US009399049B2

(12) United States Patent
Da Costa Garcia et al.

(10) Patent No.: US 9,399,049 B2
(45) Date of Patent: Jul. 26, 2016

(54) ANTIBACTERIAL PHAGE, PHAGE PEPTIDES AND METHODS OF USE THEREOF

(71) Applicants: TECNIFAR-INDÚSTRIA TÉCNICA FARMACÊUTICA, S.A, Lisbon (PT); TECHNOPHAGE, INVESTIGAçÃO E DESENVOLVIMENTO EM BIOTECNOLOGIA, SA, Lisbon (PT)

(72) Inventors: Miguel Ângelo Da Costa Garcia, Lisbon (PT); Carlos Jorge Sousa De São José, Lisbon (PT); Clara Isabel Rodrigues Leandro, Parede (PT); Filipa Maria Rodrigues Pardal Dias Antunes Marçal Da Silva, Belas (PT); Ana Raquel Martins Barbosa, Sobreda (PT)

(73) Assignees: Technophage, Investigacao E Desenvolvimento Em Biotecnologia, SA, Lisboa (PT); Tecnifar-Industria Tecnica Farmaceutica, S.A., Lisboa (PT)

( * ) Notice: Subject to any disclaimer, the term of this patent is extended or adjusted under 35 U.S.C. 154(b) by 0 days.

(21) Appl. No.: 14/943,082

(22) Filed: Nov. 17, 2015

(65) Prior Publication Data

US 2016/0074446 A1    Mar. 17, 2016

Related U.S. Application Data

(62) Division of application No. 13/823,519, filed as application No. PCT/PT2011/000031 on Sep. 19, 2011, now Pat. No. 9,222,077.

(60) Provisional application No. 61/384,015, filed on Sep. 17, 2010.

(51) Int. Cl.
*A61K 35/76* (2015.01)
*C12N 7/00* (2006.01)
*A61K 45/06* (2006.01)

(52) U.S. Cl.
CPC ............... *A61K 35/76* (2013.01); *A61K 45/06* (2013.01); *C12N 7/00* (2013.01); *C12N 2795/00022* (2013.01); *C12N 2795/00031* (2013.01)

(58) Field of Classification Search
None
See application file for complete search history.

(56) References Cited

U.S. PATENT DOCUMENTS

2010/0172918 A1    7/2010  Yoon

FOREIGN PATENT DOCUMENTS

| WO | WO 9739111 | 10/1997 |
|----|------------|---------|
| WO | WO 02/076483 | 10/2002 |
| WO | WO 03/080823 | 10/2003 |
| WO | WO 2008121830 | 10/2008 |
| WO | WO 2010023207 A2 | 3/2010 |
| WO | WO 2010/041970 | 4/2010 |
| WO | WO 2010/090542 | 8/2010 |
| WO | WO 2010090542 A2 | 8/2010 |

OTHER PUBLICATIONS

Chhibber et al., "Therapeutic Potential of Bacteriophage in Treating Klebsiella Pneumoniae B5055-Mediated Lobar Pneumonia in Mice," J. Med. Microbiol., 57, pp. 1508-1513, 2008.
Chica et al., Curr. Opin. Biotechnol., 16(4), pp. 378-384, 2005.
El Sohl et al., "Update on the Treatment of Pseudomonas Aeruginosa Pneumonia," Journal of Antimicrobial Chemotherapy, vol. 64, pp. 229-238, 2009.
"Pseudomonas phage LUZ19, Complete Genome," Nov. 27, 2007, retrieved from GenBank Accession No. AM910651.1, http://www.ncbi.nlm.nih.gov/nuccore/161168305?sat=43&satkey=10346167, 18 pages.
Rossolini et al, "Treatment and Control of Severe Infections Caused by Multiresistant Pseudomonas Aeruginosa," European Society of Clinical Microbiology and Infectious Disease, 11 (suppl. 4), pp. 17-32, 2005.
Sen et al., Appl. Biochem. Biotechnol., 143(3), pp. 212-223, 2007.
Tecnifar-Indústria Técnica Farmacêutica, S.A. and Technophage, Investigação E Desenvolvimento Em Biotecnologia, SA, Search Report for Singapore Patent Application No. 201301938-5, 6 pages, Nov. 11, 2014.
Technophage et al., English translation of the Notification of Reasons for Refusal issued for Japanese Patent Application No. 2013-529096, dated Sep. 14, 2015, 7 pages.
Ceyssens et al., GenBank Accession No. CAK25969, Oct. 12, 2006, 1 page.
Ceyssens, GenBank Accession No. CAP45518, Nov. 19, 2007, 1 page.
Ceyssens, GenBank Accession No. CAP45519, Nov. 19, 2007.
Glonti et al., GenBank Accession No. ABW23129, Jul. 25, 2007, 1 page.
Glonti et al., GenBank Accession No. ABW23119 Jul. 25, 2007, 1 page.
Glonti et al, GenBank Accession No. ABW23128, Jul. 25, 2007, 1 page.
Glonti et al., GenBank Accession No. ABY71007, Oct. 19, 2007, 1 page.

(Continued)

*Primary Examiner* — Christian Fronda
(74) *Attorney, Agent, or Firm* — Margaret B. Brivanlou; Nicole Fortune; King & Spalding LLP

(57) ABSTRACT

The present invention is directed to the field of phage therapy for the treatment and control of bacterial infections. In particular, the present invention is directed to the novel bacteriophage F387/08, F391/08, F394/08, F488/08, F510/08, F44/10, and F125/10, isolated polypeptides thereof, compositions comprising one or more of the novel bacteriophage and/or isolated polypeptides, as well as to methods for the treatment and prevention of bacterial infections using same, either alone or in combination with other antibacterial therapies, e.g., antibiotics and/or other phage therapies.

23 Claims, 758 Drawing Sheets

(56) References Cited

OTHER PUBLICATIONS

Figure 1A:
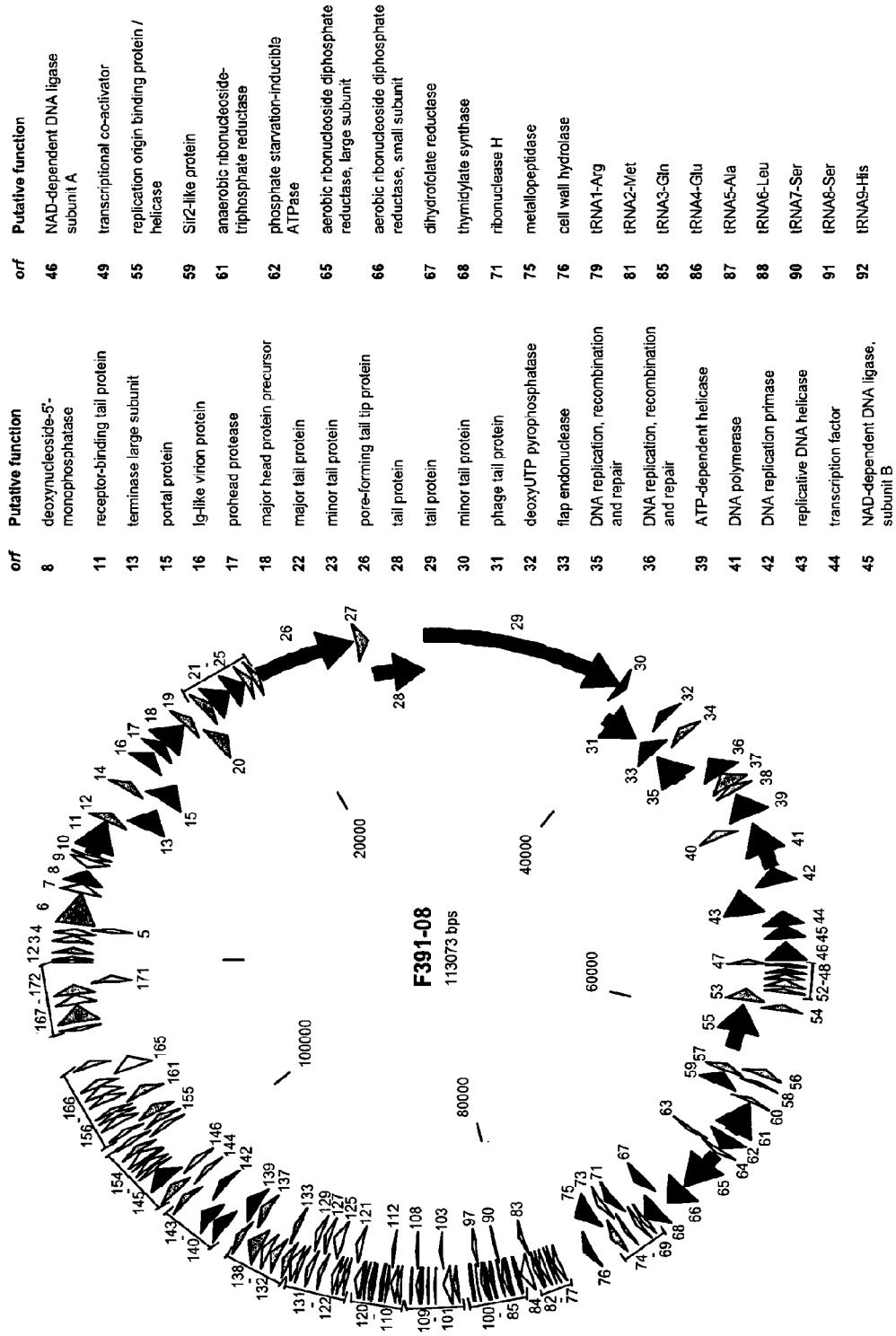

Glonti et al., GenBank Accession No. ABY71009, Oct. 19, 2007, 1 page.
Glonti et al., GenBank Accession No. ABY71011, Oct. 19, 2007, 1 page.
Kulakov et al., GenBank Accession No. CAX63154, Mar. 23, 2009, 1 page.
Lavigne, GenBank Accession No. CAD44231, Aug. 9, 2002, 1 page.
Lavigne, GenBank Accession No. CAD44229, Aug. 9, 2002, 1 page.
Lammens et al., GenBank Accession No. CAP45507, Nov. 19, 2007, 1 page.
Lavigne, GenBank Accession No. CAD44225, Aug. 9, 2002, 1 page.
Tecnifar-Industria Tecnica Farmaceutica, S.A. and Technophage, Investigacao e desenvolvimento em biotecnologia SA, Patent Examination Report No. 2 issued in counterpart Australian Patent Application No. 2011302722 on Jan. 6, 2016.
Tecnifar-Industria Tecnica Farmaceutica, S.A. and Technophage, Investigacao e desenvolvimento em biotecnologia SA, Notification of the First Office Action issued in counterpart Chinese Patent Application No. 201180054190.X on Feb. 3, 2016, 13 pages.

Fig. 1B

| orf | Putative function |
|-----|-------------------|
| 93  | tRNA10-Arg |
| 94  | tRNA11-Gln |
| 95  | tRNA12-Met |
| 98  | tRNA13-Ile |
| 99  | tRNA14-Met |
| 100 | tRNA15-Val |
| 104 | tRNA16-Asp |
| 105 | tRNA17-Asn |
| 106 | tRNA18-Cys |
| 108 | tRNA19-Lys |
| 109 | tRNA20-Phe |
| 113 | tRNA21-Leu |
| 114 | tRNA22-Pro |
| 115 | tRNA23-Thr |
| 116 | tRNA24-Gly |
| 119 | tRNA25-Trp |
| 139 | deoxynucleoside-5'-monophosphate kinase |
| 140 | ATP-dependent Clp protease |
| 141 | holin |
| 142 | lysozyme |
| 144 | thioredoxin |
| 147 | serine/threonine protein phosphatase |

Table 1 - Features of phage F391/08 gene products and assignment of putative functions.

| orf | Start position | Stop position | SEQ ID NO.: | Aminoacidic sequence | Size (aa) | Homologous/similar proteins |  |  | Predicted function | Conserved Domains |  |  |
|---|---|---|---|---|---|---|---|---|---|---|---|---|
|  |  |  |  |  |  | Name[organism] | Acc No | E value and identity |  | Name | Acc No | E value |
| 1 | 52 | 240 | 5 | MKRFVISSKPAAKLNKMASSELVK MQRDMARRYRSYQRGGQQGLPMI WDNMMRYLKSLQNNV | 62 | Hypothetical protein T5.008 [Enterobacteria phage T5] | YP_006836.1 | 4e-04 (23/54) |  | No putative conserved domains have been detected |  |  |
| 2 | 408 | 668 | 6 | MQNVKTPMIGDSVFIPFVTGDVSKP GENEKIGYIKGAAMIPFDKINAVYAE TEKAKNSDAKIYSVRVDSGDVVKVI RKDDKWLAVA | 86 | Hypothetical protein AGC_0006 [Enterobacteria phage EPS7] | YP_001836929.1 | 8e-18 (53/87) |  | No putative conserved domains have been detected |  |  |
| 3 | 1007 | 1411 | 7 | MTATKTEKFAWNETNAATAVEMYE KIASDGLEVANSQGLIDIAKAVGAE SHVKVRSKLVSAKVYQKSDKPRKV GGGSSLRKAHYVRVLTQHAIADGLI DDADGLASLEQMKLDQLDVIARMV GVQDEVKESAE | 134 | A2 [Enterobacteria phage T5] | YP_006834.1 | 8e-44 (88/133) |  | No putative conserved domains have been detected |  |  |
| 4 | 1479 | 1748 | 8 | MALIKGSVIKLTGTVVDELIQTGYQD NKVMTPPSVKVPEYIVLWVNPDAD TFGMAINREVFKPEMLELSSREIYLL NYAFSVEEKEVVK | 89 | No significant similarity found. |  |  |  | No putative conserved domains have been detected |  |  |
| 5 | 1745 | 1972 | 9 | MIFFPTESLILIAGFFAAACLYGYYN FMEIGSEQTDLLRRDFWFKKASICR RWSIIFILAVTFGISASIIPAIV | 75 | No significant similarity found. |  |  |  | No putative conserved domains have been detected |  |  |
| 6 | 2056 | 3732 | 10 | MIIAIEKQKAILTAANNLNFWGKRLR AKKLEICDELSKEHYGTAKHSSEIC DWLDSNKPVKPAAEKRAQRVAVE DSRPVAAGQLNSSVESWKVIPGRR FLLTSIQNNTFPHANFWKTLQEAAK YLGATLLVSKYAYNKKGFQNGQGN DELKYDDAFSDFICDENVFLGNRET GFAFMAEINILPTADFPLSGFGETAT AYGLKGLAIGHAKITAESVPAMKGD TVRRMYSTGTATLKNYIQQKAGQK AEALHNYGALLVEIDDNGNFFARQI ETMDESGMFYDLNHKFTVNGGEE VTGHVAALQYGDIHAEKLDHAVAFA SWGPCDDSLVNVLRPRYQIVHDVH DFTSRNHHNRASGVFLAKQYAAGR DKVIDDLIDTGRVLEAMEREFSQTVI VESNHDLALSRWLDDSKANIQQDP ANAHLYYRLNAAIYEAIENKDDTFN VLDYALRNVAGCDFAAIFLTTDESM KIAGIECGSHGH-NGINGARGNPKG FRKLGKMNTGHTHTPSIYGGVYTA GVAGSLDMGYNIGASSWSQTHLIT | 558 | A1 [Enterobacteria phage T5] | YP_006832.1 | 0.0 (402/559) |  | No putative conserved domains have been detected |  |  |

Fig 2A

| | | | YENGQRTLIDFKDGVFFA | | | | |
|---|---|---|---|---|---|---|---|
| 7 | 3801 | 11 | MKLTFIYNNRKSFTASNIVVENSLVIS RDSEGRPHVSYQKVNTVDGDTVLK ALAAILPRPAEFKESGIVSQLVAADS ILYEADICEIVEIDAAAAGLMFIVVSE NDYDDTYLLGDVMDYSSSEYTPPL AIVPVMATRIKPAELADALTLFF | 150 | No significant similarity found. | | | No putative conserved domains have been detected |
| 8 | 4253 | 12 | MAFNKLAIKAIKLWDLDGTVINSFAR VFPCMDDKGNLDLNMYREKACVH DAIMTDTLLPLVEYMRASLNDPTVL NIIVTARYMGKSDYFLRKQRIRAG RGGNIQILSRDVLHRYIGDADYKEV YYSKDGIYKTHYFEMLKAEYPNATI TMIDDNRGVLAAAAAGLQTMDAT AINDILSIGVRLAGESFIDEALDDDN DYQYLCERLAHCWEGMTEEERSD YGIKPQQFIQSLAIAS | 238 | Deoxynucleoside-5'-monophosphatase [Enterobacteria phage T5] | YP_006829.1 | 2e-81 (142/231) | deoxy-nucleoside-5-mono-phosphatase | No putative conserved domains have been detected |
| 9 | 4327 | 13 | MTIVLIFTTFFFLAAVWFGVRAHDLR NAVVAADLRNKSLHQEILQTRAER QVAISKHQRVMNDLRNDPSNPYYI PPVTPQVAKRKQKRAGSDNSRKVS GSPSSNSGSSRSDDGSTAAIIATTA AVATYSCYDSGSSYCDSGSSSSSF DSGCSF | 153 | No significant similarity found. | | | | No putative conserved domains have been detected |
| 10 | 5660 | 14 | MEVVIGALVLLSIVLFV/ITVKQGKAIK QLERTNGVLQKSYDNQTRLLHKAQ LNLSECKAELESANKIYITKGMV | 74 | No significant similarity found. | | | | No putative conserved domains have been detected |
| 11 | 5888 | 15 | MGFYAGRIGDKKVLSLTSGNNKDV NNHTNPGWDTIFHSDMPHVVVLET HERDLWDGGDWYRCTRMPDRIIQ VLSADYDRVVLTEVEFEDCTRRFIY GTSLGVGAKAYNAYFSNTVGSQAS AGTMASMKTNVCASADLHMDISFY FEETPGTINEKLRDGTGCMYTWGV NSEWGDRGPGPPVGAPIRPNFETII KAGWVLYRGAFSGNIAGSVSPPNR PLTIGVDAMRHPWMRTTGVNSICL RGETLNRNMYGHMGPRYGQSSNP VGGPYAHNIQTESYQEVQYKAGFF RGPPNNFMGWENTDNNNAGSGW GNNAIYRDNNFRVPKRVRWYITNM KYNGQGFYAENVFGSRNQEIKISP REFIVNGINLMNTGWKFINQNDINY SPGNRPDIRVIATNVARFSGNPTVG NNGYVHFNQPLTRPDNGAEFGQG NVSEMHVTTVGVYNFRSDAQWYV KSNPPEIGNQWGPVWSESTRPLRL VGGTGSSADIGGNLRTSGNASHHLA | 658 | Receptor-binding tail protein Pb5 [Enterobacteria phage T5] | YP_006985.1 | 1e-127 (269/674) | receptor-binding tail protein | No putative conserved domains have been detected |

Fig 2B

| | | SEQ ID | Sequence | Length | Description | Accession | E-value (coverage) | Short name | Domain | Pfam/E-val |
|---|---|---|---|---|---|---|---|---|---|---|
| 7989 | 8462 | 12 | TLWLGVNNSRNGACVVTLDWKND EWIAAAGIGGCYNPLEDLTQWSEVD SRLRIFGNHFQKRVHQIMCLPVNM CVPFHFIRGTVTQCGVIPGNNAMQ MKAMWAPTTNSATQGDYAIIYWLI ARADGSVEVWNVNVEMSNIMNMRVI. LPEVRIAVQRLA | | | | | | |
| 8462 | 9778 | 13 | MSNDLIVPDTMSPEGMLVIEAYLES GSDVAKAALAVGMEEPKFREIMRK PEVKAYLTDIFMESGFRNRDKFFGI LDTVLTMKMEELDETGMGSEMDIM DILKLMHKMKMDEMKMQIEYEKVK QAKAPIHQNNTQINLAGGHDSNYT DLLSRIVGAGK | 157 | Hypothetical protein T5.156 [Enterobacteria phage T5] | YP_006984.1 | 2e-42 (98/159) | | No putative conserved domains have been detected | |
| 9778 | 8462 | | MEISRSYINTTDVVDFGVDKRFFKF PVSGLLATEGIVPNGPQCAIINALED PRHRFVTACVSRRVGKSFIAYTLGF LKLLEPNVKVLVVAPNYSLANIGWA QIKGLIKKYGLQTERENAKDKEIELA NGSLFKLASAAQADSAVGRSYDFII FDEAAISDVGGDAFDIQLRPTLDKP NSKALFISTPRGGNWFKRFYEQGF REDLPQWVSIHGTYRDNPRVSLADI EEARKTVSKNYFKQEYEADFSVFE GQIYDTFSVSEHVQDLAGMGHFFA ADHEFETILGIDVGYRDPTAVLTIKY HYDQDVYYILEEYQQAEKTTAQHA MYIQHCIDRYNVDRIFVDSAAAQFR QDLAYEHEISSAPAKKSVLDGLACL AALFQQGKIIVDASCTALIHALQNYK WDFQEGEEKLSREKPRHDANSHL CDALRYGIYSISRGK | 438 | Terminase, large subunit [Enterobacteria phage EPS7] | YP_001837088.1 | 0.0 (393/438) | terminase large subunit | Terminase_6, terminase-like family | pfam03237 2e-24 |
| 9970 | 10452 | 14 | LASNVYKRDAISIMRDGIKAQYKR GNCCAICDSQENLELHHYSTVALLV KNFAKEFQLDFTDSEVVLSNRDKF YKHYWHELVEDTVTLCVFHHQTLH KVYTKEPPLFSANKQKIWVEKQRE RCMNPEAPRTSNTGERSGFAKWL PTDVKTEKSGFARFL | 160 | Hypothetical protein T5.153 [Enterobacteria phage T5] | YP_006981.1 | 6e-53 (95/145) | | No putative conserved domains have been detected | |
| 10452 | 11663 | 15 | MAIRDWLVTKLNRGQRIIRDLEDVS HRTNVKPFTTGKAYSSIEILNRSAN MVIDSAAECSYTVGEQYKTITTYGTI RSKTLETLLNVRPNPYMDSSTFRRL IVSDLLFEGCAYIHWDGSSLYHLPA ALMEVKADDKKFVNKFVFNNMIDY RVDEIIFIKDNGQNGGINSQITGQSR VATVINSLTKREKMLEFKEKFLDNG TVIGLILETDEILNKKLRERKQEELQ | 403 | Portal protein [Enterobacteria phage EPS7] | YP_001837086.1 | 0.0 (314/396) | portal protein | Phage portal protein | pfam04860 3e-23 |

Fig 2C

| | | | Sequence | | | | | | |
|---|---|---|---|---|---|---|---|---|---|
| 16 | 11660 | | LDYNPSTGQSTVLILDGGMKAKPY SQISSFKDLDFENDIARFNKDVCIAL GVPQLLIDGGNNANIRPNIELFYYM TIVPMLNKVCSSLTFFFGFKVTPNT KDVVALTPDKEKEAKFVTALVNNGI LTGNEGRIELGYEELADEQMKIRI PANVAGSATGVSGQEEGAPNKDE EKQ | | | | | | |
| | 12379 | 20 | MIDYKALKALFPNGLPEAHNVFATV KAHLTYQILRKEYGYAATNSKTWD QFKEAYAEATKPVPVASVSITGAPA SLDYTKTVQLAATVLPTNADNKTVT WKTSDATLATVSSTGLVTALSKAGT VKITATAGGKSSEVSIQVKAPVVAV TGVTMSPKTITIEAGKTGKLTGTVA PANATNKSVTYTSADTTKATVAAD GTVTVPANLAADSTVITVKTADGN KTDTAIVTVKVPTAGV | 239 | Ig-like virion protein [Serratia phage KSP90] | BAH15178.1 | 8e-21 (84/186) | Ig-like virion protein | Bacterial surface proteins containing Ig-like domains | COG5492 | 7e-07 |
| 17 | 12576 | 21 | MQNINLNAEIKSVKAVGEGDNPPLK IKGYANTITKDRAGDVILSEAWTTS NALKNFMKNPIMLFGHNHSRPIGKI LDLVPTESGLMVEGEVSAADLQIYS LIRDEVLKTFSVGFYIKDAEWDDMT ETFIIKDLELLEISVVSVPCNQDSTF SLSKSVNHNDYMELRKSFVKSSQV QPVEQPELSNLEKFLVAAGYAKG | 198 | Putative prohead protease [Enterobacteria phage T5] | YP_006978.1 | 4e-60 (117/196) | prohead protease | Peptidase_U 35, caudovirus prohead protease | pfam04586 | 2e-25 |
| 18 | 13186 | 22 | MSYDIAQLSKDLGLGLDIAEQLKGLT ASQKAEEARKFAAEQEAKELKRME DLVAKATGEDRKNLAEALELVKNLD EKSKQSAEAFVKAMNSQQEEITGL KEEIKSLLAARENGRSFVADGVAKA MFGKQEDFEDEVEKLVLLSYVMQK DVFGTKRGEAHLKAVNGSSIEVST EAYETIFSLRLRDIQAKLIGTMFEE LPMSSKLLTMMVEPEAGEASWVDA STYGTPATVGAEDKTKLSEITFKTY KLAAKAYMTDETEEDAIFTLLPIMRR RLIEAHAIAIEKAFLTGTGAAGTPKG LIQFAKDDGKVVATTAKADGSVKVT AKEIHKLRRSLGRHGLDLNKLALVV SMDAYYDLIEDEEFQDVAQVTATTA IKLQGQVGRIYGLPVLVSEFFPAKA ASAEFCVVVYRDNFIVPRQRAITVE KERQAERQRDAYYVTQRLNLMRFF ENGVVAGAYAA | 460 | Major head protein precursor [Enterobacteria phage EPS7] | YP_001837083. 1 | 0,0 (325/460) | major head protein precursor | No putative conserved domains have been detected | | |
| 19 | 14627 | 23 | MQFMTDSDWRTYGGLKRPDLESNI PMLIKAANALITQLLGIDDTANVVDV LPTKPARKKYFLSSPVPSTITKITIND | 170 | Hypothetical protein T5.148 [Enterobacteria | YP_006976.1 | 3e-65 (115/170) | | No putative conserved domains have been detected | | |

Fig 2D

| | | | | | | | |
|---|---|---|---|---|---|---|---|
| | | | QEIDKSQYKNYPDGTLLLKFSPPEG YMEVEFTQTGFTSIPDDLVLAACFL VDHWVKKDYRESRTFGGETVTFNT TKSGVPEHIRTIIEVYRRL | | phage T5] | | |
| 20 | 15139 | 15900 | 24 | VALGDLARQIVKEQLDIMSGGSHST KNTVIYSAETMDNHKDGTIGKVSFR FTKPVSEDLNVRTSSILKAVSSSLN LEGDVGVIDNLLNSITGKKSKIGRKR STGRVEVNFGDPSDADNGYAGAIS GASGRFVSNTNLRALLELVAKEYLV KDMKKAGAPLKFRTGRFANSLKIKD VLLREDAGAKTPDLNITYNYMLKPY SVFNPAVSTYRGLSLRPFPGARNP QKLIGEAIAKAARDLIHSRYRIRVNQ GT | 253 | Hypothetical protein T5.147 [Enterobacteria phage T5] | YP_006975.1 | 1e-106 (185/256) | | No putative conserved domains have been detected |
| 21 | 15900 | 16385 | 25 | MNYRTSIADALVERLKKDMDGSNP TEFFTNMYGNVSRQTYSFEQINEF PYIAVHVGTETGNYLPSAQQWVYL EIPILIYDKEKDDINMQLEKLIADVKT SIDTGGNLQYTIMKPDGSTIDSEAT DMQITSVSTDEGILSPFGFAQVNVT VRYMPLRRALDR | 161 | Hypothetical protein T5.146 [Enterobacteria phage T5] | YP_006974.1 | 8e-66 (113/161) | | No putative conserved domains have been detected |
| 22 | 16409 | 17536 | 26 | MSVQLLRNTRIFVSTVTTGFTKANT QEILVQDDVSWSQDSNSTDITLNEA GPKPTRGSQRFNDSLNAAEWSFST YILPYDDAGKQILPDYLLWHGLATG AAVNLAGTTGVFQNATNLVVNFKD NGYHELAMLNIYILTDSSWSVIRNC QVGQAEVNVDIDDIGRVTWSGNGT RLETLASQPFDKTIGIDDALYAKIQ SSYIKNKLTILKLKNNATGGKTYNIPI TGGSFTMNNNVTVYLTPNIMSRVDV PIGSFTGSFELTGSLTAYMNDAANG SIQLYKDLVSDLKAVNDFEVAILGG EYDTARPAAVLVAKHANLNIPSIETD DVLGVSIEFKAIPTQMDAGDEGYLG FSSKYTKTSIAKLISSGDGNPVTP | 375 | Major tail protein [Enterobacteria phage EPS7] | YP_001837079.1 | 9e-164 (276/377) | major tail protein | No putative conserved domains have been detected |
| 23 | 17546 | 18433 | 27 | MLYSLMRESRVVIEYDGRAYGFDA LSDYTAGTSYEEFKANRRTIHRRSN YAYSKITAQSPSSISLTLNFSSNALE GLFFELMGFIEIDGMYQMPLFSNNI EPKMFSVYIINKNTSLRFDNCFAT CDFSLDKSVPVLNVGIESGYFEEVG HPLNSYTLDQGEVLPFSLPQVSSN GRVLPGLMSAGMSFCQQOCEWRG DRSLFDINKYNNRRAIVNELNSSAL ISMYYAKSLQIDSTHNIKPDIGLPVQI RNKYIVVDFPSTRITKRLDLTDVYKI | 295 | Minor tail protein gp24 [Enterobacteria phage BF23] | BAA02256.1 | 6e-95 (171/296) | minor tail protein | No putative conserved domains have been detected |

Fig 2E

| | | | DYDVIPTEQSDPVRIKLIGE | | | | | |
|---|---|---|---|---|---|---|---|---|
| 24 | 18437 | 18859 | 28 | MSINLKDIALDTKQITIAYPGLPHFKL KVNYVSRKLSKKILEAAQENQFVNG IAVKVQNDDKFAEEFVKVAIAGWEG LTVADVEKLMLIEVPEDRLEDKVEF SIDNAMMLVRNSSAFETWMNSTVF HLDTFRGSKSEPTA | Hypothetical protein AGC_0154 [Enterobacteria phage EPS7] | YP_001837077.1 | 5e-42 (79/134) | | No putative conserved domains have been detected |
| 25 | 18933 | 19259 | 29 | MCESLGEEPNPEVLKRFVEIHDFPE IAQTALTIYNNLSDNYIPGDYPTYLG KDKSALLVFFDIYGVEDADEKSLILQ IINIFDSHAVAASRKRVEAAIKKSKM KSSSR | Hypothetical protein AGC_0153 [Enterobacteria phage EPS7] | YP_001837076.1 | 2e-25 (56/95) | | No putative conserved domains have been detected |
| 26 | 19343 | 24421 | 30 | MTDRLIRELLVDIKQRGGSKAAKQI RDVEAALDGAAQSSEGLNTSLGKL PGSFTALERSVSRTAKSLEKLSSTT SITALAASIGMLSGKFTSFEVDLAKS VLKINANLNGVTSAANKMASGFDTA ATSSVADLNRVNKALQELDAHASS VAKVLQTLKAGAGLESISSSAAKAS TDLSHLVSGVEKIGNQLARMAEQA VLAGRSLQGLKADSLGAAGEHLSK AASGISVAVSSMGEEVNKLNLLLE LAVKADLASKSIANIAPGTKLNSLGT EIQKINTSLATAANTSVAEISKIKAAL TSLVSSTATAAASMKTVGTGSGLS KLISEISAATSASTSDISKVTAALKQL NVDATAAGKALQSIKAGANLSSVPT VVGKIGTSMTQLRAQLEGSVTGIEK SLNDLSRAFATMGGTGNLNPLGNS IRGMIPSLTQLAKAAVQVNSALSKIQ AGRGVLQLPTQFKAVTASLNALETK LASTSQILERGFSKGFODMASKSTS SSTRMINNFQKVPELNAIEAAAIRS AAADKLIAKRIRLGQAGGGGNPA: FNMGALVAEMNRIVTSIEAMGNKM NTTMADMARSTDKVSDKLTDLNSG VRDVNTGLGGLNSTLTGTGSAANR ASRALGNTSGSARGATRNFAALAM VTGPMPLIIYGAIASNVYVLKAAFDQ LKLGDQLNRLEQFGSIVGAKTGTPI QSLAVALQEATGHAVSFEEAMRQA STAAAYGFDAKQISEFALVARRAAA TLGVDMTDALNRVIKGVSKQEIELL DELGVTIRLNDAYAEYVKILNAANT GITYNIQGLTSFQKQQAYANAVVAE STKRFGYLDEVLRATPWEQFAANA DSALRKVQQAAAKYLGPVIASINAA FYTSKASVSAEAATAQQESIKQMD | Pore-forming tail tip protein Pb2 [Enterobacteria phage T5] | YP_006968.1 | 0,0 (626/1196) | pore-forming tail tip protein | SMC_N, RecF/RecN/S MC N terminal domain | pfam02463 | 4e-05 |

Fig 2F

| | | | | | | | |
|---|---|---|---|---|---|---|---|
| 27 | 24536 | 25150 | 31 | GKDSNAVVMNLEASQKGLDDAVKA KEEVKNKLAALNKEIMDREAKMDM STALATAANYSGFGNLLTLGASKAN KEFTQQTADMRRQAYMLQQELAD SAGAIQKWKDARDSALSKAQKENP ELAGKLNIGQNVEASNGLYTFDNAA LDGAVALRKEFNNIKKTSGDLSNDI QNFAQDSNTASRATAALGDALKAV ESLAGGSTEKANQMTKDLNLGYST VTEMNTAYKAMSNYQKIVNDEAKS KLDVEKRIAEVYAATRNKDKAEEAG RALEMQQLSAKKEALKAVLATNKD NKAIQKELTLLETEELKVKNQGMEA TKKEKFYKDKIVGIDREIALLNNRTM TDSQYNVANLKLNLQVEKDRLALLK TQADKEKEAEQSRRNIASIEREIWK EQLDRNAKTAEMRKEEFERNQSM KPLMGESQKMQEQLAFYQEMKEF TKGNADEQARWSKEIANTTAQMAA LKAQRTAQMMDRVGQSLGADYTP TTGLEGEDKKFADMENQMASYDTA IGKLSQLNSEATATAQSMGNLANA MIQFSQGSLDTTSMIAAGMQTVSQ MISYGTNQQISAIDAIAIAAEQKRDG KSEQSKNKIKKMEAEKIKLQQESAK KQIIIQTAVAVMQAATAVPYPFSIPL MIAAGLAGALSLAQASSATGMTDIA GSGGETASYLTLGERQKNVDVSM GANAGELSYVRGDKGIGSANGFIP RAEGGNTYPGVSYKMGEHGTEVA TPMVPTKVTPADKVASETSSGGAR RPVNLNIQAMDAKSFMEYALENPA AFQAAVELALNEQGLSLKNLN | Hypothetical protein T5.139 [Enterobacteria phage T5] | 204 | YP_006967.1 | 6e-76 (130/204) | No putative conserved domains have been detected |
| 28 | 25147 | 27993 | 32 | MRLPDPFTHPQYNGLGFDKATLID NDPVIRDELPNGKVNEVKTATQYW GLNISYPVMFPDEYAVLSSAILEYK RTRGYLDVILPHYESYRVRGDANN CRIAAGQKGSTLVITNTNSLSGEPK PGDLFQLTTHPKVYKITSFKNVAGV WTLNLYPDLLLTNGSERPRFNGIL FQTKLMNGDSFSEEITVDGVYDGV NLVLRESL MRQILPSAKAYLANNDKIRLAYLVSI ELPGSTGNNAVYAYMTDYMRDINY GGILFQSGKIKTISSHKQNRTLTVGS LSFSVTGTDANEVIKLVQSGVSFLD RSISIYQAIIDDNGEILPVDPDTNGPL LFFRGKIVGGGIKESNTVSGVGTSV | Tail protein Pb3 [Enterobacteria phage EPS7] | 948 | YP_001837072.1 | 0.0 (681/949) | tail protein |

Fig 2G

| | | | | | | | |
|---|---|---|---|---|---|---|---|
| 29 | 27994 | 38385 | 33 | ITWNCSNEFYD-ERVAGRFTDDAS HRGLEIVNGELLPSHGAKRPEYQE DYGFFHANKSVNFLAKYQVKEERY KLESKKKLFGLSKSYSLKKYYETVT KEVDLDFNLAAKFIPVVYGTQKVPG IPVFADTERNNPNVVYVVYAFCEGE IEGFLDFQFGDAPMICTDQTDSTSR TCFGQKRVSGDTMARISTGLPSTS LSTHGQEYKYNDGNGDIRIWTFHG KPDQTVATVLRDIAAANNFFLQGEN GNGPEYWDSRYKLLDTAYAVIRFTI TENRTDIPEVSAELSGRKVKVYQAD GSVKMDKTSQNGVWQTFDYLTST TFGASIPIDRMVIGDWRKEADLLNII DTSYQTSWQPFWRYVGWESWTA ENRQIMQMNTILDNSNSVFKNVQE LLESFQGALNNLSGIFRITVEKDSKT PLEINFLDTYGDLDLSDTTGRNKYN SVQASLIDPTLNWKTNSITFYNSKF KNEDRGVDKKLQLSFANITNYYTAR SLADRELKKSRYSRSLSFSLPYKFL GIEPNDPVVFTYDRYGWNKKFLV DEVENTRDGKINVTLQEYGEDVFIN STQVDNSSEAVPEISNNVLPPRDFK YTPTPGGMVGDVGKNGELSWLPS LTPNVVYYSIRKSDRVDPYIVQQTA FTPNVRMFQDIVGEPAGLTIFEIRAV DINGRRSSPVTISVDLNSAKNLSMV ENFRVLNLAPDPAEWVGPDLELGW DKLQEEGLISGIEFYTLEIRDNTNKLL RSAKITSLYNYSYLLGYNKLDYKAN NSNTLGIYRALQPRIQAEGPKGEKS VAWAYI MISNIAPAKMVLQNIVTGYTIASIQH-SIFSDYDVIGRTFWLLTTGGVTTRRD FTGVDTFIATINNLIAGATYSAQGAF YDSMVDAELMAAKVGMNLSSTINF KMKTAPKITKVSSFAESVDVGVGAP MVVVELSGEAEYTIEMKPEGSST WTKYYRGPITEQIIFGGVPVGRYNI RVSGVVTMPDGVTVDVSGYDTWP SLFNLTYNFTPPSAPNLRFKTAHI QDGMERFDVRLEWDWTRGTGAN VREFIIQYISNDEFAKTGWTKANKL NVGAAKAGTITSFPYKIRHRFRVLS VAWGPDTQSITNSNEVTYIIDESTTF DNAFINETGVEMTYAGIKGKLWNS NTKQWEQTFLVDAATGAVVLGTLD | Tail protein Pb4 [Bacteriophage T5] | AAP75894.1 | 0.0 (338/580 )675 | tail protein | Collagen triple helix repeat (20 copies) | pfam013 91 | 2e-05 |

Fig 2H

ENGKAPISFDPVNKIVNVDGKVITK
DINAANVILTNLTGKDNPAIFTQGKK
YGNNAGGVWMGVDNVDGKAKFDL
GNNTQYVRWDGDTLRISGNVVIGT
PGGDVDLETGMQGKQTVFAYKLG
TSLPSRPLDQVYPPAGWSAFPPNR
TAQNQNVYVQGTLDPKKSPPALV
DGTNYSAASQWSGVPGTGGTDGS
NGDYTVQIYQISASKPTKPGNINDP
SGWSRTPPTGTPLWMCSGRFNGD
TNALTVEGWSDPIRVDGEKGATGA
TGATGPQGPQGPAGGSVEVQWSK
DGTTNWHANFTTGDIYMRQRVGT
GGWSSAIRAVGEDGTNGTPGSKG
NYIGMRFRVAAEKPATPTGQTPSG
WSDAPPQGNPLWMVKAEFNGQTN
ALVGTWSEPVRIDGEGIGVNLYPVK
KTLDQWTGMSNGTMVKNPDTLSF
TITNTESTTSSTGPGAHPVPFQGSQ
GPIVEIPYKPNTAYIFTYEVSTDSTS
FVLRDLLLEFSSITGSFTNFQELLTG
AKGKQEAKIVTRADTKFLSFRPGVR
TAGATVTYSNLKLEEGIKATAYSVE
ASDSIGEKGDQGTQGPQGPQGGNQ
GPQGNQGPQGAKGDNAKGFSLSS
LGQTFTYDAEGKLKSDATILFQAFR
QNTTANVTWSAKDEKGGNITLTST
SNTGATLTAANFKTSKSVVVTAVCD
GITDQITIVRLDDGSNALVGLLTNEG
STVLANYAGYVQNYSTGSGDFKVF
YGAKDITSECTFSTMEKNNLDADIT
SAGKYTLKGMPAGTDVINGWVDLR
AVHPTYGAVVRRVATTKSILAKGYD
RVITTSFENGNKGTWSTGSVQGVS
GATIVAAGFSKALVISARDCIEDANA
FPVVAGQKYRLGMWIMASESKVNI
NMGMRIVRAADGVVDWQGTLMIA
QGTVVPGGWSYIEKEFTVGSSNTG
IAMPWIOMAGSSGSDLGKAYVTDIH
IFALEMDGEKGDTGATGATGSQGP
QGPQGNKGDKGDTGATGAQGPA
GSSVNVQWSKDGSTNWHAGFQP
GDIFMRQQVNGVWGSAIRAVGED
GKNGADGTDGQVNGVWGSAIRAVGED
GTPTGNNPGSWSDAPPVGSPLWM
TKGTMNASGQLQGTWSNPVRLDG
TINPNLFAVRKWMAGMTGTEAGTS
KNDIEKLAHTLTRTSGTDNTAPGCY

Fig 21

ATPYLGSGAFSHPVTPGKRYTLTY
NDAASEVQTRDTIFWQANPDSGQ
STVIEELNTGTSIKVKRTFVVPTGM
NYLTLRPSALTLNVATTWSKIKLEE
GGEKTEYQVEYSDSIGIVGKSVLVQ
WSKDSSSSNWHDTFQTGDLFMRQ
NVDGVWGPAIRAIGEKGEIGPDGK
KGNYTNIIFRISDTKPAKPTGNKPTD
WFDAPPDGSPLWMATATFNGDTN
AIIGAWSDPVRIDASGVGENFLAFK
EWMMSIQRAEGTGSSVSKNPDQM
RFRVTAGPSRNDAYTTPYQGTGTH
FIEVSPNTVYTLSFEMETAVSTRMM
LLQFDNGNGGTHARNNQVISTSTGI
NSLTITTGAANTTHLSMRMSISNMGE
TNVLMKPKLELGAFPTAYVAHPSDL
LGKDGATGPQGPQGNTGATG
ATGPQGSKGDTGATGPQGPQGPK
GNAGENAKGFALTSDYQSFVYDTV
GDIKSATTILFKGLKQNTTAGITWSA
VNNTGAAVTLMNSGDNRQLTAANF
GASKWVTITATCDGLSDQITVVRLQ
DGENVLTAVMTNEAATVLANYSGY
CQSYENAKGQMRVWNYGSTDVTGQ
CTFSEGGRSNVTPSINSANGNYSV
TGMLDGTDITEGWDVKATHPKYG
AITKRFAVTKVFLAKSYEMMTNTFE
NGNKCSWAGALQSVSGPTNQSISK
ALRITARDNLEGRNTIPVAGGQKVR
IRFWYNPLGLEEEAIFRVGFIVHRKD
GGKGYPSRTVVTGPAPNSSWAYF
DQELTLSANDEGIAWPWFQLDNKT
SGSSLGYMLVADIHFEDLSMDGAD
GATGPQGPQGNTGATGPQGNKGD
TGPQGPQGPAGASVGVQWSKTGN
ASDWHTNYATGDIYMRQQVNGVW
SSAIRAVGEDGRVGADGKYTSLRF
QVAATKPARPTGNSPANWSDSPP
EGSPLWMVKGEFDSSNQLQGTWS
DPVRLDGETVNLNLFANKAWIASIT
GASGSGSVVAKNPDELRLRITAGS
GATDAYTMPSGGDGTFFTKVTAGK
RYTMSFDTDSALEMRMHVFIQAG
ANTTTSSFSWIASTTAGRTSWSFTV
PAGCDRVSVRVSLNNNPGGTNVV
SNIKLEEGDFATAFIRNELDTIGADG
SQGPQGPQGSKGDTGATGPQ
GPQGPNGTSAKAFALTSDSLSFSF

Fig 2J

| | | | Sequence | | | | | |
|---|---|---|---|---|---|---|---|---|
| 30 | 38389 | 38808 | 34 | DTSGNLKSNGTIKIDSWRQNTTAAI TWTAKNQAGSNITLGGTATNKTITS AQFGSSEYVTVTATCDGTDSITIVR LQDGVNSLVGYLTNEAANLSCNSY GFVQNWDGTGNFKVFYGTVDVT SQCTFGVEDKSNLNGNIGSSGYYA PSAMPNGLEITSGWVDYKATHPKY GTLIKRFTLKKSLPGIGYDRVFTGSF DSGNNGSWGRTVVDIATGSPGGH TKAIQCTSRDTMESSNWFPPTRKGM RYRYTAWVNNSEGEYQLRLGLHT QNSSGVNTGYPTMLAASAKDSEG WKLVTGIVTVGDGSTAETGRARPFI QMNGSASPFGNAYVAAIAIEDLSM DGADGATGPQGPQGNTGATGPQG DKGDTGPQGPQGPAGNSVNVQW SKDGSTNWHSTFTSGDLYMRQV NGSWGPAIRAVGENGANGTPGSK GNYSMKFAVMASTPSRPSGSNP AGWSDSPPPGNPLWMIKAEFNGE TNAIIGNWSDPIRLDGDSINENLFYF KAWLDSITGVAGNGSSIGKNYELLR ARIIAGTGVTDAYTLPSDGSASMFT YLPPSTTYTMSFETDNAVEVRCHV FWYAKGSNTTGGVLKTIASTTAGLS SFTFTTPANSDRISVRFSVNESGGN NVVGRCKIEKGAFVTSYVRNQYDA VGDRGPGFYTGAITNLTGWNDTQA ASFFQSTFGGPPVKYDVLTQYKSG SPQNSWTRQWNGSAWTAPALTVH GDMIVSGSITADKIIANNAFLAQIGV DILYNRAAALSSNPEGTYTMKIDLA NGYIHIR | 139 | 15kDa minor tail protein [Enterobacteria phage T5] | AAU05271.1 | 3e-43 (82/139) | minor tail protein | |
| 31 | 38808 | 40847 | 35 | MSTENRVVDIILDQNVSYGLMLQFM DIDDSAYPATETPVNLTGVTLKSSIK DSLESTGVKLADFVTVVNATQGQ ASLGLTAATVATIVSKASKERDKYN PRLRFAGYYDVIMTKGTGATATSY RVMEGSVYVSDGVTA | | | | | No putative conserved domains have been detected |
| | 38808 | | | MAITTRIIAQQVTALDGANSRVSKY PKFTVQLGYSVSSLAATELLLDAATR SAASAAAKTSETNAKASETASKN SQTAAKTSETNAAASAQVAQNLAG KASLVTPLGVMTGSAEAKIASITIAA NQSSSVHVLFALYATGNGANRDDI YNMEIVSLALPGPVTSVTADNIGSF LSHRVIGPANTNGFMVGLKSTIEGS NVTYDVYLKSRSSFRDPKMAFLSG | 679 | Hypothetical protein ACICU_01051 [Acinetobacter baumannii ACICU] | YP_001845710.1 | 1e-19 (54/139) | | No putative conserved domains have been detected |

Fig 2K

| | | | | | | | | | |
|---|---|---|---|---|---|---|---|---|---|
| | 41335 | | SISVTPPTGPLVDGTSPAWKTTGFD TDVIYVNRAQVIDDGISLARIKQLAIT NGKTDSSILLSYLNETGILSTNKKSI SLRPGGTSDSSIAATEFLPNGNIILP NGDTGNQTISWLGGPRIRVNSNGS FVLSTNNPSNQTSGFITFRPQGDQ VTSTELQIRDDGNIKQTAPQSSAGN ALIRQDAAIQHIMDKAPAAGITANPL SDLNVIPTPEGTDPWGADGVRVFQ SGVSTKNTPDGTTGRLGTILNVRHT QYRIMQFFMQSNATAPILHIRSLRA DQGNTPPAWFKVYTEYSKPNIQSDI AGITIDGNGFVKKASPIAKLIAEIPSK EDSFFWTGVETVGGYVGCNAEAQ GVFAVKTGLGKYTIKGSLGWNTEG WKFELPRDDNGNMLCFVESDWNE EEKELNIQVFTRKFDINTGNIIAGEP MEIPQGRWIDLRLEMPKVEIPEVEF PEDPEV | | Putative phage tail protein [Enterobacteria phage EPS7] | YP_001837069. 1 | 3e-09 (53/105) | phage tail protein | | |
| 32 | 40892 | 36 | MRIKLSHPDCKPHVGSSEAAGMDL RAYFGCRASDLLRAIPPGESLMIDT GVAVEIPEGWNVGIVVPRSSLGKRRL MIANTTGVIDSDYRGTIKMNLLNMS NETQPIDNFERLCQLVIVPHYNPNDI EIVDSLTDTDRGEGGFGSSGKM | | Putative deoxyUTP pyrophosphatase [Enterobacteria phage EPS7] | YP_001837067 1 | 6e-52 (100/140 ) | deoxyUTP pyro-phosphatase | Deoxyuridine 5'-triphosphate nucleotido-hydrolase (dut) | TIGR005 76 | 9e-43 |
| 33 | 41335 | 37 | MSKSWGTMKREAEQRLASRRNLM IVDGTNLGFRFKKDSGKPIAASFAN TINSLANSYDAKHTIVLGDKGKSIFR TNIFPEYKGNRDAKYADRSEAEVE ADRQFFEYLDDAFIIQLIGHHYDHIWLI RGVEADDMAAFIIQLIGHHYDHIWLI STDGDWDTLLAPNISRFSFTTRKEY HEKDMFDNHNVDTVDQFISLKAIM GDMGDNIRGVEGIGEKRGYNLIRE HGSVLDIIDALPLPGTQKFVQALNK SGELMERNLTLVDLPSFCGEAVAA AGODIYDQFYKDITAIATGEV | | Flap endonuclease [Enterobacteria phage T5] | YP_006958.1 | 1e-118 (203/289 ) | flap endonuclease | 5'-3' exonuclease | TIGR005 93 | 5e-48 |
| 34 | 42692 | 38 | MAVDSREKGKRAEYQIRDMLRKYT SLDWERVPGSGAFGQSHSLKGDV YLPPSVGKMSQYCFEIKHYADEKF NSNILNVGESQLEKWWAQAAREG EQMNMKPALIFKKDRGQWLIALDS SDPMIDNLMSRAHFIVNKRGMEIVI GLFEPWLNACEIGDLVK | | D14 protein [Enterobacteria phage T5] | YP_006957.1 | 2e-68 (118/160) | | No putative conserved domains have been detected | | |

Fig 2L

| 35 | 44527 | | MSIVINKLTISHFMSYAENVIEFDN HRYTQLIGRNGLGKSTIGTALEELL YNKNSRGIKKDDLFNWHTGSKAYT LEGQFTKOGDVYNVKVKVKSTAKV TLTKNGEDISGHTATQTYKLIEEVLA CDFTTFTKLVYQSVGSSLDFLKTTD AQRKTFLVNLFDQEQYKEVSERVK AGRKAVSAKLSGLEGSLRTAQSILS SKASLGAPQSEIPIPVFDEEPLVEEL TEAKVKVALAGKQKASIAKRSSLDM AVQAAEKTFAPFENLPAPTSKSEEL LSVTRNLTVVATRADDLKKRYDFK NAAGKTQCSACGTHLDTSAAQEA MRRTKEEYDPLYKERQKLEAEVEE LRKEDRAFKDYISKFNALEQARKNL KEFDEVNGTQDEIVDASGLAERIKAI ESSIRQGRSSVELARTHNESVVRE NAKYEAKREQIQKAEQEFDKIQAEL SLVAEEVADLDILITGLKDLVGYKLE HSVKVFEEMINHYLSIMTSGKFALG FELDETKLQVVIYNDGNRTSMVNC STGQQSRINISTLLAIRMLLSTISKVN INLLFLDEVVSYIDPDGINTLVELLQE EDQLNSIIVSHGHTHPYAHKIEWKQ DEAGLSILEA | 39 | 611 | Probable exonuclease subunit 2 [Enterobacteria phage EPS7] | YP_001837064.1 | 0.0 (377/598) | DNA replication, recombination and repair | SbcC, ATPase involved in DNA repair | COG0419 | 2e-12 |
| 36 | 45503 | | MKILFSADHHIKLGAKNVPQEWQK NRFILLGEKLDEVFGATGCDLHIIGG DIMDVSDPSSEEVELLFAFLATLQH PGIIYTGNHEMKSKTISCLDHYAAAI SDATDGLWKVVKDYRSPEFDIPYS SLHKASWKPRVSDICFTHVRGAIPP HVVPEIYLERFVEHGYSKVFAGDLH SYKNSQKIGDVDLLYPCSPLTTSFH RERTKGTNGAFIIDTVLPRDHEHYL SWIELGDLPQLIRKTIEVGEPMEAD AYDRVIYEVTGDVSQLKTLKNSELL DKKINNRVTKDAKLDLDDMSLLQEL DTYFTNVQKLDEASRTRILKRAAEY VDSN | 40 | 330 | Putative recombination endonuclease, subunit D12 [Enterobacteria phage T5] | YP_006955.1 | 1e-121 (216/328) | DNA replication, recombination and repair | Exonuclease SbcD | TIGR00619 | 4e-05 |
| 37 | 46316 | | MATKSWGSTTGGSNGDKLDYMKF NNGKNVVRIVSGVLPRYVYWIQNK EGKPAPFECLRFDREKERFIRGAS DPVHDMGFKDPEKKDGKAQPLRP KKNYLAVVIDRTDNKLKLMEVKATIL TGIHSIMAQLNLEDPGEIDITISKSGT GFDTKYDVQQIAAMQFQMAKNQP GSKEAALHEADVALIGEALYNEADE FEGFEKVPKLDVTYPVPSYDEQKK | 41 | 257 | D11 protein [Enterobacteria phage T5] | YP_006954.1 | 1e-88 (161/256) | | No putative conserved domains have been detected | | |

Fig 2M

| | | | | | | | |
|---|---|---|---|---|---|---|---|
| 38 | 46672 | | AIQAWLEGKKDEEGDESKGNEGSANSGNIDHEAASDLD | | | | No putative conserved domains have been detected |
| | 46319 | 42 | MLFYDYEKIYILARGNSSLIVQIIRRMVEDPEAHVMLTGRSFILNEDTIVYNKRKLSDRQLAEYLGLLSFRNYAEYSFSKDTSLDMQYIPPWVPRAVIEHHPLIAINKSKLTFIEEN | 117 | Hypothetical protein AGC_0138 [Enterobacteria phage EPS7] | YP_001837061.1 | 5e-40 (78/116) | | No putative conserved domains have been detected |
| 39 | 48232 | 43 | MKIVISNKIYCKPSNELWEYLLKHTSYQIFKPGAKYPLMFQNSGSVGKEIKWFPVTRLDLLESFGGKYTEIVDKRTLVPMDIPKPSFTLRPGDQLPIYEDCNDTCIINGKPGFGKTILALAIAHKLGQKTLVICTNTTIRAMWEKEVRKFFGIEPGVIGSGKFNIDSPIVISNIQTVNKHGAALAKEFGTVIVDEVHHCVATTFTKFLEQSSARYKIGLSGTLKRKDGLQVMFKDYFGTKVYSPPVNNTMPPTIHRFALKTQVSGNMNVPWAIRANDVYSQPEYFQQVVDLCELYSMAGHKVLFVSDRIDLIERYTNALELRGYKTYTITGVTSLDDREQVQIDVTNDGPCVLAASQSIFSEGVSLNALSCLVLGSLINNESLIEQLAGRYQRMADDKLDPILVDLKLGGVGFKQAAGREAVYRLNGWEVLDFNEKNMANLDKILFAKNPKV | 452 | Putative ATP-dependent helicase [Enterobacteria phage EPS7] | YP_001837060.1 | 0.0 (304/448) | ATP-dependent helicase | SSL2, DNA or RNA helicases of superfamily II | COG1061 | 4e-30 |
| 40 | 48726 | 44 | VLNFSLPVYALRAYDVLFQEGEYIVIQTRFTRYVLDNPSLPGTFSQRRLFLYGERENLPYKLYPLKKQFKYLSQINSGLKHFIDSTGKIVTWKPTTYYNIITERVRGSTRIFNGKYQCYVKNVPYPFLLSEPANYISYALVRGSPVIFDTHEEEPETPRLRVKI | 165 | Hypothetical protein T5.123 [Enterobacteria phage T5] | YP_006951.1 | 9e-52 (96/165) | | No putative conserved domains have been detected |
| 41 | 51289 | 45 | MKIAVVDKSPNNVRYQKHFELFDHEVETFFMASEKVTGRLLKKHTIGTPENPNPEDFDYVILVGADPFLKFAAKKGISDYSGKRVEHDGYANWIASISPAQLHFKPEMKPVFEATVESIHAILNGREKRSKAGDYRPIQCPDEAEYVKMVYTMCPGMIAYDSETSALYCRDGYMLGISISHQEYQGVYIDADVITENTVYYLQKLFDSPEHGWVFHNLKFDMHFYCYHLGLSFDKAAEEKRLHDTMLMHYALDERRGTHGLKSLAMKYTDMGDYDFELDQFKETYCKTHKIKEDFSYDLIPFDIMWPYAAKDTDATLRLSNFFLPKVEANPRLKSLYDVLMPGCVFLQRMEDRGVPISKDRLKE | 856 | DNA polymerase [Enterobacteria phage T5] | YP_006950.1 | 0.0 (663/856) | DNA polymerase | PolA, DNA polymerase I -3'-5' exonuclease and polymerase domains | COG0749 | 6e-84 |

Fig 2N

| | | | | | | | | |
|---|---|---|---|---|---|---|---|---|
| 42 | 52241 | | AQVQLMTALQLAKAKLYEYPEVRK LEEDQGSVFNAASVVQLRKLLFDY VGLTPTGIMTDTGADSTGADALKEL SDQHPIAKTLLEIRKISKLLSTYIEKM LISIDADGCIRTGFHIHMTTSGRLSS SGKLNLQQLPRDESVIKGCIVAPVG YRIIAWDLTTAEIYYAAVLSGDINMQ QVFINMQNDPENYSDFHGSIAHMV FALPCKPTEVKKLYPALRQAAKAIS FGILYGSGCPAKVAASVNEALLEEHM KTGKPYTECTTGDAKEYIETYFGRF PQLKKWIDKSHAQIQTNGFIYSHFG RKRRLHNINSEDRGVQGEELRSGF NAIIQSASSDSLLLGAIDTDNEIRSL GLQDEMKIIIMLVHDSVVAVREDLV DQYNEMLIRNIQVDRGISIPGCPIGI DSDSEAGGSRDYSCGKIKKQRPSV ACIEDKEFEEKVRSIIGMEDFDYAAI AANDENHPDHDKYANIKFLPEISKDI VNVRRVLGA | | | | | | |
| | 51357 | 46 | MSRITELLDLKGIEYRDTGGDILIRC LNPDHEDAHPSLRVDPDSGVFHCL SCGFGRGIPSIFHYFNEEQYRTSPR LLRVRRMISDLRTEGRSLEIPESAMI FDQDFRGIKAETFKKYFAFQQTED WEGRVVFPITDAVGRNLFFLGRNM DSSAPPKYMIRPKKVYSPPIFPVRYN TPALILVEGIFDMLNLEDKGCHNVS CCFGTHQFSLDNIADKFMPFQIAGT THVVIILDNDKSGNEAAKKLAKLIRD KTRIIPIIGNFLLPEGKDPGDLDAEE VDQLIRNVEILIAEHVKI | Putative DNA replication primase [Enterobacteria phage EPS7] | YP_001837057 1 | 294 | 8e-130 (215/293 ) | DNA replication primase | DnaG, DNA primase (bacterial type) | COG035 8 | 5e-15 |
| 43 | 52238 | 47 | MYNVQAVVLKMLLASDGKQVALET FSRLRKDHFNDAFTAIYQAVQNYYK KH-NGMPSLDALMLESNRNARLSQA LTVLANTQIPDVDISHAIHVLESEYT QDLFLNLLETDVLQDITILDQGELLD RVAALHMKLEERVTTTGKVFNADT MRVFKFRKEDSMNLISLGISNEFDA QLGGIARKETLLLGGWRGTGKSIIC SNIQVAQYYNGDIAPYFSIEMPENE VFRRNLAIMAGVSAKAMRNDSLQG IELNKLAKTRAKMFEGGLEVYNDFV SRYTLNEMSDFHDMETMLMQERP LHTPMIIVYDPELSTATIDVELTKLTS KYGDKVTIALLDYINQVRLPDTKTLD MYDWKQQMVVSSTFKSTCQKHNV AGVAPYQIDQQGNARMARGILDSC | Putative replicative DNA helicase [Enterobacteria phage EPS7] | YP_001837056. 1 | 492 | 0,0 (361/492 ) | replicative DNA helicase | DnaB, Replicative DNA helicase | COG030 5 | 3e-08 |

Fig 20

| | | | | | | | | |
|---|---|---|---|---|---|---|---|---|
| 44 | 53716 | 52238 | 48 | DMAANLNAAKQNEGHDGAIKFDFV KTRNSEGMTFMPKINWNSLRMDQ TSDLKLEDIRQMEAEFVIPLESDKP KDKPKRKKASDEDTNPTGFSSRDL | | | | No putative conserved domains have been detected |
| | | | | MAKLTWNEEITASLTAKANALNATV ISQEAVANIAAELAAETGKEVTARS VGSKLRKEGFEVQKASDVTKSPWT PGQEDELVAFLNDHPGQYTYAEIA AVVGGAYTAKQVQGKILSLELTAA VKPTEKAAAVRSFSPDQEAAFINAV ASGASVEAIAAQFERTVKQIRGKAL SLLREGRIEAMPVQEVSNAKARED VLEGLNIADMTVAEIAEATGKSERG VKSMLSRRGISAKDHDGVAKRAKL DAKSAK | 252 | Putative transcription factor [Enterobacteria phage T5] | AAU05255.1 | 5e-95 (185/240) | transcription factor | No putative conserved domains have been detected | |
| 45 | 55311 | 54562 | 49 | MKIEIPLNCHSCGSKLDLVNDQLFC RNKSMCPAQSSKLIENFCSKMKLK GFGPQTIAKLETTKVSELFFLTKEDL VRAVGDKVATKLELELETKLRQDV DFGSVLGSLSIPLIGEVAAKKLSQLY NDFQSVKAEGKAGENLASWKNTP AGQNVINLPWKFSGAREAQVTPAT ESNGVVLCITGKLNDFKNRADATKY LESLGYTVKTSVTKAVNYLICEDET KIGSSSYKKAQSLGIEVLTIKILLENK | 249 | NAD-dependent DNA ligase, subunit B [Enterobacteria phage T5] | YP_006945.1 | 5e-91 (181/254) | NAD- dependent DNA ligase, subunit B | Lig, NAD- dependent DNA ligase (contains BRCT domain type II) | COG027 2 | 3e- 30 |
| 46 | 56473 | 55511 | 50 | MQHVKEFIKLCQDAYYKGMSIISDE EYDALIRRFPLEEEIGPKGDVPHLF RMFSLQKVYPGRGEEVPFQGIETP KLDGCAISLLYIDGKFVSALTRGNG VLGNDVTHNVKLLNIPKRISQKTPV QITGEVHITKEVENMRNFASGAINL KDSGEFLSRIAEGGLMFTAYSICCE TGKVGLTATFCGDMHILQGDFVT CLDISSRVDWFPTDGVVVRMDGNN QFNAAGWTNKFPRGAYAIKEDDEG EVTTLERVEWQVGASGKVTPVGYF TPVVIDDAVISKATLNNVGYITALDL EIGCQIRVIRSGGVIPRIVERVYE | 320 | NAD-dependent DNA ligase subunit A [Enterobacteria phage EPS7] | YP_001837053. 1 | 6e-136 (234/323) | NAD- dependent DNA ligase subunit A | LIGANc, Ligase N family | smart00 532 | 3e- 56 |
| 47 | 56748 | 56473 | 51 | MQKITLNAYSSPPLQGQELVTWLE KEKGKPVVRTMSGFQMLGMWYEK NVLVCELYSPKSKRRVMSTFQAVC ENFYWEGKTQMLFDYYEAK | 91 | No significant similarity found. | | | | No putative conserved domains have been detected |
| 48 | 56866 | 56729 | 52 | MKDHEIAQLVNKLTEAAKTYAHTQ QLRAHMSRIVNEALKNAKDNA | 45 | No significant similarity found. | | | | No putative conserved domains have been detected |
| 49 | 57258 | 56950 | 53 | MNQNICQDYEGHIDDQSHVIFEDE GRQIRMTVSEFRGNLYFGFRLWLL | 102 | Putative transcriptional | AAU05252.1 | 2e-34 (66/101) | transcriptional co-activator | No putative conserved domains have been detected |

Fig 2P

| | | | | | | | | | |
|---|---|---|---|---|---|---|---|---|---|
| 50 | 57605 | | DIEDNWFPPTKSGFSFPYTLEMTSTL FRAFTKILSNSEVLHEVVRESQKTQ ASDD | | coactivator p15 [Enterobacteria phage T5] | | | | |
| | 57309 | 54 | MNKAQVVAICEKHGEFCMQYTKLR TKGVTYLYGTTEFDPKQDKYLAERI VREGLEPADKDHILVFSRSSDKFRY IPIANIKRITSLNQELDRATPVGR | 98 | Hypothetical protein AGC_0128 [Enterobacteria phage EPS7] | YP_001837051.1 | 5e-31 (62/68) | | No putative conserved domains have been detected |
| 51 | 58022 | 55 | MSTPTQWSPELEAELTSAYVAKIEL FPEDERPGVSMEIVAEIAKEHGVSP NGLRMKLSKAGVVYKKEAGKSTAK TGGDAPKAGGRTSKSDAQAELRAA FNDAGLEDGFLDESIVDKLTGKAAS HLAEAIRKITK | 134 | D3 protein [Enterobacteria phage T5] | YP_006941.1 | 5e-45 (92/137) | | Arginine decarboxylase | PRK05354 0,008 |
| 52 | 58315 | 56 | VSKYQLLNLFQIYSEGATAIRDLHYA LPMDEAEDNGWLTKYDRGLLKMY RLSPNGLVAVNQILENSVCFAAQ | 72 | No significant similarity found. | | | | |
| 53 | 59003 | 57 | MAIRKKLHANSIPDEKFKFEAIQWLE EGKTKKGACEILGVASNSTMERLIE EWKDNQRVSAEMRKKRGTKIEG AELANVIDSYLSGDSFEAIAERFYR SANMIRMVLSAHGALLRVNGEVDP LFPPAIPEESMKEVFEVGEHVWVP GYQCIGEVKKALDNPVGAYRVYLL SEARQQYVNYMYMYWDLASVEHLVAL GVDIKSLGFKWGKEDVAELVNNAV KAALKLEKRGKGE | 231 | D2 protein [Enterobacteria phage EPS7] | YP_001837048.1 | 6e-82 (152/223) | | No putative conserved domains have been detected |
| 54 | 59320 | 58 | MSKRDARWETRKFPKRDTKARKA KEIELCRVIPIRLAGMPNIYDWLEAQ RKTRLSIRINMELNMGYKSLSEFMH VTFDPTFYENRDCLEAKSVL | 94 | Hypothetical protein AGC_0124 [Enterobacteria phage EPS7] | YP_001837047.1 | 1e-10 (34/74) | | No putative conserved domains have been detected |
| 55 | 62096 | 59 | MFSILEGHAGFSRDPASGNWKEVK TTDYLFAKEFSNEHPEGKPASMPY KFNVVDTVDPKNLNEAYELMVQLT QDPHLVAVRGTCLVAEKAVRRKRT NFKIDHKSNIIAMDVDGISDTGGCD RFDIVGMGRHVIKLLNSISEDMFPL NAGFIAHASSSAGIKPGIRMHMLLE SNIPVTQGQLKFLFTSLNDSSRQKY GFDIADLAYYSSVQLHYFADPIFRD QFTDPFKAEGKPRLVKVNGARIELP NTMPDYEATRGEFKEEFLSLLNQIK GKRVASEKVEQTIAELEEAEDGYYL RIIPKLYHRALEDGVDFAWLEKEITS ALSDYINTKDNSRSLQDYFNNGRK QALKAFVNNSMRDIPESNVKGVPV HKLTSDSPDGMNYLKINRPPPEGH LTFIKASLGTGKTTAVTKWLERDQL KGNFLAVTNTRALVSSNAKKFEAG | 929 | Putative replication origin binding protein [Enterobacteria phage T5] | YP_006936.1 | 0,0 (731/929) | replication origin binding protein / helicase | DEXDc, DEAD-like helicases superfamily | smart00487 3e-05 |

Fig 2Q

| | | | | | | |
|---|---|---|---|---|---|---|
| 56 | 63090 | QYDKSVDMLNFKRGAIDRMSTTIHS IHKFKNFVGQIDVIFIDECDAVMNDL LFAPVVKQRRECISVLREILLSAKVV ILSDGDISAETIEAYGSLIDFDKPVSY YKHHRKMLSDAQAYEFPDESSIWV ALQTSLEMGEKSILVSDCGPDELNE KGLTLRNNTGAIVKEIHSNSTSDIDI RRILDYTTNELIEQQIDCLLCSPSVT SGVDFNYFDNVFVITRTANQAPNM RFCAIRRDRGAKNIFYFIDKSTSGF SAGSEQYNIDEGWLELAQQLYVKR RELESRNFISTLRYYLLDQGATIDIF SESWGKIDSSAAEYTAERVSAILSS TPDWCAPRHADAYEAKLMLVKYFH LDSIKSITQEHAEMWISKKPHKRAE FFHKLQDIFWKDIKKCSNVTISPFIE ALKKHKDFFIRTGQSANPKYARM YLTQMGINKEMETEGIVDWYRTYC SIEGISVPYEFMTDEEKALADEAQN ELGVRNEQA | | | | | |
| 56 | 62695 | MSIP-KMERISWADIPKELIDVAENLL RAALRDEELCFIIQHDVCVGLSKGS LAQDYEILFDWDDLSDLGLMVLVN NVVFHPSNFAAFREPGAGISPGFLV ADEPWTYAPEVLREGKQNASSNSI NIMGWNA | 131 | Hypothetical protein T5.107 [Enterobacteria phage T5] | YP_006935.1 | 8e-13 (48/130) | No putative conserved domains have been detected |
| 57 | 63087 | MLVNEKVVNQGVGLVPWAEIPLDV KESLLDHLRVWCDNMEVYFDYDN MHLGLWVPMDEDQDEVLDWGDLT EMGLVFALGYVCLLRESYIPVGVTG VSAGIWVGRNEDYYAPENINGWIQ VLRRFGFQVEGLTK | 133 | Hypothetical protein T5.106 [Enterobacteria phage T5] | YP_006934.1 | 2e-13 (43/124) | No putative conserved domains have been detected |
| 58 | 63475 | MYHPDDILLWPNGSWCYRSDVQD MSHLSDDYQVLRADSEQWHEFIQ MGEEYAGQ | 54 | Hypothetical protein T5.104 [Enterobacteria phage T5] | YP_006932.1 | 2e-05 (20/44) | No putative conserved domains have been detected |
| 59 | 63623 | VPTFRKGAITPLWDKYKLTEVCNIQ AFDKGFHYLNDPMPPLEALSEGSD DEPSRNLYELTHEFYNMRRQELGT VEPNIAHLRIAEWYERFPGQVVNFT TNVDDLLERAGIPHDDVIHAHGYLT EIMYRRGKDVVEDIGYTAVDYRKY EWVKPAITFFGETAPWYMGQINLF DTLTTQDLVIVVGASNQVIDFNWEL FPAHSRGTKVWVVNNGINYLEQSL YEERGIPVWYDTAANVFSNKHFIG QVEAWLEEKIYVPSR | 260 | Putative Sir2-like protein [Escherichia phage rv5] | YP_002003582.1 | 2e-64 (127/263) | Sir2-like protein | NAD-dependent deacetylase | PRK00481 | 2e-21 |
| 60 | 64442 | MKIHKTDEKRIYFMMDSGAYGSISR | 70 | No significant similarity found. | | | |

Fig 2R

| | | | | | | | | |
|---|---|---|---|---|---|---|---|---|
| | | | EDVVKLLRCRNHLWKDKVDPRTSE CLSEKAEQLRKEEMRNYMEFL | | | | | | |
| 61 | 66544 | 64715 | 65 | MNELDLIDNIYSILDNEGEEDLMFN NANKASEQFPTQRDMIAGEVSKYV VAQELPAYLLAAHNRGEIHIDHMDY RAQGYTNCCLVDLAGMFKNGTKIG GAEIETPKSISTAAAVTAQVIAQVSS CQYGGTSIDRIDEVFAPVVRKSYDK HLAIGQRWLHDSKKAAVYATEMTE KEVYDACQGLEYEVNTLFNSNGQQ PFVTFGFGLGESWEARMLQKAMLE VRIRGLGASGHTAVFPKLIFAVKEG LNKSPSDPNYDIKQLALTCTSKRMY PDYVSYERVTAVTGDFKFPMGCRS FLSAIESGETAGRNNLGVVSINLPLV AVESEGYFDRFWKLLDEYIDKAMA AHDWAIERLKRVRAKQAPILYMHG AFGVRLKANDLVWPIFEGRASVSL GYIGINELVEVMFEDTDPMSPPAIE FAVQVLNHMKDRCNKKAEETNLGF SLYATPSESLCNRFNTKIAEQYPEY DWLTDKGYLTNSHHLDVRTKVAPN VKFDYEANFTTIANGGNISFVELPE MRKFIPALEWVVDYGLSKSHYIGVN IPVDECEECGYLGESVSGEHGFVC PQCCGSGNISVTRRVCCGYLGSPGSR PFNPGKQQEVMQRVKHMNLK | 609 | Anaerobic ribonucleoside-triphosphate reductase [Enterobacteria phage T5] | AAX12030.1 | 0.0 (379/608) | anaerobic ribonucleoside-triphosphate reductase | Anaerobic ribonucleoside triphosphate reductase | PRK092 63 | <1.0 e-180 |
| 62 | 66854 | 67603 | 66 | MRKAARRKESRRNGSAKRERHEN VIPVDFEARERFQPTAKELKPKNAE QKHYISTIRNFTVTVGIGEAGTGKTF IPSVLAAQELATPGSVYEKFILVRPN EPLGKSLGMLPGDLNEKMAPWLEP IADGFKWALGERSYQGLVERKAIQ YLAIEHARGRTFNNSYVIVDEAQNIS VEAMKCILTRVGGQDCKLVICGDVAQ KDIKSDSGLQLIMDIYDQYEHVPFSL VELHDNVRSAESKAFQAIFNDMGI | 249 | Phosphate starvation-inducible protein [Enterobacteria phage T5] | AAU05235.1 | 7e-96 (173/246) | phosphate starvation-inducible ATPase | PhoH-like protein | pfam025 62 | 5e-40 |
| 63 | 67539 | 67718 | 67 | MITCVPLNPKHSRQSLTWESNMVT ELIIGYGEGITSEENWGFVGFGEGIT SHDERPDL | 59 | No significant similarity found. | | | | | No putative conserved domains have been detected |
| 64 | 67733 | 67942 | 68 | MNNVFTLNNFRTRKTKVHPVSLAT VNKYNANYPEDERRHHAAFKIANE FPNQPLGTKELVSRMKKLHFY | 69 | No significant similarity found. | | | | | |
| 65 | 68071 | 70395 | 69 | MTQRIEYVIKRDGTKEPFMAQKLND WAKYIGIRSDVPWSPVAVAVKNL PKGDVHSDDLQTMLIKSAESMIERD HRYDRFALELRLAQLRKNLFDSYTP PSLRFFHDHMVELGAWEDMSGWI | 774 | Putative aerobic ribonucleoside diphosphate reductase, large subunit | YP_006924.1 | 0.0 (534/776) | aerobic ribonucleoside diphosphate reductase, large subunit | Ribonucleotid e-diphosphate reductase subunit alpha | PRK091 03 | 9e-145 |

Fig 2S

| | | | | | | | | |
|---|---|---|---|---|---|---|---|---|
| 66 | 70492 | 70 | SDDQFEALNEVIDHSRDELFTNAGL KQFMDKYSRRNIYTEEIYETPQFAY MGMAMAMLSQPHWSMLDAIDLYN ALSLQKINVPTPPLVGLRSADRGFA SCCLVDGTDTLDSIDAAEHVVFKMV AARAGIGYHLESRSIADPVRKGAFP HSGKLPYYRHIDRSVKANTQQSRG GSATVYTAFFDPEIIQVMEAKSNRS PDEKKIDKMDYNLKFNSILLKRFLRK ENITLMSFLYAPEVYAAFDSGDVAE FERLYIAAEKRLAGVTKRGFKGEVL PVAPVIPAAELIEFWKTVRMETGRL YTMDAGEVNRNSRYKDPVRMSNL CVEIVQPTFPIPHVVDLYRTDEELD KMDVSEYGEVSLCNLGGFALGRIK TLEEWEKISYILLKFVDTIIEIQHYPF PAMKYTALRRRNVGIGLMNAAGAM AAEGLAFEGEEARNWIHREAEKAS FFLHKASVRLAKEIGPCEWFHRTHT SDGTLLIDTYKKTVDDLVSVGLEMD WESLREEIKTHGMRNSVLTASMPG ESSSVLIGVTNAVEPPRSAVTIKTS GVNKVITVAPGLDDWDTMQSYKYA FDIDRTEHIKWLAVLQKFTDQAISAN LYYDFNKYPGGIIPGTEIIKDLLNSTK YGIKNLYYANFDVDTGGSAAEQGC SSGGCTL | [Enterobacteria phage T5] | | | | |
| | | | MATVFNREWDHTESKLFLGODLGI ADYVNVRYPRLEELALLQRSQFWV ETEISLEADKKQWPNLPQHIKNKTL LNLAWQTQADSIITRAAPEDAILKLVS RPELEGMLIQWSVFENIHSRAYSNII RNVLPNPGEFIATVQANDEAFARLA LPVSVIDELAEIADIWLDARANLEIAE KEGTLEYTEEADFLALTEQVQQKIL EFYYAVYALEAIMFYASFACTFALA ENDILTGIAKNLQLIAKDEALHTVMA MEVLRILQNGEIPPHVVAAAQOANAP KILRSILETEINWAHYIFPEGEDIPGL NADLLVEYLYYNARLAFMAINIPWP EDLPVIMEDPIGWMKGWLNTKNQQ VAPQEAQITNYRVGATSQANPDDL SDEFGEFL | | | | | |
| | 71652 | | | 386 | Putative aerobic ribonucleoside diphosphate reductase, small subunit [Enterobacteria phage T5] | YP_006922.1 | 5e-118 (225/390) | aerobic ribonucleoside diphosphate reductase, small subunit | NrdB, ribonucleotide -diphosphate reductase subunit beta | PRK091 01 | 2e-63 |
| 67 | 71652 | 71 | MITALYAMRVDAAFGIFNPATMDAY GELPWGSIPEELEQFYRILDTYQVVI VGHNTYETAPPRLKKALEKKSMVY VVGSKAPVLIKNPPRNVRFITHLGS KIRDFCNEVEVVCIGGKALLETLAT | Putative dihydrofolate reductase [Enterobacteria phage EPS7] | YP_001837029. 1 | 1e-08 (40/122) | dihydrofolate reductase | Dihydrofolate reductase (DHFR) | cd00209 | 9e-07 |
| | 72215 | | | 187 | | | | | | | |

Fig 2T

| | | | | | | | | | |
|---|---|---|---|---|---|---|---|---|---|
| 68 | 72212 | | MGCLDAIYRSTIYPKAGTVPSLDHI MYLEHPILTSTPPDAVVTHIASGEN ERYRFVMEGVYL | | | | | | |
| | 73066 | 72 | VIHYINEGKRILEEGVWLENPRTGV RCLTVIGSNFEYDVLGKKFPLITTRK AYALQAIMELIGYLRGYDSAEQFRAI GCNTWNANANENEAWLVNPNRKG TDDMGRVYGVQGRTWLRPDGSHF DQLYKIYENLRRGIDDRGEILTFWN PGEFDQGCLRPCMHTHQFSLLNG NLYLDSFQRSNDFLLGQAFNMVQC YTFLALMAQITGNRAIRANQRIVNM HIYENQYYKVLMEHGQFDRKPFPAP RLEINPEIKTLEDVLTWVSKDDFKIV GYKSHDPIAYPFTA | 284 | Thymidylate synthase [Enterobacteria phage EPS7] | YP_001837028.1 | 9e-120 (204/282) | thymidylate synthase | ThyA, thymidylate synthase | PRK01827 | 2e-82 |
| 69 | 73073 | 73 | MGLFNRRPKITFSEREESQLKFLVQ SSGLHIDVILGMVKYKGMDALMRQ FAPKPPKENPPAKRDYNSNLLVPP AKLL | 77 | No significant similarity found. | | | | No putative conserved domains have been detected |
| 70 | 73404 | 74 | MSFTDAKAMAAKAKRSNDMAVIAA RRSIISNIDGSASSGKTEVDSYALN GLPIAARSQIMEDLKDAGYEVKVNH PFDQRDTESITISWGHA | 91 | No significant similarity found. | | | | No putative conserved domains have been detected |
| 71 | 73679 | 75 | MFHVYTDGGCRGNTRGVDNVGA WAMVVYNSSEEQIGTKSAPKRNTT NNEMELQAVLEALLWSNKNPGRP MTIYLDSTYVKNGCESWVWGWER KGWKKADGDTPLNLDQWKWIIDEL KKYRLNHNEIPTFVKVGHSGVEG NEAADNLLNVRMTELEMEDM | 160 | Ribonuclease H [Enterobacteria phage EPS7] | YP_001837024.1 | 7e-44 (85/160) | ribonuclease H | RnaseH | cd06222 | 6e-26 |
| 72 | 74161 | 76 | MLENLRRLVSEMKYEVLLMEPGVD RVVMKLRIARMEAQIFEAEWKALR GGDEL | 53 | No significant similarity found. | | | | |
| 73 | 74322 | 77 | MAPDLRDLFPNVPGYQLDLYAAFL EASKSGNPLRVYRQDRRHGKSWIL RWLKENEPLLKKLSERNSVQHRHT TKVGTSTSAQKSRQNISGGNRYEFI IFDDLVDENEKTQLLNAKN | 116 | No significant similarity found. | | | | No putative conserved domains have been detected |

Fig 2U

| | | | | | | |
|---|---|---|---|---|---|---|
| 74 | 74726 | 75136 | 78 | MAKQTSKKAVETKVATFPKTEANR KARLERHLRKHPADTQAASAVGKP APRRKKPVTKGSTSGYVSKIVGWS TPDKADTKEVLRKTQGRFGSVKPNI FGCEYSRENVRALCYGVGIKFTGK ANKPRNQKRKPAKKA | 136 | Hypothetical protein T5.089 [Enterobacteria phage T5] | YP_006917.1 | 8e-31 (83/170) | | No putative conserved domains have been detected | |
| 75 | 75136 | 76140 | 79 | MRNFVAKNDFNRAATHKSALDYSR VNSRELMDSCYEELEDWAADWPS MEENWDVSEDMTKPPPEVASKCD NTSRSNFNNKGNNMQNLQDRWIS VCDIESLGTPGDCKSTFIAMPFFAF VLMKDLSLDPYIVLGTPNVAQQLAL GAKVSAGTIAFWMNEARAGSAPSL SIIEALNAKDGESTVLVCNPTHESP VSKHTFMDLICPFVEAKQVIEGIIDE QGIDTRSLRHYGNGPQFDMSIYET VAAQANVFSPSDPAIVPWKFWDIS SARNPRDYFEALGGDWKALVRCA EIYAHDVIERYNLIPEGVYPSKHDPV FDALVEAYCIKTIESKLKI | 334 | Putative metallopeptidase [Enterobacteria phage T5] | YP_006915.1 | 2e-39 (96/244) | metallo-peptidase | No putative conserved domains have been detected | |
| 76 | 76205 | 76666 | 80 | MKAAILMISILTSFHAQAKIDAHEIEC IAKNAYFEARGEGVKGMTAVAQVT KNRVNYGKFPSTYCKVVYQPGQFS WVGKKKHKLDRKDEEWKQAKEIAR LVYYMDLPVDPTKGALYFHSKDTK PWWTKDKDFKRTSKIGNHVFYKLK SQLPNA | 153 | Spore cortex-lytic enzyme precursor [Enterobacteria phage T5] | AAX12015.1 | 2e-44 (96/146) | cell wall hydrolase | Hydrolase_2, cell wall hydrolase | pfam07486 | 7e-23 |
| 77 | 77991 | 78317 | 81 | MNDLSMLTKIRSDIESMVSRRSELT KAKQIISGGTQKRFTLQAGDIKFDL CGSQTRDYTFEMKPCYDMVKLGLI KALDKQIDQCTDAIKTLNVQFAAEC DRLKNSIKV | 108 | No significant similarity found. | | | | No putative conserved domains have been detected | |
| 78 | 78320 | 78496 | 82 | MVASVHTPPYERPAPNLTPEQKQLI ARRTLEFKESLHKSVGRYSEQVHD LVVKTLKLY | 58 | No significant similarity found. | | | | No putative conserved domains have been detected | |
| 79 | 78498 | 78570 | 83 | GCUUCCUUAGCUCAGAGGAuAGA GCAACGGUCGUUCUAAACCGUGG GuCACAGGUUCGAAUCCUGUAGG GAGUA | | | | | tRNA1-Arg | | |

Fig 2V

| | | | | | | |
|---|---|---|---|---|---|---|
| 80 | 78725 | 84 | MAYKIEYLKKGVLTELVIDANMARN EGTKSVFYKDGSVARMINTEDIQDL YVISDEEAGFVKDPEPAEDTPTEDT PVADTTTEEPPVEGTPEDEAAV | No significant similarity found. | | No putative conserved domains have been detected |
| 81 | 79051 | 85 | GGGCCGGUAGCCUUAAAGUuAAAG CAGUGGCCUCAUAAGCCAACGAg UGGGAGUUAGAGUCUCCCUGG CCCA | | tRNA2-Met | |
| 82 | 79147 | 86 | MSTKNAIVSFVDDSGIVLESTVTDIS PKRLLHRDGDILEILNKRSETMLVIP VNRLLSIKIWWED | No significant similarity found. | | |
| 83 | 79344 | 87 | MDAQLQTQYYMLLGMLEDAGPTV RGHYERHKAAFEALLKEVNENEGG KGSDSYAAFIIALQVFLINQLK | No significant similarity found. | | No putative conserved domains have been detected |
| 84 | 79564 | 88 | MLNIKRKGFFYKWLNFSSASFTYRL NDNRVTLCSLFWHSWWYFLLQIGV TAIAVLFSLGMGSILSTFLGLTFELGI TPWYMLVGLSLAGLSTIIAILLAIAGI GWACAKIGDRIQEWNASKSFERAQ KEYNARDEELRFGNIYQKMRIYKKD KLCPLIRVDHGE | No significant similarity found. | | No putative conserved domains have been detected |
| 85 | 80153 | 89 | AAGGGAAUAGCCAAGUGGUuACG GCAUCGGCCUUUGACUCCGAGA UcGGUAGGUUCAACUCCCUCCUUC CCUUG | | tRNA3-Gln | |
| 86 | 80239 | 90 | GCUCCUGUCGUCUAAGCuGGUuA GGACACCACUCUCUUUCACAGUGG GAACACCGGUUCGAACCCCGUU GGGAGUACCA | | tRNA4-Glu | |
| 87 | 80589 | 91 | GGGGGAUGGGUCUGCUGGAgu GGACACCGCACUUGCAAUGCGG GAAuCagAACGGUUCAAAUCCGU UAUCCUCCACCA | | tRNA5-Ala | |
| 88 | 80675 | 92 | GGGGAUGUGGCGAAAUUGGCaG CCGCGCUAGAUUUAGGUUCUAG UGGuGAAAUAUCCGUGUGGGUU CGACCCCCUCCAUCCCUACCA | | tRNA6-Leu | |

Fig 2W

| | | | | | | |
|---|---|---|---|---|---|---|
| 89 | 80779 | 81015 | 93 | MNIEIMQLDRKKNEFRKVHTFPSKE ALEFHIKCMGLVLPESEIFDLACAN GVLYVWEITYHADPDELRKEVEQIL TGE | No significant similarity found. | | No putative conserved domains have been detected |
| 90 | 81007 | 81091 | 94 | GGAGAGUAGUGCUCAUGGGAGC AAGCUGACUUGAAAUCAGUCGCC AUCGGAAACGGUGAGGUUCGA UUCCUUUAUUCUCCGCCA | | tRNA7-Ser | |
| 91 | 81099 | 81184 | 95 | GGAAAGCUGGUGAAAUGGUaGC CACGCAUCACUGCUAAUGAUGAG UCCGCAAGGGCAUGAAGGUUCA AGUCCUUCGCUUUCCGCCA | | tRNA8-Ser | |
| 92 | 81444 | 81520 | 96 | GGGAUAUUAUCAUAACUGGAUAA UGACCUCGAUUGUGGAUCGAGU CUaUCUUGUUCGAAUCCAAGAU AUCCCUCCA | | tRNA9-His | |
| 93 | 81528 | 81602 | 97 | GCACCAUUAGUUUAAUGGAuAGA AUAUAGAGCUACGAACUCUAUGG UUGAGGUUCGAUUCCUCCAUGG UGUACCA | | tRNA10-Arg | |
| 94 | 81732 | 81807 | 98 | UGGGGUAUAGCUCAGUAGGUAG AGCCGAGGUCUCUGAAGCCUAG GuCACAAGGUUCGAAUCCUUGUUGC CCCUGCCA | | tRNA11-Gln | |
| 95 | 81810 | 81886 | 99 | UGCACCGUAGAGGAGAGGCcgUC CUCGCCAGUCUCAUAAGCUGGA GAuCGCCAAGUUCGAAUCUUGCCG GAGCAUCCA | | tRNA12-Met | |
| 96 | 81900 | 82094 | 100 | MMRISFTERVLGTGVMLITSWDGD SWCNVTGLRKSEQTPENIAKIKKR MAEAASRPGAPRNGKR | Hypothetical protein [Bacteriophage 5] | CAE53211.1 | 2e-18 (41/63) | | No putative conserved domains have been detected |
| 97 | 82081 | 82260 | 101 | MVNVEVTMTRYQGMLINTHTKEIVF LAPAFHDTYNEAEEDARIAKIHPDE EICVRQQEQ | No significant similarity found. | | No putative conserved domains have been detected |
| 98 | 82262 | 82337 | 102 | GCUUCAAUAGCUCAGUUGGUAG AGCAAACGACCGAUAAUCGUUAG GuCACUGGUUCGAGUCCAGUUC GGAGUACCA | | tRNA13-Ile | |

Fig 2X

| | | | | | | |
|---|---|---|---|---|---|---|
| 99 | 82495 | 82571 | 103 | GGUCAGUUGGCAGAGAUGGUuU AUGCACUCGCUUCAUACGUGAGA CUaCAGUGGUUCGAGUCCACUAU UGACCACCA | | tRNA14-Met |
| 100 | 82575 | 82650 | 104 | ACUUGCUUAGCUCAAUCGGGAG AGCAUCGUCUUUACACGGCGAG GGuAGCUGGUUCGAAACCAGCAG CAAGUACCA | | tRNA15-Val |
| 101 | 83285 | 83566 | 105 | MEKITATGIESALVVDWAGWDGDH EWMVFYSCTLQPELWTRLTDEHA MPYGIIDVEIEINKLVGTIMVHRAEG DHKEIFRKSIKLVVSTGDFI | 93 | Hypothetical protein AGC_0078 [Enterobacteria phage EPS7] | YP_001837001. 1 | 3e-09 (31/87) | |
| 102 | 83587 | 83964 | 106 | MYTRPTNGNSAVVRLMIVQDNLSN NIESLDRRIEEYRTEMLSLMREREA KIEEQLEVCEADRLVDGTAVFMAE APAEPTFTPVAPADMQYAILPFHLE EEDGEGPSLEDVVRFLLASGFPNG GR | 125 | No significant similarity found. | | | No putative conserved domains have been detected |
| 103 | 83964 | 84179 | 107 | MDFIVVCGANTDCFELLNDALDKVD EHMQEGRTPTFIDLSQGKTYFYPSL DVEPTVLPIFMHSLSWDEEDD | 71 | No significant similarity found. | | | No putative conserved domains have been detected |
| 104 | 84374 | 84450 | 108 | GCGGCUAUGCGUGUuCAGCGGUcA ACAUACCGGCCUGUCACGUCCG AGcCACCGGUUCGAAUCCCGUUA GCCGCGCCA | | | | | tRNA16-Asp |
| 105 | 84784 | 84861 | 109 | GGGAGAGAAGCAcgUAAGUGGUAU AgGCGGUCGCCUGUUAAGCGAAU GAcAGUGAGUUCGAAUCUCACCU CUCCCGCCA | | | | | tRNA17-Asn |
| 106 | 85090 | 85163 | 110 | GCAUCAUUGGCGAGUGACUAG GCAGAGGCUUGCUAGCAAACCCUCGAA GCAUGGUUAAAAUCCAUGAUGGU GCUCCA | | | | | tRNA18-Cys |
| 107 | 85180 | 85359 | 111 | MIKYKAFVTRESQTGDSSIKFEGTT LHDTFEAALTEAETHIVSKSCYAHV WEVNTILDR | 59 | No significant similarity found. | | | |

Fig 2Y

| | | | | | | | |
|---|---|---|---|---|---|---|---|
| 108 | 85350 | 85425 | 112 | AGAUCGCUAGCUCAAUGGUuAGA GCACUCGCCUUUUAAGCGAUAG GuUCCGGGUUCGAGUCCCGGGC GGUCUACCA | | tRNA19-Lys | |
| 109 | 85601 | 85678 | 113 | GCAACUGUAGCUCAGCgaGGUgA GAGCACUGGUUUGAAAGUCCAG GGGuCCGUUCGUUCAAAUCGAACC GGUUGCACCA | | tRNA20-Phe | |
| 110 | 86126 | 86320 | 114 | MNQKILMRYNPRALWFRWEVIVSY QIFVRNGDPENNIIVLETFSNRDAA VKFLNTIDNTLIKVY | 64 | No significant similarity found. | | |
| 111 | 86323 | 86661 | 115 | MDIFTTPAINLVGVGLFQATVYRIDD STDVVTFIVPEFFLEKFFEEFEQFRE EHDAYSNMEDLAAMFPTVYGYIFE GNDLLLDKSELVELNWGISFEVGSP FPRYFQGLEIR | 112 | Hypothetical protein AGC_0081 [Enterobacteria phage EPS7] | YP_001837004. 1 | 3e-20 (48/53) | |
| 112 | 86661 | 86810 | 116 | MGGYSNFIENYINSVDSWNQETLV VVLKERFNISTLEALEAIEAYLDND | 49 | No significant similarity found. | | |
| 113 | 86812 | 86889 | 117 | ACCCACUUGGUCCAAUCuGGUaG AGCCAUGAGGCUUAAGACUUCA GGGuUCCCGGUUCGAGUCCGGG AGUGGGUACCA | | tRNA21-Leu | |
| 114 | 87022 | 87098 | 118 | UUCCCCUUAGCUCAGUCuGGCAG AGCGGGCCUUUGGGAGCGUCA GGuCAAGUGUUCAAAUCACUUAG GGGAGACCA | | tRNA22-Pro | |
| 115 | 87104 | 87179 | 119 | GCCUCAAUAGCUCAGCCGGGAG AGCAACCGCCUUGUAAGCGGUA GGuCGUGGGUUCGAAUCCCUACU UGGGGCACCA | | tRNA23-Thr | |
| 116 | 87472 | 87547 | 120 | GCGACUAACUGUACGGGuACAG CGUCCGCCUUCCAAGCGGUACU GAGuCGGGUUCGAUUCCCCCUA GUCGCUCCA | | tRNA24-Gly | |
| 117 | 87647 | 87748 | 121 | MKAFDAELVFSLLAEMEACVDRVR ALRLSMFSS | 33 | No significant similarity found. | | |

Fig 22

| | | | | | | | |
|---|---|---|---|---|---|---|---|
| 118 | 87667 | 88058 | 122 | MLTVKVMSPNGGEEIHDGSSVGFN PKQKSISIAGLDQHIFLKEDEVAYVM NQNGKTVSYYHGS | 63 | | | No putative conserved domains have been detected |
| 119 | 88063 | 88139 | 123 | AUCCCCGAGUGUUACUGGACAG CACGCCGUCCCAAAACCGuCC AGUAGGAGUUCGAGUCCUCUGG GGUUUGCCA | | Hypothetical protein ykris0001_9300 [Yersinia kristensenii ATCC 33638] | ZP_04623722.1 | 5e-18 (45/60) | tRNA25-Trp |
| 120 | 88156 | 88512 | 124 | MITYSTNFMGPVSNNWYIRMGIPYT EVTEPNRFADGGQLTRKVFAKRYA GGRIDVRGTDDYFGQEIGVPIMEAE SWNELQQFLWTFSSDKVLTLEQIV QALEDETGFRIVWFKEPACT | 118 | No significant similarity found. | | | No putative conserved domains have been detected |
| 121 | 88503 | 88883 | 125 | MYIDRNQLFKFLELDLRWPLSVNP GRATGKTFEAINTAYEFAVFKGIQA VYVASGVREMARLEKKYNELQPHV KITTYSMLEPYRIGRRFSCIMFDEPS LAIKYGVNAYVVRIARENQCPVIIFG E | 126 | No significant similarity found. | | | No putative conserved domains have been detected |
| 122 | 88885 | 89061 | 126 | VEQEFQVFVDASKRVLFIQATDEG HGLQLSFDSLEQINQIVLRAQKSLE KNTEAPPDL | 58 | No significant similarity found. | | | |
| 123 | 89156 | 89371 | 127 | MREISKMKVTMENTEEFIAICTAYA DTLPPEGMDDHTMQLVADIYRLAE LAKEQHNRLYVVKERLEMMDKE | 71 | No significant similarity found. | | | |
| 124 | 89375 | 89647 | 128 | MNELNELNELHYAERAIDELDFAGG YYTRHVNAMTAEGLNSKSAIAAELA VRDFVIDSLQKTISNLSENNKAALEA LDKLSNHLLALGIK | 90 | No significant similarity found. | | | No putative conserved domains have been detected |
| 125 | 89647 | 90189 | 129 | MNKQSLRGIRVFRSSLVDSFYIWG KATRRTVEQALDGTFYDWREKERN PVFSRPGLYHDRVSKTAWYEIEVT PGVIRAFYTDWEHEKWVWDNQIAP GDRIMNYAEYKEMKRMFELYDVPR LSRPAIFIASQEYWHTVRMKRDFNK HHLRYEKEHGTLRERYAKRKAELR EKRLEKKYGES | 180 | No significant similarity found. | | | No putative conserved domains have been detected |

Fig 2AA

| | | | | | | |
|---|---|---|---|---|---|---|
| 126 | 90176 | 90403 | 130 | MVKASLLRFTPGVGLQYKIVGGHK FQYFTPGKLYFVELHDSRAGYKLR SDANEGIWVSFTQVKRWFTVEGYN DYE | 75 | No significant similarity found. | | |
| 127 | 90390 | 90758 | 131 | MIMSKVVFVKCCRDTLELVDHKM QTCKCGASSIDGVAGAYVRFLGDK SNFMRLNEFQLEVEKNRPALEAEA ERLKDFDGNIVAYNMVSGKDFWSE LAEKLNMPRQAAKALYHGFNYSPR WN | 122 | No significant similarity found. | | | No putative conserved domains have been detected |
| 128 | 90727 | 90993 | 132 | MASTTRHVGIKFSNSNRTYVYRVP SYWKYSPEIGDVVIPGNVMFNNP RRAKVEVHGMYGKPEYKERKNIS YVELHDYLPKEERNGR | 88 | No significant similarity found. | | | No putative conserved domains have been detected |
| 129 | 90983 | 91288 | 133 | MDDKIAREAIELVRKRLEERNVEVP KIMLIGYGGIGGFPSFTDLERMERE SQASFLELESYAREMEHEHPIGNN FMPRSSRQEVTHGKTNSWPTPKR RGRK | 101 | No significant similarity found. | | | No putative conserved domains have been detected |
| 130 | 91285 | 91494 | 134 | MITTGFGYSHEELCKMVESAPFIKK LVEEQRPVCLHAACTKCHGTGVDK NGKMCVHALSCPCPKCSWSC | 69 | No significant similarity found. | | | No putative conserved domains have been detected |
| 131 | 91496 | 91933 | 135 | MDLGYCVVHEFMEQGLPDRICVVT SRNLEAAQSLVERLSGYYRDHERY QQKVFDLTKLYHQKALDMPTPQLD DLKQFSPEAWYSVKDASPVDYTVQ VFSHYGTRHWINRKWDSMVDYLN SELEKGAAEYKRKRAEAKVLKNSV AL | 145 | No significant similarity found. | | | No putative conserved domains have been detected |
| 132 | 91980 | 92303 | 136 | MSKLSIESIIRPLMHGYVQGSCVSE TEALNVIEEELVANGYNLHEGVIEDL FWQTAEDMEIFRCVNCGWWCPAF ERAENQIEEICRDCEPDLEGEVDEQ DNEGEDYE | 107 | Hypothetical protein T5.053 [Enterobacteria phage T5] | YP_006881.1 | 2e-05 (31/87) | No putative conserved domains have been detected |
| 133 | 92296 | 92568 | 137 | MNKITKVKTMSKRSIAAIIAFSMMYS GVSLAAERNKVEISDNGRVRVTTN GITKGAGKFRKSETRFGETKIYTNK TYGKPAVTLDRYGRQVEDEDDSDE | 99 | Hypothetical protein AGC_0054 [Enterobacteria phage EPS7] | YP_001836977.1 | 6e-04 (25/70) | No putative conserved domains have been detected |

Fig 2BB

| | | | | | | |
|---|---|---|---|---|---|---|
| 134 | 92561 | 92995 | 138 | MSNLHPKLQETLDWINEECAFEEA PYCVWARAGAAPSEWCTVFDNRY RITVELSLKEDKVYAKASMTALGLS GFVEMQELCMPNTHLRVQIEQLATI RLMLPEDNINDHFHKVIENEYKLRR QRRKARREVEKTRMMCNMNPHV | 144 | Hypothetical protein AGC_0053 [Enterobacteria phage EPS7] | YP_001836976.1 | 1e-14 (43/115) | No putative conserved domains have been detected |
| 135 | 93115 | 93507 | 139 | MFTLFILAVSAWMAVGINHGLDSAK LLSAKAFEFLAKFATRKDIEAIIAKG GAKDASSVLKSFDKILELRNGKHAA ELRCMSRKTIGRLCKAIFIVQGALK GPFAKYKPDSIKRAKIFNDYCVEHH PLNR | 130 | No significant similarity found. | | | No putative conserved domains have been detected |
| 136 | 93616 | 94314 | 140 | MRIISKLKDVYDLQGTMYDAERAW YREEVKEVVNVSADFEQIIFYAEILR NRTSSGYGGVNMGTLEVRPVLICG TLRWLYGYHTGLGADAVHIQTFDP VKVKEVLEEQGYYLRMGWDMNTIE KIDAHVRNATATASAFLETFNKPIA MAWDAAKSKTDPTVNITVKTDFNF HAEDFPWQEIDPNLYRWHQTLESY IFGVLGQGEPKTESTSDRDRLIAKG FDAKVSFRNMER | 232 | Hypothetical protein AGC_0049 [Enterobacteria phage EPS7] | YP_001836972.1 | 1e-34 (92/237) | No putative conserved domains have been detected |
| 137 | 94280 | 94741 | 141 | MLKFLSGIWSGKTGAILFLAIAAGTF GGAYYITNKLTDMSSSLQSLSNRN EQLEKTVGNLQTEIRNRDRNTTTYI TNLAKNQEDLDGRINKLDAARAKE GVVAAKPKLATKVAKDKVNEFQER LSCVTGNMDSCSRLQLSHPGVQN. GQTQVAQ | 153 | Hypothetical protein AGC_0048 [Enterobacteria phage EPS7] | YP_001836971.1 | 2e-20 (56/143) | No putative conserved domains have been detected |
| 138 | 94654 | 94983 | 142 | MRNWKYGLLLSAAIIASGCAERPDP SSTVTGVEPQHLPWPASLQTCPFN FEFINEEGKVYVRIPYQDWITMGKC NEQVYTYIANLTALTCTYRVSLNEY RCKPFNKETK | 109 | Hypothetical protein AGC_0047 [Enterobacteria phage EPS7] | YP_001836970.1 | 1e-19 (50/108) | No putative conserved domains have been detected |

Fig 2CC

| | | | | | | | |
|---|---|---|---|---|---|---|---|
| 139 | 94980 | 95741 | 143 | MKYVLGLIGDAGAGKDTFADMAKV WAWEVLGPEYSISKFSFAAPVYEL AAVILGVTPEKLAERRTKEIKQWFW VTQEALERTANVWKRFGIDKYADF SYVWPQFEASALYPLIAKTAPDFYQ GRETPLYPLYTSPRKMLEFVGTEL GRALVDENLWLNIVDRTATKADIS IISDVRFDNEAALVRNFPGAQNSSIL KVHAPNNIHAIQSTHASARGVAPEF IDDVVTNNFDGLENFRKNVNAFCD ERILFI | 253 | Deoxynucleoside-5-monophosphate kinase [Enterobacteria phage T5] | YP_006871.1 | 9e-54 (117/250) | deoxy-nucleoside-5-mono-phosphate kinase | No putative conserved domains have been detected |
| 140 | 95751 | 96362 | 144 | MGQINNVEQKGGNKTPNYFASLVA TKAEYNIYHYHLDGPIVDVDYYRDL SVTLATMCEGDTLNLYINSPGGYV DTAVQLCNLIMNCQGTVIGHLVGPS ASAACSIFLACHGWLVHPYVMLMG HTYRGAHYGKGKNEIQHYADQFNS FFEDMMLDLYYPFFSLEEITEMIEG GKDIWLTSKEINERVDRMAAHREQ EARKAAGQ | 203 | Putative ATP-dependent Clp protease [Enterobacteria phage T5] | YP_006870.1 | 7e-51 (96/181) | ATP-dependent Clp protease | S14_ClpP_1, caseinolytic protease (ClpP) | cd07016 | 5e-19 |
| 141 | 96520 | 97182 | 145 | MDKFIQLISILLQEAKDPASLLKRLL TLLVGLVIYLFIANTSEVMSYLKTFS TSAVLQDVKVQRTLEFPNVAREKA MILFSQTRADAVFVVKYKPEAINDY QTIIAWESNVQLDKSDVSDKAVDKT SMLYRAHLDGLNFAIDAREKRGLSK WSGTGLPPFKSANFEYVYTCPYFN LNNIYSGYVAVAWEKYPLQDEDMG MFNDYMAKICASPQRSLGRSI | 220 | Putative holin [Enterobacteria phage T5] | YP_006869.1 | 1e-82 (144/220) | holin | Bacteriophage T holin | pfam11031 | 8e-47 |
| 142 | 97179 | 97592 | 146 | MSFRFGNRSLQQLDTVDPKLKALAI RALELSPHDFTIIQGKRTVQQSAQIN IANGTSFLKDPSKSKHVTGKAIDFA PYINGKIDWNDLEAFWAIVGAFKKA ANEMNIAVRFGADWNNSGDYRDEI QRGTYDGGHVELL | 137 | Lysozyme [Enterobacteria phage T5] | YP_006868.1 | 8e-57 (104/137) | lysozyme | No putative conserved domains have been detected |

Fig 2DD

| | | | | | | | |
|---|---|---|---|---|---|---|---|
| 143 | 98142 | 98546 | 147 | MSDRFYTQMCEHFKVSPYELNIAL WDRESPEFKKIAKKSEGVMSNGKK MTRIDLNNALTKLLGVNIEGQKLSM PTLTTILEKVKAGDVKKVAVPEGRL KKPYQEAIIEAFGEKLDLDTATVKT MKALLESINNV | 134 | Hypothetical protein T5.038 [Enterobacteria phage T5] | YP_006866.1 | 1e-37 (86/141) | | No putative conserved domains have been detected | |
| 144 | 98539 | 98823 | 148 | MSKKIVFLKGSSCVPCKQFEPVFDK LTAEFNLPVEKRTDDVDSLRKFGLR TVPAVVLVDVENGREEAHHILSGAT LRSAVVSKAIQDFIDYYEE | 94 | Putative thioredoxin [Enterobacteria phage T5] | YP_006865.1 | 6e-21 (48/91) | thioredoxin | TRX_family | cd02947 | 8e-04 |
| 145 | 98925 | 99329 | 149 | MTKQAYLILNNGFAVGTTFVDLGYT KEEWQALDAAQKNQLVNEAAWEY AEAYVEAVDDELVIVVSLGAVGCDA HVHTDFQSEEEWDEDLTHQNALI NEAFWEVVDCYVAFCKDDDEANT CTNYGYEHDDVECA | 134 | Hypothetical protein AGC_0039 [Enterobacteria phage EPS7] | YP_001836962.1 | 3e-21 (49/103) | | No putative conserved domains have been detected | |
| 146 | 99329 | 99691 | 150 | MQKFSRDWSSDMARKNRAAAYYN KKIQLDKLIKGITYNVERGFSGIKVD ARSLDYSCILWAKQNGYAFKRIGNE ILIAWEPEGLVQYIYDPYRGEYVR DHRQQPTDFSLPKRYLETRY | 120 | No significant similarity found. | | | | No putative conserved domains have been detected | |
| 147 | 99691 | 100521 | 151 | MNVHETVTVPDNANIFFIGDIHGEY DMMMGALKLAGYEEGRDYVFCVG DLIDRGPKNLQVLAKFLYNPKFRSV RGNHDEFMIQDDYANWMYNGGS WTITEGFDTDTMKGIAEDMDSKMP YIMTVEHRGKKRYGVVHAGIPLRYQ AQGMGVTVPVWDDIVHEHESTPDL RRLGVLLWDRDVIQEVGFNLYRSG EKHPYFDRYASFSEECAVDVPEIVG VDYTFHGHTGVPFPIRWKNRYYLD TGGTFNGRMTVASPVLGQLYTFTT DRDDPCGSADII | 276 | Putative serine/threonine protein phosphatase [Enterobacteria phage EPS7] | YP_001836961.1 | 3e-93 (176/283) | serine/threonine protein phosphatase | PP2Ac, protein phosphatase 2A homologues, catalytic domain | cd00144 | 2e-08 |
| 148 | 100532 | 100765 | 152 | MKLFKDLEEGEVFVVAGGFELQKC VAMLDNGNSVFTDDANISVTIAPDT ETWKPKEFWEIHKDRPLDDLLDDIL FTA | 77 | No significant similarity found. | | | | No putative conserved domains have been detected | |

Fig 2EE

| | | | | | | |
|---|---|---|---|---|---|---|
| 149 | 100774 | 101142 | 153 | MKLESRYIVFKQSDAAKYLTSTAIR EINDSLSLIYKGREADGKVGFPNYIV LEEDWPEYPIAKEALEGRIVLEEFN KRAEKKRGAKAAEDHYKQHQSTEL LRGISPFCAGWNDYMRRLVIEE | 122 | No significant similarity found. | | No putative conserved domains have been detected |
| 150 | 101145 | 101264 | 154 | MYTGMGNDMAKMFIGLLILAALVGA AIVGGIWALVAFVF | 39 | No significant similarity found. | | |
| 151 | 101328 | 101756 | 155 | MKNAMIELNANMESLRHAVNTARA SFNLLMRDESIPLSARVKAFEEFAD ELLHMGDYLSDSPFNEDRRDYQHA YCNRGEIVYLTDVLESVLEYANSFM RTPDEWEDASNDYVLDEIQKNWPE IKKLVEEHIHSEVYAYRIDW | 142 | No significant similarity found. | | No putative conserved domains have been detected |
| 152 | 101838 | 102143 | 156 | MAKNTISYTTGKTADEQANTLTKDE MVAVLVILLDMSGFEGQLAKLSLPA LRALYEGTNKNAAAYNLAKNEARW AKEHQQVAERRAESFERDLKREKA KKK | 101 | Hypothetical protein T5.032 [Enterobacteria phage T5] YP_006860.1 | 2e-23 (52/81) | No putative conserved domains have been detected |
| 153 | 102143 | 102424 | 157 | MVLEILSGLLIAALVTGTGLAWVVSI LRENNRRMRLTNNGLHEKLMDQV QDADEFSAAAERLLVRLAKIEEIIGQ DSTMSKTTKMRLITEIKK | 93 | No significant similarity found. | | No putative conserved domains have been detected |
| 154 | 102421 | 102669 | 158 | MISPIVAALYLVVVGYLSGKYHGFG LKGTIKAAMLVPLYPLAILLTGYYAC VLRIFGRGKVNYDNCTALLDDIENTI KKEEK | 82 | No significant similarity found. | | No putative conserved domains have been detected |
| 155 | 102666 | 103007 | 159 | MNLNSKERQVLVDALRQVVDHDLL CDEDIVESIALIAKIELAEKDSWRPL SELPPLGLAIVVQRADGAPFNTVMV RRDLAKSYSPDIITLHTKITNEPFEF NTRHYYWRLTNA | 113 | Hypothetical protein T5.028 [Enterobacteria phage T5] YP_006856.1 | 7e-08 (40/111) | No putative conserved domains have been detected |
| 156 | 103000 | 103227 | 160 | MLNQLRIYNFLDCNFQWWRELPSR FLGWALFLSMVVSVFHNVPATFYM EAIQPVTVFIYEMYLVAINGWKDGRI N | 75 | No significant similarity found. | | No putative conserved domains have been detected |

Fig 2FF

| | | | | | | |
|---|---|---|---|---|---|---|
| 157 | 103211 | 103678 | 161 | MAASTEVLNQYFNREHQEFSDLFI QMFVNANNALDYRFFNEFHETTFS HQDINSALKELIGSKVIPFRQTANAE TLELSVVWGLFKKAYEFGKYQNAR HWIYEVYLNTEVILPRQMMLGWIAK QRPERNAKSFAPINDGNLYHASEK FDAPKSVA | 155 | Hypothetical protein AGC_0027 [Enterobacteria phage EPS7] | YP_001836950.1 | 7e-32 (65/147) | No putative conserved domains have been detected |
| 158 | 103701 | 104027 | 162 | MLLVEGLTEEDICLNSFYNCKTHVM QALDEERVELSKFMVNIATAQVHW QTQGLSADDILKHTLNAIAEYGKAR GEALLASKKEFDKSESMLKMAIDIH MEGIDGTIH | 108 | No significant similarity found. | | | No putative conserved domains have been detected |
| 159 | 104039 | 104326 | 163 | MAKKRVVVNFLEEDSGDCEYGCW NTGYGVEVMVDGKCVHRQEAWAS CTNNSSVDFDVLAHVLQGIKTKEGY PVKADHIDFGDPSDYPEEFLDLFT | 95 | No significant similarity found. | | | No putative conserved domains have been detected |
| 160 | 104378 | 104566 | 164 | MKSIDNYLRGENPVDQAAVTVEKV RKECFILTQRGGNRPNRVYLNWT QSKDLYERLKREFE | 62 | No significant similarity found. | | | |
| 161 | 104566 | 105042 | 165 | VEELRQKINQELVWEAKSFPINQFL KRDGSINHNKIKQLRPDFRQDAKNL IFNIRALDAHGVFFGYEKLVFHSLN QLVEWCPDHQDYFMQTARSHLEG NGCCKCRHRMVTRVTDYGSYTVP AYYHKFSIDGDSIIWVNNSSKLIKPL EVKDEIRFPE | 158 | ORF022 [Enterobacteria phage T5] | AAX11959.1 | 2e-50 (91/153) | No putative conserved domains have been detected |
| 162 | 105020 | 105421 | 166 | MKYDSLNNPSTNYLTDQSVSEIKFH PNYSPDSSKPSVAAISFRFRNLRFT FVGEEDKMISIIDKVKAVSELSGSDT VKFEALTSLLLTSGATVGKFELIQPH VSALTNTRNFWDQANVESLIKWDS ATEFYNK | 133 | No significant similarity found. | | | No putative conserved domains have been detected |
| 163 | 105434 | 105943 | 167 | MLFCTVDFEEANETYIVYGMSESKV RILWNQFQLEVPDDISKTPKDFFHLI DIKAVKARKKLTPYVFPGAVFVHEL TAYTNVVLKKSRQHPGYLTMLTYK VGAIHDGELVVRVDARLQOEVEEMI RQCQNKAELKQRARLFDMAAPSEA VAAYHGFYKEIAESDEDFFM | 169 | No significant similarity found. | | | No putative conserved domains have been detected |

Fig 2GG

| | | | | | | |
|---|---|---|---|---|---|---|
| 164 | 105956 | | MNEKYEVWTPVGENCSYLLRTLCT REDGTSFSEYLSECHAKAQQDNPL FKIRGEDILKVNGVPYTPVDSFAAL QVFKEHREREHRRMIERLTGREPF SHPRWNEET | 106 | No significant similarity found. | | No putative conserved domains have been detected |
| 165 | 106276 | 106276 | 168 | | | | |
| | | | MSRVEKLQHIYNLVKKADQKKLSEL SEEEYQAVLFCCSAMPAKLDGVLA KSDIHNGKETTFQPPYKWLASNIQQ MVGKVTGFSNRKTPNIFIDITPRTPE FTKDWRDALDSFPSWKVFYKPDDE TYAHLPFLKHPGYTVEDFSSGVNF KDFKCTDENIAYGLMRTSVRIAMDH ELDKQDLAVIALCKDRYIKVKRIAEK LSVLSCFETIRDCEPEGEYPKGSLY WKDVKHLGLSEEAVFLGLVVTGRF LRLQEK | 254 | No significant similarity found. | | No putative conserved domains have been detected |
| 166 | 107102 | 107431 | 170 | VGYSRDPFYRLNSLQLHRLPHRGL QDIVHSVYIIDDASEFSAKLLEKAAH KKFKPMRVNFGDKFDGHTEWFDV EPHVIEKFFLSVGAKQVPIDKLIAQE QKIRKSTKK | 109 | No significant similarity found. | | T5orf172 domain / pfam105 44 / 1e-05 |
| 167 | 109330 | 109160 | 171 | MRTLRGGSPKSRSHNTYQLNVIRD GQKKGGDGGGGEWGFRVIMVIIMT LVFLQSCQ | 56 | No significant similarity found. | | |
| 168 | 109640 | 110605 | 172 | MLQKFTPVANLPMVRGGARNLLDG SKCASIGHILGVVRSNMESRTSRAF EHSRDYVLANPGAAIVIFHDDQYLV DSQPIDLIVSTTTDAYLYKASEGKQ ASRRFCYHESELLAFTDARAWIKNL CDHLELPPARISSEMMIFVLDKDGSI LLPCDPYDIDIEEGARTGNYRYDGE LEEVAPAVTENVVNPNNFETGALQ MNTIKSTATAIVAAANKNAAVNAAKL EAGSIVLKKVSGIAASKAPFMVRGY VDTAVGRVVIANLLNFAVSQYAPNN RKAVIAADAAMQAAMLELVQSFNV GEMIDEVLKGVNLSSLIESDVAE | 321 | Hypothetical protein T5.011 [Enterobacteria phage T5] | YP_006839.1 | 3e-39 (116/324) | No putative conserved domains have been detected |

Fig 2HH

| | | | | | | |
|---|---|---|---|---|---|---|
| 169 | 110672 | 173 | MERLTATFEGEKMTIANVWQRLRQ NGDRGNFAIFIEPKNLDNLARQIDR RDCYPDTDDMLGIPLRIIGVYGYGF DICIGDSSFEIDCESGATEIEVFLINL GSLTFLDTPPAEPEPEKLEVKTSVIV SSLTMDELADIVSTYDEIHADAIKEL NNRLDTFRDKL | 164 | No significant similarity found. | | No putative conserved domains have been detected |
| 170 | 111218 | 174 | MFHVKSCVPGINYTVEAEEGLYLE GGRIESCEVAAVLKCDTNVCGTSW TDLHFLGRGIDVDSLSWEKACEHA ESMLNEDDWDDDDSDEKYANAGV EGSFYMYWPGHSCNLVNGGSPLH SVLERAIYLGYIQIVDGKAVINLRELK TFIYIPDAETILHIEEGLKSGWKVSG VVYL | 175 | Hypothetical protein AGC_0009 [Enterobacteria phage EPS7] | YP_001836932. 1 | 2e-09 (43/137) |
| 171 | 111742 | 175 | MIYIYVNKYFLAHYKTMESVIQYVSR QNARHIDEVATLKIGLRGDAINISWP LLILICRDLVAGKPVSVSALGESYPL SDDLDLYDLLTKYKTERLFYRGGSV CSSGETIETVFR | 115 | No significant similarity found. | | No putative conserved domains have been detected |
| 172 | 112942 | 176 | MLKENVMSSEIVNEFTVADAEHFIE TYLNVYDVDLAFIHKDGQI | 44 | No significant similarity found. | | |
| | >113073 | | | | | | |

Fig 2II

Table 3 - Features of phage F394/08 gene products and assignment of putative functions.

| orf | Start position | Stop position | SEQ ID NO.: | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| 1 | <2 | 268 | 177 | NPEGGQAAAAESTPADPAANVS RETKPEDLIKNDVAPAELTPAFYV VAEGRAITSKRGILAAGEAVEARD FVGGEETLNSLLERGLVE | 88 | No significant similarity found. | | | | No putative conserved domains have been detected | | |
| 2 | 265 | 720 | 178 | MNIRDLAAQDFLNIVNDKNSGFG VPVVLIAPDGNAQPLSGLTTDISS YIDPETGVLVAGRVASVTFANKAI RAACFAEMPVAVADSNKRPWVV CFRDPEGIPYLFKVKAMPDRAIS GIVLELEVYKRSIYFNGAYKFDGT TLYDGVLDLL | 151 | Hypothetical protein orf10T [Vibrio parahaemolyticus phage VP16T] | AAQ964 77.1 | 4e-17 (51/129) | | No putative conserved domains have been detected | | |
| 3 | 717 | 1394 | 179 | MNIEGFKKLQSPINKLDSFEIVRD QIAAILFLELENQKAIAGRAGIDPA RFDMKVYKERSNPWDLFDDGEN KPIINVWFSNSDFDYTNSSTVDK QKTTAIFNIDCIATAISQETATGQT LGDEMASLEVQRVAKVIRNILMS DTNTYLQLRGLVWSRRVLSLNIF QPSAENGMMQNLCAARLVLQAT FSEFSPQYEPQELEILSVTVHNCD GQILFNKEIAKNGN | 225 | Hypothetical protein orf11C [Vibrio parahaemolyticus phage VP16C] | AAQ965 42.1 | 3e-35 (87/218) | | No putative conserved domains have been detected | | |
| 4 | 1384 | 2886 | 180 | MAISTAVDISAVARVLGIKTNFKNL RDGRVVILPQRIALIGQGSTGMVF ATSKRQVTSANEVGSLYGYGSPL HLAAKQLFPNNGDGVGTIPVTVY PLSDADGSQAATGSIELLGTQLE SGAYRVVVNGIRSEQFSILINEAG QTVLNRVAAAINSVLDMPVRATA DSELQKVTLVSKWKGLSANAISV QVDGDLGQGIEFAVTQPAGGLIN PSVSGALSQFGNVWETMVLNCL NIQDTEALSAYSDFGEGRWGALV RKPLIVFTGNTEADVNSAVSVPD ARKRDRTNVQLVAPDSIDLPFVV ASRQLARIVKIANENPACDYGSQ VADGINPGEDGKQWLYNVRDMA VKKGSSTIERDNQVFIGDVVTFY HPEGEENPPYRYVCDIVKLQNIIF NLNLIFAVPEWDGAPLIPNDQPTT NPRAKKPSMAVAIASLVDSLGL | 500 | Putative tail protein orf12C [Vibrio parahaemolyticus phage VP16C] | AAQ965 43.1 | 4e-120 (228/50 1) | tail sheath protein | Mu-like_GpL, bacteriophage Mu tail sheath protein (GpL) | pfam 0627 4 | 3e-26 |

Fig. 4A

| | | | | | | | | | | |
|---|---|---|---|---|---|---|---|---|---|---|
| 5 | 2894 | 3271 | 181 | NAIISDAAFTKKNTFAQINEQNPK RLDVSTTVKLSGNTNILSVDLNFG FYFGNSVIVG MSVGGSIESLTLDGRTFSVAADA DSTRNLGGTDNEVEMNGDGTYR IVKTRVPSKLDGITVAIDDVRGDA EYLQELKDRKEGFPYSITYASGVI YQGTGTIVGETGISSQNATASITIS GSALTKQ | 125 | Hypothetical protein orf13T [Vibrio parahaemolyticus phage VP16T] | AAQ964 80.1 | 7e-28 (65/123) | 2-C-methyl-D-erythritol 4-phosphate cytidylyl-transferase | PRK1 3385 | 0.010 |
| 6 | 3328 | 3774 | 182 | VEHIENTENQTLWGLPVKVAREV AEAEFIRFCDAMDVDYNTDRMTD EDAKQFNESKGLLLLDALQIGVLEI DSDGMAVVYPKKGDIKQIKFNEL CGADYVAMDNKKDTQSFAKMFA MMGSITKLPPATFSKLKKFDAKV CLSIAKLFLV | 148 | Hypothetical protein orf14T [Vibrio parahaemolyticus phage VP16T] | AAQ964 81.1 | 2e-07 (41/133) | No putative conserved domains have been detected | | |
| 7 | 4072 | 5565 | 183 | MQSGISRFTRRAESGLRRVSDMT WNISKVSGAAAAIGGAFMAAAG GIALFVAETNRANSEINEMSKAM GVSALSARAADSLLTPLGMNWE NYTDLIEELGNKMGELKNTGEMK TFQEAIGLTNIKMKELKALKPEQQ FTRIMDSLAKMEDQQKAQFIADEI FGGEGNKFVSALKARGLTMTSLI ENYKKYNFYNEQGEKATAAFNAA LTPLTTTANSAKSQIAALTGGAMV PYIQKATEWAAANKELINSKIEVF AKGLADSLVWVVVNFSEIVTWVK RVAIGIGIFLALTAVLKTFVLIMTAV NLVMMMNPIGLIIAVVALIAVIAYLI NKFFGLQGVIAAANGVLMGIGAAI LVAMGPIGWLIGAAVLIWKNIWGV LSGFFSGLWAGIVSVFCGAQNIIM GIINGIMGAIDNVINKAVSMGSAV KGFFSFGGGGDDKQAAAAGG RVASPQERTAKSVTENNSHSTVT IQDKTGRAKMSGKPGNGVRLVKT GTM | 497 | Hypothetical protein orf16C [Vibrio parahaemolyticus phage VP16C] tail tape measure protein [Phage PY100] | CAJ2846 8.1 | 2e-05 (72/316) | tail tape measure protein | | |
| 8 | 5569 | 6801 | 184 | MSWEDRLKEAAYTAPGGTRATF LVEDVSRSFDKKTNGFTFPDASG TYYQDSGVSGFKYPLTIYFSGPD CDVEAEAFEALLRETGIGRLEHPL YGVINVYPFGTITRTDAIKTEANQ TKIELEFWETNLLYPLPQADQLS AVFEAISDVKAALSGDVLDSIDVT DASALARFKNKITGALSKYKTALG KIKNLADLPGQLMDKVNGLISPGL | 410 | Hypothetical protein orf17T [Vibrio parahaemolyticus phage VP16T] | AAQ964 84.1 | 4e-59 (153/419) | Mu-like prophage DNA circulation protein | COG 4228 | 8e-08 |

Fig. 4B

| | | | | | | | | |
|---|---|---|---|---|---|---|---|---|
| 9 | 6794 | EFISDVKAQLGDVVNSFFELATLP EQIVDSFKEKAVYKDLFSELTSFE GIFPSNEEYEAACTGVTVTLSGLV VDLVESEFNTQSEALEAAEDLLAI FDDVTGWIEEKAQGLGRTDSNAV YQRLHSAVMTAASYLVQQSFTLK KERKLVLNRSRTIIDLCAELYGEV DSALDFFITSNDLSGAEILEIPKGR EVFYYV | 185 | | | | | | |
| | 7990 | MSDVSMMIHGTRFHFWSGVRISL NIDAVATISFNAPFDHEAPGFKRN FAPFGFSPVAIDVDDQRLFTGTM LDVSPVISEDGKKEISVNAYAKCG VLQDCTAPPESMPLEFNKLNLLDI ARKMASYFGVGVVFNADPGPAF DRVACDPDKKVLEFLADLAKQRG FVIGSDENGNLLFSKSSIGGIVAKL EQGVSPLLSVSPTFNPQEYYSHIT GLSPVEVAKPAAKSTAKVKKDAA TPEKAGQGSEKATDKAGQAEIKK EPKKEEKTKKEKQKPKPTTYKKF TAIDEAPVYRPLVFKIDDAEGATD VETATKAKMARMLGNMCTYAITV STWFDASGDLWRPNTKIKLKAPD SMIYDFFEFDIKSVELSADENSQQ ANLTLCLPGSFTGEPPEIFPWEL | 398 | Putative tail protein orf18C [Vibrio parahaemolyticus phage VP16C] | AAQ965 49.1 | 2e-57 (130/39 6) | tail protein | Mu-like tail protein gpP | COG 4379 | 2e-17 |
| 10 | 7978 | VGIVATVLSNDGKDLKVDRGNGD NVTAQQFGPSCDDAPPLKNDYS VLGSAKGSGNASAVAYRDQKAE NYIAKAGEKRIYSRDESGAVKAEV YLKADGTAEIKNASGLFVMEPGG DVVINGVRITKAGVIQTPGGASMS SDFTNAGGITLGDHAADTSLHKP | 161 | Hypothetical protein orf19C [Vibrio parahaemolyticus phage VP16C] | AAQ965 50.1 | 4e-08 (38/105) | | No putative conserved domains have been detected | | |
| 11 | 8480 | MSFFDVHLFDSVDGGNVTDDLET RDGLETAVVLSLFGGNALDDGRP QNLSTWWGNIGENEAAKQYKSE AAFLLRTVPPNTANLKRIEAASR DLAWLIPEYVNKIQVKAFMPKLNA VNLTVSLDGLDPLQFRTNWGEKV KEPVYRLLPPKVSRNNGVNLEGT AETKTKLLIRADGSRLSTLVDGS GNWKFDFYPLYGGERARMYVEG VGGKISAIVTVIGVLPLRYDGMAIY DGTHKYNGVRLN | 187 | Hypothetical protein orf21T [Vibrio parahaemolyticus phage VP16T] | AAQ964 88.1 | 7e-17 (51/124) | | Mu-like protein gp46 | COG 4381 | 5e-05 |
| 12 | 9217 | MSTPTTKEISNRILSKLETTFGQS LPKSFTRVLSTVLGGVFVILYKYG GFIALQMFVSTASAKDTFNGKTI | 188 | Hypothetical protein orf22T [Vibrio parahaemolyticus | AAQ964 89.1 | 4e-68 (159/39 | baseplate protein | P2 baseplate J-like protein | pfam 0486 | 3e-12 |

Fig. 4C

| | | | | | | | | | |
|---|---|---|---|---|---|---|---|---|---|
| | | | | NPLREWGRLLIGAGDPNPAVNAIL TRIVVEKPGEILPAGTQLVNSGNG VTYITQEDIELVEGAQDIEVLAASD TSGNSGAGKAGNLNAGDVLTFA NPLGSVGRYSTVVTTIREGLDAE AIETYRARVVSRFQLRAQGGAMV DYKIWGESVSGVSRIYPYTSDLP GQVDIYVDVLEGVASQAILNQVK NAVEFDANNGLAQNRPLNALVNY LPMEFVEFNVTISGLSVEGALSVR AEIRAALEHYFNIRAPYIVGLSTDS RADRITLAASGVVDDVVNKAGG IFNDMQLFKGQTPISFYMLGIGEK ATLVNVEYL | | phage VP16T] | | 2) | | 5 | |
| 13 | 10382 | 11101 | 189 | MNMFKHLLPSGRAWNLTAEKPL KAFFRCLDVLRTDAVNYFNLLFLD INPKTTRLLLDQWEQQFGINRGFL TEAQRRERVAAAWRDVGGQSPA YIQEVLRNNGFDVYIHEWFDPAD RGEVGEKQPITPRNPLSIMSAQY AEVLPVVDCGEPLALCGEEFAHA GNYLGLVGYPLVNKFVYDADKYG YTVPVDPAYWYHFFYVCGPNFG DVAQVEATRRAEFEALILRIKPAH LWAGVIVRYV | Hypothetical protein orf23T [Vibrio parahaemolyticus phage VP16T] | AAQ964 90.1 | 2e-45 (101/242) | Uncharacterized protein conserved in bacteria (DUF2313) | pfam 1007 6 | 1e-09 |
| 14 | 11103 | 11705 | 190 | MSLVFNEKFPGKTAGATQNYPY GEARNVSGPGNGDGTPWDAALV NDIFGLLQGLLVRANIQPNGQSDT ALNSQYLQALLALFMPKQTPISGK LEQNGYLTIPFPVVINGQTVEREF TIQWGSKDWSSYPGEIQDSIVFE KPFKTACFGVFPIRKMSQHSAYG DGGVKPISVSKTGFTVSLQAYGG SVGHLLGYYWFAVGV | Putative tail-fiber protein orf24C [Vibrio parahaemolyticus phage VP16C] | AAQ965 55.1 | 1e-13 (46/108) | tail-fiber protein | | |
| 15 | 11765 | 12151 | 191 | MEPISTGGTAAFLKVYGVWLAVV TALVFVATVVLMMRLPRSPQEFL VGITTVVSSLMGGSFLILYFDLQI WANSAYGLMVIGGLYFVAGIPGW ALVRWVFNFIDAREGSTLLDIFRE FNEEFRGGKK | Hypothetical protein ACICU_01067 [Acinetobacter baumannii ACICU] | YP_0018 45726.1 | 2e-33 (66/121) | No putative conserved domains have been detected | | |
| | | | | | Hypothetical protein PAJU2_gp73 [Pseudomonas phage PAJU2] | YP_0022 84407.1 | 2e-07 (27/75) | | | |
| 16 | 12148 | 12696 | 192 | MSKIIAICAGHSDKDPGAVNGKRT EAAIVLDMRKMVASYLEKAGVKY LTDGKGGVNQPLAEAIKVAKQASI AVEFHCNAATSKKATGVELSAE | N-acetylmuramoyl-L-alanine amidase [Psychrobacter arcticus 273-4] | YP_2637 37.1 | 1e-44 (88/173) | N-acetylmur amoyl-L-alanine | N-acetylmuramoyl-L-alanine amidase or MurNAc-LAA | cd026 96 | 7e-20 |

Fig. 4D

| | | | | | | | amidase | |
|---|---|---|---|---|---|---|---|---|
| | | | | | | | | endolysin |
| | | | | | PlyB054 [Listeria phage B054] | YP_0014 68737.1 | 5e-07 (46/171) | |
| 17 | 12697 | 12954 | 193 | KNKALAKQIAAKINGVLNIPLRGE SGWKSEGSGQHSRLGFISSGGG LIVELFFISNDDDLAKWDAKKWLV AKEVAAVLIEQVKKAEAA | | | | | |
| | | | | MAALTIFNAISEVTSFAGVAREIFD TAANAMDAAQNEKKGGGNKKV WVMAYMESFINDLGENWERWAK AIFSFIDFAKSIFNSKR | 85 | No significant similarity found. | | | No putative conserved domains have been detected |
| 18 | 13318 | 13079 | 194 | MRNTADKSTIDFIEETTGDAYKPV KGCGTVRGYKAGCACNNCHKAQ IGRMADKIVKAALRTRIKSSEPTH QPKEQAWNF | 79 | No significant similarity found. | | | No putative conserved domains have been detected |
| 19 | 13809 | 13393 | 195 | MTKTELKTAIIEFSALTTLQVAGQF SIEELTGLKTHLNGQREALLMDKA PAHIKGEKEAKINAQLSDVNNLIK KANKAIGLIQVNQAELKQSKVKQ DTHFLSTFHDVAQSYLTNELYAD LKQKALNVMRIAKANGKND | 138 | No significant similarity found. | | | No putative conserved domains have been detected |
| 20 | 14092 | 13865 | 196 | MSETTNLFNPDALDANFFYENSG QALAAALDPIEKCVLEKALKYSKY NIAEVSRILGINRLTVIKMKKHGL TEI | 75 | No significant similarity found. | | | No putative conserved domains have been detected |
| 21 | 14306 | 14076 | 197 | MKQPVIQRQQLSNFSQETANHG AKIKEILSTLFCFMLAALSYMFIIK QADEIDKQAEFVAEYNAQFKEYP NERNH | 76 | No significant similarity found. | | | |
| 22 | 14582 | 15553 | 198 | VKKFNTKFKQNLDDANNNAFIPN SFQITNAFVDNIMDKISDAAVKIYLI TVRKTTGWGKQIDSISLSQYEAY SGKSRPTVVKCLKELVKVGLLVE HTGTRYGNSYSVALVNSIGFELLS ASKKILLVKSFNYTSKKSLLPLVKI FNTQKQLSKNTNQKQINKRDWFS LKTLKDELFKTGLQIEAEDLTAAK WFDREKTAFENYAPNQNLSDPQ KMYYFVDWLLKAKRKYDAAERQ QAAKAKAEGKNQNQNPEDTKTE NDPFKLSTKQISFFASQLAHLPSF AKYCTGNKGFKFEFEMWIASMLN NPENVKKWNKYLNELGYLIG | 323 | Hypothetical protein ACICU_02758 [Acinetobacter baumannii ACICU] | YP_0018 47417.1 | 9e-48 (136/365) | No putative conserved domains have been detected |
| 23 | 15572 | 15802 | 199 | MKISNFHFQMQILLLISKNTVLDFE GLKEKLAPSITDNALTECLEELM WGWVQVQKGLYMVSGVAYQIM | 76 | No significant similarity found. | | | |

Fig. 4E

| | | | GDICQC | | | | |
|---|---|---|---|---|---|---|---|
| 24 | 15843 | | | 74 | No significant similarity found. | | |
| 25 | 16069 | 200 | MEKYKYSESNAVLSPHLNCGLTS VSRVGSSGQAKHKPHKRSEIADQ AEKEICKNWALRQQAFLNNSVSN AVLGG | | | | No putative conserved domains have been detected |
| 26 | 16721 | 201 | MNKFIHEGKPTAQQVREALAMY AKDIKRPEFSLIVQRELIESFRNDT AHALKSAVAFYFKNRVIQRPGLVL ASGKDQALIVESCENKALKRHLV AVSGYSSQFLQMVIDHKTPLSAV AARDLKQALPKAEKLYKAECKEK DAKLKNICGFVACYRNGCHCTK CTTAYKKYR | 173 | No significant similarity found. | | |
| 26 | 16721 | 202 | MGVSIINLVLLVGVCLLLTNIALNC LFHTENKTYLVYACGFSAASVAG AIAGVIGCLAYGVTV | 63 | No significant similarity found. | | |
| 27 | 16912 | 203 | MKNKSILMGLFVAAAGVVFYMGA DSACNQKAVIDPGALMSLGGITV ENKKASLVRVCDTPVKENLVSFV LIKDGLRVGGVVDKSHVALIGE | 91 | No significant similarity found. | | |
| 28 | 17188 | 204 | MSLGKRPAGATHIESDGTYWKN EDADWYFWRDLWGWCQYVGPK NRNFLNKFSVLG | 55 | Hypothetical protein ACICU_02216 [Acinetobacter baumannii ACICU] | YP_0018 46875.1 | 4e-04 (23/49) | |
| 29 | 17355 | 205 | MDLYIGQIVGHSSPTWVVQGKLKI TKINEGKRSGLKIITATDESGKEFT AVYGVFFSVDRY | 61 | No significant similarity found. | | |
| 30 | 17561 | 206 | VRNENFEDYLKQTDDYAVLLNNY GSSLFIHENGVYRALPVRVAYAA WVSGGDRWGEVQHLKGKIKKMA ERAAETADFYHTKIEKLESSTVKK AGLLDMAEQWDGLELRGRDLEL NRVQESIYKRCAYLLRVAVNG | 135 | No significant similarity found. | | | No putative conserved domains have been detected |
| 31 | 17961 | 207 | MGNRWTLSGKVKGLKDLPESITA AQFREMIERGQVKNTPQAPKKR RSGKVSSPGEATLAQALKALKIEF VQEYRFCEYRKWRADFHIPGTNL LIEVEGGVRSGGRHVRPQGYIND TEKYNEAAKLGFVVLRFDTETVS RGTAINEIESYLERRGYFQNKGLT CEES | 166 | Conserved hypothetical protein [Acinetobacter calcoaceticus RUH2202] | ZP_0605 7626.1 | 6e-29 (68/112) | No putative conserved domains have been detected |

Fig. 4F

| 32 | 18448 | 18720 | 208 | VKKVKFKYDWRAVPDHINWLAT YEGGEMAWGYVNKPYRKENAGI WYETGGEWRHRVPVAPYRGHW TQSLEKRPSKAQLVEWVLNGAVV V | 90 | No significant similarity found. | | No putative conserved domains have been detected |
|---|---|---|---|---|---|---|---|---|
| 33 | 18896 | 20953 | 209 | MAENSFIQPIARKDAIALIGRDELV EGGPEGAANKQAIALANNIKYLM GLIPENWGVEKTEYGLDEVVRLS NGDVVKSVIDENINNPNENLSGW SFVTSNSVNTISDLLSIKNPKNGM KVYVLGYHKPDNFALLSPYEGGG LFIYSGNKAAENDGGVVLNGWIR QYVGDVDISWFGAKQGQDASPFI EAALKVKMSIVIRGEYKLETICGIP RQNNYAAKVIRIKGENQASLTVN CPDGAVFTSLDAKANPTSLSNIFT AKIDVFGINFVGTTVANSVLFNGD RLYNINIHHNNFKTNITIVKAYLKR EASRQYTQSVSINHNHLAEIHRVI ESDKSYNFDFAYNMCEACKGGM YIGVDAPYDPSGISITIHRNLWEA SGVLLKTNGGIIAGSVSKNYFEAN VYQDAAIDKCLIYINRSGTGAGYS GGLTFENNLFSGTSSIPDYVDVR VLGQSTETSGNSKSATTRPPVFI GNWSNSYMLTNMAQAILIGNKCS NREKMLNAYSPQEARVTYYSGY FTKQLANILTDKKLNLLKVNTSAV HAIGSSQANFKTTLDVIVFFKTSG AVGTAMATFKLDLFVYESVGLGA GNVPKANLKAVMYNFMQSTADD KITPTVNMFSAISDPLINVVDNSD GTYSIELSSFTNKGSPNWGFVSE LHIEYTAQATLIASHTSSYSAANLL TIS | 685 | No significant similarity found. | | No putative conserved domains have been detected |

Fig. 4G

| 34 | 21027 | 21707 | 210 | MFDIDTKQLHGLERRLERLNRRG LPYATRQTMNDLAFESRAVARAE LPTRMVLRNKHAINSIQVTKATSL NISQQAAHVGSTADYMATQETG GIKTKQGGAAVSIPTTTAAGQGR NAKPRTRLPRAALKMGAIHLKRIA ASRNAKNRKQRNAIAMATSDKYV FLDLGRRKGIFRKDKGGGVTMLH DLTRASVQIPKNEWLKPATEAAE RKLPGFYGRALEFQLRRF | 226 | Hypothetical protein orf62C [Vibrio parahaemolyticus phage VP16C] | AAQ965 93.1 | 7e-29 (86/232) | | No putative conserved domains have been detected | |
|---|---|---|---|---|---|---|---|---|---|---|
| 35 | 21993 | 22844 | 211 | MVKKLISRSDFAAKAGVSGAAISK ACKGPLLDAVEGKFIDLNHKSAIA YLESKKNGKTTPALEGIDSLYEEA LEVCREAGRCSQTLLRDKLMIGS DRARKLVALIQNANIQDFEKPAAE KVKREEKARPHTRGTAAKKQQAI QEDDEELFELLDRNVAQYADMTL RDIVRKFGTATRFAEYLRAMKEIS MIEDREIKIAQTKGELVHRDLVSQ LIIEPIDSAHVKLMRDGSKTIAVRM AAMHGSGADINEMQLVTSELIAS FIKPVKAKVNKIATELKRGAEA | 283 | Hypothetical protein orf2T [Vibrio parahaemolyticus phage VP16T] Likely small subunit of terminase | AAQ964 69.1 | 2e-07 (35/121) | small terminase subunit | Ftsk_gamma, directs oriented DNA translocation and forms a winged helix structure | smart 0084 3 | 0.005 |

Fig. 4H

| | | | | AAQ9647 0.1 | 4e-127 (252/65 6) | large terminase subunit | Phage terminase large subunit (GpA) | pfam 0587 6 | 1e-69 |
|---|---|---|---|---|---|---|---|---|---|
| 36 | 22847 | 24826 | 212 | Putative large terminase subunit orf3T [Vibrio parahaemolyticus phage VP16T] MNFIGMDWLCDKVENLTEYIKHV TPSQFNEENRYLPESVTSIPGFIR YDVNPFMREIVDCFDINSPVREV NLKKGVQITYSTVLESGALYYMG HVKTLPIMYMTADKELAKARIENN FIPMLAQSDMAHIVRSSDEGNSR KTGKTDNHIQFEGGGYLVPFGAI NANKMRSFSIAVMLKDEIDAWPD RVGKDGDPDKLSDDRCSAYWER RKIFRGSTPLIKGSSKIEKAYLRG DQRKYHVLCKKCSFPQELRWST PDGVGGFKWDTDEDGILKLDSVR YCCQQCGEPHFEHDKERLFSEK FGAKWIPTARPVEPGIRSVHLPAL YSPFGMQPWNYKCVIAYLDAFDPV ERKVKDIELYQVFYNNVLAEPFEI QGAKVRFETVSHHRRTVYRLGHI PNRYAVQYAGSPILFLTCQVDVH KSFLAVSVMGWAKDAKCFVIDYL RIEGEDFSDSAEPGWGKLRELIE EKQYIADDGKKYRVALTFIDSGYA NDTVVKFCSEYSSSVVPILGRDR PSKNQAIKEFADFKTQEGTTGFRI IVDHYKDRLAPVLRREWDEMGG GLQPVYHFNAPVDLSDKSLKELT VETRKEKTDASGNTSYFVWHRPG NARNELWDLLCYGHAAVEIFAWS LCVKNMEQKEVDWAWFWEFLET EAPYFEQGEPVASE | 659 | | | | | |
| 37 | 25079 | 24870 | 213 | MQYENNLEKLKGNKPEGATIVAV KGDRIAYFKEAEQKGRLLTFNRIM WVKTWFTPDHLNLKHFDFIAVL | 69 | No significant similarity found. | | | |
| 38 | 25316 | 25092 | 214 | MNNQSFNNWRGHKIEIVQAGATI QQHGYPVQITDQNTIAFDGKIYMT QNTYNSIAKNMPQCQTPNFNNQ GLNIF | 74 | No significant similarity found. | | | |
| 39 | 25582 | 25334 | 215 | MIDKKYLVFGGWVRSKHDKQSH YVAPRMVAYLYNVNPHECIFITDK TELNPRTHLPYGLNENHNLIKLGP QTNGKYNLPATN | 82 | No significant similarity found. | | No putative conserved domains have been detected | | |

Fig. 4l

| | | | | | | | | |
|---|---|---|---|---|---|---|---|---|
| 40 | 25770 | 25579 | 216 | MGQSEARQKQKSDYEKKRVIKN FSLLKERDKHLIEYIETVPNVGDL VRDLLNQHLKNEAVSKK | 63 | No significant similarity found. | | No putative conserved domains have been detected | |
| 41 | 26098 | 25883 | 217 | MLMIGNTQVKTPRELTKPLKKILG PEYKVKRDVWLMVEGKNLNEAK RIIESIGLFANDMGGFLTVFMAEE M | 71 | No significant similarity found. | | No putative conserved domains have been detected | |
| 42 | 26286 | 26540 | 218 | LDQAFLKERIEATKRQIVAYEDAV NQLSSGAVQSYSLNTGQTTQNV TRFDVARLNGDIDGLYNRLATLEA RLNGSGSTLVRPGW | 84 | No significant similarity found. | | No putative conserved domains have been detected | |
| 43 | 26544 | 28217 | 219 | MNYDFSRGLVKVPTVGLKTEFKY SGATIAPPMCGAKSDAIEINALG GGFNHSAFTGEKFIGGFGPTSLF TMDYWTLRKRSEQLFSENLYAA GLIERLVTNEINTGLTPEACPDERI LGLKPGDLEDWTELVENRFSIWA NSSEYCDFYGQNSLGEIQRIARR EALICGDVLVVLRQNQSTKMPQV QLVSGSLIRTPPDIPRKGHKIKHG VELDTQGRQCAYWVLQDDGTYK RLPAFGEKSKRRIAWMMYYGAQR RLGELRGQPLLSIVLQSLKEIDRY RDAAQRKAVVNSILAMFIEKTQDK MSTLPITGGAIRRDKVTDNSNTAA PRSFEIASQVPGVVLQELQAGEK PVGFHSQGTDINFPAFEEAVISAV AWCKQIPPEILKLSFSSNYSASQA AINEFKIYLNMVWNEWGANFCQP IYTEFLISEALLGKIDAPGFLDAWR DPVKMDIFGAWLWCDWFGSIKP STDMRKMGQGLALAVEQGWTTN AQASRQMFGTKFTKNIARQRRER ELQASLLRPMLELQKEYGISAEHL VNVAHAIGGTISAQTEETEEI | 557 | Putative capsid protein orf5T [Vibrio parahaemolyticus phage VP16T] | AAQ964 72.1 | 4e-96 (186/48 7) | portal protein | Portal_lambda, phage portal protein, lambda family | TIGR 0153 9 | 1e-25 |
| 44 | 28217 | 29368 | 220 | MDWFLTPEALKEIQELHARGLVL TAEQMTEFNALYSDDFPGSRIFQ KVGTVAQVNIAGVLTKEPNWMYR YYGGGNTAYSEIISAINEAERDPAI KEIILAIDSPGGQTNGLCSAMDAIK NTKKTVLAVVEGQAASAAYGLAS QANKIIAADRGCMVGSVGAAASIV | 383 | Putative protease orf6C [Vibrio parahaemolyticus phage VP16C] | AAQ965 37.1 | 1e-46 (137/36 8) | Clp_prote ase | Clp_protease_like superfamily | cd003 94 | 1e-07 |

Fig. 4J

| | | | | | | |
|---|---|---|---|---|---|---|
| 45 | 29414 | 29803 | 221 | VSENVVDIASTNAPKKRPDVTTD AGKAVIRETLDQIESIFIADIAAGR KVTADKVKLEFGQGGMYVAAHA LERGMIDEIKTADSSATTNAKSSA TYTASEENSTMDAATLKAQFPAV YTAIYNEGKTAENERVSAHLTLGE ASGDMQTAISAINDGSELTASIQA KYMAANMKRGQVAGRETDDTAA ANALDGVKPGATATDANAVTNM VAKNLGVA MMQVTQHTNSSINWGEVACQDD TLTLGANATLKEGTILARAATGKLI PFVKGGADGAGVPVAIAMHEIKT VAAGDVSVRAGISGQVRKNNLVI HADGNATNIDGAVTDALRSYGIV AFTVNSTNKPDNQ | | | |
| 46 | 29818 | 30903 | 222 | MTTSTIAGVYTQVAPKPLFLSGFF KAPPQNHFNTESVELDIERDSQQ VAAVVQSLGSDYNKNETGEFTNK KFTPPVYKEGFSLNAFDLLKREA GQSGFNTPSEQIRGNLITRFIKGA RKVEAKLRGIELOASOILQTGNLL LKDQEGKDAFKIDYKPKATHFVN VANVWTGANADPMKDLESLSEVI QTDGLVIPDIIIMCASALAAAKGNE KFIKNFDSRNISGNVLADMQITAR GGIYQGTLRVGNAVCELYTYGVG YQASSSAVATPFLNTNKVLMLSS ESQLDALFGAVPNIADILGVSLRE QLLPELPTRFDSNSTDLFTNVYLS ASGEQLMGGVASRPILVPTAIDSF GCLTVA | Hypothetical protein orf7T [Vibrio parahaemolyticus phage VP16T] Hypothetical protein orf8C [Vibrio parahaemolyticus phage VP16C] | AAQ964 74.1 AAQ965 39.1 | 1e-06 (38/106) 4e-57 (133/347) | No putative conserved domains have been detected No putative conserved domains have been detected |
| 47 | 30912 | >31076 | 223 | MNPLQWGFFLNLIEIFDVTKTDLI NAIKAIDSNAKTSGLDKDELQALL TELQAKA | No significant similarity found. | | | |

Fig. 4K

Fig. 5B

| orf | Putative function | orf | Putative function | orf | Putative function |
|---|---|---|---|---|---|
| 105 | Protease inhibitor | 169 | postulated decoy of host sigma70 or sigmaS | 228 | I-TevI homing endonuclease |
| 107 | EndoVII packaging and recombination endonuclease VII | 171 | DNA helicase | 229 | thymidylate synthase |
| 108 | anaerobic ribonucleotide reductase subunit | 175 | DexA exonuclease A | 232 | ribonucleotide reductase A subunit |
| 109 | anaerobic nucleotide reductase subunit | 178 | MotB modifier of transcription | 233 | ribonucleotide reductase B subunit |
| 113 | glutaredoxin | 179 | modifier of suppressor T4 tRNAs | 234 | endonuclease II |
| 126 | alpha-glucosyl-transferase | 180 | RNA metabolism moderator | 235 | RNA ligase |
| 127 | recombination endonuclease subunit | 184 | DNA topoisomerase subunit | 236 | inhibitor of host transcription |
| 130 | recombination endonuclease subunit | 186 | membrane-associated affects host membrane ATPase | 241 | dN 3'phosphatase |
| 132 | RNA polymerase binding protein | 187 | rIIB protector from prophage-induced early lysis | 248 | dCMP deaminase |
| 133 | sliding clamp DNA polymerase | 189 | endonuclease IV | 251 | head assembly cochaperone |
| 134 | clamp loader subunit, DNA polymerase accessory protein | 196 | Nucleoid disruption protein | 252 | rIII lysis inhibition accessory protein |
| 135 | clamp-loader subunit | 197 | acridine resistance protein | 261 | DNA ligase |
| 136 | RegA translational repressor protein | 198 | DNA topoisomerase subunit | 263 | adenosylribosyl-transferase packaged protein |
| 138 | DNA polymerase | 201 | activator middle promoter | 264 | Alt RNA polymerase ADP-ribosylase |
| 140 | immunity to superinfection membrane protein | 206 | inhibitor of McrBC restriction nuclease | 266 | base plate-tail tube initiator |
| 141 | dCMP hydroxymethylase | 208 | AsiA anti-sigma 70 protein | 267 | base plate |
| 142 | Endodeoxyribonuclease | 209 | holin | 268 | baseplate hub subunit, tail length determinator |
| 144 | RecA-like recombinase protein | 210 | tail fiber protein | 269 | base plate distal hub subunit |
| 145 | head vertex assembly chaperone | 211 | tail fiber protein | 270 | base plate hub subunit |
| 146 | DNA primase-helicase subunit | 212 | hinge connector long tail fiber | 271 | base plate hub assembly catalyst |
| 147 | discriminator of mRNA degradation | 213 | tail fiber hinge | 272 | baseplate hub subunit |
| 151 | spackle periplasmic protein, lysis regulation | 214 | proximal tail fiber subunit | 273 | baseplate wedge subunit |
| 154 | primase | 215 | Ribonuclease H | 274 | recombination, repair and ssDNA binding protein |
| 156 | dCTP pyrophosphatase | 216 | dsDNA binding protein | 277 | RNA-DNA and DNA-DNA helicase, ATPase |
| 159 | small outer capsid protein | 217 | late promoter transcription accessory protein | 278 | RNA-DNA and DNA-DNA helicase |
| 162 | affects phosphorylation of host sigma32 | 218 | loader of Orf146 DNA helicase | 279 | minor capsid protein |
| 163 | postulated decoy of host sigma32 | 219 | ssDNA binding, DNA repair, recombination and pre-synthesis | 280 | outer capsid protein Hoc |
| 167 | adenylribosylating enzyme | 225 | dihydrofolate reductase | 283 | RnlB RNA ligase 2 |
| 168 | adenylribosylating enzyme | 227 | thymidylate synthase | | |

Table 5 - Features of phage F488/08 gene products and assignment of putative functions.

| orf | Start position | Stop position | SEQ ID NO: | Aminoacidic sequence | Size (aa) | Homologous/similar proteins ||| Predicted function | Conserved Domains ||
|---|---|---|---|---|---|---|---|---|---|---|---|
| | | | | | | Name[organism] | Acc No | E value and identity | | Name | Acc No | E value |
| 1 | 1232 | <3 | 224 | MAKINELLRESTTTNSNSIGRPNL VALTRATTKLIYSDIVATQRTNQP VAAFYGIKYLNPDNEFTFKTGAT YAGEAGYVDREQITELTEESKLT LNKGDLFKYNNIVYKVLEDTPFA DIEESDLELALGIAIVLLKVRLFSD AASTSKFESSDSEIADARFQINK WQTAVKSRKLKTGITVELAQDLE ANGFDAPNFLEDLLATEMADEIN KDILQSLITVSKRYKVTGITDTGFI DLSYASAPEAGRSLYRMVCEMV SHIQKESTYTATFCVASARAAAIL AASGWLKHKPEDDKYLSQNAYG FLANGLPLYCDTNSPLDYVIVGV VENIGEKEIVGSIFYAPYTEGLDL DDPEHVGAFKVVVDPESLQPSIG LLVRYALSANPYTVAKDEKEARII DGGDMDKMAGRS | 410 | Gp24 precursor of head vertex subunit [Enterobacteria phage RB14] | YP_002854509.1 | 0.0 (410/410) | precursor of head vertex subunit | Major capsid protein Gp23 | pfam07068 | 5e-13 |
| 2 | 2881 | 1316 | 225 | MTIKTKAELLNKWKPLLEGEGLP EIANSKQAIIAKIFENQEKDFQTA PEYKDEKIAQAFGSFLTEAEIGG DHGYNATNIAAGQTSGAVTQIGP AVMGMVRRAIPNLIAFDICGVQP MNSPTGQVFALRAVYGKDPIAS GAKEAFHPMYGPDAMFSGGQA AKKFAALKASDTLEVGTIYTHFFQ ETGTVYLQATAAKQIDSGASDAD KLDAEIKKQMEAGVLVEIAEGMA TSIAELQEGFNGSTDNPWNEMG FRIDKQVIEAKSRQLKAAYSIELA QDLRAVHGMDADAELSGILATEI MLEINREVDWINYSAQVGKSG MTLTPGSKAGVFDFQDPIDIRGA RWAGESFKALLFQIDKEAVEIAR QTGRGEGNFIIASRNVVNVLASV DTGISYAAQGLATGFNTDTTKSV FAGVLGKYRYVIDQYAKQDYFT VGYKGPNEMDAGIYYAPYVALTP LRGSDPKNFQPVMGFKTRYGIGI NPFAESAAQAPASRIQSGMPSIL | 521 | Major capsid protein (g23) [Enterobacteria phage T4] | AAA32503.1 | 0.0 (503/521) | major capsid protein | Major capsid protein Gp23 | pfam07068 | <1.0e-180 |

Fig. 6A

| | | | NSLGKNAYFRRVYVKGI | | | | | |
|---|---|---|---|---|---|---|---|---|
| 3 | 3709 | 2900 | MLKEQIAEAQKIDASVALDSIFE SVNISPEAKETFGTVFEATVKQH AVKLAESHIAKIAEKAEEEVEKNIK EEAEEKAEKKIAEQASKFLDHLA KEWLTENKLAVDKGIKAELFESM LGGLKELFVEHNVVVPEESVDVV AEMEEELQEHKEESARLFEELNK RDAYINYVQREVALSESTKDLTE SQKEKVSALVEGMDYSDAFSSK LSAIVEMVKKSNKDESTITESINT PDTEAAGLNFVTEAVEDKSAQG AEDIVSVYAKVASRF | 226 | Gp22 prohead core scaffold protein [Enterobacteria phage RB51] | YP_0028541 29.1 | 9e-147 (268/269) | prohead core scaffold protein | No putative conserved domains have been detected | |
| 4 | 4378 | 3740 | MNEPQLLIETWGQPGEIIDGVPM LESHDGKDLGLKPGLYIEGIFMQ AEVVNRNKRLYPKRILEKAVKDYI NEQVLTKQALGELNHPPRANVD PMQAAIIEDMWNKGNDVVYGRA RVIEGDHGPGDKLAANIRAGWIP GVSSRGLGSLTDTNKGYRIVNE GFKLTVGVDAVWGPSAPDAWVT PKEITESQTAEADTSADDAYMAL AEAMKKAL | 227 | Prohead core protein protease [Enterobacteria phage T4] | AAA32501.1 | 1e-120 (212/212) | prohead core protein protease | Peptidase _U9, prohead core protein protease | pfam0342 0 | 1e-104 |
| 5 | 4803 | 4378 | MILLIPETHELVLENVEALIPEAQG RFDELSSALNKDDINTIVENMLD DETDLAVALASINENMPLNEFIVK HVSARGEITRTKDRKTRERNAFQ TTGLSKAKRRQIARKATKTKIANP AGQSRAQRKRKKALKRRKALGL S | 228 | Gp68 prohead core protein [Enterobacteria phage T4] | NP_049784. 1 | 8e-75 (141/141) | prohead core protein | No putative conserved domains have been detected | |
| 6 | 5042 | 4803 | MEGLIEAIKSNDLVAARKLFAEA MAARTTDLIKEEKIAIARNFLIEGE EPDDEDDEDSDDKDDKKDK DSDEDEDE | 229 | Gp67 prohead core [Enterobacteria phage RB51] | YP_0028541 26.1 | 2e-19 (50/51) | prohead core protein | No putative conserved domains have been detected | |
| 7 | 6616 | 5042 | MKFNVLSLFAPWAKMDERNFKD QEKEDLVSITAPKLDDGAREFEV SSNEAASPYNAAFQTIFGSYEPG MKTTRELIDTYRNLMNNYEVDNA VSEIVSDAIVYEDDTEVVALNLDK SKFSPKIKNMMLDEFSDVLNHLS FORKGSDHFRRWYVDSRIFFHKI IDPKRPKEGIKELRLRLDPRQVQY VREIITETEAGTKIVKGYKEYFIYD TAHESYACDGRMYEAGTKIKIPK AAVVYAHSGLVDCCGKNIIGYLH RAVKPANQLKLLEDAVVIYRITRA | 230 | Gp20 portal vertex protein of head [Enterobacteria phage T4] | NP_049782. 1 | 0,0 (524/524) | portal vertex protein of head | Bacteriop hage T4-like capsid assembly protein (Gp20) | pfam0723 0 | <1,0e-180 |

Fig. 6B

| | | | | | | | | |
|---|---|---|---|---|---|---|---|---|
| 8 | 7191 | 6700 | 231 | MFVDDYTRAFESGDFARPNLFQ VEISYLGQNFTFQCKATALPAGIV EKIPVGFMNRKINVAGDRTFDD WTVTVMNDEAHDARQKFVDWQ SIAAGQCNEITGKPAEYKKSAIV RQYARDAKTVTKEIEIKGLWPTN VGELCLDWDSNNEIQTFEVTLAL DYWE | Gp19 tail tube protein [Enterobacteria phage T4] | 163 | NP_049781. 1 | 1e-91 (163/163) | tail tube protein | T4-like virus tail tube protein gp19 | pfam0684 1 | 1e-83 |
| 9 | 9287 | 7308 | 232 | MTLLSPGIELKETTVQSTVVNNS TGTAALAGKFQWGPAFQIKQVT NEVDLVNTFGQPTAETADYFMS AMNFLQYGNDLRVVRAVDRDTA KNSSPIAGNIEYTISTPGSNYAVG DKITVKYVSEDVETEGKITEVDAD GKIKKINPTAKIIAKAKEVGEYPT LGSNWTAEISSSSSGLAAVITLG KIITDSGILLAEIESAETAMTAVDF QANLEKYGIPGVVALYPGELGDK IEIEIVSKADYAKGASALLPIYPGG GTRASTAKAVFGYGPQTDSQYAI IVRRNDAIVQSVVLSTKRGEKDIY DSNIYIDDFFAKGGSEYIFATAQN WPEGFSGILTLSGGLSSNAEVTA GDLMEAWDFFADRESVDVQLFI AGSCAGESLETASTVQKHVVSIG DARQDCLVLCSPPRETVVGIPVT RAVDNLVNWRTAAGSYTDNNFN ISSTYAAIDGNYKYQYDKYNDVN RWVPLAADIAGLCARTDNVSQT WMSPAGYNRGQILNVIKLAIETR QAQRDRLYQEAINPVTGTGGDG YVLYGDKTATSVPSPFDRINVRR LFNMLKTNIGRSSKYRLFELNNA FTRSSFRTETAQYLQCIKALGGIY EYRVVCDTTNNTPSVIDRNEFVA TFYIQPARSINYITLNFVATATGA | Gp18 tail sheath monomer [Enterobacteria phage RB51] | 659 | YP_0028541 23.1 | 0,0 (654/659) | tail sheath monomer | Phage tail sheath protein | pfam0498 4 | 8e-95 |

Fig. 6C

| | | | DFDELTGLAG | | | | | |
|---|---|---|---|---|---|---|---|---|
| 10 | 11151 | 9319 | 233 | MEQPINALNDFHPLNEAGKILIKH PSLAERKDEDGIHWIKSQWDGK WYPEKFSDYLRLHKIVKIPNNSD KPELFQTYKDKNNKRSRYMGLP NLKRANIKTQWTREMVEEWKKC RDDIVYFAETYCAITHIDYGVIKV QLRDYQRDMLKIMSSKRMTVGN LSRQLGKTTVVAIFLAHFVCFNK DKAVGILAHKGSMSAEVLDRTKQ AIELLPDFLQPGIVEWNKGSIELD NGSSIGAYASSPDAVRGNSFAMI YIDECAFIPNFHDSWLAIQPVISS GRRSKIIITTPNGLNIHFYDIWTA AVEGKSGFEPYTAIWNSVKERLY NDEDIFDDGWQWSIQTINGSTLA QFRQEHTAAFEGTSGTLISGMKL AVMDFIEVTPDDHGFHRFKGPE PDRKYIATLDCSEGRGQDYHAL HIIDVTDDVWEQVGVLHSNTISHL ILPDIVMRYLVEYNECPVYIELNS TGVSVAKSLYMDLEYEGVICDSY TDLGMKQTKRTKAVGCSTLKDLI EKDKLIHHRATIQEFRTFSEKGV SWAAEEGYHDDLVMSLVIFGWL STQSKFIDYADKDDMRLASEVFS KELQDMGDEYAPVIFVDSVHSAE YVPVSHGMSMV | 610 | Gp17 terminase subunit [Enterobacteria phage RB51] | YP_002854122.1 | 0.0 (608/610) | terminase large subunit | Terminase_6, terminase-like family | pfam03237 | 1e-67 |
| 11 | 11629 | 11135 | 234 | MEGLDINKLLDISDLPGIDGEEIK VYEPLQLVEVKSNPQNRTPDLE DDYGVVRRNMHFCQQMLMDAA KIFLETAKNADSPRHMEVFATLM GQMTTTNREILKLHKDMKDITSE QVGTKGAVPTCQMNIQNATVFM GSPTELMDEIGDAYEAQEAREK VINGTTD | 164 | Gp16 terminase DNA packaging enzyme, small subunit [Enterobacteria phage T4] | NP_049775.1 | 1e-91 (164/164) | terminase DNA packaging enzyme, small subunit | No putative conserved domains have been detected | | |
| 12 | 12456 | 11638 | 235 | MFGYFYNSSFRRYATLMGDLFS NICIKRQLESGDKFIRVPITYASK EHFMIKLNKWTSINSQEDVAKV ETILPRINLHLVDFSYNAPFKTNIL NQNLLQKGTTSVVSQYNPSPIKM IVELSIFTRYEDDMFQIVEQILPYF QPHFNTIMYEQFGNDIPFKRDIKI VLMSAAIDEAIDGDNLSRRRIEW SLTFEVNGWMYPPVDDAEGLIR TTYTDFHANTRDLPDGEGVFES VDSEVVPRDINPEDWDGTVKQT | 272 | Gp15 tail sheath stabilizer and completion protein [Enterobacteria phage T4] | NP_049774.1 | 1e-157 (270/272) | tail sheath stabilizer and completion protein | No putative conserved domains have been detected | | |

Fig. 6D

| | | | FTSNVNRPTPPEPPGPRT | | | | | | |
|---|---|---|---|---|---|---|---|---|---|
| 13 | 13268 | 12498 | MATYDKNLFAKLENRTGYSQTN ETEILNPYVNFNHYKNSQILADVL VAESIQMRGVECYYVPREYVSP DLIFGEDLKNKFTKAWKFAAYLN SFEGYEGAKSFFSNFGMQVQDE VTLSINPNLFKHQVNGKEPKEGD LIYFPMDNSLFEINWEPYDPFY QLGQNAIRKITAGKFIYSGEEINP VLQKNEGINIPEFSELELNPVRNL NGIHDINIDQYAEVDQINSEAKEY VEPYVVVNNRGKSFESSPFDND FMD | 236 | 256 | YP_803104. 1 | 3e-146 (255/256) | head completion protein | No putative conserved domains have been detected | |
| 14 | 14199 | 13270 | MSGYNSQNPKELKDVILRRLGAP IINVELTPDQIYDCIQRALELYGEY HFDGLNKGFHVFYVGDDEEKYK TGVFDLRGSNVFAVTRILRTNIGS ITSMDGNATYPWFTDFLLGMAGI NGGMGTSCNRFYGPNAFGADL GYFTQLTSYMGMMQDMLSPIPD FWFNSANEQLKVMGNFQKYDLII VESWTKSYIDTNKMVGNTVGYG TVGPQDSWSLSERYNNPDHNLV GRVVGQDPNVKQGAYNNRWVK DYATALAKELNGQILARHQGMM LPGGYTIDGQRLIEEARLEKEALR EELYLLDPPFGILVG | 237 | 309 | YP_0028544 96.1 | 0.0 (309/309) | neck protein | Superanti gen-like protein | PRK13345 | 0.004 |
| 15 | 15688 | 14231 | MIELKDLPFVDSVPDECQERISW IKNGEEILGASTKYGNDGSMNRP IVSVFKNVEVLDENIGILKTAIETS QKDIKTIQGVLDVSGDIEALSQIS VNKNDISNLKTLTNEHTDILTGTN NTVDKIIADIGPFNDEENSVYRTI RNDLLWIKQELGQYSGQDINGLP VVGNASTGMKHRIITNSTLLSSQ GIRLSELENKFTESDVGSLTVEV GKLRDELGNKPVDFGPNIYNRLN TIDDKQTLINSDIAEIKSSIGYPEN VSIITEINNNKSSIESINNELNQSE GVKQRLTAIETSIGSDDIPSSIKG KIKNHTTSIESLNGIVGENTSSGL RANVSWLNQIVGTDSSGGQPSP SGSLLNKVSVLEGEVSVLNNNV QNIQVEIGNNRTGIKGQVIELTSLI NGNNPDGSTVEERGLTNSIKTNE TNIAAVTHEVNTAKDNISSLQSSV QALQEAGYIPEAPKDGQAYVRK | 238 | 485 | YP_0028544 95.1 | 0.0 (480/485) | fibritin neck whiskers | Fibritin C-terminal region | pfam0792 1 | 6e-25 |

Fig. 6E

| | | | DGEWVLLSTFLSPA | | | | | | |
|---|---|---|---|---|---|---|---|---|---|
| 16 | 17248 | 15698 | 239 | MSNNTYQHVSNESKYYKFDPVG SNFPGTVTTVQSALSKISNIGVN GIPDATMEVKGIAMIASEQEVLD GTNNSKIVTPATLATRLLYPNATE TKYGLTRYSTNEETLEGSDNNSS ITPQKLKYHTDDVFRNRYSSESS NGVIKISSTPAALAGVDDTTAMT PLKTQKLAIKLISQIAPSEDTASES VRGVVQLSTVAQTRQGTLREGY AISPYTFMNSVATQEYKCVIRLG TQSEINSNLGDVAVTGETLNGRG ATGSMRGVVKLTTQAGIAPEGD SSGALAWNADVINTRGGQTNG SLNLDHLTANGIWSRGGMWKNG DQPVATERYASERVPVGTIMMF AGDSAPPGWIMCHGGTVSGDQ FPDYRNVVGTRFGGDWNNPGV PDMRGLFVRGAGTGGHILNQRG QDGYGKDRLGVGCDGMHVGGV QAQQMSYHKHAGGWGEYNRSE GPFGASVYQGYLGTRKYADWD NASYFTNDGFELGGPRDALGTL NREGLIGYETRPWNISLNYIIKVH Y | Gp12 short tail fibers [Enterobacteria phage RB14] | YP_0028544 94.1 | 0.0 (509/516) | short tail fibers | Phage short tail fibre protein gp12, middle domain | pfam0908 9 | 9e-29 |
| 17 | 17904 | 17245 | 240 | MSLLNNKAGVISRLADFLGFRTK KNDISVMNNQPVGAVTISQIAKG FYDSNVESAINDVRNMAEQQVG AVLINISGVSPTGVQQTDYWSFE GTVTDTSAKPGDPVIVNMFGIPV KATNGMTSIEFTSAVRTALQEMV VKFIAIDSEEDHPTIGNKIQVKYLD NQEHILEQYSDKGITFKQEIISPS KPGYGTWQLLGAQTVTLDSHTQ PTVFYFERIA | Gp11 base plate wedge completion tail pin [Enterobacteria phage RB14] | YP_0028544 93.1 | 3e-124 (217/219) | base plate wedge completion tail pin | GP11 baseplate wedge protein | pfam0867 7 | 1e-89 |
| 18 | 19709 | 17904 | 241 | MKQNINIGNVVDDGTGDYLRKG GIKINENFDELYYELGDGDVPYS AGAWKTYNASSGQTLTAEWGK SYAINTSSGRVTLQLPKGTVNDY NKVIKARDVFATWNVNPVTLVAA SGDTIKGSSSSVEINVQFSDLELV YCAPGRWEYVKNKQIDKIISSDIS NVARKEFLVEVQGQTDFLDVFH GTSYNVNNIRVKHRGNELYYGD VFSENSDFGSPGENEGELIPLDG FNIRLRQPCNIGDTVQIETFMDG VSQWRSSYTRRQIKVLDSKLTSK | Gp10 base plate wedge completion tail pin [Enterobacteria phage RB14] | YP_0028544 92.1 | 0.0 (590/601) | base plate wedge completion tail pin | Bacteriop hage T4 gp9/10-like protein | pfam0788 0 | 3e-79 |

Fig. 6F

| | | | | | | | | |
|---|---|---|---|---|---|---|---|---|
| 19 | 20575 | 19709 | TSLEGSIYVTDLSAMKSIPFSAFG LIPGEPINPNSLEVRFNGILQQQA GTAGYPLFLCEGANSDTQEGCIS LGGEWKESNTDYSIEYEDGKPV SLLFDRKFESGDIVITWFNNDLG TLLEKDDMIELTDDRYVSKGSSTE VTGDVALTDFDKIGWPNVEKVD SYTRTYNSISSIFDSIYPVGSIYEN AINPNNPVTYMGFGSWKLFGKG QVLVGWNDDVTDPNFALNNNDL DSSGNPSHTAGGTVGTTSVTLE NANLPATKTDERVLIEDENGSVII GGCQYDPDETGPIYTKYREDYA TTNSSHTPPTNISNIQPSITVYRW IRIA | | | | | | |
| | 21643 | 20639 | 242 | MFIQEPKKLIDTGEIGNASTGDIL FDGGNKINSDFNAIYNAFGDQRK MAVANGTGADGQIIHATGYYQK HSITEYATPVKVGTRHDIDTSTV GVKVIIERGELGDCVEFINSNGSI SVTNPLTIQAIDSIKGVSGNLVVT SPYSKVTLRCISSDNSTSVWNYS IESMFGCKESPAEGTWNISTSGS VDIPLFHRTEYNMAKLLVTCQSV DGRKIKTAEINILVDAVNSEVISSE YAVMRVGNETEEDEIANIAFSIKT NVYTATISSSTVGMRAAVKVIAT QKIGVAQ | 288 | Gp9 base plate wedge completion tail fiber socket [Enterobacteria phage RB14] | YP_0028544 91.1 | 2e-165 (287/288) | base plate wedge completion tail fiber socket | Bacteriop hage T4 gp9/10-like protein | pfam0788 0 | 9e-95 |
| 20 | | | 243 | MNDSSVIYRAIVTSKFRTEKMLN FYNSIGSGPDKNTIFITFGRSEPW SSNENEVGFAPPYPTDSVLGVT DMWTHMMGTVKVLPSMLDAVIP RRDWGDTRYPDPYTFRINDIVVC NSAPYNATESGACWMLVYRCLDV PDTGMCSIASLTDKDECLKLGGK WTPSVRSMTPPEGRGDAEGTIE PGDGYVWEYLFEIPPDVSINRCT NEYIVPWPEELKEDPTRWGYE DNLTWQQDDFGLIYRVKANTIRF KAYLDSVYFPDAALPGNKGFRQI SIITNPLEAKAHPNDPNVKAEKDY YDPEDLMRHSGEMIYMENRPPII MAMDQTEEINILFTF | 334 | Gp8 baseplate wedge subunit [Enterobacteria phage T4] | NP_049766. 1 | 0,0 (332/334) | baseplate wedge subunit | Bacteriop hage T4, Gp8 | pfam0921 5 | 5e-162 |
| 21 | 24734 | 21636 | 244 | MTVKAPSVTSLRISKLSANQVQV RWDDVGANFYVFVEIAETKTDS GENLPSDQYRWINLGYTANNSF FFDDADPLTSYIIRVATAAQDFEQ | 1032 | Gp7 base plate wedge initiator [Enterobacteria phage RB14] | YP_0028544 89.1 | 0,0 (1022/1032 ) | base plate wedge initiator | Fibronecti n type 3 domain | cd00063 | 0,009 |

Fig. 6G

| | | | | | | |
|---|---|---|---|---|---|---|
| 22 | 26713 | 24731 | 245 | SDWVYTEEFETFATNAYTFQNMI<br>EMQLANKFIQEKFTLNNSNYVNF<br>NNDTIMAALMNESFQFSPSYVDV<br>SSISNFIIGENEYHEIQGSIQQVC<br>KDINRYYLMESEGILYLFERYQP<br>VVKVSNDKGQTWKAVKLFNDRV<br>GYPLSKTVYYQSANITYVLGYDK<br>IFYGRKSTDVRWSADDVRFSSQ<br>DITFAKLGDQLHLGFDVEIFGTYA<br>TLPANVYRIAEAITCTDDYIYVA<br>RDKVRYIKTSNAPIDSDPLSPTYS<br>ERLFEPDTMTITGNPKAVCYKMD<br>SIGDKVFALIIGEVETLNANPRTS<br>KIIDSADKGIYVLNHDEKTWKRVF<br>GNTEEERRRIQPGYANMSTDGK<br>LVSLSSSNFKFLSDNVVNDPETM<br>VKYQLIGAVKYEFPREWLADKHY<br>HMMAFIADEKSDWETFTPQPMK<br>YYAEPFFNWSKKSNTRCWINNS<br>NRAVVVYADLKYTKVIENIPETSP<br>DRLVHEYWDDGDCTIVMPNVKF<br>TGFKKYASGMLFYKSSGEIISYY<br>DFNYRVRDTVEIIIWKPTGVFLKA<br>FLQNQEHETPWSPEEEHGLADP<br>DLRPLIGTMMPDSYLLQDSNFEA<br>FCEAYIQYLSDGYGTQYNNLRNL<br>IRNQYPREEHAWEYLWSEIYKR<br>NIYLNADKRDAVARFFESRSYDF<br>YSTKGIEASYKFLFKVLYNEEVEI<br>EIESGAGTEYDIIVQSDSLTEDLV<br>GQTIYTATGRCNVTYIERSYSNG<br>KLQWTVTIHNLLGRLIAGGEVKA<br>ERLPSFEGEIIRGVKGKDLLQNNI<br>DYINRSRSYYVMKIKSNLPSSRW<br>KSDVIRFVHPVGFGFIAITLLTMFI<br>NVGLTLKHTETINKYKNYKWDS<br>GLPTEYADRVAKLTPTGEIEHDS<br>VTGEAIYEPGPMAGVEYPLPDDY<br>NAENNNSIFQGQLPSERRKLMS<br>PLFDASGTTFAQFRDLVNKRLKD<br>NIGNPRDPENPTQVKIDE | MANTPVNYQLTRTANAIPEIPVG<br>GTFAEIKQNLIEWLNGQNEFLDY<br>DFEGSRLNVLCDLLAYNTLYIQQ<br>FGNAAVYESFMRTANLRSSVVQ<br>AAQDNGYLPTSKSAAQTEIMLTC<br>TDALNRNYITIPRGTRFLAYAKDT<br>SVNPYNFVSTEDVIAIRDKNNQY | 660 | gp6 base plate wedge [Enterobacteria phage RB14] | YP_0028544<br>88.1 | 0.0<br>(657/660) | base plate wedge | No putative conserved domains have been detected |

Fig. 6H

| | | | | | | | |
|---|---|---|---|---|---|---|---|
| | | FPRLKLAQGRIVRTEIIYDKLTPIII YDKNIDRNQVKLYVDGAEWINW TRKSMVHAGSTSTIYYMRETIDG NTEFYFGEGEISVNASEGALTAN YIGGLKPTQNSTIVIEYISTNGAD ANGAVGFSYADTLTNITININENP NGDPDFVGADGGGDPEDIERIR ELGTIKRETQQRCVTATDYDTFV SERFGSIIQAVQITFTDSTKPGYA FIAAKPKSGLYLTTVQREDIKNYL KDYNLAPITPSIISPNYLFIKTNLK VTYALNKLQESEQWLEGQIIDKID RYYTEDVEIFNSSFAKSKMLTYV DDADHSVIGSSATIQMVREVQNF YKTPEAGIKYNNQIKDRSMESNT FSFNSGRKVVNPDTGLEEDVLY DVRIVSTDRDSKGIGKVIIGPFAS GDVTENENIQPYTGNDFNKLANS DGRDKYYVIGEINYPADMIYWNI AKINLTSEKFEVQTIELYSDPTDD VIFTRDGSLIVFENDLRPQYLTIDL EPISQ | | | | | |
| 23 | 27015 | 26722 | 246 | MSGLSYDKCVTAGHEAWPPTVV NATQSKVFTGGIAVLVAGDPITE HTEIKKPYETHGGVTQPRTSKYY VTGKKAVQMADPISCGDTVAQA SSKVFIK | 97 | Gp5.4 conserved hypothetical protein [Enterobacteria phage T4] | NP_049763.1 | 9e-50 (97/97) | | No putative conserved domains have been detected | |
| 24 | 27510 | 27016 | 247 | MEGSSIDVTFTAQLETGETLVSIN ITSYEETPGVLVEENRLYGTYES VFGFGNDALKYRLGDEFKTAAS WEELPTDSDTQLYLWKAPQNLQ KTFTYEVTLIYDYQEQESEGGSG SNSRSSSDTTEPTDPPAPVRKTL VKNYTKTIVGNWSRWANKLRSY VYERS | 164 | Hypothetical protein RB32ORF151w [Enterobacteria phage RB32] | YP_803093.1 | 9e-90 (163/163) | | No putative conserved domains have been detected | |
| 25 | 29272 | 27545 | 248 | MEMISNNLNWFVGVVEDRMDPL KLGRVRVRVVGLHPPQRAQGDV MGIPTEKLPWMSVIQPITSAAMS GIGGSVTGPVEGTRVYGHFLDK WKTNGIVLGTYGGIVREKPNRLE GFSDPTGQYPRRLGNDTNVLNQ GGEVGYDSSSNIIQDSNLDTAIN PDDRPLSEIPTDDNPNMSMADM LRRDEGLRLKVYWDTEGYPTIGI GHLIMKQPVRDMAQINKVLSKQV GREITGNPCGSITMEEATTLFERD LADMQRDIKSHSKVGPVWQAVN | 575 | Bacteriophage T4 Cell-Puncturing Device | 1K28 | 0.0 (572/575) | baseplate hub subunit and tail lysozyme, cell-puncturing device | Bacteriop hage T4-like_lysoz yme | cd00735 | 1e-74 |

Fig. 61

| | | | | | | | |
|---|---|---|---|---|---|---|---|
| 26 | 29846 | 29256 | 249 | RSRQMALENMAFQMGVGGVAK FNTMLTAMLAGDWEKAYKAGRD SLWYQQTKGRASRVTMILTGNL ESYGVEVKTPARSLSAMAATVA KSSDPADPPIPNDSRILFKEPVSS YKGEYPVVHTMETESGHIQEFD DTPGQERYRLVHPTGTYEEVSP SGRRTRKTVDNLYDITNADGNFL VAGDKKTNVGGSEIYNMDNRL HQIDGSNTIFVRGDETKTVEGNG TILVKGNVTIVVEGNADITVKGDA TTLVEGNQTNTVNGNLSWKVAG TVDWDVGGGDWTEKMASMSSIS SGQYTIDGSRIDIG | | | | |
| | | | | MLFTFFDPIEYAAKTVNKNAPTIP MTDIFRNYKDYFKRALAGYRLRT YYIKGSPREELANTIYGNPQLY WVLLMCNDNYDPYYGWITSQEA AYQASIQKYKNVGGDQIVHVNE NGEKFYNLISYDDNPYVWYDKG DKARKYPQYEGALAAVNTYEDA VLENEKLRQIKIIAKSDINSFMNDL IRIMEKSYGNDK | Base plate wedge completion [Enterobacteria phage RB32] | YP_803091.1 | 3e-109 (193/196) | base plate wedge completion | No putative conserved domains have been detected |
| 27 | 29894 | 30346 | 250 | MAYSGKWVPKNISKYRGDPKKIT YRSNWEKFFFEWLDKNPEIIAW GSETAVIPYFCNAEGKKRRYFM DIWMKDSSGQEFFIEIKPKKETQ PPVKPAHLTTAAKKRFMNEIYTY SVNTDKWKAAQALAEKRGIKFKRI LTEDGLRALGFKGA | Head completion [Enterobacteria phage RB32] | YP_803090.1 | 5e-83 (150/150) | head completion | No putative conserved domains have been detected |
| 28 | 30346 | 31170 | 251 | MAIFGIINESTPQVPKVKQSLNEK KWIQIGLEYKKAKAKGMTGKQFA EERGIKYSTFTSAMSKYASGIKT AEKIQKLESKPMNKLNKQEROLL MINSFRQTLRDKIRNEGAAINNKT RKWFAETIKQVKGHKVVRPQPG RIYAFAYDAKHKETLPYWDKFPLI IYLGLGKHNLMYGLNLHYIPPKA RQQFLEELLKQYANTPTITNKTKL KIDWSQVKGFRGADQMIKAYIPG NIMGSLVEIAPKDWANVVLMPLQ QFVSKGKRFSANKVWSNI | Gp2 DNA end protector protein [Enterobacteria phage T4] | NP_049754.1 | 3e-158 (274/274) | DNA end protector protein | No putative conserved domains have been detected |
| 29 | 31277 | 31807 | 252 | MSQALQQIFNQANTTNFVVSIPH SNTTSAFTLNAQSVPIPGIRIPVT DTVTGPFGLGRAQRPGATFEYD PLIVRFIVDEELKSWIGMYEVML GTSNYLTGENTAQKTGPEYITLYI | Gp3 tail completion and sheath stabilizer protein [Enterobacteria | NP_049753.1 | 2e-98 (175/176) | tail completion and sheath stabilizer protein | No putative conserved domains have been detected |

Fig. 6J

| | | | | | | | | |
|---|---|---|---|---|---|---|---|---|
| 30 | 31857 | | LDNSKTEIVMSINFYKPWVSDLS EVEFSYTEDSDPALVCTATIPYTY FQVEKDGKIIAEV | | phage T4] | | | |
| | 32582 | 253 | MKLIFLSGVKRSGKDTTADFIMS NYSAVKYQLAGPIKDALAYAWG VFAANTDYPCLTRKEFEGIDYDR ETNLNLTKLEVITIMEQAFCYLNG KSPIKGVFVFDDEGQESVNSVAF NKIIDVINNIEDQWSVRRLMQALG TDLIVNNFDRMYMWVKLFALDYLD KFNSGYDYIVPDTRQDHEMDA ARAMGATVIHVVRPGQKSNDTHI TEAGLPIRDGDLVITNDGSLEELF SKIKNTLKVL | 241 | dNMP kinase [Enterobacteria phage RB32] | YP_803086. 1 | 2e-139 (240/241) | dNMP kinase | No putative conserved domains have been detected |
| 31 | 32582 | 254 | MSEQTIEQKLSAEIVTLKSRILDT QDQAARLMEESKILQGTLAEIAH AVGITGDTIKVEEIVEAVKNLTAE SADEE | 76 | Chaperone long and short tail fiber assembly [Enterobacteria phage RB32] | YP_803085. 1 | 1e-32 (75/76) | chaperone long and short tail fiber assembly | No putative conserved domains have been detected |
| 32 | 32819 | 255 | MEFKDFSTGLYVAAKFSELTLDA LEELQRSLRVPNPVPREKIHSTIC YSRVNVPYVPSSGSFEVASSGH LEVWKTQDGSTLVLVLDSEYLRC RHMYARALGATHDFDDYTPHITL SYNVGPLSFSGDVQIPVVLDREY KEPLKLDWADDLK | 151 | Hypothetical protein RB32ORF142c [Enterobacteria phage RB32] | YP_803084. 1 | 5e-84 (151/151) | | No putative conserved domains have been detected |
| 33 | 33341 | 256 | MKTFKEFATKTTITESSHGMEVK LGMALAEAERLFSRIKELAAAVD PSSFKGDQTKVKALLALCSDAGE IAKNGSKMKRLEDLK | 85 | Hypothetical protein RB32ORF141c [Enterobacteria phage RB32] | YP_803083. 1 | 1e-40 (85/85) | | No putative conserved domains have been detected |
| 34 | 33663 | 257 | MEIKMKTYQEFIAETADVKVEFIY TGKKDKMGEMPHGVLRDALDNF GQLAAEDYGDKIWVTGPAAVIEK WAAENKSIFRKK | 81 | Ip6 [Enterobacteria phage T6] | CAA84458.1 | 2e-37 (76/77) | | No putative conserved domains have been detected |
| 35 | 33967 | 258 | MKRCELIRNVAIASASAFSFSMF VGFICGLLLTTAENVFSLVVAFLIG LIAIVMDKISKGE | 61 | Trna.4 conserved hypothetical predicted membrane protein [Enterobacteria phage T4] | NP_049748. 1 | 2e-25 (61/61) | | No putative conserved domains have been detected |
| 36 | 34152 | 259 | MNVEYYVYADYENNPSKDEDNR LGVDAFDSPAAAWQWVERTDIP YRYIEVVDHAGNKYPKEAYVASG KVNFLLFAGDNYYPRGGYTDLIA KAFSEDELRDIIKENENKPMDSN | 132 | Trna.3 conserved hypothetical protein [Enterobacteria phage JS10] | YP_0029224 85.1 | 3e-67 (127/133) | | No putative conserved domains have been detected |

Fig. 6K

| | | | RFDWWQIVNANTHTIVDEG | | tRNA.2 hypothetical protein [Enterobacteria phage RB51] | YP_0028540 96.1 | 1e-46 (91/95) | | No putative conserved domains have been detected |
|---|---|---|---|---|---|---|---|---|---|
| 37 | 34553 | 34840 | 260 | MILYAKVSSIENGYKYDQDAAKA LIDDYGILTCFEVEKVYIDRSSSQ VKLVKEERKFNTVNFDFFIETEK GPLEYDIFKNPLGLECIVNMYYY KW | 95 | | | | |
| 38 | 34938 | 35010 | 261 | UGGGAAUUAGCCAAGUUGGUA AGGCACUGGAUUUUGAUUCCA GGAUgCAAAGGUUCGAGUCCU UUAUUCCCAG | | | | tRNA1-Gln | |
| 39 | 35012 | 35095 | 262 | GCGAGAAUGGCCAAAUUGGUa AAGGCACAGCACUUAAAAUGC UGCGGAAUGAAUUUCCUGUGG GUUCGAGUCCCACUUCUCGCA | | | | tRNA2-Leu | |
| 40 | 35104 | 35174 | 263 | GCGGAUAUCGUAUAAUGGUAU UACCUCAGACUUCCAAUCUGA UGAUGUGAGUUCGAUUCUCAU UAUCCGCU | | | | tRNA3-Gly | |
| 41 | 35188 | 35261 | 264 | CUCCGUGUAGCUCAGUUUGGU AGAGCGUCUGCUUUGGGAGCA GAAUGUCGUAGGUUCAAAUCC UGCCACGGAGA | | | | tRNA4-Pro | |
| 42 | 35264 | 35350 | 265 | GGAGGCGUGGCAGAGUGGUU UAAUGCACCGGUCUUGGAAAC CGGCAGUGCGCUCCGGCGACU CAUAGGUUCAAAUCCUAUCGC CUCCG | | | | tRNA5-Ser | |
| 43 | 35359 | 35431 | 266 | GCUGAUUUAGCUCAGUAGGUA GAGCAACUACUGUAAUGAG AAGGUCGGGGGUUCGAUUCC GUCAAUCAGCA | | | | tRNA6-Thr | |
| 44 | 35436 | 35507 | 267 | GGCCCUGUAGCUGGAAGGUU CAAGCAAGCGACUCAUAAUCG CCAGAUGGUGGUUCAAUUCCA CCCAGGGCCA | | | | tRNA7-Met | |
| 45 | 35520 | 35603 | 268 | GGGGAGUUAUcCCGUAGAGGU AGCCGUGUGGACUGUAAAUCC AUUGUCAUUGcGACUcGGGUG GUUCGACUCCACCACUCCCCA | | | | tRNA8-Tyr | |
| 46 | 35611 | 35682 | 269 | GGAUGUGUAGCUCAAUGGCAG AGCGAUCGCCUGUUAAGCGAU UGGUUAUAGGUUCGAAUCCUA UCACGUCCG | | | | tRNA9-Asn | |

Fig. 6L

| | | | | | | | |
|---|---|---|---|---|---|---|---|
| 47 | 35800 | 35872 | 270 | GUGGCCGUAGUUCAGUUGGU AGAACUCGAGAUUGUGAUUCU CGUAGUCAUGGGUUCGACUCC CAUCGGUCACC | | | tRNA10-His |
| 48 | 35880 | 35952 | 271 | CGGGCCAUAGCUCAGAAGGAA GAGCAAGGACCUUCUAAGUCC UAGGUCGUAGGUUCGAUCCCU ACUGCCUCGA | | | tRNA11-Arg |
| 49 | 35974 | 36324 | 272 | MKGNVYLVVHDLTFYFNHDTVI SERVINLLYQHADYVVENEYGH WQFLKNRSFGLDGYEYFDRKDL LDTIPLSTQYQNHKSLHKCRLIRN AESAYEAIDLWRKRREYIDSLKE Y | 116 | Hypothetical protein RB51ORF141 [Enterobacteria phage RB51] | YP_0028540 94.1 | 8e-60 8111/116) | No putative conserved domains have been detected |
| 50 | 36708 | 37181 | 273 | MKSYTQFLNEAVLNEASSTEIQA VAKAAIAAGKYSYKDASDESRFQ FARDMKAEGFTGNAVSMAWKSL VATGAAFAKASGKPAPKADPKA AQEKNIVKGIIAKYEAILKELLVIKT EGQKLARAYSFKDNPHVHSLEY VEDICKIIKDRIWSAKQIK | 157 | Hypothetical protein RB51ORF140 [Enterobacteria phage RB51] | YP_0028540 93.1 | 1e-83 (154/157) | No putative conserved domains have been detected |
| 51 | 37307 | 37870 | 274 | MKTYAEFLTEAAKLPSEADLTKV FFQLDPKDRGDFLKWKAKAIEM YNIDNSSFTMSQENKFNKAFFKI SKKLASGAQVPKSVLATPERAPV KISKNMFDTKKYVNALNKALDAL DDAKKAARDLQDVYTDFDRKTK GSISNSERNSVSVYSDSLDVLGD AYTEIKNRINTASKLKAAAEAIISK LGK | 187 | Hypothetical protein RB14ORF136 [Enterobacteria phage RB14] | YP_0028544 72.1 | 5e-100 (183/187) | No putative conserved domains have been detected |
| 52 | 38100 | 38363 | 275 | MDNYGELFNFFMKCVSEDFGRT VNDIKVIGPDHPMFETYAVMGNE DGQWYTVKVINMFTAEGYVKL SSKVYHDNDEIAEEYFNNMK | 87 | Hypothetical protein RB32ORF131c [Enterobacteria phage RB32] | YP_803073. 1 | 2e-44 (87/87) | No putative conserved domains have been detected |
| 53 | 38465 | 39058 | 276 | MNTLKKIVEFIRTKLGSAMAKNLS VEEQYTAAAAKLLDKIKDLKTASV KSINEEKRIRELVIEKNRQAESKE RERKLLSEGQDVTMHAKLGLLY RRTAEQLTTKADGYAEMRIEIAK KVVELDDARQELAVKLEYIRETR AANALGISTADDVVEIAALTKVDI EDTLARVETFNGNISGVETTSAD VQEYINSLK | 197 | Conserved hypothetical protein e.6 [Enterobacteria phage T4] | NP_049742. 1 | 6e-105 (194/197) | No putative conserved domains have been detected |
| 54 | 39106 | 39714 | 277 | MKMQSDFNSMFEEFQRQVDVP DQLLNALKRMAEGRNYYWGSSY | 202 | Hypothetical protein RB32ORF128c | YP_803070. 1 | 4e-112 (197/202) | No putative conserved domains have been detected |

Fig. 6M

| | | | | | | | |
|---|---|---|---|---|---|---|---|
| 55 | 39683 | 278 | ETDESLSGRFSRGKKSLIRPGILI NSIESIHSLTCDFDVEFTDFISPE WTVCVLNDDFDYLGVYSLSDAW FKRNLQKSNLFYIDTTVKFQGKK YFFTLIVDSETKHENKRILSKKNIL TIVDDLFDFKFVENPNFESDLLLEK FVKECREYVKTITIPSK | [Enterobacteria phage RB32] | | | |
| | 40075 | | MSKPSLYLPSKPVKYEPKRQIIST DVLIGPVILISFVILLIGGVLDVMT DIDSGEILVLMLILPLIVPLLLVPVN WVGYWYQGRHYRKRVRDWKA QCKKIKKEHQLKLDMYEFDEIMK FVKESRCKSQN | Hypothetical protein RB32ORF127c [Enterobacteria phage RB32] | YP_803069. 1 | 2e-64 (123/130) | | No putative conserved domains have been detected |
| 56 | 40419 | 279 | MQKPKLNKVKYSFPEALLILAVS VFTALAGSLIGLLIDCFILNIDGTVI ITEVWSELRFTIAISLFSFFGTMLY FHYDNFKINWQRKKDYKIQLKEY NSYMSYIEKESMEEFVSDCRKIK | Conserved hypothetical, predicted membrane protein e.3 [Enterobacteria phage T4] | NP_049739. 1 | 1e-49 (98/120) | | No putative conserved domains have been detected |
| 57 | 40416 | 280 | MILKTRWYDLDDGDGISVDRV DWSGCSEDTKKRLIREFRMGYQ AVKPSTVTDDKFVCIHNGRAKLT NAEWFTDKIMILWYIISLPVSSFV FYFFIKNPMDRIGDWILLTILVNIF TASILSGIWYTFIEMPWRLRRQQ KIFDEKKYTQNLNNFITECRKLK | Hypothetical protein e.2 [Enterobacteria phage RB51] | YP_0028540 86.1 | 3e-85 (152/162) | | No putative conserved domains have been detected |
| 58 | 40901 | 281 | MKTLSAGIIFMTEDKDLFMGRVT GSRKPGMMAHRWDIPKGRVES SDLNALEAAKRECLEETGFSNYN PDLLEDLGVFKYSSNKDLQLFYY TIPVEHEMFRNCHCESYFENKD GVMPEMDAFALIPRTQWQYVM GPSLYRIMNSLF | Nudix hydrolase [Enterobacteria phage RB51] | YP_0028540 85.1 | 1e-83 (144/146) | nudix hydrolase | NUDIX domain | pfam0029 3 | 5e-10 |
| 59 | 41378 | 282 | MNIFEMLRIDEGLRLKIYKDTEGY YTIGIHLLTKSPSLSVAKSELDK AIGRNCNGVITKDEAEKLFNQDV DAAVRGILRNAKLKPVYDSLDAV RRCALINMVFQMGETGVAGFTN SLRMLQQKRWDEAAVNLAKSR WYNQTPNRAKRVIATFRTGTWD AYKNL | Soluble lysozyme [Enterobacteria phage RB32] | YP_803066. 1 | 2e-92 (164/164) | soluble lysozyme | Bacteriop hage_T4-like_lysoz yme | cd00735 | 7e-64 |
| 60 | 41932 | 283 | MTRINLTLVSELADQHLIAEYREL PRVFGIVRKHVANGKRVKDFKIS SKFILGSGHVTFFYDKLEFLRKR QSDIITECLKRGFSIKDTEVPDISD IPVEWKNDYNPCKSAIKLSQQRL | Endonuclease V [Enterobacteria phage RB51] | YP_0028540 83.1 | 1e-74 (135/138) | endonuclease V | Pyrimidin e dimer DNA glycosyla | pfam0301 3 | 2e-69 |

Fig. 6N

| | | | DEKILMKPHWYKYYGKNIYI | | | | se | | |
|---|---|---|---|---|---|---|---|---|---|
| 61 | 42494 | 284 | MRTFLTGPYLSLMNAFTHHSDA RVEEICKNEYIPPFEDLLKQYCTL RLDGGRQSGKSTAVTNFAANWL YDGGTVIVLSNTSAYAKISADNIK KEFSRYSNDDIRFRLFTDSVRSFI GNKGSKFRGLSLSRILYIIDEPVK SPDMDKIYSVHIDTVHCCCNIKC CIGGITRPQFFVIGMQ | 179 | Hypothetical protein RB32ORF122c [Enterobacteria phage RB32] | YP_803064.1 | 1e-100 (176/179) | Endoribo nuclease RegB T4-bacteriop hage encoded | pfam10715 | 4e-11 |
| 62 | 43030 | 285 | MMTDQLFEYLYFSPKTKNKLV NHFEILAKNNILSEFYPKQYKLQK GVFKGCRVLCTAPNARLMNKIPY FTMEFIDGPFKGLITCSLMAYDS EPFLIKEQSWINLFFN | 109 | Unnamed protein product [Enterobacteria phage T4] | CAA28221.1 | 3e-57 (108/109) | REGB_T 4, Endoribo nuclease RegB T4-bacteriop hage encoded | pfam10715 | 1e-12 |
| 63 | 43366 | 286 | MKAYQILEGTHKGTIYFEDGIQA RIIVSKTFKEDSFVDPEIFYGLHA REIEIEQQPTVKIEGGQHLNVNVL RRETLEDAVKHPEKYPQLTIRVS GYAVRFNSLTPEQQRDVIARTFT ESL | 120 | Hypothetical protein vs.6 [Enterobacteria phage RB51] | YP_0028540 79.1 | 2e-63 (119/120) | Autonom ous glycyl radical cofactor GrcA | PRK11127 | 1e-41 |
| 64 | 43728 | 287 | MAKIIIEGSEDVLNAFAEWFSNS GEQQFNEAWNMGDINGYPTTEI SVQGYGIHEPIRLVEYDLGTGEE VKYD | 73 | Hypothetical protein RB32ORF119c [Enterobacteria phage RB32] | YP_803061 | 1e-33 (70/73) | No putative conserved domains have been detected | | |
| 65 | 43942 | 288 | MIEDIKGYKPHTDDKISKVNAIKD AEVRLGLIFDALYEDEFWEAFDSC EDDELAKNYAESLDQLTIAKMKL KEASMWACRAVFQPEEKY | 88 | Hypothetical protein vs.4 [Enterobacteria phage RB14] | YP_0028544 57.1 | 4e-42 (84/88) | No putative conserved domains have been detected | | |
| 66 | 44208 | 289 | MAQLSAGFGVEYYTAPRRVSVA PKKIQSLDDFQEVVRNAFQDYAR YLKEDSQDCLEEDEIAYYEQRLE QLKNLHEVRAEVSKSMNKLIRFK E | 92 | Conserved hypothetical protein vs.3 [Enterobacteria phage T4] | NP_049727.1 | 3e-46 (91/92) | REGB_T 4, Endoribo nuclease RegB T4-bacteriop hage encoded | pfam10715 | 3e-05 |
| 67 | 44546 | 290 | MTINTEVFIRRNKLRRHFESEFR QINNEIREASKAAGVSSFHLKYS QHLLDRAIQREIDETYVFELFHKI KD-HVLEVNEFLSMPPRPDIDEDF IDGVEYRPGRLEITDGNLWLGFT VCKPNAKFKDPSLQCRMAINSR | 153 | Site-specific RNase [Enterobacteria phage RB32] | YP_803058.1 | 8e-86 (153/153) | REGB_T 4, Endoribo nuclease RegB T4-bacteriop | pfam10715 | 2e-39 |

Fig. 60

| | | | RLPGKASKAVIKTQ | | | | | hage encoded | | |
|---|---|---|---|---|---|---|---|---|---|---|
| 68 | 45015 | 45560 | 291 | MRKALLAGLLAISMMAHSSEHTF SNVQLDNMRYAYQFGEQFSKD GKYKTHKNIHKSGLGHIMAAILW QESSAGVNLKSKPKHHAYGMFQ NYLPTMRARVKELGYNMTDAEIK RMLNKRSNSASWAYIELSYWLNI HKGDIRKAISSYNSGWNVKAGS KYASEVLEKANYLKNNKLLEIVN D | 181 | Conserved hypothetical protein vs.1 [Enterobacteria phage T4] | NP_049725.1 | 6e-101 (180/181) | | REGB_T 4, Endoribo nuclease RegB T4-bacteriop hage encoded | pfam1071 5 | 2e-27 |
| 69 | 45553 | 45894 | 292 | MTKILVLCIGLISFSVLADTSYTEI REYVNRTAADYCGKNKACQAEF AQKLIYAYKDGERDKSSRYKNDT LLKRYAKKWNTLECSVAEEKDK AACHSMVDRLVDSYNRGLSTR | 113 | Modifier of valyl-tRNA synthetase [Enterobacteria phage RB51] | YP_0028540 73.1 | 5e-59 (112/113) | modifier of valyl-tRNA synthetase | No putative conserved domains have been detected | | |
| 70 | 45891 | 46370 | 293 | MIVKYIKGDIVALFLQGNIIAHGCN CFHTMGSGVAGQLARAYPKILEI DKTTTEYGSRDKLGDMSIVFKHS PTGFGICYNLYTQYEPGPNLDYG ALVNCMIELNLGAETLLFKPVIYIP RIGCGIAGGDWDKVSKLIDMFTP DIDLIVVDYESTILPASV | 159 | Tk.4 conserved hypothetical protein [Enterobacteria phage JS98] | YP_0015952 33.1 | 5e-84 (148/159) | | Macro domain. Poa1p_lik e family | cd02901 | 5e-21 |
| 71 | 46342 | 46554 | 294 | MKVHYPHPFDPKNKYVEIIRQWER ICRTKCPINSPHDVDKDYIGTFVE YTFIDRKGRKQHVEEYCLKVTWL | 70 | Hypothetical protein tk.3 [Enterobacteria phage RB51] | YP_0028540 71.1 | 6e-33 (67/70) | | No putative conserved domains have been detected | | |
| 72 | 46551 | 46757 | 295 | MSQTSILKNAHCEKCEWPVVFAL CNDEMACDFDYWCYCSNKGCIN HKGEGFYSGFYPYPDFVKEGKP K | 68 | Hypothetical protein RB32ORF111c [Enterobacteria phage RB32] | YP_803053.1 | 6e-33 (67/68) | | No putative conserved domains have been detected | | |
| 73 | 46754 | 46927 | 296 | MNSFELQYEVLRELDNLIELAVN KGFAIGIGQKDTGHLTMEIFKQK RIILKLLEINI | 57 | RB32ORF110c hypothetical protein [Enterobacteria phage RB51] | YP_0028540 69.1 | 2e-23 (56/57) | | No putative conserved domains have been detected | | |
| 74 | 46924 | 47109 | 297 | MSLSKEQKDKLFELIHELLDEHT EANTFYDEYGPLSPEQQEEFAD RFDKKENELIAYVNML | 61 | Hypothetical protein tk.2 [Enterobacteria phage RB51] | YP_0028540 68.1 | 2e-26 (60/61) | | No putative conserved domains have been detected | | |
| 75 | 47119 | 47700 | 298 | MASLIFTYAAMNAGKSASLLTAA HNYKERGMGVLVLKPAIDTRDSV CEVVSRIGIKQEANIITDDMDIFEF YKWAEAQKDIHCVFVDEAQFLKT EQVHQLSRIVDTYNVPVMAYGL RTDFAGKLFEGSKELLAIADKLIE | 193 | Thymidine kinase [Enterobacteria phage RB32] | YP_803049.1 | 5e-110 (192/193) | thymidine kinase | Thymidin e kinase | PRK04296 | 2e-77 |

Fig. 6P

| # | | | Sequence | | | | | |
|---|---|---|---|---|---|---|---|---|
| 76 | 47743 | 47955 | LKAVCHCGKKAIMTARLMEDGTPVKEGNQICIGDEIYVSLCRKHWNELTKKLG | | | | | No putative conserved domains have been detected |
| 77 | 47968 | 48261 | MLQLTEKQLRNLTVLQLDEIRREVGNIISALRREVSLNQSPADYTRLRNFEKYLDKVKAVHRHKVNTGQK | 70 | Conserved hypothetical protein rl.1[Enterobacteria phage T4] | NP_049718.1 | 1e-32 (70/70) | | No putative conserved domains have been detected |
| 78 | 48258 | 48644 | MALKATALFAMLGLAFALSPPIEANVDPHFDKFMESGIRHVYMLFENKSVESSEQFYSFMRTTYKNDPCSSDFECIERGAEMAQSYARIMNIKLETE | 97 | Membrane protein, rl lysis inhibition regulator [Enterobacteria phage T4] | NP_049717.1 | 2e-49 (94/97) | lysis inhibition regulator, membrane protein | No putative conserved domains have been detected |
| 79 | 48740 | 48929 | MKFSDFSQSGKPSKADEYLGLLMAAQAYFHSAHFETKSYARHKAYDFIFSELPDLIDKFGEQYLGYSGRKYTPSIPDASKLPTDTIKMIDRILDQSNSIYKEMPPAIQSTIDDITGMFYQSKYLLSLE | 128 | MobD.6 hypothetical protein [Enterobacteria phage T4] | NP_049716.1 | 5e-68 (128/128) | | No putative conserved domains have been detected |
| 80 | 48928 | 49131 | MKIEALNQEGNIIYVIINGDFFVDMDEVTSEELVELLKKRYDMCDEAATHMACAIFSLSYVVE | 62 | MobD.5 hypothetical protein [Enterobacteria phage T4] | NP_049715.1 | 4e-27 (60/62) | | No putative conserved domains have been detected |
| 81 | 49134 | 49328 | MTRIEQADKIKELVALIRKADEELSDFAWFSAGIANKGIEKFEAKVDNALEALDMFLDEIIDHNTRV | 67 | Hypothetical protein RB32ORF102c [Enterobacteria phage RB32] | YP_803044.1 | 1e-26 (61/67) | | No putative conserved domains have been detected |
| 82 | 49318 | 49491 | MLTREQFEKIIKLARDIEIDSYQLAVEHCEGYSYDGIEAAKKDLDKSKAKLVQYLEMIRWNNEN | 64 | MobD.3 hypothetical protein [Enterobacteria phage RB51] | YP_0028540 61.1 | 2e-29 (64/64) | | No putative conserved domains have been detected |
| 83 | 49656 | 49841 | MKTEKQMFLMKLIEEYANAVSDYECSSRERGTAFAKEELKIMVDAHTKLQNFIENVI | 57 | mobD.2a hypothetical protein [Enterobacteria phage RB14] | YP_0028544 39.1 | 5e-25 (56/57) | | No putative conserved domains have been detected |
| 84 | 49843 | 50109 | MTSEQAFKLKELIETYSKAVHTATVIDESAFSGHANKIKYKTLMEEAKVNLDSYIETLIGE | 61 | Hypothetical protein RB14ORF101 [Enterobacteria phage RB14] | YP_0028544 37.1 | 1e-25 (59/61) | | No putative conserved domains have been detected |
| 85 | 50111 | 50644 | MGFPKLEVGDLVLTKLWNGVQSVEICQYRGATGNLMYTIYNPEILLECHLERFIKDTDSMPYSVSIVRKSDTKEYSKILEQIRANKKD | 88 | Hypothetical protein RB14ORF100 [Enterobacteria phage RB14] | YP_0028544 36.1 | 7e-42 (83/88) | | No putative conserved domains have been detected |
| 85 | 50644 | 50111 | MKRLVLEVSPLFGELAIEKVNNMYRLTQEDDMLYFTPSEIIHLTQIE | 177 | Hypothetical protein RB32ORF098c | YP_803040. | 1e-96 (169/177) | | No putative conserved domains have been detected |

Fig. 6Q

| | | | | | | | | have been detected |
|---|---|---|---|---|---|---|---|---|
| 86 | 50651 | | YPYTDKIVSINDEHKIHFYSSCPG FNIKSESMCLSVIHWDSFIDKIKY FYSNERKHSLKWLKNCNAIITN ACMQNDETLLNVSKCYEEGDVL TIRQIDDFRSHIVTFTKDEAIAKT YLDSVIPTMISK | | [Enterobacteria phage RB32] | 1 | | No putative conserved domains have been detected |
| 87 | 51172 | 309 | MFISSGSGLIRVEFKNDIFLSQGD DIIKMSYDEIKKICHALESHGKEN ATIDIGDLWVTLYEVSEGFNIEDE NNILAIDKRSDLFDVLKVYEQSN GGRKAVLVYQKPHSCGTASIISNI EDETDTYMCVLKAGGDRHPDFI SIRQNNGEISLSKSEAEAMIKYLT TVTPSMKG | 173 | Hypothetical protein RB32ORF097c [Enterobacteria phage RB32] | YP_803039. 1 | 4e-93 (166/173) | No putative conserved domains have been detected |
| 88 | 51175 | 310 | MIINENSWHYKLFKMFNDEWKR PKTLCAYFWSIVIPTFFVSFFGCT ILAGLTIICAEIIQKWLIFGSLWTLI PSAFILAILLVLLIIGSFVIPAQLHE KYKDYKWKKDYALHVENIDRAY KGLPPIQPKKSIIVEFLKARKAKV CPVIEYKAE | 153 | RB32ORF096c hypothetical protein [Enterobacteria phage RB51] | YP_0028540 56.1 | 8e-63 (139/153) | No putative conserved domains have been detected |
| 89 | 51636 | 311 | MKTVMKSYFGSHLYGTSTPESD VDFKEIFYPPARDILIGNVKEHMS KNTNNTSSKNTKDDIDHELYSLK YFFKLAADGETVALDMLHTPPEL VVKSDLPDVWKFIQDNRSRFYTT NMKSYLGYVRKQASKYGVKGSR LAALRDVLKVVNQIPEQWVDYQ EDGSIKQRRTKVEDIKHRLPENE FCEWVFHNHEKTGPQTFYTVLG RKYQTTLSLIELKQSLNKLDAEY GERARKAEANEGIDWKALSHAC RGGLQLLEIYKTGDLVYPLQDAP FILDVKLGKHPFKTVQEFLEDVV DQVEAASTEASKNGMQQKVDM SFWDDFLEKVYLENHRSYYK | 336 | Hypothetical protein RB32ORF095c [Enterobacteria phage RB32] | YP_803037. 1 | 0,0 (335/336) | Nuc- transf, Predicted nucleotidy l- transferas e | pfam1012 7 | 2e-06 |
| | | | | | | | | |
| 90 | 52764 | 312 | MKITPIEVKKLIDTEEISECFESFL EDATEDNAVYLAQKIIETYLEKNQ | 49 | No significant similarity found. | | | |
| 91 | 52910 | 313 | MTYVVDVLMNHGWKLRGHPTK NCHMFTDGDIEELHEMAEAIGMK RSWFQDKRIKHYDLHARRRQKA VELGAVEVSRREAVKWRTLK | 87 | No significant similarity found. | | | No putative conserved domains have been detected |
| 92 | 53243 | 314 | MKTVTINKGIYFGKEISGTFELLG EWFPDNAPVDAQGDGKVFVEID GKRRGVWVYKSDISYDGVKVEE VKESYEDMKTRINKRFNVMGMM | 322 | Hypothetical protein RB32ORF094c [Enterobacteria | YP_803036.1 | 0,0 (319/322) | No putative conserved domains have been detected |

Fig. 6R

| | | | | | | | |
|---|---|---|---|---|---|---|---|
| 92 | 5413 | | TNGIINGNIRSLIISGAAGIGKTYS LDKALNKANDNGYIEYKSINGKIS GIGLYEQLWNNREENSVLLIDDV DVFSDMDLNLLKAALDTGETRK VCWSTASSYLEEKGIEREFEFKG TIVFITNVDIDRELDRGTKLAPHL QALVSRSVYLDLGVHTNEEIMVR VEDVILSTDMMQKRGLSDEETYK ALSWMKVNVNRLRNVSLRTALY LADFIMTDKNGWEEIAEVTLLK | | phage RB32] | | |
| 92 | 54615 | 315 | MLYSKAREIYETKIKEAVFKFATT MRWTNDWEYSKNHKKPMVTRK AHMLVLIDREQIKAREALQNHKK AAFEWFMDNTAPETKKAVSAWF SGKNCERSFF | 100 | NrdC.9 conserved hypothetical protein [Enterobacteria phage T4] | NP_04970.1 | 8e-52 (98/100) | No putative conserved domains have been detected |
| 93 | 54676 | 316 | MNAKDIFNLVNYNDGKFKSEAQ SKFFNDISIGGEITVDGGQIYKSR WNWIVIIDEGIVEIYKNTNKNRTL HWSRDTNEQYKKDKASKLSRVT QEDIEFIKKDILMYDNLIAEEQAVI DKFDEIKASREIPDFMKESVNER YTLISERIETYKKQRAERQNTLRK FEERLKTVLA | 175 | NrdC.8 hypothetical protein [Enterobacteria phage RB14] | YP_0028544 28.1 | 9e-96 (175/175) | No putative conserved domains have been detected |
| 94 | 55259 | 317 | MKQLIIKRLNLLICCLCIAIAYGYY AINDYMHYKDYDVTVVNTITGTQ GKGSSLSFIAVYELKDGYRFSEYI SPEMYSSEKGDNITVSLRPFDV KQTLFDNIVWFFGMVLVQSVCG AYIVCSILFCIFSKIEIE | 135 | NrdC.7 conserved hypothetical, predicted membrane protein [Enterobacteria phage T4] | NP_049705.1 | 9e-66 (122/133) | No putative conserved domains have been detected |
| 95 | 55674 | 318 | MSVVINNVNAVIKSLVNKKLNEW TVLRRGEPDKFFHRFNPTLDLNV IDRDVHAEILDKFKVDIGFGLDKH LQRTNGSGMGLSNRIMKALNKIG ALSRINASEILRNYNKGYDLYGRL MPKLSFDQMIADLWENQRRLLA LGARLAKGLDKQMFKTNNTEDL KCFKFSTRGDDYIRARSTDYYN MGHHLCLAFEVLKEAGTLEYVS GAKCPIGSNCILIYRPDESSSTKL PTKPVPVRSNEKHSEQIAYFNKQ IEELNISIQQYDDEIFRLSGLSSKA KSEREKLIKIVDLLKS | 295 | NrdC.6 hypothetical protein [Enterobacteria phage RB14] | YP_0028544 26.1 | 8e-170 (291/295) | No putative conserved domains have been detected |
| 96 | 56570 | 319 | MKTRSQIEDMVRNASYTRDVMT FLCENNLDPDKVNRVIHHFKYTN SSEWVRNFSKAGYITQMTAREQ LTDFCKTIDYKNPLIVQGVGQSK | 342 | Hypothetical protein RB32ORF088c [Enterobacteria phage RB32] | YP_803030.1 | 0.0 (335/342) | No putative conserved domains have been detected |

Fig. 6S

| | | | | | | | |
|---|---|---|---|---|---|---|---|
| 97 | 57656 | VDLSSGFFNPNHYRIEWRFIALF RKQLKQILSTASRLKGSDINLKNL KFDGYTLQMEVRPLKENNRTARI SFKPNTKNSLSICECLKSQLTEAF KYMDVVAAVQSKILPRFERNIWE HTTTYELDMIVSFKYEFLRKDEIV QEKKQEVQDTLNLNLSNYLSND PKFWMYSSSNIDACKLNKVSFLP TENSNFKPVEKWHADAIEKSLKA VDDELVKATNEVLEAEKALEQAQ SRVQNLTKQRSKLNNALNALN | | | | | | |
| | 58657 | MTRNEYIKSFNSVIDDKAIPMFG QNSVLSIINQWLNSVDASIVSSTK FIHEIRKISSRVDKDVIKKTFKESR LLSYLVNRDILGNFGKEIKRTKDV VGYNWFGDVNSYHLNIKEDPENI FTRRWISNFRLFKKQILKSASKLC YGDYRQIHPLASDMIIIKEYELDK NKVSIFVNYGFFTPETNQKNINKF FSIASTITRQLETALLCMETVENIH TYPFKNICGWEGYKLVISLREVK CAYSPTDKEIYQQKCDEIVNTPK EETTLEELMECLDDSPEPIERPE VIALEKAYKEVLEISNKAQKEYEQ AKRIWEESVNRLRLREQALQLIK | 320 | NrdC.4 conserved hypothetical protein [Enterobacteria phage T4] | NP_049702. 1 | 0.0 (330/333) | | No putative conserved domains have been detected |
| 98 | 58710 | MKTRKHYIDYFDSLJTKHRNYQIG HRAVINNILRDFLDYIGWENHICK DTQNAYSHSLGSLLLEWFKRSRL LSSVIAVNNVKKFMYPSYIETNVS NASVVTFNIINDVKRTYLEEWFS KDSKEKFASEFSHEFNNNVNML FKHSRRLFCHGDNRTINVNVKD WVTAKFTPSSQNGQFELSIIICAP HEIYKNLPYMKPREANKHNETIS SLAYNLRVLLSDMDVVKSFDDNT NYGLSLFETKFVIKLKDPSEFKPT PKSNHGNDTMKEEREYLSARLIE VEKQIEEHTKVLKALTAKANGLR NAIEVLK | 321 | Hypothetical protein RB32ORF086c [Enterobacteria phage RB32] | YP_803028.1 | 1e-180 (307/308) | | No putative conserved domains have been detected |
| 99 | 59633 | MKKRLLEDIAASSNSSLIKIIMAGE EDDMEMRGKIHGCDDLDFKPPA WDAIMAMVERRERASKNVPNCP ECGTEQVCLINWRKPELEYKCR QCKHKFSKHAPEMVKLPDSTEF FKELVSVQPMPNNILD | 322 | NrdC.2 hypothetical protein [Enterobacteria phage RB14] | YP_0285442. 2.1 | 1e-70 (129/129) | tRNA synthetas es class I (K) | pfam0192 1 | 0.002 |
| 100 | 60025 | MTKRKEYMEAAEKAVRELAIAYY NEHGKFPDRYSVLKSALTRSYK | 323 | NrdC.1 hypothetical protein | YP_0028544 | 2e-39 | | No putative conserved domains |

Fig. 6T

| | | | Sequence | | | | | | have been detected | |
|---|---|---|---|---|---|---|---|---|---|---|
| 101 | 60269 | | NMLSEVSDIIYKHKEQTGQSLDY DETFKQVLGIKE | | [Enterobacteria phage RB14] | 21.1 | | | | No putative conserved domains have been detected | |
| | 60532 | 324 | MFKVYGYDSNIHKCVYCDNAKR LLTVKKQPEFINIMPEKGVFDDE KIAELLTKLGRDTQIGLTMPQVFA PDGSHIGGFDQLREYFK | 87 | NrdC thioredoxin [Enterobacteria phage T4] | NP_049698.1 | 8e-45 (87/87) | NrdC thioredoxin | GRX_GR Xb_1_3_li ke, Glutaredo xin (GRX) family | cd03418 | 2e-07 |
| 102 | 60529 | 325 | MMLEGTDYIHDYRGSAYYVGDE VAVYYGYGTLMTAKVIQIKNNRA KLEVYYSNGEKSISKWKYGDCM VKLG | 71 | RB32ORF082c hypothetical protein [Enterobacteria phage RB51] | YP_0028540 42.1 | 2e-33 (71/71) | | | No putative conserved domains have been detected | |
| 103 | 60747 | 326 | MIYDINVSRTPSMVTIPAEELDRL QKIEELLWEIESDLPSGLESWIDY EELNKLRG | 56 | Hypothetical protein RB32ORF081c [Enterobacteria phage RB32] | YP_803023.1 | 6e-23 (55/56) | | | No putative conserved domains have been detected | |
| 104 | 60883 | 327 | LIMKNLISFGVKPWWAARWETV EPEPEEPVYIDEETVYNEPTINDL IDMEMGHDYSR | 57 | Hypothetical protein RB32ORF080c [Enterobacteria phage RB32] | YP_803022.1 | 6e-24 (54/55) | | | No putative conserved domains have been detected | |
| 105 | 61040 | 328 | MITVDKWFRINRVDTGLCNYWP ELSAGTVFKVRELAKECEDDIEP DTGIIEIELSDGKIINYDKPITYWC LWNTESVENGEIEEVVERTSQD VQKPKAAFQGERISYALAKLAAQ ENNDGYEGNLMQAAAEYIEWLE TQISFSDQKIRQYKRLHQMFYNT | 161 | Inhibitor of host Lon protease [Enterobacteria phage T4] | YP_0028540 38.1 | 4e-86 (155/161) | protease inhibitor | PinA peptidase inhibitor | pfam10465 | 3e-66 |
| 106 | 61562 | 329 | MKTELVYTEKLNGGKWWKLFIKG HSTDPHMTTCVGTYSRPTKKMI RQYKRLHRMFYNT | 58 | Hypothetical protein RB32ORF078c [Enterobacteria phage RB32] | YP_803020.1 | 9e-27 (58/58) | | | No putative conserved domains have been detected | |
| 107 | 61782 | 330 | MLLTGKLYKEEKQKFYDAQNGK CLICQRELNPDVQAN-HLDHDHEL NGPKAGKVRGLLCNLCNAAEGQ MKHKFNRSGLKGQGVDYLEWLE NLLTYLKSDYTQNNIHPNFVGDK SKEFSRLGKEEMMAEMLQRGFE YNESDTKTQLIASFKKQLRKSLK | 157 | Gp49 EndoVII packaging and recombination endonuclease VII [Enterobacteria phage T4] | NP_049692.1 | 1e-87 (157/157) | EndoVII packaging and recombination endonuclease VII | Recombin ation endonucl ease VII | | 3e-20 |
| 108 | 62252 | 331 | MTIEKEIEGLIHKTNKDLLNENAN KDSRVFPTQRDLMAGIVSKHIAK NMVPSFIMKAHESGIIHFHDIDYS PALPFTNCCLVDLKGMLENGFKL GNAQIETPKSIGVATAIMAQITAQ VASHQYGGTTFANVDKVLSPYV KRTYAKHEDAEKWQIADALNYA | 605 | Anaerobic ribonucleotide reductase subunit [Enterobacteria phage RB32] | YP_0028544 13.1 | 0,0 (599/605) | anaerobic ribonucleotide reductase subunit | RNR, class III, Ribonucle otide reductase (RNR) catalyzes | cd01675 | 2e-159 |

Fig. 6U

| | | | | | | | | |
|---|---|---|---|---|---|---|---|---|
| | | | QSKTEKDVYDAFQAYEYEVNTLF SSNGQTPFVTITFGTGTDWTER MIQKAILKNRIKGLGRDGITPIFPK LVMFVEEGVNLYKDPNYDIKQL ALECASKRMYPDIISAKNNKAITG SSIPVSPMGCRSFLSAWKDSTG NEILDGRNNLGVVTLNLPRIALDS YIGTQFNEQKFTELFNERMDLCF EALMCRISSLKGVKATVAPILYQE GAFGVRLKPDDDIIELFKNGRSS VSLGYIGIHELNILVGRDIGQEILT KMNARLKQWAERTGFAFSLYST PAENLCYRFCKLDTEKYGSVKD VTDKGWYTNSFHVSVEENITPFE KISREAPYHFIATGGHISVYELPD MKNNLKGLEAVWDYAAQHLDYF GVNMPVDKCFTCGSTHEMTPTE NGFVCSICGETDPKKMNTIRRTC GYLGNPNERGFNLGKNKEIMHR VKHQ | | | the reductive synthesis | | |
| 109 | 64066 | 64536 | 332 | MNYDRFYPCDFVNGPGCRTVLF VTGCLHKCEGCYNKSTWNARN GIPFTGETLEQUECLNNDYIEGL TITGGDPLYPDNRDVIHCIVQTVK NLYPNKSIWLWTGYKFEDIKQLE MLKYYDVIIDGKYEKNLPTKKLW RGSDNCRLWSNTDGVWKHD | 156 | Anaerobic nucleotide reductase subunit [Enterobacteria phage RB32] | YP_803017.1 | 3e-87 (155/156) | anaerobic nucleotide reductase subunit | NrdG, anaerobic ribonucle oside-triphosph ate reductase activating protein | TIGR0249 1 | 4e-55 |
| 110 | 64529 | 64642 | 333 | MIKLNYIMDTINDMIFHFGPEFYS QYSLVLINAWLIN | 37 | Hypothetical protein RB32ORF074c [Enterobacteria phage RB32] | YP_803016.1 | 4e-13 (37/37) | | No putative conserved domains have been detected | |
| 111 | 64652 | 64867 | 334 | MYKFRKGLADFLTTVTFFLFMAV GAIFLIPFIAIFFVISLISPEKGLSSS EFNERLDKITNKLNAVLDKKA | 71 | Gp55.8 hypothetical protein [Enterobacteria phage RB14] | YP_0028544 11.1 | 8e-32 (71/71) | | No putative conserved domains have been detected | |
| 112 | 64870 | 65181 | 335 | MISFERYVVESWNGFDMFGNDY YFVECSLNPSFWAGREQDLEEIN ARADLLGELPTTYFTFDESGFVI QVYFPEENSGEDSVNPPYWAYQ GIISRGTKLELKE | 103 | Hypothetical protein RB51ORF079 [Enterobacteria phage RB51] | YP_0028540 32.1 | 6e-54 (103/103) | | No putative conserved domains have been detected | |
| 113 | 65153 | 65476 | 336 | VEQNSNLKNKIEVYGIPDEVGRC PGCQSVTKLLKELNAPFTFYKVL TNNGKIEYDRPLIVSLAKRAGFTS LNIRYPWIFINDSRQKNIKHFKETL | 107 | Glutaredoxin [Enterobacteria phage RB51] | YP_0028540 31.1 | 1e-55 (106/107) | glutaredoxin | Glutaredo xin | pfam0046 2 | 7e-04 |

Fig. 6V

| | | | ISLGYDRDIIED | | | | | |
|---|---|---|---|---|---|---|---|---|
| 114 | 65634 | 65816 | 337 | MVVVDKEIKKGQYYFINGNVVRV TYVNGFEVYYLILKLHKQMICDR AVFSSVAKEIKLHG | 60 | Gp55.6 hypothetical protein [Enterobacteria phage RB14] | YP_0028544 07.1 | 2e-26 (60/60) | | No putative conserved domains have been detected |
| 115 | 65809 | 66102 | 338 | MGKTYRRKDLKVRDYDYFGKRK APDGVSHKDMVENIFRSDKWRR MKGIDSEVKDELNRQLRSEVRKL KKSVYIDDDFDYNTSQRVAKRKS NECYRYS | 97 | Gp55.5 conserved protein of unknown function [Enterobacteria phage T4] | NP_049684. 1 | 6e-48 (96/97) | | No putative conserved domains have been detected |
| 116 | 66110 | 66241 | 339 | MNIKRMLFKQGLYTLNATPKGDT TKWSVNDWIKFIDENGNWEI | 43 | Gp55.4 conserved hypothetical protein [Enterobacteria phage T4] | NP_049683. 1 | 2e-16 (42/43) | | No putative conserved domains have been detected |
| 117 | 66242 | 66442 | 340 | MNPESKLSQRIAEERAKFFGNM KHNGIEDEVFLNWFWNNKYAAC EGALSLSVAMMYEGWKGAKKFS | 66 | Gp55.3 hypothetical protein [Enterobacteria phage T4] | NP_049682. 1 | 1e-31 (66/66) | | No putative conserved domains have been detected |
| 118 | 66495 | 66821 | 341 | MTIQIKNAINSYAYDKVVSLLEKG DIVTPQILDKWEKELHQTMKQND QKIGRNTVRELLVQYILSEFDVKA FGVESKAYQKHEISDKTIRRMKN QRKKKFADLKITKV | 108 | Gp55.2 hypothetical protein [Enterobacteria phage T4] | NP_049681. 1 | 6e-56 (108/108) | Hypotheti cal protein | PHA02100 0.003 |
| 119 | 66824 | 67039 | 342 | MNEALINDLRLAGYEVNTNGIGL TQIEGNGFILEYEFSQWWLYANY GELIEYVDQFDSLDAALEAAKLM NV | 71 | Gp55.1 hypothetical protein [Enterobacteria phage RB14] | YP_0028544 02.1 | 2e-32 (71/71) | | No putative conserved domains have been detected |
| 120 | 67036 | 67305 | 343 | MKLINISIAIENFGIFYVDQYMKIS FFPNKTGVGYWESHVSELNESE YVSTHKKFLDFLYRADINDHYIDI HEFKKMMEKVFQAYCLLR | 89 | Hypothetical protein RB14ORF65 [Enterobacteria phage RB14] | YP_0028544 01.1 | 2e-41 (81/89) | | No putative conserved domains have been detected |
| 121 | 67384 | 67941 | 344 | MSETKPKYNYVNNKELLQAIIDW KTELANNKDPNKVVRQNDTIGLA IMLIAEGLSKRFNFSGYTQSWKQ EMIADGIEASIKGLHNFDETKYKN PHAYITQACFNAFVQRIKKERKE VAKKYSYFVHNVYDSRDDDMVA LVDETFIQDIYDKMTHYEESTYRT PGAEKKSVVDDSPSLDFLYEAN D | 185 | Gp55 Sigma factor for T4 late transcription [Enterobacteria phage T4] | NP_049679. 1 | 7e-106 (185/185) | | No putative conserved domains have been detected |
| 122 | 67925 | 68143 | 345 | MRLTINLSGFLEEIPEVEAIPYLLK MYLREVLALDIDIDPENPYDTAFK SNGVELNYRYHLTDDDFYFILEK | 72 | A-gt.5 hypothetical protein [Enterobacteria phage T4] | NP_049678 | 2e-33 (72/72) | | No putative conserved domains have been detected |

Fig. 6W

| 123 | 68145 | 346 | MTDKPEINDEVEKLISSIEEKNRL EAERKANKLLSKNKRELNRLYKH AQIAAENNNFAQYEYAIKKSRDIL KQPYNDELISILWKTTRSQIEDMI DAYTRKIQAS | 105 | A-gt.4 conserved hypothetical protein [Enterobacteria phage T4] | NP_049677.1 | 8e-53 (105/105) | | No putative conserved domains have been detected | |
|---|---|---|---|---|---|---|---|---|---|---|
| 124 | 68431 | 347 | MLTHVKFKRLKINAGFTESLNGH LCVKISEKEYHDSSIKEVNPPIVR ADPNMKVWVDSYQVKKWWQL | 67 | Hypothetical protein RB32ORF062c [Enterobacteria phage RB32] | YP_803004.1 | 2e-32 (67/67) | | No putative conserved domains have been detected | |
| 125 | 68638 | 348 | MNTQTSEIDYNKIRSSKEEMMRR FKESHDKAKAEGTIKYKRIKFKSS NEPLYGVLCG | 57 | A-gt.2 hypothetical protein [Enterobacteria phage RB51] | YP_0028540 19.1 | 2e-24 (55/57) | | No putative conserved domains have been detected | |
| 126 | 68878 | 349 | MKVCIFMARGLECCGVTKFSLE QRDWFKNGHEVTLVYAKDKSFT RNCAHDYKSFSIPVLAKEYDKT LKLVNDCDILIINSVPATSVEEDTI NNYKKIIDNIKPSVRVVVYQHDHS SLSLRRNLGLEETIRRADVIFSHS DNGDFNKVLMKEWYPETVSLFD DIEEAPTVYYNFQPPMDIAKVRST YWKDVSEINMNINRWIGRTTTW KGFYQMFDFHEKHLKPAGLSTIM EGLERSPAFIPIKEKGIPYEYYRL HQVDQIKIAPNLPTQILDRYVNSE MLERMSKSG-GYQLSKLDKKYL QRSLEYTHLELGACGTIPVFWKS TGENLKFRVDNTPLTSHDSGIIW FDENDMESTFERIKELSSDRTLY DREREKAYEFLYQHQDSSFCFK EQFDIITK | 400 | Alpha-glucosyl-transferase [Enterobacteria phage RB51] | YP_0028540 18.1 | 0.0 (399/400) | alpha-glucosyl-transferase | No putative conserved domains have been detected | |
| 127 | 70257 | 350 | MKILNLGDWHLGVKADDEWVQS IQLDGIKQAIEYSKKNGITTWIQY GDIFDVRKATHKTMEFAREIVQ MLDDAGITLHTIVGNHDMHFKNT LTPNASTELLAKYPNVKVYDKPT TVDFDGCLIDLIPWMCEENTGEIL EHIKTSSASFCVGHWELNGFYFY KGMKSHGLEPDFLKTYKEVWSG HFHTISEAANVRYIGTPWTLTAG DENDPRGFWMFDTETERMEFIP NNTTWHRRIHYPFKGKIDYKDFT NLSVRVIVTEVDKNLTKFESELEK VVHSLRVVSKIDNSVESDDSEEV EVQSLQTLMEEYINAIPDITDSDR EALIQYANQLYVEATQ | 339 | Gp47 recombination endonuclease subunit [Enterobacteria phage RB51] | YP_0028540 16.1 | 0.0 (337/339) | recombination endonuclease subunit | Exonuclease SbcD | TIGR0061 9 | 5e-05 |

Fig. 6X

| | | | | | | | |
|---|---|---|---|---|---|---|---|
| 128 | 71273 | 71536 | MTFDEFKNVMMSQHFECEVKDD IGHKEIIEYWFEPLEVEDNCIKKV TVCTDWAVSFNFNILDNDTPKSL RDMAVSCIKDAYCEVFDI | 351 | Hypothetical protein RB32ORF057c [Enterobacteria phage RB32] | YP_802999.1 | 1e-43 (87/87) | | No putative conserved domains have been detected |
| 129 | 71517 | 71723 | VKFSTFDINDEFIANIDYTEEDSR YVGIIIYTSKTAQGVVCMAEFDEY FLDYDDMIEWSKRYIKRNLL | 352 | Hypothetical protein RB32ORF056c [Enterobacteria phage RB32] | YP_802998.1 | 9e-32 (68/68) | | No putative conserved domains have been detected |
| 130 | 71762 | 73402 | MSVGGNPIDIQLDKVQKTLITGR NGGGKSTMLEAITFGLFGKPFRD VKKGQLINSTNKKELLVELWMEY DEKKYYIKRGQKPNVFEITVNGT RLNESASSKDFQAEFEQLIGMSY ASFKQIVVLGTAGYTPFMGLSTP ARRKLVEDLLEVGTLAEMDKLNK ALIRELNSQNQVLDVVKKDSIIQQI KIYNDNVERQKKLTGDNLTRLQN MYDDLAKEARTLKSEIEEANERL VNIVLDEDPTDAFNKIGQEAVLIK SKIDSYNKVINMYHEGGLCPTCL SQLSSGDKVVSKIKDKVSECTHS FEQLSTHRDNLKVLVDEYRDNIK TQQSLANDIRNKKQSLITTVDKA KKVKAAIEKASSEFIDHADEIALL QEELDKIVKTKTNLVMEKYHRGIL TDMLKDSGIKGAIIKKYIPLFNKQI NHYLKIMEADYVFTLDEEFNETIK SRGREDFSYASFSQGEKARIDIA LLFTWRDIAEKVSGVKINTLILDE VFDSATDVEGVKAISTILDSLKNT NVFVISHRDHDPQAYGQHLQMK KVGRFTVMV | 353 | Gp46 recombination endonuclease subunit [Enterobacteria phage RB14] | YP_0028543 90.1 | 0,0 (545/546) | recombination endonuclease subunit | ABC_sbc CD, SbcCD and other Mre11/Rad50 (MR) complexes are implicated in the metabolism of DNA ends | cd03279 | 6e-08 |
| 131 | 73458 | 73646 | MEYSTGQHLLTIPEIKRYILRNNF SNEEHIVTESMILRNAFKAEYTKI MSNRNEAWTVTDYYD | 354 | Gp45.2 conserved hypothetical protein [Enterobacteria phage T4] | NP_049668.1 | 4e-29 (52/62) | | No putative conserved domains have been detected |
| 132 | 73656 | 74045 | MTKITVNYTVDVKDIQPKHVRSE SNPQNQNKIRRAWVLSLSDNAM EVIQNKIKSAPARHAYYEAIDREV SNKWIELMRKHTTESLNAGAKFI MTSCGERLEDEYCGNADERLIV AAQIVAETIAADFNR | 355 | RNA polymerase binding [Enterobacteria phage RB14] | YP_0028543 88.1 | 5e-71 (129/129) | RNA polymerase binding protein | Phage RNA polymerase binding, RpbA | pfam1078 9 | 5e-35 |
| 133 | 47101 | 74787 | MKLSKDTTALLKNFATINSGIMLK SGQFIMTRAVNGTTYAEANISDVI DFDVAIYDLNGFLGILSLVNDDAE ISQSEDGNIKIADARSTIFWPAAD | 356 | Gp45 sliding clamp DNA polymerase [Enterobacteria phage RB32] | YP_802993.1 | 2e-129 (228/228) | sliding clamp DNA polymerase | Gp45 sliding clamp, C terminal | pfam0911 6 | 5e-46 |

Fig. 6Y

| | | | | | | | | |
|---|---|---|---|---|---|---|---|---|
| | | | PSTVVAPNKPIPFPVASVVTEIKA EDLQQLLRVSRGLQIDTIAITVKE GKIVINGFNKVEDSALTRYKYSLT LGDYDGENTFNFIINMANMKMQ PGNYKLLLWAKGKQGAAKFEGE HANYVVALEADSTHDF | | | | | | |
| 134 | 74839 | 357 | MITVNEKEHILEQKYRPSTIDECIL PAFDKETFKSITSKGKIPHIILHSP SPGTGKTTVAKALCHDVNADMM FVNGSDCKIDFVRGPLTNFASAA SFDGRQKVIVIDEFDRSGLAESQ RHLRSFMEAYSSNCSIITANNID GIIKPLQSRCRVITFGQPTDEDKI EMMKQMIRRLTEICKHEGIAIAD MKVVAALVKKNFPDFRKTIGELD SYSSKGYVLDAGILSLVTNDRGAI DDVLESLKNKDVKCLRALAPKYA ADYSWFVGKLAEEIYSRVTPQSII RMYEIVGENNQYHGIAANTELHL AYLFIQLACEMQWK | 319 | NP_049665.1 | 0.0 (319/319) | clamp loader subunit, DNA polymerase accessory protein | The AAA+ (ATPases Associated with a wide variety of cellular Activities) superfamily | cd00009 | 5e-06 |
| | 75798 | | | | | | Rfc, replication factor C small subunit | PRK00440 | 1e-24 |
| 135 | 75800 | 358 | MSLFEDDIQLNEHQVAWYSKDW TAVQSAADSFKEKAENEFFEIIGA INNKTKCSIAQKDYSKFMVENAL SQFPECMPAVYAMNLIGSGLSD EAHFNYLMAAVPRGKRYGKWAK LVEDSTEVLIIKLLAKRYQVNTND AINYKSILTKNGKLPLVLKELKGL VTDDFLKEVTKNYVKEQKQLKKLA LEW | 187 | YP_002854007.1 | 2e-105 (187/187) | clamp-loader subunit | No putative conserved domains have been detected | | |
| 136 | 76365 | 359 | MIEITLKKPEDFLKVKETLTRMGI ANNKDKVLYQSCHILQKKGLYYI VHFKEMLRMDGRQVEMTEEDE VRRDSIAWLLEDWGLIEWPGQR TFMKDLTNNFRVISFKQKHEWKL VPKYTIGN | 122 | NP_049663.1 | 5e-66 (122/122) | RegA translational repressor protein | Translat_r eg, bacteriophage translational regulator | pfam01818 | 6e-46 |
| 137 | 76735 | 360 | MTAITPQEYMASLKEKYNLSATE TLFDLPENLQLKFQVEFQKLVHP EQKHFTAVVKSINADGMIIFTRQI VLI | 73 | YP_002854383.1 | 5e-34 (71/73) | RB32ORF047c hypothetical protein [Enterobacteria phage RB14] | No putative conserved domains have been detected | | |

Fig. 6Z

| | | | | | | | | |
|---|---|---|---|---|---|---|---|---|
| 138 | 77035 | 79731 | 361 | MKEFYISIETVGNNIVERYIDENG KERTREVEYLPTMFRHCKEESK YKDIYGKNCAPQKFPSMKDARD WMKRMEDIGLEALGMNDFKLAYI SDTYGSEIVYDRKFVRVANCDIE VTGDKFPDPMKAEYEIDAITHYD SIDDRFYVFDLLNSMYGSVSKW DAKLAAKLDCEGGDEVPQEILDR VIYMPFDNERDMLMEYINLWEQ KRPAIFTGWNIEGFDVPYIMNRV KMVLGERSMKRFSPIGRVKSKLI QNMYGSKEIYSIDGVSILDYLDLY KKFAFTNLPSFSLESVAQHETKK GKLPYDGPINKLRETNHQRYISY NIIDVESVQADKIRGFIDLVLSMS YYAKMPFSGVMSPIKTWDAIIFN SLKGEHKVIPQQGSHYKQSFPG AFVFEPKPIARRYIMSFDLTSLYP SIIRQVNISPETIRGQFKVHPIHEY IAGTAPKPSEEYSCSPNGWMYD KHQEGIIPKEIAKVFFQRKDWHK KMFAEEMNAEAIKKIIMKGAGSC STKPEVERYVKFSDDFLNELSNY TESVLNSLIEECEKAATLANTNQL NRKILNSLYGALGNIHFRYYDLR NATAITIFGQVGIQWIARKINEYLN KVCGTNGEDFIAAGDTDSVYVC VDKVIEKVGLDRFKEQNDLVEFM NQFGKKKMEPMIDVAYRELCDY MNNREHLMHMDREAISCPPLGS KGVGGFWKAKKRYALNVVDME DKRFAEPHLKIMGMETQQSSTP KAVQEALEESIRRILQEGEESVQ EYYKNFEKEYRQLDYKVIAEVKT ANDIAKYDDKGWPGFKCPFHIR GVLTYRRAVSGLGVAPILDGNKV MVLPLREGNPFGDKCIAWPSGT ELPKEIRSDVLSWIDYSTLFQKSF VKPLAGMCESAGMDYEEKASLD FLFG | 898 | Gp43 DNA polymerase [Enterobacteria phage RB14] | YP_0028543 82.1 | 0,0 (898/898) | DNA polymerase | DNA polymerase family B | pfam0013 6 | 4e-70 |
| 139 | 79913 | 80293 | 362 | MKIAILVIALGLTGCVAQGPVNQ SDVGKIVNCSSKFYNPNVKCYKE APKQTVEQMQANFDEAIRPDES AQAYRNSDVITREEKIENYCAEL WANWANNYQWRTGKNAPMEY VVNSYNSCVKNLTK | 126 | Imm.1 hypothetical protein [Enterobacteria phage RB51] | YP_0028540 02.1 | 3e-68 (126/126) | | | No putative conserved domains have been detected |
| 140 | 80301 | 80552 | 363 | METLVAGSIFMVLVSGVLAIIIYML | 83 | Immunity to | YP_802986.1 | 1e-38 | immunity to | | No putative conserved domains |

Fig. 6AA

| | | | | | | | | |
|---|---|---|---|---|---|---|---|---|
| 141 | 80706 | | PWFIALMRGSKSTVGIFFTSLLFN WSIIGWFITFIWSIAGETKKSAQP NQVIIREKE | | | superinfection membrane protein [Enterobacteria phage RB32] | | (83/83) | superinfection membrane protein | have been detected | |
| | | 81446 | 364 | MISDSMTVEEIRLHLGLALKEKDF VVDKTGVTIEIIGASFVADEPIF GALNDEYIQRELEVYKSKSLFVK DIPGETPKIWQQVASSKGEINSN YGWAIWSEDNYAQYDMCLAELG QNPDSRGIMIYTRPSMQFDYN KDGMSDFMCTNTVQYLIRDKKV NAVVSMRSNDCWAGYRNDYAW QKYVLDKLVSDLNAGDPSRQYK AGSIIWNVGSLHVYENQFYLVDH VWWNTGETHIAKKDYTGKWK | Gp42 dCMP hydroxymethylase [Enterobacteria phage RB51] | YP_0028539 99.1 | 2e-136 (235/246) | dCMP hydroxy- methylase | TS_Pyrim idine_HM ase, Thymidyl ate synthase and pyrimidin e hydroxy- methylas e | cd00351 | 2e-16 |
| 142 | 81437 | 82078 | 365 | MEVNVPHVYKHPKTKKWYIG SHDGHNPNYDGSGVVWQHVKK KYGIKSFNKEILYEGPMFRQVEEI ILTCLDAANCPDSYNLKNEAWG GSFPGKLNGMYGKKLSPEERYK CGNAFRGIKRPDHSKRMKGEGN PMYGKNEQAYGIINRAKENSGKT YEEIFGVEKAKIIKETMSKNRKGK PHNLIEKICPHCGLKGRGPNMTR YHFDKCKALK | Endodeoxyribonucl ease [Enterobacteria phage T4] | CAA93271.1 | 7e-66 (51/147) | endodeoxy- ribonuclease | No putative conserved domains have been detected | | |
| 143 | 82075 | 82917 | 366 | MIQFVIPSYQRYGAVSALDMFPT DYEPHIVVREHEEKAYYDAYGSK AKIVTIPDDVNGIAGTRKAITDMY AGQRIWMIDDDTTIRMSSMRKR DDRRCVDKVNQLTREQFYELIQY VEDAMDCGYYHGHARLPIFKITS SWGNYRENSYGFTNTWYDLGK LTTEQIGYGKIDLCEDMYAFLNLI NQGYPHLALFKYLVVSGKAQAP GGCSSIRSNSKHNRALEQINREF PEQARWKTSNIEKRKSLGEEDE PLKVLRMCVSRKEKSEAFHKFN AIHPIAVD | RB32ORF041c hypothetical protein [Enterobacteria phage RB14] | YP_0028543 77.1 | 5e-167 (278/280) | | No putative conserved domains have been detected | | |
| 144 | 82996 | 84177 | 367 | MSIADLKSRLIKASTSKMTAELTT SKFFNEKDVIRTKIPMLNIAISGAI DGGMQSGLTIFAGPSKHFKSNM SLTMVAAYLNKYPDAVCLFYDSE FGITPAYLRSMGVDPERVIHTPIQ SVEQLKIDMVNQLEAIERGEKVIV FIDSIGNMASKKETEDALNEKSV ADMTRAKSLKSLFRIVTPYFSIKN | RecA-like recombinase protein [Enterobacteria phage RB32] | YP_802982.1 | 0,0 (393/393) | RecA-like recombinase protein | RecA is a bacterial enzyme which has roles in homologo us recombin | cd00983 | 1e-13 |

Fig. 6BB

| | | | | | | | |
|---|---|---|---|---|---|---|---|
| | 84170 | | IPCVAVNHTIETIEMFSKTVMTGG TGVMYSADTVFIIGKRQIKDGSDL QGYQFVLNVEKSRTVKEKSKFFI DVKFDGGIDPYSGLLDMALELGF VVKPKNGWYAREFLDEETGEMI REEKSWRAKDTNCTTFWGPLFK HQPFRDAIKRAYQLGAIDSNEIVE AEVDELINSKVEKFKSPESKSKS AADLETDLEQLSDMEEFNE | | | | ation, DNA repair, and the induction of the SOS response. | |
| 145 | 84508 | 368 | MSKDDLDLEIIDESPSSEGEEER KERLFNESLKIIKSAMENVIQEIVI KLEDGSTHIVYVTKLDWVDGKVV MDFAVLDQERKAELAPHVEKCIT MQLQDAFNKRSKKKFKFF | 112 | Gp40 head vertex assembly chaperone [Enterobacteria phage T4] | NP_049655.1 | 7e-45 (104/107) | head vertex assembly chaperone | No putative conserved domains have been detected |
| 146 | 84518 | 369 | VVEIILSHLIFDQAYFSKVWPYMD SEYFESGPAKNTFKLIKSHVNEY HSVPSINALNVALENSSFTETEY SGVKTLISKLADSPEDHSWLVKE TEKYVQQRAMFNATSKIIEIQTNA ELPPEKRNKKMPDVGAIPDIMRQ ALSISFDSYVGHDWMDDYEARW LSYMNKARKVPFKLKILNKITKGG AETGTLNVLMAGVNVGKSLGLC SLAADYLQLGHNVLYISMEMAEE VCAKRIDANMLDVSLDDIDDGHI SYAEYKGKMEKWREKSTLGRLI VKQYPTGGADANTFRSLLNELKL KKNFVPTIIIVDYLGICKSCRIRVY SENSYTTVKAIAEELRALAVETET VLWTAAQVGKQAWDSSDVNMS DIAESAGLPATADFMLAVIETEEL AAAEQQLIKQIKSRYGDKNKWNK FLMGVQKGNOKWVEIEQDSTPT EVNEVAGSQQIQAEQNRYQRNE STRAQLDALANELKF | 475 | Gp41 DNA primase-helicase subunit [Enterobacteria phage T4] | NP_049654.1 | 0.0 (473/475) | DNA primase-helicase subunit | DnaB, replicative DNA helicase [DNA replication, recombination, and repair] COG0305 6e-13 |
| 147 | 86004 | 370 | MELVKVFVFMGWFKNESMFTKEI TMMKDDVQWATTQYAEVNKALV KAFIDDKKVCEVDCRG | 60 | Dmd discriminator of mRNA degradation [Enterobacteria phage T4] | NP_049653.1 | 7e-27 (60/60) | discriminator of mRNA degradation | No putative conserved domains have been detected |
| 148 | 86188 | 371 | MHIVLFKPTPYNVRKNTQFKALIA DTWELVLDIPAEESPPFGRVEFIK FAVRPTKRQIRQCKRYFRKIVKL EKQLLMLVK | 80 | Gp61.4 hypothetical protein [Enterobacteria phage RB14] | YP_0028543 72.1 | 4e-36 (74/76) | | No putative conserved domains have been detected |
| 149 | 86494 86748 | 372 | MMLVNREYQFKSEEDLEKFASG CELNRRTAKVIGLKPFTVLDCEV | 84 | No significant similarity found. | | | | No putative conserved domains have been detected |

Fig. 6CC

| | | | | | | | | |
|---|---|---|---|---|---|---|---|---|
| | | | SKFRRGCSISGHALVDGNTFFFV FSVRELLLINELEEIK | | No significant similarity found. | | | |
| 150 | 86813 | 86995 | 373 | MSKVSGYQLLTQEQRSEMDSLQ ERCQHRNNALDSFLLVEYENLC SRLEKEVVHQHEGGEE | 60 | No significant similarity found. | | | |
| 151 | 87099 | 87392 | 374 | MKKFIFAAIFALSSCAAQPAMAG YDKQLCEWSMTADQTEVETQIE ADIMNIVERDRPEMKAEVQKQLK SGGVMQYNYVLYCDKNFNNKNII AEVVGE | 97 | Sp spackle periplasmic protein [Enterobacteria phage T4] | NP_049651. 1 | 2e-49 (94/97) | spackle periplasmic protein, lysis regulation | No putative conserved domains have been detected |
| 152 | 87661 | 87762 | 375 | MLSDEINDLLNDAEKVAIPSIDDQ IFNAFMNRG | 33 | RB32ORF033c hypothetical protein [Enterobacteria phage RB51] | YP_0028539 90.1 | 1e-10 (33/33) | | No putative conserved domains have been detected |
| 153 | 87764 | 87928 | 376 | MKTFKEFIKEDMVAGDSGGNPE NISTGTTSGAVVNKGPEQIPKKK KEESKEKEE | 55 | Orf 61.1 [Enterobacteria phage T4] | AAB25712.1 | 2e-21 (54/54) | | Major capsid protein Gp23 | pfam0706 8 | 3e-04 |
| 154 | 87931 | 88959 | 377 | MSSIPWIDNEFAYRALAHLPKFT QVNNSSTFKLRFRCPVCGDSKT DQNKARGWYYGDNNEGNIHCY NCNYHAPIGIYLKEFEPDLYREYI FEIRKEKGKSRPVEKPKELPKQP EKKIKSLPSCIRLDKLAEDHPIIKY VKARCIPKDKWKYLWFTTEWPK LVNSIAPGTYKKEIPEPRLVIPIYN ANGKAESFQGRALKKDAPQKYIT IKAYPEATKIYGVERVKDGDVYV LEGPIDSLFIENGIATTGGQLDLEI VPFKDRRVWVLDNEPRHPDTIK RMTKLVDAGERVMFWDKSPWK SKDVNDMIRKEGATPEQIMEYM KNNIAQGLMAKMRLSKYAKI | 342 | Primase [Enterobacteria phage RB32] | YP_802973.1 | 0,0 (340/342) | primase | Toprim_N ,DNA primase catalytic core, N-terminal domain | pfam0827 5 | 4e-05 |
| 155 | 89156 | 88956 | 378 | MVQKLMALVNAIKGNKKRIAFTIS AMIGILLWNFVLSPVAIAHGVSIP VITLDTFVDLAFALVGLI | 66 | RB32ORF030w hypothetical protein [Enterobacteria phage RB51] | YP_0028539 87.1 | 3e-27 (61/66) | | No putative conserved domains have been detected |
| 156 | 89228 | 89746 | 379 | MAYFNECAHLIEGVDKANRAYAE NIMHNIDPLQVMLDMQRHLQIRL ANDKPETNRHPDSLETAGEVLA WLRNQDDYIADETRELYTSLGG MSNGEKEASAVWKPWKKRYSE MQSKKIQDLSPEDQLEIKFELIDQ FHFFMNKFIALGMSAEEIFKLYYL KNAENFARQDRGY | 172 | dCTPase [Bacteriophage LZ5] | AF374621_1 | 6e-98 (171/172) | dCTP pyro- phosphatase | dUTPase _2 | pfam0876 1 | 2e-18 |

Fig. 6DD

| | | | | | | |
|---|---|---|---|---|---|---|
| 157 | 89746 | 89946 | 380 | MARLNKRQLKKAHKKRIDQLFKNYDKELVCELLSNQLRAVDWVVEEGPDEIFVSEEALKLIIEHSK | Hypothetical protein RB14ORF29 [Enterobacteria phage RB14] | YP_0028543 65.1 | 1e-26 (61/66) | | No putative conserved domains have been detected |
| 158 | 89943 | 90116 | 381 | MKISKEEFIRRQKALINLHEWYAYQLKVDSSNINAVMALYKQIQDEHEFLAQVFIED | No significant similarity found. | | | | |
| 159 | 90156 | 90392 | 382 | MGGFVNIKTFTHPAGEGKEVKGMEVSVPFEIYSNEHRIADSHYQIFPSEKAAYSTVSDAADWKTKNAAMFTPTQIGG | Small outer capsid [Enterobacteria phage RB14] | YP_0028543 64.1 | 6e-38(76/78) | small outer capsid protein | No putative conserved domains have been detected |
| 160 | 90491 | 90697 | 383 | MLNRWIKPNEDLDIIISRHVMKKYELOPWSTEVVVHSFMMYADGSVEFNAEIRYDYGEKQVEFKRGFL | Mrh.2 hypothetical protein [Enterobacteria phage RB14] | YP_0028543 63.1 | 4e-33 (68/68) | | No putative conserved domains have been detected |
| 161 | 90697 | 91038 | 384 | MFIFNWFKSFFTDFFSTTPGEGVVPISNDYLPLTVVEYVYMGDGTVEAVTMTYEEAQEYYKNPWRWSTPITSSNTQNTQSSSDSYDTNVPVHWWTGDSCGSSCDSSCGSTSCD | Hypothetical protein RB32ORF026c [Enterobacteria phage RB32] | YP_802968.1 | 1e-58 (112/113) | | No putative conserved domains have been detected |
| 162 | 91047 | 91532 | 385 | MEAILFEMYISSN.SMSFAKDVPITVAVMIDKGYCDPMYLVENFVSMPVPEDAEIKLKKIGIIETVPNIPFRAIEAFTKSEYINVSAEQYNDKPISFYSYDSVYSWKIDKGNKFIIVSEDALSYFISSWNSLHPNLLKIHEFDDAPTVVLGKTNESSEENV | Mrh [Enterobacteria phage RB32] | YP_802967.1 | 2e-86 (157/161) | affects phosphorylation of host sigma32 | No putative conserved domains have been detected |
| 163 | 91507 | 91710 | 386 | MKVLKKMFEWFSRPNSMYIDDGWVEQANKEMQNESEEWMKSMISVEKEKKLERSALKLMRDIYGDKS | Postulated decoy of host sigma32 [Enterobacteria phage RB32] | YP_802965.1 | 2e-29 (65/67) | postulated decoy of host sigma32 | No putative conserved domains have been detected |
| 164 | 91707 | 91871 | 387 | VNRDMTLEEAKAKANEALDLLLKIGSKMMEENEKYIQENKIPDGPLVGKRKSHD | ModA.4 hypothetical protein [Enterobacteria phage T4] | NP_049639.1 | 1e-21 (51/54) | | No putative conserved domains have been detected |
| 165 | 91864 | 92346 | 388 | MIEVAKHYSIEFMSKEGKSVNTLDKKCSLIIPLAENPDILIKDIKERKYPENVIIIKHTEDILQNTDSPFSSSEALTIKGYKRAHEYGLFDLFEDDKVKLALNLAGQSKSKTFIIEDIKDINAFVKMVWAHFDVGLRWRMSEEERKIIEANRYFGFYR | ModA.3 hypothetical protein [Enterobacteria phage RB51] | YP_0028539 79.1 | 7e-86 (156/160) | | No putative conserved domains have been detected |
| 166 | 92355 | 92537 | 389 | MDLFEMLEDNHSTNIQNDSSDY | ModA.2 | YP_0028539 | 2e-27 | | No putative conserved domains |

Fig. 6EE

| | | | KKEYRIVLQNYGIEAPDALLEELA SYHLDPPPWAPWAK | | | | | |
|---|---|---|---|---|---|---|---|---|
| 167 | 92605 | 93228 | 390 | MIINLADVEQLSIKAESVDFQDM YKKVCEKFTDFEQSVLWQCMEA KKNKALHRQLNKIIKKHLTKSPYQ LYRGISKSTKELIKDLQVGEVFST NRVDSFTTSLHTACGFSVVEYFT EIIFRLKTDKAFNYSDHISDIILSSP NTEFKYTYEDTDGLDSERTDNL MMIVREQEWMIPIGKYKJTSISKE KLHDSFGTFKVYDIEVVE | 207 | hypothetical protein [Enterobacteria phage RB51] Adenylribosylating enzyme [Enterobacteria phage RB14] | 78.1 YP_0028543 56.1 | (60/60) 2e-117 (205/207) | adenyl-ribosylating enzyme | have been detected No putative conserved domains have been detected |
| 168 | 93225 | 93827 | 391 | MKYSAMQLKDFKIKSMDASVRA SIREELLSEGFNLSEIELLIHCITN KPDDHSWLNEIIKSRLVPNDKPL WRGVPVETKQVLNQGIDIITFDK VVSASYDKNVELHFASGLEYNT QVIFEFKAPMVFNFQEYAIKALR CKEYSPSFKFPDSHRYRNMELV SDEQEVMIPAGSVFRIADRYEYK KHSTYTIYTLDFEGFNL | 200 | Adenylribosylating enzyme [Enterobacteria phage RB51] | YP_0028539 76.1 | 3e-112 (194/200) | adenyl-ribosylating enzyme | No putative conserved domains have been detected |
| 169 | 93943 | 94689 | 392 | MKLSKNQIRKITRRLEHTQASAK RRSKDFNLDFNYIKNILDQKVCA YSGEPFDNRIEGEKLSLERFDNN VGYIKGNVIAVKKKYNTFRSDYTL EELIEKRDLFALRIGRSSAKKVHK LNLDEKKWAKIKKTYNQIKAIQKK RENRIEHISQLSKSKQTSDVKLTII ALKARIDGSRIAEGAEVVKLNVLL KGSDWKTVKKLSEAEMQYDMC DKIIQGVERYQNLSFIDKLKLKRG YPLNCSIFKLIRG | 248 | Postulated decoy of host sigma70 or sigmaS [Enterobacteria phage RB32] | YP_802959.1 | 9e-137 (243/248) | postulated decoy of host sigma70 or sigmaS | No putative conserved domains have been detected |
| 170 | 94691 | 95002 | 393 | MFYVYAIVYRDKDGFAVPVPLDE HRPAVFFEREIADKVFTTLKEQY QLALGMGIPRLVETPRKFWFNKI EVKHVKPDVDTQRLYRRILDTGR IVSIPIAGNLR | 103 | Hypothetical protein RB32OROF016c [Enterobacteria phage RB32] | YP_802958.1 | 5e-49 (96/103) | | No putative conserved domains have been detected |
| 171 | 94999 | 96318 | 394 | MTFDDLTEGQKNAFNIVMRAIKE KKHHVTINGPAGTGKTTLTKFIIE ALISTGETGIILAAPTHAAKKILSK LSGKEASTIHSILKINPVTYEENVL FEQKEVPDLAKCRVLICDEVSMY DRKLFKILLSTIPPWCTIIGIGDNK QIRPVDPGENTAYISPFFTHKDF YQCELTEVKRSNAPIIDVATDVR NGKWIYDKVVDGHGVRGFTGDT | 439 | DNA helicase [Enterobacteria phage RB14] | YP_0028543 52.1 | 0.0 (438/439) | DNA helicase | RecD_rel, recD/Tra A family | TIGR0144 8 | 3e-24 |

Fig. 6FF

| | | | | | | | | |
|---|---|---|---|---|---|---|---|---|
| | 96325 | | | ALRDFMVNYFSIVKSLDDLFENR VMAFTNKSVDKLNSIIRKKIFETD KDFIVGEIIVMQEPLIKTYKIDGKP VSEIIFNNGQLVRIIEAEYTSTFVK ARGVPGEYLIRHWDLTVETYGD DEYYREKIKIISSDEELYKFNLFLG KTAETYKNWNKGGKAPWSDFW DAKSQFSKYKALPASTFHKAQG MSVDRAFIYTPCIHYADAELAQQ LLYVGVTRGRYDVFYV | | | | | |
| 172 | 96585 | 395 | MININSKYLNRLIDGIRKKHTNKQD NLDVMVTGAELLHKLYLISDTILAI KRIEKQSYHSNTDTVITLDESVCK LLIKFEEAIRGNIN | 86 | Hypothetical protein RB51ORF017 [Enterobacteria phage RB51] | YP_002853972.1 | 7e-42 (86/86) | | No putative conserved domains have been detected |
| 173 | 96572 | 396 | VEITKDQFYLLQDKVSEIYEIAYS KNRETVKIESSKLMLQLEEIERDL IALEFFCGEVKTVTISDYVLGEISY LYKAIIND | 81 | DexA.2 hypothetical protein [Enterobacteria phage RB14] | YP_002854350.1 | 2e-36 (77/81) | | No putative conserved domains have been detected |
| 174 | 96810 | 397 | MIELSWCQFKSLMTNVKAVIEKN SGPENITREKALKIIYSLEEMQKD IESMAKFIDEPINKVYIQDYTVGQI RDLARKI | 80 | Hypothetical protein RB32ORF013c [Enterobacteria phage RB32] | YP_802955.1 | 5e-39 (80/80) | | No putative conserved domains have been detected |
| 175 | 97052 | 398 | MFDFIIDFETMGSGEKAAVIDLAV IAFDPNPEVVETFDELVSRGIKIK FDLKSQKGHRLFTKSTIEWWKN QSPEARKNIAPSDEDVSTIDGIAK FNDYINAHNIDPWKSQGWCRGM SFDFPILVDLIRDIQRLNGVSENE LDTFKLEPCKFWNQRDIRTRIEA LLLVRDMTTCPLPKGTLDGFVAH DSIHDCAKDILMMKYALRYAMGL EDAPSEEDCDPLSLPTKR | 227 | DexA exonuclease A [Enterobacteria phage T4] | NP_049629.1 | 1e-130 (226/227) | DexA exonuclease A | DEDDh exonucleases, part of the DnaQ-like (or DEDD) exonuclease superfamily | cd06127 0.001 |
| 176 | 97799 | 399 | MKIYRVESSFSILDYEDAITIRRNL CVQITPYRSIIDSWSEEWWLLHVG YDRPNFMHHSDNNKRIPLPHED KLLVKNANIVINTKFKKDYVGVEY HIPGWFIALYHFAFASEYDMMR WFTREEREELASKGFYLAVYEV PDDQVIVGGHQVMFRKSHAELV DFIEMR | 166 | Hypothetical protein RB32ORF011c [Enterobacteria phage RB32] | YP_802953.1 | 4e-93 (163/166) | | | No putative conserved domains have been detected |
| 177 | 98302 | 400 | MKFNYNPEYTPNPAAKLIDFDVV STYCPVKPLEIKEPTMTTAIEIG KTYKLVEPKIKTNALISGHKTLTD VFGEGEFIVEEFAKSEWFDKSYV IHGRRLDNNKIKKNLVYEDEFILF | 181 | MotB.1 hypothetical protein [Enterobacteria phage JS10] | YP_002922358.1 | 8e-94 (168/182) | | | No putative conserved domains have been detected |

Fig. 6GG

| | | | | | | | |
|---|---|---|---|---|---|---|---|
| 178 | 98924 | | QEVEEQDPTDLLCAAVSIRRPFD NPICGWVTDQWIEDGVELLNVV HAGDFSVVPRSAVVAILN | | | | No putative conserved domains have been detected |
| 179 | 99412 | 401 | MIINIGEIARVSDKSRSKAAGKLV EVVSIQLKHGVKDEDSEVKVRIIA KDGMSKPQFGYVRWKFLEPAFL KAVPAKGIETIDTSHVGVDFKWK LGQAIKFIAPCEFKFIKDDGKAVY TRAMCGYITDQWVEDGVKLYNV VFLGTYKVIPESWIKHYSNALYA | 162 | MotB modifier of transcription [Enterobacteria phage T4] | NP_049626.1 | 2e-84 (154/162) | MotB modifier of transcription | No putative conserved domains have been detected |
| 179 | 99587 | 402 | MKRKIVQNCTNDEFEDVLFDPDL VVVQKEHTIKFTHLTSVVYYEKV GDKQPIYGVFREITEDGTTYWKE IY | 71 | Modifier of suppressor T4 tRNAs [Enterobacteria phage RB14] | YP_0028543 44.1 | 5e-34 (71/71) | modifier of suppressor T4 tRNAs | No putative conserved domains have been detected |
| 180 | 99802 | 403 | MAIKFEVNKWYQFKNKQAQENFI KDHTDNGIYARRLGMHPFKILDV DALGRPIKIMSFAGNLVLSSGKDI LDEDFIWLSSNEAEFFNEVENPY QAAEEQEESAPITDQSKFPVMKV TIENDEQAWSLYQMLKAHFKE | 137 | RNA metabolism moderator [Enterobacteria phage RB32] | YP_802949.1 | 7e-61 (112/137) | RNA metabolism moderator | No putative conserved domains have been detected |
| 181 | 100218 | 404 | MPLYDYKCQSKDCAKEYEKIKKI SERDTDVCPDCHRIAIRLVSAPK HVNGGFYDLLKG | 58 | Hypothetical protein RB32ORF006c [Enterobacteria phage RB32] | YP_802948.1 | 2e-26 (58/58) | | No putative conserved domains have been detected |
| 182 | 100397 | 405 | MFKIGKKYRIREGEEKKYLFSAIY RNGSINAVISTSEFIVEDMKGNN VTMISTASGNDGKILHSFQSNVLI YDEEFDFFEEVPEGFAFECTITM KSGDPLSFTVKDEGSRLRIISLLQ AIKFK | 123 | Hypothetical protein RB32ORF005c [Enterobacteria phage RB32] | YP_802947.1 | 2e-58 (114/123) | | No putative conserved domains have been detected |
| 183 | 100774 | 406 | MKYINRSIAALVLAVSLVGCTDAD NATKVLSSSGFTNIEITGYNWFG CSENDFQHTGFRAIGPTGQKVE GTVCSGLFFKDSTIRFK | 86 | Gp39.1 hypothetical protein [Enterobacteria phage RB14] | YP_0028543 40.1 | 2e-43 (85/86) | | No putative conserved domains have been detected |
| 184 | 101104 | 407 | MIKNEIKILSDIEHIKKRSGMYIGS SANEMHERFLFGKWESVQYVPG LVKLIDEHIDNSVDEGIRTKFKFAN KINVTIKNNQVTVEDNGRGIPQA MVKTPTGEEIPGPVAAWTIPKAG GNFGDDKERVTGGMNGVGSSL TNIFSVMFVGETGDGQNNIVVRC SNGMENKSWETIPGKWKGTRVT FIPDFMSFETNELSQVYLDITLDR LQTLAVVYPDIQFTFNGKKVQGN | 605 | Gp60plus39 DNA topoisomerase subunit [Enterobacteria phage RB51] | YP_0028539 58.1 | 0,0 (603/605) | DNA topoisomerase subunit | GyrB, type IIA topoisomerase (DNA gyrase/topo II, topoisomerase IV), B subunit | COG0187 | 8e-81 |

Fig. 6HH

| | | | Sequence | | | | | | |
|---|---|---|---|---|---|---|---|---|---|
| | 102976 | | FKKYARQYDEHAIVQEQENCSIA VGRSPDGFRQLTYNNIHTKNG GHHIDCVMDDICEDLPQIKRKFK IDVTKARVKECLTIVMFVRDMKN MRFDSQTKERLTSPFGEIRSHIQ LDAKKISRAILNNEAILMPIIEAALA RKLAAEKAAETKAAKKASKAKVH KHIKANLCGKDADTTLFLTEGDS AIGYLIDVRNKELHGGYPLRGKV LNSWGMSYADMLKNKELFDICAI TGLVLGEKAENLNYHNIAIMTDA DHDGLGSIYPSLLGFFSNWPELF EQGRIRFVKTPVIIAQVGKKQEW FYTVAEYESAKDALPKHSIRYIKG LGSLEKSEYREMIQNPVYDVVKL PENWKELFEMLMGDNADLRKE WMSQ | | | | | | |
| 185 | 103179 | 408 | MKSYKVNLELFDKAVHREYRIIQ RFFDMGEAEEFKNRFKDIRDKIQ SDTATKDELLEVAEVIKRNMN | 67 | Hypothetical protein RB32ORF002c [Enterobacteria phage RB32] | YP_802944.1 | 1e-30 (67/67) | | TOPRIM_ TopcIIA_li ke: topoisom erase-primase (TOPRIM) nucleotidy l transferas e/hydrola se domain | cd01030 | 8e-24 |
| | | | | | | | | No putative conserved domains have been detected | | |
| 186 | 103190 105367 | 409 | MIITTEKETILGNGSKSKAFSITAS PKVFKILSSDLYTNKIRAVVRELIT NMIDAHALNGNPEKFIIQVPGRL DPRFVCRDFGPGMSDFDIQGDD NSPGLYNSYFSSSKAESNDFIGG FGLGSKSPFSYTDTFSITSYHKG EIRGYVAYMDGDGPQIKPTFVKE MGPDDKTGIEIVVPVEEKDFRNF AYEVSYIMRPFKDLAINGLDREI DYFPDFDDYYGINPERYWPDRG GLYAIYGGIVVPIDGSVIKDRNWLS IRNEVNYIKFPMGSLDIAPSREAL | 725 | Membrane-associated affects host membrane ATPase [Enterobacteria phage RB32] | YP_802943.1 | 0.0 (717/725) | membrane-associated affects host membrane ATPase | HtpG, molecular chaperon e, HSP90 family [posttrans lational modificati on, protein turnover, chaperon | COG0326 | 6e-05 |

Fig. 6II

| | | | | | | | |
|---|---|---|---|---|---|---|---|
| | | | | | | | [es] |
| 187 | 105379 | | SLDDRTRKNIIERVKELSEKAFNE DVKRFKESTSPRHTYRELMKMG YSARDYMISNSVKFTTKNLSYKK MQSMFEPDNKLCNAGVVYEVNL DPRLKRIIKQSHETSAVASSYRLF GINTTKINIVIDNIKNRVNIVRGLA RALDDSEFNNTLNIHHNERLLFIN PEVESQIDLLPDIMAMFESSDEVNI HYLSEIEALVKSYIPKVVKSAPR PKAATAFKFEIKDGRWEKEELFT LTSEADEITGVVAYMHRSDIFSM DGTTSLCHPSMNILIRMANLIGIN EFYVIRPLLQKKVKELGQCQCIFE TLRDLYVDAFDDVDYDKYVGYS SSAKRYIDKIIKYPELDFMMKYFS VDEVSEEYTRLANMVSSLQCGVY FNGGKDTIGHDIWTVTNLFDELS RNASKNSDKMVAEFTKKFRIVSD FIGYRNSLSDDEVSQIAKTMKAL AA | | | | No putative conserved domains have been detected |
| 188 | 106317 | 410 | MYNIKCLTKNEQAEIVKLYSSGN YTQQELADWQGVSVDTIRRVLK NAEEAERSKVTISGDITVKVNSD AVIAPVAKSDIIWNASKKFISITVD GVTYNATPNTHSNFQEILNLLVA DKLEEAAQKINVRRAVEKYISGD VRIEGGSLFYQNIELRSGLVDRIL DSMEKGENFEFYFPFLENLLENP SQKAVSRLFDFLVANDIEITEDGY FYAWKVVRSNYFDCHSNTFDNS PGKVVKMPRTRVNDDDTQTCSR GLHVCSKSYIRHFGSSTSRVVKV KVHPRDVVSIPIDYNDAKMRTCQ YEVVEDVTEQFK | 312 | Protector from prophage-induced early lysis rIIB [Enterobacteria phage T4] | NP_049889.1 | 0.0 (310/312) | rIIB protector from prophage-induced early lysis |
| 188 | 106346 | 411 | MLGYQARVKEEYDQLMLKINALS NFLESTKFLTVSAVEQELLLSQFI SMKSYADCLEKRIAQFK | 64 | Hypothetical protein RB32ORF269c [Enterobacteria phage RB32] | YP_803211.1 | 3e-27 (62/64) | | No putative conserved domains have been detected |
| 189 | 106604 | 412 | MQKTNPGLQRLFQIPSFTLSNSD LTSEMKVKIADTARYSLKQNPNQ DKAEVIERCRIAVYAEFFVADWL RGYVNKGQEDVNDPYTYAWDV LAHPKYCGLRVEVKTHQTDSRW ISVTTGCSGEYPYGSGINLGPILN HQVADCIIIFNTKEIHPGVIQYTPK FIGDREDLRKVVRKSNYNGWYL SI | 185 | Endonuclease IV [Enterobacteria phage RB14] | YP_002854607 | 4e-106 (183/185) | endonuclease IV | No putative conserved domains have been detected |

Fig. 6JJ

| | | | | | | | |
|---|---|---|---|---|---|---|---|
| 190 | 107235 | 107498 | 413 | MKFKFYYAKHHTGEFIAFTSTT DEGDIFTAVFLSKWESDQPYLSS REDLQRLVNGEYNDSWSYLVHD CVKKAIKQKHLEIVEIEL | 87 | Hypothetical protein RB51ORF272 [Enterobacteria phage RB51] | YP_0028542 25.1 | 9e-22 (49/87) | | No putative conserved domains have been detected |
| 191 | 107578 | 107676 | 414 | MKILNSVLIACAWWVAQVSAVVV GIHHYEYF | 32 | Ndd.5 hypothetical predicted outer membrane protein [Enterobacteria phage T4] | NP_049885. 1 | 2e-09 (32/32) | | No putative conserved domains have been detected |
| 192 | 107742 | 107855 | 415 | MKKIVKAIWNVVIILIVLSIFPIVLMI DVLNAYFGFM | 37 | Ndd.4 hypothetical protein [Enterobacteria phage RB14] | YP_0028546 03.1 | 1e-10 (37/37) | | No putative conserved domains have been detected |
| 193 | 107863 | 108060 | 416 | MKRKRSAFTFIEWFFDNIFPALFI FMLIFALGSVVVGIYLMTVVGIDIH QNGLKSVVETIWNGVK | 65 | Ndd.2a hypothetical protein [Enterobacteria phage RB51] | YP_0028542 22.1 | 3e-29 (65/65) | | No putative conserved domains have been detected |
| 194 | 108057 | 108167 | 417 | MMNLLSGWFYILMFYIGANFPY WMGWSTTAFGFYTP | 36 | Hypothetical protein RB32ORF262c [Enterobacteria phage RB32] | YP_803204.1 | 6e-12 (36/36) | | No putative conserved domains have been detected |
| 195 | 108176 | 108391 | 418 | MKIFKDVKVGEIFCLDNGDQLIRI SPLKSTSEKPTVNATLANNSNER FCIENDTETYTVEEFWELSVDCD D | 71 | Ndd.1 hypothetical protein [Enterobacteria phage RB14] | YP_0028546 00.1 | 4e-33 (70/71) | | No putative conserved domains have been detected |
| 196 | 108452 | 108910 | 419 | MKYMTVTDLNNAGATVIGTIKNG EWFLGVPHKDILSKPGFYFLVSK LDGRPFSNPCVSARFYVGNQRS KQGFSAVLSHIRQRRSQLARTIA NNNVPYTVFYLPASKMKPLTTGF GKGQLALAFIRNHHSEYQTLEEM NRMLADNFKFVLQAY | 152 | Disrupts host nucleoid [Enterobacteria phage RB32] | YP_803202.1 | 3e-84 (149/152) | nucleoid disruption protein | No putative conserved domains have been detected |
| 197 | 108998 | 109156 | 420 | MNIAKLLGVISFICWWVACVLTICID VSSVFSQALAQGMCAYLTFVLLS TND | 52 | Acridine resistance protein [Enterobacteria phage RB14] | YP_0028545 97.1 | 3e-20 (51/52) | acridine resistance protein | |
| 198 | 109294 | 110622 | 421 | MQLNNRDLKSIIDNEALAYAMYT VENRAIPNMIDGFKPVQRFVIAR ALDLARGNKDKFHKLASIAGGVA DLGYHHGENSAQDAGALMANT WNNNFPLLDGQGNFGSRTVGK AAASRYIFARVSKNFYNVYKDTE YAPVHQDKEHPPAFYLPIIPTVLL NGVSGIATGYATYILPHSVSSVK | 442 | Gp52 DNA topoisomerase subunit [Enterobacteria phage RB51] | YP_0028542 15.1 | 0.0 (442/442) | DNA topoisomeras e subunit | |

Fig. 6KK

| | | | | | | | |
|---|---|---|---|---|---|---|---|
| 199 | 110619 | 110768 | KAVLQALQGKKVTKPKVEFPEFR GEVVEIDGQYEIRGTYKFTSRTQ MHITEIPYKYDRETYVSKILDPLE DKGFITWDDACGEHGFGFKVKF RKEYSLSDNEEERHAKIMKDFGL IERRSQNITVINEKGKLQVYDNVV DLIKDFVEVRKTYVQKRIDNKIKE TESAFRLAFAKAHFIKKVISGEIVV QGKTRKELTEELSKIDMYSSYVD KLVGMNIFHMTSDEAKKLAEEAK AKKEENEYWKTTDVVTEYTKDL EEIK | | | | | |
| | | 422 | MSPFIGITSAALVSGGILLAGLGV VPAVAGGLLAFGIQRVIMTVITVM Q | 49 | MotA.1 hypothetical predicted periplasmic protein [Enterobacteria phage T4] | NP_049874. 1 | 4e-16 (48/49) | | No putative conserved domains have been detected |
| 200 | 110903 | 11130 | MKFKIENEIVKAKNALTANKLVVD GIEYDICGVREEKPGVLTFFTMIF KFKGDTEFKQFDFAHEDEIEVRN LNIK | 75 | Hypothetical protein EpJS10_0253 [Enterobacteria phage JS10] | YP_0029226 02.1 | 5e-34 (74/75) | | No putative conserved domains have been detected |
| 201 | 111236 | 111871 | MSKVTYIIKASNDVLNEKTAAILITI AKKDFITAAEVREVHPDLGNAVV NSNIGVLIKKGLVEKSGDGLIITG EAQDIISNAATLYAQENAPELLKK RATRKAREITSDMEEDKDLMLKL LDENGFVLKKVETYRSNYLAILEK RTHGIRNFEINNGNMRIFGYKM MEHHIQKFTDIGMSCKIAKNGNV YLDIKRSAENIEAVITVASEL | 211 | Activator middle promoter [Enterobacteria phage RB32] | YP_803196.1 | 7e-117 (210/211) | activator middle promoter | Transcript ion factor MotA, activation domain | pfam0911 4 | 5e-34 |
| 202 | 111882 | 112211 | MNKLEIVNELRRCVEPTQEGWDI WYHGAYLGTIVKIKTGKYMIRES KDAPVGIRNNFMAAISSFTDAAY EIYLADYKEFQESQPVIRSIGVNK AQQKTLWQRIKGWFK | 109 | Arn.4 hypothetical protein [Enterobacteria phage RB14] | YP_0028545 92.1 | 8e-58 (107/109) | | No putative conserved domains have been detected |
| 203 | 112208 | 112669 | MNPFINRLRKMLNVPLSRETPESL VEKFKAHGYKCTEEDILKEVPEIC WQTAYWDENQKYQRRIVCAAN RFKLKDGRTLIIPGARHYSKDMA EVLDVVKPQLVTQQVCDDDQGF IDQYSNYWTREEAMIIATYAGQV RIERGGSEKELYSEDLY | 153 | Arn.3 conserved hypothetical protein [Enterobacteria phage T4] | NP_049871. 1 | 4e-34 (151/153) | | No putative conserved domains have been detected |
| 204 | 112669 | 112965 | MNIKKFQIDGITNQIKALEYANKM MSTNWGIYANEPAFKFCDMEFT KKLVGKDHVCPFSSPVNGMLKP ALRDLYIAMNEEMIKELKRQLKVI | 98 | Arn.2 hypothetical protein [Enterobacteria | YP_0028542 10.1 | 8e-50 (95/98) | | No putative conserved domains have been detected |

Fig. 6LL

| | | | | QFGQGN | | phage RB51] | | | | |
|---|---|---|---|---|---|---|---|---|---|---|
| 205 | 112949 | 428 | | LAREINSKSDYFNSLNDKDKNLIR HFIVEMGYTDTHDLREHIFECGV AKKFSFTCKCLREVIQHYEQFSR KT | | Arn.1 conserved hypothetical protein [Enterobacteria phage RB69] | NP_861950. 1 | 1e-22 (52/72) | | No putative conserved domains have been detected | |
| 206 | 113251 | 429 | | MIIDSQSVVQYTIKIDILEKLYKFL PNLYHSIVNELVEELHLGNNDFLI GTYKDLSKAGYFYIIPAPGKSIDD VLKTIMVVHDYEIEDYFE | | Inhibitor of MrcBC restriction nuclease [Enterobacteria phage RB51] | YP_0028542 08.1 | 8e-44 (90/92) | inhibitor of MrcBC restriction nuclease | No putative conserved domains have been detected | |
| 207 | 113526 | 430 | | MSHNLEKVIEHNVAQERKSFKEF VEKIFEENTTDQFTNQASDDIITK STN | | AsiA.1 hypothetical protein [Enterobacteria phage T4] | NP_049867. 1 | 9e-19 (48/50) | | No putative conserved domains have been detected | |
| 208 | 113691 | 431 | | MNKNIDTVREIITVASILIKFSREDI VENRANFIAFLNEIGVTHEGRKL NQNSFRKIVSELTQEDKKTLIDEF NEGFEGVYRYLEMYTNK | | AsiA anti-sigma 70 protein [Enterobacteria phage T4] | NP_049866. 1 | 5e-44 (90/90) | AsiA anti-sigma 70 protein | AsiA, anti-sigma factor A | pfam0901 0 | 3e-30 |
| 209 | 114620 | 432 | | MAAPRISFSPSDILFGVLDRLFKD NATGKVLASRVAVVILLFMMAIV WYRGDSFFEYYKQSKYETYSEII EKERNARFESVALEQLQIVHISSE ADFSAVYSFRPKNLNYFVDIIAYE GKLPSTISEKSLGGYPVDKTMDE YTVHLNGRHYYSDSKFAFLPTKK PTPEINYMYSCPYFNLDNIYAGTI TMWYWYRNDHISNDRLESICAQAA RILGRAK | | Holin [Enterobacteria phage RB32] | YP_803187.1 | 7e-125 (216/218) | holin | No putative conserved domains have been detected | |
| 210 | 115433 | 433 | | MAVVGVPGWIGSSAANETGQR WMSQAAGQLRLGVPCWMSQFA GRSREIIHTVGANHNFNGQWFR DRCFEAGGAPIVFNIVGDIVSYSK DVPLFFMYGDTPNEVVQLNIHGV TMYGRGNGGSNSPGSAGGHC IQNDIGGRLRINNGGAIAGGGGG GGGGYYSPFSQMRLTFGGGGG RPFGAPGGSIDMQSGATGGTIS APGSGSVNGIYNGGNGGEVGSA GGRCNIRGGQSEYNGGAAGYA VIGSAPTWQNVGAIYGPRV | | Tail fiber protein [Enterobacteria phage KEP10] | BAF95751.1 | 2e-107 (254/260) | tail fiber protein | Phage tail fibre adhesin Gp38 | pfam0526 8 | 2e-76 |
| 211 | 118418 | 434 | | MATLKQIQFKRSKTAGQRPAASV LAEGELAINLKDKTIFTKDDSGSV IELGLKYGGTINGSLEVTENITGT LIGNSSTATKLQTPRKINGISFDG SKDITLTPSDINVNSTTFIKNNGE LPTDANLDTYGPIEEYLGWSKS | | Tail fiber protein [Enterobacteria phage KEP10] | BAF95750.1 | 0,0 (921/982) | tail fiber protein | No putative conserved domains have been detected | |

Fig. 6MM

| 212 | 119077 | | | | | | | | |
|---|---|---|---|---|---|---|---|---|---|
| | 118427 | 435 | TSTNAQPANKFPEENAVGVLEVF VAGQFAGTQRYTVRSGNVYIRS LSAKWNGVDGPWGVWRNVQAS TRPLSQTIDLDSLGELEHCGLWR NSSSAIASFDRHYPEEGSAAQGF LEIFEGGLYTRTQRYTRMGMVY TRCLAAAWDASAPKWEEWKQV GHGTPATFYDGDLNDFKTPGLY NILGTDAVINCPTGEGLPTVIVGL LEVKQRASGGAIFQRFTTAGTGA TTRDRIFERAYTGGAWGAWNEV YTSYSLPITLGMGGIKAQLAELD WQTFDFVPGSMFSVPLNKIKNM PANMDWGTIDGNLVMFSVGPSE HTGTGRTVQVWRGTVSQANYR YFVVRIAGNPGSSRTNTCRRVVLE DGSHTWTAQQNFRGLLNITAAV NLGANQKISLAPGAYIQAPASGS GSNTYANQNTTIAPLYQAIDDSN KNQFAPIVKQKNTVTNITMASGM DIASSEYRIVAQGDLSATGTTATE LATWRFLPSGRFMSQSRVYAGA AFLNTDGNIAGSMVKKYNDATNL DAALNTRLGKGGDTMTGRLTINA PNDSIVLSTTASNSLHIRGDIDGT GNWYIGKGGADNSLAFYSYASQ AAVHITNNGEIALNPQ

| 213 | 120255 | 119140 | 436 | MEKFMAEFGQGYVQTPFLSESN SVRYKISIAGSCPLSTAGPYVKF QDNPVGNQTFSAGLHLRVFDPS TGALVDSKSYAFSASNNTTSAAF VSFMNSLSNNRLVAILTSGKVNF PPEVVSWLRGAGTSVFPSDSVL SRFDVSYAAFYTSSKRAIALEHV KLSNRKSTDDYQTILDVVFDSLE DVGATGFPKRTYESVEQFMSAV GGTNNEIARLPTSAAISKLSDYNL IPGDVLYLKAQLYADADLLDLGTT NISIRFYDASNGYISSTQAEFTGQ AGSWELKEDYVVVPENAVGFTIY AQRTAQAGQGGMRNLSFSEVS RNGGISKPAEFGVNGIRVNYYCE SASPPDIMVLPTQASSKTGKVFG QEFREV | 371 | Tail fiber hinge [Enterobacteria phage RB32] | YP_803183.1 | 0.0 (365/371) | tail fiber hinge | No putative conserved domains have been detected |
| 214 | 124133 | 120264 | 437 | MAEIKRKFRAEDGLDAGGDKIIN VALADRTVGTDGVNVDYLIQENT VQQYDPTRGYLKDFVIIYNNRFW AATDNIPKPAGNFNRIRWKALRT DAVYTTVSSGPYQLKSGEAISVD TSVGNDIEFTLPPSPLDGETVIIQ DIGGKPGINGVKINSSNQSIVNFR GEQVRSVLMTHPKSQMIFIFNNR LWQMYVADYSREAAIVTPSTAY QAQSNDFIVRRFTSAAPINVKLP RFANHGDIINFVDLDKLNPLYHTI VTTYDETTSVQEVGTHSIEGRTSI DGFLMFDDNEKLWRLFDGDSKA RLRIITTNSNIRPNEEVMVFGANN GTTQTIELQLPTDISVGDTVKISM NYMRKGQTVKIKAAGEDKIASSV QLLQFPKRSEYPPEAEWVTVQE LVFNGETNYVPVLQLAYIEDSDG KYMVVQQNVPTVERVDSLNAST RARLGVIALATQAQANADLENSP QKELATPETLANRTATETRRGIA RIATTAQVNQNTTFSFADDLIITP KKLNERTATETRRGVAEIATQQE TNTGTDDTTIITPKKLQARQGSE SLSGIVTFVSTAGATPASSRELN GTNVYNKNTNNLVVSPKALDQY KATPTQQGAVILAVESEVIAGQS QEGWANAVVTPETLHKKTSTDG RIGLIEIATQSEVNTGTDYTRAVT PKTLNDRRATESLSGIAEIATQVE FDAGVDDTRISTPLKIKTRFNSTD | 1289 | Gp34 proximal tail fiber subunit [Enterobacteria phage RB14] | YP_0028545 78.1 | 0.0 (1280/1289 ) | proximal tail fiber subunit | No putative conserved domains have been detected |

Fig. 600

| | | | | | | | |
|---|---|---|---|---|---|---|---|
| | | | RTSVVALSGLVESGTLWDHYTL NILEANETQRGTLRVATQVEAAA GTLDNVLITPKKLLGTKSTESQE GVIKVATQSETVTGTSANTAVSP KNLKWIVQSEPTWAATTLIRGFV KTSSGGLLTFVGNDTVGSTQPLES YEKNGYAVSPYELNRVLANYLPL KAKAVDSNLLDGLDSLQFIRRDIA QTVNGSLTLTQQTNLGAPLVSSS TATFGGSVSANSTLTISNTGTAT RLIFEKGPQTGTNPAQTMTVRV WGNQFSGESDTTRSTVFEVSDE TSSHFYSQRNKAGNITFNINGTV TPINVNASGTLNANGVATFGNSV TATGEIISRSANAFRAINGNYGFI VRNDGSVTNFMLTASGDQTGGF NGLRPLAINNASGQVTIGESLIIAK GATINSGGLTVNSRIRSQGTKTS DLYTRAPTSDTVGFWSIDINDSA TYNQFPGYFKMVEKTNEVTGLP YLERGEEVKSPGTLTQFGNTLDS LYQDWTYPTTPEARTTRWTRT WQKTKNSWSSFVQVFDGGNPP QPSDIGAIPSDNGIIGNLTIRDFLR IGNVRIIPDPVNKTVKFEWVE | | | | |
| 215 | 124238 | | MDLEMMLDEDYKEGICFIDFSQI ALSTALVNFPDKEKINLSMVRHLI LNSIKFNVKKAKTLGYTKIVLCIDN AKSGYWRDFAYYYKKNRGKA REESTWDWEGYFESSHKVIDEL KAYMPYIVMDIDKYEADDHIAVLV KKFSLEGHKILIISSDGDFTQLHK YPNVKQWSPMHKKWVKKSGSA EIDCMTKILKGDKKDNVASVKVR SDFWFTRVEGERTPSMKTSIVEA IANDREQAKVLLTESEYNRYKEN LVLIDFDYIPDNIASNIVNYNSYK LPPRGKIYSYFVKAGLSKLTNSIN EF | 305 | RNaseH [Enterobacteria phage RB32] | YP_803181.1 | 4e-178 (305/305) | ribonuclease H | RNaseH_C, T4 RNase H, C terminal | pfam09293 | 9e-40 |
| 216 | 125164 | 125433 | 439 | MAKKEMVEFDEAIHGEDLAKFIK EASDHKLKISGYNELIKDIRIRAKD ELGVDGKMFNRLLALYHKDNRD VFEAETEEVVELYDTVFSK | 89 | DsbA dsDNA binding protein, late transcription [Enterobacteria phage T4] | NP_049858.1 | 5e-43 (89/89) | dsDNA binding protein | No putative conserved domains have been detected |
| 217 | 125411 | 125749 | 440 | MTQFSLNDIRPVDETGLSEKELSI KKEKDEIAKLLDRQENGFIIEKMV EEFGMSYLEATTAFLEENSIPET | 112 | Gp33 late promoter transcription accessory protein | NP_049857.1 | 4e-57 (112/112) | late promoter transcription accessory | No putative conserved domains have been detected |

Fig. 6PP

| | | | | | | | | | |
|---|---|---|---|---|---|---|---|---|---|
| 218 | 125746 | 126399 | 441 | QFAKFIPSGIIEKIQSEAIDENLLR PSVVRCEKTNTLDFLL | | | | | |
| | | | | MIKLRMPAGGERYIDGKSVYKLY LMIKQHMNGKYDVIKYNWCMRV SDAAYQKRRDKYFFQKLSEKYK LKELALIFISNLVANQDAWIGDISD ADALVFYREYIGRLKQIKFKFEED IRNIYFSKKVEVSAFKEIFEYNP KVQSSYIFKLLQSNIISFETFILLD SFLNIIDKHDEQTDNLVWNNYSIK LKAYRKILNIDSQKAKNVFIETVK SCKY | 217 | [Enterobacteria phage T4] | NP_049856. 1 | 4e-121 (217/217) | loader of Orf146 DNA helicase | T4-helicase_ C, T4 gene 59 helicase, C terminal | pfam0899 4 | 3e-35 |
| | | | | | | | | | T4-helicase_ N, T4 gene 59 helicase, N terminal | pfam0899 3 | 3e-34 |
| 219 | 126500 | 127408 | 442 | MFKRKSTAELAAQMAKLAGNKG GFSSEDKGEWKLKLDNAGNGQ AVIRFLPSKNDEQAPFALLVNHG FKKNGKWYIETCSSTYGDYDSC PVCQYISKNDLYNTDNKEYSLVK RKTSYWANILVVKDPAAPENEGK VFKYRFGKKIWDKINAMIAVDVE MGETPVDVTCPWEGANFVLKVK QVSGFSNYDESKFLNQSAIPNID DESFQKELFEQMVDLSEMTSKD KFKSFEELSTKFSQVMGTAAMG GAAATAAKKADKVADDLDAFNV KFKTKTEDDFMSSSSGSSSSA DDTDLDDLLNDL | 302 | ssDNA binding, DNA repair, recombination and pre-synthesis [Enterobacteria phage RB32] | YP_803177.1 | 4e-172 (296/302) | ssDNA binding, DNA repair, recombination and pre-synthesis | Gp32 DNA binding protein like | pfam0880 4 | 6e-41 |
| 220 | 127553 | 127783 | 443 | MAKVDIDIVDFEYIEEIIRNRYPEL SITSIHDDPNYCNFSIVIEGPLEDL TRFMANEYCDGMDSEDAEFYM GLIEQ | 76 | Frd.3 hypothetical protein [Enterobacteria phage RB51] | YP_0028541 94.1 | 1e-36 (76/76) | | Bacteriop hage FRD3 protein | pfam0579 8 | 3e-33 |
| 221 | 127829 | 128194 | 444 | MYIGKKYELVPRLIDTFINVRPRS NSSIVKIIQENGGWFEVKEAFFV DGFRVIKHECANGKHFYFNVCE DEFHCFREYKEPTSEEDGAEDIV SGVTKIHCIVDENNVDEIIELLRKT FKK | 121 | Frd.2 hypothetical protein [Enterobacteria phage RB14] | YP_0028545 71.1 | 6e-62 (118/121) | | Bacteriop hage FRD2 protein | pfam0319 7 | 2e-36 |
| 222 | 128333 | 128575 | 445 | MRLQRQSIKDSEVRGKWYFNIIG KDSELVEKAEHLLRDMGWEDEC DGCPLYEDGESAGFWIYHSDVD | 80 | Frd.1 conserved hypothetical protein [Enterobacteria | NP_049851. 1 | 3e-39 (79/80) | | No putative conserved domains have been detected | | |

Fig. 6QQ

| | | | QFKADWKVKKSV | | phage T4] | | | | |
|---|---|---|---|---|---|---|---|---|---|
| 223 | 128586 | 128918 | 446 | MSGIHVTGIAQVNIRCQFKTVPG VTHITLSHDPYSRGRQLTGVIKFF GGIGGSEFTIGDDEIVGCKLKVQ KGVLELFSDEVFDEISRAVNKGM LTLIKMIKASGYVTDPF | 110 | Hypothetical protein RB51ORF237 [Enterobacteria phage RB51] | YP_002854190.1 | 2e-34 (78/116) | | No putative conserved domains have been detected |
| 224 | 128930 | 129175 | 447 | MIFVFEFMNDEFDYAIFNALHNP DLSEFNEMFSDALSMSEEYCGE CQRVCVTVFENKEKTYEELFFDA NKATEWFVERGFA | 81 | Hypothetical protein RB32ORF231c [Enterobacteria phage RB32] | YP_803173.1 | 7e-39 (79/80) | | No putative conserved domains have been detected |
| 225 | 129175 | 129756 | 448 | MIKLVFAYSPTKVEGFNELAFG LGDGLPWGRIKKDLQNFKARTE GTILIMGAKTFQSLSTLLPGRSHI VVCDLARDYPVTKDGDLAHFYIT WEQYITYISGGEIQVSSPNAPFE TMLGQNSKVSVIGGPALLYAALP YADEVVSRIVKRHRVNSTVQLD ASFLDDISKREMVETHWYKIDEV TTLTESVYK | 193 | Dihydrofolate reductase [Enterobacteria phage RB14] | YP_002854568.1 | 8e-109 (190/193) | dihydrofolate reductase | DHFR_1, dihydrofolate reductase | pfam00186 | 2e-30 |
| 226 | 129753 | 129959 | 449 | MSNKLKVKDVPNAMALFICRQM HQGPMTPKQYLKGERSLGFTRK AKQMVKLGYKPNFAKYPSTYSW MN | 68 | No significant similarity found. | | | | |
| 227 | 129959 | 130510 | 450 | MKQYQFLIKDILENGYETDDRTG TGTIALFGTKLRWDLTKGFPAVT TKKLAWNACISELLWFLSGSTNV NDLRLIQHNSLIQGKTVWDENYE NQAKDLGYHSGELGPIYGKQWR DFGGVDQIIEVIDRIKKLPNDRRQ IVSAWNPAELKQMALPPCHMFY QFNVRNGYLDLQWYQRSVDVFL G | 183 | Thymidylate synthase [Bacteriophage RB23] | AAP86753.1 | 2e-101 (177/183) | thymidylate synthase | Thymidylate synthase, thyA | PRK01827 | 6e-67 |
| 228 | 130639 | 131376 | 451 | MKSGIYQIKNTLNNKVVVGSAKD FEKRWKRHFKDLEKGCHSSIKL QRSFNKHGNVFECSILEEIPYEK DLIIERENFWIKELNSKINGYNIAD ATFGDTCSTHPLKEEIIKKRSETV KAKMLKLGPDGRKALYSKPGSK NGRWNPETHKFCKCGVRIQTSA YTCSKCRNRSGENNSFFNHKHS DITKSKISEKMKGKKPSNIKKISC DGVIFDCAADAARHFKISSGLVT YRVKSDKWNWFYINA | 245 | I-TevI homing endonuclease [Enterobacteria phage T4] | NP_049849.3 | 3e-141 (245/245) | I-TevI homing endonuclease | Group I intron endonuclease, grpIintron_endo | TIGR01453 | 5e-39 |
| 229 | 131521 | 131835 | 452 | MLPFNIASYATLVHIVAKMCNLIP GDLIFSGGNTHIYMNHVEQCKEI | 104 | Thymidylate synthase | AAP86755.1 | 7e-55 (103/103) | thymidylate synthase | Thymidylate | PRK01827 | 8e-26 |

Fig. 6RR

| | | | | | | | |
|---|---|---|---|---|---|---|---|
| 230 | 131859 | | LRREPKELCELVIGGLPYKFRYL STKEQLEYILKLRPKDFVLKDYQ SHGVLKGKMAV | | | | synthase, thyA |
| | 132122 | 453 | MILRFKDTSGAVLFTLPNPSELEV PGPNQPIIYGKKYYTHKMTREYF DNKISTVKTSSDCYYDITVLTEKQ YDELSPRGPSMPGSE | 87 | [Bacteriophage RB3] | AAP78917.1 | 2e-43 (86/87) | No putative conserved domains have been detected |
| 231 | 132076 | 454 | MTNYHRAGRLCQVVNIKYKSDFD VNIHRGTFWGNYVGKDAGSREA AIELFKKDFIRRIKSGEITKAHLEP LRGMRLGCTCKPKPCHGDIIAHI VNRLFKDDFQVEDLCN | 108 | NrdA.2 [Enterobacteria phage T2] | ABI48941.1 | 5e-57 (106/108) | No putative conserved domains have been detected |
| 232 | 132393 | 455 | MQLINVIKSSGVSQSFDPQKIIKV LSWAAEGTSVDPYELYENIKSYL RDGMTTDDIQTIVIKAAANSISVE EPDYQYVAARCLMFALRKHVYG QYEPRSFIDHISYCVNEGKYDPE LLSKYSAEEITFLESKIKHERDME FTYSGAMQLKEKYLVKDKTTGQI YETPQFAFMTIGMALHQDEPVD RLKHVIRFYEAVSTRQISLPTPIM AGCRTPTRQFSSCVVIEAGDSLK SINKASASIVEYISKRAGIGINVGM IRAEGSKIGMGEVRHTGVIPFWK HFQTAVKSCSCQGGIRGGAATAY YPIWHLEVENLLVLKNNKGVEEN RIRHMDYGVQLNDLMMERFGKN DYTLFSPHEMGGELYYSYFKDQ DRFRELYEAAEKDPNIRKKRIKA RELFELLMTERSGTARIYVQFIDN TNNYTPFIREKAPIRQSNLCCEIAI PTNDVNSPDAEIGLCTLSAFVLD NFDWQDODKINELAEVQVRALD NLLDYQGYPVPEAEKAKKRRNL GVGVTNYAAWLASNFASYEDAN DLTHELFERLQYGLIKASIKLAKE KGPCEYYSDTRWSRGELPIDWY NKKIDQIAAPKYVCDWSSLREDL KLFGIRNSTLSALMPCESSSQVS NSTNGIEPPRGPVSVKESKEGSF NQVVPNIEHNIDLYDYTWKLAKK GNKPYLTQVAIMLKWVCQSASA NTYYDPQIFPKGKVPMSIMIDDLL YFWVFGGKNFYYHNTRDGSGT DDYEIETPKAEDCSSCKL | 754 | Ribonucleotide reductase A subunit [Enterobacteria phage RB51] | YP_0028541 83.1 | 0.0 (753/754) | ribonucleotide reductase A subunit | Ribonucle otide-diphosph ate reductase subunit alpha | PRK09103 | <1.0e-180 |
| 233 | 134709 | | | | | | |
| | 135887 | 456 | MSTVFNTNPVDVLKEPMFFGSG LGIARYDIQRHKVFEDLTEKQLSF | 392 | Ribonucleotide reductase B subunit | YP_0028545 | 0.0 | ribonucleotide reductase B | Ribonucle otide- | PRK09101 | 4e-141 |

Fig. 6SS

| | | | | | | | | | |
|---|---|---|---|---|---|---|---|---|---|
| | | | FWRPEEVNLMMDAAGFNKLPQY QQNIFTNNLKYQSLLDSIQGRAP SAVLMSLISDPSLDTWWATWTFS ETIHSRSYTHIMRNLYTDPSKVF DEIVLDEAIMKRAESIGRYYDDVL IKTRYWENAKADIEYQKEINADE DVIEDAIEHETYWKRELMKSLYL CLHVINALEAIRFYVSFACTFNFH KNMEIMEGNAKIMKFIARDEQLH LKGTQYIRQLQLGTDGDEWVKI AQECEQEAVDIFMEVNRQEKDW AVHLFKDGDVPGLNTNSMWSFI DYLTVSRMKQCGLPCPITDAPVK HPYPWIREYLNSDNVQSAPQEV ELSSYLVAQIDNDVDDKVMMSFK KYF | | [Enterobacteria phage RB14] | 62.1 | (387/392) | subunit | diphosph ate reductase subunit beta | | |
| 234 | 135915 | | | | | | | | |
| | 136325 | 457 | MKEIATEYSFIKYTELELDYNGSI KQLSIPNKYNVIYAIAINDELVYIG KTKNLRKRINYYRTAINRKDKTS DSTKSALIHAALKEGSKVEFYAR QCFNLSMTNELGTMTIATIDLEEP LFIKLFNPPWNIQHKKK | | Endonuclease II [Enterobacteria phage RB51] | YP_0028541 81.1 | 7e-73 (135/136) | endonuclease II | GIY-YIG type nucleases (URI domain) | smart0046 5 | 1e-05 |
| 235 | 136378 | 458 | MQELFNNLMELCKDSQRKFFYS DDVSASGRTYRIFSYNYASYSD WLLPDALECRGIMFEMDGEKPV RIASRPMEKFFNLNENPFTMNID LNDVDYILTKEDGSLVSTYLDGD EILFKSKGSIKSEQALMANGILMN INHHRLRDRLKELAEDGFTANFE FVAPTNIRVLAYOEMKIILLNVRE NETGEYISYDDIYKDAAALRPYLVE RYEIDSPKWVEEAKNAENIEGYV AVMKDGSHFKIKSDWYVSLHST KSSLDNPEKLFKTIIDGASDDLKA MYADDEYSYRKIEAFETTYLKYL DRALFLVLDCHNKHCGKDRKTY AMEAQGVAKGAGMDHLFGIIMS LYQGYDSQEKVMCEIEQNFLKN YKKFIPEGY | | RNA ligase [Enterobacteria phage RB51] | YP_0028541 80.1 | 0.0 (373/374) | RNA ligase | RNA ligase, T4 RnlA family | TIGR0230 8 | <1.0e-180 |
| 236 | 137567 138070 | 459 | MDLQLITTEMVVEAYGDTTDGIS VFKGNRRVGYITDLKKDLAKQVK RKTTIKEYRNRRLEQARDMLPDA VEEMKVFLENGQLAKYDCDVFINQ TQPNVHINSCKCYIIVNPLTGKHR LGISNPNRSASDMAEDVEACFKI SKSPAEHHILINGLSQDDIIEVIKT LCM | | Alc inhibitor of host transcription [Enterobacteria phage T4] | NP_049838. 1 | 3e-93 (164/167) | inhibitor of host transcription | | | |
| | | | | | | | | No putative conserved domains have been detected | | |

Fig. 6TT

| | | | | | | | | |
|---|---|---|---|---|---|---|---|---|
| 237 | 138061 | 138414 | 460 | MHVSNFTAGLLLLVIAFGGTSIILK NKVERLETSVTETFKTANENALAL NNLRIQYNYIDAMNKNREAIAAI ERENEKLRKDAKKADVVAHKPG LVEKQINNSFNKFAEDIQDLSK | 117 | PseT.3 conserved hypothetical predicted membrane protein [Enterobacteria phage T4] | NP_049837. 1 | 2e-59 (116/117) | | No putative conserved domains have been detected |
| 238 | 138411 | 138710 | 461 | MIKLSAVILSIGLLVGCSTKPLEVK KETV-HPNWPVQIKSYDEAKLSW QVKVIDGKAWVGMPFEDSQEFR IWLNDVKRYVHDQKTMICYYRQ ELKEDKCK | 99 | Hypothetical protein RB32ORF219c [Enterobacteria phage RB32] | YP_803161.1 | 1e-51 (99/99) | Outer membran e assembly lipoprotei n YfiO | TIGR0330 2 | 0.002 |
| 239 | 138707 | 138937 | 462 | MISWYQFEHLKGLIYESEMAAMI YGRQIQRLESLPPTNDVLLAQSR ANLKNEYQNKWGKASKDLHDYI QSLVEKNK | 76 | PseT.1 hypothetical protein [Enterobacteria phage RB51] | YP_0028541 76.1 | 2e-37 (76/76) | | No putative conserved domains have been detected |
| 240 | 138934 | 139236 | 463 | MKTLLERYIECSDRYIDVCHDNA SSISEDIEHAKALDDAGKALRKEA KARGFDMYQLKNHMIKFISSNVQ SKSVNQSTAELYKGRREHNIRIL EVFLGIK | 100 | RB32ORF217c hypothetical protein [Enterobacteria phage RB14] | YP_0028545 55.1 | 3e-49 (96/100) | | No putative conserved domains have been detected |
| 241 | 139233 | 140138 | 464 | MMKKIILTIGCPGSGKSTWAREFI AKNPGFYNINRDDYRQSIMAHEE RDEYKYTKNKEGIVTYMQHDVA NMILCQDATKGVIVSDTNLNPER RKVWEEFAKELGHQIEYKVFDVP WTELVKRNSKRGTKAVPIDVLRS MYKSMREYLGLPVYKGTPGKPK AVIFDVDGTLAKMNGRGPYDLEK CDIDINPMVVELSKMYALMGYQI VVVSGRESGTEEDPTKYYRMTR KWVEDIAGVPLVMQCQREQGDT RKDDVVKEEIFWKHIAPHFDVKL AIDDRTQVVEMWRRIGVECWQV ASGDF | 301 | dN 3'phosphatase [Enterobacteria phage RB51] | YP_0028541 74.1 | 1e-170 (290/300) | dN 3'phosphatas e | COG4639 | 8e-12 |
| 242 | 140158 | 140334 | 465 | LGFVIVNSGLVGTSNGQFCVFTS ENRAWEECLKLREKNPDVELVV KKTKLPLPWKTYE | 58 | Cd.5 hypothetical protein [Enterobacteria phage T4] | NP_049833. 1 | 2e-24 (55/57) | | No putative conserved domains have been detected |
| 243 | 140327 | 140527 | 466 | MNNLEKIYRLCDKIEKEKKYLFCL WPIVDGRVGLDVLDYETEDKVD GATFDNALDVIDWLEENYVR | 66 | Hypothetical protein RB51ORF219 [Enterobacteria phage RB51] | YP_0028541 72.1 | 2e-29 (64/66) | | No putative conserved domains have been detected |
| 244 | 140530 | 140805 | 467 | MFPTYSKIVEVVFSQIIANNMFEK LDNAAELRIHAQVTHVLNALLPD | 91 | Hypothetical protein RB32ORF215c | YP_803157.1 | 2e-45 (91/91) | | No putative conserved domains have been detected |

Fig. 6UU

| | | | | | | | |
|---|---|---|---|---|---|---|---|
| 245 | 140868 | 468 | QVDSIAITLYPGSAHIIVVFGLDAE LVIKGDIRFESQTSEFKAI | [Enterobacteria phage RB32] | | | No putative conserved domains have been detected |
| 246 | 141395 | | MSEWFEEDKVYRFKAGYKDIFN ETCGANKRIAQFIGENSFKVKIDP AKNVISIKREIDDCWYKAVDVMG ESYKVSPLFSIAYMLEYSFFEEV QKDDSVSKFEIKTDKEIKWKVVGI TGCMFYIYAQTDTKEEAKKKALE YLEEHEEGPVMITQDAELVSVKL VKNVESKELGSTC | 175 | Hypothetical protein RB32ORF214c [Enterobacteria phage RB32] | YP_803156.1 | 5e-95 (173/175) | No putative conserved domains have been detected |
| 246 | 141389 | 469 | MLSEKPITVKEFQEKVKLFAQEL VNKVSERFPETSVRVITETPRSV LVIVNPGDGDQISHLKLDFDGLV EAQRVYGVL | 78 | Hypothetical protein RB32ORF213c [Enterobacteria phage RB32] | YP_803155.1 | 5e-37 (78/78) | No putative conserved domains have been detected |
| 247 | 141622 | 470 | MMNLTDIIDNCLENDTGDHRALD SETAQFIRITLMNDTLVNSIHPSV YDAIIVTKYPVELHKKMTGAVFID KKNRFKDGQNITSSVIKSITKLRH EIYRVETAKSAYLVIMK | 112 | Cd.1 hypothetical protein [Enterobacteria phage T4] | NP_049829.1 | 2e-58 (111/112) | No putative conserved domains have been detected |
| 248 | 141957 | 471 | MKASTVLQIAYLVSQESKCCSW KVGAVIEKNGRIISTGYNGSPAG GVNCCDYAAEQGWLLNKPKHTII QGHKPECVSFGSTDRFVLAKEH RSAHSEWSSKNEIHAELNAILFA ARNGSSIEGATMVVTLSPCPDCA KAIAQSGIKKLVYCETYDKNKPG WDDILRNAGIEVFNVPKKNLNKL NWENINEFCGE | 193 | dCMP deaminase [Enterobacteria phage RB32] | YP_803153.1 | 3e-110 (193/193) | Deoxycyti dylate_de aminase | dCMP deaminase | cd01286 | 1e-37 |
| 249 | 142538 | 472 | MKFRLVKLTAISSYSNENISFAVE YKKYFFSKWKQYYKTDWTSIDR PYSWKSDLEKCQKLLSTLKERG TTHIKTVIGK | 78 | Gp31.2 hypothetical protein [Enterobacteria phage RB51] | YP_0028541 67.1 | 1e-37 (78/78) | No putative conserved domains have been detected |
| 250 | 142775 | 473 | MKLTTEQKVAIREILKTKLSMGIS NVVFEKSDGTIRIMKCTRDADFM PTMQTGKLTESTRKESTDMIPVF DVELGAWRGFSIDKLISVNGMKV EHLLQFIGK | 102 | Gp31.1 conserved hypothetical protein [Enterobacteria phage T4] | NP_04826.1 | 2e-50 (99/102) | No putative conserved domains have been detected |
| 251 | 143140 | 474 | MSEVQQLPIRAVGEYVILVSEPA QAGDEEVTESGLIIGKRIQGEVP ELCVVHSVGPDVPEGFCEVGDL TSLPVGQIRNVPHPFVALGLKQP KEIKQKFVTCHYKAPCLYK | 111 | Gp31 head assembly cochaperone with GroEL [Enterobacteria phage T4] | NP_049825.1 | 1e-56 (110/111) | head assembly cochaperone | Chaperon in 10 Kd subunit | pfam0016 6 | 8e-06 |
| 252 | 143623 | 475 | MIKQLQHALELQRNAWNNGHEN YGASIDVEAEALEILRYFKHLNPA | 82 | rIII lysis inhibition accessory protein, | NP_049824. | 6e-40 | rIII lysis inhibition | No putative conserved domains |

Fig. 6VV

| | | | | | | | | accessory protein | have been detected | | |
|---|---|---|---|---|---|---|---|---|---|---|---|
| | | | QTALAAELQEKDELKYAKPLASA ARKAVRHFVVTLK | | rapid lysis phenotype [Enterobacteria phage T4] | | (82/82) | | have been detected | | |
| 253 | 144226 | 144444 | 476 | MPISPAFSFKREFIMAKQVAKK AVEKKVGDSKRAGYKRGSNSRI NQTVEKIMRRARAVLRDDASRF GKQKA | 72 | Unnamed protein product [Enterobacteria phage T4] | CAA35653.1 | 2e-32 (71/72) | | No putative conserved domains have been detected | | |
| 254 | 144555 | 144920 | 477 | MNYINFERKYVSNGIAGSIDTICL WKHQNGSVCEIDQYMTPNYVY MRFENGITVSITKEGSNFKIALDD DFRERDLGTHPCWNGVHRKLLI KTWIRHILSNKAKPEHLEAIFDVV LNEFDI | 121 | Protein gp30.7 [Bacteriophage K3] | CAC42995.1 | 2e-64 (116/121) | | Phage_T 4_Gp30_ 7, Phage Gp30.7 protein | pfam0691 9 | 3e-66 |
| 255 | 144949 | 145236 | 478 | MFMTTYFDTRKNFCEVVFSKAP KDLPAHLQPTSESIKNYVNVVCP LEFRTVNGRDTLAITKLNREIDID PSIAREINSSDINGGNVKSHGFQ MRF | 95 | Gp30.6 hypothetical protein [Enterobacteria phage RB14] | YP_0028545 39.1 | 1e-47 (91/95) | | No putative conserved domains have been detected | | |
| 256 | 145236 | 145433 | 479 | MKFFLGQTVELKGVGIPGLISKVL PPFKWSGIQIKEAYIVSWVDGNE DLRMGDELSPIYGLKELV | 65 | Gp30.5 hypothetical protein [Enterobacteria phage T4] | NP_049819. 1 | 5e-29 (65/65) | | No putative conserved domains have been detected | | |
| 257 | 145430 | 145636 | 480 | MNIINKIFGIQYIKVTYKVTDKNPY TDEHEEPQVKSIILEKGSDWPVE FRLPNYGHWADVEIISIENV | 68 | Gp30.4 hypothetical protein [Enterobacteria phage RB51] | YP_0028541 58.1 | 5e-29 (64/68) | | No putative conserved domains have been detected | | |
| 258 | 145629 | 146087 | 481 | MSELEIRSNFKWPSCALSNFAQ WPFVMDGIQFGGLEGFLQGCKV KNVEQORRIFGLSGLAAQOAGR SYARAQDRGTLFWLGVPFSRYS PAWKELYTNAYFEAAIONKGFRD ALHASKGKVLKHSMASGLTKDD TILTEAEFIDVLNLLRDSL | 152 | Gp30.3 protein [Bacteriophage Pol] | CAD30242.1 | 5e-85 (152/152) | | Bacteriop hage protein GP30.3 | pfam0801 0 | 6e-71 |
| 259 | 146084 | 146923 | 482 | MKPTILTDIDGVCLSWQSGLPYF AQKYNLPLEHILKMQDEKFISPG KLFNCDEELGVKLIEKYNRSDFIR YLSPYKDALCVINKLKEDYNFVA VTALGDSIDALLNRGFNLNALFP GAFSEVLMCGHDSSKEELFKKA KEKYNVICYIDDLAHHCDHASEIL NVPVYWMARGERDSIPKTAQRV YTWNDVENKLFSPKENKESFDS EKAIKDVIEKMIKNDSFPWNTTW RTPGFNPYNHLYHPYQTHPFQT | 279 | Hypothetical protein RB32ORF199c [Enterobacteria phage RB32] | YP_803141.1 | 2e-163 (276/279) | | No putative conserved domains have been detected | | |

Fig. 6WW

| | | | | | | | | |
|---|---|---|---|---|---|---|---|---|
| 260 | 146923 | | WNYIKPGGIEYLYNRPTSGDNIFQGAF | | | | | |
| | 147192 | 483 | MFVVHTIYENEGNTTRDYGHVN QFFRCNPEFRAQKDERIFKKCVE QGFIYVKHWMQGNKVRTTYHRS LTELNDELIYNRAVNQTLKDEQ | 89 | Hypothetical protein RB32ORF198c [Enterobacteria phage RB32] | YP_803140.1 | 1e-46 (89/89) | | No putative conserved domains have been detected |
| 261 | 148652 | 484 | MILKILNEIASIGSTKQKQAILEKN KDNELLKRVYRLTYSRGLQYYIK KWPKPGIATQSFGMLTLTDMLDF IEFTLATRKLTGNAAIEELTGYITD GKKDDVEVLRRVMMRDLECGAS VSIANKVWPGLIPEQPQMLASSY DEKGINKNIKFPAFAQLKADGAR CFAEVRGDELDDVRLLSRAGNE YLGLDLLKEELIKMTTEARQIHPE GVLIDGELVYHEQVEKEPEGLDF LFDAYPEISKAKEFAEVAESRTA SNGIANKSLKGTISEKEAQCMKF QVWDYVPLVEIYGLPAFRLKYDV RFSKLEQMTSGYDKVILIENQVV NNLDEAKVIYKKYIDQGLEGIILKN TDGLWENARSKNLYKFKEVIDVD LKIVGIYPHRKDPTKAGGFILESE CGKIKVNAGSGLKDKASVKSHEL DRTRIMENQNYYIGKILECECNG WLKSDGRTDYVKLFLPIAIRLRED KTKANTFEDVFGDFHEVTGL | 487 | Gp30 DNA ligase [Enterobacteria phage RB51] | YP_002854154.1 | 0.0 (482/487) | DNA ligase | DNA_liga se_A_M, ATP dependen t DNA ligase domain | pfam0106 8 | 3e-26 |
| 262 | 148837 | 485 | MKAYLETIVVAQKEGGDVSTSVS QVILEFVDAYAYNKFTETFDAYE KGPKFEIYRTLLPLDY | 62 | Alt.1 conserved hypothetical protein [Enterobacteria phage T4] | NP_049812.1 | 1e-26 (57/62) | | No putative conserved domains have been detected |
| 263 | 148890 | 486 | MELITELFDEDTTLPITNLNPKKKI PQIFSVHVDDAIEQPGFRLCTYT SGGDTNRDLKMGDKMMHIVPFT LTAKGSIAKLKGLGPSPINYINSV FTVAMQTMRCYKIDACMLRLKS KTAGQARQIQVIADRLRSRSGG RYVLLKELWDYDKKYAYILIHRKN VSLEDIPGVPEISTELFTKVESKV GDVYINKDTGAQVTKNEAIAASIA QENDKRSDQAVIVKVKISRRAIA QSQSLESSRFESELFQKYESTAA NFNKPATAPLIPEAEEMKIGINSL ASKTKAAKIIAEGTADELHYDYKF FPMSQVGEVSEKIKEVIFNAIKNE PTTSIKCLEKYAAAANQLFEEYK DNWLDKHNKTRKGQPDEVWEE | 697 | Adenosyl ribosyl-transferase packaged protein [Enterobacteria phage RB14] | YP_002854531.1 | 0.0 (682/697) | adenosylribos yl-transferase packaged protein | VIP2; A family of actin-ADP-ribosylatin g toxin | cd00233 | 1e-36 |

Fig. 6XX

| 264 | 150987 | 487 | MTKNSWNAAKTKFLKRMIYSFS GIGAGPMIDITIARDGSKYTPSQK RGIREYCGSGYTDINNLLGRYD PERYEVMSEKEIEAATNLDSAFE NGDRIPEGITVYRAQSMTAPIYE ALVKNKVFYFRNFVSTSLTPIIFG RFGITHAGIGLLEPEARNELTVDK NEEGITINPNEIRAYKENPEYVKV QIGWAIDGAHKVNVVYPGSLGIA TEAEVILPRG

| | | | | | | | |
|---|---|---|---|---|---|---|---|
| 265 | 153105 | 153395 | 488 | MKSSLRFLGQELVVEGVIPADNA FNEAVYNEFIKFGTDKKFGIFPS ENFSKPEQTESIFQGVTGKFES EAPVKIEVYIEDSLVASVAAFISFR K | 96 | [Enterobacteria phage T4] | NP_049808 | 3e-46 (95/96) | | No putative conserved domains have been detected |
| 266 | 154389 | 153424 | 489 | MYSLEEFNNQAINADFQRNNMF SCVFATTPSTKSSLISSISNFSY NNLGLNSDWLGLTQGDINQGITT LITAGTQKLIRKSGVSKYLIGAMS QRTVQSLLGSFTVGTYLIDFFNM AYNSSGLMIYSVKMPENRLSYET DWNYNSPNIRITGRELDPLVISFR MDSEACNYRAMQDWVNSVQDP VTGLRALPQDVEADIQVNLHSRN GLPHTAVMFTGCIPISVSAPELSY DGDNQITTFDVTFAYRVMQAGA VDRQAALEWLESAAINGIQSVLG NSGGVTGLSNSLSRLSRLGGTA GSISNINTMTGIVNSQSKILGAI | 321 | Base plate-tail tube initiator [Enterobacteria phage RB32] | YP_803134.1 | 0.0 (320/321) | base plate-tail tube initiator | |
| 267 | 155483 | 154389 | 490 | MAIVKEITADLIKKSGEKISAGQS TKSEVATKTYTAQFPTGRASGN DTTGDFQVTDLYKNGLLFTAYN MSSRDSGSLRTMRSNYSSSSSS ILRTARNTISNTVSKLSNGLISDN NSGTISKVPVANILLPRSKSDVDT SSHRFNDVQDSLITKGGGTATG VLSNMASTAVFGALESITQGIMA DNNEQIYTTARSMYGGAENRTK VFTWDLTPRSTEDLMAINIYQYF NYFSYGETGKSQYAAEIKGYLDE WYRSTFIEPLTPEDAVKNKTLFE KMTSSLTNVLVVSNPTIWMVKNF GATSKFDGKTEIFGPCQIQSIRFD KTPNGNFNGLAIAPNLPSTFTLEI TMREITLNRASLYAGTF | 364 | Gp48 base plate [Enterobacteria phage RB51] | YP_0028541 48.1 | 0.0 (358/364) | base plate | |
| 268 | 157264 | 155492 | 491 | MKKPQEMQTMRRKVISDNKPTQ EAAKSASNTLSGLNDISTKLDDA QAASELIAQTVEEKSNEIIGAIDN VESAVSDTTAGSELIAETVEIGNN INKEIGESLGSKLDKLTSLLEQKI QTAGIQQTGTSLATVESAIPVKV VEDDTAESVGPLLPAPEAVNND PDADFFPTPQPVEPKQESPEEK QKKEAFNLKLSQALDKLTKTVDF GFKKSISISDKISSMLFKYTVSAAI | 590 | Gp29 baseplate hub subunit, tail length determinator [Enterobacteria phage T4] | NP_049805. 1 | 0.0 (567/590) | baseplate hub subunit, tail length determinator | |

Fig. 6ZZ

| | | | | | | | | |
|---|---|---|---|---|---|---|---|---|
| | | | EAAKMTAMILAVVVGIDLLMVHF KYWSDKFSQAWDLFSTNFTKFS SETGTWGPLLQSIFGSIDKIKKLW EAGDWGGLTVAIVEGLGKVLFNL GELIQLGMAKLSAAILRVIPGMKD TADEVEGRALENFQNTTNASLSK EDQEKVANYQYKRMNDDLGPIA KGLDKIANWKTRASNWIRGVDN KEALTTDEERAEEEEKLKQLSPE EAKIALMKANEARAAMNRFDEYA NSADMSKDSTVKSVEAAYEDLK KRMDDPDLNNSPAVKKELAARF SKIDATYQELKKNQPNAKPQTSA KSPEAKQVQVIEKNKAQQAPIQQ ASPSINMTNNVIKKNTVVHNMTP VTSTTAPGVFDATGVN | | | | | |
| 269 | 157794 | 157261 | 492 | MNLKLILPLKKVVLPISNKEVSIPK MGLKHYNILKDVKGPDENLKLLID SICPNLSPAEVDFVSIHLLEFNGK IKSRKEIDGYTYDINDVYVCQRLE FQYQGNTFYFRPPGKFEQFLTV SDMLSKCLLKVNDEVKEINFLEM PAFVLKWANDIFTTLAIPGPNGPI TGIGNIIGLFE | 177 | Base plate distal hub subunit [Enterobacteria phage RB32] | YP_803131.1 | 9e-97 (176/177) | base plate distal hub subunit | No putative conserved domains have been detected |
| 270 | 158914 | 157742 | 493 | MSMLQRPGYPNLSVKLFESYDA WSNNRFVELAATITTLTMRDSLY GRNEGMLQFYDSKNIHTKMDGN EIIIQISVANANDINNVKTRIYGCKH FSVSVDSKGDNIIAIELGTIHSIEN LKFGRPFFPDAGESIKEMLGVIY QDRTLLTPAINAINAYYPDIPWTS TFENYLSYVREVALAVGSDKFVF VWQDIMGVNNMDYDMMINQEP YPMIVGEPTLIGQFVQELKYPLAY DFVWLTKSNPHKRDPMKNATIY AHSFLDSSLPMITTGKGENSIWVS RSGAYSEMTYRNGYEEAIRLQT MAQYDGYAKCSTVGNFNLTPGV KIIFNDSKNQFKTEFYVDEVIHEL SNNNSVTHLYMFTNATKLETIDP VKVKNEFKTDTTTEESSSSDK | 390 | Gp27 base plate hub subunit [Enterobacteria phage RB51] | YP_002854145.1 | 0.0 (390/390) | base plate hub subunit | Phage-tail_1, Baseplate structural protein, domain 1 | pfam09097 | 2e-98 |
| | | | | | | | | | | Phage-tail_2, Baseplate structural protein, domain 2 | pfam09096 | 9e-86 |

Fig. 6AAA

| | | | | | | | |
|---|---|---|---|---|---|---|---|
| 271 | 159663 | 494 | MANIIRCKLPDGVHRFKPFTVED YRDFLLVRNDIEHRSPQEEKEIIT DLIDDYFGDYPKTWQPFIFLQVF VGSIGKTKVPVTFVCPKCKKEKT VPFEIYQKELKEPVFDVANVKIKL KFPSEFYENKAKMITENHSVQV DEIWYDWKEISESSQIELVDAIEI ETLEKILDAMNPINLTLHMSCCDK YIKKYTDIVDVFKLLVNPDEIFTFY QINHTLVKSNYSLNSIMKMIPAER GFVLKLIEKDKHQ | 250 | Gp51 base plate hub assembly catalyst [Enterobacteria phage RB14] | YP_0028545 23.1 | 3e-141 (247/249) | base plate hub assembly catalyst | No putative conserved domains have been detected |
| 272 | 159714 | 495 | MYEYKFDVRVGSKIINCRAFTLK EYLELITAKNNGSVEVIVKKLIKD CTNAKDLNRQESELLLIHLWAHS LGEVNHENSWKCTCGTEIPTHIN LLHTQIDAPEDLWYTLGDIKIKFR YPKIFDDKNIAHMIVSCIETIHANG ESIPVEDLNEKELEDLYSIITESDI VAIKDMLLKPTVLAVPIKCPECG KTHAHVIRGLKEFFELL | 208 | Gp26 baseplate hub subunit [Enterobacteria phage T4] | NP_049801.1 | 7e-118 (208/208) | baseplate hub subunit | No putative conserved domains have been detected |
| 273 | 160340 | 496 | MANIINKLYSDIDPEMKMDWNKD VSRSLGLRSIKNSLLGIITTRKGS RPFDPEFGCDLSDQLFENMTPL TADTVERNIESAVRNYEPRIDKLA VNVIPVYDDYTLIVEIRFSVIDNPD DIEQIKLQLASSNRV | 132 | Gp25 baseplate wedge subunit [Enterobacteria phage T4] | NP_049800.1 | 2e-70 (132/132) | baseplate wedge subunit | Baseplate wedge subunit gp25 / PHA00415 / 3e-54 |
| 274 | 160805 | 497 | MRLEDLQEELKKDVFIDSTKLQY EAANNVMLYSKWLNKHSSIKKE MLRIEAQKKVALKAKLDYYSGRG DGDEFSMDRYEKSEMKTVLSAD KDVLKVDTSLQYWGILLDFCSGA LDAIKSRGFAIKHIQDMRAFEAGK | 137 | UvsY [Enterobacteria phage RB51] | YP_0028541 41.1 | 3e-73 (137/137) | recombination, repair and ssDNA binding protein | No putative conserved domains have been detected |
| 275 | 161218 | 498 | MRYNIDDAFNYEEEFETEIQFLM KKHNLKRQDIRILADHPCGEDVL YIKGKFAGYLDEYFYSKDMGIDM HMRVV | 74 | UvsY.-1 conserved hypothetical protein [Enterobacteria phage T4] | NP_049798.1 | 1e-35 (73/74) | | No putative conserved domains have been detected |
| 276 | 161471 | 499 | MSDKICVVCKTPIDSALVVETDK GPVHPGPCVNYIKELPVSESSEE QLNETQLLL | 55 | UvsY.-2 conserved hypothetical protein [Enterobacteria phage T4] | NP_049797.1 | 1e-23 (55/55) | | No putative conserved domains have been detected |
| 277 | 161924 | 500 | MILEFKQFLYEASIDEFMGKIASC QTLEGLEELEAYYKRVKETELK DTDDISVRDALAGKRAELEDSDD EVEESF | 76 | UvsW RNA-DNA and DNA-DNA helicase, ATPase [Enterobacteria phage T4] | NP_049796.1 | 2e-35 (76/76) | RNA-DNA and DNA-DNA helicase, ATPase | No putative conserved domains have been detected |

Fig. 6BBB

| | | | | | | | | | |
|---|---|---|---|---|---|---|---|---|---|
| 278 | 163461 | 161950 | 501 | MTDIKVHFYDFSHVRIDCEESTF HELRDFFSFEADGYRFNPKYKY GHWDGRIRLLDYNRLLPFGLVG QIKKFCDNFGYKAWIDPQINEKE ELSRKDFDEWLSKLEIYSGNKRI EPHWYQKDAVFEGLVNRRRILN LPTSAGKSLIQALLARYYLENYE GKILIVPTTALTTQMADDFVDYR LFSHAMIKKIGGGASKDDKYKND APVVVGTWQTVVKQPKEWFSQ FGMMMNDECHLATGKSISSIISG LNNCMFKFGLSGGSLRDGKANIM QYYGMFGEIFKPVTTSKLMEDG QVTELKINSIFLRYPDEFTTKLKG KTYQEEIKIITGLSKRNKWIAKLAI KLAQKDENAFVMFKHVSHGKAIF DLIKNEYDKVYVSGEVDTETRN IMKTLAENGKGIIIVASYGVFSTGI SVKNLHHVVLAHGVKSKIIVLQTI GRVLRKHGSKTIATVWDLIDDCG VKPKSANTKKKYKVVHLNYLLKHGI DRIQRYADEKFNYVMKTVNL | RNA-DNA and DNA-DNA helicase [Enterobacteria phage RB51] | YP_0028541 37.1 | 0,0 (503/503) | RNA-DNA and DNA-DNA helicase | SSL2, DNA or RNA helicases of superfami ly II | COG1061 | 8e-27 |
| 279 | 163512 | 164192 | 502 | MIDKDYIAELKALDDNKEAKAKLA EYAEQFGIKVKKNKSFDNIVNDIE EALQKLASEPMPETDGLSIKDLID AADAAEGLKYDDEEVNPEAALLI DSPVKSDIKIEVVETDKIPENTDV LIEDTPFVEEKFEQAVAEIIESEKP SVFTLPENFSPNLQLIGKNPGFC TVPWWIYQWIAETPDWKSHPTS FEHASAHQTLFSLIYYINRDGSVL IRETRNSSFVTLK | Minor capsid protein inhibitor of 21 protease [Enterobacteria phage RB14] | YP_0028545 14.1 | 4e-125 (224/226) | minor capsid protein | | TIGR0043 7 | 2e-04 |
| 280 | 164202 | 165620 | 503 | MTFTVDITPKTPTGVIDETKQFTA TPSGETGGGTITYAWTVDDAPQ EETSATFSYVLKGPAGGKTIKVV ATNQVAESEPETAEISTTITVQNK TQTTTLAVTPGSPDAGVIGTPIEF TAALASOPSGANATYQWYVDGS PVGEATSTTFNYTPDASGVKTIK CVAQVTATDYDTKEVTSNEVSLT VNKKTQTTTLAVTPDSPPAGVIG TPVQFTAALASQPDGASATYQW YVDDSQVGGETNSTFSYTPTTS GVKRIKCVAQVTAENYNEKEVTS NEVSLTVNKKTMNPQVTLTPPSI NVQQDASATFTANVTGAPEEAQI TYSWKKDSSPVEGSTNVTVDT | Outer capsid protein Hoc [Bacteriophage RB30] | AAM52483.1 | 0,0 (428/472) | outer capsid protein Hoc | PKD domain | pfam0080 1 | 0,001 |

Fig. 6CCC

| | | | | | | | | |
|---|---|---|---|---|---|---|---|---|
| 281 | 165722 | 165925 | 504 | SSVGSQTIEVTAVVTATDYDSKTI TAEGQVTDKVAPEPEGELPY VHPLPHRTSAYIWCGWWVMDEI QKMTEEGKDWKTDDPDSKYYLH RYTLQKMMKDYPEVDVQESRN GYIIHKTALETGIIYTYP MRTEVVVFTLHESGKSFIEIAREL NLQAKEVAVLWARAMTAKNKFE TREKVVYRKRHINKKVKNGTV | 67 | Hypothetical protein RB32ORF177c [Enterobacteria phage RB32] | YP_803119.1 | 4e-30 (67/67) | | No putative conserved domains have been detected |
| 282 | 165912 | 166190 | 505 | MEQYDLYENESFANQLREKALK SKQFKLECFIKDFSELANKAAEQ GKTHFSYYCIARDKLITEEIGDWL RKEGFSFKVNSDQRDGDWLEIT F | 92 | Gp24.2 conserved hypothetical protein [Enterobacteria phage T4] | NP_049791.1 | 3e-46 (91/92) | | No putative conserved domains have been detected |
| 283 | 166200 | 167204 | 506 | MFKKYSSLENHYNSKFIEKLYSL GLTGGEWVAREKIHGTNFSLIIER DKVTCAKRTGPILPAEDFFGYEII LKNYEDSIKAVQDIMETSAVVSY QVFGEFAGPGIQKNVDYGDKDF YVFDIIVTTESGDVTYVDDYMME SFCNTFKFKIMAPLLGRGKFEELI KLPNDLDSVYQDYNFTVDHAGL VDANKCVWKAEAKGEVFTAEGY VLKPCYPSWLHNGNRVAIKCKN SKFSEKKKSDKPIKAKVELSEAD NKLVGILACYVTLNRVNNVISKIG EIGPKDFGKVMGLTVQDILEETS REGITLTQADNPSLVKKELVKMV QDVLRPAWIELVS | 334 | RnlB RNA ligase 2 [Enterobacteria phage T4] | NP_049790.1 | 0.0 (329/334) | RnlB RNA ligase 2 | RNA ligase | pfam09414 | 4e-132 |

Fig. 6DDD

Table 7 - Features of phage F510/08 gene products and assignment of putative functions.

| ORFs | Start position | Stop position | SEQ ID NO.: | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| 1 | 1 | 124 | 507 | LLNEAVASKVLNSRLG WSAVGEYVELFNRTQ SRVAGLIPE | 40 | Hypothetical protein PPLUZ19_gp49 [Pseudomonas phage LUZ19] | YP_001671995.1 | 1e-14 (40/40) | | No putative conserved domains have been detected | | |
| 2 | 641 | 432 | 508 | MLSRQDRGERAWHQ QDAAWQRQIATWAAQ DHRHYAAPWRKRQAS QEYAVALTKHREALER SRHYGQPKG | 69 | No significant similarity found. | | | | No putative conserved domains have been detected | | |
| 3 | 1175 | 1528 | 509 | VGSRSVEFALSSRNNA STGSLETGLTHCQGIG RVRSQNDGRLQPSKR GTSHRRKGHGKLLGQ EPQCVRPAGITEGIDTV QDTRYSSHHLMATQQ KGLCQRTGRTNPRQRI DKTSASL | 117 | Hypothetical protein PT2_gp01 [Pseudomonas phage PT2] | YP_002117780.1 | 4e-31 (68/73) | | No putative conserved domains have been detected | | |
| 4 | 2012 | 2296 | 510 | MAHFKAKAPKSPFAAQ VAYWRDWEAKRTKLIA QDNVEGRKELRKMRD VRYATDPEPAPGRYHN PEQKAFVKGSEGKAR NILKGWNAKKSQGKGL | 94 | Hypothetical protein PPLUZ19_gp1 [Pseudomonas phage LUZ19] | YP_001671943.1 | 5e-48 (94/94) | | No putative conserved domains have been detected | | |
| 5 | 2296 | 2523 | 511 | MPRVNELTPRQRKAAK ARRDKARRIDLAHRMP KGADCPIFRKAEQAQA KQPRVDTLTTPRSAGY LAAAAYLNKSI | 75 | Hypothetical protein PPLUZ19_gp2 [Pseudomonas phage LUZ19] | YP_601671944.1 | 3e-35 (75/75) | | No putative conserved domains have been detected | | |
| 6 | 2534 | 3073 | 512 | MTNAISKTVIAFRGTEEI NRAIDAIRVRGKELDEA IQLTGLSIIHHIDQCGDV TVVKALYEAMPKGSRR NALVEWLVLHGKVQVN TDKKSNKDLPFLYNKF GKTDLVGATNSPWYSF KPEKALDQEFNLAAAL ATIKKQVLQAQTKGKVI VGMELLGDLEALAAKA APIAEQSKRAAAH | 179 | Hypothetical protein PT2_gp04 [Pseudomonas phage PT2] | YP_002117783.1 | 3e-100 (179/179) | | Hypothetical protein | PHA017 82 | 3e-72 |

Fig. 8A

| | | | | | | | |
|---|---|---|---|---|---|---|---|
| 7 | 3441 | 3809 | 513 | MQALNTLLIAIPKDPTA GMHAADKVLCAHGFR MGDLNTAHVLTPGGFV VVGAGVTVNRYDEAY RMSRNLDSEGFDVLLV QGSPLSGRVTCQAYG WINAEYHKGCANGRPI FDIAGTSYHVIA | Hypothetical protein PPLUZ19_gp4 [Pseudomonas phage LUZ19] | YP_0016 71946.1 | 2e-65 (120/122) | No putative conserved domains have been detected |
| 8 | 3796 | 4020 | 514 | MSSRDPYRIGHRVGLV NYSDRYLGADAAGTK GIIEAITRPSRCMTVYH VRCERTLRLIEAEARNV RFIRQRAER | Hypothetical protein PPLUZ19_gp5 [Pseudomonas phage LUZ19] | YP_0016 71947 | 2e-34 (72/74) | No putative conserved domains have been detected |
| 9 | 4199 | 4459 | 515 | MTLVATVVDSAHNLEV DDLTAGNLYAASSPSG NMFIVVVGNHNGRRLP VVLSSTDTRTIGDVISN TGFRYSEIAGFSVNLA QGDYD | Hypothetical protein PPLUZ19_gp6 [Pseudomonas phage LUZ19] | YP_0016 71948.1 | 9e-42 (86/86) | No putative conserved domains have been detected |
| 10 | 4459 | 4749 | 516 | MVTRTVVVTPEDPTPPI LSVGRLAPGELYKVVA PSSAEGIVLATKQTPA LAQAAVVLHSMNPAQY PAGSAILNTAWKCRRL GVGEYVKLVQGEED | Hypothetical protein PPLUZ19_gp7 [Pseudomonas phage LUZ19] | YP_0016 71949.1 | 3e-48 (96/96) | No putative conserved domains have been detected |
| 11 | 4749 | 4988 | 517 | MAVAILILAVWLIGGALL FLPFDLVVSPRLPLSDE ALNRTALYTVLWPVTL PTLIAITVVMLHSAYR GAIELYQEMKS | Hypothetical protein PPLUZ19_gp8 [Pseudomonas phage LUZ19] | YP_0016 71950.1 | 1e-27 (66/69) | No putative conserved domains have been detected |
| 12 | 4985 | 5278 | 518 | MIRTHTHNVERTPHRL YRHTELASGELYRVVQ PDSKRGTLVVGVAAW DSOGRPAVLPVVIHDD GDAKVTCARPTVLRND GWRMVLADKGTQVTL TAE | Hypothetical protein phiKMvp09 [Pseudomonas phage phiKMV] | NP_8774 48.1 | 9e-39 (80/97) | No putative conserved domains have been detected |
| 13 | 5357 | 5773 | 519 | MTNVNTTTETTTAAVL GAKLIKKPATVEDFRN NVVFHHSALTKLTEVY NEAVAALQTAERLSSL VAGDVITFDHGKGEKA EVLSGEVISVVAGVYQ VLVRFSDSAPAKLLDV KASAIRAVQSSAAQAA TLDEAIAQGE | Hypothetical protein PPphiKF77_gp11 [Pseudomonas phage phiKF77] | YP_0027 27830.1 | 1e-58 (114/123) | No putative conserved domains have been detected |

Fig. 8B

| | | | | | | | | |
|---|---|---|---|---|---|---|---|---|
| 14 | 5842 | 6201 | 520 | MSKRNPEHINGTVRSV SVQKLAATQELEDRLE AALAVCQQRAEDIDLL SRRLQAAERARRWEID EIRNHQATIRLLQNDLN AAHDAHEAQERRARK ATIMAWVCLLTAGLAV TLKLAGV | 119 | Hypothetical protein PPLUZ19_gp11 [Pseudomonas phage LUZ19] | YP_0016 71953.1 | 2e-60 (119/119) | | No putative conserved domains have been detected | |
| 15 | 6204 | 7013 | 521 | MQCKDLYTNLASGMF NVPCSQVTPEMRRVA KSRAFAHAYTPKKQAS GGTYTARVSGVTCDG GKVEVRLDNVERVSTF DYAELETRVAASLCQA DAKRAAEYEKLLLKAF PSVSPKDGPLSAKDFE LRLHDLCSTHKLVVLRAL RDAGIEMDGPLRSRVR KLADRNNVMGAELFSL KQELAQLVAVGQKAGL NWDGAETQRLLTVAPT KALCRLISALTGVRYTH HTVVAKAEAEARERAK AEAKDSLQAATFAAAIA GGWVGSALMFLLG | 269 | Hypothetical protein PPLUZ19_gp12 [Pseudomonas phage LUZ19] | YP_0016 71954.1 | 3e-145 (260/268) | DNA polymera se | DNA_pol_A, DNA polymerase family A, 5'-3' polymerase domain | cd08444 | 5e-05 |
| 16 | 7284 | 7826 | 522 | MSKTSLYPLNLHPGLIQ IRTIHVFSIQAPSNAEN WWQWFLWGRKYHPL RESLSPAGELSASIAEC VLHLRRNGWQDSDIW RKKGGVLALGAFDLSG LMVGSCLVVGGELKAL CVDDRHSRGGIGAELV RAAELAGAEYLTCFEF LEPFYADLGWSTTHRE ANWTAGEPDVLHMRA PGHDV | 180 | Hypothetical protein PT5_gp14 [Pseudomonas phage PT5] | YP_0021 17736.1 | 6e-102 (180/180) | | No putative conserved domains have been detected | |

Fig. 8C

| | | | | | | | | |
|---|---|---|---|---|---|---|---|---|
| 17 | 8012 | 8836 | 523 | MALRRDSWLKQAQSL AVGQAGRFRHVLGCQ SMSRGGTNMTCKNLP DRWVAYCYSCQEGGV VEKTHVRRVQCADQE RFMPWPEDASDWTQA DCYQSLYGLLLSKGIDY NVMTPGLPLLYSERQH RLIFPTDAGWIGRATAD QNPKWVGYGYPAPDY HGWPQELSMGRPWVL TEDYLSALKVRWACPE VFAVGLNGTRLRDRLA AIMLQQTCKRAFIFLDG DRAGVRGSAGVMRRL RSLLIEGQVIPTPDGFD PKDLTREQIRSLVIGRI DASRTE | 274 | Primase [Pseudomonas phage LUZ19] | YP_0016 71958.1 | 2e-158 (271/274) | primase | Putative DnaG-like primase | PHA02031 | 6e-148 |
| 18 | 8805 | 10073 | 524 | LDVLTLHALSDRDRFR TLRSVVPEGMMGPET CFVIDWEQYWKVYPA HQKVDPQALRELIKLR GGYQPEQLAVVLNLVN QLDKPVDPDSLQGVVS QLNELDFSGRVDALLA QYNQGEDIDLAYELRR LSDEALRGGVSTPTD YVTDDVFDILAEEQGD HGIKLPGLVLPAYMKG LHAGASVLVAAPPDAG KTSFMAWIAVHIAPQLK RYFDPGRPILWLNNEG KGRRIKPRLYSAALGM TVGEILALDPEEVRRM YAEKIGGDSELIRIKDF HIGGSLAQAEQVIDAMK PSVVFWDMMAHVKGG QRKDQNRTDEMEYKV AEVREMAVRHDFISFM TWQISNDGHDQLFPPQ SCLKDSKTAVQGAVDV QIHLGRLNGADQQVM RGLSLPKNKFQMDGK PSNVEAMINFDAARCR FFESVDHAS | 422 | DNA_B Helicase [Pseudomonas phage LUZ19] | YP_0016 71959.1 | 0.0 (395/397) | DNA_B helicase | DnaB helicase C terminal domain | cd00984 | 2e-06 |

Fig. 8D

| | | | | | | | | |
|---|---|---|---|---|---|---|---|---|
| 19 | 10063 | 10683 | 525 | MQAKHSRVLEGTKEIP LGSIEPLLGSVAGLLLC LYSDATHEEGVALAGG FPRDLMHGATPKDVDV ALYSMTWGRAEHLIQK ALPVLNPIFVRDGGWR SDYADGGDGIFKGV MSLVGCRGLNGMDLD FNYYDADSLGRVMESF DFTINQVGIAYNWPDP EGGPRLGAYLHKDVT WGVNKEVGAGSRLPE RCEKMRAKAAYYGWE NV | 206 | Hypothetical protein PPLUZ19_gp16 [Pseudomonas phage LUZ19] | YP_0016 71960.1 | 7e-111 (196/206) | | Hypothetical protein | PHA01806 | 7e-92 |
| 20 | 10683 | 11630 | 526 | MSKRDVVLDIEKGIWR GVDQNDKAVEAIIKKN GYVIVEPKIDGCRAIVG AHGVVSRSGRRFPALD GLEDRIIERLARPGLDS GLVLDCEMYLAGMPFS EATGRMSSKTPLTEEE LECLHFAVFDATHIDVL RKARTSHLVYEERRAM ASSLLAACRLSDTPTFF QVGFTVCRRMSDVYR QYKFNREVGYEGSME KDPSLVYRNGKVAGCY KRKPGITVDGRIVGYV MGKTGKNVGRVVGYR VELEDGSGTVAATGLS EEHIQLLTYAHLNAHID EAMPNYGRIVEVSAME RSANTLRHPSFSRFRD LASNPGVKV | 315 | ATP-dependent DNA ligase [Pseudomonas phage phikF77] | YP_0027 27838.1 | 5e-159 (275/315) | ATP-depende nt DNA ligase | ATP-dependent DNA ligase | PHA00454 | 1e-99 |
| 21 | 11627 | 11911 | 527 | MKIRKSRNRNYPEDMV YHATNRDSLLYPKYVM GSVFISODGTFRICVM AGTWDHVGSEVLHHA RDIQSLGAGRRKLHRV MRRLRRNLQCVGVKV | 94 | Hypothetical protein PPphikF77_gp20 [Pseudomonas phage phikF77] | YP_0027 27839.1 | 1e-46 (91/94) | | No putative conserved domains have been detected | | |
| 22 | 11908 | 12243 | 528 | MRMPTEEERTIRCLLA DIHEPLNLLFPGIRVKA ETMPLGWGDSICALVL RVSYEHLTLGRLEYMH EVPILHLSQWGRDGLL QHLMNEIPRRVLDGML RQAQKYSQSNWYSK | 111 | Hypothetical protein PT2_gp22 [Pseudomonas phage PT2] | YP_0021 17801.1 | 4e-58 (109/111) | | No putative conserved domains have been detected | | |

Fig. 8E

| 23 | 12240 | 14663 | 529 | MTTIRLDLETESVEHK GRKASPFDPRNYIVMA GWRDDVDGKVGQKVE HRFRSRAEAEDPNNR WFNLDGVDVIVAHNAM FESNWFFTRYRDEYLA FLRRGGRVWCTQGAE YLLSHQTWLYPALDEL APKYGGTHKVDGIKML WDQGVLTSEMDCDLL SEYLSGPCGDIENTAL VFYGGQLMKLQARGMW AGYLERCEALIGFSAM ECAGLKVDLEVAKVNH AKQLEEVAGIEAELKKL MPDFPEYFEFKYTSLY HMSAWLYGGEVRYKG RVPYEDGRMEKADFV RFGTAKRGTPIESTSV RVPIHEVTDQGEWHW PTITELATKHGPVITFSA GKNKGSVKVFREDTDI PATKWDDDQRFRFPG LINLTNLPEVVREKFLG KRPEFQCALTLADGSP VFSTSGDALKALEKOG FEAAKLLMRLAELHKD NSSFYITHTYNKDGTIK DTKGMLQYVDDDGIIH HSLNTTATATTRLSSS RPNLQQLPSKDEDDPE AGSRVKEMFVSRFGA DGMIGETDYTALEVVM LAALSKDRNLLAKLMA GTDMHLYRLAGKHNN WNGFDYDQLVAIKKDP NHPWHGRMMQARKNI KPKAFSAQYGASAAGI AFNTGCTVEEAQEFLD NEAALFPESIAFRQIVR DSAEATSLVMYKAEDQ MPAGAFSEMGPDGNW RQYRRGFWQAPGGTC YSFRQQERWDKEQRK TVMDFKDTQIANYWNQ GEAGFMMTVSVGRIFR WMLHRPGFMVTEFLIN NVHDAVYTDCHKDTAA EVNKGVRDIMADAARY MSERLGYDIADVPFPA | 807 | Putative DNA directed DNA polymerase [Pseudomonas phage phiKMV] | NP_8774 58.1 | 0.0 (806/807) | DNA polymerase | DNA polymerase family A, 5'-3' polymerase domain | cd06444 | 2e-20 |
|---|---|---|---|---|---|---|---|---|---|---|---|

Fig. 8F

| | | | VAEMGPNMFNMEVIQ | | | | | | |
|---|---|---|---|---|---|---|---|---|---|
| 24 | 14660 | 14971 | 530 | VKELHPLHTPEFVKTFL DQTGCLPGVRRTGRT TGIALQAIGMALSHPRE TLTFVDHPDGSAAALV ASIETILATLGYKNVLVR PTTRADGRSVSIVFKTL PNA | 103 | Hypothetical protein PPphikF77_gp23 [Pseudomonas phage phikF77] | YP_0027 27842.1 | 2e-52 (102/103) | | No putative conserved domains have been detected | |
| 25 | 15026 | 16075 | 531 | MTQQLNALQAALALAN KAAETATIDMSETSTG GGGGRIFPAGTAMGR FCIYIELGDHAKEFOGK LKNPAPQIRLGFALWG DVNPQAGNPQSRPDD LFHTYEADGSIKPGLFR TFEMTLGNNEKSKTKL AFDKMNWSGQHTHFA QMLGQAFIIPIKRTKITK GNNAGKERNDIDWGGI MKPYNPVDGSPYNVP ELPMDILQYFFFDAPT KETWDALYIEGTSDNG KSKNFLQETIRSATNFP GSALHIMLGGGDDLIIK PTSQAAGSNLPAVPNV AADAGVAAAPAVPAVP QAVAQTAPSVPQVANV AAPVVGTAEAQNVLPD VPQVAQTAAPAAVEVP AVPVPAVPQV | 349 | Hypothetical protein PPLUZ19_gp21 [Pseudomonas phage LUZ19] | YP_0016 71965.1 | 0,0 (347/349) | | Hypothetical protein | PHA02030 | 4e-138 |
| 26 | 16075 | 17016 | 532 | MRLPSEEFLAGLSAQF DRSMAGGTLVCDADG PAYVAAATAKTLDTAL RRFWKLILEQQFLAHC TGTRVHLTAAGGAKAY RDTYPTMKPYQGQRK GKAKPALLEPLRRAVA DVHERGGAPEGIDVIL HTFFEADDGMMMDAY AMQDKAIIRSDDKDLR MITIYPYWEIDTACVSRI EGGFGYLKEAYTPSGQ FKLKGHGRKFFLAQWL GGDTADNIRGIDRFNG KLCGMKTAFDILHPITD EDEAIDMILEAYAKIKQ NPLAEAEVLWMRRTPT DNAAQYLLSRDLRPAF | 313 | 5'-3' exonuclease [Pseudomonas phage LUZ19] | YP_0016 71966.1 | 0,0 (313/313) | 5'-3' exonucle ase | 53EXOc, 5'-3' exonuclease | cd00008 | 0,006 |

Fig. 8G

| | | | | | | | | | |
|---|---|---|---|---|---|---|---|---|---|
| 27 | 17006 | 17446 | 533 | RQWIIELDAYHEALLQKRRESDYDE | | | | | |
| | | | | MTSEPKVYQIPRSQQRTFTLKLWAEQNKLCPLCGKPIDISVKGEAVMDHDHETGLVRGVLHRSCNTAEGKITNAAGSWGCKSMKYSDIIPYLRALLTYLEGPKHPLIYPLHKTDEEKHEAKLAKRRQAAAKRKAAMAVAKHNARNV | 146 | Putative DNA endonuclease VII [Pseudomonas phage phiKF77] | YP_002727845.1 | 8e-81 (144/146) | DNA endonuclease VII | Endonuclease_7, Recombination endonuclease VII | pfam02945 | 8e-10 |
| 28 | 17443 | 18489 | 534 | MSKLRKQFTNEYLRNVYVELGLKKGAEHLTEHSRFGEVSRQCFRNWCIKLGFHDSRTRGMYAKKGAMHWLGRKAAEVVRKFPGAVGNVVGQGPKVLSLDIETSPIEGWVWSLWKQNVGLNQIKRDWTILSFCCAKWMHSDEVIYMDCQGDPLDDMHLLVALHKLLDEADIIIVQNGKRFDVPKINARFFLNKMPPPRPFKVIDTLIIAKQQFAFTSRKLEYMTHKACTIKKRLHGKFPGFDLWAACLQDNPEAWEEMRLYNIDDVRSMEELYILMRPWFVGHPNVAVYFNDAEPTIRCPKCGDTDVKQEGWVHTQTGKYEHYHCGCGGWSRGRYTRNTSEQRKALLSN | 348 | Hypothetical protein PPLUZ19_gp24 [Pseudomonas phage LUZ19] | YP_001671968.1 | 0,0 (346/348) | 3'-5' exonuclease activity | DEDDy exonucleases, part of the DnaQ-like (or DEDD) exonuclease superfamily | cd06126 | 3e-04 |
| 29 | 18499 | 18870 | 535 | MSLAFPDSYESTITTEPYRKGASLEERKVGKLPMHLVVEGFPLLKRELARMMQWAAEVKGYLPHDWKKMTVGEFKSAQHRHESKRLIDGPLDDESNLMHLVHEAFNAMAAAEVALMDREKGNE | 123 | Hypothetical protein PPLUZ19_gp25 [Pseudomonas phage LUZ19] | YP_001671969.1 | 2e-66 (123/123) | | No putative conserved domains have been detected | | |
| 30 | 18863 | 19213 | 536 | MSKICWCTRPHETDEGVRVIWAFNERGIGVNYVTAYITPAMVSHRDWSDVILPDILREMAERLEREVKLVELRWFRAEILSCGEWRDYRAMTLEGAV | 116 | Hypothetical protein PPLUZ19_gp25.1 [Pseudomonas phage LUZ19] | YP_001671970.1 | 2e-60 (116/116) | | No putative conserved domains have been detected | | |

Fig. 8H

| 31 | 19222 | 21672 | 537 | SLAEAEWGPEDIGRVIERR<br>MDLQQQAHEEALVG<br>AAQNDARIALEKAIAQG<br>SIDRIPRARIMLMRMLPI<br>VTEAIFAHQEAKAAGP<br>AAKLRHLLRIIDAQDLA<br>VMALRAGLSMLINYPTI<br>TATKYYTHMGKILCREI<br>EVRLAFKVNQPYYDRT<br>LDYLKTSRTTRSVRHIQK<br>TMDALLDAVLPEEARID<br>LPDGDYLRLGKFIGDPL<br>IQCGLFEPNRFTGRGG<br>TSVHLEPSPEAKEFLQ<br>DPSAAMTWGGPGRSV<br>MLAPPRPWNDWCDG<br>GYYSAKAQKHHVLVRR<br>TKHQTKRARQMQLRH<br>LGRDKMPRVYEAVNAL<br>QSVAYEINHDVYEIIER<br>VFTSGGGVLGIPQRTY<br>PDKPEFPLGDEWAKE<br>NASEQELEAFNRWKR<br>SVHRWYTGEREHTAK<br>LREFAALYRVVREHHG<br>KAVYFPMHVDSRGRM<br>YYWGTPNPQGSDIAKA<br>CLRFHEKRALGKRGLY<br>WLKVHVANSLGCDKV<br>YFDDRAAWVDERWDD<br>FQRALDEGPENYPNLF<br>PEDESPLCAIAGLLELR<br>AAYASGNPEGYASGFI<br>VHMDATCSGLQHYSAI<br>LRDEIGGAYVNLLPPGL<br>AKADIYSRVLGLVNESL<br>ERDRAEGADGEARGY<br>AILWDKAGLTRSLTKKP<br>CMTLVYGTTFKGVVDH<br>CLDYLDESGVEIPEGV<br>PSYRLGSYMATLILDAI<br>RETVPSAVFAMEWLQ<br>RLARALPDASKDLHWT<br>TPLGMQVFQSYPKTEE<br>VRVRLRAEAVEYVTLY<br>EAKDELDPVRNANGIA<br>PNFVHGLDSSHLGLTA<br>LACAAEGIPIQAIHDSM | 816 | Putative phage-specific RNA polymerase [Pseudomonas phage phiKF77] | YP_0027 27849.1 | 0.0 (799/816) | RNA polymerase | T3/T7-like RNA polymerase | PHA00452 | <1.0e-180 |

Fig. 8I

| | | | | | | | |
|---|---|---|---|---|---|---|---|
| | | | GTYAADVDRMHVHIRE QFIAMYSGPCVLVELA KQLGIEATPPRRGSLN LEAVRDSWAFFC | | | | No putative conserved domains have been detected |
| 32 | 21845 | 22096 | 538 | MATMKTHRPTVMSPT VEGSRTGKGTARPVTF TSQQIEWLEQTFPEHQ IGPGTTMEDIQFQAGR RDVVRAVRLRRRDAIA VELK | Hypothetical protein PPLUZ19_gp27 [Pseudomonas phage LUZ19] | YP_0016 71972.1 | 1e-40 (83/83) | |
| 33 | 22096 | 22569 | 539 | MNKSIWRVHAKAGTPS ELQGLCWLAIQELEEF TLFRSKDDALNAMLDSI EGNDRTELLYFRDGQL AGGACIVFEDDPHVGP CVTAQWQYYLPRYRN TGVVREFIRELHRQAG WGQIPLVCWSHRESD SRYTIHYRRAKPYGQE SKEGAGQDHHRQTR | Hypothetical protein PPLUZ19_gp28 [Pseudomonas phage LUZ19] | YP_0016 71973.1 | 5e-88 (154/157) | Hypothetical protein | PHA01807 | 2e-70 |
| 34 | 22514 | 22810 | 540 | MGKKVKKVLGKTIIGKL ADGLLGTDLSGAQSDA RKMEEQNRLMQQQAD QLARNQQVDLTAENVA QVDLGAMADATGTGT RRRRNQAGTGVSQTL GINY | Hypothetical protein PT2_gp34 [Pseudomonas phage PT2] | YP_0021 17813.1 | 2e-47 (98/98) | Putative structural protein | PHA01808 | 8e-14 |

Fig. 8J

| 35 | 22822 | 24354 | 541 | MKTTAAMLWEKLRDG SVESRAIEFAKTTLPYL MVDPMSGSRGVVEHD FQSAGALLVNNLAAKL ARSLFPTGIPFFRSELT DAIRREADSRDTDITEV TAALARVDRKATQRLF QNASLAVLTQVIKLLIVT GNALLYRDSAAATVVA WSLRSYAVRRDATGR WMDIVLKQRYKSKDLD EEYKQDLMRAGRNLS GSGSVDLYTHVQRKK GTAMEYAELYHEIDGV RVGKEGRWPIHLCPYI VPTWNLAPGEHYGRG HVEDYIGDFAKLSLLSE KLGLYELESLEVLNLVD EAKGAVVDDYQDAEM GDYVPGGAEAVRAYE RGDYNKMAAIQQSLQA VVVRLNQAFMYGANQ RDAERVTAEEVRITAE EAENTLGGTYSLLAEN LQSPLAYVCLSEVDDA LLQGLITKQHKPAIETG LPALSRSAAVQSMLNA SQVIAGLAPIAQLDPRI SLPKMMDTIWAAFSVD TSQFYKSADELEAEAE QQRQQAAQAQAAQET LLEGASDMTNALAGV | Head-tail connector protein [Pseudomonas phage LUZ19] | YP_0016 71975.1 | 0.0 (510/510) | head-tail connecto r protein | Head-tail_con, bacteriopha ge head to tail connecting protein | pfam12236 | 5e-103 |
| 36 | 24358 | 25326 | 542 | MTQPNDQQLPPGLAN LVANVPPAAAPTPSHV QVLPNPVIQPQAPVQP GQVGAPQQLAIPTQQP QPVPTSAMTPHYQPVA VPVAGQPVVPQAPAQ PAPVAPPAAGAVLPEN LEVPPPPAFTPNGEIVG TLAGNLEGDPQLAPSIS YLEAFSDKLDTVRAFG KAAENRDPRFIDEHYL KEVLGPAQAQHVINVA KGVLTYDAQTKAVLN QTYAAVGGEAVLKQAA GVFNQHADPATKAAIG RLMDSGDAQAMQYAA KQIVAFAQGSGAVVQA TGQPLGAAAPALAALS | Hypothetical protein PT2_gp37 [Pseudomonas phage PT2] | YP_0021 17816.1 | 4e-174 (316/322) | scaffoldin g protein | Putative scaffolding protein | PHA01929 | 2e-92 |

Fig. 8K

| | | | | | | | | |
|---|---|---|---|---|---|---|---|---|
| 37 | 25379 | 26386 | AEQYRLEVSKLPLNAS EAEMAALRERRKAGM AQGI | | | | | |
| | | | | | | | | |
| | | 543 | MSFLNDLTRPNYAGKN ADVDIHLEEHLGIVDKH FAYTSKFAPLMNIRDLR GSNVVRLDRLGNVEAK GRRAGEELERSRVVN DKWNLTVDTLLYLRHQ FDHQDEWTQSFDMRK EVAELDGQELARKFDQ ACLIQVIKAAAMDAPVD LEDAFSPGVLEKLDLT GLTAKQAADKIVRMHR RVVETFIDRDLGDAVY SEGLTPMSPRVFSLLL EHDKLMNVEYQATGAT NDYVKSRVAILNGVKV LETPRFATKAIAAHPLG RHFNVSAEESERQIAL FLPSKTLITAQVAPVQA KLWEDNEKFSWVLDTF QMYNIGARRPDTAGAI ELKGIGAFDITA | 335 | Major capsid protein [Pseudomonas phage LUZ19] | YP_0016 71977.1 | 0.0 (335/335) | major capsid protein | Capsid protein | PHA02004 | 3e-177 |
| 38 | 26483 | 27037 | MLLLDAVNVILRKIGEL PIPSMDETYPTMAIALP ELEDQRIQLLTQGWWF NTWWKHKLTPDPQGR INLPKDTLAFYPDSPDL QWDGLGVRDANTGDD RIGKSVEGRLVLSREW DRIPEIAQRVIAHQAAL AVYTHEIGPDETAQVIA QELQAYQNELSRMHT RSRPLNTQAKRSFSR WRRSLRT | 184 | Putative tail tubular protein A [Pseudomonas phage LKD16] | YP_0015 22825.1 | 2e-102 (183/184) | tail tubular protein A | Tail tubular protein A | | |
| 39 | 27040 | 29520 | MSYKQSAYPNLLMGV SQQVPFERLPGGQLSEQ INMVSDPVSGLRRRSG IELMAHLLHTDQPWPR PFLYHTNLGGRSIAML VAQHRGELYLFDERDG RLLMGQPLAHDYLKAD DYRQLRAATVADDLFIA NLSVKPEADRTDVKGV DPNIKAGWLYIKAGQYS KAFSMTIKVKDNATGT TYSHTATYVTPDNAST | 826 | Tail tubular protein B [Pseudomonas phage LUZ19] | YP_0016 71979.1 | 0.0 (821/826) | tail tubular protein B | | PHA00428 | 7e-66 |
| | | 544 | | | | | | | No putative conserved domains have been detected |
| | | 545 | | | | | | | |

Fig. 8L

| | | | | | | | | |
|---|---|---|---|---|---|---|---|---|
| 40 | 29520 | 30065 | 546 | NPNLAEAPFQTSVGYI AWQLYGKFFGAPEYTL PNSTKKYPKVDPDANA ATIAGYLNQRGVQDGY IAFRGDADIVVEVSTDM GNNYGIASGGMSLNAT ADLPALLPGAGAPGVG VQFMGGAVMATGSTK APVYFEWDSANRRWA ERAAYGTDWVLKKMP LALRWDEATDTYSLNE LEYDRRGSGDEDTNPT FNFVTRGITGMTTFQG RLVLLSQEYVCMSASN NPHRWFKKSAAALND DDPIEIAAQGSLTEPYE HAVTFNKDLIVFAKKYQ AVVPGGGIVTPRTAVIS ITTQYDLDTRAAPAVTG RSVYFAAERALGFMGL HEMAPSPSTDSHYVAE DVTSHIPSYMPGPAEYI QAAASSGYLVFGTSTA DEMICHQYLWQGNEK VQNAFHRWTLRHQIIG AYFTGDNLMVLIQKGQ EIALGRMHLNSLPARE GLQYPKYDYWRRIEAT VDGELELTKQHWDLIK DASAVYQLQPVAGAY MERTHLGVKRETNTKV FLDVPEAVVGAVYVG CEFWSKVEFTPPVLRD HNGLPMTSTRAVLHRY NVNFGWTGEFLWRISD TARPNQPWYDTTPLRL FSRQLNAGEPLVDSAV VPLPARVDMATSKFEL SCHSPYDMNVRAVEY NFKSNQTYRRV MAFWILPLLAAGGMSAL CQGLANKEERNKIKAE NKARLKTDLDNLGAAA RDIANLGVMAASYRKQ AVASQVEAKRQGMLA GGSAEAQAGAFGVKG ASVDAVALDIEREVGE ALIQIDDNLDNCMWNL AEQAHSIQAQAKAGLL GQKSTTAGQRSPLVA | 181 | Internal virion protein [Pseudomonas phage LUZ19] | YP_0016 71980.1 | 2e-97 (181/181) | internal virion protein | Putative internal virion protein A | 2e-66 PHA01547 |

Fig. 8M

| 41 | 30065 | 32761 | 547 | GLMSAGSLYASQYFKF GATPKGGN | 898 | Internal virion protein [Pseudomonas phage LUZ19] | YP_0016 71981.1 | 0.0 (895/898) | internal virion protein, T4-like lysozyme | | | |
|---|---|---|---|---|---|---|---|---|---|---|---|---|
| | | | | MAESQRASQELGINVG QTQLQPGQSARRGVR DSEVNYSGPSVGSQIL DGILGAGQQIAGKWFE HNVQQEVLRGERARM AGEAEEAVDSNVLAKP FVKGGWRKQDYRIAQ ADFSLKMQRFIANKGR EMTPEEFRRKYLSQEAT HVLDSTEGMNPNDAL CALAQQQKAEEQLFG MQAKAYMDWSIDQAA RGFRTQGNSILAKAVQ AQATGDELSRQLSLEE AGLFYTNIMTSEDIPLE VRDKVGMQFLAASLD MNQRGIYEGLRDAGFL DSMSFDDRRALNGLYE KSKAQTRAKESMATLR ADADFQQRVANGAITD LAEVEAYSRGMVEEG RWSDAQAISFMTKAMT GLGNAQRMQGIMAAL EAGDINALHTLGTNVTE ALEQWDKMQAANGSS LTDRLVQGTQLGLRLG TFPKTYGESVGSAVRM IQAAKEGEANPELVNTL NSIFEQVASAQEINPSA GNVMLSGIPEAEQGAV AWALKQMKMGIAPAQ ALREFSANAEVVKQMD EFEKGQNTKAFKDNLG KQVNDKFVNNIFGRAW NMLTGESDLSNNEAVL SMYRRATIDEANWILAS DRKHAGLLTSDTGREA LEIAAANVRNRTIQVG EGRNLKEGDLFSRRDS APLILPRGTTAEQLFGT NDTETIGTVLAEQHKP HVEGLLGYKSVVAFEY DRTRGSLLAVEYDENG VALDRTRVDPQAVGNE VLKRNADKLNAMRGAE YGANVKVSGTDIRMNG GNSAGMLKQDVFNWR | | | | | | | | cd00735 | Bacteriopha ge_T4-like_lysozy me | 2e-10 |

Fig. 8N

| | | | | | | | | |
|---|---|---|---|---|---|---|---|---|
| 42 | 32765 | 36778 | 548 | KELAQFEAYRGEAYKD ADGYSVGLGHYLGSG NAGAGTTVTPEQAAQ WFAEDTDRALDQGVR LADELGVTNNASILGLA GMAFQMGEGRARQFR NTFQAIKDRNKEAFEA GVRNSKWTQTPNRA EAFIKRMAPHFDTPSQI GVDWYSAATAE MAKQFKGRMTPKYPL DQVQLDEAQVQGQLD AVPTVGFDALTGGEIG ERNVAAGQRANAREL ERIVADQELPALDRAS ALWNQSTLVGRWVDA LQLDADLAANSTGEVD PNFDAGTYGVQALQAA GIQPTDNYLQIMARAG NAEDAAYLLSRIQRYE QDEQIVRDNPYWNFAV GMLDPAALAVDAVTFG AGRALRLGRAGMAAA GGAGQVGVYAGLDAA GADVDAGTYIVAGALG AGVGALLGSGAGRIAA EAPTQPHVPEVSAPTV GLPEVAMTAEEAAARG FKAGDVVDLLDEGTVL SRVSARVEQAEIPAIPR RDTAFGDELHSLSGRK LSEVLDHIKTHAEVPKP LQGIAAKVADTIRTLEG LGQRTAFRVVQGGDT ASSAFLKPGTAGIHST QGLDTLVQVRGSTAPG RVGTNPVTVLHEAVHA ATVGVMNAALRNPGA MSPKVAQAMQTLENV RGNVLNALKQDRAAG RQLSEFEETLLAGNSN TLANVKELVAWGLTDT RFQRTLNRLRYSDGGP GLWSRFVEGIRTLLGL RSDADTALSRVLAASE TIMEAMPGYTKAQAKW ANKGAPVTEEASLETIV RSTRERAREGAGFVN RFFSEADLLAQPGEGA RRLLSRLIDDPVRRDG | 1337 | Internal virion protein [Pseudomonas phage LU219] | YP_0016 71982.1 | 0.0 (1327/1337) | internal virion protein | Virion protein | PHA02006 | <1.0e-180 |

Fig. 80

| 43 | 36780 | 37535 | 549 | FSTNDMAASYLRRYRN EFEGYVKSYDEMMAK AMAEQGVGLTARALNS RRAMAVRDQLNEQVT RELLRRDREWTAYGS VRVDPNLPPTIKALADR SDEIHGLMGQRAREAG VRGFENFAPRPGYFHR SWNWSKMAQMDEAA PGLARRAISEAVFRGIP GLERADADTIAQAIVQR ARDRATGIRSEFMGAM GVADTAFIRQALEEAN VSQAKFDSIMAKIEQK CSDQGTVKYGKGRLS LDMTAEINHNGTVYRV QDLIDRDLDRLMENYA GSMSGRSALARAGMP GDSEIEAFIREYQREAA HLGTDKVQELTGQLRG VFGDFTGNVPREHQL GPVAQRASGLTSATML GFSGVYQLAELATMAH RQGVFNVMKAMLNSR LGDFVGAMRRDPDLA DEMQTVLGLNLANDIR MKPWKRQFDTFLVSQ DTFMDRFLHAGKQAVP VLNGMKFIHNWQSRM NANLTLNKVARAAQGD EAALRVLQQYGKDVD WTPVLARVRGYVTYR GRNARSMNWGAWSQ ADVNTVMNTALRIMDD SLLYGRVGQNSGFARS PVGQILGQFRSFVAFA HNKLLRGTYENSGVLG VASLLAFQYPLTALMM GAKAAINGKFDTSDEGI RKMAIDGIGYTAGLGFT ADMWGVITGHSRMSA PVFGLAEHSNEVFRGV KDLVTGDDPAAATGDI VNGAAGALPFVNVFPA TKLLLESIKGE | 251 | Tail fiber protein [Pseudomonas phage phiKMV] | NP_8774 77.1 | 9e-144 (248/251) | tail fiber protein | Phage T7 tail fibre protein | pfam03906 | 4e-05 |
|---|---|---|---|---|---|---|---|---|---|---|

Fig. 8P

| | | | | | | | | |
|---|---|---|---|---|---|---|---|---|
| | | | QGIPFLPRYIDANNKQL LYAVQEGINTANLALD GVLDAIRIAEEARRLAQ EALDAANEALRRALGF AEIRTVTEDSDIDPSWR GYWNRCITSEQSLTLT MQMEDPDEPWIEFSE VHFEQAGIRDLNIVAGP GVTINRLQNTTMQLYG ENGVCTLKRLGPNHWI-IFGAMEDD | | | | | | |
| 44 | 37535 | 37975 | 550 | MRGIIAGVVASQIRRPK PVLTTITYPQSSSDRG GMTFHAIAGIIQDTVKF ADSKDLGSYEMLVRDA TLKSMVITLTEVKDSSV WSMGVLSAAIKSVVQF LTPVEEKSSLDMSIIHG EHKQSVIPYSRWAEAG SLSMGITEGKVYVP | 146 | Hypothetical protein phiKMVp39 [Pseudomonas phage phiKMV] | NP_8774 78.1 | 3e-76 (142/146) | | No putative conserved domains have been detected |
| 45 | 37965 | 38843 | 551 | MYHSSTIRGEFDLEIVR PDGTVRQHLHFKNLIT DLALEAMSSKGVPSGG WTNMFAGTGNRTPVP ADVSLVAPVANASASL NYGNRAVWDSTTGEK VHTGTFRAGSFQG QSLAEVGIGRVVSELY SRSLIKDANGDPTTITV LVDEELRVTYTLRIAPP ASSEVKITMKGIEYTLS MRDRRTFRDLSPEPAA EFGTRGSLSWSAISAP DSNGQTKTANLSGDA GTGIIQVPAQSAQIMRI QPADANWTEGIQYLR WETPAGRELEIKLDPP LVKNSLERVDITVTHIF NRV | 292 | Putative tail fiber protein [Pseudomonas phage PT2] | YP_0021 17825.1 | 4e-164 (284/292) | tail fiber protein | |
| 46 | 38840 | 39430 | 552 | MIQFKFGDYRTRVPFQ GARDRRDINDRSDYVD GGVAIQDPSQGLLYQE WHAELLEDGIYLTPEK ERVTTRIGPGINEGVAS MAVTFDQNMNYVLVYT KQGEGFIDFFDSATEE RNVMNLGPVDYIKTDL DDRRPEGSAWAQVLV CYTRQGNFYVRASSTR | 196 | Hypothetical protein phiKMVp41 [Pseudomonas phage phiKMV] | NP_8774 80.1 | 1e-70 (129/130) | | No putative conserved domains have been detected |

Fig. 8Q

| | | | | | | | | |
|---|---|---|---|---|---|---|---|---|
| 47 | 39430 | 39735 | 553 | FTEEELIVGTGKVTRPI VKCGMAANWRFQVLF RGRM MSKKQTASAERLGLLH ELVCTAIERNFKWYMD NDIPIPASDIAAATKFLK DNEITCDPSDTINIDRL REEMRQAQAENRRIAL EGFIAGETDDEMERLY TH | Terminase small subunit [Pseudomonas phage LUZ19] | 101 | YP_0016 71987.1 | 2e-53 (101/101) | terminas e small subunit | Hypothetica l protein | PHA02046 | 9e-36 |
| 48 | 39745 | 41550 | 554 | MTPQERFQIAHEVRDM YPRFRDFCLDAMLFLG FKMTWMQLDIADFMQ DSPNKAMVAAQRGEA KSTIACIYVVWCITQNP ATRAMLVSGSGDKAEE NGQLITKLIMHWDLLAY LRPEARMGDRTSATSF DVNWALKGVEKSASIN CIGITAALQGYRADILIP DDIETTKNGLTATERAK LTRQSCEFTSICTHGKI LYLGTPQSRESIYNGLP ARGFLMRIWPGRFPTL DEQERYGDWLAPSILA RIARLEEKGHNPRTGK GLDGTRGWAADPQRY NEEDLLDKELDQGPEG FQLQYMLDTSLADEQR MQLKLRDLLFIDATHES VPEQVAWAADERFKLK FDAHRFPVIKPELYLPA LMAGGWAPLQQMTMF VDPAGDGGDELSYAV GGTLGPYIHVVSIGGW KGGFAEENLEKCIALAA RYGVKVIVYVEKNLGAG AVGQLFRNHMRSIDPD TNKPRYEGIGVEDRQK SGQKERRIIDTLRPIMQ RHRLIFHVSAMDSDHV ACQQYPADKRNERSV FHQIHNITTDRGSLPKD DRIDALEGLVRELAPTL VKDDEAATRAREEAAK KEWLNPMGYTKSVL RSLGMGRERRKGRPK GRRL | Putative DNA maturase B [Pseudomonas phage PT5] | 601 | YP_0021 17769.1 | 0.0 (597/601) | DNA maturase B | No putative conserved domains have been detected | | |
| 49 | 41547 | 41747 | 555 | MMLDTATEAGKGTLAV | Holin [Pseudomonas phage | 66 | YP_0016 | 2e-29 | holin | No putative conserved domains have | | |

Fig. 8R

| | | | | | | | | | been detected | |
|---|---|---|---|---|---|---|---|---|---|---|
| 50 | 41744 | 42226 | 556 | TGVGIAVYSPYEIASLC AAVLTALYVGAQLITLL PKMLDSIAELRRRFKK VNKPLRGAALAAALAG LVALEGSETTAYRDIAG VPTICSGTTAGVKMGD KATPEQCYQMTLKDY QRFERIVLDAIKVPLNV NEQTALTFFCYNVGPV CTTSTAFKRFNQGRAT EGCQALAMWNKVTIN GQKVVSKGLVNRRNA EIKQCLEPSSQYSSLL W | 160 | Endolysin [Pseudomonas phage LUZ19] | YP_0016 71990.1 | 2e-89 (159/160) | endolysin | Endolysin_ autolysin | cd00737 | 5e-34 |
| 51 | 42184 | 42513 | 557 | MPRTIVAILVLAVVALG ASYGFVQSYRALGIAQ EEIKRQTARAEALEVR YATLQRHVKEVAARTN TQRQEVDRALDQNRP WADRPVPAAVVDSLC NRPGARCAVRTPTD | 109 | Rz protein [Pseudomonas phage LUZ19] | YP_0016 71991.1 | 2e-55 (108/109) | lambda Rz1-like protein | Phage lambda Rz1-like protein | PHA020 47 | 3e-32 |
| 52 | 42603 | 42917 | 558 | MANTREQYLAGRNTG LTFYQVCQPGTDNRIA LHDMDEADVKAKATAV IAAATALGGEGGATPP DPLTAYKVKNGDTLPV DGGGSVKVTVANGAIT KVVYTAPAG | 104 | Hypothetical protein PT2_gp53 [Pseudomonas phage PT2] | YP_0021 17832.1 | 2e-52 (104/104) | | No putative conserved domains have been detected | | |
| 53 | 42967 | 43212 | 559 | MATFAAATQKDLRAFA GAIENLIRPLEEAALGS GFTEVITITKGTDGNET RTSERKVRPELVANLD ALMAAVETAKAAVYK | 81 | Phage particle protein [Pseudomonas phage LUZ19] | YP_0016 71994.1 | 1e-36 (79/81) | phage particle protein | No putative conserved domains have been detected | | |

Fig. 8S

Table 9 - Features of phage F44/10 gene products and assignment of putative functions.

| orf | Start position | Stop position | SEQ ID NO.: | Aminoacidic sequence | Size (aa) | Name[organism] | Acc No | E value and identity | Predicted function | Name | Acc No | E value |
|---|---|---|---|---|---|---|---|---|---|---|---|---|
| 1a | 467 | 1 | 561 | MKKIYILEEEIEEMDYDLWEEDT VYTTSYEVLGYTDSLEDAEYIK NNYGTSNPIFINEYPYLTKDKLI EEQRYRYRNSAIELKRVDGYFE VYEINDLNVTECFSINKDDISFD CPFSIDMFSSDRNSIFIEFMMY SEYDNKKDTIEKEKNSFLMK | 155 | hypothetical protein KgORF8 [Staphylococcus phage K] | YP_024439.1 | 2e-62 (131/155) | | PHA02241, hypothetical protein | PHA022 41 | 8.06e-17 |
| 2 | 689 | 471 | 562 | MKKIINFLVDYNINFSYSEDSLN VMGNSYLVDKHGTQDYEIIGNY GHITGVFSYQTEEEVIAKLKNLI GVWE | 72 | ORF201 [Staphylococcus phage G1] | YP_241058.1 | 3e-31 (68/72) | | No putative conserved domains have been detected | | |
| 3 | 884 | 690 | 563 | MRDKRIHSELLYNIIGKHIQEEE NITPYIEAIYVDIMNIIVVEYTFYN ENGTRMLGQYPIGEVM | 64 | ORF218 [Staphylococcus phage G1] | YP_241059.1 | 7e-28 (62/64) | | No putative conserved domains have been detected | | |
| 4 | 1611 | 874 | 564 | MNLEKSFLLSTIEFGSTYQGTS DEYSDKDYMSLVVQPLSDTIFR NSEKASKHTEVSRYYAVERFIS LVLKSGFDNVLNLCAQLEQAKN TRFNKTVLDLFYDDFIFLTVVRA NFKPIAYSVIGNINNILKKEELAG KDLVKFYTFYNHLEYYNDLLDD LDNLNVSYKDFAKVKYMPKEVL DNKRSNVSIENKKDLVTKVEPLI QEVKDKLKSNESNIKHYKDAM ELVEKSLKDKTVSFLTEVYNER | 245 | hypothetical protein KgORF9 [Staphylococcus phage K] | YP_024440.1 | 1e-124 (238/245) | | No putative conserved domains have been detected | | |
| 5 | 1778 | 1674 | 565 | MKYILGLITLGVILFKIYEYFKYIQ DEVDTTEDI | 34 | ORF437 [Staphylococcus phage G1] | YP_241061.1 | 9e-08 (29/34) | | No putative conserved domains have been detected | | |
| 6 | 2027 | 1800 | 566 | MDFYQFLNHENVRVNSITPSQ KNFIRENIDYTNLDTVDIDFMNS KQAKKEIEKIIRTKNEEEYDMA MDALSGWEG | 75 | gp ORF020 [Staphylococcus phage A5W] | ACB89011.1 | 4e-29 (61/73) | | No putative conserved domains have been detected | | |
| 7 | 2415 | 2029 | 567 | MFGKAPEHIMEIIDKEDNILGED LTLNIDYKGINLTVKRHPHSGHL NGYINVPTNITKEQFNSIEDCSH GGITYDEHEGDYRVLGFDCAH YSDMTPYAVISFSDSYYRDLKY VLNTLKDMADCLKEGE | 128 | gp ORF021 [Staphylococcus phage A5W] | ACB89012.1 | 4e-39 (79/130) | | No putative conserved domains have been detected | | |
| 8 | 2685 | 2512 | 568 | MEKVNHEFLAELAKSNSPVLNS | 57 | ORF245 | YP_241064.1 | 3e-26 | | No putative conserved domains have been detected | | |

Fig. 10A

| | | | | | | | | |
|---|---|---|---|---|---|---|---|---|
| 9 | 3208 | 2726 | 569 | KPLQDGDYNIEFDYDGFHFEFS QKNGYWQWKYNAK MANEKELIRMVNYLIDNMSMW HINYARAVLIPSEVEKIIKEHEKF DDLLKKRGEWLVKGSDTDNID DLETYNQIMNNQKDEMMIQEID IYTQGKTIKVDNKHYSSNELNE VINKIEQSEDIKIKSNYKLLCIDY TKVIGYEVTYASSYEEKFKNDL EKDL | [Staphylococcus phage G1] hypothetical protein KgORF11 [Staphylococcus phage K] | YP_024442.1 | 5e-78 (144/160) | (55/57) | PHA0224, hypothetical protein | PHA022 43 | 5.15e-24 |
| | | | | | | | | have been detected |
| 10 | 3800 | 3258 | 570 | MDRRIIGKHNLTQDLRLGDKVEV YDAHKFKENEDGTIELGDKVTE GIVVDYKGDFTGNTSGLVTLDS SEEELIIGEHNFKLIEEGNLQAV YDSVSKNKVESLSEDYDMYRK LLGVKSGELEDISYELERLIMEY NKKVDNYNGLLTLSKEKARELS LLTGDRKMIPHMKNKRLELGTE ADF | hypothetical protein KgORF12 [Staphylococcus phage K] | YP_024443.1 | 1e-188 (166/180) | | No putative conserved domains have been detected | | |
| 11 | 4333 | 3800 | 571 | MVYDSIISRTMAVSILNKWIAELI TDVDLDKCKFTEEEYGKVVTN SINKIQDVLIEKNYEVTDGELYDI VCTELINPIKNNTEEEKHNEKN DLLEHLEDLAFRHDIDLGYVSD GSYNLTVTHWLMQDEFTDVNI KVNKDEDFYTITIPESKYFWLPI TKENLEMFLTQDPINKGEIE | hypothetical protein KgORF13 [Staphylococcus phage K] | YP_024444.1 | 1e-95 (173/177) | | No putative conserved domains have been detected | | |
| 12 | 4500 | 4336 | 572 | MKNLIKFLSMVVVTILTFSLTYVI LKKETNNKRNGVAPFDFSLED HIHLNKEIK | hypothetical membrane protein MbpP [Staphylococcus phage A5W] | ACB89017.1 | 5e-20 (50/54) | Membrane protein MbpP | | | |
| 13 | 4781 | 4503 | 573 | MVNNIWAVVLSIIIILLIILLWFLF RKKVNGGSSKNVEIQKAEEGN DNKEQEVEEAQYRELNEEEKE KNENSSKDYKYDKEKVKNKLK ELE | hypothetical membrane protein MbpR [Staphylococcus phage A5W] | ACB89018.1 | 5e-24 (89/92) | Membrane protein MbpR | | | |
| 14 | 5626 | 4781 | 574 | MGRRLIDNSELNVIKYDGLPDF FSALKKNRVSGRENSSDTGSY DFTGTHSFQEAYNLMVKGDRE SYDMVVKLKKMTDALFRMDKS VKRKPVVAPEGYQPHVPNAIK GLPNSMMSQQRVKAEKKVIDV FYNSSISWMEDPENLAYRGAIM LSAIQTLETKGYSINLYLGKLSN SEYENKLTGFVVNIKHSYQRLN VFKSSFYLVNPSFLRRISFRVLE | hypothetical protein KgORF14 [Staphylococcus phage K] | YP_024445.1 | 5e-160 (277/281) | | No putative conserved domains have been detected | | |

Fig. 10B

| | | | | | | | | | | |
|---|---|---|---|---|---|---|---|---|---|---|
| 15 | 6756 | 5638 | 575 | VEPDMVDLTNHGYGSVVSKSS YGNKLTEHILDNAVIFDSSIGIDI NNDSSENLRAVKKLFGGRL MAKQDTIERLERLVEQQMETT ADLAKKLGEKNSNPYEQAIVDA IVEKAGTESREIIITDVKKQIEEY VEEQLSNLPVKIELQQEGKTIK DISGIFHYRYQDILKLVNQNIPV FLKGGAGSGKNHVLEQVAEAL DLDFYFSNAITQEFKLTGFIDAN GKFHETQFYKAFTKGGLFFLDE MDASIPEVLLILNSAIANKYFDF PIGRVTAHEDFRVVSAGNTMG TGADHYVGRQQLDGATLDRF AQVEFDYDTKVEHQLSSNEDL VNFVQQLRHENDEKGLPYVFS MRAIINGSKLDGVMEDEFVVES IIFKSVPKDEINQFISSLPEGNRY TEATRKLLGMQQEPKQEPRKS NSTSKDSMDFDTIMDKLGLE | 372 | YP_024446.1 | 2e-109 (193/194) | ATPase | ATPase-like protein | PHA022 44 | 2.63e-175 |
| 16 | 7233 | 6907 | 576 | VSKRTDNFIYFCKYYFSEYLPS LGVEVLNHNETSHGTMEGVRK YYIANILYEGQELTVTIDLEEFN NATSMHNMLEIMNSHTYNCMF MYDMDTHGTKDIDDFFKLMYF | 108 | YP_241072.1 | 3e-55 (105/108) | | No putative conserved domains have been detected | | |
| 17 | 7642 | 7226 | 577 | MNAKEFMKTQAQVEDYLDKLK VTIIEDALSVSKEWSNDSNDLG YALSSLGESIGLLEDYYNIQVDA HLPEHYKGSKDVISFLEEHFSY DGFVDSMIFNIVKYTTRLGRKD AVDKEVQKIKTYYVRLERNIKY GDSTRV | 138 | YP_024447.1 | 2e-74 (138/138) | | No putative conserved domains have been detected | | |
| 18 | 8077 | 7775 | 578 | MEKVELIKQWAKDRNLQTGKP EGQMLKLLEEAGELASGIAKSN DHVTRDSVGDIFVVLTVLCLQL DIDIEECIDMAYDEIKERKGKLIN GVFVKEEDLKK | 100 | YP_024448.1 | 2e-49 (99/100) | Pyrophosph o-hydrolase | MazG | | |
| 19 | 8265 | 8077 | 579 | MEKFQEDYYNIDIRVKAYVRVG YRYEEDITNNLHELVEDNLNVT SDSDNLIIKDTEIKGDIE | 62 | YP_241075.1 | 2e-26 (62/62) | | No putative conserved domains have been detected | | |
| 20 | 8470 | 8309 | 580 | MVKPVITLEPEDVKVLLDYLSFL EDDMRNYEGMRELYEELHKKY QLAKGNYSD | 53 | YP_241076.1 | 3e-22 (53/53) | | No putative conserved domains have been detected | | |
| 21 | 10518 | 8470 | 581 | MAITYKQKGLTEQEIINLPKVNK GCIYIGEEDVFLKKKNNINLG | 682 | YP_024449.1 | 0.0 (639/682) | | | pfam03 819 | 4.19e-03 |

Fig. 10C

| | | | | [Staphylococcus phage K] | | | | |
|---|---|---|---|---|---|---|---|---|
| | | | SKELFRDIHNIFSFDTATEIHLFL ALCGNKEVTNFEGDPYETVEK LVEGVIGNNKGRNYKEYIEADR GERKDFPLYGSRRRKQIQSKG YVEEKIKELENENRLWGYEAR QLDEYKEAVDSLNNDIMDVLD QGKYVLINSSIIVMNEDIEKGSS EYYKEMSDSLYSRVWYMHPST ENNSSFGLKVRHIRDKHNMGN KWVLENKSSFDVKTGAVKVFL TDSLVNKEIALNLYKDDISKSEY KNELTLSVLLNVILKNYSQPNLN RGIIIKIIEQTLEHHNFDFSSWCP DNIDVYGHINYRGDKYRIFIGEN STSNYLITLTDIVKNIDKINNLEE FGLFERNALLFHIPKNPKWKVH EAFNLTKQTYKKLLTLNKFEQG NYLRFANTLYKNYNHLHNEVNL HQLFDDTFLMVRDSRDVTNAL KVKPIVNEILSISFANYKKMTHY LDVDAQDRQRITGYALDNYYLD YLHDLSILIREGYRTLESVNLTP FSLKLEHDIVTDEKQSIQQQLD DAELKAKYDNKLEKIIDKTYKLK DGRKVKFLPADTVSKLKDEGK MLSHCVGGYANRILKNSCLILL ARLEEDLDNSWFTVEIRITDNG YVLGQQQSIDAYKLPNELKEAL EKDIKKINKEEFKEVA | | | | | | |
| 22 | 10596 | 582 | MSIEKKEEIIAHNEVVFRSLTQG LYVKEVDIYSDVVSYTKDVDEA LAMPNTINFKNSRKYEKLIRNLD LEPLNKIQKVIYETHLEEL | gp ORF038 [Staphylococcus phage A5W] | ACB89029.1 | 8e-41 (85/87) | | No putative conserved domains have been detected |
| 23 | 11049 10876 | 583 | LNDLIKEGNKYYHKVRAGETLW TISKNYDVEIKKLQELNINIKSVS LTNLEYLVCVE | gp ORF039 [Staphylococcus phage A5W] | ACB89030.1 | 9e-24 (56/57) | Peptidoglyc an binding protein | LysM | pfam01 476 | 5.26e-06 |
| 24 | 11634 11056 | 584 | MDNLSHYLSILYAILVTVGYIPG LIALVKSDSVHKGVSSYFWYLVA TVGISFYNLLLTDATMFQVVSV GLNLTLGIVCLLVASYRKKDYF SIPFIIVFSLLLFLLSDFTALTQTV ATITILAYVTQITTFYKTKSAEG TNRFLFLNGLGLASLIVSMVLTH TYVHIIATEFVNFVLILICYLQAN YYSRR | gp ORF040 [Staphylococcus phage A5W] | ACB89031.1 | 13-93 (183/192) | | PHA02246, hypothetical protein | PHA022 46 | 6.35e-42 |
| 25 | 12250 | 585 | MVNKIKDKVYMGGHILNEAMV DYRDKQHKEVDGIVGVTPYSP | hypothetical protein KgORF20 | YP_024451.1 | 6e-92 | | No putative conserved domains | | |

Fig. 10D

| | | | | | | | | | |
|---|---|---|---|---|---|---|---|---|---|
| 26 | 13139 | 12243 | 586 | HKDKSINDKANAEQTKLAERILT NDFKAMQESDIFVFDVLNEGLG TIAELGILLGMKHQAQETIKQLK EQSELFKFNEIDELSETYDILQG QIGEQEYILKKPVLIYCSDIRQG HGKPYNDPDRAEFSTNQFVYG MVLELTNGEGFISWEEVTNRLE KLGEQDG MKSYTVKVKNKGIVLDKFKERGL VVQEKLDGSNASFTVENGELV CFSRRKKLNENETLNGFYDWV HENINVRNTYVSALEKYIIFGEW LVKHKIQYKEEFYNNFVVFDVY DKENEVYLSIEDMNVIAHHLGL KTVKTLLVAKPSHYLNDLKPEEI QELVGKSDMTYKPDKGEGIVIK YLDGKSEYDDYFKLVSNEFKEF SRQKMKTEVKKNESVADYAITR ARMEKMFRAIEEDRLSEDDLE LENFGLIMKQVGQNFVDDIMEE EKENILKIVDKQIKKKMPHILREI LEEKGDTIDG | [Staphylococcus phage K] putative DNA ligase [Staphylococcus phage K] | (172/209) 5e-169 (296/298) | | DNA ligase | have been detected ATP-dependent DNA ligase | COG14 23 | 9.05e-03 |
| 27 | 13363 | 13139 | 587 | MNYLAKVFINNNWLVKLITIVLL TLFLSGLVVISAISLFLSTVLNL PGLVVLAFLASVSLILFSIVHNS KEDN | No significant similarity found. | | | | No putative conserved domains have been detected | | |
| 28 | 14172 | 13432 | 588 | MAIQLKELDFKLKDYPNVRYNM GEHLIFNEFLEKATTEQLDFCE DFFNDNVEILWNESQAGTGKT MCSVACAYADYLNKNRKLVFII SPVSEDLGSRFGNQTEKEMAY FMGLHDALIELNMNPEQQITEM LMMEDNVKEDKLGDCWVSQIS HLFLRGGNLRDATIIINEAQNFK RSELKKVLTRVHTKNSTVIVEG NFKQIDLKNESKSGFGDYMEY FKNYEGAVFHNFTVNFRSKLA QYADNFKW | putative PhoH-related protein [Staphylococcus phage K] | 8e-144 (245/246) | | ATPase | PhoH-like protein | pfam02 562 | 1.46e-21 |
| 29 | 14838 | 14224 | 589 | MKKINSVIKGEGKKVQTADVRK ISYYVKDYNPCMTVDDANDYN ATSQYLVSDNGKFIAKYNKDM NAVGFYEESGDTVKHLTHTTP ERLEGTVFTIEEETEIDLINDTLP QGDILIKFSDGSIYLPDNESVLD SVNYLADNDWDSVDDIIYTGLS KGNSENCIVDFNYNNYDIGYDD VEDEDVCDNYPECECSNYCSS | hypothetical protein KgORF23 [Staphylococcus phage K] | 3e-113 (204/204) | | | PHA02248, hypothetical protein | PHA022 48 | 9.28e-98 |

Fig. 10E

| | | | TGEYIGN | | | | | | |
|---|---|---|---|---|---|---|---|---|---|
| 30 | 15279 | 14854 | 590 | MQDSVNIYTDGSSSYNKGKVG SGAVLVSKEGNIISEISKSVDKP GLIKYNNVAGEILACCYGIEEAI KLGYNQAIVYIDYIGLIHWYEGT WSARNILSKTYINMIREYQKVID INFVKVKSHSNDKWNDYADNL AKKSIDI | 141 | putative ribonuclease [Staphylococcus phage K] | YP_024455.1 | 5e-74 (141/141) | Ribonuclease | RnaseH | cd06222 | 4.11e-18 |
| 31 | 15460 | 15269 | 591 | MKKGVFTVIADGFKFNVIAKDK KEVQEHCFKCFDFNYISVSFCR EVYSDCEFPQFMEDYKYAG | 63 | ORF222 [Staphylococcus phage G1] | YP_241086.1 | 1e-28 (63/63) | | No putative conserved domains have been detected | | |
| 32 | 16124 | 15483 | 592 | MENNNLVNFLMTTDDIDDTIEM VDSFELQDINKVLGEDTFLTIME ITDSLPDNQYKIVILLSSLDKLLN TDRKELVEYDEEFPTIRKHNVS ELKRDTVNSVIDSYMNTNIEILY TEYPTISNYSVVVDSVKVLNTL YLIESKNGKIEATLSEDGEDLHE YISEEGYSVTDILNKFDDVEDLF DEDDSLINFFSDIDEGKNKTIKS FIELVINLK | 213 | hypothetical protein KgORF25 [Staphylococcus phage K] | YP_024456.1 | 7e-113 (212/213) | | No putative conserved domains have been detected | | |
| 33 | 16344 | 16114 | 593 | MDEKKESKPLNLQKIRVEKGHT LRSLASEIGVHYSLISYWEYGK KKPRSANLVRLEKALNTPGKEL FKELEEDDGE | 76 | ORF187 [Staphylococcus phage G1] | YP_241088.1 | 5e-36 (76/76) | DNA binding protein | HTH_XRE - helix-turn-helix XRE-family like proteins | smart00530 | 4.91e-08 |
| 34 | 16574 | 16347 | 594 | MNIKFKRWFRINVLKKETLLFKV YWRYESPSLKKPHVFHIELYAK SKAEARNKSQEYILKNAKESED FKFLKVEEK | 75 | ORF190 [Staphylococcus phage G1] | YP_241089.1 | 6e-34 (74/75) | | No putative conserved domains have been detected | | |
| 35 | 17375 | 16683 | 595 | MKKTIFATLALGTATTFGGIATN EASADEIDYNKLAEQAKSNSAE VNTKPIQEGNYDFSFSDGEFTY HFYNYNGNFGYEYHSGSTQVD NTVSRLAGEEQTPEQKVDQQQ AQFDTQNKQDTKKEVQTTSAP VQKETKQPTQSTSSTGGSVAE QIRQAGGDEAMIEIAMRESTMN PNAVNASSGAQGLFQGLGKS WSGGSIAEQTKGAKQYMIDRY GSTSGALAYHNAHNSY | 230 | hypothetical protein KgORF26 [Staphylococcus phage K] | YP_024457.1 | 1e-130 (229/230) | | LT_GEWL - lytic transglycosylase and goose egg white lysozyme domain | cd00254 | 4.34e-03 |

Fig. 10F

| | | | | | | | | |
|---|---|---|---|---|---|---|---|---|
| 36 | 18367 | 17573 | 596 | MRKSVVISGVLGFLAIIGFIILLM CITKIPQGHVGVYSVNGVKED TKSPGWHLTAPFDKVNKYPTK TQTHKYKDLNVATSDGKNLQM DIDVSYKVDATKAVDLFNRFGS ADIEELEKGYLRSRVQDNVRQ AVSKYSVIDAFGVKTGEIKKDTL DSLNDNLEKQGFVIEDIALSSPK ADKNTQKAIDSRVKANQELERT KVDKQIAEQNAKKKEVEANGD KKANEIRESSLSDKILRQQLIEK WDGKQPIQIIGDGTIVDVTGK | hypothetical protein KgORF28 [Staphylococcus phage K] | YP_024459.1 | 2e-133 (229/261) | | Band_7 domain of flotillin (reggie)-like proteins | pfam01 145 | 5.79e-24 |
| | | | | | | | HflC, membrane protease subunits | COG03 30 | 1.86e-13 |
| 37 | 18675 | 18367 | 597 | MALLLTYFAIFIVFLVLVGFGISY LFDFLSMKEKKSNIRKQYRELV RQGTLDEYGLEQYVKYKKQFL NDRRQSIVTRADKQEIDQEEKA LNSLIKEIEKGEM | hypothetical protein KgORF29 [Staphylococcus phage K] | YP_024460.1 | 1e-50 (102/102) | | No putative conserved domains have been detected | | |
| 38 | 20276 | 18789 | 598 | MAKTQAEINKRLDAYAKGTVDS PYRVKKATSYDPSFGVMEAGAI DADGYYHAQCCDLITDYVLWL TDNKVRTWGNAKDQIKQSYGT GFKIHENKPSTVPKKGWIAVFT SGSYEQWGHIGIVYDGGNTST FTILEQNWNGYANKKPTKRVD NYYGLTHFIEIPVKAGTTVKKET AKKSASKTPAPKKKATLKVSKN HINYTMDKRGKKPEGMVIHND AGRSSGQQYENSLANAGYARY ANGIAHYYGSEGYVWEAIDAK NQIAWHTGDGTGANSGNFRFA GIEVCCQSMSASDAQFLKNEQA VFQFTAEKFKEWGLTPNRKTV RLHMEFVPTACPHRSMVLHTG FNPVTQGRPSQAIMNKLKDYFI KQIKNYMSNGTSSSTVVKDGK TSSASTPATRPVTGSWHKNQF GTWYKPESATFVNGNQPIVTRI GSPFLNAPVGGNLPAGATIVYD EVCIQAGHIWIGYNAYNGNRVY CPVRTCQGVPPNQIPGYAWGV FK | putative lysin [Staphylococcus phage K] | YP_024461.1 | 0.0 (491/495) | Endolysin | CHAP | pfam05 257 | 1.22e-15 |
| | | | | | | | | SH3_5, bacterial SH3 domain | pfam08 460 | 2.54e-14 |
| | | | | | | | | N-acetylmura moyl-L-alanine amidase | COG56 32 | 7.60e-05 |
| 39 | 20779 | 20276 | 599 | MANETKQPKVVGGINLSTRTKS KTFWVAIISAVALFANQITGAFG LDYSAQIEQGVNIVCSILTLLAG LGIIVDNNTKGLRDSDIVQTDYV KPRDSKDPNEFVQWQTNANN ASTFEIDSYENNAEPDTDSDE | putative holin [Staphylococcus phage K] | YP_024463.1 | 6e-89 (162/167) | Holin | Phage_holin_1 | pfam04 531 | 3.49e-25 |

Fig. 10G

| | | | | VPAIEDEIDGGSAPSQDEEDTE EHGKVFAEEEVK | | | | | |
|---|---|---|---|---|---|---|---|---|---|
| 40 | 21049 | 20864 | 600 | MASAKQLYYTESLVGKAIINNK VSNKEEVWDKLELLPETKLEDL DNKQMSEVIKKLNQINE | 61 | ORF233 [Staphylococcus phage G1] | YP_241098.1 | 9e-26 (61/61) | | No putative conserved domains have been detected |
| 41 | 21282 | 21211 | 601 | ACACCCUAGUAUAAUUAGU AGUACAAGGGUCUCCAAAAC CCUUAGUCUUUGUGCAAAUC AAAGAGGGUGUG | | | | | tRNA4-Trp | |
| 42 | 21361 | 21289 | 602 | GGUUCUUAGCUCAGAUGGU AGAGCACUAGAUUGAAGCUC UAGGUGUCAUUGGUUCAAAU CCAAUAGAAACCA | | | | | tRNA3-Phe | |
| 43 | 21441 | 21368 | 603 | GGCUCAUUGGUGUAACUGGU UAACACUGCCCUGUCACG GCAGAGAGUACGAGUUCGAG UCUCGUAUGGGUCG | | | | | tRNA2-ASP | |
| 44 | 22812 | 22594 | 604 | MKRQKMFYSSLICKECGNVFK VPRKRANKREEGHIKDIYCIKC CKTTKHEDNRSEAERRWDAIQ EELTKDN | 72 | ORF200 [Staphylococcus phage G1] | YP_241099.1 | 8e-35 (72/72) | | No putative conserved domains have been detected |
| 45 | 23499 | 23290 | 605 | MSKHIEITMSSGAKYFLVSTDE KSYNRQDIDYMLRGMDETSIKV YTESAITSPQVYINPNRIESFKIV F | 69 | ORF207 [Staphylococcus phage G1] | YP_241100.1 | 1e-32 (69/69) | | No putative conserved domains have been detected |
| 46 | 23844 | 23512 | 606 | LDKEINNLVSQVETIKSKIQEGN YIDRGTFKDLEVEVAELRKMIV SIDKDVAVNSEKQSAIYVQLER LDEKISELAGSTKTKDTKKKDT TEKVLLLVLGAILSFVFNKFA | 110 | ORF209 [Staphylococcus phage G1] | YP_241101.1 | 3e-52 (107/110) | | PHA02414, hypothetical protein / PHA024 14 / 1.54e-30 |
| 47 | 23857 | 24183 | 607 | LTKYKDILKLEFKDALAHFKRDR RYFHVYRIDRVLINGSIIYFDYY YLPSDDPNIVIKELDLQSFGKLR FEIDTKTSYGKVVTDNYMEIIND FLENYDIHSESETVRP | 108 | hypothetical membrane protein MbpC [Staphylococcus phage A5W] | ACB89047.1 | 4e-53 (105/108) | Membrane protein MbpC | No putative conserved domains have been detected |
| 48 | 24623 | 25009 | 608 | LNNNIAIFIFKTLVIIIFLLLLSVIN SLSLIYSIRPSVVMTYFIFGGIVS NVALTVTDKFLLKKEDPLPEYV LKKVEINDKEIRIKKIIESNYGIT AEEIKVRAKAQRRIEEDSKKED YDENKERN | 128 | hypothetical membrane protein MbpD [Staphylococcus phage A5W] | ACB89048.1 | 4e-48 (125/128) | Membrane protein MbpD | No putative conserved domains have been detected |
| 49 | 24987 | 25265 | 609 | MKTKKEIKEQRKELKDGATSVS LVKKGDKRIASPSRICSLCGQQ LSGMNYTKGKALSKVNHFHLQ | 92 | ORF161 [Staphylococcus | YP_241104.1 | 5e-47(92/92) | | No putative conserved domains have been detected |

Fig. 10H

| | | | YSKYIYFDICADINNCYKNLRKRGEMD | | phage G1] | | | | | |
|---|---|---|---|---|---|---|---|---|---|---|
| 50 | 25262 | 25672 | 610 | LSAENIRDINKKKLEEEDTRKYIADGFMNGIGKLMYEFNKKVDNKEIEVKDPNDLYKLFVIFSQMQNMVNETSEGGAIPQLSRPQQELFDEITTEDSNGESTVDLQKISEMSAEDITAMISEKEKVMNEENSETF | 136 | ORF133 [Staphylococcus phage G1] | YP_241105.1 | 2e-71 (135/136) | | | No putative conserved domains have been detected |
| 51 | 25687 | 27504 | 611 | MDGKELIKIAQETFQTEKITREQIDHIINMLNPSTYMLKYHTLRGHPITFSIPNRDRSKAQAHRPWQTRIVNDTHPNKAVIKSRQLGLSEMGVMEMVHFADMHSYANAKCLYTFPTNEQMKKFVQSRLNPVLEKEYFRDIVDWDKDSLGFKKIRNSSLFFRTSSKASTVEGVDIDYLSLDEYDRVNLLAESSALESMSSSPFKIVRRWSTPSVPGMGIHKLYQQSDQWYYGHRCQHCDYLNEMSYNDYNPDNLEESGNMLCVNPEGVDEQAKTVQNGSYQFVCQKCGKPLDRWYNGEWHCKYPERTKGNKGVRGYLITQMNAVWISADELKEKEMNTESKQAFYNYILGYPFEDVKLRVNEEDVYGNKSPIAETQLMKRDRYSHIAGIDWGNTHWITVHGMLPNGKVDLIRLFSVKKMTRPDLVEADLEKIIWEISKYDPDIIIADNGDSGNNVLKLINHFGKDKVFGCTYKSSPKSTGQLRPEFNENNNRVTVDKLMQNKRYVQALKTKDISVYSTVDDDLKTFLKHWQNVVIMDEEDEKTGEMYQVIKRKGDDHYAQASVYAYIGLTRIKELLKEGNGTSFGSTFVSTDYNQEGNKQFYFDE | 605 | gp74 [Listeria phage A511] | YP_001468454.1 | 0,0 (308/503) | Terminase large subunit | Terminase_GpA | pfam05876 | 4.8e-22 |
| 52 | 27497 | 28318 | 612 | MNRGEIDLTDKLFYGTISNEEINKSVLNLLGEELSLDYVSKNSDTLDVKYEHYYKSLGFDNFFDCFLYANREPEIVHKGGDKNLGGLNKVKRTVIRNGKEMEMTVYEDGNKENDSKEKQEGKEEVSRSAVGARAISNGEEGKVNPKKVANSLSNLSKKGVDVSHINTNSSLYKEFVDDNGDTLGITSFKRTENDILESYASSHDSDGVGARAIMEL | 273 | hypothetical protein KgORF36 [Staphylococcus phage K] | YP_024466.1 | 3e-153 (273/273) | | | No putative conserved domains have been detected |

Fig. 101

| | | | | | | | | | |
|---|---|---|---|---|---|---|---|---|---|
| 53 | 28296 | 28478 | 613 | LRLSIKENKNAVVYDIELPEAVE YLKTLGFKPNKDGYILRKKDVK QFLGDYSDFI | | | | | |
| 54 | 28475 | 28954 | 614 | VIIVILFSTIVIYSIVFILYIVLKTIYI KSNMSRIDNTTELLKILQEDIEG KIKKEGRNK | 60 | ORF235 [Staphylococcus phage G1] | YP_240894.1 | 3e-23 (59/60) | | No putative conserved domains have been detected |
| | | | | MTLEENKLTLEESITPLSKEEKE DSIKEFSSLLCEMVNRLYKSYN VFRQDPMDETQRLDGSLMVFQ SRLNDPLTGDLHDKMYKLAFS KRIDIFEANKQFRKDVEAGKAIE LGDVAIIDTALSNILSGNEFQGSI SFMLRKDFEEKERIRKEEEEKL NNL | 159 | hypothetical protein KgORF37 [Staphylococcus phage K] | YP_024467.1 | 5e-86 (159/159) | | No putative conserved domains have been detected |
| 55 | 28996 | 29322 | 615 | LKKKPQGNEVIITIITVMIAVFVVI MTIFFNKYQDAKEDKDRYQRL VEIYKKADNDGETKKKYVKRL NKAEEELKKVKKKQIIKIIIRSQV KKDKKIKKLERKYMM | 108 | hypothetical protein KgORF38 [Staphylococcus phage K] | YP_024468.1 | 4e-26 (68/69) | | No putative conserved domains have been detected |
| 56 | 30117 | 30221 | 616 | VDEEDKNEDTTDDKQPTEQPD DNNIDNEDKTEEE | 34 | hypothetical protein KgORF38 [Staphylococcus phage K] | YP_024468.1 | 2e-08 (34/34) | | No putative conserved domains have been detected |
| 57 | 30306 | 30647 | 617 | MNNITSLSVVFTCLSLLTLMIFVH SKFSSKNVFVLYVIYIAIIGITYI VLTMFQTTSVLIKNDVIDSIENT EHYIGFNDPIIIFTISFIGAILGGI WYKMMKIIKKSNFKDKK | 113 | hypothetical membrane protein MbpE [Staphylococcus phage A5W] | ACB89055.1 | 5e-56 (113/113) | Membrane protein MbpE | |
| 58 | 30665 | 31036 | 618 | LIFSKDKKWDEAKDFIKGCGQM QDNWIEIVDYYRQIGGKHVAVF IALNKVKYMILEATKDNKVILVD KDNNILLEDYDIVMESKKMFYYI EEPFEVKINIPGHIRDVTYNNTV VLTTVRGSRGD | 123 | hypothetical protein KgORF40 [Staphylococcus phage K] | YP_024470.1 | 2e-64 (122/123) | | No putative conserved domains have been detected |
| 59 | 31040 | 32731 | 619 | LADLFKQFRLGKDYGNNSTIAQ VPIDEGLQANIKKIEQDNKEYQ DLTKSLYGQOQAYAEPFIEMM DTNPEFRDKRSYMKNEHNLHD VLKKFGNNPILNAIILTRSNQVA MYCOPARYSEKGLGFEVRLRD LDAEPGRKEKEEMKRIEDFIVN TGKDKDVDRDSFQTFCKKIVR DTYIYDQVNFEKVFNKNNKTKL EKFIAVDPSTIFYATDKKGKIIKG GKRFVQVVDKRVVASFTSREL | 563 | putative portal protein [Staphylococcus phage K] | YP_024471.1 | 0.0 (562/563) | Portal protein | Phage_port al | pfam04 860 | 1.13e-13 |
| | | | | | | | | | | PHA02256, hypothetical protein | PHA022 56 | 6.49e-28 |

Fig. 10J

| | | | | | | | | | |
|---|---|---|---|---|---|---|---|---|---|
| | | | AMGIRNPRTELSSSGYGLSEVE IAMKEFIAYNNTESFNDRFFSH GGTTRGILQIRSDQQQSQHALE NFKREWKSSLSGINGSWQIPV VMADDIKFVNMTPTANDMQFE KWLNYLINIISALYGIDPAEIGFP NRGGATGSKGGSTLNEADPGK KQQQSONKGLOPLLRFIEDLVN RHIISEYGDKYTFQFVGGDTKS ATDKLNILKLETQIFKTVNEARE EQGKKPIEGGDIILDASFLQGTA QLQQDKQYNDGKQKERLQMM MSLLEGDNDDSEEGQSTDSSN DDKEIGTDAQIKGDDNVYRTQT SNKGQGRKGEKSSDFKH | | | | | |
| 60 | 32925 | 33698 | LEEIKFNAFVPMDLKKSVSTAS DTNEYSIVSGWASTPSMDLQN DIVNPKGIDIEYFKSQGYINYEH QSDKVVGIPTENCYVDIEKGLFI EAKLWKNDENVVKMLDLAEKL EKSGSGRRLGFSIEGAVKKRNI NDNRVIDEVMITGVALVKNPAN PEATWESFMKSFLTGHGTSPD TQVDAGALRKEEIASSITNLAYV TKIKDLKEFNDVWNGVVEDLSK SNSMGYEESVLTLQLAKGLSR KDAELAVMDINKQKLE | 620 | hypothetical protein KgORF42 [Staphylococcus phage K] | 257 | YP_024472.1 | 9e-147 (256/257) | Prohead protease | Peptidase_U35 | pfam04 586 | 8.72e-05 |
| 61 | 33717 | 34667 | MSKEMQNILEEYDKLNAQEAV SKSVEDDEKNTVESTEEQVAE TTEEPAKEPEKVSEEDAKEAQ EQGEKVESEEVAEGNEDEEVE KSAKESKDPVDQKOTKTENKD NEKRKNKDKKEDSDDEDKDT DDDKDKKEDKKEKTSKSISDED ITTVFKSILTSFENLNKEKENFA TKEDLSEVSKSINELSAKISEIQ AEDVSKSVDTDEEAVEKSVTST NGEQEKVEGYVSKSVDTEEQA ETGEAKSEEAEEVQEDNTFKG LSQEERTKFMDSYKAQAKDPR ASKHDLQSAYQSYLNINTDPTN ASEKDIKTVKDFAQI | 621 | hypothetical protein KgORF43 [Staphylococcus phage K] | 316 | YP_024473.1 | 4e-170 (316/316) | | No putative conserved domains have been detected | | |
| 62 | 34783 | 36174 | MTIEKNLSDVQQKYADQFQED VVKSFQTGYGITPDTQIDAGAL RREILDDQITMLTWTNEDLIFYR DISRRPAQSTVVKYDQYLRHG NVGHSRFYKEIGVAPVSDPNIR | 622 | putative capsid protein [Staphylococcus phage K] | 463 | YP_024474.1 | 0,0 (463/463) | Capsid protein | No putative conserved domains have been detected | | |

Fig. 10K

| | | | | | | | |
|---|---|---|---|---|---|---|---|
| | | | QKTVSMKYVSDTKNMSIASGL VNNIADPSQILTEDAIAVVAKTIE WASFYGDASLTSEVEGEGLEF DGLAKLIDKNNVIINAKGNQLTE KHLNEAAVRICKGFGTATDAY MPIGVHADFVNSILGRQMQLM QDNSGNVNTGYSVNGFYSSR GFIKLHGSTVMENELILDESLQP LPNAPQPAKVTATVETKQKGA FENEEDRAGLSYKVVVNSDDA QSAPSEEVTATVSNVDDGVKL SINVNAMYQQQPQFVSIYRQG KETGMYFLIKRVPVHDAQEDGT IVFVDKNETLPETADVFVGEMS PQVVHLFELLPMMKLPLAQINA SITFAVLWYGALALRAPKKWAR IKNVRYIAV | | | | |
| 63 | 36266 | 36562 | 623 | MLYYKKLLDKKMATVYGTVEID KDGVVKGLTKEQEKEFANVPG FEFEEEKKTTRKQSASTSKEEE PKEEEKKASTRKTTSTTRKSTA RKTTAKKDENK | 98 | ORF151 [Staphylococcus phage G1] | YP_240904.1 | 7e-46 (97/98) | No putative conserved domains have been detected |
| 64 | 36575 | 37483 | 624 | MVNSMFGGDLDPYEKSLNYEY PYHPSGNPKHIDVSEIDNLTLA DYGWSPDAVKAYMFGIVVQNP DTGQPMGDEFYNHILERAVGK AERALDISILPDTQHEMRDYHE TEFNSYMFVHAYRKPILQVENL QLQFNGRPIYKYPANWWKVEH LAGHVQLFPTALMQTGQSMSY DAVFNGYPQLAGVYPPSGATF APQMIRLEYVSGMLPRKKAGR NKPWEMPPELEQLVIKYALKEI YQWWGNLIIGAGIANKTLEVDGI TETIGTTQSAMYGGASAQILQI NEDIKELLDGLRAYFGYNMIGL | 302 | hypothetical protein KgORF45 [Staphylococcus phage K] | YP_024475.1 | 2e-177 (302/302) | No putative conserved domains have been detected |
| 65 | 37497 | 38375 | 625 | MEKPYMIGANSNPNVINKSTTY TTTTQADEQDKPKYTTRLEFDT IDMIRFINDRGIKVLWEEAYFCP CLNPDTGHPRVDCPRCHGKGI AYLPPKETIMAIQSQEKGTNQL DIGILDTGTAIGTTQLEKRISYR DRFTVPEVLMPQQMIYFVNKD RIRKGIPLYYDVKEVTYATQDG TVVEEDYEIKNNRLYLNEKYEN HTVTLKILMTLRYVVSDILKESR YQYTKFNQPKSKFENLPQKLLL | 292 | hypothetical protein KgORF46 [Staphylococcus phage K] | YP_024476.1 | 2e-170 (290/292) | No putative conserved domains have been detected |

Fig. 10L

| | | | | | | | | |
|---|---|---|---|---|---|---|---|---|
| 66 | 38375 | 38995 | 626 | KREDVIVLQDPYKNDGIEEDL EIQVDDPKASASNPSNLGGFF GGAFK MPVHGKRPNLFKNKNYKQVGK RTIDGMRSEVLDKLQATAQQV ENTSIKRMPTYLQITEKKLEKEG VVDLKKAFAHSSKKKTSKDGG WYLTVPIRIKTSRMNNSTYQDM RTLKVDKGTGSVSKITDYLEGR RKNVSHPSMKPEPMTHNMTKV KRGKQSSYFIFRTVSSKSPASS WILNRDKVNEDNFSKTTLKTVK QLMNWKMKNLN | 206 | hypothetical protein KgORF47 [Staphylococcus phage K] | YP_024477.1 | 1e-116 (206/206) | | No putative conserved domains have been detected |
| 67 | 39014 | 39850 | 627 | MAITSVDSYLLSEIKPRLNTVLE NCYIIDEVLKDFDYQTRESFKE AFCGKNAQHEVTVGFNFPKFK NNYEAHYLIQLGQQETKNSL GSIQSSYFEATGDTLVESSTAIR EDDKLVFTVSKPIGELIKVEDIE FAKYDNLQVEGNKVSFKYQTN EDYENYNANIIFTEKKNDSKGL VKGFTVEEQVTVVGLSFNVDV ARCLDAVLKMILISMRDSIEEQQ TFQLQNLSFGDIAPIIEDGDSMI FGRPTIIKYTSSLDLDYTITQDIN KLTFKERKDWK | 278 | hypothetical protein KgORF48 [Staphylococcus phage K] | YP_024478.1 | 3e-160 (278/278) | | No putative conserved domains have been detected |
| 68 | 39852 | 40067 | 628 | MARKKTPENNTPKFNGYVHIDT FLDTAKTLFNMKDSQVAGFKA YMEGSHYLFSEQEFLPSLEKYL GRKLDI | 71 | ORF202 [Staphylococcus phage G1] | YP_240909.1 | 2e-34 (70/71) | | No putative conserved domains have been detected |
| 69 | 40094 | 41857 | 629 | MAVEPFPRRPITRPHASIEVDT SGIGGSAGSSEKVFCLIGQAEG GEPNTVYELRNYAQAKRLFRS GELLDAIELAWGSNPNYTAGKI LAMRIEDAKPASAEIGGLKVTS KIYGNVANNIQVGLEKNTLSDS LRLRVIFQDDRFNEVYDNIGNIF TIKYKGEEANATFSVEHDEETQ KASRLVLKVGDQEVKSYDLTG GAYDYTNAIITDINQLPDFEAKL SPFGDKNLESSKLDKIENANIK DKAVYVKAVFGDLEKQTAYNGI VSFEQLNAEGEVPSNVEVEAG EESATVTATSPIKTIEPFELTKLT GGTNGEPPATWADKLDKFAHE GGYYIVPLSSKQSVHAEVASFV KERSDAGEPMRAIVGGGFNES | 587 | major tail sheath protein [Staphylococcus phage 812] | ABL87117.1 | 0.0 (583/587) | Major tail sheath protein | Phage_sheath 1 pfam04984 6.04e-09 |

Fig. 10M

| | | | | | | | |
|---|---|---|---|---|---|---|---|
| | 41930 | | KEQLFGRQASLSNPRVSLVAN SGTFVMDDGRKNHVPAYMVA VALGGLASGLEIGESITFKPLRV SSLDQIYESIDLDELNENGIISIE FVRNRTNTFFRIVDDVTTFNDK SDPVKAEMAVGEANDFLVSEL KVQLEDQFIGTRTINTSASIIKDF IQSYLGRKKRDNEIQDFPAEDV QVIVEGNEARISMTVYPIRSFKK ISVSLVYKQQTLEA | | | | |
| 70 | 42334 | 630 | MASEAKQTVHTGNTVLLMIKGK PVGRAQSASGQREYGTTGVYE IGSIMPQEHVYLRYEGTITVERL RMKKENFADLGYASLGEEILKK DIIDILVVDNLTKQVIISYHGCSA NNYNETWQTNEIVTEEIEFSYL | 134 | capsid protein [Staphylococcus phage 812] | ABL87118.1 | 3e-73 (134/134) | Capsid protein | No putative conserved domains have been detected |
| 71 | 42754 | 631 | MGKNQYTFNIKENKNKWYEW CKLQNVKPLVEYENAQQIFYFE FLEGKFKGLIGKTYWASINRGS NMRMSCLTSESKDKYLKNLGK RKGIEVVEDYKGGRKLKHKFIV LEGKYQGCEGYITLNDLENLGR VDNRSLSEKGRKQYFDKQARL RDCIILEYPKDYRIKTKDKIVVKD KEGHVHNIIVQDFFEKSSLLELS CASEGEKIVKEILTKNSIKFEKE KSFRNKEGKVQRFDFYINENN KEYAIEYNGAQHYIDSTGYLKD TLETTQKRDKLKKEYSKDKGIN LLIIPYTITDKKEMEKIILNFLNK | 309 | ORF018 [Staphylococcus phage Twort] | YP_238556.1 | 2e-19 (79/239) | | No putative conserved domains have been detected |
| 72 | 43741 | 632 | MNNRQAKLKGYNQFHYYDFPT TKGKFKDIMKRKSRTELKKDLQ KERKYYLDK | 52 | ORF245 [Staphylococcus phage Twort] | YP_238558.1 | 3e-11 (37/52) | | No putative conserved domains have been detected |
| 73 | 43889 | 633 | LTNKRKTIGKMSNTRATWNINP VTKVKKDKTKYSRKNKHKGLD NYN | 46 | ORF293 [Staphylococcus phage G1] | YP_240912.1 | 1e-10 (44/46) | | No putative conserved domains have been detected |
| 74 | 44074 | 634 | MRIYISNDYNKELLDKCLSDINK DKGNINYSINYGEGNIKEADVEI IKLDKNLLETESRAFAYSKFVED CIFLFPYKIALLRGGKIELRFDW NEIL | 96 | No significant similarity found. | | | | |
| 75 | 44364 | 635 | MSTFWSERRTTNKDRQVKKHY TQMSMYERKKCVELLQETITEN RIINFTRHSAKKVKGKPTTNIPK LIGFIFKNKFAYENIIEYNNTDYN GNIERRIVVKHPKVITVEGKLSY | 152 | hypothetical protein KgORF51 [Staphylococcus phage KJ] | YP_024481.1 | 2e-83 (151/152) | | PHA02264, hypothetical protein | PHA022 64 | 2.05e-29 |

Fig. 10N

|    |       |     |     |     |     |     |     |     |     |
|----|-------|-----|-----|-----|-----|-----|-----|-----|-----|
|    |       |     | QFLTISLEDARVITWYNSVDDTHRTLDLNYYSKDLTIQ | | | | | | |
| 76 | 44856 | 45050 | 636 | MGLTIVNGYFFLSSIIFNVSILNGKGTVTRESLAMSQALVIITSIQFLAFLIINGIYYSLKYM | 64 | ORF215 [Staphylococcus phage G1] | YP_240914.1 | 4e-19 (49/64) | | No putative conserved domains have been detected | | |
| 77 | 45066 | 45218 | 637 | MEIYIVIDLRGSTEEETSMDFKAFRKLQDAITYVDGNGNRDLHIIPLELE | 50 | No significant similarity found. | | | | No putative conserved domains have been detected | | |
| 78 | 45286 | 45597 | 638 | MSQDKLRAIYTEMKVELHKFPKEVDVTSKSTAIAINQILDKFKTLTEQAGKITRKYLEGQEILTIDYEYYDSLQEYYIYLLRNSEKIEQSLQEITKRTGEYVK | 103 | hypothetical protein KgORF52 [Staphylococcus phage K] | YP_024482.1 | 3e-51 (102/103) | | PHA0_2265, hypothetical protein | PHA022 65 | 2.51e-17 |
| 79 | 45730 | 46188 | 639 | MAEEIKKEQDVQETTKEEKKDVSKMTPEEIDKLKYQDKQEKEQVINKVIKGVNDTWEKEYNFEELDLRFKVKIKLPNAREQGNIFALRSAYLGGMDMYQTDQVIRAYQMLATLQEVGIEVPKEFQDPDDIYNLYPLTVMYEDWLGFLNSFRY | 152 | hypothetical protein KgORF53 [Staphylococcus phage K] | YP_024483.1 | 2e-82 (152/152) | | No putative conserved domains have been detected | | |
| 80 | 46232 | 46768 | 640 | MESIVKQPLSRNLWAIMKEFNVLPTEQRFKDLDDYQIEFIIGNMNRDVYEHNKQLKQAQKGGKFDSQFEDDDSSWWNESHEDFDPVPDFLDADDLAQQMEAKLSDRDKEERAKRNDAELNDETEGLTTQHLAMMEYIRQKQQELDDEVGNGKTSEDDATISQDSVNKALEDLDDDWYM | 178 | hypothetical protein KgORF54 [Staphylococcus phage K] | YP_024484.1 | 8e-99 (178/178) | | No putative conserved domains have been detected | | |
| 81 | 46821 | 50879 | 641 | MMAMNDDYRLVLSGDSSDLENSLKAIELYMDSLESKNIDAPLDNFLKLKVIAKEVKNVQNAMDKQDGKSVISSKDMDESIKSTQSATKNINELKKALDDLQKENISKGIAPDPEVEKAYAKMGKVVDETQEKLEKMSSQKIGSDASIQNRIKEMKTLNQVTEEYNKISKDSSATKDYTKRLRANRNMTRGYMERSEGTGRLTYDQGARVRSELGKVSSYESQRKQNQRNLGQAREQYSNYRNQQQDLTKRRASGQINKAQYEQELASIKQEMKAREELISNYEKLGAELDKTVQYYKGSVQKDFQSRDVDQQRGTFGRMVQERLPSIGSHAMMGTTAMATGLYMKGASILSETNRPMVTSLGQN | 1352 | hypothetical protein KgORF55 [Staphylococcus phage K] | YP_024485.1 | 0.0 (1343/1351) | | Smc, chromosome segregation ATPases | COG11 96 | 8.71e-06 |

Fig. 100

| 82a | 50957 | 52159 | 642 | MKRLRRPKVRIEIVTDDNTFTL SDNMDIDSVRNAYGDLSIDNKL GYNSTDMLKMATSYEASVGHK SDEDTMAGTKQLAIGGRSLGIK DQEAYQESMGQIMHTGGVNS DNMKEMQDAFLGGIKQSGMV GRQDEQLKALGSIAEQSGEGR TLTKDQMSNLTAMQSTFAESG SKGLQGEQANAINSIDQGLKN GMNSSYARIAMGWGTQYQGL EGGYDLQKRMDEGISNPENLT DMADMATQMGGSEKEQKYLF NRSMKEIGANLTMEQSDEIFKD SKEGKLSKEELAKKAKKMEKE GKKEGEDNATDYKESKSGKND QNKSKTDDKAEDTYDMAGPLR DAHSALAGLPAPIYLAIGAIGAF TASLIASASQFGAGHLIGKGAK GLRNKFGRNKGGSSGGNPMA GGMPSGGGSPKGGGSPKGG GTRSTGGKILDSAKGLGGFLVG GAGWKGMFGGESKGKGFKQT SKEAWSGTRKVFNRDNGRKA MDKSKDIAKGTGSGLKDIYNDS IFGKERRQNLGEKAKGFGGKA KGLYGKFADIKFGDGGKNGILS QSPKAGGSGIGKLGKLAGGLG KGAGVLGVATSALSLIPALASG DSKAIGGGIGSMGGGMAGASA GASIGALFGGVGAIPGALIGGAI GSFGGGAVGEKVGDMAKKAN TKEGWNLGWTNGDKDGKNKF QDSLLGKPISKAWSGITGLFDN DAEASEENSKDKKKGVKGVKG DTKKKEKMTAEQLREKNNQSE TKNLKIYSDLLDRAQKIIESAKGI NIDGGTSDSGSDSGGSASDVG GEGAEKMYKFLKGKGLSDNQV GAVMGNLQQESNLLDPNAKNPS SGAFGIAQWLGARKTGLDNFA KSKGKKSSDLDVQLDYLWKEM QSDYESKNLKNAGWSKGGSLE QNTKAFATGFERMGANEAMM GTRVNNAKEFKKKYGGSGGG GGGGAMSSTYQEAMSNPVLTT GSNYRGSNDASNASTTNRITV NVNVQGGNNPEETGDIIGGRIR EVLDSNMDIFANEHKRSY | 400 | hypothetical protein | YP_024486.1 | 0.0 | Tail lysin | No putative conserved domains |
|---|---|---|---|---|---|---|---|---|---|

Fig. 10P

| | | | | | | | | |
|---|---|---|---|---|---|---|---|---|
| | | | RFEDTRDYNGDEFGAKLLGFQ TKNSMEDDSSVFQINMAGDTY WDKLVMANDIIRIFITFNDDPND KEGRQERLIQVGMVSQVSKVG SYGNDGTQFRITGQSFVKPFM KFGLGVIQEVQAVLPEVGWLID GDGDNEVKFTGSSAHEVMTGII RRFVPYMKYNYTEKTYNTIDSY LDYDDLSSWDEFENLTEVSAFT NFDGSLKQLMDMVTARPFNEL FFKNSEKTPGKAQLVLRKTPFN PTEWRALDMIKVPTEDFIEEDV GKSDVETYSIFTATPAGMLKEL NGDVFSKPQFHPELTDRYGYT KFEVENIYLSTKSGSATEDSDS SGDDNGTERGTYSKIMKDLSN YGRDNISKGIDKYTSKLSSKYK NLKKPKLKKL | | KgORF56 [Staphylococcus phage K] | (390/400) | | have been detected |
| B2b | 52258 | 52368 | 643 | LTKDKLKSILKEKFKTQDDFNN SKKRKLKQMHLKN | 36 | | 7e-04 (23/23) | |
| B2c | 52365 | 53381 | 644 | LTTKYRFGNKTHATTLLDEYIKY KGEPPNDEAFDKYLKAIEGVSN IATDTGSDASDSPLVMFSRMLF NWYHGNPNFYAGDIIVLGDPKY DLGKRLFIEDKQRGDTWEFYIE SVEHKFDYKQGYYTTVGVTRG LKDAILEDGKGSPHRFAGLWN QSSDFMGGLMGEDTSKELKEK GVSEKQSSGDKDGGSDSGGA QDGGSLDSLKKYNGKLPKHDP SFVQPGNRHYKYQCTWYAYN RRGQLGIPVPLWGDAADWIGG AKGAGYGVGRTPKQGACVIW QRGVQGGSAQYGHVAFVEKV LDGKKIFISEHNWATPNGYGT RTIDMSSAGKNAQFIYDKK | 338 | | 0.0 (334/338) | CHAP | pfam05 257 | 2.48e-13 |
| B3 | 53395 | 54282 | 645 | MATDKEAKDVIDKFIDNVFNFD VLTMERVKEKDEEIKKITTDDM YEKVVYIRPYVGVIQSLNPQHV QYESFSNNGYDIEAELSFRKVS YLVDKGSIPTDSLSTLTVHLVER NQELLIDYFDEIQDVLYGEYME EEYVFDEDVPLSTILALDLNDNL KSLSNIKYMFKGAPKENPFGTD KDVVIDTYNLLYWLYLGEDEEL AYPMNINYFFTEGRFFTIFGKG HKYKVDVSKFIVGDILFFGRSD | 295 | hypothetical protein KgORF57 [Staphylococcus phage K] | YP_024487.1 | 9e-166 (292/295) | No putative conserved domains have been detected |

Fig. 10Q

| | | | | | | | | |
|---|---|---|---|---|---|---|---|---|
| 84 | 54282 | 56828 | 646 | TNIGIYVGDGEFISMGKFPKDE TPIGKYKLDDYWNEFNGRVMR FDEEVYI MVVRFQSSMGRSLKRVDSDDL NVKGLVLATVSKINYKYQSVEV KVNNLTLGSRIGDDGSLAVPYP KSFIGRTPEGSVFGTKPLITEGS VVLIGFLNDDINSPIILSVYGDNE QNKMINTNPLDGGKFDTDSVY KYSSALYEILPSLNYKYDDGEG TSIKTYNGKSFFSMTSGEEEKP QATDFYTGTEYQDLFTSYYGN KTLIEPRIQKAPNMLFKHQGVF YDDGTPDNHITTLFISERGDIRA SVLNTETQKRTTQEMSSDGSY RVIKQDDDLMLDEAQVWIEYGI SEDNKFYIKNDKHKFEFTDEGI YIDDKFPMLENLDESIAEAMKNL NEIQKELDDINYLLEGVGKDNL EELIESTKESIEASKKATSDVNR LTTQIAEVSGRTEGIITQFQKFR DETFKDFYEDASTVINEVNQNF PTMKTDVNTLKTKVDNLEKTEI PNKTRLTELENNNNNADKIISD RGEHIGAMIQLEENVTVPTRNV MPIPWSKVTYNNAEFWDSNNP TRLVVPKGTKVRVAGNVLWDS NATGQRMLRILKNGTYSLGLPY TRDVAISTAPQNGTSGVIPVKE GDYFEFEAFQDSEGDRQFRAD PYTWFSIEAIELETETMEKDFM LIGHRGATGYTDEHTIKGYQMA LDKGADYIELDLQLTKDNKLLC MHDSTIDRTTTGTGKVGDMTL SYIQTNFTSLNGEPIPSLDDVLN HFGTKVKYIETKRPFDANMDK ELLTQLKAKGLIGIGSERFQVIIQ SFARESLINIHNQFSNIPLAYLT STFSESEMDDCLSYGSYAIAPK YTTITKELVDLAHSKGLKVHAW TVNTKEEVQSLIQMGVDGFFT NYLDEYKKI | putative glycerophosphoryl diester phosphodiesterase [Staphylococcus phage K] | YP_024488.1 | 0.0 (838/848) | Glycero- phosphoryl diester phospho- diesterase | GDPD_SaG lpQ like, glycerophos -phodiester phospho- diesterase domain | cd08601 | 1.70e- 60 |
| 85 | 56935 | 57726 | 647 | MPQSDGISNLHRIALRFPKEGG GYDMYRFKVNPENYTIDSPQR TTAIKTKSDIVIEDYGKDIEVINF TGTTGFRPVREADGLKTGKQK MEELQSRVSEYAMQGGSGNV | hypothetical protein KgORF59 [Staphylococcus phage K] | YP_024489.1 | 1e-150 (262/263) | | No putative conserved domains have been detected | | |

Fig. 10R

| | | | | | | | |
|---|---|---|---|---|---|---|---|
| 86 | 57726 | 58250 | 648 | SGSYLQFFNFTDDSYYKVHLAP QGLKITRSKDEPLLFRYEITLVVI GSLTEADRSAVTTEEFGNVKP NASQRVDEGIKELDKNARKTR DRNNQEISKRENTIPKSTGDNT NEGNRLKQSFPSSSIYNPRQST NGLKGNIDNMALIIGYGDGGVS s | | | No putative conserved domains have been detected |
| | | | | MNNFIPQPQGLLRFLNALDADL TSSHMNLLDEEVSFSVSKFYTPQ LQLSELAKKVLTNIKTDDIPVLE REFNDNTIIHKANDTLLKVQAP RMYMILQSIVLEAYAIVNCFVEN PSSLKYLTEEDVSITRENLNYV ADYLGNYDDYNSVVLDLRDLD LCFSAIELQLPLIKKEANV | 174 | ORF078 [Staphylococcus phage G1] | YP_240925.1 | 8e-95 (173/174) | |
| 87 | 58250 | 58954 | 649 | MRFKKHVVQHEETMQAIAQRY YGDVSYWIDLVEHNNLKYPYLV ETDEEKMKDPERLASTGDTLIIP IESDLTDVSAKEINSRDKDVLVE LALGRDLNITADEKYFNEHGTS DNILAFSTNGNGDLDTVKGIDN MKQQLQARLLTPRGSLMLHPN YGSDLHNLFGLNIPEQATLIEM EVLRTLTSDNRVKSANLJDWKI QGNVYSQQFSVEIKSVEESINF VLGQDEEGIFALFE | 234 | putative bacteriophage baseplate protein [Staphylococcus phage K] | YP_024491.1 | 2e-134 (234/234) | Baseplate protein | DUF1371, Protein of unknown function | pfam07 115 | 7.96e-04 |
| 88 | 58969 | 60015 | 650 | MKTRKLTNILSKLIDKTMAGTSK ITDFTPGSASRSLLEAVSLEIEQ FYILTKENIDWGIQEGIIEAFDFQ KRQSKRAYGDVTIQFYQPLDM RMYIPAGTTFTSTRQEYPQQFE TLVDYYAEPDSTEIWVEVYCKE TGVAGNVPEGTINTIASGSSLIR SVNNEYSFNTGTKEESQEDFK RRFHSFVESRGRATNKSVRYG ALQIPDVEGVYVYEETGHITVF AHDRNGNLSDTLKEDIIDALQD YRPSGIMLDVTGVEKEEVNVSA TVTISNKSRIGDTLQKHIEGVIR SYLNNLKTSDDLIITDLIQAIMNI DDVLIYDVSFDNLDENIIVPPQG IIRAGEIKVELK | 348 | hypothetical protein KgORF62 [Staphylococcus phage K] | YP_024492.1 | 0.0 (347/348) | | XkdT, Un-characterize d homolog of phage Mu protein gp47 | COG32 99 | 3.44e-05 |
| 89 | 60036 | 62600 | 651 | VANFLKNLHPLLRRDRNKKDN QDPNFALIDALNEEMNQVEKD AIESKLQSSLKTSTSEYLDKFG DWFGVYRKTDENDDVYRARIIK | 854 | hypothetical protein KgORF63 [Staphylococcus phage K] | YP_024493.1 | 0.0 (498/545) | | No putative conserved domains have been detected |

Fig. 10S

| | | | | | | | | |
|---|---|---|---|---|---|---|---|---|
| 90 | 62711 | 63232 | 652 | YLLLKRGTNNAIIDAIKDYLGRD DIDVSVYEPTNIFYTNKSHLNG EDHLMGYYRFAVINVSIGDYF PVEIIDVINEFKPAGVTLYVTYD GASTIRGGAIIKWLDGLPKIETY QEFDRFTGYDDTFYGHINMNQ SKDTDNSTSDIFKTNHSLINSLD VLTGSSSVGRQYVNYGYITSYV YNPGMTSSVNQISASTEGRGQ EVPTDYYMYTSTKNNNTVELS MQTSGVSYLYNNFNFRDYMS KYRPQVNLQSDEARRIVSDYIK ELSIDYYLSAVIPPDESIEIKLQV YDFSINRWLTVSINNLSFYEKNI GSNIGYIKDYLNSELNMFTRLEI NAGKRDSVDIKVNYLDLMFYYY ERGIYTIKPYKALVENYLDISRE TYVEAFKISSLSNGDIITKTGYL PIGYLRVSGDIDNLSNHIEIITD NNTNSITSTLLEDDSNSLILSYG NVKTNIHSFELNSDASISNIKFE YSYYGDAWEELTVLTEISEGET IVPNLIDLYGLQTVDYSNINPM SKVSLRSIWNVKLGELNNKEGS LSNMPNDYFNAVWQDIDKLSDI DLGSMRMIKDTEGGVFDGATG EIIKATLFNVGVVTDLDMLAYTL TNYTEPITLGSSRLISELKEELLT SESFNVDNRIKVIDSISEQLPNN NILSNSYQTQTITQNGFAKYNL KEPIEQRKQYNLRIHGDFKEGL ERLAIGNSNGSFNEVFVYPENI KDGIVDITYTSRDDNYAEGKQR LNNDYRVYAQPYDSEWTIYSL ELIKV MAIATYNSHVELAKYLVSKADS VYLTIGKSTPWSNETNPPQPDE NATVLQEVIGYKKATKVTLVRP SKSPEDDNKNLISYGNKSWVE VTPENAKDEGAKWVYLESSIV GDELPLGTYRQVGFVMDLVAK SGISKFNLVPSEVESTGTLLFFD NKQFQNRSEQTTAKERFIVEV | phage K] hypothetical protein KgORF64 [Staphylococcus phage K] | YP_024494.1 | 3e-95 (172/173) | Baseplate structural protein | Phage-Gp8, bacteriopha ge T4 baseplate structural proteins | pfam09 215 | 6.79e-04 |
| 91 | 63253 | 66711 | 653 | MAINFKGSPYLDRFDPSKDRTK VLFNPDRPLQQAELNEMQSID QYYLKNLGDAIFKDGDKQSGL GFTLSEDNVLTVNPGYVYINGK | hypothetical protein KgORF65 [Staphylococcus phage K] | YP_024495.1 | 0.0 (1147/1152) | | No putative conserved domains have been detected | | |

Fig. 10T

IRYYDNDDSVKITGVGKETIGIK
LTERIVTPDEDASLLDQTSGVP
SYFSKGADRLEEKMSLTVNDP
TSATIYTFMDGDLYIQSTNAEM
DKINKVLAERTYDESGSYKVNG
FELFSEGNAEDDHVSVVVDA
GKAYVKGFKVDKPVSTRISVPK
SYDLGTAENESTIFNKSNNSISL
ANSPVKEIRRVTGQVLIEKERV
TRGAQGDGQDFLSNNTAFEIV
KVWTETSPGVTTKEYKQGEDF
RLTDGQTIDWSPQGQEPSGGT
SYYVSKYKNKRMEVGKDYEVT
TQGEGLSKKWYINFTPENGAK
PIDQTVMLVDYTYYLARKDSVFI
NKYGDIAILPGEPNIMRLVTPPL
NTDPENLQLGTVTVLPDSDEAV
CISFATRLSMEDLQKVKTRVD
NLEYNQAVNALDDGAMEGQN
PLTLRSVFSEGFISLDKADITHP
DFGIVFSFEDAEATLAYTEAVN
QPKIIPGDTTAHIWGRLISAPFT
EERTIYQGQASETLNVNPYNIP
NKQGVLKLTPSEDNWIDTENVT
ITEQKTKKVTMKRFWRHNESY
YGETEHYLYSNLQLDAGQKWK
GETYAYDREHGRTGTLLESGG
QRTLEEMIEFIRIRDVSFEVKGL
NPNDNNLYLLFDGVRCPITPAT
GYRKGSEDGTIMTDAKGTAKG
KFTIPAGIRCGNREVTLKNANS
TSATTYTAQGRKKIVQDIIIRTR
VTVNLVDPLAQSFQYDENRTIS
SLGLYFASKGDKQSNVVIQIRG
MGDQGYPNKTIYAETVMNADD
IKVSNNASAETRVYFDDPMMA
EGGKEYAIWIITENSDYTIMVVG
TRTKPKIDKPNEVISGNPYLQG
VLFSSSNASTWTPHQNSDLKF
GIYTSKFNETATIEFEPIKDVSA
DRIVLMSTYLTPERTGCTWEM
KLILDDMASSTTFDQLKWEPIG
NYQDDLDVLGLARQVKLRATFE
SNRYISPLMSSSDLTFTTFLTEL
TGSVVGRAIDMTEAPYNTVRFS
YEAFLPKGTKVVPKYSADDGK
TWKTFTKSPTTTRANNEFTRYV
IDEKVKSSGTNTKLQVRLDLST

Fig. 10U

| | | | ENSFLRPRVRRLMVTTRDE | | | | No putative conserved domains have been detected | |
|---|---|---|---|---|---|---|---|---|
| 92 | 66760 | 66918 | 654 | MPREVRDPYSQAKLFIPTVEEK SIKELEKTYKEKIDEATKLINELK KERGEK | 52 | ORF262 [Staphylococcus phage G1] | YP_240931.1 | 3e-20 (52/52) | | |
| 93 | 66919 | 68833 | 655 | MAFNYTPLTETQKLKDMYPKV NDIGNFLKTEVNLSDVKQISQP DFNNILASIPDSGNYVTNSKG APSGEATAGFVRLDKRNVNYY KIYYSPYSSNKMYIKTYANGTV YDWISFKLDEGNLYNEGNTLNV KELTESTTQQVTLVNPPKENLN TGWVNYKESKNGVSSLVEFNP VNSTSTFKMIRKLPVQEQKPNL LKDSLFVYPETSSSNIKTDNWN TPPFWGYTANSGRSGVRFRG ENTIQIDDGSSTYPTAMTNRFK MGNELSVGDTITVSVYAKINDP ALLKDNLVVFELAGYDMVDRT DNPYTGGRREITASEITTEWKK YSFTFTIPENTIGASGVKVNYVS LLLRMNCSSSKGNGAVVYYAL PKLEKSSKVTPFITHATDVRKY DEIWSNWQEVISKDELKGHSP VDIEYNDYFKYQWWKSEVNEK SLKDLAMTVPQGYHTFYCQGSI AGTPRGRSIRGTIQVDYDKGDP YRANKFVKLLFTDTEGIPYTLYY GGYNQGWKLLKQSETSTLLWE GTLDFGSTEAVNLNDSLDNYDL IEVTYWTRSAGHFSTKRLDIKN TSNLLYIRDFNISNDSTGSSVDF FEGYCTFPTRTSVQPGMVKSIT LDGSTNTTKVASWNEKERIKVY NIMGINRG | 639 | hypothetical protein KgORF66 [Staphylococcus phage K] | YP_024496.1 | 0.0 (617/640) | PHA01818, hypothetical protein | PHA018 18 | 6.90e-04 |
| 94 | 68862 | 69236 | 656 | MAVKYDIGNNEIVLHLREGKYIT GFTTVGGYDKELGQVKVNREIL PAYFFDNFAYERYLYYSKPEEV IENKNYVPPQINNGDEESQONT VPKEQYDSLKEELELMRKQQE AMMEMLQKLLGQKG | 124 | hypothetical protein KgORF67 [Staphylococcus phage K] | YP_024497.1 | 3e-63 (121/124) | DUF2977, Protein of unknown function | pfam11 192 | 2.94e-12 |
| 95 | 69243 | 70619 | 657 | MALNFTITENNVIKDLTTQVNN IGEELTKERNIFDITDDLVYNFN KSQKIKLTDDKGLTKSYGNITAL RDIKEPGYYYIGARTLATLLDRP DMESLDVVLHVVPLDTSSKVV QHLYTLSTNNNQIKMLYRFVSG NSSSEWVQFIQGLPSNKNAVISG | 458 | hypothetical protein KgORF68 [Staphylococcus phage K] | YP_024498.1 | 0.0 (445/458) | PHA01818, hypothetical protein | PHA018 18 | 0.0 |

Fig. 10V

| | | | | | | | | |
|---|---|---|---|---|---|---|---|---|
| 96 | 70709 | 72457 | 658 | TNILDIASPGVYFVMGMTGGMPSGVDSGFLDLSVDANDNRLARLTDAETGKEYTSIKKPTEVYTAWKKEFEPKDMEKYLLSSIRDDGSASFPLLVYTSDNKTFQQAIIDHIDRTGQTTFTFYVQGGVSGSPMSNSCRGLFMSDTPNTSSLHGVYNAIGTDGRNVTGSVVGGNWTSPKTSPSHKELWTGAQSFLSVGTTKNLADDISNYSYVEVYTKHKTVEKTKGNDDSGTICHKFYLDGSGTYVCSGTFVSGDRTDTKPPVTEFYRVGVSFKGSTWTLVDSAVQNSKTQYVTRIIGINMPMRLRIKNLYTYVEFEEDDKYLKDIFLKRVHTTIGARQEGFQYSPAYKRGSWDGYVDFYVYEEDKFPTGLLFKIELLLGELQSRYNFQFETIDERDESFLSEEDIDDEITLLDNNVGQITLRDYQYEAVYNSLTFYNGIAHLATNGGKTEVASGIIDQLLPQLEKGERVAFFTGSTEIFHQSADRLQERLNIPIGKVGAGKFDVKQVTVVMIPTLNAMLKDPTQGVKVTPKQNISKKIAQEILPKFEGGTNQKKLLKVLLDNTTPKTKVEQNVLSALEIIYQNSKTDAEVLLNLRNHNAHFQKIVREKNEKKYDKYQDMRDFLDSVTVMIVDEAHHSKSDSWYNNLMTCEKALYRIALTGSIDKKDELLWMRLQALFGNVIARTTNKFLIDEGHSARPTINIIPVANPNDIDRIDDYREAYDKGITNNDFRNKLIAKLTEKWYNQDKGTLIIVNFIEHGDTISEMLNDLDVEHYFLHGEIDSETRREKLNDMRSGKLKVMIATSLIDEGVDISGINALILGAGGKSLRQTLQRIGRALRKKDDNTTQIFDFNDMTNRFLYTHANERRKIYEEEDFEIKDLGK | putative helicase [Staphylococcus phage K] | YP_024499.1 | 0,0 (582/582) | | Helicase | HELICc, helicase superfamily c-terminal domain | cd00079 | 1.80e-12 |
| 97 | 72469 | 74082 | 659 | MATKTQRKLYQYLEENATENKFHISTKKELADSLGVSISALSNNLKKLEEENKVVTVSKRGRKNGGVIITLVREYDTEELKEFNNSTDNIITSDLQYAKALREKHFPSYRYERKEQRRRTKIEMAQYNAIKDEK | putative Rep protein [Staphylococcus phage K] | YP_024500.1 | 0,0 (531/537) | | Transcription regulator protein | HTH_ARSR subfamily of helix-turn-helix bacterial transcription | cd00090 | 4.28e-03 |

Fig. 10W

| | | | | | | | | | |
|---|---|---|---|---|---|---|---|---|---|
| | | | RRIIADMNFYSEGLPYPSKDIFN MSYDPEGFYKAYILCKLYDQYA ISHMDAKHTSHLKAMSKATTKD EYDYHQHMSEYYRNKMIQNLP RNSVSDNFFGSKMFNTFYNFY LKIKDKNINVFKYMKNVFKNVTF YYENGMQPNPIPSPNFFSSDK YFKNYNNYIKGIKKGINSTNRHL GDTDSIINSSDYVKNPAVLHLH QLYTGLNSTLHDIDTMFEQAL DLENASYGLFGDMKHIIILQYN SMIEEEIKNLPIEEKDIINKYYKQ CIINNYSPTSISPSAARLSMFTMQ KEHIVYNKQLNKGIKREDLLPLS LGGIVNKDSLSSMDIQNLEQNG NEYLYMRQHTSTYYILRMFGD YLGYEVNLREVKYNVEKYNLIDK IPLTKEGMLDYNKLIHLVEEEVN NYE | | | | | | |
| 98 | 74075 | 75517 | 660 | MSKKIKELILHKSMKDIHFAREV LDNLPKNLFSAESEDMGYLFTA IKRTAHISDKMSNEALAIKVEQL MGNNKEDEEKVTKTLTYLEDLY KVDVNEKDESVNYEIEKYIKTE MSKEVLVKFIAENKQEDSDNLH ELVDKLKQIEVSDISGGNGEFID FFEDTEKKQELLSNLATNKFST GFTSIDNHIEGGIARGEVGLIIAP TGRGKSLMASNLAKNYVKSGL SVLYIALEEKMDRMVLRAEQQ MAGAEKSQIVNQDMSLNNKVY DAICNHYQKNRKLLGDFYISKH MPGEVTPNQLEQIIVNTTIKKDK NIDVVIIDYPHLMRNPYAKYHSE SDAGGKLFEDIRRLSQQYGFV CWTLAQTNRGAYGSDVITSEH VEGSRKIVNAVEVSLAVNQKDE EFKSGFLRLYLDKIFRNSSNTGE RFVNLKVEPTKMVRDETPEEK QEHIQLLSDNGKEDTSKFQNK DNKIEAINNTFGGLPGV | 480 | putative helicase [Staphylococcus phage K] | YP_024501.1 | 0.0 (480/480) | Helicase | 41 helicase | regulatory proteins | PHA025 42 | 1.06e-05 |
| 99 | 75596 | 76621 | 661 | MKFVFFTDSHFHLFTNYAKPDN EFVNDRFKEQIEALQKVFDIAK KEEATVIFGGDLFHKRNSVDTR VYNKVFSTFAKNNEVPVLLLRG NHDATTNSLYTDSSIDTFEYLP NVNVIKSLNTILKDNVNIVFTAY | 341 | putative exonuclease [Staphylococcus phage K] | YP_024502.1 | 1e-172 (294/345) | Exonuclease | MPP_Mre11_N nuclease, N-terminal metallo-phosphatas | cd00840 | 3.56e-21 |

Fig. 10X

| | | | | | | | | | |
|---|---|---|---|---|---|---|---|---|---|
| | | | GDETKEIKTYINSNYDKDMVNIL VGHLGVEGSLTGKGSHRLEGA FGYQDLLPDKYDFILLGHYHRR QYFQNPNHFYGGSLMQQSFS DEQEANGVHLIDTDKMTTEFIPI HTRRFITIQGEDIPDNFEQLIEE DNFIRVIGTANHAKVLEMDDSM KDKNVEVGIKKEYTVEKRIDSD VSDDPLTIASTYAKQYSPESEQ EILECLKEVL | | | | | | e domain | |
| 100 | 76621 | 76998 | 662 | MKKYREYLNKTDAENLAEDWE KVTEDLWKVFKDMKPKINTLDI SNVGSKDLDKSKPILQFQDSD GVIENICNVEGLEDGLSKMKKIF DDSNFEKHYYNRVVDHDGYY WIDYGSHHCFFRVTKGDK | 125 | hypothetical protein KgORF73 [Staphylococcus phage K] | YP_024503.1 | 3e-65 (123/125) | | PHA02275, hypothetical protein | PHA022 75 | 2.14e-21 |
| 101 | 76998 | 78917 | 663 | MVVFKQVEVNNFLAIKEATLEL DNRGLILIEGENKSNESFHSNG SGKSTLISAITYALYGKTEKGLK ADDVVNIEKKNTSVKLKFDIG EDSYLIERYRKDKENKNKVKLF VNEKEITGSTNDVTDKQIQDLF GIEFNTYVNAIMYGQGDIPMFS QATDKGKKEILESITKTDVYKQ AQDVAKEKVKVEEEQQNNIRQ EIYKLGYQLSTKDEYFQREIEQ YNQYKEQLVQIENSNKEKDRL REQEEKQIEAQIEQLASQIPTIP EDEFKHSEEYNKASQSLDLLSN KLTELNQVYSEYNTKEQVLKSE IATLSNSLNQLDINDHCPVCGS PIDNSHKLKEQENSNQIENKK QEITSVLEMKDTYKEAIDKVKD KSQEIKDKMSQEDQQEREHNN KINSIIQEASRIKSDISSLENNKT YLVKYQHQSVQGLEREEPSK EKHEEDKKELQESIDKHEENIV QLETKKGKYQQAVDAFSNKGI RSVVLDHFITPFLNEKANEYLQTL SGSDIEIEFQTQVKNAKGELKD KFDVIVKNNKGGGSYKSNSAG EQKRIDLAISFAIQDLIMSKDEIS TNIALYDECFDGLDTIGCENVIK LLKDRLNTVGTIFVITHNTELKP LFEQTIKIVKENGVSKLEEK | 639 | putative exonuclease [Staphylococcus phage K] | YP_024504.1 | 0.0 (636/639) | Exonuclease | 46 endonuclease subunit | PHA025 62 | 1.68e-26 |
| 102 | 78917 | 79513 | 664 | MKLKILDKDNATLNVFHRNKEH KTIDNVPTANLVDWYPLSNAYE | 198 | hypothetical protein KgORF75 | YP_024505.1 | 2e-111 (197/198) | | No putative conserved domains have been detected | |

Fig. 10Y

| | | | | | | | | | |
|---|---|---|---|---|---|---|---|---|---|
| 103 | 79528 | | YKLSRNGEYLELKRLRSTLPSS YGLDDNNQDIIRDNNHRCKIGY WYNPAVRKDNLKIIEKAKQYGL PVITEEYDANTVEQGFRDIGVIF QSLKTIVVTRYLEGKTEEELRIF NMKSEESQLNEALKESDFSVD LTYSDLGQIYNMLLLMKKISK | | [Staphylococcus phage K] | | | | |
| | 80595 | 665 | MRFEDFLTQELGEPKENTIGEL RYCCPFCGEKSYKFYVKQALD SSNGQYHCKKCDETGNPITFM KTYYNITGKQAFDLLESKNIDIE RAPLLTTNNKDLTESEKLILMLR GVHQDKGTTSIKPPRLPEGYKL LKDNLNNKEIPFLKYLKGRGITL EQIINNNIGYVINGSFYKVDGES KVSLRNSIIFFTYDNNGNYQYW NTRSIEKNPYIKSINAPAKQDEV GRKDVIFNLNIARKKKFLVITEG VFDALTFHEYGVATLGKQVTEN QIKKIIDYVSIDTSIYIMLDTDALD NNIDLAYKLKTHFNKVYFVPHG DEDANDMGTRKAFELLKQNRV LVTPESIQSYKIQQKLKL | 355 | putative primase [Staphylococcus phage K] | YP_024506.1 | 0.0 (352/355) | DNA primase | DnaG, DNA primase (bacterial type) | COG03 58 | 1.08e-12 |
| 104 | 80661 80999 | 666 | MSNSKKDILEFVDEYITALRVG NEQROHQLEEMGKEETATLTD VAKAITNLMLGVNEQMTDLEYN NELNLNILIDALYKAELINEDVLD YIQESIDKSQEEPKNEEEKGEQ E | 112 | ORF127 [Staphylococcus phage G1] | YP_240943.1 | 2e-55 (111/112) | | No putative conserved domains have been detected | |
| 105 | 80999 81451 | 667 | MEKNISTHTKGISQADMEKWIE AVVQGTVDGKQVDEKTAKQLD RIGSRSVSLEEATRIAKVLNAVT AQEVTGDFNDAFNAIDLMMIM EDELGVTQEKVGKAKDKLNEK REAYLKEKQEELRQKQQEEAQ KETESDSNEKVIQLKKNDEQ | 150 | ORF098 [Staphylococcus phage G1] | YP_240944.1 | 2e-78 (149/150) | | PHA02277, hypothetical protein | PHA022 77 | 9.45e-43 |
| 106 | 81438 82046 | 668 | MTNSKKKGDTFERKIAKELTAW WGYQFNRSPQSGGASWGKD NNAVGDIVVPQEANFPLVVECK HREEWTIDNVLLNNREPHTWW EQVINDSSKVDKTPCLIFTRNR AQSYVALPYDEKVYEDLRNNE YPVMRTDFIIDNIRKDKFFYDVLI TTMNGLTSFTPSYIISCYDKKDI KPYKKVESNLSEVSKHEDELIN DLLSDI | 202 | ORF064 [Staphylococcus phage G1] | YP_240945.1 | 2e-115 (201/202) | | No putative conserved domains have been detected | |

Fig. 10Z

| | | | | | | | | | |
|---|---|---|---|---|---|---|---|---|---|
| 107 | 82063 | 82455 | 669 | MTSKERPLIVYFSGTGQTERLV NKININNSFETFRVKSGKEKVN KPFILTPTYMKGAIPKQIERFLE INGSPKEVIGTGNKQWGSNFC GASKKISEMFKIPIIAKVEQSGH FNEIQPILLEHFSNKYKVA | 130 | putative NrdI protein [Staphylococcus phage K] | YP_024509.1 | 4e-68 (129/139) | Ribonucleoti de reductase protein | Flavodoxin_ NdrI | pfam07 972 | 2.44e-29 |
| 108 | 82470 | 84584 | 670 | MATYGKWIELNNEITQLDDNGK NKLYKDQEALDEYLKYIEDNTR KFNSEVERIRVLTKEGTYDKIFD KVPDTIIDEMTKLAYSFNFKFPS FMAGQKFYESYASKQYDENKK PIFVEDYEQHNVRVALYLFQND YVKARELLVQLMEQTFQPSTPT YNNSGQANRGELSSCYLFVVD DSIESLNFVEDSVANASSNGG GVAIDLTRIRPKGAPVRNRPNS SKGV/AFAKAIEHKVSIYDQGGV RQGSGAVYLNIFHNDILDLLSS KKINASESVRLDKLSIGVTIPNK FMELVKEGRPFYTFDTYDINKV YGKYLDELNIDEWYDKLLNNDS IGKVKHDAREVMTDIAKTQLES GYPYVFYIDNANDNHPLKNLGK VKMSNLCTEISQLQEVSEIYPY SYSNQNVINRDVVCTLGSLNLV NVVEKGLLNESVDIGTRALTKV TDIMDLPYLPSVQKANDDIRAIG LGSMNLHGLLAKNMISYGSRE ALDLVNSLYSAINFQSIKTSMLM AKETGKPFKGFEKSDYATGEY FVRYIRESNQPKTDKAKKVLDK VYIPTQDDWDELAKAVKVHGL YNGYRKAEAPTQSISVVQNATS SIMPVPSAIENRQYGDMETYYP MPYLSPITQFFYEGETAYKIDN KRIINTSAVVQKHTDQAVSTILY VESEIPTNKLVSLYYAWEEQGL KSLYYTRSRKLSVIECETCSV | 704 | putative ribonucleotide reductase large subunit [Staphylococcus phage K] | YP_024510.1 | 0.0 (701/704) | Ribonucleoti de reductase large subunit | RNR_I, ribonucleotide reductase | cd01679 | 3.18e-130 |
| 109 | 84598 | 85647 | 671 | MDITQKVKQHNKNAVLKATNW NIEDDGMSDIYWEQGISQFWT PEEFDVSRDLSSWNSLTESEK NTYKKVLAGLTGLDTKQGGEG MNLVSYHEPRPKYQAVFAFMG GMEEIHAKSYSHIFTTLLSNKET SYLLDTWVEENDFLKVKAQFIG YYYDQLLKPNPTVFDRYMAKV ASAFLESALFYSGFYYPLLLAG | 349 | putative ribonucleotide reductase minor subunit [Staphylococcus phage K] | YP_024511.1 | 0.0 (347/349) | Ribonucleoti de reductase minor subunit | RNRR2, ribonucleotide Reductase | cd01049 | 1.74e-63 |

Fig. 10AA

| | | | | | | | | | |
|---|---|---|---|---|---|---|---|---|---|
| 110 | 85665 | 85994 | 672 | RGQMTQSGAIIYKITQDEAYHG SAVGLTAQYDYNLLTEEEKKQA DKETYELLDILYTNEVAYTHSLY DPLESEDVINYVQYNFNRALQ NLGREDYFNPEPYNPIVENQTN VDRLRNVDFFSGKADYEKSTNI KDIKDEDFSFLDSKEYNTAKEF L | | | | | |
| | | | | MDRKEAMDLLSKAEILFKKHDE FSCVSDINDPMKLFSSSKDAKA DDTSKSFQLEFMHDMTMYTLS YGSGQLKLIDLAEGYEAQKATV VNSFPEIIKTLEKDDSEDGKNE | 109 | hypothetical protein KgORF82 [Staphylococcus phage K] | YP_024512.1 | 4e-55 (106/109) | | No putative conserved domains have been detected |
| 111 | 85978 | 86298 | 673 | MEKMNSLVDLNTAIRQKKDVIV MITQDNCGKCEILKSVIPMFQE SGDIKKPILTLNLDAEDVDREKA VKLFDIMSTPVLIGYKDGQLVK KYEDQVTPMQLQELESL | 106 | thioredoxin-like protein [Staphylococcus phage K] | YP_024513.1 | 8e-54 (106/106) | Thioredoxin-like protein | PHA02278, thioredoxin-like protein | PHA022 78 | 1.12e-45 |
| 112 | 86505 | 87101 | 674 | MDELISKSRRYIMRDENHYMLF NEKYNNDRLIEKVCKHGGKVT YYTDSVLPYYVLKDLSSHPDSE VVYRMRNGFTAKEVDNIALSF MGTKVIIDISVVFPYVNPYDIIRS LHDIKTNVDEVHLSFPRILEVDE KQEKFYFFDGFAYDLKPEYKV DFADKIRVSLSVWKMYYILTSS RDFEDVDNVITKLKQQRKIKI | 198 | hypothetical protein KgORF84 [Staphylococcus phage K] | YP_024514.1 | 5e-109 (196/198) | | No putative conserved domains have been detected |
| 113 | 87111 | 87416 | 675 | MSTANRRDIARKISENTGYYIQ DVEEILSAETDAISDLLEEGYTK VKNHKFMQIEVIERKGKKAWD GLNKEYFHLPNRKAIKFKPLKE LEEVIDRLNEEEK | 101 | putative integration host factor [Staphylococcus phage K] | YP_024515.1 | 2e-51 (101/101) | DNA binding / bending protein | Bac_DNA binding | pfam00 216 | 4.22e-12 |
| 114a | 87492 | 88364 | 676 | MKVLILFDHIREEHFSVSKDGS VKSNVLNTPNGKTLKKLLEKCS NLKRDKTNRDYDIDFLYNAVPT PIRNDYGKIIKYQDVKQAEVKP YYERMNNIIIDNSYDMVIPVGKL GVKYLLNVTAIGKVRGVPSKVTI ENETSSHDVWVLPTYSIEYTNV NKNSERHVVSDLQTVGKFVEQ GEEAFKPKEVSYELVDNIERVR EIFNKEVKNDNYDGVDITAWDL ETNSLKPDKEGSKPLVLSLSW RNGQGVTIPLYKSDFNWENGQ DDIDEVLELLKNWLASKEDIKVA HNGK | 290 | putative DNA polymerase [Staphylococcus phage K] | YP_024516.1 | 6e-167 (269/290) | DNA Polymerase | DNA_polA_I Ecoli_like exonuclease e | cd06139 | 3.30e-09 |

Fig. 10BB

| | | | | | | | | |
|---|---|---|---|---|---|---|---|---|
| 115* | 88530 | 677 | VYQLNRGGTVKKDYMTSVKNN KKVCRRCNEELDLSNFKTYKK NDKIYYOSMCIPCRKEYNKLDK TKNTIKKCYDKNGDKYRKQGN EYNTSDRGRELNKKRSRKYRE NNSLKAKARNSVRTALRNGSLL RPSKCSECNKECIPEAHHPDY NKPLEIKMLCKSCHEDTHHKK | 170 | hypothetical protein KgORF87 [Staphylococcus phage K] | YP_024517.1 | 4e-79 (145/156) | | No putative conserved domains have been detected |
| 114b | 89178 | 678 | MSTENFKDFESIQDTKVGWYL AVTQEVKESLRLSDLAYEVTDV GGYDKPLEDFKLWFVTKLLRFF SDKIKEIQKENKKIAKKEYDVKA PEYKEWLENKLNETVVELDDT EKKFRVSELEKKYIQLGLSPEIV NMNLVMNNDEFISIAEQSPEYM GLSDYAKSYTLNTAINLINEYRD VKDVVNDIDGGNFNYDWFPIEL MHPYASGDTDVCRRIHCDVVK KLKEQDRPKSMHLLEVNYPRL TKSLARIESNGLYCDLDYMKEN DESYESEMAKNHATMREHWA VKEFEEYQYNLYQMALEEHEK KPKDRDKDIHQYRDKFKDGKW MFSPSSGDHKGRVIYDILGIQL PYDKEYVKEKPFNANVKEADLT WQDYKTDKKAIGYALDNLELKD DVRELLELLKYHASMQTKRNSF TKKLPNMINKQKRTLHGSFSET GTETSRLSSSNPNLQNLPAHTS DVNKFDYKHPIKRSFVSRFENG VILLGADYSALEMRIGLFTKDPD MLQSFLNGEDIHKATASIVYNK PVEEVTKEERQATKAVNFGLAF GESPPSFAGKNNMEVSEAEEIF EKYFQTKPSVKTSIDNVHEFVQ QYGYVDTMHGHRRFIRSAQST DKKIKNEGLRQSFNTIIOGSGSF LTNMSLTYLDDFIQSRNLKSKVI ATVHDSILIDCPPEEAKIMAKVTI HIMENLPFDFLKAEIDGKEVQY PIEADMEIGLNYNDMAVEYDEEE IDTFNSYQGYIKYMMNLQTLED YKESGKLTDEQFEKATNVVKS EKHIYQEI | 776 | putative DNA polymerase [Staphylococcus phage K] | YP_024516.1 | 0.0 (770/776) | DNA Polymerase | DNA_pol_A pol_I_C | cd08637 | 8.00e-72 |
| 116 | 91577 91819 | 679 | VNTGEIRFNRSMIDEWIITSMYQ DELGDMNIVVTFYNREENKHG STVLPTESSTGEVTEELANLEE | 80 | ORF181 [Staphylococcus phage G1] | YP_240959.1 | 7e-37 (77/80) | | No putative conserved domains have been detected |

Fig. 10CC

| | | | EYPLALPLSSISVNI | | | | | | |
|---|---|---|---|---|---|---|---|---|---|
| 117 | 91836 | 92318 | 680 | MEIHDSLDFTNFTIKDRNGNSQ EFDITDELRITEYTIQEDFMQQS AKYAFWASILEKVRAYSEMEQ RNLETIGSKLNLTIRQEYEQQG KKPTKDMIESSVYIHDSYQQQL KVVEAWNYKVKQLQYVVKAFE TRRDMMIQLGAELRQTNKNGG ITNPFSH | hypothetical protein KgORF91 [Staphylococcus phage K] | YP_024519.1 | 5e-90 (160/160) | | No putative conserved domains have been detected | |
| 118 | 92405 | 93676 | 681 | MDFNQFINNEASKLESNNSSFN NNVESYKPKNPVLRLGNIKDAN GNKVVKENAFVRVLPPAQGTN VFFKEFRTTGINYSKKDGSQGF TGLTLPAEEGSSVLDPYIQDWI TNGVQFSRFPNKPGVRYYIHVI EYFNNNGQIQPKTDAQGNVMI QPMELSNTGYKELLANLKDTM LKPSPNAPHSFISANEAFLVNIV KAKKGEMSWKVSVYPNAPLGA LPQGWEQQLSDLDQLAKPTEE QNPNFVNFLINNVNNTELSHDN FKFNRETNVLGEEPSEPKQAP TQQDVDSQMPSNMGGQPNQP QQGQVGQYAQQGQSNGQCQ QLQGTQQPINNTQFGQGTPSG QQPSNTGSVDWDNLAQQOSQ PDSNPFNDFDVSSVDDSQVPF ETQPQNTQQAPEPHQTTQEPP KQKQTQSIDDVLGGLDLNL | hypothetical protein KgORF92 [Staphylococcus phage K] | YP_024520.1 | 0.0 (421/423) | | No putative conserved domains have been detected | |
| 119 | 93736 | 94992 | 682 | MARAKKGKEVDLTDLNTIDLGK ELGLTLLSDTNRADIKNVIPTMV PQYDYILGGGIPLGRLTEVYGL TSGKSTFAVHLSRIATQLGVIT IWIDIEGTADNNRMEQLGVDVS KLFSIQSGEGRLKNTVELSVEQ VGKELEYWIDTFNEKIPGVPIVF IWDSLGATRTQKEIDGGIDEKQ MGLKASATQKVINAVTPKLNDT NTGLIVINQARDDMNAGMYGD PIKSTGGRAFEHSASLRIKVHK ASOLKQKSELTGKDEYHGHIM RIETKKKSKLSRPGQKAEADLLS DYMVGKEDDPILLNGIDLEHTV YKEAVERGLITKGAWRNYVTLN GEEIKLRDAEWPVLKDNRELY LELFSRVYGEHFPNGYSPLLNN KVIVTQLEEYQALENYYKEWAT | putative DNA repair protein [Staphylococcus phage K] | YP_024521.1 | 0.0 (417/418) | DNA repair protein | recA | cd00983 | 1.99e-34 |

Fig. 10DD

| | | | DNKQEEQEEELKGESQEKDSE | | | | | |
|---|---|---|---|---|---|---|---|---|
| 120 | 94996 | 683 | MDNLIDKNMSQVKESLGNANS SDVLPLPYKDIAKKFEEVKEKG ESIIIEEGGFPYTDSTVMYIEHV TDRWAGGYSLIRHEGEEVKVP KTIHFSDIYVKDKSHKVRIIFEGA NPYEES | 117 | ORF121 [Staphylococcus phage G1] | YP_240963.1 | 3e-61 (116/117) | | No putative conserved domains have been detected |
| 121 | 95336 | 684 | MKKANNGNRYVIDIDGIPVDFE RDLDSLLNRYKNLRWSLYHRY AGILSNDFERQELREYIDEQFIK LVKEYNIRSKVDFPGYIKAKLTL RVQNSYVKKNEKYKRTEIIGKK DYTVESLTEDLNEDFEDNQIMS YVFDDIEFTEVQSELLKELLINP EREDDAFIVSQVAEKFDMKRK EVASELTELRDYVRFKINAYHE YYAKKELNNHRVNTENHIWEN | 220 | putative sigma factor [Staphylococcus phage K] | YP_024522.1 | 1e-122 (220/220) | Sigma factor | No putative conserved domains have been detected |
| 122 | 96126 | 685 | MAKKVNDVLQQESVTVADKY LQVKVNRDGYTRTHEGQYAYK VVSEGEELFLYPVQTDGKGTL NVMKKSPIAYTDGDNIHFVVNT VVDPYNHSFIRTEDIKGLDKGK QLIQAFLAFVEDRFKFGVYNVF VANNKEDVLSIVDPTDNDADEV KDSLEHAHEDVIADFPASPARK DVKGVDSSEGQGDTSEPSAPK NVQVTPKEDGADVSAE | 210 | hypothetical protein KgORF95 [Staphylococcus phage K] | YP_024523.1 | 1e-117 (210/210) | | PHA02283, hypothetical protein | PHA022 83 | 5.30e-71 |
| 123 | 96781 | 686 | LAKLNLYKGNELLNSVEKTEGK STITIENLDANTDYPKGTFKVSF SNDSGESEKVDVPQFKTKAIKV ISVTLDVDSLDLTVGDTHQLST TITPSEASNKNVSFESDKSGVA SVTSEDLIEAVSAGTANVTVTT EDGSHTDIVAVTVKEPIPEAPA DVTVEPGENSADITV | 170 | putative major tail protein [Staphylococcus phage K] | YP_024524.1 | 3e-88 (168/170) | Major tail protein | Big_2 bacterial surface proteins containing Ig-like domains | pfam02 368 | 1.61e-03 |
| 124 | 97308 | 687 | MEKTLKVYSNGEVVGSQVANN DGATTVSITGLEAGKTYAKGDF KVAFANDSGESEKVDVPEFTT KTPTEEPSGDA | 75 | ORF189 [Staphylococcus phage G1] | YP_240967.1 | 1e-34 (75/75) | | No putative conserved domains have been detected |
| 125 | 97631 | 688 | MDIPTILFRNPYDYTKVKKLME NKEQYIVVKFDSVSVHNLNVQ GMMNVIQDYLHIYGYRVKEYG QENSSKDDERDVKGYLYERVG E | 86 | ORF174 [Staphylococcus phage G1] | YP_240968.1 | 2e-42 (86/86) | | No putative conserved domains have been detected |
| 126 | 97895 | 689 | MGIIVNSNHIQSDTLYEYDSFFD | 251 | hypothetical protein | YP_024525.1 | 1e-141 | | PHA02284, | PHA022 | 1.74e- |

Fig. 10EE

| | | | | | | | | hypothetical protein | 84 | 41 |
|---|---|---|---|---|---|---|---|---|---|---|
| 127 | 98643 | 99893 | 690 | IEKVDTFEEGLLSIQDEPTVLAG FIYDDITFNKVINSNSDIDDYIKN NDIYYVSDIGLLPDTFITVDSDR KYYSLLQQITELSKDPFPKWVE DDAKGLTKYYNFQDFEDVFDL NSFYKKEVDMVREKCYNNGNV YLLYEVLPDYKLPLAYSLLSNK EHGIVIIGSQTRSNNDILTFYVK GMDAKAIASMFNVEHDYDSNIF HTFVNSHINILGNQITKFIREKG SSYE | | KgORF97 [Staphylococcus phage K] | | (251/251) | | | |
| | | | | MSNYKTIEEVQAVIGVLFKDEG KIITSKFNKITKEFGLDRIGKDDL KEIVEDIRQDAYLNELKNKAIKG KVTLGDLKDVADNQVFEGNNY HEEVSTYVVAKEKELSHLREQ RKHNRHTAYPQIMFDELKEHM VKELQGETLVEHHGSKANINDT ELIVLLSDFHIGSIVSDMTNGKY DFEVLKARLNHFINTTVKEIEDR EISNVTVYFVGDLVEHINMRDV NQAFETEFTLAEQISKGTRLLID ILNVLSNVVSGELRFGIIGGNHD RMQGNKMQKIYNDNIAYVVLDS LLLFQEEQGLLNGVDIIDNREDIY TIRDTFGGKSIIINHCGDLKGKG NHINKFILDSHIDLLITGHVHHFS VKQEDFNRMHIVASSPMGYNN YAKELHLSKTKPSQQLLFINKE NKDIDIKTVFLD | 416 | hypothetical protein KgORF98 [Staphylococcus phage K] | | 0.0 (413/416) | | No putative conserved domains have been detected | |
| 128 | 99907 | 100275 | 691 | MDTIFHGVAFITFATFNIVFRLFD LWTTEKKMVSQGQPPLSNFEY YHVIVPYLVGVIVIILSIIFRDSLY SAQSGFGVIITSFYMLVYVIIGL VGSFVLTIFQARKARQYQTQED NNEVQ | 122 | hypothetical protein KgORF99 [Staphylococcus phage K] | | 5e-63 (122/122) | | No putative conserved domains have been detected | |
| 129 | 100262 | 100573 | 692 | MKFNDIYEQLIKNDTVQNIHES QDDKGNIYTIQFDKGNDKYLFN VINDGFLKEMTNGMVDHPEGQ PYSVSLINKETPSMSVKQYLTD VEDIVPTIRKMEKDFL | 103 | hypothetical protein KgORF100 [Staphylococcus phage K] | | 5e-53 (103/103) | | No putative conserved domains have been detected | |
| 130 | 100637 | 101173 | 693 | MDFNFSAFDNSSLAMRISEGV YYFNDTPYYFIEHVEEEMSEYV IVYDIHDREEKENPGKKYRIEPY QRTIPGGTPLSNLIKSMMPQRK YPKKVTEDPIFVANVIPLGTDTV TGKTGKCFFERDKDRTIYSQKE | 178 | ORF075 [Staphylococcus phage G1] | | 8e-100 (178/178) | | No putative conserved domains have been detected | |

Fig. 10FF

| | | | PTKVHGQYTGVFIGLTSVKW NRTYPLESVVEYKRVKGDR LNV | | | | |
|---|---|---|---|---|---|---|---|
| 131 | 101166 | | | | | | |
| | 101933 | 694 | MSNDVVKFYEKDIKDLRTKKH MFKDDEITSDINDIRIFNEKVICQ GKCRTDCLVLDRNGTVMGIEIK TERDSTQRLNNQLKYYSLVCK YVYVMCHDKHVPKVEQILKRY KHNHVGIMSYISFKGKPVVGKY KDATPSPHRSPYHTMNILWKT NLMTILRLIRDPHTYRTGYSYN ASGRYSGGEGNFSQTTQSKR MKKPAIINQIIHYVGVDNTYKLF TRGVIYGYNNRWEVIEEDFFNT MKNGVRVINEQRQTK | 255 | hypothetical protein KgORF101 [Staphylococcus phage K] | YP_024529.1 | 5e-149 (255/255) | No putative conserved domains have been detected |
| 132 | 101911 | | | | | | |
| | 102357 | 695 | MSKDKPNRRKEIQHQPVNFAP TNTLTGANNSFFAKNPSEPKDA TSVIEYRILFIKRFDNVTSTDVKL QKKYALNLISEALDVKETYLSLK QIKGKKTESILHTDRVYYVHRGK KLIGKCSIREQRTFKGKHLIFFK TRHRVKAERKDK | 148 | hypothetical protein KgORF102 [Staphylococcus phage K] | YP_024530.1 | 2e-80 (147/148) | No putative conserved domains have been detected |
| 133 | 102357 | | | | | | |
| | 103220 | 696 | MLKGFSEHVDKPTTSKTLYKTL TSGKVELLGVSYDSDYFPSGV TVQSYIEDIGNEDEGLQFVNKV NVVESMKQAVVGMNNQLGSS GLGYVRTEQLKKELEETGLMT DLLARGTNLTSTKKVDIVSTFIE PEVTYQNITIAKDIKLRLYKVEE ESPLNGYTHIVYLLTTEKLYDG QTLFGMLSKKDKLSKGDTDKLL AFFRNNSLISKSVFCVKKLLSKD YYFNLYNTHETGIFFLEDTDVITI ACGQSYVKVNTKDIKSSVVKIE DKTHKLTELVINLKGDDTLTILF | 287 | ORF036 [Staphylococcus phage G1] | YP_240976.1 | 1e-160 (286/287) | No putative conserved domains have been detected |
| 134 | 103592 | | | | | | |
| | 104323 | 697 | MARKKNLRNKNSDIKVVPDKE KESILSKLYHNKLLRSKVDNAL DEDMSYDDIIELCKEYDELSK SAITRYKSKRKEAIENGWDLGE LIDKRKKTSVKDIKEKETPILEEE QLSPEQSKHHTQTYQDIQVL DMIISKGAKGLEFVETLDPALMI RAMETKDKITGNQLKGMSFIGL RELQLKQTAQDTAMSEVLLEFI PEEKHEEVLQRLEELQNEFYK NLDLDEESRKLKEALDRVGYTI | 243 | hypothetical protein KgORF103 [Staphylococcus phage K] | YP_024531.1 | 6e-136 (243/243) | No putative conserved domains have been detected |

Fig. 10GG

| | | | | | | | | | |
|---|---|---|---|---|---|---|---|---|---|
| 135 | 104341 | 104799 | 698 | MADEISLNPIQDAKPIDDIVDIMT YLKNGKVLRVKQDNQGDILVR MSPGKHKFTEVSRDLDKESFY YKRHWVLYNVSVNSLITFDVYL DEEYSETTKVKYPKDTIVEYTR EDQEKDVAMIKEILTDNNGNYF YALTGETMLFDENKLNKVKD | 152 | ORF094 [Staphylococcus phage G1] | YP_240978.1 | 3e-82 (151/152) | | No putative conserved domains have been detected |
| 136 | 104864 | 105307 | 699 | MFISLNQEEKELLTKEESKYTPL ETSREFNTPKEEFIVTSYNEGK PLDYIAKEAKVSMGLIYTVLNYY KVGKRNKKSPVEERIAHILKDK NLVKEIIKDYQYMNLQDIYSKYN LHKNGLYYILDLYHVERKSELK DKALEEDNIVVE | 147 | hypothetical protein KgORF105 [Staphylococcus phage K] | YP_024533.1 | 2e-77 (147/147) | | No putative conserved domains have been detected |
| 137 | 105324 | 106028 | 700 | MRNKKSFQEQLNDMRNKEKW VSEEEFTEEVAPSEEPEVEEEK LYTLNELKENLLDAQGLKDVVA DFPASKDLYEPNKLYICTIPKGY RSTEVQPGQYIGISTGSLLSESE DFSHLRGQMPRNLYETSHVLK PLVRINNTNLEYQQHELLEDIKD DKKIYDVELEDLRLVTGEEISHL EIVDSKFFESRINEILDRYTELT DSDDLLIYYSKLRELVGSDKMIY CSLLDKCVKIID | 234 | ORF106 [Staphylococcus phage K] | YP_024534.1 | 3e-118 (223/234) | PHA02290, hypothetical protein | PHA022 90 | 4.62e-30 |
| 138 | 106091 | 106489 | 701 | MSRKASIFYILVIVLAFSISSYYI SSFMYHDKAKNEVSTELSNTG KIKEEKNVEFVGDYTLKKVENN KAYFMETLPTYLPGRTGDNSID MRYYKTSRFKEGVNFKLIRVYT EDGEDNPIHKYRFEAVPTKK | 132 | hypothetical protein KgORF107 [Staphylococcus phage K] | YP_024535.1 | 5e-70 (131/132) | PHA02291, hypothetical protein | PHA022 91 | 7.32e-18 |
| 139 | 106636 | 106878 | 702 | MEMADLERFDTFVRLVSDDEL SEERALELSVDLLNPILEGGTA YQAKKRIRSKFGKIEAKNFKRN YKFLLKSIAQIDQRR | 80 | ORF182 [Staphylococcus phage G1] | YP_240982.1 | 2e-35 (74/80) | | No putative conserved domains have been detected |
| 140 | 106883 | 107440 | 703 | MIEREKLVKEIEDANRDIQLRLK EVDDYKDSIRSKGTRNYVSTKV LDSVMVGLISFFILVMLRVLEYF VTGNAVYSPLAPAVIIMFVLALG TWKVSKMNKIVSYRGTIKMYW ELSNAEQNQAKVFKYPNDEVDI VSKHNLRQITFSEINILHLKYMR YNKAVEQHTKLSKELFKKDKET VDKNK | 185 | hypothetical protein KgORF108 [Staphylococcus phage K] | YP_024536.1 | 1e-66 (120/135) | | No putative conserved domains have been detected |
| 141 | 107476 | 107652 | 704 | MVIPSIKAQNKFKNELEYYKQG | 58 | ORF240 | YP_240984.1 | 8e-25 | | No putative conserved domains have been detected |

Fig. 10HH

| | | | | | | | |
|---|---|---|---|---|---|---|---|
| 142 | 107645 | 705 | HISESKMLELAFDYIQELEQNN EYVTNLLEEERYGE | | [Staphylococcus phage G1] | (58/58) | have been detected |
| 143 | 107893 | 706 | VSKFIGVYLFNLLVVALIYTVGF LFFYGVASLVIILTHATIDPFVLA TFLGIGFLVIRTAHRIMARVIND AVAKAIKDKENE | 82 | No significant similarity found. | | No putative conserved domains have been detected |
| 144 | 107886 | 707 | MNKGEFIMDKTLPKFSVYEVIV KTVIMTPTEGSSDLESFYFSTR ELAERFVEENTVETKNGKRVSF AVKERKVNQPG | 77 | No significant similarity found. | | No putative conserved domains have been detected |
| 145 | 108200 | 708 | MKVSEEVKQSYLENRANTKMD KISWSELRSSPLGITLGDIIFYSV VIIDNIAIILTLTLIGTITDSIES TL AQIIVGMFIIITYGILSALIPILVHK AVSPGWSYTEWNESYYIRLPG EENYKYYSKWYLDLLGVKEFY YKRDNGEEVKEKIYHGLFKLK | 162 | ORF076 [Staphylococcus phage G1] | YP_240985.1 | 2e-52 (104/112) | No putative conserved domains have been detected |
| 146 | 108724 | 708 | LLTNRPLTILEYKKLKKLDKESEI RKQEDLEEYKQYNSN | 39 | ORF076 [Staphylococcus phage G1] | YP_240985.1 | 5e-13 (39/39) | No putative conserved domains have been detected |
| 147 | 108858 | 709 | MISSFDSILLVIYIIIAFAVAMAIIY LVFKGMTILLDKLMMLLLSKTTL DVEACSMIMAVISTIVFGIIVLLI WLAVNNILL | 82 | No significant similarity found. | | No putative conserved domains have been detected |
| 148 | 109118 | 710 | MDFNDFINSESDRVGKPKQKK KVENKLPSSTPIEDKEKKLKEIR KKSLYIDLRRKRND | 58 | ORF241 [Staphylococcus phage G1] | YP_240986.1 | 1e-23 (58/58) | No putative conserved domains have been detected |
| 149 | 109287 | 711 | MTKETNVLYKDKYRDYTIVVRL AGNIIVTEVDKKHKTAFTPIIFDN GVEGVELVMRIGSVELSMTDL REFTKEVSTAQKALEYFNKKLY IKGLTDEAF | 98 | ORF152 [Staphylococcus phage G1] | YP_240987.1 | 1e-48 (97/98) | No putative conserved domains have been detected |
| 150 | 109631 | 712 | MLLGILWFIWGFVSYFVLMFGI EFWKDRWMPGVIGAGALLLFL FWIMKSIHNAMTVVYLY | 60 | hypothetical membrane protein MbpK [Staphylococcus phage A5W] | ACB89144.1 | 3e-25 (60/60) | Membrane protein MbpK |
| 151 | 109826 | 713 | MIDILVIHYEETNKRVLKETIQTI QNHLNDEHGLVKMTATKLSRE NIEKRFNNYNIVIAEDDPDNSYH YGEAVEDADFIIDIPISYLDIHAGI EWDVDNPVDMLDRNPDFIEAV NKLNEDLML | 123 | ORF119 [Staphylococcus phage G1] | YP_240989.1 | 9e-63 (119/122) | No putative conserved domains have been detected |
| 151 | 110210 | 714 | MLNEKLKNLEDTKVYMINSIASL LSASTGKSSKVFFDEGTIKIVSG | 115 | ORF124 [Staphylococcus | YP_240990.1 | 9e-60 | No putative conserved domains |

Fig. 10ll

| | | | | | | | |
|---|---|---|---|---|---|---|---|
| | | | ETKAVEVIDNLVHPHSGRLPIKT TERIALGRLTDSLQFVISEIEVV KDQIIDEENEAYIDFVMEDWNW D | | phage G1] | (115/115) | have been detected |
| 152 | 110557 | 110835 | 715 | MPMDLLTIASVAFIAVVIIDLIND DMSYMLTGTAILNIWAGFYGW FFLLQAGMLLFLLLARKVKDDK ESILYSSASLICALGMIINLLSFS | 92 | ORF162 [Staphylococcus phage G1] | YP_240991.1 | 1e-43 (92/92) | No putative conserved domains have been detected |
| 153 | 110905 | 111210 | 716 | MSKETIRRQFSNAIEIMATTKE WWNFPKSFDTNKEFKIKTFKN DTLVFEVREGSRNLGSFVVFTN IDFDYDKLEGTSTQYMINYFAK KLTKDMFNYHKLQL | 101 | ORF140 [Staphylococcus phage G1] | YP_240992.1 | 4e-52 (101/101) | No putative conserved domains have been detected |
| 154 | 111225 | 111575 | 717 | MREELKPFNRKQVNVKGYLDD VKYSKRRRHKGNQHGCVKITV TDVKINGIPIDHVNIEVGISFYEK LKELQGKRIQFVGTVYKVKHA RGRKGRIKGFYKEDYSVTLDKK LQKEEK | 116 | ORF122 [Staphylococcus phage G1] | YP_240993.1 | 2e-59 (116/116) | No putative conserved domains have been detected |
| 155 | 111575 | 111754 | 718 | MTEWYALCYDKVGKKKIPRQ VRAHRDISVLEELKERLEERNP NTEYSIKTTKEFDEER | 59 | ORF237 [Staphylococcus phage G1] | YP_240995.1 | 6e-21(46/59) | No putative conserved domains have been detected |
| 156 | 111980 | 112390 | 719 | VKLEDKVLERIDSLGGKLGDIS QHAWEALVKYQIIYGIIDLIVGIV VIALTLFLVWKVFINQHKKVNDM DRDDDYSLLFEDCEDLSGIGLF YVIVTSLISLFAFIYLYGIPMDIIK ILNPEVFAVKDLIEQAKGGN | 136 | ORF107 [Staphylococcus phage G1] | YP_240996.1 | 3e-34 (81/136) | No putative conserved domains have been detected |
| 157 | 112392 | 112685 | 720 | MKQRDFEFEEDFVLTYECEDC KHFEDWGHDEEPEECSECGS SDLINNTSHEDTECDMCKGYID MWQDGYRYMGDNKAYLEKED SGLICEDCYEKLDI | 97 | gp ORF160 [Staphylococcus phage A5W] | ACB89153.1 | 4e-47 (93/97) | No putative conserved domains have been detected |
| 158 | 112701 | 112988 | 721 | MNKAVEQASNAVGQGFSAMV WHQVLVGLGFILLGLILSLLVWV LVKKFHVPPFNHPTAFVVYSIML VSIVASFIWGGLHVINPEYYAIL ELKGFIK | 95 | ORF157 [Staphylococcus phage G1] | YP_240999.1 | 3e-37 (93/95) | No putative conserved domains have been detected |
| 159 | 112999 | 113112 | 722 | MTKEELEQRVKELEAENKELKK QIERFEDEGGKTKDE | 37 | ORF362 [Staphylococcus phage G1] | YP_241000.1 | 6e-10 (36/37) | No putative conserved domains have been detected |
| 160 | 113105 | 113371 | 723 | MNSRQKKILTLTVSNFLILALDT VALIRYKKGKIKQENYNTGQITR MIATTANSLGILYLEEQERKEVK | 88 | ORF170 [Staphylococcus phage G1] | YP_241001.1 | 2e-31 (68/86) | No putative conserved domains have been detected |

Fig. 10J

| | | | | DIKVGTFEIGALKRFTNNK | | | | | |
|---|---|---|---|---|---|---|---|---|---|
| 161 | 113449 | 113754 | 724 | MKGIIIFYKEETKEDLGYFLGFIN FKLEGLSYTTEGTLVDNDVVVL KDNQINEDNLEQFSMSNNNLVI GILGHSSLSVRIYEKGIRQEFDR VEEYLEELRQ | 101 | No significant similarity found. | | | No putative conserved domains have been detected | |
| 162 | 113754 | 114155 | 725 | MIFILFGLLFILSLLGIFIYSVLR KKKQLIEERESFGIYNRTKEKL GDVTRLGYEEDVYKLIHNQSNK TIIEDKKSKVVDTIKKMYELELT SVDVSKVEGLSPLDTEPMTNM KLLSYKLDREGLYSLSKFI | 133 | No significant similarity found. | | | No putative conserved domains have been detected | |
| 163 | 114166 | 114402 | 726 | MEFIDKNNVIKAYDIPNVYLKGY VLQACDKNGDTTAYDGYDQIH YKEGRVLTFPFDKPLRKINVLS GYYKLFKKEDII | 78 | No significant similarity found. | | | No putative conserved domains have been detected | |
| 164 | 114399 | 114926 | 727 | MIYFVSDLHFGHDNIREFEAPT RSHWNSVEEMNEGLIELWNNT ITNNDIVYNIGDFFFNMKPSKVE DILNRLNYKEMILIAGNHDHKKL IKLYERNGITVKYADMIKKDGKR FYLSHYPTLIGRKNMFNHGHIH SQLMGTEYHINVGYDVEGKIAY SFDDIISRAGEYNGEIQR | 175 | phage protein [Staphylococcus aureus subsp. aureus TW20] | CBI49957.1 | 1e-66 (124/165) | Phospho-esterase or phospho-hydrolase | MPP_AQ15 75, melametallo-phosphatas e family | cd07390 | 2.83e-37 |
| | | | | | | gp43 [Listeria phage A511] | YP_001468613.1 | 2e-18 (65/174) | | | |
| 165 | 114907 | 115218 | 728 | MEKFKGKDLYKTRIRKQTIKNL VIKTEKLHNKHGKYRPIGHVYY YPKTKEFTLSKPEQKIFIEYMKA LGFSVKHKRRKKIIIVYKNVLDE YLSMYQEAIESTC | 103 | No significant similarity found. | | | No putative conserved domains have been detected | |
| 166 | 115264 | 115443 | 729 | MKHFLILIGIVILVIALGIVLPAWIL QLVLSAFGVKVSIWVCIGIFILIS AVGSMFSRN | 59 | ORF236 [Staphylococcus phage G1] | YP_241002.1 | 3e-22 (58/59) | | No putative conserved domains have been detected | |
| 167 | 115458 | 115721 | 730 | MAKYESNNINGENYIATPSQALR EALAELIREEKNFAEYQTKGEE QYESQLQLRHFDSMISQYEEAI RVLEDRYSPQIFIPKDNKEEK | 87 | ORF171 [Staphylococcus phage G1] | YP_241003.1 | 3e-39 (80/86) | | No putative conserved domains have been detected | |
| 168 | 115724 | 116041 | 731 | MKAESIARFFQDKVLQIEGYKV RFTGASSSYILDIDTMDESVLFL DTVVFTLSGKYLLDTHITINKPE TLSSNELYTEISNKLQEIVGDQT KTDIELSKYFKEVK | 105 | ORF137 [Staphylococcus phage G1] | YP_241004.1 | 4e-42 (88/105) | | No putative conserved domains have been detected | |

Fig. 10KK

| | | | | | | | |
|---|---|---|---|---|---|---|---|---|
| 169 | 116042 | 116722 | 732 | MSSEAITNHLNLNQIKIKEYNIH AYIKKSVCSGIFNADFEVRINYI ADKDPNYIRTINSIIFVDYSNRN PKEILLQFKEKILSIVKEQVEIDN DFIEAIKDINTNHELEKLEPFINK EYYSMFKSSIEKEVPVALSSEV LNRCTGKTSTLAYLAIEKDLPLI VSNNSMMKMLKKDYPSVKVSS VEDFSNYNIKGEIVLIDEVDVDQ LYSADRVSVDALLVGIIKN | 226 | ORF055 [Staphylococcus phage G1] | YP_241006.1 | 4e-84 (158/226) | No putative conserved domains have been detected |
| 170 | 116800 | 116958 | 733 | MVGIIILVGLILFLASGYKLVLGK YYDDIDLKMLFTIFGICAILLLTG FIL | 52 | ORF263 [Staphylococcus phage G1] | YP_241007.1 | 4e 12 (38/52) | No putative conserved domains have been detected |
| 171 | 116974 | 117198 | 734 | MNYKEVLEVIKKNKPCKVRFTG SILAIVNKEFNADTDKGILQIDVS NINKNDYIKLQQYCLERDDYTV AGAILF | 74 | No significant similarity found. | | | No putative conserved domains have been detected |
| 172 | 117211 | 117411 | 735 | MNYRDFITDCISCGYKVHSVTE KRVHIISEMTSASYPKKEINLDE LQAYVYYMNNFGSQITTEGL | 66 | ORF211 [Staphylococcus phage G1] | YP_241008.1 | 5e-30 (64/66) | No putative conserved domains have been detected |
| 173 | 117412 | 117702 | 736 | MELVINIIAVLIGMYGIYFYVTKF STGLSGILIVLGMAVGLYFYIDY LNVRENVIRLVSVMFGAFLFSIE MIYNKIMFEIKKSKYDKTVRTYR GDQ | 96 | hypothetical membrane protein MbpO [Staphylococcus phage A5W] | YP_241009.1 | 3e-40 (85/96) | No putative conserved domains have been detected |
| 174 | 117853 | 118206 | 737 | MNARKARKNTKNHKDSSVVTK EQHLTYIYKINYLIANSSSQGK TYVMNLRTGYPDEFSLSKLKY LKEIKQHYKDLGFTVQIQVRKS RWSEKSIIRYFNLGYIDSVLVP IIHISW | 117 | hypothetical protein KgORH-115 [Staphylococcus phage K] | YP_024543.1 | 4e-57 (107/117) | No putative conserved domains have been detected |
| 175 | 118225 | 118398 | 738 | MDNPNLNKKTLRAVIREMDKDI EERAEALRREETRLSIARDNRK RLYIELESILELE | 57 | No significant similarity found. | | | No putative conserved domains have been detected |
| 176 | 118401 | 118625 | 739 | MDFNLKDYAVRPITDKEGNMV VRTVVVCLKREYSDWVVDKVY GRQESSETWLKFMQEIRNIERA KLRVEKWQVN | 74 | No significant similarity found. | | | No putative conserved domains have been detected |
| 177 | 118652 | 118810 | 740 | MSLSELLEYHKNSGKERAEYIS DNGNCRVAIMHYDKWAVVGDL ENAVFTIEK | 52 | No significant similarity found. | | | No putative conserved domains have been detected |
| 178 | 118816 | 118917 | 741 | MYLFAKIIIISIDVIPLMSIIVVQLIT DYNDRH | 33 | ORF445 [Staphylococcus phage G1] | YP_241021.1 | 2e-04 (24/33) | No putative conserved domains have been detected |

Fig. 10LL

| | | | | | | |
|---|---|---|---|---|---|---|
| 179 | 119523 | 742 | MIIPLILMMTFGTFAFSYVAHDA YRVDEKGIMYAMVVGIVVINVIG LEMIIVECL | 56 | No significant similarity found. | | No putative conserved domains have been detected |
| 180 | 119709 | 743 | MIDIYLHSEYDKDKLKFILKAIRD FSPRELTYDFRNPKADVSIQEL LGDDIDIFESIALDYPNDINILVG DSGYSIVYQNDFLTISGLSTAM KEVIG | 97 | gp ORF182 [Staphylococcus phage A5W] | ACB89175.1 | 2e-08 (38/92) | No putative conserved domains have been detected |
| 181 | 119999 | 744 | MIGFTILSTIMVILVIAMYTQVLV DMIQSIRYDRFDKVLNIVTFIVM TVVLVSGILIMFDI | 61 | ORF231 [Staphylococcus phage G1] | YP_241023.1 | 7e-11 (37/61) | No putative conserved domains have been detected |
| 182 | 120293 | 745 | MKAIVYCAKRYSKHTLKHILEEL EAENSDLTFSTEISDLGEVDIVV QHTKLPFSELMIDLCSKVSKGS DRFYVFVGNHSGYYINGDLYIN EIGKFITSRETNVMM | 104 | No significant similarity found. | | | No putative conserved domains have been detected |
| 183 | 120621 | 746 | MEIRLVEGYDKSQLKFMLKKIK RVAPRELTYDIEAGIDSVDVNIE DVLPHKSPQEYERYSMLLEED LWIVILESGYIAYWDGKKYGGE ALDDIIYNMFKGRGRL | 105 | hypothetical protein KgORF117 [Staphylococcus phage K] | YP_024545.1 | 1e-22 (56/99) | No putative conserved domains have been detected |
| 184 | 120938 | 747 | MIEVFLSKDYDKDLLKAYLEYIR KSASRELKYNTNHTKGTDVNIE NIISYTNOEVHHFSSYGMYRDD LCVFIDNTRVSEYLNGEPVGVD TIYKYIKEM | 98 | gp ORF185 [Staphylococcus phage A5W] | ACB89178.1 | 6e-19 (48/98) | No putative conserved domains have been detected |
| 185 | 121238 | 748 | MFKVYTVYHRQSMKTIKDKLD RSGLIYFLYETWYKDINNVCPS NYNPEFGSLNKDIDIDRLIEAVN EEGILLINHGNYYTVEEW | 85 | ORF175 [Staphylococcus phage G1] | YP_241027.1 | 2e-33 (70/85) | No putative conserved domains have been detected |
| 186 | 121593 | 749 | MIDIEIKIWDETLRMGVEEEDVL SFLSKFKNKTTGDKEESYGVGL DESKWKVHPFYTRYEVHPEGY VRLKDTKTPVIFTKYRKELHHK PQFISSNIMDDEGKHTVALHKL VADTFIPIPWYYLQGYNYTDLSV GLKDGDYENKEAVKAYNLAWY VGRIRGNAPMIKLMDLEDDRVL YFASIPQIENFIRDNKLDPKRFN YKTE | 202 | No significant similarity found. | | | No putative conserved domains have been detected |
| 187 | 122567 | 750 | MEFKFEGTKEELNKEVHNLLKK VNYVYQVNIFENELRNLIDVKE KDYLFSLSVDYNWLMEEKQKD GYNDLASAIYEEYIETYLN | 84 | No significant similarity found. | | | No putative conserved domains have been detected |

Fig. 10MM

| | | | | | | | |
|---|---|---|---|---|---|---|---|
| 188 | 123008 | 123316 | 751 | MDVKEIANTIMELWQMDGYRCTEPPLYESTLNHTRTYTALIVSIKGNYDTVQMFRKTPIMSMRGQAQPASMLVNVIDDVIIIVYENVVYGVQNKEIKFIEEI | 102 | ORF145 [Staphylococcus phage G1] | YP_241031.1 | 5e-52 (99/102) | No putative conserved domains have been detected |
| 189 | 123520 | 123807 | 752 | MTNKNYLYEEAHTVQGNEITAFRIPNDANGNPRYVVHFMDLNIKLADYDNINKLYGFNKYRAKWFGGGVVFQSYNIEDTLNFALDKVKEIEAVKN | 95 | ORF159 [Staphylococcus phage G1] | YP_241032.1 | 1e-38 (76/88) | No putative conserved domains have been detected |
| 190 | 123857 | 124048 | 753 | MKFKIEKNNSDIKTLWNLAKNGYMSYQTVHNIFKNESDEFIIFNSKQTYNKFMELRYNRSAIQ | 63 | ORF221 [Staphylococcus phage G1] | YP_241033.1 | 6e-28 (62/63) | No putative conserved domains have been detected |
| 191 | 124566 | 124724 | 754 | MLKFKWKNKTIKSTQKTDNILLIIGGLVATITPKLVNWFLLLQDNINIFLR | 52 | ORF253 [Staphylococcus phage Twort] | YP_238667.1 | 0.012 (21/38) | No putative conserved domains have been detected |
| 192 | 124794 | 124925 | 755 | MKKITTTLNLIGMKNNERFTEELKNYRQDVTFLKANKIVKYSK | 43 | ORF297 [Staphylococcus phage G1] | YP_241036.1 | 1e-15 (43/43) | No putative conserved domains have been detected |
| 193 | 125091 | 125414 | 756 | MKFIKTIENLLTKAENKGQAILNGRYYDGYRNGELEEKYAIEIEGNKLVMRHWGTQTIEIDLGMKEIVSYYGESNSDRDSLNTLVYCLGIAPNFRYLPSKDLFIYEN | 107 | ORF135 [Staphylococcus phage G1] | YP_241037.1 | 2e-50 (97/107) | No putative conserved domains have been detected |
| 194 | 125514 | 125915 | 757 | MFKLQNKVEIIVPKYTNSGKEISSPAIKEAVNNATKICGGCTITEIKGQWWSDDEQRIMEDDNLNLEWYYDKGMQDMNDQQGLLQALSKIARQLIVFVEQEAISKINGTLYIIDYEDLDLLSYDLYELMFKN | 133 | No significant similarity found. | | | No putative conserved domains have been detected |
| 195 | 126409 | 126630 | 758 | MNRLEIVKDTAMEYILMMDNSVMDGVWMTQEEYNEAVSFEKVYDYTLSEANQECKFLGGKVLTFLVHEAIEEYA | 73 | No significant similarity found. | | | No putative conserved domains have been detected |
| 196 | 126711 | 126848 | 759 | MRYEIVTLVNGELFMFATFKKAEAENKYQEWCDLYGQENVSMEKN | 45 | No significant similarity found. | | | No putative conserved domains have been detected |
| 197 | 126919 | 127083 | 760 | MTKTIKQLESQLERLERKSDEQLANGYYEAFERTCAQIRELDLQIELKKNSETV | 54 | No significant similarity found. | | | No putative conserved domains have been detected |
| 198 | 127321 | 127557 | 761 | MKLLNRDNEIVISIATLESVKQALIWEYIDHIDNNILDSEIYDQEAVVVTSKTLQSIKFADTMEDLCEYI | 78 | gp ORF194 [Staphylococcus phage A5W] | ACB89187.1 | 1e-30 (66/78) | No putative conserved domains have been detected |

Fig. 10NN

| | | | | | | |
|---|---|---|---|---|---|---|
| 199 | 127649 | 762 | ADINWKLV MTNTIKGFLQTEEASTVKDVAT HGVQSGAIGRLIYTSDVVKFFD RHYSDIEAVVLDFLEGFTGQRY YDLLDYDLMRELEEHANVEFE DEDEYNNIQFDLAENIASDEIEG FEDMDEAEQADAVIEAMDDVE LEILDTDKVQFVNLAVEIVAQQ MQEA | 157 | ORF092 [Staphylococcus phage G1] | YP_241038.1 | 3e-63 (120/154) | No putative conserved domains have been detected |
| 200 | 128202 | 763 | MTIKEIINQLQAVENKELELFVC DKEGNNISIKDITLFDSEAEHTE NNPLGINY | 54 | hypothetical protein EFP_gp130 [Enterococcus phage phiEF24C] | YP_001504239.1 | 0.001 (23/55) | No putative conserved domains have been detected |
| 201 | 128378 | 764 | LNIREVHNVVKSAKSKLLQEQN NINNVMIDDYITEELHRRTQRS GTIQMNNNTASYSNGSYGSLE EIREAYDLSSLSTNEIKELLETF V | 89 | ORF166 [Staphylococcus phage G1] | YP_241041.1 | 7e-33 (70/89) | No putative conserved domains have been detected |
| 202 | 128732 | 765 | MRDLQERKRELKTLLFNLAIEK NRATDETLRSVLEEAHQEVGN QLRKVRKEIEILVEEKEREFWN DFDFNGLD | 73 | gp ORF003 [Staphylococcus phage A5W] | ACB88994.1 | 2e-28 (64/73) | No putative conserved domains have been detected |
| 203 | 131537 | 129258 | 766 | MPHLKAYDKEGNILAIGYNVYT EQGSVIIPNLKPHTKYPQGEFY VSWEGDNYESEKTVVPEFTTL ESSYKEITFYAKDILTVKPKTAY DIAVDNGFTGTEEEWVKSIKGE PGEPGKPGEPGKPGEPGKTG EPGKDFTFDRFTEEQLDSLRVF VNPSDSNLQEVNKTMEDSLIVY PDNGEDIRLYPSTVDKTYFSNIT IRNSIPENTMNPDGSFTLNSNG WLFYTVKAVEKLAPGKTFSAKII TDDVPDPKASFEYSIQDSDGSY IQTITQLNKINDTTFAINNINIPEN SSKISLRIDTRQVTSPVNIKQFL LFDGSSTKKIQTVNNEEFIKGLI KEIDNMKISMKKETSYKIPVFTP VDYLIKDHPLVNNIFTDGLGKFS TSLNMENFKLRGGKSYYVDGE NGNDTNDGLSQSTPFKTFKKA QGIINNGDTLYVSDGDYFRVGG TLLPPISNKSINIIGLGSNVNLFM ADEPTWTKTSGRDSTYEFTRS AVRRVVDFNNDREFTNVTSLD KVDTTLFSWYSDGTKVYVNNG | 759 | ORF002 [Staphylococcus phage 37] | YP_240100.1 | 4e-105 (251/690) | No putative conserved domains have been detected |

Fig. 100O

| | | | | | | |
|---|---|---|---|---|---|---|
| 204 | 131859 | 131602 | 767 | SIEPNKKVVPLLSSQHLIVSSVP TDFYIENLNLYGGARPARFELN QDNSVVINNCVLSYASQVNGN GLEIVGGKEVIVNNSVANNNYM DGFNYHIGADSSKPLVIEINCTA LENGFEKGTAGTKSNNGSTTH DGLKAIRVNGIYARNDGGNVAD VNEGTESWNLGCTAFESYQGK DFQTSSGSHMWLDSCIAYGST NSINSSDPNSKIYTRLGSYQNK LILGEEIKY MKLYQVEHDNCEPYEDNFHFR EDNVYTNKEKLIKRIKEEGYRE ETNYRGEQEFIKGDPRGFDGM DMITIHELNIVDCDINIKKGN | 85 | gp ORF004 [Staphylococcus phage A5W] | ACB89995.1 | 8e-31( 65/76) | No putative conserved domains have been detected |
| 205 | 132119 | 131874 | 768 | MEFFIDRTSTINKKPIEGAYIKKL ELVDQKGNPFTLERWCVEINSL EELTEISKHEGEVIINTRGDSPF SPYLEIYDYYRE | 81 | No significant similarity found. | | | No putative conserved domains have been detected |
| 206 | 132289 | 132119 | 769 | MERFKVKRIITTEEVRYIDAETE EDAWYSEYEDEGTDTAHFNA EYGEWSYEKEEN | 56 | gp ORF005 [Staphylococcus phage A5W] | ACB88996.1 | 1e-19 (49/56) | No putative conserved domains have been detected |
| 207 | 132773 | 132291 | 770 | MNKTFFKAIGKNTLEYSKQGLG FLVALLIMLILSVFLAFIIGIPAGII YGLYALDINNYFITMLVTVEWFII LYGIVRTQDNKKPFVKLKLKDY LLTILYLTITATSVLESVLLFKVL PFTGDTRAVITLLSFLLFLAVNR GICKIVIKSYKEYKEEN | 160 | ORF087 [Staphylococcus phage G1] | YP_241049.1 | 4e-65 (129/160) | No putative conserved domains have been detected |
| 208 | 133017 | 132766 | 771 | MIFKKHKEEEVKKDINFIRIHDV SGTSTIIKQKDTKTNLNSFIGGL VFNGVKFLESNKGDTSIWFKD NIIHIDTVVYKEVADE | 83 | No significant similarity found. | | | No putative conserved domains have been detected |
| 209 | 133262 | 133017 | 772 | MAYEYKNKIQDIITDNENYWCID NEKELEELGEVYQKAEAFDEIV NEFHYQLQNLESWNTLDQKDC QTLKQILEENIKEEE | 81 | ORF103 [Staphylococcus phage G1] | YP_241047.1 | 3e-17 (46/51) | No putative conserved domains have been detected |
| 210 | 133682 | 133266 | 773 | MNIKYIDLVLENCDVVRLEPKD VKRFHVDGITEGIDYYGTSHISR TRRCTYFGILIDNPKEISQVGFA YPDNTNAYEMITAYSDITAIDIIY DDDTNEYTYVDFNEYNDYYNIN QKNEYYNNMLEVTITESNSIEE EG | 138 | hypothetical protein KgORF2 [Staphylococcus phage K] | YP_024433.1 | 2e-61 (121/141) | No putative conserved domains have been detected |

Fig. 10PP

| | | | | | | | | | |
|---|---|---|---|---|---|---|---|---|---|
| 211 | 134191 | 133697 | 774 | MKETKEYIMFWGKEDIYSNFYP ITFKHKGRTFNNSEQAFMWRK AQYFKDWQIAGEILNAKHPNHA KSLGRKVRNFNEEQWNKVRY DIMVEVVKDKFMTTHLKQKILD TDLRKDFVEASPYDKIWGVGIK ANDPKILDESNWKGQNLLGKV MEDVRVHCVYNRFK | 164 | hypothetical protein KgORF4 [Staphylococcus phage K] | YP_024435.1 | 1e-84 (146/162) | | Riboflafusio n conserved hypothetical protein, ribA/ribD-fused | TIGR02 464 | 2.80e-55 |
| 212 | 134602 | 134204 | 775 | MKKRYFKGLKLNDFEKEVFGL KKNKKYKKMNKELGRNEPKYW NYDMSFFIQLYADLNAFVESSN HVDMEYH1FTDIEGKERTQIDM IKHILSLIQFYHESMDSFDVDNE DEIEQVQNKILDNFKIVLPSLWN | 132 | hypothetical protein KgORF5 [Staphylococcus phage K] | YP_024436.1 | 2e-55 (114/132) | | No putative conserved domains have been detected | | |
| 213 | 135306 | 134599 | 776 | MAIYVVPDIHGEYCKLLTIMDKI NNERKPKETIVFLGDYVDRGKR SKDVVNYIFDLMSNDDNVVTLL GNHDDEFYNVMENVDRLSIYDI EWILSRYCIETLNSYGYSVTLK YSSVEENLRSNYDFIKSELKKL KESDDYRKFKILMVNCRKYYKE DKYIFSHSGGVSWKPVEEQTID QLIWSRDFQPRKDGFTYYCGH TPTDSGEVEINGDMLMCDVGA VFRDIDLPFIKLEGNS | 235 | putative protein phosphatase [Staphylococcus phage K] | YP_024437.1 | 1e-130 (227/232) | Phosphatas e | Putative protein phosphatas e | PHA022 39 | 6.31e-126 |
| 214 | 135957 | 135406 | 777 | MVNVLPSVYDAEKGEWTLLA KPIAEEVFKIMKADYLEHKGNIG FFISKYKDGDSSIEQHNVVFY NEKDYDTMELTESELTDALNEY IDYTLDGKYKPFSLNNFINYLED YGYRLPVNFEVDVTIILSDGQK FTYPRTSSITNNASIVDALKSED QYIEVKYINDHAIDDKKLAHGN DTLK | 183 | hypothetical protein KgORF7 [Staphylococcus phage K] | YP_024438.1 | 6e-99 (180/183) | | No putative conserved domains have been detected | | |
| 215 | 136293 | 135976 | 778 | VERTLNLYDSKGKLLKSSEKIT GASAKIIEKLTPNTVYSQGSFKI SWTINGKESILTDVPEFTTKSN EDKQEIVFNTLNIDSNSFVVSET EPSDKSKLWFKPIN | 105 | ORF138 [Staphylococcus phage G1] | YP_241056.1 | 1e-51 (104/105) | | No putative conserved domains have been detected | | |
| 216 | 136999 | 136928 | 779 | GGACUCUUAGCUUAAAGGUA AAGCCAACCGCUCAUAACG | 26 | | | | tRNA1-Met | | | |
| 1b | >137359 | 137279 | 780 | KYLLKHSKEADIRSTSKIMDSID KLT | 26 | hypothetical protein KgORF8 [Staphylococcus phage K] | YP_024439.1 | 2e-14 (25/26) | | No putative conserved domains have been detected | | |

Fig. 10QQ

| orf | Putative function | orf | Putative function | orf | Putative function |
|---|---|---|---|---|---|
| 29 | tail completion and sheath stabilizer protein | 127 | EndoVII packaging and recombination endonuclease VII | 192 | DNA topoisomerase subunit |
| 30 | deoxynucleoside monophosphate kinase | 128 | anaerobic NTP reductase large subunit | 196 | rIIA protector from prophage-induced early lysis |
| 38 | tRNA1-Tyr | 130 | anaerobic NTP reductase small subunit | 197 | rIIB protector from prophage-induced early lysis |
| 39 | tRNA2-Lys | 133 | glutaredoxin | 199 | endonuclease IV |
| 40 | tRNA3-Asn | 142 | sigma factor | 202 | nuclear disruption protein |
| 41 | tRNA4-Asp | 147 | alpha-glucosyl-transferase | 205 | topoisomerase II medium subunit |
| 43 | tRNA5-Met | 148 | recombination endonuclease subunit | 207 | activator middle promoter |
| 44 | tRNA6-Gln | 149 | recombination endonuclease subunit | 217 | AsiA anti-sigma 70 |
| 46 | tRNA7-His | 151 | RNA polymerase binding | 218 | holin |
| 47 | tRNA8-Ser | 152 | sliding clamp DNA polymerase | 219 | distal long tail fiber assembly catalyst |
| 48 | tRNA9-Ile | 153 | clamp-loader subunit | 220 | L-shaped tail fiber protein |
| 49 | tRNA10-Trp | 154 | clamp-loader subunit | 221 | hinge connector of long tail fiber distal connector |
| 50 | tRNA11-Gly | 155 | translation repressor protein | 222 | hinge connector of long tail fiber proximal connector |
| 51 | tRNA12-Pro | 157 | DNA polymerase | 223 | long tail fiber proximal subunit |
| 56 | tRNA13-Met | 159 | immunity to superinfection membrane protein | 224 | RNaseH ribonuclease |
| 60 | tRNA14-Leu | 160 | thymidylate synthase and pyrimide hydroxymethylase | 225 | dsDNA binding protein |
| 61 | tRNA15-Arg | 161 | beta-glucosyl-HMC-alpha-glucosyl-transferase | 226 | late promoter transcription accessory protein |
| 62 | tRNA16-Thr | 163 | RecA-like recombinase protein | 227 | loader of DNA helicase |
| 71 | nudix hydrolase | 164 | head vertex assembly chaperone | 228 | ssDNA binding protein |
| 73 | lysozyme | 165 | DNA primase-helicase ATPase | 235 | dihydrofolate reductase |
| 75 | internal head protein | 167 | protein spackle precursor | 237 | thymidylate synthetase |
| 79 | autonomous glycyl radical cofactor | 170 | DNA primase subunit | 240 | aerobic NDP reductase large subunit |
| 81 | RegB site-specific RNA endonuclease | 172 | dCTPase pyrophosphatase | 241 | homing endonuclease |
| 83 | valyl-tRNA synthetase modifier | 174 | small outer capsid protein | 242 | aerobic NDP reductase small subunit |
| 87 | thymidine kinase | 178 | ADP-ribosylase | 243 | endonuclease II |
| 90 | putative lysis inhibition regulator | 179 | Srd anti-sigma factor | 244 | RNA ligase A |
| 92 | putative lysis inhibition regulator | 181 | DNA helicase | 245 | inhibitor of host transcription |
| 120 | thioredoxin | 183 | exonuclease A | 250 | polynucleotide 5'-kinase and 3'-phosphatase |
| 125 | protease inhibitor | 186 | cef modifier of suppressor tRNAs | 254 | dCMP deaminase |

Fig. 11B

| orf | Putative function |
|---|---|
| 257 | head assembly cochaperone with GroEL |
| 258 | lysis inhibition accessory protein |
| 268 | DNA ligase |
| 270 | RNA polymerase ADP-ribosylase |
| 272 | baseplate tail tube initiator |
| 273 | baseplate tail tube cap |
| 274 | baseplate hub subunit, tail length determinator |
| 275 | base plate distal hub subunit |
| 276 | baseplate hub subunit |
| 277 | baseplate hub assembly catalyst |
| 278 | baseplate hub subunit |
| 279 | baseplate wedge subunit |
| 280 | recombination, repair and ssDNA binding protein |
| 282 | RNA-DNA and DNA-DNA helicase, ATPase |
| 283 | RNA-DNA and DNA-DNA helicase, ATPase |
| 284 | minor capsid protein |
| 285 | outer capsid protein |
| 286 | DNA primase-helicase subunit |
| 289 | RNA ligase |
| 291 | precursor of head vertex subunit |
| 292 | precursor of major head subunit |

Fig. 11C

| orf | Start position | Stop position | SEQ ID NO.: | Aminoacidic sequence | Size (aa) | Homologous/similar proteins ||| Conserved Domains ||||
|---|---|---|---|---|---|---|---|---|---|---|---|---|
| | | | | | | Name[organism] | Acc No | E value and identity | Predicted function | Name | Acc No | E value |
| 1 | 1321 | 2 | 782 | MKKNKLIEKWQPLLENEALPEIV GASKKALIAKIFENQEADINQAP EYRDEKIAEAFGSFLSEAEIGGD HGYDAQNIAAGQTSGAVTQIGP AVMGMVRRAIPNLIAFDICGVQ PMSNPTGQVFALRAVYGKDPL AAGAKEAFHPMYAPDAMFSGQ GATEKFEAVKAGAALTVGDIVV HDFAQTGRAHLQVVEDFTVDA GATDAAKLDAAVTAALEAGKVV EIAEGMATSVAELQEAFNGSKD NPWNEMGFRIDKQTIEAKSRQL KAQYSIELACDLRAVHGMDADA ELSSILATEIMLEINREVVDWINY SAQVGKSGMTQTVGSKAGVFD FQDPIDIRGARWAGESFKALLF QIIDKESAEIARQTGRGEGNFIIA SRNVVNVLAAVDTNVSPAAQG LGRGYNTDTTKAVFAGVLGGR YRVYIDQYARQDYFTIGYKGAN | 440 | gp23 major head protein [Enterobacteria phage IME08] | YP_003734314.1 | 0,0 (379/400) | major head protein | Major capsid protein | PHA02541 | 0,0 |
| 2 | 2154 | 1342 | 783 | MLKELLMTEAKTIDASVALDSIF ESVQLSPEAKANFSTVFEATVK KHAVALAESHIEKIAEKAEEKVE EEKEKAKEEAREELKEAASKYF DHIAAEWMAENQLAVDRGIKAD LFESMFVGMKELFVEHNVVIPE ESVDVVAEMEEELAEQKAETA RLFEEVSKRDEYINYAQREYAI QEATRELTDTQKEKVVSLTEGM DYSDAFSTKLKAIVEMVQGSVE QSVTESADINTIDKEADGLNFTT EAVEETPATKTPSVMDAYVAQA ARLS | 270 | gp22 prohead core scaffold protein [Enterobacteria phage IME08] | YP_003734313.1 | 1e-89 (187/272) | prohead core scaffold protein | Prohead core protein | PHA02557 | 5,11e-58 |
| 3 | 2837 | 2187 | 784 | MENLNEQLLIEHWGQPGDVIDG KPMLESIIVEGENESGLKPGLYI EGVFMQAEVVNRNKRLYPKRIL ETAVSRYIKEQVATRQALGELN HPPRANVDPMQAAIIEDMWWK GNDVYGRARIIEGDHGPGDKLA ANIRAGWIPGVSSRGLGSLKDS GKGYNIVQEGFRLTVGVDAVW GPSAPDAWVQPKQISENTSAQ VANSADDAFMALAEKLKAL | 216 | Prohead core scaffolding protein and protease [Enterobacteria phage RB69] | NP_861875.1 | 4e-95 (175/212) | prohead core scaffolding protein and protease | Peptidase_U9 | pfam03420 | 2,86e-88 |

Fig. 12A

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 4 | 3262 | 2837 | 785 | MLILPENHELVIDTVEALLPEAQ ARFDKLSAALSKDDINKIVENLV VSEPDLAIALGSINESLQLNEFIV KHVDSKGTITRTKDRKTRERNA FQTTGLSKAKRRQIARKAVKSK RANPSAQTRGLRKRKKALKRR QALGLS | 141 | gp68 prohead core [Enterobacteria phage RB51] | YP_002854127.1 | 8e-48 (105/141) | prohead core protein | Prohead core protein | PHA02586 | 2.69e-42 |
| 5 | 3486 | 3262 | 786 | MENYISAIESRDLVAAKKAFGAI MAERTSGLIEERKKFIAASVMIE GEEPDEDEDEDEDKSDKD EDDEEDE | 74 | gp67 prohead core [Enterobacteria phage RB51] | YP_002854126.1 | 2e-05 (29/50) | prohead core protein | Prohead core protein | PHA02608 | 2e-07 |
| 6 | 5054 | 3486 | 787 | MAFHILDLFAPWEKRDEAEYKQ QINNDLESITAPKFDDGAREVE SNENEIQYNSFNQMMFGSNEP GMKTTADLINTYRSLMNNYEVD NAVEEIVSDAVVYEDGHPVVSL DLDSTDFSQAIKDRILEEFNTVL TCLNFERKGADHFRRWYVDSR IFFHKIVNTKKMKDGIQELRRLD PRNLQFIREIVTADDAGTKIVKG YKEYFIYDTGKESYYADGRLYS AGTKIKIPRDAIVYAHSGLVDCS GQNIIGYLHRAVKPANQLKLLED ALVIYRITRAPDRRVFYIDTGNM PSRKAAAHMQHIMNTMKNRVV YDASTGKIKNQQHNMSMFEDY WLQRRDGKAVTEVDTLPGMSG MSDMDDVRYFRTALYMALRVP LSRMPDANNQGGVQFDAGTAI TRDELDFAKFIRRLQHKFEEIML DPLRTNLILKKVLSKDEWEDEIN NIKIVFHKDSYFTELKDAEVMER RINMLTMAEPFIGKYISHKTAMK DFLQMSDEEIEQEAKQIELESK EARFQDQENEEDF | 522 | gp20 portal vertex protein of head [Enterobacteria phage JS10] | YP_002922513.1 | 0,0 (404/502) | portal vertex protein of head | Portal vertex protein | PHA02531 | 0,0 |
| 7 | 5672 | 5085 | 788 | MFCTYLTIYTGNKLPRRYIGSTS VSRIIDENYHGSVKSKKYKDLW KSEQHDNPHLFKTRILNTYETR EEASKAELELQIKYDVVKSSSYI NMALAQPNGFFGMSTKGRKMS EESKEKQRHQRLGIKRPDHSIK LSGRKRPDHSKAMSGERNPMF GKEHPNKGKKINQPRMTCPVC | 195 | No significant similarity found. | | | | No putative conserved domains have been detected |||

Fig. 12B

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | GVESTRSAIMRYHKACLSSI | | | | | | | | |
| 8 | 6203 | 5712 | 789 | MELTDITRAFESGDFARPNLFE VEIPYLGRNFSFKCKAAPMPAG IVEKVPVGYMNRKINVAGDRTY DDWTVTIYNDDKHEVRKAIIAW QAQAHAQGNDISGMTPADYKK VATVRQFSRDGKTITNEHTITGL WPTNVGEVQMDWDSNNEIETF ETTFAIDWWE | 163 | Tail tube protein gp19 [Klebsiella phage KPP95] | ASS46617.1 | 2e-92 (162/163) | tail tube protein | Tail tube protein | PHA025 51 | 5,59e -72 |
| 9 | 8304 | 6331 | 790 | MPLVSPGIELKETSVGSTVVLN ATGRAAIVGHKFQWGPAYQVTQI TNEVELVDMFGGPNNQTADYF MSAMNFLQYGNDLRTVRVNR EAAKNASPLVDNIEWTITTAGS NYEVGDKITVKYADQTVDDTGS VTEVDSDGKIKSVFIPTSKIIAYA KSINQYPDLGSSWTTITSQSS GVSAVITLGKIISESTVLLTEHET AHEEMTKTEFQTALAQYKMPGI VAAYPGELGNQLEIEIVSKAAFD KGEQLTIYPSGGQRASTAKAVF GYGPQTDTQYAIIVRRDGAVVE SAVLSTSRQDKDIYGNNIFMDD YFSKGSSRYVFATAQGWPEGF SGVIRLGGGVSANESVTAGDLI QGWDLFGDREALRVNLLIAGAC AGETDEIASTVQKHVSSIADER QDCLALISPPRSTIVNIPLTRAVD NLIDWRQGDGTYDSANMNINTT YAAIDGNYKYQYDKYNDVNRW VPLAADIAGLCARTDDIAQPWM SPAGYRRGQILNCIKLAIEPRQA HRDRMYQAGINPVTGQGTGEG FILFGDKTATTVPTPFDRINVRR LFNMLKNNIGDSSKWQLFELND NFTRSSFRMETSQYLAGIKALG GVYDFRVVCDTTNNTPAVIDRN | 657 | Tail sheath protein gp18 [Klebsiella phage KPP95] | ASS46616.1 | 0,0 (645/657) | tail sheath protein | Tail sheath protein | PHA025 39 | 0,0 |

Fig. 12C

| off | Start position | Stop position | SEQ ID NO.: | Aminoacidic sequence | Size (aa) | Homologous/similar proteins ||| Conserved Domains ||
|---|---|---|---|---|---|---|---|---|---|---|
| | | | | | | Name[organism] | Acc No | E value and identity | Predicted function | Name | Acc No | E value |
| | | | | EFVASFYIKPARSINYITLNFVAT ATGADFDELIGPQ | | | | | | | | |

Fig. 12D

| orf | Start position | Stop position | SEQ ID NO.: | Aminoacidic sequence | Size (aa) | Homologous/similar proteins ||| Conserved Domains |||
| --- | --- | --- | --- | --- | --- | --- | --- | --- | --- | --- | --- |
| | | | | | | Name[organism] | Acc No | E value and identity | Predicted function | Name | Acc No | E value |
| 10 | 10176 | 8338 | 791 | MEQTQPFNVLSDAHPLNDGKL TVIRHPSEMETKIENGVRFFKS QWDDKWYPEKFEDYLKLHGIV KIRLQGEDPAHFQTFKDKNNKR TRYMGLPNLKRANIKMQLTREI VAEWKKCRDDIVYFAETYCAIT HIDYGTIKVQLRDYQRDMLEIM AAKRMTCCNLSRQLGKTTVVAI FLAHFVCFNKDKAVGILAHKGS MSAEVLDRTKQAIELLPDFLQP GIVEWNKGSIELDNGSSIGAYA SSPDAVRGNSFAMIYIDECAFIP NFIDAWLAIQPVISSGRRSKIIIT TPSGLNHFYDIWTAAVEGKSGF TPYTAIWNSVKERLYNDEDMFD DGWQWSLQTISASSLEQFKQE HCAEFHGTSGTLISGMKLANMD WIEVTPDSHGFYKFKEAEADHK YIATLDSAEGRGDYHALNIIDV TTSEWEQVGVLHSNTISHLILPD IVIKYLMEYNEAPIYIELNSTGVS VAKSLYMDLEYENVICDSIVDLG MKQTKRSKAVGCSALKDLIEKD KLIIHHRATVQEFRTFSEKGVS WAAAEDGYHDDLIMSLVIFAMLT TQQKFADFVDKDEMRLASEVF KRELEDMNDDYAPVVFVDAVN SAEYAPQEHGLSFV | 612 | gp17 terminase DNA packaging enzyme, large subunit [Enterobacteria phage T4] | NP_049776.1 | 0.0 (506/608) | terminase DNA packaging enzyme, large subunit | Large terminase protein | PHA02533 | 0.0 |
| 11 | 10663 | 10154 | 792 | MSELQLDMAKLLDIEGIPGIEGQ EIPVYEKLELVEVKSNPNDRKP DLEDDYSVVRKNMHFQQQML MDAAKIFLETAKNADSPRHMEV FATLMGQMTTTNKEILKLHKEM KDITSEQVGTGKGANPQQGMN IQNATVFVGSTADMMDEFGDA YEAQEAREKIVNGTDSTV | 169 | gp16 terminase DNA packaging enzyme, small subunit [Enterobacteria phage T4] | NP_049775.1 | 0.0 (130/160) | terminase DNA packaging enzyme, small subunit | Small terminase protein | PHA02585 | 2.22e-59 |

Fig. 12E

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 12 | 11484 | 10660 | 793 | MFGHWVNSSLRRYIVLLGDLFS HVQIARWREDTGLKYIKVPITYA SKEKFLSQLGKWTAIQSTENKA KIETVLPRMNLHLVDMQYNAMY KTSQLNRTKSYKTPSKITSQYN PTPIKMIFELGIYTRNQDDMYQII EQIVPYFQPHFNTITITELYDKDT SFNRDVRIVLQSFSQDEAVDGD NITRRRLEWSLMFEVNGWLYP PVAEIDGEIRTIYLDFFANSKELT PEGNFESVDSEVTPRDVQHEN WDGSSKQTYSHDIPIPVNPEAP GPRGEK | 274 | gp15 tail sheath stabilizer and completion protein [Enterobacteria phage JS10] | YP_00292250 8.1 | 4e-113 (194/273) | tail sheath stabilizer and completion protein | Tail sheath stabilizer and completion protein | PHA025 56 | 3,5e-117 |
| 13 | 12302 | 11526 | 794 | MSTFDSRLFAKLEDYRGYNKTN ETEILNPYVNFYNHRNSQTLAD ALSAEAIQMRGIEFYFLPREYNN PDLLFGEDPSSKFTKAWKFAAY LDSFEGYSGDNTFFSKFGMMV NDEVNLTINPNLFKHQTNNSEP KAGDLIYFPMDNSLFEINWVQP YDPFYQLGQNVQRKITAQKYIY SGEQLQPELQRNEGINIPEFSE LDLEPIKNIDALADISDIQYAESD EINKEASEYVHPYYVNNGRGLE SPPKADSFDDGFFE | 258 | gp14 neck protein [Enterobacteria phage JS98] | YP_00159529 0.1 | 4e-115 (199/258) | neck protein | T4_neck-protein | pfam11 649 | 7,29e-94 |
| 14 | 13247 | 12306 | 795 | MSYNTYNPKTLKDAILRRLGAP VINVEVTEDQIYDCIQRALELYG EYHFNGLNKGYQVFYIGKDEAD NARFLNGVFDLRGRNVFAVTQI VRTNVGSLTSMDGNATYPWFT DFLMGMAGINGGMGSSCNKSY GPNAFGADLGYFTQLMTYWSM MQDLLAPLPDYWYNSDNEMLK VMGNFMKGDIIVCECWTKSFM NTDAMVGNTAGYGFAGPQTAD HWGLGDRYQNPDLRNNGQYA GEGNTNREGAYNNRWVKDYA TALTKKLWGEILFKHQGLQLAG GVTVDGQTLKVEAQEEIERLRE ELDLDPGCPILLG | 313 | gp13 neck protein [Enterobacteria phage JS98] | YP_00159528 9.1 | 2e-123 (223/314) | neck protein | Neck protein | PHA025 54 | 9,45e-117 |

Fig. 12F

| orf | Start position | Stop position | SEQ ID NO.: | Aminoacidic sequence | Size (aa) | Homologous/similar proteins ||| Predicted function | Conserved Domains |||
| | | | | | | Name[organism] | Acc No | E value and Identity | | Name | Acc No | E value |
| --- | --- | --- | --- | --- | --- | --- | --- | --- | --- | --- | --- | --- |
| 15 | 15071 | 13305 | 796 | MTKLVDSLPFVDGIPDDFQQRI NWIKNTEPLNGASTRYGNDGE LNRASVQIQKNVVQVHNDLNNV GTAVENIQVDVDQIKKSLEITGS SDAIEQVYINKKNIEKHDGQILKL EEDTEKLRTDLDFLEEDVGVYD SSKDDYYRTVRDNIVWVKREIG AYPGQDINGQPKQDSPGSGMK YRIINNASAIVKHDERIQALEDAY NDSDVGSLTIEVNDLRKEVGPK SGATSASIYARLVNNADAISAAN NEIFAINQAIDFTNPVKIGARTTR LENDYRIVDATLNFAQTGLVPR VNNIDARLGSSDKPDTIEGKISS LSTDQGYISDVVGRDTSSGLQG QVAWINQQVGIVPSEQPIPPGSI LARMTNVEGMQNSQQSAIQDI QVELGNNNEGLKGSVFTLQTQ MNGDFSSENPVQRDGVYATVV ELQDKFVTAVTDVEQAGAYLRK QGEWFKKPSSIGEFSKEDFTVD LSSDALVNPNSLVAAPFNAGIRI VDDIVVDDDGVFCVETDTVIEA SDSDKGVKIVILVNNIEVFSYGL GVKAVTGEQLIKTKKLIEFSSGD AIKIVYRAASEESQVLVKIKSLDI TIHPAV | 588 | Fibritin [Klebsiella phage KPP95] | ABH10666.1 | 3e-124 (221/225) | fibritin | wac, fibritin | PHA026 07 | 3.25e -111 |

Fig. 12G

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 16 | 16426 | 15080 | 797 | MAQNNYNHYSDLAKYTIFDPTN TQWPVAIKDVQSALELIGSWAR TDTGLPVASPTVAGVIRTATQA EVDAGTIGNAAVTPATLKSTVT RPEATTTVLGLTRYATNTEAAA LTAGNRTITAAALGHVFKTVKA QENVDGTVRLTTAAQAQAGTD ETTAVTPKRVVEMIGKFSVSPP SYTSATESNLGLVRVATQAQVA AGAVHDGYAVTPKTFMASKAS DSVFGIVKFAKDSDVASATSNN LAVTPKSLQALKSTKDKYGLTR LSGSPTTDASLAAAATDAVFKT RRINGKTLDNDITITNNDINCYT RQESDGRYMPAGTRVGNVTW VEGQSWISRGATFTCNAPWEA SSRLALNVNVKFERNNDGYDN RIFRFVVIVNGSQWGGELTLNIE NTKGGRNGHSWRFEAYASSNF FFNNIPPNATVQIRPTEDSRIIFY DCMLTFCTNRP | 448 | gp12 short tail fibers [Klebsiella phage KP15] | YP_00358004 3.1 | 2e-52 (123/310) | short tail fibers | Long tail fiber, proximal subunit | PHA025 84 | 3.81e -17 |
| 17 | 17097 | 16426 | 798 | MTIETKTREGAKVNSRLAAFSE YRVDPQNIAVGNTAPIGSLTFE QMDLGVWYPNTEAAINDLMSL QSAEIGTIICNDTGISPQPAQQIT RATFSGVVALEPKEDGSVGDP VIIHILGLPIRIANGDDFAAVATR WYDKVKELEAVGKVVQQVTQS PATPQYVDIIHLDYQNHNFETYK KYGLTVEFTITSPAKAGYGQWD AIGNESKTFGANTFTFHYFRRM G | 223 | gp11 base plate wedge completion tail pin [Enterobacteria phage RB51] | YP_00286411 5.1 | 5e-27 (68/215) | base plate wedge completion tail pin | Baseplate wedge subunit and tail pin | PHA025 8 | 4.15e -49 |

Fig. 12H

| orf | Start position | Stop position | SEQ ID NO.: | Aminoacidic sequence | Size (aa) | Homologous/similar proteins | | | Conserved Domains | | | |
|---|---|---|---|---|---|---|---|---|---|---|---|---|
| | | | | | | Name[organism] | Acc No | E value and identity | Predicted function | Name | Acc No | E value |
| 18 | 18922 | 17099 | 799 | MKQNLIVGQSVDDGSGDYLRK GGLKINNNFDDLYSELGDGSVP FAAGAWKTFKASPTGTTLNAKF GQAFAINTQAARVNVQLPKGTA NDYNKVIKLRDVWSTWRLSPIT VIPAQGDTLKGSASPKIFNTNFQ DLELYYCAPGRWEYIENKTVDK LTNGNLSTVAKKSIIATAGQTDF LNIFDGVEYNEDSLNVYRRGNIL YYGETSVMDKANADYGSPGTV AGQLVELNGKDIRLKVPCVEGE VITFETFLDGIGVYRSSYNKLAI QIRDSAQTTSQTIPGSIIVDNLTA LRRITLDDMGVLPGVGVNPNSL EISLNGKELLEAGTAGLPLFYCE GAEGGYAEDCINNGGQWVNS NQDYRLEFDSTGTNVEAIIFGEA FEDKDLLTVRWFNNNIGTTMDI DDIMAETDQVYMNAEQLVTLKN RIEYTNYDEPNQKNMRPVADDI MIKVNNIAAFFDVIYPIGTIYENA HNHANPADYMGFGVWKLYSQ GRVTAGWNNDSSDPYFSRNN NNLNENGQPSLTAGGTVGDLT FTLGKEHIPELMSRDKVLISDPE HGSVVIGGCQLDPDAQGPGYS KYREDTVAVNNGVVPNDITKIQ PTITVYRWIRVG | 607 | gp10 baseplate wedge subunit and tail pin [Klebsiella phage KP15] | YP_00358004 1.1 | 0,0 (323/611) | baseplate wedge subunit and tail pin | Baseplate wedge subunit and tail pin | PHA025 82 | 0,0 |
| 19 | 19833 | 18922 | 800 | MYTDKGKKIIDVGEIGNASTGDI LYDGGVKINDNFDAIYNAFADQ RLFAAGGGALNQKIHATSYYQK IKFGDANSAGTVPMGSCIDADC SEGAVQIRLSKGKAGEAVFVVN SNGSASKARSIKITTNGEGVAD AFKDGSRELIINTPRCRIELWCV EVKANGAAVWDYSISSMFGST YSPLEATYNLTSSPINIRLGYND DYSTVKLLLSFSANPGGGTIKR QSSEVMLMIDPTITSSAPNGRV FDTEYAVLRSGESSENEKMYSI SYSINAQKDLICTASTSYGNARL AVKVIATQTVGVSQ | 303 | gp9 baseplate wedge tail fiber connector [Enterobacteria phage JS98] | YP_00159528 4.1 | 6e-60 (134/302) | baseplate wedge tail fiber connector | Baseplate wedge tail fiber connector | PHA025 81 | 6,6e-67 |

Fig. 12I

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 20 | 20924 | 19899 | 801 | MSNSTRASSTRSTIYRAIITSKF RTEKMYTFYKSIGPGTDQNTLY VSFGKSTPWSDNESEPGFAPP YPADNGDGVVDVWTNMMGAV KIESSMLDCVVPRRDWGDTRY PNPRTFLIGDIVVANSAPYNRTD AGFGWMVYRCIDVPKDGMCSI GNLTSKEECIKLGGKWTPSTIS GSAPRGRGDANGTVDLGDGYL WEYLYEIPADVSINRCTNEYIVV PWPEEIEESPARWGFQNNLTW QQNDFNLIYRMKCNTIRFKAYL DAVYFPEFSLPGNTGFRQLSIIT NPLEVKPMFNSPNVKAEKGWY SASGLERQSGEMIYMENRQPII RSMDQTEELNLIFEF | 341 | gp8 baseplate wedge subunit [Enterobacteria phage JS98] | YP_001595283.1 | 9e-146 (238/330) | baseplate wedge subunit | Baseplate wedge subunit | pha02580 | 1,08e-164 |
| 21 | 24015 | 20917 | 802 | MTIAPPFVTSLRIHKLSANQVNIR WDDVGANFYYFVELAETRNRA GEIIPADNLSWSSLGYTADNDW FEQNRIEPLTYYKMRVQTTSAG FEPSEWVETEEFQTFEENAYTF EHMQEFSLVKEFIKQKFSLNNM SYVNFNTSAMMASLMTESFQF SPEYSHLSAIENFVVGESGYHEI QGPIEAVCVDKNRTMLGEIDGIL YLFERFQHMVKVSNDKGQNW QYVQLFNDRVGNPVSRVVIYQS STTSYVLGYDKIFYGRKSSDVR WSSNEVKFSDNEVTFAKLGDQ LKLGFEVELFGTYASLPADVTK YAEAFTCNDDHLYVVAKDTVRR VKLKDAPIDTDPLSPTFGEKVFE KEASHITGNPKSVCFKMDSVG GKIFALITGEVKTLGLDPTDPRN VVDSATKGVVVYQEDTNTWKR VFGNTDEEKRRIEHLWTSMSTD GKEIFFSSANFKTTEYTQDIELE TKYPELISTAVKNVNPIQYHSDK HYHMMSFRADEFSRWETFVPG PMRFYAEPWFVWMAREGNRC WISTADHAVVIYNDILYQKRVDA AAQGTTERVLSEVWDKGDATF YCPPVSFNGFLQYASGIMFHEP | 1032 | gp7 baseplate wedge initiator [Enterobacteria phage IME08] | YP_003734295.1 | 0,0 (667/1029) | baseplate wedge initiator | Baseplate wedge subunit | PHA02579 | 0,0 |

Fig. 12J

| off | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and Identity | | Name | Acc No | E value |
| | | | | DGKLIGYYAFDYRVRDQVTLN WKPTDVMFKAFLQNQTREEDW TPEHTPGLRDPDLRPYLTKMM PDSYLLQDSNFEQFCKYYLQFL SDGNGTHYNSLVNLVKNKYPR EENAWEYLWSEVYKRNIYLSKD ARDAVVRFFEARKNDFYATKGI EDSYKFLFKLLYNEDVEIDIESK NTTEYDIIVESTNISDDLVGRTIY TASGRSNVTYIEREYRDGRLLW RITIHNLSGRFIEGQEIKSERTDF EGIIVQGVRGKDMLSNNIDYINR SRSYYVMKIKSQLPTSRFRDDV LRFVHPVGFGFIGITLLTMFINS GLNMKHVETIINKLKNYKWDAG LPSVYPDRVAIIASDDTIERDPIT NEPRYSSRAQAGEPFPLPANY NQENNNSIIAGQNPGQRRKPLS PTFDQSAVTFANYRDLVNQRLK DDAGNPRDPENPTQVKIDE | | | | | | | | |

Fig. 12K

| orf | Start position | Stop position | SEQ ID NO.: | Aminoacidic sequence | Size (aa) | Homologous/similar proteins ||| Predicted function | Conserved Domains ||
|---|---|---|---|---|---|---|---|---|---|---|---|
| | | | | | | Name[organism] | Acc No | E value and identity | | Name | Acc No | E value |
| 22 | 25970 | 24012 | 803 | MAIKEPLNYQLTRTANAIPDAFT GATFDEIKNQLINWLSGQKEFQ DFDFAGSRLNVLLDLLAYNTLYI QQFSNTALYESFIGTANLRSSV VQAAQQNGYLPSSKSAATASIM LEVTHMNPSSTLRVVIPRGTKF LAYSKSDKANPYNFVVTENVVA IRDNDQKYWPIVNLAQGRIIRTQ LSYDPKKPIVIRDQSIDRKQVKL WVDGAEWTNWTDRSMVHASS ISTYYMRETVDGNTEFFFGEG VAEASVAGGVLESNFIGGLKPT KGAQVVIEYIRTDGEAANGATE FSYADTLQYIVVNRIIENWSDSP DYYGADGGGEPEDIERIRELAQ IKRESQMRCVSKTDYESFVSSR FGSIVQAVQCFTDQDKPGYAFI AIKPKSGLQLTAVQREDIQDYLK PFCLAPITPSVMSPDYLFIRHNI KASYALNKLQESEQWLQSKIID SINRYYVDEVEMFNKNFSKSKL LTYIDDTDHSIIGSSVDIQMVREI VNYFTLPSAGIKYYNTITPRTLR SGDLVFTVTPTAEPYSVNIVGT DPDKNGKGNMVIGPFKPGDIKE NTHIQPYTENDFDRTTIGERTR WYKIGEVDYYGDNIYWSLGAIG ADPLQFEDQSIELYSTPTQDIVF ARDGTLIVFENDLRPQYTTIKLE PITQ | 652 | gp6 baseplate wedge subunit [Enterobacteria phage JS98] | YP_001595281.1 | 0.0 (443/650) | baseplate wedge subunit | Baseplate wedge subunit | PHA02553 | 0.0 |
| 23 | 26263 | 25997 | 804 | MAGLSFNKCLTAGHSAYPPTEV NATQSKVFTGGIAVLVDGDSITP HTKTVDPHDTHGGVVQPRTSK VFVTGKKAVQMADPISCGDTVA QSSSKVFIH | 97 | gp5.4 conserved hypothetical protein [Enterobacteria phage JS98] | YP_001595280.1 | 9e-39 (76/76) | | No putative conserved domains have been detected |||
| 24 | 26767 | 26264 | 805 | MADILPINTLREVIEGEYVEQY FTAQLSTNETLKSINIIDYQPVSD ISVSETHYKGNYNSVFTFGNDV LKYREGDELKSASAWEDLPNP KTADLYLWKAPRTLEKTFYTV EIIYTVTEESSGGSSGGSSAPIIT EHKKQKIYSQTVKGNWSRWGD QLRAYVYAGN | 167 | Hypothetical protein EME08_gp142 [Enterobacteria phage IME08] | YP_003734292.1 | 2e-40 (86/177) | | Hypothetical protein | PHA02606 | 4.54e-48 |

Fig. 12L

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 25 | 28500 | 26770 | 806 | MIEMNDSLKWFTGVVEDRQDP LKQGRVRVRVYGLHPFEKVQG AITGLPTEDLPWMSVIQPTNSA GISGVGSSITGMVEGTSVFGLW LDEFKTAGLVIGTYSAHRKTKP NYTEGFSDPTGQYPRQVGSDT NPLVQGDETGYSAIPNIIQDRNL DIGINPDDADLSDIPEDPNPAITI TDMLNRDEGLRLKVYWDTEGY PTVGIGHLIMAQKVRDMSVINKT LSNQVGRTVTGNPGIITMDEAV ALFKKDRDKMLSDIKTNSRVGP VYAKVNKSRQMALENMSFCMG VGGLAKFGKMLDAMLIGDWKT AYTEARNSWWFNQTKGRASRV SMILTGNMESYGVPAPKPEGK NLSAAYVEPKSGGNPEDPWTP EDSRILFKEPESSYNGQYPYVH TMETESGHIQEFDDTPGYERYR IVHPTGSYEEVAPDGRRTRKTV ADLYDMTQGDGNILISGDKKVN VGGNETYYNMYNRRQQIDGDN TLYVRGNETKTIEGNGTIFVKGN IKIVVEGNADIQVNGDATTKVDG NHDVTVGGNLTWQVAGTVNW NVGGAWTETMASMSSIAQGQY TVDGSRIDVG | 576 | Base plate hub subunit and lysozyme [Enterobacteria phage RB32] | YP_803092.1 | 0,0 (391/576) | base plate hub subunit and lysozyme | Bacteriophag e_T4-like_lysozym e | cd00735 | 4,39e -65 |
| 26 | 29135 | 28497 | 807 | MLFSFFSPIDYSAKTVKGAKAK AIPTADIFRNYRKYFDTVAENYL LQTYYISGAPRPEELAYILYGNS QLYWILLMCNNVYDPFRDWIKT QDACYQFAQQKYADVGGDQIL YHVDAYGNRYYNLEQYPENSG VWYDKGDFNHQYPQYTGALAG VDIYEDSIIENEKLRQININPSDI EAFLSDIIREMEKAPDSEYESG RYKSQTTIGEVL | 212 | gp53 baseplate wedge subunit [Enterobacteria phage JS98] | YP_00159527 7.1 | 1e-66 (121/199) | baseplate wedge subunit | Baseplate wedge subunit | PHA025 78 | 4,62e -75 |
| 27 | 29185 | 29634 | 808 | MAYSGKFMPQNLHKYKGDFRK ITYRSTWEQYMMRWLDNHPDV VQWNSEEVVIPYFSNADGKKR RYFMDFWAKFSNGCQFFFEVK PKKETRPPVKPTKLTTSAKKRYI DEIYTWSVNVDKWKAAQATAS | 149 | gp4 head completion protein [Enterobacteria phage JS98] | YP_00159527 6.1 | 2e-67 (122/149) | head completion protein | Head completion protein | PHA025 52 | 1,15e -63 |

Fig. 12M

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | KMGIEFRLITEDSLKKLGWKG | | | | | | | | |
| 28 | 29634 | 30461 | 809 | MAIFEFITEAAESPKAKSRSENQ WVALGVEYSAARKKGMTSKSF AESKGINPATFSKAMARHASRI KTAIKVAEIEKKPANKMTKQERA LVMVNSFRSSIKDKIRNEGAAV NNKSAKWFAETIKKNIRGHSVT KPQPGKLYAYMYDAKHKDTLP FWDKFPLIVYLGLGKQGTTTLM YGLNLHYIPPKARQFLEELLK QYANTPVISNKTRLKINWSQVK GFAGADKMIKAYIPGNIKGALIEI KPADWANVVMLPLQQFMSKGK RYSATSVWKS | 275 | gp2 DNA end protector protein [Enterobacteria phage IME08] | YP_00373428 8.1 | 1e-188 (200/277) | DNA end protector protein | DNA end protector protein | PHA025 77 | 7.34e -107 |
| 29 | 30461 | 31063 | 810 | MSTGLFNQTNTNFILEVPDGG LTQAFKANLQTAVVPGIHIPATD TVGSPQGMHRAKLPGSTFEFD AVPVRFLVDENLDSWVQMYKW MLSCQNYIDRDKSGWNNGGE GFPGAVLMHVLDNDKHDIVLTV RYIGGWVSDLSEIEYSLTEESD PAMVCVATLQYKYIEVEKDGIIIT GRPSVNDTRESQYQQKVMGM HPSMR | 200 | gp3 tail completion and sheath stabilizer protein [Enterobacteria phage JS98] | YP_00159527 4.1 | 2e-61 (111/197) | tail completion and sheath stabilizer protein | Tail completion and sheath stabilizer protein | PHA025 76 | 7.95e -65 |
| 30 | 31068 | 31811 | 811 | LKLLFLIGKKRSGKDTTADYIMD NYNATKHQLAGPIKDALADAML TEWYRDTSREFPRITRSMIEGID YDREQDLNLSTKDVIRIMANAIE YVHHDLPLPGVVYDNKRKILDG DTMEVIRKVVINKPVEPWSIRRL MQTLGTDIVCDKLDRMYWVKR FTLVMADTFGDYDYFIVPDTRQ DHELDVARAMGATVIHVVRPEQ EGSKKDTHVTERGLPIREGDIVI TNDGSLEELYSKINTILGIQNDY | 247 | gp1 dNMP kinase [Enterobacteria phage RB14] | YP_00285448 0.1 | 3e-69 (140/252) | deoxy-nucleoside monophosphate kinase | Deoxy-nucleoside monophosphate kinase | PHA025 75 | 2.45e -65 |
| 31 | 31801 | 32034 | 812 | MTTEQLQAQVDTLKVRVFDLSE TIQGLSALRAQYEEVLQKLIAVS GVEIGEDGQVKLDDLVAKIEAQ | 77 | No significant similarity found. | | | | No putative conserved domains have been detected | | |

Fig. 12N

| orf | Start positi on | Stop positi on | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | FAEETTEESE | | | | | | | | |
| 32 | 32034 | 32489 | 813 | MKFSDFSTGLYVAAKFSEKTLD AIEDLQRELKVPNPVPRHKIHTT ICYSRVHVPYVCASGSFEVATS GKLEVWDTQDGRTLVLKLDSE YLKFRHQYARALGATHDFPDYS PHITLSYNVGPAHFEGEVQVPV VLDREYQEPLKLNWSEDLK | 151 | gp57B conserved hypothetical protein [Enterobacteria phage T4] | NP_049750.1 | 6e-67 (120/151) | | Hypothetical protein | PHA025 74 | 4.25e -65 |
| 33 | 32486 | 32869 | 814 | MKSYQEFLMETEALLESTLPDY MIVKSFNVKNGYVIKFPIASVKP GADMSNDAGISVKVNVQFINYN SAKKSYDAKMTFSGGEKVVKNI KLDYDESAESVKKRFGDKLVKS IMVHPTFKRDFTELYK | 127 | No significant similarity found. | | | | No putative conserved domains have been detected | | |
| 34 | 32935 | 33114 | 815 | MKRCELIRNVASAICLTAVGTSI FGAIFMGAKEIMVVLVAAFLMG SISFIMDKISHEKD | 59 | Trna.4 conserved hypothetical predicted membrane protein [Enterobacteria phage JS98] | YP_00159527 0.1 | 5e-07 (31/59) | | No putative conserved domains have been detected | | |
| 35 | 33101 | 33280 | 816 | MKKIKQWFVKTYDLGREEVTKY DYVTLGVGLGALLAALHSSLLAI AVLILAHYSWKRK | 59 | No significant similarity found. | | | | No putative conserved domains have been detected | | |
| 36 | 33280 | 33465 | 817 | MYALLTWSNYYPAPGSDQIRG VYSTVEECYEALQGTYQDYFEI LNSRFETVAKGSTEAYKD | 61 | No significant similarity found. | | | | No putative conserved domains have been detected | | |
| 37 | 33482 | 33832 | 818 | MNIIRAAFNTFYQENYKLLSHEY YDAQGVPIPSDLVTPKHVKTDS LDNEIQPGDLVSYYCGGSLSAA SVGILLGFTPKGYRVVPFHTSPI PEHRVLLSHMDSPHRVFLVKSK SSPIV | 116 | No significant similarity found. | | | | No putative conserved domains have been detected | | |
| 38 | 33915 | 33998 | 819 | GGGGAGUUAGACCGUAGGGG UAGCGGGACAGAGACUGUAAAU CUGUUGCUCAAAAGGCUCGA GUGGUUCGACUCCAUUACUC CCCA | 84 | | | | tRNA1-Tyr | | | |
| 39 | 34009 | 34082 | 820 | GGGAUACUAGCUCAGUUGGU UAGAGCACCGGACUCUUUAAU CCGGGUGUACGAAGUUCGAA UCUUCGUGUCCCA | 74 | | | | tRNA2-Lys | | | |

Fig. 120

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 40 | 34091 | 34172 | 821 | GGGUCGUUGGCUGAGAGGG UAAGCGACGGACUGUUAAUC CGUGUCAGAAAUGACUAGGC AGGUUCGAUACCUGCACGGC CCG | 82 | | | | tRNA3-Asn | | | |
| 41 | 34429 | 34502 | 822 | AGUGCUGUAGUCGAGAUGGU UAAGACACUCCCCUGUCACG GGAGAGAUCGCGGUUCGAC ACCCGUCAGCACUG | 74 | | | | tRNA4-Asp | | | |
| 42 | 34586 | 34984 | 823 | LTFDEWLSWWKATGKYHLRGR ASDNYCMCRKGDVGPYSLDNI YCATNAQNAKDAGANGRIISTG FTGHNHSDETKIKISENHAHKLN ADEISLRIDLYNSIDFTQRGALV KFANKLGISHTQARKFINKFIK | 132 | PHG31p119nc [Aeromonas phage 31] | YP_238848.1 | 2e-31 (67/134) | | No putative conserved domains have been detected | | |
| 43 | 35138 | 35211 | 824 | UGCGGAGUAACUUCAGUUGG UAGAAUGUUGGGCUCAUAUC CCGACACGCGCAGGUUCGAG UCCUGCCUCCGCCU | 74 | | | | tRNA5-Met | | | |
| 44 | 35221 | 35292 | 825 | UGAAUCAUAGCCAAGUUGGU AAGGCAGUAGGUUUUGAUCC UACGAUCCCUGGUUCGAGUC CAGGUGGUUCAG | 72 | | | | tRNA6-Gln | | | |
| 45 | 35367 | 35540 | 826 | MMDGVNIDVVVVQLVEPEVVIL DVTDSNSVGHPNNEGMVEKYT ARKTLWLSLSELCL | 57 | No significant similarity found. | | | | No putative conserved domains have been detected | | |
| 46 | 35391 | 35463 | 827 | GUGGUCGUAGUUCAGUUGGU AGAACCCGAGGUUGUGAUCC UCGAUGUCACGGAUUCGAAU UCCGUCGGCCACC | 73 | | | | tRNA7-His | | | |
| 47 | 35564 | 35645 | 828 | GGAGAGUAGCGCUAGUGGUA GCAAACCCGACUUGAAAUCC GGGCCACCGGAAACGGUGAG GGUUCAACUCCCUUUACUCUC CG | 82 | | | | tRNA8-Ser | | | |
| 48 | 35715 | 35787 | 829 | GGGAGUAUAGCUCAUUUGGU AGAGCUCUCGACCGAUAAUC GAGCGGUGACUGGUUCGAGU CCAGUUACUCCCA | 73 | | | | tRNA9-Ile | | | |

Fig. 12P

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 49 | 35797 | 35868 | 830 | AGGUUCUUAGUAUAAUGGCU AUAAUGCUGGGCCUCCAAACC CAGUGAUGAGGGUUCGGAUUC CUUCAGGGCCUG | 72 | | | | tRNA10-Trp | | | |
| 50 | 35877 | 35948 | 831 | GCAUCCAUCGUAUAGCGGAU AUAUGUCUGGGCUUCCACCC AGAAGAUGGAGGUUCGGAUUC UCCCUGGAUGCU | 72 | | | | tRNA11-Gly | | | |
| 51 | 35957 | 36030 | 832 | CUCCGUAUAGCUCAGCCUGG UAGAGCCUCCAUUUGGGAU GGAGAGGUCGAAUGUUCGAG UCAUUCUAUGGAGA | 74 | | | | tRNA12-Pro | | | |
| 52 | 36209 | 36361 | 833 | MKYYGFKTSHFGKAYRTENIDR RRAYYESLHKAGRSRARQEGQ KQAKEIE | 50 | Hypothetical protein RB43ORF088w [Enterobacteria phage RB43] | YP_239064.1 | 5e-13 (35/48) | | No putative conserved domains have been detected | | |
| 53 | 36358 | 36723 | 834 | MNIFIGVANNVNAITVKLQWNR PTNFALGLCKSERDLMLHADFA YTFDERKGMWVWIKCRYEALIK YEYFSERDIQEVIAYHSGCKVS KLRQVIPFTNASNVEELITDFKRI YQAKYDERF | 121 | No significant similarity found. | | | | No putative conserved domains have been detected | | |
| 54 | 36707 | 36940 | 835 | MMMDSKGRDVQVGDIVFYGER TYNKGGRGSMRCGRITDIASGL AKVDNDYVAMRSKSFVKVSPM FATMWENGTIFEI | 77 | Hypothetical protein Ea21-4_gp102 [Erwinia phage phiEa21-4] | YP_00245612 5.1 | 7e-04 (25/72) | | No putative conserved domains have been detected | | |
| 55 | 36995 | 37219 | 836 | MKRIALIVDQEAMFAATGKFHP VSKFVARSEKIVGLVETVAGDVI VSIKTSEISPVVKVAVENDFWEV ADFMCE | 74 | No significant similarity found. | | | | No putative conserved domains have been detected | | |
| 56 | 37298 | 37371 | 837 | GGGCCUGUAGCUCAAUUGGU AGAGCGUUCCCUCAUAAGG GAUUGGUUGCAUGUUCGAGU CUUUGCCAGGUCA | 74 | | | | tRNA13-Met | | | |
| 57 | 37394 | 37594 | 838 | MMRLVKVVVEESEYMGDSRMI EEFVTVEADSESEIVDKVYRHF DNMSDSYGTMYSIYRLDVIVHIN | 66 | No significant similarity found. | | | | No putative conserved domains have been detected | | |

Fig. 12Q

| orf | Start positi on | Stop positi on | SEQ ID NO.: | Aminoacidic sequence | Size (aa) | Homologous/similar proteins ||| Conserved Domains ||
|---|---|---|---|---|---|---|---|---|---|---|
| | | | | | | Name[organism] | Acc No | E value and identity | Predicted function | Name | Acc No | E value |
| 58 | 37605 | 38162 | 839 | MHIRFGQVIPKGLAMAITTWEN DADRYSTQMVYGLEKEEINQVI HVLEWFSSNGRRGEYLGNNDY NHEAILEKLHTEQKYVTPEFSKK FFGVDVPAYDCTDEEFDAYLDN HYSCSNEVMYAIQAWLGNPIEY DYDFMRVFEKVEIFDIKEEIRIPD APVAFHVGITYKQKESPLKVDW LKYVKEK | 185 | Hypothetical protein EpJS98_gp138 [Enterobacteria phage JS98] | YP_00159526 7.1 | 2e-20 (63/162) | | No putative conserved domains have been detected ||
| 59 | 38162 | 38611 | 840 | MDIGSGSSYPSCALSNFAPHKF IYDGVECASMEGFLQSLKFSSP EMQAHVCTLVGKSAKFKGKKK RWWPTQTLYWKGVPIHRASEA YQNLLTGAYDALSKNEGFRKAL AATRNATLTHSMGKNKISETILT EREFCNQLYRLRNAINNQ | 149 | Hypothetical protein KP-KP15p076 [Klebsiella phage KP15] | YP_00357995 2.1 | 4e-57 (114/146) | | Phage_30_3 proteins | pfam08 010 | 4.60e -65 |
| 60 | 38757 | 38840 | 841 | GCGUCGAUGUUGGAAUUGGU AGACAAAGGAGACUUAAAAUC UCCCGGGAUUAAACCCGUAC GAGUUCGAGUCUCGUUCGAC GCA | 84 | | | | tRNA14-Leu | | | |
| 61 | 38846 | 38918 | 842 | GCCCUUAUAGUGUAAAUGGAU AGCACACGAUCGUUCUAAGG UCGGUAGUCCGGGUUCGAGU CCUGGUGGGGUA | 73 | | | | tRNA15-Arg | | | |
| 62 | 38923 | 38995 | 843 | GCCGAUUUAGCUCAGUUGGU AGAGCGCUUCACUUUGUAAUG AAGAUGCCCCGGGUUCGACU CCUGCAAUCGGCA | 73 | | | | tRNA16-Thr | | | |
| 63 | 39268 | 39852 | 844 | MKFKDFLTEEELFEAAPGRMTK SKWRDALVLVPRGERHDFSKF AASVEKIYGIGISDPKDYAKVAA AFESLGGKVTTPARGASPAQA PAAKPAPVKAKPKNIPGLKISGD HGDIIGSGELFKAIDKALPLVRD NGPLYKAVQFYFDNLWKYRES QGAKPSARETQHIGEVKTLLAK LNHHLVELSRQTELSYNV | 194 | No significant similarity found. | | | | No putative conserved domains have been detected ||
| 64 | 40040 | 40330 | 845 | MSKFNFIQIERGYNNYGTPDRY RAIWIKGEHEHAVFNVAETREL KDLIKHVRKDWPAVEEYYVRVY HEEAPTETVQIKFAKTASALTKR IEAVINC | 96 | Hypothetical protein RB51ORF009 [Enterobacteria phage RB51] | YP_00285396 4.1 | 7e-08 (40/93) | | No putative conserved domains have been detected ||

Fig. 12R

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 65 | 40378 | 40971 | 846 | MSILKKLVEFIRSKFGTFVAQNT SVEDQYTMAANRIIDEITKLRTT HVKSVNEEKRLLKLADEKDQAG ASKEREIRRLMAEGMNVETHAK LGLLYRRTAKALRDKAAEYKEM RAQIEETVVKLDDQRLDLAVKL EYIRETRNASALGITSADDVIEIA ELAKVDVQDIMMKVETFSGTQP GIETTADVQEYLESLK | 197 | Hypothetical protein EME08_gp126 [Enterobacteria phage IME08] | YP_003734276.1 | 7e-68 (128/197) | | No putative conserved domains have been detected | | |
| 66 | 41042 | 41602 | 847 | MATPQIKELIAAGFPTEITDLGK FAYPDTRPENWKTRYNGYNTT VLPRAIVLKDYSKLKNLISNISSI SDGVKLVDIFALRYGIYSFNDSP SNLKSARTNAGEYSTSGSTTYT IMEIIHNKNSYRLGINLVKYVTS QDDYSNYLNYCVNELPSKVMS MFDSNNMVGKQLIIDEFIKYCRE RVQK | 186 | No significant similarity found. | | | | No putative conserved domains have been detected | | |
| 67 | 41599 | 41958 | 848 | MSNLYLPSEPPVYNYYKFDQI DYALVPGICATVGAMCTFAAIDI MHLTDITPAVLFGILLAWWGTSL LIMGLIECSRWVKWSRNNYKRK AEWKEQCKNLTLEWNRKKSFE FIKEVRRK | 119 | No significant similarity found. | | | | No putative conserved domains have been detected | | |
| 68 | 41955 | 42251 | 849 | MNEYKPDGFWNQDGLAPGFGI VTWLLYCAFVIVGGTFFGLNVS EFMIMLFLGVFAFSLMWMLIIA LINCCTFLAYRMKYKKWKEKED FNTWIRSCRK | 98 | No significant similarity found. | | | | No putative conserved domains have been detected | | |
| 69 | 42248 | 42574 | 850 | MIKTCYRGMIKSDEPGYFFLFLL IWFSLSAFVGFGTFWGFYFFSP VFGDALYYIGWMSGVGTWFAIL ARWLQFVSQRQRGVFDKPKVK KEKSKDDSRSETLSWIKEMK | 108 | No significant similarity found. | | | | No putative conserved domains have been detected | | |
| 70 | 42574 | 42810 | 851 | MAVAVHVKFENGDTRLLCYSD NESLSGIEISLKEELLGINGPICD FSVEGSDNCNDDLESMVYTAM EDILEESWNECQ | 78 | No significant similarity found. | | | | No putative conserved domains have been detected | | |

Fig. 12S

| orf | Start position | Stop position | SEQ ID NO: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 71 | 42801 | 43253 | 852 | MPMKELSAGILFFTDDKRLLMG RMTNTYVQGRGSRWDIPKGHV EPGETPKEAAIRECKEETGFTE FDQDLLYDLGRHDYASNKDIHL FGYMLPVSPEMFRNCRCTAYH KDENGINFPEIDAFALIKPSQWK YVMGPSLYKIMTQMYSTAQ | 150 | NudE nudix hydrolase [Enterobacteria phage RB69] | YP_861819.1 | 6e-47 (89/144) | nudix hydrolase | Nudix_Hydro lase | cd02883 | 3,28e -15 |
| 72 | 43261 | 43569 | 853 | MEEAVELGIPHIYKHELRFIHDG KWISIFHPRDKMSRILMKSRYVF SDSEYIKSAYYIAEQLYPGFSEL PEDDKRDYVWWKDKWTPYEK CSLELFIAKCRAK | 102 | No significant similarity found. | | | | No putative conserved domains have been detected | | |
| 73 | 43599 | 44093 | 854 | MDIFGMLRIDEGYDSKIYKDSE GYWTIGIGHLLTKDPSKSLAISN LDKLVGRSTGGQITQAEAEVIFA KDVEKAIKGIVANATLSPVYNIL DDVRRAALINMVFQMGVSGVA GFPASMKLLLAKKWDAAAKELA NSRWVYRQTPNRARRVIETMRT GTWAAYQGK | 164 | Chain A, E108v Mutant Of T4 Lysozyme | 1QUG A | 3e-57 (108/162) | lysozyme | Bacteriophag e_T4- like_lysozym e | cd00735 | 5,01e -45 |
| 74 | 44094 | 44573 | 855 | MKTYQEFLNESRLATVGVMTE SVGSNLLKFKKGQKMTATLED GTEIEMDVVGYNYVDGKLYNK SHAKFDSFDDFVSSVEDESSRK AVASGDARSLMAHGHMRIKSK QNKPGEDNFALVGYQSGKTSN GYQRTVTMYMRNGKIAFVNDR GAIRYAKSIK | 159 | Hypothetical protein RB32ORF123c [Enterobacteria phage RB32] | YP_803065.1 | 3e-60 (111/159) | | No putative conserved domains have been detected | | |
| 75 | 44766 | 45068 | 856 | MKTYKEFITEARVSAGKLEAAIN KKAHSFHDLSDKDRKKLVSLYI DKERILALPGANEGKQAKPLNA VEKKIDNFASKFGMSMDDLQQ AAIEAAKVIKGK | 100 | IpII internal head protein [Enterobacteria phage IME08] | YP_00373425 9.1 | 4e-47 (93/100) | internal head protein | No putative conserved domains have been detected | | |
| 76 | 45272 | 45805 | 857 | MKYLTPIYLTLMHAFKDAADRR LNNPNYSFYEPSCLMREYGTLR LDGGRQTGKTAALCQFATDWL LEDGSVIILSTRYTQSSELMEGI LREYNSSHLINKLPANEIAKSIVP MTIREFLSNDSSYKFRGRKLGR ALIIIEEPMKVPDMMKFYDMYQ EAIRWSMPNDTLPLFFVIGMQ | 177 | Vs.8 conserved hypothetical protein [Enterobacteria phage JS10] | YP_00292245 8.1 | 3e-40 (91/180) | | Terminase_6 | pfam03 237 | 1,09e -03 |

Fig. 12T

| orf | Start position | Stop position | SEQ ID NO.: | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| 77 | 54802 | 46113 | 858 | MMTQTEIVDMITVMENTGFADM KQLITMVTAGNLLEYKRYKFLS GPFKGAEFISNAPNTKWMNRY PNFRIEFISGKLKGVISSSLITYD QRIQEKTMQWLKLL | 103 | Vs.7 conserved hypothetical protein [Enterobacteria phage JS10] | YP_002922457.1 | 2e-10 (29/54) | | No putative conserved domains have been detected | | |
| 78 | 46095 | 46439 | 859 | MAEIVIRCPPHLVESFCEWFSN SGEQDFYEAHQNGTWNETTKQ WEEATTYIGTRGYVNEPIEIVE YDKETDEEVTYHEDKITYLEAA AKFHSDEWNKMSVITAYMRGW NKESN | 114 | Vs.5 conserved hypothetical protein [Enterobacteria phage RB69] | NP_861809.1 | 2e-10 (36/77) | | No putative conserved domains have been detected | | |
| 79 | 46448 | 46810 | 860 | MKAYQILEGELKGTIYIEDGDDA RVIVSKVLKEDTITDAETFYGYK AREVEIEYQPTVKIEGGQHLNV NVLRRETLLDAVEHPEKYPQLTI RVSGYAVRFNSLTPEQRDVIA RTFTEAL | 120 | Autonomous glycyl radical cofactor [Enterobacteria phage AR1] | BAI83131.1 | 2e-51 (100/120) | autonomous glycyl radical cofactor | Autonomous glycyl radical cofactor GrcA | PRK11127 | 1,37e-40 |
| 80 | 46810 | 47091 | 861 | MAIEDIKGYKPHTDEKIGKVNAI KDAEIRLGLIFKALEEEHVEKYM NLDVSTMSDKEFDLAHERITQIR NAIQHLKEASMWACRSVFQPE EKY | 93 | Vs.4 conserved hypothetical protein [Enterobacteria phage JS98] | YP_001595237.1 | 1e-35 (72/91) | | No putative conserved domains have been detected | | |
| 81 | 47155 | 47613 | 862 | MSTNPEVFIRRTKLRRKFEEAF RSLNLSVRARAKAEGKEPFFTK YSDHLLDRAIQREIDEEYVFSVL SKIPNHLKEINEFLAMPWLPIDP KDIDENIEYKPMRLEITDGNLWL GFTMDIPRPGKGPSIKCRMAFV NDKRLKGKISTKVIHIN | 152 | RegB site-specific RNA endonuclease [Enterobacteria phage JS98] | YP_001595236.1 | 2e-43 (90/148) | RegB site-specific RNA endonuclease | REGB_T4 | pfam10715 | 1,91e-20 |
| 82 | 47621 | 48166 | 863 | MKKALIGLMALCSTAFGSEPTF SNVQLDNLHYAYNFGEQYQKS GKEKSPHNRYDNNGLGYIMAAI SWKESSAGANLKAGKGHHSYG VFQNYLPTVKARAKLEGKNLSD SEIRKMLKSRQNSAEWAYIELS YWLNIHNGNMRKALASYNAGW NVKRGNSYASDVLEKANFLKKH KMLHTKVE | 181 | Vs.1 conserved hypothetical protein [Enterobacteria phage RB69] | YP_861805.1 | 5e-59 (115/180) | | REGB_T4 | pfam10715 | 1,00e-18 |
| 83 | 48166 | 48486 | 864 | MVKYAALLGLVLAFSANAENSM TDSLRIAKTFCNTNSECVDILAL ELDSAFSDGVKDSRSPAQWTT LINRKAKSMKDLCVNAPNENICL MYRDQLMARYMSGLSSK | 106 | Vs valyl-tRNA synthetase modifier [Enterobacteria phage Phi1] | YP_001469436.1 | 4e-13 (34/80) | valyl-tRNA synthetase modifier | No putative conserved domains have been detected | | |

Fig. 12U

| orf | Start position | Stop position | SEQ ID NO.: | Aminoacidic sequence | Size (aa) | Homologous/similar proteins ||| | Conserved Domains |||
|---|---|---|---|---|---|---|---|---|---|---|---|---|
| | | | | | | Name[organism] | Acc No | E value and identity | Predicted function | Name | Acc No | E value |
| 84 | 48483 | 48875 | 865 | MKKAAILLCCAFSVNAWEKLPG YPETVLAAQGTKIESNGPFKNNI EIAFVPSSRKLLMSFYNYQDKD DQVIVPLVEYNARGCGMQSDG VSVDGVMHPKEQGVLNPILNC NNAIFLRVYNNLNEYATYKIP | 130 | No significant similarity found. | | | | No putative conserved domains have been detected |||
| 85 | 48884 | 49351 | 866 | MITGYIKGNIVELFMKHECDIAH GCNCFTTMGAGVAGQLAKAYP PILDIDIDEDRYYDNNLAKLGTH TRAIHKKGTAYCYNLYTQYAPG PNVDYGAIFNAFHELNSGRIVY NRPLYIPKIGAGIAGGDWELIEK LINLATPDIDIMVVEYEEAKS | 155 | Tk.4 conserved hypothetical protein [Enterobacteria phage JS10] | YP_0029224 5.1 | 3e-41 (89/157) | | tk.4 | PHA025 95 | 6,30e -49 |
| 86 | 49375 | 49542 | 867 | MITEEQKTKLWQLIDDYAGAEQ VVAISAIYGNGLPEEYDELIRSK NAISDFMETL | 55 | No significant similarity found. | | | | No putative conserved domains have been detected |||
| 87 | 49542 | 50141 | 868 | MAQLYFNYASMNAGKSANLLT AAHNYKERGMGTLILKPAIDTR DSATEVTSRIGLRHEANTVDESI DILEFFKWAQTQRDIHCVFVDE AQFLTAEHVLQLCKIVDLYDVPV MAYGLRTDFRGELFEGSKALLS VADKLVELKGVCHCGRKATMV ARIDENGNAITDGEVVELGGED KYVSLCRKH-WCELVGVYNEAK NV | 199 | Tk thymidine kinase [Enterobacteria phage RB69] | YP_861801.1 | 3e-81 (137/192) | thymidine kinase | Thymidine kinase | PRK042 96 | 3,20e -80 |
| 88 | 50122 | 50316 | 869 | MKPRTYNTILMLVLSMLFIWMG VAASIQSDRREELQNRLDSGCK VLAQGKDFIANTNGCYIKYE | 64 | No significant similarity found. | | | | No putative conserved domains have been detected |||
| 89 | 50600 | 50983 | 870 | MSRTIRRKGWHVVKSSKWNDQ NNNEFAYIKSYNEYVKTQKDKE NQQKYVELRISENSERPLEAKK LIAKSKRDGFWKTLRWTRYAM PVPRLFHKAEIKRALKYDEEYN WDEAGARTIEQGICEWLWD | 127 | No significant similarity found. | | | | No putative conserved domains have been detected |||
| 90 | 51030 | 51242 | 871 | MQHLSEKQLRNLTVEQLDELR REIGHGISHLQEEIRQHSSKADY TRKRT_LEKYLKEVKAVLQHKRN TGQK | 70 | rI.1 conserved hypothetical protein [Enterobacteria phage RB69] | NP_861800.1 | 1e-20 (51/69) | putative lysis inhibition regulator | No putative conserved domains have been detected |||

Fig. 12V

| orf | Start position | Stop position | SEQ ID NO.: | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and Identity | Predicted function | Name | Acc No | E value |
| 91 | 51254 | 51541 | 872 | MAFNHICLALVLGCGISFPAASH DDISDYNSYVEGALQVYAKFKE PSKQESEQFYAFVQSKWKSES CSKDCDSLGRSAGEEYANRMR IQFDNEVQ | 95 | Hypothetical protein Acj133p120 [Acinetobacter phage 133] | ADJ19435.1 | 4e-13 (36/82) | | Hypothetical protein | PHA020 54 | 3,47e-06 |
| 92 | 51528 | 51914 | 873 | MKFNDFVKDGKLTPQDEFIGLL MVSQAYFHSAHFDTKSYARHK AYEVFFNEIPDLIDAFGEQWLG FSGKSYTPALPSQKELPKDTIE MLDFILAKADGIYKSVPAALQSV LDDITGLCYKTKYLLSLQ | 128 | MobD.6 hypothetical protein [Enterobacteria phage T4] | NP_049716.1 | 2e-43 (79/128) | putative lysis inhibition regulator | rl.-1 hypothetical protein | PHA026 04 | 6,38e-44 |
| 93 | 52019 | 52507 | 874 | MIKLTTELQPGKIFYHVCGVNRT ETKPGEITRYIVASGTYDVELGL SGVYSRKSPFFQVICEYENYAG QTESYSTERSAHDMGIFKPGEK RSYHNLNRGFWTREEAEOQFIKE LQENKFSDPDDQAYADRLTPS EDFRRQQEFMDSYLDSCDYDY YDFDDGEE | 162 | No significant similarity found. | | | | No putative conserved domains have been detected | | |
| 94 | 52599 | 52865 | 875 | MNGWGPSDDGFATREATIADG IEWARLQKQLQEQRESEEFCV DCDEEIPVARRLLVKGCQRCVE CQGKWDTVMTSAYNRRGSKD SQLR | 88 | Conserved hypothetical bacterial protein [Acinetobacter phage 133] | ADJ19431.1 | 1e-24 (54/88) | | Hypothetical protein | PRK110 19 | 4,8e-16 |
| 95 | 52868 | 53059 | 876 | MESILDSTNLDNPYSDVHVKVV NSYFTKKLSRVVLKQGNDIIHLD TKQIDSLIQFLIEAKDGE | 63 | No significant similarity found. | | | | No putative conserved domains have been detected | | |
| 96 | 53049 | 53282 | 877 | MASKLVWDGKPRKGDAVIEDE SPHVIDLYLTVFHTYEHNTIIEIE RDGDCVAIDKSDAIELVKYLTA MIPTMKQDNL | 77 | No significant similarity found. | | | | No putative conserved domains have been detected | | |
| 97 | 53282 | 53782 | 878 | MNINKNSWHFKMNLWFKSGNI WKMPKTLCGYFWTTVLHILFSS AIAIFIGSVAWMFGWPLIAQTGIL AWIGVSLLSAFWLNVVAVPVGAV FIATFVLAFVAIVFGFIFGLEKFK EYRKNKQFTKKLARVKAGLPAE SEPLVFIQYLKARKRKVCPMIDY VEGKTSEE | 166 | RB69ORF104c hypothetical protein [Enterobacteria phage RB69] | NP_861794.1 | 2e-14 (55/163) | | No putative conserved domains have been detected | | |
| 98 | 53772 | 53996 | 879 | VKNDQVYIVNGRKAVFRAKTER GIISTYPIAEFTFEDGEQIKKYV PLSQTYRFIGGEIDLDIYYEGGV WKLKS | 74 | No significant similarity found. | | | | No putative conserved domains have been detected | | |

Fig. 12W

| orf | Start position | Stop position | SEQ ID NO.: | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| 99 | 53978 | 54400 | 880 | MEIEIVTTKKKLSMSLLKQMKM ASSSEIKFAMFDRVHRVLGYVN AFKWNKMDIQVAIINTGNDWAL VPMYDTHVIKTARREPHPDGQ EYHFHDVVYYHTMQKIGNVHR NSKKSTDKEHVEACAKASNDLI KFAKGNHIYL | 140 | No significant similarity found. | | | | No putative conserved domains have been detected | | |
| 100 | 54397 | 55407 | 881 | MKTIVKSYFGSHLYGTSTPESD VDFKEIFVPHPRDILMCQAMNH TNCNTNNSATKNTKDDVDHELF SLKYFFKLAADGETVALDMLHT PPELVVASDLPEVWKFIQDNRA RFYTTDMKAYLGYVRKQAGKY GVKGSRLADLHKVLDVIRDVPE WKYDDRPQQKGINERWKVQDI AEKLPLGEFLEWTTFVDHKSGE QKFYNVLGRKFQTTTIKEMKYS LEKLDAEYGERARKAEANEGV DWKALSHALRAGLQLQEIYMTG DLQFPLTHAKMVKMVKAGELPF KEVQELLESVVDEVEILAHTAEK NGMPKKVDMKFWDDFVEKVYL ENHNSYYK | 336 | NrdC.11 conserved hypothetical protein [Enterobacteria phage JS10] | YP_00292243 8.1 | 7e-132 (241/336) | | nrdC.11 hypothetical protein | PHA026 03 | 8,18e -142 |
| 101 | 55412 | 55600 | 882 | MKVFLNYGRPHKGRRWYLEAV CRETGRRENAKFSARPTRKQIH QFMSWAGETLRFSLYWAEI | 62 | No significant similarity found. | | | | No putative conserved domains have been detected | | |
| 102 | 55597 | 55836 | 883 | MILLWSVVPIVVAIIYFIVGWSV CKHLIKNGTIEKVGEYWFYLIFW FPAFIVGAIIMFFRWAGKLPKRI AENAINKHA | 79 | No significant similarity found. | | | | No putative conserved domains have been detected | | |
| 103 | 55955 | 56170 | 884 | MKTLEIVVNNIDKAFKAAEAHGV EFEPMMVGEAFSKLAIIRGETD NLIDFVDDFYLGSKVRPYYINEIL EK | 71 | No significant similarity found. | | | | No putative conserved domains have been detected | | |

Fig. 12X

| orf | Start position | Stop position | SEQ ID NO.: | Aminoacidic sequence | Size (aa) | Homologous/similar proteins ||| Conserved Domains |||
| --- | --- | --- | --- | --- | --- | --- | --- | --- | --- | --- | --- |
| | | | | | | Name[organism] | Acc No | E value and identity | Predicted function | Name | Acc No | E value |
| 104 | 56248 | 57225 | 885 | MSTITIKKGIYFGKEISGTYELLG EWFPDSLSAEDSRQGDGKVFV ELNGKKRGVWVFKDDITIDGVA AKIEVVESVDEMKERIKKRFNV MGLMTNGLIHGNIRSLIISGAAGI GKTYSLDKALQHAHDTNAIDYK SVNGKISGIGLYCRLWESREAN SVLLIDDVDVFSDMDILNLLKAA LDSGEKRKVCWSTASSFLEDK GIPNEFEFEGTVVFITNVDIDRE LERGSKLAPHLQALVSRSVYLD LGVHTNEEIMVRVQDVIMTTSM LQNRGLRNSEVIEVLEFMKDNV NRLRNVSLRTALYIGDFVATDR KNWRTIAEVTMLK | 325 | Hypothetical protein T4Tp097 [Enterobacteria phage T4T] | ADJ39814.1 | 2e-138 (243/325) | | No putative conserved domains have been detected | | |
| 105 | 57268 | 57414 | 886 | MATLISNDVKRVLFKGGMYIVD TPKGDTSSWTINEWINYIDENG AWVQ | 48 | Hypothetical protein [Enterobacteria phage AR1] | BAI83080.1 | 6e-07 (23/40) | | No putative conserved domains have been detected | | |
| 106 | 57411 | 57836 | 887 | MSLAAIKDIECWLNDIKVYPPGH IFAGKPKGKAEKACEAICEKLYK FNFGDKKNVLAEVHSSYHELRV MVNVFRAPPFIELRKEYANKVF DTFLANVQDAVKHLDEMHKQH QDLNAYYKPWRKSYQELKNRIE LIRYEVLK | 141 | No significant similarity found. | | | | No putative conserved domains have been detected | | |
| 107 | 57833 | 58171 | 888 | MKNWVMTESEAYAAYYSPDDR RSELFGYYGSYCVAEEAAVKGQ SWWGSDGTVNRKPTELITFTD ENGESWTFPKSAAISVQEETPE AKRKRLEKIKESALAKLNPDER EALGL | 112 | Hypothetical protein Aeh1p086 [Aeromonas phage Aeh1] | NP_943964.1 | 1e-07 (36/107) | | No putative conserved domains have been detected | | |
| 108 | 58168 | 58488 | 889 | MSKEFSTTRMVDAFGYPCNGY REFIHPEVENQFKEVVRNILLNA FKTQGTNPRDLGIYLEEAIRDV QKSVSAKLHWAEENIAWSNKK RSDLNWPADREQIVNYAKG | 106 | No significant similarity found. | | | | No putative conserved domains have been detected | | |
| 109 | 58492 | 58782 | 890 | MFNTIVSIHAYYEGQLNAARTK YKRGMEESVECLKDIQTFAQKT QNLILMDRKQVSLAEELKASKMI IEDNRKHQLKLLKRRQHQSPW FNSDFRSF | 96 | No significant similarity found. | | | | No putative conserved domains have been detected | | |

Fig. 12Y

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 110 | 58863 | 59027 | 891 | MKAPTWNELQEMFNTEEAFGTI SEMVENLVDSPSEDNLLCLAQF IIETYIENQK | 54 | No significant similarity found. | | | | No putative conserved domains have been detected | | |
| 111 | 59024 | 59290 | 892 | MTVYVDVLMNHGWKMRGHQV KNCHMFSDNLDELHAMAEAIG MKRSWFQDKRVPHYDLRDVR RKQAVALGAVEVSRRDAVLLW RKFFTK | 88 | Bcep22gp48 [Burkholderia phage Bcep22] | NP_944277.1 | 4e-07 (31/79) | | No putative conserved domains have been detected | | |
| 112 | 59348 | 60136 | 893 | MKTLTEIISALVEENRVARQAHR AKVEKRAEELNAGWAKTRFGR EYFDKVVAPTWGKDDRPHAPF DGYLWENELGEVEAYHAGSYL PYVTELDSLDKPEYTGDHGWW KIRLTQEEYKELREYGYPLEVRI PYKEWKLQDGTNVVMAEVRAH KSILEAIQEHSKEVFDNIFNELN KNKGDAPEGRVTVSGTVTSVK VYEDYYGVQCKMMVVLENGAT VYGSLPKSIPFEYRGKVQFTAT FELAKDDKTHAFYKRPSKVIML DE | 262 | No significant similarity found. | | | | No putative conserved domains have been detected | | |
| 113 | 60207 | 61181 | 894 | MNKNELKMFVEAAEFNKLKDKTL TKREKHVKVLSALHDLNPRAYD VAIAGNVARRVLNSMASHEANY AGFVVENIRRSRWLGAMSAEK QLKKFAIGNAKIYGQRYSFAAG AFKTEERHDRSAAQIFCSEFNA NLRRILNRSICLLKGDDRVKYQA SSTSSRNPKGVSFIRAEELDNV TVRIHINSHLSSGKYPARALLAQ VRTALDHMDVVKKSCCKQQGE NSSVLEVHLDPFKIFPKTLSTTP VIDEDVAHMYLNVVKPLPTPV NHIEIAKNSITAEMESYKRFIDTK EAELAKHELTMADLVKSLNEYK ERYESLEYARSLL | 324 | No significant similarity found. | | | | No putative conserved domains have been detected | | |
| 114 | 61178 | 61438 | 895 | VKNQLKEDMVVDDNDLEIEFEY PPVPEFKIDWDACLEMVDRRE AAAKQVVPCEKCGSIQVQLVD WTTDILKMKCRTCKHRFERKLK | 86 | NrdC.2 conserved hypothetical protein [Enterobacteria phage T4] | NP_049700.1 | 2e-11 (34/78) | | No putative conserved domains have been detected | | |

Fig. 12Z.

| orf | Start positi on | Stop positi on | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 115 | 61435 | 61749 | 896 | MITKTITGANTKFFVEYANNLIK DKNFDNIIADMILDAYESGIDPM QLKEYLRATMDFTVLNMMLRT DTEFNEMIARRNEGKFNLTDDE VLACAAHEAWKKVIK | 104 | No significant similarity found. | | | | No putative conserved domains have been detected | | |
| 116 | 61746 | 62081 | 897 | MKTTGALWKEFYNDEAFWEGY YHDDTLILFDDVEVEEYEDPSP DAVVKIESGYVYKTDDDSFTSH DLSLETFFKRWKKQTTRTMVV TVDKDDFAKVFETISNIPGVKKV K | 111 | Hypothetical protein phiSboM-AG3_gp129 [Shigella phage phiSboM-AG3] | YP_00335861 6.1 | 7e-09 (41/115) | | No putative conserved domains have been detected | | |
| 117 | 62078 | 62590 | 898 | MIDIKLDTYAVRQLFPEGTAARA QLQQSVINNVKEMVLKDSQNK LKQAVQSEVNIAAVTIPDVRAEV KKQVQQMFHTRGWNDMSAKE EMSQMMRNAAQSCAKNAIDDM VRQTIDDAVKQAEGRIKMSIER ANLRIQEIIVNAMNKNFADQINA AIAAKLAEHFPVTANG | 170 | Hypothetical protein KP-KP15p225 [Klebsiella phage KP15] | YP_00358010 1.1 | 1e-05 (43/173) | | No putative conserved domains have been detected | | |
| 118 | 62583 | 62756 | 899 | MDKIDFSKLNIPRMGIPDDIAKQ LASVQPMPDNCIKDIFDALDGK TLVITTKAENGS | 57 | No significant similarity found. | | | | No putative conserved domains have been detected | | |
| 119 | 62746 | 63036 | 900 | MARKRYMEEAERVMLLMYSVY YNETGQIVDSSKLKGAMTRGR GFAQAAIDKEIISRLGIKYSSKM YLHPGWNVQAQVFKEIEEDV HSFWLRQQHP | 96 | No significant similarity found. | | | | No putative conserved domains have been detected | | |
| 120 | 62999 | 63268 | 901 | MFTVFGYDSNIHKCVFCDNAKR LLDVKKQEYAFINVMPEKGVFD EVVISDLLRRLGRESQVGLTMP QIFAPDGTHIGGFDELRKFKFN A | 89 | NrdC thioredoxin [Enterobacteria phage JS98] | YP_00159521 1.1 | 2e-34 (68/85) | thioredoxin | GRX_GRXb _1_3 like | cd03418 | 1,52e -08 |
| 121 | 63261 | 63449 | 902 | MHDYRGTLLREGDIVALYYGYG GLETGEIKQIKNHRAKVEVTYS NGVKVMSKWKYGECMVKL | 62 | Hypothetical protein RB32ORF082c [Enterobacteria phage RB32] | YP_803024.1 | 9e-16 (42/62) | | No putative conserved domains have been detected | | |
| 122 | 63468 | 63638 | 903 | MSYDIGDLKAPCTVTISAEEFIR LQAIEELLWEIECALPSGLESWI DDEDLQKLRG | 56 | RB32ORF081c hypothetical protein [Enterobacteria phage RB14] | YP_00285441 8.1 | 6e-15 (42/56) | | No putative conserved domains have been detected | | |

Fig. 12AA

| orf | Start position | Stop position | SEQ ID NO.: | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| 123 | 63640 | 64029 | 904 | MTNAELVKEIKHIAGVTGEWDD NYDFEYPPNAPDDAEEIFVLV EDDEWTQDHKYQSRSQIWYP ARGVHFMVSESRSGSYHTDWY YNPPEVDIVTRHEKVVTRTEVE WRIEYDSVNDSAPAPCKAAKA | 129 | Hypothetical protein RB51ORF087 [Enterobacteria phage RB51] | YP_002854040.1 | 2e-12 (39/90) | | No putative conserved domains have been detected | | |
| 124 | 64008 | 64166 | 905 | MQSSKGIKPWYTARWETVEPE EDAIPEEDYNTSEPTINELLDYE DKVNGTYW | 52 | No significant similarity found. | | | | No putative conserved domains have been detected | | |
| 125 | 64150 | 64602 | 906 | MELIGKQFEVIENDDELTEQFP QFVPGFKFQVINAVNEDDLETC GITAVIDLLTNKIITINDPTPFGES WFWCFYSEDTMHQIKEIGQGE DVPNISEIKLDHFHGKIVPITKAL YAFAGQENCDSEEYDLMQKAA DYIVALETRLGVQYV | 150 | Pin protease inhibitor [Enterobacteria phage RB69] | NP_861778.1 | 1e-10 (50/144) | protease inhibitor | Inhibitor_I24 | pfam10465 | 4.84e -11 |
| 126 | 64595 | 64903 | 907 | MSKSCVTKTITVKILDFCDIHRIA REILRSHGYKIGDIIKFSNGYYD DDIGGMAWPKMSIIHKETNSYIE FNADDYEGIYAFCTSFCIKESNH NIYSSYSLI | 102 | No significant similarity found. | | | | No putative conserved domains have been detected | | |
| 127 | 64940 | 65413 | 908 | MLLTGKLYKEEKEKLYQAQNGL CPCCKRPLDEDIQKNHLDHDHA LEGDNAGKVRGLLCNLCNAAE GQMKHKFNRSGLKGQDIDYLE WLENILLVYLRQNRKDSNIHPQY VADMAKRFSRLGKPEMIAEMEL HGFTYEESDGKSQLASKYKKQ LRKSLK | 157 | gp49 EndoVII packaging and recombination endonuclease VII [Enterobacteria phage JS98] | YP_001595204.1 | 6e-61 (115/157) | EndoVII packaging and recombinatio n endonucleas e VII | Endonuc-dimeriz | pfam09124 | 1.60e -16 |
| | | | | | | | | | | Recombinati on endonucleas e VII | PHA02565 | 2.43e -62 |

Fig. 12BB

| orf | Start position | Stop position | SEQ ID NO.: | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| 128 | 65410 | 67248 | 909 | MNIELEIQGLINKTNKDLLNENA NKDSRVFPTQRDLMAGIVSKHI ANQVIPFSVMEAHKEGVIHFHD MDYSPALPFTNCCLVDLKGML QNGFKLGNAQIETPKSIGVATAI MAQITAQVASHQYGGTTFANV DLVLAPYYVEKTFAKHVRDARKY QVALVKDYAISKTEKDVFDAFQ AYEYEVNTLFSSNGQTPFVTITF GMGTSWEEKLIQRAILDNRIRG LGRDGITPIFPKLVMFVEEGINL RKEDPNYDIKQLALECAAKRMY PDIISARNNRAITGSETPVSPMG CRSFLGAWRDSSGKPVLDGRN NLGVVTLNLPRIALDANYKSSD DSNKLFKLLDERLDICKEALLTRI KSLEGVTASVAPILYQEGAFGV RMKPDDEILELFKNGRSSISLGY IGIHEFDMLTFKGSGKLVLKYIN TKLNKWTEETGYAFSLYSTPAE SLCYRFCKIDQAKFGDVKGVTD KGWYTNSFHVSVEENLSPFEKI DREAPYHSIAKGGHISYVELPD MKRNLEGLEVVWDYAIEKLDYF GVNMPVDKCLSCGSTHEMTPT ENGFTCSICGETDPKKMNTIRR TCGYLGNPSERGFNLGKNKEIM HRVKHVRETNEAS | 612 | NrdD anaerobic NTP reductase, large subunit [Enterobacteria phage AR1] | BAI83088.1 | 0.0 (478/604) | anaerobic NTP reductase large subunit | Anaerobic ribonucleosid e triphosphate reductase | PRK092 63 | 0.0 |
| 129 | 67220 | 67453 | 910 | MLEKPMKQVDWNQLSEWGLI WKINKEVLHPLGIAITRDPESGL SAGAIQTDEPWKYDAEVEARN EVRFNEFRQNLPF | 76 | Hypothetical protein RB16p170 [Enterobacteria phage RB16] | YP_00385847 0.1 | 1e-13 (37/66) | | No putative conserved domains have been detected | | |
| 130 | 67425 | 67895 | 911 | MNFDRIYPSDFVNGPGCRVVLF VTGCLHKCEGCYNKSTWNARN GQLFTMNTVKEIASHLSKSYIQ GLTLTGGDPLYPQNREEISNLV SWVKARFPEKDIWMMVTGYKFE DIKDLDLLQHIDVIIDGKYEKSLP TTKNWRGSDNQRLWVRNGST WTHD | 156 | NrdG anaerobic NTP reductase, small subunit [Enterobacteria phage T4] | NP_049688.1 | 1e-77 (135/156) | anaerobic NTP reductase small subunit | nrdG, anaerobic ribonucleotid e reductase-activating protein | PRK111 21 | 8,77e -46 |
| 131 | 67870 | 68004 | 912 | MVLPGHMIEEIYMLTYKIMFTLN HMATELFGPEFLAMTAFILTI | 44 | No significant similarity found. | | | | No putative conserved domains have been detected | | |

Fig. 12CC

| orf | Start position | Stop position | SEQ ID NO.: | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| 132 | 68013 | 68225 | 913 | MKFINAIRKFISNVIALVALTAGA FVAIPFIVLIIIADWINPTKKDEKL SNEEFQKRVNTLTAKLQQVMK | 70 | No significant similarity found. | | | | No putative conserved domains have been detected | | |
| 133 | 68222 | 68524 | 914 | MIEIYGIPEEVWRCPGCKAVRD LLDKLQLPYEFYNVINEVDGQP VYDRPLIESLAKRIGCYPSLAIR YPVIFMDNVKQYDIPTFKTNLIA AGHDPDIIED | 100 | NrdH glutaredoxin [Enterobacteria phage IME08] | YP_00373422 0.1 | 7e-26 (62/99) | glutaredoxin | Glutaredoxin | pfam00 462 | 6,62e -03 |
| 134 | 68710 | 68898 | 915 | MNWLNWQEALEAMSKGCKVK HVHFTDDEYFLMKNKVICDENG YDMTRWYKGESWQNEHWYIA | 62 | Hypothetical protein AGC_0014 [Enterobacteria phage EPS7] | YP_00183693 4.1 | 3e-04 (26/59) | | No putative conserved domains have been detected | | |
| 135 | 68895 | 69137 | 916 | MKTFAVGDIVRTRIWDGLQFEV VVYVGSDGVLLHRINNLIKWHL ERFVKYHEFNSYHCTVAPVASK EYYDMLEELKSLKD | 80 | Hypothetical protein RB14ORF100 [Enterobacteria phage RB14] | YP_00285443 6.1 | 7e-04 (28/81) | | No putative conserved domains have been detected | | |
| 136 | 69202 | 69534 | 917 | MSQAIKNALNAFAYYKVSAMLE EGRCVTPSLLDQWEVELHGTM KEEGQKIGKARIRELVVAYLLSE FGIKAFGVEPIVVGVGEISESAIR KMKNQRKKGFRDVKAVKAAK | 110 | gp55.2 hypothetical protein [Enterobacteria phage T4] | NP_049681.1 | 4e-29 (61/107) | | No putative conserved domains have been detected | | |
| 137 | 69531 | 69806 | 918 | MKLNQNGCPSRVRFCILELRSN IVVIDEYTTIVGVQQYLDRRFDT RTHMKYGFPGKCKFYPMSADH QSVVNDEYKWAEGLTLKELEE YLDA | 91 | No significant similarity found. | | | | No putative conserved domains have been detected | | |
| 138 | 69799 | 70080 | 919 | MRKVILYTEIFTSRWVFDSVRIS NASKEDVRNAQRLAYDEAGKS PAFVKIEYIITDSALIHNVSESVL KKFCVDRINKGTSMEYFLLARE LKW | 93 | No significant similarity found. | | | | No putative conserved domains have been detected | | |
| 139 | 70074 | 70298 | 920 | MVEEQIAEIGLLGWFVSKTKDG RNLIETPEGEFIIEEDFDAFWIYE RSGENEYTSVDAFSKFEDAIDS VKAWLK | 74 | No significant similarity found. | | | | Formyl-methanofura n-tetrahydro-methanopteri n formyl-transferase | PRK021 14 | 1,51e -03 |
| 140 | 70286 | 70564 | 921 | MAKVNQIMIVVEGIGGFTIDSYM GVWFDNEEGMYWETHASMLN ETHYESLYSSFMEMMHEVDES DWFELSLVEFKRIMEQLFQCYR | 92 | Hypothetical protein RB14ORF65 [Enterobacteria | YP_00285440 1.1 | 3e-08 (32/89) | | No putative conserved domains have been detected | | |

Fig. 12DD

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | IMKGEL | | phage RB14] | | | | | | |
| 141 | 70561 | 70806 | 922 | MKIQLTLTHENIKGVFCLENSQI TFAQDGTYWYAESDDIAGYGM ERVFEDFEAVIDVPLDFTYNDF YRIMMKLIACAELIK | 81 | No significant similarity found. | | | | No putative conserved domains have been detected | | |
| 142 | 70873 | 71421 | 923 | MSNYVNNKELYKSICSWKEKC RESEAAGGPRVVKQNDTIGLAI MLIAEGLSKRFNFSGYTQSWK QEMISDGIEAAIKGLINFDETKY DNPHAYTQACFNAFVQRIKKE RKEMAKKYSYFVHNVYDSRDD DMVALADETFIQDIYDKMTQYE STAYKAPGSAKKSEPTSDGPNL EFLYEAED | 182 | gp55 Sigma factor for T4 late transcription [Enterobacteria phage T4] | NP_049679.1 | 4e-76 (139/180) | sigma factor | RNA polymerase sigma factor | PHA025 47 | 1,38e -71 |
| 143 | 71405 | 71635 | 924 | MRLKINLDGFLEDVQDLDAIPYL LKMYLREVLDLDIHIDPKNPHDA DFRSDSAIIEHSYNWTDTEFTFE INYHPKE | 76 | a-gt.5 hypothetical protein [Enterobacteria phage T4] | NP_049678.1 | 2e-15 (40/68) | | No putative conserved domains have been detected | | |
| 144 | 71637 | 71939 | 925 | MNNITQEERDELQQKLMEAAE EQAIARANKIVRKNRREIERLKA HAGDAVLDNNFFPAYKYAIEKLR TILKQPFTDEILLTCWNTSRKSV WDILNAGTSKI | 100 | a-gt.4 conserved hypothetical protein [Enterobacteria phage JS98] | YP_001595190.1 | 2e-20 (51/99) | | a-gt.4, hypothetical protein | PHA025 71 | 1,02e -22 |
| 145 | 71917 | 72114 | 926 | MLVQVKFKRVRKDAGFTLNTAT GTMAVKVADNQYRVLGSTEGC KLIDKNSLVWVDTFQVKRWYE W | 65 | a-gt.3 conserved hypothetical protein [Enterobacteria phage RB69] | NP_861758.1 | 7e-08 (31/66) | | No putative conserved domains have been detected | | |
| 146 | 72146 | 72391 | 927 | MGSNPGHDWPEGNYACRCSN CSERYTGPKRSYFCYKCDTAR REAPAPDYEAIRNAKIDMLKRF EEAKRICEAAGYVVKKI | 81 | No significant similarity found. | | | | No putative conserved domains have been detected | | |

Fig. 12EE

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 147 | 72461 | 73657 | 928 | MKINILMARGLEGCGVTKFSLE HREWLVKHGHEVNIIYAKDKAF TRNRAHSYKDVTIPVSLADDYD KTLSLLNACDILINSVPAVNAPE AAIDNYKKLIENIKPEVRVVVYQ HDHRALSLRRNAGLEETVKRA DVLFSHSSNGDFNTVLMEEYFP SGGLSFFDDSDSAPPVYNFQP AMNIKAIRDKYWKDFSAIDFDIH RWIGRTTTWKGYFLMFDFHES HLRPAGKTTILEGLERSPAFINK ERYEIDYCRHYHQVKTGPGLNP QVLDRYVNSEMLERMSOSGFG YQLSRLPDKFLERSLEYTHLEL GACGTIPVFHKATGDALKFRVD GKPLTSHDSGILWLNDENKNEV FERMKHLSSDQKLYDKERNKA FEFLVEHQDSEHCFKEQFELMT K | 398 | Alpha-glucosyl-transferase [Enterobacteria phage RB32] | YP_803002.1 | 6e-164 (273/401) | alpha-glucosyl-transferase | AGT, alpha-glucosyl-transferase | pfam11440 | 1.80e-143 |
| 148 | 73728 | 74750 | 929 | MKIIHSGDWHLGVRADDPWVQ DVQRHGIKQHDYAKKHGIKTII QYGDIFDVRKAITHKTMEFAREI AESLEKEGINLITIVGNHDMHYK NTLTPNASTEVLGKYKHITVIEK PVTMDFDGTLIDLCPWMCEEN TSEIMKHIKESSAEYCIGHWELN GFYFYKGMKSHGLEPDFLKKY KQVWSGHFHTISSAANVKYIGT PWTLTAGDENDPRGFWVQDTE LSTFDFVPNEITWHRKLIYPVTG QVDFEEFRNLAVRIIITAVDEDL PKFESELEKVVHELRTVSKVDN SVESEDGEEVEVKSLLDLMEEY IQALEDLSADDIKALKVMSKQLY IEAQNQ | 340 | gp47 recombination endonuclease subunit [Enterobacteria phage RB32] | YP_803000.1 | 6e-144 (237/337) | recombination endonuclease subunit | Endonuclease subunit | PHA02546 | 2.02e-136 |

Fig. 12FF

| orf | Start position | Stop position | SEQ ID NO.: | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| 149 | 74747 | 76429 | 930 | VKTFKLNRVKYKNIMSVGQAAI DIQLDKCQKTLITGKNGGGKST MLEAITFALFGKPFRDIKKGQLI NSFNKKDSVVELWMEYDGHSF YIKRGQKPNVFEILRDGNKLDE AASSKDFQSYFESLIGMSYTSF KQIVVLGTAGYTPFMGLSTANR RKLVEDLLEVSLLADMDKLNKT QIREINQQIQVNDVQREALTNEI KTHHEYAEKQKKLSGDNVARL QAMYDEQVNEARGYKAELETL QRELLELVIGDDPAESIQEVQG KTFKIRSKIESYSKVLGLYDKGG HCPTCLQDLHSNDTLITKINHHV EECNTILGELKTRQSELDELAR EYNTVRARARDIKTQMGSLKQ MTITAVEKARRIKAAIDKASQEFI DNSDKIKLLQEELDKIILVKTNLV MEKYRRGILTEMLKDSGIKGAII KKYIPMFNKQINSYLKIMEADYS FTLNEEFSETIKSRGREEFSYAS FSQGEKARIDIALLFTWRDIAEK VSGVKINCLFLDEVYDSATDAE GVKAITAILNKMVDANVFIISHRD HDPQAYGQHLQMKKVGRFTV ME | 560 | gp46 recombination endonuclease subunit [Enterobacteria phage RB14] | YP_00285439 0.1 | 0.0 (382/563) | recombination endonuclease subunit | Endonuclease subunit | PHA02562 | 0.0 |
| 150 | 76426 | 76620 | 931 | MNEFTTGQHLLAFPELKRYVLV NLFSDERHLVTEEMLRDAFTGN EYNRVMSNRNPGWMVEDYYD | 64 | gp45.2 hypothetical protein [Enterobacteria phage RB51] | YP_00285401 1.1 | 3e-17 (41/64) | | No putative conserved domains have been detected |||
| 151 | 76631 | 77008 | 932 | MINFVDVKDIQVKNVRADSNPN NQNRIRKSWVLALTEETKQAIK DKIKDSEARFAFYKSIDDEVAEK WIELMRKHYNESIKAGAKIVTDR HGGERLENDYCVDADEQLVAA GQIVAEELTATFAA | 125 | RNA polymerase binding [Enterobacteria phage RB32] | YP_802994.1 | 5e-35 (71/123) | RNA polymerase binding | Phage_Rpb A | pfam10789 | 1.19e-28 |

Fig. 12GG

| orf | Start position | Stop position | SEQ ID NO.: | Aminoacidic sequence | Size (aa) | Homologous/similar proteins | | | Predicted function | Conserved Domains | | E value |
|---|---|---|---|---|---|---|---|---|---|---|---|---|
| | | | | | | Name [organism] | Acc No | E value and identity | | Name | Acc No | |
| 152 | 77044 | 77745 | 933 | MKFSKETLNILKNFSTINSGIML KPPGNFIMTRAVNGTTYAEATIS DTIDTDVAIYDLNSFLSILSLVGD DADIIMQEDGNLAIKDARSTIFW PAADPSTIVFPTKPIPFPVANVII DFKGEDLQQLMRVSRGMQIDTI AITNVDGKIVLRGYNKVEDAALT RPKYSLTLGDYEGEGNFNIIN MSNMKMTIGDYKLMLWAKMNG SKKQTAAKFEGASASYVVAME ADSTFDFE | 233 | gp45 sliding clamp DNA polymerase [Enterobacteria phage RB32] | YP_802993.1 | 1e-94 (173/232) | sliding clamp DNA polymerase | Sliding clamp | PHA025 45 | 1,26e -86 |
| 153 | 77794 | 78756 | 934 | MKLTVNEADFMWEQKYRPGTI SECVLPAEDKEIFSALVAKGKIP HLILHSTSPGTGKTTVAKALCN DINAEMMFVNGSDCKIDFVRGP LTAFASSASIAGKQKIIVIDEFDR AGLAESQRHLRSFMEAYSTNC TIIITANNLDGIIKPLQSRCRVINF GKPSPSDVKPMQIEMLKRCLAI CENEGVVVEDKKVVAALVKKNF PEFRKTINMLDHYSSKGVIDAGI LSIVLNDRGSIEDVIEAIKTKNIKE LRALAPKYAADYTWFVDKLSSE LYTMVTGPSIIRMYEIIGENNQY HGIAASIELHLVYMLIQLVVEMQ WK | 320 | gp44 clamp-loader subunit [Enterobacteria phage RB32] | YP_802992.1 | 1e-140 (231/318) | clamp-loader subunit | Clamp loader, small subunit | PHA025 44 | 3,56e -154 |
| 154 | 78756 | 79322 | 935 | MSLFEDDQYNEHQIAWLGKD WTKVQELSDSYKEKAENQFFTII GSINEKQEHLNSTMDYSKFMV ENALSQHPDCMPSVYYMNLVG QGLSDQAHYNYMMASVPRGR RYGKWAKLTENIQDALILQVIMT YYKVNAIDARMYRETLEAKNKL KPALKKMKGLVTDELVKTITKNV KEQKNLKTALEW | 188 | gp62 clamp-loader subunit [Enterobacteria phage RB51] | YP_002854007.1 | 2e-65 (118/188) | clamp-loader subunit | Clamp loader small subunit | PHA025 93 | 4,34e -63 |
| 155 | 79316 | 79687 | 936 | MVKMIEITLKQPEDFLKVKETLT RMGIANNKDKVLYQSCHILOKQ GRYYIVHFKEMLKLDGRPVTIDL EDEIRRDSIAQLLADWGLLSINR GQTLAQMQNNFRVITFKQKHE WTLKSKYTIGA | 123 | Translation repressor protein [Enterobacteria phage RB69] | YP_861747.1 | 4e-48 (96/124) | translation repressor protein | regA, translation repressor protein | PHA025 43 | 1,68e -55 |

Fig. 12HH

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 156 | 79687 | 79887 | 937 | MTDQEFYDKLKNIRITAPEWFS LPIDEQIQYQVKETLEKYPGRKV MMCFTYDKNRVPRIQKQVIEV | 66 | No significant similarity found. | | | | No putative conserved domains have been detected | | |
| 157 | 79980 | 82688 | 938 | MKEFYISVESLGNDIVERYIDST GEERMRRVPYSPVMFSHCMEE TKYKDIYGKYCKKNTFPTMKDA RDWMRRMEDMGMEAMGMDD FKLAYISDTYGSEIVYNKKFIRIA NCDIEVTASQFPDPMKAEYEID AITHYDSVDDKFYVFDLLHSLY GSVSEWDKKLAARLDSEGGDE VPQHILDRVVYMPFNSEKEMML EYINLWEQKCPAIFTGWNIEGF DIPYIMNRVKQILGERAMKRFSP LNKVSSKIITNMYGDKEIYSIMG VTILDYMDLYKKFSFTNQPTYKL DFIAYYETKKGKLAYDGPINKLR ETNHQRYISYNIIDVESVQAIDA VRGFIDLAISMSYYAKMPYQGV MSPIKTWDAIIFNSLKEQDKVIP QSRSHVKQSYPGAYVKEPVPA AYRYIMSFDLTSLYPSIIRQVNIS PETIVGQFKLHPLGEYINKTAPR PSDEYSCSPNGWMYRKDVDG VIPVEIAKVFYQRKEWKNKMMG AKRNQELIKKVLNDKKFGTIDKF AEVNVYEDFSDDMKAELLTYTE ECLDKLMFECKHAEILGNTNQL NRKILINSLYGALGNIYFRYYDL RNASAITLFGQMAIQWIERKYN EYLNKVCGTEGHSFVVAGDTD SIYVCVDKVIEKVGLERFKETND LVEFLNQFGKKKMEPWIDQSY REMCEYMNNKEHLMFMDREAI SCPPLGSNGIGGFWKAKKRYA LNVYDMEGTRYAEPHLKIIMGM ETQQSSTPTAVQNALEESIRRM LQEGEESLQQYYKQFESEYRE LDYKVIAEVKTANNIGKYDDGA GYPDKGTPYHVKGALAYNRAT AGFEGITPIMEGEKVMIPLREG NPYGEKCMAWPSGTELPQEIR QEVLVWLDHSVLFQKSFVKPLT | 902 | gp43 DNA polymerase [Enterobacteria phage T4] | NP_049662.1 | 0,0 (675/900) | DNA polymerase | DNA polymerase | PHA025 28 | 0,0 |

Fig. 12II

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | GMSEAAGLDYEEKSSLLDMFDF | | | | | | | | |
| 158 | 82758 | 83201 | 939 | MKSLLAVIVALTLTGCQMPQGD IVPASSVGQVRAIGGTVGYYRA SNQVSAESLAVERRLAKEKANP NRQLSAMELDMIEQNKHELEEI KRLRKTCKERTCTAQAAAVND QIRLTDFANGGLSYNEHKQRM EQLKSLQNHIYNKCMSN | 147 | No significant similarity found. | | | | No putative conserved domains have been detected | | |

Fig. 12JJ

| orf | Start position | Stop position | SEQ ID NO: | Aminoacidic sequence | Size (aa) | Name[organism] | Acc No | E value and identity | Predicted function | Name | Acc No | E value |
|---|---|---|---|---|---|---|---|---|---|---|---|---|
| 159 | 83212 | 83418 | 940 | MEAVFGLIILFFIYFLPTFVACSR KHKSRGGIFITNLVFGWSIIGWLI ALIWSASNAQQNTIIIQQVK | 68 | Immunity to superinfection membrane protein [Enterobacteria phage RB32] | YP_802986.1 | 9e-08 (31/61) | immunity to superinfection membrane protein | No putative conserved domains have been detected | | |
| 160 | 83427 | 84161 | 941 | MIVTPMTVQDIRQEFADALLNK EFVIDKTGVKTIEIVGASFIADEN LIFGAVNDGYIARELEWYKSQS LFVKDIPGETPAIWKAIASKHGEI NSNYGWAVWSTQNYSQFANC AKELINNPDSRRGIMIYTRPQM QYDFERDGMSDFMCTNNVQYL IRDNRVHAVVNMRSNDVFGY RNDYAWQLYVLEQLTKLLNAS GKNYSVGDIIWNVGSLHVYSRH FYLVDNYAHTGETHIAKKDYKG EWK | 244 | gp42 dCMP hydroxymethylase [Enterobacteria phage RB51] | YP_002853999.1 | 2e-103 (177/246) | thymidylate synthetase and pyrimidine hydroxy-methylase | Thymidylat_synt | pfam00303 | 1,55e-21 |
| 161 | 84158 | 84994 | 942 | MIQFVIPSYKRAGAVTALTMFPE GYVPHLVVRESEKEAYETWHG HAAKIVTVPDDVDGIAGTRRLIT EMYAGQRIWMLDDDTTIHLTEI RERDRRVPLGVGEAMSQEVF DDMVKYVETAMDCGYYHGHA RLPIFKITSSWGHYRENSFGFT NTFYDLTKLTAEDIGYGIIDLNED AYAFLKLINMGHPHLALFKYLVK SGKVQSPGGCSTQRDTARQN RALEQLHAAFPNQARWKSKDG ERRGLFGDDEPLKSIRMCINTR VKSQAFHEFGKVEPYL | 278 | Beta-glucosyl-HMC-alpha-glucosyl-transferase [Enterobacteria phage AR1] | BAI83052.1 | 4e-106 (180/277) | beta-glucosyl-HMC-alpha-glucosyl-transferase | No putative conserved domains have been detected | | |
| 162 | 84991 | 85242 | 943 | VRAKALQGPLMNIYDKSDVAGN IFKAEEFRCFVCKSDEFVHEGT TGSDGMHCWWHGMCVGCKIH YEIDMETVVYNTKKKWNFC | 83 | No significant similarity found. | | | | No putative conserved domains have been detected | | |

Fig. 12KK

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 163 | 85325 | 86500 | 944 | MSDLKSRLIKASTSKMTAELTK SKFFNEKDVVRTKIPMLNIAISG ALDGGMQSGLTIFAGPSKHFKS NMSLTMVSAYLNKYPDAVCLFY DSEFGITPAYLKSMGVDPDRVI HTPVQSVEQLKIDMVNQLEAIE RGEKVIVFIDSIGNMASKKETED ALNEKSVADMTRAKSLKSLFRI VTPYFSIKNIPCVAVNHTIETIEM FSKTVMTGGTGPMYSADTVFII GKRQIKDGSELEGYQFVLNAEK SRTVKEKSKFFIDVKFDGGIDPY SGLLDMALDIGFVVKPKNGWYA REFLDVETGEMIREEKSWRAK DTSSTEFWGPLFKHEPFRDAIK ARYQLGAIDSNAAVDEAVAEMI NSKVSTKVDGVKLPESGSVSAA EVEDELENFMNED | 391 | RecA-like recombinase protein [Enterobacteria phage RB32] | YP_802982.1 | 0.0 (342/387) | RecA-like recombinase protein | recA | cd00983 | 4,14e -13 |
| 164 | 86490 | 86840 | 945 | MKTEFDLESELEKFEQESPSEE GDFERQERVFKKSHEIIQEAMK TVIQEIVIKLNGQSHLLYVHKLNI SPSGEVTIEFSTPSEAHKDELY PHVEACVKQQIQSALKTKKKSL WKIF | 116 | gp40 head vertex assembly chaperone [Enterobacteria phage IME08] | YP_00373418 7.1 | 1e-13 (47/108) | head vertex assembly chaperone | Phage_head _chap | pfam11 113 | 2,81e -12 |
| 165 | 86850 | 88289 | 946 | VVETILANLIYNQAFFTKVWPYM DKEYFEQGPAQTVFNIIKKHVN EYTAIPSKTALCVALDNSSITET EHEGAKKLIDKLSDAPEDLNWL VKETEKYVQEKAMYNATSRIIEI QTNAQLEPNKRDKRLPDIGAIP DIMREALSVSFDSYIGHDWMED YEARWLSYQNKARKVPFKLSIL NKITKGGAETGTLNVLMAGVNV GKSLGLCSLAADYLQMGHNVL YISMEMAEEVCAKRIDANLLDV SLDDIDDGCVSYAEYKGKMEK WRSSSTLGRLIIKQYPTGGANA NTFRALLNELKLKKNFKPTVIIID YLGICASCRIRQYTENSYTLVKA IAEELRALAVESETVLWTAAQV GRSAWDASDMDMSDIAESAGL PATADFMLAVIETPELAQMKQQ LIKQIIKSRYGDKNINNKFSMGVH | 479 | 41 helicase [Enterobacteria phage RB69] | NP_861732.2 | 0.0 (386/484) | DNA primase-helicase ATPase | Helicase | PHA025 42 | 0,0 |

Fig. 12LL

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | KANQRWVEIEQQNDPTKPNPS NTVREGAGAQNRVAESNRQER VSRSKLDALAEELKF | | | | | | | | |
| 166 | 88300 | 88533 | 947 | MIFVFSVIRDQSGRSFVVTASD SVHRGVIAYNKADLSSYDYGEV KAYNDEGIWVNSAIYLPTKNLTS DEVLEKLFKR | 77 | No significant similarity found. | | | | No putative conserved domains have been detected | | |
| 167 | 88594 | 88887 | 948 | MKKIVLALIFAVSSCSAVPALAN YDKDLCEWSMTADEKDVAEQI RADVGHIIDNTDPSKMKEVQAEI SNDGAAIKLNYALYCDANFDNF TIASWILG | 96 | Protein spackle precursor [Enterobacteria phage AR1] | BAI83046.1 | 6e-21 (47/96) | protein spackle precursor | No putative conserved domains have been detected | | |
| 168 | 88884 | 89102 | 949 | MITYYLVMAIMTGAGGVSTEKL SFTGMNESSLAQKCEDAGKQF TGIKADSGFGSPSVYTTYKCIRI DGGNNK | 72 | No significant similarity found. | | | | No putative conserved domains have been detected | | |
| 169 | 89115 | 89282 | 950 | MKTFKEFVKLNEEMVAGDAGG NPQNIASGTTSGAVVNKGPETL PKKKRDKSKPET | 55 | gp61.1 hypothetical protein [Enterobacteria phage JS98] | YP_00159515 6.1 | 6e-13 (38/48) | | Gp23 | pfam07 068 | 3.47e -05 |

Fig. 12MM

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 170 | 89322 | 90344 | 951 | MSWVDNEFAIRAISHLPKFRHV TTSSTFKLNCRCPICGDSOKDI NKARFWIFDAGOGLRCHCFNC EYNKWLSQYLKDNEPDLYREY LLEKRKEQVFDKPKTVEPSEKI NAKLPVIEKLNFCERLDRLPKEH PIVKYVTARCIPSTSWKRLWFT NQWPSLVNSVNPGTYKNETNE PRLVPIFNKKGEIESFQGRALR KNAPQKYITIKAHEHATKIYGLD TIDESKLVFVMEGPIDSLFIDNAI AITGGSLDLAQVPCHDNRAWIM DHEPRHPDTIKRMKRLVDAGEK VVFWDKSPWKSKDINDMIMKE GATASEITDYINQNISQGLMAKL RLDKYAKI | 340 | gp61 DNA primase subunit [Enterobacteria phage JS98] | YP_001595155.1 | 2e-143 (243/344) | DNA primase subunit | DNA primase | PHA02540 | 9.49e-155 |
| 171 | 90554 | 90363 | 952 | MSEVKRECKDKGGFGRYLYVG IATAALAAWNYVVPLASTHGL VLPPMPLEKVVSFIMTGGLL | 63 | No significant similarity found. | | | | No putative conserved domains have been detected |||
| 172 | 90621 | 91142 | 953 | MPHFNECSQLIAGADKAEARYA GIVRKVGGDPLQVMLDMOKSL QVRLANDKPGTNMHPDELAQA GDIVQWLRNQKDYIDDEFRELL TSLGGMSNGEKAASAVWKPW KSDHVKMQETYIKDLSDKDQLE IKFEMIDILHFVLNMFMALGLDS EEIFKLYYLKNAENFARQDSGY | 173 | gp56 dCTPase [Enterobacteria phage JS98] | YP_001595154.1 | 1e-73 (136/173) | dCTPase pyro-phosphatase | dCTP pyro-phosphatase | PHA02602 | 1.24e-79 |
| 173 | 91142 | 91279 | 954 | MAKRISKRRLKIIRKQKERALVL ALREEITREIDKEILKALTAAI | 45 | No significant similarity found. | | | | No putative conserved domains have been detected |||
| 174 | 91310 | 91546 | 955 | MAYVNIKTFDHTTADGEVKGTE VSVAFKVYSDSHRIANAQYQIF PSEKAAYSTVVDDAATWATTN AKMFEAVPSDAEV | 78 | Soc small outer capsid protein [Enterobacteria phage RB69] | NP_861717.1 | 2e-19 (48/73) | small outer capsid protein | No putative conserved domains have been detected |||
| 175 | 91625 | 91816 | 956 | MICYTKPWYQSSLKKSHFDCW YRGVRAAALLLKAAPALIKAND KWFEDNNMTEGALCGKRKNL | 63 | No significant similarity found. | | | | No putative conserved domains have been detected |||
| 176 | 91794 | 92318 | 957 | VANAKIYNAKIYKVSLQRAVQS RSDANGVLRLDODRIFTVALYS TFDKDFKDLVNKFEAFGWCPS EDYGIIKTAHVFDVDTVPGSPVA ILRALHLKGYTNVCHETSLYEYE NDIISRGKKIIIDSTDSLIEFTKLV WLYMGADFIKLTPSPLLQKAAD | 174 | No significant similarity found. | | | | No putative conserved domains have been detected |||

Fig. 12NN

| orf | Start position | Stop position | SEQ ID NO.: | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| | | | | GYNSSSCLYRNNEWFM | | | | | | | | |
| 177 | 92318 | 92506 | 958 | MDLFEMMEEPQEEVQVHPVIS KDIKDEYRIIQKYGIKAPEALLD ELASIWSDPPPWSPWAK | 62 | ModA.2 hypothetical protein [Enterobacteria phage T4] | NP_049637.1 | 7e-12 (36/62) | | No putative conserved domains have been detected | | |
| 178 | 92578 | 93267 | 959 | MAISLNPSISVKLLSKVIPIEKPIRS IDVLNFARESKGLPLYDLSVWE ALANRFDCKEQSILWQCMNNKI GEEFHKKLDSIVRRHQIDNSDIL YRGLSCRESKAFYDALIKGEKF GFGKVASFTTDETIAREFAGKW HYSTFVVIEVNNCHQSFDYHTN MKSLLITAPDSEFMRPNDVIDNI AQRRSADIEMIDKEQERMLPM GTKFKVVGHNKVEKSGLLMDY FSVTIA | 229 | ModB ADP-ribosylase [Enterobacteria phage RB69] | NP_861709.1 | 5e-19 (59/178) | ADP-ribosylase | No putative conserved domains have been detected | | |
| 179 | 93345 | 94103 | 960 | MMKFTAETAKIYTRLITTLGSAQ RRNKEFNLTPEYLFNIMQQTHC AYSGEKFGTVKGNHPDSMTLE RWNNDLGYVMGNVIPVKQKYN TLRGNNTIEGLERKANEIAARIV RSSDSVKPTSDKEASRLEKIRE YEKTITSIKTNLHNRENHLSQFV QKEKNGTATSADLELINALRTRI SGGKSELAKVERKLSAILASVP NRPSDAEIRVQSIRLIVSSLRRL EECSMLDKLKLKKGLPLTASFF QLLRGKM | 252 | Putative Srd anti-sigma factor [Enterobacteria phage RB69] | NP_861707.1 | 3e-34 (96/246) | Srd anti-sigma factor | Seryl-tRNA synthetase | PRK05431 | 1.55e-04 |
| 180 | 94103 | 94417 | 961 | MQHYGYVVAYKDKDGFDHPVT TDMYDGERCVVFTNEESANKA RIRTMSVLTDKLAKGNFTGKSK TKGMLWWKTTELVYEPLSDVE REKLKAKIKNLHVVRVKVA | 104 | No significant similarity found. | | | | No putative conserved domains have been detected | | |

Fig. 120O

| orf | Start positi on | Stop positi on | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 181 | 94414 | 95745 | 962 | MITFDQLKESQKAIFNKVIEMVK QGAKGQHITINGPAGTGKTLT KFIIDALISQGISGIALAAPTHGA KKVLSKLSGMQASTIHSLLKINP TTYEENVLFEQKKVPDMASIRV LICDEASMYDRKLFKILMATIPA WCIVIAIGDKAQIRPVEPGSNEP ALSPFFTHKDFLQLHLTEVMRS NAPIIEVATEIRNGGWIRDCVVD GHGVRGFTKGTALKDFMLNYF NLVKTPEDLFENRMLAFTNKSV DKLNEIIRRRIYETERPFVVGEIV VMQEPLTKELKFEGKKFSEILFN NGQFVRILDAIETTSFLGARGVP GEYLVRHWVLDIETYGDDEEYA REKICVISSEEMNKFQFFLAKT ADTYKNWNKGGKAPWSEFWD AKRKFHKVKALPASTFHKAQGI SIDRSFIYTPCIHMADASLAQQL LYVGTTRGRYDVFYV | 443 | DNA helicase [Enterobacteria phage RB14] | YP_00285435 2.1 | 0.0 (323/442) | DNA helicase | DUF889, PIF1 helicase | pfam05 970 | 5,03e -08 |
| | | | | | | | | | | recD | TIGR01 447 | 4,61e -15 |
| 182 | 95752 | 96006 | 963 | MFELKLEDLQTMIVGLQESKFE APDNVKRAINIKIDIVLNELRDIA DNANAITWFTGYDPKVYLSEYI GCCLREIKFMLEAQNG | 84 | No significant similarity found. | | | | No putative conserved domains have been detected | | |
| 183 | 95999 | 96688 | 964 | MAKDFIIDFETFGNVSSSSVIDL ALITFDSDPEVLESFDELVKRGH RIKFDLKSOKGHRLFGKSTLEW WKKQSAEARANLASTPDDLSVI AGIKEAQQYLIDNGIHPWDSFG WCRGQSFDFPIFVDCLRDVQR AQGISEEEIDTFKEEPCKFWNQ RDIRTAIESLLLLTRGLTTTPLPKG TLNGFIAHDSIHDCAKDILMLKY AQRYALGLSEAPSPEDTDPLSL PKGRG | 229 | Exonuclease A [Enterobacteria phage RB32] | YP_802954.1 | 8e-89 (154/225) | exonuclease A | dexA, exonuclease | PHA025 70 | 4,05e -86 |
| 184 | 96688 | 96855 | 965 | MEEFEFDENFEEWFNREILPKI SPTMVLVAKALMAKGWDAGYM FGVDVGCEISHR | 55 | No significant similarity found. | | | | No putative conserved domains have been detected | | |

Fig. 12PP

| orf | Start positi on | Stop positi on | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 185 | 96916 | 97359 | 966 | MMKNLVVGENVKVIGGKHIGKE GVIVGIFNRSNKMSSYLLQLEN EDKAVYSLQKFVVALESRDLLD SMFNESYLRKWVHVNSLDNVIT QSVSSTNSATNLSLHKNVLVTD EWEEDGKTLVNVVFQGNYAVL PKADVEPTESQRQGLV | 147 | No significant similarity found. | | | | No putative conserved domains have been detected | | |
| 186 | 97424 | 97639 | 967 | MKTENTVKITAEAFEDILFNPDLI VVQKEKTFGKEEHWTWLYVFA NHGDIVPVRTFARVITVDGPEY MEIV | 71 | Cef modifier of suppressor tRNAs [Enterobacteria phage JS10] | YP_00292223 5.1 | 3e-07 (32/64) | cef modifier of suppressor tRNAs | No putative conserved domains have been detected | | |
| 187 | 97639 | 98004 | 968 | MNFKEGVQYKFVNDEAEEFS SRYEVNEDFVYELYENGGSFTV TKVDRQNNRVSGIMWANGTEC DEVGGEDLVIFDSEFKYFTEVG TSANVIPTDLVMNLSIHNRGQAI AAIAALQSAYQC | 121 | No significant similarity found. | | | | No putative conserved domains have been detected | | |
| 188 | 97998 | 98333 | 969 | MLNLAPIFEASKLSYPIPNRSIG NVMLQLSSETGEMCDWINRPW RQKEEFEGECADVINCVVDAL WLHFRNRHKNDTHVSDDEISM MVTRALNEQIMVKTQKWKDAV NANV | 111 | Hypothetical protein 44RRORF011c [Aeromonas phage 44RR2.8t] | NP_932366.1 | 3e-10 (37/102) | | No putative conserved domains have been detected | | |
| 189 | 98320 | 98496 | 970 | MPMYDYKCEVCGKKIEIMRKIS HRDYTVNCFNPKCEGQMKRVV SAPAVHYDGLKSGDY | 58 | No significant similarity found. | | | | CxxC_CxxC _SSSS | TIGR02 605 | 5,16e -07 |
| 190 | 98582 | 98830 | 971 | MKKILITALAFMMIGCTDADNAT RVLENAGFTEVDITGYKFFSCS EDDFQHTGFKAVGPTGKTVKG TVCSGIFLKNSTIRFE | 82 | Hypothetical protein T4Tp006 [Enterobacteria phage T4T] | ADJ39724.1 | 8e-26 (52/81) | | No putative conserved domains have been detected | | |
| 191 | 98913 | 99110 | 972 | MKYIILTLIALVISIGVLVSLADST ESSNEVQKSSIGIGVNGQVGVK ISDNLCVNPSTGAAEVCF | 65 | No significant similarity found. | | | | | | |

Fig. 12QQ

| orf | Start position | Stop position | SEQ ID NO.: | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| 192 | 99151 | 100989 | 973 | MIKNEIKILSDREHIIKRSGMYIG SSACEAHDRFLFGKFQSVKYVP GIIKLIDEIIDNSVDEAIRTNFKHA NKISVDIKGNKIIVTDNGRGLPQ APVVTPEGETIPGPVAAWTRPR AGGNFGDDAERKTGGMNGVG SALTNIFSVSFTGATCDGKNEII VRCSNGSENISWEEHPAKDKE FIKDKTGTVVSFIPDFSHFESTG LTDVDQSIIHDRLMTLAVVYPDI EFKFMGKRVQGKFKAYAQMYD ENAVVQDSDTCAIAIGRSDDGF RQLSYVNNIHTKNGGTHVDLVL DELSNELIPALKRKYKLEVNKAR IKECLTVIMFIRDMSNMRFDSQT KERLTSPWGEIRSHIDIDYKKLA NAIMKSEDIHMPIIEAMLARKLA AEKAAETKAAKKAQKAKVAKHI KANKYGKDADTTLFLTEGDSAI GYLLTTRDRELHGGYPLRGKF MNTWGMSAADAMKNKEVFDIC AITGLTIGEPAENTNYRNIAIMTD ADVDGVGSIFPSLLAFFSNWPE LFEQGRIRFVKTPVIILTKGKEQ RWFYSLGEYEDHKDDFKGWKL RYIKGLGSLEEDEYERVIQDPV YDVVSLPENWKELFELIMGNDA APRKTWMSE | 612 | gp60plus39 DNA topoisomerase subunit [Enterobacteria phage RB51] | YP_002853958.1 | 0.0 (441/612) | DNA topoisomerase subunit | DNA topoisomerase II large subunit | PHA02569 | 0.0 |
| 193 | 101030 | 101182 | 974 | MQRYWITLVSGDYGYMFAEKK PLPGTWVTIWVENSDGSKHEV YGRVSRVH | 50 | No significant similarity found. | | | | No putative conserved domains have been detected | | |
| 194 | 101223 | 101471 | 975 | MKSTIISILRTEALKYSVDPSNEY QELLIKRLLNSIADRLESNQSVPI NHSLFAMKVIRFLRPDIKIADMV KVIKSSGAVKC | 82 | No significant similarity found. | | | | No putative conserved domains have been detected | | |
| 195 | 101465 | 101674 | 976 | MLKKSYVPNKELFDDAIYREYRI IQRFFDIQAAEEFKDRFKQISDKI FTTNTATAEELLEVAEIIKRHN | 69 | Conserved hypothetical protein [Enterobacteria phage AR1] | BAI83010.1 | 7e-16 (45/65) | | No putative conserved domains have been detected | | |

Fig. 12RR

| orf | Start position | Stop position | SEQ ID NO.: | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| 196 | 10168 5 | 10386 2 | 977 | MKIKCDDEVIIGSSDAEDSTFTIK ASGKAFDILSNKLYKYKVRAVV RELSTNCDDAHKLNGNENRPF YIKAPTRLDPRFVIRDYGPGLNH NDMMTMYKTFFESTKNNSNDFI GALGLGSKSPLSYTSTFNVVSY HNGKATGYTVMKNRGEPTIRP MFVDDMKEDEETGLEITVPVKV EDIDTWHYEIAYILRTFGAVPPK VDSLRREIEYFPVDKTDWFSVN SSYESYGLYAVYGKIVYPISGV DVKADWLLNRYGKVYVHFPLG ELDITPSREELSLDEETIANIQKR VNALEEEVITADIKAFEAYESDR EFLREFNKLSSKERSILQSRGITI GNRDIKQVVAKYNLDKIRSYYV DNEVSYYVSCDEPARRKVSSS SWHRHNQVNISDICGVDRTKAF VLIDDKAGKRIATVRALCKSGLV PIWAHITVIKDNEDELHVIDELKK IMDTDEVVVFRVSELEAQRKAL PDYDTGPKEKRPKSPNVSLHWI DKDGYWEEDRQTLLSSEITELE GYAIGRNRDEIHTFPDNVWWW NMSITDMRSLAEACGIKKFYAIR PSAMKAAAKADGLLSFDRFIIDQ YIKCIDKVDYDQYMPSNATGNR ICGNIAHYDKLNFLSSKFTASGM KNPFLTKLNKIAKVCRTSKIKDE NDENNDLALCNKIYNKLSSDAE TIFYKKIEQFKDDYPVIASVLDT WRTDSKLVDDIVKIMELLDGAS TQNSENKGE | 725 | rIIA protector from prophage-induced early lysis [Enterobacteria phage IME08] | YP_00373415 1.1 | 5e-99 (250/754) | rIIA protector from prophage-induced early lysis | HSP90 family protein | PRK140 83 | 1,11e -03 |

Fig. 12SS

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 197 | 103863 | 104774 | 978 | MAVTCLSEIQKDAIVKNFKNGLY TKKELAENYGVSRDTIRRVFKE REARAAAAVPAKVEAPVEREF KWAASSKFISITEGRTTYNADS QHPGFKSALQKLVDGDIAGAID HINLEQGIKKFVQGNVRIEDGTL FYKDIELKSGLTERIVRAMEDGE DFKRYLPFLENLMLNPSRRAVY RLFDFLNANDIDITDDGHFIGWK VVRSNYFDCASNTFDNSPGKT VTMPRNQVDEDDQRTCSTGLH VCSKSYIGHFGSGSDRIVSVKV HPRDVVSIPVDYNDAKMRTCG YVVLEDVTDRWGSELR | 303 | rIIB protector from prophage-induced early lysis [Enterobacteria phage JS98] | YP_001595395.1 | 3e-93 (169/318) | rIIB protector from prophage-induced early lysis | No putative conserved domains have been detected | | |
| 198 | 104817 | 105113 | 979 | MINPFNVSHSKVVNLRGTHHAA TVFCHHVVKHEGDVHYAWLHC DELVELGDDFVVEPDTCNHDD RVYFGELHIRGIYGIDEQSPAEI EPTPDIYPRFE | 98 | RB69ORF272c hypothetical protein [Enterobacteria phage RB69] | NP_861962.1 | 1e-20 (52/96) | | No putative conserved domains have been detected | | |
| 199 | 105046 | 105633 | 980 | MALMNKALQRLNQLRTFTLDLN KLRGEAKVKIIDTARYSLDIDPS QDRIDVLKRCRIAIPAEYVVADF LDGYNDQVVDHNNNDPYEW AWDVLAHPHYQGVRVEVKTHF VHDRANHKPWINVTTGKDGPF PDGSGINLGPMFKHKVADCIIIF VAEEVSQNVIRYTPMFAGGIEQ LMEVVKPSRVGAGGYIMHKF | 195 | Endonuclease IV [Enterobacteria phage RB14] | YP_0028546 07.1 | 2e-49 (104/183) | endonuclease IV | No putative conserved domains have been detected | | |
| 200 | 105698 | 105937 | 981 | MSYLELKSLRAKRGNASIKAEL LKEYRILESMNWHYAIIACDNG DSTYGGLYPNGAAAARDEHKD KVKALEEKIRNLCI | 79 | No significant similarity found. | | | | No putative conserved domains have been detected | | |
| 201 | 106126 | 106317 | 982 | MIRSSFDRRFNLMRTVVLSFIVA VALGIVAIFGFGIYFAIQAVDIIQT DGLKSLVETVWEGQK | 64 | No significant similarity found. | | | | No putative conserved domains have been detected | | |
| 202 | 106462 | 106917 | 983 | MRNIMTFADLLDNAGAELIGSIRN GDWAAGAPSREITEREGFYFL MFNDGKAGYIGASARFFVAKQ RSKAGFESVLSHIRSRSQLGR TLRSNCVTYGVFWIPANKMKPL TTGYGKGQLALAFTRQHSSAA QTYSELNRILNDNFIFTLQKY | 151 | Nuclear disruption protein [Enterobacteria phage AR1] | BAI83281.1 | 1e-42 (87/148) | nuclear disruption protein | Phage_T4_N dd | pfam06 591 | 7,83e -46 |

Fig. 12TT

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 203 | 107087 | 107230 | 984 | MIKGIAGGIWAALCVSTLTTGET SVISQALAQGTLSILIIAAFSND | 47 | Hypothetical protein EpJS98_gp256 [Enterobacteria phage JS98] | YP_001595385.1 | 5e-05 (24/47) | | No putative conserved domains have been detected |||
| 204 | 107223 | 107363 | 985 | MIKKILIGAALVAALLLILYYGMIY GMIYIVLFISDVIVQIGSLIW | 46 | Hypothetical protein RB32ORF257c [Enterobacteria phage RB32] | YP_803199.1 | 5e-04 (29/47) | | No putative conserved domains have been detected |||
| 205 | 107369 | 108757 | 986 | MDIFDTLLKQAGSIDDLAKASNL RHRDLKSIIDNEAKEYAIYTVEN RAIPNLIDGFKPVQRFVIARALD LARGNKEKFHKLASVAGGVADL GYHHGETSAQDAGALMANTW NNNYPLLDGCQGNFGSRLVQSA AASRYIFCRISDNFRKIYKDTEIA PVHKDKEHVPPAYYLPVIPTVLL NGVRGIATGYSTSILPHSFESVL ECTKAALRGEMMEPEVQFPKF NGKIVQTEDGSVELHGVYKETS RNSIYISEIPYKFERASYVEKVL DPLEDAGYITYDDDCSKTGFGF KVKFRKDYALSEDPEQRHAKIM KDFKLIEKMSQYIVVIDENGKLN DKFKTSGELIRHFVEVRKTFTAK RIEHKIAETKQAFNLAQAKAQFI KEVIAGNIVIQGKTRKQLTKEIE QNELFKDHSEKLVSMNIYHITD DEAKKLAQEAKRLAQEVKYWE KTTPEAEYLKDLEEL | 462 | gp52 topoisomerase II medium subunit [Enterobacteria phage IME08] | YP_003734396.1 | 2e-175 (304/462) | topoisomerase II medium subunit | DNA topoisomerase II medium subunit | PHA02592 | 0,0 |
| 206 | 108985 | 109248 | 987 | MITSLKSDIKNILYISTQADGTRL SHYVKGNIVVLDEFEVNREYPM RQVIQASNYEDGEEYQVVLCVY DDFWVLKLENGDKFLIFNV | 87 | No significant similarity found. ||| | | | |
| 207 | 109373 | 110017 | 988 | MSKVTYIIKASEDALNEKTAAILV QVAKKDFITSSELREILEETMNA SSVNSNIGVLIKKGLIEKSGDGLI ITGEAQDIHSKAAVIYAEENKPEL LKKRNTRKARPLTEDMNEHKDL MMKLLGEMEDILPLKELTVYRS NYIAVLEKRTFGIRSLEVNNKGT FRIFGYKISEEHQKHFTDLGMS | 214 | Activator middle promoter [Enterobacteria phage RB32] | YP_803196.1 | 3e-76 (145/214) | activator middle promoter | MotA_activ | pfam09114 | 3,76e -32 |

Fig. 12UU

| orf | Start position | Stop position | SEQ ID NO.: | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| | | | | CRVAATGNTYLDIARTAENIETII RSIKEL | | | | | | | | |
| 208 | 110017 | 110187 | 989 | MELWEIIYEDDVNIRGSIFIKALD KYHAIELFEQLQQQTYINESRYL IKLAMFLVE | 56 | No significant similarity found. | | | | | | |
| 209 | 110187 | 110528 | 990 | MNKFKVLNELQRCVEKVNLNA NIPTDCWDVWFRGHFIGYIDKK FTKCYAIYNADGKHIMDVDNYQ KALAKFVPLAEAVNSMEWLEKI QGEPVIRQIGIREKKSLWQKIKG FFK | 113 | Arn.4 conserved hypothetical protein [Enterobacteria phage JS98] | YP_00159538 0.1 | 3e-13 (43/117) | | No putative conserved domains have been detected | | |
| 210 | 110525 | 110950 | 991 | MSKFSEQMNKFVDASRHGALI NEPEEVSIPEICFKVADWWDGR LLQRRIVCAANRFELKSGGTIVV PGTRHYSVDMANVLDMFRDKL VSDHVHGDNQGFVDQWGEYF TREEALIIATHAGQVNTVRPKSG PANELFSEDLY | 141 | Hypothetical protein EME08_gp240 [Enterobacteria phage IME08] | YP_00373439 1.1 | 1e-36 (73/113) | | No putative conserved domains have been detected | | |
| 211 | 110950 | 111252 | 992 | MISTLKNNITLLKIQRKSLQRSLE MMDDNWGTYTNEAGFKMADS KFMKTLMDKEYICPFSHPFNGG AKPFLAEMYKIMTEEMIKDIDYYI KELECKEDKV | 100 | Hypothetical protein RB32ORF250c [Enterobacteria phage RB32] | YP_803192.1 | 6e-15 (38/80) | | No putative conserved domains have been detected | | |
| 212 | 111249 | 111461 | 993 | VRAISAKADYFNSLNRSEKAQIK RFILELGYVHAGDLKAHIQECGI AKRFDITRNCLNEVIAHVQPSSE E | 70 | Arn.1 conserved hypothetical protein [Enterobacteria phage RB69] | NP_861950.1 | 3e-14 (37/67) | | No putative conserved domains have been detected | | |
| 213 | 111436 | 111561 | 994 | MYNPVAKNDFNKGGAHKDKKR AAKESKRKQKHKGKDNAHSE | 41 | Hypothetical protein RB43ORF288c [Enterobacteria phage RB43] | YP_239264.1 | 7e-05 (24/35) | | No putative conserved domains have been detected | | |
| 214 | 111701 | 111823 | 995 | MVHDWNNGTFTVAIIANVEPEE VLEQFQKCVDAYDIGDYL | 40 | No significant similarity found. | | | | | | |

Fig. 12VV

| orf | Start position | Stop position | SEQ ID NO: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 215 | 111820 | 112146 | 996 | MNTETLRREDEAKAYHKRVELL SAIKVEYTLQVRLKVLNSWAND LEVKHLEQAVMFTFTQEASKPF SLSADFHTYGIITIKAKDRGDIIS GVEYIESILGNRGEVVLA | 108 | No significant similarity found. | | | | No putative conserved domains have been detected | | |
| 216 | 112143 | 112409 | 997 | MSHINLESVIESQRYLEALMNKI ALGSLIDLSFQEAMDVCHWMN RRVRPIGKEWVLTAKVKDGRY GLWMSSGAEYITTKEDLNSRW ELA | 88 | No significant similarity found. | | | | No putative conserved domains have been detected | | |
| 217 | 112477 | 112749 | 998 | MTKFEIVQEIVTVASILTKFNAEH IMEKRDEFIAFLNEIGIKNEQGR QLNQSNFRKMVSELTDEEKRIL VEEYNEGFESIYRTMAMHSNK | 90 | AsiA anti-sigma 70 protein [Enterobacteria phage RB69] | NP_861947.1 | 2e-22 (53/85) | AsiA anti-sigma 70 | AsiA, Anti-sigma factor A transcriptional inhibitor | pfam09 010 | 1,02e -19 |
| 218 | 113406 | 112750 | 999 | MASKQSIPFFDMFLGLLELLFKD GATGRVLFSRVFVILLALLAFA GYKSDSLITAYVDSTYDKYDKL VQKDRDTRFDNTALEQLQIVHI SSGADFSAVFTFRPKNLNYFVD LIAYEGTLPSTVDSKNLGGYPID KTSAEYSTHLSGRYFWTDKEFV FLPTKRKPPEISYMFSCPYFNL DNVYAGTVEMYWYNSKPALSN ERLTSICGQAVRALGRAK | 218 | t holin lysis mediator [Enterobacteria phage RB69] | NP_861946.1 | 4e-75 (132/217) | holin | Phage_holin_T | pfam11 031 | 8,03e -75 |
| 219 | 113974 | 113435 | 1000 | MAVTGPWVGSSAKAETGEPW MAQAGAKLRLGTPFWMSNMIG RSVFNFSLTVQYRNWNNIYR GSWQVGGWNWSPKPTTKNTV QGNFEGKEVTLFVSVSGQGGV NYWNGDPQGTTLGIRNGDAINL RVMMSDGTTFDFTPGKMDGDV RNYQIASNDEANKLKNWFSDR TDQYWQGLITRR | 179 | gp38 distal long tail fiber assembly catalyst [Enterobacteria phage RB16] | YP_00385856 0.1 | 8e-23 (73/183) | distal long tail fiber assembly catalyst | GP38 | pfam05 268 | 8,30e -12 |

Fig. 12WW

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 220 | 118588 | 114011 | 1001 | MADQNLKQIQFKRTSTENKAPG ADIVARGEIVLNTHGRTLAIYTK DEADNVVQLAGKGVPFLDTAG NLNVDGITTLKDNVTISPNKAIN FEATDLSGAIVRHIVGKCATND GWYIGAGGTSNSGILEIGTIDDG AETIQFVQRGSGNVEARKLVLL DGSGNTTLPGDLRLSTNKTVKI NNGSTLVLEMGVGSNDAYIKN QRGVGVLQLTNDSNLTFRNSQ VYYAMNGRGPGKSGTLLTNVE NNRQAWQYVISAATAGTPRWV KVATIKHPGDASSQLDLMITGGI DSGHGRHYVDFITLSGRNLTS WSTSNLDNWVEWRRIGSPNKG NVPEYYVVKNDAATDSEASFDF YAKVPRYGNGLYVTVLNTAEYN GQDSGKVIIYETGQDTGATTPS GSILVSMKQVFDSISKPDFSDTT GTLPVNRGGTGATNVGDARNN LGLRTAAVRDVGESSGNVMEV GAFGIGGNGKSLVDITSDVDLM TRLKALGGTTFRANVASGYTGA PYYSHGAGFFSRTGDTMSALNI DYATGNVRVFAINDSGLASGRV NSNVLYGTANKPSKADVGLGN LTNDTQVKKAGDTMTGDLTVP NLHASGTGTASVYYNAGSGNA HVWFRTGGNERGVIWATPNTA DLGQINIRAKTTGDVSAGDFSF RSDGRLDVPVAVKVGGAAMLT KDGNITSGSMFGGNLNNYLTSI KNDITTGDSKQVSKTGDTMTG NLTINANLKVENPNGSMVDLGS ENSDKYSRLTLARKVGSGAAVA MLKITPEGYVQFGYQDAVATPA PSKYIRVKPDGLDVEGDLVFNQ TYRGTEDAINITDKTNDLNNMVI KGSDLGTRQLYKCVSSGGGSN ISNKPTSDGNFVLEVLSLRKISD SDWTCKQTFTTKNGNVEGTYV RYCQNGTWSAWKEVVAGVQPI NLGGTGATSVAAARNNLGVGE GQSVKFGWLVVNGVGTSDPTI | 1525 | L-shaped tail fiber protein [Klebsiella phage KP15] | YP_003580110.1 | 6e-137 (386/1138) | L-shaped tail fiber protein | No putative conserved domains have been detected | | |

Fig. 12XX

| orf | Start position | Stop position | SEQ ID NO.: | Aminoacidic sequence | Size (aa) | Homologous/similar proteins ||| Conserved Domains |||
| --- | --- | --- | --- | --- | --- | --- | --- | --- | --- | --- | --- |
| | | | | | | Name[organism] | Acc No | E value and identity | Predicted function | Name | Acc No | E value |
| | | | | TFKNGAVVREAQGGSTGALIMS ASATAAASAKYIAFRPFGDSSG SEIRVKANGSEPLLEWSYGPGI RSNDSGAFVIYAKTGQALHLRP NGDDSNQATVIDQKGKMTVGG EFEAQNSKITGNLNVSEDNRMI VLGKNSDIGLVKKNGMPGKMAI GKSNSFTVMVSANTNNQINPAD TFSDIFKVDASGNQTVYGNAQI NRQLTVTSNTNLNSDLIVKGNS RFSGVINADGNINVASGKFVIAG QAPTDNSHLTNKKYVDDKVAS AISNAGDTYLPLAGGTVTGTLIV TGNQLKTTSLWTTGDAAVNGV LTVDGKARFNQEFSVSTSVNV QNTGNSHVFFRKADGTEKGLL WADEPGNVSIRAGGASGPVWN FWASGSCQFPGAISNYNGISST TNYPAGQPNGTYNNTAGLVSR FSNGAYASLYFQEYVGNFHQAI INVNGFGRDDSFYFRAGGDFIC TRNGSFDNVEIRSDRRAKSDIK VIENALEKVETLSGNTYELHNTS GGTTRSAGLIAQEVQEVLPEAV TQDIEADGGLLRLNYNSVIALLV ESVKELSAEVKGLKAEIEELKSK | | | | | | | |
| 221 | 119260 | 118598 | 1002 | MADLKAGSTVGGNPIWHAGTF PLVPAGNSLTYRGKKVYTEIDK PQAADNDFVSKANGGSYSRTV TFETGLRVQTTGSGGMELVNG GVDGATLNGVNAKIKTWWGLG FESNSGSNGITIAFDLRSGNITT KGGITSNNQVSVAAAAPTANSH LTRKDYVDELINTVSNVANAAV KKAGDTMTGVLRANAGVIVNK ATSGEYAPRLDQVISRGVTIDF GTY | 220 | Hinge connector of long tail fiber distal connector [Klebsiella phage KP15] | YP_003583010 9.1 | 1e-59 (120/223) | hinge connector of long tail fiber distal connector | Phage_T4_g p36, phage T4 tail fibre | pfam03 903 | 9.26e -51 |

Fig. 12YY

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 222 | 120454 | 119318 | 1003 | MADPILMAAFGEDFVETRILSEA NSVKYWLKAYATHSNAVPNKP ELNINGAFDMTSSLRRGINVVQ VNGDRFINFKTFDVTTDDNNAN NKAFVEYANGLTSGLYIIMTHER FQSSPLIDRWFKNKWSASWPG SDFSKSFPNSAYVGVLGAAKG RILIESFYGNDGKVKEDSRAKV DTVYDNVGDVGYTGCPYRSIE DTNEYSDSTGYEYKRYPVQNE SISKIADYGLSPGDSVFLVCDM YASKSLLDAGSTTRASLRWFKG TSLLSSNVSLEVPKNGADRWLR FERFTAVPTDADGFTIVVSRYP KTSVVGDSKIKNLVFVQTSHGE QLNSVIQEFGVNGIRMNKGVEG GTTMIMELPNSKVDPSGVIPVQ SFRETSD | 378 | gp35 hinge connector of long tail fiber proximal connector [Klebsiella phage KP15] | YP_003580108.1 | 9e-110 (203/371) | hinge connector of long tail fiber proximal connector | No putative conserved domains have been detected | | |

Fig. 12ZZ

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 223 | 124299 | 120454 | 1004 | MSDLLKQHFRATNGLDAGGNK VINVALADRNVKTDGVSVEYVI QENTIQKYDPTRGYLTDFAVTY GRRIWIANKDIPKPAGEFNQAN WTSLRVDPNWIYTVRKGEFEIQ SGQFINVDSNAAGNATLLLPLA PDEGDTIVVRDIGGRPGYNGILI KAQDTGASIVFGESRLREVRLT RPYSQIMLTFSNGAWRASLTDF GDTAKMVVPNGIVPTQVQSGD NVVRRYTSNSEIFITLPLFANSN DIINFTDLDGTSPINHMTVRTFD PTISIGTPGQTEIQVRTSGSGFL VYDAIDKIWRIFENDLRTRVRIIT SDVTLMPNEHISVFGADNSTVK TINITLPTDVAVGDTVKIAMNYM RKGQTVVIKASDGDTIASNLNLL QFPKRSEYPPDAAWVQSSSITF NGTTSYVPVLELAYIEDKASGK SYWIVTESDPTVERVDAKDNTT RARLGVIALATQAQANAESNPE KELAITPETLNGRRSTETQTGIA RIATSGEVNQATTASYLDNVIVT PKKLNERSATETRRGLAEIASN AKMDAGTDDFTIVTPKKLLYRT TSDSRLGVIQLVKTGGAPNTTA DRSSAGTGIFDHSDYKNAVTPK TLREYKATVNQSGIVWLASDSE VRNGTPASSNIPTVVTPESLHK KVATDGAIGLIQIATQTEVNAGG VTNKAVTPKTLNDRTATNDRTG IARFATPGAQGEFEAGTSSTVM VNPKLLFDKFANTSRIQVNTSS GLTITGNLWDHYTINIQEASTSQ RGTTTLATAAEVRTGTDAKKIVT AATLHAKTATEGAIGLAQYATQ AQVDAGTLSDRIVPPAYLKQTIQ VTESWQATDSVRGTVRLSTGD GTWKGNDTNGSTLPDNGYASK GVAVSPYELNLTLKHYLPRLGK AYDTGMLGGQTPDKYARRDIA QTISGAWTFSQDTVFNMNISVQ NILYANGGEVKISPTADTGNAH VRFQNRDGTERGIIYAETQTAS | 1281 | gp34 long tail fiber proximal subunit [Klebsiella phage KP15] | YP_003580107.1 | 0.0 8596/1309) | long tail fiber proximal subunit | Long tail fiber, proximal subunit | PHA02584 | 0.0 |

Fig. 12AAAA

| orf | Start position | Stop position | SEQ ID NO.: | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| | | | | AGNLKVRVKNGTGTTAASQTY TFGGNGTLDVPNEVSTKTLRSS GNTIVGGTVMVKDTVLLTIETQN AIIGARSHSAFIDTRDADTQIFAR DNTNSYPILTTKNYARLADGRY VKKAGDTMTGNLNINSSAIVITG SESWYVPTNDTVLRQGSWTAE IKDATKLKGLRGYMVPIRTPIDP ANPSTLVVTGYEEKTAAGGVLT QVGVTTNNTYQLWTPYPPTE TADKRFAHTVWMRIYNPNLNKF DDWMRVFTSATPPTAADIGAPS SVSTQVKTLEVLEWIKLGPVKI WPDRPNQTLKFEWVGD | | | | | | | | |
| 224 | 12437 5 | 12530 1 | 1005 | MSDLNCLFAEEDQVKEGVLIDL SQIAMATILHTYKEGDKLTTPMV RHLILSTLKFNAFKWKKDGYTKI VICVDNAVNGYWRRDVAYYYK KNRAKAREESNWDWEGYFEG LRTVIDEFKQYMPYYVIDIDKAE ADDSIAVLTKKFSLEGHPVMVS SDGDFTQLHKYPNVKQWSPM QKKLVKSKTGSPALDCMVKIIK GDKKDNVASIKVRSDFWYTHV DGERTPSTKMTFVEECLDAGE NIKDLLTEEQYKRFLENRVLIDF DYIREDIVANILDCYNNYQLPGR GKIYSYFVKSGLSKLMKEINNF | 308 | RNaseH ribonuclease [Enterobacteria phage T4] | NP_049859.1 | 2e-114 (202/306) | RNaseH ribonuclease | rnh, RnaseH | PHA025 67 | 4,40e -127 |

Fig. 12BBB

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 225 | 125312 | 125584 | 1006 | MAKKEKEQVVFDEAVHGQALR DMIKEASGNKLKAESYLELNKDI KDRAKKELGVEGKLFNQLLALF HKGTRDRFETEKDEVVEAYDSI FA | 90 | DsbA dsDNA binding protein [Enterobacteria phage IME08] | YP_0037343 8.1 | 1e-21 (54/86) | dsDNA binding protein | Double-stranded DNA binding protein | PHA025 99 | 1,94e -24 |
| 226 | 125565 | 125864 | 1007 | MTLFSLKDEGDTSPSESINQLL DKQANGFAIESMVTELGMGYLE ATTQWLEENSIPEGNFSRYIPP AIIEKIMSEALEENMLRPSFSQT HKTNSLDFLL | 99 | gp33 late promoter transcription accessory protein [Enterobacteria phage RB69] | NP_861938.1 | 5e-25 (54/84) | late promoter transcription accessory protein | No putative conserved domains have been detected | | |
| 227 | 125861 | 126523 | 1008 | MIRLRMPQNNNRYVNGKSVYL LYLMLKQHFAGRYDVVKYNWV MRVSDKAYQKRRDKYFFEKLA EKYTLKELTLIFMSNLVANQDA WIGDISDADALIFYREYIGKLKQI KTTFSEDVKNIYYFAKKVNVDKL HDIFEYNEKVGTSYVFKLLQSN VISFETFIMLDSFLDIINTHDTAT DNLVWSNYSTKLKAYKKLLNVD GAEAKKLFISIIKSCKEISI | 220 | gp59 loader of gp41 DNA helicase [Enterobacteria phage JS98] | YP_0015953 6.1 | 8e-95 (166/216) | loader of DNA helicase | T4-helicase_N | pfam08 993 | 2,06e -36 |
| | | | | | | | | | | T4-helicase_C | pfam08 994 | 2,67e -28 |
| 228 | 126591 | 127508 | 1009 | MFKRKNPAQLQQQLAGLGKGGS SFSNEDKNEWKLKTDNAGNGQ AVIRFLPGKDENSLPFVKLINHG FKHAGKWYIENCTSTHGDFDS CPVCAHLSKNDSYNSNPAEYKL LKRKTSFWSNILVKDPANPENE GKVFKFRFGQKIMDKINAMVEV DVDMGETPVDVTCVYEGANFV MKVKKVGGFQNYDECKFLGQS EIANINDEETQKFLTENMADLSE IVAPSQFKSFEVNEAKFKQIMG TAALGGAAAKAAAQADKIGDDL DSFDKDLSDFESKPTSSRSADD IMGDAGDSVGDDDLNDILNDL | 305 | gp32 single-stranded DNA binding protein [Enterobacteria phage JS98] | YP_0015953 6.1 | 9e-104 (202/284) | ssDNA binding protein | Single-stranded DNA binding protein | PHA025 50 | 5,68e -109 |
| 229 | 127634 | 127891 | 1010 | MGKLNIDIVAEPYINKSGFCTDLI FEDGSRFYDTDHGIDFDLVIKE GPGGWPNIDLRGSKEAVRAW LEANEWEDIDLMMEDWKE | 85 | No significant similarity found. | | | | No putative conserved domains have been detected | | |

Fig. 12CCC

| orf | Start position | Stop position | SEQ ID NO.: | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| 230 | 127933 | 128154 | 1011 | MAQVTVEIYDYEHFIETIEKYGLI EVSNKSAPWGGNEITVEGDTP TLWLWLEQEYFPGMDDECRED TLTTFSG | 73 | No significant similarity found. | | | | No putative conserved domains have been detected | | |
| 231 | 128158 | 128523 | 1012 | MKLNTEYRIIPSLAAEWDLSSS GNRRMRLMIEEHGGSFFPTKM LDEDNSFHTEVKFKDGTTADAE GFGDAYFEISDYEFKYFEPVYEI GSAIQPGPTRLDLIVTPENAEE MIDLIKKVFKK | 121 | Frd.2 conserved hypothetical protein [Enterobacteria phage RB69] | NP_861934.1 | 3e-08 (45/130) | | Bacteriophage FRD2 protein | pfam03 197 | 3,59e-11 |
| 232 | 128580 | 128858 | 1013 | MKLQRQSIKLGSEYRGKWNFCI CDKNPEELERVEEVLCQMEAP FTMGGETVYWNDYCDNCPCY EDGYGSGFWIPVEDVEEFKKAF KLAKAKK | 92 | Frd.1 conserved hypothetical protein [Enterobacteria phage RB16] | YP_003858463.1 | 4e-25 (53/89) | | No putative conserved domains have been detected | | |
| 233 | 128937 | 129257 | 1014 | MSKFSVTGYPRVNIRCQFDEIP GVTHIELVFDPHSRCNQVSGKI DSAYGEFLINDQVVVSAISGEQ AGSLYILKREVFEEISEAIKEGFK TLQSMIKASEYKSCGF | 106 | Hypothetical protein RB51ORF237 [Enterobacteria phage RB51] | YP_002854190.1 | 6e-06 (39/114) | | No putative conserved domains have been detected | | |
| 234 | 129340 | 129504 | 1015 | MENFAVDDYDDLIWWDGREW VTICAMSNIDSAIKRLQELQQK WEDGNVERVEFY | 54 | No significant similarity found. | | | | No putative conserved domains have been detected | | |
| 235 | 129512 | 130111 | 1016 | MIQIVYAFAPTKTVDGKNENAF GLGDGLPWKHISODMKNFANR TRDTILICGAKTFMSFPEPLPGR KTIVVQDMSRALATAKNGFFAD AYVSELEFIGFLGGDIMAAHTSY NSTITFNRDLNYSIIGGAGIIQKA YPYADRVIQTIIRKSHRVNSDVT LPAEFVTAPTWPESGFITKENH WYHIDEVTNISEVVYERKL | 199 | Frd dihydrofolate reductase [Enterobacteria phage IME08] | YP_003734372.1 | 4e-44 (91/197) | dihydrofolate reductase | DHFR_1, Dihydrofolate reductase | pfam00 186 | 2,29e-14 |
| 236 | 130095 | 130412 | 1017 | MSANYDITQLSEDKVQKRWKR FPFKHGIHLLVFSYNGLSTYNG STTVYNRRNGNIPIEIERDYKKMF IGMSHGNVTVNDDVVSIIGRFE KRGDQLFFTPLQEKFNA | 105 | RB32ORF229c hypothetical protein [Enterobacteria phage RB14] | YP_002854567.1 | 1e-06 (36/116) | | No putative conserved domains have been detected | | |

Fig. 12DDDD

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 237 | 130405 | 131265 | 1018 | MREYQELIKDIFENGYETDDRT GTGTIAKFGTQHRFDLQEGFPA VTTKRLAWKACIAELIWFMCGS TNVHELRLIQHDSLLEGKTVWD DNYENQAKDMGYSGGELGPVY GKQWRDFMGVDQLKLIIDRIKQ LPYDRRQIVTAWNPVDLDKMAL PPCHLLYQFNVRQGHLDLQWY QRSVDVFLGLPFNIASYAALVHII AKMTNLKPGHLVFTGGNTHYL NHIEQCKEILRREPKELCELEIA FPDTYETWQTSSQIRWLEQFA RPHHFELVGYKSHPTIKGKMAI | 286 | Thymidylate synthetase [Enterobacteria phage RB32] | YP_803170.1 | 3e-134 (217/286) | thymidylate synthetase | thyA, thymidylate synthase | PRK01827 | 3.21e-96 |
| 238 | 131262 | 131468 | 1019 | MNIRFVRKGHQSKTVLGEMQD AFSSDLPEVNDTIVFDGTEQRV LSVIKSYEWSIGKTQLICWFEVD IT | 68 | No significant similarity found. | | | | No putative conserved domains have been detected | | |
| 239 | 131465 | 131770 | 1020 | MKICRVVNKYHSDFDVNIQRGT MWGNYVGKDCDNRPDAIAAFK DDFIAKIRNGEIKREHLETLRGM RLGCTCKPLPCHGDIIALVVNKL FKDTFELEDLCK | 101 | NrdA.1 conserved hypothetical protein [Enterobacteria phage T4] | NP_049846.1 | 2e-36 (71/99) | | No putative conserved domains have been detected | | |
| 240 | 131761 | 134007 | 1021 | MQVIKSSGVSQEFDMQKIIKVLE WACEGTKVDPPYELYEIIKSHLR DGMSTADIQKTIVKVAANSISID EPDYQYVASNAAMFEIRKRVYG QFEPPAFIDHISRCVNANKYDK EILSKWSAEEITLLDSYIKHERD FTMTYAGTMQLIEKYLVKDRHT GELYETPQFAFMLIGMCLHQDD GENRLANVIRFYDAVSTKKISLP TPIMSGVRTPTRQFSSCVVIEG GDSLNSINEAAASITKYISKRAGI GINAGMIRAEGSKIGFGEVKHT GVIPFWKHFQTAVKSCSCQGGV RGGAATLYYPIWHLEVENLLVL KNNKGVDENRIRHLDYGVQINN LMIERLIKNDYITLFSPDVCLGAL YTEYFRDAQAFRTLYEELEKNP DIRKKRIKARELFELFLTERAGT ARIYPYMVDNVGEYGPFIRDVA TVKQSNLCLEIALPTSDVGQED GEIALCTLAAFVLDNFNWQDQE | 748 | NrdA aerobic NDP reductase, large subunit [Enterobacteria phage JS10] | YP_002922571.1 | 0.0 (572/751) | aerobic NDP reductase large subunit | nrdA, ribonucleosid e-diphosphate reductase subunit alpha | PHA02572 | 0.0 |

Fig. 12EEE

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | EVNEIAEVMVRALDNLLDYQDY PVDKALKAKDRRALGVGITNYA AWLASNFASYADANDITHEMM ERIQYALIKASVKLASEKGPCAL YKETRYGRGELPIDWVNKRIDQ LAAPNYVCDWELLREDLKRYGI RNSTLSALMPCESSSQVSNST NGIEPPRGPVSVKESKEGSFNQ VVPNVEHNASLYDYAWQLAKQ GNKPYLNQVLIMQKFVDQSISA NTYYDPANFPKGKVEMSVMMD DLLYFWYFGGKTLYYHNTRDG SGNDDMIQDSADCAACKL | | | | | ATP_cone | pfam03477 | 3.83e-12 |
| 241 | 13400 7 | 13464 8 | 1022 | MNYQNVYNSLISRARARESLLG YKETHHIIPRCIGGSDDKENLVE LTGREHFIAHWLLCKIYEAPGLK KAFGLMCLTGKNRSYKYSSQL YELGKRRLSEAATGRKASIETR EKISKSLKGREFTEEHLANMRK PKTEETKKNIAAAKVGVLNPMY GKISPTRDVPHTKETRDVISLRT KQGTEYPPCPHCGKKVNKGNA | 213 | Putative homing endonuclease [Enterobacteria phage LZ7] | ABA03236.1 | 4e-113 (193/213) | homing endonuclease | HNHc, HNH nucleases | cd00085 | 2.82e-04 |

Fig. 12FFF

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | LRWHYDKCKFKDPK | | | | | | | | |
| 242 | 13464 5 | 13578 7 | 1023 | MSTVFNKEPVDIMNEPMFLGS GLGIARYDVQRHKVFEELIEKSL SFFWRPEEVNVMMDRGQFEKL PEHQRNIFTDNLKYQSLLDSIQ GRAPAAVLSALISDPSLDTWNQ TWTFSETIHSRSYTHIMRNLYV DPAKIFDEIVLDEAIMKRAESIGV YYDDVIAKTRAWENAKNRCFN QDNIEIKEAKRDLMKSLYLCLHV INALEAIRFYVSFACTFNFHKNM EIMEGNAKIMKFIARDEQLHLKG TQYILRQLQTGTDGEEWVEIAK ECEQEAIEIFMEVNRQEKDWAI HLFRNGGLPGLNVKILHDFIDYL TVSRMRSCGLPCPITDAPTRHP IPWIREYLNSDAVQSAPQEVEIS SYLVAQIDNDVTDDVLIGFKRYL | 380 | NrdB aerobic NDP reductase, small subunit [Enterobacteria phage T4] | NP_049841.1 | 0,0 (306/388) | aerobic NDP reductase small subunit | nrdB, ribonucleotid e-diphosphate reductase subunit beta | PRK091 01 | 3,79e -147 |
| 243 | 13581 5 | 13623 1 | 1024 | MNDIANEFSFIKYVQLELEPDFS IKPVLVANKLNVVYAIAVDDELV YIGKTKNLRKRINYYRTAINRKD QTSDSAKSAKIFEALMAGKKVE FYARQCFNLLINNELGEMSIST MDLEEPMFIKKFNPPWNTQHK VKKC | 138 | DenA endonuclease II [Enterobacteria phage JS98] | YP_00159535 1.1 | 1e-58 (108/137) | endonucleas e II | denA, endonucleas e II | PHA025 98 | 3,38e -49 |

Fig. 12GGG

| orf | Start position | Stop position | SEQ ID NO.: | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| 244 | 136225 | 137376 | 1025 | MLELYKNLMNLCESSEVAKFFY KDFTGPMDGKFRVFSYHYASY SEWLKPDALECRGIMFEMDGD TPIRIASRPMEKFFNLNENPLTM GIDISDVEYIMDKADGSLVSSYV DDGYLYLKSKTSLYSDQARQAS ALINSEEYSSLHQVILELALDGY TVNMEFVSPNNRVVLAYQEPQ LFVLNVRNNTTGEYIKYDDLYA NAKIRPYLINAYGISDPTTWVEG VRELEGVEGYIAVLNTGQRFKV KTEWYSALHHTKDSITSNERLF ASVVSANSDDLRSLFAGDEYTI KKISAFEQAYLDYLGKSLELCQ SFYDEYRGRARKDYAIAAQKAT VNQRHLFGVIMIMYEGTVDVD KLLKDLERVFLKYWAGYVPKEY EKEIEISEE | 383 | RNA ligase A [Enterobacteria phage RB69] | NP_861926.1 | 8e-109 (188/376) | RNA ligase A | rnIA, RNA ligase A | PHA02589 | 6,98e -147 |
| 245 | 137439 | 137948 | 1026 | MDMQAITLDMVVNKYGTHSDGI FWNGTKKVGFVTDLRTHMAR KEAARKKQKEYTNRVNEQRAE ALPEAVDEMIDFLDNHLAKYGA EVFKNITQPNVHANGCKCYVIV DPIYGKHRLGIMHRELNYSEMA EYVEACFKCSPSESSDRHILISG LSRDDIVEVILKLCSK | 169 | Inhibitor of host Transcription [Enterobacteria phage T4T] | ADT39948.1 | 2e-46 (94/167) | inhibitor of host transcription | | | No putative conserved domains have been detected |
| 246 | 137936 | 138289 | 1027 | MLKINTTWLLIGVLALSAGGLKY LSWRVENLKADLKVVQDESDR QAKEIENIGVSIKNLQTTYKGYQ ENRAARDTSNAKMNKDSKRGN VVAAKPGLVEKQINASFNKFAE DIQEATR | 117 | PseT.3 conserved hypothetical predicted membrane protein [Enterobacteria phage RB69] | NP_861924.1 | 1e-12 (47/119) | | Hypothetical protein | PHA02141 | 3,41e -03 |
| 247 | 138286 | 138573 | 1028 | MKRSLLAMCIISLLAGCSSSAPD VPVLHPEWPDPIQKWEGHWEV KVIDGKAWVGMPFEESQEYRI WMNDILRYTKDANGMICYYRSE LKEPRCVK | 95 | PseT.2 conserved hypothetical protein [Enterobacteria phage JS10] | YP_002922565.1 | 4e-24 (53/95) | | OM_YfiO | TIGR03302 | 6,31e -03 |

Fig. 12HHH

| orf | Start position | Stop position | SEQ ID NO.: | Aminoacidic sequence | Size (aa) | Homologous/similar proteins ||| | Conserved Domains |||
|---|---|---|---|---|---|---|---|---|---|---|---|
| | | | | | | Name[organism] | Acc No | E value and identity | Predicted function | Name | Acc No | E value |
| 248 | 138595 | 139080 | 1029 | MEPSHFYSYFVKDASHLLSIKN TQLRNMLAVGSCQLTPLAKKAT VIPENISNGYVYTVRVSVPGALK ERLFELNDQTRISFDVWFKLFM VEFMYPDFLKFVQRKEALKEAI SELEDASIEFGKALQFVESGGV EQDAVNGFLKKYGKRRSLAHR NLSKMVM | 161 | No significant similarity found. | | | | No putative conserved domains have been detected ||
| 249 | 139080 | 139292 | 1030 | VNQEQYETLKGLIAENELACIVF GRAAENYDKNDILSMNKPLRAI KEKYRANWGEKSKALHDFIDTL KDV | 70 | PseT.1 conserved hypothetical protein [Enterobacteria phage T4] | NP_049835.1 | 2e-05 (26/71) | | No putative conserved domains have been detected ||
| 250 | 139292 | 140185 | 1031 | MKKLVLTQGAPGSGKTTWANE YVAANPGWNYVLSRDDLREGIF GLDKRNDYKYSKLREKSVSVC QFSMAKTLLEMETTKGVIIADTN LNPTTIKKWQELAYEIDGVKWEI KRFDVPWTELVKRNLYRGANA VPIEVLRSFYSKMHPYDLYIPDE SLPKAVIFDLDGTLADNNHRSP YDLAKCGKDHPKEMVIEFKML RNKGYKILTVSGRESGTKEDPT VYQRITKKWLLDHVGETGEHFQ RKQGDSRKDDVVKEEIFWDRIA DRYNVKLAVDDRAQVVEMWR RIGVECWQVAHGDF | 297 | Polynucleotide 5'-kinase and 3'-phosphatase [Enterobacteria phage AR1] | BAI83237.1 | 4e-92 (175/301) | polynucleotide 5'-kinase and 3'-phosphatase | HAD_like, Haloacid dehalogenas e-like hydrolases | cd01427 | 3,38e -08 |
| | | | | | | | | | | pseT,poly-nucleotide kinase | PHA025 30 | 2,64e -105 |
| 251 | 140197 | 140481 | 1032 | MFPKYSEVVKVSFTQVVANHLT DEFTPAEVAKMHAEFLSAMINAL IPNGEVVKFSIDRLGGSSEIKISC GEGEHDWFIVGIIANFETQQVE TYVV | 94 | Cd.3 conserved hypothetical protein [Enterobacteria phage RB69] | NP_861916.1 | 2e-06 (34/90) | | No putative conserved domains have been detected ||
| 252 | 140471 | 140707 | 1033 | MLSDAKFSHDEFISKVKIFAQEV ANRVPGSKVTLRRESSFNYVD AYITVNNGKSNQHTQLALTGT | 78 | No significant similarity found. | | | | No putative conserved domains have been detected ||

Fig. 12III

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | GQVEMTNILGHI | | | | | | | | |
| 253 | 140707 | 141051 | 1034 | MTLREAVEALLIEHARGIKAEIS PNGIRLISAVIGSDQGVWSIPRE EYDAILYSNVNVKEGQPMYGYV FSDSLERGNHPFPDGTGIRTSR VESFASPTDELKLVKTNNTTYL VI | 114 | No significant similarity found. | | | | No putative conserved domains have been detected |||
| 254 | 141052 | 141621 | 1035 | MKASTVLQIAYLVSQESKCCSW KVGAVIEKNGRIISTGYNGSPSG GVNCCDHAAEOGWIGEIPYKST GLRQDGFQVKKVGLLKEHRAA HSAWSKVNEIHAELNALFAAR NGSSIDGATMYVTLSPCPDCAK AIAQSGIKKLVYCETYDKNEPG WDDILRSAGIEVFNVPKRNLDK LNWYNIKEFCGIE | 189 | dCMP deaminase [Enterobacteria phage RB32] | YP_803153.1 | 7e-83 (155/193) | dCMP deaminase | cd, deoxycytidyl ate deaminase | PHA025 88 | 1,13e -81 |
| 255 | 141621 | 141821 | 1036 | MKLRIVEINKLNLSGDVVISYSV ERRYWFKWKPLATFKFEDQAV RLLKELSKRKSVIIKTIKETSK | 66 | gp5 [Enterobacteria phage N4] | YP_950483.1 | 3e-06 (29/63) | | No putative conserved domains have been detected |||
| 256 | 141818 | 142126 | 1037 | MKLTTEQNIHIRETLKAVLSMGE SQIVFEKADGTIRTLRCTRDKDII PSDLVESTTKSARAESTTSLPV YDTEKEGWRSFAFDKLISVNG MKVEHLLQMIGK | 102 | gp31.1 hypothetical protein [Enterobacteria phage RB14] | YP_002854654 | 2e-29 (65/102) | | DUF2693 | pfam10 902 | 2.25e -22 |
| 257 | 142184 | 142507 | 1038 | MELPIKALGEYVILVSEPAQQG DEIVSPSGIILGKEEQGQLPDMC EIYSIGDDVPKGFVEVGDLTPLP VGNIRNVPHPLVAAGVKKPKEI RQKFVTCHYKSLACVYK | 107 | gp31 head assembly cochaperone with GroEL [Enterobacteria phage IME08] | YP_003734352.1 | 3e-40 (78/107) | head assembly cochaperone with GroEL | Cpn10 | pfam00 166 | 2,77e -03 |
| 258 | 142623 | 142871 | 1039 | MNKQLTKALELQRNAWNSGHE NYGASIDIYAEALEVLKGFKHLN PAQAEFRDTLEAMDELKYAKHL GSAARKAVRHFVVTLK | 82 | rIII lysis inhibition accessory protein rapidlysis phenotype [Enterobacteria phage IME08] | YP_003734351.1 | 6e-29 (63/82) | lysis inhibition accessory protein | No putative conserved domains have been detected |||
| 259 | 143224 | 143415 | 1040 | MEDDKMAKQAKTAVKEVVG TSKRAGYKRGSNKRINQTVEKI MRRARAVLRDDASRFGKPKA | 63 | Uncharacterized 11.1 kDa protein in Gp30-rIII intergenic region | PI7310.1 | 1e-14 (41/44) | | No putative conserved domains have been detected |||

Fig. 12JJJ

| orf | Start positi on | Stop positi on | SEQ ID NO.: | Aminoacidic sequence | Size (aa) | Homologous/similar proteins ||||| Conserved Domains |||
|---|---|---|---|---|---|---|---|---|---|---|---|---|---|
| | | | | | | Name[organism] | Acc No | E value and identity | Predicted function | | Name | Acc No | E value |
| 260 | 143537 | 143896 | 1041 | MNFTNFNRKYVQNNAWDVSTT LLWEHNNGTVAQIDMYWEDNY VFFSFENGPTLDIQFNGSEIKVG FHDEVRKRDLSSHPSWNTNRQ LLVKIYLRHILGRKTTEEQREAI WDIVSNEIKF | 119 | gp30.7 conserved hypothetical protein [Enterobacteria phage T4] | NP_049821.1 | 3e-26 (58/118) | | | Phage_T4_ Gp30_7 | pfam06 919 | 2,72e -27 |
| 261 | 143936 | 144418 | 1042 | MEKGKFYKLKKTPSLSPGALIK GVFEQIGNNPIKITRTFKYAENT GLVEFEIKPDGEYKRVSIDEVR FSRMWCIITNQEFQHYFEETTH KEPEPKTDDGSNDWGVWTSN KGNDTYKGGLTKEEAVNLAKV QRLNATKDTKVVIMQPFAVPVV HVNIRPF | 160 | No significant similarity found. | | | | | No putative conserved domains have been detected | | |
| 262 | 144431 | 144709 | 1043 | MIVSAFYDSRKKKVETIISDTRD GTPANKNGVKAYIDKYCPPEFR MIDGVDSLSINIINAKIEFINETVP IGYSDGDGSNAKMPKEKFITKF | 92 | Hypothetical protein EME08_gp196 [Enterobacteria phage IME08] | YP_00373434 7.1 | 7e-05 (24/66) | | | No putative conserved domains have been detected | | |
| 263 | 144720 | 144890 | 1044 | MIVSVPKSKDGIFSCGLKNHPM VDIMSANVKQHTVEYEIDAPDF FELPEWAVRLDA | 56 | No significant similarity found. | | | | | No putative conserved domains have been detected | | |
| 264 | 144887 | 145087 | 1045 | MKYHIFNTVRLANGIPGVVCDT APAIKAYSVEPWYEVNWVDGN RSIHAESELYPITQLRAANDDVY | 66 | No significant similarity found. | | | | | No putative conserved domains have been detected | | |
| 265 | 145077 | 145286 | 1046 | MSINPHFGHMVARRITREMLKT AEYYNIELIDIEPSDAPGLIWFNF TGAANSVAKFKQALRNFPECQ NQ | 69 | No significant similarity found. | | | | | No putative conserved domains have been detected | | |
| 266 | 145271 | 146113 | 1047 | MSKPVIATDVDGIIVKWQSGLP YFAQKYNLPVEHILDMMTTEKFI KPAELFDCEEDLAVKLLLKYNN SDFIRYLAPYADALATVNKLKEK YDFVAITALGNSVDANLNRRFN LNALFPDAFTEIMVCDYDESKD ALLEKAKVKYGDRIVCYVDDLP KHIAAASKVFEDTETRVFYMPR GEREGSVTAPGIMVEDWHQIVT CLESLESVKKPQKSLSRLWEEA IKDQIRKEQHPFNWPPRQVPG DWWKQPIIPFSPSPHVPPGND WVNNGRITCDNHQINC | 280 | gp30.2 protein [Bacteriophage Ox2] | CAG29240.1 | 5e-62 (132/267) | | | 30.2 hypothetical protein | PHA025 97 | 8,07e -59 |

Fig. 12KKK

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 267 | 146155 | 146361 | 1048 | MFVVHTKVGKRWLSCDYGHVN QFYRWNPIWREAKACPIWNECI NNGFVYIDGLTYHRSVSELSKE LGE | 68 | gp30.1 conserved hypothetical protein [Enterobacteria phage T4] | NP_049814.1 | 2e-08 (34/75) | | DUF3045 | pfam11243 | 3.18e-12 |
| 268 | 146361 | 147833 | 1049 | MIFDIIKAIEDAKGSKAKTQILIDN KDNVDLKRAYLLAYSGRFKFFIK KVPEYTPVKYPNVPSKTFSDGL DYLQDILAARVLTGNMAIQGLV DLLSKMNEGDASVLVRVLLKDM RCGASGSIANKVWKKLIPEMPQ MLASAYSEKALSYIKFPAFAQLK ADGARCFAEIRGDDLDDVTLLT RSGNEYLGLDKLKRQLIEMTKE ARERHPNGVMIDGELVYHVEV KEEENDLFDMFKEPELPELSKA KEFQQTARTESNGLANKAIKGTI SAEEAEGMRFQVWDYVPLDVV YSEGKVPGFAYDVRFRALEMM SKGYDKILIENHVVHNIHEARAI YKTYVDQGLEGIILKNIGAYWED KRSKNLVKFKEVITVDLKCVGS YEHRKQPGKMGGLMFVSECG RIRVNAGSGLKDKPEELHELDR THLWKIRDSLPGTIWELECNGW VTAEGRDDGTVGLFLPIIKQRR YDKEVANTFEAAFGVNFTEATG IK | 490 | gp30 DNA ligase [Enterobacteria phage T4] | NP_049813.1 | 1e-147 (287/503) | DNA ligase | DNA ligase | PHA02587 | 8.32e-169 |
| 269 | 147830 | 148009 | 1050 | MKVLYEVIAKTDDGRGGISVHT EVLDFDNIDVFKNFKENIEEYES VNGLQVWRTATIIN | 59 | No significant similarity found. | | | | No putative conserved domains have been detected |||

Fig. 12LLL.

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 270 | 148062 | 150188 | 1051 | MELLNEVFDEENSKIYPVENVK PKLKVPQVFLIKVPGNNNLMIRL VHGSGQGDAVKNIKMGDKFIQ VYVFSVSEKGNIGALKGGLGQD PIGAINTIFETVNKVVKQIKADAV MFRFNPKKMQGQDKAIQRILAR LITTRTGGRFNLMKDMAYYKGK YAYSIMVHKGKKLEEIEGIPEISD ELYTKVESKVGEIYVSKETGES VTKAEALANSIGEKEDKKSELA VMSKMKVSRKDLIRAQYGKFVS YVDEDWPENKRERWYELTTNT PVLNAEGDTVDLQKDIKAGLEK SIPFYVDDIKHYRVRGGYGSNF GDAVERLFVGQMISRMHDDWK VFIPSGSDKMKIAEQRISDVADV IAQAKNPASMETMRKIVEVATR GFDMPPADDFGALRQYQNLVN YMISAYVSIVGDSISKAIEYNRE MQSRLSEEERDAIHHYCGSGY SFVNNYLIGMESLGDPIIDKKIRP LDSAFEKGLRLEPGTLLYRGQR GKYEDFKDNIESKMFYFQNYVS TSLSPIIFGAYSNAGDSLMPDAP SSDLENKETTANAVSSVIGTDN LERVDRGEEVAYGDEFKFGFVI HGADKVKVVIPGVLSSFSDEAE VILPRGLAMKVNKVWVWGTPFRN GVGVANNKTFMVEMTVVPPEQ IDESVHLYDGDILMEQGKVEPL EESKFKGFLMEIYFSPDRSTDK VSYTRTMELLAGAINLDGIPEKL A | 708 | Alt RNA polymerase ADP-ribosylase [Enterobacteria phage JS10] | YP_00292254 2.1 | 4e-115 (261/745) | RNA polymerase ADP-ribosylase | alt, ADP-ribosyl-transferase | PHA025 66 | 1,89e -145 |
| 271 | 150252 | 150530 | 1052 | MKHVFRFNGIEWSADVKDAEK FNEEVLIMLEGFNEGTPTVLIQD IFRKPTEPSFVEAVLNGKAEGII PVKVVWTTKEMKLLRTEPGFIG CIA | 92 | No significant similarity found. | | | | No putative conserved domains have been detected | | |

Fig. 12MMM

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 272 | 151478 | 150552 | 1053 | MFTLEEFKSQAADIDFQRTNMF SVVFATVPSSKTQALLNDFGGE LYNNMGLDGNWLGLTPGEFNQ GITTIVTQGTRQVVRKSGVNTF MIGAMTQRVVQSLLGEFTVGTY LLDFFNMAFPTAGLMVYSAKIP ENRLSYEMDKFHNAPNIKITGR DMEPLVLSFRMDPEASNYRAM QDWVNAVEDPVTGLRGLPQDV ECDIQVNLHARNGLPHTVCLFS GAMPVACGAPEFTYDGENTIAV FDVTFAYRSMQTGSVGKQAAM DWLEDKTIQKIETINPNQGLSTS ASRLSRLGGAGGGISNITTSTS RII | 308 | gp54 baseplate tail tube initiator [Enterobacteria phage JS98] | YP_00159532 0.1 | 1e-117 (190/303) | baseplate tail tube initiator | 54,baseplate subunit | PHA026 05 | 4,28e -126 |
| 273 | 152530 | 151478 | 1054 | MIFEELADGLENIKKSGTRISQG KSKLTNAPTTKVAQFPAERSAG NDSAQDMRVHDLYRNGLLFTA YDFKGRTTPDLRSFRRDVMLS SVFDSPMSALANSSSSTTSTAP VANILLPRSKSDVDSVSHKFND VGDSLVTRGSGTATGVLSNVA STAVFGSIESLTQGLMADNGEQ IYNTARSMYAGPDNRTKVFTW DLTPRSADDLIQIIRYEIFNYYSY GVTGNSSYAKEVKAAIDEWYK GTLKSAAPDGAKVENTVFEQIT SFLSNVIVVSNPTIWTVRNFGYS TSMDGREDIFGPCQIQSIRFDK TPNGHFNGLAIAPNLPSTFTLEI TMREILTLNRGNVYIGGIE | 350 | gp48 baseplate tail tube cap [Enterobacteria phage JS98] | YP_00159531 9.1 | 2e-126 (225/363) | baseplate tail tube cap | Baseplate subunit | PHA026 13 | 2,88e -137 |

Fig. 12NNN

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 274 | 154273 | 152540 | 1055 | MTKKSEMNSMRRRVIADSAPQ KKAESQADAQINTLEDIGRRLD DQQASTDLISDVIETKSNEIIKSV EDVSAGVELTAEASERTTDAVS KLNDTASLINDKLTKLADLLSKK HDVQQDVQKTGTGTSLETITEQ VPDAPVQQPLEELLERLIPPQD DRRPDADFFPNTEEQEERKEP NKETEDKNKKFLGLKFGELIKSV KSGFGKTISLTDKISSMLFSYTV SALAQMAKTAAMVLGVIMLIDLI KVHFNYWTKLFEKNFVEFNKQ AKEWGPLLTAISEMSNEIVKSFV KGDWGGLAKAIGSGLVDVIDKL GETIMLGMSKLLAGMLRALGFN DSADNIEGAALDRFQTVTGAEL DEEDAKMRAKYVDRQEREYDE QPEWKRKLSAKFQKFTGQIDD DEYNKLLSGEKKQSAYADLPED ERLKIITARNNAEAELKRTKAYV EKTDASDSTRLDSAKDAVQSTT TRYKELEKLSPEVAKDLKVELD QLQKLLDSKISEPAPTAEAIPAT EQPEVKQSASIKAADSREAAR TRESNTQSQPIQVNTAVNKNST YVYRTPPQTSTAAPGMQGAMK TS | 577 | gp29 baseplate hub subunit, tail length determinator [Enterobacteria phage RB69] | NP_861896.1 | 2e-77 (225/613) | baseplate hub subunit, tail length determinator | BAR_Vps5p | cd07627 | 8.94e-03 |
| 275 | 154797 | 154270 | 1056 | MNLNVILPIKKIVINEKTISIPKLG LKHHNLMKDVKGPDENMNLL DSICPGLTAAESDIVVLHLLAFN NRIKETVVKDDFTYDLNKYYICQ RLTQRLDGKEFKFRAPPRYSKL GSVDSILSEFLESVDGKPMDINF MKLPAFVTKWADDLVNTIAIDG PEGPIKGMLNVMEIFE | 175 | Base plate distal hub subunit [Enterobacteria phage RB32] | YP_803131.1 | 2e-48 (93/177) | base plate distal hub subunit | Phage_hub_GP28 | pfam11110 | 3.47e-53 |

Fig. 12000

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 276 | 155911 | 154769 | 1057 | MTAQRLGYPNISIKLYSGYDAW LANRFVELAATFITLTMRDSLRG TNEGLLQFYDSKNMHTRMNGD ELVQISVANSNTSRTQTRIYGIK HFTVGVDDKGDSIITLQLGTLHD IMNLKFSRAFFSSAYETIKEMIG AMYVDQPLIAPPINGINAYVPRV PWTSTLKDYLRYVRNVGISTDN DQFIFAWEDITGINMMDYESMIS QNPNVFMFGAPQTIGQFAAGL KYPLAWDFEWLVKSNRYNRNP MKNATFYAHSFVDKDVTRIING EGQNSVFINRSGGYSDMIFRNG YEEALRISTMAQYDGYAQTKCY GNFELTPGMKINFVDLKDQFRT DFYYDEVIHEISNNTSITNLYMF TNGSALEPVDLIKVKNELKRDS SY | 380 | gp27 baseplate hub subunit [Enterobacteria phage IME08] | YP_003734332.1 | 1e-145 (236/377) | baseplate hub subunit | baseplate hub subunit | PHA02612 | 1,76e-159 |
| 277 | 156666 | 155908 | 1058 | MANIVRCELPDGVQRFKPFTVE DYRDLLLVRNDMNTKSEEEQK QLIAELMDDYFHDHPAEYRPYIF LKVFLSSIGKTKIPVRMKCPKCG KYKQYLFNLNQPPLVNPKVEVA GLTLKFKKPIEIIDDTGKMILDNII SVKDSSGEYAWNELSDSNKLT VIDAIDVETLEKILSQMKPFNFEL KTSCCDTTTILKYDNIVDIFKLLL HPDEIFTFYQINHRLVSQGKYDL NSIMKMLPIERGITLSLIEKDLKS | 252 | gp51 baseplate hub assembly catalyst [Enterobacteria phage JS10] | YP_002922535.1 | 3e-81 (145/251) | baseplate hub assembly catalyst | Baseplate hub assembly protein | PHA02611 | 7,69e-87 |
| 278 | 156718 | 157347 | 1059 | MNITYKFETRINGKNIQCRAFTL EEYANLIAAKKNGTIDECIKALLR ECTNATELNKQESELLIVILWAH SIGEVNHEYTWNCTCGRKIPVP LNYTHAQIDPPEDLWYDLKGFK IKFKYPSLFDDSDIPMMISKCIDY IVVGNEQIYFNDLNDAEIDDLYS AITTEDVVNIKNIMLLKPQVQLAV PITCECGISIHIVIKGLKEFFKIM S | 209 | gp26 baseplate hub subunit [Enterobacteria phage JS10] | YP_002922534.1 | 4e-54 (103/207) | baseplate hub subunit | T4_baseplate | pfam12322 | 5,28e-51 |

Fig. 12PPP

| orf | Start position | Stop position | SEQ ID NO.: | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| 279 | 157344 | 157754 | 1060 | MSNIDKLYSDLDPEMRLAWDT DVSKTVGARSVKNSLLGIITTRK GSRPFDPAFGCDITNELFENMT PLTGDTIKRNIVSAVRNYEPRIN RLSVDVLPLYDDNAIIVTVQFSIV DDPDTLERIRIQMRSNANSSSR V | 136 | gp25 baseplate wedge subunit [Enterobacteria phage JS98] | YP_001595313.1 | 2e-52 (98/128) | baseplate wedge subunit | Baseplate wedge subunit | PHA00415 | 3,87e -46 |
| 280 | 157796 | 158212 | 1061 | MRLEELQDELDNDLIIDQTKLQY EAANNPVLYGKWVRKHSTCRK EMLRLDALKKQNLKARLDYYTG RGEVGGEVCMDVYEKSEMKTV LSADKEILGVDTKLQYWGILLEF CSDAMDAIKSRGFSIKHIIDLRQ FEAGA | 138 | UvsY recombination, repair and ssDNA binding protein [Enterobacteria phage T4] | NP_049799.2 | 6e-51 (99/137) | recombination, repair and ssDNA binding protein | UvsY | pfam11056 | 4,75e -42 |
| 281 | 158243 | 158410 | 1062 | MSNTVCVVCKGPIDEALVVQTD KGPVHPGACYNYAIELPVTEDT EEQLQETQLLI | 55 | UvsY.-2 conserved hypothetical protein [Enterobacteria phage T4] | NP_049797.1 | 1e-16 (41/55) | | uvsY.-2, hypothetical protein | PHA02610 | 3,92e -10 |
| 282 | 158712 | 158470 | 1063 | MIKFEDIYEATIREATIDNFMSKI NACQTLDGLKELEKYYDKRSKE TTLADSDDIIVRDALAGRRQALE ADSEDDEDEF | 80 | UvsW RNA-DNA and DNA-DNA helicase, ATPase [Enterobacteria phage T4] | NP_049796.1 | 2e-15 (44/73) | RNA-DNA and DNA-DNA helicase, ATPase | uvsW.1 | PHA02609 | 7,25e -18 |

Fig. 12QQQ

| orf | Start position | Stop position | SEQ ID NO.: | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| 283 | 160211 | 158709 | 1064 | VHDIQVKFKDFSHVHIECDDSIF YELRDYFSFEADGYRFNPKYRY GHWDGRIRLLDYNRLLPFGLVG QIRKFADQFGYKVYFDPAIFEQ ETLSREDFDNWLSTKEIYSGLT KIEPHWYQKDAVYEGLVNRRRI LNLPTSAGKSLIQALLARYYVEN YEGKVLIIVPTTALVDQMIDDFC DYRLFPRNAMLGIRGGTARDS NALVYVSTWQTAVKQPKEWFS QFGMMMNDECHLATGKSISTII AGLTNCMFKYGLSGSLKDGKA NIMQYVGMFGEIFRPVSTSKLM EDGQVTELKINTIFLRYPDAAAN ALKGKTYQEEIKFITNVKKRNR WIANLATKLAARDENAFVMFKH VAHGKELFEMIKAAGHEHVYYV SGEVNTETRNALKAMAENGKGI IIVASYGVFSTGISVKNLHHVILA HPVKSKIIVLQTIGRVLRKHKDK SLATVWDIIDDLGVKPKSANAK KKYTHLNVCLKHALERIQRYAD EKFNYVMKTVNL | 500 | UvsW RNA-DNA and DNA-DNA helicase, ATPase [Enterobacteria phage JS10] | YP_002922529.1 | 0,0 (392/497) | RNA-DNA and DNA-DNA helicase, ATPase | UvsW helicase | PHA02558 | 0,0 |
| 284 | 160269 | 161063 | 1065 | MLDKDYIKEIQALDKKEAKDKLD EYAQTFGIKLKKTRSFDNMVAD LEKELAKLANEPMPEDNDGLSI ADLIQADDEIEGKAVFKDEASD EAKLLFDAPVNVGIKIHDIDPGF YKETPKVNDPGFEVKTPSINDK GFYAEAPIGDSVIHIDDEGQVTN IPVSITDPEEFSKAMDKVVKIIKT DEIIELPENFSPNMQLLGKNPG YITLPWWIYQWKDNPDWKSRP TSFEHPSAHQTLFSLIYYIKRNG SVMIRETRNSSFVTLK | 264 | Minor capsid protein inhibitor of 21 protease [Enterobacteria phage RB51] | YP_0028541 36.1 | 2e-64 (144/265) | minor capsid protein | No putative conserved domains have been detected | | |

Fig. 12RRR

| orf | Start position | Stop position | SEQ ID NO.: | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 285 | 161073 | 162482 | 1066 | MAYSVSIAPLAASAVIGATTNFT ATTSGAAAEGTETFWTVNGV KQSSVTAAMNYTAGPAGSKT VKVVATVTPAEGEVETAEAETT LTVKNKTMPAITLTLSPTSVSKEI GQSQVVTADVTGAPSGASIAYV WKRGSSVISGQTGKTITLTEST ETSYTLNCEVTVSAPDYNNGTA TKGIAVAFTKKTMSGVSVTLSP TSVSKEIGQSQVVTANVVGAPE GASIAYVWKRGTVVIEGQTAKTI TITESAEANYTLNCEATVSAPDY NPVTVSKGASVTITKKTMSGVS VTLTPESITVEQGSDASFKADVI GSPEGASGTYSWTKDGSPVEG STSTLVIDTSDIGSQVIGVSVEV SAEDYNSVTVTTTGNVTITKRV APTPNGELPYIHPLPFRETAYIW CGWWVMDEIQRMTVEGKDWK LDDPDSDYYLLHRYTLAKMLDDY PEVDVQESRNGYIVHRTALEAG IIYP | 469 | Hoc head outer capsid protein [Enterobacteria phage JS10] | YP_002922527.1 | 1e-164 (295/468) | outer capsid protein | No putative conserved domains have been detected |||
| 286 | 162561 | 162788 | 1067 | MKAIQAHLMHESGKDFQEIARA LDITPAEAAKLWVSVEKAHERF KQKEKVVYRKRLTNVGIKSRHK KLVKHMRTL | 75 | DNA primase-helicase subunit [Klebsiella phage KPP95] | ABH10667.1 | 8e-35 | DNA primase-helicase subunit | DUF2774 | pfam11242 | 6,15e-16 |
| 287 | 162785 | 163111 | 1068 | MMSKVDPIVVERFEEMLSKKFT PAANGVNVWLFASKFVSKMMA VQSSYYYKSGARKITDLINERY GKIDWMLMDKDIPLVLEVGSKS QFEIMLTKSGYIMYRFVPSGY | 108 | No significant similarity found. | | | | No putative conserved domains have been detected |||
| 288 | 163226 | 163483 | 1069 | MNLADRMANTAINVATEELSAA KEEVLTQIEKTALAGKRELIMYP SSLVKKHITNVLNYLHDEGFVT NYTSAQRNGDTDFMKITF | 85 | No significant similarity found. | | | | No putative conserved domains have been detected |||

Fig. 12SSS

| orf | Start position | Stop position | SEQ ID NO.: | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| 289 | 163494 | 164501 | 1070 | MFAKYSSLENHYNNKFIEKIRG AGFDMHTVEWVAREKIHGTNF SVIITPTEIVPAKRTGPILEGESF FGHEIIMKKYKDSFVKMQNMLN TMDLVSVQIFGEFAGGGIQKGV DYGDKDFYVFDILSDSGNEKVY WDDYVVESFATGLGLKLAPLLG RGSFAELSQYVNDFKSIVNYYN ELVDTTDLEHANKHVFGPQASS ETGVAEGYVLKPVNPKFFNNGT RVAIKCKNSKFSEKAKSDKPIKA KVELTDTDKRVLEIFSEYVTWN RVSNVLSHIGTVTAKDFGRVMG LTMKDIINEAAREGHDMLFADN PSAVKKELTTLIQNTIRSKWHEV LE | 335 | RNA ligase [Enterobacteria phage RB14] | YP_002854510.1 | 1e-104 (195/336) | RNA ligase | RNA_lig_RN L2 | TIGR02307 | 1,30e-77 |
| 290 | 164501 | 165049 | 1071 | MRLALIGSREAPRRVLSLMTIIG QRLSEEGHFSYSGGAPGSDEA WLAKYDRSNSCRIIPYSGFCGH VPDTGVVVWSELSNEAKIKSIIK AREVTSYWDECSKIVQTLFARN SMQVLGLECTEPVDKVLYWAP EKRCGSVSGGTRVAVDIARRH GIECVNLYDKNVFKSLEEEYSP RFDIFSL | 182 | Hypothetical protein KP-KP15p208 [Klebsiella phage KP15] | YP_003580084.1 | 5e-25 (64/116) | | No putative conserved domains have been detected | | |
| 291 | 166359 | 165079 | 1072 | MAKINELLRESTTTSSNLIGRPN LVALTRATTKLIYTDLVATQRTK QPVAALYGIKYLNPNGDLTFNT GATYAGQIGAPERESIEELTMA NKDSFNKDDMFKYQNVVFKVL KDSPFTDTAETDEFGIVSEAVA ANNIRMLSDAAVTEKFEGPDSD PITEASFKIDKWQTQVKSRKLKT DLTVELAQDLEANGFDAPELID DLLATEMAEDINKDILQSLITVSS RFKVAGVSDKGVLDLTKQDSA PEQGRTLYRFICEMNSAVQRNT SYSGTYAVASTRCAAVLAASG WLTQKNDGSIPENAYGMLNNG LPLYCDTNSPVDYVIVGVKAEF GGKETVGSLFYAPYTEGLDLDD PEHVGAFKVIVDPASLQPSVAL LVRYALSVNPYTVGLDEDEARV | 426 | gp24 precursor of head vertex subunit [Enterobacteria phage RB51] | YP_002854131.1 | 2e-163 (293/428) | precursor of head vertex subunit | Capsid vertex protein | PHA02548 | 1,38e-178 |

Fig. 12TTT

| orf | Start positi on | Stop positi on | SEQ ID NO.: | Aminoacidic sequence | Size (aa) | Homologous/similar proteins ||| Predicted function | Conserved Domains |||
| --- | --- | --- | --- | --- | --- | --- | --- | --- | --- | --- | --- | --- |
| | | | | | | Name[organism] | Acc No | E value and identity | | Name | Acc No | E value |
| | | | | INAADMDKMAGRSKMSVLLGV KLPKLIAD | | | | | | | | |
| 292 | 16667 7 | 16644 1 | 1073 | MDAGIYYAPYVALTPLRGSDPK NFQPVMGFKTRYGIGINPFADS AAQQPKGRITSGMPSIVNSVGK NAYFRRVWVKGI | 78 | gp23 precursor of major head subunit [Enterobacteria phage RB51] | YP_00285413 0.1 | 6e-35 (70/78) | precursor of major head subunit | Major capsid protein | PHA025 41 | 7,51e -38 |

Fig. 12UUU

Fig. 13B

| orf | Putative function |
|---|---|
| 183 | tail lysin |
| 185 | glycerophosphoryl diester phosphodiesterase |
| 188 | baseplate protein |
| 197 | helicase |
| 198 | transcription regulator protein |
| 199 | helicase |
| 200 | exonuclease |
| 202 | exonuclease |
| 204 | DNA primase |
| 208 | ribonucleotide reductase protein |
| 209 | ribonucleotide reductase large subunit |
| 210 | ribonucleotide reductase minor subunit |
| 212 | thioredoxin-like protein |
| 214 | DNA binding / bending protein |
| 215 | DNA polymerase |
| 219 | DNA repair protein |
| 221 | sigma factor |

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name [organism] | Acc No | E value and identity | | Name | Acc No | E value |
| 1b | 2 | 310 | 1075 | FVQIPIFSLIPILRYKLEEQ GIGLIETEESYTSKTSFIDN EKPIKHNVYKGKRVKRGL FKTEEGRILNADVNGAFQI MKKVFPDVEIPRDNGFVY NPFLINC | 102 | IS element Dka2 orfB [Hyperthermophilic Archaeal Virus 2] | YP_003773391.1 | 5e-18 (109/405) | Transposase | orfB_IS605, probable transposase | pfam01385 | 2,87e-36 |
| 2 | 475 | 1107 | 1076 | MAKKNVNDVLQQESVTV ADKYLQVKVNRDGYTRT HEGQYAYKVVSEGEELFL YPVQTDGKGTLNVMKKS PIAYTDGDNIHFVVNTVV DPYNHSFIRTEDIKGLDKG KQLIQAFLAFVEDRFKFG VYNVFVANSKEDVLSIVD PTDNDADEVKDSLEHAHE DVIADFPASPARKDVKGV DSGEGQGDTSEPSAPKNV QVTPKEDGADVSAE | 210 | hypothetical protein KgORF95 [Staphylococcus phage K] | YP_024523.1 | 6e-177 (209/210) | | PHA02283, hypothetical protein | PHA02283 | 4,55e-71 |
| 3 | 1121 | 1642 | 1077 | MVNLAKLNLYKGNELLN SVEKTEGKSTITIENLDAN TDYPKGTFKVSFSNDSGE SEKVDVPQFKTKAIKVISV TLDVDSLDLTVGDTHQLS TTITPSEASNKNVSFESDK SGVASVTSEGLIEAVSAGT ANVTVTTEDGSHTDIVAV TVKEPIPEAPADVTVEPGE NSADITA | 173 | putative major tail protein [Staphylococcus phage K] | YP_024524.1 | 1e-88 (168/169) | Major tail protein | Big_2, bacterial Ig-like domain (group 2) | pfam02368 | 2,14e-04 |
| 4 | 1657 | 1884 | 1078 | MEKTLKVYSNGEVVGSQ VANNDGATTVSITGLEAG KTYAKGAFKVAFANDSG ESEKVDVPEFTTKTPTEEP | 75 | ORF189 [Staphylococcus phage G1] | YP_240967.1 | 3e-33 (73/75) | | No putative conserved domains have been detected | | |

FIG. 14A

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | SGEA | | | | | | | | |
| 5 | 1979 | 2239 | 1079 | MDIPTLFRNPYDYTKVK KLMENKEQYIVVKFDSVS VHNLNVQGMMNVIQDYL HIYGYRVKEYGQENASK DDERDVKGYLYERVGE | 86 | ORF174 [Staphylococcus phage G1] | YP_240968.1 | 5e-42(86/86) | | No putative conserved domains have been detected | | |
| 6 | 2243 | 2998 | 1080 | MGHVNSNHIQSDTLYEYD SFFDIEKVDTFEEGLLSIQ DEPTVLAGFIYDDITFNKV INSNSDIDDYIKNNDIYYV SDICLLPDTFITVDSDKKY YSLLQQVVELSKDPFPKW VEDDAKGLTKYNFQDF EDVFDLNSFYKKEVDMV REKCYNNGNVYLLYEVL PDYKLPLAYSLLSNKEHGI VIIGSQTRSNNDILTFYVK GMDAKAIASMFNVEHDY DSNIFHTFVNSHINILGNQI TKFIREKGSSYE | 251 | hypothetical protein KgORF97 [Staphylococcus phage K] | YP_024525.1 | 2e-140 (248/251) | | PHA02284, hypothetical protein | PHA02 284 | 5,61e-42 |
| 7 | 2991 | 4241 | 1081 | MSNYKTIEEVQAVIIGVLF KDEGKIVTSKFNKITKEFG LDRIGKDDLKEIVEDIRQD AYLNELKNKAIKGKVTLG DLKDVADNQVFEGNNYH EEVSTYVVAKEKELSHLR EQRKHNRHTAYPQIMFDE LKEHMVKELQGETLVEH HGSKANINDTELIVLLSDF HIGSIVSDMTNGKYDFEV LKARLNHFNTTVKEIEDR EISNVTVYFVGDLVEHIN | 416 | hypothetical protein KgORF98 [Staphylococcus phage K] | YP_024526.1 | 0,0 (415/416) | | No putative conserved domains have been detected | | |

FIG. 14B

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | MRDVNQAFETEFTLAEQI SKGTRLLIDILNVLSNVVS GELRFGIIGGNHDRMQGN KNQKIYNDNIAYVVLDSL LLFQEQGLLNGVDIIDNRE DIYTIRDTFGGKSIIINHGD GLKGKGNHINKFILDSHID LLITGHVHHFSVKQEDFN RMHIVASSPMGYNNYAK ELHLSKTKPSQQLLFVNK ENKDIDIKTVFLD | | | | | | | |
| 8 | 4255 | 4623 | 1082 | MDTFIIGVAFITFATFNIV FRLFDLWTTEKKMVSQG QPPLSNFEYYHVIVPYLV GVIVITLSIIFRDSLYSAQS GFGIITSFIYMLVYVIIGL VGSFILTIFQARKARQYQT QEDNNEVQ | 122 | hypothetical membrane protein MbpG [Staphylococcus phage A5W] | ACB89126.1 | 5e-62 (119/122) | Membrane protein MbpG | No putative conserved domains have been detected | | |
| 9 | 4610 | 4921 | 1083 | MKFNDIYEQLIKNDTVQN IHESQDDKGNIYTIQFDKG NDKYLFNVTNDGFLKEMT NGMVDHPEGQPYSVSLIN KETPSMSVKQYLTDVEDI VPTTIRKMEKDFL | 103 | hypothetical protein KgORF100 [Staphylococcus phage K] | YP_024528.1 | 5e-53 (103/103) | | No putative conserved domains have been detected | | |
| 10 | 4985 | 5521 | 1084 | MDFNFSAFDNSSLAMRIS EGVYFNDTPYYFIEHVE EEMSEYVIVYDIHDREEK ENPQKKYRIEPYQRTIPGG TPLSNLIKSMPQRKYPK KVTEDPIFVANVIPLGTDT VTGKTGKGFFERDKDRTI YSQKEPTKVVHGQYTGV | 178 | ORF075 [Staphylococcus phage G1] | YP_240973.1 | 1e-99 (178/178) | | No putative conserved domains have been detected | | |

FIG. 14C

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | FIGLTSVKWNRTYTPLES VVEYYKRVKGDRLNV | | | | | | | | |
| 11 | 5514 | 6281 | 1085 | MSNDVVKFYEKDIKDLIR TKKHMFKDDEITSDINDIR IFNEKVICQGKCRTDCLVL DRNGTVMGIEIKTERDST QRLNNQLKYYSLVCKYV YVMCHDKHVPKVEQILK RYKHNHVGIMSYISFKGK PVVGKYKDATPSPHRSPY HTMNILWKTNLMTILRLI RDPHTYRTGYSYNASGRY SGGEGNFSQTTQSKRMKK PAIINQIIHYVGVDNTYKL FTRGVIYGYNNRWEVIEE DFFNTMKNGVRVINEQRQ TK | 255 | hypothetical protein KgORF101 [Staphylococcus phage K] | YP_024529.1 | 6E-149 (255/255) | | No putative conserved domains have been detected | | |
| 12 | 6259 | 6705 | 1086 | MSKDKPNRRKEIQHQPVN FAPMNTLTGANNSFFAKK PSEPKDATSVIEYRILFIKR FDNVTSTDVKLQKKYAL NLISEALDVKETYLSLKQ KGKKTESILHTDRVYYVH RGKKLIGKCSIREQRTFKG KHLIFIFKTRHRVKAERKD K | 148 | hypothetical protein KgORF102 [Staphylococcus phage K] | YP_024530.1 | 3e-80 (147/148) | | No putative conserved domains have been detected | | |
| 13 | 6705 | 7568 | 1087 | MLKGFSEHVDKPTTTKTL YKTLTSGKVELLGVSYDS DYFPSGVTVQSYIEDIGNE DEGLQFVNKINVVESMKQ AVVGMNNQLGSSGLGYV RTEQLKKELEETGLMTDL | 287 | ORF036 [Staphylococcus phage G1] | YP_240976.1 | 1e-159 (283/287) | | sepiapter_re d, sepiapterin reductase | TIGR01 500 | 8,02e-03 |

FIG. 14D

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | LARGTNLTSTKKVDIVSTF IEPEVTYQDTTIAKDIKLRL YKLEEESPLNGYTHIVYLL TTEKLYDGQTLFGMLSKK DKLSKGDTDKLLAFFRNN SLISKSVFCVKLLSKDYYF NLYNTHETGIFFLEDTDVI TIACGQSYVKVNTKDIKS SYVKIEDKTHKLTELVINL KGDDTLTLF | | | | | | | | |
| 14 | 7940 | 8671 | 1088 | MARKKNLRNKNSDIKVV PDKEKESILSKLYHNKLLR SKVDNALDEDMSYDDIIE LCKEYDLELSKSATRYKS KRKEAIENGWDLEELIDK RKKTSVKDIKEKETPILEE EQLSPFEQSKHHTQTIYDD IQVLDMIISKGAKGLEFVE TLDPALMIRAMETKDKIT GNQLKGMSFIGLRELQLK QTAQDTAMSEVLLEFIPEE KHEEVLQRLEELQNEFYK NLDLDEESRKLKEALDRV GYTI | 243 | hypothetical protein KgORF103 [Staphylococcus phage K] | YP_024531.1 | 6e-135 (242/243) | | No putative conserved domains have been detected | | |
| 15 | 8689 | 9147 | 1089 | MADEISLNPIQDAKPIDDI VEIMTYLKDGRVLRVKQ DNQGDILVRMSPGKHKFT EVSRDLDKESFYYKRHW VLYNVSVNSLITFDVVYLD EEYSETTKVKYPKDTIVE YTREDQEKDVAMIKEILT DNNGNYFYALTGETMLF | 152 | ORF094 [Staphylococcus phage G1] | YP_240978.1 | 7e-81 (148/152) | | No putative conserved domains have been detected | | |

FIG. 14E

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| | | | | DENKLNKVKD | | | | | | | | |
| 16 | 9212 | 9655 | 1090 | MFISLNQEEKELLTKEESK YTPLETSREFNTPKEEFIV TSYNEGKPLDYIAKEAKV SMGLIYTVLNYYKVGKR NKKSPVEERIAHLKDKNL VKEIIKDYQYMNLQDIYS KYNLHKNGLYYILDLYH VERKSELKDKALEEDNIV VE | 147 | hypothetical protein KgORF105 [Staphylococcus phage K] | YP_024533.1 | 3e-77 (147/147) | | No putative conserved domains have been detected | | |
| 17 | 9672 | 10376 | 1091 | MRNKKSFQEQLNDMRNK EKWVSEEEFTEEVAPSEEP EVEEEKLYTLNELKENLL DAQGLKDVVADFPASKD LYEPNKLYICTIPKGYQST EVQPGQYIGISTGLLSESE DFSHLRGQMPRNLYETSH VLKPLVRINNTSIFYQQHE LLEDIKEDKNVYDVELED LRLATGEEISYLEIVDSKF FESRINEVLDFYHELTDSD DLLEYYNKLRELVGNDR MIYCPLLNKCVKIID | 234 | hypothetical protein KgORF106 [Staphylococcus phage K] | YP_024534.1 | 2e-113 (215/234) | | PHA02290, hypothetical protein | PHA02290 | 2.24e-29 |
| 18 | 10522 | 10836 | 1092 | MYHDKAKNEVSTELSNT GKIKEEKNVEFVGDYTLK KVEDNKAYFMETLPTYLP GRTGDNSIDMRYYKTSRF KEGVNFKLIRVYTEDGED NPIHKYRFEAVPTKK | 104 | hypothetical protein KgORF107 [Staphylococcus phage K] | YP_024535.1 | 2e-54 (104/104) | | PHA02291, hypothetical protein | PHA02291 | 2.86e-15 |
| 19 | 10983 | 11225 | 1093 | MEMADLERFDAFVRLISD DELSEERILELSVDLLNPIL | 80 | gp ORF144 [Staphylococcus phage | ACB89137.1 | 6e-37 | | No putative conserved domains | | |

FIG. 14F

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| | | | | EGGTAYRAKKRIKSKFGKLEAKNFKRNYKFLLKSIAQIDQRR | | ASW] | | (79/80) | | have been detected | | |
| 20 | 11230 | 11787 | 1094 | MTEREKLIKEIEANRDIQLQLKEVDNYKDSIRSKGTRNYISTKVLDSITVGFIVSFLILIIMRVLEYFVTGNAVYSPLAPAVIIMFVLALGTWKVSKMNKIVSYRGTIKMYWELSNAEQKQAKVFKYPNDEVDIVSKHNLRQITFSEINILHLKYMRYNKAVEQHTKLSKELFKKDKETVDKNK | 185 | hypothetical protein KgORF108 [Staphylococcus phage K] | YP_024536.1 | 1e-71 (133/135) | | No putative conserved domains have been detected | | |
| 21 | 11823 | 11999 | 1095 | MVIPSIKAQNKFKNELEYYKQGHISESKMLELAFDYIQELEQNNEYVTNLLEEERYGE | 58 | ORF240 [Staphylococcus phage G1] | YP_240984.1 | 1e-24 (58/58) | | No putative conserved domains have been detected | | |
| 22 | 11989 | 12240 | 1096 | MVSKFIGVYLFNLLVVALVYTVGFLFFYGVASLVIILTHATIDPFVLATFLGIGFLVIRTAHRIMARVINDAVAQAIKDKENE | 83 | No significant similarity found. | | | | No putative conserved domains have been detected | | |
| 23 | 12233 | 12466 | 1097 | MNKGEFIMDKTLPKFSVYEVIVKTVIMTPTEGSSDLESFYFSTRELAERFVEENTVETKNGKRVSFAVKERKVNQPG | 77 | No significant similarity found. | | | | No putative conserved domains have been detected | | |
| 24 | 12548 | 13192 | 1098 | MKVSEEVKQSYLENKANTKMDKISWSELKASPLGIT | 214 | hypothetical membrane protein MbpJ | ACB89141.1 | 4e-88 | Membrane | No putative conserved domains | | |

FIG. 14G

Table 11 - Features of phage F125/10 gene products and assignment of putative functions.

| orf | Start position | Stop Position | SEQ ID NO. | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| | | | | LGDIIFYSVVIIDNIIAIILTL TLIGTTTDSIESTLAQIIVGV FIIITYGILSALIPILIHKAV SPGWSYTEWNESYYIRLP GEENYKYYSKWYLDLLG VKEFYYKRDSGEEVKEK NISWAFQAEVKRPEDVNH WKNQLLTNRPLTILEYKK LKKLDKESEIRKQEDLEE YKQYNSN | | [Staphylococcus phage A5W] | | (162/173) | protein MbpJ | have been detected | | |
| 25 | 13207 | 13455 | 1099 | MISSFDSILLVIYIIIAFAVA MAIIYLVFKGMTILLDKL MMLLSKTTLDVEACSMI MAVISTIVFGIIVLLIWLAV NNILL | 82 | No significant similarity found. | | | | No putative conserved domains have been detected | | |
| 26 | 13467 | 13643 | 1100 | MDFNDFINSESDRVGNPK QKKKVENKLPSSPIEDRE KKLKEIRKKSLYIDLRRKR ND | 58 | ORF241 [Staphylococcus phage G1] | YP_240986.1 | 5e-22 (55/58) | | No putative conserved domains have been detected | | |
| 27 | 13636 | 13932 | 1101 | MTKETNVLYKDKYRDYT IVVRLAGNIIVTEVDKKH KTAFTPIIFDNGVEGVELV MRIGSVELSMTDLRFFTK EVSTAQKALEYFNKKLYI KGLTDEAF | 98 | ORF152 [Staphylococcus phage G1] | YP_240987.1 | 1e-48 (97/98) | | No putative conserved domains have been detected | | |
| 28 | 13980 | 14162 | 1102 | MLLGILWFIWGFVSYFVL MFGIEFCKDRWMPGVIGA GALLLFLFWIMKSIHNAM TVVYLY | 60 | hypothetical membrane protein MbpK [Staphylococcus phage A5W] | ACB89144.1 | 3e-24 (59/60) | Membrane protein MbpK | No putative conserved domains have been detected | | |

FIG. 14H

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| 29 | 14175 | 14543 | 1103 | MDILIHYKETNKRVLKET IQTIQNFILNDEHGLVKMT ATKLSRENIEKREFNNYNIV IAEDDPDNSYHYSEAVEE ADFIIDIPISYLDIHAGVEW DVDNPVDMLDRNPDFIEA VNKLNEDLML | 122 | ORF119 [Staphylococcus phage G1] | YP_240989.1 | 1e-62 (119/122) | | No putative conserved domains have been detected | | |
| 30 | 14556 | 14903 | 1104 | MLNEKLKNLEDTKVYMI NSIASLLSASTGKSSKVFF DEGTIKIVSGETKAVEVID NLVHPHSGRLPIKTTERIA LGRLTDSLQFVISEIEVVK DQIIDEENEAYIDFVMED WDWD | 115 | ORF124 [Staphylococcus phage G1] | YP_240990.1 | 5e-59 (114/115) | | No putative conserved domains have been detected | | |
| 31 | 14909 | 15181 | 1105 | MDLLTIASVAFIAVVIIDLI NNDMSYMLTGTAILINIW AGFYGWFFLLQAGMLLF LLLARKVKDDKESILYSS ASLICALGMIINLLSFS | 90 | hypothetical membrane protein MbpI [Staphylococcus phage A5W] | ACB89147.1 | 8e-42 (90/90) | Membrane protein MbpI | No putative conserved domains have been detected | | |
| 32 | 15251 | 15556 | 1106 | MSKETIRRQFSNAIFIMAT TKEWWNFPKSFNTSKEFK IKTFKNDTLVFEVREGSR NLGSFVIFTNIDFDYDKLE GTSTQYMINYFAKKLTKD MFNYHKLQL | 101 | ORF140 [Staphylococcus phage G1] | YP_240992.1 | 8e-51 (98/101) | | No putative conserved domains have been detected | | |
| 33 | 15571 | 15921 | 1107 | MREELKPFNRKQVNVKG YLDDVKYSKRRRHKGNQ HGCVKITVTDVKINGIPID HVNIEVGISFYEKLKELQG KRIQFVGTVYKYVKHAR GRKGRIKGFYKEDYSVTL | 116 | ORF122 [Staphylococcus phage G1] | YP_240993.1 | 2e-59 (116/116) | | No putative conserved domains have been detected | | |

FIG. 141

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| | | | | DKKLQKEEK | | | | | | | | |
| 34 | 15921 | 16523 | 1108 | MIKRRKHLDHSLQPEKG WRTVPFNGYYEAHPTGLI RNKVTKKLIKGTQTRKNH PKWTAHEIVYLINPKKTS YSRGVVIAHTFPEMISQSR GDLKNGHVCFKDGDRSN CHVDNMFIGKGNVNKNI YKLNDSYLTRKDIEEDVN NLVNERLFSQLELLIKKNE PERITPSNHFIKRDNNVFSI TDLSKNSLVEFELEIKNIK | 200 | ORF065 [Staphylococcus phage G1] | YP_240994.1 | 2e-113 (200/200) | | No putative conserved domains have been detected | | |
| 35 | 16537 | 16716 | 1109 | MNEWYALCYYDKVGKK KIPRQIKAHRDVSVLEDL KDRLEEQNPKEEYKIKTT KEFDKER | 59 | ORF237 [Staphylococcus phage G1] | YP_240995.1 | 2e-25 (57/59) | | | | |
| 36a | 16943 | 17218 | 1110 | MKLEDKVLERIDSLGNKA GNLSNQAMESLVKYQITY GHDIVVSILVIALTIFLGKV YLKEYKKVKMDLKESLL YDDYDILSLRNSCRYTN | 91 | hypothetical membrane protein MbpM [Staphylococcus phage A5W] | ACB89152.1 | 1e-35 (81/87) | Membrane protein MbpM | No putative conserved domains have been detected | | |
| 36b | 17223 | 17291 | 1111 | MRLINPEVYAVKDLIEQV KGGN | 22 | | | 2e-12 (22/22) | | No putative conserved domains have been detected | | |
| 37 | 17293 | 17586 | 1112 | MKQRDFEFEEDFVLTYEC EDCKHFEDWGHDEEPEEC SECGSSDLINNTSHEDTEC DMCRGYIDMWQDGYRY MGDNKEYIEKEESGLICE DCYEKLDI | 97 | gp ORF160 [Staphylococcus phage A5W] | ACB89153.1 | 2e-48 (97/97) | | No putative conserved domains have been detected | | |

FIG. 14J

Table 11 - Features of phage F125/10 gene products and assignment of putative functions.

| orf | Start position | Stop Position | SEQ ID NO. | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| 38 | 17603 | 17890 | 1113 | MNKAVEQASNALGQGFS AMVWHQVLAGLGFILLG LVLSLLVWVLVKKFHVPF NHPTAFVVYSIMLVSIVAS FIWGGLHVINPEYYAILEL KGFIK | 95 | hypothetical membrane protein MbpL [Staphylococcus phage A5W] | ACB89154.1 | 2e-45 (94/95) | Membrane protein MbpL | No putative conserved domains have been detected | | |
| 39 | 17901 | 18017 | 1114 | MTKEELEQKVKELEAEN KELKKQIERFEDEGGKTK DEQ | 38 | ORF362 [Staphylococcus phage G1] | YP_241000.1 | 1e-10 (38/38) | | No putative conserved domains have been detected | | |
| 40 | 18007 | 18273 | 1115 | MNSRQKKILTLTVSNFLIL ALDTVALIRYKKGKIKQE NYNTGQITRMIATTANSL GILYLEEQERKEVKDIKV GTEIGALKRFTNNK | 88 | ORF170 [Staphylococcus phage G1] | YP_241001.1 | 3e-31 (68/86) | | No putative conserved domains have been detected | | |
| 41 | 18351 | 18656 | 1116 | MKGIIIFYKEETKEDLGYF LGFINFKLEGLSYTTEGTL VDNDVVVLKDNQNEDN LEQFSMSNNNLVIGILGHS SLSVRIYEKGIRQEFDRVE EYLEELRQ | 101 | No significant similarity found. | | | | No putative conserved domains have been detected | | |
| 42 | 18656 | 19057 | 1117 | MIFILIFGLLFILSLLGIFIYF IVLRKKKQLIEERESFGIY NRTKEKLGDVTRLGYEED VYKLIHNQSNKTIIEDKKS KVVDTIKKMYELELTSVD VSKVEGLSPLDTEPMTNM KLLSYKLDREGLYSLSKFI | 133 | No significant similarity found. | | | | No putative conserved domains have been detected | | |
| 43 | 19068 | 19304 | 1118 | MEFIDKNNVIKAYDIPNV YLKGYVLQACDKNGDTT AYDGYDQIIHYKEGRVLTF | 78 | No significant similarity found. | | | | No putative conserved domains have been detected | | |

FIG. 14K

Table 11 - Features of phage F125/10 gene products and assignment of putative functions.

| orf | Start position | Stop Position | SEQ ID NO. | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| | | | | PFDKPLRKINVLSGYYKLF KKEDII | | | | | | | | |
| 44 | 19301 | 19828 | 1119 | MIYFVSDLHFGHDNIREFE APTRSHWNSVEEMNEGLI ELWNNTITNNDIVYNIGD FFFNMKPSKVEDILNRLN YKEMILIAGNHDHKKLIK LYERNGITVKYADMIKKD GKRFVLSHYPTLIGRKNM FNHIGHIHSQLMGTEYHIN VGYDVEGKIAYSFDDIISR AGEYNGEIQR | 175 | phage protein [Staphylococcus aureus subsp. aureus TW20] | CBI49957.1 | 2e-66 (124/165) | | MPP_AQ15 75, Aquifex aeolicus AQ1575 and related proteins, metallophos phatase domain | cd07390 | 2,83e-37 |
| 45 | 19809 | 20129 | 1120 | MEKFKGKDLYKTRIRKQT IKNLVIKTEKLHNKHGKY RPIGHVYYYPKTKEFTLS KPEQKIFIEYMKELGFNV KHRRRKKTLJIYKNAFTE YISMYHEAIEQIEGGT | 106 | No significant similarity found. | | | | No putative conserved domains have been detected | | |
| 46 | 20129 | 20359 | 1121 | MEYLFLFIGIGMIIWGFIAP YLAFVVYYKHVRENING FSDEESLEEATVLGMGFM FIAFIPIGILVVIEEIKILFF | 76 | No significant similarity found. | | | | No putative conserved domains have been detected | | |
| 47 | 20412 | 20618 | 1122 | MKHFLILLGIVILVIALGIVI LVIALGIVLPAWILQLVLS AFGVKVSIWVCIGIFILISA IGSMFSRN | 68 | ORF236 [Staphylococcus phage G1] | YP_241002.1 | 5e-20 (59/68) | | No putative conserved domains have been detected | | |
| 48 | 20633 | 20896 | 1123 | MAKYESNINGENYIATPS QALREALAKLITEEKSFAE YQTKGGEQYESQLQLRHF DAMISQYEEAIRVLEDKY | 87 | ORF171 [Staphylococcus phage G1] | YP_241003.1 | 1e-41 (85/87) | | No putative conserved domains have been detected | | |

FIG. 14L

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| | | | | RPQIFPKDNKEEN | | | | | | | | |
| 49 | 20899 | 21216 | 1124 | MKAESIARFFNDKVLQIE GYKVRFPQASSSYILDIDT VDESVLFLDAQVSTLSGK HLLDTAITIERPETLSAKE LYTEISNKLQAIVGDQTKT TIELSRYFKEEK | 105 | ORF137 [Staphylococcus phage G1] | YP_241004.1 | 2e-51 (102/105) | | No putative conserved domains have been detected | | |
| 50 | 21217 | 21897 | 1125 | VSNKTITNHLLNLKGINIE TYSIIARIKKQTSWGDKG DSFEISISYKADKDPRTVR YITTETIDYSSNNPKEILL QLKDKIFSIVEEQVETDND FIESIKEINSTKALERLKPY INNEYYSMFKSSIEKEIPV ALSSEVLNRCTGKTSTLA YLALEKDLPLVVSNEPMR KMLKNKPPHLRVSSAEDY SNYDIKGEIVLIDEVDIDQ LYSADKVSVDALLVGIIK N | 226 | ORF055 [Staphylococcus phage G1] | YP_241006.1 | 5e-116 (210/226) | | No putative conserved domains have been detected | | |
| 51 | 21975 | 22133 | 1126 | MIPIVILIGLIILFLSSGYKL VLGKYYDDVDLKILFTIF GVGIALLLGGFIL | 52 | hypothetical membrane protein MbpN [Staphylococcus phage A5W] | ACB89160.1 | 3e-17 (51/52) | Membrane protein MbpN | No putative conserved domains have been detected | | |
| 52 | 22149 | 22373 | 1127 | MNYEEVLRTIKENKPCKV RFTGNILAIVNEEFNADTD KGVLQLDVSNINKEGYIR LQQYCLERDDYTVVGAIL F | 74 | No significant similarity found. | | | | No putative conserved domains have been detected | | |

FIG. 14M

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| 53 | 22386 | 22586 | 1128 | MNYRDFITDCISGGYNVH ISVTEKRVHIISEMTSASYP KKEINLDELQAYVYYMN NFGSQITTEGL | 66 | ORF211 [Staphylococcus phage G1] | YP_241008.1 | 2e-31 (66/66) | | No putative conserved domains have been detected | | |
| 54 | 22587 | 22877 | 1129 | MELVINIVAVLVGMYAIY FYVTKFSTGLSGILIVLGM AIGLYFYLDYLNVRENVI RLVSVMFGAFLFSIEMIYN KIMFEIKKSNVQKTVRVY DKEQ | 96 | ORF155 [Staphylococcus phage G1] | YP_241009.1 | 7e-46 (96/96) | | No putative conserved domains have been detected | | |
| 55 | 22971 | 23279 | 1130 | MYPEIDVEKLAYKLKSTR EYLESKIKEVEIYEIYHLK TGKLVFKGEYIEVKELLR KMYKENLTLVDVDTMLSI GKGFIDVIKNISAENVFQI TYKKELSTK | 102 | hypothetical protein KgORF109 [Staphylococcus phage K] | YP_024537.1 | 2e-47 (99/102) | | No putative conserved domains have been detected | | |
| 56 | 23276 | 24184 | 1131 | MIKIFSEVDKEYKPIITEKF PNGEINFKYDDLKYLVEE NLRFDVFFKWENDADLM HLYMFTKYLEQLGIKDKA EFLEIAYLPYSRMDRVEE GHNNMFSLKYITEFINNL NYKSVWVVEPHSPVTEEL LTNSVAIDVTLKLLNQYIE MSEEPVTIVLPDKGAYDR YLFDVERILMESNIESYSI VYGEKKRDFETGKIKGIKI IKDKNTLYDNCIILDDLTS YGGTFVGCKKALDKLKV SSVSLILTHAERAFAEGAL LSSGFKDIIVTDSMFPKNN WEKAIAKHRARINGTELQ | 302 | putative ribose-phosphate pyrophosphokinase [Staphylococcus phage K] | YP_024538.1 | 2e-172 (299/302) | Ribose-phosphate pyrophospho-kinase | RibP_PPkin, ribose-phosphate pyrophosph o-kinase | TIGR01 251 | 8.54e-17 |

FIG. 14N

Table 11 - Features of phage F125/10 gene products and assignment of putative functions.

| orf | Start position | Stop Position | SEQ ID NO. | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| | | | | IKDIERYL | | | | | | | | |
| 57 | 24202 | 25671 | 1132 | MLNPTLMCDFYKLSHRE QYPEGTEIVYSTLVPRSNK YYEHSDNIVVFGIQSLVK KYFIDMFNKEFFNRPKEE VINEYKRTVKFTLGQENP DAKHLEQLHDLGYLPIDV RALKEGTVVHPNTPVMTI ENTHSDFFWLTNYLETIIS TQTWQAMTSATLAYDMR KMLDKYAMETVGNIEAV DFQGHDFSMRGMSSLETA QLSSAGHAISFKGSDTVPV VDFLESYYNADVEKEMV VASIPATEHSVMCANGNY ETMDEYETYKRMLTEIYP TGIFSIVSDTWDFWGNMT KTLPRLKDIIMERDGKVVI RPDSGDPVKIICGDPDADT EYERKGAVEVLWDTFGG TETEKGYKVLDEHVGLIY GDSINYERAQQICEGLKE KGFASINVVLGVGSFSYQ FNTRDTHGFAIKATYAKI KNEEKLIYKNPKTDSGKR SHKGRVAVYKDGSWEDN LTLHQWLNKQNVNQLER VFEDGKLYRDQSLSEIREII KNN | 489 | nicotinamide phosphoribosyl transferase [Staphylococcus phage K] | YP_024539.1 | 0.0 (488/489) | Nicotinamide phosphoribosyl transferase | PBEF_like, pre-B-cell colony-enhancing factor (PBEF)-like | cd01569 | 2,88e-163 |
| 58 | 25750 | 25995 | 1133 | MIYKISKHNYYSRFEYSSY LPDEGFAYIDYVDVILIGV DNPRKRKVITLKADEFNP SDFKVGHKYNIIKILWFEK | 81 | ORF178 [Staphylococcus phage G1] | YP_241013.1 | 5e-35 (70/81) | | No putative conserved domains have been detected | | |

FIG. 140

Table 11 - Features of phage F125/10 gene products and assignment of putative functions

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| | | | | WEWLQP | | | | | | | | |
| 59 | 26012 | 26404 | 1134 | MIIDKLNGVKLEIGGHVV SFSVSKFKTINGERQLLDY HHIKRRKQKYFRTTEEFY NEYKEIKPDKNEIDEMFES LGYVDTKLEDVVRNQEK VTEILGVSEQYLNQLSYK AIEEYVDKIVTLEIKELKG EK | 130 | ORF113 [Staphylococcus phage G1] | YP_241014.1 | 3e-63 (121/130) | | No putative conserved domains have been detected | | |
| 60 | 26406 | 26603 | 1135 | MSNSWEKEGVNYWENED CPREYLEKAFIELVEYVEG VTVPSRDVQQLREDKLRE DIGFYEYVADK | 65 | ORF194 [Staphylococcus phage G1] | YP_241015.1 | 8e-26 (58/63) | | No putative conserved domains have been detected | | |
| 61 | 26668 | 26964 | 1136 | MMNGKQIYVFLSDQYSK DILSLQLGLIKEWSRRELT YSDDVGSDADVVICTDIV RDDFVKKLSKNNSNALFV FISSFYWIGYKGGEFVAV QDYVKGM | 98 | No significant similarity found. | | | | No putative conserved domains have been detected | | |
| 62 | 26968 | 27279 | 1137 | MKKLLILFTLASTLLLAGC TPDNHEGKVLGTGEYREP TTYIKSGSVTVPVIGEMK YYVDLETDKGEDRVYLN REVYHKFDKGDDFSNVG KKVYKNDELIYKGD | 103 | hypothetical protein KgORF113 [Staphylococcus phage K] | YP_024541.1 | 2e-51 (102/103) | | No putative conserved domains have been detected | | |
| 63 | 27285 | 27584 | 1138 | MKQFIHDKKDSYNSTNRN FDIQYYKGIPLQQIDRGYG QARARRFTINNTNQNIWIP MTYLKPNGTLKNNIDIDW ILVKEKCSLKKAGLVIKIK | 99 | hypothetical protein KgORF114 [Staphylococcus phage K] | YP_024542.1 | 2e-50 (98/99) | | No putative conserved domains have been detected | | |

FIG. 14P

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | ITGDVL | | | | | | | | |
| 64 | 27584 | 27823 | 1139 | MYILERTIRGFAGQTEDIL PYYFKSKKEIVNFLKLME ELKEETNYWVKKNGNYTI IIRAKRILYIEEHIQKLKEW ENDL | 79 | No significant similarity found. | | | | No putative conserved domains have been detected | | |
| 65 | 27813 | 27968 | 1140 | MTYDVYVLYKRGEPIAQ GSMEHCLDVYYWERVHG YSNKGYELLPMGYEQEE | 51 | No significant similarity found. | | | | No putative conserved domains have been detected | | |
| 66 | 27972 | 28166 | 1141 | MINIEHDYTIRTVDNRKY TYYSKHESPVTLYKNIIGK DCIEVTKYGKDKKVIIAT KYIVSIERW | 64 | gp ORFI79 [Staphylococcus phage A5W] | ACB89172.1 | 5e-23 (55/64) | | No putative conserved domains have been detected | | |
| 67 | 28184 | 28537 | 1142 | MNARKARKNTKNYKDSN VVTKEQIHLTYIYNKLNYL IANNSSQGKTYVVMNLRT DYPDEFSLSKLKYLKEIKQ HYKDLVFNVKTQVRKAQ WSEKSIIRYYFNLGYIDSV LVPIIHISW | 117 | hypothetical protein KgORF115 [Staphylococcus phage K] | YP_024543.1 | 3e-58 (110/117) | | No putative conserved domains have been detected | | |
| 68a | 28556 | 28744 | 1143 | MFFKKKKLSNVEKQIRQN RNKEDKERKEHQDKLDT DMYKTYELDKIVEEHLRK LNTISLEEL | 62 | hypothetical protein KgORF116 [Staphylococcus phage K] | YP_024544.1 | 8e-24 (58/62) | | No putative conserved domains have been detected | | |
| 68b | 28754 | 28942 | 1144 | VCLGTRLVYYYSIGKDW NKQVYSLNELEYMKKKF KKLGFETQITNEDIGFQPY IYLRLLWDA | 62 | | | 7e-29 (61/62) | | | | |

FIG. 14Q

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 69 | 29627 | 29788 | 1145 | MNLTFEDKLEDLLKKVRS GEIEPIEYSQVNDEHPNGK TTCGVTFKFDIDTPTK | 53 | No significant similarity found. | | | | No putative conserved domains have been detected | | |
| 70 | 29883 | 30188 | 1146 | MILFTQDYDKTLMKVIL GDINTMRPNWKYSVNHP EKEEDVHIQAYEGEDIFD DIEELSDSTQDIVIGVTED DCISESPYDFNGGLRLVTK HIKEHIEKFL | 101 | No significant similarity found. | | | | No putative conserved domains have been detected | | |
| 71 | 30200 | 30499 | 1147 | MIDIYLGEGYNKEYLSKA LRLINDHAPRELSYDFNN VEADVNIHTMLYVKPEDR YVYKDISYDFPGDLJICIVE DDAIVYHQGKQVSGISILR IIEELI | 99 | gp ORF182 [Staphylococcus phage A5W] | ACB89175.1 | 5e-47 (91/98) | | No putative conserved domains have been detected | | |
| 72 | 30596 | 30889 | 1148 | MIEIYLSENYDKDLLKAE LKWIKETASRELTYDVNR NPNLDVHVSPFRYTKDEV KEISLIPQFEDDVCVFIAE TWIHEYHRGKSIGVDSME EYVKEM | 97 | gp ORF185 [Staphylococcus phage A5W] | ACB89178.1 | 5e-39 (80/97) | | No putative conserved domains have been detected | | |
| 73 | 30892 | 31149 | 1149 | MFKVYTVYHKGSMKTI KDKLDRSSLIYFLYDTWY KDISNVFPNHYNKEFGSN SDDIDIDKLIEAVNEEGILL INRGNYVTIREW | 85 | ORF175 [Staphylococcus phage G1] | YP_241027.1 | 6e-41 (83/85) | | No putative conserved domains have been detected | | |
| 74 | 31267 | 31506 | 1150 | MVTLTYTIIHKESDRVIAS GLDELEVINLVQRMVNTN LVTDISLDDYIRRPSGDID VLNLLVDIRRQGVFDFNH | 79 | gp ORF187 [Staphylococcus phage A5W] | ACB89180.1 | 4e-32 (69/79) | | No putative conserved domains have been detected | | |

FIG. 14R

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| | | | | TWHVG | | | | | | | | |
| 75 | 31517 | 31864 | 1151 | MIVIYTDVSKDYLKDEFL PWLNERDRYLEDYKDELP EDIDSSYIVSVVYCKDME GLLERKDIVIGNSYNEPVA LLGVPEFFGNYSNYFYYR GESISKHDLGEIVRLKAW QRMGGD | 115 | hypothetical protein KgORF118 [Staphylococcus phage K] | YP_024546.1 | 1e-57 (112/115) | | No putative conserved domains have been detected | | |
| 76 | 32761 | 32069 | 1152 | MKHNINNIEMFSKYYIKE NKVYSKKTNKELKKDKN NFYRMTDDINKARKVKID TLLQYNLKDYNSINNLPN EKWKRIENNINNIFNYSVS NYGRIKRHGNYYMIEKLV KPHNHKQGYKIVKJNYKH HSIHRLVYEYFGNDFNQD YHIHHIDGNKQNNHINNL QCISPTEHNNLHHKDETIN NFKRGKSLTDNERKNIYK LYTEKGFTQEELSNMYNV SRITINRNIKRFK | 230 | ORF085 [Staphylococcus phage G1] | YP_241035.1 | 3e-37 (83/165) | | HNHc, HNH nucleases | Smart00507 | 5,48e-03 |
| | | | | | | | | | | Sigma 70_r4 | pfam04545 | 6,44e-03 |
| 77 | 32902 | 33210 | 1153 | MEIKEIADTIMYLFNMDG YRCAEPPLYESTLNHTRT HTALIVSIKGNYDTVQMF RKTPIMSMRGQSQPASML VNVIDDVIIIVYFNVVYGV QNKEJKFIEEI | 102 | ORF145 [Staphylococcus phage G1] | YP_241031.1 | 9e-49 (94/102) | | No putative conserved domains have been detected | | |

FIG. 14S

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 78 | 33417 | 33704 | 1154 | MTNKNYLYEETHTVQGQ DITAFRIPNDTNGNPRYVV HFMDLNIKLADYDNINKL YGFNKYRAKWFGGGVVF QSYNIEDTLNFALDKVKEI EAVKN | 95 | ORF159 [Staphylococcus phage G1] | YP_241032.1 | 2e-39 (78/88) | | No putative conserved domains have been detected | | |
| 79 | 33754 | 34026 | 1155 | MILEIETKPVKTLKAIKDD TKNIKNSIAEHLGLNREQF KLSNGLITLKGYSEEFKC WYNLTSTIGNFPKYLKSE LYNEYKLYCNVELKTK | 90 | No significant similarity found. | | | | No putative conserved domains have been detected | | |
| 80 | 34550 | 34708 | 1156 | MLKFKWKNKTKSTQKT DNILLIGGLVATITPKLV NWFLLLQDNINIFLR | 52 | No significant similarity found. | | | | No putative conserved domains have been detected | | |
| 81 | 34875 | 35255 | 1157 | MFKLQNKVEIIVPKEDNN GVEIADKRJKEYVNSITME AGGCTITEIKGQWYSEDE KRIMEDNNLNLEWYYIPD RAKFMTVELKGIVRRLIE VYGQEAISIKVNGTLYIVD QSDIEELHTTLLNIMK | 126 | No significant similarity found. | | | | No putative conserved domains have been detected | | |
| 82 | 35747 | 35968 | 1158 | MNRLEIVKDTAMEYILM MDNSVMDGVMTQEEYN EAVSFEKVYDYTLSEANK ECKFLGGKVLTFLVHEAI EEYA | 73 | No significant similarity found. | | | | No putative conserved domains have been detected | | |
| 83 | 36049 | 36186 | 1159 | MRYEIVTLVNQELFMYAT FNKQEAEAKYSEWCELY GQENVSMEKN | 45 | No significant similarity found. | | | | No putative conserved domains have been detected | | |

FIG. 14T

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 84 | 36215 | 36493 | 1160 | MIILNYTKEKEMIQMKLL NQENQIVISIATLESVKQA LIWEYIDHIDYNIWNNEL DDTEAVVKISGILQSIKFA DTMEDLQEYIGDIGWKLI | 92 | gp ORF194 [Staphylococcus phage A5W] | ACB89187.1 | 3e-24 (56/78) | | No putative conserved domains have been detected | | |
| 85 | 36584 | 36823 | 1161 | MKKNVKASTIEWLELTQ GHGEFDGFDEEDMDFRK LDDEDIKWYFENWYFTEE KQEQIIDEIGQEEFEEAYS DDIKEYNN | 79 | No significant similarity found. | | | | No putative conserved domains have been detected | | |
| 86 | 36898 | 37158 | 1162 | MTKFKLIDKNSFYVNDNY NNETYLTSQIVLSGEAGR LLDDMIEDCEDEHDKDN YKKLDTNNIDDIDYILECA NVYIYPYNKTEFKY | 86 | No significant similarity found. | | | | No putative conserved domains have been detected | | |
| 87 | 37176 | 37349 | 1163 | MNTRRANKALNEAVRLL DKQIEDTQKTMQELNKQL EQQIKAKQELMTLVDVM TGDDE | 57 | gp ORF002 [Staphylococcus phage A5W] | ACB88993.1 | 2e-19 (50/57) | | No putative conserved domains have been detected | | |
| 88 | 37349 | 37618 | 1164 | MNIKEAHKVVRSAKSKLL QEQEHITNHIIEDYIIEELH RRTQGSGTIQMNNNTASY SNGSYGSLEELREAYDLS SLSTGEIKELLETFV | 89 | ORF166 [Staphylococcus phage G1] | YP_241041.1 | 2e-33 (71/89) | | No putative conserved domains have been detected | | |
| 89 | 37720 | 37971 | 1165 | MKEQIKQFEKELEMAVN NLFVLHDCGVSQAKIEEQ NQKVVYLKAIVENMKAY EEIRVEPKSEEQFFKELEE ELEEEKILKGI | 83 | No significant similarity found. | | | | No putative conserved domains have been detected | | |

FIG. 14U

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| 90 | 38522 | 38259 | 1166 | MKLYQVEHDNCEPYEDN YSYREDKVYTNKENLIKR IKAEGYEEKISGYLQDGY TYYYKDNIEDVPLFREDM ITIHELEVINNTSEEE | 87 | gp ORF004 [Staphylococcus phage A5W] | ACB88995.1 | 5e-19 (52/83) | | PRK14902, 16S rRNA methyltransf erase B | PRK14 902 | 6.40e-03 |
| 91 | 38955 | 38524 | 1167 | MENYKNFIIEEMNKAHIL VTKAEQIKGDRKLAETEL EEVYRKAEAFDEIVNELL YQLQNLESWDTLDQKDC QTLKQILEENIKEEKQME RFKVKRIITTEEVRYIDAE TEEDAWYSVEYEDEGTD TAHFSAEYGEWSYEREDN | 143 | ORF103 [Staphylococcus phage G1] | YP_241047.1 | 1e-67 (129/142) | | No putative conserved domains have been detected | | |
| 92 | 39149 | 38958 | 1168 | MIEISWTYLITFLLLWSA GTLYINYLVYRIRLTNKER KEMSKEHHRNREEIKQRI ENRRDK | 63 | ORF224 [Staphylococcus phage G1] | YP_241048.1 | 1e-26 (61/63) | | No putative conserved domains have been detected | | |
| 93 | 39394 | 39146 | 1169 | MRYDINEKCYDEKDFVL QIIYENYSDETDREVETIY NKAEAWDKLCEMLKDK DMSDGHFEEEMFKLFSRT GKSFTIDKEESQ | 82 | No significant similarity found. | | | | No putative conserved domains have been detected | | |
| 94 | 39876 | 39394 | 1170 | MNKTFFKFLGKNTLEYSK QGLGFLVALPIMLIIFSVFL AFIIGIPAVIIYALHALNID NDFIIQLVPVMWFIILYGI VRTDEHKKPFVKLKLKD YLLSILYLTTITAISVLESY LLFQLLPFTGDVRAVITLL SFIVFVAVNRGICKIAIKSY | 160 | ORF087 [Staphylococcus phage G1] | YP_241049.1 | 5e-81 (153/159) | | No putative conserved domains have been detected | | |

FIG. 14V

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | KEYKEEL | | | | | | | | |
| 95 | 40300 | 39869 | 1171 | MNIKYIDLVLENCDVVRL ESKDVSRFHISGITEGIDY YGTYKETSNISRTRHCTYF GILIDKPMEIPQVGFAYPD NTNAYEMITAYSDITAIDII YENDANEYIYVDFNEYND NYNINQKNDYYNMLEIT ITESNSREEEDE | 143 | hypothetical protein KgORF2 [Staphylococcus phage K] | YP_024433.1 | 7e-74 (139/143) | | No putative conserved domains have been detected | | |
| 96 | 40856 | 40314 | 1172 | MDKINLNKKHDGSTVVNI SNNIMLKIQCTDLRKECD DSEAPTTYTHFKAYIVYNI FIVVNDRKQKKKVKYDY YNDHVGRGNVKDLLKVK DVIFQLSTQLNTNEIIKISG ADERRYKIYKYFIEKDIRF EDNMYYSKSNIWIINNFSL LQKFQWNTVVTKDGDYN KKELKKVDKEWKELLI | 180 | ORF073 [Staphylococcus phage G1] | YP_241051.1 | 8e-96 (177/180) | | No putative conserved domains have been detected | | |
| 97 | 41356 | 40868 | 1173 | MRETSEYIMFWGKEDIYS NFYPIKFKHQGRTFNNSE QAFMWRKARYFNDFQIA GEILNAKNPNHAKSLGRK VRNFNEEQWNKVRYDIM VEVVKDKFMTTHLKQRIL DTDVRKDFVEASPYDKIW GVGLKANDPKILEQSNW KGQNLLGKVMEDVRVHC IYNK | 162 | hypothetical protein KgORF4 [Staphylococcus phage K] | YP_024435.1 | 2e-90 (160/162) | | Ribofla_fusion, conserved hypothetical protein, ribA/ribD-fused | TIGR02 464 | 2.28e-60 |
| 98 | 41767 | 41369 | 1174 | MKKKYFKGLKLNDFEKE VFGLKKNKYKMKKKL | 132 | hypothetical protein KgORF5 | YP_024436.1 | 8e-69 | | No putative conserved domains | | |

FIG. 14W

Table 11 - Features of phage F125/10 gene products and assignment of putative functions.

| orf | Start position | Stop Position | SEQ ID NO. | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| | | | | GRNEPKYWNYDMSFFIQL YADLNAFVESSNHVDME YHTFDVDGKERTQIDMI KHILSLIKYYHKEMDFD MDKYDELEQVQSKILDNF KIVLPSLWN | | [Staphylococcus phage K] | | (130/132) | | have been detected | | |
| 99 | 42471 | 41764 | 1175 | MAIYVVPDIHGEYQKLLTI MDKINNERKPEETIVFLG DYVDRGKRSKDVVNYIF DLMSNDDNVVTLLGNHD DEFYNIMENVDRLSIYDIE WLSRYCIETLNSYGVSTV TLKYSSVEENLRNNYDFI KSELKKLKESDDYRKFKI LMVNCRKYYKEDKYIFSH SGGVSWKPVEEQTIDQLI WSRDFQPRKDGFTYVCG HTPTDSGEVEINGDILMC DVGAVFRNIDFPFIKLEVK K | 235 | putative protein phosphatase [Staphylococcus phage K] | YP_024437.1 | 5e-134 (234/235) | Phosphatase | MPP_PPP_ family, phospho protein phospha- tases of the metallo- phosphatase superfamily, metallo- phosphatase domain | cd00014 4 | 6,21e-23 |
| 100 | 44413 | 42563 | 1176 | MTKKLKLYDYENNLLKS SENIEDSIGQIVIENLNPDT TYEAGHFKICWDINGEESI KVDIPKFVTLTSSQDKLI1 VTYNEVEPMNIKAENIIGL QDVIDTQFNDHIKEEFMA EINKLIADNKPTQQPSTTTI SPLKDKKVIFIGDSITEVN ARTTKNYHQFIADRTGLI NVNKGTSGTGYQDRKNV AYTITDKPDLICVMLGTN DYGLVGGKTKPLGTAKE HSYTTVAGSIYYTYYQLS KVFPTVPIVVLTPTPRIESN | 616 | lipase/acylhydrolase domain protein [Staphylococcus epidermidis RP62A phage SP-beta] | AAW54968.1 | 2e-149 (277/503) | Hydrolase | SGNH_ hydrolase_ like_2, SGNH hydrolase subfamily | cd01834 | 2,31e-08 |

FIG. 14X

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | PFKEVENGQGYTLGQLVD VIKEIAKQFSPVLDLYRE SNIRVWDNNVNKTFFAW KEGMEDGLHPNAKGHEFI SYTIQSFLESKGTVGAIAS PPSIDTSVKDLGNGVYSK LIRPTGMRWKKDTSFVM NMSTDDIDLTANKILNVS YNGKSLINPEGYTSNSPY WYTLPAYEDGNKYNRISE VQNFLNAFTIDDNAQGL EFMRDYIKVIYVDKTKTN IVGEYTQVGYKDTTASTP PTGDTSGTITPVSNGDGTY TATFTPTAIYWKEDQSFMI NIDKTKLDLTGKSVTKLE YNGKTLVNNTSLASNSPY WLTVPTATEGTTNNRTPE VKDFVSVLTLESTGTDGR KKYKNVEIKLTYK | | | | | | | |
| 101 | 45043 | 44972 | 1177 | GGACUCUUAGCUUAAAG GUAAAGCCAACCGCUCA UAACGGUUGACUGUA GGUUCGAGUCCUGCAGA GUCCA | | | | | tRNA4-Met | | | |
| 102 | 45871 | 45323 | 1178 | MEKIYILEEIEEMDYDL WEEDTVYTTSYEVLGYT DSLEDAEYIRDNYGTSNPI FINEYPYLTKEKLIEEQRY FRYNSYLELKRVNGYFEIS EINELHVTEDFSINKDDKN FDSPFSINMFSHNRNSIGIE FIMFSEYNDKEDIIEKEKN SFLMKLKYLLKHSREADI | 182 | hypothetical protein KgORF8 [Staphylococcus phage K] | YP_024439.1 | 4e-88 (162/169) | | PHA02241, hypothetical protein | PHA02 241 | 1,20e-23 |

FIG. 14Y

Table 11 - Features of phage F125/10 gene products and assignment of putative functions.

| orf | Start position | Stop Position | SEQ ID NO. | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| | | | | RSTSKIIDSIDKLT | | | | | | | | |
| 103 | 46093 | 45875 | 1179 | MKNIINFLVDYNINFSYSE DSLNVMNNSYLVDKHGT QDYEIVGNYEHITGVFSY QTEEEVIAKLKNLIGIWE | 72 | ORF201 [Staphylococcus phage G1] | YP_241058.1 | 4e-33 (71/72) | | No putative conserved domains have been detected | | |
| 104 | 46288 | 46094 | 1180 | MRDKRIHSELLYDIIGKHI QEEENTPYIEAIYVDMM NIIVVEYTFYNENGTRML GQYPIGEVM | 64 | ORF218 [Staphylococcus phage G1] | YP_241059.1 | 8e-29 (64/64) | | No putative conserved domains have been detected | | |
| 105 | 47015 | 46278 | 1181 | MNLEKSFLLSTIEFGSTYQ GTSDEHSDKDYMSLVVQ PLSDTIFRNNEKASKHTEV SRYYAVERFISLVLKSGFD NVLNLCAQLEQAKNTRF NKTVLDLFYDDFIFLTYV RANFKPIAYSVIGNINNIL KKGELTGKDLVKFYTFYN HLEYYNDLLDDLDNLNV SYKDFAKVKYMPKEVLD NKRSNVSIEKKKDLVNKV EPLIQEVKDKLKYNESNIK HYKDAMELVEKSLKDKT VAFLTEVYNER | 245 | hypothetical protein KgORF9 [Staphylococcus phage K] | YP_024440.1 | 2e-135 (243/245) | | No putative conserved domains have been detected | | |
| 106 | 47182 | 47078 | 1182 | MKYILGLITLGIILFKVYE HFKYKQDEVDTEEDI | 34 | ORF437 [Staphylococcus phage G1] | YP_241061.1 | 4e-10 (34/34) | | No putative conserved domains have been detected | | |
| 107 | 47442 | 47194 | 1183 | MSNMDFYQFLNHENVRV NSITPSQKNFIRENLELTN LEDTDIDFISSKKAKEEIEK IIRIKNEEEYDMAMDALA | 82 | gp ORF020 [Staphylococcus phage A5W] | ACB89011.1 | 6e-40 (80/82) | | No putative conserved domains have been detected | | |

FIG. 14Z

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | GWVTKHGY | | | | | | | | |
| 108 | 47824 | 47435 | 1184 | MFKKAPQYIMEKVEKEN NILGEDLSLDIYYKGVKLT VKRHPETGHLNGYTLPS DINEKEYDSLERRAHRGIT YDDYDYEGKRVLGFDCA HAWDMTPYAIIGSLDDQY RDLEYVLSILKDMAEYVK KDE | 129 | hypothetical protein KgORF10 [Staphylococcus phage K] | YP_024441.1 | 2e-69 (129/129) | | No putative conserved domains have been detected | | |
| 109 | 48096 | 47923 | 1185 | MEKVNHEFLAELAKSNSP VLNSKPLQDGDYNIEFDY DGFHFEFSQKNGYWQWK YNAK | 57 | ORF245 [Staphylococcus phage G1] | YP_241064.1 | 7e-25 (55/57) | | No putative conserved domains have been detected | | |
| 110 | 48619 | 48137 | 1186 | MANEKEIIRMVNYLIDNM SMWHINYARAVLIPSEVE KIIKEHEKFDDLLKKRGE WLVKGSDTDNIDDLLETYN QIMNNQKDEMMIQEIDIY TQGKTITIDNEHYSSDDLN EVLNKLEQSEDIKIKSNYK SLYVGYTNVVGYEVTYA SSYEETFKNDLEKDL | 160 | hypothetical protein KgORF11 [Staphylococcus phage K] | YP_024442.1 | 2e-85 (159/160) | | PHA02243, hypothetical protein | PHA02 243 | 2,31e-36 |
| 111 | 49211 | 48669 | 1187 | MDRIIGKIHNLTQDLRLGD KVEVYDAHKFKENEDGTI ELGDKITEGIVVDYKGDF TGNTSGLVTLDSSEKELII GEYNFKLIEEGNLQAVYD SVSKNKVESLSEDYDMYR KLLGVKSGELAGIEDELE YLVRQYNSKVDNYNGLL TLSKEKARELSLLTGNKK | 180 | hypothetical protein KgORF12 [Staphylococcus phage K] | YP_024443.1 | 1e-94 (177/180) | | No putative conserved domains have been detected | | |

FIG. 14AA

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
|  |  |  |  | TIPHMKNRRLELGKEADF |  |  |  |  |  |  |  |  |
| 112 | 49744 | 49211 | 1188 | MVYDSIISRTMAVSILNK WIAELITDVDLDKCKFTE EEYGKVVTNSINKIQDVLI EKNYEVTDGELYDIVCTE LINPIKNNTEEEKHNEKND LLEHLEDLAFRHDIDLGY VSDGSYNLTVTHWLMQD EFTDVNIKVNNDEDFYTV TIPESKYFWLPITKENLEM FLTQDPINKGEVK | 177 | hypothetical protein KgORF13 [Staphylococcus phage K] | YP_024444.1 | 4e-97 (177/177) |  | No putative conserved domains have been detected |  |  |
| 113 | 49911 | 49747 | 1189 | MKNPIKLLSIAVVTILTFSL TYVILKKETNNKRNGVAP FDFSLEDHIHLNKEIK | 54 | hypothetical membrane protein MbpP [Staphylococcus phage A5W] | ACB89017.1 | 2e-22 (54/54) | Membrane protein MbpP | No putative conserved domains have been detected |  |  |
| 114 | 50192 | 49914 | 1190 | MANNIWAVVLSIIILLIILLI LWFLFRKKVNGGNSKNV EIQKAEENNDNKEQEVEE AQYRELNEEEKEKENENSS KDYKYDKEKVKNKLKEL E | 92 | hypothetical membrane protein MbpR [Staphylococcus phage A5W] | ACB89018.1 | 2e-41 (92/92) | Membrane protein MbpR | No putative conserved domains have been detected |  |  |
| 115 | 51037 | 50192 | 1191 | MGRRLIDNSELNVIKYDG LPDFFSALKKNRVSGRDN SSDTGSYDFTGTHSFQEA YNLMVKGDRESYDMVV KLKKMTDALFRMDKSVK RKPVVAPEGYQPHVPNAJ KGLPNSMMSQORVKAEK KVIDVFYNSSISWREDPEN LAYRGAIMLSAIQTLETK GYSINLYLGKLSNSGYED | 281 | hypothetical protein KgORF14 [Staphylococcus phage K] | YP_024445.1 | 8e-161 (280/281) |  | No putative conserved domains have been detected |  |  |

FIG. 14BB

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | KLTGFVVNIKHSYQRLNV FKSSFYLVNPSFLRRISFR VLEVEPDMVDLTNHGYG SVVSKSSYGNKLTEHILD NAVIFDSSVGIDINNDSSE NLRAVKKLFGGRL | | | | | | | | |
| 116 | 52167 | 51049 | 1192 | MAKQDTIERLERLVEQQ METTADLAKKLGEKNSN PYEQAIVDAIVEKAGTESR EIIITDVKKQIEEYVEEQLS NLPVKIELQQEGKTIKDIS GIFHYRYQDILKLVNQNIP VFLKGGAGSGKNHVLEQ VAEALDLDFYFSNAITQEF KLTGFIDANGKFHETQFY KAFTKGGLFFLDEMDASI PEVLLILNSAIANKYFDFPI GRVTAHEDFRVVSAGNT MGTGADHIYVGRQQLDG ATLDRFAQVEFDYDTKVE HQLSSNEDLVNFVQQLRH ENDEKGLPYVFSMRAIIN GSKLDGVMEDEFVVESIIF KSVPKDEINQFISSLPEGN RYTEATRKLLGMQQEPK QEPRKSDSTSKDSMDFDTI MDKLGLE | 372 | putative ATPase [Staphylococcus phage K] | YP_024446.1 | 9e-110 (194/194) | ATPase | PHA02244, ATPase-like protein | PHA02 244 | 1.23e-175 |
| 117 | 52645 | 52319 | 1193 | VSKRTDNFIYFCKYYFSE YLPSLGVEVLNHNETSHG TMEGVKKYYIANILYEGQ ELTVTIDLEEFNNATSMH NMLEIMNNHTYNCMFMY DMDTHETKDIDDFFKLM | 108 | ORF134 [Staphylococcus phage G1] | YP_241072.1 | 6e-56 (106/108) | | No putative conserved domains have been detected | | |

FIG. 14CC

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| | | | | YF | | | | | | | | |
| 118 | 53054 | 52638 | 1194 | MNAKEFMKTQAQVEDYL DKLKVTIIEDALSVSKEWS NDSNDLGYALSSLGESIGL LENYYNIQVDAHLPEHYK GSKDVISFLEEHFSYDGFV DSMIFNIVKYTTRLGRKD AVDKEVQKIKTYVVRLER NIKYGDSTRV | 138 | hypothetical protein KgORF16 [Staphylococcus phage K] | YP_024447.1 | 7e-74 (137/138) | | No putative conserved domains have been detected | | |
| 119 | 53488 | 53186 | 1195 | MEKVELIKQWAKDRNLQ TGKPEGQMLKLLEEAGEL ASGIAKSNDHVTRDSVGD IFVVLTVLCLQLDIDIEECI DMAYDEIKDRKGKLINGV FVKEEDLKK | 100 | hypothetical protein KgORF17 [Staphylococcus phage K] | YP_024448.1 | 9e-50 (100/100) | Pyrophospho-hydrolase | MazG | pfam03 819 | 7,10e-03 |
| 120 | 53676 | 53488 | 1196 | MEKFQEDYVNIDIRVKAY VRVGYRYEEDITNNLHEL VEDNLNVTSDSDSLIIKDT EIKGDIE | 62 | ORF228 [Staphylococcus phage G1] | YP_241075.1 | 5e-26 (61/62) | | No putative conserved domains have been detected | | |
| 121 | 53881 | 53720 | 1197 | MVKPVITLEPEDVKVLLD YLSFLEDDMRNYEGMRE LYEFLHKKYQLAKGNYS D | 53 | ORF259 [Staphylococcus phage G1] | YP_241076.1 | 4e-22 (53/53) | | No putative conserved domains have been detected | | |
| 122 | 55932 | 53881 | 1198 | MAITYKQKGLTEQEIINLP KVNKGCIYIGEEDVFLKK KKNNINLGSKELFRDIFN IFSFDTATEIHLFLALCGN KEVTNFTGNPYETIEKLVE GVIEENKGRSYKEYIASSR EERKEFPLYGSKRITQIKS | 683 | hypothetical protein KgORF18 [Staphylococcus phage K] | YP_024449.1 | 0,0 (591/683) | | No putative conserved domains have been detected | | |

FIG. 14DD

Table 11 - Features of phage F125/10 gene products and assignment of putative functions.

| orf | Start position | Stop Position | SEQ ID NO. | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| | | | | KGYVEEKIKELENETRLR WYESRQLDEYKEVVDSL NNDIMDILYQGKYGLIKS SITSRLNEDTEKGSSKYYK EISDSLYSSTWYMHPSTE NSSSFGLKVRHIRDKYNM GNRWVLENKSSFDVKTG EVKVFLTDSLVNKEITLNL YKDDISKSEYKNELNLAV LLNVILKNYSTPNLSKNVI IKIIEETLRNDGFGLSSWC LDEVDVYGRVNYGGNKY KPLKGENSTSNYLTLTDI VKNIDKINNLEEFELFERN SLLFHIPKNPKWKIHEAFN LTKQTYKKLLTLNNFEQS NYLRFSDTLYNYYNHLH NEVNLHQLFDDTFLMVQ DVRNVTDALKVKPIVNEI LSISFANYKKMTHYLDVD AQDRQRITGYALDSYYLD YLHDLSILIREGYRTLESV NLTPFSLKLEHDIVTDEKQ SIQQQLDDAELKSKYENK LEKIIDKTYKLKDGRKVK FLPADTVSKLKNEGKMLS HCVGGYANRIIKNSCLILL ARLEEDLDNSWFTVEIRIT DNGYVLGQQQSIDAYKLP NELKEALEKDIKKINKEEF KEVA | | | | | | | | |
| 123 | 56273 | 56010 | 1199 | MSIEKKEEVVAHNEVVFK SLTQGLYVKEVDIYSDVIS YTKDIDEALAMPNTINFK NSRKYEKLIRNLDLKPLN | 87 | gp ORF038 [Staphylococcus phage A5W] | ACB89029.1 | 5e-39 (79/87) | | No putative conserved domains have been detected | | |

FIG. 14EE

Table 11 - Features of phage F125/10 gene products and assignment of putative functions.

| orf | Start position | Stop Position | SEQ ID NO. | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| | | | | KIQKVIYETHLEEL | | | | | | | | |
| 124 | 56465 | 56292 | 1200 | LNDLIKEGNKYYHKVRA GETLWTISKNYGVDIKKL QELNNIKSVTLTSLEYVLV CVE | 57 | gp ORF039 [Staphylococcus phage A5W] | ACB89030.1 | 1e-21 (52/57) | Peptidoglycan binding protein | LysM | pfam01476 | 8,09e-07 |
| 125 | 57050 | 56472 | 1201 | MDNLSHYLSILYAILVTV GYIPGLIALVKSDSVKGVS SYFWYLIVATVGISFYNLL ITDATMFQVVSVGVNLTL GIVCLLVASYRKKDYFSIP FIIVFSVLLFLLSDFTALTQ TIATITILAYVTQITTFYK TKSAEGTNRFLFLJIGLGL ASLILSMVLSHTYVHIIAT EFVNFVLILICYLQANYYS RR | 192 | gp ORF040 [Staphylococcus phage A5W] | ACB89031.1 | 5e-92 (177/192) | | PHA02246, hypothetical protein | PHA02246 | 2,51e-33 |
| 126 | 57636 | 57043 | 1202 | MVNYTKDKVCYMGGIIL LNQAMVEYRTKQHEQVE GIVGVTPYSPHQDKSIND KANAEQTGLAERILNNDF KAMQESDIFVFDILNEGL GTIAELGILLGMKHQAOK IIDKYEDIDFRDLEPLTQY DILEAYNIVNKPVLIYCSD IROGHGKGYDDPDRAEFS TNQFIYGCVLSLTNGEGFI SWEEVLKRLLEKLGGQDG | 197 | hypothetical protein KgORF20 [Staphylococcus phage K] | YP_024451.1 | 8e-79 (153/210) | | No putative conserved domains have been detected | | |
| 127 | 58522 | 57629 | 1203 | MKSYTKVKNKGLSLDKF KDRGFVVQEKLDGSNASF TTENGELVCFSRRKKLNE NETLNGFYNWVHENMTD | 297 | putative DNA ligase [Staphylococcus phage K] | YP_024452.1 | 8e-134 (237/298) | DNA ligase | RNA_lig_ RNL2, RNA ligase, Rnl2 | TIGR02307 | 1,21e-07 |

FIG. 14FF

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | KLDLSILEGIIIFGEWLVKH KVNYKEECYNNFYVFDV YDKDSETYLPYSEVISLSE TLGLKTVKTLMIIEPSFYL NKLNPQEIQDLVGKSDMT VKPNTGEGIVIKYLDGKS EHDDYFKLVSKEFKEFSR KKMKSEVRSNDSVADYAI TKSRMEKMIFRAIEENRLS KDDLELENFGLIMKQVGQ NFVDDIMEEEKENMMKII EKQIKKKMPHILRGILEEK GDTIDG | | | | | | family | | |
| 128 | 58750 | 58526 | 1204 | MNYLAKVFINNNWLVKLI TIVLLTLLLGGLVYVISAV ALFLSTVLNLPGLVVLAF LASVSLILFSIVHNSKEDN | 74 | No significant similarity found. | | | | No putative conserved domains have been detected | | |
| 129 | 59558 | 58818 | 1205 | MAIQLKELDFKLKDYPNV RYNMGEHLVFNEFLEKAT TEQLDFCEDFFNDNVEIL WNESQAGTGKTMCSVAC AYADYLNKDRKLVFIISP VSEDLGSRPGNQTEKEMA YFMGLHDALIELNMNPEQ QTEMLMMEDNVKEDKL GDCWVSQISHLFLRGGNL RDSTIIINEAQNFKRSELK KVLTRVHTKNSTVIVEGN FKQIDLKNESKSGFGDYM EYFKKYDGAVFHNFTVNF RSKLAQYADNFKW | 246 | putative PhoH-related protein [Staphylococcus phage K] | YP_024453.1 | 4e-142 (242/246) | ATPase | PhoH-like protein | pfam02562 | 3.99e-21 |

FIG. 14GG

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| | | | | | | Homologous/similar proteins | | | | Conserved Domains | | |
| 130 | 60224 | 59610 | 1206 | MKKINSVIKGEGKKVQTT DVRKISYYVKDYNPCMT VDDANDYNSTSQYLVSD NGKFIAKYNKDMNAVGF YEESGDTVKHLTHTTPER LEGTVFTIEEETKIDLINDT LPQGDILKFSDGSIYLPDN ESVLDSVNYLADNDWDS VDDIIYTGLSKGNSENCIV DFNYNNYDIGYDDVEDEE VCDNYPECECSNYCSSTG EYIGN | 204 | hypothetical protein KgORF23 [Staphylococcus phage K] | YP_024454.1 | 3e-111 (200/204) | | PHA02248, hypothetical protein | PHA02 248 | 2.68e-96 |
| 131 | 60665 | 60240 | 1207 | MQDSVNIYTDGSSSYNKG KVGSGAVLVSKEGNIIAEI SKSVDKPGLIKYNNVAGE ILACCYGIEEAIKLGYNQA IVYIDYIGLIHWYEGTWSA RNILSKTYINMIREYQKVI DINFVKVKSHSNDKWND YADNLAKKSIDI | 141 | putative ribonuclease [Staphylococcus phage K] | YP_024455.1 | 1e-73 (140/141) | Ribonuclease | RNase_HI_bacteria_HBD | cd09277 | 8.50e-30 |
| 132 | 60846 | 60655 | 1208 | MKKGVFTVIADGFKFNVI AKDKKEVQEHCFKCFDF NYISVSFCREVYSDCEFPQ FMEDYKYAG | 63 | ORF222 [Staphylococcus phage G1] | YP_241086.1 | 2e-28 (63/63) | | No putative conserved domains have been detected | | |
| 133 | 61510 | 60869 | 1209 | MENNNLVNFLMTTDDID DTIEMVDSFELQDINKVL GEDTFLTIMEITDSLPDNQ YKIVILSSLDKLLNTDRK ELVEYDEEFPTIRKHNVSE LKRDTVNSVIDSYMNTNV EILYTEYPTISNYSVVVDS VKVLNTLYLIESKNGKIEA | 213 | hypothetical protein KgORF25 [Staphylococcus phage K] | YP_024456.1 | 7e-113 (213/213) | | No putative conserved domains have been detected | | |

FIG. 14HH

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | TLSEDGEDLHEYISEEGYS VTDILNKFDDVEDLFDED DSLINFFSDIDEGKNKTIKS FIELVINLK | | | | | | | | |
| 134 | 61730 | 61500 | 1210 | MDEKKESKPLNLQKIRVE KGHTLRSLASEIGVHYSLI SYWEYGKKKPRSANLMR LEKALNTPGKELFKELEE DDGE | 76 | ORF187 [Staphylococcus phage G1] | YP_241088.1 | 6e-36 (76/76) | DNA binding protein | HTH_XRE, Helix-turn-helix XRE-family like proteins | cd00093 | 9.43e-07 |
| 135 | 61960 | 61733 | 1211 | MNKFKRWFRINVLKKETL LFKVYWRYESPSLKKPHV FHIELYAKSKAEARDKSH EYILKNAKASEDFKFLKV EEK | 75 | ORF190 [Staphylococcus phage G1] | YP_241089.1 | 2e-33 (73/75) | | No putative conserved domains have been detected | | |
| 136 | 62778 | 62071 | 1212 | MKKTIFATLALGTAITFGG MATNEASADEIDYNKLAE QAKSNSVEVNTKPIQEGN YDFSFSDGEFTYHFYNYN GNFGYEYHSGSTQVDNT VSRLAGEEQTPEQKVDQQ QAQFDTQNKAVEQPKQE TTTQEAPKSVEAPKVETK TTATKSTGGSVAEQIRQA GGDEAMIEIAMRESTLNP NAVNPTSGAQGLFQGLG KSWSGGSIAEQTKGAKQY MIDRYGSTSGALNFHNAN GNY | 235 | hypothetical protein KgORF26 [Staphylococcus phage K] | YP_024457.1 | 3e-110 (201/235) | | No putative conserved domains have been detected | | |
| 137 | 63768 | 62974 | 1213 | MRKSVVISGVIGFLAIIGFI ILLMCITKIPQGHVGVVYS VNGVKEDTKSPGWHLTA | 264 | hypothetical membrane protein MbpS [Staphylococcus phage] | ACB89042.1 | 1e-137 (237/261) | Membrane protein | Band_7_Hfl C domain of flotillin | cd03405 | 3.25e-11 |

FIG. 14II

Table 11 - Features of phage F125/10 gene products and assignment of putative functions.

| orf | Start position | Stop Position | SEQ ID NO. | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| | | | | PFDKVNKYPTKTQTHKY KDLNVATSDGKNLQMDI DVSYKVDATKAVDLFNR FGSADIEELEKGYLRSRV QDNVRQSVSKYSVIDAFG VKTGQIKKDTLDSLNDNL EKQGFVIEDIALSSPKADK NTQKAIDERVKANQELER TKVDKQIAEENAKKKEVE AKGEKKANDIRSESLTDE VLQQQLIEKWDGKQPIQI GGDGTIVDVTGK | | A5W] | | | MbpS | (reggie) like proteins | | |
| 138 | 64077 | 63769 | 1214 | MALFLTYFAIFIVFLVLVG FGMSYYVFDFLSMREKKSN IRKQYRELVRQGTLEEYG LEQYVKYKKQFLNDRRQ SLVTKADKQEIDKEEKAL NSLIKEIEKGEM | 102 | hypothetical protein KgORF29 [Staphylococcus phage K] | YP_024460.1 | 3e-47 (94/102) | | No putative conserved domains have been detected | | |
| 139 | 64810 | 64190 | 1215 | MENIIGKKIEKLFVEEYVG SDKIKGKLYLCLCDCGMD RVLSKSQLYYYKSCGCM KSRNGSKKHPEYTVWRK MKERCYNKNQDSYPYYG GRGIEVCDRWKNSFFSFL YDMGKRPSDKYQLDRKD NDGNYSPENCRWTTRSEN IVNRPSKLEGLKNIQERTN GKYRVSITRNNIRYQSYQ VDSIKEAINLRDRMLKEY EETKSITIFK | 206 | hypothetical protein KgORF27 [Staphylococcus phage K] | YP_024458.1 | 3e-34 (88/211) | | No putative conserved domains have been detected | | |
| 140 | 66363 | 64873 | 1216 | MAKTQAEINKRLDAYAK GTVDSPYRVKKATSYDPS | 496 | putative lysin [Staphylococcus phage | YP_024461.1 | 0,0 | Endolysin | PGRP, Peptidoglyc | cd0658 | 3,07e- |

FIG. 14J

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | FGVMEAGAIDADGYYHA QCQDLITDYVLWLTDNK VRTWGNAKDQIKQSYGT GFKJHENKPSTVPKKGWI AVFTSGSYEQWGHIGIVY DGGNTSTFTILEQNWNGY ANKKPTKRVDNYYGLTH FIEIPVKAGTTVKKETAKK SASKTPAPKKKATLKVSK NHINYTMDKRGKKPEGM VIHNDAGRSSGQQYENSL ANAGYARYANGIAHYYG SEGYVWEAIDAKNQIAW HTGDGTGANSGNFRFAGI EVCQSMSASDAQFLKNEQ AVFQFTAEKFKEWGLTPN RKTVRLHMEFVPTACPHR SMVLHTGFNPVTQGRPSQ AIMNKLKDYFIKQIKNYM DKGTSSSTVVKDGKTSSA STPATRPVTGSWKKNQY GTWYKPENATFVNGNQPI VTRIGSPFLNAPVGGNLPA GATIVYDEVCIQAGHIWIG YNAYNGNRVYCPVRTCQ GVPPSHVPGVAWGVFKG | | K] | | (492/495) | | an recognition proteins (PGRPs) | 3 | 10 |
| | | | | | | | | | | CHAP domain | pfam05 257 | 1,42e-15 |
| | | | | | | | | | | Bacterial SH3 domain | pfam08 460 | 6,49e-14 |
| 141 | 66866 | 66363 | 1217 | MANETKQPKVVGGINLST RTKSKTFWVAHSAVALFA NQITGAFGLDYSAQIFQG VNIVGSILTLLAGLGIIVD NNTKGLKDSDIVQTDYLK PRDSKDPNEFVQWQANA NNASTFEIDSYENNAEPDT DDSDEVPAIEDEIDGGSAP SQDEEDTEEHGKVFAEEE | 167 | putative holin [Staphylococcus phage K] | YP_024463.1 | 6e-90 (165/167) | Holin | Phage_holin_1 | pfam04 531 | 1,53e-25 |

FIG. 14KK

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | VK | | | | | | | | |
| 142 | 67136 | 66951 | 1218 | MASAKQLYYTESLVGKAI INNKVSNKEEVWDKLELL PETKLEDLDNKQMSEVIK KLNQINE | 61 | ORF233 [Staphylococcus phage G1] | YP_241098.1 | 1e-25 (61/61) | | No putative conserved domains have been detected | | |
| 143 | 67369 | 67298 | 1219 | ACACCCUUAGUAUAAUU AGUAGUACAAGGGUCUC CAAAACCCUUAGUCUUU GUGCAAAUCAAAGAGG GUGUG | | | | | tRNA3-Trp | | | |
| 144 | 67448 | 67376 | 1220 | GGUUCUUAGCUCAGAU GGUAGAGCACUAGAUU GAAGCUCUAGGUGUCAU UGGUUCAAAUCCAAUAG AAACCA | | | | | tRNA2-Phe | | | |
| 145 | 67528 | 67455 | 1221 | GGCUCAUUGGUGUAACU CGUUAACACACUGCCCU GUCACGGCAGAGAGUAC GAGUUCGAGUCUCGUAU GGGUCG | | | | | tRNA1-Asp | | | |
| 146 | 68901 | 68683 | 1222 | MKRQKMFYSSLICKECGN VFKVPRKRANKREEGHIK DIYCIKCCKTTKHEDNRS EAERRWDAIQEELTKDN | 72 | ORF200 [Staphylococcus phage G1] | YP_241099.1 | 1e-34 (72/72) | | No putative conserved domains have been detected | | |
| 147 | 69593 | 69384 | 1223 | MSKHIEITMSSGAKYTLVS TDEKSYNRQDIDYMLRG MIDETSIKVYTESAITSPQV YINPNRIESFKIVF | 69 | ORF207 [Staphylococcus phage G1] | YP_241100.1 | 1e-32 (69/69) | | No putative conserved domains have been detected | | |

FIG. 14LL

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Conserved Domains Name | Acc No | E value |
|---|---|---|---|---|---|---|---|---|---|---|---|---|
| 148 | 69939 | 69606 | 1224 | LDKEINNLVSQVETIKSKI QEGNYIDRGTFKDLEVEV AELRKMIVSIDKDVAVNS EKQSAIYVQLERLDEKISE LAESTKTKDTKKKDTTEK VLLVLGAILSFVFNKFA | 110 | ORF209 [Staphylococcus phage G1] | YP_241101.1 | 5e-53 (108/110) | | PHA02414, hypothetical protein | PHA02414 | 8.04e-30 |
| 149 | 70277 | 69951 | 1225 | LTKYKDILKLEFKDSLAH FKRDRRFFHMYRIDRLLIN GSIIYFDYYYLPSDDPNIVI KELDLQDFGKLRFEIDTK TSYGKVVTDNYMEINDF LENYDIHSESETVRP | 108 | hypothetical membrane protein MbpC [Staphylococcus phage A5W] | ACB89047.1 | 6e-51 (100/108) | Membrane protein MbpC | No putative conserved domains have been detected | | |
| 150 | 70717 | 71103 | 1226 | LNNNIAIFIFKTLVIIIFLLL FLSVVNSLSLIYSIRPSVV MAYFTFGGIVSDVALTMT DKFLLKKEDPLPEYVLKK VEINDKEISIIKKIIESNYDI TSEEIKVRAKAQQRLEED SKEEDNDENEERN | 128 | hypothetical membrane protein MbpD [Staphylococcus phage A5W] | ACB89048.1 | 7e-42 (112/128) | Membrane protein MbpD | No putative conserved domains have been detected | | |
| 151 | 71081 | 71359 | 1227 | MKTKKEIKEQRKELKDG ATTVSLVRKGDKRIASPS RICSLCGQQLSGMSYTKG KALSKVNHFHLQYSKYIY FDICADINNCYKNLRKRG EMD | 92 | ORF161 [Staphylococcus phage G1] | YP_241104.1 | 3e-46 (90/92) | | No putative conserved domains have been detected | | |
| 152 | 71356 | 71766 | 1228 | LSAENIRDIINKKKLEEED TRKYIADGFMNGIGKLMY EFNKKVDNKEIEVKDPND LYKLFVIFSQMQNMVNET SEGGAIPQLSRPQOELFEEI TTEDSNGESTVDLQKISE | 136 | ORF133 [Staphylococcus phage G1] | YP_241105.1 | 2e-69 (132/136) | | No putative conserved domains have been detected | | |

FIG. 14MM

Table 11 - Features of phage F125/10 gene products and assignment of putaive functions.

| orf | Start position | Stop Position | SEQ ID NO. | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| | | | | MSAEDITEMISEKEKVMN EENSKTF | | | | | | | | |
| 153a | 71782 | 72021 | 1229 | MDGKELIKIAQETFQTEKI TREQIDHIINMLNPSTYML KYHTLRGHPITFSIPNRDR SKAQAHRPWQVRKHTMR TINLF | 79 | hypothetical protein KgORF35 [Staphylococcus phage K] | YP_024465.1 | 5e-34 (68/69) | Terminase large subunit | No putative conserved domains have been detected | | |
| 153b | 72255 | 72398 | 1230 | MIVNDTHPNKAVIKSRQL GLSEMGVMEMVHFADM HSYANAKCLYTFN | 47 | | | 2e-19(45/45) | | No putative conserved domains have been detected | | |
| 154* | 72647 | 73558 | 1231 | MGKKLTNTEFLNRVFQLV SDEYSFLEEYKGRHTKLR CKHNLCSYEWDVEPGAF LGNKNKAGSRCPSCYGN VTKTTDKFKKEIYNLTKD EYRLLSEYINAKTKVKIK HSKCGNTFSMTPNTFINGS RCPECNPQKPYNTDSAKD RINKETNGTFELVSEYKG CYELMKLKHHECGNIVEI NMQSIDSNRLNCPYCYNR SRGELLVSSFLLSKNIPFE VQKRFDGFKKYPYDFYIA DYNTVIEYHGEQHYKPIK FYGGEDRLVRQKNIDLKK KNFVEGKGINYLEIPYTLN NQNKVNEFLINYFK | 303 | ORF031 [Staphylococcus phage Twort] | YP_238727.1 | 5e-49 (119/307) | | No putative conserved domains have been detected | | |
| 153c | 73663 | 75123 | 1232 | MKKFVQSRLNPVLEKEYF RDIVDWDKDSLGFKKIRN SSLFFRTSSKASTVEGVDI DYLSLDEYDRVNLLAESS | 486 | hypothetical protein KgORF35 [Staphylococcus phage K] | YP_024465.1 | 0,0 (486/486) | Terminase large subunit | Terminase_GpA | pfam05876 | 5,63e-17 |

FIG. 14NN

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | ALESMSSSPFKIVRRWSTP SVPGMGIHKLYQQSDQW YYGHRCQHCDYLNEMSY NDYNPDNLEESGNMLCV NPEGVDEQAKTVQNGSY QFVCQKCGKPLDRWYNG EWHCKYPERTKGNKGVR GYLTQMNAVWISADELK EKEMNTESKQAFYNYILG YPFEDVKLRVNEEDVYG NKSPIAETQLMKRDRYSH IAIGIDWGNTHWITVHGM LPNGKVDLIRLFSVKKMT RPDLVEADLEKIIWEISKY DPDIIIADNGDSGNNVLKL INHFGKDKVFGCTYKSSP KSTGQLRPEFNENNNRVT VDKLMQNKRYVQALKTK DISVYSTVDDDLKTFLKH WQNVVIMDEEDEKTGEM YQVIKRKGDDHYAQASV YAYIGLTRIKELLKEGNGT SFGSTFVSTDYNQEGNKQ FYTDE | | K] | | | | | | |
| 155 | 75116 | 75937 | 1233 | MNRGEIDLTDKLFYGTIS NEEINKSVLNLLLGEELSL DYVSKNSDTLDVKYEHV YKSLGFDNFFDCFLYANR EPEIVHKGGDKNLGGLNK VKRTVIRNGKEMEMTVY EDGNKENDSKEKQEGKE EVSRSAVGARAJSNGEEG KVNPKKVANSLSSLSKKG VDVSHINTNLSLYKEFVD DNGDTLGITSFKRTENDII | 273 | hypothetical protein KgORF36 [Staphylococcus phage K] | YP_024466.1 | 2e-150 (270/273) | | No putative conserved domains have been detected | | |

FIG. 1400

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | LESYASSPDSDGVGARAI MELLRLSIKENKNAVVYD IELPEAVEYLKTLGFKPNK DGYILRKDVKQFLGDYS DFI | | | | | | | | |
| 156 | 75915 | 76097 | 1234 | VIVILFSTIVIYSIVFILYIV LKTTYIKSNMSRIDNTTEL LKILQEDIEGKIKKEGRNK | 60 | ORF235 [Staphylococcus phage G1] | YP_240894.1 | 4e-23 (56/60) | | No putative conserved domains have been detected | | |
| 157 | 76094 | 76573 | 1235 | MTLEENKLTLEESITPLSK EEKEDSIKEFSSLLCEMVN RLYKSYNVFRQDPMDET QRLDGSLMVFQSRLNDPL TGDLHDKMYKLAFSKRID IFEANKQFRKDVEAGKAI ELGDVAIIDTALSNILSGN EFQGSISFMLRKDFEEKER IRKEEEKLNNL | 159 | hypothetical protein KgORF37 [Staphylococcus phage K] | YP_024467.1 | 6e-86 (159/159) | | No putative conserved domains have been detected | | |
| 158 | 76615 | 77826 | 1236 | LKKKPQGNEVIITITVMIA VFVVIMTIFFNKYQDAKE DKDRYQRLVEIYKKADD NDGETKKKYVKRLNKAE EELKKVKKETNYKDYNK KSSKERQKEDKETREKIY DVTGDDDLILVKNNIDFS DKVDKPEILISEDQIGTITV PVDSGYEKQTVGSIITSVL GSPFLSPGSNSIDGLSVIND NVYPNTVDSIVEDTKPSIN LPMDNPIITNPVEPTIPSDT IPIDNPSVPVFPENPVDN NQGNTDNPNPPPGYTDE DGGRGSGGGNSEPPSTE | 403 | hypothetical membrane protein MbpF [Staphylococcus phage A5W] | ACB89054.1 | 2e-163 (375/403) | Membrane protein MbpF | No putative conserved domains have been detected | | |

FIG. 14PP

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | EPSDNGNTGGDWEEKP DPGEEPSDNGNTGGNGGE VTPEPDPTPSEPEQPNENS DEGNEEKPSEPSDNPDEN GGWETEPTEPSPSEPDD KVDEEDKNEDTTTDDKQP TEQPDDNNIDNEDKTEEE | | | | | | | | |
| 159 | 77969 | 78253 | 1237 | MIFVHSKFSSKNVFVLYVI YAIIGTYIVLTMFQTTS VLIKNDVIDSIENTEHYIGF NDPIIIFTISFIGAILGGIWY KMMKITKKSNFKDKK | 94 | hypothetical membrane protein MbpE [Staphylococcus phage A5W] | ACB89055.1 | 2e-45 (94/94) | Membrane protein MbpE | PHA02256, hypothetical protein | PHA02 256 | 8.96e-22 |
| 160 | 78262 | 78642 | 1238 | VNRLIFSKDKKWDEAKDF IKGQGMQDNWIEIVDYYR QHGKHVAVFIALNKVKY MILEATKDNKVILVDKDN NILLEDYDIVMESKKMFY YIEEPFEVKINIPQHIRDVT YNNTVVLTTVRGSRGD | 126 | hypothetical protein KgORF40 [Staphylococcus phage K] | YP_024470.1 | 2e-64 (122/123) | | No putative conserved domains have been detected | | |
| 161 | 78646 | 80346 | 1239 | LADLFKQFRLGKDYGNNS TIAQVPIDEGLQANIKKIE QDNKEYQDLTKSLYGQQ QAYAEPFIEMMDTNPEFR DKRSYMKNEHNLJIDVLK KFGNNPILNAILTRSNQV AMYCQPARYSEKGLGFE VRLRDLDAEPGRKEKEE MKRIEDFIVNTGKDKDVD RDSFQTFCKKIVRDTYIYD QVNFEKVFNKNNKTRLE KFIAVDPSTIFYATDKKGK IIKGGKRFVQVVDKRVVA | 566 | putative portal protein [Staphylococcus phage K] | YP_024471.1 | 0.0 (555/566) | Portal protein | Phage_porta 1 | pfam04 860 | 1,00e-13 |

FIG. 14QQ

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | SFTSRELAMGIRNPRTFLS SSGYGLSEVEIAMKEFIAY NNTESFNDRFFSHGGTTR GILQIRSDQQQSQHALENF KREWKSSLSGINGSWQIP VVMADDIKFVNMTPTAN DMQFEKWLNYLINIISAL YGIDPAEIGFPNRGGATGS KGGSTLNEADPGKKQQQ SQNKGLQPLLRFIEDLVN RHIISEYGDKYTFQFVGG DTKSATDKLNILKLETQIF KTVNEAREEQGKKPIEGG DIILDASFLQGTAQLQQD KQYNDGKQKERLQMMM SLLEGDNDDSEEGQSADS SNDDKSNPEVGTDSQIKG DSNVYRTETSNKGQGKK GEKSSDFKH | | | | | | | | |
| 162 | 80364 | 81518 | 1240 | MSVIYKDNNWIDLTNVPY LQKGDSGYRKDIPRKNW KKCLNTEVSFSYKGKKGL FYVTYRKEDKGKVKVEY DKYVKIIDPHDLKTLNINK IVNPPNKAKYREQEVING DTVRNIRKVKNTGIVYTM LCSEYEEYDIRESDLLRG RGSPYKSGRKVCYNNSLY SVENLREYICDLEYAKTV TKFSHKDIKCKCPICSEEK VMKVNKLVNNGFSCHRC SSTITYPERLMIGLLELNN LNYEYQKVFKDLPNRKFD FYLPKLNMVIETHGLQHY RELNGYMNHEKTKESDL | 384 | conserved phage protein [Staphylococcus phage CNPH82] | YP_950629.1 | 6e-53 (133/332) | | No putative conserved domains have been detected | | |

FIG. 14RR

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | | | EKYNYCKNNNIDYIEIDCS YSDLSFILSNVENSKLNSIL KNKNYDNLSNYIIRSKND DVKYNIYLDYCKGLSKKE LKDKYNKTSYYINRSIEIF KH | | | | | | |
| 163 | 81712 | 82485 | 1241 | LEEIKFNAFVPMDLKKSV STASDTNEYSIVSGWASTP SMDLQNDIVNPKGIDIEYF KSQGYINYEHQSDKVVGI PTENCVDIEKGLFIEAKL WKNDENVVKMLDLAEKL EKSGSGRRLGFSIEGAVK KRNINDNRVIDEVMITGV ALVKNPANPEATWESFM KSFLTGHGTSPDTQVDAG ALRKEIASSITNLAYVTK IKDLKEFNDVWNGVVED LSKSNSMGYEESVLTLQL AKGLSRKDAELAVMDIN KQKLE | 257 | hypothetical protein KgORF42 [Staphylococcus phage K] | YP_024472.1 | 1e-146 (256/257) | Prohead protease | Peptidase_U35 | pfam04586 | 8.72e-05 |
| 164 | 82504 | 83460 | 1242 | MSKEMQNILEEYDKLNA QEAVSKSVEDDEKNTVES TEEQVAETTEEPAKEPEK VSEEDAKEAQEQGEKVES EEVAEDNEDEEVEKSAKE SKDPVDQKDTKTENKDN EKRKNKKDKKEDSDSDD EDKDTDDDKDKKEDKKE KTSKSISDEDITTVFKSILT SFENLNKEKENFATKEDL SEVSKSINELSAKISEIQAE DVSKSVDTDEEAVEKSVT STNGEQEKVEGYVSKSVD | 318 | ORF029 [Staphylococcus phage G1] | YP_240902.1 | 9e-170 (317/318) | | No putative conserved domains have been detected | | |

FIG. 14SS

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | TEEQAETGEAKSEEAEEV QEDNTFKGLSQEERTKFM DSYKAQAKDPRASKHDL QSAYQSYLNINTDPTNAS EKDIKTVKDFAQI | | | | | | | | |
| 165 | 83576 | 84967 | 1243 | MTIEKNLSDVQQKYADQF QEDVVKSFQTGYGITPDT QIDAGALRREILDDQITML TWTNEDLIFYRDISRRPAQ STVVKYDQYLRHGNVGH SRFVKEIGVAPVSDPNIRQ KTVSMKYVSDTKNMSIAS GLVNNIADPSQILTEDAIA VVAKTIEWASFYGDASLT SEVEGEGLEFDGLAKLID KNNVINAKGNQLTEKHL NEAAVRIGKGFGTATDAY MPIGVHADFVNSILGRQM QLMQDNSGNVNTGYSVN GFYSSRGFIKLHGSTVME NELILDESLQPLPNAPQPA KVTATVETKQKGAFENEE DRAGLSYKVVVNSDDAQ SAPSEEVTATVSNVDDGV KLSISVNAMYQQQPQFVS IYRQGKETGMYFLIKRVP VKDAQEDGTIVFVDKNET LPETADVFVGEMSPQVVH LFELLPMMKLLPLAQINASI TFAVLWYGALALRAPKK WARIKNVRYIAV | 463 | putative capsid protein [Staphylococcus phage K] | YP_024474.1 | 0,0 (462/463) | Capsid protein | No putative conserved domains have been detected | | |
| 166 | 85059 | 85355 | 1244 | MLYYKKLLDKKMATVY GTVEIDKDGVVKGLTKEQ EKEFANVPGFEFEEKKT | 98 | ORF151 [Staphylococcus phage] | YP_240904.1 | 9e-46 | | No putative conserved domains | | |

FIG. 14TT

Table 11 - Features of phage F125/10 gene products and assignment of putative functions.

| orf | Start position | Stop Position | SEQ ID NO. | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| | | | | TRKQSASTSKEEFPKEEEK KASTRKTTSTTRKSTARK TTAKKDENK | | G] | | (97/98) | | have been detected | | |
| 167 | 85368 | 86276 | 1245 | MVNSMFGGDLDPYEKSL NYEYPYHPSGNPKHIDVS EIDNLTLADYGWSPDAVK AYMFGIIVQNPDTGQPMG DEFYNHILERAVGKAERA LDISILPDTQHEMRDYHET EFNSYMFVHAYRKPILQV ENLQLQFNGRPHYKYPAN WWKVEHLAGHVQLFPTA LMQTGQSMSYDAVFNGY PQLAGVYPPSGATFAPQM IRLEVSGMLPRKKAGRN KPWEMPPELEQLVIKYAL KEIYQVWGNLIIGAGIAN KTLEVDGITETIGTTQSAM YGGASAQILQINEDIKELL DGLRAYFGYNMIGL | 302 | hypothetical protein KgORF45 [Staphylococcus phage K] | YP_024475.1 | 3e-117 (301/302) | | No putative conserved domains have been detected | | |
| 168 | 86290 | 87168 | 1246 | MEKPYMIGANSNPNVINK STIYTTTTQADEQDKPKY TTRLEFDTIDMIRFINDRGI KVLWEEAYFCPCLNPDTG HPRVDCPRCHGKGIAYLP PKETIMAIQSOEKGTNQL DIGILDTGTAIGTTQLEKRI SYRDRFTVPEVLMPQQMI YFVNKDRIKKGIPLYYDV KEVTYIATQDGTVYEEDY EIKNNRLYLNEKYENHTV TLKILMTLRYVVSDILKES RYQYTKFNQPKSKFENLP QKLLLKREDVIVLQDPYK | 292 | capsid protein [Staphylococcus phage 812] | ABL87113.1 | 1e-170 (291/292) | Capsid protein | No putative conserved domains have been detected | | |

FIG. 14UU

Table 11 - Features of phage F125/10 gene products and assignment of putative functions.

| orf | Start position | Stop Position | SEQ ID NO. | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
| | | | | VNDGIEEDLEIQVDDPKA SASNPSNLGGFFGGAFK | | | | | | | | |
| 169 | 87168 | 87788 | 1247 | MPVHGKRPNLFKNKNYK QVGKRTIDGMRSEVLDKL QATAQQVENTSIKRMPTY LQITEKKLEKEGVVDLKK AFAHSSKKKTSKDGGWV LTVPIRIKTSRMNNSTYQD MRTLKVDKGTGSVSKITD YLEGRRKNVSHPSMKPEP MTHNMTKVKRGKQSSYF IFRTVSSKSPASSWILNRD KVNEDNFSKTTLKTVKQL MNWKMKNLN | 206 | hypothetical protein KgORF47 [Staphylococcus phage K] | YP_024477.1 | 1e-116 (206/206) | | No putative conserved domains have been detected | | |
| 170 | 87807 | 88643 | 1248 | MAITSVDSYLLSEIKPRLN TVLENCYIIDEVLKDFDY QTRESFKEAFCGKNAQHE VTVGFNFPKFKNNYEAHY LIQLGQGQETKNSLGSIQS SYFEATGDTLVESSTAIRE DDKLVFTVSKPIGELIKVE DIEFAKYDNLQVEGNKVS FKYQTNEDYENYNANIIF TEKKNDSKGLVKGFTVEE QVTVVGLSFNVDVARCL DAVLKMILISMRDSIEFQQ TFQLQNLSFGDIAPIIEDG DSMIFGRPTIIKYTSSLDLD YTITQDINKLTFKERKDW K | 278 | hypothetical protein KgORF48 [Staphylococcus phage K] | YP_024478.1 | 4e-160 (278/278) | | Crotono- betainyl- CoA:carniti ne CoA- transferase | PRK03 525 | 8.14e- 03 |
| 171 | 88645 | 88860 | 1249 | MARKKTPENNTPKFNGY VHIDTFLDTAKTLFNMKD | 71 | ORF202 [Staphylococcus phage | YP_240909.1 | 2e-34 | | No putative conserved domains | | |

FIG. 14VV

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | SQVAGFKAYMEGSHYLFS EQFFLPSLEKYLGRKLDI | | G] | | (70/71) | | have been detected | | |
| 172 | 88887 | 90650 | 1250 | MAVEPFPRRPITRPHASIE VDTSGIGGSAGSSEKVFCL IGQAEGGEPNTVYELRNY AQAKRLFRSGELLDAIEL AWGSNPNYTAGKILAMRI EDAKPASAEIGGLKVTSKI YGNVANNIQVGLEKNTLS DSLRLRVIFQDDRFNEVY DNIGNIFTIKYKGEEANAT FSVEHDEETQKASRLVLK VGDQEVKSYDLTGGAYD YTNAIITDINQLPDFEAKL SPFGDKNLESSKLDKIENA NIKDKAVYVKAVFGDLE KQTAYNGIVSFEQLNAEG EVPSNVEVEAGEESATVT ATSPIKTIEPFELTKLTGGT NGFPPATWADKLDKFAH EGGYYIVPLSSKQSVHAE VASFVKERSDAGEPMRAI VGGGFNESKEQLFGRQAS LSNPRVSLVANSGTFVMD DGRKNHVPAYMVAVALG GLASGLEIGESITFKPLRVS SLDQIYESIDLDELNENGII SIEFVRNRTNTFFRIVDDV TTFNDKSDPVKAEMAVG EANDFLVSELKVQLEDQF IGTRTINTSASIIKDFIQSYL GRKKRDNEIQDFPAEDVQ VIVEGNEARISMTVYPIRS FKKISVSLVYKQQTLQA | 587 | major tail sheath protein [Staphylococcus phage 812] | ABL87117.1 | 0.0 (584/587) | Major tail sheath protein | Phage_sheath_1 | pfam04984 | 2.11e-07 |

FIG. 14WW

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 173 | 90723 | 91127 | 1251 | MASEAKQTVHTGNTVLL MIKGKPVGRAQSASGQRE YGTTGVYEIGSIMPQEHV YLRYEGTITVERLRMKKE NFADLGYASLGEEILKKDI IDILVVDNLTKQVIISYHG CSANNYNETWQTNEIVTE EIEFSYL | 134 | capsid protein [Staphylococcus phage 812] | ABL87118.1 | 3e-73 (134/134) | Capsid protein | No putative conserved domains have been detected | | |
| 174 | 91547 | 92476 | 1252 | MGKNQYTFNIKENKNKW YEWCKLQNVKPLVEYEN AQQIFYFEFLEGKFKGLIG KTYWASINRGSNMRMSC LTSESKDKYLKNLGKRKG IEVVEDYKGGRKLKHKFI VLEGKYQGCEGYITLNDL ENLGRVDNRSLSEKGRKQ YFDKQARLRDCIILEYPKD YRIKTKDKIVVKDKEGHV HNIIVQDFFEKSSLLELSC ASEGEKIVKEILTKNSIKFE KEKSPRNKEGKVQREDFY INENNKEYAIEYNGAQHY IDSTGYLKDTLETTQKRD KLKKEYSKDKGINLLIIPY TITDKKEMEKIILNFLNK | 309 | ORF018 [Staphylococcus phage Twort] | YP_238556.1 | 2e-19 (79/239) | | No putative conserved domains have been detected | | |
| 175 | 92534 | 92692 | 1253 | MNNRQAKIKGYNQFHYY DFPTTKGKFKDIMKRKSR TELKKDLQKERKYYLDK | 52 | ORF245 [Staphylococcus phage Twort] | YP_238558.1 | 5e-11 (36/52) | | No putative conserved domains have been detected | | |
| 176 | 92682 | 92822 | 1254 | LTNKRKTIGKMSNTRAT WNINPVTKVKKDKTKYS RKNKHKGLDNYN | 46 | ORF293 [Staphylococcus phage G1] | YP_240912.1 | 1e-10 (44/46) | | No putative conserved domains have been detected | | |

FIG. 14XX

Table 11 - Features of phage F 125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
| 177 | 92864 | 93322 | 1255 | MSTFWSERRTTNKDRQV KKHYTQMSMYERKKCVE LLQETTENRIINFTRHSAK KVKGKPTTNIPKLIGFIFK NKFAYENIIEYNNTDYNG NIERRIVVKHPKVITVEGK PSYQFLTISLEDARVITVW YNSVDDTHRTLDLNYYS KDLTIQ | 152 | hypothetical protein KgORF51 [Staphylococcus phage K] | YP_024481.1 | 2e-84 (152/152) | | PHA02264, hypothetical protein | PHA02 264 | 1.25e-30 |
| 178 | 93335 | 93526 | 1256 | MGITIVNSYFILSNIFLIILTI LNGKGTVTRESLTMSKIL VVITSIQFLACLINGIYWS LKF | 63 | ORF215 [Staphylococcus phage G1] | YP_240914.1 | 3e-25 (62/63) | | No putative conserved domains have been detected | | |
| 179 | 93599 | 93910 | 1257 | MSQDKLRAIYTEMKVEL HKFPKEVDITSKSTAIAIN QILDKFKTLTEQAGKITRK YLEGQEILTIDYEYYDSLQ EYYIYLLRNSEKIEQSLQEI TKRTGEYVK | 103 | hypothetical protein KgORF52 [Staphylococcus phage K] | YP_024482.1 | 3e-51 (103/103) | | PHA02265, hypothetical protein | PHA02 265 | 2.50e-17 |
| 180 | 94042 | 94500 | 1258 | MAEIKKEQDVQETTKEE KKDVSKMTPEEIDKLKYQ DKQFKEQVINKVIKGVND TWEKEYNFEELDLRFKVK IKLPNAREQGNIFALRSAY LGGMDMYQTDQVIRAYQ MLATLQEVGIEVPKEFQD PDDIYNLYPLTVMYEDWL GFLNSFRY | 152 | hypothetical protein KgORF53 [Staphylococcus phage K] | YP_024483.1 | 2e-82 (152/152) | | No putative conserved domains have been detected | | |
| 181 | 94544 | 95080 | 1259 | MESIVKQPLSRNLWAIMK EFNVLPTEQRFKDLDDYQ IEFIIGNMNRDVYEHNKQ | 178 | gp ORF080 [Staphylococcus phage] | ACB89073.1 | 1e-98 (178/178) | | No putative conserved domains have been detected | | |

FIG. 14YY

Table 11 - Features of phage FI25/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | LKQAQKGGKFDSQFEDD DSSWWNESHEDFDPVPDF LDADDLAQQVEAKLSDR DKEERAKRNDAELNDETE GLTTQHLAMMEYIRQKQ QELDDEVGNGKTSEEDAT ISQDSVNKALEDLDDDW YM | | A5W] | | | | | | |
| 182 | 95136 | 99191 | 1260 | MAMNDDYRLVLSGDSSD LENSLKAIELYMDSLESK NIDAPLDNFLKKLKVIAK EVKNVQNAMDKQDGKS VISSKDMDESIKSTQSATK NINELKKALDDLQKENIS KGIAPDPFVEKAYAKMG KVVDETQEKLEKMSSQKI GSDASIQNRIKEMKTLNQ VTEEYNKISKDSSATKDY TKRLRANRNMTRGYMER SEGTGRLTYDQGARVRSE LGKISSYESQRKQNQRNL GQAREQYSNYRNQQQDL TKRRASGQINKAQYEQEL ASIKQEMKAIREELISNYE KLGAELDKTVQYYKGSV QKDFQSRDVDQQRGTFG RMVQERLPSIGSHAMMG TTAMATGLYMKGASLSE TNRPMVTSLGQNSDNMDI DSVRNAYGDLSIDNKLGY NSTDMLKMATSYEASVG HKSDEDTMAGTKQLAIG GRSLGIRDQEAYQESMGQ IMHTGGVNSDNMKEMQD AFLGGIKQSGMVGRQDE | 1351 | ORF001 [Staphylococcus phage G1] | YP_240918.1 | 0,0 (1348/1351) | | COG4372, un-characterized protein conserved in bacteria with the myosin-like domain | COG43 72 | 9,12e-03 |

FIG. 14ZZ

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 183 | 99270 | 101696 | 1261 | MRRIRRPKVRIEIVTDDNT FTLRFEDTRDYNGDEFGA KLLGFQTKNSMEDDSSVF QLKALGSIAEQSGEGRTL TKDQMSNLTAMQSTFAES GSKGLQGEQGANAINSID QGLKNGMNSSYARIAMG WGTQYQGLEGGYDLQKR MDEGISNPENLTDMADM ATQMGGSEKEQKYLFNR SMKEIGANLTMEQSDEIF KDAQSGKLSKEELAKKA KKMEKEGKKLEGEDNA1D YKESKSGKNDQNKSKTD DKAEDTYDMAQPLRDAH SALAGLPAPIYLAIGAIGA FTASLIASASQFGAGHLIG KGAKGLRNKFGRNKGGS SGGNPMAGGMPSGGGSP KGGGSPKGGGTRSTGGKI LDSAKGLGFLVGGAGW KGMFGGESKGKGFKQTS KEAWSGTRKVFNRDNGR KAMDKSKDIAKGTGSGL KDIYNDSIFGKERRQNLG EKAKGFGGKAKGLYGKF ADKFGDGGKNGILSQSPK AGGSGIGKLGKLAGGLGK GAGVLGVATSALSLIPAL ASGDSKAICGGIGSMGGG MAGASAGASIGALFGGV GAIPGALIGGAIGSFGGGA VGEKVGDMAKKANTKEG WNLGWTNGDKDGKNKF QDSLLGKPI | 808 | hypothetical protein KgORF56 [Staphylococcus phage] | YP_024486.1 | 0.0 (806/808) | Tail lysin | CHAP domain | pfam05 257 | 1,02e-14 |

FIG. 14AAA

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | | QINMAGDTYWDKLVMA NDIIRIFITPNDDPNDKEGR QERLIQVGMVSQVSKVGS YGNDQTQFRITGQSFVKP FMKFGLGVIQEVQAVLPE VGWLIDGDGDNEVKFTG SSAHEVMTGIIRRFIPYMK YNYTEKTYNTIDNYLDYD DLSSWDEFEKLTEVSAFT NFDGSLKQLMDMVTARP FNELFFKNSEKTPGKAQL VLRKTPFNPTEWRALDMI KVPTEDFIEEDVGKSDVE TYSIFTATPAGMLKELNG DVFSKPQFHPELTDRYGY TKFEVENIYLSTKSGSATE DSDSGDDNGTERGTYSK IMKDLSNYGRDNISKGID KYTSKLSSKYKNLKKAQ AKKIIEKFVKEGKVTEKE YEKITGNKVDDELTSDNR PKLTKDKLKSILKEKFKT QDDFNNSKKKKKAKTDA LKELTTKYRFGNKTHATT LLDEYIKYKGEPPNDEAF DKYLKAIEGVSNVATDTG SDASDSPLVMFSRMLFNW YHGNPNFYAGDIIVLGDP KYDLGKRLFIEDKQRGDT WEFYIESVEHKFDYKQGY YTTVGVTRGLKDAILEDG KGSPHRFAGLWNQSSDF MGGLMGEDTSKELKEKG VAEKQSSGGKDGGSDSG GAQDGGSLDSLKKYNGK LPKHDPSFVQPGNRHYKY | K] | | | | | | |

FIG. 14BBB

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name [organism] | Acc No | E value and identity | | Name | Acc No | E value |
| | | | | QCTWYAYNRRGQLGIPVP LWGDAADWIGGAKGAG YGVGRTPKQGACVIWQR GVQGGSPQYGHVAFVEK VLDGGKKIFISEHNYATPN GYGTRTIDMSSAIGKNAQ FIYDKK | | | | | | | | |
| 184 | 101710 | 102597 | 1262 | MATDKEAKDVIDKFIDNV FNFDVLTKERIKEKDEEIK KITTDDMYEKVVYIRPYV GVIQSLNPQHVQYESFSN NGYDIEAELSFRKVSYLV DKGSIPTDSLSTLTVHLVE RNQELLIDYFDEIQDVLY GEYMEEEYVFDEDVPLST ILALDLNDNLKSLSNIKY MFKGAPKENPFGTDKDV YIDTYNLLYWLYLGEDEE LAYPMNINYFFTEGRFFTI FGKGHKYKVDVSKFIVGD ILTFGRSDTNIGIYVGDGE FISMMGKFPKDETPIGKY KLDDYWNEFNGRVMRFD EEVYI | 295 | hypothetical protein KgORF57 [Staphylococcus phage K] | YP_024487.1 | 4e-167 (295/295) | | No putative conserved domains have been detected | | |
| 185 | 102597 | 105143 | 1263 | MVVRFQSSMGRSLKRVD SDDLNVKGLVLATVSKIN YKYQSVEVKVNNLTLGS RIGDDGSLAVPYPKSHIGR TPEGSVFGTKPLITEGSVV LIGFLNDDINSPIILSVYGD NEQNKMINTNPLDGGKFD TESVYKYSSSLYEILPSLN YKYDDGEGTSIRTYNGKS FFSMTSGEEEKPQATDFY | 848 | putative glycerophosphoryl diester phosphodiesterase [Staphylococcus phage K] | YP_024488.1 | 0.0 (845/848) | Glycero-phosphoryl diester phospho-diesterase | GDPD_SaGlpQ_lik e, glycero-phosphodiester phospho-diesterase domain | cd08601 | 1,43e-60 |

FIG. 14CCC

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | TGTEYQDLFTSYYGNKTL IEPRIQKAPNMLFKHQGV FYDDGTPDNHITTLFISER GDIRASVLNTETQKRTTQ EMSSDGSYRVIKQDDDL MLDEAQVWIEYGISEDNK FYIKNDKHKFEFTDEGIY1 DDKPMLENLDESIAEAMK NLNEIQKELDDINYLLEG VGKDNLEELIESTKESIEA SKKATSDVNRLTTQIAEV SGRTEGIITQFQKFRDETF KDFYEDASTVINEVNQNF PTMKTDVKTLKTKVDNL EKTEIPNIKTRLTELENNN NNADKIISDRGEHIGAMIQ LEENVTVPMRKYMPIPWS KVTYNNAEFWDSNNPTR LVVPKGITKVRVAGNVL WDSNATGQRMLRLKNG TYSIGLPYTRDVAISTAPQ NGTSGVIPVKEGDYFEFE AFQDSEGDRQFRADPYT WFSIEAIELETETMEKDFM LIGHRGATGYTDEHTIKG YQMALDKGADYIELDLQ LTKDNKLLCMHDSTIDRT TTGTGKVGDMTLSYIQTN FTSLNGEPIPSLDDVLNHF GTKVKYYIETKRPFDANM DKELLTQLKAKGLIGIGSE RFQVIIQSFARESLNIHNQ FSNIPLAYLTSTFSESEMID DCLSYGSYAIAPKYTTITK ELVDLAHSKGLKVHAWT VNTKEEMQSLIQMGVDG | | | | | | | | |

FIG. 14DDD

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | FFTNYLDEYKKI | | | | | | | | |
| 186 | 105250 | 106041 | 1264 | MPQSDGISNLHRIALRFPK EGGGYDMYRFKVNPENY TIDSPQRTTAIKTKSDIVIE DYGKDIEVINFTGTTGFRP VREADGLKTCKQKMEEL QSRVSEYAMQGGSGNVS GSYLQFFNFTDDSYYKVH LAPQGLKITRSKDEPLLFR YEITLVVIGSLTEADRSAV TTEEFGNVKPNASQRVDE GIKELDKNARKTRDRNNQ EISRRENTIPKSTGDNTNE GNRLKQSFPSSSIYNPRQS TNGLKGNIDNMALIIGYG DGGVSS | 263 | hypothetical protein KgORF59 [Staphylococcus phage K] | YP_024489.1 | 7e-151 (263/263) | | No putative conserved domains have been detected | | |
| 187 | 106041 | 106565 | 1265 | MNNFIPQPQGLLRFLNAL DIDLTSSHMNLLDEEVSF VSKFYTPQLQLSELAKKV LTNIKTDDIPVLEREFNDN TIIHKANDTLLKVQAPRM YMILQSIVLEAYAIVNCFV ENPSSLKYLTEEDVSITRE NLNYVADYLGNYDDYNS VVLDLRDLDLCFSAIELQL PLIKKEANV | 174 | ORF078 [Staphylococcus phage G1] | YP_240925.1 | 3e-95 (174/174) | | No putative conserved domains have been detected | | |
| 188 | 106565 | 107269 | 1266 | MRFKKHVVQHEETMQAI AQRYYGDVSYWIDLVEH NNLKYPYLVETDEEKMK DPERLASTGDTLIIPIESDL TDVSAKEINSRDKDVLVE LALGRDLNITADEKYFNE | 234 | putative bacteriophage baseplate protein [Staphylococcus phage K] | YP_024491.1 | 2e-134 (234/234) | Baseplate protein | COG3628, phage baseplate assembly protein W | COG36 28 | 1.50e-03 |

FIG. 14EEE

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | HGTSDNILAFSTNGNGDL DTVKGIDNMKQQLQARL LTPRGSLMLHPNYGSDLH NLFGLNIPEQATLIEMEVL RTLTSDNRVKSANLIDWK IQGNVYSGQFSVEIKSVEE SINFVLGQDEEGIFALFE | | | | | | | | |
| 189 | 107284 | 108330 | 1267 | MKTRKLTNILSKLIDKTM AGTSKITDFTPGSASRSLL EAVSLEIEQFYILTKENID WGIQEGIIEAFDFQKRQSK RAYGDVTIQFYQPLDMR MYIPAGTTFTSTRQEYPQ QFETLVDYYAEPDSTEIV VEVYCKETGVAGNVPEG TINTIASGSSLIRSVNNEYS FNTGTKEESQEDFKRRFH SFVESRGRATNKSVRYGA LQIPDVEGVYVYEETGHIT VFAHDRNGNLSDTLKEDII DALQDYRPSGIMLDVTGV EKEEVNVSATVTISNKSRI GDTLQKHIESVIRSYLNNL KTSDDLIITDLIQAIMNIDD VLIYDVSFDNLDENIIVPP QGIIRAGEIKVELK | 348 | hypothetical protein KgORF62 [Staphylococcus phage K] | YP_024492.1 | 0,0 (348/348) | | XtrcT, uncharacterized homolog of phage Mu protein gp47 | COG3299 | 2,38e-05 |
| 190 | 108351 | 111410 | 1268 | VANFLKNLHPLLRRDRNK KDNQDPNFALIDALNEEM NQVEKDAIESKLQSSLKTS TSEYLDKFGDWFGVYRK TDENDDVYRARIIKYLLL KRGTNNAIIDAIKDYLGR DDIDVSVYEPFTNIFYTNK SHLNGEDHLMGYYYRFA | 1019 | hypothetical protein KgORF63 [Staphylococcus phage K] | YP_024493.1 | 0,0 (1006/1019) | | No putative conserved domains have been detected | | |

FIG. 14FFF

Table 11 - Features of phage F125/10 gene products and assignment of putative functions.

| | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| orf | | | | VINVSIGDYFPVEIIDVINE FKPAGVTLYVTYDGASTI RGGAIIKWLDGLPKIETYQ EFDRFTGYDDTFYGHINM NQSKDTDNSSSDIFKTNHS LINSLDVLTGSSSVGRQYI NYGYVTSYVYNPGMTSS VNQISASTEGRGQEVPTD YYMYTSTKNNNTVELSM QTTSGVSYLYNNFNFRDY MSKYRPQVDLQSDEARRI VSDYIKELSIDYYLSAVIPP DESIEIKLQVYDFSINRWL TVSINNLSFYEKNIGSNIG YIKDYLNSELNMFTRLEIN AGKRDSVDIKVNYLDLM FYYYERGIYTIKPYKALIE NYLDISRETYVEAFKIASL SNGDIITKTGFQPIGYLKL VGNYENTRPSTINIVAKDT DNNPIESNELDVVNTVEN RNLLQSYKGANTIAREITS TKEFTVSGWAKEIYSTNY LSKVLKPGKVYTLSFDIEI TGNDLTLKSYSDNHGIYL YSNTKGIVVNGVKSMERT IGNKVSVTQTFFTAPTITDH RLLIYTGRYTSDGKASTPP VFFNTVKITELKLLSEGTSN LEYSPAPEDKPNVIEKGIK FNNILTNIQTLSNSDTILK NVTLYSYYGDNWVELK TLGNISTGETTETNNLIDL YGLQTVDYSNINPMSKVS LRSIWNVKLGELNNQEGS LSNMPNDYFNAVWQDID | | | | | | | |

FIG. 14GGG

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | KLSDIEIGSMRMVKDTEG GVFDGATGEIIKATLFNV GSYTDLDMLAYTLTNYTE PLTLGSSRLISELKEELTS ESFNVDNRIKVIDSIYEELP NTSIIKNGFVEREVTGSKY LDYGLYEPIEDGTRYKLIV EGEFKDNIEFIYLYNSNPN FNETFYPSEIINGVAEKEF IAKPSTEDKPRLNTDVRIY IRPYDSTISKVRRVELRKV | | | | | | | | |
| 191 | 11152 | 11204 2 | 1269 | MAIATYNSHVELAKYLVS KADSVYLTIGKSTPWSNE TNPPQPDENATVLQEVIG YKKATKVTLVRPSKSPED DKNLISYGNKSWVEVTP ENAKAEGAKWVYLESSIV GDELPLGTYRQVGFVMD LVAKSGISKFNLVPSEVES TGTLLFFDNKQFQNRSEQ TTAKERFIVEV | 173 | hypothetical protein KgORF64 [Staphylococcus phage K] | YP_024494.1 | 6e-96 (173/173) | | Bacterio-phage T4, Gp8 | pfam09 215 | 2.26e-03 |
| 192 | 11206 3 | 11552 1 | 1270 | MAINFKGSPYLDRFDPSK DRTKVLFNPDRPLQQAEL NEMQSIDQYYLKNLGDAI FKDGDKQSGLGFTLSEDN VLTVNPGYVYINGKIRYY DNDDSVKITGVGKETIGIK LTERIVTPDEDASLLDQTS GVPSYFSKGADRLEEKMS LTVNDPTSATIYTFMDGD LYIQSTNAEMDKINKVLA ERTYDESGSYKVNGFELF SEGNAEDDDHVSVVVDA GKAYVKGFKVDKPVSTRI | 1152 | hypothetical protein KgORF65 [Staphylococcus phage K] | YP_024495.1 | 0.0 (1151/1152) | | No putative conserved domains have been detected | | |

FIG. 14HHH

Table 11 - Features of phage F125/10 gene products and assignment of putative functions.

| orf | Start position | Stop Position | SEQ ID NO. | Aminoacidic sequence | Size (aa) | Homologous/similar proteins | | | | Conserved Domains | | |
|---|---|---|---|---|---|---|---|---|---|---|---|---|
| | | | | | | Name[organism] | Acc No | E value and identity | Predicted function | Name | Acc No | E value |
| | | | | SVPKSYDLGTAENESTIFN KSNNSISLANSPVKEIRRV TGQVLIEKERVTRGAQGD GQDFLSNNTAFEIVKVWT ETSPGVTTKEYKQGEDFR LTDGQTIDWSPQGQEPSG GTSYYVSYKYNKRMEAG KDYEVTTQGEGLSKKWYI NFTPSNGAKPIDQTVVLV DYTYYLARKDSVFINKYG DIAILPGEPNIMRLVTPPL NTDPENLQLGTVTVLPDS DEAVCISFATRLSMEDLQ KVKTRVDNLEYNQAVNA LDDGAMECQNPLTLRSVF SEGFISLDKADITHPDFGIV FSFEDAEATLAYTEAVNQ PKIIPGDTTAHIWGRLISAP FTEERITYQGQASETLNV NPYNIPNKQGVLKLTPSE DNWIDTENVTITEQKTKK VTMKRFWRHNESYYGET EHYLYSNLQLDAGQKWK GETYAYDREHGRTGTLLE SGGQRTLEEMIETIRIRDV SFEVKGLNPNDNNLYLLF DGVRCAITPATGYRKGSE DGTIMTDAKGTAKGKFTI PAGIRCGNREVTLKNANS TSATTYTAQGRKKTVQDI IIRTRVTVNLVDPLAQSFQ YDENRTISSLGLYFASKG DKQSNVVIQIRGMGDQG YPNKTIYAETVMNADDIK VSNNASAETRVYFDDPM MAEGGKEYAIVIITENSDY | | | | | | | | |

FIG. 14III

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | TMWVGTRTKPKIDKPNE VISGNPYLQGVLFSSSNAS TWTPHQNSDLKFGIYTSK FNETATIEFEPKDVSADRI VLMSTYLTPERTGCTWE MKLILDDMASSTTFDQLK WEPIGNYQDLDVLGLAR QVKLRATFES | | | | | | | | |
| 193 | 115570 | 115728 | 1271 | MPREVRDPYSQAKLFIPT VEEKSIKELEKTYKEKIDE ATKLINELKKERGEK | 52 | ORF262 [Staphylococcus phage G1] | YP_240931.1 | 3e-20 (52/52) | | No putative conserved domains have been detected | | |
| 194 | 115729 | 117651 | 1272 | MAFNYTPLTETQKLKDM YPKVNDIGNFLKTEVNLS DVKQISQPDFNNILASIPD SGNYYVTNSKGAPSGEAT AGFVRLDKRNVNYYKIY YSPYSSNKMYIKTYANGT VYDWISFKLDEGNLYNEG NTLNVKELTESTTQYATL VNPPKENLNTGWVNYKE SKNGVSSLVEFNPVNSTST FKMIRKLPVQFQKPNLLK DSLFVYPETSYSNIKTDN WDTPFWGYSSNSGRSGV RFRGENTVQIDDGSNTYP LVVSNRFKMGKELSVGD TVTVSVYAKINDPALLKD NLVYFELAGYDTVDDTSK NPYTGGRREITASEITTEW KKYSFTFTIPENTIGASGV KVNYVSLLLRMNCSSSKG NGAVVYYALPKLEKSPK VTPFITHENDVRKYDEIW SNWQEVISKDELKGHSPV | 640 | hypothetical protein KgORF66 [Staphylococcus phage K] | YP_024496.1 | 0,0 (633/640) | | PHA01818, hypothetical protein | PHA01 818 | 5,89e-04 |

FIG. 14JJJ

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| | | | | | | DIEYNDYFKYQWWKSEV NEKSLKDLAMTVPQGYH TFYCQGSIAGTPKGRSIRG TIQVDYDKGDPYRANKFV KLLFTDTEGIPYTLYYGG YNQGWKLLKQSETSTLL WEGTLDFGSTEAVNLNDS LDNYDLIEVTYWTRSAGH FSTKRLDIKNTSNLLYTRD FNISNDSTGSSVDFFEGYC TFPTRASVQPGMVKSITL DGSTNTTKVASWNEKERI KVYNIMGINRG | | | | | | | |
| 195 | 117673 | 118044 | 1273 | MAVKYDIGNNFIVLHRE GKYITGFTTVGGYDKELG QVKVNREILPAYFFDNFA YERYLYYSKPEEVIENKN YVPPQINDDEESQQITVPK EQYDSLKEELELMRKQQE AMMEMLQKLLGQKG | 123 | hypothetical protein KgORF67 [Staphylococcus phage K] | YP_024497.1 | 2e-63 (123/124) | | DUF2977, protein of unknown function | pfam11 192 | 2.73e-12 |
| 196 | 118051 | 119427 | 1274 | MALNFTTITENNVIRDLTT QVNNIGEELTKERNFDIT DDLVYNFNKSQKIKLTDD KGLTKSYGNITALRDIKEP GYYIGARTLATLLDRPD MESLDVVLHVVPLDTSSK VVQHLYTLSTNNNQIKML YRFVSGNSSSEWQFIQGLP SNKNAVISGTNILDIASPG VYFVMGMTGGMPSGVSS GFLDLSVDANDNRLARLT DAETGKEYTSIKKPTGTY TSWKKEFEPKDMEKYLLS SIRDDGSASFPLLVYTSDN | 458 | hypothetical protein KgORF68 [Staphylococcus phage K] | YP_024498.1 | 0.0 (448/458) | | PHA01818, hypothetical protein | PHA01 818 | 0.0e-00 |

FIG. 14KKK

Table 11 - Features of phage F125/10 gene products and assignment of putative functions.

| orf | Start position | Stop Position | SEQ ID NO. | Aminoacidic sequence | Homologous/similar proteins ||| Predicted function | Conserved Domains |||
|---|---|---|---|---|---|---|---|---|---|---|---|
| | | | | | Name[organism] | Acc No | E value and identity | | Name | Acc No | E value |
| | | | | Size (aa) | | | | | | | |
| | | | | KTFQQAIIDHIDRTGQTTF TFYVQGGVSGSPMSNSCR GLFMSDTPNTSSLHGVYN AIGTDGRNVTGSVVGGN WTSPKTSPSHKELWTGAQ SFLSVGTTKNLADDISNYS YVEVYTKHKTVEKTKGN DDSGTICHKFYLDGSGTY VCSGTFVSGDRTDTKPPV TEFYRVGVSFKGSTWTLV DSAVQNSKTQYVTRIIGIN MP | | | | | | |
| 197 | 119517 | 121265 | 1275 | 582 | MRLRIKNLYTYVEFEEDD KYLKDIFLKRVHTTIGAR QEGFQYSPAYKRGSWDG YVDFYVYEEDKFPTGLLF KIELLLGELQSRYNFQFET IDFRDESFLSEFDIIDFITL LDNNVGQITLRDYQYEAV YNSLTFYNGIAHLATNGG KTEVASGIIDQLLPQLEKG ERVAFFTGSTEIFHQSADR LQERLNIPIGKVGAGKFD VKQVTVVMIPTLNANLK DPTQGVKVTPKQNISKKI AQEILPKFEGGTNQKKLL KVLLDNTTPKTKVEQNVL SALEIIYQNSKTDAEVLLN LRNHNAHFQKIVREKNEK KYDKYQDMRDFLDSVTV MIVDEAHHSKSDSWYNN LMTCEKALYRIALTGSID KKDELLWMRLQALFGNV IARTTNKFLIDEGHSARPTI NIIPIANPNDIDRIDDYREA | putative helicase [Staphylococcus phage K] | YP_024499.1 | 0,0 (580/582) | Helicase | HELICc, helicase superfamily c-terminal domain | cd00079 | 1,74e-13 |

FIG. 14LLL.

Table 11 - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name [organism] | Acc No | E value and identity | | Name | Acc No | E value |
| | | | | YDRGITNNDFRNKLIAKL TEKWYNQDKGTLIIVNFIE HGDTISEMLNDLDVEHYF LHGEIDSETRREKLNDMR SGKLKVMIATSLIDEGVDI SGINALILGAGGKSLRQTL QRIGRALRKKKDDNTTQI FDFNDMTNRFLYTHANER RKIYEEEDFEIKDLGK | | | | | | | | |
| 198 | 12127 7 | 12289 0 | 1276 | MATKTQRKLYQYLEENA TENKFHISTKKELADSLG VSISALSNNLKKLEEENK VVTVSKRGKNGGVIITLV REYDTEELKEFNNSTDNII TSDLQYAKALREKHFPSY RYERKEQRRRTKIEMAQY NAIKDEKRRIIADMNFYSE GLPYPSKDIFNMSYDPEGF YKAYILCKLYDQYAISHM DAKHTSHLKAMSKATTK DEYDYHQHMSEYYRNK MIQNLPRNSVSDNFFGSK MFNTFYNFYLKIKDKNIN VFKYMQNVFKNVTFYYE NGMQPNPIPSPNFFSSDKY FKNYNNYIKGIKKGVNST NRHLGDTDSIINSSDYVK NPAVLHLHQLYTTGLNST LHDIDTMFEQALDLENAS YGLFGDMKHILLQYNSM IEEEIKNLPREEKDIINKYV KQCIINDYSPTSISPSARLS MFTMQKEHIVYNKQLNK GIKREDLLPLSLGGIVNKD SLSGMDIQNLEQNGNEYL | 357 | putative Rep protein [Staphylococcus phage K] | YP_024500.1 | 0.0 (536/537) | Transcription regulator protein | IITH_2, Helix-turn-helix domain | pfam12 840 | 2.66e-03 |

FIG. 14MMM

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | YMRQHTSTYYILRMFGD YLGYEVNLREVKYIVEKY NLIDKIPLTKEGMLDYNK LIHLVEEEVNNYE | | | | | | | | |
| 199 | 122883 | 124325 | 1277 | MSKKIKELLHKSMKDIHF AREVLDNLPKNLFSAESE DMGYLFTAIKRTAHISDK MSNEALAIKVEQLMGNN KEDEEKVTKTLTYLEDLY KVDVNEKDESVNYEIEKY IKTEMSKEVLVKFIAENK QEDSDNLHELVDKLKQIE VSDISGGNGEFIDFFEDTE KKQELLSNLATNKFSTGF TSIDNHIEGGIARGEVGLII APTGRGKSLMASNLAKN YVKSGLSVLYIALEEKMD RMVLRAEQQMAGAEKSQ IVNQDMSLNNKVYDAIQN HYQKNRKLLGDFYISKH MPGEVTPNQLEQIIVNTTI KKDKNIDVVIIDYPHLMR NPYAKYHSESDAGGKLFE DIRRLSQQYGFVCWTLAQ TNRGAYGSDVITSEHVEG SRKIVNAVEVSLAVNQKD EEFKSGFLRLYLDKIRNSS NTGERFVNLKVEPTKMIV RDETPEEKQEHIQLLSDN GKEDTSKFQNKDNKIEAI NNTFGGLPGV | 480 | putative helicase [Staphylococcus phage K] | YP_024501.1 | 0.0 (480/480) | Helicase | 41 helicase | PHA02 542 | 1,01e-9 |
| 200 | 124401 | 125421 | 1278 | MKFVFFTDSHFHLFTNYA KPDNEFVNDRFKEQIEAL QKVFDIAKKEEATVIFGG | 341 | putative exonuclease [Staphylococcus phage | YP_024502.1 | 2e-172 | Exonuclease | MPP_Mre11 _N,Mre11 nuclease, N- | cd00084 | 1,01e- |

FIG. 14NNN

Table 11 - Features of phage F125/10 gene products and assignment of putative functions.

| orf | Start position | Stop Position | SEQ ID NO. | Aminoacidic sequence | Size (aa) | Name[organism] | Acc No | E value and identity | Predicted function | Name | Acc No | E value |
|---|---|---|---|---|---|---|---|---|---|---|---|---|
|  | 4 | 9 |  | DLFHKRNSVDTRVYNKV FSTFAKNDEVPVLLLRGN HDATTNSLYTDSSIDTFEY LPNVSVIKSLNTILKDNVN IVFTAYGDETKEIKTYINS NYDKDMVNILVGHLGVE GSLTGKGSHRLEGAFGYQ DLLPDKYDFILLGHYHRR QYFQNPNHFYGGSLMQQ SFSDEQEANGVHLIDTEK MTTEFIPIHTRRFITIQGEDI PENFEQLIEEGNFIRVIGTA NHAKVLEMDDSMKDKN VEVQIKKEYTVEKRIDSD VSDDPLTIASTYAKQYSPE SEQEILECLKEVL |  | KJ |  | (295/345) |  | terminal metallo-phosphatase domain | 0 | 20 |
| 201 | 12542 9 | 12580 6 | 1279 | MKKYREYLNKTDAENLA EDWEKVTEDLWKVFKD MKPKINTLDISNVESKNL DKSKPILQFQDSDGVIENI CNVEGLEDGLSKMKKVF DDSNFEKHYYSRVVDHD EYYWIDYGSHHCFRVTK GDK | 125 | hypothetical protein KgORF73 [Staphylococcus phage KJ] | YP_024503 1.1 | 7e-65 (121/125) |  | PHA02275, hypothetical protein | PHA02 275 | 1,65e-21 |
| 202 | 12580 6 | 12772 5 | 1280 | MVVFKQVEVNNFLAIKEA TLELDNRGLILIEGENKSN ESFHSNGSGKSTLISAITY ALYGKTEKGLKADDVVN NIEKKNTSVKLKFDIGEDS YLIERYRKDKENKNKVKL FVNEKEITGSTNDVTDKQI QDLFGIEFNTYVNAIMYG QGDIPMFSQATDKGKKEI LESITKTDVYKQAQDVAK | 639 | putative exonuclease [Staphylococcus phage KJ] | YP_024504.1 | 0,0 (638/639) | Exonuclease | 46, endo-nuclease subunit | PHA02 562 | 1,71e-21 |

FIG. 14OOO

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | EKVKEVEEQQNNIRQEIY KLGYQLSTKDEYFQREIE QYNQYKEQLVQIENSNKE KDRLREQEEKQIEAQIEQL ASQIPTIPEDEFKHSEEYN KASQSLDLLSNKLTELNQ VYSEYNTKEQVLKSEIAT LSNSLNKLDTNDHCPVCG SPIDNSHKLKEQENINNQI ENKKQEITSVLEMKDTYK EAIDKVKDKSQEIKDKMS QEDQQEREHNNKINSIIQE ASRIKSDISSLENNKTYLK VKYQHQSVQGLEREEPSK EKHEEDKKELQESIDKHE ENIVQLETKKGKYQQAV DAFSNKGIRSVVLDFITPF LNEKANEYLQTLSGSDIEI EFQTQVKNAKGELKDKF DVIVKNSKGGGSYKSNSA GEQKRIDLAISFAIQDLIM SKDEISTNIALYDECFDGL DTIGCENVIKLLKDRLNT VGTIFVTHNTELKIPLFFQ TIKIVKENGVSKLEEK | | | | | | | | |
| 203 | 12772 5 | 12832 1 | 1281 | MKLKILDKDNATLNVFHR NKEHKTIDNVPTANLVD WYPLSNAYEYKLSRNGE YLELKRLRSTLPSSYGLD DNNQDIIRDNNHIRCKIGY WYNPAVRKDNLKIIEKAK QYGLPVITEEYDANTVEQ GFRDIGVIFQSLKTIVVTR YLEGKTEELRIFNMKSEE SQLNEALKESDIFSVDLTY | 198 | hypothetical protein KgORF75 [Staphylococcus phage K] | YP_024505.1 | 2e-111 (197/198) | | No putative conserved domains have been detected | | |

FIG. 14PPP

Table 11 - Features of phage F125/10 gene products and assignment of putative functions.

| orf | Start position | Stop Position | SEQ ID NO. | Aminoacidic sequence | Size (aa) | Homologous/similar proteins | | | Conserved Domains | | |
|---|---|---|---|---|---|---|---|---|---|---|---|
| | | | | | | Name [organism] | Acc No | E value and identity | Predicted function | Name | Acc No | E value |
| | | | | SDLGQIYNMLLLMKKISK | | | | | | | | |
| 204 | 128336 | 129403 | 1282 | MRFEDFLTQELGEPKENTI GELRYCCPFCGEKSYKFY VKQALDSSNGQYHCKKC DESGNPITFMKTYYNITG KQAFDLLESKNIDIERAPL LTTNNKDLTESEKLILML RGVHQDKGTTSIKPPRLPE GYKLLKDNLNNKEIIPFLK YLKGRGITLEQINNNIGY VINGSFYKVDGESKVSLR NSIIFFTYDNDGNYQYWN TRSIEKNPYIKSINAPAKQ DEVGRKDVIFNLNIARKK KFLVITEGVFDALTFHEY GVATLGKQVTENQIKKIID YVSIDTSIYIMLDTDALDN NIDLAYKLKTHFNKVYFV PHGDEDANDMGTRKAFE LLKQNRVLVTPESIQSYKI QQKLKL. | 355 | putative primase [Staphylococcus phage K] | YP_024506.1 | 0,0 (354/355) | DNA primase | dnaG, DNA primase, catalytic core | TIGR01391 | 1,95e-16 |
| 205 | 129469 | 129807 | 1283 | MSNNKKDILEFVDEYITA LRVGNEQRQHQLEEMGK EETATLTDVAKAITNLML GVNEQMTDLEYNNELNL NILIDALYKAELINEDVLD YIQESIDKSQEEPKNEEEK GEQE | 112 | ORF127 [Staphylococcus phage G1] | YP_240943.1 | 7e-56 (112/112) | | No putative conserved domains have been detected | | |
| 206 | 129807 | 130259 | 1284 | MEKNISTHTKGISQADME KWIEAVVQGTVDGKQVD EKTAKQLDRIGSRSVSLEE ATRIAKVLNAVTAQEVTG | 150 | ORF098 [Staphylococcus phage G1] | YP_240944.1 | 2e-78 (149/150) | | PHA02277, hypothetical protein | PHA02277 | 9,45e-43 |

FIG. 14QQQ

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains |||
|---|---|---|---|---|---|---|---|---|---|---|---|
| | | | | | | Name[organism] | Acc No | E value and identity | Predicted function | Name | Acc No | E value |
| | | | | DFNDAFNAIDLMMIIMED ELGVTQEKVGKAKDKLN EKREAYLKEKQEELRQKQ QEEAQKETESDSNEKVIQ LKKNDEQ | | | | | | | | |
| 207 | 130246 | 130854 | 1285 | MITNSKKKGDTFERKIAKE LTAWGYQFNRSPQSGG ASWGKDNNAVGDIVVPQ EANFPLVVECKHREEWTI DNVLLNNREPHTWWEQV INDSSKVNKTPCLIFTRNR AQSYVALPYNEKVYEDL RNNEYPVMRTDFHDNIRK DKFFYDVLITTMNGLTSF TPSYIISCYDKKDIKPYKK VESNLSEVSKHEDELINDL LSDI | 202 | ORF064 [Staphylococcus phage G1] | YP_240945.1 | 2e-115 (201/202) | | No putative conserved domains have been detected | | |
| 208 | 130844 | 131263 | 1286 | VIYKEGKISMTSKERPLIV YFSGTGQTERLVNKININN SFETFRVKSGKEKVNKPFI LITPTYKKGAIPKQIERFLE INGSPKEVIGTGNKQWGS NFCGASKKISEMFKIPLIA KVEQSGHFNEIQPILEHFS NKYKVA | 139 | putative NrdI protein [Staphylococcus phage K] | YP_024509.1 | 1e-68 (130/130) | Ribonucleotide reductase protein | Flavodoxin_NdrI | pfam07972 | 1,62e-29 |
| 209 | 131278 | 133392 | 1287 | MATYGKWIELNNEITQLD DNGKNKLYKDQEALDEY LKYIEDNTRKFNSEVERIR VLTKEGTYDKIFDKVPDTI IDEMTKLAYSFNFKFPSF MAGQKFYESYASKQYDE NKKPIFVEDYEQHNVRVA | 704 | putative ribonucleotide reductase large subunit [Staphylococcus phage K] | YP_0245101 | 0,0 (699/704) | Ribonucleotide reductase large subunit | PRK07632, ribo-nucleotide-diphosphate reductase subunit | PRK07632 | 0,0e-00 |

FIG. 14RRR

Table 11 - Features of phage F125/10 gene products and assignment of putative functions.

| of | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 210 | 133406 | 134455 | 1288 | MDITQKVKQHNKNAVLK ATNWNIEDDGMSDIYWE QGISQFWTPEEFDVSRDLS LYLFQNDYVKARELLVQL MEQTFQPSTPTYNNSGQA NRGELSSCYLFVVDDSIES LNFVEDSVANASSNGGGV AIDLTRIRPKGAPVRNRPN SSKGVIAFAKAIEHKVSIY DQGGVRQGSGAVYLNIFH NDILDLLSSKKINASESVR LDKLSIGVTIPNKFMELVK EGRPFYTFDTYDINKVYG KYLDELNIDEWYDKLLD NDSIGKVKHDAREVMTDI AKTQLESGYPYVFYIDNA NDNHPLKNLGKVKMSNL CTEISQLQEVSEIYPYSYS NKNVINRDVVCTLGSLNL VNVVEKGLLNESVDIGTR ALTKVTDIMDLPYLPSVQ KANDDIRAJGLGSMNLHG LLAKNMISYGSREALDLV NSLYSAINFQSIKTSMLMA KETGKPFKGFEKSDYATG EYFVRYIRESNQPKTDKA KKVLDKVYIPTQDDWDE LAKAVKVHGLYNGYRKA EAPTQSISYVQNATSSIMP VPSAIENRQYGDMETYYP MPYLSPITQFFYEGETAYK IDNKRIJNTSAVVQKHTDQ AVSTILYVESEIPTNKLVS LYYYAWEQGLKSLYYTR SRKLSVIECETCSV | 349 | putative ribonucleotide reductase minor subunit [Staphylococcus phage] | YP_024511.1 | 0.0 (348/349) | Ribonucleotide reductase | NrdF, ribonucleotide-diphosphate alpha | PRK09614 | 4.21e-80 |

FIG. 14SSS

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | SWNSLTESEKNTYKKVLA GLTGLDTKQGGEGMNLV SYHEPRPKYQAVFAFMG GMEEIHAKSYSHIFTTLLS NKETSYLLDTWVEENDFL KVKAQFIGYYYDQLLKPN PTVFDRYMAKVASAFLES ALFYSGFYYPLLLAGRGQ MTQSGAIIYKITQDEAYH GSAVGLTAQYDYNLLTEE EKKQADKETYELLDILYT NEVAYTHSLYDPLELSED VINYVQYNFNRALQNLGR EDYFNPEPYNPIVENQTN VDRLRNVDFFSGKADYE KSTNIKDIKDEDFSFLDSK EYSTAKEFL | | K] | | | minor subunit | reductase subunit beta | | |
| 211 | 13447 3 | 13480 2 | 1289 | MDRKEAMDLLSKAEILFK KHDEFSCVSDINDPMKLF SNSKDAKADDTSKSFQLE FMHDMTMYTLSYGSGQL KLIDLAEGYEAQKATVVN SFPEIIKTLEKDDSEDGKN E | 109 | hypothetical protein KgORF82 [Staphylococcus phage K] | YP_024512.1 | 1e-55 (107/109) | | No putative conserved domains have been detected | | |
| 212 | 13478 6 | 13510 6 | 1290 | MEKMNSLVDLNTAIRQK KDVIVMITQDNCGKCEIL KSVIPMFQESGDIKKPILT LNLDAEDVDREKAVKLF DIMSTPVLIGYKDGQLVK KYEDQVTPMQLQELESL | 106 | thioredoxin-like protein [Staphylococcus phage K] | YP_024513.1 | 1e-53 (106/106) | Thioredoxin-like protein | PHA02278, thioredoxin-like protein | PHA02 278 | 2,95e-30 |
| 213 | 13531 | 13590 | 1291 | MDELISKSRRYIMRDENH YMLFNEKYNDRLIEKVC | 198 | hypothetical protein KgORF84 | YP_024514.1 | 7e-109 | | No putative conserved domains | | |

FIG. 14TTT

Table 11 - Features of phage F125/10 gene products and assignment of putative functions.

| orf | Start position | Stop position | SEQ ID NO. | Aminoacidic sequence | Size (aa) | Homologous/similar proteins Name[organism] | Acc No | E value and identity | Predicted function | Conserved Domains Name | Acc No | E value |
|---|---|---|---|---|---|---|---|---|---|---|---|---|
|  | 3 | 9 |  | KHGGKVTYYTDSVLPYY VLKDLSSHPDSEVVYRMR NGFTAKEVDNIALSFMGT KVIIDISVVFPYVNPYDIIR SLHDIKTNVDEVHLSFPRI LEVDEKQFKFYFFDGEAY DLKPEYKVDFADKIRVSL SVWKMYIYILTSSRDFED VDNVITKLKQQRKIKI |  | [Staphylococcus phage K] |  | (196/198) |  | have been detected |  |  |
| 214 | 135919 | 136224 | 1292 | MSTANRRDIARKISENTG YYIQDVEEILSAETDAISD LLEEGYTKVKNHKFMQIE VIERKGKKAWDGLNKEY FHLPNRKAIKFKPLKELEE VIDRLNEEK | 101 | putative integration host factor [Staphylococcus phage K] | YP_024515.1 | 2e-51 (101/101) | DNA binding / bending protein | Bac_DNA_binding | pfam00216 | 4,57e-12 |
| 215 | 136300 | 139518 | 1293 | MKVLILFDHIREEHFSVSK DGSVKSNVLNTPNGKTLK KLLEKCSNLKRDKTNRDY DIDFLYNAVPTPIRNDYG KIIKYQDVKQAEVKPYYE RMNNIIDNSYDMIIPVGK LGVKYLLNVTAIGKVRGV PSKVTIENGTSSHDVWVL PTYSIEYTNVNKNSERHV VSDLQTVGKFVEQGEEAF KPKEVSYELVDNIERVREI FNKEVKNDNYDGVDITA WDLETNSLKPDKEGSKPL VLSLSWRNGQGVTIPLYK SDFNWENGQDDIDEVLEL LKNWLASKEDIKVAHNG KYDIKFLMSTENFKDFESI QDTKVGWYLAVTQEVKE SLRLSDLAYEVTDVGGYD | 1072 | putative DNA polymerase [Staphylococcus phage K] | YP_024516.1 | 0,0 (1065/1072) | DNA polymerase | DNA_pol_A _pol_I_C, Polymerase I | cd08637 | 7,32e-72 |

FIG. 14UUU

Table 11 - Features of phage F125/10 gene products and assignment of putative functions.

| orf | Start position | Stop Position | SEQ ID NO. | Aminoacidic sequence | Size (aa) | Homologous/similar proteins ||| Conserved Domains ||
|---|---|---|---|---|---|---|---|---|---|---|
| | | | | | | Name[organism] | Acc No | E value and identity | Predicted function | Name | Acc No | E value |
| | | | | KPLEDFKLWFVTKLLRFF SDKIKEIQKENKKIAKKEY DVKAPEYKEWLENKLNE TVVELDDTEKKFRVSELE KKYIQLGLSPEIVNMNLV MNNDEFISIAEQSPEYMG LSDYAKSYTLNTAINLNE YRDVKDVVNDIDGGNFN YDWFPIELMHPYASGDTD VCRRIHCDVVKKLKEQDR PKSMHLLEVNYPRLTKSL ARIESNGLYCDLDYMKEN DESYESEMAKNHATMRE HWAVKEFEEYQYNLYQM ALEHEKKPKDRDKDIHQ YRDKFKDGKWMFSPSSG DHKGRVIYDILGIQLPYDK EYVKEKPFNANVKEADLT WQDYKTDKKAIGYALDN LELKDDVRELLELLKYHA SMQTKRNSFTKKLPNMIN KQKRTLHGSFSETGTETS RLSSSNPNLQNLPAHTSD VNKFDYKHPIKRSFVSRFE NGVLLGADYSALEMRIIG LFTKDPDMLQSFLNGEDI HKATASIVYNKPVEEVTK EERQATKAVNFGLAFGES PFSFAGKNNMEVSEAEEIF EKYFQTKPSVKTSIDNVH EFVQQYGYYDTMHGHRR FIRSAQSTDKKIKNEGLRQ SFNTHQGSGSFLTNMSLT YLDDFIQSRNLKSKVIATV HDSILIDCPPEEAKIMAKV TIHIMENLPFDFLKAEIDG | | | | | | | |

FIG. 14VVV

Table 11 - Features of phage F125/10 gene products and assignment of putative functions.

| orf | Start position | Stop Position | SEQ ID NO. | Aminoacidic sequence | Size (aa) | Homologous/similar proteins | | | Predicted function | Conserved Domains | | |
|---|---|---|---|---|---|---|---|---|---|---|---|---|
| | | | | | | Name[organism] | Acc No | E value and identity | | Name | Acc No | E value |
| | | | | KEVQYPIEADMEIGLNYN DMVEYDEEEIDT | | | | | | | | |
| 216 | 139588 | 139830 | 1294 | VNTGEIRFNRSMDEWIITS MYQDELGEMNIVVTFYN REENKHGSTVLPTESSTGE VAEELASLEEEYPLALPLS SISVNI | 80 | ORF181 [Staphylococcus phage G1] | YP_240959.1 | 2e-36 (77/80) | | No putative conserved domains have been detected | | |
| 217 | 139847 | 140329 | 1295 | MEIHIDSLDFTNFTIKDRN GNSQEFDITDELRITEYTIQ EDFMQQSAKYAFWASILE KVRAYSEMEQRNLETIGS KLNLTIRQEYEQGKKPT KDMIESSVYIHDSYQQQL KVVEAWNYKVKQLQYV VKAFETRRDMMIQLGAEL RQTNKNGGITNPFSH | 160 | hypothetical protein KgORF91 [Staphylococcus phage K] | YP_024519.1 | 6e-90 (160/160) | | No putative conserved domains have been detected | | |
| 218 | 140416 | 141687 | 1296 | MDFNQFINNEASKLESNN SSFNNNVESYKPKNPVLR LGNIKDANGNKVVKENA FVRVLPPAQGTNVFFKEF RTTGINYSKKDGSQGFTG LTLPAEEGSSVLDPYIQD WITNGVQFSRFPNKPGVR YYIHVIEYFNNNGQIQPKT DAQGNVMIQPMELSNTG YKELLANLKDTMLKPSPN APHSFISANEAFLVNIVKA KKGEMSWKVSVYPNAPL GALPQGWEQQLSDLDQL AKPTEEQNPNFVNFLINN VNNTELSHDNFKFNRETN VLGEEPSEPKQAPTQQDV | 423 | hypothetical protein KgORF92 [Staphylococcus phage K] | YP_024520.1 | 0,0 (421/423) | | No putative conserved domains have been detected | | |

FIG. 14WWW

Table 11 - Features of phage F125/10 gene products and assignment of putative functions.

| orf | Start position | Stop Position | SEQ ID NO. | Aminoacidic sequence | Size (aa) | Homologous/similar proteins | | | Conserved Domains | | |
|---|---|---|---|---|---|---|---|---|---|---|---|
| | | | | | | Name[organism] | Acc No | E value and identity | Predicted function | Name | Acc No | E value |
| | | | | DSQMPSNMGGQPNQPQQ GQVGQYAQQGQSNGQGQ QLQGTQQPINNTQFGQGT PSGQQPSNTGSVDWDNL AQQQSQPDSNPFNDFDVS SVDDSQVPFETQPQNTQQ APEPHQTTQEPPKQKQTQ SIDDVLGGLDLDNL | | | | | | | |
| 219 | 14174 9 | 14301 4 | 1297 | MARAKKGKEVDLTDLNT IDLGKELGLTLLSDSNRA DIKNIVPTMVPQYDRILGG GIPLGRLTEVYGLTGSGKS SFAVHLSRISTQLGVITIWI DIEGTADNNRMEQLGVD VSKLFSIQAGEGRLKNTV ELSVETVGKELDYWIDTF NEKAPGVPILFIWDSLGAT RTQAEIEEGVDHRKLGTK ATATQKVINAVSPKLNDT NTGLIVINQARDNLNMSN PYDDPIKSTGGRAFEHGA SLRLKITKGKESDLKQSDS MTGKPTYKGHVMRVETK KSKLSRPGQKAEADLLSG YEVGSGSDITQLNGIDPYH TIYKEAVERGLITKGTWR NYITLNGEEIKLYDKDWV PRLIDDHELYLELFSRVYG EHFPNGYSPLLNTKVIVTQ LEEYQALENYYEEWAKD NKQEEQEEESKGESQEKD SE | 421 | putative DNA repair protein [Staphylococcus phage K] | YP_024521.1 | 0,0 (351/421) | DNA repair protein | RecA | cd00098 3 | 6.13e-22 |

FIG. 14XXX

Table II - Features of phage F125/10 gene products and assignment of putative functions.

| orf | Start position | Stop Position | SEQ ID NO. | Aminoacidic sequence | Size (aa) | Homologous/similar proteins ||| Predicted function | Conserved Domains |||
|---|---|---|---|---|---|---|---|---|---|---|---|---|
| | | | | | | Name[organism] | Acc No | E value and identity | | Name | Acc No | E value |
| 220 | 143018 | 143371 | 1298 | MYNLIDKNMRQVKESLG NANSSDVLPLPYKDIAKK FEEVKEKGESIIIEEGGFPY TDSTVMYIEHVTDRWAG GYSLIRHEGEEVKVPKTIH FSDIYVKDKSHKVRIIFEG ANPYEEG | 117 | ORF121 [Staphylococcus phage G1] | YP_240963.1 | 2e-59 (114/116) | | No putative conserved domains have been detected | | |
| 221 | 143358 | 144020 | 1299 | MKKAKNGNRYVIDIDGIP VDFERDLDSLLNRYKNLR WSLYHKYAGILSNDFERQ ELREYIDEQFIKLVKEYNI RSKVDFPGYIKAKLTLRV QNSYVKKNEKYKRTEIIG KKDYTVESLTEDLNEDFE DNQIMSYVFDDIEFTEVQS ELLKELLNPEREDDAFIV SQVAEKFDMKRKEVASE LTELRDYVRFKINAYHEY YAKKELNNHRVNTENHI WEN | 220 | putative sigma factor [Staphylococcus phage K] | YP_024522.1 | 2e-121 (218/220) | Sigma factor | No putative conserved domains have been detected | | |
| 1a | 144114 | 144994 | 1300 | VRIEKHHKIKNNKVINEMSI TANNLYNHANFILRQNFF NNKTNKGYRKFLNYNTIH RILKNMNEENVIKLPRQTS QQVLRDLINNWSSFRKSE KDYFKNPNKYRNRPKPPK YKAKGGKGTIKFTNQQCR IHKKDGLIHLPTPLQDITIK PYKAKNIRELVCIPKSDYF EVLVCYKEENSNKTLNDN ENIASIDLGLDNLITMVSI VDKPIINGKGLKSKNKYF NKKIRYYQSLLQNNSYSS KRILKYWEKRHNIILDYF | 293 | IS element Dka2 orfB [Hyperthermophilic Archaeal Virus 2] | YP_003773391.1 | 5e-18 (109/405) | Transposase | orfB_IS605, probable transposase | pfam01385 | 2.87e-36 |

FIG. 14YYY

Table 11 - Features of phage F125/10 gene products and assignment of putative functions.

| orf | Start position | Stop Position | SEQ ID NO. | Aminoacidic sequence | Size (aa) | Homologous/similar proteins ||||  Conserved Domains |||
|---|---|---|---|---|---|---|---|---|---|---|---|---|
| | | | | | | Name[organism] | Acc No | E value and identity | Predicted function | Name | Acc No | E value |
| | | | | HKATNEVVKYCVKNDIS KVVIGYNKQQKYKSKLK | | | | | | | | |

FIG. 14ZZZ

FIG. 15A

```
                              sequence.txt
                           SEQUENCE LISTING <110>  DA COSTA GARCIA, MIGUEL ANGELO
       SOUSA DE SAO JOSE, CARLOS JORGE
       RODRIGUES LEANDRO, CLARA ISABEL
       RODRIGUES PARDAL DIAS ANTUNES MARCAL DA SILVA, FILIPA MARIA

<120>  ANTIBACTERIAL PHAGE, PHAGE PEPTIDES AND METHODS OF USE THEREOF

<130>  16395-105003US1

<140>
<141>

<150>  61/384,015
<151>  2010-09-17

<160>  1300

<170>  PatentIn version 3.5

<210>  1
<211>  113073
<212>  DNA
<213>  Unknown

<220>
<223>  Description of Unknown: Bacteriophage F391/08

<400>  1
```

| | | | | | |
|---|---|---|---|---|---:|
| attatgcaaa | ctaaacgaaa | tcatacactc | cactaattaa | aggttgacaa | catgaaacgc | 60 |
| tttgtaatat | catctaaacc | ggcggcaaaa | ttgaacaaaa | tggcaagctc | ggaactggtc | 120 |
| aaaatgcagc | gcgatatggc | gcggcgttac | cgctcttatc | agcgcggagg | tcagcaaggc | 180 |
| ttaccgatga | tttgggataa | catgatgcgt | tatctaaaat | ctttacaaaa | taacgtttga | 240 |
| caatctgccg | ataacgcttt | attatagaat | ctcaataagc | aacaccgctc | tttaaaaatt | 300 |
| tggaaaagtc | gattctctca | gtaagggtaa | ttgagttttc | tgttaacact | ctagcagtaa | 360 |
| aagagtgtta | accggataac | ccaataaact | aaactggagt | aagaaacatg | caaaacgtta | 420 |
| aaaccccaat | gatcggtgat | tccgttttta | ttcctttcgt | tactggcgac | gtaagtaagc | 480 |
| cgggcgaaaa | tgaaaaaatc | ggatatatca | aaggggcggc | gatgatcccg | tttgataaaa | 540 |
| ttaatgcggt | atacgccgaa | acggaaaaag | caaaaaacag | cgacgcgaag | atttacagcg | 600 |
| tccgggtaga | ttccggcgac | gtggtgaaag | tcattcgcaa | agatgataaa | tggttggctg | 660 |
| tcgcttaaca | gccaataagt | ttaaccccgg | caataatgg | gatgcttccc | ctatgttaga | 720 |
| cttccgatgt | atattccatg | cagcgcaagc | aatgttatgg | tgcgcaaatt | aaacttatgt | 780 |
| gctggaactt | atatcatgct | ttgaacggca | attgtgagtt | aacacgaatc | tatagcgtga | 840 |
| aatagacgta | atagcgtaat | tattaaaggc | agcgtatata | tacaatgccg | ctttaaatag | 900 |
| ctttaaattg | aaaactaaaa | taaagagttt | tcgttatata | ttctagctag | aatatatagc | 960 |
| ggctaacttt | ctagccttaa | cccttaaata | aaactggaga | tatatcatga | ctgctactaa | 1020 |

FIG. 15B sequence.txt

```
aaccgaaaaa ttcgcatgga acgaaacaaa cgccgctacc gccgttgaaa tgtacgaaaa    1080
gatcattgct tccgatggtc tggaggtggc taactcgcaa ggtcttattg atattgcaaa    1140
ggctgtaggt gctgaatcgc atgttaaagt gcgctctaaa ctggttagcg caaaggtgta    1200
tcagaagtcc gataagccgc gcaaagtcgg cggcggctcc tccctgcgta aagctcacta    1260
tgtgcgcgtt ctcactcagc acgccattgc tgacggcctg attgatgatg ccgatggtct    1320
ggcaagtctg gaacaaatga agctcgacca actggacgtt atcgcccgta tggttggcgt    1380
tcaggatgaa gtaaaagaat cagcagaata attataatgc gcctccctag cggggcgcat    1440
aattaaatat tttgtccccc ataactggag aaataaaaat ggctttaatt aaaggctccg    1500
ttattaaatt aacgggaacc gttgtggatg aattaatcca acggggtat caggataata     1560
aggttatgac gcccccaagc gttaaagtac ctgaatatat tgttttgtgg gttaaccctg    1620
atgcggatac tttcgggatg gctattaacc gcgaagtctt taagccggaa atgctggaat    1680
tatcttcccg cgaaatttac cttctcaatt acgctttcag cgtagaagaa aaggaggttg    1740
taaaatgatc ttttcccta ctgaatcctt aattcttatc gctggctttt tcgccgccgc     1800
ttgtctctat ggttactata atttcatgga ataggcagc gaacaaacgg atttattacg     1860
ccgtgacttc tggttcaaga aagcgagtat ttgccgccgc tggtcaataa tctttattat    1920
tctagcggta actttcggaa tatcagcaag cattatcccg gcaatagttt agagtcgcaa    1980
attataacgc caccagcaac aaggcgttat atttggcaat tctgcctata tcccattaac    2040
tggagaattt agataatgat cattgcaatt gagaaacaaa aagctatttt aaccgctgct    2100
aacaacctca atttttgggg taaacgcctg cgcgctaaaa agctggagat ctgcgacgaa    2160
ttgagcaaag agcattacgg gacggcgaaa cactctagcg aaatttgcga ttggctggat    2220
agtaacaagc ctgttaaacc cgctgctgaa aaacgcgccc aacgtgttgc ggtggaagat    2280
tcccgccccg ttgccgctgg tcagcttaat tccagcgtcg aaagctggaa ggtaattccg    2340
ggccgccgtt ttctgctaac gtcgattcaa aataatacct tccctcatgc taatttctgg    2400
aaaactttac aggaggccgc gaaatatctc ggcgctactc tgttagtaag caaatacgcc    2460
tacaacaaaa aaggcttcca aaacgggcaa ggcaacgatg aactgaaata tgatgatgct    2520
ttctcagatt tcatttgtga tgaaaacgtg ttttgggca accgcgaaac cggattcgca     2580
ttcatggcgg aaattaatat tctgccaact gctgattttc cgctgtccgg ctttggcgag    2640
actgcgaccg cctacggcct gaaagggctg ctattggtc acgctaaaat caccgccgaa     2700
agtgtcccgg caatgaaggg cgacactgtg cgccgtatgt attcaactgg cacagcgacg    2760
ctgaaaaatt atattcagca aaaagcgggc caaaaggccg aagcgctgca taactatggc    2820
gctttgctgg tagagatcga cgacaacggc aacttctttg ctcgccaaat cgaaacgatg    2880
```

FIG. 15C sequence.txt

```
gacgaaagcg ggatgtttta cgatcttaat cataaattta ctgttaacgg tggcgaggag    2940
gtaacgggcc acgttgccgc gctgcaatat ggtgacattc acgccgaaaa gctggatcac    3000
gctgtcgcct ttgcttcatg ggggccgtgt gatgattctc tagtgaacgt cctgcgccct    3060
cgttaccaga ttgtgcatga tgtgcatgac tttacatcac gaaaccatca taaccgcgct    3120
agtggcgttt tccttgcgaa acaatatgcc gccggacgtg acaaggtaat tgacgatctt    3180
atcgataccg ggcgcgtact agaagcaatg gaacgtgaat tcagtcaaac ggtcattgtt    3240
gaatcgaacc acgatcttgc gctttctcgc tggctggatg atagtaaagc taacattcaa    3300
caagacccgg cgaacgccca tctttattat cgcctgaatg ctgcgattta tgaagcaatc    3360
gaaaacaagg acgatacttt taacgtacta gattacgccc tgcgcaatgt tgctggctgc    3420
gattttgctg cgatcttctt aaccacggat gaatctatga aaattgcggg catcgaatgc    3480
ggttcccacg gtcacaacgg cattaacggc gctcgcggca acccgaaggg attccgcaag    3540
ctcggcaaga tgaacactgg ccatacgcat acgcccagca tttacggcgg cgtttatacc    3600
gctggcgtcg ctggttccct cgatatgggt tacaacatcg gcgcgtctag ctggtcacaa    3660
acgcatttga tcacctatga aaacgggcaa cgtaccttga ttgactttaa agacggcgtt    3720
ttctttgcat aacaaaaaag ccggggtaat tgccccggca ataataacc cataaataaa    3780
taaataagct ggagaaacaa atgaaactta ctttcatcta taacaatcgt aaatctttca    3840
ccgcgtccaa cgtcgtagaa aatagccttg ttatttcccg cgatagtgaa gggcgcccgc    3900
atgttagcta tcagaaagtt aacacggtgg acggcgacac tgttttaaaa gctctagccg    3960
ctatcctccc gcgcccgct gaatttaaag aatccggcat tgtgtcgcaa ttagtcgccg    4020
ccgattctat tctttatgag gctgatatct gcgagatcgt agagattgac gccgccgccg    4080
ctggccttat gtttatcgtc gtaagcgaaa atgattatga tgatacctat ctgctcggcg    4140
acgtgatgga ttattcttct agcgaatata cgccgccgct ggcaattgtc ccggtaatgg    4200
ctacccggat taaaccggct gaattagccg atgccttaac tttattcttc tgataattaa    4260
caaagcgagt tataatatag ctcgcttgat taattaccaa caaccccgaa accggagaaa    4320
tgaaaaatgg cttttaataa actggcaatt aaggcaatta agttatggga tttagacgga    4380
actgttatta attcctttgc ccgcgtgttc ccgtgtatgg atgataaagg gaacttagat    4440
ttaaacatgt accgggaaaa ggcttgcgta catgatgcaa ttatgaccga cactcttta    4500
ccgctggttg aatatatgcg ggcatcgctt aacgatccca ctgtattaaa cattattgtc    4560
accgctcgtt atatgggtaa gagtgactac tatttcctac gcaaacaacg tatccgggcg    4620
gggcgcggtg gtaatatcca gatactgtcc cgcgatgtat tgcaccgata tattggcgat    4680
gctgattata aagaggtgta ctattcgaaa gatggtatct ataaaacgca ttatttcgaa    4740
atgcttaaag ctgaatatcc gaacgctact atcactatga ttgacgataa tagaggcgtg    4800
```

FIG. 15D sequence.txt

| | | | | | | |
|---|---|---|---|---|---|---|
| ttggctgctg | ctgctgctgc | tggccttcaa | acgatggacg | ctaccgcaat | taacgatatt | 4860 |
| ctatctattg | gtgtgcgcct | tgcgggtgag | tcattcatag | atgaagcgct | ggatgatgat | 4920 |
| aatgattatc | aatatctttg | cgagcgttta | gctcattgct | gggaaggtat | gaccgaagaa | 4980 |
| gaaagaagcg | actacggaat | taagccgcaa | caatttattc | aatcgttagc | catcgcatca | 5040 |
| taagaaagct | aatagtaccc | tagcgaaata | gttagggtac | taatagttag | ctaggggggt | 5100 |
| aatcggacta | ccataccacc | ccccgaccct | ctaagcccac | ctccatgtgt | aactttatga | 5160 |
| aatttggaga | aaaggctaaa | gggagtactt | aggcaaactt | agaacgagca | gcccgaatca | 5220 |
| aagctactac | tgctactgcc | gctgtcgcaa | taagaacttc | ccgagtcata | cccgctatac | 5280 |
| gttgcaactg | ccgcagttgt | agctatgatt | gctgcagtcg | acccatcatc | gctccgagaa | 5340 |
| cttcccgagt | tcgatgaagg | acttcccgaa | actttccgag | aattatccga | gcctgcccgt | 5400 |
| ttttgcttgc | gtttcgcgac | ctgtggtgtc | actggaggga | tgtagtacgg | gttgctcggg | 5460 |
| tcattccgaa | gatcgttcat | gactcgttgg | tgttttgaga | tcgctacttg | acgttctgcc | 5520 |
| cgagtttgaa | ggatctcttg | atgcagactt | tgttacgaa | gatctgccgc | tactaccgcg | 5580 |
| ttccgcaggt | catgtgcccg | cacaccaaac | caaactgctg | ccaggaaaaa | gaatgttgtg | 5640 |
| aaaattaata | caatagtcat | gttttacacc | atacccttag | taatgtagat | tttgtttgct | 5700 |
| gattctagtt | ctgccttgca | ttcagacagg | tttaactgtg | ccttatgcag | caaacgggtt | 5760 |
| tgattgtcat | aagacttctg | cagcaccccg | ttagtgcgtt | ctagctgttt | gattgcctta | 5820 |
| ccctgcttta | cggtaatgac | gaatagtacg | attgagagta | aaacaagtgc | tcctataact | 5880 |
| acttccatag | tggtcctcct | agatggtttt | aaaaaatctg | gtttacttgg | cggttgattt | 5940 |
| aatttataat | aatattatat | tataaaagtc | acttgttagc | aagtgagatt | tgaggtttt | 6000 |
| tatgggcttt | tatgcaggaa | ggataggcga | caaaaaagtg | ttgtctctta | cctctggcaa | 6060 |
| caataaagac | gttaataacc | acactaatcc | aggttgggat | actatattcc | atagcgatat | 6120 |
| gcctcacgtt | gtagttttag | aaactcacga | aagagacctc | tgggatggtg | gtgattggta | 6180 |
| tcgttgtact | agaatgccag | acagaattat | tcaggtactg | tccgcagact | acgacagggt | 6240 |
| tgtcttaact | gaagttgagt | ttgaggatgg | caccagacgt | ttcatttatg | gtacatccct | 6300 |
| gggtgtgggc | gctaaagcgt | ataacgctta | ctttagtaat | actgtcggtt | cccaggcttc | 6360 |
| tgcaggtact | atggctagta | tgaagactaa | cgtttgtgct | tctgcagact | tacacatgga | 6420 |
| tattagtttc | tatttcgaag | agacgccagg | tactattaac | gagaagctac | gagacggtac | 6480 |
| tgggtgtatg | tacacctggg | gcgttaactc | agaatgggga | gacagagggc | ctgggccgcc | 6540 |
| ggttggagct | cctatacgtc | ctaactttga | gactattatt | aaagctggat | gggtgctcta | 6600 |
| taggggggct | tttagtggca | atatagccgg | ttctgtgtct | ccgcccaata | gacccttac | 6660 |

FIG. 15E sequence.txt

```
tattggtgtt gatgctatgc gccacccgtg gatgcgtact actggtgtta acagtatatg    6720
tttgcgtggt gagactctca accgtaatat gtacggacat atggggccta gatatgggca    6780
gagctccaat cccgttggtg gtccttatgc tcataacatc cagactgagt cttatcagga    6840
ggttcagtac aaagcaggtt ttttccgtgg tccgcccaat aactttatgg ggtgggaaaa    6900
cacagataac aacaatgctg gtagtggttg gggtaacaat gccatttacc gtgacaataa    6960
cttccgtgtt cctaaacgtg ttcgctggta tattactaat atgaaataca atgggcaggg    7020
gttctacgca gagaacgtat ttggctcccg caaccaggag attaaaatca gccctagaga    7080
gttcattgta aacggtataa acctaatgaa cactgggtgg aagttcataa accagaacga    7140
tataaactac agcccaggta ataggcctga tatccgagtt attgcaacca acgtcgccag    7200
atttagtggc aaccctactg ttggtaataa tggatatgtt cactttaatc agcctctaac    7260
tcgaccagat aatggtgctg agtttggaca aggtaacgtg agtgagatgc atgtaaccac    7320
tgtaggggtt tacaatttta gatctgatgc acagtggtac gtaaaatcta acccgccgga    7380
aatcggaaac cagtggggtc cagtatggtc tgaatcaact cgacctctcc gcctagtggg    7440
cggtaccggc tctgctgata ttggagggaa cctacgtact agcggtaatg ctagtcacca    7500
cctggctacc ttgtggttag gggttaataa ctcccgaaat ggggcttgcg tcgtcactct    7560
agactggaaa aatgatgagt ggattgctgc tgcagggatt ggatgttata accctctaga    7620
agatcttacc cagtggagcg aggtggatag taggctgaga attttcggaa atcacttcca    7680
gaaacgtgtg catcaaatca tgtgtttgcc cgttaacatg tgtgtgccgt tccactttat    7740
acgcgggacc gtaacccagt gtggggttat tcctgggaac aacgccatgc aaatgaaggc    7800
tatgtgggca cctactacta ccaactctgc cactcagggc gattatgcca ttatctattg    7860
gctgatagct agggctgacg gtagtgttga agtttgggtt aacgttgaga tgagcaatat    7920
catgaatatg cgagtaattc ttcctgaggt taggattgct gtgcaaaggc ttgcctaaag    7980
gaggcaatat gagcaatgat ttaattgtac cagatacaat gtctccggaa ggcatgctag    8040
ttatagaggc ctacctggag tctggcagcg acgttgcgaa agcagcgtta gctgttggca    8100
tggaggaacc taaattccgg gagattatgc gtaaacctga ggtcaaagcg taccttacgg    8160
atatcttcat ggaatctggc ttccgtaacc gtgataaatt cttcggcatt ctagacactg    8220
ttctaactat gaaaatggag gaactggatg aaactggaat gggttcagag atggatatta    8280
tggatatcct caaactcatg cacaaaatga agatggatga gatgaagatg cagatcgagt    8340
atgagaaggt gaagcaagct aaagctccaa tacaccaaaa taatactcag atcaacctgg    8400
cagggggtca cgactctaat tacacggacc ttctgtcacg cattgtggga gcaggtaagt    8460
aatggaaatc tcacgtagtt atattaatac gactgacgtg gtggattttg gtgttgataa    8520
acgattcttt aaattcccgg tgtccggctt gctggccacc gagggatcg ttccaaatgg    8580
```

FIG. 15F sequence.txt

| | | | | | |
|---|---|---|---|---|---|
| cccgcagtgc | gcaatcataa | acgcactgga | agacccacgt | caccgtttcg | ttacagcatg | 8640 |
| cgtatcacgt | cgtgttggca | agtcgttcat | tgcgtatact | ctaggcttcc | ttaaactcct | 8700 |
| agagccgaac | gttaaggtgc | tcgtagtagc | tccgaactac | tccctggcaa | acatcgggtg | 8760 |
| ggcgcagatc | aaaggtctga | ttaagaaata | cgggcttcaa | actgagcgtg | agaacgccaa | 8820 |
| agataaagag | attgaacttg | ctaacggttc | gctctttaag | ctggcttctg | ctgcgcaggc | 8880 |
| tgactccgca | gttggtcgtt | catacgactt | tattatcttt | gacgaagcag | cgatctccga | 8940 |
| cgttggtggg | gacgcttttg | atattcagct | ccgtcctaca | ctagacaaac | ctaactctaa | 9000 |
| agctctgttt | atctctactc | ctcgtggcgg | taactggttc | aagcgcttct | atgaacaggg | 9060 |
| attcagagag | gatcttccgc | aatgggtatc | aatccacggt | acataccgag | ataaccctcg | 9120 |
| cgtatctctt | gcagatatcg | aggaagcacg | taagactgta | tctaagaact | acttcaaaca | 9180 |
| ggagtatgag | gcggacttct | ccgtattcga | aggtcagatt | tacgacacct | tcagcgtttc | 9240 |
| cgagcacgta | caggatcttg | caggtatggg | gcacttcttt | gctgcggacc | atgagttcga | 9300 |
| aaccattcta | ggtatcgacg | ttggttacag | agacccgaca | gcagtactta | ccattaagta | 9360 |
| ccactatgac | caagatgtgt | actacatcct | tgaggagtac | cagcaggcag | agaagactac | 9420 |
| agcacagcat | gccatgtaca | tacaacactg | catagaccgg | tataacgtag | accgtatctt | 9480 |
| cgttgactcc | gcggctgcac | agttccgaca | ggacttagca | tacgagcatg | aaatatcctc | 9540 |
| tgctcctgcc | aaaaaatctg | ttctagatgg | cctggcatgc | ctagctgctc | tattccagca | 9600 |
| gggtaagatc | attgtcgacg | cctcgtgcac | tgcgttaatt | cacgcactcc | agaactacaa | 9660 |
| gtgggacttc | caagaagggg | aggaaaagct | ctccagagag | aaacctcgtc | acgatgccaa | 9720 |
| ctctcactta | tgtgacgcac | tgcgttacgg | catctactcg | atttcccgtg | gcaaataaga | 9780 |
| gctgagttgg | aacggatagt | agtgagtaca | aattccgttc | caactttata | aaattcactt | 9840 |
| tacaatttcg | tgtgtggcag | ttataatata | ttcataccttt | gagagatctc | atagacatca | 9900 |
| gggtgaatga | gaggaatatt | taattgctat | acccgaagta | gtattttccc | aactaagagg | 9960 |
| aggaacactt | tggcttccaa | tgtaaaatat | aagagagatg | caatctccat | aatgcgtgac | 10020 |
| ggaatcaaag | cccagtacaa | aagaggcaac | tgttgcgcca | tttgtgactc | acaggaaaac | 10080 |
| ctggagctac | accactactc | gactgtggcc | ttactagtta | aaaactttgc | taaagaattc | 10140 |
| caactggatt | tcactgactc | agaagtcgtc | ctaagtaatc | gggataagtt | ctataaacat | 10200 |
| tattggcatg | agctagtaga | ggacacggtc | accttatgtg | tctttcatca | tcagacctta | 10260 |
| cacaaggtct | atacgaaaga | acctccgttg | ttttcagcta | acaaacagaa | gatttgggtt | 10320 |
| gagaaacaac | gtgaaagatg | tatgaatcca | gaggcacctc | gtacaagcaa | cactggcgaa | 10380 |
| agatcaggct | ttgcgaagtg | gcttccgact | gacgtcaaga | ctgagaaatc | aggattcgca | 10440 |

FIG. 15G

```
                              sequence.txt
aggttcctat aatggctatt cgtgactggt tagttactaa actaaaccgc ggacaacgca    10500
taatcaggga cttggaggat gttagtcacc gtactaacgt caagccattc acgactggca    10560
aagcctattc gtctattgag atccttaata gatccgcgaa catggtaatt gacagcgccg    10620
ctgagtgctc ctacaccgta ggtgaacagt ataaaacaat aacaacctat ggcacgatca    10680
ggagtaaaac tcttgagacg ctgcttaatg ttcgccctaa cccgtacatg gattccagta    10740
cttttagacg cctaatagtg tctgaccttc tattcgaagg gtgcgcgtat atccattggg    10800
acggttcgtc tctgtaccat ctgcctgctg ccctaatgga agtaaaagca gatgacaaaa    10860
aattcgttaa caaattcgtc tttaataata tgatcgacta tcgcgttgat gaaattatct    10920
tcatcaaaga taatggccag aatggtggta ttaactccca gattacgggt caatctcgtg    10980
tggctaccgt aattaactcg cttactaagc gtgagaaaat gcttgagttc aaggagaaat    11040
tcctggacaa tggtacggtt atcggtctta ttctagaaac agatgaaatc ctaaataaaa    11100
agctccgtga acgtaaacaa gaagagcttc agctggacta taaccctagt accggccaat    11160
caactgtgct cattctagac ggcgggatga aggctaagcc atactcccaa atctcctcct    11220
ttaaagatct cgatttcgag aacgatatcg ctcgttttaa taaagacgta tgtatcgctc    11280
tcggagtccc acaactattg atcgatgggg gtaacaacgc caatattcga ccgaacattg    11340
agctgttcta ctacatgact attgtgccta tgctcaataa agtatgtagc tctcttacgt    11400
tcttcttcgg ttttaaagta acgcccaata ctaaagacgt agtagcacta actcctgaca    11460
aggagaaaga ggctaaattc gtaactgcac tggtcaacaa cggtatcctt accggtaacg    11520
aaggtcgtat agagcttggt tacgaggagc tggctgacga gcagatgaag aaaattcgca    11580
tccctgccaa cgtagctgga tcagctaccg gagtaagtgg acaagaaggt ggcgctccca    11640
ataaagacga ggaaaaacaa tgattgacta taagcatta aaagcactat tccctaatgg    11700
tctccccgag gcacataacg tgtttgcaac cgttaaggca catctcactt accagattct    11760
gcgtaaggag tatgggtacg ctgctactaa cagtaaaacc tgggatcagt ttaaggaagc    11820
ctacgcggaa gcaactaagc cagtaccggt agcttctgtt agtatcacgg gcgctcctgc    11880
atccttagac tatactaaga ctgtacagct tgccgcaact gtcctaccaa caaacgcaga    11940
taataaaact gtaacgtgga agactagtga tgctacccta gctactgtga gctcaacagg    12000
attagtaaca gccctgtcta aggcaggcac tgttaaaatt actgccactg caggtggtaa    12060
atctagtgaa gtgtctattc aggtcaaggc tcctgttgta gcagttaccg gtgtcactat    12120
gtcacctaag actattacaa tcgaagcagg taagaccggc aaacttactg gtaccgtagc    12180
cccggctaac gcaaccaata agtctgtaac ttacttcct gctgatacca ccaaagctac    12240
cgtagctgcg gacggtacgg taactgttcc tgctaacctg gctgcggata gtaccgtagt    12300
tattactgtt aaaacagctg acggcaataa gaccgacact gcaatagtaa cagttaaggt    12360
```

FIG. 15H sequence.txt

| | | | | | |
|---|---|---|---|---|---|
| tcctacagcg | ggtgtgtaat | atctgttaac | tggggagctt | cggctcccca | tttttctatg | 12420 |
| ctagtgcata | actattttca | gtgtaaccaa | tttcgactac | ctactaattc | cacacaccgt | 12480 |
| gtgggatttt | caaatatctt | ttgacattcg | cgatttggta | tgtaataata | gtatctgaaa | 12540 |
| actgaggaac | aacacgaaag | tgtttggagc | aaacgatgca | gaatattaat | cttaatgctg | 12600 |
| agattaaatc | tgttaaagct | gtcggtgagg | gtgataatcc | tcctttaaaa | atcaaagggt | 12660 |
| atgctaacac | gattaccaaa | gaccgcgccg | gcgacgttat | tctctccgaa | gcgtggacta | 12720 |
| ccagtaacgc | cctcaagaat | tttatgaaga | acccgatcat | gcttttcggc | cataaccata | 12780 |
| gccgcccaat | tggtaagatc | ctagacctgg | taccaaccga | gtccggactt | atggttgagg | 12840 |
| gtgaggtaag | tgctgctgat | ctacagattt | actcattaat | acgtgatgag | gttcttaaaa | 12900 |
| cgttctcggt | aggcttctat | attaaagacg | ccgaatggga | cgatatgact | gaaacgttca | 12960 |
| ttattaaaga | tctggagtta | ctcgagatct | ctgtagtctc | ggttccctgc | aaccaagact | 13020 |
| caacttttag | cctttcgaag | tctgtaaacc | ataatgatta | catggagctt | cgtaagtctt | 13080 |
| ttgtaaaatc | ttcgcaggtc | cagcctgttg | aacaacctga | actttctaat | ttagagaaat | 13140 |
| tcctagtagc | cgctggttac | gctaaggat | aatggagaaa | taataatgtc | ttacgatatc | 13200 |
| gcacaactgt | ctaaagatct | gggcctgggt | gacattgctg | agcagcttaa | aggtctaacc | 13260 |
| gcctctcaga | aagctgaaga | agctcgcaaa | tttgctgctg | agcaggaagc | taaagaactc | 13320 |
| aagcgtatgg | aagacctggt | tgctaaagca | actggtgaag | accgtaaaaa | cctggcagaa | 13380 |
| gctctggagc | ttgtaaaaaa | cctggatgag | aaatccaaac | agtccgctga | agcgttcgtt | 13440 |
| aaagcaatga | actcccagca | ggaagaaatc | actggtctga | agaagaaat | caaatctctg | 13500 |
| ctggccgctc | gtgaaaatgg | tcgctctttc | gtagctgatg | gcgttgctaa | ggcaatgttt | 13560 |
| ggtaagcagg | aagatttcga | agacgaagtt | gagaaactgg | ttcttctgtc | ctacgtaatg | 13620 |
| cagaaagatg | tattcggtac | taagcgtggc | gaagcccacc | tgaaagctgt | taacggctct | 13680 |
| tcttctatcg | aagtttctac | cgaagcatac | gaaaccatct | tctccctgcg | tatcctgcgt | 13740 |
| gacattcagg | ctaaactgat | tatcggtacc | atgttcgaag | aactgccgat | gtctagcaaa | 13800 |
| ttgctgacca | tgatggttga | gccggaagct | ggtgaagcta | gctgggttga | cgcctctact | 13860 |
| tacggtactc | ctgctactgt | tggtgcggaa | gacaaaacca | agctgtctga | aatcaccttc | 13920 |
| aagacctaca | aactggctgc | taaagcgtat | atgaccgacg | aaacagaaga | agatgctatc | 13980 |
| ttcactctgc | tgccgatcat | gcgtcgtcgt | ctgattgaag | ctcacgctat | cgcaatcgaa | 14040 |
| aaggcgttcc | tgaccggtac | tggtgctgcg | ggtactccga | aaggcctgat | ccagttcgct | 14100 |
| aaagacgatg | gtaaagtggt | tgctaccact | gctaaagctg | acggttctgt | taaagttacc | 14160 |
| gctaaagaaa | ttcacaagct | gcgtcgttcg | ctgggccgcc | acggtctaga | cctgaacaaa | 14220 |

FIG. 15I sequence.txt

```
ctggctctgg ttgtttcgat ggatgcttac tacgatctga tcgaagacga agaattccag    14280
gacgttgcac aggttaccgc taccaccgct atcaaactgc agggtcaggt tggtcgtatc    14340
tacggtctgc cggtactggt ttctgagttc ttcccagcta aggctgcaag cgctgagttc    14400
tgtgtagttg tttaccgtga caacttcatc gttcctcgtc agcgtgcaat cactgttgag    14460
aaagagcgtc aggctgaacg tcagcgcgat gcgtactacg ttactcagcg tctgaacctg    14520
atgcgtttct tcgagaacgg cgtagttgct ggtgcttacg ctgcttaatt tggctatact    14580
gccgactaaa ggagagcttc ggctctcctt ttttattggg taaaatatgc aattcatgac    14640
agattctgat tggagaacat atggaggcct taaacgtcct gacttagagt caaatatccc    14700
aatgttaatc aaagcagcca atgctctgat tactcagctt ctaggtattg acgacactgc    14760
taacgttgta gacgttctgc ctactaaacc agcacgcaaa aagtacttcc tgtcttctcc    14820
cgtgcctagc acgatcacta aaattacgat taacgatcag gagatcgata agtcgcaata    14880
taagaactac ccggatggta cgctcttgct gaaattctcc cctccagagg ggtatatgga    14940
agtagagttt actcagaccg gcttcacctc gatccctgac gacctggtac tagcagcctg    15000
cttcctagtt gatcactggg tcaagaagga ctaccgcgag tctcgtacat tcggcggaga    15060
aaccgttact ttcaatacca ctaaatctgg cgtaccggaa cacattcgta ctataatcga    15120
agtataccgg aggctgtagt ggcgttgggc gatctagctc gacagatagt taaagaacag    15180
ctggacatta tgagtggtgg tagccactct accaagaaca ccgtgatata tagtgcggaa    15240
actatggata accacaaaga tggcaccata ggcaaggtat ccttccgatt taccaagccg    15300
gtatcggagg atttactgaa tgttcggacg tcctctattt taaaagctgt ctcgtcgtca    15360
cttaatctgg aaggtgacgt tggtgttatc gataaccttc taaatagtat cactggtaaa    15420
aaatccaaaa taggaagaaa acggtctacc ggtagggtag aggttaactt tggagatcct    15480
tcagatgctg acaacggtta cgctggtgct atttctggcg cttctgggcg tttcgtctca    15540
aacacaaacc ttagagcgtt acttgaactc gtagcgaaag aatacttagt caaggatatg    15600
aaaaaagctg gggcacccct taaatttaga acggggcgtt tcgctaattc cttgaagatt    15660
aaagacgtgc tgttaagaga agacgcaggg gcaaagactc ctgacctcaa catcacgtat    15720
aactacatgc ttaagcctta ctctgtgttc aaccctgccg tctctaccta ccgcggactt    15780
tccttacggc cttccctgg tgctaggaac ccgcagaagc tgatcggcga ggcaatcgct    15840
aaggctgcaa gagaccttat ccattctaga taccggataa gagtaaatca gggtacataa    15900
tgaattacag aacaagtatt gctgatgccc tagtggaacg actgaagaag gacatggatg    15960
ggagtaatcc cacagagttc ttcactaata tgtatgggaa cgtatcccgc cagacttatt    16020
cgtttgagca gatcaatgag ttcccttaca tagcagtcca tgtgggtacc gaaactggaa    16080
actacctgcc gtctgcacag cagtgggttt accttgaaat tcctattctt atctatgata    16140
```

FIG. 15J sequence.txt

```
aagaaaagga tgatattaac atgcaacttg agaaactcat agcggatgta aaaacctcta     16200
ttgacactgg aggaaattta caatatacta taatgaaacc tgatggttca actatcgatt     16260
ctgaagccac tgacatgcag atcacgtcgg tgtccacaga cgagggtata ctgtccccgt     16320
ttggttttgc tcaagttaac gtaacagtcc ggtatatgcc tctgagaaga gcgctggata     16380
gataagttac agctcaggag aaatttaaat gtctgtacaa ctattacgta atacacgaat     16440
cttcgtgtca accgttacta cggggttcac taaggccaac actcaggaga tcctagttca     16500
ggatgatgtc tcctggagcc aggacagtaa ctccactgat attaccctaa atgaggctgg     16560
ccctaagccg acccgcggtt cgcagcgctt taacgattca ttgaacgctg ctgagtggag     16620
cttctccact tatatcctac cgtatgacga tgcaggtaaa cagatcctgc cggactacct     16680
actgtggcac ggactggcaa ctggagctgc cgtgaatcta gcaggtacta ctggcgtatt     16740
ccagaatgct actaacctgg ttgtcaactt taaagacaac gggtaccacg aactggccat     16800
gttgaacatc tacatcctaa ccgatagctc ttggtctgtg atccgtaact gccaggttgg     16860
gcaggctgag gttaacgtag atattgatga tatcgggcgt gtaacctggt caggtaatgg     16920
tactcgcttg gagaccctag cttctcagcc gttcgaccct aaaaccatag ggatagacga     16980
cgctctttat gctaagattc agagttctta tatcaagaac aaactgacca ttcttaagct     17040
gaagaacaac gctaccggcg gaaaaaccta taacatcccg atcacgggag gttctttcac     17100
tatgaacaac aacgtgacgt acctgactcc taacatcatg tctcgtgttg acgttcgcat     17160
cggttcattc actggttcct tcgagctgac tggttccttg acagcgtata tgaatgatgc     17220
tgccaacggc tctatccagc tgtacaaaga tctggtttcc gacctgaaag ctgtgaacga     17280
cttcgaagtt gcaatcatcc tgggtggaga gtatgatact gctcgtccgg cagctgttct     17340
ggtggctaag cacgctaacc tgaacatccc gtcaatcgaa actgatgacg tgctgggtgt     17400
gtctattgag ttcaaggcta ttccgactca gatggacgca ggggatgaag gttatctggg     17460
cttctcttcc aagtacacca agacttcgat cgcgaagctg atcagctctg gtgacggtaa     17520
ccctgtcaca ccataaggat aactaatgct atactcccta atgcgggagt ctagagtagt     17580
catcgagtac gatggcaggg cgtacggatt tgacgccctg tctgattaca ctgctggaac     17640
gtcctacgaa gagtttaaag caaatcgtag gacgattcac agacgcagta actacgccta     17700
ttcgaagata actgctcagt ctccttcttc aatttctcta actcttaact tctctagcaa     17760
tgctctcgaa ggtctatttt tcgagttgat gggggtttata gagatagacg gaatgtatca     17820
gatgcccttg ttcagtaata atattgagcc taaaatgttc tccgtatata ttattaacaa     17880
gaacacgagc ttacgtttcg ataactgttt tgctaccacc tgcgactttt ctctagataa     17940
gagtgtcccg gtgctaaacg ttggtatcga gtcgggatac tttgaggaag taggccaccc     18000
```

FIG. 15K sequence.txt

```
actcaacagc tatacgcttg atcaaggtga ggtgctacca ttttcattac ctcaggtatc    18060
ttcgaatggg agagtgctcc caggacttat gtcagccggt atgtcattcc agcagcaatg    18120
cgaatggcga ggtgacagaa gtttattcga tatcaataag atttataata atagaagggc    18180
aatcgttaac gaattgaact catccgcttt gatatcgatg tactatgcaa agagtcttca    18240
gatagactct acgcataaca ttaaacctga tattggccta ccggtacaaa tcagaaataa    18300
atatattgtg gtggatttcc cttccactcg aatcacaaaa cgcctagact taaccgacgt    18360
gtacaagatc gattatgacg taatacctac tgagcaatca gatcctgtcc gaatcaagct    18420
aattggagaa taacaaatga gtattaacct aaaagatatt gcactggata ccaaacagat    18480
caccattgca taccctggcc taccacactt caaactgaaa gttaactacg tctcccgtaa    18540
gctctccaag aaaattctgg aagctgcaca agagaaccag tttgttaatg gtatcgctgt    18600
taaagtgcaa aacgatgaca aattcgcaga agagttcgtc aaagtggcta ttgcaggttg    18660
ggaaggtctg accgtcgcag atgttgagaa actaatgctg atcgaagttc cagaagatcg    18720
tctggaagac aaagtcgaat ttagtatcga caacgcgatg atgttggtgc gtaactccag    18780
tgccttcgag acttggatga acagcactgt cttccaccta gacactttc gtggctcaaa    18840
atcggaacct actgcttaag gaaatagatg cctttgcaga acgatgtgtc aaaggagggg    18900
actccaaaat tacacgggag cagtatctga cgatgtgcga atccctcggg gaggaaccta    18960
accccgaggt acttaaacgt ttcgtagaga tccatgactt ccctgaaatc gcacagaccg    19020
ctctaacaat atataacaac ttatcggata actatatccc cggagattat ccaacctatt    19080
taggcaagga taagagtgct ttactagttt tcttcgatat ctacggagtc gaagacgctg    19140
atgagaagag ccttatactc caaatcatca atatattcga ctcacatgcc gtggcagcct    19200
ctcgtaaacg cgttgaagca gctattaaga agtctaaaat gaagtcttct agtaggtagt    19260
gagttacagt ttcctccaac gggcgttcca cgtgaggctt ggcctagggt taatgcccta    19320
ggcctttta ttggaaaaaa tcatgacaga tagactaata cgagaattac ttgtagatat    19380
caagcagcgt ggtggatcca aagccgctaa acaaatcagg gatgttgaag ctgctttaga    19440
cggggctgct cagagctcag agggtctaaa tacaagcttg ggcaaacttc ctgggtcttt    19500
cacggcgctg gaacgatctg tatcacgtac tgctaagtcg ctggagaaat tatcctcgac    19560
caccagcatt acagcattag cagcgtctat cggcatgcta agcggcaagt ttacctcgtt    19620
cgaggttgac ttggctaaat ccgtactaaa aatcaacgca aacctaaacg gggtgacttc    19680
cgccgctaac aaaatggcct ctggttttga cactgcagcc acttcttcgg ttgcggactt    19740
aaaccgcgtc aataaggctc ttcaggagtt agatgcgcac gcctcttcag tagctaaagt    19800
gttgcagacc ttgaaggcgg gggccgggtt agaatctatt agctctagtg ctgctaaggc    19860
tagtacggat cttagccacc tagtatctgg ggtggaaaag ataggtaacc aattagctag    19920
```

FIG. 15L sequence.txt

```
aatggcggag caagccgtgc tggcaggcag gtctcttcag gggctgaaag ccgactcctt    19980
aggggctgcc ggagagcatc tgagtaaggc tgcgtccggg atttccgtag ctgtatcttc    20040
tatgggcgaa gaggtgaaca agctaaacaa actacttctt gagttggcag taaaggctga    20100
tttagcgagt aaatctatag caaatattgc accagggacc aaactgaata gtctgggaac    20160
tgaaatccag aagattaata ctagtttagc cactgcagcc aatacctcgg tagctgagat    20220
atctaagatt aaagcagccc ttacgtcttt agtatcctct accgctacag ctgccgcttc    20280
aatgaaaacc gtaggaaccg gtagtggtct gagcaagcta atctcagaga tatcagcagc    20340
cacctcagct tccacttcgg atatctctaa agtaacagcc gctttaaaac agcttaacgt    20400
agatgctacg gcagcaggaa aagcactgca aagtattaaa gcaggcgcaa atctttcttc    20460
tgtacctaca gttgttggaa agataggtac ttcaatgacg cagttgcgtg ctcagttaga    20520
aggatctgta accggtatcg agaaaagcct aaatgatcta tctagagctt ttgccactat    20580
gggaggtacg ggaaacctga atccactggg taactccatc agaggtatga tcccgtcact    20640
cacccagctg gctaaggccg ctgtgcaagt taactccgct ctgtcaaaaa tacaggcagg    20700
caggggcgta cttcaattac ctacccaatt caaagcagta acggcctcat taaatgccct    20760
ggagactaaa ctggcctcta cgtctcaaat actagagcgc ggattctcca agggatttca    20820
ggatatggcg tctaaatcaa cctcgtcatc tacgagaatg attaacaact tccagaaagt    20880
ggtaccggag ctcaacgcta ttgaagctgc tgctatacgt tctgctgctg caatagacaa    20940
gctaatagcc aaacgtatac gcctcggaca agctggggga gggggtaacc ctgcagcgtt    21000
caatatgggt gccttagtag cggaaatgaa caggattgta acctccattg aagctatggg    21060
caacaaaatg aataccacca tggctgatat ggcacggagt acggacaagg tatctgacaa    21120
attaacagat ctaaactcgg gagttcggga tgttaatact ggtttaggtg ggttgaattc    21180
aacgttaacg ggtacgggta gcgctgctaa tagggcgtcc agagcgttgg gaaatacttc    21240
aggatctgct cgcggagcta ctaggaactt cgcagcacta gctatggtga ctggccctat    21300
gcctcttatc tacggtgcta tagcctctaa cgtatacgtg cttaaagcag cgttcgatca    21360
gctaaaactt ggagaccagc tgaaccgctt agaacagttt ggatctatcg taggagcgaa    21420
gacaggtaca cctattcagt cccttgctgt ggcactgcag gaagctaccg ccacgcggt    21480
atcctttgaa gaggcaatgc gtcaggcatc tactgcggcc gcgtatggtt tcgacgctaa    21540
acagattagc gagtttgctc tagttgcacg tagggcagcg gctactcttg gcgttgatat    21600
gaccgatgca ctcaaccgtg taatcaaggg tgtgtccaag caggaaattg agcttctaga    21660
cgaattaggt gtaaccatcc gtttaaatga tgcgtatgcc gaatacgtta aaatacttaa    21720
tgcggctaac actggtataa cgtataacat tcagggtcta acttccttcc agaagcagca    21780
```

FIG. 15M

```
                                    sequence.txt
ggcatatgct aatgcggtag tagcagagtc taccaaacgc ttcggctacc ttgatgaggt    21840
actacgagca accccatggg agcaatttgc ggctaatgcg gattctgcat tacgcaaggt    21900
tcaacaagca gctgctaaat atctaggtcc agttattgca tctataaacg cagcattcta    21960
tacgtctaag gcttcggtat ctgcagaggc agctactgcc cagcaagagt cgattaagca    22020
aatggacggt aaagactcta acgcagtggt catgaacctt gaggcttctc agaaaggctt    22080
ggatgatgca gtcaaagcaa aagaggaagt aaaaaataaa ctcgcagctc ttaataagga    22140
gataatggat agagaggcga agatggatat gtccactgca ctggccacag ccgccaacta    22200
tagtgggttc ggtaatctgc ttaccctggg agcctctaaa gctaacaaag aatttacaca    22260
acagactgca gatatgcgta gacaggcgta tatgttacag caggagttag cagattctgc    22320
gggagctatc caaaaatgga agacgccag ggactccgct ctatctaagg ctcagaaaga    22380
gaacccagaa ctggcgggga aacttaatat agggcagaac gttgaagcaa gtaatggact    22440
atacccttt gacaacgcag cattagacgg ggcagttgct ctacggaagg agttcaataa    22500
tataaagaaa acttccggag atctgagcaa cgatatccag aactttgcac aggactctaa    22560
cactgcgtct cgagctactg cagcactggg tgatgcactt aaggcggttg agtcattggc    22620
gggtggatct acggaaaaag ccaatcaaat gaccaaggac cttaatttgg gctattccac    22680
cgtaaccgag atgaacactg cgtataaagc catgtctaac tatcagaaga tagtgaatga    22740
tgaggctaag tctaagctag atgttgagaa acgtatagcg gaggtctacg ctgccactcg    22800
taataaggat aaggcggaag aagctggtag agccctagaa atgcagcaac ttagcgcgaa    22860
gaaagaggca ttgaaagctg tgctggcgac gaacaaggac aacaaggcta ttcaaaaaga    22920
gttgaccctg ttagagacgg aagagctcaa agtgaagaac cagggcatgg aagcgactaa    22980
gaaggagaaa ttctataagg ataagatagt aggcatagat cgagaaatag cactcctaaa    23040
taatcgcact atgacagatt ctcagtataa cgtggcgaac cttaaattaa atctacaagt    23100
agagaaagat aggttagcct tactgaagac tcaggcagat aaggagaagg aagccgaaca    23160
gtctagacgt aacattgcct ctattgaaag ggaaatctgg aaagagcagc ttgaccgtaa    23220
tgccaaaact gctgagatgc gtaaagaaga attcgagcgc aatcaaagca tgaagcctct    23280
aatgggagag tcacagaaaa tgcaggagca gctagcgttc taccaagaaa tgaaggaatt    23340
cacgaaaggt aacgctgatg aacaggcgcg ttggagcaag gaaattgcta acactactgc    23400
gcaaatggcg gctctcaaag ctcagcgtac tgcacagatg atggatcgcg taggacagtc    23460
cttgggcgca gactatacgc ctactactgg cctggagggg aggataaga aattcgccga    23520
catggaaaac cagatggcgt catacgatac cgctatcggt aagctctctc agctaaattc    23580
ggaggctact gctactgctc aaagtatggg gaacttagct aacgctatga tccagttctc    23640
tcaaggatct ctggatacta cgtccatgat tgcagcgggc atgcagacag ttagccagat    23700
```

FIG. 15N sequence.txt

| | | | | | |
|---|---|---|---|---|---|
| gatcagctac | ggtactaacc | agcagatttc | agcaattgat | gcagctatag | cggcagagca | 23760 |
| gaagcgtgac | ggtaaatctg | agcagtctaa | gaacaagatc | aaaaagatgg | aagcggagaa | 23820 |
| gattaaactt | cagcaggaat | ctgctaagaa | gcaaatcatt | atccagacag | cagtagcggt | 23880 |
| aatgcaggca | gcaacagctg | ttccgtatcc | gttctctatt | cctctgatga | tcgcggctgg | 23940 |
| gcttgcaggt | gctctgtctc | tagcacaggc | gtctagtgct | accggaatga | ccgatatagc | 24000 |
| aggatctggt | ggtgaaaccg | cctcttacct | aaccttaggt | gagcgccaga | aaaacgtaga | 24060 |
| cgttagcatg | ggcgcaaacg | caggtgaact | atcttacgtt | cgcggcgata | aaggcatagg | 24120 |
| tagtgctaac | ggatttatcc | ctcgtgcaga | aggtggtaat | acctacccag | gtgtctccta | 24180 |
| taagatgggt | gaacacggaa | cggaagttgc | aactcctatg | gtgcctacca | aggtaactcc | 24240 |
| agcggataaa | gtggcttctg | aaacttcttc | tggcggtgct | agaagaccgg | ttaatctgaa | 24300 |
| catccaggca | atggacgcta | agagctttat | ggagtacgca | ttggaaaacc | ctgcggcatt | 24360 |
| ccaggcagct | gtagagttag | ccttgaatga | acaagggctg | agcttaaaga | acctgaatta | 24420 |
| actaaactaa | agggaggacg | taattgtcct | cccttctttt | tggaatttat | aaaattatct | 24480 |
| tgaaaatttt | tcttgatatg | actataatat | taacattgag | aggagaaaac | aaaacatgag | 24540 |
| attaccagat | cccttacac | atcctcagta | taacggcctt | gggtttgata | aagctacgct | 24600 |
| gatcgataat | gatccagtga | tcagagacga | gctaccaaac | ggcaaggtta | acgaagttaa | 24660 |
| aacagccact | cagtactggg | gtcttaacat | tagttatcct | gtgatgtttc | ccgacgagta | 24720 |
| tgctgtactt | tcgtcagcaa | ttctagagta | taagcgtacc | agaggctatc | tcgacgttat | 24780 |
| actcccacat | tacgagtctt | accgagtaag | aggggatgcg | aacaactgtc | gcattgccgc | 24840 |
| tggacaaaaa | ggctccacac | tggttatcac | caatacgaat | tccttatctg | gagaacctaa | 24900 |
| gccaggtgat | ttattccagt | taaccacaca | tccaaaggtg | tataagatta | catcttttaa | 24960 |
| aaacgtagca | ggagtatgga | cacttaatct | ataccctgat | ctgttgctca | ctaccaacgg | 25020 |
| ctccgagaga | ccacgtttca | atgggattct | tttccaaact | aaattaatga | acggagattc | 25080 |
| attcagcgaa | gagatcacag | ttgatggtgt | atacgacggg | gttaacctag | ttctgagaga | 25140 |
| aagtctatga | gacagatcct | tccttctgcg | aaagcctacc | ttgccaacaa | tgacaagata | 25200 |
| cgattagcgt | atcttgtctc | tatcgaactc | cggggtcca | cgggtaataa | cgctgtttat | 25260 |
| gcttatatga | cggactatat | gagagatatc | aactatggtg | gtatactctt | ccaatcaggg | 25320 |
| aaaattaaaa | caattagcag | ccacaaacaa | aaccgtacgt | taaccgtcgg | cagtttgagc | 25380 |
| tttagtgtta | ctggtacgga | tgccaacgaa | gtcattaagc | tcgtgcaaag | tggtgtatca | 25440 |
| ttttttagatc | gctctatttc | tatatatcag | gcgatcatcg | acgacaatgg | ggaaatcctt | 25500 |
| ccagtggacc | cagatactaa | tggccccttta | ctcttcttta | ggggtaagat | tgtaggtggt | 25560 |

FIG. 150 sequence.txt

```
ggtatcaaag aaagtaatac agtatccgga gttggtactt ctgttataac ctggaactgt    25620
tctaatgaat tctatgattt tgagcgggtt gctggacgct tcacagatga cgcttcccac    25680
cgaggacttg agattgtaaa tggagaatta ctgccttctc acggtgccaa acgaccggaa    25740
taccaagaag actatggatt cttccacgcc aacaagagcg ttaacttcct agctaaatat    25800
caagtaaaag aagaacgata caagctagaa tctaagaaga aattattcgg tctctccaag    25860
agctacagcc ttaaaaagta ttatgagact gttactaaag aagtagacct ggacttcaac    25920
cttgcagcca aatttattcc tgtagtatac ggtactcaaa aagttcctgg tatcccggtt    25980
ttcgcggata cagagagaaa caatccaaac gttgtgtacg tggtttacgc gttctgtgag    26040
ggtgagattg aaggattcct agacttccag tttggggacg cccccatgat ctgtactgat    26100
caaactgaca gtacatctcg tacatgcttt ggacaaaaaa gggtgtcggg agatactatg    26160
gcaagaattt ccacagggct cccatcaaca tctctctcca cgcatggtca agaatacaag    26220
tataatgacg gtaacggaga tatacgaatc tggacattcc atggcaagcc agaccaaacg    26280
gtagctacgg tactaagaga cattgctgct gctaacaatt tcttccttca aggagagaac    26340
ggtaatggtc cggagtactg ggattctagg tacaagttat tagacaccgc atacgctgtc    26400
atacgtttca ctatcacgga gaacagaact gatattcctg aagtatccgc agaattaagc    26460
ggacgcaaag tgaaagtata ccaggcagat ggttctgtta aaatggataa aacgagtcag    26520
aatggtgtgt ggcaaacatt tgactaccta acctccacca cctttggtgc aagtatcccg    26580
atagacagaa tggtgattgg tgactggaga aaagaggccg atctattaaa cattatagac    26640
acctcttatc aaactagttg gcaacctttc tggagatacg ttggatggga gagctggaca    26700
gccgaaaaca gacaaataat gcaaatgaac acaatcctgg ataactccaa ctctgtgttc    26760
aaaaacgtgc aggagctatt agaatccttc caggggcgt tgaataacct atcaggtatc    26820
ttccgcatca ccgtagagaa agattcaaaa actccgctag aacttaattt cctagatact    26880
tatggggacc tggatctatc agatactaca ggccgtaata agtacaactc agttcaggca    26940
tctctgattg atcctaccct gaactggaaa accaactcta taacgttcta taattctaag    27000
tttaagaatg aagatcgtgg agttgacaag aaacttcaac tttcttttgc taacataacc    27060
aactactaca ctgctagaag cttggcagat agagagctta agaagtctcg ttactctcgc    27120
tctctgagtt tctctttacc ttacaaattc cttggtatag aacctaacga tcctgtagta    27180
ttcacctacg atcgttatgg ctggaataag aagttcttcc tagtagatga ggtggagaac    27240
acaagggatg gtaagataaa cgtaactctt caggagtatg gtgaggatgt atttattaac    27300
tcaacgcagg tggataacag tagcgaggcc gttcctgaaa tatccaataa cgtcctgcca    27360
ccaagagact ttaagtacac ccctacacca ggtggaatgg taggtgatgt tggcaaaaac    27420
ggagagcttt catggcttcc tagcttgaca cctaacgtag tctattactc gatacgtaaa    27480
```

FIG. 15P sequence.txt

| | | | | | |
|---|---|---|---|---|---|
| tccgaccgcg | tggatcctta | tattgtgcag | cagactgctt | tcacacctaa | cgttagaatg | 27540 |
| ttccaagata | tcgtgggtga | gcctgctggc | ctgactattt | tcgagatccg | cgccgttgat | 27600 |
| attaatggtc | gtcgtagctc | tccagtaaca | atttctgtag | atttgaactc | agctaaaaac | 27660 |
| cttagtatgg | tggaaaactt | ccgagtgctt | aaccttgccc | ctgaccctgc | tgaatgggta | 27720 |
| ggacctgact | tagagttagg | gtgggacaag | ctgcaagaag | aggggctgat | ttcagggatt | 27780 |
| ttctacacgc | ttgaaataag | ggacaacact | aataaactgc | ttagatccgc | aaagatcacc | 27840 |
| agtttatata | actacagcta | cctgttgggc | tataataagc | tcgactacaa | ggccaacaac | 27900 |
| tcgaatactt | tggggattta | cagagcactt | cagccaagaa | ttcaggcgga | gggaccaaag | 27960 |
| ggcgagaagt | cggttgcatg | ggcatatatc | taaatgattt | caaacatagc | accagctaaa | 28020 |
| atggtactgc | agaatatcgt | gaccggctat | acgattgcga | gtattcagca | ctcaatcttt | 28080 |
| tccgattacg | acgtaattgg | tagaactttc | tggctaacta | cgggtggggt | aactacccgt | 28140 |
| agggacttta | ccggcgttga | tacattcatt | gccacaatta | acaatctaat | cgctggcgct | 28200 |
| acctactctg | cccagggtgc | tttctatgac | tcgatggttg | atgcagagct | gatggctgct | 28260 |
| aaagtaggta | tgaacctctc | tagcaccatt | aacttcaaga | tgaaaactgc | tccgaagatt | 28320 |
| accaaagtgt | cctcttttgc | agaatctgtt | gacgtgggtg | tgggtgctcc | tatggttgtc | 28380 |
| gtagagcttt | ctggggaggc | cgaatacgtt | accatcgaaa | tgaaacctga | gggctctagc | 28440 |
| acctggacta | aatactaccg | tggtccaatc | actgagcaga | tcatctttgg | gggtgttcca | 28500 |
| gttggcagat | acaatatccg | ggtatctggt | gttgtcacta | tgccagatgg | tgttactgtg | 28560 |
| gatgtttctg | ggtatgatac | ctggccgtca | ctgtttaacc | tgacctacaa | cttcactcca | 28620 |
| ccgtctgccc | caactaacct | gcgtttcaaa | actgcccaca | tccaagatgg | tatggagcgt | 28680 |
| tttgacgttc | gcctggaatg | ggattggact | cgtggtacgg | gtgctaacgt | tcgtgaattt | 28740 |
| atcatccagt | atattagtaa | cgatgagttt | gcaaaaactg | gatggactaa | ggccaacaag | 28800 |
| ctaaacgtgg | gtgcagctaa | agctggtact | atcactagct | tcccttacaa | aatccgccac | 28860 |
| cgcttccgtg | tactatcggt | tgcttgggc | ccagatactc | agtctataac | taactctaac | 28920 |
| gaggttactt | atattataga | cgagagcacc | actttcgaca | atgcattcat | taacgagacc | 28980 |
| ggtgtagaaa | tgacctacgc | aggtatcaag | ggtaaactct | ggaactctaa | caccaaacag | 29040 |
| tgggagcaga | cttttcttagt | cgatgctgct | acaggtgcag | tagttcttgg | tacactcgat | 29100 |
| gaaaatggta | aagcgccgat | ttcattcgac | cctgttaata | agattgtaaa | cgtcgatggt | 29160 |
| aaagttatca | ctaaagacat | taatgctgct | aacgtaattc | ttactaacct | gaccggtaaa | 29220 |
| gataacccgg | caatcttcac | tcagggtaag | aagtacggta | ataacgcagg | tggtgtctgg | 29280 |
| atgggtgttg | acaacgttga | cggtaaggcc | aaatttgacc | tcggtaataa | cactcagtat | 29340 |

FIG. 15Q sequence.txt

| | | | | | |
|---|---|---|---|---|---|
| gtgcgctggg | acggtgatac | tcttcgcatt | tctggtaacg | ttgtaatcgg | tactcctgga | 29400 |
| ggcgatgtag | accttgaaac | cggtatgcag | ggtaagcaga | ctgtatttgc | ttataaactt | 29460 |
| ggtacatctc | tgccaagtcg | cccgcttgac | caagtttatc | caccagctgg | atggtccgca | 29520 |
| ttcccgccta | accgcactgc | tcagaatcag | aacgtgtacg | ttgtgcaggg | tactctggat | 29580 |
| cctaagaaga | gtcctcctgc | tctagtagac | ggtaccaact | actcagctgc | atcccagtgg | 29640 |
| tctggtgtcc | caggtactgg | tggtactgat | ggttctaacg | gtgattacac | tgttcagatt | 29700 |
| taccagatca | gtgctagtaa | gcccacgaaa | ccaggcaata | tcaatgaccc | tagcggttgg | 29760 |
| agtcgtaccc | caccgactgg | aacccctctt | tggatgtgtt | ctggtagatt | caatggcgat | 29820 |
| actaacgctc | taactgttga | gggttggtca | gacccgatcc | gagtagacgg | cgagaaaggg | 29880 |
| gctactggtg | ctactggtgc | tactggtcct | caaggtcctc | aaggtccggc | aggtggttca | 29940 |
| gtagaagtac | agtggtctaa | agatggtact | actaactggc | atgcaaactt | tactactggt | 30000 |
| gatatctaca | tgcgtcagcg | tgttggtaca | ggtgggtgga | gttcagctat | ccgtgcagtt | 30060 |
| ggggaagatg | gtactaatgg | tactcctggg | tctaagggta | actacattgg | gatgcgcttc | 30120 |
| cgagtggcgg | ctgagaaacc | tgccactccg | actggccaga | cccccttcagg | ttggtcagat | 30180 |
| gcacctcctc | agggaaaccc | tctatggatg | gttaaagctg | agttcaacgg | tcaaaccaac | 30240 |
| gccctagtag | gtacgtggtc | agaaccagtt | cgtattgatg | gcgaaggtat | tggagtaaac | 30300 |
| ctgtatccgg | ttaagaaaac | actggatcag | tggaccggaa | tgagcaacgg | tactatggtt | 30360 |
| aagaacccag | ataccctcag | ctttaccata | accaacacag | agagcactac | ctcctctacc | 30420 |
| ggaccgggtg | cacatcctgt | tccgttccag | ggttcacaag | gtcctatagt | tgagattcca | 30480 |
| gtaaagccga | atacagcgta | catcttcact | tatgaggtta | gtactgatag | caccagcttt | 30540 |
| gttctgagag | acctgttact | agagttctct | agcattaccg | gaagttttac | caacttccaa | 30600 |
| gagttactga | ctggagccaa | aggtaagcag | gaagctaaga | ttgtcactcg | tgctgatact | 30660 |
| aagttcctga | gcttccgtcc | aggtgtccgc | actgccggag | ctacggttac | ttattctaat | 30720 |
| ctaaaacttg | aagaaggcat | taaagctacc | gcttacagcg | tagaggcttc | cgacagtatc | 30780 |
| ggtgagaaag | gagaccaagg | tactcagggt | ccacaagggc | ctcagggtaa | tcagggtcca | 30840 |
| cagggtaatc | aaggcccgca | aggtgctaag | ggtgataatg | caaaggatt | cagcctctct | 30900 |
| tctctcggtc | agacgtttac | gtacgacgca | gaaggtaaac | tgaagtccga | tgcaaccatc | 30960 |
| ctgttccagg | ctttccgtca | gaatactact | gcaaacgtta | cttggtcagc | caaggacgag | 31020 |
| aaaggtggga | acatcactct | gacaagtact | agcaatactg | gtgctacact | gaccgccgct | 31080 |
| aacttcaaaa | catcgaagtc | tgtagtagtt | acagccgtct | gtgatggtat | caccgatcag | 31140 |
| atcactattg | tgcgtctaga | cgatggttcc | aacgctctcg | tagggcttct | gaccaacgaa | 31200 |
| ggttccacag | ttctagcgaa | ctatgctggt | tacgtgcaaa | actatagtac | tggttctggt | 31260 |

FIG. 15R sequence.txt

```
gacttcaaag tattctatgg ggcgaaggat atcacctcag aatgcacctt cagtactatg    31320
gagaagaata accttgatgc tgatattact tcagcgggca aatatacttt aaaaggtatg    31380
ccggctggta ctgatgttat caacggctgg gtcgacttac gtgctgtaca ccctacttac    31440
ggtgccgtgg tccgcagagt ggcaactact aaatctatcc ttgcaaaagg ttatgatcgc    31500
gttattacca cttcattcga gaacggaaat aagggtacct ggtcgactgg tagtgtccaa    31560
ggggtttctg gtgccacaat tgtagccgca ggtttcagca aggccctagt gatctctgct    31620
agagactgta tagaagatgc taacgcattc cctgtagtag ctggtcagaa atatagactg    31680
ggcatgtgga taatggctag tgagtctaaa gtcaatatca acatgggaat gcgaattgta    31740
agggcggccg acggagttgt tgattggcaa ggaacccta tgattgcaca aggtactgta    31800
gtacctggtg gctggtccta catcgaaaaa gagtttactg ttggcagttc taataccggt    31860
atagcaatgc cgtggatcca gatggctggg tcttctggta gtgacttagg taaagcttac    31920
gttaccgata ttcacatttt cgccctagaa atggatgggg agaaaggtga tactggtgca    31980
actggtgcta caggttctca aggtccacaa ggtccacagg gtaataaagg ggacaaaggt    32040
gatactggtg caactggtgc tcaaggccct gctggtagct ctgtaaacgt ccagtggtct    32100
aaggatgggt ctactaactg gcatgctggt ttccaacctg gcgatatttt catgcgtcag    32160
caggttaatg gagtttgggg cagtgctatt cgtgcagttg gcgaagacgg taaaaatggt    32220
gctgatggta ctgacggtga ctacatttca atgaagttta tcgttcagga taccaaacct    32280
ggcacaccta ctggtaacaa cccaggtagc tggagtgatg ctcctccagt tggtagccct    32340
ttatggatga ctaagggcac tatgaatgct agcggtcaac tacagggtac gtggtctaat    32400
ccggtccgcc tagacgggac tatcaaccct aacctgttcg cagtacgtaa gtggatggca    32460
gggatgactg gtacggaagc cggcacatct aagaacgata tcgagaagct agcgcatacc    32520
ttgactcgta cttccggaac tgataatacg gctccagggt gctatgcgac cccgtatcta    32580
ggtagtgggg cgttttccca tccagtgact ccaggtaaac gctacactct aacctataat    32640
atcgacgcgg ctagcgaggt ccagacccga gatactatat tctggcaggc taatccagac    32700
tcaggacaat ccacctacat agaggaactg aataccggga cgtctataaa ggttaagcgt    32760
acctttgtag ttcctacagg tatgaactac ctaaccctac gcccttctgc tctgacactt    32820
aacgtagcga ctacgtggag caagattaag ctggaagaag gcggagagaa aactgagtat    32880
caagtagaat actcagacag tatcggtata gtaggtaaat cagttttagt acagtggtct    32940
aaggatagct cttctagtaa ctggcatgat accttccaaa caggtgactt gttcatgcgt    33000
cagaacgttg acggtgtttg gggtcctgcg attcgtgcta taggtgagaa aggtgagatt    33060
ggtcctgacg gtaagaaagg taactacacc aatatcatct tccgtatttc ggatactaaa    33120
```

FIG. 15S sequence.txt

```
ccagctaaac ctactggtaa caaacctacg gattggtttg atgctccacc tgatggttcc   33180
cctctttgga tggcaacagc aacgtttaat ggggatacta acgctatcat tggtgcttgg   33240
tctgaccctg tgcgaatcga tgcttccggc gtaggcgaaa acttcttagc gttcaaagag   33300
tggatgatgt ctattcagag ggctgagggg acgggctctt cagttagcaa gaatccggac   33360
cagatgagat tccgggtaac agctgggcca tccagaaatg acgcgtacac tacccccttac   33420
caaggaaccg gcacacattt tatagaagtg tcgcctaata ctgtgtatac tttatcattt   33480
gaaatggaaa ctgctgtgtc cactagaatg atgctgttgc agtttgataa tggtaatggg   33540
ggcacgcacg cacgtaacaa tcaggttata tcaaccagta ctggtataaa cagtctgact   33600
attactacgg gtgctaacac tacccacctg tctatgcgta tgtcaatctc taacatggga   33660
gagactaacg tactgatgaa acctaagctg gaactcgggg cgtttcctac ggcatacgtg   33720
gcgcatccta gtgatctact tggtaaagat ggtgctactg gagctactgg tcctcaaggt   33780
ccgcagggta acactggtgc tactggtgct acaggcccac aaggtagtaa aggtgacaca   33840
ggggctactg gtcctcaagg tcctcaaggt ccgaaaggta acgcaggtga aaacgctaaa   33900
ggattcgccc taacgtcaga ttatcagtca ttcgtgtatg atactgtagg ggacattaaa   33960
tccgctacta ctattctgtt caagggacta aaacagaata ctactgcagg gatcacgtgg   34020
agtgctgtaa ataatacggg agctgcagta acactgatga attctggaga taaccgtcag   34080
ctaaccgctg cgaacttcgg cgcctctaag tgggttacga taacagcaac ctgtgatggt   34140
ttatcagatc aaattactgt ggttcgtttg caggacggtg agaacgtgtt gaccgctgtt   34200
atgacaaatg aggcagctac ggtacttgct aactactccg gatattgcca gagttacgaa   34260
aacgccaaag gtcagatgag agtttggtac ggaagcaccg atgttactgg tcagtgcact   34320
ttctctgagg gcggaagaag taacgtaact cctagcatca actcagcaaa tgggaactac   34380
tccgttactg gtatgttgga tgggaccgat attaccgaag gttgggtgga cgttaaggct   34440
actcatccaa aatatggagc aattaccaag cgttttgcgg taactaaggt attcctagcc   34500
aagagctatg agatggttat caccaatacc ttcgagaatg gtaacaaagg ttcatgggca   34560
ggagctctgc agagtgtttc cggcccaaca aaccagagca tctctaaggc gctgcgtatc   34620
acagctagag ataacctaga gggtaggaac accatcccag tagcaggggg gcaaaaagtc   34680
cgtatcagat tctggtacaa cccactagga ttagaggaag ccatttttag agtaggcttt   34740
attgttcacc gcaaagatgg gggcaaaggt taccctcca gaactgtggt tacgggcccc   34800
gctcctaata gctcctgggc gtacttcgat caagagttga ctctaagtgc taacgatgag   34860
ggtattgcct ggccgtggtt ccagttagat aacaaaactt ctggttcttc attagggtat   34920
atgcttgttg ctgacataca cttcgaagat ctatccatgg atggtgcaga cggagctact   34980
ggtcctcaag gtccgcaggg taacactggt gctacaggtc ctcaaggtaa caaggggggat   35040
```

FIG. 15T sequence.txt

| | | | | | | |
|---|---|---|---|---|---|---|
| actggtccac | agggtccaca | aggtcctgca | ggagcttcag | ttggtgttca | gtggtctaaa | 35100 |
| accggcaacg | cgagcgattg | gcacacaaac | tatgctactg | gcgacattta | tatgcgtcag | 35160 |
| caagttaacg | gtgtgtggtc | ttcggcaatc | cgcgcagttg | gcgaggatgg | gcgggttggt | 35220 |
| gctgatggta | aatatacctc | cctgagattc | caagtagctg | caactaaacc | tgctagacct | 35280 |
| acagggaact | ctccggctaa | ctggtctgat | tcacctccag | aaggttcccc | actctggatg | 35340 |
| gttaaaggtg | agtttgactc | cagcaaccaa | cttcagggaa | cctggtcaga | tccagttcgt | 35400 |
| ctggacggtg | agacggtcaa | cctcaacctg | tttgctaaca | aagcatggat | tgcgtctata | 35460 |
| acgggtgcca | gtggtagtgg | atctgttgta | gccaaaaacc | ctgacgaact | acgcttacgc | 35520 |
| attaccgcag | gttctggtgc | aactgacgcg | tataccatgc | ctagtggtgg | tgatggtacg | 35580 |
| ttcttcacta | aagttaccgc | aggtaagcgc | tacactatgt | cgttcgacac | ggatagtgct | 35640 |
| ctggaaatga | gaatgcatgt | gttctttatc | caggcaggag | caaatactac | tacctcatca | 35700 |
| ttctcttgga | tagcgtcaac | aactgctggc | agaactagct | ggtcgttcac | tgttcctgca | 35760 |
| ggatgtgata | gggtatctgt | ccgtgtgtca | ctgaacaaca | acccaggtgg | aaccaacgtt | 35820 |
| gtttccaata | tcaagctgga | agagggagat | ttcgccacag | cgttcattag | gaacgagctg | 35880 |
| gatactattg | gtgctgatgg | ttcacaaggc | ccacaaggtc | cacagggtag | taaaggtgat | 35940 |
| aaaggggaca | caggagctac | tggtccacaa | ggtccgcagg | gtccaaatgg | tactagcgcc | 36000 |
| aaagcctttg | ccttaacatc | cgatagcctg | tcctttagct | tcgatactag | tggtaacctg | 36060 |
| aaatctaatg | gtactatcaa | gatcgatagc | tggagacaga | ataccactgc | tgcaataacc | 36120 |
| tggactgcca | agaaccaagc | agggagtaat | ataactttag | gtggcactgc | tactaacaag | 36180 |
| actataacct | ctgctcagtt | cggaagctca | gagtacgtaa | cagtaaccgc | gacgtgtgat | 36240 |
| ggaataaccg | attccattac | aatagttagg | ctgcaagacg | gggtgaactc | tctagtcggg | 36300 |
| tacttaacta | acgaagcggc | taacctgtcg | tgtaactcct | acggttttgt | gcagaattgg | 36360 |
| gatggcacta | cgggtaactt | taaggtgttc | tacggaacgg | tagatgttac | cagtcagtgt | 36420 |
| accttcggag | tggaggataa | gagcaatctt | aacggcaaca | tagggtcaag | cggttattat | 36480 |
| gccccctagcg | ctatgccaaa | cgggctggaa | attacctctg | ggtgggtaga | ttataaggct | 36540 |
| acgcatccta | agtacggaac | acttattaag | aggtttacac | tcaaaaagag | cctgcccggg | 36600 |
| attggttacg | acagagtgtt | cacggggtcc | tttgactctg | gtaacaatgg | atcgtgggga | 36660 |
| cgtacggtag | ttgacatcgc | tacgggcagt | cccggaggac | acaccaaggc | tatacagtgc | 36720 |
| acctctaggg | acaccatgga | aagtagtaac | tggttcccta | ctcgtaaggg | gatgcgctac | 36780 |
| cgtgtaactg | catgggtgaa | caactctgag | ggtgagtatc | agctaaggtt | aggcctccat | 36840 |
| acccagaact | cttctggcag | cgttaacact | ggttacccaa | ctatgctagc | cgcatcagct | 36900 |

FIG. 15U sequence.txt

| | | | | | | |
|---|---|---|---|---|---|---|
| aaggattccg | agggatggaa | actagtaact | ggtattgtca | cggtaggaga | tgggtctact | 36960 |
| gcggagactg | gtagggcaag | accatttatc | cagatgaatg | gtagtgctag | cccccttcggc | 37020 |
| aacgcttacg | tagctgctat | agcgatcgaa | gacctatcta | tggatggtgc | agatggggca | 37080 |
| acagggccgc | agggtccaca | aggtaatact | ggtgccactg | gtccgcaagg | tgataaaggg | 37140 |
| gatactggtc | ctcagggtcc | acagggtcct | gcaggtaact | ctgtaaacgt | tcaatggtct | 37200 |
| aaggacgggt | ctactaactg | gcacagtacg | ttcacttcag | gtgatctgta | catgcgtcag | 37260 |
| caggtgaatg | gatcctgggg | tcctgcgatc | agagcagtag | gtgagaacgg | ggctaatggt | 37320 |
| acgccaggtt | ctaagggtaa | ctatgtgagt | atgaagttcg | ccgtaatggc | tagcactcct | 37380 |
| agtaggcctt | ctggtagtaa | tccggctggc | tggtcagata | gccctcctcc | aggtaacccg | 37440 |
| ttatggatga | ttaaagcgga | gtttaatggg | gagactaatg | ctattatagg | taattggtca | 37500 |
| gatcctattc | gcctagatgg | ggatagtatt | aacgagaacc | tgttctactt | taaagcctgg | 37560 |
| ttagactcga | ttaccggagt | tgcaggcaac | ggttcatcta | taggtaagaa | ctacgagtta | 37620 |
| ctaagggcta | ggataatcgc | aggtacagga | gttaccgatg | cgtatacctc | cccatcagat | 37680 |
| ggatccgcct | ccatgttcac | ctaccttcct | ccaagcacca | catatacgat | gtcttttcgag | 37740 |
| actgataacg | ctgtagaagt | tcgttgtcac | gtattttggt | acgctaaggg | aagcaatacc | 37800 |
| actggaggag | tgctgaagac | tattgcatct | actactgcag | gtttgagcag | cttttaccttc | 37860 |
| accacgccgg | ctaattcgga | taggatatcc | gttaggttct | cagttaacga | atctggggga | 37920 |
| aataacgttg | taggaaggtg | taagattgaa | aagggagcct | tcgtaacgtc | atatgttcgt | 37980 |
| aaccagtatg | acgctgtagg | ggatcgtggt | ccagggttct | atactcaggc | gatcacaaac | 38040 |
| ttaaccggat | ggaacgatac | tcaggcagca | tctttcttcc | agtcaacatt | tggtggacct | 38100 |
| ccggttaagt | atgacgtact | aactcagtat | aagtcgggct | ctccgcagaa | ctcctggact | 38160 |
| cgtcaatgga | atggctcggc | atggacagct | cctgcattaa | ctgttcatgg | tgatatgatc | 38220 |
| gtctccggtt | ctatcactgc | tgataagatt | attgcaaaca | acgcgttcct | ggcgcagatt | 38280 |
| ggtgttgaca | tcctttacaa | tagggccgcc | gcactaagct | ctaacccaga | gggcacttac | 38340 |
| acaatgaaaa | tagacctggc | taacgggtac | attcatataa | ggtaacaaat | gagcacggaa | 38400 |
| aacagagtag | ttgatattat | ccttgatcaa | aacgtgtcat | acggattgat | gctacagttc | 38460 |
| atggatatcg | atgactctgc | gtacccagca | acggaaaccc | ctgtcaatct | gacaggggta | 38520 |
| acccttaagt | cttcaattaa | agactctctg | gaatccactg | gggtaaaatt | agcagatttc | 38580 |
| gtcgtaacag | tagtaaacgc | tacacaaggt | caggcgtcgc | taggattaac | tgcggctacc | 38640 |
| gtggcaacaa | tcgttagtaa | agcaagtaaa | gaacgagata | aatataatcc | tagacttcgg | 38700 |
| ttcgcaggtt | actatgatgt | aatcatgacc | aaaggaacag | gagctaccgc | tacctcttat | 38760 |
| agagtcatgg | aggggagcgt | gtacgtcagt | gatggagtaa | ccgcgtaatg | gctattacaa | 38820 |

FIG. 15V sequence.txt

| | | | | | |
|---|---|---|---|---|---|
| caagaattat | tgcacaacag | gttaccgctc | ttgacggagc | taactcaagg | gtaagtaagt | 38880 |
| acccaaaatt | taccgtacag | ctaggatact | cagttagttc | tctggctgct | acagaattac | 38940 |
| tagatgctgc | cactagatcg | gcagcatccg | ccgccgccgc | taaaacttcg | gaaaccaatg | 39000 |
| ctaaggcttc | tgaaaccgct | agtaaaaatt | cccagacagc | agctaagact | tcagaaacta | 39060 |
| acgcggcagc | atccgcccaa | gtagctcaga | atttggcagg | taaagcgtcc | ctagtaacac | 39120 |
| cactaggagt | gatgaccggc | tcggcagaag | ctaagattgc | atctataaca | atagccgcaa | 39180 |
| atcagtcttc | tagcgttcac | gtattatttg | cgctctacgc | tacaggtaat | ggagccaaca | 39240 |
| gggatgatat | atacaatatg | gagatagtat | ccctggcatt | acctggtcct | gtaacctctg | 39300 |
| taaccgcgga | caacatcggc | agcttcctta | gtcatcgagt | aataggtccg | gccaacacta | 39360 |
| atggatttat | ggtaggactt | aaatctacta | ttgagggtag | caacgtgacc | tatgatgtat | 39420 |
| acctcaaatc | tcgtagtagt | ttcagagacc | ctaagatggc | attcttatcc | ggctccatat | 39480 |
| ctgttactcc | acctaccgga | cctttggtgg | acggaacatc | ccctgcgtgg | aaaactacag | 39540 |
| gttttgatac | tgatgttatc | tatgtaaata | gggcgcaagt | aattgatgat | ggcattagtt | 39600 |
| tagcccgcat | caaacaacta | gctataacta | acggtaaaac | cgatagctct | atacttcttt | 39660 |
| tatcctattt | aaatgaaaca | ggtatactat | ctaccaataa | gaagtctatt | tccctccggc | 39720 |
| caggaggtac | gagtgactct | agtattgcag | ctacggagtt | tctacctaac | gggaatataa | 39780 |
| ttctgcctaa | tggggatact | gggaaccaaa | ctattagttg | gttaggtggt | ccccgcatac | 39840 |
| gagtcaactc | caacgggtct | tttgttcttt | ctactaataa | tcccagtaat | caaactagtg | 39900 |
| ggtttataac | tttcaggcca | caaggtgatc | aagtaacttc | cactgagctt | cagattaggg | 39960 |
| atgatggtaa | cattaagcag | acagctccac | agtcatcggc | aggcaatgca | cttatacgcc | 40020 |
| aggatgcggc | tattcaacat | atcatggata | aggctccggc | tgccggtatt | actgctaacc | 40080 |
| ccctaagcga | cttgaacgta | atacctacgc | ctgaaggtac | agatccttgg | ggagcagacg | 40140 |
| gtgtacgtgt | attccaatca | ggggtatcaa | caaaaaatac | tccggacgga | actactggtc | 40200 |
| ggcttggaac | tatcctcaac | gttaggcaca | cccagtaccg | tataatgcag | ttcttcatgc | 40260 |
| agagtaatgc | tactgcacct | attctgcata | ttagatcatt | aagggctgat | cagggtaata | 40320 |
| ccccaccggc | atggtttaaa | gtttatacag | aatactctaa | acctaacatt | cagtctgaca | 40380 |
| tagcaggtat | tactatagac | ggcaatggtt | tcgttaagaa | agcctccccg | atcgccaagc | 40440 |
| tcatagccga | aattcctagc | aaagaggatt | cattcttctg | gacaggcgtg | gaaactgtgg | 40500 |
| gaggttacgt | agggtgtaac | gcagaggctc | aaggtgtatt | tgctgtaaaa | actggactag | 40560 |
| gcaagtatac | tattaaaggg | agtttaggct | ggaacacgga | aggatgaaaa | tttgagctac | 40620 |
| caagagatga | taacggcaat | atgttgtgct | tcgtggaatc | ggattggaat | gaggaagaga | 40680 |

FIG. 15W sequence.txt

| | | | | | | |
|---|---|---|---|---|---|---|
| aagagctaaa | catacaggtg | ttcacccgta | agtttgatat | taacacaggt | aatatcatcg | 40740 |
| ctggtgaacc | tatggagata | ccacaaggtc | gttggattga | tctacgtctg | gaaatgccaa | 40800 |
| aagtggaaat | accagaagtg | gaatttccag | aagatccaga | agtataataa | aataaaaccc | 40860 |
| cagtcggagc | aatccgctgg | ggttttttcta | tttacatctt | accagaactt | ccgaagccac | 40920 |
| cttcgccacg | atcagtgtcg | gtcagactat | cgacaatttc | aatgtcattg | gggttataat | 40980 |
| gaggtacgat | caccaactga | cacagacgct | caaagttatc | aatcggttgt | gtctcgttgc | 41040 |
| tcatattcaa | caggttcatc | ttgatggttc | ctcgataatc | tgagtcaatc | accctgttg | 41100 |
| tattggcaat | cattagccga | cgtttcccta | gagaacttct | cggaaccacg | attcctaccc | 41160 |
| agccttcggg | aatctcaacc | gcaactccgg | tatcaatcat | caatgactcc | ccaggaggta | 41220 |
| tggcacgcaa | taggtcggaa | gcacgatctc | cgaagtaggc | ccgtagatcc | ataccggctg | 41280 |
| cttccgagct | tccaacgtga | ggtttacaat | cggggtgaga | taatttaata | cgcattatac | 41340 |
| ttctcctgtg | gcaatagccg | taatgtcttt | aacaaattga | tcgtagatat | cttgtcctgc | 41400 |
| tgcggcaact | gcttccccac | agaaacttgg | gagatctact | agagttaggt | tacgttccat | 41460 |
| aagttcgcct | gatttattca | gagcctggac | gaattttga | gttcctggga | gcggtagtgc | 41520 |
| atcaataatg | tctagcacgc | taccatgttc | ccggattagg | ttgtagccac | gttttcgcc | 41580 |
| gataccttca | acaccacgaa | tgttatcccc | catatcgccc | ataatggctt | ttaatgagat | 41640 |
| aaactgatct | acagtatcta | cgttatggtt | gtcgaacata | tctttctcgt | gatattcttt | 41700 |
| acgagtagta | aacgagaagc | gggagatatt | cggagcaagc | agggtatccc | agtcaccgtc | 41760 |
| tgtggagatg | agccagatat | gatcgtagtg | atgacctatc | agctgaataa | tgaaagccgc | 41820 |
| catgtcatct | gcttctactc | cgcggattcg | gaaagtaggg | aattggcttg | caataagatc | 41880 |
| aaacgcatcg | tctaagtatt | caaagaattg | acgatccgcc | tctacttccg | cttcggagcg | 41940 |
| atcggcgtac | ttagcgtctc | ggttgccctt | atactccggg | aaaatattgg | tacggaagat | 42000 |
| actcttccct | ttatccccta | gaacgatagt | gtgcttcgca | tcgtaggagt | ttgccaaaga | 42060 |
| gttgatggtg | tttgcaaagg | atgctgcaat | aggcttacca | ctatctttct | tgaagcggaa | 42120 |
| gcctaagttc | gtaccgtcaa | caatcataag | attacggcgt | gaggcgaggc | gttgttctgc | 42180 |
| ctctcgtttc | attgttcccc | aggatttact | catttaacta | aatctccaat | ttcacatgcg | 42240 |
| tttaaccacg | gctcaaaaag | accgataaca | atttccattc | cacgttatt | aactatgaaa | 42300 |
| tgtgctctac | tcatgaggtt | atcaatcata | gggtcgctac | tatccagagc | gataagccat | 42360 |
| tgaccacgat | cttcttaaa | gatcagggcg | ggtttcatgt | tcatttgctc | accttcacgt | 42420 |
| gcggcttggg | cccaccattt | ttctagctgg | gattctccaa | cgtttaggat | attgctatta | 42480 |
| aattttcgt | ctgcgtagtg | tttgatctca | aaacagtatt | ggctcatttt | acctacgcta | 42540 |
| ggtggcagat | acacatcccc | ctttagggag | tgggattggc | caaaagctcc | tgaaccagga | 42600 |

FIG. 15X sequence.txt

| | | | | | | |
|---|---|---|---|---|---|---|
| acacgttccc | agtccaagga | ggtatattta | cgcagcatat | cacggatttg | gtattccgcg | 42660 |
| cgttttcctt | tctcgcgact | atctacggcc | attaggcctc | caaaattgat | aagccagctt | 42720 |
| cgtcttgttt | aacctcaatc | ttatgtgcat | acggatgtgt | gtgcccgtga | gatacgatga | 42780 |
| ttgagttcag | ctgatcttct | tcctgtagaa | gttctacgag | ggtattaatt | ccatccgggt | 42840 |
| caatataact | tacaacttca | tcaaggaaga | gcaggttgat | attaacttta | ctaatcgttg | 42900 |
| aaagcaacat | tcgaattgct | aatagcgtgg | aaatattgat | acggctctgc | tgaccagtgg | 42960 |
| agcagttgac | catagaagtc | ctgttaccat | cattgtagat | gacaacctgt | agcttcgtct | 43020 |
| cgtctaactc | gaaccctaga | gcaaatttac | cgctggtcat | gatagagaga | taatgattga | 43080 |
| tcatctcttc | aaataccttg | acactatgct | ccagcttata | ccctaccaga | tcttttagcc | 43140 |
| cggtaattaa | gatatctaga | tccgctactt | cttctgcaac | taaggacagt | tcagcctgga | 43200 |
| tcttatcaaa | ctcctgctcg | gccttttgaa | tctgttcacg | cttagcttca | tatttcgcat | 43260 |
| tttcacgtac | aactgattcg | ttatgggttc | ttgcaagttc | taccgaggat | ctgccttgac | 43320 |
| gaatgctaga | ctcaatagct | ttgatacgct | cagctaaccc | gctagcgtct | acgatttcat | 43380 |
| cctgcgttcc | attgacctca | tcaaattcct | tgaggttttt | gcgagcctgt | tccagagcgt | 43440 |
| taaacttaga | gatataatcc | ttaaacgccc | tatcttcctt | cctaagttct | tcaacttctg | 43500 |
| cttccagctt | ttgacgttct | ttatagagcg | gatcatactc | ctccttagtt | cgtctcatag | 43560 |
| cttcttgggc | ggcggaggta | tctaagtgag | ttccgcacgc | agaacactga | gttttacctg | 43620 |
| cggcattttt | gaaatcgtag | taacgtttct | tcaaatcatc | cgctctagtt | gccacgaccg | 43680 |
| ttaggttacg | cgtaacactc | aggagttcct | cagatttcga | ggtgggcgca | ggtaaatttt | 43740 |
| cgaatggtgc | aaaagttttt | tcggcagctt | gtacggccat | gtccaaagag | ctacgttttg | 43800 |
| caatactggc | ttttttgcttc | tgagccagtg | ctaccttgac | ttttgcttcg | gttaattctt | 43860 |
| cgactagtgg | ctcttcatcg | aaaacaggga | ttgggatctc | tgattgaggt | gcgccaagcg | 43920 |
| aggcttttga | ggaaagtata | gattgggcag | ttcgcaggct | accttccaat | ccggacagtt | 43980 |
| ttgccgagac | ggctttacgt | cccgctttaa | cacgttcaga | aacttcctta | tattgttcct | 44040 |
| gatcaaacag | gttaacgagg | aaagtcttgc | gctgagcatc | cgtagtcttg | aggaagtcga | 44100 |
| gactggatcc | aactgactga | tatacgagct | tagtaaatgt | cgtaaaatca | caggcgagta | 44160 |
| cctcttctat | cagcttatac | gtttgggttg | cggtgtgtcc | gctgatatct | tcaccgtttt | 44220 |
| tagtgagagt | tactttggcg | gttgacttca | caactttctt | gacgttgtac | acgtcaccgt | 44280 |
| cttttgtgaa | ctgaccttct | agcgtatagg | ccttggagcc | agtatgccag | ttaaacaggt | 44340 |
| cgtccttctt | gataccacgt | gagttcttat | tataaagaag | ctcctctaga | gctgtaccaa | 44400 |
| ttgttgattt | acccagcccg | ttacgcccga | ttaactgagt | tacgcggtga | ttatcaaatt | 44460 |

FIG. 15Y

```
                                    sequence.txt
ctatcaccac gttctcagca tatgacataa aatggctgat tgtcaattta ttaattacta    44520
tcgacatact cagcggctct ctttaatatg cgtgttctag acgcttcgtc tagtttctgc    44580
acgtttgtga aataagtatc cagctcctgt agcagtgaca tatcgtctag atctaactta    44640
gcatctttgg tgacacggtt attgatcttc ttatctaaca gttcgctgtt ctttaacgtt    44700
ttgagttgtg atacgtcgcc ggtgacttcg tatataactc tgtcatacgc atcggcttcc    44760
attggctcgc cgacttcaat agttttcgt atgagctgtg aagatctcc cagttcaatc    44820
cacgaaaggt agtgctcatg gtctcttggc aagaccgtat cgatgataaa agctccgtta    44880
gttcctttg tcctttctct gtgaaacgaa gttgtaagcg gagatccggg atagagcagg    44940
tcaacatccc cgatcttttg gctgttcttg tagctgtgga gatcgcctgc aaatactttg    45000
gagtacccat gttcgacgaa tctttcgagg tagatttctg gtacgacatg aggcgggatt    45060
gcacctctga catgcgtgaa gcaaatgtct gaaactctgg gcttccaact agctttgtga    45120
aggctgctgt aagggatgat atcgaactct ggagatcggt agtctttgac gactttccaa    45180
agtccatctg ttgcgtcgct aattgctgct gcatagtgat ccaggcaaga aatcgtttta    45240
gatttcattt cgtggttccc ggtgtaaata ataccaggat gttggagggt agctaggaat    45300
gcaaacagta gttcaacttc ttctgaagac gggtctgaaa catccatgat gtcaccacca    45360
ataatgtgaa ggtcacatcc agtagctcca aacacttcgt ccagcttttc accgagaaga    45420
ataaaccgat ttttctgcca ttcctgagga acgttcttcg ctcctagctt gatgtgatga    45480
tctgctgaga aaagtatttt catagtcaaa ataaaggga gccgaagctc cccttgtttg    45540
gattaatcga ggtcagaagc tgcttcgtga tcgatgttac cggagttcgc ggaaccttca    45600
ttacctttag attcgtcgcc ctcctcatct ttcttacctt ccagccatgc ctggattgct    45660
ttcttctgct catcatagga cggaaccggg taggtaacat ccagtttagg cacttttttcg    45720
aagccttcga attcgtctgc ttcgttgtac agagcctcac caatcagagc aacgtcggct    45780
tcatgcaggg cggcctcttt agaacccggc tgattttag ccatctggaa ctgcattgca    45840
gcgatctgct gtacatcgta cttggtatcg aagccagtac cagatttgga gatagtgata    45900
tcgatctcac ccggatcttc cagattcagc tgggccatga tggagtggat accggtcagg    45960
atggttgcct taacttccat cagcttcagt ttgttatcag tacgatcgat aacaacggcc    46020
aggtagtttt tcttaggacg cagcggctga gccttaccat ctttcttctc cggatctttg    46080
aagcccatgt cgtgaaccgg atcggatgct ccacggatga aacgctcttt ttcacggtcg    46140
aaacgcaggc actcgaacgg agccggttta ccttccttat tctgaatcca gtacacataa    46200
cgcgggagaa cgccggaaac gatacgtaca acgttcttac cgttgttgaa cttcatgtag    46260
tccagtttgt cgccgttaga accgccagta gtagaacccc aagatttagt agccatattt    46320
aattttcctc gataaatgtc aattttgact tgttgattgc gattagtggg tggtgctcga    46380
```

FIG. 15Z sequence.txt

| | | | | | |
|---|---|---|---|---|---|
| taactgctct | aggaacccac | ggtggaatat | attgcatatc | cagtgatgta | tccttcgaga | 46440 |
| agctatattc | ggcatagttt | ctaaaactca | aaagtcctag | atactcagcc | aactgtcggt | 46500 |
| ctgacagctt | tcgtttatta | taaacgattg | tatcttcgtt | caagataaat | gatctacccg | 46560 |
| ttaacataac | atgagcttcg | ggatcttcaa | ccattcgtct | gataatctgt | acaatcagcg | 46620 |
| atgagttacc | tcgtgctaat | atgtaaattt | tttcgtaatc | ataaacaac | atgattatta | 46680 |
| tacaccattt | tgagagaatt | tagcaactaa | gttttattt | ttctgcttcg | gactttccga | 46740 |
| agattcagtt | gctgttccca | ttaatttata | cagatattat | atcgtatttt | tgaggactca | 46800 |
| gcaactgaaa | tttttaacta | tttgcttaac | tcttctttgt | aaatctgtct | ctcagttcaa | 46860 |
| tataaatatt | atatcaaact | ttggggttct | tagcaaacag | aattttatct | aagtttgcca | 46920 |
| tattcttctc | gttaaagtca | agaacttccc | acccattgag | acgatatacc | gcttctctac | 46980 |
| ccgccgcctg | cttaaatcct | acacctccta | gcttcagatc | cacgaggatt | gggtctaact | 47040 |
| tatcatctgc | catacgttgg | acacgacctg | ccaactgttc | gattagagat | tcgttattta | 47100 |
| ttaaagagcc | taacactaaa | cacgataaag | catttaatga | tacaccctcc | gagaagatgc | 47160 |
| tttgggaagc | cgctaacaca | cacggaccgt | cattggtcac | gtcaatctgt | acttgctccc | 47220 |
| tatcatcgag | cgaagttaca | ccggtgatcg | tgtaggtctt | cacaccctg | agttccaaag | 47280 |
| cattcgtaac | tctctcaatt | agatctatac | gatcggacac | aaacaggact | ttatggcctg | 47340 |
| ccatcgaata | tagctcgcac | aagtcaacaa | cctgttgaaa | gtattctggc | tgcgaatata | 47400 |
| catcgttagc | tcttatcgcc | cacggcacat | tcatatttcc | agaaacctgc | gttttagcg | 47460 |
| caaacctatg | gatagtaggt | ggcatagtgt | tatttaccgg | aggactatat | actttcgttc | 47520 |
| caaaatagtc | cttaaacata | acctgcaaac | catccttacg | ttttaatgta | ccggatagcc | 47580 |
| cgattttata | tcgtgccgaa | gactgctcta | gaaacttggt | aaacgtggtg | gcaacgcagt | 47640 |
| gatgcacttc | gtcaacaata | acggtgccga | attcttttgc | caaagcggct | ccgtgtttgt | 47700 |
| taactgtctg | tatattacta | ataacgatag | gagaatcgat | attaaatttg | ccagacccaa | 47760 |
| taactcctgg | ctcaatccca | aagaacttgc | gtacctcctt | ctcccacata | gctcgaatgg | 47820 |
| tagtgttggt | acatataact | aacgttttct | gcccaagttt | atgggcgata | gcaagagcaa | 47880 |
| ggattgtttt | accgaaccca | ggcttaccat | taataataca | cgtatcatta | cagtcttcat | 47940 |
| atatagggag | ctgatcccct | ggtcgcaggg | tgaacgatgg | ctttggaata | tccataggaa | 48000 |
| ccagagtacg | tttatctacg | atctctgtca | cttttttgccc | gaaagattct | agaagatcta | 48060 |
| atctggttac | gggaaaccac | ttgatctctt | tacctaccga | tcctgagttc | tggaacatta | 48120 |
| gaggatactt | tgccccaggt | ttaaagatct | ggtatgaagt | gtgttttaat | aagtattccc | 48180 |
| acagttcgtt | gctgggttta | caatagattt | tattagatat | aactatcttc | atatcttaac | 48240 |

FIG. 15AA sequence.txt

| | | | | | |
|---|---|---|---|---|---|
| tctaagtcta | ggagtttctg | gctcctcttc | gtgcgtgtca | aaaataactg | gtgaaccgcg | 48300 |
| aaccaacgcg | tacgaaatat | agttggcagg | ttcactaagt | aagaaaggat | atggaacgtt | 48360 |
| cttgacataa | cactggtact | ttccgttgaa | gattctagtt | gatcctctaa | cgcgttccgt | 48420 |
| gataatgttg | taataagtcg | taggtttcca | tgttactatc | ttacctgtgg | agtcgatgaa | 48480 |
| atgctttagt | ccagagttta | ttatctgaga | taagtacttg | aactgtttct | ttaaaggata | 48540 |
| gagcttataa | ggtaaatttt | cccgctcacc | ataaagaaaa | agccttcgct | gagagaatgt | 48600 |
| cccaggaagg | cttggattgt | ccagcacata | ccttgtaaat | ctcgtctgga | taacaatgta | 48660 |
| ctcccctct | tggaagagta | catcataagc | ccttaaagca | tatactggta | agctaaagtt | 48720 |
| aagcaccaag | aaccctgcga | acgttgacaa | tatctttgct | gatttccggc | aaaaacttaa | 48780 |
| tattggcgta | cttatcgtga | tcagggtggt | tttcatcgtt | agccgcaata | gcagcgtagt | 48840 |
| cgaagtcctc | cataccgata | atactacgta | ctttctcctc | aaactccttg | tcctcaatgc | 48900 |
| aagcaacaga | aggacgctgt | ttcttgatct | taccacagga | gtaatcacga | gaaccgccag | 48960 |
| cctcggagtc | agagtcgata | ccaataggac | agcccggaat | actaatacca | cggtctacct | 49020 |
| gaatgttacg | gattagcatc | tcgttatact | gatcaactaa | atcctcacga | acaatggcaa | 49080 |
| ccacggagtc | gtgaaccagc | atgataatct | tcatttcgtc | ctgcagaccc | agagagcgaa | 49140 |
| tctcattatc | ggtatcgata | gcgcctagca | ggagactatc | agaagatgca | gactgaatga | 49200 |
| tggcgttgaa | accagaacgc | agttcttcac | cctgtacacc | acggtcttcg | gagttaatgt | 49260 |
| tgtgcagacg | acgcttacga | ccaaagtggc | tgtaaatgaa | gccgttagtt | tggatctggg | 49320 |
| catgagattt | atcgatccat | ttcttaagct | gagggaatcg | gccaaagtag | gtttcgatgt | 49380 |
| actctttcgc | atcaccagta | gtacattcag | tgtacggttt | accggtcttc | atgtgctctt | 49440 |
| ctaggagagc | ttcgtttact | gacgctgcta | ctttagccgg | gccagaaccg | taaagaatac | 49500 |
| cgaatgaaat | agcttttgca | gcctgtcgta | gtgcaggata | cagttttta | acctcagtcg | 49560 |
| gtttacacgg | cagagcaaat | accatgtgtg | caattgaacc | gtggaagtct | gagtagtttt | 49620 |
| ccgggtcgtt | ctgcatgttg | ataaacactt | gctgcatgtt | aatgtcacca | gacagtacag | 49680 |
| cggcgtagta | aatctcagca | gttgttaagt | cccatgcgat | aatacgataa | cctacagggg | 49740 |
| caacaataca | acctttaata | acagactcat | cacgaggtaa | ctgctgaagg | ttcagcttac | 49800 |
| cagacgaact | cagacgaccg | gatgtagtca | tatggatatg | gaatccagta | cgaatgcaac | 49860 |
| cgtcagcatc | aatactgatc | agcatcttct | cgatatacgt | cgagagcagc | ttggagatct | 49920 |
| tacgaatctc | tagcagagtc | ttagctatcg | gatgctggtc | cgaaagctct | ttcagggcat | 49980 |
| ctgcgccggt | ggaatctgca | cccgtatctg | tcatgatacc | cgtcggggtt | aagccaacat | 50040 |
| aatcgaacag | gagcttacga | agctgtacaa | cagaggctgc | gttaaatact | gagccctgat | 50100 |
| cttcctctag | cttacgaact | tctggatact | catacagctt | agcttttgca | agctgtagcg | 50160 |

FIG. 15BB sequence.txt

| | | | | | |
|---|---|---|---|---|---|
| cagtcattaa | ctgaacctga | gcctctttca | gacgatcttt | ggagatcggt | acaccacggt | 50220 |
| cttccatacg | ctgtaggaat | acacatcccg | gcatcagtac | atcgtaatac | agagacttca | 50280 |
| gtcgagggtt | agcttcgact | tttggcagga | agaaattgga | tagacgcagt | gttgcatcgg | 50340 |
| tatccttcgc | tgcgtaaggc | cacatgatat | caaacggaat | gagatcatac | gagaaatcct | 50400 |
| ctttcttgat | cttatgcgtc | ttgcaatacg | tctccttgaa | ctggtcgagt | tcaaaatcgt | 50460 |
| agtcccccat | atcggtatac | ttcatcgcca | aagatttcaa | accgtgtgta | ccacgtcgtt | 50520 |
| catctagggc | gtagtgcatc | agcatggtat | cgtggaggcg | tttctcttct | gctgccttat | 50580 |
| caaaggatag | acctaagtga | tagcagtaga | agtgcatatc | aaacttcaag | ttatggaaca | 50640 |
| caacgccatg | ctccgggcta | tcgaacagtt | tctgtaagta | atagacggta | ttttctgtga | 50700 |
| tgacgtctgc | atcaatatat | acgccctgat | actcttggtg | ggagattgag | atccccagca | 50760 |
| tgtaaccatc | tcggcagtat | agcgcactgg | tttcggagtc | atatgcgatc | atgccaggac | 50820 |
| acatggtata | caccatcttc | acatacgctt | cggcttcgtc | cgggcactga | atcgggcggt | 50880 |
| aatcccctgc | tttagagcgt | ttttcacgac | cattgagaat | ggcatgaatg | ctctctactg | 50940 |
| tggcttcaaa | tacaggcttc | atttccggtt | taaagtggag | ctgggccgga | ctgatacttg | 51000 |
| caatccagtt | agcataccca | tcatgctcaa | cacgtttacc | tgagtaatcg | gaaatgccct | 51060 |
| ttttagctgc | aaacttcaag | aacgggtctg | cacctaccag | aataacgtaa | tcaaaatctt | 51120 |
| ccggattgaa | cgggttctcc | ggtgttccga | tagtgatatg | tttcttgagc | agtcgcccgg | 51180 |
| ttactttctc | actagccatg | aagaaggtct | caacctcatg | gtcaaagagt | tcgaagtgtt | 51240 |
| tctgatagcg | gacgttattc | ggtgatttgt | ctacaactgc | gattttcatt | gatttctcct | 51300 |
| attaggtaag | caagtaaaac | gtcagtgttt | cttctcaaac | ttacccaatt | attatatcaa | 51360 |
| atcttgacat | gttcagcaat | caagatttct | acgtttctga | tgagttggtc | gacttcttca | 51420 |
| gcatctaggt | ctccagggtc | tttgccctct | ggaagcaaga | agttacctat | aattggtata | 51480 |
| attctagtct | tatcacggat | taatttggcc | aacttcttag | ccgcctcatt | accggactta | 51540 |
| tcattgtcca | atatgatgac | tacgtgagta | gtaccggcga | tttggaacgg | catgaattta | 51600 |
| tctgcaatgt | tatctagtga | gaactggtga | gtaccaaaac | aacatgaaac | gttatggcaa | 51660 |
| cctttatctt | ctagattcaa | catgtcgaat | ataccttcga | ctaggattag | gctggggtg | 51720 |
| ttatagcgaa | cagggaagat | tggggggag | accttcttag | gtctaatcat | atatttcgga | 51780 |
| ggggcagagc | tatccatatt | acggcctaag | aagaataagt | ttctccctac | ggcatccgta | 51840 |
| ataggaaaca | ctacacgacc | ttcccagtcc | tctgtttgtt | ggaatgcaaa | gtatttcttg | 51900 |
| aaagtctctg | ctttgatacc | acgaaagtct | tgatcgaata | tcatggctga | ttctggaatt | 51960 |
| tctagactgc | gaccctcagt | tcggaggtca | ctaatcattc | tgcgaactct | caggagtcta | 52020 |

FIG. 15CC sequence.txt

| | | | | | | |
|---|---|---|---|---|---|---|
| ggcgacgtcc | tgtactgttc | ttcattgaag | taatgaaaga | tgcttggtat | accacgacca | 52080 |
| aatccgcagc | ttaggcagtg | gaaaaccccg | gaatcgggt | caacacgcaa | actaggatga | 52140 |
| gcatcctcat | gatcaggatt | gagacagcgg | atgaggatgt | ccccacccgt | atctctgtat | 52200 |
| tcaatccctt | tgagatctaa | aagctcggtt | attctactca | taagtctctt | gaggattctc | 52260 |
| cggtgggatt | agtatcctca | tccgaagcct | ttttcctttt | tggtttgtct | ttcggtttat | 52320 |
| cgctttcaag | tgggataaca | aactctgctt | ccatctgacg | aatgtcctct | agcttaaggt | 52380 |
| cagaagtctg | atccatacgc | agtgagttcc | agttgatctt | cggcatgaat | gtcataccct | 52440 |
| cggagttacg | agtttttacg | aagtcgaact | tgattgcacc | gtcatgcccc | tcgttctgtt | 52500 |
| tagcagcatt | taggtttgca | gccatatcac | aggaatcgag | aatacctctt | gccatacggg | 52560 |
| cgttaccctg | ttggtcaatc | tggtaagggg | ctacaccagc | aacgttatgc | ttttggcacg | 52620 |
| tagacttgaa | tgtagaggag | acaaccatct | gctgcttcca | atcgtacata | tctagtgtct | 52680 |
| tcgtatccgg | caaacgtacc | tggttgatgt | agtctagcag | ggcgattgtt | accttatctc | 52740 |
| catacttgga | ggttagctta | gttagttcaa | catcgatggt | tgctgtacta | agttccggat | 52800 |
| catacacaat | gatcatcgga | gtgtgcaggg | gtctttcctg | cattagcata | gtctccatgt | 52860 |
| catggaaatc | actcatctcg | ttgagcgtat | aacgtgatac | aaaatcgtta | tatacttcca | 52920 |
| gaccgccttc | aaacattttt | gcacgagtct | tcgcaagttt | gttgagttca | ataccttgta | 52980 |
| aggagtcatt | gcgcatagcc | ttagcggaaa | caccggccat | aatggctagg | ttacgtctaa | 53040 |
| agacctcatt | ctctggcatt | tcgatggaga | aatatggggc | gatatcccg | ttgtaatatt | 53100 |
| gggctacttg | aatgttagaa | cagatgattg | atttacctgt | accacgccat | ccaccgagta | 53160 |
| gcagtgtttc | ttttctggca | attccgccaa | gttgagcatc | aaattcgttt | gagatgccga | 53220 |
| gagagataag | atttaacatg | gagtcttctt | ttctcttgaa | aacacgcata | gtatcggcgt | 53280 |
| tgaagacctt | accagtcgtt | gttactcgtt | cctctagctt | catgtgcaga | gccgctactc | 53340 |
| gatcaagtaa | ttctccctga | tccagtatgg | taatatcctg | caacacatca | gtttctagca | 53400 |
| gattcaggaa | tagatcctgt | gtgtattccg | actctaggac | atgaatcgca | tgcgatatgt | 53460 |
| caacgtctgg | aatctgagtg | tttgctaaaa | cagttagtgc | ttgagacaac | cttgcgtttc | 53520 |
| tgttagactc | tagcattaga | gcatctaacg | aaggcattcc | gttatgcttt | ttgtaataat | 53580 |
| tctggacagc | ttggtagatc | gcggtaaatg | cgtcattgaa | gtgatctttg | cgcagtctag | 53640 |
| agaatgtctc | tagggccacc | tgcttttgat | cggaggctag | gagcattttc | aaaactactg | 53700 |
| cttggacgtt | atacataaga | tactctctac | gccgcgttag | cgtctactta | aacgaaaaag | 53760 |
| gggagaggaa | caaaattcct | ctccccctcag | gtcaaatcaa | ttacttggcg | gatttagcgt | 53820 |
| caagtttagc | gcgcttagca | acaccatcgt | gatccttagc | agagatacca | cggcggctca | 53880 |
| gcatagactt | aacaccacgc | tcggatttac | cagttgcttc | tgcgatctca | gcaacggtca | 53940 |

FIG. 15DD sequence.txt

```
tatcggcgat attcagacct tccagaacgt cttcgcgtgc cttagcatta gagacttcct   54000
ggaccggcat agcttcgata cggccttcac gcagcaggct cagagcttta ccacggatct   54060
gcttaacggt acgttcgaac tgagcagcga ttgcttcaac ggacgcgcca ctggcaacgg   54120
cattaatgaa agcagcttcc tgatccgggc taaagctacg tacagcagcg gccttttcag   54180
tcggcttaac agccgcagtc agttccaggc tcaggatttt accctgtact tgtttagcgg   54240
tataagcacc accaactaca gcagcagcga tttcagcgta ggtatactga cccggatgat   54300
cgttcaggaa tgcaaccagt tcatcttcct gacccggagt ccacggagat tggttacgt    54360
cggatgcttt ctgtacttcg aagccttctt tacgcagttt agaaccaacc gaacgggcgg   54420
taacttcttt accagtttca gcagccagtt cagcagcgat gttagcaacg cttcctgag    54480
agataacggt cgcgttcaga gcgttagctt tagcggtcag ggatgcagtg atttcttcgt   54540
tccaggttaa tttagccatt tttatttatt ctccagtaga attttaatcg tcaagacttc   54600
gatgcccagc gattgtgctt ttttgtatga agaagaaccg atcttggttt catcttcgca   54660
gattaagtag tttacagcct tagtcacgga ggttttcacc gtatacccaa gactttccag   54720
atatttggta gcgtccgcac gattttgaa gtcgttgagc ttaccagtaa tgcaaagaac    54780
aactccgttg gattcagtcg ccggggtaac ttgagcttcc cgcgccccac tgaatttcca   54840
tggtagatta attacgttct gtcctgccgg tgtattcttc cacgaagcta agttttctcc   54900
agctttacct tccgctttca cagattggaa atcgttgtaa agctgggata atttcttagc   54960
agcaacttca ccgataagag ggatactaag agatccaaga accgaaccaa agtcaacatc   55020
ttgtctcagc ttagtttcca actctagctc aagtttcgtg gcgactttat cacctacagc   55080
tctgaccaaa tcttctttag tcaggaaaaa gagttctgaa actttcgtga tttccagttt   55140
agcaatcgtc tgtgggccaa agccctttaa cttcatcttt gagcagaagt tctcgattaa   55200
tttactgctt tgagctggac acatagactt gttacggcag acaactgat cgttaactaa    55260
gtccagtttc gaaccacaag agtggcaatt cagtggaatt tcaattttca ttgattttct   55320
tcctcatcaa tttatataaa tattatagca agaaaatcag gactaagcaa tcgaaatttt   55380
tcagaattta gctcagtctc tcaccaaata tttctttccc tcaactgaat gataatagta   55440
tacaccctgg cgatgaaaat gtcaataact actttaaaaa atcatcacgg tgtatctatt   55500
gaatcaagtg ttactcgtaa acacgttcta cgatgcgagg gatgaccca ccactacgaa    55560
ttacgcgaat ctggcaaccg atttctaggt caaggcagt gatataacca acgttattca    55620
gggtagcttt tgaaatgaca gcgtcgtcga tgactaccgg ggtgaagtat ccgacaggag   55680
taactttacc ggaagcccca acttgccatt ctacccgttc gagcgtagta acctcgcctt   55740
catcatcttc tttgatggcg tacgcaccac gcgggaactt gttagtccaa cctgctgcgt   55800
```

FIG. 15EE sequence.txt

```
taaattggtt gttgccatcc atacgaacca ccacgccgtc cgttgggaac caatctactc    55860
gactggagat atccagacag gtaacaaaac catcaccctg gaggatatgc atatctccac    55920
agaaagtagc ggtcaggcca actttgccgg tttcacactg aatactatat gccgtgaaca    55980
tcaggccacc ttccgcaata cgggagagaa actctccaga atctttcagg ttaatagcac    56040
cagaggcgaa gttacgcata ttttcaactt ctttggtgat gtgtacttca ccagtaatct    56100
gcaccggagt cttttgggag atccgtttag ggatgttcag taacttcaca ttatgagtta    56160
catcattacc taagacgccg ttaccacggg ttaacgcaga aacgaacttt ccgtcaatat    56220
acagaagtga aatagcacag ccatcgagct tcggcgtttc aatgccctgg aagggtactt    56280
cttcgccgcg gcctgggtac actttctgta gggagaacat acggaatagg tgaggtacat    56340
cacctttagg gccaatttct tcctctagcg gaaaacgacg gattaaggca tcatactctt    56400
catcagagat aatcgacatg cctttgtagt acgcgtcttg gcacagctta ataaattctt    56460
taacgtgttg cattatttgg cctcgtagta atcgaacagc atctgagtct tcccttccca    56520
gtaaaagttt tcgcataccg cctggaaggt ggacattacc ctacgcttag attttggact    56580
gtacaattcg catactagta cgttcttctc ataccacatg cctagcatct ggaagcctga    56640
cattgtccgt actacaggtt tgcccttctc tttctctaac caggttagga ctagctcctg    56700
accctgaagt ggcgggctgg agtatgcgtt aagcgttatc ttttgcattc tttaatgcct    56760
cgttaacaat tctagacatg tgtgctctca gctgttgagt gtgagcatac gtcttagcag    56820
cttcggtcag cttattaact aattgagcga tttcatgatc tttcataaag atctccttta    56880
aactatgaga atattatatc aaggtttaaa acactaagca attgagattt taaagaaaaa    56940
gccagcaact tagtcgtcac tggcttgggt cttttgagat tcacggtaaa cttcatgaag    57000
aacctctgaa ttgcttagta ttttagtaaa tgcacggaat agcgtgctgg tcatttctaa    57060
cgtgtacggg aacgagaagc ctgatttagt agggaaccag ttatcttcaa tatctagtaa    57120
ccataatcgg aaaccaaagt ataaattgcc tctaaactcc gagacagtca tacgaatctg    57180
tcgcccttca tcttcaaaga taacgtggga ctgatcatca atatgtcctt cgtaatcctg    57240
acaaatgttt tgattcattt ttattgttct cagataaaca aaaagccccc gaaggggctg    57300
attgcgtctt aacgacctac tggagtagct cgatcaagtt cttggttgag gctggtgatg    57360
cgcttaatat tcgcaatcgg aatatagcgg aatttatcgc tagagcggct aaagaccagg    57420
atatgatctt tgtcagcggg ttccaggcct tcacggacga ttcgctcggc cagatattta    57480
tcttgcttag gatcgaactc agtcgtaccg tagaggtaag ttaccccctt ggtacgcagt    57540
ttggtgtatt gcatgcaaaa ctcaccgtgt ttctcacaga tagctacgac ttgtgcttta    57600
ttcattgcaa taccctctta tttagtgatt ttacggatag cttcagccag gtgagaggca    57660
gctttaccgg tcagtttgtc aacgatcgat tcgtccagga agccatcttc cagtccagcg    57720
```

FIG. 15FF sequence.txt

| | | | | | |
|---|---|---|---|---|---|
| tcgttaaatg | cagcgcgcag | ttcagcctga | gcatcagact | tagaagtacg | gccaccagct | 57780 |
| ttaggggcat | caccaccagt | tttagcggta | gacttaccag | cttctttctt | gacgtatacg | 57840 |
| ccagctttgg | acagcttcat | acgaaggccg | ttcggggaaa | caccgtgctc | tttggcgatc | 57900 |
| tcagctacga | tctccatgga | aacgccagga | cgctcatctt | ccgggaagag | ttcgattttg | 57960 |
| gcgacgtagg | cagaagtcag | ttcagcttcg | agttcaggag | accattgagt | tggagtagac | 58020 |
| atatttatta | cttccttatt | tattgttaaa | aagagttttt | aagttttgtt | tcagactatg | 58080 |
| agaatattat | aacaagttac | tgagctgcaa | agcaaacaga | attttctagg | atttggttaa | 58140 |
| cagctaccaa | accattaggg | gacaaacgat | acatcttcag | caaaccacga | tcgtatttgg | 58200 |
| taagccagcc | attatcttct | gcttcgtcca | tgggaagtgc | atagtgcaga | tcccggatag | 58260 |
| ctgtagcacc | ctcggaatag | atctgaaata | agttcaggag | ttgatattta | ctcaccttta | 58320 |
| cctctctttt | ctagtttcag | ggctgctttt | acagcgttat | taaccagttc | agctacgtct | 58380 |
| tctttacccc | acttgaaccc | cagggacttg | atatcaacac | caagtgctac | cagatgttcg | 58440 |
| acagacgcca | gatcccaata | catgtagtta | acatactgct | ggcgggcttc | ggacagcagg | 58500 |
| taaacacgat | acgcgcctac | cggattatcc | agagcttttt | taacttcgcc | aatacactga | 58560 |
| tagccaggaa | cccaaacgtg | ttcgcctact | tcgaatacct | cttTcattga | ttcttctgga | 58620 |
| atcgcaggtg | gaaagagcgg | gtcaacctcg | ccattaacac | gaagcagagc | accgtgagca | 58680 |
| gacagaacca | ttctgatcat | gtttgcggaa | cggtagaaac | gctcggcaat | tgcctcaaaa | 58740 |
| ctatcacctg | acaggtacga | atcgataacg | ttggccagtt | cagccccttc | gattttagta | 58800 |
| ccacgtttct | ttttacgcat | ttcagcggaa | acacgctggt | tatctttcca | ttcctcgata | 58860 |
| aggcgttcca | tcgtggagtt | agacgctacg | ccgaggattt | cgcaagcgcc | tttcttggtt | 58920 |
| ttgccttcct | ctagccactg | aatcgcttcc | ttaaacttTt | cgtccggat | gctattagca | 58980 |
| tgaagttttt | tgcggattgc | catgttcttt | atcctctctc | gaatttatga | aactattata | 59040 |
| atacagattt | agcttctaag | caatcgcgat | tttcatagaa | cgtagggtcg | aaagtaacgt | 59100 |
| gcatgaattc | agatagactc | ttgtacccca | tgttaagttc | catgttgatg | cgtatagaaa | 59160 |
| ggcgtgtctt | tcgctgagcc | tctagccaat | catagatatt | tggcatctgt | gctaagcgaa | 59220 |
| taggtattac | tctacacaat | tctatctctt | tagctttccg | tgctttcgta | tcgcgtttgg | 59280 |
| gaaacttcct | tgtttcccag | cgggcatcac | gcttgctcat | tacgtactcc | aagttcgttt | 59340 |
| tgcgcttcat | cggccagcgc | cttctcctcg | tccgtcataa | actcatacgg | tacagagata | 59400 |
| ccctcgatag | aacagtacgt | gcgataccag | tctacgatct | gctccgtctc | catttcctta | 59460 |
| ttaataccca | tttgggttaa | gtacatacgg | gcatatttag | ggttggcaga | ctgtcccgtc | 59520 |
| ctaataaaga | agtccttctt | gtgtttcttc | agggcttcaa | taagggggct | aatcgtcacg | 59580 |

FIG. 15GG sequence.txt

| | | | | | | |
|---|---|---|---|---|---|---|
| ttagaacact | tcttaatatc | cttccagaat | atatcttgaa | gtttatggaa | gaactccgcc | 59640 |
| cgcttgtgtg | gtttcttact | aatccacatc | tccgcatgtt | cctgtgtgat | actcttgata | 59700 |
| gagtccaggt | ggaagtactt | gaccaacatt | agcttggctt | cgtatgcgtc | cgcatgacgt | 59760 |
| ggtgcacacc | aatccggggt | actactcaaa | atagcagaga | ctcgttcagc | agtatactct | 59820 |
| gcggccgagc | tatcaatctt | accccagctt | tcactgaaga | tatcgatagt | tgctccctga | 59880 |
| tccagcagat | aataccgcag | agtactgata | aagttacggg | actctagttc | acgacgttta | 59940 |
| acatacagct | gctgagctaa | ttctagccaa | ccctcatcga | tgttatactg | ctccgaaccc | 60000 |
| gcagagaatc | cgctggtgga | cttatcgatg | aaatagaaga | tattcttagc | tccccggtcg | 60060 |
| cgcctgattg | cctggaagcg | catgtttggc | gcctggttag | cggtacgagt | aataacgaat | 60120 |
| acgttgtcga | agtaattaaa | gtcaacacca | ctcgttactg | acggactgca | cagtagacaa | 60180 |
| tcaatctgct | gttcaattaa | ctcattcgtt | gtataatcca | agatacgacg | aatatctata | 60240 |
| tcagatgtag | agtttgagtg | aatctcttta | acaatcgcac | ctgtattgtt | tcttagcgtc | 60300 |
| aggcctttct | cgtttaactc | atccggccca | cagtcggaca | ccagaataga | tttctctccc | 60360 |
| atctctaggg | acgtttggag | ggcaacccaa | atactggatt | catcagggaa | ctcatacgcc | 60420 |
| tgagcatccg | agagcatctt | acgatggtgt | ttataataag | agaccggctt | gtcaaaatct | 60480 |
| atgagagatc | catatgcctc | aatggtttct | gcgctgatat | ccccgtcaga | caggataacg | 60540 |
| acttttgcag | atagcagaat | ttcacgaaga | actgagatac | actcacgacg | ttgtttaaca | 60600 |
| actggagcaa | ataacaggtc | attcataact | gcgtcgcact | catcgataaa | gataacatcg | 60660 |
| atctgcccaa | caaagttttt | aaacttgtgg | attgagtgaa | tagtagtaga | catacgatca | 60720 |
| atggcaccgc | gcttgaagtt | taacatatct | acggacttat | catactgtcc | ggcttcaaac | 60780 |
| ttcttagcgt | tagatgaaac | cagggcacgg | gtgttagtaa | ctgcaaggaa | attacctttc | 60840 |
| agctgatcac | gttctagcca | cttcgtcact | gcggtggttt | tacccgtacc | tagagaagcc | 60900 |
| ttgataaacg | ttaaatgccc | ttccggtggt | ggacggttga | tcttcaaata | attcatcccg | 60960 |
| tctgggctat | cagaggtcaa | cttgtgtaca | ggaacgcctt | taacattcga | ctcaggaata | 61020 |
| tctcgcatcg | agttgttcac | aaacgctttt | aatgcctgct | tacgaccgtt | attgaagtaa | 61080 |
| tcctgaagac | tgcgggaatt | atccttcgtg | ttgatataat | cggacaaagc | tgaggtaatt | 61140 |
| tctttctcaa | gccaggcgaa | atcaacaccg | tcctccagag | ctctgtggta | cagtttagga | 61200 |
| ataatacgca | gataaacacc | atcctctgct | tcttccagct | ctgcaatggt | ttgttccact | 61260 |
| ttctcagagg | ctacgcgctt | gcctttaatc | tgattaagta | gggatagaaa | ctcttctttta | 61320 |
| aattccccac | gagtggcttc | ataatctggc | atagtattgg | gcagttcaat | cctagcaccg | 61380 |
| ttaactttaa | ccagacgtgg | cttaccctcc | gctttaaacg | gatcggtaaa | ctgatcccgg | 61440 |
| aaaatcgggt | cagcgaaata | gtgtagctgt | acagatgaat | aataagctaa | gtcggcaata | 61500 |

FIG. 15HH sequence.txt

| | | | | | | |
|---|---|---|---|---|---|---|
| tcaaaaccat | acttctgccg | agagctatca | ttgagggacg | taaatagaaa | ctttaactga | 61560 |
| ccctgagtaa | cgggaatatt | actctctaat | agcatgtgca | tacgaatccc | cggcttaatt | 61620 |
| ccagccgaag | acgacgcatg | ggcaataaac | cctgcgttaa | gcgggaacat | gtcctcgctg | 61680 |
| atgctattta | ataacttaat | gacatgacgt | cccataccca | caatgtcaaa | cctgtcgcat | 61740 |
| cctccggtat | cagagattcc | atcgacgtcc | atagcaataa | tattgctctt | atggtcgatt | 61800 |
| ttgaagttag | tacgtttacg | acgcacggcc | ttctctgcaa | ctaagcatgt | acctcgtact | 61860 |
| gctacgagat | gtggatcttg | agtgagctga | accatcagct | catacgcttc | attaagattt | 61920 |
| ttggggtcaa | ctgtatccac | tacgttaaat | ttgtagggca | ttgaggctgg | cttaccttct | 61980 |
| ggatgctcgt | tagaaaactc | cttcgcaaaa | aggtaatcag | ttgtcttcac | ttccttccag | 62040 |
| tttccggaag | cgggatcgcg | ggaaaaaccc | gcgtgtcctt | ctagaataga | aaacattacg | 62100 |
| ttttctccta | tgttgaagaa | taaagcgatc | tcgaactatc | aaggatagaa | cagcttaaaa | 62160 |
| gtccactgac | tcaacaaatt | tccttataga | tggaggggtg | gtcacttcct | cattgctaga | 62220 |
| actggccgct | tcgcacaact | cccacacagc | atgtaatcgc | cgctaagctc | catgtggttg | 62280 |
| acccctattc | gtcgctattg | cgcagaggta | cgttgctact | tacagcttca | cttcttggtc | 62340 |
| atttcagacc | gcggtgctat | ttgctccaca | tgactaacga | acaaatatct | gagagcctcg | 62400 |
| cgatgccaac | ctctcttacc | cgcattctag | atcaattatc | tataattccg | ttcggaatca | 62460 |
| atttcccaat | aagccaaacc | caaccaagca | tgtagcagcc | ggactgttct | gtatgctcgg | 62520 |
| aagtgaatga | gaggaattat | gtcagttttg | taactcacat | catttctctc | aacctatgaa | 62580 |
| tatattatat | aaaaatcgtg | gcgagattgc | aagtaaaata | tttaaatacg | tggtaggtaa | 62640 |
| ctgggtttaa | gcatagaaaa | gaccagagga | taatcccctg | gtctaagcgt | tcaactaggc | 62700 |
| attccaaccc | ataatattaa | ttgagttaga | agaggcattt | tgtttgccct | cacgaagaac | 62760 |
| ctctggagca | tacgtccaag | gctcatcagc | taccaagaac | cccggagaaa | tacctgcccc | 62820 |
| cggttcccgg | aatgctgcaa | aattagaggg | gtggaacaca | acgttgttca | ccagaaccat | 62880 |
| tagccccaga | tccgagaggt | catcccaatc | aaagaggatc | tcataatcct | gggccaaact | 62940 |
| acctttggac | aaaccaacac | acacgtcatg | ctggatgatg | aagcaaagct | cctcgtccct | 63000 |
| caacgcggct | cgcagcagat | tctctgctac | atcaatcaat | tccttgggga | tatccgccca | 63060 |
| ggagatacgt | tccattttag | gaatactcat | ttagttaacc | cttcaacttg | gaaaccgaag | 63120 |
| cgacgcagca | cctggatcca | accgttaata | ttttccggag | cataataatc | ttcattacgt | 63180 |
| ccgacccaaa | tacctgctga | aacacctgta | accccaaccg | ggatatagga | ctcacgcagc | 63240 |
| agacacacgt | agccagtgc | aaacaccagc | cccatctcag | tcagatcgcc | ccagtctagg | 63300 |
| acttcatctt | gatcttcgtc | cataggaacc | catagcccca | ggtgcatgtt | gtcataatcg | 63360 |

FIG. 15II sequence.txt

| | | | | | | |
|---|---|---|---|---|---|---|
| aagtagacct | ccatattatc | gcaccacaca | cgaagatggt | ccagcagaga | ctcttttacg | 63420 |
| tccagaggaa | tttcagccca | gggaactagc | ccaaccccctt | gattaacaac | cttttcattg | 63480 |
| accagcatat | tcttccccca | tttggatgaa | ttcgtgccac | tgctcagagt | ccgctcgtaa | 63540 |
| aacctgatag | tcgtccgata | ggtgactcat | atcttgtaca | tcactgcgat | aacaccaact | 63600 |
| accgttgggc | cataacagga | tatcatcggg | atggtacata | aattttctcc | tccagccaag | 63660 |
| cctcaacttg | acctatgaaa | tgtttgttgc | taaatacatt | ggcagcagta | tcataccaaa | 63720 |
| cggggatccc | gcgttcttcg | tacaaactct | gctccaggta | gttaataccg | ttgttcacta | 63780 |
| cccacacctt | agtacctcga | ctatgggctg | gaatagttc | ccaattaaag | tcgattactt | 63840 |
| ggttactagc | accaacaacg | attaccagat | cctgggttgt | cagggtatca | aacaggttga | 63900 |
| tctgccccat | ataccacgga | gcggtttccc | cgaagaacgt | aattgcaggc | ttaacccact | 63960 |
| catacttacg | gtaatcaacc | gcagtgtacc | cgatatcttc | cacgatcaca | tccttacctc | 64020 |
| ggcgatacat | tatctccgta | aggtagccat | gagcatggat | cacatcatca | tggggaatgc | 64080 |
| cagcacgctc | tagtagatca | tccacgttag | tagtaaagtt | aacgacttga | ccagggaagc | 64140 |
| gctcatacca | ctcagcaatt | ctcaagtgag | caatgttagg | ctccaccgta | cccagctcct | 64200 |
| gtcgccgcat | gttgtagaac | tcatgggtta | gctcgtacag | gttgcgacta | ggctcatcat | 64260 |
| cagatccctc | agaaagggct | tctaacgggg | gcatagggtc | gttcagatag | tgaaacccct | 64320 |
| tatcgaacgc | ctgaatattg | catacttcgg | ttagtttgta | tttatcccac | aggggagtga | 64380 |
| tggcacccctt | acggaacgtt | ggcactcaat | ccagcaccac | ttacgataat | caatctacgc | 64440 |
| attacaggaa | ctccatatag | tttctcattt | cttctttccg | caactgctca | gccttttcgg | 64500 |
| acaagcactc | agaggttctg | ggatcgactt | tatctttcca | caagtggtta | cggcatcgca | 64560 |
| gaagttttac | cacgtcttct | cgggaaatag | atccgtatgc | tccagagtcc | atcataaagt | 64620 |
| agatacgctt | ttcatcagtt | ttatggattt | tcataaatcc | tccgtttctc | aattacaact | 64680 |
| atcttatcaa | aaacggaggt | atttagcaag | tgatttattt | caaattcatg | tgtttgaccc | 64740 |
| tttgcattac | ttcctgttgc | ttaccagggt | taaagggtct | actaccagga | ctacctaagt | 64800 |
| acccacaaac | gcgacgggta | accgagatat | tccccgaccc | acattgagga | catacaaagc | 64860 |
| cgtgctctcc | ggatacagac | tctcctagat | atccgcactc | ttcacattca | tcaactggaa | 64920 |
| tgttaacccc | tatgtagtga | gatttactta | atccataatc | aacaacccac | tctagtgcag | 64980 |
| ggataaactt | acgcatctcc | ggaagttcca | caaggatat | attaccccca | ttggcgatgg | 65040 |
| tggtaaaatt | agcctcatag | tcaaacttca | cgttaggggc | aacttttgta | cggacatcca | 65100 |
| ggtggtggct | attagtcagg | tatcccttat | ccgttagcca | gtcgtactca | gggtactgtt | 65160 |
| cggcaatttt | agtattgaac | ctattgcaca | gagactcact | aggggtagca | taaaggctga | 65220 |
| atccaagatt | agtttcctca | gcttttttgt | tacaacggtc | tttcatgtgg | ttgagaacct | 65280 |

FIG. 15JJ

```
sequence.txt
gtacagcaaa ttcaatcgca ggtggggaca tggggtcggt atcctcaaac attacttcaa      65340
ccagctcgtt aataccgata tatcccaaag acactgatgc cctgccttca aagatgggcc      65400
atacaagatc attggctttc aaccgtaccc caaaagctcc gtgcatatag agaattggtg      65460
cctgtttagc acgcacacgc ttcaaccgct caatagccca atcgtgggca gccatcgctt      65520
tatcaatgta ttcgtccaac aacttccaga acctatcgaa gtatccctca gactctacag      65580
caactagcgg caggttaatg gatacaaccc ctaggttatt gcgccccgca gtctcccggg      65640
actcaatagc tgaaaggaaa gaccgacaac ccatagggaa cttaaaatca cctgtaacag      65700
ccgttactct ttcataactc acgtaatccg ggtacatcct cttagaagtg caggtgagcg      65760
ccagctgttt gatatcgtag ttgggatcgc tgggagattt attaagcccc tctttaactg      65820
cgaaaataag tttaggaaat acagcagtat gccctgaagc acccaggcct cttatacgaa      65880
cttccagcat agctttctgc aacatgcgtg cctcccagga ttctcctaga ccaaacccaa      65940
atgtcacaaa tggctgctga ccattagagt tgaacaacgt attaacttcg tactctagcc      66000
cctggcacgc atcatatact tcttttttctg tcatttcagt agcatacact gctgccttct      66060
tactatcgtg aagccaacgc tggccaatag ctaagtgctt atcataggac ttacggacat      66120
acggggcaaa gacctcgtca atacgatcga tagacgtacc cccatactga cacgagctta      66180
cctgggcaat aacttgggca gttactgcag ctgcagtaga gatagatttt ggagtttcaa      66240
tctctgctcc accaatttta gttccattct taaacatccc cgctaaatct accaggcagc      66300
agttagtata cccctgcgct cggtagtcca tatcgtgaat gtgtatctct cctctattat      66360
gagccgccaa taggtatgct ggaagctcct gtgctaccac atacttagag acttccccag      66420
ctatcatgtc cctctgtgta gggaattgct cgcttgcctt attggcatta ttaaacataa      66480
ggtcttcttc accctcgtta tcaaggatac tatagatatt atcaatcagg tctaattcgt      66540
tcatatattc ctccagttag gcatatatta taccaaatag acacaactat gtcaacctta      66600
ttttattata atcaacagta acttgatctg gatcatcaaa acaataaaaa ctggaaaatt      66660
ttatttgctt attcacccta ttttatatta ttcgtgtgcg cccgcgcatc gcgcgaataa      66720
aggaaaggat ccgtcctcca tatcatccta gaaaatttca gttgcaatcc acgccaaaac      66780
ttggtatact ggtattctaa attgataaac atggtcgaaa tttgaccctc tgtagacctc      66840
taaggagatc gcaatgagaa aagcagcacg tcgtaaggag tcgcgccgta acggtagcgc      66900
aaaacgtgaa cgtcacgaaa acgtcatccc cgttgatttt gaagcacggg aacgttttca      66960
accaaccgca aaagaactca agccgaagaa cgctgagcaa aagcactata ttagcaccat      67020
ccgtaacttt acggtgacag ttggtattgg agaagcaggt acgggtaaaa cgtttatccc      67080
atctgttctc gctgctcaag agttagcaac gcctggttct gtgtacgaga agttcatcct      67140
```

FIG. 15KK sequence.txt

| | | | | | | |
|---|---|---|---|---|---|---|
| agtccgtccg | aacgaacctc | ttggtaaatc | cctagggatg | ttgccaggag | atctgaacga | 67200 |
| gaagatggca | ccgtggttag | aaccaatcgc | tgacggcttc | aagtgggcct | taggggaacg | 67260 |
| ttcttatcag | gggctggttg | aacgcaaggc | aatccaatac | cttgctatcg | aacatgcacg | 67320 |
| cggtcgtacc | ttcaacaatt | cttatgtaat | tgttgacgaa | gctcaaaata | tctccgtaga | 67380 |
| agcaatgaag | tgtattctaa | cccgcgtagg | tcaggattgc | aaattagtaa | tctgtggcga | 67440 |
| cgtagcgcag | aaagacatta | aatccgactc | tggtctgcaa | ctgatcatgg | atatctacga | 67500 |
| tcagtacgaa | catgtgcctt | tctccttagt | agagttgcat | gataacgtgc | gttccgctga | 67560 |
| atccaaagca | ttccaggcaa | tctttaacga | tatgggaatc | taatatggtt | actgaactga | 67620 |
| tcattggtta | tggtgagggt | attacctctg | aagaaaactg | gggctttgta | ggcttcggtg | 67680 |
| aaggtatcac | ttctcacgac | gaacgtcctg | acctctaact | ctaggagcgc | gtatgaacaa | 67740 |
| cgtatttaca | ctgaacaact | tccgcactcg | taaaacgaaa | gtgcatccag | tatccctggc | 67800 |
| aacagtcaat | aaatacaatg | ctaactatcc | tgaggatgag | cggcgacacc | atgccgcttt | 67860 |
| caagatagca | aacgaatttc | ctaaccaacc | cctcggtact | aaagagttag | ttagtcgaat | 67920 |
| gaaaaaatta | cacttttatt | aaagtagacc | gacacacagg | cagcctcgaa | aggggttgcc | 67980 |
| tgttttgtc | tgtaaaatct | catttgcaaa | atggccgaaa | acaaagtaga | atatctttta | 68040 |
| aatcctgaca | acttccaaaa | ggagttacca | atgacccaac | gtattgaata | cgttatcaag | 68100 |
| cgtgacggta | caaaagaacc | gttcatggcc | cagaagctga | atgactgggc | aaaatacatc | 68160 |
| ggaatccgaa | gcgatgttcc | gtggtctccg | gtagcggtag | ccgcagttaa | gaacctgccg | 68220 |
| aaaggtgatg | tacactcaga | cgatctgcaa | acaatgctga | ttaagtctgc | cgaatcaatg | 68280 |
| atcgagcgtg | atcatcgtta | cgaccgattc | gccctagagc | tgcgtttagc | ccagctccgt | 68340 |
| aagaacctgt | ttgattctta | cacccccgcc | tctctgcgtt | tcttccacga | ccacatggta | 68400 |
| gagctgggag | cgtgggaaga | tatgagcggc | tggatctctg | acgaccagtt | cgaagctcta | 68460 |
| aacgaagtta | tcgaccacag | ccgtgacgaa | ctattcacta | atgctggtct | gaagcagttc | 68520 |
| atggataaat | actctagacg | taatatctat | acggaagaga | tctatgaaac | tccgcagttt | 68580 |
| gcctacatgg | gtatggcaat | ggcaatgctt | tctcaacctc | actggagtat | gctcgatgca | 68640 |
| atcgaccttt | ataacgcgct | gtcgctacag | aaaatcaacg | tcccaactcc | gccgctcgtg | 68700 |
| ggccttcgga | gtgctgacag | gggcttcgct | tcttgctgtc | ttgttgatgg | tactgacacc | 68760 |
| ctggactcca | ttgacgcagc | agagcacgtc | gtcttcaaaa | tggtcgctgc | ccgagcaggg | 68820 |
| atcggctatc | atcttgagag | tagatcaatt | gctgatccgg | tgcgaaaagg | cgcgttccca | 68880 |
| cactctggaa | aactgccata | ttatcgacac | atcgaccgct | ccgtaaaagc | taacactcag | 68940 |
| cagtcccgtg | gcggttctgc | aaccgtttac | actgcgttct | tcgatccgga | aatcattcag | 69000 |
| gtaatggaag | ctaagagcaa | ccgttcccct | gatgaaaaga | aaatcgataa | gatggactac | 69060 |

FIG. 15LL sequence.txt

| | | | | | | |
|---|---|---|---|---|---|---|
| aacctgaagt | ttaacagtat | tctcctgaaa | cgcttcctgc | gtaaagagaa | catcacactg | 69120 |
| atgagcttcc | tgtacgctcc | agaagtatac | gcagcattcg | actctggtga | tgtagcagaa | 69180 |
| tttgaacgcc | tgtacatcgc | agccgaaaaa | cgtctagcgg | gcgttaccaa | acgtggtttc | 69240 |
| aagggtgaag | ttctccctgt | agccccagtg | attcctgccg | cagaactgat | tgagttctgg | 69300 |
| aaaactgtac | gtatggaaac | tggccgcctg | tacactatgg | acgctggtga | agtgaaccgc | 69360 |
| aacagccgtt | acaaagatcc | ggtgcgtatg | tccaaccttt | gtgttgagat | tgtacagcca | 69420 |
| acgttcccga | tccctcacgt | agtagatctg | taccgtacag | acgaagaact | ggataaaatg | 69480 |
| gatgtttcag | agtatgggga | agtatctctg | tgcaacttag | gcgggttcgc | cctaggtcgt | 69540 |
| atcaaaactc | tggaagagtg | ggagaagatc | tcttacatcc | tgttgaagtt | cgttgatacc | 69600 |
| atcatcgaga | ttcagcacta | tccgttccca | gctatgaagt | acacggcatt | acgccgccgt | 69660 |
| aacgtaggta | ttgggctgat | gaacgccgca | ggagcgatgg | ccgctgaagg | cctggcattc | 69720 |
| gaaggcgaag | aagcccgtaa | ctggattcac | cgtgaagcag | agaaggcatc | attcttcctt | 69780 |
| cataaagcgt | ctgtacgtct | ggcaaaagag | atcggcccat | gtgaatggtt | ccatcgtact | 69840 |
| cacacttctg | atggtacact | gttaatcgat | acttacaaga | agactgtgga | tgacctggtt | 69900 |
| tccgtaggtc | tggaaatgga | ctgggagagc | ctccgtgaag | agatcaaaac | tcacggtatg | 69960 |
| cgcaactctg | ttctgacggc | aagtatgccg | ggagagtcca | gctctgttct | gattggtgtt | 70020 |
| accaacgcag | tagagcctcc | tcgcagtgcg | gtaactatca | agacttcggg | cgttaacaaa | 70080 |
| gtaattactg | tagctccggg | tctagacgat | tgggacacca | tgcagtccta | taagtatgcg | 70140 |
| ttcgatattg | accgtactga | gcacattaag | tggttagcag | ttctgcagaa | gttcacggat | 70200 |
| caggctatta | gtgccaacct | gtactacgac | tttaacaaat | atcctggagg | tattattccg | 70260 |
| ggtactgaga | ttatcaaaga | tctccttaac | tccactaaat | atgggattaa | gaacctctac | 70320 |
| tacgcaaact | ttgacgtaga | taccggaggc | tctgcagcag | agcagggttg | ttccagtggc | 70380 |
| ggttgtactc | tgtaattaag | ctcgatccaa | ccgaaagcaa | aatttatttt | gcaagtaggt | 70440 |
| tggatttttt | gttataatat | tcgtatatta | aatgagagag | gaaattaaac | aatggcaaca | 70500 |
| gtatttaacc | gcgaatggga | tcacactgag | tctaaactat | tcctgggcca | agacctggga | 70560 |
| atcgccgact | atgtaaacgt | tcgctatcct | cgtttagagg | aacttgcatt | actgcaacgc | 70620 |
| tcgcagttct | gggttgagac | tgagatctcc | ctggaagccg | ataagaaaca | atggcctaat | 70680 |
| ctgccacaac | atattaaaaa | caaaaccctg | ctgaacttag | cctggcaaac | ccaagccgac | 70740 |
| tccattatca | cccgtgctcc | ggaagatgcc | attctgaaac | tggtatctcg | ccctgaactg | 70800 |
| gaaggtatgc | ttattcagtg | gagctacttt | gagaatattc | atagccgtgc | gtattccaac | 70860 |
| attattcgta | acgttctccc | taatccgggt | gagttcattg | caaccgtaca | ggctaacgac | 70920 |

FIG. 15MM

```
                                  sequence.txt
gaagcattcg cacgtctagc actgccggtt tctgttattg atgagttggc cgaaattgcc    70980
gacatttggc tggacgctag agccaatctg gaaatcgctg agaaggaagg tactctggaa    71040
tacaccgaag aggcagactt cttagcactt actgaacaag tacagcagaa gattctggag    71100
ttctactacg ctgtatacgc tctagaagcc attatgttct acgcgtcgtt tgcgtgcacc    71160
tttgctctgg cagaaaacga tatcctaacc ggtattgcaa agaacttaca gctgatcgct    71220
aaagatgagg cactccatac cgttatggct atggaagttc tccgtattct tcaaaatggg    71280
gaaattcccc cacatgtagt ggcagcagct caggctaacg ccccgaagat cctgcgcagt    71340
attctggaga cagaaattaa ctgggcgcat tatattttcc cggaaggcga agatattcca    71400
ggcctgaacg ccgatttgct ggtagagtac ctgtactaca acgcacgcct ggcatttatg    71460
gcgatcaaca ttccgtggcc ggaagatctc ccggtaatta tggaagaccc gattggctgg    71520
atgaaaggtt ggctgaacac caagaaccag caagtagctc cgcaagaagc acagattacc    71580
aactatcgtg ttggtgcaac ctctcaggct aacccggacg atctgtctga tgaatttgga    71640
gagttcctgt aatgattaca gctttatacg caatgcgagt tgacgccgcc ttcgggattt    71700
ttaatccggc tacaatggat gcctacgggg aacttccctg gggctccatt cccgaggagc    71760
tagaacagtt ctacagaatc ctggatacct atcaggttgt tatagtgggc cataatacct    71820
acgaaacagc ccctccacga ctgaaaaagg cactggagaa gaaatccatg gtgtacgtag    71880
taggttctaa ggctccagtt ctgataaaaa accctccccg taatgtgcgg tttattaccc    71940
acttgggttc caaaattcgg gacttctgta atgaagttga ggtagtctgc ataggaggga    72000
aagctctgct agaaacccta gcaactatgg gctgtctgga tgcgatttat cgctccacca    72060
tttatcctaa ggccggtaca gtaccaagcc tagaccacat catgtatctg gaacacccga    72120
tacttacgtc cactcctccg gatgctgtag taactcatat agcttctggg gaaaatgagc    72180
gctatcgttt tgttatggaa ggagtctatc tgtgattcac tatattaatg aaggcaaacg    72240
cattcttgaa gaaggtgtat ggctggagaa ccctcgaacg ggggttcgtt gtttaaccgt    72300
aatagggtca aactttgaat atgatgtact cggaaagaaa ttcccactta tcacaactcg    72360
taaagcgtat gctcttcagg ccatcatgga gcttatcgga tatctgcgag gatatgattc    72420
cgcagagcaa ttccgtgcta tcggctgcaa tacgtggaac gctaacgcca acgaaaacga    72480
ggcgtggttg gtcaaccota acagaaaggg aaccgacgat atgggtagag tctatggagt    72540
acagggcaga acgtggcttc gaccggatgg ttcccacttt gaccaactct ataagatcta    72600
tgagaattta cgacgaggca ttgatgaccg cggagagatt ctcaccttct ggaaccctgg    72660
cgaatttgat caaggatgct tacgaccgtg catgcatacc caccagttct cgctgctcaa    72720
tggaaatctg tatctcgact ccttccagag atccaatgac ttcctattgg acaagccttt    72780
taacatggtc caatgctaca cgtttcttgc gcttatggcc cagatcacag ggaaccgggc    72840
```

FIG. 15NN sequence.txt

```
aatcagagca aaccaacgta tagtaaatat gcacatctac gagaatcagt acaaggttct      72900
catggaacat gggcaatttg accgcaaacc tttcccggct cctcgtctag agatcaaccc      72960
ggagataaaa accctagagg acgtactcac ctgggtttct aaggacgact ttaaaatcgt      73020
ggggtataag tctcatgacc ctattgcata tccgttcact gcgtgaggac ttatgggatt      73080
atttaacaga cgccccaaaa taaccttctc cgaaagggag gagtctcagc tgaagtttct      73140
ggttcaatcc tcgggattac acatagatgt tatcctaggg atggtaaagt acaagggcat      73200
ggacgcacta atgcgtcagt ttgcccctaa accacctaaa gaaaaccctc cagccaagcg      73260
ggactataac agtaatttac tggttcctcc agctaaatta ctataactaa ggtggccttc      73320
gggccactta tattaaaaat tcatttgcaa accacgtgaa tttctaatat aatagattca      73380
taaatttgag agaggaaata aatatgtctt ttactgatgc aaaagcaatg gcagctaaag      73440
ccaaaaggtc taacgatatg gcagttatag cagctcgcag atctattata tcaaatattg      73500
atggatcagc ttcttcaggt aaaacagaag tagattctta cgcattgaat ggcctgccta      73560
tcgccgcacg gtctcagatt atggaagacc taaggacgc gggctatgaa gtaaaagtaa      73620
atcatccgtt tgaccaacgc gatactgaat caattaccat ttcctggggg cacgcataat      73680
gtttcatgtt tatactgatg gtggttgccg cggtaatacc cgtggggtag acaacgttgg      73740
tgcttgggct atggtagttt acaactccag cgaagagcaa atcggcacca agtctgctcc      73800
caaacgcaac acaactaaca acgagatgga gcttcaagca gtcctagagg ctctgctatg      73860
gtctaacaaa aaccctggcc gaccaatgac aatctatctg gactcaacct acgttaagaa      73920
tggttgtgag tcctgggttt ggggctggga acgtaaaggc tggaagaagg cagatggtga      73980
tacacctctg aacttagacc agtggaagtg gattatcgac gaactcaaga agtatcgtct      74040
aaaccacaat gagatcccaa ctttcgttaa ggttaagggc cactctggtg tagaaggtaa      74100
tgaggccgca gataacctgc taaatgttcg aatgaccgaa ctggaaatgg aggatatgtg      74160
atgttggaga atttacgccg cctagttagt gaaatgaaat atgaagtgct cctgatggag      74220
cctggtgtgg atcgagtagt aatgaaattg cgaatcgcac gtatggaagc ccaaatctt      74280
gaagcggagt ggaaagctct gaggggtgga gatgaattat aatggcacca gatttgaggg      74340
atttgttccc aaacgtacca cagtaccagc tcgatctcta cgccgcgttt ctggaagcgt      74400
caaaatcggg gaaccctcta cgcgtctacc gccaagaccg caggcacggg aaatcctgga      74460
tcctgagatg gctgaaagag aacgagccgc tcttaaagaa attgagcgaa agaaactctg      74520
tacagcaccg gcatacaaca aaggtgggta ccagtacatc agctcagaag agcaggcaaa      74580
acatatcggg cggtaacaga tacgagttca tcatcttcga tgatcttgta gatgaaaatg      74640
aaaaaacgca gttgctaaac gctaaaaatt aacgtataat agattcataa attaacgaaa      74700
```

FIG. 1500

```
                              sequence.txt
ccaatcaaaa caaaggaaat aaatcatggc taagcagacc tctaaaaaag cagtagaaac    74760
caaagttgca acttttccca aaactgaagc gaatcgcaaa gcacgtctgg agcgtcatct    74820
gcgtaaacat ccggctgata ctcaagcagc atcagctgta ggcaaaccgg ccccgcgtcg    74880
taagaaaccg gtaactaagg gttctacctc cggctacgtc tccaagatcg tcggttggag    74940
tacgccggat aaggcagaca ccaaagaagt cctgcgcaag acccagggcc gtttcggtag    75000
cgtcaagccg aatatcttcg gttgcgaata cagccgtgag aatgttcgcg ctctgtgcta    75060
cggcgtaggt attaaattta cgggcaaggc aaataagccc cgtaatcaaa aacgcaaacc    75120
agctaagaag gcataatgcg aaattttgta gctaaaaacg atttcaatcg tgcagcgaca    75180
cataagtcgg ccctagatta ttctagggtc aactcccggg aactgatgga ttcgtgctac    75240
gaagaactcg aagattgggc ggctgactgg ccgtcgatgg aagaaaactg ggatgtgtcc    75300
gaagatatga ctaagccacc accggaggtg gcttctaaat gtgataacac atctagaagc    75360
aactttaata acaaaggaaa caatatgcaa aacttacaag accgctggat ctctgtttgt    75420
gatatcgaat ccctgggaac tccgggagat tgcaagagca cctttatcgc tatgccgttt    75480
ttcgctttcg tactgatgaa agatctatcg ttagatccgt atatcgttct aggcactcct    75540
aacgttgccc agcagttggc cctcggtgct aaagtctccg ccggaactat tgcattctgg    75600
atgaatgagg ctcgtgctgg tagtgctccg tcgctgtcca ttattgaagc tctgaacgct    75660
aaagacggtg agtctactgt tctggtctgc aatccgactc atgaatcacc ggtatccaag    75720
catacgttca tggatctgat ctgcccgttc gtagaggcaa acaggtaat cgaaggcatt     75780
atcgatgagc aaggtatcga cactcgttcc ctgcgccact acggtaatgg cccgcagttc    75840
gatatgtcta tttacgaaac agtggcggct caggctaatg tcttctctcc gtctgatcct    75900
gcaatcgttc cgtggaaatt ctgggatatc tccagcgccc gtaacccgcg tgactatttc    75960
gaggctctcg gaggagactg gaaagcattg gtacgttgtg ctgaaatcta cgcacacgac    76020
gtaatcgagc gttacaacct gattcctgag ggggtctatc cgtcgaaaca tgatccggtg    76080
tttgacgccc tggtagaagc gtactgtatt aaaactatcg aatcgaaatt gaaaatttga    76140
tttgactaaa tggctgattt cttgatatac tattattctt gaatcaaaga gtaaaggaga    76200
aataatgaaa gcagccattc taatgatctc catcctcact agcttccatg cgcaggcaaa    76260
gattgatgcg catgagatag agtgcatagc taaaaatgcg tactttgaag ctagagggga    76320
aggagttaaa ggaatgaccg cagttgcaca agtaacgaaa aatcgtgtta actatggaaa    76380
attcccgtcc acatattgta aagtagtcta tcaaccaggg cagttcagct gggttggtaa    76440
gaagaaacat aaactcgatc gtaaagacga agagtggaaa caagctaaag agatagctag    76500
actagtttac tatatggatc ttccagtaga tccgacgaag ggagctttgt actttcacag    76560
taaagatact aaaccttact ggacaaaaga caaggacttc aaaagaacaa gtaaaattgg    76620
```

FIG. 15PP sequence.txt

| | | | | | | |
|---|---|---|---|---|---|---|
| caaccatgtg | ttctataaat | taaaatctca | gttgcctaat | gcttaaaaag | ttgatataat | 76680 |
| agtttcataa | attagagaga | acagcgggcc | gattacgctg | aacttgtttt | aatgtaagac | 76740 |
| tcgtcgagca | ttaagattcg | ttgaatagaa | tcggtgagtt | aagagtgatc | acctgacaaa | 76800 |
| gttcgtgcat | ccagtccgga | taccggccag | ggagcgtatt | ggacgggcgt | aggttagaga | 76860 |
| tctcttgtaa | aactcgggag | ctgtcccgga | gtctcgtaaa | ctcttctcct | gatttataga | 76920 |
| aaatggtgga | atctcacttt | aacctgttcg | accagaatga | agcatggtgc | gtggcctgcc | 76980 |
| ggagaggtgg | ggagctgagc | ctgagaaact | cgtatagctc | ccacactgac | ctgcctaggc | 77040 |
| cgcaaattgg | agacatgtgt | atagcgtctg | gtgctagtta | ttgccaccat | agtggggtgt | 77100 |
| cgaaatcact | tatgtagcaa | cactgccgtc | ctaagttaat | tggtagactt | ctgcacgcgg | 77160 |
| gggagctatc | cccagatgcg | gaaagtgcag | gttcgaatcc | tgcggtcgga | aagagttaga | 77220 |
| taactgatgg | ttctattggc | gaaccactcg | ctgctggagt | acctcctccc | ctcccaggga | 77280 |
| aagacttggg | agactcgcgg | gaacgaaaca | gctaaaccac | gaaggactag | gatgctgatt | 77340 |
| tggctaccct | tacctgatat | atgcccaaat | caaaagaaga | actttaggcg | gtagcctaga | 77400 |
| tagtgaagtt | tttcctccac | gaggagtcgt | ttttcaagct | atcaaaactt | cacatcgaaa | 77460 |
| attcggaggt | gtgattttaa | cagaccgcgt | ggaggatggc | tctccagaag | tgccaaagtt | 77520 |
| agtccttaaa | tacggcatga | tgatcgtatg | aactttggcg | aggtgggatc | tcgcctgatt | 77580 |
| ctaagtggga | aagagtattc | ggatagccgt | tcgtacaaac | ggtggctccg | agacctaagt | 77640 |
| gggacacggt | tgagtataca | gctccgcgga | agctcgtata | ccctgtgtaa | gcatgtgaca | 77700 |
| atggagtcat | gaccggagtc | accccgagcg | aaagcataac | cactatttat | agcaccctta | 77760 |
| cacaggctag | aagtgcccct | gtttggagtg | tgccctcgcc | tagaccgcat | tagccgacgg | 77820 |
| atatccgttg | gccgggatct | ggcaaggtat | attagtcacc | ttgactataa | ctggaagata | 77880 |
| cgtctgacag | aagggccgca | tagcttaaac | aggggaaggc | ccctacctac | tggcggtatc | 77940 |
| tttaagagct | ttcacgagag | ttcttaaaga | tactaattga | cgaggtctat | atgaacgatt | 78000 |
| taagtatgtt | aactaagata | cgctctgata | ttgagtctat | ggtctctcgt | cgtagtgagc | 78060 |
| tgactaaggc | taaacagatc | atcagcggtg | gtacacagaa | acgcttcaca | ttgcaagccg | 78120 |
| gggatattaa | gtttgaccta | tgtggcagcc | agactcgaga | ttcactttc | gaaatgaaac | 78180 |
| cgtgttacga | tatggtgaag | ctggggctta | tcaaagctct | agacaaacaa | atagatcagt | 78240 |
| gtacggacgc | aatcaaaacc | ctaaacgtcc | agttcgccgc | tgaatgcgat | cgtctcaaaa | 78300 |
| actctatcaa | ggtataataa | tggtggcatc | tgtgcatact | cctccgtatg | aacgtccagc | 78360 |
| acctaatctg | acacctgaac | agaaacagct | aatcgccagg | cgcactctag | agtttaaaga | 78420 |
| gtcgctgcat | aagagcgttg | gccggtattc | tgaacaggtt | catgatctgg | ttgtcaaaac | 78480 |

FIG. 15QQ sequence.txt

| | | | | | | |
|---|---|---|---|---|---|---|
| acttaaactt | tattaatgct | tccttagctc | agaggataga | gcaacggtct | tctaaaccgt | 78540 |
| gggtcacagg | ttcgaatcct | gtagggagta | ccactttaat | cgctgcccac | acgtaatatt | 78600 |
| cagtgggcag | cggcagaaag | cccgcagggc | gcagattaag | attgattcta | caaaattttt | 78660 |
| cttgcaattt | tgtcagaaat | tttgtataat | agttctttaa | atcaaagaga | aagtagagga | 78720 |
| taaaatggct | tacaaaattg | aatatttaaa | gaaaggggtt | ctcactgagc | tggttatcga | 78780 |
| tgcgaacatg | gctcgcaacg | agggcactaa | atccgtattc | tataaagacg | gtagcgtagc | 78840 |
| tcgtatgatc | aataccgaag | acattcagga | tctgtacgtg | atctccgacg | aagaagcagg | 78900 |
| tttcgtaaaa | gatcctgagc | cggctgaaga | tactccaact | gaagacactc | cggtagcgga | 78960 |
| taccactact | gaagaacctc | cggtggaagg | cactccggaa | gatgaagcag | cagtataaat | 79020 |
| aactaagggc | tagaaatagc | ccttctcctt | gggccggtag | cttaaagtta | aagcagtggc | 79080 |
| ctcataagcc | aacgagtggg | agttagagtc | tcccctggcc | caccaatttc | ataacaggag | 79140 |
| actaaaatgt | ctactaaaaa | cgcaatcgta | tccttcgtgg | atgacagtgg | tatcgtccta | 79200 |
| gagtccacag | taacagatat | cagtcctaaa | cgtctgctcc | atcgtgatgg | ggatatcctg | 79260 |
| gaaatcctta | ataaacggtc | tgagactatg | ctggtcattc | ctgtaaatcg | tcttctctcg | 79320 |
| attaaaatcg | tgtgggagga | ctaatggacg | ctcaattaca | aacccagtac | tatatgcttt | 79380 |
| taggcatgtt | agaggatgct | ggcccgacag | tcagagggca | ctatgagcgt | cacaaagcag | 79440 |
| cttttgaagc | cctactaaaa | gaagttaatg | agaacgaagg | tggtaaaggc | tctgactcct | 79500 |
| atgccgcatt | cattatcgcg | ctacaagttt | tcctaatcaa | tcaactcaag | taataggcta | 79560 |
| aatatgctga | atattaaacg | taaaggtttt | ttctacaagt | ggcttaattt | ctcttccgcg | 79620 |
| tctttcacct | accggctgaa | cgacaacaga | gtcaccttgt | gtagcctatt | ttggcactca | 79680 |
| gtgtggtatt | tcctgctaca | gattggcgta | actgctattg | ctgtactctt | ctccttgggg | 79740 |
| atgggaagta | tcttatctac | gttcttgggt | ctcacctttg | agctgggaat | tactccctgg | 79800 |
| tacatgcttg | tagggttaag | tctagcagga | ctatctacga | taatagcgat | tctgctggcg | 79860 |
| atagctggga | tcggctgggc | ctgcgctaag | ataggggatc | ggatccagga | atggaacgcg | 79920 |
| agtaaatcct | ttgaaagggc | acagaaagag | tataatgctc | gcgatgaaga | gctccgcttc | 79980 |
| ggtaatatct | accagaagat | gcgaatctat | aagaaggaca | aactttgtcc | gctcattcgt | 80040 |
| gtagaccacg | gcgagtagtt | tgcatagtga | cctgcgttgc | cgggtcacta | ccaaaatact | 80100 |
| tgaaaaattc | aattgctaaa | tgctctagaa | tttgagataa | tatttatatt | gaaagggaat | 80160 |
| agccaagtgg | ttacggcatc | ggcctttgac | tccgagatcg | gtaggttcaa | ctcctccttc | 80220 |
| ccttgccaaa | tttaaaatgc | tcctgtcgtc | taagctggtt | aggacaccac | tctttcacag | 80280 |
| tgggaacacg | ggttcgaacc | ccgttgggag | taccaaattt | actgaaaaat | tcagttgcta | 80340 |
| aatgcttaac | aaattgatat | aatatttata | tagtttgtta | aggaattaat | ctgatactga | 80400 |

FIG. 15RR sequence.txt

```
gccggaacca aaaaacacgc ttgcagcttg ctcggtcatt gtactgaggg ttcgcaagaa    80460
tagcggagtg gctctccgaa acgcctggta agcgtagagt gtatcgtatt tgtgaagagc    80520
gggtatcctc gcatggctaa ttgcttaggg tattacgcgc accggattaa ttgccttaac    80580
aaattattgg gggatgggtc tgctgggagt ggacaccgca cttgcaatgc gggaatcaga    80640
acggttcaaa tccgttatcc tccaccaaac aaatggggat gtggcgaaat tggcagccgc    80700
gctagattta ggttctagtg gtgaaatatc cgtgtgggtt cgaccccctc catccctacc    80760
aaataacggg agttcgtgat gaacatagaa atcatgcagt tggatcgtaa gaaaaatgag    80820
ttccgtaagg tccatacctt tccgagtaaa gaagctctag agtttcatat taagtgtatg    80880
ggactggtgc taccggaaag cgagatcttc gacttagcat gtgctaacgg agttctgtac    80940
gtctgggaaa tcacgtatca tgctgatcct gatgaactcc gtaaagaagt agagcaaata    81000
ctaactggag agtagtgctc atgggagcaa gctgacttga aatcagtcgc catcggaaac    81060
ggtgagggtt cgattccttt attctccgcc aaacaacagg aaagctggtg aaatggtagc    81120
cacgcatcac tgctaatgat gagtccgcaa gggcatgaag gttcaagtcc ttcgctttcc    81180
gccaaacaat ggcccgacga gtaacggttg ccccttttcta gagaattttc tgggcgaaaa    81240
tccagaagta atcaactagt tgtaagtggg aagagtttct tagggccgcc aaatttgagt    81300
atcattggta ttgtaggagt cgtacgctgg gactacgtag tacactgagt gtcctatgcc    81360
cagtacgcgg tctaaccaaa tacggtgtgc gatgtgcatt ttatttgtgg aggtctgatc    81420
agccctcgat ggtactcaaa tttgggatat tatcataact ggataatgac ctcgattgtg    81480
gatcgagtct atcttggttc gaatccaaga tatccctcca gattactgca ccattagttt    81540
aatggataga atatagagct acgaactcta tggttgaggt tcgattcctc gatggtgtac    81600
cataaaatct ctgctgagag tgacgaggtt agccctctgg gtcacatccc tcttctagcc    81660
gcctcccata aatgcaagca tttatgttct ggccctagac acaacgttgt actcagcaga    81720
gtgcgcataa ttggggtata gctcagtagg tagagcggag gtctctgaag ccttaggtca    81780
caagttcgat tcttgttgcc cctgccaatt gcaccgtaga ggagaggccg tcctcgccag    81840
tctcataagc tggagatcgc aagttcgaat cttgccggag catccaattc taggagaaga    81900
tgatgagaat ctctttcaca gaacgagtac taggtactgg agtaatgcta atcacttcct    81960
gggatggaga tagctggtgt aacgtgacag gcttacgtaa gtcagaacaa acacccgaga    82020
atatcgctaa aatcaagaaa cgaatggcag aagctgctag tcgtcctgga gcacctcgta    82080
atggtaaacg ttgaggtaac tatgactcgc tatcaaggta tgctaattaa tacccacaca    82140
aaagagattg tattcttggc accggctttt cacgacacct acaatgaagc cgaggaagac    82200
gctaggatcg ctaaaataca cccggacgag gaaatctgcg tccgtcagca agaacaataa    82260
```

FIG. 15SS sequence.txt

| | | | | | | |
|---|---|---|---|---|---|---|
| tgcttcaata | gctcagttgg | tagagcaaac | gaccgataat | cgttaggtca | ctggttcgag | 82320 |
| tccagttcgg | agtaccaatt | tttgccccct | ataggatatt | tcatcggaat | atcctccagc | 82380 |
| gatggtacgt | agtatagtac | ttacctgtta | agcctagaca | aagttacttt | gtgggcaaaa | 82440 |
| taggtataga | taggagaaga | atagtagcgt | aagattcttg | aggcaaattc | tttaggtcag | 82500 |
| ttggcagaga | tggtttatgc | actcgcttca | tacgtgagac | tacagtggtt | cgagtccact | 82560 |
| attgaccacc | aaatacttgc | ttagctcaat | cgggagagca | tcgtctttac | acggcgaggg | 82620 |
| tagctggttc | gaaaccagca | gcaagtacca | atttacagtg | agacttcggt | cagggccgtc | 82680 |
| aaacgtccga | gaagctgtaa | tttctgatgg | ggatgatccc | agattcgtaa | gaatacccca | 82740 |
| tccttacctt | cacaggtttt | agcgcaatgc | tgagtaaaag | tctagggaat | cgactccatg | 82800 |
| ccatccagga | gtataaatgg | cgaatctagg | gacttagacg | gtcattgccc | tagcgcgttg | 82860 |
| atgccgtgcc | ggaatcggta | tacggggctt | cctaaagggc | gtaagcagaa | catccactct | 82920 |
| gcataagata | cccgaaaacg | aggctgagat | aaatggtcta | tcttgtgaag | gttcgatccc | 82980 |
| ttccggggtt | agcgtgtagt | ggggctaatc | aatccccacg | ttaaacgttc | aagttaagat | 83040 |
| ttgttagttg | cagaagcggg | gaggctatca | accttcagtc | cctgaaagct | ctcagcgctt | 83100 |
| ggaactcttt | cgtccgtaag | gaatagatcc | cctttcgctt | tgactcgcaa | acttcaaacc | 83160 |
| aagtgtaact | aacagctgca | agcctggatt | accgctctcc | ggagcggata | attcaaaaat | 83220 |
| ttatttgcta | aacgctctta | tttactgtat | aatagttaca | taaattaatg | agaggagtta | 83280 |
| gcaaatggaa | aagattactg | caactggtat | tgaatctgca | ctggtggttg | attgggccgg | 83340 |
| atgggacgga | gatcacgaat | ggatggtctt | ttatagctgt | acgcttcagc | cagaactatg | 83400 |
| gactaggctt | accgatgagc | atgctatgcc | ctacggtatc | atagatgtag | aaattgagat | 83460 |
| taacaaactg | gttggcacca | ttatggtgca | tcgagccgaa | ggcgatcaca | aggaaatctt | 83520 |
| ccgtaaaagc | attaaactgg | tagtttctac | cggtgacttt | atttaacaat | taactgagga | 83580 |
| aatactatgt | acacacgtcc | tactaatgga | aattctgctg | tagtccgcct | gatgattgtt | 83640 |
| caggacaacc | tgtccaacaa | catcgagtct | ctagaccgtc | gtattgagga | gtatcgcact | 83700 |
| gagatgctgt | ctctgatgcg | cgaacgtgag | gccaagatcg | aagagcagct | agaggtttgc | 83760 |
| gaagctatcg | accgcctggt | tgacgaaacc | gcagtattta | tggcggaagc | tcccgcagag | 83820 |
| cctaccttca | ccccggtagc | accagctgac | atgcagtatg | ctattctgcc | tttccatctg | 83880 |
| gaagaagaag | atggcgaagg | cccgtcgctg | gaagacgttg | ttcgcttcct | gcttgcctcc | 83940 |
| ggtttcccga | acggaggtcg | ttaatggatt | ttatcgttgt | ttgcggagcg | aatactgact | 84000 |
| gcttcgagct | gttaaacgac | gccctagaca | aggttgatga | acacatgcag | gaaggcagaa | 84060 |
| ctcctacatt | cattgacctg | tctcaaggta | aaacttactt | ctacccgtct | cttgacgtag | 84120 |
| agcctacagt | tctacctatc | ttcatgcact | ccctctcgtg | ggacgaagaa | gacgattaat | 84180 |

FIG. 15TT sequence.txt

| | | | | | |
|---|---|---|---|---|---|
| gaaaaaattc | atttgcctag | tactctgaaa | tttagtataa | tatttatatt | gaaacgaaag | 84240 |
| aggaaaagca | aatggaagat | gaagttaaat | tgtacatttg | ttcagattgc | ggtgagttaa | 84300 |
| gtgaatgtca | ttgggagtgt | ccgacttgtg | agtcagacga | cttaatggaa | tacgaaccgg | 84360 |
| aataacaaat | taagcggcta | tggtgttcag | cggtcaacat | accggcctgt | cacgtcggag | 84420 |
| ccacgggttc | gaatcccgtt | agccgcgcca | aattctctct | gggctaagag | atatgaccgt | 84480 |
| ctagaggtat | cctcggacac | aagggtcagc | cctagacaca | ataagttagc | aaatatctcg | 84540 |
| tttcgacgag | gtatttgaag | aggttcttac | gagagcttct | tcaaatacgg | gggaatattc | 84600 |
| tgtaagtggt | agcagagcgg | tctgtaaaat | cgttgccatt | gcggctcggg | tggttcgact | 84660 |
| ccatcttccc | ccaccaattt | tgacaatcaa | agagatccgg | gttcgaatcc | cgcgtacgca | 84720 |
| acaggcggca | taaaggcctt | gtagcttaaa | tggacaaaag | cgctttggtt | gttaaatcta | 84780 |
| tttgggagag | aagcagtaag | tggtataggc | ggtcgcctgt | taagcgaatg | acagtgagtt | 84840 |
| cgaatctcac | ctctcccgcc | aattttactg | aaaaggttat | ttaattaacc | taggcacgcg | 84900 |
| taggaatact | gccaccgcaa | ttgaaagatg | tggcccggtt | tggagaggta | tgccgctaca | 84960 |
| cgctacggtg | ctaactccgt | ctaggtgaaa | atcctagtca | gtaatacagt | attagggtaa | 85020 |
| gaacagcgac | ttaggttgca | gtgaagcgtt | agcaatcggt | ggaactccgg | tgcgccctaa | 85080 |
| ttaaacaatg | catcattggc | cgagtgacta | ggcagaggct | tgcaaaccct | cgaagcatgg | 85140 |
| ttaaaatcca | tgatggtgct | ccaattacca | gaggtactca | tgattaagta | taaggcgttt | 85200 |
| gtaacaagag | agtcccaaac | aggagattca | agtattaaat | tcgaaggtac | aacgttacat | 85260 |
| gatacatttg | aagccgcttt | aacagaggcg | gaaacccata | tagtatcgaa | aagctgctat | 85320 |
| gctcatgtat | gggaagtaaa | cactatttta | gatcgctagc | tcaatggtta | gagcactcgc | 85380 |
| cttttaagcg | ataggttccg | ggttcgagtc | ccgggcggtc | taccacatta | tgggacttca | 85440 |
| gctaatcggc | taagcatcat | agatagcggg | gaatcccggt | ctgtgagggg | agtaacacgt | 85500 |
| agtctcccaa | gttccaccaa | acatcagagc | agcgtgatgt | actgcaaaga | cccaaagacc | 85560 |
| ggggtggact | tcttgattca | aaggagcagg | cacgaattac | gcaactgtag | ctcagcgagg | 85620 |
| tgagagcact | ggtttgaaag | tccaggggtc | gttcgttcaa | atcgaaccgg | ttgcaccaaa | 85680 |
| ttaatagtat | caatagctta | tggagctgaa | tagtcctaaa | gctcacggta | aagcagctgg | 85740 |
| ccgttagtga | gcagacttgg | aaacgtctgg | tgatctctag | gttagccggt | gcgttggttc | 85800 |
| gaatccaact | gatacttcca | aatcccaagt | agcccgttac | aggctctctg | attaaactca | 85860 |
| gacaagcagg | taatgggtga | caggataaaa | taagccactg | atttccggcc | gtttgacgtg | 85920 |
| gtaaagtcct | ccagtcaaga | agaatttctg | cgtgcagaaa | tcactgaaag | caatggggca | 85980 |
| gacaacttga | gatagattgc | ctataacgtc | tcaagtagtg | gcattgactt | agggtggcat | 86040 |

FIG. 15UU sequence.txt

| | | | | | | |
|---|---|---|---|---|---|---|
| tttcccgaaa | gttcgaaaaa | ttcatttgct | aaacgctctt | atttataata | taatatttat | 86100 |
| ataaattaat | gagagggctt | acctaatgaa | tcaaaaaatt | cttatgcgat | ataatccacg | 86160 |
| agctttatgg | ttccgctggg | aagtgattgt | atcgtaccag | atacgagtgc | gtaacggtga | 86220 |
| tcctgagaac | aacattatcg | tgctggagac | attctctaat | agagatgcgg | cagttaagtt | 86280 |
| cctgaacacc | atcgacaata | ctttaatcaa | ggtatattaa | taatggatat | ctttactact | 86340 |
| cctgctatca | acttggtcgg | tgtcggccta | ttccaggcaa | cggtctatcg | tattgatgat | 86400 |
| agcactgacg | ttgtaacgtt | cattgtaccg | gagttcttcc | ttgagaagtt | ctttgaagag | 86460 |
| tttgagcaat | tccgtgaaga | gcatgatgct | tactccaata | tggaagatct | agcagcgatg | 86520 |
| ttcccaactg | tatacggcta | catctttgaa | ggcaatgatc | tgcttttgga | taagtcagag | 86580 |
| ctggtggaac | tcaactgggg | cattagcttt | gaagtgggct | ctccgttccc | gcggtatttc | 86640 |
| caaggtctgg | agattcgata | atgggcggct | actctaattt | catcgagaat | tacattaatt | 86700 |
| ccgtagattc | ctggaatcag | gaaactctag | tggtagtgct | taaagagaga | ttcaatatct | 86760 |
| ctactctgga | agccctagag | gctatagaag | cctacttgga | taacgattaa | cacccacttg | 86820 |
| gtccaatctg | gtagaggcat | gaggcttaag | acttcagggt | tcccggttcg | agtccgggag | 86880 |
| tgggtaccaa | attatggggc | acgactgatg | gggaagtcgg | cctggctagg | gttgagatac | 86940 |
| ggttcgattc | cgtaggcaaa | tggtctcgta | attccgcaca | ggtgatggaa | ggttcgagtc | 87000 |
| cttctcccat | aactatacaa | attcccctta | gctcagtctg | gcagagcggg | cgctttggga | 87060 |
| gcgtcaggtc | aagtgttcaa | atcacttagg | ggagaccaat | cttgcctcaa | tagctcagcc | 87120 |
| gggagagcaa | ccgccttgta | agcggtaggt | cgtgggttcg | attcctactt | ggggcaccat | 87180 |
| tttcgctggt | tatggttaca | gtgtgattaa | gtttacattg | tcattaaatt | ccggttcaat | 87240 |
| tccggaagcc | agcaacccta | aaaggtaagc | atatgaggat | tcttttccata | gaagatgtta | 87300 |
| tgtgtgacag | atgctacggc | tccatattct | ctggtggctg | tagttgtaag | taatctatct | 87360 |
| aatgaccttc | tgtagatgta | aaataaatat | gaagggtcga | tgctcgcggc | taccgacaga | 87420 |
| tcgtaatgat | caagtagtag | tctgaggtga | agagactagc | ccattaattc | cgcgactaac | 87480 |
| tgtacgggtt | acagcgtccg | ccttccaagc | ggtactgagt | ggggttcgat | tcccctagt | 87540 |
| cgctccaaat | tcggtaaaat | gaccgtcccc | tgacgttacg | gggaattaaa | caaggaactg | 87600 |
| ggagccggta | aggccatttt | atcgatacta | cttgagaggt | acaacaatga | aagcctttga | 87660 |
| tgcagaacta | gtgttctcac | tcttagctga | gatggaagcc | tgcgtagatc | gtgtacgtgc | 87720 |
| gctgcgtctt | agtatgttta | gctcttaaat | tatttgctgt | tctagagcca | atgtagtccg | 87780 |
| gggtgccgac | gtctgcctgg | aactcgactc | taggatagtc | aggacgtcac | ttaacagcca | 87840 |
| gagatggcaa | actataggag | aagcaaatgt | taacagttaa | ggtaatgtca | cctaacggtg | 87900 |
| gcgaagaaat | tcacgatggt | tcaagcgttg | ggtttaatcc | taagcagaag | agcatctcta | 87960 |

FIG. 15VV sequence.txt

| | | | | | | |
|---|---|---|---|---|---|---|
| ttgctggtct | tgatcagcat | atcttcctga | aagaagatga | ggtagcctac | gttatgaatc | 88020 |
| agaatggtaa | gacagtatcc | gtctaccacg | gtagctaatt | ttattccccg | agtgttactg | 88080 |
| gacagcacgc | cggtctccaa | aaccgtgcag | taggagttcg | agtctcctgg | ggtttgccag | 88140 |
| tttaaaggag | tgatcatgat | cacttatagc | accaatttta | tggggccagt | ctccaacaat | 88200 |
| tggtacatcc | gtatgggtat | tccgtatacg | gaagtaaccg | agccgaatcg | ttttgcagat | 88260 |
| ggcgggcaac | taactcgaaa | agtatttgcc | aaacgatatg | ccggtggtcg | cattgacgtt | 88320 |
| cgtggtactg | atgactattt | cggccaggaa | atcggtgttc | cgattatgga | ggccgagtct | 88380 |
| tggaatgaac | tacagcagtt | tctctggaca | ttctcgtccg | ataaggttct | gacattggag | 88440 |
| caaattgtac | aggctctaga | ggacgagaca | ggttttcgca | ttgtttggtt | taaggagcca | 88500 |
| gcatgtacat | agatcgtaac | caactgttca | agttcctaga | gcttgacctt | cgttggcctc | 88560 |
| tatcagtcaa | tccgggacga | gctactggca | agacgttcga | ggctattaat | acagcctatg | 88620 |
| agtttgcagt | atttaaaggt | attcaagcag | tatacgtagc | atccggtgtc | cgtgaaatgg | 88680 |
| cacgcctaga | gaagaagtat | aacgagcttc | aacctcatgt | taaaattaca | acgtatagca | 88740 |
| tgttagaacc | ctaccgtata | ggtcgtcgat | tcagctgcat | catgtttgac | gaacctagct | 88800 |
| tggctattaa | gtacggcgta | aacgcttacg | tggttcgtat | agccagagaa | aaccagtgtc | 88860 |
| ctgtaattat | ttttggagag | taaagtggaa | caagaatttc | aagtcttcgt | agacgcctct | 88920 |
| aagagagttt | tattcataca | agccaccgat | gaaggtcatg | gcctgcaact | ttccttcgac | 88980 |
| tctctggagc | aaataaacca | gattgttctg | agggcacaaa | aatcattaga | aaagaacact | 89040 |
| gaggcacctc | ctgacctcta | aacaaaagcc | ccttgtctct | ttgagcgagg | ggcttttttct | 89100 |
| ttataaattc | acttgcaaaa | atgccaattt | tgccgtataa | tagatttata | aattgatgag | 89160 |
| agagatttcc | aagatgaaag | taacaatgga | aaacacagaa | gagtttattg | ctatctgtac | 89220 |
| tgcgtatgca | gatacgcttc | cacctgaggg | tatggacgac | catacaatgc | agttagtggc | 89280 |
| ggatatctac | agattagcag | agttagctaa | agaacaacac | aacaggctgg | tgtacgtcaa | 89340 |
| agaacgcctc | gaaatgatgg | ataaggagta | atcaatgaac | gaactcaatg | aactgaatga | 89400 |
| attgcattac | gctgaacgtg | ctattgacga | gctggatttc | gctggtggtt | attatacccg | 89460 |
| acacgtcaac | gcaatgaccg | ccgaagggct | taatagtaag | tctgcgattg | ctgcggagtt | 89520 |
| agcagttcgg | gactttgtta | ttgatagtct | ccagaagact | attagcaact | tgagcgaaaa | 89580 |
| caacaaagct | gctctggaag | ccctggataa | gctgtccaac | catcttctcg | cattggggat | 89640 |
| caaataatga | ataagcaatc | tctacgtggt | atccgagtat | ttcgctctag | ccttgttgat | 89700 |
| tccttctata | tctggggcaa | ggcaactcga | cgcactgttg | agcaagcact | agacggtacg | 89760 |
| ttctatgatt | ggcgagaaaa | agagcgaaac | cccgtattca | gccgcccagg | gctgtatcac | 89820 |

FIG. 15WW sequence.txt

```
gatcgtgtat ctaagacagc gtggtacgaa attgaagtaa ctcctggcgt tatcagagcg      89880
ttctatacgg attgggagca cgaaaagtgg gtttgggaca atcagattgc tcccggtgat      89940
cgtattatga actatgccga atataaagaa atgaagcgca tgttcgagct atacgatgtt      90000
cctaggctgt ctcgcccggc tatcttcatt gctagccaag agtactggca tactgttcgt      90060
atgaagcgtg attttaacaa gcatcacctg cgctatgaga aagaacacgg cacactgcgg      90120
gaacgtgtgg ccaagagaaa agccgaactg cgtgaaaaac gcctggagaa gaaatatggt      90180
gaaagctagt ctcttacgct tcactcctgg agttggcctc cagtataaaa ttgttggggg      90240
ccacaagttc caatacttca ccccgggtaa gctctacttc gtcgagctac acgatagtag      90300
agcaggctac aaattacgaa gcgacgcaaa tgagggcatt tgggtgagct tcacacaagt      90360
taaacgctgg tttacagttg aaggatataa tgattatgag taaagttgta tatttcgtaa      90420
aatgctgccg tgacacctta gagttggtcg accacaaaat gcagacctgt aaatgtggtg      90480
cttcctccat agatggtgta gccggagcct acgtccgttt tctaggcgac aaaagtaact      90540
tcatgcgtct gaatgagttc cagctcgaag ttgaaaagaa tcgaccggct ctagaggcag      90600
aggctgagcg tctcaaagat ttcgatggga acatcgtagc atataacatg gtaagcggta      90660
aagacttctg gtctgaactg gctgaaaaac ttaacatgcc gcggcaggcg gctaaggctt      90720
tatatcatgg cttcaactac tcgccacgtt ggaattaagt tttccaacag taacagaact      90780
tacgtttacc gagtacctag ttattggaaa tactcccggg agataggtga tgtagtagtc      90840
ataccgggga atgttatgtt taataatcct cgtcgcgcca aagtagtaga agtgcatggt      90900
atgtatggta agccagagta taaagaaaga aagaacatct cttatgtaga gctgcatgat      90960
tacttaccga aggaggaacg taatggacga taaaattgct cgggaagcaa tagaacttgt      91020
tcgtaaacga ctggaagaac gtaatgtcga ggtgccgaaa ataatgctta ttggctacgg      91080
cggcatcggc ggatttccca gcttcactga cctagaaaga atggaacgag agtcccaagc      91140
cagctttcta gagttagaat cctacgctcg ggaaatggaa cacgaacatc cgattggtaa      91200
taactttatg ccacgtagct cccgccagga ggttactcac ggcaagacta attcctggcc      91260
cactccgaaa cgcagaggta gaaaatgatt actacaggat ttggatattc tcacgaagaa      91320
ttgtgcaaaa tggttgaaag cgctccgttt attaagaagt tagtcgaaga gcaacgaccg      91380
gtgtgtttac atgctgcctg taccaagtgt cacggtactg gtgttgataa aaacggcaag      91440
atgtgcgtac atgcactgtc ctgcccgtgt cctaaatgta gctggagctg ttaatatgga      91500
tctaggatat tgtgtagtac atgaattcat ggagcagggg ttgccggatc gtatttgcgt      91560
tgtaacctct cgtaatctgg aagcagccca atcactagtg gagcgactct ctggctacta      91620
tcgtgaccat gaacgttacc agcagaaagt atttgacctg acaaaactgt accatcaaaa      91680
agctctggat atgccaactc cacagctgga cgatctcaag cagtttagtc ctgaggcctg      91740
```

FIG. 15XX sequence.txt

| | | | | | | |
|---|---|---|---|---|---|---|
| gtatagcgtc | aaagacgcca | gtccggtaga | ctataccgta | caggtattct | cgcattatgg | 91800 |
| tactcgtcac | tggataaacc | gtaaatggga | ttccatggtt | gactaccttg | attcggaact | 91860 |
| cgaaaagggg | gctgccgaat | acaaaagaaa | gcgtgccgaa | gccaaagtat | tgaaaaattc | 91920 |
| agttgcattg | taggcgattt | ttcgatataa | tagttacata | aattgatagg | gagagcttca | 91980 |
| tgagcaaact | aagtattgaa | agcattatcc | gcccgttaat | gcacgggtat | gtacaaggtt | 92040 |
| cctgtgtaag | cgaaactgaa | gctctcaatg | ttatcgaaga | agagctggtg | gctaacgggt | 92100 |
| ataatcttca | cgaaggtgtt | atcgaggatc | tcttctggca | gaccgcggaa | gatatggaga | 92160 |
| tctttcggtg | cgtgaattgc | gggtggtggt | gtcctgcttt | tgaaagggcg | gagaaccaaa | 92220 |
| tagaggaaat | ctgccgggac | tgcgagccag | acctcgaagg | tgaagtggat | gaacaagata | 92280 |
| acgaaggtga | agactatgag | taagcgttca | attgcagcaa | tcatcgcatt | cagtatgatg | 92340 |
| tactctggag | tatctctggc | cgcagagcgt | aacaaagtag | agatctctga | taacgggcgg | 92400 |
| gttcgtgtaa | caacgaatgg | gattactaaa | ggagctggta | agtttcgtaa | atctgaaacc | 92460 |
| cgttttgggg | aaactaagat | ctacacgaac | aaaacctatg | gcaagcccgc | tgtgacactg | 92520 |
| gaccgctatg | gtcgtcaggt | agaagacgag | gatgatagcg | atgagtaatc | ttcaccccaa | 92580 |
| acttcaagag | accctagact | ggattaatga | agagtgtgct | tttgaggaag | ctccttactg | 92640 |
| tgtctgggca | agagctggtg | cagcccctc | ggagtggtgt | actgtgtttg | ataatcgcta | 92700 |
| ccggataaca | gttgaactaa | gcctaaaaga | ggacaaagta | tacgctaaag | cctctatgac | 92760 |
| cgcgctagga | ttatccgggt | tcgtggagat | gcaagagctc | tgtatgccta | acactcacct | 92820 |
| tcgggttcag | atcgagcagt | tggcaacaat | tcgtttgatg | ttgccggaag | ataacatcaa | 92880 |
| tgaccatttc | cataaggtta | ttgaaaatga | atacaaacta | cggcggcaac | gtcgcaaagc | 92940 |
| acgacgggaa | gtagagaaga | ctcggatgat | gtgtaacatg | aatccacacg | tataacggta | 93000 |
| gggccgttat | aggagtcacc | ttcctgttcc | tatccggagt | cgtgccgcg | atgaacgaag | 93060 |
| tggtgagttg | gtcgccgacc | actaactaat | tcaaagacaa | actgaggaag | caaaatgttt | 93120 |
| actttattta | tactggcagt | atcggcgtgg | atggcagttg | gtatcaatca | tggtctggac | 93180 |
| tctgctaagc | tgctgtcagc | taaagccttc | gagttcctgg | ctaagtttgc | cacccgtaaa | 93240 |
| gatatcgagg | ccatcatcgc | aaaaggcggt | gccaaagatg | catcgagtgt | cctgaagtcc | 93300 |
| ttcgataaga | tcctagagct | tcgtaacggt | aagcatgccg | cagagctacg | ctgtatgagt | 93360 |
| cgcaagacca | taggcagact | gtgtaaggcc | atcttcatcg | tacaggggc | gttgaaaggc | 93420 |
| ccattcgcta | agtataaacc | ggatagtatc | aagcgagcca | agatctttaa | cgattactgt | 93480 |
| gtggaacacc | acccgttaaa | tcgctaacta | cccaagccca | gcatcgaaag | gtgttgggct | 93540 |
| tttctttttt | aaaaattact | tgcgctctcg | cttaaaatgt | tgtataatag | ttttataaat | 93600 |

FIG. 15YY sequence.txt

| | | | | | | |
|---|---|---|---|---|---|---|
| gagaggagaa | ctaacatgcg | tattatctct | aaattaaagg | acgtatatga | tctacaaggt | 93660 |
| actatgtatg | atgcagaaag | agcatggtat | cgcgaagaag | tgaaagaggt | tgtaaacgta | 93720 |
| tccgctgatt | tcgaacaaat | tattttctac | gctgaaatct | tgcgtaaccg | cacttcctct | 93780 |
| ggatatgggg | gtgttaatat | gggaactctg | gaagttcgtc | cagtattgat | ttgtggtaca | 93840 |
| ctacgctggc | tgtacggtta | tcacactggc | ctaggagcag | atgctgtgca | tatccagact | 93900 |
| ttcgatccag | ttaaggtaaa | agaggtactg | gaagaacaag | gatactacct | gcggatgggt | 93960 |
| tgggacatga | atacgattga | gaagatcgac | gctcatgttc | gtaacgcaac | cgccacggct | 94020 |
| tctgcgttcc | tggagacttt | caacaagccc | attgcgatgg | catgggatgc | cgcaaagtct | 94080 |
| aagacagacc | caacggttaa | tattaccgtt | aaaactgatt | tcaacttcca | tgcggaagat | 94140 |
| ttcccgtggc | aggaaattga | tccaaacctg | tatcgctggc | accagacctt | agaatcatat | 94200 |
| atcttcggtg | tgctgggtca | aggggaacca | aagaccgagt | ctacgtctga | tcgtgatcgg | 94260 |
| ttaattgcta | agggcttcga | tgctaaagtt | tctttcagga | atatggagcg | gtaagactgg | 94320 |
| agcaattctg | tttctggcaa | ttgcagcagg | caccttcggg | ggtgcctact | acattaccaa | 94380 |
| taagctaaca | gatatgtcca | gttctttaca | gtccctatca | aaccgtaatg | aacaactaga | 94440 |
| aaagacagtt | ggtaatctcc | aaacagagat | tcgaaatcga | gatcgcaata | ccactaccta | 94500 |
| cataaccaac | ctagctaaga | accaggaaga | tctggatggg | cgtattaata | aactggatgc | 94560 |
| agctagagcc | aaagagggcg | tggttgccgc | taaacctaaa | cttgctacca | aagtggcaaa | 94620 |
| agacaaagtt | aatgagttcc | aggagagact | ttcatgcgta | actggaaata | tggactcctg | 94680 |
| ctctcggctg | caattatcgc | atccgggtgt | gcagaacggc | cagacccaag | tagcacagta | 94740 |
| acggggttg | agccacagca | cctaccgtgg | ccagcaagcc | tacagacttg | cccgtttaat | 94800 |
| tttgagttca | taaacgaaga | agggaaagtg | tatgttcgca | taccttacca | agattggatc | 94860 |
| acgatgggca | agtgtaatga | gcaggtctac | acctacattg | ccaatctgac | tgcattaacg | 94920 |
| tgtacctatc | gcgtgtcact | taatgaatat | cgttgcaaac | cgttcaataa | ggaaacaaaa | 94980 |
| tgaaatacgt | tttaggatta | attggtgatg | ccggcgcagg | caaagacacc | tttgctgaca | 95040 |
| tggctaaggt | ttgggcctgg | gaagtcctcg | gtccggagta | ttctatcagt | aaatttagtt | 95100 |
| ttgcagctcc | agtttacgaa | ctcgcggctg | taatccttgg | agtcacgcca | gaaaagctgg | 95160 |
| cagagcgcag | gacaaaagag | attaagcagt | ggttttgggt | gactcaggaa | gcccttgagc | 95220 |
| gtactgctaa | cgtctggaag | cgttttggga | tcgacaagta | cgccgatttc | tcttacgttt | 95280 |
| ggcctcagtt | tgaagcgtca | gcactatatc | cgttgattgc | taagactgcc | ccagactttt | 95340 |
| atcaaggtcg | tgagaccccg | ttgtacccat | tatacacgtc | ccctcgtaaa | atgctagaat | 95400 |
| ttgttggcac | ggagttagga | cgcgctctgg | tggatgagaa | cttgtggttg | aatattgtgg | 95460 |
| tagatcgtat | cactgctacc | aaagctgaca | ttagtattat | ttctgatgtt | cgttttgata | 95520 |

FIG. 15ZZ sequence.txt

| | | | | | |
|---|---|---|---|---|---|
| atgaagccgc | gctagttcgg | aacttccccg | gtgcgcagaa | ctctagtatt | cttaaagttc | 95580 |
| acgcccctaa | caacatccac | gctatccaat | ctactcatgc | ctccgctaga | ggtgttgcac | 95640 |
| ctgagtttat | tgatgatgtg | gtaacaaata | actttgacgg | actggaaaat | ttccgtaaaa | 95700 |
| atgtaaacgc | attttgcgac | gagaggattc | tctttatata | aggtaacaat | atgggacaaa | 95760 |
| ttaataacgt | agagcagaaa | ggtggcaata | agactcctaa | ttacttcgcc | tccctagtgg | 95820 |
| cgactaaggc | agagtataat | atttaccact | atcatctcga | tgggccgata | gtcgatgtag | 95880 |
| actactaccg | cgacctatca | gtcactctgg | caactatgca | agagggagac | actcttaatc | 95940 |
| tttatattaa | tagtcccggc | gggtacgttg | atacagcagt | tcagttgtgc | aaccttatca | 96000 |
| tgaactgcca | gggaaccgta | attgggcacc | tggttgggcc | atcagcatca | gctgcctgct | 96060 |
| caatcttcct | agcatgtcat | ggttggctgg | tgcacccta | cgttatgttg | atgggtcata | 96120 |
| cctatcgtgg | tgcgcactat | ggtaagggca | aaaatgagat | ccagcactat | gctgatcagt | 96180 |
| ttaactcgtt | cttcgaggat | atgatgctag | acctgtacta | cccgttcttc | tctctagaag | 96240 |
| agatcactga | gatgatagaa | ggtggtaagg | atatttggct | gacctccaaa | gaaatcaacg | 96300 |
| aacgtgtaga | tcgtatggct | gcgcaccgag | aacaagaagc | tcgtaaggct | gcgggtcaat | 96360 |
| aaaactaagt | aggccagggc | tttttagctc | tggccttttt | ctttatctaa | attctacttg | 96420 |
| acatttgtct | caaagtatga | tccgagcaat | aactataaat | ttttattgca | acttcctcca | 96480 |
| ataaagggta | taattataaa | tggttagagg | aggttcttaa | tggataaatt | tatacagttg | 96540 |
| atatcgctgt | tactacaaga | agcgaaggat | ccagcttctc | ttcttaaacg | tttgctaacc | 96600 |
| ttactggttg | gtctagttat | ctacctcttt | atagctaata | cgagtgaagt | catgtcgtac | 96660 |
| ttaaagactt | tctctacttc | ggcggtccta | caagatgtta | aagtacaacg | cacactagag | 96720 |
| tttccaaatg | tggcacgaga | gaaggcaatg | atcctattct | cacagactcg | agctgatgcc | 96780 |
| gtcttcgtgg | ttaaatacaa | gcctgaggct | ataatgatt | accaaactat | catagcttgg | 96840 |
| gaaagcaacg | ttcagttgga | taaatccgat | gtatccgaca | aagcagttga | caagacgtct | 96900 |
| atgctctacc | gagcgcattt | agacggtctg | aactttgcaa | ttgatgcaag | ggaaaaacga | 96960 |
| ggtttatcga | agtggtctgg | aacgggtttg | ccaccgttca | agagtgcaaa | tttcgagtat | 97020 |
| gtgtacacgt | gcccatattt | taaccttaat | aacatctact | ctggatatgt | tgccgtcgcg | 97080 |
| tgggagaagt | atccccctaca | agacgaagac | atgggtatgt | ttaatgacta | tatggcaaaa | 97140 |
| atctgcgcat | cgccgcagag | atcattaggg | agatcaatat | gagtttcaga | tttggaaacc | 97200 |
| gtagtctcca | gcagctcgat | actgtagatc | ctaaactcaa | ggctctagct | attcgtgctc | 97260 |
| tggaactctc | accgcacgat | tttaccatca | ttcagggcaa | acgtaccgta | caacagagtg | 97320 |
| cccagaacat | tgctaatggt | acttcatttt | tgaaagaccc | tagcaagtct | aaacacgtta | 97380 |

FIG. 15AAA sequence.txt

| | | | | | | |
|---|---|---|---|---|---|---|
| cgggcaaagc | cattgacttc | gccccatata | tcaatggtaa | gattgactgg | aatgacttag | 97440 |
| aagcattctg | ggctatcgtc | ggtgcattta | aaaaggccgc | aaatgagatg | aacattgccg | 97500 |
| ttcgtttcgg | agcggattgg | aataactctg | gcgactaccg | tgatgaaatc | caacgtggta | 97560 |
| cttatgacgg | cggacacgta | gagttactgt | aacattaagg | ggagctttta | ggctcccctt | 97620 |
| ctttgtatgg | agcaagcaaa | taggaggtgg | ttatgtttgc | aagtttagta | actataatgc | 97680 |
| tactcaagat | atttcaattc | ggtatagtat | tcttttccgc | aacatggatt | ttaatacgcg | 97740 |
| gtgccattta | ttttcgcaga | acacgcttag | ctagggttgc | tagatggctt | ctacacttcg | 97800 |
| tatttggtat | tttcggtgtg | ttccgctgcc | catgtgagaa | aaagagggga | acagggttct | 97860 |
| gctggctctg | gttaggtcta | gagaattgct | tctcattgtc | cttagcgcta | ctatttggta | 97920 |
| tgatagtcct | agctataacg | ctagcattta | taccactaat | gtacgcaggt | ggggtgacgt | 97980 |
| ctatcctaac | ccttacttct | cctgtgttga | tgtactcagt | atacccatt | acactatttt | 98040 |
| tcgtaagacg | aggcaagcac | tgcaattaat | gaaaaattca | attgactttc | cgctcgattt | 98100 |
| agcgtataat | atatttataa | attcgagaga | ggagatacaa | aatgtcagac | agattctaca | 98160 |
| ctcaaatgtg | cgagcatttt | aaagtatctc | cctacgagtt | aaatatagct | ttgtgggatc | 98220 |
| gtgaatcacc | ggagtttaag | aaaattgcta | agaaatcgga | gggtgttatg | tccaacggta | 98280 |
| agaaaatgac | ccgaattgac | cttaacaatg | cgctaaccaa | actgctcggc | gttaacattg | 98340 |
| agggccagaa | gctctctatg | ccaactttga | ctactatttt | ggagaaagtc | aaggctggag | 98400 |
| atgttaaaaa | agtagcagtg | cctgagggtc | gtctgaaaaa | gccgtatcag | gaggctataa | 98460 |
| ttgaggcttt | cggagaaaag | ctagacctgg | ataccgcaac | cgtaaaaaca | atgaaagcac | 98520 |
| tactggagag | tattaataat | gtctaagaaa | attgtattcc | ttaaaggttc | tagctgcgtt | 98580 |
| ccttgcaagc | aatttgaacc | agttttgat | aaactcaccg | ctgagttcaa | cctgcccgtt | 98640 |
| gaaaaacgca | cggacgacgt | agattcccta | cgtaagttcg | gccttcgcac | tgtacccgca | 98700 |
| gtagtcctgg | tggatgtgga | aacggacgt | gaagaagcac | atcacattct | tagtggtgcc | 98760 |
| acgcttcgct | ctgcagtagt | tagtaaagct | atccaagact | ttatcgacta | cgtagaagaa | 98820 |
| taatacctaa | ccccggctca | atacgagacc | ggggtttttt | attatttgct | aaacgcttaa | 98880 |
| aattttgata | taatatttat | attgaattga | gagaggatta | cacaatgact | aagcaagcat | 98940 |
| atcttatcct | gaataatggt | tttgcagttg | gtactacctt | cgttgatctg | gggtatacaa | 99000 |
| aagaagagtg | gcaagctctc | gatgctgccc | agaagaatca | gcttgttaat | gaagccgcct | 99060 |
| gggagtatgc | agaggcttac | gtggaggcgg | tagatgacga | gttagttatt | gtcgtttccc | 99120 |
| ttggtgccgt | aggttgtgat | gctcatgtac | atacagactt | ccagagcgaa | gaagagtggg | 99180 |
| atgagttaga | tctaacccac | caaaatgctc | tgattaacga | agcgttctgg | gaagttgtag | 99240 |
| actgctacgt | tgcgttctgt | aaggacgatg | atgaagctaa | cacctgcact | aactatggct | 99300 |

FIG. 15BBB sequence.txt

| | | | | | | |
|---|---|---|---|---|---|---|
| atgaacacga | cgatgtggag | tgtgcataat | gcaaaaattc | tctagagact | ggtcttctga | 99360 |
| tatggcccgt | aaaaatcgag | ctgctgccta | ctataataag | aaaatacagc | tcgataagtt | 99420 |
| aataaagggt | atcacctaca | atgtagagag | gggctttttct | ggtataaaag | tagatgctag | 99480 |
| gagcctggac | tactcgtgca | tactgtgggc | taagcagaat | gggtacgcgt | ttaaacgaat | 99540 |
| aggcaatgag | atactgattg | cctgggaacc | cgaaggtcta | gtgcaatacg | taatatacga | 99600 |
| cccttatcga | ggggaatatg | taagagatca | caggcagcag | cccacagact | tctcgctgcc | 99660 |
| aaaacgttac | tatttagaga | cgaggtatta | atgaacgtac | atgaaacagt | taccgtgccc | 99720 |
| gacaatgcta | atatcttctt | cattggggat | attcatggcg | agtacgacat | gatgatgggt | 99780 |
| gccctgaaac | ttgcagggta | cgaggaaggt | cgtgactacg | tgttctgtgt | aggggatctt | 99840 |
| atcgaccgtg | gcccgaaaaa | cttacaggtt | ctagcgaagt | tcctgtacaa | cccgaaattc | 99900 |
| cgctctgttc | gcgggaatca | tgacgaattc | atgatccaag | acgactacgc | taactggatg | 99960 |
| tataatggcg | gtagctggac | tatcacgaaa | ggtttcgata | cggataccat | gaaaggtatc | 100020 |
| gcggaagaca | tggacagcaa | gatgccatac | attatgaccg | ttgaacaccg | tggcaagcgt | 100080 |
| tacggggtag | ttcatgctgg | tatccctctg | cgctaccagg | ctcaaggtat | gggtgtaact | 100140 |
| gtaccggtgt | gggacgacat | tgtgcacgaa | cacgaatcta | caccagattt | acgtcgtttg | 100200 |
| ggtgtactgc | tgtgggatcg | tgatgtaatc | caagaagttg | ggtttaatct | gtatcgtagt | 100260 |
| ggggagaagc | atccgtactt | cgatcgctac | gccagcttct | ccgaggagtg | cgcagtcgat | 100320 |
| gtgcctgaaa | tcgtgggagt | agactacacg | tttcatggcc | atactggtgt | cccgttcccc | 100380 |
| attcgctgga | agaaccgtgt | ctatttggac | acaggtggca | cctttaacgg | tcgtatgacc | 100440 |
| gtggcgtcgc | cggttctagg | tcaattatac | acattcacca | cagatcgtga | tgatccttgt | 100500 |
| ggttccgctg | acattattta | ataggtgaaa | catgaaactt | ttcaaagatc | tggaagaagg | 100560 |
| tgaagtattc | gtagttgctg | gtggcttcga | gttgcagaaa | tgtgtagcaa | tgctggacaa | 100620 |
| cggaaactcc | gtgtttacag | acgacgcgaa | tatctcggtt | actattgccc | cggacactga | 100680 |
| aacctggaaa | cccaaagaat | tctgggagat | ccataaagat | cgtccattgg | acgacctact | 100740 |
| ggacgacatt | ctattcacag | cctgaggtaa | atcatgaaac | tcgaatctcg | ttatattgta | 100800 |
| tttaagcagt | cagatgccgc | taagtatcta | accagcactg | ctattcggga | gataaacgac | 100860 |
| agcttatccc | tgatctataa | aggccgagag | gctgacggca | aggtaggatt | cccgaactat | 100920 |
| atcgttctag | aagaggattg | gccggagtat | cctatcgcta | agaagctct | agaaggacgt | 100980 |
| atcgtgctgg | aagagtttaa | taaaagggcg | gagaagaaac | gtggggctaa | ggctgcagaa | 101040 |
| gatcactata | agcagcacca | gtctacggaa | ctactccggg | gtatttctcc | attctgtgca | 101100 |
| gggtggaacg | actacatgag | aagactggta | atcgaggagt | aaccatgtat | actggaatgg | 101160 |

FIG. 15CCC

```
                                        sequence.txt
gaaatgatat ggccaagatg tttattggcc tcttaatcct ggctgcgtta gtcggtgcag    101220
caattgtagg cggaatctgg gcgctcgtag catttgtatt ttaaattcag ttgcttccga    101280
gccaattttt ctgtataata gctgtataaa ttgatgagga agcaaatatg aaaaacgcaa    101340
tgatcgaact gaatgcaaat atggaatccc ttcgccacgc agttaacacc gcccgtgctt    101400
cttttaacct gctgatgcgc gatgagagca taccgctgtc cgctcgtgtc aaggcatttg    101460
aggagttcgc cgatgagctt cttcatatgg gagactatct cagcgactcc ccgtttaatg    101520
aagatcgccg ggattatcaa cacgcctact gcaatcgtgg ggaaatagtt tacctgaccg    101580
atgttctgga gagtgtgctg gagtatgcga actctttcat gcgaactcct gacgaatggg    101640
aagacgcttc gaacgactat gttctagacg agattcaaaa gaactggcca gaaattaaga    101700
aactggtaga agaacacatt cattctgaag tttacgctta ccggatcgat tggtaaaaag    101760
tttaaaaatt cacttgctaa gtagttagaa tttcggtata atatacgcat aaattaacga    101820
aacggacgga aatcattatg gctaagaaca ctatctctta caccactggt aaaactgctg    101880
acgaacaagc taacaccctg accaaagacg aaatggttgc ggtactggta atcctgctgg    101940
atatgagtgg gttcgaaggt cagcttgcta aactgtctct cccggcactt cgtgctctgt    102000
acgaaggcac taacaaaaat gctgcggcct acaacctcgc taaaaatgaa gcgcgctggg    102060
ccaaggaaca ccagcaggtt gctgaacgtc gtgctgagag tttcgaacgt gacctgaaac    102120
gtgaaaaggc gaagaaaaag taatggtact agaaattctc tccgggctgt taatagcagc    102180
cctagtaact ggaacgggtc tggcggtttg ggtatcgata ctgcgggaaa ataaccggag    102240
aatgagatta accaacaacg ggctacacga gaagttgatg gatcaagtac aagatgctga    102300
tgaattctct gctgcggctg agcgactttt agttcgcctg gcgaagattg aagagattat    102360
cggccaagat tccacaatgt cgaagacaac caaaatgcgg ttgatcacgg agattaagaa    102420
atgatctcac caattgtagc ggcactttac ttagtagttg ttggctacct gtccgggaag    102480
taccacggct tcggtttaaa aggtactatt aaggcagcaa tgctggttcc tctgtatcct    102540
ctggcaattc tgttaaccgg gtactacgcc tgtgttttaa gaatctttgg ccggggcaaa    102600
gttaactacg ataactgcac agcgttgctg gacgatattg aaaacaccat taagaaggaa    102660
gaaaaatgaa ccttaactcc aaagaacgcc aagtgttagt agatgctctg cgtcaggtag    102720
tagaccacga tttgctttgt gatgaagata tcgttgagtc aattgcccta atcgccaaga    102780
ttgagcttgc tgagaaggac tcatggcgtc ctttgagtga gcttcctcct ctaggcttgg    102840
caatcgtagt acaacgtgct gatggcgctc cgtttaacac tgtgatggtt cgcagagatc    102900
tggcaaagtc ctactccccg gatatcatca cgttgcacac taagatcacc aacgaacctt    102960
tcgagtttaa tactcgtcac tattactgga gactgaccaa tgcttaatca gcttcgaatc    103020
tataatttcc tggattgcaa cttccaggtc tggcgagaac tccccagccg tttcctaggc    103080
```

FIG. 15DDD sequence.txt

```
tgggcattat tcctctccat ggtggtttca gtcttccata acgtcccagc gacgttctat    103140
atggaagcaa ttcaaccagt cactgtattc atttacgaga tgtacctcgt agcaattaac    103200
gggtggaaag atggccgcat caactgaagt tttaaatcaa tattttaatc gtgagcacca    103260
agagttcagc gatctgttca tccagatgtt cgtcaacgct aataacgctc tggactatcg    103320
tttcttcaac gagttccatg agaccacgtt cagccatcag gatattaact ccgctctgaa    103380
agaactcatt ggctctaaag tgataccatt ccgacagact gcaaatgcag agacactaga    103440
gcttagtgtc gtttggggct tgttcaagaa agcatatgag tttggcaagt atcagaacgc    103500
acgtcactgg atttacgagg tgtatctaaa cactgaagtc attctacctc gccaaatgat    103560
gttgggctgg attgcaaaac aacgtcctga acgcaatgca aaatcattcg caccaattaa    103620
cgacgggaac ttataccatg caagtgaaaa atttgatgct ccaaaatccg tggcttgatc    103680
gcctggcgca agtagagaag atgcttctgg ttgaaggtct gaccgaagaa gacatttgtc    103740
tgaactcctt ctacaactgc aaaactcatg taatgcaggc gctagacgaa gaacgtgttg    103800
aactgagtaa gtttatggtg aacatcgcca cagctcaagt tcactggcaa acccagggct    103860
tatccgccga cgatatcctg aaacataccc tgaacgctat tgcagagtat gggaaagctc    103920
gtggtgaagc tctcttggct tcaaagaaag agtttgataa atcggagtca atgctgaaaa    103980
tggcaatcga tatccatatg gaaggcatcg acggtactat tcactaagag ggtgacaaat    104040
ggctaagaaa cgcgttgtgg taaacttcct agaggaagat tctggggact gcgagtacgg    104100
ttgctggaat actggctacg gtgttgaggt tatggtggat ggcaaatgcg tccaccgtca    104160
ggaagcctgg gcaagctgca ctaacaacag cagcgtagac tttgacgtat tggcccatgt    104220
tcttcagggc atcaagacga agaaggcta cccggtcaaa gcagatcaca tcgactttgg    104280
agatccttcc gattatccag aggagtttct ggatctgttc acctaacaaa gaggccaggg    104340
ctaattgctc tggccttttcg tggtttaagg atattaaatg aaatctatag acaactattt    104400
gcgcggggaa aaccctgtag atcaagcagc agttactgtt gaaaaggtca ggaaagagtg    104460
ttttatactt actcaacgtg gaggtggtaa tcggcctaat cgagtgtatc ttaattggac    104520
tcagtccaaa gacctgtatg agaggttgaa aagggaattt gagtagtgga agaattaaga    104580
cagaagataa atcaagagct agtatgggaa gctaaatcct tccccattaa tcaattcctt    104640
aaacgtgacg gttcgatcaa ccataataag ataaagcaac ttaggccaga tttcaggcaa    104700
gatgctaaga acctcatctt tattaaccgt gctctagacg ctcatggagt attcttcgga    104760
tatgagaagc tagtgttcca cagcctaaat cagctggtgg aaatatggtg tcccgaccat    104820
caagattact ttatgcaaac tgctagaagc caccttgagg gtaacggttg ccaaaaatgc    104880
aggcaccgca tggttaccag agttacggat tatggaagtt acaccgtgcc agcatactat    104940
```

FIG. 15EEE sequence.txt

```
cacaaatttt caattgacgg agactccatt atttggtata ataactccag taaattgata    105000
aaacctttgg aggttaaaga tgaaatacga ttccctgaat aatccgagca ccaactatct    105060
gactgaccag tcagtttctg agatcaagtt ccatccgaac tactccccgg actctagcaa    105120
gccgagtgta gcagctatct ccttccgctt ccgcaatctg cgctttacgt tcgttggaga    105180
ggaagacaag atgatctcta taattgacaa ggttaaagca gtaagcgagc tgtccggtag    105240
cgataccgtt aagttcgaag cattaacctc gttgctgctg actagtgggg ctaccgttgg    105300
taagttcgaa cttattcagc cgcatgtttc tgcactgacc aataccagaa acttctggga    105360
tcaagccaat gtcgagagtc tcataaaatg ggatagtgct actgagttct acaacaagta    105420
agagggctag gatatgttat tctgtacagt tgattttgaa gaagctaacg aaacgtatat    105480
tgtctacggt atgtctgaaa gcaaagtacg tatcctctgg aatcagttcc aattagaagt    105540
accggacgac atatccaaga ctccgaaaga cttctttcat ttaatagata ttaaggcagt    105600
aaaagctcgt aagaagctaa ctccttatgt gttcccaggt gcagtattcg tccatgagtt    105660
aacagcgtat actaacgtgg ttctcaaaaa gtctcgacag cacccaggct atctcacgat    105720
gttgacgtac aaagttggag ctattcacga cggtgagctg gtggttcggg tagatgcacg    105780
cttgcagcaa gaagtcgaag aaatgattag gcagtgccaa ataaagcag aattaaaaca    105840
aagagcacgc ctattcgaca tggcagcacc tagcgaggca gttgccgcat atcacggctt    105900
ttataaagaa atagctgaat ccgatgaaga tttctttatg taagaggata acacaatgaa    105960
cgagaaatat gaagtatgga ctccggttgg ggagaattgt agctatcttc ttcgtaccct    106020
gtgtactcgg gaagatggca catctttctc agaatacttg agtgaatgcc acgctaaggc    106080
ccagcaggac aacccgctat ttaagatcag aggagaggat atcctcaaag ttaacggcgt    106140
gccgtacacg ccagtggaca gtttcgccgc tcttcaggtg tttaaggaac acagagagcg    106200
ggagcaccgg aggatgattg aacgcttgac aggtagagag ccgttttcac atcctaggtg    106260
gaatgaggag acataatgag cagagttgaa aagctacaac atatctataa cctggttaag    106320
aaagctgacc aaaagaaact ctcagagctg agtgaagaag agtatcaagc agtcctcttc    106380
tgttgttcgg caatgccagc gaagctcgat ggagtactgg caaagtcaga catccacaac    106440
ggtaaggaaa caactttcca gccgccgtat aaatggctag cgtccaacat ccagcaaatg    106500
gtgggtaaag ttacgggatt ctcaaataga aagacgccta acatctttat tgacattact    106560
cctagaaccc ctgagtttac gaaggactgg agagacgcat tggattcatt tccgtcatgg    106620
aaagtctttt ataaacctga cgatgaaacg tatgcacatc ttcccttttt gaagcaccca    106680
ggctacacag ttgaagaccc aagttctggg gttaatttca aagacttcaa gtgtactgac    106740
gagaacattg cttacggact catgagaaca tccgtgagga ttgcaatgga tcatgaacta    106800
gacaaacaag atctagcagt cattgcactt tgtaaggatc gttatattaa agttaagagg    106860
```

FIG. 15FFF sequence.txt

| | | | | | |
|---|---|---|---|---|---|
| atcgcagaga | aactttccgt | actttcttgc | tttgaaacaa | tccgagattg | tgaaccagag | 106920 |
| ggtgaatatc | ctaaaggttc | cctctactgg | aaagatgtta | aacatctagg | actatcagaa | 106980 |
| gaagccgtat | tcctaggctt | agtagttacg | ggaagattcc | tgaggctaca | ggagaaataa | 107040 |
| tttgtacttc | gtctatattt | tcgctaatga | agatcagcgg | cttatccta | ggcggaccaa | 107100 |
| ggtgggttac | tcgcgtgacc | cattttatcg | tctaaattcg | cttcaacttc | acagactacc | 107160 |
| tcatcgtgga | ttacaggata | tcgttattca | ttctgtctat | ataatagatg | acgccagcga | 107220 |
| gttctcagca | aagttgctag | agaaggccgc | gcataaaaag | tttaagccta | tgcgagttaa | 107280 |
| tttcggtgac | aagtttgatg | ggcatacaga | atggtttgat | gttgaacctc | acgttattga | 107340 |
| gaagttcttc | ctgtcagttg | gggcaaaaca | agtacctatt | gacaaactca | tagcccaaga | 107400 |
| acaaaagatt | cgtaaatcca | cgaaaaagta | gttgaaaaaa | aataaaacgc | atgttataat | 107460 |
| aatctcatag | attacataca | atttgaaaaa | tttatgaagc | taggcggatt | atgaaccaga | 107520 |
| atcctggact | cggggcgacc | aagcctacga | tgtcacagag | actttctggt | ctcacataat | 107580 |
| ccgcatgcct | agcgcttcgt | aatctcacat | gaacgatgga | gaacctataa | ctataataaa | 107640 |
| actaaggaga | aaatagggaa | acgtgggaat | gaactcacga | ttactcacgt | ttaaaagtag | 107700 |
| gtaatcctta | cacaccatcg | tttcgcggct | ctagggttga | actctagtca | tctttctata | 107760 |
| cagggcggtt | cttttctacac | acctaagggg | agggcggtta | ttttccaacc | ctaaaaatcc | 107820 |
| ataaccattt | tctggaattg | cacaaatttt | cacaccgtct | cacatatccc | acgaagccct | 107880 |
| cacacatctc | acgcaatccc | tctagtacgc | ccaagttcta | agcgtcactc | cacaaagtcc | 107940 |
| tcacgaagtc | cccacacaaa | cccacgtcat | tcacccaagt | tctaagcgtc | aaacattatc | 108000 |
| ggatttgcac | attgctccta | gatattaaag | aagccaagca | tttctagatt | tctagcaatt | 108060 |
| gtcggatttg | cacatgacaa | aacgattgtc | ggaaatgcac | attaactctg | aatccaaaaa | 108120 |
| cacggtcgaa | tttgcacata | taaaaactac | tatcggattt | gcacatactc | aaacgcttgt | 108180 |
| cggaaatgca | cattattact | gaagtacggt | agctgtggat | caaaatcttc | gattctgcga | 108240 |
| atataaaata | tctcctgaaa | tttcaagcct | ttttacacgg | tgtgtcaccg | tgagttcgct | 108300 |
| tgttttttag | agccacagga | attttttctg | tgtcaacccc | tttaccccca | tttaactcat | 108360 |
| aatatttcc | cttatctgcc | ccctgccccc | atcatcccg | aattgcccca | attacccccc | 108420 |
| tttatccctc | ccccaaaaat | acccatcgga | tttgcacata | ctcacccaaa | ctcgcgccca | 108480 |
| ccgctgcgct | gcagcaaact | gcgcgccttc | cccctaaaaa | ttattatcgg | ttttgcacat | 108540 |
| attagtatcg | gatttgcaca | tgcccctagg | gcggtaaaaa | taaattttca | tcggatttgc | 108600 |
| acatacccta | gcagcctcac | gtaatatttt | gcttgacaca | ttgtcggatt | cgcacataag | 108660 |
| cgcaggaagg | gccggggtc | ggaaatgcaa | atacgaatga | gagtgattcg | catttgagaa | 108720 |

FIG. 15GGG

```
                                  sequence.txt
gttgaatgcg aatgataatt attctcgttt gataagctga atacgaatga gaatgattcg    108780
cattccggaa aggaagtgag aaacactatc atttaagtta tcaccagagt tatacaaaat    108840
tgtaaattag cttgacgctt gagaaggtcg cagacgagtt atccacagac ttattaacag    108900
gttatcctac tggttattta tacagtagtt cccggcaaca ctttctgcta atgtcgattt    108960
taagcgccct aggaagcgtt ctaagcgatt taaatttcgt ggggtatttt tagtaagggg    109020
tcacgcggtg gaggagggcg gcgacactct tacatatcgc cgtggaaaca ctcaggccaa    109080
aagtgattta caactgaaac tattagcagg gtaatgattg cgctaataac tatcatgccc    109140
aaaaacatta ggccgctcat tattggcagc tctgcaaaaa gactagggtc ataataataa    109200
ccatgatgac acgaaaaccc cactcaccgc cgccaccgtc accgcctttc ttctgaccgt    109260
cacgaataac gttcaattgg taagtattgt ggctacggct tttgggacta ccaccgcgta    109320
aagttcgcat taaaaagcct ccttattaaa caaggtatca tagagggcat agccgcaaaa    109380
agcgataaaa cccaaaacca tcatagaacc aactaaaccg agcgccaaca ttgaaaaagc    109440
cattttcga tctcctatat gggtgagtca taataataac ataactctag cgggaagcaa    109500
ctactatttt tagtagtaga caagcaaatc cgatttccct atagtttgat ctcccggcaa    109560
gcatagaaaa attttgcttg ctaaaaagcg gagaatcttg ctataataga ttctcagcca    109620
aacaaaggag taacagaaga tgttacagaa atttacccccc gttgcaaatt tgcctatggt    109680
tcgcggtggc gctcgcaacc tgttagatgg tagtaaatgc gcctctatcg gtcatatttt    109740
aggcgtttac cgctcgaata tggaaagtag aaccagccgc gcttttgaac atagccgcga    109800
ctacgttcta gccaacccccg gcgctgcgat tgttattttt cacgacgatc aatatttagt    109860
tgacagccag cctattgatc tgatagtatc taccactacg gacgcttatt tgtataaggc    109920
atccgaaggt aagcaagcgt caagacgttt ttgctaccat gaaagcgaac tgctcgcttt    109980
caccgatgcc cgcgcatgga ttaaaaacct gtgcgatcat ctggaactac caccagcacg    110040
aatttctagc gaaatgatga ttttgtgct tgacaaagac ggaagcatcc tgctaccatg    110100
tgacccttac gatattgata tcgaagaagg ggcaaggact ggaaattatc gttatgatgg    110160
cgagctagaa gaagtcgccc cggctgttac tgaaaatgta gttaacccta ataatttga    110220
gactggagca ttacaaatga atactatcaa atctaccgct accgctatcg ttgccgctaa    110280
caaaaacgct gctgtaaacg ctgctaaact ggaagccggt tctatcgtcc tgaaaaaagt    110340
ttccggcatc gccgccagca aagcgccgtt tatggttcgc ggttatgttg acacggcggt    110400
aggtcgtgtg gtaattgcta acctgctgaa tttcgcggtt agccagtatg cgccgaacaa    110460
ccgcaaagcg gtgattgcgg ctgacgctgc aatgcaagcc gccatgttgg aactggtaca    110520
aagtttcaat gtaggcgaaa tgattgacga agtattgaaa ggcgtcaatc tttctagcct    110580
gattgaaagc gacgtagcag aataattata tctagcgcct ctataatggg gcgctataat    110640
```

FIG. 15HHH sequence.txt

| | | | | | |
|---|---|---|---|---|---|
| aattaccctg | ctaactaact | ggagacaaaa | aatggaacgg | ctaaccgcta | ctttcgaagg | 110700 |
| cgaaaagatg | acgatcgcta | atgtatggca | gcgcctgcgc | cagaatggcg | atcgtggcaa | 110760 |
| ttttgctatt | ttcatcgagc | caaaaaactt | ggataatctg | gctcgccaga | ttgaccgccg | 110820 |
| ggactgctac | ccggatacag | atgatatgct | gggaatcccc | ttgcggatta | tcggggtata | 110880 |
| tggttacggc | tttgatatct | gtattggtga | tagtagcttt | gaaatcgact | gcgaatccgg | 110940 |
| cgctaccgaa | atcgaagtat | tcctaattaa | tttaggctcg | ctaacgtttt | tggatacgcc | 111000 |
| accagcggaa | ccggaaccgg | aaaagctgga | ggtgaaaacg | tccgttattg | ttagttcgct | 111060 |
| aactatggat | gagctggcgg | atatcgtgtc | aacgtatgac | gaaattcacg | ccgacgcgat | 111120 |
| taaagagcta | aacaaccggc | ttgatacttt | ccgcgataag | ctgtaaaatc | cctcccggcg | 111180 |
| gctaaatctc | tagccgcccc | cattattgga | gaaaaccatg | tttcatgtga | aatcttgcgt | 111240 |
| accgggcatt | aattatacgg | tagaagcgga | agaaggttta | tatttagagg | gcgggcgaat | 111300 |
| tgagtctcag | gaagtcgccg | ccgtcctcaa | atgtgacact | aacgtttgcg | gtacgtcctg | 111360 |
| gactgacctt | cattttttag | gtcgtggaat | tgacgtcgat | tccctttcct | gggaaaaggc | 111420 |
| ttgcgaacat | gctgaaagta | tgctaaacga | ggatgattgg | gatgatgacg | acagcgacga | 111480 |
| aaaatacgcg | aatgctgggg | tagaagggtc | gttttatatg | tactggcccg | gtcattcctg | 111540 |
| caacctcgtt | aatggtggtt | cgcccctcca | ttccgttcta | gagcgggcaa | tctatttggg | 111600 |
| ctatatccag | atagttgacg | gaaaggcagt | cattaatctg | cgcgaattga | aaacgtttat | 111660 |
| ctatatcccg | gatgctgaaa | ctatccttca | tattgaggaa | ggtttaaaat | ccggttggaa | 111720 |
| ggttagcggg | gtcgtatacc | tatgatttac | atctatgtca | acaaatattt | tctggcgcac | 111780 |
| tataaaacga | tggaatctgt | gatccagtac | gttagccgcc | agaatgcaag | gcatattgat | 111840 |
| gaagtggcta | ccctcaaaat | cggattgcgg | ggcgatgcta | tcaatattag | ctggcctttg | 111900 |
| ctaattctga | tttgccgtga | tcttgtagcg | ggtaaacctg | tttccgtttc | cgcgctgggg | 111960 |
| gaatcttacc | cgctttccga | tgatctggat | ctctatgatc | tgctaaccaa | atataaaact | 112020 |
| gaacgcctgt | tttatcgtgg | cgggtcggta | tgctctagcg | gcgaaacaat | agaaacggta | 112080 |
| ttccgctaat | agttagctaa | ctaatgataa | gcctgcttat | aatgagcggg | cttttattt | 112140 |
| ttctgcgccc | ctctagcaat | ggcctttaat | atggcctcta | aatttaaagc | gcttagaatg | 112200 |
| cgttatagag | cgttctagag | gcatattaga | gtattaccgc | tgccggaata | tactgtataa | 112260 |
| atatacagta | ggataacctg | tggataagtc | tggggatatc | tcgttatacc | gcttctcagc | 112320 |
| ttgtcaagtc | aaaacgtgct | gtggataact | tgcccggaaa | acaggagtgc | agcataaaat | 112380 |
| aaacgcaagc | attattttgc | gttttcataa | aaataatcgt | tgtctagtg | gataactaat | 112440 |
| taaatttcat | ttttgctttt | tgtataagtt | attaacaggg | tctaaaacgc | cctagaatcg | 112500 |

FIG. 15III

```
                                        sequence.txt
attctaagcg gttttagata aaagccgatg aatcataccg ggtatgaggc gatctcctca    112560
cctcgtgtga aatagatttt gtcaacccct tttgaagaaa aatagtaaaa atattcgttg    112620
actttcttta aatattgtgt cacgtgcgcg cgcttcctat ctatcgtggg cctgttttct    112680
ctttacgctt ctttacaatt ctccgcttgc ggctaaacgc cattgtgtta ttatttatct    112740
cgtagggcgg caagacgaaa cggaaacacg aaagcgtttc actagtagtt aggtatctgg    112800
aggcggcaac attgccccga ctaccgcgaa aggaaaggcc gaaacgatat agtctgcccc    112860
cgccctacac tgctctttaa aaatttggga ttctataaaa agcgttatcg gctttcttta    112920
cttaataagg gaaccgaaaa catgttaaaa gaaaacgtaa tgagtagcga gattgtaaac    112980
gagtttacag tagcagacgc cgaacatttt atagagactt atttaaatgt gtacgacgta    113040
gatttagcct tcattcataa agacggccaa atc                                 113073
```

FIG. 16A sequence.txt

```
<210> 2
<211> 31078
<212> DNA
<213> Unknown

<220>
<223> Description of Unknown: Bacteriophage F394/08
<400> 2
aacccggag   caaggccaag   cagcagccgc   agaaagtacg   ccagcagatc   cggcggctaa      60
tgtttcacgt  gaaacgaagc   ccgaagattt   aataaaaaac   gacgtggccc   cggctgaatt     120
aaccccggct  ttttatgtgg   tggctgaagg   tcgcgcgatt   acgtcaaaac   gtggcatttt     180
ggccgctggt  gaagcagtag   aggcccgcga   ctttgtaggc   ggtgaagaaa   cgctaaacag     240
cctttttagag cgtggtttag   ttgaatgaat   atccgagatt   tagcggccca   agatttcctt     300
aatatcgtga  atgataaaaa   tagcggtttt   ggcgttcccg   tggtgttaat   tgccccggat     360
ggtaacgcgc  agccgttaag   cggattaacc   acggatatat   cgagctatat   tgatccggaa     420
acgggcgttt  tagttgcggg   ccgtgttgca   tcggtcacat   tcgcaaacaa   ggcaatccgt     480
gccgctggat  tcgcagaaat   gcccgtagcg   gtggccgatt   caaataaacg   cccgtgggtg     540
gtgtgctttc  gtgatcctga   aggcatcccg   tatttgttca   aagtggttaa   ggctatgccg     600
gatcgcgcga  ttagtggcat   agttttagaa   ttggaagttt   ataagcgttc   tatttacttc     660
aatggggctt  ataaatttga   tgggacgacg   ttatacgatg   gagttttaga   cttgttatga     720
atatagaagg  ctttaaaaaa   ctgcaaagcc   cgattaacaa   gctagatagt   tttgaaatag     780
tccgcgacca  gatcgcggct   attttatttc   ttgagcttga   aaatcaaaaa   gccattgctg     840
ggcgcgcgca  gattgacccc   gctagatttg   atatgaaagt   ttataaagag   cgttctaatc     900
cgtgggatct  attcgacgat   ggcgaaaata   agcccattat   taacgtgtgg   tttagtaata     960
gcgatttcga  ttacaccaat   agcagcacag   tcgataagca   gaaaaccacg   gctattttta    1020
atattgattg  catagcgacg   gctataagcc   aagaaacagc   gaccgggcaa   acgctgggcg    1080
atgaaatggc  atctttagag   gtgcagcgcg   tggctaaagt   gatccgaaat   attttaatgt    1140
cagatacaaa  tacatatttg   caattgcgcg   ggcttgtttg   gtcgcgccgt   gtgctgtcat    1200
taaacatatt  tcagcccagc   gcagaaaatg   gaatgatgca   aaatctatgc   gcggcccggc    1260
ttgtacttca  ggcgacgttt   agcgagtttt   cgccgcagta   tgaaccccaa   gagctagaga    1320
ttttgtccgt  aactgtccat   aattgcgatg   gacaaatttt   atttaacaag   gagattgcta    1380
agaatggcaa  ttagtaccgc   tgttgatata   agcgcggtgg   cccgcgtttt   aggtatcaaa    1440
acaaatttta  aaaatttgcg   ggatggtcgt   gtggtgattt   tgccgcagcg   gatcgcctta    1500
```

FIG. 16B sequence.txt

```
attggtcaag gttccacggg gatggtgttt gcaacgtcaa aacgacaagt aacaagcgcc  1560
aatgaggtgg gttcgctata tggttatggt tcaccgcttc acttagcagc taaacaacta  1620
tttccgaata atggcgacgg agtggggacg atcccggtaa cggtttaccc gttaagtgat  1680
gcggacggat cgcaagcggc gaccggatca attgagcttc tagggacgca attagaatcc  1740
ggggcttata gagttgttgt gaacggtatc cgttcggaac aatttcaat tttgattaat  1800
gaggccgggc aaactgttct aaatcgagtt gcggcggcta ttaactccgt tttagatatg  1860
ccagtacgtg cgacggcaga ttcggaactt caaaaagtaa cgcttgtttc aaaatggaag  1920
ggtttaagcg ctaatgctat ttctgtccaa gttgatgggg atttagggca aggtatcgaa  1980
tttgcagtaa cgcagccagc gggcgggctt attaatccga gtgtttccgg tgcgctttcg  2040
cagtttggca acgtatggga acaatggtt ttaaactgtc ttaatattca ggataccgaa  2100
gcattaagcg cttattctga ttttggggaa gggcgctggg gtgcgttggt gcgtaaaccg  2160
cttattgtat ttacggggaa tactgaagcc gacgtaaata gcgccgtttc agtcccggac  2220
gcgcgaaaac gtgatcggac aaatgttcaa cttgtggccc cggattctat cgatttgccg  2280
ttcgttgttg cgtcccgtca attggcccgt attgtaaaaa ttgcaaacga aaacccggct  2340
tgtgattacg gcagccaagt agccgacggc attaaccccg gcgaagatgg gaaacaatgg  2400
ctttataacg tgcgtgatat ggccgttaaa aaaggcagtt caactattga aattcgggac  2460
aatcaagtat ttatcgggga cgttgtaacc ttctatcatc ctgaaggtga agaaaatccg  2520
ccgtatcgtt acgtttgcga tattgtgaag ctgcaaaaca ttattttaa cttaaatcta  2580
attttgccg tgccggaatg ggacggagcg ccgttaattc caaacgatca gccgaccaca  2640
aacccacgcg ccaaaaagcc ttctatggcc gttgccgcta ttgccagcct tgtggatagc  2700
ttgggcctaa atgccattat tagcgatgcg gcatttacca agaaaaacac gtttgcacaa  2760
attaatgaac aaaatccgaa gcgtttagac gtttcgacga ctgtaaaact tagcggaaat  2820
acaaacattt taagtgtgga tcttaatttt ggtttctatt tcggtaattc ggtaattgtg  2880
gggtaaataa cttatgtcag ttggtggcag cattgagagc ttaactttag acggccgaac  2940
cttcagcgta gcagcggacg cggattcaac gcgcaattta ggcggcacgg ataacgaagt  3000
agaaatgaac ggggatggta cttatcgaat tgtaaaaacg cgcgtaccgt caaaactaga  3060
cggtatcacg gttgcaattg atgacgtgcg cggggatgca gaatacttgc aagagctaaa  3120
agatcgaaaa gagggctttc cctattcgat tacatacgcc agcggtgtga tttatcaagg  3180
tacggggaca atcgtaggag aaacgggaat ttctagccaa aacgcgaccg cttcgattac  3240
tatttcggga tcggctttaa ctaagcagta atttacagcg cggccataag attggccgcc  3300
cttctttaat catttagggg gtttcacgtg gaacatatcg aaaatactga aaatcaaact  3360
ttgtggggct tgcctgttaa ggttgcgcgt gaagttgcgg aggctgaatt tatccgcttt  3420
```

FIG. 16C sequence.txt

| | | | | | | |
|---|---|---|---|---|---|---|
| tgtgatgcta | tggacgtgga | ttacaacacg | gatcgaatga | cggacgaaga | tgcaaaagac | 3480 |
| tttaacgaaa | gtaaagggct | tttgcttgat | gcgctgcaaa | ttggcgtttt | ggaaattgat | 3540 |
| agcgacggca | tggccgttgt | ttacccgaaa | aaaggcgata | ttaagcaaat | taaatttaat | 3600 |
| gagctttgcg | gggcggatta | cgtggcaatg | gacaataaaa | aggatacgca | aagtttcgct | 3660 |
| aaaatgttcg | caatgatggg | atctattacc | aagttaccgc | ccgcgacttt | ctcaaaactt | 3720 |
| aaaaagtttg | atgcaaaagt | ttgtttgtcg | attgctaaac | ttttttttggt | ctagtcgata | 3780 |
| ccgttttaat | cataaagggg | ggcgaggttc | gcctatcccc | ttcgagagat | tcggatggta | 3840 |
| tcgagcgcgg | gaataatacg | agatttcaag | tttattcaac | gatgcttatg | cagatcctaa | 3900 |
| gagattataa | cttgccgaat | tttagaacct | taacaagttc | agaaattcgg | ttttttatga | 3960 |
| cggattgcgg | gccgagttga | agaaacaac | aaaaccgagg | aattaatgag | ccgttacagc | 4020 |
| gtagaaacaa | tatttagggc | cgtggatcgc | atgacggccc | ccatatcccg | gatgcaatcg | 4080 |
| ggaattagtc | gatttactcg | ccgggctgaa | agcggactta | ggcgcgtttc | agatatgacg | 4140 |
| tggaatatat | ccaaagtatc | aggcgcagca | gccgcggcca | ttggtggcgc | atttatggcg | 4200 |
| gccgctggtg | gtattgccct | ctttgtcgca | gaaacaaacc | gggccaattc | agaaataaat | 4260 |
| gaaatgtcca | aagctatggg | ggtttccgcg | ttatccgcaa | gggccgcaga | ttccttgctt | 4320 |
| acaccgcttg | ggatgaattg | ggaaaattac | acggatctta | ttgaagaatt | gggaaataag | 4380 |
| atgggtgaat | taaaaaacac | gggggaaatg | aaaacatttc | aagaggctat | tggacttact | 4440 |
| aatattaaaa | tgaaggaatt | aaaagcctta | agccggagc | agcaatttac | aagaattatg | 4500 |
| gattctttgg | caaaaatgga | ggatcagcaa | aaagcccaat | ttattgcaga | tgaaattttc | 4560 |
| gggggtgagg | gtaataaatt | cgtttcagcg | ttaaaggcgc | gcggcttgac | tatgacgagc | 4620 |
| ttgattgaaa | attataaaaa | gtacaatttt | tataatgagc | aaggcgaaaa | agcaacggcc | 4680 |
| gctttttaatg | cagctttaac | cccgctaacc | acgacggcaa | attcggcaaa | atcgcagatc | 4740 |
| gcggccttaa | ctggtggcgc | gatggttcca | tatattcaaa | aggcgacgga | atgggctgcg | 4800 |
| gcaaataagg | aattaattaa | tagcaaaatc | gaagtattcg | ccaaaggctt | ggcggattcg | 4860 |
| cttgtttggg | tggtggttaa | ttttttccgag | attgtgacgt | gggttaaacg | tgtcgctatt | 4920 |
| ggtatcggca | tattcttagc | gcttacagcc | gttttaaaaa | ctttcgtttt | gattatgacg | 4980 |
| gccgttaatt | tagtaatgat | gatgaacccg | ataggctaa | tcattatcgc | cgtggtcgcg | 5040 |
| cttattgctg | tcattgcgta | tctgattaat | aagtttttttg | ggttgcaagg | tgtcattgcc | 5100 |
| gcggctaatg | gtgtgcttat | ggggattggg | gccgctattt | tggtggcgat | ggggccaata | 5160 |
| ggctggctaa | ttggggccgc | tgtcttgatt | tggaaaaatt | ggggcgtttt | aagtggtttc | 5220 |
| tttagtggtt | tatgggcggg | tatcgtttca | gttttcagg | gcgcgcaaaa | tattattatg | 5280 |

FIG. 16D

```
                              sequence.txt
gggatcatta acgggattat gggcgcaatt gataacgtga ttaataaagc ggtttcgatg    5340
ggttcggctg ttaagggctt ttttagcttt ggcggcggtg gtggtgatca aaagcaagca    5400
gcagcagcgg gcggacgtgt ggcaagccca caagagcgaa ccgcaaaaag cgtaacggaa    5460
aataatagcc attcaacggt aacgatccaa gacaaaaccg gacgcgcgaa aatgtcaggt    5520
aaaccgggga atggggttcg attggttaaa acggggacta tgtaaacaat gagttgggaa    5580
gatcgtttaa aggaggcggc ttacaccgcc cccggaggta cacgggccac gttcttagtt    5640
gaggacgttt cccgtagttt tgataaaaaa acaaatggtt tcacgttccc ggatgcgtcc    5700
gggacttatg ttcaagattc aggcgtaagc gggtttaaat atccgctgac tatctatttt    5760
agtgggccgg attgcgatgt ggaggccgaa gcgtttgaag cgcttttgag agaaacggga    5820
atagggcgtt tagagcatcc gctttatggc gttattaacg tggttccgtt cggtacgatt    5880
acccgtaccg atgcaattaa aaccgaggca aaccaaacaa aaatagagct ggaattttgg    5940
gaaacaaacc ttttaattta cccattaccg caagccgacc aattaagcgc cgtatttgag    6000
gctatttccg acgttaaggc ggctttaagc ggtgatgtgc tagatagtat cgacgtaacc    6060
gacgcgagcg ccctagcgcg atttaaaaac aaaataacgg gggctttaag caaggtaaaa    6120
accgctttag ggaaaattaa gaatttagcg gacttgccgg ggcaattaat ggacaaggta    6180
aacggcttaa tttcgcccgg ccttgagttt atttccgatg ttaaagccca gcttggcgat    6240
gtggttaatt cattttttga gcttgccacg ttgcccgaac aaattgtcga ttcattcaaa    6300
gagaaaatag cggtctataa ggatctcttt agcgaattaa cttcattcga gggcatattc    6360
cccagcaatg aagaatacga ggcagcttgt accggggtaa cggtgacttt atccggctta    6420
gtagtggatt tggttgaatc tgaatttaat acacaaagcg aagcattgga ggcggccgag    6480
gatctattag ccattttttga tgatgtaacg ggatggattg aagaaaaggc gcaaggcttg    6540
ggccgtaccg attcaaacgc ggtttatcag cgcttacata gcgccgtgat gaccgcggcc    6600
agctatttgg ttcagcaatc ttttaccttta aaaaagagc gtaaattggt tttaaaccgt    6660
agccgtacaa ttattgattt atgcgcggag ttatacgggg aagtcgatag cgctttagat    6720
ttctttatta cgtcgaatga tttaagcggg gctgaaatat tggaaattcc gaaagggcgc    6780
gaggttttt attatgtctg acgtttctat gatgatccac gggacgcgct ttcattttg    6840
gagtggtgta aggatctctt taaatattga cgcggtggca acgattagtt ttaacgcccc    6900
gtttgaccat gaggccccg gatttaagcg caatttcgcg ccgtttggat tttccccggt    6960
tgctatcgac gtggacgatc agcgcttatt taccggaacc atgttggacg tttccccggt    7020
gattagtgaa gatggtaaaa aagagatttc cgtaaatgct tatgcaaaat gcggagtgct    7080
tcaggattgc accgccccgc ctgaatccat gccattagag ttcaataaat taaacctgtt    7140
ggatattgct agaaaaatgg cctcttattt tgggtgggt gtggtatta atgcagatcc    7200
```

FIG. 16E sequence.txt

| | | | | | |
|---|---|---|---|---|---|
| gggaccggct | tttgatcgcg | tggcgtgtga | cccggataag | aaagttttag | aatttttagc | 7260 |
| ggatctcgca | aaacaacgcg | gctttgtgat | cggtagcgat | gaaaacggca | atttactttt | 7320 |
| ttctaaaagt | tcaatcggcg | gcattgttgc | taagttggag | caaggcgtat | ccccgctttt | 7380 |
| aagtgtatcc | cctacttttta | acccgcagga | atattattcg | catattacgg | ggctatcccc | 7440 |
| tgtcgaagtg | gcaaagcccg | cggccaaaag | cacggccaaa | gtaaaaagg | acgctgcaac | 7500 |
| gcctgaaaaa | gcagggcagg | ggagcgaaaa | ggcgaccgat | aaggcgggcc | aagccgaaat | 7560 |
| taaaaaggaa | ccaaaaaaag | aggaaaaaac | caaaaaggaa | aagcaaaaac | caaagcccac | 7620 |
| gacttataaa | aagtttacag | ctatcgacga | ggcccccgta | tatcggccat | tggttttttaa | 7680 |
| aattgatgat | gcagaaggcg | cgaccgatgt | agaaacggcc | acaaaagcaa | aaatggcccg | 7740 |
| aatgcttggc | aatatgtgta | cttatgcaat | tacggtttcg | acgtggttcg | atgcgtccgg | 7800 |
| ggatttatgg | cggcccaata | ctaaaattaa | actcaaggcc | ccggattcaa | tgatttatga | 7860 |
| tttttttcgag | tttgatatta | aaagcgtgga | attgtcggcc | gatgaaaaca | gccaacaagc | 7920 |
| aaatttaact | ttatgtttac | cgggttcgtt | tacgggcgaa | cccccggaga | ttttcccgtg | 7980 |
| ggaattgtag | cgactgtatt | aagtaatgat | ggtaaggatt | taaaagtaga | tcggggcaac | 8040 |
| ggggacaacg | taacggccca | gcagttcggc | ccgtccggtg | atgatgctcc | cccgcttaaa | 8100 |
| aatgattatt | cggttttagg | atcggccaaa | ggttcaggca | atgccagcgc | cgtggcctat | 8160 |
| cgtgaccaaa | aggccgaaaa | ctacatagcc | aaagcagggg | aaaaacggat | ttattcgcgg | 8220 |
| gatgaatcgg | gggcggtaaa | agctgaagtt | tatttaaaag | cggacggaac | cgcggagatt | 8280 |
| aaaaacgcca | gcgggctttt | tgttatggag | ccgggcggtg | atgtggtaat | aaatgggggtt | 8340 |
| agaattacta | aagccggagt | tattcaaacg | ccgggcgggg | cttcaatgag | ttctgatttc | 8400 |
| acaaacgcgg | gcggaataac | tttgggcgac | catgcggccg | atacaagttt | acataagcca | 8460 |
| taaggggggaa | tagtttttaa | tgtctttttt | tgatgtgcat | ttatttgatt | cagtcgatgg | 8520 |
| cggcaatgta | acggatgatt | tagaaacgcg | ggacggccta | gaaacggctg | tttatctaag | 8580 |
| tcttttttggc | ggtaatgcct | tagatgatgg | aaggccccaa | aaccctttcga | cgtggtgggg | 8640 |
| gaatattggg | gagaatgaag | cggcaaagca | atataaaagc | gaagccgctt | ttttgcttcg | 8700 |
| cacggttccg | ccgaatacag | ccaatttaaa | gcgaatcgaa | gcggctgcat | cgcgggatct | 8760 |
| tgcttggttg | attcctgaat | atgtgaataa | gattcaagtt | aaggcgttta | tgcctaaatt | 8820 |
| gaatgcggtt | aatttaacgg | tttctttgga | tggtttagat | ccgttgcaat | tccgtacaaa | 8880 |
| ttgggggcgaa | aaggttaaag | agcctgttta | tagactattg | ccgcctaaag | tttcccgaaa | 8940 |
| taatgggggtt | aatttagaag | gcacagcaga | aacaaaaact | aaactaattc | ttatccgtgc | 9000 |
| cgatggatca | agattaagta | cgctggttga | tggttcaggg | aattggaaat | ttgattttta | 9060 |

FIG. 16F sequence.txt

| | | | | | |
|---|---|---|---|---|---|
| ccctttatat | ggtggtgaac | gtgcccggat | gtatgttgag | ggtgtagggg | gtaaaatatc | 9120
| cgctattgtt | acagttatcg | gggttttacc | gcttcgctat | gatgggatgg | caatttatga | 9180
| cggtacgcac | aaatataacg | gagttagatt | aaattaatga | gtacgccaac | gactaaagaa | 9240
| atatcgaacc | gtatttatc | caagttagaa | acgacattcg | ggcaaagttt | gcctaagtct | 9300
| tttacacgtg | ttttatccac | ggttttgggg | ggtgtgtttg | taattttata | taaatacggt | 9360
| ggttttattg | ctttgcaaat | gtttgtttca | acggccagcg | ctaaagatac | ggactttaac | 9420
| ggcaaaacaa | ttaacccatt | acgcgaatgg | ggccgcctca | ttggggcggg | tgatcctaat | 9480
| ccagccgtta | atgccattat | tttaacgcgg | attgtagtag | aaaagccggg | cgagatattg | 9540
| cccgcaggga | cgcagctagt | aaacagcggc | aacggtgtta | catacattac | caagaagat | 9600
| attgagctag | tcgaagggc | gcaagatatt | gaagttttag | cggcttcgga | tacttcggga | 9660
| aattcaggcg | caggcaaagc | gggcaattta | aatgcggggg | atgttttgac | ttttgcgaac | 9720
| ccgcttggat | cggttggccg | ttattcgact | gtggtaacta | caattcggga | aggcctggac | 9780
| gctgaagcta | tcgaaacata | tcgcgcccgt | gttgtttcac | gtttccaatt | gcgcgctcaa | 9840
| ggcggggcaa | tggtggatta | taagatttgg | ggcgaatctg | tttccggggt | tagtcgaatt | 9900
| tatccttata | cgtccgattt | gccgggccaa | gtggatattt | atgtagatgt | tttggagggc | 9960
| gtagcaagtc | aagcgatttt | aaatcaggtt | aaaaacgccg | tcgaatttga | tgcaaataac | 10020
| gggcttgcac | aaaaccgccc | tttaaatgcg | ctggtaaatt | atttaccgat | ggagtttgta | 10080
| gaatttaacg | taacgattag | cggtttaagt | gttgagggcg | cgctatctgt | tagggctgaa | 10140
| attagagcag | ctttagaaca | ttatttaat | atccgtgcgc | cgtatattgt | gggcctttct | 10200
| actgattcgc | gcgcggaccg | aatcacattg | gcggccgcgt | ccggtgttgt | ggacgatgtt | 10260
| gttaataaag | ctggggcat | ttttaacgat | atgcagttat | ttaaggggca | aacgccaatt | 10320
| tcttttttata | tgttggggat | tggtgaaaag | gcgactttgg | taaacgtcga | gtatctataa | 10380
| tatgaatatg | tttaagcact | tgttacccag | cggccgcgct | tggaacctaa | ccgcggaaaa | 10440
| gccactaaag | gcttttttcc | gttgcttgga | tgttttgaga | acggacgcag | taaattattt | 10500
| taatttgctt | tttttagata | taaacccaaa | aacaacgcgc | ttacttgatc | aatgggagca | 10560
| gcaattcggc | attaaccgag | gatttttaac | cgaggcccag | cgccgggaac | gtgtcgcggc | 10620
| cgcttggcgt | gatgtgggcg | gacaatcccc | ggcctacatt | caagaagttt | taagaaataa | 10680
| tggctttgat | gtttatattc | acgaatggtt | cgatccggca | gatcgcgggg | aagtaggtga | 10740
| aaaacagcct | ataacgccac | gtaacccgct | gtcgattatg | tcggcccaat | atgccgaggt | 10800
| tttgcccgtt | gtggattgtg | gcgaaccgct | ggcgctatgt | ggtgaagaat | ttgcacatgc | 10860
| cggaaattat | ttgggccttg | ttgggtatcc | gcttgttaat | aagttcgttt | atgacgcgga | 10920
| taaatacggc | tacactgtcc | ccgttgatcc | ggcttattgg | tatcactttt | tttatgtttg | 10980

FIG. 16G sequence.txt

```
tggccctaat tttggcgatg tggcccaagt tgaagcaacg cgacgcgctg aatttgaagc   11040
gctaattttg agaattaaac ccgcgcactt atgggcgggc gttattgtga gatacgttta   11100
atatgtcttt agtgtttaat gagaaatttc ccggaaaaac ggcaggggct acacaaaatt   11160
acccgtatgg cgaagcgcgt aacgtatcag gccccggaaa tggtgacggt acgccgtggg   11220
atgcggccct agtgaatgat attttggat tacttcaagg gcttttagtt cgtgccaata    11280
ttcagccgaa cggccagtcg gacacggctt taaactcgca atatttacaa gccttgcttg   11340
ccctgtttat gccgaaacaa acgccaattt ccggaaagtt agagcaaaac ggatatttaa   11400
ctatcccttt ccctgttgta ataaacggcc aaacggtaga gcgtgaattt acaattcaat   11460
ggggttctaa ggattggtct agttatccgg gtgaaattca agattctatt gttttgaaa    11520
agccttttaa aacagcctgt tttggtgttt ttccaatccg aaaaatgtcg cagcattccg   11580
cttatggtga tggtggtgtt aagcctattt ctgtttctaa aaccgggttt acagtttctt   11640
tgcaagccta cggggttct gtgggccact tgttgggtta ttattggttc gctgttggtg    11700
tttaagttag ttctgatttt atggggtaaa tgatgaatct atttatacaa ggcatttatt   11760
tactatggaa ccaatttcaa cgggtggcac agccgctttt ttaaaggttt atggggtgtg   11820
gttggcggtt gttaccgctt tggtgtttgt tgctactgtc gttttaatga tgcgtttacc   11880
acgtagccca caagagttcc ttgtgggcat tattacgact gtcgtttcaa gtctaatggg   11940
cggatctttt ttaattcttt attttgattt acagatttgg gccaattcag cttatggcct   12000
tatggtaatt ggtgggcttt actttgtggc gggtattccc ggctgggctt tggttcgctg   12060
ggtgtttaat tttattgatg cgcgggaagg ttccacacta ttggacattt tccgcgaatt   12120
taatgaagaa tttagaggcg ggaaaaaatg agtaaaatta ttgcgatttg cgcggggcat   12180
agtgataaag atccgggcgc ggtaaatggt aaacgtaccg aggcggccat tgttttagat   12240
atgcgtaaga tggttgccag ttatttggaa aaagcgggcg tgaaatattt aacagacggc   12300
aaaggcgggg ttaatcagcc attggccgaa gctatcaaag tggcaaaaca agccagtatt   12360
gctgttgaat ttcactgtaa tgccgctaca tcgaaaaaag cgaccggggt ggaggttttta  12420
tccgctgaaa aaaataaggc cctagcgaag caaatagcgg ccaaaattaa cggggttta    12480
aatattccgt tacgtgggga agtggttgg aagtctgaag gatcagggca gcatagccgc    12540
ttaggtttta ttagttccgg gggcggttta attgttgaat tgttctttat ttccaatgat   12600
gacgatttag cgaaatggga cgcgaaaaaa tggcttgttg ccaaagaagt ggcggccgta   12660
ttgattgaac aagtaaaaaa ggcggaggcg gcataaatgg cagcattaac gatatttaac   12720
gcgatttcag aagttacaag ttttgcaggg gtggcccgtg agattttcga cacagcagcc   12780
aatgcaatgg acgcggccca aaatgagaaa aaaggcggag gaaataaaaa agtttgggta   12840
```

FIG. 16H

```
                              sequence.txt
atggcttaca tggaatcatt tattaatgat ttgggcgaaa attgggaacg atgggccaaa     12900
gctatttttt cttttattga ttttgccaag tcgattttta atagtaagcg ctaataaaaa     12960
agccccgtat taattcgggg cttttttatg gttccacgtg aacggttta gcttttcttt     13020
ttgcttgccg ggtttcttaa taaacgatct tttttgatct cgcttacaat cccgtcgatt     13080
aaaaattcca tgcttgttcc tttggttggt gggttggttc agatgattta attcgagttc     13140
ttagggccgc ttttacaatc ttatccgcca tgcgccctat ttgcgccttg tggcagttat     13200
tacacgcgca tccggcctta tatcccgaaa cggttccgca gcctttaacg ggcttatatg     13260
cgtcccctgt cgtttcttca ataaaatcta tggttgattt gtccgccgtg tttcgcatcc     13320
tttaccccta agccgcagcg ggagcaacgg ccatttttaa ataaggtgaa tgtttggcaa     13380
ataaaacaaa agttagtcat ttttgccgtt tgccttagcg attcgcatta cattaagggc     13440
cttttgcttt agatccgcgt atagctcatt agtaaggtaa ctttgtgcta catcgtgaaa     13500
agtagataaa aaatgcgtgt cttgttttac cttgctttgt ttaagttccg cttggtttac     13560
ctgaattaag ccaatagctt tgtttgcctt tttgattaag ttattcacgt cgcttaattg     13620
cgcgtttatt ttggcctctt tttcgccttt tatgtgtgct ggggccttat ccatcaaaag     13680
ggcttcacgt tggccgttta ggtgggtttt taggcccgtt aattcctcta ttgagaattg     13740
ccccgccact tgcaaagtgg ttaatgctga aaattcaatg attgcggttt taagttctgt     13800
tttagtcatg ggtagcactt catttaaaaa gtattaagcc cagcagcagc cgggcaatgg     13860
tgggttagat ttcggttaag ccgtgttttt tcattttctt ataacggtt aatcggttaa      13920
tgcctaatat tcgggatact tcggcaatat tatatttga atatttaagc gcttttttcca    13980
aaacgcactt ttcaatagga tctaatgcag ccgctagagc ttggccggaa ttttcataaa     14040
aaaaattcgc gtccaaagca tccgggttaa ataaattagt ggtttcgctc attcggatat     14100
tccttaaatt gcgcgttata ttcagcgaca aattccgctt gtttgtcgat ttcatcggct     14160
tgtttgataa tgaacatata agacaaagcc gcaagcataa aacagaaaaa caacgtgctt     14220
aaaatctctt ttatttttgc gccgtggttc gctgtttctt gtgaaaaatt gcttaattgt     14280
tgacgctgaa taactggctg tttcataata atcggactcc atgaaattag aaaaaagccc     14340
cgtagccgtc caaagttccg ggctttttg ctgtctatgt gttgcataat atacaatata     14400
aataaaaagt aaatagagaa attatagata ataaatazаa taataaaat agataaaaag      14460
tattagtttt aattgtggca tgaatatttg ataagtgtta aaatttgttc taagcaatca     14520
tgctgaaaat aaaaaacccg ccggacgggg cgggttttag tttgtcttga gggtataaga     14580
cgtgaaaaag tttaacacga aatttaagca aaatcttgat gatgcaaata caacgcatt      14640
tattccgaac agctttcaaa ttacaaatgc tttcgttgat aacatcatgg ataaaatttc     14700
ggatgcagca gtaaagatct atttaattac agtgcgtaaa acaacgggct ggggtaagca     14760
```

FIG. 16I sequence.txt

```
gatagattcg atttctttaa gccaatatga agcgtatagc ggcaagtcgc gccctactgt    14820
tgttaagtgt ttaaaagagt tggttaaggt gggtttattg gtagagcata ccgggacacg    14880
gtacggtaat tcgtattcgg tggcgcttgt aaatagcatc ggtttcgagc ttttatctgc    14940
tagtaaaaaa attttactag taaaaagttt taactacact agtaaaaaat ctttactgcc    15000
actagttaaa attttttaaca cacaaaaaca actatcaaaa aacactaatc aaaaacaaat    15060
aaataagcgc gattggtttt ctttaaaaac tttaaaagat gaattgttta aaaccgggtt    15120
gcaaattgag gctgaagatc taacagcggc taaatggttc gatagagaga aaacagcctt    15180
tgaaaactat gcacctaatc aaaacctttc agatccgcaa aaaatgtatt acttcgttga    15240
ttggctttta aaagcaaagc gcaagtacga cgcagcagag cgccagcaag cagctaaggc    15300
aaaagcggaa ggcaaaaacc aaaatcaaaa ccctgaagat acaaaaacag aaaacgaccc    15360
ttttaaactt tctactaaac aaatttcatt ctttgctagt cagttagccc atttaccatc    15420
atttgcaaaa tattgcactg gtaacaaagg ctttaaagaa tttgaaatgt ggattgcttc    15480
aatgttgaac aatcctgaaa atgttaaaaa gtggaataaa tatttaaatg aattgggtta    15540
tttgatcggg taatcagggg gattaaaaac aatgaagatt tcaaactttc attttcaaat    15600
gcaaatttta cttttgattt ctaaaaacac ggttttagat tttgagggat taaaagagaa    15660
gttagcgccg tcgattacag acaacgcatt aacggaatgt ttagaagaat tattgatgtg    15720
gggatgggta caagtacaaa agggccttta catggtttca ggcgttgctt atcagatcat    15780
gggggatatt tgccaatgct gatagacaaa tatttctatt aatcggcttc gatacggatg    15840
caatggaaaa atacaagtat tcagaatcaa acgccgtatt aagcccgcat ttaaattgcg    15900
gcctaacttc agttagtcgc gttggatctt caggccaagc aaagcataaa ccgcataagc    15960
gaagtgaaat agcagatcag gcagaaaaag agatttgcaa gaattgggcg ttaagacaac    16020
aagcattttt aaataacagc gtaagcaacg cggtactagg gggctaatat gaacaagttt    16080
attcacattg agggcaaacc aacggcccag caagtacgcg aagcgctggc aatgtatgca    16140
aaagacatta acgcccgga attttctttta attgttcagc gtgagcttat cgaatcattc    16200
cgcaacgata cggcccacgc ccttaaatcc gcagttgcct tttatttaa aaatcgtgtg    16260
atccaacgcc ccggccttgt gttggcaagt ggtaaagatc aagcgcttat tgttgagagt    16320
tgcgaaaata aggcattaaa gcgccacttg gtcgcggtgt cggggtattc atcgcaattt    16380
ctgcaaatgg tgatagatca taaacgcca ctttcagccg ttgccgcgcg ggatctaaag    16440
caggcattac caaaagcgga aaaactctat aaggccgaat gcaaggaaaa agatgcaaaa    16500
ttaaaaaaga atatttgcgg ttttgtcgct tgctatagaa atggctgtca ttgcacaaaa    16560
tgcaccacgg catataagaa atatcgctaa aagcaagcct atcttttaaa gagaaaaagc    16620
```

FIG. 16J

```
                                    sequence.txt
gcagttcgcg ccgtggccgc ttagtgtttc acgtggaacc aaacaacgcc ccggattaaa    16680
cgtccgggga tctaaaaaag agtaaggaaa aggaataaaa atgggtgttt cgattattaa    16740
tttagtttta ttggttggtg tttgcttatt gctaacaaat atcgccttaa attgtttgtt    16800
tcataccgaa aataaaacat atctagtcta tgcgtgtggt tttagtgcgg cttcggtggc    16860
gggtgccatt gctggcgtta ttggttgttt ggcttatggg gtaacagtgt aatgaaaaat    16920
aaatcaattc ttatgggcct attcgttgcg gccgctggtg tggtgtttta tatggggggcg    16980
gatagtgctt gcaatcaaaa ggctgttata gatccgggcg cgcttatgtc gcttggtggt    17040
atcactgttg aaaataaaaa agcctcattg gttcgcgtat gtgatacgcc agtaaaagaa    17100
aaccttgtga gctttgtttt gattaaagac ggcttgcgcg tgggtggtgt ggtcgataaa    17160
agccatgttg cgctcatagg tgaataaatg agtttaggaa aacgccccgc aggtgcgacg    17220
catatagaga gcgacggcac atattggaaa aatgaggacg cggattggta ttttggcgt     17280
gacttgtggg gctggtgtca atatgtcggg ccaaagaata gaaattttt aaataagttt     17340
tcggtgttgg ggtgatggat ttatatattg gtcagattgt cggcatagt tcgcccactt     17400
gggttgttca gggaaaattg aagataacca aaattaacga gggtaagcga agcggtttaa    17460
agattattac ggctacagat gaatcgggta aggaatttac cgcagtttat ggcgtgtttt    17520
ttagtgttga tagatattaa ttaaaatttt ggggtaatac gtgagaaacg aaaactttga    17580
agattattta aaacaaacgg atgattacgc cgtattactg aataattacg gatctagtct    17640
atttatccat gaaaatggcg tttatcgcgc tttgcctgtc cgggtggctt atgccgcttg    17700
ggtatcgggc ggggatcgct ggggagaggt gcagcacttg aaaggcaaaa ttaagaaaat    17760
ggccgaacgt gcagcagaaa cagcggattt ttaccatacc aaaatagaaa aattggaaag    17820
tagcacggtt aaaaaggcgg gtttattgga tatggccgaa caatgggacg gtttagagtt    17880
gcgcggacgt gatttggaat taaaccgggt gcaagaatca atttataagc gttgtgctta    17940
tttgttgcgg gtggctgtta atgggtaatc ggtggacgtt aagcggaaag gtaaagggt     18000
taaagatttt gcccgaaagt ataaccgcgg cacaattcag ggaaatgata gaacgggggc    18060
aagtcaaaaa cacgccacaa gccccaaaaa agcgccgtag cggaaaagta agtagtccgg    18120
gggaggctac attagcccaa gccttaaaag cgcttaaaat cgaatttgtg caagagtatc    18180
gcttttgtga atatcgcaaa tggcgcgcag atttccatat accggggaca aaccttttaa    18240
ttgaggtaga aggggcgta agatccggcg ccgccacgt gcgaccacaa ggctatataa     18300
acgacacgga aaaatataat gaggcggcta agttgggctt tgttgtattg cgctttgata    18360
cggaaacggt ttcacgtgga accgcaataa acgaaataga agttatttta gaaaggcgcg    18420
gatatttcca aaataagggg cttacttgtg aagaaagtta aaaagtttaa atacgattgg    18480
cgcgccgtgc cggatcatat taattggctt gcaacgtatg aaggcgggga aatggcctgg    18540
```

FIG. 16K sequence.txt

| | | | | | |
|---|---|---|---|---|---|
| gggtatgtga | ataaaccata | tagaaaagaa | aacgcgggga | tatggtacga | aacgggcgga | 18600 |
| gagtggcggc | atcgtgtacc | tgttgcccca | tatcgcggcc | attggacgca | atcattagaa | 18660 |
| aaacgaccta | gcaaggccca | gctagtcgag | tgggttttaa | atggggctgt | agtggtttaa | 18720 |
| tattcacgaa | ccctcataga | gtgttttata | acattctgtt | ttacaagcct | cattgcctat | 18780 |
| agtgaggctt | tttttttgctt | tgcggtttga | ttggattttt | aattgttctg | tgaattttgg | 18840 |
| gctaatatta | gaaaaccgca | taggcggcaa | cgattgataa | attagagagt | aaataatggc | 18900 |
| tgaaaatagt | tttattcaac | caattgcaag | aaaggacgcg | attgcccctta | ttggccgtga | 18960 |
| tgagcttgtg | gaaggtgggc | cggaaggggc | agcgaataaa | caagcaattg | cacttgcaaa | 19020 |
| taatattaag | tatttaatgg | gcttaattcc | tgaaaattgg | ggggtggaaa | aaaccgaata | 19080 |
| tggtttagat | gaagttgtaa | ggctttcaaa | tggtgacgtt | gttaaatctg | ttattgatga | 19140 |
| aaatatcaat | aatccgaacg | agaaatttgtc | gggttggtct | tttgttacaa | gtaattcagt | 19200 |
| aaatactatt | tctgatttat | taagtattaa | aaatccgaaa | aatggaatga | aagtttatgt | 19260 |
| tcttggatac | cataaaccgg | ataattttgc | tcttttaagc | ccgtatgaag | ggggcgggct | 19320 |
| tttcatatat | agcgggaata | aggcagcgga | aaatgatggc | ggcgtggttt | taaatggctg | 19380 |
| gattcgtcaa | tatgttggcg | atgtggatat | ttcttggttc | ggagcaaaac | aaggtcaaga | 19440 |
| cgcttcgccg | tttattgaag | cagctttaaa | agtgaaaatg | tcaattgtga | ttcgtggaga | 19500 |
| atacaagtta | gaaacaattt | gcggcatacc | aagacaaaat | aactatgcgg | caaaagttat | 19560 |
| tagaattaag | ggggaaaatc | aggcttcgct | tactgtaaat | tgcccggatg | gtgctgttttt | 19620 |
| tacttcgtta | gatgcaaaag | caaaccctac | aagtttatcc | aatattttta | ccgcaaaaat | 19680 |
| tgacgtattc | gggattaact | ttgtaggtac | aacggttgca | aattctgttc | tgtttaatgg | 19740 |
| tgatcgttta | tacaatatta | atattcatca | caataatttc | aaaacaaata | ttacaattgt | 19800 |
| taaagcgtat | ttaaagcgcg | aggcatcaag | acaatatacg | caaagcgttt | ctattaatca | 19860 |
| taatcactta | gcggaaattc | accgggttat | tgagtcggac | aagtcttata | acttcgattt | 19920 |
| tgcatacaat | atgtgtgaag | cgtgtaaagg | tggcatgtat | atcggtgttg | atgcgcctta | 19980 |
| tgatccttca | ggtatttcta | taacaattca | tcgaaattta | tgggaagcca | gcggggtttt | 20040 |
| attaaaaaca | aatggcggga | ttattgctgg | tagtgtttca | aaaaactatt | ttgaagctaa | 20100 |
| cgtatatcaa | gatgcagcaa | ttgataaatg | cttaatatat | atcaaccgaa | gcggaacggg | 20160 |
| ggcgggttat | tccggtggtt | taacttttga | aaataattta | ttttcaggga | cttcgtcgat | 20220 |
| tccggattat | gttgatgtgc | gcgttttggg | tcaaagtaca | gaaacatcgg | gaaattcaaa | 20280 |
| atctgctact | acgcgaccgc | ctgtatttat | tggtaactgg | tcaaatagtt | acatgctaac | 20340 |
| aaatatggcc | caagctattt | tgatcggtaa | taagtgttct | aaccgcgaaa | aaatgctgaa | 20400 |

FIG. 16L

```
                              sequence.txt
tgcttacagc ccgcaagaag cgcgcgttac ttactattcc ggctattta  ctaagcaatt    20460
ggctaatatt ttaaccgata aaaagttaaa tttattaaag gtgaatactt cagcagttca    20520
tgctattggt tcctctcaag ctaactttaa aactacatta gacgttattg tattctttaa    20580
aacatccggc gcagttggaa cagcaatggc gacttttaaa ttagatttat ttgtttacga    20640
atcagtcgga cttggcgctg gcaatgttcc aaaagcaaac ttaaaagccg tgatgtataa    20700
ttttatgcaa tccaccgcag acgacaaaat tacaccaacg gttaatatgt tttcggctat    20760
ttctgatccg ttaattaatg ttgttgataa ctcagacgga acgtatagca ttgagctttc    20820
gagttttact aataaatcat cgccaaactg ggggtttgtt tctgaattgc atattgaata    20880
cacggcccaa gcgacgctta tagcttcgca tacatccagt tattcagcgg ctaacttatt    20940
aaccatttca taaacttaat taatagctaa ctaaggggga gcgccaattt tgtttttaag    21000
attggcgctt ttttttattgg ggttttatgt ttgatataga tacaaagcaa ttgcacggcc    21060
tggagaggcg tttagagcga ttaaaccgcc gtggcttgcc ttatgccact aggcaaacaa    21120
tgaacgatct agcgtttgaa tctcgcgccg tggcccgtgc cgagttacca acgcgcatgg    21180
ttttaagaaa taaacacgcg attaatagca ttcaagtaac taaagcaaca tcgctaaaca    21240
tttcccagca agccgcgcat gttggatcta cagccgacta tatggcaacg caagaaacgg    21300
gaggcattaa aaccaaacaa ggcggggccg ccgtgtctat tccgaccacg acggcagcag    21360
ggcagggcag aaacgcaaag ccccgaaccc gtttaccacg tgcagcgctc aaaatgggcg    21420
ctattcacct aaagcgtata gcggcaagcc gtaacgctaa gaatcgtaaa caacgcaatg    21480
ccattgctat ggctacatcg gataaatatg tatttctcga tttgggccgc cgtaaaggta    21540
ttttagaaa  ggacaagggg ggaggggtaa caatgttgca tgatcttaca cgcgcatcgg    21600
tgcagatccc taagaatgaa tggctgaagc ccgcgaccga ggcagccgaa cggaagttac    21660
cgggattcta tggccgtgct ttagagttcc aattaaggcg cttttaatta accaaaaact    21720
taacttcggg cggttcgggc gggtagccgc ccgcggttaa gttaaagaat ttttcgcaca    21780
aaaagccacg gttcgcgccg tggtttttat ttgtctttat cattcacgtg atgaatggat    21840
ttatttttaa aatcaatagt ctgaaataaa aaaaggtact gtgccgaccc cccacccct    21900
tgccgttttg attgcgacgc gcgggccgcg cacaaattca gaatttttaa cttgtcttaa    21960
cttcgggcgg gttaaatgtt aaatttcgca tcatggttaa aaagttaatt tctcgcagcg    22020
attttgctgc taaggcgggg gttagcgggg cggcaatcag taaggcatgt aaagggccgt    22080
tattagatgc tgttgagggt aaattcatcg acttaaacca taagtcggct atcgcttact    22140
tagaatcaaa gaaaaacggc aagacaacgc cagcacttga ggggattgat tcgctatatg    22200
aggaagcatt agaagtttgc agagaagcgg gccgatgctc gcaaacattg ttgcgtgaca    22260
aattaatgat aggcagcgac cgggctagaa agttggtcgc tttaattcaa aacgcaaata    22320
```

FIG. 16M sequence.txt

| | | | | | |
|---|---|---|---|---|---|
| tccaagattt | tgaaaaacca | gcagccgaaa | aggtaaaaag | agaggagaaa | gcgcgcccgc | 22380 |
| atacccgcgg | gacggctgca | aaaaaacagc | aagcaattca | agaggacgac | gaagaattat | 22440 |
| ttgagctgtt | agatcggaac | gtagcgcaat | atgcagatat | gacgctaagg | gacattgtta | 22500 |
| ggaaattcgg | gacggcaacg | cgatttgcgg | aatatcttag | agcaatgaaa | gaaatatcaa | 22560 |
| tgattgaaga | tcgggaaatt | aaaatagccc | aaacaagggg | cgagctagtc | catagggatc | 22620 |
| tagttagtca | attgatcatt | gagccgatag | attcggccca | tgtaaaactt | atgcgggacg | 22680 |
| gatctaaaac | aatagccgtg | cgaatggcag | caatgcacgg | cagcggggcg | gacattaacg | 22740 |
| aaatgcagtt | agtcacatca | gaattaattg | caagtttcat | taaacccgta | aaagccaaag | 22800 |
| taaataaaat | cgcaacggaa | ttaaaacgag | gggctgaagc | gtgaatatga | attttatagg | 22860 |
| tatggattgg | ctttgcgata | aagtcgagaa | tctaaccgag | tatattaagc | acgtaacgcc | 22920 |
| cagccaattt | aatgaagaaa | atagatattt | gcccgaatct | gtgaccagta | ttccgggctt | 22980 |
| tatccgttac | gacgtaaacc | cgtttatgcg | tgaaattgtc | gattgctttg | atattaattc | 23040 |
| acctgtccgg | gaagtgaatt | taaaaagggg | cgtacaaatt | acatattcca | cggttttaga | 23100 |
| atccggggct | ttgtactata | tgggccacgt | taaaaccttg | cccattatgt | atatgacggc | 23160 |
| cgacaaggaa | ttagcaaagg | cccgtattga | aaacaacttt | atcccaatgc | tggcacagtc | 23220 |
| ggacatggcc | cacattgtcc | gatcaagcga | cgaaggtaac | agcagaaaaa | cgggtaaaac | 23280 |
| cgataatcat | atccaatttg | agggcggcgg | ctatttggtt | ccattcgggg | ccattaatgc | 23340 |
| aaataaaatg | cgttcgtttt | ctattgctgt | catgctcaag | gatgagattg | acgcgtggcc | 23400 |
| ggatcgcgtc | ggaaaagatg | gcgacccgga | taagttgagt | gatgaccgtt | gtagcgccta | 23460 |
| ttgggaacgt | cgaaagattt | tccgaggttc | cacgccctta | atcaaaggat | cttcaaaaat | 23520 |
| tgaaaagca | tacttgcgcg | gggatcaaag | aaaatatcac | gtactttgta | aaaaatgcag | 23580 |
| tttcccgcag | gaattgcgat | ggagtacgcc | ggacggtgta | ggcggtttta | aatgggacac | 23640 |
| ggacgaggac | ggaattttaa | aacttgattc | ggtgcgctac | tgttgccagc | aatgcgggga | 23700 |
| gccacatttc | gagcatgaca | aagagcgcct | atttagtgag | aaattcgggg | caaaatggat | 23760 |
| accaacggcc | cgccctgttg | agccggggat | tcgttcctat | catttacccg | cgttatattc | 23820 |
| gccgtttggg | atgcaaccgt | ggtacaagtg | cgtgattgct | tatttagacg | cattcgaccc | 23880 |
| ggtagagcgc | aaagtaaaag | acatagagct | ttaccaagta | ttttataaca | acgtattggc | 23940 |
| ggaaccgttc | gagattcaag | gtgctaaggt | tcgctttgaa | acggtttcgc | atcatcgccg | 24000 |
| cacagtgtac | cgattgggcc | atattccgaa | ccgttacgcg | gttcaatatg | ctggatcgcc | 24060 |
| tatcctatt | ctaacctgtc | aagtggacgt | acataaatca | ttcttagccg | tttccgtgat | 24120 |
| gggttgggcc | aaagatgcta | aatgttttgt | tattgattat | ttgcggatcg | agggcgagga | 24180 |

FIG. 16N

```
                                    sequence.txt
cttttccgat agcgcggaac cggggttgggg taaattgcgc gagctaatcg aagaaaagca        24240
atatattgcc gatgacggta aaaaataccg cgttgctttg accttcatag attcgggtta        24300
tgctaacgat accgtcgtta aattttgttc tgaatattcg agttcagtct atccaatttt        24360
gggccgtgac cgaccaagta aaaaccaagc aattaaagaa tttgccgact ttaaaacgca        24420
agaagggaca acgggcttta gaattattgt cgatcattat aaggatcgtt tggccccggt        24480
gttgcgtcgt gaatgggacg agatgggcgg aggtttacag cctgtttatc attttaatgc        24540
gcctgtcgat ttgtctgata agtcattaaa agaattgacc gtagaaacgc gcaaggagaa        24600
aaccgacgca agcggcaata cttcatattt ttggcatcgc cccggcaatg cacgaaatga        24660
gctttgggat ttgctttgct atggacatgc agccgtcgag attttcgcgt ggtcgctatg        24720
cgttaaaaat atggaacaaa aggaagtgga ttgggcttgg ttttgggaat ttttggaaac        24780
agaagccccg tattttgagc aaggcgaacc cgtcgccagt gagtaacaaa aagcccgcta        24840
aattagcggg cttgtttca cgtggaacct tataaaacgg ctataaaatc gaaatgcttt         24900
aggtttaagt gatccggggt aaaccaagtt ttaacccaca taatgcgatt gaaggttagc        24960
aagcggcctt tttgttcagc ctccttaaaa taggcgattc gatccccttt tactgcgacg        25020
atggtcgcgc cttcgggttt atttcccttc agcttttcta aattattttc atattgcatt        25080
ttgttagatc cttaaaaat gtttaaacct tgattattaa aattaggcgt ttggcattgc         25140
ggcatatttt tagcgatgct gttgtaagtg ttttgcgtca tgtaaatttt accgtcaaaa        25200
gcaatcgtgt tttgatcggt gatttgcacc gggtagccgt gttgctggat cgttgcgcca        25260
gcttgtacga tttcgatttt atggccgcgc caattgttaa aagattggtt attcatgagt        25320
ttggttcctt aaattaattt gttgctggta ggttatattt accgtttgtt tgtgggccta        25380
atttaataag attgtgattc tcattaagcc cataaggtaa atgggttcgc gggtttaatt        25440
cggttttatc agtaataaaa atacattcat gcggattcac gttgtaaaga taggcgacca        25500
tgcgcggggc tacataatgg gattgcttat catgttttga gcgaacccag ccgccgaaaa        25560
ctaaatattt tttatctatc attttttgga aacagcctca tttttaagt gttggttaag         25620
cagatcccgg acaagatcgc ccacgtttgg cactgtttca atgtattcga ttaaatgctt        25680
atcgcgttcc ttgagtagag aaaaattttt aattacgcgc ttttctcat aatcgctttt         25740
ttgcttttgc cttgcttcgc tttggcccat tatttacacc gttttacagc ttggttatat        25800
tgatttcttg caatgttgga gagcgttgta gttttggaat tattccgacc cgcttggcgt        25860
gatgaaccaa gcgggctttt ttttacattt cttcagccat aaacacggtt aagaagccac        25920
ccatatcatt ggcaaaaagg ccgatagatt caataatgcg ctttgcttcg tttagatttt        25980
taccttcaac cataagccaa acatcgcgtt tcactttata ttcagggcct agaattttt         26040
taagtggctt ggtcaattcg cgtggtgttt ttacttgagt gtttccgatc attaacattt        26100
```

FIG. 16O sequence.txt

| | | | | | | |
|---|---|---|---|---|---|---|
| tgcaaaactc | ttatttatct | atttgatgtg | tcaattatgt | cgtattacga | caagcaaggc | 26160 |
| aatagggaat | gtataaaaaa | tatatatttt | ttaaaatggt | tccacgtgga | accgtggcgg | 26220 |
| gcgtttatgt | tgcgctttcg | ctttattgat | atactaaaaa | caacatagcg | ggagtattta | 26280 |
| aaaaattgga | tcaagcattt | ttaaaagaaa | ggatcgaagc | gacaaagcgg | caaattgtgg | 26340 |
| cctatgagga | tgcagtaaac | cagctttcaa | gcggtgcggt | tcaatcgtac | tcattaaaca | 26400 |
| cggggcagac | gacgcaaaac | gtgacgcgct | ttgatgttgc | gcgcctaaat | ggggatattg | 26460 |
| acgggcttta | taatcgcttg | gcgacgcttg | aggcgcgttt | aaatggttcg | ggttctactt | 26520 |
| tggttcgtcc | gggatggtaa | tagatgaatt | atgattttag | ccgtgggctg | gtaaaggttc | 26580 |
| cgacggtggg | tttaaaaacc | gagtttaaat | attcaggggc | tacaattgca | ccgccgccaa | 26640 |
| tgcagggcgc | aaaatccgac | gctatcgaaa | taaacgcgct | gggcggtggg | ttcaatcatt | 26700 |
| ccgcttttac | cggggaaaaa | tttataggcg | gtttcgggcc | tacaagttta | tttactatgg | 26760 |
| attattggac | gttacgcaaa | agatccgagc | agctatttag | cgaaaactta | tacgcggccg | 26820 |
| gattaatcga | gcgtttagta | acaaatgaaa | taaacacagg | attaaccccg | gaggcttgtc | 26880 |
| ccgatgaacg | gattttggga | ttaaagccgg | gtgatttaga | agattggacg | gaattagtag | 26940 |
| aaaaccgatt | ttctatttgg | gccaatagtt | cggaatattg | cgacttttac | ggacaaaaca | 27000 |
| gcttagggga | aattcagcgg | atcgcaagac | gcgaagccct | tatttgtggt | gatgtgctgg | 27060 |
| tggtgttacg | ccaaaaccaa | agtaccaaaa | tgccgcaagt | tcagcttgta | agcggatctt | 27120 |
| taatccgaac | cccgccggat | atcccgcgca | aaggccacaa | aattaaacac | ggtgtcgaat | 27180 |
| tagatacgca | aggccgccag | tgtgcttatt | gggttttaca | agacgatgga | acctataagc | 27240 |
| gtttgcccgc | gtttggtgaa | aaatcaaagc | gccgcattgc | gtggatggtg | tacggagcgc | 27300 |
| aaagacgttt | aggcgaattg | cgcggccagc | cgcttttaag | tatcgttttg | cagagcttaa | 27360 |
| aagaaattga | ccgataccgc | gacgcggccc | agcgtaaagc | cgttgtaaat | tctatttgg | 27420 |
| caatgtttat | tgaaaaaacg | caggataaaa | tgtccacgtt | gccaattacc | ggggcgcaa | 27480 |
| tccgacgtga | taaggttacg | gataattcaa | acaccgcggc | cccgcgtagc | tttgaaatag | 27540 |
| cttcgcaagt | tccgggcgtg | gtattgcaag | aattacaagc | gggagaaaag | cccgtaggtt | 27600 |
| tccatagtca | aggcacagat | attaactttc | ccgcgtttga | ggaggccgtg | attagtgcgg | 27660 |
| ttgcttggtg | caagcagatc | ccgccggaga | ttctaaaact | gtcgtttagt | tctaattatt | 27720 |
| cggcaagtca | ggcagccatt | aacgaattta | aaatttattt | aaatatggtc | tggaatgaat | 27780 |
| ggggcgctaa | cttttgccag | ccgatctata | ccgagttttt | aattagtgag | gcgcttttag | 27840 |
| ggaaaattga | cgcgccgggc | ttttggacg | catggcgcga | cccggtaaaa | atggatattt | 27900 |
| ttggggcttg | gttgtggtgc | gactggttcg | gcagtattaa | accgagtaca | gacatgcgta | 27960 |

FIG. 16P sequence.txt

| | | | | | | |
|---|---|---|---|---|---|---|
| aaatggggca | aggcttggcg | cttgccgtgg | aacaaggttg | gacgaccaac | gcccaagcat | 28020 |
| cgcggcaaat | gttcgggact | aagttcacta | aaaacattgc | aagacaacgc | cgcgaacgtg | 28080 |
| aattacaagc | cagcctttta | aggccaatgc | ttgagctgca | aaaagaatac | ggcataagcg | 28140 |
| cggagcattt | agtaaatgta | gcccatgcga | ttggcgggac | aatttcggca | caaactgaag | 28200 |
| aaacagagga | aatttaatgg | attggttttt | aacgcctgaa | gccctaaaag | aaattcagga | 28260 |
| attacacgcc | cgcggcttgg | ttttgaccgc | ggagcaaatg | acggaattta | acgcgcttta | 28320 |
| ttcggatgat | ttccccggat | cgcgtatttt | tcaaaaagtg | gggacggttg | cacaagtaaa | 28380 |
| cattgccgga | gttctaacaa | aggaacctaa | ttggatgtat | cgctattacg | gtggcggtaa | 28440 |
| tacagcatat | agcgaaatta | tttccgcgat | taatgaggcg | gagcgcgacc | cagccattaa | 28500 |
| agaaattatt | ttggcgattg | atagccccgg | cggacaaaca | aacgggcttt | gttcagcgat | 28560 |
| ggacgcaatt | aaaaacacga | aaaaaaccgt | tttggccgtg | gtggaaggtc | aggcagcaag | 28620 |
| cgccgcttat | ggccttgcat | cgcaagcaaa | taagattatt | gccgcggatc | gcggttgcat | 28680 |
| ggtcggaagt | gtaggcgcgg | ccgcttcgat | tgttgttagc | gaaaatgttg | tcgatattgc | 28740 |
| cagtaccaac | gcgccaaaga | aacgcccgga | cgtgaccaca | gacgcgggta | aagcggtaat | 28800 |
| acgtgaaaca | ttagatcaaa | ttgaaagtat | ttttattgct | gatattgccg | ccgggcgcaa | 28860 |
| ggtaacggcc | gataaagtta | aacttgagtt | tggtcagggt | ggtatgtatg | ttgcggccca | 28920 |
| tgcccttgag | cgtggtatga | ttgacgaaat | taaacggct | gattctagcg | ctacaacaaa | 28980 |
| cgcgaaaagt | tcagcaactt | acacagcaag | cgaggaaaat | tcaacaatgg | atgcagcaac | 29040 |
| tttaaaggcg | caattcccag | cagtttacac | agcaatttat | aacgaaggca | aaaccgcaga | 29100 |
| aaatgagcgc | gtatccgcgc | atttaacgct | gggcgaggct | tcaggcgata | tgcaaacggc | 29160 |
| tatttctgca | attaacgacg | gttcagaatt | aaccgcaagc | attcaagcca | agtatatggc | 29220 |
| ggcaaatatg | aagcgcggcc | aagttgctgg | gcgtgaaaca | gacgacacgg | ccgcggctaa | 29280 |
| tgctttggat | ggtgttaaac | cgggcgcgac | tgctacagat | gcgaatgcag | ttacaaacat | 29340 |
| ggttgctaaa | aatttgggcg | ttgcataagc | ccaaaccgta | aagacatttt | agaaataaag | 29400 |
| gggtaacagt | tgcatgatgc | aggtaacgca | gcacacaaac | agttcaatta | attggggtga | 29460 |
| agtagcttgt | caggatgaca | cgctaacttt | aggcgcaaac | gcaacgctaa | aagaaggcac | 29520 |
| aattttagcc | cgtgcagcaa | cgggaaaact | tatcccgttt | gttaagggtg | gcgcagatgg | 29580 |
| ggcgggggtt | cctgttgcta | ttgctatgca | cgaaattaaa | accgtggccg | ctggtgatgt | 29640 |
| ttcagtacgt | gcgggcattt | ccggccaagt | gcgtaaaaat | aacttagtga | tccatgccga | 29700 |
| tggaaacgcg | accaatatcg | acggagcagt | aacagacgct | ttgcgtagtt | atggcattgt | 29760 |
| cgctttcaca | gtaaacagca | caaacaaacc | ggataaccaa | taaggaattt | ttgatttatg | 29820 |
| actactagca | caattgccgg | ggtatataca | caagttgcac | caaagccgct | attttatcg | 29880 |

FIG. 16Q sequence.txt

```
ggctttttca aagcaccgcc acagaatcat tttaatactg aatctgtcga gctggacatt       29940
gagcgcgatt cgcagcaagt ggccgcggtt gttcaatcgc ttggcagcga ctacaacaaa       30000
aacgaaacgg gtgaatttac caataagaaa tttacgccgc cagtttataa agaaggcttt       30060
tcgcttaatg cgttcgattt gcttaaacgt gaagcgggcc aaagcggttt taatacgcct       30120
agcgaacaga tccgcggcaa tttgattacc cgctttatta aggcgcgcg aaaagttgaa        30180
gcaaagattt tacgcggtat tgagttgcaa gcatcgcaaa ttttgcaaac gggtaatttg       30240
ttgctgaagg atcaagaagg caaagacgct tttaaaattg attacaagcc aaaagcaacg       30300
cattttgtga atgttgcgaa tgtttggacg ggtgcgaatg ccgacccgat gaaagatctt       30360
gaatcattgt ccgaagtaat ccaaaccgac ggccttgtaa ttcccgatat tatcattatg        30420
ggcgcttcag cactggcagc ggctaagggt aacgagaagt ttattaaaaa ctttgattct       30480
cgcaatattt cgggcaatgt tttagctgat atgcaaatta cggcccgcgg tggtatctat       30540
caagggacgt tgcgcgtagg taatgccgtt tgtgagcttt acacttatgg cgtgggttat       30600
caggcttcat cttcagcagt tgcaacgccg ttttttaaata ccaataaagt gcttatgctt      30660
agttctgaat cgcaattaga cgcgcttttt ggtgcggttc caaacattgc ggacattttg       30720
ggcgtgagct tgcgcgaaca gcttttaccg gaattgccga cgcgctttga ttcaaacagt       30780
accgatttat ttacaaatgt gtatttgtcg gcaagtggtg agcagcttat gggcggggtt       30840
gctagtcgcc ctattcttgt cccgacggct attgattcat tcggctgttt aactgttgca       30900
taaaaattaa aatgaacccc cttcaatggg ggttttttct tttaaatttg gagatattcg       30960
acgtgactaa aaccgattta attaacgcaa ttaaagccat tgattcaaac gcgaaaacgt       31020
ccggccttga taaagacgaa ttacaagccc ttttaacaga attacaagcc aaagcgac         31078
```

FIG. 17A sequence.txt

<210> 3
<211> 167285
<212> DNA
<213> Unknown

<220>
<223> Description of Unknown: Bacteriophage F488/08

<400> 3

| | | | | | |
|---|---|---|---|---|---:|
| tctgaacgac | ctgccatttt | atccatgtct | ccaccgtcaa | ttattcttgc | ttcttttca | 60 |
| tcttttgcta | cagtgtaagg | atttgctgat | aaagcatatc | taactaataa | accgatagat | 120 |
| ggctgcaaac | tttctgggtc | aactacaact | ttaaatgcac | ctacatgttc | agggtcatct | 180 |
| aagtcaagac | cttctgtata | cggagcatag | aaaattgatc | caacaatttc | tttttcaccg | 240 |
| atattttcta | ctacaccaac | gattacataa | tctaatgggc | tgttagtatc | gcaataaagc | 300 |
| ggtaaaccat | tagctaagaa | cccataggca | ttttgtgaaa | gatatttatc | atcttctggt | 360 |
| ttatgtttta | accaacctga | tgcagcaaga | atcgcagcag | cacgagctga | agcaacacag | 420 |
| aacgttgctg | tataagttga | ttcttttgg | atatgcgaaa | ccatttcaca | taccattcgg | 480 |
| tataatgaac | gaccagcttc | aggtgcagat | gcataactca | aatcgatgaa | tccagtatca | 540 |
| gtaattcctg | taactttata | gcgttttgac | actgtaatca | aagactgcag | aatatcttta | 600 |
| ttgatttcat | ctgccatttc | agttgcaagc | aaatcttcca | agaaattagg | agcatcgaat | 660 |
| ccatttgctt | ctaaatcttg | tgctaattca | actgtgatac | cagttttaag | tttacgagat | 720 |
| ttaactgcgg | tttgccattt | attaatctgg | aatctagcat | ccgcaatttc | actatcagag | 780 |
| ctttcaaatt | tgcttgttga | cgctgcgtca | gaaatagac | gaacctttaa | agaacaatt | 840 |
| gcaatctgaa | gagctaattc | taaatcgctt | tcttcaatat | cagcaaatgg | tgtatcttct | 900 |
| aatactttat | aaacgatatt | attatatttg | aataaatcgc | ccttattgag | agttaattta | 960 |
| gactcttctg | ttaattctgt | gatttgttct | cggtctacat | atccagcttc | gccggcgtaa | 1020 |
| gtagcaccag | ttttaaatgt | aaattcgtta | tccgggttaa | ggtatttgat | accataaaaa | 1080 |
| gcagcaacag | gttgattagt | tctttgcgtt | gctacaatgt | cagaatatat | taatttagtg | 1140 |
| gtagcgcgag | tcaaagcaac | gagatttggg | cgaccgattg | agttgctatt | cgttgtggtt | 1200 |
| gattcgcgca | gaagttcgtt | gattttagcc | attgcgcttt | cctttcagtt | tatatgattt | 1260 |
| atttatacca | taaaaacaac | taaagggacc | cgaaggtccc | ttaaatcgtc | aaagattaga | 1320 |
| tacctttaac | atatacacgg | cggaagtaag | cgttttacc | aaggctattc | agaatagaag | 1380 |

FIG. 17B sequence.txt

```
gcataccgct ctggatgcga gaagccggag cctgagcagc ggattctgca aatgggttga      1440
taccgatacc gtaacgagtt ttgaatccca ttaccggttg gaagttcttc ggatcagaac      1500
cacgcagcgg agtcagagct acatatggag catagtaaat accagcatcc atttcgttcg      1560
gacctttata acctacggtg aaataatcct gtttagcata ctggtcgata tatacacggt      1620
atttaccacc cagaacacca gcaaatactg acttggtagt atcagtgtta aagccagtag      1680
ccagaccttg tgcagcataa gaaatgccgg tatcaactga agccagaacg ttaactacgt      1740
tacgggaagc gataatgaag ttaccttcgc cgcgaccagt ctgacgagca atttcaactg      1800
cttctttgtc aatctggaac aacagagctt taaaggattc acctgcccag cgagcaccac      1860
gaatatcgat tgggtcctgg aagtcaaata caccagcttt agaacccgga gtcagggtca      1920
taccagattt accaacctga gcggagtagt taatccaatc aacaacttcg cggttgattt      1980
ccagcataat ttcggtagcc agaataccag acagttcagc atcagcatcc ataccgtgaa      2040
cagcgcgaag gtcttgtgct aattcaatag agtaagcagc tttcagctga cgagatttag      2100
cttcgataac ttgtttatcg atacggaagc ccatttcatt ccatgggtta tcggtagaac      2160
cgttgaaacc ttcctgaagt tcagcgatag aagtagccat accttcagcg atttctacca      2220
gtacaccagc ttccatttgt ttcttaattt cagcatctaa tttgtctgcg tcagatgcgc      2280
ctgaatcaat ttgtttagct gctgtagctt gcagatatac tgtaccagtt cctggaaga       2340
agtgagtgta aatagttccg acttcaagag tatcacttgc tttcaaagca gcgaatttct      2400
tagcagcacc ctgaccagag aacattgcat ctggaccata cattgggtgg aatgcttctt      2460
tagcgccgga agcgattgga tctttaccat atactgcgcg cagcgcgaat acctggccag      2520
tcgggctgtt cattggctga acaccacaaa tatcgaaagc aatcaggtta ggaatagcac      2580
gacgtaccat acccataaca gctgggccaa tctgagttac tgcgccagaa gtctgacctg      2640
cggcgatgtt ggtagcattg taaccgtggt caccaccgat ttcagcttct gttaagaaag      2700
aaccgaatgc ctgagcaatt ttttcgtctt tatattccgg agctgtctgg aaatcttttt      2760
cctggttttc aaagatttta gcgataatcg cttgtttgct attagcaatt ccggtaaac       2820
cttcaccttc cagtaatggc ttccatttgt tcaaaagttc agctttagtt ttgatagtca      2880
tttgtgttaa cctttaaaat tagaaacgag atgcgacttt cgcatataca cttacaatat      2940
cttctgcacc ttgtgcagat ttatcttcta cagcttcagt gacgaaattc agtccggctg      3000
cttcagtatc aggagtattt atactctcag taatagtgct ttcatcttta ttagatttct      3060
tcaccatttc tacgattgca ctcaatttac ttgagaatgc atctgaataa tccatacctt      3120
cgaccagagc agagactttt tcttttgag actcagtcag atctttagta ctttcgctca       3180
atgccacttc acgctgcaca taattgatat atgcgtcacg cttattgagt tcttcgaaca      3240
gacgagctga ttcttcttta tgttcttgca gttcttcttc catttcagct acaacatcaa      3300
```

FIG. 17C

```
sequence.txt
ctgattcttc tggaacaaca acgttgtgtt caacgaagag ctctttcaat ccaccaagca    3360
tggattcaaa cagttcggct ttgatacctt tatctactgc taatttattt tcagtgagcc    3420
attcttttgc aagatggtca aggaatttag aagcttgctc agcgattttc ttctcagctt    3480
tttcttctgc ttccttcttta ttttttttcta cttcttcttc tgcttttttca gcaattttag    3540
cgatatgaga ttcagctaat ttaacggcgt gctgcttgac ggtagcttcg aatacagtgc    3600
cgaaagtttc ttttgcttcc ggagaaatat taactgattc gaaaatacta tcaagagcaa    3660
cggaagcatc aattttctgc gcttcggcaa tcagttgttc tttaagcatt ttgtagtcct    3720
gttgtttaga taataatatt tataacgctt ttttcatggc ctctgcgaga gccatatagg    3780
cgtcatcggc acttgtatcg gcttccgccg tctgtgattc ggtaatttcc ttaggagtta    3840
cccatgcatc tggagcactt ggaccccata ctgcatcaac acctacagtt aatttgaatc    3900
cttcgtttac gatacgataa cctttatttg tgtcagtcaa tgaacctaat ccacgagaag    3960
aaactcctgg aatccatccg gcacgaatat tagctgctaa tttatctcca ggaccgtggt    4020
caccttcaat aacacgagct cgtccgtata cgtcatttcc tttccaccac atatcttcta    4080
taatgatagc ggcttgcatc gggtcaacat tagcgcgtgg aggatgattt aattctccga    4140
gagcttgttt agttaaaact tgctcattaa tatagtcttt taccgctttt tctaatatac    4200
gttttggata aagacgttta tttctattga cgacttccgc ttgcatgaat attccttcga    4260
tgtataaacc cggttttaaa cctaagtctt ttccatcatg agattcaagc attggtacgc    4320
catcaataat ttcgccaggt tgaccccaag tttcaattag taattggggt tcattcatta    4380
gcttaatcct aatgctttac ggcgtttaag agcttttta cgcttacgct gagcacgaga    4440
ttgacctgct ggattggcaa tcttcgtttt ggtagcttta cgagcaattt gtctacgttt    4500
tgctttagac aacccggtag tttgaaatgc attacgttcg cgggttttgc gatctttagt    4560
gcgagtaatt tcaccacggg cagaaacatg tttaacgata aattcattta acggcatatt    4620
ttcattaata gaagctaatg caaccgctaa atcagtttca tcatcaagca tattctcgac    4680
aattgtattt atatcgtctt tatttaaagc agaagacaat tcgtcaaagc gaccctgtgc    4740
ttcaggaata agtgcttcga cattctcgag aactaattca tgagtttcag ggatcagaag    4800
cattattcat catcctcgtc ttcgtcagag tctttgtctt ttttgtcgtc tttatcatca    4860
ctatcttcgt cttcgtcatc atcctcgtca tcaggttctt caccttcgat taagaaatta    4920
cgagcgatag cgattttttc ttctttaatt aaatcagtcg ttcttgcagc catggcttca    4980
gcaaataatt tacgagcggc tacgaggtcg tttgatttaa tagcttcaat taaaccttcc    5040
attaaaaatc ctcttgttct tggtcggggt cttggaaacg agcctcttta gactcttctt    5100
caatttgctt ggcttcttgt tctatttctt catcagtcat ctgcaaaata tctttcatag    5160
```

FIG. 17D

```
                                  sequence.txt
cagttctgtg agaaatatat ttaccaataa atggttctgc catggttagc atattaattc      5220
ttcgttccaa aatttctgct tctttgagct cagcaaagta gctatcccga tgaaattcta      5280
tcttaatatt atttatttca tcattccact catcttctgt gattatacct ttaagcaaaa      5340
gatttgtttt aagtggatct aggaaaactt cttcaaactt gtgctgtaac tcacgaataa      5400
atttagcaaa cgttaattca tcacgtgtaa tgctagttcc agaatcaaac atcacaccgc      5460
cttgttggtc ttgtggaatg cgtgaaagag gaacacgtaa tgccatgtaa agagcttgtc      5520
taaaccaacg aatatcttcc atattgccag tattatcagc accaggaaga gtatcaactt      5580
ctgtcacagc tttaccatca cggcgctgca accaatagtc ttcggtcata gacatattat      5640
gttgttgatt ttttatttta cctgttgatg catcatatac tacacggttt ttcatcgtgt      5700
tcataacatg ttgcatgtgc tcagcagctt tacgagcagg catattacct gtgtctacat      5760
accaaacacg acggtcagga gcacgagtaa tgcgataaat gactacagca tcttctaata      5820
attttaattg gttagcaggt ttaacagcac gatgtaaata cccgatgata tttttgccac      5880
agcaatcgac taatccagaa tgggcataaa caacagcagc ttttggaatt tttattttg     5940
tgccagcttc atacattcta ccatcacatg catatgactc atgggcagta tcatatataa      6000
aatattcttt gtaacccttta actatttttg tgccagcttc agtttctgtt ataatttcgc      6060
gaacatactg aacttggcga gggtctaatc tacgtaattc ttttatgcct tcttttggac      6120
gttttggatc aatgatttta tgaaagaaaa ttcttgaatc aacataccaa cgtctaaaat      6180
gatcagaacc ttttcgttga aacgatagat gatttaatac atcactaaat tcatctaaca      6240
tcatattttt aattttgga ctaaatttag atttatccaa atttaacgct acgacttcag      6300
tatcatcttc gtagacgata gcatctgaaa cgatttctga aactgcatta tctacttcat      6360
agttattcat gagattacga tatgtatcaa taagctcacg agtagttttc attcctggtt      6420
catatgaacc aaaaattgtt tggaatgcag cattataagg agaagcagct tcattcgagc      6480
ttacttcaaa ttctcttgct ccatcatcaa gctttggggc tgtaatggaa acaagatctt      6540
cttttcttg gtctttaaaa tttcgttcgt ccatttagc ccatggagca aacaaactta      6600
atacattaaa tttcattgta ttctccaaat gggaattata gttatattta taatggactt      6660
ctctgcttta agcaggatgg ggatttctcc ccattcattt tattcccaat aatcgagagc      6720
aagagttact tcaaaggttt ggatttcatt gtttgaatcc caatctaatt gaagttcacc      6780
cacgttagta ggccacagac ctttaatttc aatttctttt gttactgttt tagcatcacg      6840
agcatattga cgaacaatag cgctcttttt atactctgca ggttttccac cagtaatttc      6900
gtttccttga ccagcagcaa tgctttgcca atcaacaaac ttctggcgag catcatgagc      6960
ttcatcgttc attactgtaa cagtccagtc atcgaatgta cgatcgcctg ctacgttaat      7020
tttacggttc ataaatccga ctggaatttt ttctacaata ccagctggta aagcagtggc      7080
```

FIG. 17E sequence.txt

```
tttacattgg aatgtaaaat tttgtccaag ataagaaatt tctacttgga ataagttagg    7140
tcgagcaaaa tcaccagatt caaacgctcg tgttacatca tctacaaaca tattagcctc    7200
tgtagtattt atatccctat gtttaaccta gggcatatag aattaaagaa ttaaggatat    7260
agtgtattta tatggcctgc cgaaacaggc ctttagaatg caccgtatta accagcaaga    7320
ccagttaact catcgaaatc tgcaccagta gcagttgcta cgaagttcaa ggtaatgtag    7380
ttaatgcttc tagccggttg aatgtagaat gttgcaacaa actcatttct atcaattact    7440
gacggagtgt tatttgttgt atcgcaaact acacgatatt cataaattcc accgagagct    7500
ttaattccct gtaagtattg ggcagtttct gtgcggaatg atgaacgagt aaacgcgttg    7560
tttaattcga acaaacgata ttttgaacta cgtccgatat tcgttttcaa catattaaac    7620
agacgacgaa cgttaatacg atcaaatgga gaaggaacag aagtagctgt tttatcacca    7680
tacaatacgt aaccatcgcc acctgtacca gttactggat taatagcttc ttggtataaa    7740
cggtcgcgct gagcttggcg agtttcaata gcaagtttaa taacgttaag aatctggcca    7800
cgattataac cagctggaga catccaagtc tgagatacgt tatcagttct tgcgcataaa    7860
ccagcaatat cagctgctaa tggaacccaa cgattcacat cattatattt gtcatactga    7920
tatttgtagt taccatcaat tgctgcgtag gttgaactga tattaaagtt attatcagtg    7980
tatgaacctg ctgcagttct ccagttaact aaattatcta ctgcacgagt tacaggaatt    8040
ccaactacag tttcacgcgg aggtgagcac aatactaagc aatcttgacg agcatcacca    8100
attgaaacaa catgtttttg gacagtagat gctgtttcaa gagattcacc ggcacaagaa    8160
cccgcaataa acaactgaac gtcaacagat tcgcggtcag caaagaagtc ccaagcttcc    8220
atcaaatctc ctgctgttac ttcagcattt gatgataatc caccagacag agttaaaatt    8280
ccagagaagc cttctggcca gttttgcgca gttgcgaaaa tatattctga accacctttt    8340
gcgaaaaagt catcaatata gatgttacta tcgtaaatat cttttccacc acgcttagtt    8400
gaaagaacaa cgctttgaac aatagcatca tttcgacgaa ctataatagc gtactgtgag    8460
tcagtctgcg gcccatatcc aaatactgcc ttggcagtag atgcacgagt accaccacct    8520
ggataaattg gcagtaatgc agaagcgcct ttcgcatagt cagctttaga tacgatttca    8580
atttcaattt tatcgcctaa ttcgcctgga tagagagcta ctactcctgg aattccatat    8640
tttttcaagat ttgcctgaaa atcaactgct gtcatagcag tttcagcgct ctcgatttca    8700
gctaataaaa taccggaatc agtaataatt tttccaagag ttattactgc agctaaaccg    8760
gaagaagatg aagaaatttc tgcagtccag ttagaaccta atgttgggta ttcgccaact    8820
tctttagctt tagcaataat ttttgcagta ggaatattaa ttttcttaat ttttccatca    8880
gcatctactt cggtaatttt accttctgtt tcaacatctt ctgaaacata tttgaccgtg    8940
```

FIG. 17F sequence.txt

```
attttatctc caaccgcgta gttactacct ggggtagaaa ttgtgtattc aatattacca     9000
gcaatcggag atgagttttt agcggtatct ctatcgacag cgcgcacaac tcgcaaatca     9060
tttccatatt gtaagaaatt cattgcagac ataaaatagt cagcagtttc agctgtaggt     9120
tgaccaaaag tattaactaa atctacttcg tttgtaacct gtttaatctg aaaagcagga     9180
ccccactgga atttaccggc caaagctgct gtaccagtag agttattaac cacggtgctt     9240
tgaaccgtag tttctttgag ctcaatgccc ggagataata aagtcatttt taatcctctt     9300
taatatgctt taatatattt ataccattga cataccatga gatactggaa catactcagc     9360
agaatgaacc gaatcaacaa atataactgg agcgtattca tcccccatat cttgaagctc     9420
ttttgaaaac acttcagatg ctaatcgcat gtcatctttg tcggcataat caataaattt     9480
tgattgtgtt gataaccatc caaaaattac taaagacatt actaaatcgt catgataacc     9540
ttcttcagcc gcccaagaca cgccttttc actaaacgtt ctaaattctt gaatagttgc      9600
acggtgatga ataataagct tatctttttc aataaggtct tttaatgtag agcatcctac     9660
tgctttcgtt cgtttagttt gcttcattcc taaatcagta tatgaatcgc aaataacgcc     9720
ttcgtattct aaatccatgt aaagtgattt cgcaactgac acaccagtac tatttaattc     9780
aatataaact gggcattcat tatattctac taaataacgc ataacgatgt caggcagaat     9840
taaatgagaa atggtatttg aatgtaaaac accaacctgt tcccacacat catcggtaac     9900
atcaataata tgtaaagcgt ggtaatcttg cccacgacct tctgaacagt ctaaagttgc     9960
aatgtatttt ctatctggtt caggtccttt aaatcgatga aaccatgat catctggagt     10020
tacttcaatg aaatccataa cagccaattt cattcctgaa attaatgtac cagaagtccc     10080
ttcaaacgct gcggtatgtt cttgacggaa ttgtgctaaa gtagaaccat taatggtttg     10140
tatgctccat tgccatccat cgtcaaaaat atcttcatca ttataaagac gttctttaac     10200
tgaattccaa atagcagtgt atggttcaaa tcctgattta ccttcaacag cagcagtcca     10260
aatatcataa aaatgattta atccattagg agtcgtagta ataataattt ttgaacgacg     10320
accagatgaa attactggtt gaatagcaag ccaggaatca tggaagtttg gaataaatgc     10380
acattcgtca atataaatca ttgcgaatga gttaccacga actgcgtcag gagaggaagc     10440
ataagcgcca attgaagaac cattatctag ttcaatagac cctttattcc attcaactat     10500
accaggctgt aaaagtcag gaagcagttc aattgcttgc ttagtacggt ctaaaacttc     10560
cgcagacatt gagcctttgt gcgcaagaat acctacagct ttatccttgt taaaacatac     10620
aaagtgtgca agaaaaatag ctactacagt tgtttttacca agctgacgtg atagattaca     10680
aacagtcata cgtttagatg acattatttt gagcatatca cgctgatagt cacgtaattg     10740
aacctttatg acaccatagt cgatatgagt aatggcgcag tatgtttctg caaaatatac     10800
aatatcatct cggcattttt tccattcctc aaccatttca cgagtccatt gtgttttaat     10860
```

FIG. 17G sequence.txt

```
attagctcgt tttaagttag gaagacccat ataccgagat cttttattat tcttatcttt    10920
ataagtttga aataattcag gcttatcaga attatttggg atttttacta ttttgtgtaa    10980
acgaagataa tcactgaatt tttcaggata ccatttcca tcccactgtg attttatcca    11040
atgaattcca tcttcatctt ttctttctgc taagcttggg tgttttatta aaattttcc    11100
agcttcattt aatggatgga aatcatttaa tgcattaatc ggttgttcca tttatcacct    11160
tctcacgagc ttcttgagcc tcgtaagcat caccaatttc gtccattaat tctgttggtg    11220
aacccatgaa tactgtcgcg ttctgaatat tcatttgacc tgtaggaaca gcgcctttag    11280
tgccaacctg ctcagatgta atatctttca tatctttatg aagcttcagt atttctctgt    11340
tcgtcgtagt catttgcccc ataagagttg caaatacttc catgtgacga ggagaatcag    11400
cattctttgc cgtctcaaga aaaatcttgg ctgcgtccat tagcatttgt tgttgaaaat    11460
gcatatttcg acgaactact ccataatcat cttctaagtc aggagtacgg ttttgaggat    11520
tgcttttaac ttctactaat tgtagaggtt catatacttt aatttcctcc ccgtcgattc    11580
cggggaggtc agaaatatct aaaagtttgt ttatatcaag accttccata ataacctcta    11640
tgttcttggg ccaggaggtt ctggcggtgt tggtctattt acattgctag tgaaagtttg    11700
ttttactgtt ccatcccagt cctctgggtt aatatctcga ggaacaactt cgctatcaac    11760
agattcaaaa acaccttcgc catcaggcaa atctcttgta ttggcgtgaa aatctgtata    11820
agtagtacga attaatcctt ctgcatcatc tactggagga tacatccatc cgtttacttc    11880
aaatgttagt gaccattcga ttctacgacg agataaatta tctccatcta tagcttcatc    11940
tatagcagca gacatcagta caattttaat atccctttta aatggaatat catttccaaa    12000
ctgttcgtac atagttgtat taaaatgagg ttgaaaatat ggaagaatct gttcaactat    12060
ttgaaacata tcgtcttcgt aacgagtaaa gatactcaat tcataaatca ttttaatagg    12120
agatggatta tactgcgata ctacagaagt tgtacctttt tgcagtaaat tctgatttaa    12180
aatgtttgtt ttaaatggag cgttatagct aaaatcaact aaatgcaaat ttatacgagg    12240
tagaatagtt tcaaccttgg ccacatcttc ttgtgaattt atcgatgtcc atttattcaa    12300
tttcatcata aagtgttcct ttgatgcata cgtaatagga acacgtataa acttatcacc    12360
agattctaac tgacgtttga tttggatatt tgaaaacaaa tcgcccatca aggtagcata    12420
tcgtctaaaa gacgaattat aaaaataacc aaacatgatt tctcctaatc tgggctttaa    12480
ttagtttata atatttatta atccatgaaa tcattatcaa atgggctaga ttcaaaagat    12540
ttgcctctgt tattgacaac aacataaggt tcaacatatt ctttagcttc agaattaatt    12600
tgatctactt cagcatattg atcaatatta atatcatgaa taccgttaag attgcgaaca    12660
ggatttagtt ctaattcact aaattctgga atgttaattc cttcattttt ctgtagaact    12720
```

FIG. 17H sequence.txt

```
ggattaattt cttctccaga ataaatgaat ttacctgctg taattttacg aatagcgttt    12780
tgacctaatt gataaaatgg atcatatggt tcaacccagt taatttcaaa taagctgtta    12840
tccataggaa aatatatcaa atcgccttct ttcggttctt ttccattaac ttggtgttta    12900
aacaagtttg gattaatgga caaagtaact tcatcctgta cttgcatacc aaagttacta    12960
aagaacgatt tagctccttc atatccttca aatgaattta aatatgcagc gaatttccaa    13020
gctttagtaa atttatttt taagtcttcg ccaaatatca aatcagggga aacatactct    13080
cttggaacat aatagcattc tacacctcgc atttgaatgc tttcagctac taatacatca    13140
gctaatattt gactgttttt ataatgattg aaatttacat aaggatttag tatttcagtt    13200
tcattggtct gagaataacc agtgcggttt tccaatttag caaaaagatt tttatcataa    13260
gtagccatat taacctacca aaattccaaa tggaggatcg agcaagtata attcttcacg    13320
taatgcttct ttttctaatc gagcttcttc tattaagcgt tgtccatcaa tcgtaacacc    13380
gccaggaagc atcatacctt ggtggcgtgc taaaatttga ccattcaatt ctttagctaa    13440
agcagtagca tagtctttca cccaacgatt attataagca ccctgtttaa catttgggtc    13500
ttgaccaaca acacgaccaa ctaaattgtg gtctgggtta ttatatcgtt cagataatga    13560
ccagctatct tgtggaccga ctgttccata tcctactgta tttccaacca tttattagt    13620
atcaatgtat gatttagtcc agctttctac gataattaaa tcatattttt ggaagtttcc    13680
catgactttg agctgttcat ttgctgaatt aaaccaaaag tctggaatag gagagagcat    13740
atcttgcatc attcccatgt aactggtaag ctgggtaaaa tatcctaaat cagctccaaa    13800
ggcatttggt ccataaaatc tattacaaga agtccccata ccgccattaa taccagccat    13860
tcctaaaaga aaatcagtaa accatggata tgtagcgttt ccgtccattg acgttattga    13920
tccaatattt gttcgcaaaa tgcgagttac tgcgaataca tttgaacctc ttaaatcgaa    13980
gactccagtt ttatatttt cttcgtcatc tcctacataa aatacatgaa aacctttgtt    14040
aagtccatca aaatggtatt caccgtataa ttctagggca cgctggatac aatcataaat    14100
ttgatcgggt gttaactcaa cattaataat tggagccccct aaacgtctta gaatgacatc    14160
tttgagttcc tttggattct gagaattata tcctgacatt taaaatcctt tggggccttg    14220
cggccccatg ttatgctggt gataaaaagg tagaaagtag tacccattcg ccgtctttac    14280
gaacgtaagc ttggccatct tttggagctt caggaatata acccgcttct tgtagagctt    14340
gaacgctgct ctgtaaagag gatatattgt cttagctgt atttacttca tgcgtgactg     14400
ccgcaatgtt agtttcattc gtttttatag aattagttaa tcctcgttct tcaacagttg    14460
atccgtcagg attatttcca tttataagtg aagtaagttc aataacttga ccttttaattc   14520
ctgttctatt atttcctatt tcaacttgta tattttgaac attattgttt aaaactgaaa    14580
cttctccttc aagcactgaa actttatta atagagatcc agaaggagac ggttgtcctc    14640
```

FIG. 17I sequence.txt

| | | | | | |
|---|---|---|---|---|---|
| cgctggagtc | agttccaaca | atttgattta | accacgaaac | attcgctctt | aaaccagacg | 14700 |
| aagtgttttc | accaacaatt | ccgtttaaag | actcaataga | agttgtgtga | tttttaattt | 14760 |
| ttcctttaat | actagaagga | atatcatctg | aacctataga | agtttcaata | gccgttaagc | 14820 |
| gctgtttaac | accttcactc | tgatttaatt | cattattaat | agattcaatg | ctactttgt | 14880 |
| tattattaat | ttctgttatt | atagaaacat | tttctgggta | tccaatagaa | gatttaattt | 14940 |
| ctgctatatc | agaatttatt | aaagtttgtt | tatcatctat | agtgtttaat | ctattataaa | 15000 |
| tatttggtcc | aaaatctact | ggtttattac | caagttcatc | gcgtaattta | ccaacttcaa | 15060 |
| ccgtcaatga | tcctacgtca | gattcagtaa | atttattttc | taattcactt | aaacgaatgc | 15120 |
| cttgtgaaga | taataatgta | ctatttgtta | ttattctatg | tttcattcct | gtgctagcat | 15180 |
| taccaacaac | aggaagaccg | ttaatgtctt | ggccagaata | ttgccctagt | tcttgtttaa | 15240 |
| tccacaataa | atcatttcta | attgttctat | aaacagagtt | ttcttcatca | ttaaatggac | 15300 |
| ctatatcagc | aataattttg | tcaactgtat | tattagttcc | agttaatata | tcagtgtgtt | 15360 |
| cattagtaag | tgtcttaaa | tttgatatgt | cattttatt | aacactgatc | tgcgatagtg | 15420 |
| cttctatatc | tcctgataca | tctaaaactc | cttgaattgt | tttaatatct | ttctgcgatg | 15480 |
| tttcaatggc | agttttaaga | attcctatat | tttcgtcaag | aacctcaaca | tttttaaaca | 15540 |
| cggaaacaat | tggtctattc | attgatccat | cgtttccata | cttagtgcta | gctcctagta | 15600 |
| tttcttcacc | attttaatc | catgaaatac | gttcctgacc | ttcatcagga | acgctatcaa | 15660 |
| caaaaggtaa | atcttttaat | tcaatcattt | gtaatcctta | gtaatgaact | ttaataatat | 15720 |
| agtttaatga | tatattccat | ggtctagttt | cataaccaat | taatccttca | cgattaagtg | 15780 |
| taccaagggc | atctctcggt | ccgcctaatt | caaatccatc | attagtgaag | tatgaagcat | 15840 |
| tatcccagtc | ggcatatttt | ctagttccaa | gatatccttg | ataaacagac | gcgccaaatg | 15900 |
| ggccttcact | tctgttatat | tccccccaac | caccggcgtg | tttatggtat | gacatttgtt | 15960 |
| gtgcttgaac | accaccaaca | tgcattccgt | cacatcctac | gccaagtcta | tcctttccat | 16020 |
| aaccatcttg | tcctcgttga | tttaaaatat | gaccgcctgt | gccagctcct | ctgacgaaaa | 16080 |
| gaccccgcat | atcaggaacg | ccaggattat | tccaatcgcc | accaaatctt | gttccaacta | 16140 |
| cgtttctata | atcaggaaat | tggtcacctg | acacggttcc | accatgacac | ataatccaac | 16200 |
| ctggaggtgc | tgaatcaccc | gcaaacatca | taatagttcc | aaccggaact | cgttcggacg | 16260 |
| catatctttc | agtggcaaca | ggttgatcgc | cattttccca | cattccaccg | cgtgaccaaa | 16320 |
| ttccatttgc | tgtaagatgg | tctaaattta | aagaaccatt | aatagtttgt | ccaccacgcg | 16380 |
| tattaattac | atctgcgttc | cacgctaatg | ctccagaact | atcaccttca | ggggcaatac | 16440 |
| cggcttgcgt | cgttaattta | actactccac | gcatagaacc | agtagctcct | cgaccattta | 16500 |

FIG. 17J

```
                                    sequence.txt
gtgtttcacc tgttactgca acatctccta aattactgtt aatttccgat tgtgttccta    16560
aacgtataac acccttatat tcttgtgttg caacagaatt cataaaggta tacggagaaa    16620
ttgcatatcc ttcgcggaga gttccttgac gagtttgcgc aacagttgat aattgaacca    16680
cacctctcac agattctgat gcagtatctt cggaaggagc tatttgtgaa attaatttta    16740
ttgcgagttt ttgggttttt agcggagtca tcgccgtagt atcatcaaca ccagccaaag    16800
ccgcaggcgt agatgatatt ttaataaccc cgtttgatga ctcagatgaa tatctatttc    16860
ggaacacatc atcagtatgg tatttcagtt tttgcggcgt tattgatgaa ttattatctg    16920
agccttctaa tgtttcttca tttgttgaat agcgcgttaa accatattta gtttcagtag    16980
catttggata caataatctt gttgctaatg tagctggtgt aacgatttta gaattatttg    17040
ttccatctaa aacctcttgc tctgatgcaa tcattgctat tcctttaact tccatagttg    17100
catcaggaat accatttacg ccgatattac ttattttga taatgcagac tgtactgtcg    17160
taacagtgcc aggaaaattc gatcctactg gatcgaattt aacatatttt gattcatttg    17220
atacgtgctg atatgtattg ttactcatgc tattctctca aaataataaa atactgtagg    17280
ttgtgtgtga ctatctagcg taacagtttg cgcacctaat aattgccaag ttccataccc    17340
gggtttagaa ggagaaatta tttcttgttt gaaagtaatt cctttatcag agtattgttc    17400
taagatatgt tcttggttat ctaaatactt aacttgtatt ttattcccta tggtaggatg    17460
gtcttcaaat gaatcaattg caataaattt tacaaccatt tcctgtagag ctgttctaac    17520
agcactagta aattcaattg aagtcattcc attagtagct ttaactggaa taccaaacat    17580
gttaacaata actgggtcac ctggtttggc tgaagtatca gtaacagttc cttcaaatga    17640
ccaatagtcg gtttgttgca cgccagtagg agatacgccg cttatattaa ttaatacagc    17700
tccaacctgt tgctctgcca tatttctaac atcattgata gcagattcta catttgagtc    17760
ataaaaacct tttgctattt gtgaaattgt tacagcgcct accggctgat tattcataac    17820
cgaaatatca tttttcttag ttctaaaacc aagaaaatct gctaagcggg aaataactcc    17880
cgctttatta ttaagtaaac tcattatgca atccttatcc aacggtatac agtaatagac    17940
ggttgaatat tactaatatt agtaggagga gtatgtgaag agtttgttgt tgcgtagtct    18000
tcacgatatt ttgtatatat aggaccagtt tcgtctgggt catattgaca tcctccaata    18060
ataactgatc cattttcgtc ttcaattaaa actctttcat cagttttagt cgcaggaaga    18120
tttgcgtttt caagcgttac tgatgttgta ccaactgttc caccggcagt atgtgaagga    18180
tttccgctag aatctaaatc attattgttt aaagcaaagt ttggatccgt aacatcatca    18240
ttccatccta ctaaaacttg tcctttacca ataatttcc atgaaccaaa tcccatataa     18300
gtcaccggat tatttgggtt tatagcattt tcataaattg aaccaacagg ataaatgctg    18360
tcgaaaatag atgatattga attatacgtt ctagtataag aatcaacttt ttcaacattt    18420
```

FIG. 17K sequence.txt

```
ggccaaccga ttttatcaaa atctgttaag gctacatccc cagtaacttc agtagatgat   18480
cctttactaa cataacggtc atcagttaat tcaataatgt catcttttc taaaagagtt    18540
cctaaatcat tattaaacca tgttataacg attatatcac ctgattcaaa ttttctatca   18600
aataaaagac tgacaggttt tccatcttca tattctatag aataatctgt gtttgattct   18660
ttccattcgc caccaagaga tatacatcct tcttgcgtat ctgaattagc gccttcgcac   18720
aaaaacagag gatacccagc tgttccagcc tgttgctgta aaattccatt aaaacgaacc   18780
tcaagagaat taggattaat gggttcgcca ggaattaatc caaaagctga aatggaatt    18840
gatttcatcg ccgataaatc agtaacataa atgcttcctt ctaaagaagt ctttgatgtt   18900
agttttgaat ctagcacttt tatttggcgt cttgtatatg aacttctcca ttgtgataca   18960
ccatccataa acgtttcaat ttgaacagtg tcgccaatat tacaaggctg tcttaaccta   19020
atattaaatc catcaagagg aattaattct ccttcatttt cccccggaga gccaaagtca   19080
ctgttttcac taaatacatc gccgtaatat aattcgttac cgcggtgttt tactctgatg   19140
ttattgacat tataactagt tccatggaaa acatctaaaa agtcagtttg tccttgaact   19200
tctactaaaa attctttgcg agctacatta ctaatatctg aactaataat tttatcaatt   19260
tgtttgtttt tgacatattc ccaacgtcct ggagcacaat aaactaactc taaatcgcta   19320
aattgaacat taatttcaac tgatgacgat gatcctttaa tagtatcacc agaagcggct   19380
actagagtaa ctggattaac attccatgtt gcaaatacat ccctagcttt aattacttta   19440
ttataatcat taacggttcc tttaggaagt tgtagagtta ctcttccaga tgaagtgtta   19500
atagcatatg attttcccca ttctgctgtt aatgtttgtc ctgatgaagc attataagtt   19560
ttccaggcac cggctgaata tggaacatct ccatccaccaa gctcgtaata aagctcatca   19620
aagttttcat ttattttat accacctta cgcaggtagt caccggtacc atcatctaca    19680
acattaccga tattaatatt ttgtttcatt attgagccac cccgattttc tgcgtagcga   19740
taactttaac tgctgctctc ataccgacag ttgaagaact tatagtcgct gttacataat   19800
ttgttttaat actaaatgca atattagcga tttcgtcttc ttcagtttca ttcccaactc   19860
gcatgacagc atattcagaa gaatgacttt ctgaattaac agcatctaca agaatattta   19920
tttctgccgt tttaatttt cttccatcta ccgattggca cgtaactaac aatttagcca    19980
tattgtattc agtgcgatga aatagtggaa tatcaactga tccggatgta gaaatattcc   20040
atgtaccttc agctggtgat tccttttgtc caaacatact ttcaatagaa taattccaaa   20100
ccgatgtaga attatcagat gaaatacagc gtaaagttac tttactatat gggctagtta   20160
ctactaaatt acctgaaaca cctttaattg aatcaatagc ttgaattgtt aaaggattag   20220
taactgatat tgatccatta gagttaatga attcaacaca atcgccgagt tcgcctcttt   20280
```

FIG. 17L

```
                                     sequence.txt
caataataac tttaacacct acagtagagg tatcaatatc atgtctagtg ccaactttca    20340
ctggagttgc gtactctgta atagagtgtt tttgataata cccagtagca tggataattt    20400
gaccatctgc tccagtgcca tttgctactg ccattttacg ctgatcgcca aacgcattat    20460
aaattgcgtt aaaatcacta ttaattttat taccaccgtc gaataagata tcaccagtag    20520
aagcgttacc aatttcgccg gtatcaatca atttctttgg ttcttgaatg aacatagcgg    20580
tttccttatg agtttatagt atttataaag aaaaagggag cccatgggct cccttaattt    20640
aaaatgtaaa cagaatattg atttcttctg tttgatccat tgccataata ataggtggcc    20700
tattttccat ataaatcatt tcgcccgaat gcctcattaa atcttctggg tcataataat    20760
ccttttcagc tttaacgttt gggtcatttg gatgagcttt agcttcaaga ggattcgtga    20820
ttattgatat ttgtctaaat cctttatttc ctggcaatgc agcatcagga aaataaactg    20880
aatctaaata tgctttaaaa cggatagtat ttgccttaac ccggtaaatt aatccaaaat    20940
catcttgttg ccaagtgaga ttatcttcat atccccatct agtcgggtct tcttttaatt    21000
cctcaggcca aggaaccaca atatattcat tcgtgcatct atttatagat acatcgggtg    21060
gaatctcaaa aagatattcc catacatacc cgtccccagg ttcaattgtt ccttcagcat    21120
ctcctcgacc ttcaggagga gtcattgacc taacagaagg tgtccatttt ccgcctaatt    21180
taaggcattc atccttatca gttaaagatg caattgaaca cattccagta tcaggaacat    21240
ctaaacaacg atatactaac cagcctgcgc ctgattcagt agcgttgtaa ggagctgagt    21300
tacacactac aatatcgtta attctaaatg tgtatggatc cggatatcta gtatctcccc    21360
aatctcgacg aggaataact gcgtcaagca ttgatggaag aacctttact gttcccatca    21420
tatgcgtcca catgtcagtt acgcctaata cagaatcggt tggataaggt ggggcaaagc    21480
ccacctcatt ttcatttgat gaccacggtt ctgatcttcc aaatgtgata aagatagtgt    21540
ttttatccgg accacttcca attgaattat aaaaattcaa catttttct gttctaaatt     21600
ttgaagtaac tatcgcacga tagataacac ttgaatcatt catctatttt aacctgtgtt    21660
ggattttcag ggtctcttgg atttcctata ttatctttta gacgtttatt aactaaatct    21720
ctaaattgcg caaatgttgt tccagatgca tcaaataaag gactcattaa tttacgtcgt    21780
tcagacggca attgaccttg aaatattgaa ttattatttt cagcattata gtcatcagga    21840
agaggatatt ctacaccagc cattgggcca ggctcataaa ttgcttcgcc tgttactgaa    21900
tcatgctcaa tttcaccggt tggagttaat ttagctactc tatcagcata ttcagtaggc    21960
aatccagaat cccatttata gttttatat ttattaatta ttgtctctgt gtgtttaaga     22020
gttaaaccaa cattaataaa catcgttaaa agggtaattg ctataaatcc aaatcctact    22080
ggatgaacaa aacgaataac gtcagatttc cagcgggaag aaggtaaatt ggatttaatt    22140
ttcattacat agtatgatct acttctatta atatagtcta tattgttttg aagcaaatcc    22200
```

FIG. 17M sequence.txt

| | | | | | | |
|---|---|---|---|---|---|---|
| tttcctttaa | ctccacgaat | aatttcgcct | tcaaaactag | ggagtctttc | tgctttaact | 22260 |
| tcttgaccag | caattaatct | tcccaaaaga | ttatgaatag | ttacggtcca | ttgcaattta | 22320 |
| ccattagaat | aacttctttc | tatataagta | acattacatc | ttcctgttgc | cgtataaatc | 22380 |
| gtttgtccta | ctaaatcttc | agtcaaagaa | tcagattgaa | cgattatgtc | atattcagta | 22440 |
| ccggccccag | attcaatttc | aatttcaact | tcttcattat | aaagaacttt | aaaaagaaac | 22500 |
| ttgtatgatg | cttcaattcc | tttagtagaa | taaaaatcat | agctacgtga | ttcaaagaat | 22560 |
| ctcgcaacag | catcacgttt | atcagcattt | aaataaatgt | ttcttttata | tatctctgac | 22620 |
| cacaaatatt | cccacgcatg | ctcttctcgt | ggatattggt | tacgaattaa | atttcgtaaa | 22680 |
| ttgttatact | gagttccata | tccatcagaa | agatactgaa | tatatgcttc | gcaaaatgcc | 22740 |
| tcaaaattcg | aatcctgcaa | caaataagaa | tcaggcatca | ttgtgccaat | taatggtctt | 22800 |
| aaatcaggat | cagctaatcc | atgctcttct | tctggtgacc | aaggagtctc | atgctcttgg | 22860 |
| ttttgtaaaa | atgcttttaa | aaatactcca | gtcggcttcc | aaataatttc | tactgtatct | 22920 |
| ctcacacgat | agttaaaatc | atagtaagaa | attatttcac | cagaagattt | ataaaaaagc | 22980 |
| atcccagacg | catatttttt | aaatcccgtg | aatttaacat | ttggcattac | tatcgtacaa | 23040 |
| tcaccatcat | cccagtattc | atgaactaat | ctatctggtg | atgtttccgg | aatatttttct | 23100 |
| ataactttag | tgtatttttaa | atcagcataa | actactacag | ctctattaga | gttgtttatc | 23160 |
| caacagcgtg | tgttagattt | tttagaccaa | ttaaagaacg | gttctgcgta | gtatttcatt | 23220 |
| ggttgaggag | taaaagtctc | ccaatcagat | ttttcatccg | ctataaatgc | catcatatga | 23280 |
| taatgcttat | cagctaacca | ttcacgggga | aattcatatt | taacagcacc | gattaactga | 23340 |
| tatttcacca | tagtttcagg | gtcattaaca | acattatcac | ttaaaaattt | aaaattactc | 23400 |
| gaagacagag | aaactaattt | accgtcagtt | gacatgtttg | cgtatccagg | ttgaatacgt | 23460 |
| cttctttctt | cttcggtatt | accgaaaact | cttttccatg | tttttttcgtc | atgatttaaa | 23520 |
| acatatattc | ctttatcagc | agaatcaatt | attttttgaag | ttctcggatt | ggcatttaat | 23580 |
| gtttcaactt | caccaataat | aagagcaaaa | actttatcac | cgatagaatc | cattttatag | 23640 |
| catactgctt | taggatttcc | agttatagtc | attgtatcag | gttcaaaaag | tcttttccgag | 23700 |
| tatgttggtg | ataacgggtc | agaatctata | ggtgcattac | tcgttttttat | atatctaact | 23760 |
| ttatctctgg | caacaacata | gatataatca | tccgtacaag | taatggcttc | agctatacga | 23820 |
| tatacattcg | ctggtaaagt | cgcataagta | ccaaagattt | ctacatcaaa | tcctaaatgt | 23880 |
| aactggtcgc | caagtttagc | aaatgttata | tcctgcgaac | tgaatctgac | atcatctgct | 23940 |
| gaccatctaa | cgtcagtcga | tttacggcca | tagaaaatct | tgtcgtatcc | tagaacgtat | 24000 |
| gttgtgttcg | cagattggta | atatactgtc | ttagataaag | gatatcctac | acggtcattg | 24060 |

FIG. 17N

```
                                   sequence.txt
aagagcttca cagctttcca ggtttgtcct ttatcattag atactttaac cacgggttga    24120
taacgctcaa aaagatatag aatcccttct gattccatca aataaactcg gttaatatcc    24180
ttacatactt gctgaatgga accttgtatt tcatgatact cattttcacc aataataaaa    24240
ttactgattg atgaaacatc aacatatgat gggctgaatt ggaacgattc attcatcaat    24300
gcagccatta tagtgtcatt attaaaattg acataattag aattgttaag agtaaatttt    24360
tcctgaatga atttattggc taattgcatt tcaatcatgt tttgaaatgt gtaagcattc    24420
gtagcaaaag tttcaaactc ttccgtataa acccaatcag attgctcaaa atcttgtgca    24480
gctgtagcta ctctaatgat gtatgatgtt agtggatcag catcatcaaa aaagaaacta    24540
ttgtttgctg tatatcctaa attaatccaa cgatattgat cactcgggag attttccccc    24600
gagtctgttt tgtctcagc gatttctaca aaatagtaga aattagcacc aacgtcatcc     24660
cagcgtactt gcacctgatt tgcggataac ttggaaattc tgagactagt gactgaaggt    24720
gcttttactg tcattgtgat ataggctcca aatcgatagt taagtattgc ggacgtaaat    24780
cattttcaaa tacaatcagt gaaccatcac gggtaaagat aacatcatcg gttgggtcag    24840
aatataattc aatagtctga acctcaaatt tttcagatgt taaattaatt ttagcgatat    24900
tccaataaat catgtcagcc ggataattta tttcaccgat aacatagtat ttgtcgcgtc    24960
catcagaatt tgctaattta ttaaaatcat tgcctgtata tggctgaatg ttttcatttt    25020
ctgtaacatc gccagaagca aatggaccaa taataacttt accaattcct ttagaatctc    25080
ggtctgttga tactatacga acatcatata atacatcttc ttctaaacca gtatcaggat    25140
ttacaacctt tcgtccagaa ttaaatgaaa acgtattaga ttccatagaa cgatcttta    25200
tttgattatt gtatttaata cctgcttcag gtgttttata gaagttttgt acttcacgaa    25260
ccatttgaat agtcgctgat gaaccaatga cagaatgatc tgcatcatct acataagtta    25320
acatcttaga tttagcgaaa gacgagttaa aaatttctac atcttcggta taatagcgat    25380
caattttatc aattatttga ccttcaagcc actgctcgga ttcttgtagt ttatttaaag    25440
catatgtgac ttttaaatta gtcttaataa aaagataatt aggagaaata attgatggcg    25500
taataggagc taaattatag tctttgagat aattttttaat atcttcacgc tgtacagtag    25560
ttaaatacag acctgattta ggtttagcag caataaatgc atacccaggt ttagtagaat    25620
cagtgaaagt ctgaactgcc tgaataatag aaccaaatct ctctgaaacg aatgtatcgt    25680
agtcagtcgc agttacgcat cgttgctggg tttcgcgttt aatagtaccc aattcgcgaa    25740
tacgctcaat atcttctgga tcaccgcctc catctgcccc aacaaaatct gggtcaccgt    25800
ttggattttc attaatattg atgatagtta tatttgttaa tgtatctgcg tatgaaaatc    25860
cgactgctcc gttcgcgtca gcaccattag tactaatgta ctcaataaca atcgtagagt    25920
tctgagtagg tttgagacct ccgatataat tagcggtcaa agctccttca gaagcattaa    25980
```

FIG. 170 sequence.txt

| | | | | | |
|---|---|---|---|---|---|
| cagaaatttc | accttcacca | aaatagaatt | cagtgtttcc | atcaatagtt | tcacgcatgt | 26040 |
| agtaaattgt | tgatgtagaa | ccagcatgaa | ccattgactt | tcttgtccag | ttaatccatt | 26100 |
| ccgctccatc | aacgtataat | ttaacctggt | ttctatcaat | attttatca | taaatgataa | 26160 |
| taggtgtcaa | tttatcataa | atgatttcag | ttcttactat | acgtccttgg | gccaatttta | 26220 |
| atcgtggaaa | atattggtta | tttttatcac | gaatagcaat | aacatcttcg | gtagatacaa | 26280 |
| agttatatgg | attaacagaa | gtatcttttg | catatgctaa | aaagcgagtt | ccgcgaggaa | 26340 |
| ttgtaatgta | attcctattc | aatgcgtcgg | tgcatgttaa | cataatttcg | gtctgcgcag | 26400 |
| cggattttga | agtaggtaaa | tatccgttat | cttgtgcagc | ttgaacaact | gaacttcgta | 26460 |
| agttagcagt | acgcataaag | ctttcataca | cagcagcatt | accaaactgc | tgaatgtaca | 26520 |
| atgtattata | agccaaaagg | tcacacagaa | cgtttaatct | tgagccttca | aaatcataat | 26580 |
| ccaaaaattc | attttggcca | ttaagccatt | caatgaggtt | ttgttttatt | tcagcaaacg | 26640 |
| taccccgac | gaatatctcg | ggaatagcat | ttgctgttct | tgttaattga | taatttacag | 26700 |
| gggtatttgc | cattttaaat | cctatttaat | gaatacttta | gatgatgcct | gagccacagt | 26760 |
| atcaccgcat | gatattggat | cagccatttg | aacagctttc | tttccagtga | catatacctt | 26820 |
| agaagttctg | ggttgtgtca | ctccgccatg | tgtttcatat | ggcttttaa | tttctgtatg | 26880 |
| ttctgtaatt | ggatcacctg | ctacgagaac | agcaattcct | ccagtgaata | ctttactttg | 26940 |
| tgtggcattc | acaactgttg | gaggccatgc | ttcatggcca | gcagtaacac | acttatcata | 27000 |
| acttaatcct | gacatctatg | acctctcata | cacatagctt | cttaatttat | tagcccaacg | 27060 |
| actccaattt | ccaactatag | tttttgtgta | attttaact | agagtttttc | ttactggagc | 27120 |
| aggaggatcc | gtcggttcag | tagtatcaga | ggatgaccta | gaattactgc | cagaacctcc | 27180 |
| agattcactt | tgttcttggt | agtcatatat | taatgttact | tcgtaagtga | atgtcttctg | 27240 |
| gaggttttga | ggagctttcc | ataaatacaa | ctgagtatca | gaatcagtag | gaagttcttc | 27300 |
| ccatgaagca | gcagttttaa | attcatcgcc | taaacgatat | ttcaacgcgt | catttccaaa | 27360 |
| tccaaacaca | gattcatatg | ttccgtataa | gcgattttct | tctactaaaa | ccccaggagt | 27420 |
| ttcttcgtaa | ctagttatat | ttatagatac | taacgtttca | cctgtttcta | attgagcggt | 27480 |
| aaaggtgacg | tcgatagaag | aaccttccat | ggattctcct | aaatcagcgc | tcattggaag | 27540 |
| tatattagcc | aatgtcaatc | ctcgatccat | caattgtgta | ttgaccagat | gaaatagaac | 27600 |
| tcatagatgc | catttttct | gtccaatcac | caccaacgtc | ccaatcaact | gtcccagcaa | 27660 |
| ctttccaaga | aagatttcca | tttactgtgt | tagtttgatt | tccttcaact | aaagtggtag | 27720 |
| catctccttt | aactgtaatg | tcagcattac | cttcaactac | aatagtaaca | ttacctttaa | 27780 |
| ctaggatagt | tccattgcct | tcaactgtct | tagtttcatc | gccacgtaca | aatattgtat | 27840 |

FIG. 17P sequence.txt

```
tgcttccatc tatttggtga agacgattat ccatgttgta ataaatttct gatccaccga    27900
cgttagtctt tttatcaccg gctaccaaaa aattaccatc agcgttggtt atatcataca    27960
aattatcgac agttttcttt gttcttcttc ctgacggtga tacttcttca taagttccag    28020
tcggatgaac taatctgtat cgttcttgcc caggagtatc atcaaattcc tgaatatgtc    28080
cgctttcagt ttccattgta tgcacataag gatattcacc tttatatgaa gaaactggtt    28140
ctttgaataa aattctcgag tcatttggaa taggagggtc agccgggtca gaagatttag    28200
ctacagtagc agccattgct gatagagacc tagctggggt tttcacttca acaccatatg    28260
attccaaatt ccccgtaaga ataatcatgg taacacggga tgcacggcct tttgtttgtt    28320
gataccacaa tgaatcacga ccggctttat atgcttttc ccaatctccg gctaacatag    28380
cagttaacat tgtgttaaat ttagctacac cgccaacacc catttgaaat gccatatttt    28440
ctaacgccat ttgacgagaa cggttgacag cttgccagac tggtcctact ttagaatgtg    28500
atttaatgtc ccgttgcata tcagccaaat cacgttcaaa taaagtcgtc gcctcttcca    28560
tcgtaataga acctgggttt ccagtaattt cacgaccaac ttgttttgat aaaactttat    28620
taatttgagc catatcacga actggctgct tcatgataag atgaccaata ccaattgtcg    28680
gatatccttc agtatcccaa taaacttta gtcttaatcc ttcatcacgg cgaagcatgt    28740
cagccattga catatttgga ttatcatcgg ttggaatctc tgatagtggt ctatcatcgg    28800
gatttattgc agtgtctaag ttactatctt ggataatgtt agaagacgaa tcatatccta    28860
cttctccgcc ttggtttaat acattagtat catttcctaa acgtctagga tattgcccag    28920
ttgggtcaga aaatccttca agtctattcg gttttcgcg aactattcca ccatacgtgc    28980
caaggacaat tccgttagtt ttccatttgt ctaaaaaatg accataaact ctagttcctt    29040
ctaccggtcc agtaacagaa cctccaattc cagacattgc tgcagaagtt ataggttgaa    29100
taactgacat ccatggtaat ttttcagttg gaatacccat tacatcgcct tgtgctcttt    29160
gaggtggatg cagaccaacc acacgaacac gaacacgacc taattttaat gggtccattc    29220
tatcttcaac aacaccaaca aaccaattaa ggttattact tatcatttcc ataagatttc    29280
tccattatac gtataaggtc gttcataaat gaattaatgt ctgattttgc tattattttt    29340
atttgacgaa gttttcatt ttcaagaaca gcatcttcat acgtattaac agcagcaagt    29400
gctccttcat attgaggata ttttctagct ttatcacctt tatcatacca aacatatgga    29460
ttatcatcgt atgatattaa attataaaat ttttcaccgt tctcattcac atgatatact    29520
atttggtctc cacctacatt tttgtatttt tgtatagatg cttgataagc tgcttcttgt    29580
gaagtaatcc atccataata cgggtcataa ttatcattac acatcaataa aacccaatac    29640
aactgtggat ttccatatat agtatttgct aattcttccg ggcgtggtga acctttgata    29700
taataagtac gtaagcggta tcccgcaaga gcgcgtttaa aatagtcttt atagtttcta    29760
```

FIG. 17Q

```
sequence.txt
aaaatatctg tcataggaat agtcggcgcg tttttattca ccgttttggc cgcatattca    29820
atcggatcaa aaaatgtaaa gagcatgggc cctcctgttt ataaatatat tatctattta    29880
taaggagaat ccaatggcat attctggaaa atgggttcct aaaaatatat caaagtatag    29940
aggtgaccct aaaaaaatta cgtatagatc aaattgggaa aaattctttt ttgaatggtt    30000
agataaaaat ccagaaatta ttgcatgggg tagtgaaaca gcagtaattc cttattttg     30060
taatgcagaa gggaaaaaac gtagatactt catggatatt tggatgaaag attcttctgg    30120
acaagaattt tttattgaaa taaaacctaa aaaagaaaca caaccaccag ttaaaccagc    30180
acatctaaca actgcagcga agaaaagatt tatgaatgaa atttatacat attccgttaa    30240
tactgacaaa tggaaagcag ctcaagcttt agctgaaaag cgtggaataa aatttagaat    30300
tttaacagaa gatggattac gagctcttgg ctttaagggg gcataatggc tatttttcaa    30360
ataattaatg aaagcactcc ccaagttcca aaggttaagc aatcattaaa cgaaaagaaa    30420
tggattcaga taggtcttga atataaaaag gccaaagcaa aaggaatgac cggaaagcaa    30480
tttgctgaag aaagaggaat caaatactct acgtttactt cagcaatgtc aaaatatgct    30540
tcaggaatta aaacggctga aaagattcaa aagcttgaat caaaaccaat gaataaactc    30600
aataagcaag aaagacaact gcttatgata aattcattca gacaaacatt gcgcgataaa    30660
attcgtaatg aaggcgcagc aattaataat aaaaccagaa agtggtttgc tgaaactatt    30720
aagcaagtaa aaggacataa agttgttcgc ccgcagccgg gacgaatata tgcttttgct    30780
tatgatgcta aacacaagga aactcttcct tactgggata aatttccttt gataaattac    30840
cttggtttag gtaagcataa tttaatgtac ggattgaact tgcactatat tccacctaaa    30900
gctcgtcaac agtttctaga agagcttta aagcaatatg caaatacacc tactattact    30960
aataaaacga aattaaaaat tgattggagt caagtgaaag gatttagggg tgcagaccaa    31020
atgattaagg catatatacc tggtaatatt atgggtagcc ttgttgaaat cgccccgaaa    31080
gactgggcga acgttgtgtt aatgccactt cagcagttcg tttcaaaagg aaaacgtttc    31140
tctgcaaaca aagtctggtc aaatatctaa ttctattatc ttccattctt ttctgttgtt    31200
tgttctaaat ggaattgaat ggaagggact tagacccatt ataccaccaa cagttataaa    31260
gcattatgag gaatatatgt cgcaagcact gcaacaaatt tttaaccaag caaatacaac    31320
taactttgta gtatcaatac cacatagtaa tactacatct gcttttactt taaatgctca    31380
gtcagttcct attccaggaa ttagaatacc tgttactgat accgtgactg ggccgtttgg    31440
actgggccga gcacaacgtc caggtgctac atttgagtac gatccactca tcgtgagatt    31500
tatagttgat gaagaactta agtcatggat aggaatgtat gaatggatgc taggaactag    31560
caactatctt acaggtgaaa atactgccca aaaacaggt cctgaataca ttacgcttta    31620
```

FIG. 17R

```
                              sequence.txt
cattttagat aatagcaaaa ctgaaatcgt gatgtcaata aatttttata agccttgggt    31680
ttctgacctg tctgaagtag aatttagcta cacagaagat tcagacccgg ctttagtatg    31740
tacagcaacg attccttata cgtattttca agtagaaaaa gatggaaaaa ttatagcgga    31800
agtttaatgc ttcagtttca tgtgttataa tcttaactaa atttgaggag aaacatatga    31860
aactaatctt tttaagcggt gtaaagcgta gtggaaaaga tactactgct gattttatca    31920
tgagcaatta ttctgcagtt aaataccaac ttgctggtcc tattaaggat gcattggctt    31980
atgcatgggg agtatttgca gcaaataccg actatccttg cttaactcgt aaagagtttg    32040
aaggaattga ctatgatcgt gagactaatt taaatctaac taaattagaa gtaatcacga    32100
ttatggaaca agcattttgc tatcttaatg gtaaaagccc aattaaaggt gtgtttgttt    32160
ttgatgacga aggacaagaa tcagttaatt ccgtagcatt taacaagatt attgacgtta    32220
taaataatat tgaagatcaa tggtcagtcc gtcgtctgat gcaagcccta ggtacggatt    32280
tgattgttaa taacttcgac cgcatgtact gggtaaaatt atttgcttta gattatcttg    32340
ataaatttaa ctcaggttat gattattata tcgttcctga tacccgtcaa gatcatgaaa    32400
tggatgcggc tagggcgatg ggtgctacag taattcatgt agttcgtcct ggtcaaaaat    32460
ccaatgatac acatattaca gaagctggat tgccaattcg tgatggcgat ttagtaatta    32520
caaacgatgg ttctcttgaa gaacttttt ctaaaattaa aaatacacta aaggtactat    32580
aatgtctgaa caaactattg aacaaaaact gtctgctgaa atcgtaactc tgaaatctcg    32640
tattcttgat acgcaggacc aagcggctcg tctgatggaa gaatccaaaa ttctgcaagg    32700
aactttggct gaaattgctc atgcagtagg tatcactggc gatactatta agttgaaga    32760
aatcgttgaa gctgtcaaga atcttactgc tgaatctgca gatgaagaat gatggaattt    32820
aaagactttt caacgggtct ttatgtagca gctaagtttt cagaattaac acttgacgcg    32880
ctggaagaac tccagcgctc tttacgtgtt cctaatccag ttcctagaga aaaaattcat    32940
tcgactatat gttattcaag agtaaatgtt ccatatgttc catcgagtgg aagttttgaa    33000
gtagcttctt ctggacattt agaagtgtgg aaaacacaag atggatcgac tcttgtactt    33060
gtgctagatt ctgaatatct gcgctgtcga cacatgtatg cgcgggcact aggtgctaca    33120
cacgattttg atgattacac accgcatata acattgtctt ataatgttgg gcccttatca    33180
tttagcggtg atgtacaaat tccggttgta cttgaccgtg aatacaaaga gcctcttaaa    33240
ctcgattggg cagatgattt aaaataattt cacaagttg tttacatact gatgaggtag    33300
tgatactatt acctcatcaa aattaattag gaaaataaaa atgaaaactt caaagagtt    33360
tgctacaaaa actactatca ctgaatcttc ccacggtatg gaagtaaagc ttggaatggc    33420
tttagctgaa gctgagcgtc ttttctctcg tattaaagaa cttgctgctg cggtcgatcc    33480
ttcatctttt aaaggagacc aaactaaagt taaagcactt ttagcattat gctccgatgc    33540
```

FIG. 17S sequence.txt

```
aggagaaatt gctaaaaatg gttctaagat gaagaaacga ttagaagatt taaaataatt    33600
tcacaaagtt gtttacatag ggttttagtt gtgatactat taccctatca aaacaaaacc    33660
aaatggaaat caaaatgaaa acttaccaag aatttattgc tgaaactgct gatgtaaaag    33720
ttgagtttat ttacactggc aagaaagata aaatgggtga aatgcctcat ggagttcttc    33780
gtgatgcatt agataatttc ggtcaactcg ccgcagaaga ttacggtgat aaaattgttg    33840
ttactggtcc tgctgcagtt attgaaaaat gggcagcaga aaataaatca attttcgta     33900
aaaaataagt ttacttttag atagggtagt gatactatta ccctatctac tactgaggag    33960
aataaaatga aacgttgtga attaattcga aatgttgcta ttgcaatttc tgcttccgct    34020
ttcagttttt caatgtttgt tggatttata tgcggattat tgactacggc agaaaatgtt    34080
ttttcacttg tagtagcatt tttaattggt ttaattgcta ttgttatgga taaaatttct    34140
aaaggtgaat aatgaacgtt gaatattatg tatatgcgga ttacgaaaat aatccgtcta    34200
aagatgaaga taatcgttta ggtgtagatg ctttcgattc ccctgcggcg gcatggcaat    34260
gggttgaaag aaccgatatt ccttaccgtt atattgaagt ggttgaccac gcaggaaaca    34320
agtatcctaa ggaagcatat gttgcttccg ggaaggtaaa tttcctttg tttgcaggtg     34380
ataattatta tccccgtggt gggtataccg atttaattgc taaagcattc tctgaagatg    34440
aactccgtga cattatcaaa gaaatgaaa acaaaccgat ggattctaat cgctttgatt     34500
ggtggcaaat cgtaaatgct aatactcaca ctattgttga tgaaggctga taatgattct    34560
ttatgcgaaa gtatcatcca ttgaaaatgg atataaatat gatcaagacg cggctaaagc    34620
tttgattgat gattatggca ttttaacatg ttttgaagtt gaaaaggttt acattgaccg    34680
ttcatcttct caagttaaat tagtgaagga agaacgtaaa tttaatacag taaattttga    34740
tttctttatt gaaacagaaa aaggtcctct tgaatatgat attttcaaga atcctttggg    34800
tcttgaatgc atcgtaaata tgtattatta taatggtaa atatgcttta agaattattt     34860
gttattatta actcatatcg cactgattaa taccctctat catcaagggt tcttgcttaa    34920
gagcctttgt taataattgg gaattagcca agttggtaag gcactggatt ttgattccag    34980
gatgcaaagg ttcgagtcct ttattcccag cgcgagaatg gccaaattgg taaaggcaca    35040
gcacttaaaa tgctgcggaa tgatttcctt gtgggttcga gtcccacttc tcgcaccaaa    35100
tttgcggata tcgtataatg gtattacctc agacttccaa tctgatgatg tgagttcgat    35160
tctcattatc cgctccaatt taatttactc cgtgtagctc agtttggtag agcgtctgct    35220
ttgggagcag aatgtcgtag gttcaaatcc tgccacggag actggaggcg tggcagagtg    35280
gtttaatgca ccggtcttga aaaccggcag tcgctccggc gactcatagg ttcaaatcct    35340
atcgcctccg ccagttttgc tgatttagct cagtaggtag agcaactcac ttgtaatgag    35400
```

FIG. 17T

```
                                sequence.txt
aaggtcggcg gttcgattcc gtcaatcagc accaaggccc tgtagctgga aggttcaagc       35460
aagcgactca taatcgccag atggtggttc aattccaccc agggccacca aattaatttg       35520
gggagttatc ccgtagaggt agcggtgtgg actgtaaatc cattgtcatt gcgactcggg       35580
tggttcgact ccaccactcc ccaccaattt ggatgtgtag ctcaatggca gagcgatcgc       35640
ctgttaagcg attggttata ggttcgaatc ctatcacgtc cgccaaattt gtgacaactg       35700
tcacattaat atctacttga cgcgattata ggggttgaac tgatcactct tctcttaatt       35760
tcgtgtgaag acatcttgat tgttggagta ggtattaatg tggccgtagt tcagttggta       35820
gaactcgaga ttgtgattct cgtagtcatg ggttcgactc ccatcggtca ccccaattac       35880
ggggcatagc tcagaaggaa gagcaaggac cttctaagtc ctaggtcgta ggttcgatcc       35940
ctactgcctc gaccaattat aagtgaggaa aatatgaaag gtaatgttta tttagtagtt       36000
catgatttaa cattctattt taatcataat gatactgtta tttctgaacg tgtaattaat       36060
ttgctttatc agcatgcaga ttatgtttat gtcgaaaacg aatatggtca ttggcaattt       36120
ctcaaaaatc gttcatttgg tttagatggt tacgaatatt tgatcgtaa agacctttta       36180
gatacaattc cgttatctac acaatatcaa aatcataagt ctttacataa atgccggcta       36240
attcgaaatg ctgaatccgc gtatgaagca attgatttgt ggcgtaaacg ccgtgaatat       36300
attgattctt taaaagaata ttaagaaacc gggtcgctac cggtaagtcg tcggactgat       36360
gttccctgga gtatagtttc ctcccacagt tttactgtgt tctggctctt tactatcaca       36420
gcagaaacgg cgcaccgaat tatcgattcg aggaaatatc tttgccgtaa gccgagtagc       36480
gttttttgacg gaacgttcgg atatggtcga gatatggcct tttaaaaata ttgagtagcg       36540
tcaactactt aataaccggg ttcgaatccc ggcgtttcgt acaaacactt gccttagcag       36600
gtggaacccc gacaaggttg ccgcaaggct tagccccgac cgaaaggttg gggcttttttg     36660
gtataaatat tagtatatta aatctacaaa ttaaaacagg aaataagatg aaatcatata       36720
ctcaattttt aaatgaagcg gtgttaaatg aagcatctag caccgaaatt caagctgttg       36780
caaaagctgc cattgccgcg ggtaaatatt cctataaaga tgcttctgat gaatcgcgat       36840
tccagtttgc acgcgacatg aaagcggaag gatttacggg aaatgcagtt agtatggcct       36900
ggaaaagttt agttgctact ggcgctgctt ttgcaaaggc ttcgggtaaa cctgctccta       36960
aagcagatcc taaagcggca caagaaaaaa atatcgttaa aggaattatc gctaaatatg       37020
aagctatcct taaagagctt ttagtaatca aaccgaagg ccaaaagtta gcccgtgctt        37080
atagtttcaa agataatcca catgttcact ctcttgagta tgttgaagac atccaaaaaa       37140
ttattaaaga ccgcatttgg tctgctaaac aaatcaaatg acattcttag ccccgaccga       37200
aaggttgggg cttttttagtt tgaatcactc ggataacgct gttacggata gtaacaaagt       37260
aataaataat taataaccaa ccgataaatt atttcaagga ttttaaatga aacctatgc       37320
```

FIG. 17U sequence.txt

| | | | | | |
|---|---|---|---|---|---|
| cgaattttta | accgaagcag | caaaattacc | atctgaagca | gatcttacta | aagtattctt | 37380
| ccaattggac | ccaaaagacc | gcggcgattt | tcttaagtgg | aaagctaaag | ctattgaaat | 37440
| gtacaacatc | gataatagtt | cttttacaat | gagtcaagaa | aataaattca | ataaagcatt | 37500
| tttcaaaatt | tctaagaaat | tggcatctgg | cgctcaggtt | cctaaatctg | tgttagctac | 37560
| tcctgaacgc | gcacctgtta | aaatttctaa | gaatatgttc | gacactaaaa | aatacgttaa | 37620
| tgctttgaat | aaagctcttg | atgcattgga | tgatgcaaag | aaggcagccc | gcgatcttca | 37680
| agacgtgtac | accgattttg | accgcaaaac | taaaggttct | atttcaaata | gcgaacgcaa | 37740
| tagtgtaagt | gtttattctg | atagccttga | tgttcttggc | gatgcgtata | ctgaaattaa | 37800
| aaatcgtatt | aacactgcat | ctaagctaaa | agctgctgca | gaagctataa | taagtaaact | 37860
| aggtaaataa | ttttaaatcc | ctatctaaat | gatagggctt | tttggtatct | aggcctttct | 37920
| ggacctctct | aggcatcatt | tagtttatac | cctttataat | atattatcct | atcctttaat | 37980
| tgcccatccc | tgccctagaa | ttccctaaaa | atttttcac | aaaactgttt | acatctctgt | 38040
| tcttccatgg | tactatacaa | ctatcaacta | ctgatacaga | aaacaacttg | gagaatgaaa | 38100
| tggataatta | cggcgaactg | ttcaacttct | ttatgaaatg | cgtttcagaa | gatttcggtc | 38160
| gtacagtgaa | tgatattaaa | gttatcggtc | ctgatcatcc | gatgtttgaa | acttacgcag | 38220
| taatgggtaa | tgaagacggt | cagtggtata | ctgtaaaagt | tgtgattaat | atgttcacag | 38280
| cagaaggtta | tgttaaactg | tcttctaaag | tttaccatga | taacgacgaa | atcgcggaag | 38340
| aatatttcaa | taatatgaaa | taagtttacg | caggctcatg | attgagatat | tatgagccta | 38400
| taatttgacg | atagagtatt | atactcctac | ggatttaaa | tctcaattaa | cctaaggaaa | 38460
| tactatgaac | acactgaaga | aaattgttga | gtttattcgc | actaaacttg | gttctgctat | 38520
| ggctaaaaat | ctatctgtcg | aagaacagta | tactgctgca | gcagcaaaac | tacttgataa | 38580
| aattaaagat | ctaaaaactg | cttctgttaa | atctattaac | gaagaaaaac | gtattcgtga | 38640
| acttgttatc | gaaaagaatc | gacaggccga | atcaaaagag | cgtgaaattc | gtaaacttct | 38700
| ttccgaaggc | caagatgtaa | caatgcatgc | taaactcggt | ttactatatc | gtcgaacagc | 38760
| tgagcagttg | actactaagg | ctgacggtta | tgctgaaatg | cgaattgaaa | tcgccaagaa | 38820
| agtagttgag | ttagatgatg | ctcgtcaaga | acttgcggtt | aaattggaat | atatccgtga | 38880
| aactcgtgca | gcaaatgccc | ttggaattag | tactgctgat | gatgtagttg | aaattgcagc | 38940
| actgactaag | gttgatattg | aagataccct | tgctcgagtt | gaaacctta | acggtaatat | 39000
| ttctggggtt | gaaactacct | ctgccgatgt | tcaggaatac | attaattctc | tgaaataatg | 39060
| ataaggggct | tcggccccctt | atacttggag | taaataggaa | tgaaaatgaa | aatgcaaagt | 39120
| gatttcaatt | caatgtttga | agagttccaa | agacaggttg | atgttccaga | ccaattacta | 39180

FIG. 17V

```
                              sequence.txt
aatgctctta aacgcatggc agaaggacgt aattactatt gggggtcttc atatgaaact   39240
gatgaaagcc tttccggaag attttctaga ggtaaaaagt ctttaatacg tcctggaata   39300
ctcattaaca gtattgaatc aattcattca ttgacgtgtg attttgatgt tgaatttact   39360
gatttcattt ctcctgaatg gacggtttgt tatttaaacg acgattttga ttatctcggt   39420
gtttatagtt taagtgacgc atggtttaaa cgtaatttac aaaagtcaaa tttattttat   39480
attgatacta ctgtaaaatt tcagggcaag aaatatttct ttactcttat agttgattct   39540
gaaacgaagc atgaaaataa acgtattctt agtaaaaaga atatcttaac tattgttgat   39600
gatcttttg ataaatttgt agaaaatccc aattttgaaa gtgatttatt actagaaaaa   39660
tttgttaagg aatgtagaga atatgtcaaa accatcacta taccttccaa gtaaacctgt   39720
gaagtatgaa ccaaagcgtc agataatttc tactgatgtg ttaataggtc ctgttatact   39780
catatcattt gtaattctat tgattattgg aggtgtttta gatgttatga ctgatattga   39840
ttctggcgaa atacttgtgt taatgctaat tcttccatta atagttccac ttttattagt   39900
acccgtaaat tgggtaggat actggtatca aggaagacat tatcgtaaac gtgtacgtga   39960
ttggaaagct cagtgtaaaa agattaaaaa ggaacaccag cttaagctag atatgtatga   40020
atttgatgaa attatgaaat tgttaagga atcacgatgc aaaagccaaa actaaataaa   40080
gtcaaatatt cgtttcctga ggcactatta attcttgctg tatcagtatt tacagctctt   40140
gcgggtagtc ttattggatt gttaattgac tgttttattt taaatatcga cggcacagta   40200
attataacag aggtttggag tgaacttcgt tttactatag cgatttcatt attttcattc   40260
tttggtacca tgttatattt tcattatgat aattttaaaa taaattggca agaaaaaaag   40320
gattacaaaa tacaattaaa ggaatataat agctatatgt cttatattga aaaagaatca   40380
atggaagagt ttgtgagtga ttgtaggaaa attaaatgat tttaaaaact cgctggtatg   40440
atttagatga tggggacgat ggcatttcag ttgatagagt tgactggagc ggctgttctg   40500
aagatacaaa gaaacgatta attagggagt ttagaatggg atatcaagca gttaagccat   40560
ctactgtaac agatgataaa ttcgtgtgta ttcataatgg tcgtgctaag ttaacgaatg   40620
ctgaatggtt cacagataag attatgattc tgtggtatat cattagtctt cctgtgtcat   40680
cattcgtatt ttacttttt ataaaaatc caatggacag aataggagat tggattcttt   40740
taaccatact tgttaatatt tttacagcat caatattatc tgggatatgg tacacgttca   40800
ttgaaatgcc atggcggcta cgcagacaac aaaagatttt tgatgaaaag aaatatactc   40860
aaaatttaaa taactttatc actgaatgca ggaaattaaa atgaaaacat tatcagctgg   40920
tattatcttc atgacagaag ataagatttt atttatgggt cgggttactg ttctcgtaa   40980
gcctggaatg atggcacatc gctgggatat tccaaaggga cgtgtagaaa gttctgatt   41040
gaatgcactg gaagctgcaa aaagagaatg cttagaagag accggtttta gcaattataa   41100
```

FIG. 17W

```
sequence.txt
tccagacctt ctagaagacc taggtgtatt taaatattct agtaataaag acttacagtt    41160
attttattat acgattccag tagagcatga gatgtttaga aattgccatt gcgagtctta    41220
ttttgaaaat aaagatggcg ttatgattcc agagatggat gcttttgctc ttattcctcg    41280
tactcagtgg caatatgtga tgggtccttc actttaccga ataatgaaca gcctctttta    41340
atttataaat accttctata aatacttagg aggtattatg aatatatttg aaatgttacg    41400
tatagatgaa ggtcttagac tcaaaatcta taaagacaca gaaggctatt acactattgg    41460
catcggtcat ttgcttacta aaagtccatc actaagtgtt gctaaatctg aattagataa    41520
agctattggg cgtaattgta atggtgtaat tacaaaagat gaggccgaaa aactctttaa    41580
tcaggatgtt gatgctgctg ttcgcggaat tctgagaaat gctaaattaa accagtttta    41640
tgattctctt gatgctgttc gccgctgtgc attgattaac atggtcttcc aaatggggga    41700
aaccggcgta gcaggattta ctaattcttt acgcatgctc cagcaaaaac gctgggatga    41760
agcagcagtt aacttagcta aaagtagatg gtataatcaa acacctaatc gcgcaaaacg    41820
agtcattgca acgtttagaa ctggcacttg ggacgcgtat aaaaatctat aaagttgttt    41880
actttctcct agaattgtga tagtatattc acagttactt ggagggataa aatgactcgt    41940
attaatttga ctttagtatc tgaacttgct gatcaacatt taatcgcaga ataccgtgaa    42000
ttgccgcgtg tttttggtat agttcgtaag catgtggcaa acggtaagcg cgttaaagat    42060
tttaaaatat cttctaaatt tattttaggt tctggtcatg ttactttctt ttacgataag    42120
ttagaatttt tgcgaaagcg tcaatcggac attataacgg aatgcttaaa acgcgggttc    42180
agtataaaag atactgaagt tcctgacatc agcgatattc cagtagaatg gaaaaatgat    42240
tataatccat gcaaatcagc tattaagttg agtcaacaac gactcgatga aaaaatttta    42300
atgaagccac actggtataa gtattacggc aaaaatattt acatttaaat aacatgggaa    42360
taacctggac ctcatgattc tgtgagggat tcccgccaac ctgtaataag gtcgagccca    42420
agtgcggtaa tgggtaaata cagaaatgga caattcatgc gccatggaat ggcccaaacc    42480
tagagagaac aaaatgagaa cattttaac tggtccttat ctatccctga tgaatgcttt    42540
tacacaccat tctgatgcta gagtagaaga aatttgtaaa acgaatata  tcccgccatt    42600
tgaagactta cttaaacagt attgtacact tcgactagat ggtgggcgtc aatctggtaa    42660
atcaactgca gtaactaatt ttgccgctaa ttggttgtat gacggtggaa cagttattgt    42720
tctttctaat acttcagctt acgctaaaat ttccgcagat aatattaaaa aggaattttc    42780
gcgttattct aatgatgata tacgttttcg tttatttact gattctgtgc gcagttttat    42840
tggtaataaa ggaagcaagt tcagaggttt atcgctttcg cgaattttgt atataattga    42900
tgagcctgtc aaatctcctg atatggataa gatttatagt gtccatattg acactgtaca    42960
```

FIG. 17X

```
                                     sequence.txt
ctgctgctgt aatattaaat gttgcattgg tggtattact cgtccacagt tttcgtaat      43020
cggaatgcaa tgatgacaga cactcagctt ttcgaatatc tttattttc gccaaaaact      43080
attaaaaata aattggtgaa tcattttgaa attttggcaa aaaataacat tttgagcgaa      43140
ttttatccca agcaatacaa attacaaaaa ggcgtattca aaggatgcag agttttgtgc      43200
acggctccta atgcacggct aatgaataaa attccatatt ttaccatgga atttattgat      43260
gggccttta aaggactaat cacacagagt ttaatggcat atgattctga gccatttta      43320
attaaagaac aatcttggat aaatttattt tttaattgag gttatatgaa agcatatcaa      43380
attcttgaag gcacacataa aggtactatt tattttgaag atggtattca agcacgaatt      43440
attgtctcta aaacctttaa agaggactct tttgtagacc cagaaatttt ctatggtttg      43500
catgcccgtg aaattgaaat tgagcaacag cctacagtta aaattgaagg tggtcaacac      43560
ctgaacgtta acgttctgcg tcgtgaaact ctggaagatg cagttaagca tccggaaaaa      43620
tatccgcagc tgaccatccg tgtatccggt tatgcagttc gctttaactc tctgactccg      43680
gaacagcagc gcgacgttat cgctcgtacc ttcaccgaga gtttgtaatg caaagataa      43740
ttattgaagg ttctgaagat gtgctaaatg ctttcgccga gtggtttagt aattcaggcg      43800
aacagcaatt taacgaagca tggaacatgg gtgatattaa tggaattat cctacgacag      43860
aaatttctgt tcaaggatat ggcattcatg aacctattcg tttagttgaa tatgatttgg      43920
gaacaggtga ggaagtaaaa tatgattgaa gacattaaag gttataaacc acatactgac      43980
gataaaatca gtaaagtgaa tgctatcaaa gatgctgaag ttcgtttagg gcttatcttt      44040
gatgctttat atgatgaatt ctgggaagca tttgatagct gtgaagatga tgaactcgcg      44100
aagaattacg ccgaaagcct cgatcagtta actattgcta aaatgaaact caaagaagcc      44160
agtatgtggg cttgtcgcgc agtgttccaa ccagaggaaa aatactaatg gctcaattaa      44220
gcgcagggtt tggttatgag tattatactg cccctcgtcg tgtatctgtt gctcctaaga      44280
aaattcaaag tcttgatgac ttccaggaag tagttcgtaa cgcttttccag gactatgcac      44340
gttatcttaa agaagattca caggactgtc tcgaagaaga tgaaattgct tactatgagc      44400
agcgtcttga acagctcaaa aatctacatg aggttcgtgc agaagtttca agtctatga      44460
ataaattgat tagatttaaa gaataactgt ttactttcc tcttgactgt ggtataattt      44520
ttctatcagt taagaggaga ataacatgac tatcaataca gaagtttta tccgtcgaaa      44580
taagcttcgt cgtcactttg agtcggagtt tcgtcaaatt aacaatgaga ttcgtgaggc      44640
atcaaaagca gcaggagtct catcgtttca tctaaaatat tctcaacatc ttcttgatcg      44700
tgcaattcaa cgggagattg atgagacata tgttttgaa ttattccata aaataaaaga      44760
ccatgtttta gaagttaatg aattcctgag tatgcctccg cgtcctgaca ttgacgagga      44820
ttttattgat ggggttgaat atcgtcctgg acgtttagaa atcacagatg gaaatctttg      44880
```

FIG. 17Y sequence.txt

| | | | | | | |
|---|---|---|---|---|---|---|
| gcttggattt | acagtttgta | aacctaacgc | gaagttcaaa | gacccgtcac | ttcaatgtag | 44940 |
| gatggcaatt | atcaacagtc | gtcgtttacc | aggaaaggct | tctaaagcag | taattaaaac | 45000 |
| tcaatgaggt | aagcatgaga | aaagcactac | tcgctggtct | attggccatt | tcaatgatgg | 45060 |
| cacatagctc | cgagcatact | ttcagtaatg | tccaactcga | taacatgcgt | tacgcgtatc | 45120 |
| aattcgggga | acaattttct | aaggatggaa | aatataaaac | acacaaaaac | atccataaga | 45180 |
| gcggattggg | tcatataatg | gctgctattt | tgtggcaaga | aagctctgcc | ggagttaatt | 45240 |
| taaaatctaa | accaaagcat | catgcctatg | gaatgttcca | aaattatttg | cctactatgc | 45300 |
| gagcgagagt | caaggaactt | ggttataata | tgaccgatgc | tgaaataaaa | agaatgttga | 45360 |
| ataaacggtc | caattcagct | tcctgggcgt | acattgaact | ttcttattgg | ttaaatatac | 45420 |
| ataagggtga | tataagaaaa | gcaatatcat | cttataattc | gggatggaat | gttaaagcag | 45480 |
| gttctaaata | tgcttctgaa | gtcctagaaa | aggctaatta | ccttaaaaat | aataaacttt | 45540 |
| tggaaatagt | aaatgactaa | aattttggtt | ttatgtatag | gattaatttc | attttctgtg | 45600 |
| ttagcagata | catcatatac | tgaaattaga | gagtatgtaa | accgtactgc | agcggattat | 45660 |
| tgcgggaaaa | ataaagcatg | ccaagctgaa | tttgcgcaga | aattaatata | tgcatataaa | 45720 |
| gacggagaaa | gagataaatc | aagcagatac | aaaaatgata | cattgttaaa | acgatatgct | 45780 |
| aaaagtggaa | ataccttaga | atgttcagtt | gcggaggaga | aagataaagc | cgcttgtcat | 45840 |
| tcaatggttg | accgtttagt | agattcttat | aatcgaggat | tgagtactag | atgattgtaa | 45900 |
| aatatatcaa | gggcgatatt | gtcgccctat | ttcttcaagg | taatattatt | gcgcacgggt | 45960 |
| gcaattgctt | ccacacaatg | ggctctggcg | tagcgggtca | attagcaaga | gcctatccca | 46020 |
| aaattttaga | aatagataaa | accactaccg | agtacggttc | tcgtgataaa | ttaggcgata | 46080 |
| tgtctattgt | ttttaaacat | agtcctacgg | gatttggtat | atgctataac | ctgtatacac | 46140 |
| aatacgaacc | gggtcctaat | cttgattatg | gtgctttagt | aaactgcatg | atagaattaa | 46200 |
| atctacaggc | agaaacccct | ttgtttaaac | cagtaattta | cattccacgc | ataggttgcg | 46260 |
| gtattgctgg | cggcgattgg | gataaggttt | ctaaattaat | cgacatgttt | actcctgata | 46320 |
| ttgatttaat | agtggtggat | tatgaaagta | cattacccgc | atccgtttga | tcctaaaaac | 46380 |
| aaagtggaaa | ttattcgtca | atgggaacgc | atttgccgta | ctaaatgccc | aattaatagt | 46440 |
| ccacatgatg | tagataaaga | ctatattgga | acattcgttg | aatataccctt | tattgatagg | 46500 |
| aaaggtcgta | acaacatgt | agaagaatat | tgtttaaagg | ttacatggtt | atgagccaaa | 46560 |
| ctagtattct | taaaaatgcc | cactgcgaaa | agtgtgaatg | gccagttgtt | tttgctttat | 46620 |
| gtaatgatga | aatggcttgt | gatttcgatt | attggtgcta | ttgttctaat | aaaggatgca | 46680 |
| tcaatcataa | aggtgaagga | ttttattcag | gattttatcc | ttatcctgat | ttcgttaaag | 46740 |

FIG. 17Z

```
                                   sequence.txt
aaggtaaacc gaaatgaata gttttgagtt acagtatgaa gtgttacgtg agcttgataa    46800
tttaattgaa ctcgctgtca ataaaggttt tgccattgga atcggtcaaa aagatactgg    46860
tcatttaact atggaaatat ttaagcaaaa gcgaattatt ttaaaactcc tggaaattaa    46920
tatatgagtc tgagtaaaga acaaaaagat aaattgtttg agcttatcca tgaacttcta    46980
gatgagcata cagaagcaaa caccttttat gatgaatacg gcccgctatc tcccgaacag    47040
caagaagaat ttgctgatcg gtttgataag aaagaaaacg aattaatagc ttatgtgaat    47100
atgctttaag aaggtgatat ggcgagttta attttactt acgcagcaat gaatgctgga    47160
aaatctgctt ctcttttgac tgctgcacat aattataaag aacgcggaat gggtgtatta    47220
gttcttaagc ctgctattga tactcgcgat tctgtctgtg aagtcgtttc tcgcattgga    47280
attaagcagg aagcgaatat tattacggat gatatggata tttttgagtt ctataaatgg    47340
gctgaagcac aaaaagatat tcattgtgta tttgtagatg aagctcagtt tttaaaaact    47400
gaacaggtgc atcaattaag tcgaattgtt gatacatata atgttcctgt tatggcttat    47460
gggctaagga ctgatttcgc tggaaaatta tttgaaggtt ctaaagaact tttggcgatt    47520
gcagataaac ttattgaact aaaggcagtt tgtcattgtg gtaaaaagc tattatgaca    47580
gctcgattaa tggaagatgg aacaccagtt aaagaaggta atcaaatctg tattggtgat    47640
gaaatttatg tttctttgtg tagaaaacat tggaacgaat taactaaaaa gctcggttag    47700
tgcaaaagtt ataataggt ttatctaact aaagggggtat atatgctaca attaactgaa    47760
aagcaacttc gcaatcttac tgttcttcaa ttagatgaaa ttcgtaggga agttggaaat    47820
atcatttcag ctttgcgtcg agaagtatca ctcaaccaat ctccggcaga ctatactaga    47880
ttgcgaaatt ttgaaaaata ccttgataaa gttaaggccg tgcatcggca taaagtaaat    47940
acaggacaaa aatgatagga ggcctttatg gccttaaaag caacggcact atttgccatg    48000
ctaggattag cgtttgcttt atctccacca attgaagcga atgtcgatcc tcattttgat    48060
aaatttatgg aatctggtat tagacacgtt tatatgcttt ttgaaaataa aagcgtagaa    48120
tcatctgaac agttctatag ttttatgcga acgacttata aaaatgaccc gtgctcttcc    48180
gatttttgaat gtatagagcg aggcgcggag atggcacaat catacgctag aattatgaac    48240
attaaattgg agactgaatg aaattcagcg acttttcaca aagtggaaaa ccttcaaagg    48300
cagatgaata cttaggttta ttaatggctg cacaagctta ttttcattct gcgcattttg    48360
aaactaaaag ttatgctaga cacaaagcat acgattttat tttctctgag ttgccagatt    48420
tgattgataa atttggtgag caatatttgg ggtattctgg tagaaaatac acgccttcta    48480
ttccagatgc cagtaaactt cctaccgaca caattaaaat gattgatcgc atactagacc    48540
aatctaacag catttataaa gaatgcctc cagccattca aagcacgata gatgatatta    48600
ctgggatgtt ttaccagagt aaatatcttc tttccctcga ataacattag tctccttcgg    48660
```

FIG. 17AA sequence.txt

| | | | | | |
|---|---|---|---|---|---|
| gagactttt | tcattttacc | ggtttacttt | ccatttgagc | tgtgatacta | tacaactatc | 48720 |
| ggataaagag | gagaacatca | tgaaaattga | agcacttaat | caagaaggaa | atatctacgt | 48780 |
| catcattaat | ggtgatttt | tcgtcgacat | ggatgaagtt | actagtgaag | aacttgtaga | 48840 |
| acttcttaag | aaacgttatg | atatgtgtga | tgaagctgca | actcatatgg | cgtgtgcaat | 48900 |
| attctctctt | tcatatgtgg | tggaataatg | actagaattg | aacaagcaga | taaaattaaa | 48960 |
| gaattggtag | ctttaattcg | caaagcagat | gaggaactta | gtgactttgc | ttggttttcg | 49020 |
| gcaggcattg | caaataaagg | tattgaaaaa | tttgaagcta | aagttgataa | tgctttagaa | 49080 |
| gcgttagata | tgtttcttga | tgaaattatc | gatcataata | cgagagtgta | agtatgctaa | 49140 |
| cacgcgaaca | gtttgaaaaa | atcattaaat | tagcacgtga | tattgaaata | gattcatatc | 49200 |
| aattagcagt | tgagcattgt | gaaggatatt | catacgatgg | tatagaagca | gctaaaaagg | 49260 |
| atttggataa | atctaaagct | aagttagttc | aatatcttga | aatgattagg | tggaataatg | 49320 |
| aaaactgaaa | agcagatgtt | tttaatgaag | ctaattgaag | aatatgctaa | tgcagtttct | 49380 |
| gactatgaat | gttcttctcg | tgaaagaggt | acagctttcg | ctaaagaaga | attgaaaatc | 49440 |
| atggttgatg | ctcatacaaa | gcttcagaat | tttattgaaa | acgtcattta | atggtttaca | 49500 |
| agttggcaag | gttatggtat | agtaatcttg | tcaactgcca | aggagaagag | aatgaaagtt | 49560 |
| ttgtttgttg | tgtatgtgat | gattcaatat | aattacccaa | tgtttactta | taatctggtg | 49620 |
| aacaacatta | ttgatattat | tcaaaggagt | atgtaatgac | aagtgagcag | gcttttaaat | 49680 |
| taaaagaatt | aattgaaaca | tatagcaaag | ctgttcatac | agcaacagtt | attgatgaat | 49740 |
| cagctttctc | cggacatgct | aacaagatta | aatacaaaac | tcttatggaa | gaagctaaag | 49800 |
| taaatcttga | ttcttatatt | gaaactttaa | ttggtgaata | acatgggctt | tcctaaatta | 49860 |
| gaagtaggtg | atttagtttt | aacaaaatta | tggaatggtg | ttcaatcagt | agaaatctgc | 49920 |
| caatatcgtg | gagcaacagg | taatttgatg | tacacgattt | ataatccaga | aattttgtta | 49980 |
| gagtgtcatt | tggaacgctt | tataaagac | accgatagta | tgccttatag | tgtatcaatt | 50040 |
| gtacgtaaat | ctgatacaaa | ggaatattct | aaaattttag | aacaaattcg | tgccaataaa | 50100 |
| aaggattaat | atgaaacgat | tagtattaga | agttagtccg | ctttttggtg | aattggctat | 50160 |
| agaaaaagta | aataacatgt | atcgtttgac | gcaagaagac | gatatgctat | attttacgcc | 50220 |
| tagtgaaatc | attcatttaa | cccaaattga | atatccttat | actgataaaa | tagtaagcat | 50280 |
| caatgatgag | cacaaaattc | attttattc | ttcatgccca | ggatttaata | ttaaaagtga | 50340 |
| gtcaatgtgt | ttatcagtta | tccattggga | tagtttttata | gataagatta | aatatttta | 50400 |
| ttattctaat | gaaagaaaac | atagtttaaa | atggctcaaa | aattgcaatg | ctattattac | 50460 |
| taacgcttgc | aatcagaatg | atgaaactct | tttaaatgta | tcaaaatgtt | atgaagaggg | 50520 |

FIG. 17BB sequence.txt

```
agatgtctta actattcgcc aaattgacga ttttcgatca catattgtca catttaccaa      50580
agacgaagct attgcgttaa agacttatct tgattctgtc attccaacta tgatttcaaa      50640
gtgaggaaat atgtttattt caagtggaag cggtttaatt cgtgttgaat ttaaaaatga      50700
catctttctt agtcaaggag atgatattat taaaatgagt tatgacgaaa tcaagaaaat      50760
ttgtcatgct cttgaaagtc atggaaagga aaatgctact atcgatatag gtgatttatg      50820
ggtgacactt tatgaagtat ccgaaggatt taacattgaa gatgaaaaca acattttagc      50880
tattgataaa agaagtgatt tgtttgatgt attaaaagtt tatgaacagt caaatggtgg      50940
aagaaaagct gtattagttt atcaaaaacc acattcatgt ggaactgctt caatcatttc      51000
aaatattgaa gatgaaactg atacttatat gtgtgtttta aaagctggtg gtgaccgtca      51060
tccggatttt atttctattc gtcaaaataa tggagaaatt tcattatcaa aatcagaagc      51120
tgaagctatg attaagtatt taacaactgt tacaccttca atgaaaggat aattatgatt      51180
attaatgaaa actcttggca ttataaatta ttcaaaatgt ttaacgacga atggaaacga      51240
cctaagacac tttgtgcata tttttggtct attgttatcc ctacatttttt cgtttctttt      51300
ttcggatgta ctatactcgc aggtctaact attatctgtg cagaaatcat acagaaatgg      51360
cttatttttg gtagtttatg gactcttatt ccatcagcat ttatacttgc cattttgctt      51420
gtttttactta ttatcggttc atttgttatt cctgcacaac tacatgaaaa atataaagat      51480
tataaatgga aaaggatta tgctttacat gtagaaaata ttgataggggc gtataaaggt      51540
ttacctccta ttcaacccaa gaaatctatt atcgtcgaat ttttaaaagc gcgtaaagct      51600
aaagtatgtc ctgttattga atataaggct gaatgatgaa acagtaatg aaaagctatt      51660
ttggtagtca tctttatgga acttctactc cagaatctga tgtagatttt aaagaaatct      51720
ttgttcctcc tgctcgcgat attcttatcg gaaatgttaa agagcatatg agtaaaaaca      51780
ctaacaacac atcatctaaa aacactaaag atgatattga ccatgaacta tacagtctta      51840
aatatttctt taaattagca gcagatggtg aaactgtagc gttagatatg cttcacactc      51900
cacctgagtt agtggttaaa tctgatttgc ctgatgtgtg gaagttatt caagacaacc      51960
gttctcgttt ttatacgact aacatgaaat cctatttagg atatgtccgt aagcaagctt      52020
ctaaatacgg cgttaagggt tctcgtttgg ctgcattacg tgatgtattg aaagtagtta      52080
atcaaatccc tgagcagtgg gttgattacc aagaagatgg ttctattaag cagcgtcgta      52140
ctaaagttga agatattaag catcgtcttc cagaaaacga attctgtgaa tgggtgttcc      52200
ataatcatga gaaaacaggc ccacagacgt tctacacagt gttgggtcgt aaatatcaga      52260
caacgctttc tcttattgag cttaagcagt cactgaacaa attagatgct gaatatggtg      52320
aacgcgctcg taaggccgaa gccaatgaag gtattgactg gaaagctctg agtcatgctt      52380
gccgtggtgg actccaacta ttggaaattt acaaaactgg tgacttggtt tatccactcc      52440
```

FIG. 17CC sequence.txt

| | | | | | |
|---|---|---|---|---|---|
| aagatgctcc | atttattctc | gacgtgaagt | tgggtaaaca | tccatttaaa | acggttcaag | 52500 |
| agtttttgga | agatgtggtc | gatcaagtag | aagcagcatc | tactgaagct | tctaagaacg | 52560 |
| gtatgcagca | aaaagtagac | atgagtttct | gggatgactt | ccttgagaag | gtctatcttg | 52620 |
| aaaaccatcg | aagttattat | aaatgatagg | gagccttcgg | gctcccttt | ttatttaaa | 52680 |
| aattttttca | caaaactgtt | tacaagcata | aagctttatg | gtactataca | actatcaaaa | 52740 |
| caaacactta | aacggaaaac | aaaatgaaaa | ttacaccaat | tgaagtaaaa | aagttgattg | 52800 |
| atacagaaga | aatttcagag | tgttttgaaa | gtttcttaga | agacgcaact | gaagataacg | 52860 |
| cggtttatct | cgcccagaaa | attatcgaaa | cttatttgga | gaagaatcaa | tgacagttta | 52920 |
| cgtagatgtt | ttaatgaatc | atggatggaa | acttcgcggt | catccaacta | aaaattgtca | 52980 |
| tatgttcact | gatggagata | ttgaagagct | tcatgaaatg | gcagaagcaa | taggaatgaa | 53040 |
| acgttcttgg | tttcaagata | aacgcattaa | acattatgac | ttacacgctc | gccgacgcca | 53100 |
| aaaagctgta | gaacttggag | ctgtagaagt | atctcgccgt | gaagcagtaa | aaatttggcg | 53160 |
| aacgttaaaa | taaattgttt | acagaagggt | agtagtgtga | tactattacc | ctatcaaaac | 53220 |
| aaatgtgaga | ttggagaata | aaatgaaaac | tgtaactatc | aataagggta | tctacttcgg | 53280 |
| taaagaaatc | tctggaactt | ttgagctctt | aggtgaatgg | ttcccagata | atgctccggt | 53340 |
| agatgcacaa | ggagatggta | aagtttttgt | tgaaattgac | ggtaagcgtc | gcggtgtttg | 53400 |
| ggtttacaaa | tcagacattt | catatgatgg | tgtaaaagtt | gaagaagtta | aagaatcata | 53460 |
| tgaagatatg | aaaacccgca | ttaataaaag | atttaatgtt | atgggaatga | tgacgaatgg | 53520 |
| tattattaac | ggaaacattc | gttcattaat | tatctctggt | gcggcgggta | ttggtaaaac | 53580 |
| gtattcttta | gataaagctt | tgaataaagc | aaatgataat | ggatacattg | aatataaaag | 53640 |
| cattaacggt | aaaatctccg | gtatcggtct | ttatgaacaa | cttggaata | atcgtgaaga | 53700 |
| gaattctgtc | cttttgattg | atgatgtgga | tgttttctct | gatatggaca | ttcttaatct | 53760 |
| tctgaaagct | gctctggaca | ctggagagac | ccgtaaagtc | tgctggagca | ccgcatcttc | 53820 |
| ttacttagaa | gaaaaaggca | ttgagcgtga | gtttgaattt | aaaggaacga | ttgttttat | 53880 |
| cacaaacgtt | gacattgacc | gcgaattaga | ccgtggtact | aaacttgctc | cacatttaca | 53940 |
| agcattagtg | tcccgctcgg | tttatttgga | tttgggtgtt | cacactaatg | aagaaattat | 54000 |
| ggtcagggtt | gaagatgtta | ttctttcaac | tgacatgatg | caaaagcgcg | gtctttctga | 54060 |
| tgaagaaact | tataaagcat | tatcatggat | gaaagttaat | gttaatcgtt | tacgcaatgt | 54120 |
| ttcactgcgt | actgctcttt | atcttgctga | ctttattatg | accgacaaaa | acggttggga | 54180 |
| agaaattgct | gaggttactc | ttctgaaata | attcataaga | ggacttctat | gacaaaaagg | 54240 |
| cagttcagaa | atagattata | tggactgcca | ttaaaaagat | gactagaatt | aaactggtga | 54300 |

FIG. 17DD sequence.txt

```
atggaggtaa tgatgttata ctcaaaggct cgtgaaattt acgaaactaa aattaaagaa    54360
gcagtattta agttcgcaac gacaatgcga tggacaaatg actgggagta ttcaaaaaat    54420
cataagaagc ccatggtgac aagaaaggct catatgttag tgttaataga ccgtgagcag    54480
attaaagccc gagaagccct ccagaatcat aaaaaggctg cctttgaatg gtttatggat    54540
aacactgctc ctgagactaa gaaagcggta agcgcatggt tcagtggaaa aaattgtgaa    54600
agaagtttct tttagtggtt tacaagactg ttcctctgtg gtactataca actatcaact    54660
acggaggaac acaaaatgaa cgctaaagat attttcaacc tggtaaatta caacgatggt    54720
aaatttaaat ctgaagcaca agtaagttc tttaatgaca tctcaatcgg aggtgaaatc    54780
acggttgacg gaggacaaat ttacaaatct cgttggaatt ggatcgttat tatcgatgag    54840
attggtattg tagaaattta caagaatacg aataaaaatc gtacattaca ctggtctcgt    54900
gatactaacg aacagtacaa aaaggataaa gcatctaaat tatctcgtgt aactcaagaa    54960
gatattgagt tcatcaagaa agatattttg atgtatgata acttaattgc tgaagagcaa    55020
gctgttattg ataaatttga tgagattaaa gcttctcgtg aaattcctga ttttatgaaa    55080
gaatcagtaa atgaacgata cactctcatt tcagagcgta ttgaaactta caaaaagcaa    55140
agagctgaac gccagaatac tcttcggaag tttgaagaac ggttaaagac ggtactcgca    55200
taaccgcttt ataccaagga tggtataatg gttctaagcc cttttaattg agattattat    55260
gaaacagttg ataattaaaa gattgaattt attgatatgt tgtttatgta tagcaattgc    55320
atatggttat tacgcaatta atgattatat gcattataaa gattatgatg ttactgtagt    55380
taataccatt acaggaacac aaggaaaagg gtctagttta tcgtttattg ccgtatatga    55440
actcaaagat ggttatagat ttagtgaata tatttcccca gagatgtatt catcaataga    55500
aaaaggtgat aatattactg taagtttacg tcctttcgac gtaaaacaga cattgtttga    55560
taatattgtt tggttctttg gaatggtatt agttcaatct gtgtgtggtg cttatatagt    55620
ctgttccatc ttattctgta tatttagtaa aattgaaatt gagtgaggaa aatatgtcag    55680
tagtaattaa taatgtcaat gcagtaatta atctttagt taataaaaaa ttaaatgaat    55740
ggactgtact tcgtcgtgga gagccagata aatttttca tagatttaac ccaactttgg    55800
atttgaatgt tattgacaga gatgttcatg ctgaaatttt agataaattt aaagttgata    55860
ttgggtttgg gttagataaa catttgcaac gaacaaacgg atctggaatg ggtttatcta    55920
atcgcatcat gaaagcccct aataaaattg gagcgttgtc tcgtattaat gcgagtgaaa    55980
tccttcgcaa ttataataaa ggatatgacc tttatggtcg actaatgccg aaattatcat    56040
ttgaccaaat gattgcggat ttgtgggaaa atcaacgacg attattagca ttaggcgctc    56100
gattagctaa aggtctagat aaacaaatga tttttaagac caataataca gaagacctta    56160
aatgctttaa atttagtact cgtggagatg attattacat cagagctcgc tctacagatt    56220
```

FIG. 17EE sequence.txt

| | | | | | | |
|---|---|---|---|---|---|---|
| atgttaatat | ggggcatcat | ctctgtttag | cttttgaagt | tttaaaagaa | gccggaacat | 56280 |
| tagaatatgt | gtctggtgct | aaatgtccga | ttggttcaaa | ttgcatttta | atttatcgcc | 56340 |
| cagatgaatc | cagttcaact | aaattaccta | caaaacctgt | accagttcgc | agtaatgaaa | 56400 |
| aacattctga | acaaattgct | tattttaata | agcagattga | agagctaaat | atttctattc | 56460 |
| agcaatatga | tgatgaaatt | ttcagactat | ctggattgag | tagtaaagct | aaatctgagc | 56520 |
| gtgaaaaatt | aattaaaatc | gttgatttac | ttaaatctta | aggaacacca | tgaaaactcg | 56580 |
| ttctcaaatt | gaagatatgg | ttcgtaatgc | cagctatact | cgtgatgtta | tgacattttt | 56640 |
| gtgtgaaaat | aatttagacc | ctgataaagt | taatcgtgtt | attcatcact | ttaagtatac | 56700 |
| gaatagcagt | gaatgggtgc | gtaattttag | taaagcaggg | tatattacac | aaatgactgc | 56760 |
| tcgtgaacag | ctcaccgatt | tctgtaaaac | tattgattat | aaaaatcctt | tgattgttca | 56820 |
| aggcgttggt | caaagtaagg | tcgatttatc | atctggatt | ttcaatccaa | atcattatcg | 56880 |
| tattgaatgg | agatttattg | ctctattccg | taaacaatta | aagcaaattt | tgtctactgc | 56940 |
| tagtcgatta | aaaggctctg | atattaactt | aaagaacctg | aaatttgatg | gttatactct | 57000 |
| tcagatggaa | gtaagaccgt | taaaagaaaa | taatagaact | gcacgaatta | gctttaagcc | 57060 |
| taatactaaa | aattctcttt | caatttgtga | atgtcttaaa | tcacagctga | cagaagcatt | 57120 |
| taagtatatg | gatgttgttg | ctgctgttca | atctaagatt | ttacctcgtt | ttgagcgaaa | 57180 |
| ttgggaacat | acaacaacat | atgaacttga | tatgatcgtt | tcatttaaat | atgaatttt | 57240 |
| gagaaaggat | gaaattgttc | aagagaaaaa | gcaggaagtg | caagatacct | aaatttaaa | 57300 |
| tttatccaat | tacttatcaa | acgatcctaa | attttggatg | tatagctcaa | gcaatataga | 57360 |
| tgcatgtaaa | cttaataaag | tgagttttct | tcctactgaa | aattcaaatt | ttaaacctgt | 57420 |
| agaaaaatgg | cacgctgacg | cgattgagaa | gtctcttaag | gcagtagatg | atgaactcgt | 57480 |
| taaagcgacc | aatgaagtgc | tagaagctga | aaaggcgtta | gaacaagctc | agtcaagggt | 57540 |
| tcaaaatctg | acaaagcaac | gttctaaact | gaacaatgca | ctaaatgcac | tgaactagtt | 57600 |
| tactttgcca | caaggatgtg | gtataatgtt | tttactttct | actgaggaga | ttattatgac | 57660 |
| tcgtaacgaa | tatatcaaat | cattcaatag | cgttattgat | gataaagcta | taccgatgtt | 57720 |
| tggccaaaat | agcgttcttt | ctattatcaa | tcaatggctc | aatagtgttg | atgcaagtat | 57780 |
| tgtttcttct | actaaattta | ttcatgaaat | tcgtaaaatt | tctagccgtg | tagataaaga | 57840 |
| tgttatcaag | aaaacctta | aagagtctcg | tcttctttca | tatttggtta | atcgggatat | 57900 |
| tcttggtaat | tttgggaaag | aaattaaacg | aactaaagat | gtagtaggat | acaattggtt | 57960 |
| cggtgatgtt | aattcttatc | atcttaatat | taaagaagac | cctgagaata | tttttactcg | 58020 |
| tcgttggatc | agtaatttca | gactttttaa | gaaacaaatt | ctaaaatcag | cttctaaatt | 58080 |

FIG. 17FF sequence.txt

```
atgttatggc gattatcgtc aaattcatcc tttggcttct gatatgatta tcataaaaga    58140
atatgaactt gataaaaata aagtatctat ttttgtgaat tatggatttt ttacaccaga    58200
aactaaccaa aagaatatta ataaattttt ctcaattgct agcactataa ctcgtcaatt    58260
agagaccgca ttactttgta tggaaacagt agaaaatatt catacatatc cttttaagaa    58320
tatatgcggt tgggaaggat ataaactcgt aattagcctt cgtgaagtga aatgtgctta    58380
ttcacctact gataaagaaa tttaccaaca aaaatgtgat gaaattgtga atactcctaa    58440
agaagaaact acccttgagg aactaatgga atgtcttgat gattcacctg aaccgataga    58500
aattcgtcca gaagttattg cactagaaaa agcttataaa gaagttctag aaatttctaa    58560
taaagcgcag aaagaatatg agcaggctaa aaggatttgg gaagaatctg ttaatcgtct    58620
tgatcgtctg gaacaagctt tacagttaat taagtaattt aaagccaagg atggctcgga    58680
gtataaatca ttaccaagt gagaagaaca tgaaaactcg taaacattat attgattatt    58740
ttgacagtct tattactaaa catcgtaatt atcagatagg acacagagca gtaatcaata    58800
atattcttcg tgatttttta gactatattg gatgggaaaa ccatatttgt aaagatacac    58860
aaaatgcgta ttcacattct cttggttctt tgctcgagtg gttcaaacgt tcccgattac    58920
tatcttctgt gatagctgtt aataatgtta aaaaatttat gtatccaagc tacattgaga    58980
ctaatgtatc aaatgctagt gttgttacat ttaatattat taacgacgtg aaaagaactt    59040
atttagaaga atggttttct aaagatagta aagaaaaatt tgctagtgaa ttttcacacg    59100
aattcaataa taacgtgaat atgctttta agcattctcg tagactgttt tgtcatggtg    59160
ataaccgtac tattaatgtg aatgtaaaag actgggttac ggctaaattc actccatcgt    59220
cccagaatgg gcaatttgaa ttgtcaatta tcatttgtgc tccgcacgag atatataaaa    59280
accttccgta tatgaaacca cgcgaagcta ataaacacaa tgaaactatt agttctttgg    59340
cttataattt acgcgtgtta ttatctgata tggatgtagt caaatccttt gatgataata    59400
cgaattatgg tctttcgctg tttgaaacta aatttgttat taaattaaag gaccctagtg    59460
aatttaaacc tacaccaaaa tccaatcatg gaatgatac tatgaaagaa gaacgcgaat    59520
atctcagtgc ccgtttgatt gaagttgaaa aacagattga agagcatact aaagttctta    59580
aggctttaac cgccaaagca aatggtttac gtaatgctat tgaggtattg aaatgaaaaa    59640
gcgtttatta gaagacattg cagcttcaag taattccagt ttaattaaaa ttattatggc    59700
tggtgaggaa gatgatatgg aaatgcgtgg aaagattcac ggctgcgacg atttagattt    59760
taaacctcca gcatgggatg ctattatggc tatggttgaa cgacgtgaaa gagcttctaa    59820
aaacgttcct aattgccctg aatgcggtac tgaacaagtt caattgatta actggcgtaa    59880
accagagctt gaatataaat gccgtcaatg taaacataaa ttcagtaagc atgctccgga    59940
aatggttaaa ttgcctgact ctactgagtt cttaaagaa cttgtgagtg ttcaaccaat    60000
```

FIG. 17GG sequence.txt

```
gcctaataat attttggatt aaaaatgacc aagcgtaaag aatatatgga ggctgctgaa      60060
aaggcagtcc gtgaattagc aatagcttat tataatgaac atggtaaatt tcctgataga      60120
tacagcgtgc ttaaatctgc tttaactcgt tcatataaaa atatgctatc agaagtaagt      60180
gatattatat acaaacataa agaacaaacg ggccaaagtc ttgattacga cgagactttt      60240
aaacaagtac taggaattaa ggaataatat gtttaaagta tatggttatg atagcaacat      60300
tcataaatgt gtgtattgcg ataatgcaaa acgtcttttg accgtgaaga aacagccgtt      60360
tgaatttatc aacattatgc cggaaaaagg tgttttttgat gatgagaaaa ttgctgagct      60420
tctgactaaa ctaggtcgtg atactcaaat cggcttgaca atgccccagg tatttgctcc      60480
tgatggaagt catattggtg gatttgacca actgcgagaa tattttaaat gatgctcgaa      60540
ggaactgact atattcatga ttaccgcgga agcgcggtat atgtaggtga tgaagttgca      60600
gtttattatg ggtatggaac tttgatgaca gccaaggtta ttcaaattaa aaataatcgt      60660
gctaaactcg aagtttatta ttctaatggt gaaaagtcta tttctaagtg gaaatacggc      60720
gattgtatgg ttaaattggg gtaaatatga tttacgatat taatgtatca agaactccgt      60780
caatggttac tattccagcc gaagaactag atcgtcttca gaaaattgaa gagcttcttt      60840
gggaaattga atctgatttg ccatcaggat tagaatcctg gattgattat gaagaactta      60900
ataagcttcg gggttaaacc ttggtgggcg gctagatggg aaactgtaga gccagagccg      60960
gaagaaccgg tttacattga tgaagaaaca gtatataatg aaccaacgat aaatgactta      61020
attgatatgg agatgggaca tgattacagt agataagtgg tttagaatta atcgtgttga      61080
tacagggcta tgtaattact ggccggaact tagtgcaggt actgtcttta aagttcgtga      61140
acttgcaaaa gaatgcgaag atgatataga acctgatact ggaattattg aaattgaact      61200
ttccgacgga aagattatta acatctatga taagccaatt acatactggt gtttgtggaa      61260
tactgaatcc gttgaaaatg gcgaaattga agaagttgta gagagaacta gccaagatgt      61320
tcagaagcct aaagccgctt ttcaaggtga acgtatttca tacgcattag ctaaattagc      61380
tgcgcaagaa aataacgatg gctatgaagg taacctgatg caagctgccg cagagtacat      61440
tgaatggctt gaaactcaaa tttctttttc tgaccaaaag attcggcaat ataagcgatt      61500
gcatcaaatg ttttacaata cttgaaaaaa ctcaaaattc tttttctgac aggacatttt      61560
aatgaaaacc gaattggttt atactgaaaa gttaatggcg gtaaggttt ggaaactttt      61620
tattaaagga cattctacgg accctcatat gaccacttgc gtaggaacct attctcgtcc      61680
tactaaaaag atgattcgac agtataaacg attgcatcga atgttttaca atacttaaaa      61740
ataataaata cccttatcta tttaaggtaa gggtatttat tatgttattg actggcaaat      61800
tatacaaaga agaaaaacaa aaattttatg atgcacaaaa tggtaaatgc ttaatttgcc      61860
```

FIG. 17HH

```
                              sequence.txt
aacgagaact aaatcctgac gttcaagcta atcatcttga tcatgaccat gaattaaatg    61920
gaccaaaagc aggaaaggta cgtggattgc tttgtaatct ctgcaatgct gcagaaggtc    61980
aaatgaagca caaatttaat cgttctggct taaagggaca aggtgttgat tatcttgaat    62040
ggttagaaaa tttacttact tatttaaaat ccgattacac ccaaaataat attcatccta    62100
actttgttgg agataaatca aaggaatttt ctcgtttagg aaaagaggaa atgatggccg    62160
agatgcttca aagaggattt gaatataatg aatctgacac caaaacacaa ttaatagctt    62220
catttaagaa gcagcttaga aagagtttaa aatgacaatt gaaaagaaa ttgaaggatt     62280
gattcataaa actaataaag accttttaaa cgagaatgct aataaagatt ctcgtgtttt    62340
tccaactcaa cgggacctta tggctggtat tgtgtctaaa cacattgcca aaaatatggt    62400
cccgtctttt attatgaaag cgcatgaaag cggaattatt catttccatg atattgatta    62460
ttcccctgct cttccattta ctaattgttg tttagtagat ttaaaaggaa tgcttgaaaa    62520
cggatttaag cttggtaatg cacagattga aactcctaaa tcaattggcg ttgctactgc    62580
aattatggcg caaattactg cacaggttgc ttctcaccaa tacggcggaa cgacttttgc    62640
taatgtagat aaagtacttt ctccttatgt taaacgcacc tatgcaaaac atattgagga    62700
tgcagaaaaa tggcaaatcg ctgatgcgtt aaattatgct caatctaaaa cagaaaaaga    62760
tgtatacgat gcattccaag cttatgaata tgaagtaaat actctcttta gttcaaacgg    62820
acagactcct tttgtaacaa ttacatttgg tacgggaact gactggactg aacgaatgat    62880
tcagaaagca attctgaaaa atcgtattaa aggtctcggt cgtgatggga taactcctat    62940
tttccctaag cttgttatgt tcgttgaaga aggcgttaat ctttataaag acgatccgaa    63000
ctatgatatt aagcagcttg ctttagagtg tgcaagcaaa aggatgtatc ctgatattat    63060
ttcagctaag aacaataaag ctatcaccgg ctcatctatt cctgtttctc caatgggttg    63120
ccgcagtttc ttgagcgcgt ggaaagattc aaccggtaat gaaattcttg atggacgtaa    63180
taatcttggt gttgtaacac tgaatcttcc tcgtattgcg ttggattctt atattggaac    63240
acagttcaat gaacagaaat ttactgaatt gttcaatgag cgaatggatt tatgttttga    63300
agctttgatg tgtagaatta gttccttaaa aggagttaaa gcgactgttg ctcctattct    63360
ttaccaagaa ggtgcattcg gggttcgtct taaacctgat gacgacataa ttgagttatt    63420
taaaacggt agaagttcag tgtctttagg atacattggt attcatgaat gaatattct     63480
tgtcggtcgt gatattggac aagaaatttt aactaaaatg aatgctcgtc ttaaacagtg    63540
ggctgaaaga actgggtttg cttttagttt gtattcgact cctgctgaaa acctttgtta    63600
tcgcttctgt aaacttgata cagaaaaata tggaagtgta aagatgtta ccgataaagg     63660
atggtacact aacagtttcc atgtttcagt agaagaaaat attactccgt ttgaaaagat    63720
ttctcgcgaa gccccatatc atttcattgc gacaggtggt cacatttctt atgttgaact    63780
```

FIG. 17II sequence.txt

| | | | | | |
|---|---|---|---|---|---|
| tcctgatatg | aaaaataacc | taaaaggtct | tgaggctgtc | tgggattatg | ctgcacaaca | 63840 |
| tttagattat | tttggtgtta | atatgccagt | agataagtgt | tttacatgcg | gaagtaccca | 63900 |
| tgaaatgact | cctactgaaa | acggatttgt | ttgttctatt | tgtggagaaa | ctgatcctaa | 63960 |
| aaagatgaac | acaataagaa | gaacatgtgg | ttatttggga | aatccgaacg | aacgcggatt | 64020 |
| taatctcggc | aaaaataaag | aaatcatgca | tagggttaag | caccaatgaa | ttatgataga | 64080 |
| ttttatcctt | gcgattttgt | taatggtcct | ggctgcagga | ccgttctttt | cgttacaggt | 64140 |
| tgtttgcata | aatgtgaagg | gtgttataat | aaatcaacat | ggaatgctag | aaatggtatt | 64200 |
| ccattcactg | gtgaaacact | agaacaatta | attgaatgtt | tgaataatga | ttatatagaa | 64260 |
| ggattaacta | taaccggagg | tgaccctctt | tatcctgata | acagagacgt | gattcattgc | 64320 |
| atcgttcaaa | cagtaaaaaa | tctttatccc | aataaaagca | tttggttgtg | gacaggatat | 64380 |
| aagtttgaag | atattaaaca | actagaaatg | cttaaatatg | ttgatgttat | tattgatggg | 64440 |
| aagtatgaga | aaaatcttcc | gactaaaaag | ctgtggcgag | gatcagataa | tcagcgactt | 64500 |
| tggtcaaata | ccgatggggt | gtggaaacat | gattaaattg | aattatatta | tggatactat | 64560 |
| aaatgatatg | attttcatt | ttggtccaga | attttattcc | caatatagtt | tagtgcttat | 64620 |
| caatgcttgg | ttaattaatt | aagggtaaaa | tatgtataaa | tttcgtaaag | gtttagctga | 64680 |
| ttttcttaca | actgtaacat | tctttctgtt | tatggcagtt | ggagctattt | tccttattcc | 64740 |
| ttttattgct | atatttttcg | tgattagttt | aatttctcca | gaaaagggct | tatcttctag | 64800 |
| tgagtttaat | gagcgtctgg | ataaaattac | taacaagctg | aatgctgttc | ttgataaaaa | 64860 |
| ggcttaatta | tgattagttt | tgagcggtat | gtagtagaga | gttggaatgg | ttttgatatg | 64920 |
| ttcggtaatg | actattattt | ctatgaatgt | agtctgaacc | caagcttctg | ggctggacgt | 64980 |
| gaacaagacc | tcgaagaaat | caacgctcgt | gccgatttgt | taggtgaact | gcctactact | 65040 |
| tatttcacct | ttgatgaatc | cggcttcgtt | atccaggttt | attttcctga | agaaaactct | 65100 |
| ggtgaggatt | ctgttaatcc | tccttattgg | gcttaccaag | gaattatttc | tcgtggaaca | 65160 |
| aaactcgaac | ttaaagaata | agattgaagt | ctatggaatt | ccagatgaag | taggtcgttg | 65220 |
| tcctggatgt | caatcagtta | caaaacttct | aaaggagctc | aatgctcctt | ttactttcta | 65280 |
| taagttctt | acaaataatg | gtaagattga | gtatgatcgt | ccactgattg | tatctcttgc | 65340 |
| taaacgcgct | ggattcacat | ctcttaacat | tcgttatcca | gtcatttttca | ttaatgattc | 65400 |
| tagacaaaag | aacattaaac | acttcaaaga | aactctcatt | tcacttggat | atgatagaga | 65460 |
| tatcatagaa | gactaagacg | ggccctctgg | gcctttctt | ctcacattct | gtatattacc | 65520 |
| attctaagct | atcgttccct | tcttatcatt | ccctaaaata | atttcacaaa | gttgtttaca | 65580 |
| acaagttcaa | actgtggtat | tattaacata | tgaattgcct | ttgaggattt | gatatggttg | 65640 |

FIG. 17JJ

```
                                    sequence.txt
tggttgataa agagattaaa aagggacaat attattttat taatggtaat gttgttcgtg    65700
ttacttatgt aaacggtttt gaagtttatt atcttatact caagttacat aaacagatga    65760
tttgtgatcg tgctgtattt agttcagttg ctaaggaaat taaactccat gggtaaaacg    65820
tatcgtcgta aagatttaaa agtacgtgat tatgactatt tcggaaagcg taaagctcct    65880
gatggtgtaa gtcataaaga tatggttgaa aacattttc gctctgataa atggcgtaga     65940
atgaaaggca ttgattcaga agttaaagat gagctaaatc gtcaattacg tagtgaagta    66000
agaaagttga aaaaatcagt ttacattgac gatgattttg attacaatac ttctcaacga    66060
gttgctaagc gcaaatcaaa cgagtgttat cgttatagct gaggaaaata tgaatatcaa    66120
acgcatgctt tttaagcaag ggctatatac tttaaatgct actccaaaag gcgatacaac    66180
taagtggtca gtaaatgact ggattaaatt tattgatgaa aacggtaatt gggaaattta    66240
aatgaatcct gaatctaaat tatcgcagcg aattgctgaa gaacgcgcca aattttccca    66300
gaacatgaaa cacaatggta ttgaggatga agtttttcta aattggttct ggaataataa    66360
gtatgcagca tgcgaaggag ccttgtcatt gtcagtcgca atgatgtacg aaggctggaa    66420
gggtgccaaa aagtttagct aagggcttcg gccctttttg gataataaaa ttttaatgca    66480
attgaggata atgtatgact attcaaatta aaaacgccat caattcttac gcatatgata    66540
aagtagtttc tctgctagaa aaaggcgata ttgtaactcc tcaaattttg gataaatggg    66600
aaaaagagct tcatcagacg atgaaacaga atgatcagaa gattggacgc aatactgtcc    66660
gtgaattgtt ggttcaatat atcttgtcag aatttgatgt taaagctttt ggtgtagaat    66720
ctaaagctta tcaaaagcat gaaatttccg ataaaactat tcgtcgtatg aaaaatcaac    66780
gcaagaaaaa atttgcagac ctgaaaatta ctaaggtata attatgaacg aagctcttat    66840
taacgatttg cgtcttgccg gatatgaagt aaatacaaat ggcattggtt taactcaaat    66900
tgaaggaaac ggattcatcc ttgagtatga atttagccaa tggtggttat atgccaatta    66960
cggcgaattg attgaatatg ttgaccaatt tgattcacta gatgcagctc ttgaagcggc    67020
taagttgatg aatgtatgaa attaattaat atttctattg ctattgaaaa ttttggtatt    67080
ttctatgttg accaatacat gaaaatttca tttttcccaa ataaaactgg tgttggatat    67140
tgggaaagcc atgtttctga attaaatgaa agtgaatatg ttagtacaca taaaaagttt    67200
ttagactttt tatatcgcgc tgatattaat gatcattaca tagatattca tgaatttaaa    67260
aagatgatgg agaaagtgtt ccaagcatac tgcttactta gataactgat atcctctatg    67320
ctttaagata gatcttcaaa tattatgata taatagatct atgaattgag ctaagaggtg    67380
aaaatgtcag aaactaagcc taagtataat tacgtaaaca ataaagagct tttacaagct    67440
attattgatt ggaaaacaga attagcaaat aataagacc caaataaagt agttcgtcag     67500
aatgatacta tcggattagc cattatgctt attgcagaag gcttatctaa acgtttcaac    67560
```

FIG. 17KK sequence.txt

| | | | | | | |
|---|---|---|---|---|---|---|
| ttttcaggat | acacccagtc | ttggaaacaa | gaaatgattg | cagatggtat | agaagcttct | 67620 |
| attaaggggc | ttcacaattt | tgatgaaacg | aaatataaaa | acccacatgc | gtatataact | 67680 |
| caagcttgtt | ttaatgcatt | tgtccaacgt | attaaaaaag | aacgtaagga | agttgcaaag | 67740 |
| aaatatagtt | acttcgttca | caatgtctat | gacagtcgtg | acgacgatat | ggttgcgtta | 67800 |
| gtagatgaaa | cttttattca | agacatctac | gataaaatga | cgcattacga | agaatcaacc | 67860 |
| tatagaacac | cgggggctga | aaagaaaagt | gttgtagacg | attctcctag | tttggatttt | 67920 |
| ttatatgagg | ctaacgatta | acctctccgg | attcttggaa | gaaatacctg | aagttgaagc | 67980 |
| tattccctat | ttacttaaaa | tgtatctcag | ggaagtttta | gctcttgaca | ttgatattga | 68040 |
| tccagaaaat | ccgtatgata | ccgcttttaa | atctaatggt | gtagaattaa | actatcggta | 68100 |
| tcatttaaca | gatgatgatt | tttattttat | attagagaaa | taatatgact | gataaacccg | 68160 |
| aaattaatga | tgaagtggaa | aagcttattt | cttctattga | agaaaagaac | cgtcttgaag | 68220 |
| cagaaagaaa | agcaaataag | ttattgtcta | aaaacaaacg | cgaactgaat | cgtctttata | 68280 |
| agcacgctca | gatcgcagct | gaaaacaata | attttgctca | atacgaatat | gctatcaaga | 68340 |
| aaagtcggga | tattctgaaa | cagccatata | acgatgaact | catcagtatt | ctttggaaga | 68400 |
| ctactagatc | gcagattgag | gatatgattg | atgcttacac | acgtaaaatt | caagcgtctt | 68460 |
| aaaattaatg | caggatttac | tgaatctttg | aatggtcatc | tttgtgtgaa | aatttctgaa | 68520 |
| aaagaatacc | atgatagttc | aattaaagaa | gttaatcctc | ctattgtaag | agcagacccc | 68580 |
| aatatgaaag | tgtgggttga | ttcttatcaa | gtcaaaaaat | ggtggcagtt | atgaaagatg | 68640 |
| aacacccaga | cttctgaaat | agattataat | aaaattcgtt | cctctaaaga | ggaaatgatg | 68700 |
| agacgcttta | aagagtctca | tgataaagct | aaagcagaag | gaactataaa | atataagcgc | 68760 |
| ataaaattta | aaagttctaa | cgagcctctg | tatggcgtat | tatgtggata | ggagcttcgg | 68820 |
| ctcctatatt | gctttataaa | ttttggtaa | aataaaccaa | acaaagagg | atattaaatg | 68880 |
| aaagtatgta | tttttatggc | tcgaggtctt | gaaggttgcg | gtgtaactaa | attttctctt | 68940 |
| gagcagcgtg | attggtttat | taaaaatggt | catgaagtaa | ctttggttta | tgctaaagat | 69000 |
| aaatcattta | ctcgtaattg | tgcgcatgat | tataaatcat | tttcaattcc | ggttttatta | 69060 |
| gcaaaagaat | acgataaaac | acttaagctg | gtaaatgatt | gtgatattct | aattatcaat | 69120 |
| tcagttcctg | ctacttcggt | tgaagaagac | actattaata | actataaaaa | aattattgat | 69180 |
| aacattaaac | cttctgttcg | tgttgtagtt | tatcaacatg | accattcttc | tctttctttg | 69240 |
| cgccgaaatt | tgggattaga | agaaactatt | cgtcgagctg | atgttatttt | tagccattct | 69300 |
| gataatggtg | attttaataa | agttctgatg | aaagaatggt | atcctgaaac | agtttctctg | 69360 |
| tttgatgata | ttgaagaagc | accgacagta | tataactttc | agcctcctat | ggatattgcg | 69420 |

FIG. 17LL sequence.txt

| | | | | | | |
|---|---|---|---|---|---|---|
| aaggttcggt | caacctactg | gaaagatgtt | tctgaaatta | acatgaatat | caaccgttgg | 69480 |
| attggtcgta | cgactacatg | gaaaggtttt | tatcagatgt | ttgattttca | tgaaaaacat | 69540 |
| cttaaacctg | caggactaag | tactattatg | gaaggtctgg | aacgttctcc | agcgttcatt | 69600 |
| cctattaaag | aaaaaggaat | tccatacgag | tattatcgtc | ttcatcaagt | agaccaaatt | 69660 |
| aaaattgctc | ctaatttgcc | aacgcaaatt | cttgaccgtt | atgtaaatag | cgaaatgctt | 69720 |
| gaacgcatga | gtaaatccgg | atttggttat | cagctgagta | agttggacaa | aaaatatcta | 69780 |
| caacgttctt | tagaatatac | tcatctcgag | cttggtgcat | gtggaacaat | tccggtattt | 69840 |
| tggaaatcta | ctggcgaaaa | tttaaaattc | cgtgttgata | atactccttt | gacctcgcat | 69900 |
| gatagcggta | tcatttggtt | tgatgaaaat | gacatggaat | caacatttga | acgtattaaa | 69960 |
| gaactgtcat | ctgaccgaac | tctttatgac | cgtgaacgcg | aaaaagctta | tgaattttg | 70020 |
| tatcagcatc | aagattcaag | cttctgcttt | aaagaacagt | ttgacattat | tacaaaataa | 70080 |
| agggcttcgg | ccctttagct | ttatacggag | tttgatataa | tgatatttct | tggatatgtg | 70140 |
| atactttttc | ttgcatttta | tctattcact | agagcatgtt | ggattgggtt | ctttagcacg | 70200 |
| ccagatgggt | ttatttcaat | aattttattt | tgcatttcaa | tgacggttct | tgatatatga | 70260 |
| aaatttaaa | tttaggtgat | tggcatttag | gcgttaaagc | cgatgatgag | tgggttcaat | 70320 |
| ccattcagtt | ggatggaatt | aaacaagcaa | tagaatattc | taagaaaaat | ggaattacta | 70380 |
| cctggattca | atacggtgat | atttttgatg | tgcgaaaagc | aatcacacac | aaaactatgg | 70440 |
| agttcgcccg | tgaaatagtt | caaatgcttg | atgatgctgg | tattaccta | catactattg | 70500 |
| taggaaacca | tgatatgcac | tttaaaaata | ctttaactcc | aaatgcctct | actgagcttt | 70560 |
| tggctaaata | tcctaatgtt | aaagtatatg | ataagcctac | tacagtagat | tttgacggat | 70620 |
| gtttaattga | tttaattcct | tggatgtgtg | aagaaaatac | tggtgaaatt | cttgagcata | 70680 |
| tcaaaacttc | atctgcttct | ttttgtgttg | gtcactggga | actgaatgga | ttttatttt | 70740 |
| ataaggaat | gaaatctcac | ggtcttgaac | ctgatttcct | taagacttat | aaagaggtgt | 70800 |
| ggtctggtca | cttccatact | atctctgagg | ctgctaacgt | cagatatatt | gggacaccat | 70860 |
| ggacactaac | tgcaggtgac | gagaatgacc | ctcgtgggtt | ctggatgttt | gatacagaaa | 70920 |
| cagaacgaat | ggaatttatt | ccaaacaata | ctacctggca | tcgtagaatt | cattatccat | 70980 |
| ttaaaggaaa | aattgactat | aaagatttta | caaatctatc | agtacgtgtt | atagtaactg | 71040 |
| aagtagacaa | aaatctgacg | aagttcgaat | ctgaactaga | aaaagttgtg | cattcattac | 71100 |
| gagttgtgtc | aaagattgat | aactctgtcg | agtcagatga | cagtgaagaa | gttgaagttc | 71160 |
| aatctcttca | gacgttgatg | gaagaataca | ttaatgcaat | tccagacatc | actgattctg | 71220 |
| accgtgaagc | acttattcaa | tatgcaaatc | agttatatgt | agaggcaaca | caatgacttt | 71280 |
| tgatgaattt | aaaaatgtta | tgatgagtca | gcattttgaa | tgcgaagtaa | aagatgatat | 71340 |

FIG. 17MM sequence.txt

| | | | | | |
|---|---|---|---|---|---|
| tggtcataaa | gaaattattg | aatattggtt | tgaaccgcta | gaggttgaag | ataattgtat | 71400 |
| taaaaaagtt | acggtctgta | cagattgggc | tgtatctttt | aacttcaaca | ttttagataa | 71460 |
| tgacacacct | aaatcattgc | gagatatggc | cgtatcttgt | attaaggatg | catactgtga | 71520 |
| agttttcgac | atttgacatt | aatgatgaat | tcatagcaaa | cattgattat | accgaagaag | 71580 |
| attctagata | tgttggaata | atttatatta | catcaaaaac | agcacaaggt | gttgtttgca | 71640 |
| tggctgaatt | tgatgaatac | tttttagatt | atgatgatat | gatagaatgg | tctaaaagat | 71700 |
| acattaaaag | gaatcttttg | tgaagaattt | taaactaaac | cgagttaggt | accaaaatat | 71760 |
| aatgtcagta | ggtggaaatc | ctattgacat | tcaattagat | aaggttcaaa | aaactcttat | 71820 |
| tactggacga | aatggtggtg | gtaagtctac | tatgttagaa | gccatcacat | ttgggctttt | 71880 |
| tggcaagcca | tttcgtgatg | taaagaaagg | tcaattaata | aacagcacaa | ataagaaaga | 71940 |
| actttagtt | gaactgtgga | tggaatatga | tgagaaaaag | tactatatca | aaagaggaca | 72000 |
| aaaccgaac | gttttcgaaa | tcaccgttaa | cggtacacgt | cttaatgaat | ctgccagcag | 72060 |
| taaagatttc | caagcagaat | ttgaacagct | tatcggaatg | tcatatgcca | gtttcaagca | 72120 |
| gattgttgtc | cttggtacag | cagggtatac | ccctttcatg | ggtttgtcga | cccctgcgcg | 72180 |
| aagaaagctt | gtggaagact | tgcttgaggt | aggaacatta | gctgaaatgg | ataagcttaa | 72240 |
| taagcacta | atacgcgaat | taaattcaca | aaaccaagtg | cttgatgtta | aaaagatag | 72300 |
| tattatccaa | caaattaaaa | tatataatga | taacgttgaa | cgccagaaaa | aattaacggg | 72360 |
| tgacaacctt | actcgtctgc | aaaatatgta | tgatgatttg | gcaaagaag | ctagaacgct | 72420 |
| aaaatcggaa | atagaagaag | ctaatgaaag | attagttaat | attgttttag | acgaagaccc | 72480 |
| gactgatgca | tttaataaaa | tcggtcaaga | agcagtttta | attaaatcaa | aaattgactc | 72540 |
| gtataataaa | gtcattaata | tgtatcacga | aggtggatta | tgcccaacct | gtttgtcaca | 72600 |
| attaagttcc | ggtgataaag | ttgtttctaa | aattaaagat | aaagtttctg | aatgcacaca | 72660 |
| ttcatttgaa | cagctttcaa | cgcatcgtga | taatttaaaa | gttcttgttg | atgaataccg | 72720 |
| agataatatt | aaaacccaac | agtcgttggc | aaatgatatc | cgcaataaaa | agcaatctct | 72780 |
| aatcacgacg | gtagataaag | ctaaaaaagt | taaagcggct | atagaaaaag | catcttctga | 72840 |
| gtttattgac | catgctgatg | aaatagcact | gcttcaagaa | gaacttgata | aaattgttaa | 72900 |
| gacaaaaact | aatttagtaa | tggaaaaata | ccaccgagga | attttgactg | atatgctcaa | 72960 |
| agattctggt | attaaggtg | ctattattaa | aaagtacatt | ccattattta | ataagcagat | 73020 |
| taaccattat | cttaaaataa | tggaagcgga | ttatgtgttt | acattagatg | aagaatttaa | 73080 |
| tgagacaatt | aaatcccgtg | gtcgtgaaga | ttttagttat | gcttcattca | gtcaaggtga | 73140 |
| aaaagcacga | attgatattg | ctcttttatt | tacttggcgt | gatattgctg | aaaaagtttc | 73200 |

FIG. 17NN

```
                                   sequence.txt
aggtgttaaa ataaacacac taattcttga tgaagttttt gattcagcga ccgacgttga    73260
aggtgtaaaa gctatttcaa ctatttttaga tagtttaaaa aatactaacg tttttgttat    73320
ttcgcataga gaccatgacc cgcaagcata cggtcagcat cttcaaatga agaaagttgg    73380
tcgatttact gtaatggttt aatttataag agattatgct ttaatttatt agagtataat    73440
ctctatggag gaaaaacatg gaatattcaa ccggacagca tctattaact attcctgaaa    73500
taaaacgata tattctgaga aataattttt ctaatgaaga gcatatagtt actgaatcta    73560
tgcttaggaa tgcatttaaa gcagaatata caaaaataat gtccaataga aatgaagctt    73620
ggactgttac tgattattat gactaaaggt gtattatgac taaaattact gtgaattata    73680
ctgttgatgt aaaagatatt cagccaaaac acgtgcgttc tgaatcaaat ccacaaaacc    73740
aaaataaaat tcgtcgagca tgggttttgt ctctttctga taacgcaatg gaagttattc    73800
agaacaaaat taaatctgca cctgctcgtc atgcgtatta tgaagctatc gatcgtgaag    73860
taagtaataa atggattgaa ctaatgcgca aacatactac agaatcccta aacgctggtg    73920
ctaaatttat tatgacttca tgtggtgaac gccttgaaga tgaatattgt ggcaatgcag    73980
atgaacgtct gattgttgcc gctcaaattg ttgccgaaac aatcgcagct gattttaatc    74040
gttaattgct ttattaaatt agttataaaa ttaaatctca tttgaattga aggaaattac    74100
atgaaactgt ctaaagatac tactgctctg cttaaaaatt tcgctactat taactctggt    74160
attatgctta aatccggtca atttattatg actcgcgcag ttaatggtac aacttatgcg    74220
gaagcaaata tttctgacgt tattgatttt gatgtagcaa tttacgattt gaacggtttt    74280
ctcggtattc tgtctctagt taatgatgat gcagaaattt cccagtcaga agatggaaat    74340
attaaaattg ctgatgcccg ctcaacaatt ttttggccag cagccgatcc gagtacagta    74400
gttgctccta ataaaccaat tccattcccg gtagcatctg ttgttactga aattaaagct    74460
gaagaccttc aacaactgtt gcgtgtatct cgtggtctgc aaattgatac aattgctatc    74520
acggtaaaag aaggtaaaat cgtaattaac ggttttaata agtagaaga ttctgctttg    74580
actcgtgtta aatattcttt gactcttggt gattatgatg gtgaaaacac atttaatttc    74640
attatcaata tggcaaatat gaaaatgcaa ccaggaaatt ataaacttct gctttgggca    74700
aaaggtaaac aaggcgctgc taaatttgaa ggtgaacatg cgaattatgt agtagctctt    74760
gaagctgatt ctacccatga tttttaatag agggcttcgg ccctttataa tttacactaa    74820
aacttgaatg aggaaattat gattaccgta aatgaaaaag aacacattct tgaacagaaa    74880
tatcgtccat ctactatcga tgaatgtatt cttcccgcct tgataaaga aacctttaaa    74940
tctattacaa gtaaaggtaa gattccacat attattcttc attctccttc tccaggaaca    75000
ggtaaaacaa ctgtagcaaa agcattgtgt catgatgtaa atgctgatat gatgtttgtg    75060
aatggatcag actgtaaaat tgatttcgtt cgtggtcctt tgactaattt tgctagtgca    75120
```

FIG. 1700 sequence.txt

| | | | | | | |
|---|---|---|---|---|---|---|
| gcttcatttg | atggtcgtca | aaaagtaatc | gttattgatg | aatttgaccg | ttcaggttta | 75180 |
| gcagaatctc | agcgacatct | tcgttccttt | atggaagctt | atagttcaaa | ctgtagtatt | 75240 |
| attattactg | ctaacaatat | tgatggtatt | attaaaccac | ttcagtcacg | ctgccgagtt | 75300 |
| attacgttcg | gtcaaccgac | cgatgaagat | aaaattgaaa | tgatgaagca | gatgattcgt | 75360 |
| cgattgactg | aaatctgtaa | gcatgaagga | attgctatag | ctgatatgaa | agttgtagca | 75420 |
| gctttggtta | aaaagaattt | tcctgatttt | cgtaaaacta | ttggcgagct | cgatagttat | 75480 |
| tcatctaaag | gtgttttgga | tgctggtatt | ttatcactgg | ttactaacga | tcgtggtgct | 75540 |
| attgatgatg | ttcttgagtc | tctcaaaaat | aaagatgtta | acaactcag | agctttagca | 75600 |
| ccaaaatatg | cagccgatta | ttcgtggttc | gtgggtaaac | ttgccgaaga | aatctattca | 75660 |
| cgtgtaactc | cacagagtat | tattcgtatg | tacgaaattg | tcggcgaaaa | taatcagtat | 75720 |
| catggtattg | cagctaatac | tgaattgcat | ctagcttatc | ttttcattca | gttagcatgt | 75780 |
| gaaatgcagt | ggaagtgata | tgagcttatt | tgaagatgat | attcaattaa | acgagcatca | 75840 |
| agttgcttgg | tattcaaaag | attggacagc | cgtccaatcc | gctgctgatt | cttttaaaga | 75900 |
| aaaagctgaa | aatgagtttt | ttgaaataat | tggagctatt | aataataaaa | ctaaatgctc | 75960 |
| tattgctcaa | aaagattatt | caaaattcat | ggttgaaaat | gcattatcac | aatttccaga | 76020 |
| gtgcatgcca | gctgtatatg | caatgaattt | aatcggttct | ggattaagtg | atgaagctca | 76080 |
| ttttaattat | ctaatggctg | ctgttcctcg | tggtaaaaga | tatggtaaat | gggcaaaact | 76140 |
| ggttgaagat | tccaccgaag | tattgattat | taagttactt | gctaagcggt | atcaagttaa | 76200 |
| tacaaatgat | gcaattaact | ataaatcaat | tcttactaaa | aatggaaaac | ttcctttagt | 76260 |
| attaaaagaa | ctaaaaggtt | tagtcacgga | tgatttttg | aaagaagtga | ctaagaacgt | 76320 |
| aaaagaacag | aaacaactca | aaaaactagc | attggaatgg | taaaatgatt | gaaattactc | 76380 |
| ttaaaaaacc | tgaagatttt | ctgaaagtaa | aagaaacttt | gactcgtatg | ggaattgcta | 76440 |
| ataataaaga | taaagttctg | tatcagtcct | gtcatattct | tcagaaaaaa | ggactatact | 76500 |
| atatcgttca | ttttaaagaa | atgcttcgta | tggatggccg | tcaagttgaa | atgacagaag | 76560 |
| aagatgaagt | tcgtcgtgat | tcgattgcat | ggctgttaga | agattggggg | ctgattgaaa | 76620 |
| tcgttcctgg | tcaaagaact | tttatgaaag | atttaactaa | taacttccga | gttatttctt | 76680 |
| ttaaacaaaa | acatgaatgg | aaactcgttc | ctaaatatac | gattggtaat | taatatgact | 76740 |
| gctataactc | cacaagaata | catggcgtct | cttaaagaaa | aatataatct | ttctgcaaca | 76800 |
| gaaacacttt | tgatttacc | agaaaacctc | caattaaaat | ttcaggtaga | atttcaaaaa | 76860 |
| ttagttcacc | cagaacaaaa | acattttact | gcagtcgtta | agtcaattaa | tgcagatgga | 76920 |
| atgataattt | tcacccggca | aatagtacta | atttaagcaa | ggggcttcgg | ccccttattt | 76980 |

FIG. 17PP sequence.txt

```
ggagtataat atatcaagag cctaataact cgggctataa actaaggaat atctatgaaa    77040
gaattttata tctctattga aacagtcgga aataacattg ttgaacgtta tattgatgaa    77100
aacggaaagg aacgtactcg tgaagtagaa tatcttccaa ctatgtttag gcattgtaag    77160
gaagagtcaa agtacaaaga catctatggt aaaaactgcg ctcctcaaaa atttccatca    77220
atgaaagatg ctcgagattg gatgaaacga atggaagaca tcggtctcga agctctcggt    77280
atgaacgatt ttaaactcgc ttatatcagt gatacatatg gttcagaaat tgtttatgac    77340
cgaaaatttg ttcgtgtagc taactgtgac attgaggtta ctggtgataa atttcctgac    77400
ccaatgaaag ctgaatatga aattgatgct atcactcatt acgattcaat tgatgatcgt    77460
ttttatgttt tcgaccttt gaattcaatg tacggttcag tatcaaaatg ggatgcaaag    77520
ttagctgcta agcttgactg tgaaggtggt gatgaagttc ctcaagaaat tcttgaccga    77580
gtaatttata tgccattcga taatgagcgc gatatgctca tggaatatat caatctttgg    77640
gaacagaaac gacctgctat ttttactggt tggaatattg agggatttga cgttccgtat    77700
atcatgaatc gcgttaaaat ggttctcggt gaacgcagta tgaaacgttt ctctccaatc    77760
ggtcgagtaa aatctaaact tatccaaaat atgtacggta gcaaagaaat ttattctatt    77820
gatggcgtat ctattcttga ttatttagat ttgtataaga aattcgcatt tactaatttg    77880
ccgtcattct ctttggaatc agttgctcaa catgaaacca aaaaaggtaa attaccatac    77940
gacggtccta ttaataaact tcgtgagact aatcatcaac gatacattag ttataacatc    78000
attgacgtag aatcagttca agcaattgat aaaattcgtg ggtttatcga tctagtttta    78060
agtatgtctt attacgccaa aatgcctttt tctggtgtaa tgagtcctat taaaacttgg    78120
gatgctatta ttttttaactc attgaaaggt gaacacaagg ttattcctca acaaggttcg    78180
cacgttaaac aaagttttcc gggtgcattt gtatttgaac ctaaaccaat tgctcgtcga    78240
tatattatga gttttgactt gacgtctctg tatccgagca ttattcgtca ggttaacatt    78300
agtcctgaga ctattcgtgg gcaatttaaa gttcatccaa ttcatgaata tatcgcagga    78360
acagctccta agccaagtga agaatattct tgttctccga atggatggat gtatgataag    78420
catcaagaag gtatcattcc aaaggaaatc gctaaagtat ttttccagcg taaagactgg    78480
aaaaagaaaa tgttcgctga agaaatgaat gccgaagcta ttaaaaagat tattatgaaa    78540
ggcgcagggt cttgttcaac taaaccagaa gttgaacgat atgttaagtt cagtgatgat    78600
ttcttaaatg aactatcgaa ttatactgaa tctgttctca atagtctgat tgaagaatgt    78660
gaaaaagctg ctacacttgc taatacaaat cagctgaacc gtaaaattct cattaacagt    78720
ctttatggcg ctcttggtaa tattcatttc cgttactatg atttgcgaaa tgctactgct    78780
atcacaattt tcggccaagt tggtattcag tggattgctc gtaaaattaa tgaatatctg    78840
aataaagtat gcggaactaa tggtgaagat ttcatcgcag caggtgatac tgattcggta    78900
```

FIG. 17QQ sequence.txt

| | | | | | | |
|---|---|---|---|---|---|---|
| tatgtttgtg | tagataaagt | tattgaaaaa | gttggtcttg | accgattcaa | agagcagaac | 78960 |
| gatttagttg | aattcatgaa | tcagttcggt | aagaaaaaga | tggaacctat | gattgatgtt | 79020 |
| gcatatcgtg | agttatgtga | ttatatgaat | aaccgcgagc | atctgatgca | tatggaccgt | 79080 |
| gaagctattt | cttgccctcc | acttggttca | aagggtgttg | gtggattttg | gaaagcgaaa | 79140 |
| aagcgttatg | ctctgaacgt | ttatgatatg | gaagataaac | gatttgctga | accgcatcta | 79200 |
| aaaatcatgg | gtatggaaac | tcagcagagt | tcaacaccaa | aagcagtgca | agaagctctc | 79260 |
| gaagaaagta | ttcgtcgtat | tcttcaagaa | ggtgaagagt | ctgtccaaga | atactacaag | 79320 |
| aacttcgaga | aagaatatcg | tcaacttgac | tataaagtta | ttgctgaagt | aaaaaccgcg | 79380 |
| aacgatatag | cgaaatatga | tgataaaggt | tggccagggt | ttaaatgccc | gttccatatt | 79440 |
| cgcggtgtgc | taacttatcg | tcgagctgtt | agtggtctgg | gtgtagctcc | aattttggat | 79500 |
| ggaaataagg | taatggttct | tccattacgt | gaaggaaatc | catttggtga | caagtgtatt | 79560 |
| gcttggccgt | cgggcacaga | acttccaaaa | gaaattcgtt | ctgacgtact | gtcttggatt | 79620 |
| gactactcaa | ctttgttcca | aaaatcgttt | gttaaaccgc | ttgcgggtat | gtgtgaatcg | 79680 |
| gctggtatgg | actatgaaga | aaaagcttcg | ttagacttcc | tgtttggctg | atagaataaa | 79740 |
| tctagggacc | tccgggtccc | tttttcatac | aagtaatata | aatctatact | tatgaaaaac | 79800 |
| agatgattct | ggacctttag | aattccctaa | aaaattttc | acaaaactgt | ttacaagact | 79860 |
| gttcctctgt | ggtactatac | aactatcaac | taatacggat | ttggagaatg | aaatgaaaat | 79920 |
| cgctattttg | gttattgcat | taggtcttac | tggttgtgta | gctcaaggac | cggtagtaaa | 79980 |
| tcagtctgat | gtaggaaaaa | ttgtaaactg | ttcaagcaaa | ttttataatc | ctaatgtcaa | 80040 |
| gtgttataaa | gaagctccaa | agcaaacagt | agaacaaatg | caggcgaatt | ttgacgaagc | 80100 |
| tattcgtcca | gatgaatctg | ctcaagcata | tcgtaattct | gatgtaatta | cacgcgaaga | 80160 |
| aaaaattgaa | aactactgcg | cagagctttg | ggcaaattgg | gctaataatt | accaatggcg | 80220 |
| tactggtaaa | aatgctccga | tggagtatgt | agtgaattct | tataattcat | gcgtaaaaaa | 80280 |
| tttgactaag | tgaggaaaag | atggaaactt | tagtagcagg | ttcaatttt | atggttttag | 80340 |
| tttcaggcgt | gttggctatt | attatataca | tgcttccatg | gttcatcgcc | ttgatgcgtg | 80400 |
| ggtcaaaatc | gacagtagga | atcttttca | cgtctttact | gtttaactgg | tcaattattg | 80460 |
| gttggtttat | tacatttatt | tggtcaattg | cgggtgaaac | taaaaagtct | gcacaaccaa | 80520 |
| accaggtaat | tatcatcaga | gagaaggaat | gaaaagcaaa | attataacag | tgttgctttt | 80580 |
| aatcttgatg | attataataa | gtatatacta | tagtgtaacg | gttcctctta | tgattccaac | 80640 |
| tattatttta | ggttggggtt | tattactgtt | acaagttaaa | tatgaatgta | tcaattgagg | 80700 |
| tttaaatgat | tagtgactct | atgacagttg | aagaaatccg | tcttcatttg | gggcttgcat | 80760 |

FIG. 17RR sequence.txt

| | | | | | |
|---|---|---|---|---|---|
| taaaagaaaa | agatttcgta | gttgataaaa | ctggtgttaa | aactattgaa | attattggcg | 80820 |
| catcatttgt | agcagatgaa | ccgtttattt | ttggcgctct | taatgatgaa | tacattcagc | 80880 |
| gtgaacttga | atggtataaa | tctaagagct | tgtttgttaa | agatattcca | ggtgaaacac | 80940 |
| caaagatttg | gcagcaggta | gcatcttcta | aaggcgaaat | taactcgaat | tatggttggg | 81000 |
| ctatttggtc | agaagataac | tatgcccagt | atgatatgtg | tttagctgaa | cttggtcaaa | 81060 |
| atcctgattc | tcggcgtggt | atcatgattt | atactcgtcc | atccatgcaa | tttgactaca | 81120 |
| ataaagatgg | tatgtcagat | ttcatgtgta | ctaatacagt | acagtacctg | attcgtgata | 81180 |
| agaaagtcaa | tgcggttgtt | agcatgagaa | gcaatgattg | ctgggcaggc | tatcgtaatg | 81240 |
| attatgcttg | gcaaaaatac | gtactagata | aattagtatc | tgatttgaat | gcaggcgacc | 81300 |
| catcgcggca | atataaagca | ggttctatta | tatggaacgt | tggaagtctt | catgtgtacg | 81360 |
| aaaatcagtt | ttatttagtt | gaccattggt | ggaacaccgg | tgagactcat | attgctaaaa | 81420 |
| aggattatac | tggaaaatgg | aagtaaatgt | gccgcatgtt | tataagtata | aacatcctaa | 81480 |
| aactaaaaag | tggtatatag | gaagtcatga | tggtcacaac | ccgaattatg | atggttcggg | 81540 |
| tgtagtttgg | caacatgtta | aaaagaaata | tggaataaaa | tcctttaata | aagaaatatt | 81600 |
| atatgaagga | ccaatgttta | gacaggttga | agaaattatt | ttaacttgtt | tagatgctgc | 81660 |
| taattgtccg | gattcatata | atttaaagaa | tgaagcatgg | ggaggaagtt | ttccaggcaa | 81720 |
| attaaatgga | atgtacggta | aaaaactatc | tccagaagaa | agatataagt | gcggaaatgc | 81780 |
| ctttcgtgga | atcaagcgtc | ctgatcattc | taaaagaatg | aaaggcgaag | gtaatccaat | 81840 |
| gtatggtaaa | aatgagcagg | catatggaat | tataaatcga | gccaaggaaa | attctggtaa | 81900 |
| aacttatgaa | gaaatttttg | gcgtagaaaa | agctaaaata | attaaagaaa | cgatgtctaa | 81960 |
| aaatcgtaaa | ggaaaacctc | ataatttgat | agaaaaaata | tgtccgcatt | gcggactaaa | 82020 |
| aggacgtggg | ccaaatatga | caagatacca | ttttgataaa | tgtaaggcac | ttaaatgatt | 82080 |
| caattcgtaa | ttccgagcta | tcaacgtgta | ggggcagttt | ctgcccttga | tatgtttccg | 82140 |
| actgattatg | aacctcatat | cgtagtacgt | gaacatgaag | aaaaagctta | ttatgatgcc | 82200 |
| tatgggtcta | aagctaaaat | tgtaactatt | cctgatgatg | ttaatggaat | tgccggtact | 82260 |
| cgtaaagcaa | ttactgatat | gtatgcaggt | caacgaatct | ggatgattga | cgatgatact | 82320 |
| actattcgta | tgagttcaat | gcgaaaaaga | gatgatcgtc | gttgtgtgga | taaagtcaat | 82380 |
| caattgactc | gtgaacagtt | ctatgaattg | attcaatacg | tcgaagatgc | catggattgt | 82440 |
| gggtattatc | acggtcatgc | tcgcctacca | atttttaaaa | ttacttcatc | ttggggtaat | 82500 |
| tatcgtgaaa | attcatatgg | attcacgaat | acatggtatg | accttggaaa | acttacgaca | 82560 |
| gaacaaattg | ggtatggaaa | aattgatttg | tgcgaagata | tgtatgcatt | tctcaattta | 82620 |
| attaatcaag | gttatccgca | tttggccttg | ttcaaatatc | tggttgtatc | tggaaaagca | 82680 |

FIG. 17SS sequence.txt

| | | | | | |
|---|---|---|---|---|---|
| caagctcctg | gagggtgcag | ttcaattcgt | agtaattcta | aacataatag | agcgcttgag | 82740 |
| caaatcaata | gagagtttcc | agagcaagct | cgttggaaaa | cttctaatat | tgaaaaacga | 82800 |
| aaatcgttgg | gtgaagaaga | cgagccatta | aaggttcttc | gcatgtgcgt | ttcgcgtaaa | 82860 |
| gaaaaatcag | aagcatttca | taagtttaat | gctattcatc | caatagcagt | tgattaatgc | 82920 |
| ctaaatttat | tgtgttataa | ttactctatc | tttaaccagt | gaggaaaata | taatgatgcc | 82980 |
| tatggaaaaa | aatgaatgtc | tattgcagat | ttaaaatccc | gtttgattaa | agcttccact | 83040 |
| tctaaaatga | ctgctgaact | gactacatct | aaattcttta | atgaaaagga | tgtaattcgt | 83100 |
| acaaaaattc | caatgcttaa | tattgctatt | tctggtgcga | ttgatggcgg | tatgcagtct | 83160 |
| ggtttaacta | ttttcgcagg | gccttctaaa | cactttaaat | caaatatgtc | tttgactatg | 83220 |
| gttgcggcat | atttgaacaa | atatcctgac | gcggtttgtc | tattctatga | tagtgaattt | 83280 |
| ggtattactc | cagcttattt | gcgatccatg | ggagttgacc | cggaacgagt | aattcatacg | 83340 |
| ccaatccagt | cagttgaaca | gctgaaaatt | gatatggtga | atcagcttga | agctattgag | 83400 |
| cgtggtgaaa | aagttattgt | attcatcgac | tcaatcggta | atatggcttc | taagaaagaa | 83460 |
| acggaagatg | ccttgaatga | aaaatctgtg | gcagatatga | ctcgtgctaa | atcactgaag | 83520 |
| tcattattcc | gtattgttac | tccttacttt | agcattaaaa | atattccatg | tgttgcggtt | 83580 |
| aaccatacaa | ttgaaacaat | tgaaatgttt | agtaaaaccg | tgatgacagg | tggtacaggc | 83640 |
| gtaatgtatt | cggctgatac | tgtattcatt | atcggtaagc | gtcagattaa | agatggttct | 83700 |
| gatcttcagg | ggtatcaatt | tgttctaaat | gtagaaaaat | ctcgtaccgt | taaagaaaaa | 83760 |
| agtaaattct | ttattgatgt | taaatttgac | ggtggtattg | atccttattc | tggattgtta | 83820 |
| gatatggctc | tagaattagg | atttgtagta | aaacctaaaa | atggttggta | tgctcgtgaa | 83880 |
| tttcttgatg | aagaaaccgg | cgagatgatt | cgcgaagaaa | atcttggcg | tgcaaaagat | 83940 |
| accaactgca | ctacattctg | gggtcccttta | tttaagcatc | aaccattccg | agatgctatt | 84000 |
| aaacgtgctt | atcagttagg | tgctattgat | agtaatgaaa | ttgttgaagc | tgaagttgat | 84060 |
| gaattgatta | actcaaaggt | tgaaaaattt | aaatctccag | aaagtaaaag | taaatcagca | 84120 |
| gctgatttag | aaactgacct | cgagcagtta | agtgatatgg | aagaatttaa | tgagtaaaga | 84180 |
| tgatttagat | ttagaaatta | tcgatgaatc | ccctcttcg | gagggggaag | aagaaagaaa | 84240 |
| agaacgtctt | tttaatgagt | ctcttaagat | aattaaatcc | gctatggaaa | atgttatcca | 84300 |
| ggagattgtc | attaaactag | aagatggttc | tacacacatt | gtgtatgtga | caaaattaga | 84360 |
| ttgggttgat | ggaaaagtcg | taatggactt | tgctgttctt | gaccaagaaa | gaaaagctga | 84420 |
| gttagctcct | catgtagaaa | aatgtattac | aatgcaacta | caagatgcat | ttaataaaag | 84480 |
| gtcaaagaaa | aaatttaaat | tcttttaagg | agtaagtgtg | gtagaaatta | ttctttccca | 84540 |

FIG. 17TT sequence.txt

```
tctcatattt gatcaagctt attttttcaaa agtttggcca tatatggatt cagaatattt    84600
tgaaagtggt ccagctaaaa atacattcaa attaattaaa tctcatgtta atgagtacca    84660
tagcgttcca tctattaatg cgttaaatgt tgcattagaa aatagttcat ttactgaaac    84720
agaatattct ggtgtaaaaa cacttatttc aaaactagcc gattctccgg aagaccacag    84780
ctggttagta aaagaaacag aaaaatatgt tcagcaaagg gcgatgttta atgctacgtc    84840
taaaataatt gaaattcaaa ctaatgctga gcttcctccg gaaaaacgaa ataagaaaat    84900
gccagatgta ggtgctattc ctgacatcat gcgccaagca ttatcaattt catttgatag    84960
ttacgttggt catgattgga tggatgacta cgaagcacgt tggctatctt atatgaataa    85020
agctcgtaag gttccattta aactcaaaat tctaaataaa attactaaag gcggagctga    85080
gactggaaca ctgaacgttt taatggctgg tgttaacgtt ggtaagtcat taggattgtg    85140
ttcattggca gcagattatt tacagctcgg tcataatgtt ctttacattt ccatggaaat    85200
ggcagaagaa gtctgtgcta acgtattga cgctaatatg cttgatgttt ctcttgatga    85260
cattgatgat gggcatattt cttacgctga gtataaagga aaaatggaaa aatggcgtga    85320
gaaatctact ctcggtcgtt taatcgttaa gcaatatcct actggtggag cagacgctaa    85380
tacatttcga tctctttttaa acgaattgaa gctcaagaag aattttgttc caacaatcat    85440
tattgttgac tatctgggta tttgtaaatc ttgccgcatc agagtttatt cggaaaatag    85500
ttacacaact gttaaagcta tcgcagaaga attgcgtgct ctggctgttg aaactgaaac    85560
tgttctttgg actgcagcac aggttggtaa gcaagcttgg gattcttctg atgttaacat    85620
gagcgatatt gcggaatctg ccggtcttcc agcaacagcc gattttatgc ttgcggtcat    85680
tgaaaccgag gagttagcag ctgctgaaca acaactcatt aagcaaatca aatcacgata    85740
tggtgataag aataaatgga ataagttttt gatgggtgtt caaaaaggaa atcagaaatg    85800
ggtagaaatt gaacaagatt ctactccaac tgaagtgaac gaagtagcag gttcacaaca    85860
gatacaagct gaacagaacc gctatcaaag aaacgaatcc actcgagctc agttagatgc    85920
tttggcgaat gaattaaaat tttagtttac aagctgacaa gactatggta tagtagtctt    85980
gttggttaaa tgaggagatt gttatggaat tggtaaaggt agtttttatg gggtggttta    86040
agaatgaaag catgtttact aaagaaatca caatgatgaa agatgacgtt caatgggcta    86100
ctactcaata tgctgaagtt aataaagcgc tagttaaagc tttcattgat gacaagaaag    86160
tatgtgaagt ggattgccga ggataatatg cacattgttt tatttaaacc tactccgtat    86220
aatgtcagga aaaatactca attcaaagca cttatcgcag atacgtggga attggtgtta    86280
gatattccag cagaagaaag tcctccattt ggtcgagtgg aatttattaa gtttgctgtg    86340
cgccctacga agcgacagat tcgccaatgc aaaagatact ttcgtaaaat cgtcaagtta    86400
gagaaacagt tattgatgct agtaaaatag tagtttacaa gctgatagag ttgtgttata    86460
```

FIG. 17UU sequence.txt

| | | | | | | |
|---|---|---|---|---|---|---|
| gtaattctat | cagctaatcg | cggagaaaag | aaaatgatgc | tagttaatag | agaatatcag | 86520 |
| tttaaatcag | aagaagattt | ggaaaaattc | gcgagtggtt | gtgaactgaa | tagacgcaca | 86580 |
| gctaaagtca | taggattaaa | acctttaca | gttctagatt | gtgaagtttc | taaattccgc | 86640 |
| agagggtgtt | ctattagcgg | tcatgctctg | gttgatggaa | acacattttt | ctttgttttt | 86700 |
| agcgtcagag | aacttttatt | gattaacgaa | cttgaggaaa | taaaatagtt | tactttttgtt | 86760 |
| ttaaacatgt | tattatagac | ctatcaaaac | aaacgagtaa | atggagaaca | aaatgtctaa | 86820 |
| agtatcaggt | tatcaattat | taacacaaga | acaacgttca | gagatggatt | ctttacaaga | 86880 |
| acggtgtcag | catagaaata | acgcacttga | ttcatttta | ttagttgaat | atgaaaactt | 86940 |
| gtgctctaga | cttgaaaaag | aatatgttca | tcaacatgaa | ggaggagaag | aatgaaactg | 87000 |
| aaatcaccaa | ttattgcaat | ttgtctgttt | gcttctacta | gtgtttactt | ttgttgaaaa | 87060 |
| ttgagatact | ataaacataa | actactgagg | agattatcat | gaaaaaattt | atctttgctg | 87120 |
| caattttttgc | tttatcttct | tgcgctgctc | agcctgctat | ggcgggttat | gacaaagatt | 87180 |
| tgtgtgagtg | gtctatgact | gcagatcaga | ctgaagttga | aactcaaatt | gaagcggata | 87240 |
| ttatgaatat | cgttgagcgt | gatcgtcctg | aaatgaaagc | tgaagtgcaa | aaacagctca | 87300 |
| agtctggtgg | tgtaatgcag | tataattacg | ttctgtattg | tgataaaaac | ttcaataata | 87360 |
| aaaatatcat | cgctgaagtg | gtaggtgagt | aattagaggt | taatatgtat | agttctgaat | 87420 |
| tttcatattt | aaaaatggaa | aaaaatttca | tacgatttta | tagatgaaaa | ggtttattac | 87480 |
| agtttccatg | aaccacgttt | taatagtgag | gttgggttta | ttgcagtaaa | agacaatttc | 87540 |
| atttaaaaa | tatattcggc | attaaaggat | tttcactacg | aaaatattaa | cctaaaattt | 87600 |
| gataaagaaa | acgttcgtaa | ttgcgcagta | acaattacag | gaaataaagg | tacatgcgtt | 87660 |
| atgctatctg | atgaaattaa | tgatttgcta | aatgatgccg | aaaaggttgc | tattccatcg | 87720 |
| attgatgacc | aaattttaa | tgcttttatg | aatagaggtt | aatatgaaaa | cgtttaaaga | 87780 |
| atttatcaaa | gaagatatgg | tcgctggaga | ttcaggtggt | aatcctgaaa | atatctctac | 87840 |
| tggaacaacg | tcaggcgctg | tagtaaataa | aggtcctgaa | cagattccta | aaaagaaaaa | 87900 |
| agaggaatct | aaagaaaaag | aagagtaaaa | atgtcatcga | taccttggat | tgataatgag | 87960 |
| tttgcatatc | gtgcattagc | tcatttacct | aaattcacac | aagtaaataa | tagttcaact | 88020 |
| tttaaattgc | ggtttagatg | ccctgtttgt | ggagattcaa | aaaccgacca | aaataaagcc | 88080 |
| cgtggatggt | attatggtga | taataatgaa | ggaaatattc | attgttataa | ctgtaactat | 88140 |
| catgcaccaa | tcggaatata | tttaaaggag | tttgaacctg | atttatatcg | tgagtatatc | 88200 |
| tttgaaataa | gaaaagaaaa | aggtaaaagt | cgtccagtag | aaaaacctaa | agaacttcct | 88260 |
| aaacaacctg | agaagaaaat | aattaaatct | cttccgtcat | gcattagatt | agataaattg | 88320 |

FIG. 17VV

```
                              sequence.txt
gcggaagacc atccaattat aaaatacgta aaagctcgct gtattccaaa ggataaatgg    88380
aaatatcttt ggtttacaac tgaatggcct aaattagtta atagcatagc accaggaaca    88440
tataaaaagg aaatacctga gcctcgtctt gttattccaa tttataatgc taatggaaaa    88500
gctgagtctt ttcaagggcg tgcattaaag aaagatgctc cccaaaaata tatcaccatc    88560
aaagcttatc ctgaggcaac aaaaatctat ggtgttgaac gggttaaaga tggtgatgta    88620
tatgttctag aaggacctat agattcgctt tttattgaaa atggtatagc tattacgggt    88680
ggtcaattag acctagaaat tgttccattt aaagatagac gtgtatgggt tttagataat    88740
gaacctcgtc accctgacac tattaaacga atgactaaat tagttgatgc aggagaaagg    88800
gttatgtttt gggataaatc tccctggaaa tcaaaagatg tcaatgatat gattagaaag    88860
gaaggtgcaa cccctgaaca aattatggaa tatatgaaaa ataatattgc ccaagggttg    88920
atggctaaaa tgcggctatc taaatatgct aagatttaaa ttaacccaac caaagcaaat    88980
gctaaatcta cgaatgtatc aagagtaatt actggaatac taacgccatg agcaatagca    89040
actggcgata aaacaaaatt ccaaagtaaa attcctatca tagcagaaat agtaaaagct    89100
atacgttttt tattacctt gatggcatta acaagtgcca ttaatttttg taccatatgt    89160
cctccttatt gctttatata tttattgtat aattaatcta ctaatccatg aattgaaagg    89220
aaaaataatg gcatacttta atgaatgcgc tcatttgatc gaaggtgttg ataaagcaaa    89280
tcgtgcatat gctgagaata ttatgcacaa tattgacccg ctgcaggtta tgcttgatat    89340
gcagcggcat ttacaaattc gtttggctaa cgataaacca gaaacaaatc gtcatcccga    89400
ttcacttgaa actgcgggag aagttcttgc ttggctgcga aaccaagacg attatatcgc    89460
agacgaaact cgcgagctat atacttctct tggtggtatg agtaatggtg aaaaagaagc    89520
ttctgctgta tggaacctt ggaagaaacg ttattctgaa atgcaatcca agaaaattca    89580
agatttatct cctgaagatc agcttgaaat taaatttgaa ctgattgatc aatttcactt    89640
tttcatgaat aaatttattg ctcttggaat gtcagctgaa gaaatcttta acttattta    89700
tctgaaaaat gctgaaaatt tcgctcgtca agatcgaggt tattaatggc tcgtttaaat    89760
aaacgccagc ttaagaaagc ccacaagaaa cgtattgacc agctatttaa aaattatgac    89820
aaagagctcg tgtgtgagct cttatctaat cagcttcgtg cggttgattg ggttgtagaa    89880
gaaggtcctg atgaaatttt tgtcagcgaa gaagccttaa aattaattat agagcattca    89940
aaatgaaaat atccaaagaa gaatttatta gacgacaaaa agctttaatt aatttacacg    90000
agtggtatgc ttaccagctt aaagtagata gctctaatat aaatgctgta atggctttat    90060
ataaacaaat tcaagatgaa cacgaattcc tggcacaagt tttcattgaa gactgatata    90120
aatacacctg taattaaaca ataaaggagt ttattatggg tggtttcgtt aacatcaaga    90180
cctttactca tccagcgggt gaaggcaaag aagttaaagg tatggaagtt tctgttccgt    90240
```

FIG. 17WW sequence.txt

| | | | | | | |
|---|---|---|---|---|---|---|
| ttgaaattta | ttctaacgag | catcgtatcg | cagattctca | ttatcagatc | tttccgtcag | 90300 |
| aaaaggcagc | atattctact | gtagtttctg | atgcagctga | ttggaaaact | aagaatgctg | 90360 |
| caatgtttac | gcctacacaa | ataggtggtt | aataattcaa | ggactcctcc | gggagtcctt | 90420 |
| ttttcatttt | actggtttac | tttccaaaat | gagtatggta | taataaaatt | atcttataga | 90480 |
| ggagagcact | atgttaaatc | gttggattaa | accaaatgaa | gatttagata | ttatcatttc | 90540 |
| acggcatgta | atgaagaaat | atgaactgca | gccatggtct | acagaagttg | ttgtgcattc | 90600 |
| atttatgatg | tacgcagatg | gttctgtcga | atttaatgca | gaaattcgat | atgattatgg | 90660 |
| cgagaagcaa | gtcgaattca | agagaggctt | tttgtaatgt | ttatctttaa | ttggtttaaa | 90720 |
| agcttcttta | cagattttt | ctctacaact | cctggagaag | gtgtagttcc | tatttcaaat | 90780 |
| gactaccttc | ctttaactgt | agttgaatat | gtttatatgg | gagatggaac | agtagaagca | 90840 |
| gttactatga | cttatgaaga | agcccaagaa | tattataaaa | atccttggcg | ctggtcaaca | 90900 |
| cctattacat | catctaatac | acagaataca | cagtctagtt | ctgattcata | tgacactaat | 90960 |
| gttcctgttc | atgtatggac | gggcgattcg | tgtggaagtt | cttgtgattc | tagttgttca | 91020 |
| tctacatctt | gtgattgagg | aaaattatgg | aagcgatttt | gtttgaaatg | tatattagca | 91080 |
| gtaatagtat | gtcgtttgct | aaagacgttc | caattaccgt | agcagtaatg | attgataagg | 91140 |
| gttattgtga | cccaatgtat | ctcgtagaaa | atttcgtttc | aatgccagtt | ccagaagatg | 91200 |
| ctgaaataaa | acttaaaaag | attggtatta | ttgaaactgt | accaaatatt | ccgtttagag | 91260 |
| caattgaagc | atttactaaa | tccgaataca | ttaatgttag | cgcagaacaa | tataatgata | 91320 |
| aacctatatc | tttctattcg | tatgattcag | tatatagttg | gaaaatagat | aaaggaaata | 91380 |
| aatttataat | tgtgagtgaa | gatgctttat | catactttat | ttcttctata | tggaatagtt | 91440 |
| tacatccaaa | tttgctaaaa | attcatgaat | tcgatgatgc | tcctactgtt | gttttaggta | 91500 |
| aaacaaatga | aagttctgaa | gaaatgtttt | gaatggttca | gtagaccaaa | ctcaatgtac | 91560 |
| attgatgatg | gttgggttga | acaagcaaat | aaagaaatgc | agaacgaatc | agaagaatgg | 91620 |
| atgaaatcaa | tgattagcgt | tgagaaagaa | aagaaattag | aacgctcagc | gcttaaattg | 91680 |
| atgagagaca | tttatgggga | taaatcgtga | acagagatat | gacgctagaa | gaggctaaag | 91740 |
| ctaaagcaaa | tgaagcttta | gatttgcttc | ttaaaattgg | cagtaaaatg | atggaagaaa | 91800 |
| atgagaaata | tatccaggaa | aacaaaattc | ctgatggtcc | attagtaggc | aaaaggaaat | 91860 |
| cgcatgattg | aagtagcaaa | acattattca | atagaattta | tgtctaaaga | aggtaaatca | 91920 |
| gtaaatacac | ttgataaaaa | gtgctcatta | attattcctt | tagcagaaaa | tccggatatt | 91980 |
| ttaattaaag | atataaaaga | aagaaaatat | ccagaaaatg | ttattctaat | tataaagcat | 92040 |
| actgaagata | ttttgcagaa | tactgattca | ccgttttctt | cttctgaagc | tttaactatt | 92100 |

FIG. 17XX sequence.txt

| | | | | | | |
|---|---|---|---|---|---|---|
| aaaggctata | aaagagctca | tgaatatggt | cttttgacc | tgtttgaaga | cgataaagtt | 92160 |
| aaattagcac | ttaatttagc | aggtcaatct | tctaaaagta | aaacattcat | tattgaagat | 92220 |
| attaaagata | taaatgcatt | tgttaagatg | gtctgggctc | attttgacgt | tggactacgc | 92280 |
| tggagaatgt | ccgaagaaga | aagaaaaatt | attgaagcta | atcgttattt | tggtttttat | 92340 |
| cgctaggaat | taatatggat | ttatttgaga | tgttagaaga | taatcattct | acgaatatcc | 92400 |
| agaatgattc | tagtgattat | aagaaagagt | accgtatagt | attacagaat | tatggaattg | 92460 |
| aagccccaga | tgctcttcta | gaagaactag | cttcatacca | tcttgaccct | ccgccctggg | 92520 |
| ctccctgggc | aaaataattc | aaaaagttgt | ttactttcct | tcctaacaat | gatatgatag | 92580 |
| cttctgaagt | atatggaggc | tatcatgatt | attaatcttg | cagatgttga | acagttatct | 92640 |
| ataaaagctg | aaagcgttga | ttttcaatat | gatatgtata | aaaaagtctg | tgaaaaattt | 92700 |
| actgactttg | aacaatcagt | tctttggcaa | tgtatggaag | ccaaaaagaa | taaagctctt | 92760 |
| catcggcagt | tgaataaaat | cattaaaaag | catttaacta | aatcacctta | tcagctatat | 92820 |
| cgtggtatat | caaaatcgac | aaaagaactc | attaaagatt | tacaagttgg | agaagtgttt | 92880 |
| tcaacgaaca | gagtagattc | atttactact | agtttgcaca | cagcgtgcgg | tttttcttat | 92940 |
| gttgagtatt | tcactgaaat | aatatttcgc | ttaaaaactg | ataaagcttt | taattattct | 93000 |
| gaccatatca | gcgatattat | actttcttct | cctaatactg | agtttaagta | tacatatgaa | 93060 |
| gatactgatg | gattagattc | agaacgtact | gataacttaa | tgatgattgt | gcgtgaacaa | 93120 |
| gaatggatga | ttccaattgg | aaagtataaa | ataacttcta | tttcaaaaga | aaaattacac | 93180 |
| gattcatttg | gaacatttaa | agtgtatgat | attgaggtag | ttgaatgaaa | tattcagcaa | 93240 |
| tgcaattaaa | agattttaaa | atcaaatcaa | tggatgcatc | ggtgcgtgct | tctattcgtg | 93300 |
| aagaattact | ttctgaagga | tttaatttat | ctgaaattga | acttttaatt | cattgtatta | 93360 |
| ctaataagcc | agacgatcat | tcttggttaa | atgaaataat | caaatctcgt | ttggttccaa | 93420 |
| acgataaacc | tctttggaga | ggtgttccag | ttgagactaa | gcaggtgtta | aatcaaggaa | 93480 |
| ttgatattat | tacatttgat | aaagtagtat | cagcttcata | tgataaaaat | gtagagctac | 93540 |
| attttgcttc | tggattagaa | tacaacacgc | aagttatttt | tgaattcaaa | gctcctatgg | 93600 |
| tatttaattt | ccaggagtat | gctataaaag | ctctacgttg | taaagaatat | agtccgagtt | 93660 |
| ttaagtttcc | agatagccat | cgttatcgta | atatggaatt | agtttcagat | gaacaagaag | 93720 |
| taatgatacc | agctggaagt | gtatttagaa | ttgcggatag | atacgagtat | aaaaagcatt | 93780 |
| caacatacac | tatctatact | cttgactttg | aaggatttaa | tctataatgg | aaggacttag | 93840 |
| attcattata | ccatgaaagt | tttaaagcat | ttttcataaa | gttgtttaca | agctgaagta | 93900 |
| aaaatgttat | agtataagta | gttaaccgtc | cgtgagaaaa | atatgaaact | gtctaaaaat | 93960 |
| caaattcgta | aaattacacg | tcgtttagag | catactcagg | catctgctaa | aagacgttct | 94020 |

FIG. 17YY sequence.txt

| | | | | | | |
|---|---|---|---|---|---|---|
| aaagatttta | acttagactt | caattacatt | aagaacattt | tagatcagaa | agtttgcgct | 94080 |
| tactcgggag | aaccttttga | taatcgtatt | gaaggagaga | aattatcatt | agaacgtttt | 94140 |
| gataataacg | ttggatacat | taaagggaat | gttattgcag | taaagaaaaa | gtataataca | 94200 |
| tttcgttctg | attatacttt | agaagagttg | attgaaaagc | gtgatttatt | tgctttgcga | 94260 |
| attggtcgtt | catctgcgaa | aaaagttcat | aaactaaatt | tagatgaaaa | gaaatgggct | 94320 |
| aaaatcaaaa | agacttataa | tcaaattaaa | gctatacaga | aaaaacgtga | aaccgaatt | 94380 |
| gagcacattt | ctcagctttc | taaatcaaaa | caaacttctg | acgttaagct | aacgattata | 94440 |
| gcacttaaag | ctcgtattga | tggttctcgt | atagcagaag | gcgctgaagt | tgttaaattg | 94500 |
| aacgttcttc | ttaaaggctc | ggattggaaa | actgtgaaaa | agctgtcaga | agcagaaatg | 94560 |
| caatatgata | tgtgtgataa | aattattcaa | ggtgtagagc | ggtatcaaaa | cttgtctttt | 94620 |
| attgataaac | ttaaactgaa | aagaggatac | ccgctaaatt | gttcaatttt | taaacttatc | 94680 |
| cgaggataat | atgttttatg | tatatgcgat | agtgtataga | gataaagatg | gatttgcggt | 94740 |
| gcctgttcct | cttgatgaac | atcgccctgc | tgtatttttt | gaaagggaga | ttgctgataa | 94800 |
| agtatttaca | actcttaaag | agcagtatca | actagcttta | ggtatgggaa | ttccgagatt | 94860 |
| agttgagact | ccacgcaagt | tttggtttaa | taaaatagaa | gttaaacatg | ttaagcctga | 94920 |
| tgtagacacg | caaagattat | atcggcgaat | tttagatact | gggcgtattg | ttagtatacc | 94980 |
| aattgcaggg | aatttacgat | gacatttgat | gatttgacag | aaggccagaa | aaatgccttt | 95040 |
| aacatcgtta | tgagggctat | caaagaaaag | aaacatcatg | taactattaa | tggacctgcc | 95100 |
| ggtactggta | aaactactct | tactaagttc | atcattgaag | ctttaatatc | tacgggcgaa | 95160 |
| actggcatta | ttttagcagc | tcctacacat | gcagctaaaa | agattctttc | aaaactgtca | 95220 |
| gggaaagaag | cgagtactat | tcatagtatt | cttaaaatta | accccgtaac | atacgaagaa | 95280 |
| aacgttcttt | ttgaacaaaa | agaagtaccg | gatttagcca | aatgtagagt | attaatctgc | 95340 |
| gacgaagtgt | caatgtatga | tagaaagcta | tttaaaattc | tgctttcaac | tatcccgcca | 95400 |
| tggtgtacta | taattggaat | aggcgataat | aagcaaatta | gacctgttga | cccagggaa | 95460 |
| aacactgctt | atatcagtcc | attctttaca | cataaagatt | tttatcagtg | tgaactcact | 95520 |
| gaagttaaac | gcagtaatgc | tcctattatt | gatgtagcta | ctgatgttcg | caacggtaag | 95580 |
| tggatttatg | ataaagttgt | tgacggacat | ggagtacgtg | gatttactgg | tgataccgct | 95640 |
| ttacgcgatt | ttatggtaaa | ttatttttca | atcgttaaat | cactagatga | tttgtttgaa | 95700 |
| aatcgcgtaa | tggcatttac | gaataaatct | gttgataagt | taaatagcat | tattcgtaaa | 95760 |
| aagatttttg | aaactgataa | agattttatt | gtcggtgaaa | ttattgtaat | gcaggaaccg | 95820 |
| ttaattaaaa | catataaaat | tgatggaaag | cctgtgtcag | aaattatttt | taataacgga | 95880 |

FIG. 17ZZ sequence.txt

```
caattagttc gtattataga agcagaatat acatcaacat ttgttaaagc tcgtggcgtt    95940
cctggagaat atctaattcg tcattgggat ttaacagtag aaacttacgg cgatgatgaa    96000
tattatcgtg aaaagattaa aataatttca tctgatgaag agctgtataa gtttaactta    96060
tttttaggta aaacagcaga aacttataaa aactggaata agggtggaaa agctccatgg    96120
agtgattttt gggatgctaa atcacagttt agtaaagtga agcacttcc tgcatcaaca     96180
ttccataaag cgcagggtat gtctgtagac cgtgctttca tctatacacc ttgtattcat    96240
tatgcagatg ctgaattggc tcaacaactt ctttatgttg gtgttacccg tggtcgttat    96300
gacgtatttt atgtgtgagg atatatgatt aacatcaatt caaaatattt aaatcgtcta    96360
atagatggta taaggaagca tactaataag caagataatc tcgatgttat ggtaacagga    96420
gctgagctcc ttcataagct ttatcttata agtgatacta tattagcaat taaacgaatt    96480
gaaaaacaat catatcacag taatacagat acggtaatta cactagatga agtgtctgt     96540
aaattactaa ttaaatttga ggaagctatt cgtggaaata actaaagacc agttttatct    96600
gcttcaagat aaagtgagcg aaatttatga aatagcttat agtaaaaatc gtgaaactgt    96660
aaaaattgaa tctagtaagt tgatgcttca attagaagaa attgaacgag atttaattgc    96720
gttagaattc ttttgtggtg aagtgaaaac tgtcacaatc agtgattatg ttttaggtga    96780
aattagctat ctttataagg cgattattaa tgattgaatt aagttggtgt cagtttaaat    96840
ctcttatgac aaatgttaaa gctgtcattg agaaaaattc tggtcctgaa aatattacta    96900
ttcgcgaaaa agctttaaag ataatataca gtcttgaaga gatgcaaaaa gatattgaat    96960
ctatggcaaa atttattgat gaacctatta ataaagttta tattcaagac tatactgtag    97020
gccaaattcg cgatttagcg aggaaaattt aatgtttgat tttattatag attttgaaac    97080
aatgggaagt ggtgaaaaag cagctgttat tgatttagct gtaattgctt ttgaccctaa    97140
cccagaagta gttgaaacat ttgatgaatt agtttcacgc ggcattaaaa tcaaatttga    97200
tttaaaaagc caaaaaggac atcgtctttt tactaaaagc actatcgaat ggtggaaaaa    97260
tcagtctcct gaagctcgaa aaaatattgc accgtccgat gaagatgtaa gcactatcga    97320
cggtattgcg aaatttaatg attacatcaa tgcacataat atcgatcctt ggaaatctca    97380
aggctggtgc cgtggaatgt cgtttgattt tccaattta gtcgatctca ttcgtgatat     97440
tcaacgtctt aatggtgttt ctgagaatga acttgacaca tttaagttag aaccatgtaa    97500
attctggaat cagcgtgata ttcgtaccag aattgaagca cttctgcttg ttcgtgatat    97560
gaccacgtgt cctcttccaa aaggaacttt agatggattc gttgcgcatg attctattca    97620
tgactgcgcg aaagacatcc tgatgatgaa gtacgctttg cgatatgcta tgggtcttga    97680
agatgctcca tcagaggaag attgcgatcc tctatctctt ccaacaaaac gataaaaagt    97740
tgtttacttc ctcggttagt tgtggtatta taacaccata gctactgagg ataataaaat    97800
```

FIG. 17AAA sequence.txt

| | | | | | | |
|---|---|---|---|---|---|---|
| gaaaatttat | cgtgttgaat | catcgtttag | tattcttgat | tatgaagatg | ctataacaat | 97860 |
| acgtcgaaat | ctttgtgttc | aaataacgcc | gtacaggagt | ataatagatt | catggagcga | 97920 |
| agagtggcta | ttacacgtag | gttatgacag | acctaatttt | atgcatcata | gcgataataa | 97980 |
| taaaagaatt | cctttaccac | acgaagataa | actattagtt | aaaaacgcta | atatagtaat | 98040 |
| taatactaag | ttcaagaaag | attatgttgg | agtagaatat | catattccag | gatggtttat | 98100 |
| agctctttat | cattttgctt | tcgctagcga | atatgatatg | atgagatggt | tcacacgaga | 98160 |
| agagcgtgaa | gaattagctt | cgaaaggatt | ttatcttgct | gtatacgaag | taccagatga | 98220 |
| ccaagttatc | gttggcgggc | atcaagtaat | gttccgtaaa | tcccatgctg | aacttgtaga | 98280 |
| ttttattgaa | atgagataat | tatgaaattt | aattataatc | ctgaatacac | accgaatccg | 98340 |
| gcagctaaac | tgattgattt | tgacgttgta | agtacttatg | tatgccctgt | taaaccactg | 98400 |
| gaaattaagg | aacctactat | gactaccgct | attgaaatcg | gcaaaaccta | caaactggtt | 98460 |
| gaacctaaaa | ttaaaactaa | tgccttgatt | tctggtcata | aaactctgac | tgatgttttt | 98520 |
| ggcgaaggcg | aatttattgt | tgaagaattt | gccaaaagtg | agtggtttga | caaatcttac | 98580 |
| gtcatccacg | gtcgccggtt | agataataac | aaaataaaga | aaaacctggt | ttatgaagat | 98640 |
| gagttcatcc | tgttccaaga | agttgaagaa | caagacccta | cagacctgtt | gtgtgctgct | 98700 |
| gtgtctatcc | gtcgtccttt | tgataatcct | atctgtggtt | gggtaacaga | ccagtggatt | 98760 |
| gaagatggtg | ttgagcttct | gaacgttgtc | catgcaggag | attttagtgt | agtacctcgt | 98820 |
| agtgcggtgg | tagctatttt | gaattaatag | tttacaaact | cttgggacca | gagtataatg | 98880 |
| gtcctgtgga | gtataaaatc | tttttaacaa | gtgagagata | actatgatta | ttaatattgg | 98940 |
| tgaaattgct | cgtgtatctg | ataaatcccg | ttctaaagca | gcaggaaaat | tggtcgaagt | 99000 |
| tgtaagcatt | cagcttaaac | acggtgttaa | agatgaagat | tctgaagtaa | aagtacgtat | 99060 |
| cattgctaaa | gatggaatgt | ctaagcccca | gtttggttat | gttcgatgga | aatttcttga | 99120 |
| gcctgcgttt | ttgaaagctg | ttcctgctaa | aggaattgaa | acgattgata | cttcgcatgt | 99180 |
| aggtgtagac | tttaagtgga | aactcggtca | agctatcaag | ttcattgctc | cttgtgaatt | 99240 |
| taaatttatc | aaagatgatg | gaaaggctgt | ttatactcgc | gctatgtgtg | gatacattac | 99300 |
| cgatcaatgg | gtagaagatg | gcgttaagtt | gtacaacgtg | gtattttag | gaacatataa | 99360 |
| agtcattcct | gaaagttgga | ttaaacacta | cagcaatgct | ctctatgcat | aaagtttaaa | 99420 |
| atttttcat | aaaactatat | acatcagtag | ttgattatgg | tactatatca | atatcaacta | 99480 |
| ctgatacaga | aaacaacttg | gagaataaaa | tggataattc | gttaaaggtg | cgctgatact | 99540 |
| cttctgaaac | gcatcgctcc | aatgttcaat | taatgaggaa | attatgatga | aacgtaaaat | 99600 |
| tgttcagaat | tgcactaatg | atgaatttga | agatgtatta | ttcgatccag | atttggtagt | 99660 |

FIG. 17BBB sequence.txt

| | | | | | | |
|---|---|---|---|---|---|---|
| agttcaaaag | gaacacacta | tcaagtttac | tcacttgact | tcggtttatg | tgtatgaaaa | 99720 |
| ggttggggat | aaacaaccaa | tttacggtgt | atttcgtgaa | atcactgaag | atggtacaac | 99780 |
| ttactggaag | gaaatttatt | aatggctatt | aaatttgaag | ttaataaatg | gtatcaattt | 99840 |
| aaaaataaac | aagctcaaga | aaatttatt | aaagaccata | ctgataacgg | aatctatgca | 99900 |
| cgccgtttag | gtatgcatcc | ttttaaaatt | ttagatgtgg | atgctcttgg | gcgtcctatt | 99960 |
| aaaattatgt | catttgctgg | aaatttagta | ctatcttctg | gtaaagatat | tttggatgaa | 100020 |
| gattttattt | ggctttcatc | gaatgaagct | gaattcttta | atgaagttga | aaatccatac | 100080 |
| caggcagctg | aagagcagga | agaatctgca | ccgataactg | atcaatctaa | attccctgta | 100140 |
| atgaaagtta | ctattgaaaa | tgatgaacag | gcatggtcct | tgtatcagat | gttgaaagct | 100200 |
| cactttaagg | aataattatg | ccgctttatg | attataaatg | tcaatcaaaa | gactgcgcaa | 100260 |
| aagaatacga | aaaaatcaag | aaaatttctg | aaagagatac | tgatgtatgt | cctgattgtc | 100320 |
| atcggattgc | tattcggtta | gtctctgccc | ctaagcatgt | gaatggcgga | ttttacgact | 100380 |
| tacttaaagg | gtaattatgt | ttaaaatcgg | taagaaatat | cgcattcgcg | aaggtgaaga | 100440 |
| aaagaaatat | ctattttctg | ctatttatag | gaatggttct | attaatgctg | taatatctac | 100500 |
| aagcgaattt | atcgttgaag | atatgaaagg | taataatgtt | acaatgatta | gtacagcatc | 100560 |
| tggaaatgac | ggaaaaattc | ttcacagttt | tcagagtaat | gttctaattt | atgatgaaga | 100620 |
| atttgacttc | ttcgaagaag | ttcccgaagg | ttttgctttt | gaatgcacta | tcactatgaa | 100680 |
| atctggtgac | cctctttctt | ttacagttaa | agatgaagga | agtcgcttga | gaattattag | 100740 |
| tcttcttcaa | gccattaaat | ttaagtgaaa | attatgaaat | atattaatcg | ttctatcgcg | 100800 |
| gcattagtat | tagcagtgtc | tttagtagga | tgtactgatg | ctgataatgc | aaccaaagtt | 100860 |
| ttgtcttcaa | gcggttttac | taatattgaa | atcactggat | ataactggtt | cggttgttct | 100920 |
| gaaaatgatt | tccaacatac | tggatttcgt | gctattggac | ctactgggca | gaaagtagaa | 100980 |
| ggaacagtat | gttctgggct | gttctttaag | gattcaacta | ttcgttttaa | ataaaaggcc | 101040 |
| ttcgggcctt | tagctttatg | attaccggag | tataatattc | ccgaaaccaa | acgaggataa | 101100 |
| gtgatgatta | agaatgaaat | taaaattctg | agcgatattg | aacatatcaa | aaagcgtagc | 101160 |
| ggcatgtata | ttggctcttc | tgctaatgaa | atgcatgagc | gctttctgtt | tggtaaatgg | 101220 |
| gaaagtgttc | agtatgtacc | tggtcttgtt | aagcttattg | atgaaattat | cgataactca | 101280 |
| gtagatgaag | gtattcgtac | taagtttaaa | ttcgcaaata | aaattaatgt | tactattaaa | 101340 |
| aacaatcaag | taacagttga | agataacggt | cgcggtattc | cacaagcgat | ggttaaaaca | 101400 |
| cctactggtg | aagaaattcc | tggtccagtt | gctgcgtgga | ctattccaaa | agcaggtggt | 101460 |
| aactttggtg | atgataaaga | acgcgtcacc | ggtggtatga | atggtgttgg | ttctagttta | 101520 |
| actaacattt | tttctgtgat | gtttgtcggt | gaaactggcg | atggtcaaaa | taatattgta | 101580 |

FIG. 17CCC sequence.txt

| | | | | | |
|---|---|---|---|---|---|
| gttcgttgtt | caaatggcat | ggaaaataaa | tcatgggaaa | ctattcctgg | aaaatggaaa | 101640
| ggaactcgtg | ttactttcat | tccagatttt | atgtcatttg | aaactaatga | attatctcaa | 101700
| gtttatcttg | acattacatt | agatcgtctc | cagacacttg | ctgttgttta | tcctgatatt | 101760
| caatttacct | ttaatggtaa | aaaggttcag | ggcaatttta | agaaatatgc | acgccaatat | 101820
| gatgagcatg | ctatcgttca | agaacaagaa | aactgttcta | ttgcagttgg | tcgttcaccg | 101880
| gatggttttc | gtcaattaac | atacgttaat | aacattcata | ctaagaatgg | tggccatcac | 101940
| attgactgtg | ttatggatga | tatttgtgaa | gaccttattc | cacaaatcaa | acgtaagttc | 102000
| aaaattgatg | tgactaaagc | acgcgttaaa | gaatgtttga | caatcgttat | gtttgttcgt | 102060
| gatatgaaaa | acatgcgatt | tgattctcaa | actaaagagc | gtttgacttc | tccatttggt | 102120
| gaaatccgta | gtcatattca | gcttgatgct | aaaaagattt | cacgtgctat | tttgaataat | 102180
| gaagcaattc | tgatgccaat | tattgaagct | gctttggctc | gtaaattggc | ggcagaaaaa | 102240
| gcagcagaaa | ctaaagcagc | taaaaaggca | tctaaagcta | aggttcataa | acatatcaaa | 102300
| gcgaatcttt | gtggtaaaga | tgctgatact | acattgttct | tgactgaggg | tgattctgct | 102360
| atcggatatc | ttattgatgt | tcgtaataaa | gaacttcatg | gtggttatcc | attacgtggt | 102420
| aaagttctca | acagttgggg | tatgtcatat | gctgacatgc | ttaaaaacaa | agaactgttt | 102480
| gatatttgcg | caatcactgg | attagttctc | ggtgaaaaag | ctgaaaactt | gaattatcat | 102540
| aatattgcta | ttatgactga | tgctgaccat | gatggtctag | gaagcattta | tccttctctg | 102600
| cttggatttt | ttagtaattg | gccagaactg | tttgagcaag | gaagaattcg | cttcgtcaaa | 102660
| actcctgtaa | tcatcgctca | ggtcggtaaa | aaacaagaat | ggttttatac | agtcgctgaa | 102720
| tatgagagtg | ccaaagatgc | tctacctaaa | catagcatcc | gttatattaa | aggacttggc | 102780
| tctttggaaa | aatctgaata | tcgtgagatg | attcaaaacc | cagtatatga | tgttgttaaa | 102840
| cttcctgaga | actggaaaga | gcttttgaa | atgctcatgg | gagataatgc | tgaccttcgt | 102900
| aaagaatgga | tgagccagta | gtttacttta | ccacaaggat | gtggtataat | taattgggca | 102960
| aatgaggata | ttgaaatgaa | atcatataaa | gtaaatttag | aacttttga | taaagcagtt | 103020
| catcgagaat | atagaatcat | tcaacgcttt | ttcgatatgg | gagaagctga | agagtttaaa | 103080
| aaccgcttta | aggatattag | agataaaatt | caatccgaca | ccgcaactaa | agatgaacta | 103140
| ctagaagttg | ctgaagttat | taaacgcaat | atgaattaat | gaggaaatta | tgattatcac | 103200
| cactgaaaaa | gaaacaattc | ttggtaatgg | ttctaaatca | aaagcattta | gcatcacagc | 103260
| atctcctaaa | gtatttaaaa | ttctatcatc | tgatttgtac | acaaacaaga | ttcgcgcagt | 103320
| agtccgtgaa | ttgattacca | acatgattga | tgcccatgct | ctcaatggaa | atcctgaaaa | 103380
| atttatcatt | caagttcctg | gacgtttaga | cccacgattt | gtttgtcgag | attttggtcc | 103440

FIG. 17DDD sequence.txt

```
gggtatgagt gattttgata ttcagggtga tgataattct cctgggttgt ataattcata    103500
cttcagttca tctaaagctg aatctaatga ctttattggc ggatttggtt taggttctaa    103560
atctccgttt agttatactg atacgtttag tattacttcg tatcataaag gtgaaattcg    103620
tggttatgta gcttacatgg atggtgatgg cccacagatt aaacctacat tcgtaaaaga    103680
aatgggtcca gatgataaaa ctggtattga aatcgtagtt ccagttgaag aaaaagactt    103740
tagaaacttt gcttatgaag tttcttatat catgcgacca ttcaaagatt tggctatcat    103800
taatggtctt gaccgcgaaa ttgattattt tccggatttt gatgattatt acggcataaa    103860
tccagaaaga tactggcctg atcgtggtgg attatatgct atctatggcg gtattgttta    103920
tcctatcgat ggtgttatta aagaccgtaa ctggctaagc attcgtaatg aagtgaatta    103980
cattaagttt ccaatgggtt cgcttgatat tgctccatca cgcgaagctc tttcactaga    104040
tgatcgtact cgtaaaaata ttattgaacg agttaaagaa ctcagtgaga aagcatttaa    104100
tgaagatgta aaacgattta aagaatctac atctcctcgt cacacatatc gtgaattgat    104160
gaagatggga tattctgctc gagattatat gattagtaat tcagtcaaat tcacgactaa    104220
aaatctgtca tataaaaga tgcagagcat gtttgaacct gacaataagt tatgtaatgc    104280
aggagttgtg tatgaagtaa atcttgatcc tcgactgaag cgcattaagc aaagtcatga    104340
aacttcagcc gttgcatcaa gttatcgtct gtttggtatt aatacaacaa aaattaatat    104400
cgttattgat aatattaaaa atcgtgttaa tattgttcgt ggattagcac gagcgttaga    104460
tgatagtgaa tttaataaca ctttgaatat tcatcataat gagcgtcttc tgtttattaa    104520
tccagaagta gaatcgcaga ttgatttgct tcctgatatt atggcgatgt ttgaaagtga    104580
tgaagttaac attcattatt tgtcagaaat tgaagcttta gttaaaagct atattccaaa    104640
ggtagttaaa agtaaagctc ctcgtcctaa agctgctaca gcatttaagt ttgaaattaa    104700
agacgggcgc tgggaaaaag aggaattatt tacgctcaca tcagaagcag atgaaattac    104760
tgggtatgta gcgtatatgc atcgttctga tatttctct atggatggta ctacatctct    104820
ttgtcatcca tctatgaata ttttgattcg tatggctaat cttattggca ttaatgagtt    104880
ttatgttatt cgtccgcttt tgcagaaaaa ggtaaaagaa ctcggtcagt gccaatgtat    104940
ttttgaaact ctgcgtgatt tatatgtaga tgcttttgat gatgtagatt atgataagta    105000
tgtaggttat tcaagttcag ctaaacgata tattgataaa attattaagt atcctgaact    105060
agattttatg atgaagtact tcagtgtaga tgaagttttct gaagaatata cacgactcgc    105120
taatatggtt agttcattac agggtgtata tttcaacggt ggaaaagata ccatcggtca    105180
tgacatctgg acagtaacta atcttttga tgaattatca cgtaatgctt caaaaaacag    105240
tgataaaatg gttgctgagt ttaccaagaa attccgtatt gtttccgact tcatcggata    105300
tcgcaactct ttaagtgatg atgaagtttc ccaaatcgct aaaactatga aggcccttgc    105360
```

FIG. 17EEE sequence.txt

| | | | | | | |
|---|---|---|---|---|---|---|
| ggcctaataa | ggaaaattat | gtacaatatt | aaatgcctga | ccaaaaacga | acaagctgaa | 105420 |
| attgttaaac | tgtattcaag | tggtaattac | acccagcagg | aattggctga | ttggcaaggt | 105480 |
| gtatcggttg | acacaatccg | tcgtgttttg | aaaaatgctg | aagaagcaga | acgctctaaa | 105540 |
| gttactatta | gcggtgacat | tacagttaaa | gttaatagcg | atgcagttat | tgctccagtt | 105600 |
| gctaaatctg | acattatttg | gaatgcatct | aaaaaattca | tttcaattac | tgttgacggt | 105660 |
| gtaacttata | cgcaactcc | taatactcat | tcaaacttcc | aggaaattct | taatctgctt | 105720 |
| gtagcggata | agttggaaga | agcggcacaa | aaaattaatg | ttcgtcgcgc | tgttgaaaaa | 105780 |
| tatatttccg | gcgatgttcg | aattgaaggt | ggaagcttat | tctatcaaaa | tattgaattg | 105840 |
| cggtctggtt | tggttgatcg | tattcttgat | tcgatggaaa | aaggcgaaaa | ctttgaattt | 105900 |
| tattttccgt | tcttggaaaa | tctgctggaa | aacccaagcc | agaaagcggt | atctcgactc | 105960 |
| tttgatttct | tggtagcaaa | cgatattgaa | attacagaag | atggttactt | ctatgcttgg | 106020 |
| aaagtagttc | gtagcaatta | ctttgattgt | cactcaaaca | cttttgataa | cagtcctggt | 106080 |
| aaagtagtta | aaatgccgcg | tactcgtgtg | aatgacgatg | atacgcaaac | ttgttcccgc | 106140 |
| ggtttgcatg | tatgttctaa | atcttatatt | cgtcactttg | gcagttcaac | cagccgagtc | 106200 |
| gtaaaagtta | aagtacatcc | gcgtgatgta | gtatcaattc | cgattgatta | caacgatgct | 106260 |
| aaaatgcgta | cctgccaata | cgaagtagtt | gaagacgtta | ctgaacaatt | taaataaggg | 106320 |
| cttcggccct | taactaagga | aaattatgtt | aggttatcaa | gcacgagtaa | aagaagaata | 106380 |
| cgatcaatta | atgctcaaaa | ttaatgcact | tagcaatttt | ttagaaagca | caaagtttct | 106440 |
| aacggttagt | gcagttgagc | aagaattgct | actttcgcag | tttatctcaa | tgaaatctta | 106500 |
| cgcagattgt | ttagaaaaaa | gaattgcaca | attcaaataa | aataagggct | tcggcccttt | 106560 |
| tgttttaagg | gaaattatga | ttccgacata | aaggaaagtt | taaatgcaga | aaacgaatcc | 106620 |
| gggtttgcag | agactatttc | agattccgtc | atttacccta | tcgaacagtg | acttgactag | 106680 |
| tgaaatgaag | gtcaaaattg | ctgatactgc | aagatactct | ttaaaacaaa | acccgaacca | 106740 |
| ggataaagca | gaagttatcg | aaagatgtcg | tatcgctgtg | tacgcagagt | ttttttgtggc | 106800 |
| agattggcta | agagggtatg | ttaacaaagg | ccaagaggat | gttaatgacc | cgtatacata | 106860 |
| cgcatgggat | gtactggcgc | atccaaaata | ctgcgggctt | cgtgtagaag | ttaagacaca | 106920 |
| tcaaactgac | tcacgttgga | tttcggtaac | aacaggatgc | agcggagagt | atccatatgg | 106980 |
| ttctggaata | aatctagggc | ccattctaaa | tcatcaagtc | gctgactgta | taattatatt | 107040 |
| caacactaaa | gaaattcatc | caggtgtcat | ccagtacact | ccgaagttca | tcggtgacag | 107100 |
| agaagacctt | cgtaaggttg | taagaaaaag | caactacaat | ggatggtatc | tttccattta | 107160 |
| aaattttca | caaacggtt | tacataccac | aaggactgtg | gtactataca | actatcagct | 107220 |

FIG. 17FFF

```
                                     sequence.txt
acggaggagt aaaaatgaaa tttaaatttt attacgctaa acataaaatt accggtgaat    107280
ttattgcatt tacgacttca actacagatg aaggagatat ttttactgca gtatttttat    107340
caaaatggga atcagatcaa ccttacttat catcacgtga agatctccaa cgattagtta    107400
atggagaata taatgattca tggtcatatt tagtccatga ttgtgttaaa aaggcaataa    107460
aacaaaaaca cttggaaatc gttgagattg aactatgagt tcattatggt ggtgtttcgt    107520
ttggttaatt agtattccat taatttgttt aacatttact tttgtgatga ggttattatg    107580
aaaattttga attctgtgct tattgcttgt gcgtggtggg ttgcgcaagt ttcagcagta    107640
gtagttggta ttcacattta ttacgaatat ttttaaaaaa gttgtttaca agactgttct    107700
tccgtggtat tattaccta tcaactacgg aggaacagaa aatgaaaaag attgttaaag     107760
ctatatggaa tgtagttata atactaatag ttttgagtat attcccaatc gttttaatga    107820
ttgatgtatt aaacgcttac tttggattta tgtgaggaaa atatgaagcg taaacgcagt    107880
gcttttacat ttattgaatg gttttcgat aatattttc cggctttatt cattttcatg      107940
ctgattttg ctttaggttc agttgtagtt ggaatctatt tgatgacagt agtcggaatt     108000
gatattcatc aaaatggttt aaaatccgta gttgaaacaa tttggaacgg tgtaaaatga    108060
tgaatttgct gagcggttgg ttttatattc ttatgtttta cattggcgca aattttccat    108120
attggatggg atggtcaaca actgcgtttg gattttatac tccttgaggt gaattatgaa    108180
aatctttaaa gatgtaaaag ttggtgaaat tttctgttta gataacggtg atcagttaat    108240
tcgtatttca cctcttaaga gcactagcga gaaaccgaca gttaacgcta ctttagcaaa    108300
caatagtaat gaacgtttct gtattgaaaa tgatactgaa acttataccg tagaagagtt    108360
ttgggaattg agcgtcgact gcgacgatta atttaatggc cgtgtgtatt catgcggcct    108420
tggagtagaa aataaattag aggaaattaa tatgaaatac atgactgtta ctgatctgaa    108480
taatgcaggc gctaccgtta ttggtacaat caagaacggt gaatggtttt tgggagttcc    108540
acataaagat attttatcta aacctggatt ttactttta gtaagtaaat tagatggtcg     108600
tccatttagt aatccatgtg tgtctgcacg attttatgta ggtaatcagc gttctaagca    108660
aggatttagt gcggttctaa gtcatattcg tcaacgtcgg tctcagcttg cgcgtactat    108720
tgcaaataac aatgttccat acacagtatt ttatctgcct gcttctaaga tgaaacctct    108780
gactacggga tttggaaaag gtcagttagc tttggcgttt attcgtaatc atcattctga    108840
gtatcaaaca cttgaagaaa tgaaccgtat gttggctgat aactttaaat tcgttttgca    108900
ggcatattaa tgagtaattt ccacaacgaa catgtgatgc agttctatcg taataatttt    108960
aaaactaaag gcgtcttcgg acgccagtga ggaaaatatg aatattgcaa aattattagg    109020
agttatttca tttatttgtt ggatagtagc atgtgtttta actatctgta ttgatgtcag    109080
cagtgtgttt tcgcaagctt tagctcaggg tatgtgtgca tatttaacat ttgtgttgtt    109140
```

FIG. 17GGG sequence.txt

| | | | | | | |
|---|---|---|---|---|---|---|
| atctactaat | gattaagaaa | atcttgggct | attcattagc | ccttgctatt | ttattgatag | 109200 |
| cattatatta | cggaataatg | ttcggattaa | ttcaagtcgt | gcttttcatt | tctgatgtta | 109260 |
| ttatggcact | acattcacta | gtatggtaaa | tttatgcaac | tgaataatcg | tgatttaaaa | 109320 |
| agtatcattg | ataatgaagc | attggcttat | gctatgtaca | cggttgaaaa | tcgtgccatt | 109380 |
| ccaaatatga | ttgacggatt | taagccagtt | caacgatttg | ttattgctcg | agctcttgat | 109440 |
| ttggcacgag | gaaataaaga | taagtttcac | aaactcgctt | ctatcgcagg | cggtgtagcg | 109500 |
| gaccttggat | atcatcatgg | tgaaaactct | gcgcaagacg | caggtgcttt | gatggctaac | 109560 |
| acttggaata | ataactttcc | tctgttagac | ggtcaaggaa | actttggttc | tcgtactgtc | 109620 |
| caaaaggcag | cagcaagtcg | ttatattttt | gctcgtgtaa | gtaaaaattt | ctataacgta | 109680 |
| tataaagata | ctgaatatgc | tccagtacat | caagataaag | aacacattcc | gcctgctttc | 109740 |
| tatttgccta | ttattcctac | tgttcttctt | aatggcgttt | ccggtattgc | aactggttat | 109800 |
| gcaacttaca | ttcttcctca | tagtgtttct | tctgtcaaga | aagctgtact | gcaagctctt | 109860 |
| caaggaaaga | aagtaactaa | accgaaggta | gaattcccag | aatttcgtgg | tgaagtcgtt | 109920 |
| gaaattgatg | ggcaatatga | aattcgtgga | acatataagt | ttacttcacg | aactcaaatg | 109980 |
| catatcactg | agattccata | taagtatgat | cgtgaaactt | atgtgagtaa | aatcttagac | 110040 |
| ccgcttgaag | ataaaggctt | cattacatgg | gatgatgctt | gtggtgagca | tggctttggc | 110100 |
| ttcaaagtta | aattccgaaa | agaatactct | ttgagcgata | atgaagaaga | acgccatgca | 110160 |
| aaaattatga | aagacttcgg | gttgattgag | cgtcgttccc | agaatattac | cgtcattaat | 110220 |
| gagaaaggaa | agctgcaagt | ttacgataat | gtagttgatt | taatcaaaga | cttcgttgaa | 110280 |
| gttcgtaaaa | cttatgtcca | aaaacgaatt | gataacaaaa | tcaaagaaac | tgaatcagca | 110340 |
| tttcgtttag | cttttgccaa | ggcacatttc | attaagaaag | taatttcagg | tgaaattgtt | 110400 |
| gtacaaggta | aaactcgcaa | agaactgacc | gaagaacttt | ctaaaattga | tatgtattct | 110460 |
| tcttatgttg | ataaactagt | tggaatgaac | atttttcata | tgacttccga | cgaagcaaag | 110520 |
| aaacttgctg | aagaagctaa | agccaaaaaa | gaagaaaacg | aatattggaa | aactactgat | 110580 |
| gtagttacag | aatacaccaa | agatttagag | gaaatcaaat | gagtccattc | attggtatca | 110640 |
| caagcgctgc | attagtatct | ggtggcattt | tactggcggg | tttaggtgtt | gttcctgccg | 110700 |
| tagcaggagg | tcttcttgcg | ttcggaattc | aacgtgttat | catgacagtt | atcacagtca | 110760 |
| tgcagtaatt | ttagggagag | cctcggctct | cccttttat | ttcaaaaatt | ttttcacaaa | 110820 |
| acggtttaca | accaaagcat | actgtggtac | tatacaacta | tcaaataaat | gaactgaaac | 110880 |
| aaacaacccg | gagatacaaa | aaatgaaatt | taaaatcgaa | aacgaaatcg | ttaaagctaa | 110940 |
| aaatgctctg | actgctaaca | aactggttgt | agatggtatt | gaatatgata | tctgtggagt | 111000 |

FIG. 17HHH sequence.txt

```
tcgtgaagaa aaacctggtg ttctgacttt cttcacaatg attttaaat ttaaaggtga    111060
cacagaattc aaacagtttg attttgccca tgaagacgaa atcgaagttc gtaatctgaa    111120
cattaagtaa gtactttatt agagctcttg aaaaagagtg caaaaaagtg tttacttctg    111180
ctttaaacat gatactatag acctatcaaa taaatgaact gaaacggaga ttaaaatgtc    111240
taaagtaact tacatcatca aagcttctaa cgatgttctg aatgaaaaaa ctgctgcgat    111300
tttaattacc attgctaaga aagatttcat tacagccgca gaagttcgtg aggtgcatcc    111360
agatttaggt aacgcagtag ttaatagtaa tattggggta ttgattaaaa aaggcctggt    111420
ggagaaatct ggtgatggat taatcattac tggtgaagct caagatatta tttcaaacgc    111480
agcaaccttta tacgcgcagg aaaatgctcc ggaactactg aaaaaacgtg ctactcgtaa    111540
agctcgtgag attacttctg atatggaaga agataaagac ctcatgttaa aactttaga    111600
tgaaaatgga tttgttctta aaaaggttga aacttatcgt agtaattatc ttgccatttt    111660
agaaaaacgc actcacggaa ttcgtaattt tgaaattaac aataatggaa atatgcgaat    111720
ttttggatac aaaatgatgg aacatcatat tcagaaattt actgatatcg gaatgtcatg    111780
taaaatcgct aaaaacggta atgtgtatct tgacattaaa cgctcggcag aaaacattga    111840
agctgtaatc actgtagcat ctgaactgtg aggaataaat aatgaacaag ttagaaattg    111900
tcaatgaact tcgtcgttgt gtagaaccta ctcaagaggg ttgggacatc tggtaccatg    111960
gagcttatct tggaactatc gtaaagatta agactggtaa atacatgatt attcgtgaaa    112020
gtaaagatgc tccagtaggt attcgcaata attttatggc agcgataagt tcatttacag    112080
atgcagctta cgaaatttac cttgccgatt ataagaatt ccaggaatct caaccggtta    112140
ttcgttcaat tggtgttaac aaagctcagc agaaaacttt gtggcagcgt attaaaggat    112200
ggtttaaatg aacccattta ttaatcgttt aaaaatgctg aatgttcctt tatctcgtga    112260
aactccagaa agtcttgttg aaaaatttaa agcgcatggt tataaatgca cagaagaaga    112320
tattctgaaa gaagttcctg aaatctgttg gcagactgcg tactgggatg aaaaccaaaa    112380
gtatcaacga cgaattgtct gcgcagctaa tcgttttaaa ttaaagatg gacgaactct    112440
tattattcca ggtgctcgtc attattctaa agatatggca gaagttttag atgtagttaa    112500
acctcaatta gttactcaac aagtttgtga tgatgaccaa ggatttattg accaatatag    112560
taattattgg acacgtgaag aagcaatgat tattgcaact tacgccggac aagtacgtat    112620
tgaacgtggt ggtagtgaaa aagaactta ctctgaggac ctttactaat gaatattaaa    112680
aagtttcaaa ttgatggaat tacgaatcaa attaaggcat tggaatatgc caataaaatg    112740
atgtcaacta attggggaat ttatgcgaat gagccagcat ttaaattttg tgatatggaa    112800
tttaccaaaa agcttgtagg aaaagatcat gtatgcccat ttagttctcc ggtaaatgga    112860
atgctaaaac ctgctttacg cgatctttat attgcgatga acgaagaaat gataaaagag    112920
```

FIG. 17III sequence.txt

| | | | | | | |
|---|---|---|---|---|---|---|
| ctaaaacgtc | aactgaaggt | gattcaattt | ggccagggaa | attaattcaa | aatcagatta | 112980 |
| ttttaactct | ctcaatgata | aagataaaaa | tctaatacgg | cattttattg | ttgagatggg | 113040 |
| atataccgat | acacacgatt | taagagaaca | tatatttgaa | tgtggtgtag | ctaaaaagtt | 113100 |
| ttcattcacg | tgcaaatgtt | taagagaggt | aattcaacac | tatgaacaat | ttagtcgcaa | 113160 |
| aacataattt | taataaagct | tctgtccata | aagataagaa | gaaagcgttt | aaagaatcta | 113220 |
| atcgcaaaca | gaaacataag | gggaaggtct | atgattattg | attctcaatc | tgtagttcaa | 113280 |
| tatacaatca | aaattgatat | tctagaaaag | ctatataagt | ttctaccaaa | tttataccac | 113340 |
| tcaattgtta | atgaattagt | tgaagaactg | catcttggga | ataatgattt | cttgattgga | 113400 |
| acttataaag | acctctcaaa | agcaggatat | ttttacataa | ttccagctcc | aggaaaaagt | 113460 |
| attgatgatg | tattaaaaac | tataatgatt | tatgtccatg | attatgaaat | tgaagattat | 113520 |
| ttcgaatgag | tcataatctt | gaaaaagtaa | tcgagcataa | tgtagctcag | gaacgtaagt | 113580 |
| cgttcaagga | attcgtagaa | aaattttg | aagaaaatac | cacagaccag | tttacaaatc | 113640 |
| aagcgtctga | tgatattata | acaaagtcaa | ctaattgagt | ggtatagtta | atgaataaaa | 113700 |
| atattgatac | agttcgtgaa | attattactg | ttgcgtctat | tttgattaaa | ttttccagag | 113760 |
| aagatattgt | tgagaatcgc | gctaatttta | ttgcatttct | gaatgagatt | ggagtaacgc | 113820 |
| atgaaggtag | aaagttaaat | cagaattcat | tccgtaaaat | tgtttctgaa | ttaactcaag | 113880 |
| aagataagaa | aaccctcatc | gacgaattca | acgagggttt | tgagggtgta | tatcgatatc | 113940 |
| tagagatgta | tacgaacaaa | taattattta | gcccttccta | atattctggc | cgcctgagca | 114000 |
| catattgatt | caaggcggtc | attacttata | tgatcatttc | tataccagta | catggttatt | 114060 |
| gttccagcat | agatattatc | caaattaaaa | tatggacaac | tgtacatgta | gtttatttcg | 114120 |
| ggagtaggct | ttttagttgg | taaaaaagca | aattttgagt | cggaataata | atgacgtcca | 114180 |
| tttaaatgaa | ctgtatattc | atccatagtt | ttatcaacag | gatatcctcc | aagtgatttt | 114240 |
| tcacttattg | ttgaaggtaa | ttttccttca | tatgctataa | tatcaacaaa | atagtttaag | 114300 |
| tttttagggc | ggaaagaata | caccgcacta | aagtctgcct | cagatgatat | atgaactatc | 114360 |
| tggagttgtt | ccagggcgac | agattcaaag | cgtgcatttc | tttccttttc | aataatttca | 114420 |
| ctgtatgttt | catactttga | ttgcttatag | tactcaaaga | aactatctcc | cctataccaa | 114480 |
| acaatcgcca | tcataaataa | aagaattacg | acagctaccc | gggaagcaag | aactttcccg | 114540 |
| gtagcgttat | ctttgaacaa | gcgatctaga | acaccaaaca | gaatatcaga | gggcgaaaat | 114600 |
| gatattctag | gtgctgccat | agaccctcct | tttaagggta | tttattcaca | ttatactctt | 114660 |
| ggaccatata | ttgctccaac | attttgccat | gttggagcgg | accctatgac | agcataacca | 114720 |
| gcagcgccgc | cattatattc | agatccttga | ccgcgaatat | tgcatctacc | tcccgcggaa | 114780 |

FIG. 17JJJ sequence.txt

```
cctacttcac caccgtttcc accattatag ataccattca cggatcctga gccaggtgca  114840
gaaatagtac cgccagtcgc gcctgattgc atatcaatag atcctcctgg cgcaccaaaa  114900
ggacgaccgc caccaccacc aaaggtcaat ctcatttgtg aaaaaggaga ataatatccg  114960
ccgccgccac cgccgccacc gcctgcaata gctccgccat tattaattct tagtctccca  115020
ccaatatcgt tttgaataca atgacctcca gctgagccag gactattgct accgccatta  115080
cctccacgac catacatcgt tacgccatgt atatttaact gaacatattc atttggtgta  115140
tctccgtaca tgaagaataa aggaacatct ttagaataag aaacgatatc accaacaata  115200
ttgaatacaa taggtgcacc gccagcttca aagcatctat cacggaacca ctgaccatta  115260
aaattgtggt ttgctcctac agtatgaata atttctcgtg agcgacctgc aaattgactc  115320
atccagcaag gaacacccaa tcttaattga ccagctgctt gactcatcca gcgctgtcct  115380
gtttcatttg cggctgaact tccaatccaa ccaggaacac caactactgc cataatttat  115440
actccaaagg gggcatttcc cccttgttgt tagaatttaa aatatttact aattttgcga  115500
gcaattttag taaagagagg cgttttcaat tctttaattt cttcactcat ttcctgaata  115560
gccttaatta aaagagcatt cacagcagag ttagaaattg tcagaacatc agatccatca  115620
acttcaactt tagatacagc ttccggtaat tccttttcaa ggtcctgagc aataatacca  115680
acttcacgtt taataacact acggtcttta atagacttaa ctttatcgta aatataaact  115740
ttcagtcggc aaacttttc gactgctcca tattctaatt cttctttatt aatcttgaga  115800
cgggagtcag aacgaatata cacatcgcta aagctaccat ttcctggtgt ataaaagaat  115860
ccatcatgat ggaattcaaa cacagcttgt gggtgtccag catcaggaga agcctccgtg  115920
gatccgacac gaatgattgc ttgccccac tgtgatggaa tacgacgcat accaaagtca  115980
acagcggtgc tatatccttg attggttata acgcttcttg ctttaagaat aggataataa  116040
ctatcttgac caacataacc atgatcaacg aataatggag cttctactcg ccattggttg  116100
ccccaatcac ccggttgtct agcaatccat ccagaaccgt taatgtgtac acggtacgg   116160
ttaacgttaa ccattgcggt attttgcggg tttaacgcaa tctcaccatt gtttgtgata  116220
tgtactgccg cctgagaagc atagctataa aatgctagcg aattatcagc accacccttg  116280
ccaatatacc agttaccagt cccgtctatg tcaccgcgaa tatgcaaaga attactagca  116340
gttgttgata atacaataga atcattaggt gcattgattg ttaaccgacc tgtcatcgta  116400
tcaccgcctt tacctaggcg agtattcaag gcagcatcta aattggttgc atcgttgtat  116460
ttcttccaga ttgaaccagc aatgttacca tcagtgttca agaatgctgc gccagcataa  116520
actcggcttt gtgacatgaa tcggccagac ggcaagaaac gccatgtagc taattcagtg  116580
gctgtagttc cagtagcgga taaatcaccc tgagcaacga tacgatattc tgaactagca  116640
atatccatac cagaagccat agtaatattt gttacagtgt ttttctgttt aacaattggc  116700
```

FIG. 17KKK sequence.txt

```
gcaaactggt ttttatttga atcgtcaata gcctgatata atggcgcaat ggtagtattc   116760
tgatttgcgt aagtattaga accagaaccg ctagcagggg cttgaatata tgctcctgga   116820
gcaagtgaaa ttttctgatt agcaccaaga ttaacagcag cagtgatatt cagcaatccc   116880
ctaaagtttt gttgagcagt ccaagtatgt gatccgtctt caagaacaac acgacgacaa   116940
gtattagtcc tacttcctgg attaccagcg atacgaacaa cgaaataacg atagttcgcc   117000
tgagatacag taccgcgcca cacttgaaca gttcgacccg ttccggtatg ttcgctagga   117060
ccgacagaaa acataaccag gtttccatca atcgtgcccc aatccatatt tgctggcata   117120
ttctttattt tgttcaaagg aacactaaac atactaccag ggacaaaatc aaaggtttgc   117180
caatctaact ccgctaattg agctttaata ccacccatac ccaaagtaat tggcagagaa   117240
taagatgtat atacttcgtt ccatgcaccc cacgcaccac cagtatatgc acgctcaaaa   117300
atacgatcgc gagtagttgc acccgttcct gcggtagtga acgttggaa aatagcaccg    117360
ccagaagcac gctgtttaac ttccagcaaa ccaacaataa cagtcggcaa accttcacct   117420
gtaggacagt taataacggc atcagtgcct aaaatattat ataacccggg agttttaaaa   117480
tcattcagat ctccatcata gaaagtcgct ggtgtgccat gaccaacctg cttccattcc   117540
tcccacttag gtgcactagc atcccatgca gcagcgagac aacgagtata aaccataccc   117600
atgcgggtag tataacgctg agttctcgtg tataaaccac cttcaaatat ttctaaaaat   117660
ccttgtgcgg ctgatccttc ttctggataa tggcgatcaa atgatgcgat tgcgcttgaa   117720
ctgtttcgcc ataagccaca atgttctaat tctcccaagc tatcaaggtc aatcgtttgt   117780
gaaagtggac gagttgacgc ttgaacatta cgccacacac cccatggacc atcgacgcca   117840
ttccatttag cagataagga acgaatatag acgttaccag atcttacagt ataacgctga   117900
gtgccagcaa attggccggc cacaaacact tctagtacac ctacggcatt ttcttctggg   117960
aatttatttg ctggttgcgc atttgttgaa gtagatttcg accaaacacc aagatattct   118020
tcaatgggcc catacgtatc taaattagca tcagtaggta attcgccatt attttttata   118080
aatgttgtgc tattgacatt tatgtcagat ggagttaagg taatgtcctt tgacccatca   118140
aaagatatac cattaatttt cctaggtgtt tgcaatttag tagctgtgct agaatttcca   118200
attaaagttc cagttatatt ttctgtaacc tctaaagacc catttatagt tcctccatat   118260
tttaaaccta attctataac actacctgag tcatcttttg tgaaaattgt tttatctttt   118320
aagtttatag ccaattcacc ttcggctaat actgaagcag caggacgttg acctgcagtt   118380
ttgcttcttt taaattgtat ttgttttaaa gtagccataa gtcctcttaa taatagccga   118440
aatcttgaac agaatcctta attacgattt ggtcaaatcg tggaacgtgt gaaggttgag   118500
atgcaggatt ctgtgaaaaa aggtttggcg cagttaaatt tcctgtcata gtgtctccag   118560
```

FIG. 17LLL

```
                                    sequence.txt
agcgtaatac cctagagttt gcatttgctg taacagtatt tattgctcca tcaacataat    118620
ctttgcgagt aacatcagat gctgcggaag gagtagatgt aacagttacc gatggagccg    118680
ttacagccct ggtaaatgtt gtcaaacctt ctggcgtaat agtaatttgt ccagtagtga    118740
tttcactacc tgcaggtcta aaactaatac caccggaaga gccgccaact acaagagtat    118800
taccagtgcc gccaccagaa cgaattcgga tagggtttc attattactt aattgaagat     118860
aactatttac cccgtaatta atagtaattg gaccggcgta agtaccacca ttagctttag    118920
aaacgaaatc gttatcagct gcctgcggtt tattatattc tgaatatatt ttaaatgatt    118980
tgtagagtac atcgtcaccg gctgaattca atggaaaatt ccttgatgc caaatgacag      119040
atccacccac agttgaacct acttttaaat cagccattat atgccccttt attttaatat    119100
tatttataaa gaaaaaggga acccgaaggc tccctcagtt taaacttctc taaattcctg    119160
tccaaacact ttgccagttt tagaagaggc ttgtgtagga agtaccatta tatctggagg    119220
tgaagccgat tcacagacat aattaacgcg aataccgttg acgccaaatt cggcaggttt    119280
tgaaatgccg ccatttcttg atacttcaga aaaacttaaa tttctcatgc cgccttgacc    119340
tgcttgagca gttctttgtg catatatcgt aaatcctacg gcgttttctg gaacaactac    119400
atagtcttct tttaattccc aagacccagc ttgcccagta aactcagctt gggtcgagga    119460
aatatatcca tttgatgcat cataaaaacg aatggatatg tttgtagttc caagatcaag    119520
taaatcagca tcagcatata actgtgcttt aagataaaga acatcaccag gaattaaatt    119580
atagtcagaa agtttactta tagcagctga agttggcaat cgcgcaattt cgttattagt    119640
tccaccaact gctgacatga attgctctac actttcataa gttcttttg gaaatcctgt     119700
cgctccgacg tcttctaaac tatcaaatac aacatctaaa atagtttgat aatcatctgt    119760
gcttttctcta ttacttagtt taacatgctc taatgcaata gctcttttag aagaagtata   119820
aaaagcagca tatgatacgt caaatcttga caatactgaa tctgatggaa aaactgaagt    119880
tcctgctccc cttaaccaag ataccacttc aggaggaaaa ttaaccttc cgctagttaa     119940
tatagcaaca agtctattgt ttgacaaaga attcatgaaa ctgacaaaag cggcagatgt    120000
tgtattgttt gaagcagaaa aagcatatga cttgctatca actaatgctc ccgtagaagg    120060
gtcaaaaact cttaaatgaa gacctgcact aaatgtttga tttccaacgg gattatcctg    120120
aaatttaaca tatggccccg cagtagaaag cgggcaagaa cccgctatgc ttattttgta   120180
tcttactgaa ttactttccg ataaaaatgg cgtttggacg tatccttgtc caaactctgc    120240
cataaatttt tccataatac ctcttattca acccattcaa atttaacagt tttattcact   120300
gggtcaggaa taatgcgaac attaccaatt cgtaagaaat cacgaatagt aagattacct    120360
attattccat tatcagatgg gattgctcct atatccgaag gttgaggagg gttacctcca    120420
tcaaatacct gaacaaaact tgaccaagaa tttttagttt tctgccatgt acgcgtccag    120480
```

FIG. 17MMM sequence.txt

| | | | | | | |
|---|---|---|---|---|---|---|
| cgagtggtac | gtgcttctgg | ggtcgttgga | taagtaatcc | aatcttggta | aagcgaatca | 120540 |
| agtgtgttac | caaactgagt | caatgtacca | ggagatttaa | cttcttcgcc | acgttctaag | 120600 |
| tatggaagcc | cagtcacttc | attagttttt | tcaaccattt | taaaataacc | cgggaactgg | 120660 |
| ttataagtgg | ctgaatcgtt | aatatcaatt | gaccagaatc | ctacagtatc | agatgttgga | 120720 |
| gcgcgggtgt | ataaatcaga | tgttttagtg | ccctgagaac | gaattctcga | gttaacagtc | 120780 |
| aaaccgcctg | aatttatagt | agcacctttg | gcaatgatta | agctttcacc | aatcgttact | 120840 |
| tggccagatg | cattattaat | agctaaagga | cgtaatccat | taaatccacc | agtctgatca | 120900 |
| cccgatgcag | taagcataaa | attcgttact | gatccatcat | tgcgaacaat | gaaaccataa | 120960 |
| tttccgttaa | tagcacggaa | agcatttgcg | cttcgagaaa | taatttcacc | agttgcagtg | 121020 |
| actgaattac | caaatgttgc | tacaccattt | gcattcaatg | ttcctgaagc | attaacattt | 121080 |
| atcggtgtta | ctgtaccgtt | gatattaaat | gttatatttc | cagctttatt | acgctgagaa | 121140 |
| taaaaatgac | tagacgtttc | atcactaact | tcaaatacgg | tagaacgtgt | tgtgtctgat | 121200 |
| tccccgctaa | attgatttcc | ccacactctg | actgtcatcg | tttgagccgg | gtttgttcca | 121260 |
| gtttgaggtc | ctttctcaaa | aatcagacga | gttgccgttc | cagtattaga | aatagttaat | 121320 |
| gtactatttg | ctgaaactga | tccaccgaat | gtagcagtac | tagatgatac | aagaggggca | 121380 |
| cccagattcg | tttgttgggt | taaggttagt | gaaccattaa | ctgtttgtgc | aatgtcccta | 121440 |
| cgaatgaact | ggagcgaatc | tagaccatct | aataaattac | tatctacagc | ttttgctttt | 121500 |
| aatggcaaat | aatttgctaa | tacgcgattt | aattcatatg | gtgatactgc | ataaccattt | 121560 |
| ttctcatatg | attctaatgg | ctgtgttgaa | cctaccgtat | cattaccaac | aaacgttaat | 121620 |
| gaaccagaag | aagttttaac | aaaccctctt | atcagagtag | ttgctgccca | agttggttca | 121680 |
| ctctgcacaa | tccattttaa | attttttgga | gatacagcag | tatttgctga | cgttccagtc | 121740 |
| acagtttcag | actgagttgc | aactttaata | acaccttctt | gcgattcggt | agatttagta | 121800 |
| cctaaaagct | ttttaggagt | tattaaaaca | ttatctaatg | ttcctgcagc | agcttcaact | 121860 |
| tgtgtagcta | cacgaagtgt | accacgctgt | gtctcatttg | cttcaagaat | attaagggta | 121920 |
| taatggtccc | agagagttcc | tgattcaact | aatccagata | gagcaacaac | agaagtacga | 121980 |
| tcagtactat | taaatctggt | tttaattttt | aatggtgtag | agatacgagt | atcgtcgacg | 122040 |
| cctgcgtcga | attcaacttg | cgtagcaatt | tcagctatac | cacttaaact | ttcagttgct | 122100 |
| ctacggtcat | ttaaagtttt | aggagtgact | gcgcgagtat | aatcagttcc | tgtattaact | 122160 |
| tcgctttgcg | tagcaatttc | aattaaacca | attcttccat | cagttgatgt | cttttatgt | 122220 |
| aacgtttctg | gtgttacaac | cgcatttgcc | catccttctt | ggctttgtcc | agcaattact | 122280 |
| tcactttcaa | ctgctaaaat | tactgcgcct | tgttgcgttg | gagtagcttt | atactgatcc | 122340 |

FIG. 17NNN sequence.txt

```
aaagctttag gtgaaacaac taaattatta gtgtttttat tataaacatt cgtaccattt    122400
aattcacgac tagaagctgg agtagctcct gcggtagata caaaagttac aataccagat    122460
aatgattcag aaccttgacg agcttgaagc tttttaggag tgatgattgt agtatcatca    122520
gtacctgtat tagtttcctg ctgcgtagca atttcagcga cacctctacg agtttctgta    122580
gcagttcttt cattcagctt tttaggagtg atgataaggt catctgcaaa agagaatgtg    122640
gtgttctgat ttacttgagc agtagttgct attcttgcaa tacctctgcg agtttcagta    122700
gcagtacgat tagctaacgt ttctggagta attgccaatt cttttttgcgg agaattttct   122760
aaatcagcat ttgcttgagc ttgtgtagct aaagcaatta cgcctaatct tgctctagta    122820
gaagcattta aagagtctac tctttctaca gttggaacgt tttgctgtac aacccagtat    122880
tttccatcag aatcttctat ataagcaagt tgtaaaactg aacataatt agtttcaccg     122940
ttaaaaacta attcttgaac tgttacccat tcagcttcag gcggatattc tgaacgtttt    123000
gggaattgca gcaattgaac tgaagaagca attttatctt caccagcagc tttgatttta    123060
actgtttgtc cttttctcat gtaattcatg gaaattttaa cagtatcacc aacagaaata    123120
tcagtcggaa gctgaagttc aattgtttgg gttgttccat tattcgcgcc aaataccatg    123180
acttcttcat ttggacgaat atttgaatta gttgttataa tgcgtaaacg tgctttacta    123240
tccccgtcaa acaatctcca caatttctca ttatcgtcaa acatcaagaa accgtcaatc    123300
gatgtacggc cttcaatgga atgagttcca acttcttgta ctgaagtcgt ttcatcgtat    123360
gtagtaacaa ttgtatgata aagtggattc agtttatcta aatcaacgaa attaataata    123420
tcgccatgat tagcaaatct cggaagttta acattaattg gtgcagcaga agtaaatcta    123480
cgtacgataa aatcattaga ttgtgcttga tacgcagtcg atggagtaac aatcgcagct    123540
tctctgctat aatcagcaac atacatttgc cacaaacgat tattaaaaat gaatatcatc    123600
tgtgactttg gatgagtcat taaaactgaa cgtacttgtt cacctctaaa attgacaata    123660
ctctgatttg aagaatttat tttaacctga tttatgccag gttttccacc gatatcttga    123720
attattacgg tttctccatc aagcggagaa ggtggtaaag taaactcaat gtcattgcca    123780
actgatgtat ctactgaaat tgcttctccg gattttaatt gatatggtcc agatgataca    123840
gttgtatata cagcatcagt acgtaatgct ttccaacgaa ttctattaaa atttccagca    123900
ggttttggaa tattatccgt tgctgcccaa aaacgattat tataaatgat tacaaaatct    123960
tttaaatatc cacgagttgg atcatattgc tgaactgtgt tttcttgaat taagtaatca    124020
acgttaacac cgtcagttcc tacggtacga tcagctaaag ctacgttgat tattttatcg    124080
ccacctgcgt ccagaccatc ttctgctctg aactttcttt taatctcggc cattctcccg    124140
ggctcctatt gtgttttcaa taataagtat ttatacctgt ttactttaag atttagatag    124200
tatataatag aaatctcact aattgaacga ggttcatatg gatttagaaa tgatgctgga    124260
```

FIG. 17OOO sequence.txt

```
tgaagattac aaagaaggaa tttgctttat tgactttagt caaattgctc tttcaactgc   124320
tctggtaaac ttcccagata aagaaaaaat taatttatcg atggttcgtc atttgatatt   124380
gaactcaatt aagtttaatg tcaaaaaagc aaaaacgctt ggatacacta aaattgtgct   124440
gtgtattgat aacgcgaaat ctggatactg gcgtcgtgat tttgcttact attacaagaa   124500
aaaccgtgga aaagcacgag aagaatctac ttgggactgg gaaggttatt ttgaatccag   124560
tcataaagtt atagatgaat tgaaagctta tatgccatac attgttatgg atattgataa   124620
gtatgaagca gatgaccaca ttgctgttct tgttaaaaag ttctctttag aaggacataa   124680
gattttaatc atttcatcgg acggtgactt tacacagctt cacaaatatc caatgttaa    124740
gcaatggtca ccgatgcata agaaatgggt taaaattaaa agcggttctg ctgaaattga   124800
ctgtatgact aaaatcctta aaggcgacaa aaaggataac gttgcttcag ttaaagtacg   124860
atctgacttt tggtttacca gagttgaagg tgaacgaacc ccttcaatga aaacttcaat   124920
cgttgaagct attgctaatg accgtgagca agctaaggtg cttctcacag aatctgaata   124980
taatcgttat aaagaaaatt tagttctaat tgattttgat tatattcctg ataatattgc   125040
ttcaaacatt gtgaattact ataattcata taattacca ccgcgtggca aaatttattc    125100
atattttgta aaagcgggtc tttctaaatt aactaatagc attaatgaat tttgaggtga   125160
ataatggcta aaaagaaat ggttgaattt gatgaagcta tccatggcga agacttggct    125220
aaatttatta agaagcatc tgatcataaa ctgaaaattt ccggttataa tgaactgatt    125280
aaagatattc gaattcgtgc taaagatgaa cttggcgttg atggtaagat gtttaatcgt   125340
ctattagctt tgtatcataa agataaccgt gatgtgtttg aagctgaaac tgaagaggta   125400
gttgaacttt atgacacagt tttctctaaa tgatattcgc ccggtcgatg agaccggtct   125460
ttcagaaaaa gaactttcaa ttaagaaaga aaaggatgaa attgcaaagc ttcttgaccg   125520
ccaagaaaat ggatttatta ttgaaaaaat ggtagaagaa tttggaatga gttatcttga   125580
agctacgaca gcattcttgg aagaaaactc tattcctgaa actcaatttg ctaaatttat   125640
tccttcgggt ataattgaaa aaattcagtc agaagccatt gacgaaaatc ttttacgtcc   125700
ttctgttgtt cgttgtgaaa aaactaatac attagatttt ctgctatgat taaactccgc   125760
atgcctgctg gtggtgaaag atacattgat ggtaaatcag tttataaatt atacttaatg   125820
ataaaacagc atatgaatgg aaagtatgat gtaattaagt ataattggtg catgcgggtg   125880
tctgatgccg cttatcaaaa gcgaagggat aagtattttt tccagaagtt atcagaaaaa   125940
tataaattaa aggaacttgc tttaatttt ataagtaatt tggttgctaa ccaagatgct    126000
tggattggtg acatctctga cgctgatgca cttgtgtttt atcgtgaata tatcggacgc   126060
ttaaagcaaa ttaaatttaa gtttgaagaa gatattcgca atatttacta ttttagtaaa   126120
```

FIG. 17PPP sequence.txt

```
aaagttgaag tttctgcttt taaagaaatc tttgagtata atccaaaagt tcaatcaagt    126180
tatattttta aactacttca atcgaatata atttcgtttg aaacgtttat cttgcttgat    126240
tcgttttaa  atataattga taaacatgat gaacagactg ataatttagt ctggaataat    126300
tattctataa agttaaaggc ttatagaaaa attttaaata ttgattcaca gaaagctaaa    126360
aatgttttca ttgaaactgt gaaatcttgc aagtattaat tgcttattat aaataagatt    126420
ataattatct cactgaccag ctatgaggtc atacatcgtc atagcaccaa ctgttaatta    126480
aattaaaaag gaaataaaaa tgtttaaacg taaatctact gctgaactcg ctgcgcaaat    126540
ggctaaactg gctggaaata aaggtggttt ttcttctgaa gataaaggcg agtggaaact    126600
gaaactcgac aatgcgggta acggccaagc agtaattcgt tttcttccgt ctaaaaatga    126660
tgaacaagca ccattcgcac ttcttgtaaa tcacggtttc aagaaaaatg gtaaatggta    126720
tatcgaaaca tgctcatcta cctacggtga ttacgattct tgtccagtat gtcagtacat    126780
cagtaaaaat gatttgtaca acactgacaa taaagagtac agtcttgtta acgtaaaac    126840
ttcttactgg gctaacattc ttgttgtaaa agacccagct gctccagaaa acgaaggtaa    126900
agtatttaaa tatcgtttcg gtaagaaaat ctgggataaa atcaatgcaa tgattgcagt    126960
tgatgttgaa atgggtgaaa ctccggttga tgtaacttgt ccgtgggaag gtgctaactt    127020
tgtactgaaa gttaaacaag tttctggttt tagtaactac gacgaatcta aattcctgaa    127080
tcaatctgcg attccaaaca ttgacgatga atctttccag aaagaactgt tcgaacaaat    127140
ggttgacctt tctgaaatga cttctaaaga taaattcaaa tcatttgaag aactgagcac    127200
taagttcagt caagttatgg gaactgctgc aatgggtggt gccgctgcaa ctgccgctaa    127260
gaaagctgat aaagttgctg atgatttgga tgcattcaat gttgatgact caaaacaaa    127320
aactgaagat gatttatga gctcaagctc tggcagttca tctagtgctg atgacacgga    127380
tctagatgac cttttgaatg acctttaaca gattatatta ctaattaatt ggggacccta    127440
gaggtcccct ttttatttca aaatttttt cacaaaactg tttacatcct tgtccttcca    127500
tggtactata caactatcgg caatactgct gataattaaa gaggaaaata atatggctaa    127560
agttgatatt gacatcgttg attttgaata tattgaagaa attattcgta atcgttatcc    127620
tgaacttagt atcacaagta ttcacgatga tcccaattat tgcaattttt ctattgtcat    127680
tgaaggtcct cttgaagacc tcacccgctt tatggctaat gaatattgtg atggtatgga    127740
ttctgaagac gcagaatttt acatgggatt gattgaacaa taattatcaa ggggctatta    127800
caagccccgt taaaatgagg aaaacgtaat gtatattggc aaaaagtatg agcttgttcc    127860
aagacttatt gatacattta ttaattatcg cccacgttct aattcatcga tagttaaaat    127920
tattcaagaa aatggtggat ggtttgaagt taaagaagct ttctttgttg atggatttag    127980
agtaataaaa cacattgaat gcgcaaatgg aaagcatttt tactttaacg tttgtgaaga    128040
```

FIG. 17QQQ sequence.txt

| | | | | | |
|---|---|---|---|---|---|
| cgaatttcat | tgttttcgtg | agtataaaga | accgacttct | gaagaagatg | gagccgaaga | 128100 |
| catagtttct | ggcgtaacaa | aaattcactg | cattgttgac | gaaaataatg | tagatgaaat | 128160 |
| cattgaactt | ttgcgaaaaa | ctttcaaaaa | gtagtttaca | acagggtagt | agtgtgatac | 128220 |
| tattaccccta | tcaaaactaa | tggagaaaag | aaaatgttcg | caccttatat | tatggcagca | 128280 |
| gttatgttgg | tctgtttata | tcttttgatt | aaagcttgct | aaggagaata | aaatgagatt | 128340 |
| acaacgccag | agcatcaaag | attcagaagt | tagaggtaaa | tggtatttta | atatcatcgg | 128400 |
| taaagattct | gaacttgttg | aaaaagctga | acatctttta | cgtgacatgg | gatgggaaga | 128460 |
| tgaatgtgat | ggatgtcctc | tttatgaaga | cggagaaagc | gcaggattct | ggatttatca | 128520 |
| ttctgatgtt | gatcagttta | aagctgattg | gaaaattgtg | aaaaagtctg | tttgaggaaa | 128580 |
| ataatatgtc | tggcattcat | gtaactggaa | ttgctcaagt | aaacatccgc | tgccaattta | 128640 |
| aaactgtacc | tggggtgact | catattactt | tatcacacga | cccatattct | cgtggaagac | 128700 |
| agttaactgg | cgtaattaag | tttttcggcg | gaattggcgg | aagcgaattt | actataggag | 128760 |
| atgacgaaat | tgttggctgt | aaattaaaag | ttcagaaggg | cgtgttagaa | cttttttagtg | 128820 |
| atgaagtttt | tgatgaaatc | tcacgagcag | ttaacaaagg | aatgttaacg | ttaattaaaa | 128880 |
| tgattaaagc | tagcggatat | gttactgatc | cttttaata | ggaggcaata | tgatttttgt | 128940 |
| atttgaattt | atgaatgatg | aattcgatta | tgcaattttt | aacgcattgc | ataatcctga | 129000 |
| tttaagtgaa | tttaatgaaa | tgttttctga | cgctttgagt | atgtcagaag | aatactgtgg | 129060 |
| agaatgtcaa | cgtgtttgtg | tgacagtctt | tgaaaacaaa | gaaaagacct | atgaagaatt | 129120 |
| attctttgat | gctaataaag | ccactgaatg | gtttgttgaa | agaggttttg | cgtaatgatt | 129180 |
| aaattggtat | tcgcttattc | tccaactaaa | acggtcgaag | gctttaatga | attagcattc | 129240 |
| ggtttaggtg | atggtttacc | atggggacga | attaaaaagg | acctccagaa | ttttaaagct | 129300 |
| cgtacagaag | gtacaatttt | gattatgggt | gctaaaacgt | tccagtcatt | atctacatta | 129360 |
| cttcccggtc | gtagccatat | tgtggtgtgt | gaccttgcgc | gtgattatcc | tgtaactaaa | 129420 |
| gacggcgatt | tagcacattt | ctatattact | tgggaacagt | acataactta | catttctggc | 129480 |
| ggcgaaattc | aagtttcaag | tcctaatgca | ccattcgaga | ctatgcttgg | tcagaattcc | 129540 |
| aaagtaagtg | taattggcgg | gcctgctctg | ttatatgctg | cgttacctta | tgcggatgaa | 129600 |
| gtagttgttt | ctcgcatcgt | taaaaggcat | cgtgttaatt | caacggttca | attagacgca | 129660 |
| agttttcttg | atgatataag | caagcgtgaa | atggttgaaa | cgcattggta | taaaatagat | 129720 |
| gaagtaacaa | cccttacgga | atcagtatat | aaatgagcaa | taaattaaaa | gttaaggatg | 129780 |
| ttcctaatgc | tatggccctt | tttatttgta | ggcagatgca | tcaagggcct | atgacaccaa | 129840 |
| aacaatatct | taaaggtgag | cgttctttag | gatttactcg | caaagcaaaa | caaatggtta | 129900 |

FIG. 17RRR sequence.txt

| | | | | | | |
|---|---|---|---|---|---|---|
| aattaggata | taagcctaac | tttgccaaat | atccttctac | atattcttgg | atgaactaat | 129960 |
| gaaacaatac | caatttttaa | ttaaagatat | cctggaaaat | ggctacgaaa | ccgatgaccg | 130020 |
| aacaggcaca | ggaacaattg | ctttgttcgg | tactaaatta | cgctgggatt | taactaaagg | 130080 |
| ttttcctgca | gtaacaacta | agaagctcgc | ctggaatgca | tgtatttctg | agttattgtg | 130140 |
| gttcttatca | ggaagtacta | acgtaaatga | tttgcgatta | attcaacata | attcattaat | 130200 |
| tcaaggcaaa | acagtttggg | atgaaaatta | cgaaaatcaa | gcaaagatt | taggatacca | 130260 |
| tagcggtgaa | cttggtccaa | tttatggaaa | acagtggcgt | gattttggtg | gtgtagacca | 130320 |
| aattatagaa | gttattgatc | gtattaaaaa | attgccaaat | gataggcgtc | aaattgtttc | 130380 |
| agcatggaat | ccagctgaac | tcaagcagat | ggcattaccg | ccttgtcata | tgttctatca | 130440 |
| gtttaatgtg | cgtaatggct | atttggattt | gcagtggtat | caacgatcag | tagatgtttt | 130500 |
| cttgggttaa | ttgaggcctg | agtataaggt | gacttatact | tgtaatctat | ctaaacgggg | 130560 |
| aacctctcta | gtagacaatc | ccgtgctaaa | ttgtaggact | gccctttaat | aaatacttct | 130620 |
| atatttaaag | aggtatttat | gaaaagcgga | atttatcaga | ttaaaaatac | tttaaacaat | 130680 |
| aaagtatatg | taggaagtgc | taaagatttt | gaaagagat | ggaagaggca | ttttaaagat | 130740 |
| ttagaaaaag | gatgccattc | ttctataaag | cttcagaggt | cttttaacaa | acatggtaat | 130800 |
| gtgtttgaat | gttctatttt | ggaagaaatt | ccatatgaga | aagatttgat | tattgaacga | 130860 |
| gaaaattttt | ggattaaaga | gcttaattct | aaaattaatg | gatacaatat | tgctgatgca | 130920 |
| acgtttggtg | atacatgttc | tacgcatcca | ttaaaagaag | aaattattaa | gaaacgttct | 130980 |
| gaaactgtta | aagctaagat | gcttaaactt | ggacctgatg | gtcggaaagc | tctttacagt | 131040 |
| aaacccggaa | gtaaaaacgg | gcgttggaat | ccagaaaccc | ataagttttg | taagtgcggt | 131100 |
| gttcgcatac | aaacttctgc | ttatacttgt | agtaaatgca | gaaatcgttc | aggtgaaaat | 131160 |
| aattcattct | ttaatcataa | gcattcagac | ataactaaat | ctaaaatatc | agaaaagatg | 131220 |
| aaaggtaaaa | agcctagtaa | tattaaaaag | atttcatgtg | atggggttat | ttttgattgt | 131280 |
| gcagcagatg | cagctagaca | ttttaaaatt | tcgtctggat | tagttactta | tcgtgtaaaa | 131340 |
| tctgataaat | ggaattggtt | ctacataaat | gcctaacgac | tatcccttg | gggagtaggg | 131400 |
| tcaagtgact | cgaaacgata | gacaacttgc | tttaacaagt | tggagatata | gtctgctctg | 131460 |
| catggtgaca | tgtagctgga | tataattccg | gggtaagatt | aacgaccta | tctgaacata | 131520 |
| atgctaccgt | ttaatattgc | atcatatgct | acgttagttc | atattgtagc | taagatgtgt | 131580 |
| aatcttatcc | caggagattt | gatattttct | ggtggtaata | ctcatatcta | tatgaatcac | 131640 |
| gtagaacaat | gtaaagaaat | tttgcgtcgt | gaacctaaag | agctttgtga | actggtaata | 131700 |
| ggcggattgc | cttataaatt | ccgctatctt | tctactaaag | aacaattgga | atacattctt | 131760 |
| aaactcaggc | ctaaagattt | cgttctcaaa | gattatcagt | cccacggcgt | cttgaaagga | 131820 |

FIG. 17SSS sequence.txt

| | | | | | |
|---|---|---|---|---|---:|
| aaaatggcgg | tgtaatttca | atttaattgc | gaggatatat | gattttacga | tttaaagata | 131880 |
| cttctggtgc | agttctttt | acacttccta | atccaagtga | gctagaagtt | ccaggaccaa | 131940 |
| atcagcctat | tatcatttat | ggcaaaaaat | attatactca | taaaatgact | cgtgagtatt | 132000 |
| ttgataataa | aatttctaca | gttaaaactt | cttctgattg | ttactatgat | attactgttt | 132060 |
| taacggaaaa | acaatatgac | gaattatcac | cgcgcgggcc | gtctatgcca | ggtagtgaat | 132120 |
| aaatataaat | ccgactttga | tgtcaatatt | caccgcggta | cattttgggg | aaattacgtc | 132180 |
| ggtaaagatg | ctggcagccg | ggaggctgcc | attgaattat | tcaaaaaaga | ttttatacgt | 132240 |
| cgaattaaat | ccggagaaat | aactaaagca | catttagagc | ctttacgtgg | aatgaggcta | 132300 |
| ggatgcacat | gtaaaccaaa | gccgtgtcat | ggtgatataa | tagctcatat | agttaaccga | 132360 |
| ttgtttaaag | acgattttca | agttgaggac | ttatgcaatt | aattaatgtt | atcaaaagta | 132420 |
| gtggtgtttc | tcagagcttt | gacccacaaa | aaattattaa | agttttatct | tgggcagctg | 132480 |
| aaggaacatc | agtagatcct | tatgaattat | atgaaaatat | taaatcatat | ctccgtgatg | 132540 |
| gaatgacaac | tgatgatatt | cagactattg | tcattaaggc | cgctgcgaat | tctatttcgg | 132600 |
| ttgaagaacc | tgattatcaa | tatgtagctg | cacgttgttt | aatgtttgct | cttcgtaagc | 132660 |
| atgtttacgg | gcagtatgaa | ccgcgttcat | ttattgacca | tatttcttac | tgtgtaaatg | 132720 |
| aaggtaaata | tgaccctgaa | ttgttgtcaa | aatattcagc | agaagaaatt | acatttttag | 132780 |
| aatcaaaaat | taagcacgag | cgggatatgg | aatttactta | ttccggggcg | atgcaattaa | 132840 |
| aagaaaaata | tctcgttaaa | gataaaacca | ctggtcaaat | ttatgaaact | ccgcagtttg | 132900 |
| catttatgac | tattggaatg | gcattgcatc | aagatgaacc | tgttgataga | ttaaaacatg | 132960 |
| ttattcgttt | ttatgaagca | gtatctactc | gacagatttc | attaccaact | cctattatgg | 133020 |
| ctggttgtcg | tactccgact | cgacagttta | gttcatgtgt | tgttattgag | gcaggtgatt | 133080 |
| cgctgaagtc | tatcaataag | gcttccgctt | cgattgttga | atatatctct | aaacgcgctg | 133140 |
| gaattggtat | taacgttggt | atgattcgtg | ccgaaggttc | taagattggc | atgggtgaag | 133200 |
| tacgccatac | tggtgttatt | cctttttgga | aacatttca | gactgcagtt | aaatcatgtt | 133260 |
| cacagggtgg | aattcgtggc | ggcgctgcta | ctgcttatta | tcctatttgg | catttggaag | 133320 |
| ttgaaaatct | tctcgtttg | aaaaataaca | aaggcgtaga | agaaaccgc | attcgtcata | 133380 |
| tggattatgg | tgttcaactg | aatgatttga | tgatggaacg | attcggaaag | aacgattaca | 133440 |
| ttactttgtt | cagtccgcat | gaaatgggtg | gagagcttta | ttattcttat | tttaaagacc | 133500 |
| aagaccgttt | ccgtgaatta | tacgaagcag | cagaaaaaga | ccctaatatt | cgtaaaaagc | 133560 |
| gtattaaagc | ccgtgaacta | tttgaattgc | tcatgactga | acgttcagga | acagcaagaa | 133620 |
| tttatgtaca | gttcattgat | aatacgaata | actatactcc | gtttattcgt | gaaaaggcac | 133680 |

FIG. 17TTT sequence.txt

```
ctattcgtca gagtaacttg tgctgtgaaa ttgctattcc aacaaatgat gtgaatagtc   133740
ctgatgctga aattggattg tgtactctct ctgcattcgt actagataat tttgactggc   133800
aagaccaaga taaaattaat gaattggcag aagttcaagt tcgtgctctt gataatcttt   133860
tggattacca aggatatcca gttcctgaag cagaaaaagc taaaaagcgt cgtaacctcg   133920
gtgtaggtgt taccaactat gcagcttggc tggcaagtaa cttcgcttct tatgaagatg   133980
ctaacgattt aacacatgaa ctatttgaga gattacagta tggactcatt aaagcatcca   134040
ttaagctcgc caaagaaaaa ggaccttgcg aatattattc agacactcgt tggtctcgag   134100
gcgaattacc tatcgactgg tacaataaaa agattgacca aatcgcagct ccaaaatacg   134160
tttgtgactg gtcgtcgctg cgggaagacc ttaagctctt tggcatccgt aatagcacac   134220
tatcagcact tatgccatgt gagtcatctt cccaagtttc taacagtaca acggtatcg    134280
agcctccacg tggaccagtc tctgttaaag aatcaaaaga gggttccttt aatcaagtcg   134340
tgcccaatat tgaacataac atagacctat atgattatac atggaaatta gctaagaaag   134400
gtaataaacc ttatcttacg caagtagcta ttatgctgaa atgggtatgt caatcagctt   134460
cagcgaatac atactatgac ccgcagattt ttccaaaagg aaaggttcca atgtcaataa   134520
tgattgatga ccttttgtat ttttggtatt ttggcggaaa aaatttctat tatcataata   134580
cccgtgatgg ttctggtact gatgattatg aaatagaaac tccaaaagct gaagattgtt   134640
catcctgtaa attatgatat aatttgactc acggacgagt caccaactat taactaagcg   134700
gaaaatttat gagcacagtt tttaatacaa atccagttga tgttttaaaa gaacctatgt   134760
ttttggttc aggtcttggt attgcgcgtt atgatattca acgccataaa gtttttgaag    134820
atttgaccga aaagcaatta tcattttct ggcgtcctga agaagtaaac ttaatgatgg    134880
atgctgcaca gtttaataag cttcctcaat atcagcagaa tatttttact aataatctga   134940
agtatcaatc acttctagat agcattcagg gtcgtgcacc gtctgctgta cttatgtcat   135000
tgatttcaga cccaagcctt gatacatggg ttgctacatg gacttttagt gaaactattc   135060
acagtcgttc atatactcat atcatgcgaa atctttatac tgatccatcg aaggtatttg   135120
atgaaattgt attagatgaa gctattatga acgtgctga atctattgga cgttattatg    135180
atgatgttct gattaaaact cgttattggg aaaacgctaa agctgatatc gaataccaaa   135240
aagaaattaa tgcagacgaa gacgttattg aagatgctat tgagcatgag acatattgga   135300
agcgtgagct aatgaaatct ctttacctct gtttgcatgt aatcaacgca ttggaagcta   135360
ttcgttttta tgtatctttt gcatgtacct taacttcca taagaacatg gaaatcatgg    135420
aaggtaatgc caagattatg aagttcattg cacgtgatga gcagcttcac cttaaaggca   135480
cccaatatat tattcgtcaa cttcaacttg gcactgatgg cgatgaatgg gttaaaattg   135540
ctcaagagtg tgaacaagaa gcagttgata ttttcatgga agttaaccgc caagaaaaag   135600
```

FIG. 17UUU sequence.txt

| | | | | | | |
|---|---|---|---|---|---|---|
| attgggcagt | tcatttattt | aaagatggtg | atgttcctgg | attaaataca | aatagcatgt | 135660 |
| ggagctttat | tgattactta | actgtatctc | gtatgaagca | gtgtggtctt | ccatgcccaa | 135720 |
| ttaccgatgc | tccggttaaa | catccatatc | cttggattcg | tgaatatctt | aattctgata | 135780 |
| atgttcaatc | tgcgccacaa | gaagtagaat | tgtcatctta | ccttgttgca | cagattgata | 135840 |
| atgatgttga | tgataaagtt | atgatgagtt | ttaaaaaata | cttttaagga | gtgggccgca | 135900 |
| aggcccattt | tattatgaaa | gaaattgcaa | cagaatattc | atttattaaa | tatactgagc | 135960 |
| tagaattaga | ctacaacgga | agtataaaac | aattatctat | tccaaacaag | tataacgtaa | 136020 |
| tttatgctat | tgctataaat | gatgaacttg | tttatattgg | aaaaactaaa | aatttacgca | 136080 |
| aaagaataaa | ctattataga | actgctatta | accgtaaaga | caaaacgtct | gattctacta | 136140 |
| aatctgcatt | aattcatgct | gcgctaaagg | aaggaagcaa | agttgaattt | tacgcccgcc | 136200 |
| aatgttttaa | tctttctatg | acaaatgagt | taggtacaat | gacaatcgcg | acgattgacc | 136260 |
| tagaggaacc | actattcatt | aagctgttta | acccgccttg | gaatattcaa | cataagaaaa | 136320 |
| aatgatgctt | ccacatggag | tgtggtacta | tattcaaaac | acaaagagg | atacacaatg | 136380 |
| caagaacttt | ttaacaattt | aatggaacta | tgcaaggatt | cacagcgtaa | gttttttac | 136440 |
| tcggatgatg | taagtgcgtc | tggaagaact | tacagaattt | tctcatataa | ttatgcatct | 136500 |
| tattctgatt | ggttacttcc | agacgcattg | gaatgtcgtg | gaatcatgtt | tgaaatggat | 136560 |
| ggagaaaaac | cagtaagaat | tgcttctcgt | cctatggaaa | agttttttaa | cttgaatgaa | 136620 |
| aatccattca | cgatgaatat | cgatttaaat | gatgttgatt | acattctaac | aaaagaagat | 136680 |
| gggtctttgg | tatcaactta | tttagacggt | gatgaaattc | tgttcaaatc | aaagggttca | 136740 |
| atcaaatccg | aacaggcttt | aatggctaat | ggtattttga | tgaatattaa | tcaccatcgg | 136800 |
| ttgcgtgata | gacttaaaga | attagctgaa | gatggattta | ctgctaactt | cgaattcgtt | 136860 |
| gctccgacga | atagaatcgt | tcttgcttac | caagaaatga | aaattatttt | actgaatgtt | 136920 |
| cgtgaaaacg | aaacgggtga | atacatttca | tatgatgata | tttataaaga | tgctgctctt | 136980 |
| cgtccatatc | tagttgaacg | atacgaaatc | gatagcccta | aatgggtaga | agaagctaaa | 137040 |
| aatgcggaaa | acatcgaagg | ctatgttgct | gtgatgaaag | atggttctca | ttttaaaatt | 137100 |
| aagtctgact | ggtatgtgtc | tcttcatagc | acaaaaagtt | cattagataa | tccagaaaaa | 137160 |
| ttgtttaaga | ctattattga | tggtgcatca | gatgatctta | aagcaatgta | tgctgacgat | 137220 |
| gaatattcat | acagaaaaat | tgaagcattt | gaaacgactt | atctgaagta | cttagaccga | 137280 |
| gctctgtttt | tagttcttga | ctgtcataat | aagcattgtg | gtaaggatag | aaagacttat | 137340 |
| gcgatggaag | cgcaaggtgt | tgctaaaggt | gctggaatgg | atcacttgtt | cggtatcatc | 137400 |
| atgagcttat | accaggggta | tgatagtcaa | gagaaggtta | tgtgtgaaat | cgaacagaat | 137460 |

FIG. 17VVV sequence.txt

| | | | | | | |
|---|---|---|---|---|---|---|
| tttttgaaaa | attataaaaa | atttatccca | gaaggatact | aagctgttta | caagtccctc | 137520 |
| gtgttgtgtt | acagtagtct | tactgacata | acatgaggac | tttatgatgg | atttgcagct | 137580 |
| cattactact | gaaatggtcg | ttgaagcata | cggtgatact | acagatggga | tttctgtatt | 137640 |
| taaaggaaac | cgtcgagttg | gatatatcac | cgatcttaag | aaagatttag | ctaagcaagt | 137700 |
| caagcggaaa | acgaccatta | aagaatatcg | aaatcgtcgt | cttgagcaag | cccgtgatat | 137760 |
| gcttcctgat | gcggttgaag | agatgaaagt | cttttagaa | aatcagcttg | cgaaatatga | 137820 |
| ttgtgatgta | tttattaatc | agactcaacc | taatgttcat | atcaatagtt | gtaaatgcta | 137880 |
| tatcatcgtt | aatcctttga | ctggaaagca | tcgtcttgga | attagtaatc | caaatcgtag | 137940 |
| tgcatcggat | atggcagaag | atgttgaggc | atgctttaaa | atttctaaat | ctccagctga | 138000 |
| acatcatatt | ttaattaacg | gtctttctca | agacgatatt | atagaggtta | ttaaaacttt | 138060 |
| atgcatgtaa | gtaattttac | agctggattg | ctattacttg | taatagcatt | tggcggaaca | 138120 |
| tctattattt | taaaaaataa | ggtagaaaga | ttagaaacat | cagttactga | aattacaaaa | 138180 |
| acagccaatg | aaaacgcctt | agcattaaat | aatttgcgaa | ttcagtataa | ttatattgat | 138240 |
| gcgatgaata | ataaaaatcg | tgaggcaatt | gctgctattg | agcgtgaaaa | tgaaaaactg | 138300 |
| cgcaaagacg | caaagaaggc | ggatgtggtg | gctcataagc | caggattggt | tgaaaaacaa | 138360 |
| atcaacaact | ccttcaacaa | gttcgcagaa | gacatccagg | acctttctaa | atgattaaac | 138420 |
| tatcagcagt | aatattatct | attggtcttc | tagttggttg | ttcgacaaag | cctctagaag | 138480 |
| taaagaaaga | aacagttcat | cctaattggc | ctgtgcaaat | aaagtcatat | gacgaagcta | 138540 |
| aactatcttg | gcaagttaaa | gttattgatg | gtaaagcttg | ggtaggtatg | ccatttgaag | 138600 |
| attctcagga | atttcgtatt | tggcttaatg | atgtaaaacg | atatgtacat | gaccagaaaa | 138660 |
| ctatgatatg | ttattatcgt | caagagctaa | aagaggataa | atgtaaatga | tttcatggta | 138720 |
| tcaatttgaa | catctaaaag | gattaattta | tgaatccgag | atggctgcaa | tgatttatgg | 138780 |
| acgacagatt | caacgattag | aatctttacc | tccaactaat | gatgttttat | tagctcaatc | 138840 |
| acgtgctaat | ctcaaaaatg | aatatcaaaa | taagtggggt | aaagcatcta | aagacttgca | 138900 |
| tgattatatt | caatcattag | ttgagaaaaa | taaatgaaaa | ctctgctaga | acgttatatt | 138960 |
| gaatgctcgg | accgttacat | tgatgtatgc | catgacaatg | catcaagcat | tagcgaagac | 139020 |
| attgaacatg | ctaaagcttt | agatgatgct | ggtaaagccc | tacgaaaaga | agcaaaagct | 139080 |
| cgtgggtttg | atatgtatca | gcttaaaaat | cacatgataa | aatttatttc | atctaatgtt | 139140 |
| cagagcaaat | cggtgaatca | atcaacagct | gaattatata | aagggcggcg | tgagcataat | 139200 |
| attcgtattc | ttgaagtttt | cttaggaatt | aaatgatgaa | aaagattatt | ttgactattg | 139260 |
| gctgtcctgg | ttctggtaag | agtacttggg | ctcgtgaatt | tattgctaaa | aatccagggt | 139320 |
| tttataatat | caatcgtgat | gactatcgcc | aatctattat | ggcacatgaa | gaacgcgatg | 139380 |

FIG. 17WWW sequence.txt

| | | | | | |
|---|---|---|---|---|---|
| agtacaagta | taccaaaaat | aaagaaggta | tcgtaactta | catgcagcat | gatgttgcta | 139440 |
| acatgattct | ctgccaagac | gcaacgaagg | gtgtaattgt | ttcagatact | aatctgaatc | 139500 |
| ctgaacgacg | taaggtttgg | gaagagtttg | ccaaagagct | tgggcatcaa | attgaatata | 139560 |
| aagtgtttga | tgttccttgg | actgaattgg | ttaaacgtaa | ctcaaaacgc | ggaactaaag | 139620 |
| cagtaccaat | tgatgtttta | cgctcaatgt | ataaaagcat | gcgagagtat | ctcggtcttc | 139680 |
| cggtatataa | agggactcct | ggtaaaccaa | aagcagttat | ttttgatgtt | gatggcacgt | 139740 |
| tagcaaaaat | gaatggtcgt | ggtccttatg | accttgaaaa | atgcgatatc | gatattatta | 139800 |
| atccaatggt | cgttgaacta | tccaagatgt | atgctcttat | gggttatcaa | atcgtagtcg | 139860 |
| tttcaggccg | tgaaagtgga | accgaagaag | atccaacgaa | atattatcgt | atgacccgta | 139920 |
| aatgggttga | ggacattgct | ggtgttccat | tagtcatgca | gtgtcaacgc | gaacaaggcg | 139980 |
| atacccgtaa | agatgatgta | gttaaagaag | aaattttctg | gaaacacatc | gcaccacatt | 140040 |
| ttgatgtgaa | attagctatt | gatgaccgaa | ctcaagtagt | tgaaatgtgg | cgccgcatcg | 140100 |
| gtgttgaatg | ctggcaagtc | gcttcgggag | atttttaatg | gcttggcacc | atgaaacttg | 140160 |
| ggctttgtta | ttgtaaatag | cggtttagtt | ggtactagta | atgggcaatt | ttgtgtattt | 140220 |
| actagtgaaa | atagagcatg | ggaggaatgc | cttaaattaa | gagaaaagaa | tcctgatgtt | 140280 |
| gaactagtag | taaagaaaac | taaactgcct | ttaccatgga | aaacgtatga | ataacctaga | 140340 |
| aaagatttat | cgtctttgtg | ataaaattga | aaaagaaaag | aaatatctat | tttgtctatg | 140400 |
| gcctattgtt | gacggaagag | taggcctaga | tgttcttgat | tatgaaacag | aagacaaagt | 140460 |
| agatggcgca | acttttgata | acgctttgga | tgttattgat | tggctcgaag | aaaattatgt | 140520 |
| gaggtaaata | tgtttccgac | ttactctaaa | atcgtagaag | tagtgtttag | ccaaattatc | 140580 |
| gctaataaca | tgtttgaaaa | gcttgataat | gcagctgaac | ttcgaatcca | cgctcaagtg | 140640 |
| actcatgtat | tgaacgcttt | gcttccagac | caggtggatt | ctattgccat | tacgttgtat | 140700 |
| ccaggttccg | cgcatatcat | tgttgtattt | ggtcttgatg | ctgagctagt | tatcaaaggc | 140760 |
| gacattcgct | ttgaatcaca | gacatcagaa | ttcaaagcaa | tttaatagtt | tactttacgg | 140820 |
| tagagttgtg | atattatagc | tctaccaaaa | caaatgagga | aattgaaatg | agcgaatggt | 140880 |
| ttgaagaaga | taaggtttat | cgctttaaag | ctggatataa | agatattttt | aatgaaactt | 140940 |
| gcggggctaa | taaacgaatt | gcccagttta | ttggggaaaa | ttcatttaaa | gtaaaaatag | 141000 |
| atcctgcgaa | aaatgttatt | agcattaaac | gtgaaattga | tgattgttgg | tataaagctg | 141060 |
| ttgatgtaat | gggtgaatcc | tataagtta | gcccgttatt | ttcaattgct | tatatgttag | 141120 |
| aatattcttt | tttcgaagaa | gttcaaaaag | atgattctgt | aagtaaattt | gaaattaaaa | 141180 |
| ctgataaaga | aattaagtgg | aaagtagtag | gtattactgg | ttgtatgttc | tatatctatg | 141240 |

FIG. 17XXX sequence.txt

| | | | | | | |
|---|---|---|---|---|---|---|
| ctcaaactga | tacgaaggaa | gaagctaaaa | agaaagctct | agaatatctt | gaagagcatg | 141300 |
| aagaaggtcc | ggtaatgatt | acccaagatg | ctgaattagt | ttctgtcaaa | ttagttaaaa | 141360 |
| atgttgaaag | taaggagcta | ggatcaacat | gctaagcgaa | aaaccaatta | ctgttaaaga | 141420 |
| attccaagaa | aaagttaaac | tatttgctca | agaattggta | aataaggttt | ctgaacgatt | 141480 |
| tcctgaaacg | tcggttcgtg | ttattaccga | aactcctcgt | tcagtattag | taattgtgaa | 141540 |
| tccaggtgat | ggcgatcaaa | tatcgcatct | taaactggat | tttgatggat | tagttgaagc | 141600 |
| acaaagggtg | tatggcgtac | tatgatgaat | ttaactgata | taattgataa | ttgtcttgaa | 141660 |
| aatgatactg | gcgatcatag | agcgcttgat | tctgaaacag | cacagttcat | tagaataact | 141720 |
| ttaatgaatg | atactctggt | gaatagtatt | catccttctg | tgtatgatgc | tattattgtg | 141780 |
| acgaagtatc | cggttgagct | tcacaaaaag | atgactggcg | cagtttttat | tgataagaaa | 141840 |
| aaccgcttta | agatgggca | gaatataact | agttctgtta | ttaaaagtat | aactaaactt | 141900 |
| cgtcacgaaa | tttatcgtgt | tgaaactgct | aaatctgctt | atctggtgat | tatgaaatga | 141960 |
| aagcgagtac | agtacttcaa | attgcatatt | tagtatcaca | ggaatcaaaa | tgttgctcct | 142020 |
| ggaaggtagg | agcagtaatt | gaaaagaatg | gacgtattat | ttctactggg | tataatggtt | 142080 |
| cacccgcagg | cggtgtgaac | tgttgtgatt | atgctgctga | gcaaggttgg | ttgctgaata | 142140 |
| agcctaaaca | cactatcatt | caaggccata | agcctgaatg | cgtatcattt | ggttcaactg | 142200 |
| atcgctttgt | cttggcgaaa | gaacatcgta | gtgctcactc | ggaatggtca | tctaaaaatg | 142260 |
| aaattcatgc | tgaactaaat | gcaatttgt | ttgctgcacg | aaatggttct | tctattgaag | 142320 |
| gcgctactat | gtatgtaaca | ctttctcctt | gtccggattg | cgcaaaagcg | atagctcaat | 142380 |
| ctggtattaa | aaagctggtt | tattgtgaaa | catacgataa | aaataaacct | ggctgggatg | 142440 |
| atattctgcg | aaatgcaggt | attgaagtgt | taatgttcc | taagaaaaac | ttgaataagt | 142500 |
| taaactggga | aaatatcaac | gaattctgtg | gtgaataatg | aaatttcgtt | tggtaaagct | 142560 |
| cacagcaatt | agttcttatt | ctaacgagaa | catctcattt | gctgtagagt | ataagaaata | 142620 |
| ttttttctct | aaatggaaac | agtattataa | aactgattgg | actagtattg | ataggccata | 142680 |
| tagttggaaa | tctgatttag | aaaaatgcca | aaaattactt | tccactctta | agaacgtgg | 142740 |
| aacaactcat | attaaaactg | taataggtaa | atgaatgaaa | ctgacgactg | aacagaaagt | 142800 |
| agcaattcgt | gaaattttga | aaactaaatt | gtccatgggt | atttcaaacg | tagtttttga | 142860 |
| aaagtctgat | ggtactattc | gtattatgaa | atgtactcgt | gatgcagact | ttatgccaac | 142920 |
| catgcaaact | ggtaaattga | ctgaatctac | tcggaaagaa | tctactgata | tgattccagt | 142980 |
| atttgatgtt | gaacttggtg | cgtggcgagg | ttttctatt | gacaaattga | tttccgttaa | 143040 |
| tggtatgaaa | gttgagcatt | tgctccaatt | tattggtaaa | taaatgcttt | aagaattatt | 143100 |
| tgttattatt | aattcatctg | ttaacaaaaa | ggaaaaacga | tgtctgaagt | acaacagtta | 143160 |

FIG. 17YYY sequence.txt

```
ccaattcgtg ctgtcggtga atatgttatt ttagtttctg aacctgcaca agccggtgat   143220
gaagaagtta cagaatcagg acttattatt ggtaaacgta tccaaggcga agttcctgaa   143280
ctgtgtgtag ttcactctgt cggtcctgat gttcctgaag gtttctgcga agttggtgat   143340
ttgacttctc ttccagttgg tcaaattcga aatgttccgc atccttttgt agctctgggt   143400
cttaagcagc caaaagaaat taaacaaaaa tttgttacct gtcactataa agctattccg   143460
tgtctttata agtgatataa ataataatat gaattgggtg tcggaataat aagttaaccg   143520
aacaattcta tgtggtagtc tacaactgag agatctgtcg aaagaagatg aaattcagaa   143580
gaacgtgact accgagtttt aatctctaac gagaattttt aaatgattaa acaattacaa   143640
cacgctcttg aactgcaacg aaacgcatgg aataatggtc acgaaaacta tggcgcatct   143700
attgatgttg aagccgaagc tcttgaaatc ctgcgttatt tcaaacatct gaatcctgct   143760
caaactgcat tagctgctga gcttcaggaa aaagatgaac ttaaatatgc taagcctctg   143820
gcttctgctg cacgaaaagc agttcgtcat tttgtggtaa cactgaagta atttattgga   143880
gattcactgc cttagtgtga gctaaatcga ggagccgtcg aactgtctga ttaatgattt   143940
gcgaatcatt atagttttaa gaccccggca gttttacggt gtacctcttg aatgttattt   144000
tatagcggca agtgcatgct accccgaggt gatggccaat cgggagtacg cctcaaggcc   144060
tatatatcca tcagtatata tcttatcctc gagtaatcgg acccggaacc tttaagctaa   144120
cggtgtgcaa cagataagag ctataaggta tgttgacgag gtttatggtt atcctgtcgg   144180
taaatattca aaacctaagt acccctttga gggattgcgc aggcaatgcc aataagtcct   144240
gcatttcat ttaaaagaga atttataatg gcaaaacaag ttaaagcaaa gaaagcagtt   144300
gaaaagaaag ttggtgattc taaacgcgct ggctacaagc gtgggtcgaa ctctcgtatc   144360
aatcaaactg ttgagaagat catgcgccga gcacgtgcgg ttcttcgaga tgatgcttct   144420
cgttttggta agcagaaagc ataagttgag gactccttcg ggagtccttt tttatttttcc   144480
aaagattgca caaagttgtt tacagtacgg ttcctttgtg atagtattat cttacacaaa   144540
caaaggagaa taaaatgaac tacatcaact ttgaacgtaa atatgtttct aatggtattg   144600
caggttctat tgatactatt tgtctctgga acatcaaaaa cggatcagta tgcgaaatcg   144660
atcagtatat gactcctaat tacgtttata tgcgatttga aaatggcatc acggtttcaa   144720
tcactaagga aggttccaac tttaaaatcg ctctagatga tgatttccgt gaacgcgatt   144780
tagggactca tccttgttgg aatggcgttc atcgcaagct tctgattaaa acttggattc   144840
gtcatattct gagtaacaaa gctaaacctg agcatcttga agcaatcttt gatgtagttc   144900
ttaacgaatt tgatatttaa gcttcggccc cttactgagg aaaatattat gtttatgact   144960
acttattttg atacccgcaa aaatttctgt gaagttgttt tctcaaaggc gcctaaagac   145020
```

FIG. 17ZZZ

```
                                    sequence.txt
cttcctgcac atttgcaacc taccagtgaa tcgattaaaa actacgttaa tgtagtctgc    145080
cctttagagt tccgtactgt aaatgggcgc gatactttag ctatcactaa actcaatcgc    145140
gaaattgaca ttgatccctc aattgcacgt gaaattaata gttctgatat taatggcggt    145200
aatgttaaat cgcacggttt tcagatgagg ttttaatgaa attcttttta ggtcaaactg    145260
ttgaattaaa gggagttggt atacctggat taatttctaa ggttctacct ccgtttaaat    145320
ggagtggtat tcaaataaaa gaggcttata ttgtttcttg ggtagatgga aatgaagacc    145380
ttcgtatggg cgatgaatta tctcctatct acggattaaa ggaattagta tgaatataat    145440
taataagatt tttggaattc agtacattaa ggtcacatat aaagtaacag ataaaaatcc    145500
gtatactgat gaacacgaag aaccgcaagt taagtctatt atattagaaa aaggcagtga    145560
ctggccagtt gaatttcgtc taccaaacta tggtcattgg gctgatgttg aaattataag    145620
cattgaaaat gtctgagtta gagattagaa gcaattttaa atggccatca tgtgcattaa    145680
gtaatttcgc ccaatggcct ttcgttatgg atggtattca atttggaggt cttgaaggat    145740
tcctccaagg atgcaaggtg aaaaatgttg aacaacaacg tcgtatattt gggttatccg    145800
ggcttgccgc ccaacaagct ggaaggtctt atgctagagc tcaggaccgt gggaccctct    145860
tctggcttgg agttccgttt tcaagatact ccccagcatg gaaagaatta tacacaaatg    145920
catattttga agcagcgatc caaaacaagg gctttcgtga tgcattacac gcctcgaaag    145980
gaaaagtttt gaagcacagc atggctagtg gtctaacaaa agatgataca atattaaccg    146040
aagctgaatt tattgatgtg ttaaacctat taagagactc tctatgaagc ctactatttt    146100
aactgatatt gatggagtat gtttaagctg gcaatcaggc cttccttatt ttgctcagaa    146160
ataatcttt ccgttagaac atattttaaa aatgatccaa gatgagaaat ttatttctcc    146220
aggtaaactc tttaattgtg acgaagaact tggcgtcaag ttaattgaaa aatacaatcg    146280
ttcagatttt attcgttact tgtctccata taaagatgct ctgtgtgtaa ttaacaaatt    146340
aaaagaagat tataattttg tagctgttac agcattgggt gattctattg acgctctgct    146400
gaatcgtcaa tttaatttga acgctctttt tcctggtgcc ttctcagaag tactgatgtg    146460
tggtcatgat tcttcaaaag aagagttgtt taaaaaggca aaagagaaat ataacgtgat    146520
ttgttatatt gacgatctcg ctcaccattg cgatcatgcg agtgaaatat taaatgttcc    146580
tgtttattgg atggctcgag gggaacgtga cagtattcca aaaactgcac agcgagttta    146640
tacatggaat gatgtagaaa ataagctttt ttccaaaag gaaaataaag aaagttttga    146700
tagtgaaaaa gctataaaag atgtaattga gaagatgatc aaaacgatt cttttccttg    146760
gaacactacc tggagaactc ctggatttaa tccttataat catctatatc atccatatca    146820
gacacatccg tttcagacat ggaactatat taaacctggt ggcatagagt atttgtataa    146880
tagacctact agtggtgata atattttcca aggagcattc taatgtttgt tgttcatact    146940
```

FIG. 17AAAA sequence.txt

```
atttatgaaa atgaaggtaa tactacacgt gattacggtc acgtaaatca atttttaga    147000
tgcaatccag aattccgagc tcaaaaagac gaacgaattt ttaaaaaatg tgtagagcaa   147060
ggtttcattt acgtcaagca ctggatgcaa ggaaataaag ttagaaccac gtaccacagg   147120
tctttgactg agcttaatga tgaattgatt tataatagag ctgtaaacca aactctaaag   147180
gatgaacaat gattcttaaa attctgaacg aaatagcatc tattggttca actaagcaga   147240
agcaagcaat tcttgaaaag aataaagata atgaattgct taaacgagta tatcgtctga   147300
cttattctcg tgggttacag tattatatca agaaatggcc taaaccgggt attgctaccc   147360
agagttttgg aatgttgact cttaccgata tgcttgactt cattgaattc acgttagcta   147420
ctcggaaatt gactggaaat gcggcaattg aggaattaac tggatatatt actgacggta   147480
aaaaagatga tgttgaagtt ttgcgtcggg tgatgatgcg agaccttgaa tgcggtgctt   147540
cagtatctat tgcaaacaaa gtttggccag gtttaattcc tgaacaacct caaatgcttg   147600
caagttctta tgatgaaaaa ggcattaata agaatatcaa atttccagcc tttgcccagt   147660
taaaagctga tggagctcgg tgttttgctg aagtcagagg tgatgaatta gatgatgttc   147720
gtcttttatc acgagctggt aatgaatatc taggattaga tcttcttaag gaagagttaa   147780
tcaaaatgac tacagaagct cgccagattc atccagaagg tgtgttaatt gatggcgaat   147840
tggtatacca tgagcaagtt gaaaaggaac cagaaggcct agattttctt tttgatgctt   147900
atcctgaaat tagtaaagct aaagaattcg ccgaagtagc tgaatcacgt actgcatcta   147960
atggcatcgc caataaatct ttaaagggaa ccatttctga aaaagaagct caatgcatga   148020
agtttcaggt ctgggattat gtcccgttgg tagaaatata cggtcttcct gcatttcgtt   148080
tgaaatatga tgtacgtttt tctaaactag aacaaatgac atcaggttat gataaagtaa   148140
ttttaattga aaaccaggta gtaaataacc tagatgaagc taaggtaatt tataaaaagt   148200
atattgacca aggtcttgaa ggtattattc tcaaaaatac cgatggattg tgggaaaatg   148260
ctcgttcaaa aaatctctat aaatttaaag aagtaattga tgttgattta aaaattgtag   148320
gaatttatcc tcaccgtaaa gaccctacta aagcgggtgg atttattctt gaatcagagt   148380
gtggaaaaat taaggtaaat gctggttcag gcttaaaaga taaagccagt gtaaaatcgc   148440
atgaacttga ccgtactcgc attatggaaa accaaaatta ttatattgga aaaattctag   148500
agtgcgaatg caacggttgg ttaaaatctg atggccgcac tgattacgtt aaattatttc   148560
ttccgattgc gattcgttta cgtgaagata aaactaaagc taatacattc gaggatgtat   148620
ttggtgattt tcatgaggta actggtttat gaaagcttac ttagaaacaa ttgtcgtggc   148680
tcaaaagaa ggtggagatg tttctacttc tgtatcacaa gtcattctcg aatttgtaga   148740
tgcatacgct tataataaat ttacagaaac atttgatgcc tatgaaaaag gaccaaagtt   148800
```

FIG. 17BBBB sequence.txt

| | | | | | |
|---|---|---|---|---|---|
| tgaaatatat | cgtactctct | taccactaga | ttactaaagg | ccttcgggcc | tttaatttta | 148860 |
| taaatagaat | aaacactaga | gaggctatga | tggaacttat | tacagaatta | tttgacgaag | 148920 |
| atactactct | tccgattaca | aacttaaatc | caaagaagaa | aataccgcaa | attttttcag | 148980 |
| ttcatgttga | tgatgcaatt | gaacagccag | gctttcgttt | atgtacatat | acatctggag | 149040 |
| gtgatactaa | tcgcgattta | aaaatgggcg | ataaaatgat | gcatattgtt | ccttttacat | 149100 |
| taactgctaa | aggttcaatt | gctaaattaa | aaggtcttgg | tccaagccca | attaattata | 149160 |
| tcaattcagt | ttttactgtt | gcaatgcaaa | caatgcgcca | gtataaaatt | gatgcttgta | 149220 |
| tgcttcgtat | tcttaagtct | aaaaccgctg | gtcaagctcg | acaaattcaa | gttattgctg | 149280 |
| atagacttat | ccgtagccgt | tcaggtggca | gatacgtcct | tcttaaggaa | ctctgggatt | 149340 |
| atgataaaaa | gtatgcatat | attcttatac | atcgcaaaaa | tgtatcacta | gaagacattc | 149400 |
| caggagttcc | ggaaattagt | accgagctct | ttactaaagt | tgaatcgaaa | gtcggcgatg | 149460 |
| tttacatcaa | taaagatact | ggagctcaag | taactaaaaa | tgaggcaatt | gcagcatcta | 149520 |
| ttgcacaaga | aaatgataaa | cgttctgacc | aagctgtaat | cgttaaagtt | aaaatttccc | 149580 |
| gtagagcaat | tgcgcaaagt | caatcattgg | aatcttctag | atttgaaagt | gaattattcc | 149640 |
| agaagtatga | atctacagca | gctaatttta | ataaaccagc | tactgcacct | ttaattcccg | 149700 |
| aagcagaaga | aatgaaaatt | ggaattaatt | cattagcttc | taaaacaaag | gcagcaaaaa | 149760 |
| ttattgctga | aggaacggca | gatgaacttc | actatgatta | taaattcttt | ccaatgagtc | 149820 |
| aagtcggtga | agtttcagaa | aaaattaaag | aagtaatttt | taatgcaatt | aaaaatgaac | 149880 |
| caactacttc | aataaaatgt | ttagagaaat | acgcagcagc | tgctaatcaa | ctctttgaag | 149940 |
| aatataaaga | taattggctt | gataaacata | ataaaactcg | taaagggcag | ccagatgaag | 150000 |
| tctgggaaga | aatgactaaa | aattcctgga | acgcagcaaa | aactaaattc | ctcaaaagaa | 150060 |
| tgatttatag | ttttttctgga | attggtgcag | gtccaatgat | tgatattact | attgcccgtg | 150120 |
| atggttctaa | atatactcca | tcacaaaagc | gcggcattag | agagtattgt | ggttcagggt | 150180 |
| atactgacat | caataatctt | cttttgggtc | gttatgatcc | agaacgttat | gaagtaatga | 150240 |
| gtgaaaaaga | aattgaagct | gctataacta | atttagattc | tgcttttgaa | aatggtgatc | 150300 |
| gtataccaga | aggcattaca | gtttatcgtg | ctcaaagtat | gactgctcct | atatacgaag | 150360 |
| cactagttaa | aaataaagta | ttctatttca | gaaattttgt | atctacttct | ttaactccta | 150420 |
| tcattttttgg | acgttttgga | attacacatg | ctggtattgg | tctttttagaa | ccagaagctc | 150480 |
| gcaatgaatt | aacagttgat | aaaaatgaag | aaggaataac | tattaatcca | aacgaaataa | 150540 |
| gagcgtataa | agaaaatcct | gaatacgtta | aagttcaaat | aggatgggca | attgatggag | 150600 |
| ctcataaagt | taatgttgta | tatccaggaa | gtctcggaat | agcaacagaa | gctgaagtta | 150660 |
| ttctaccgcg | tggattgatg | gtcaaagtta | ataaaataac | tgatgcttct | aataatgacg | 150720 |

FIG. 17CCCC sequence.txt

| | | | | | | |
|---|---|---|---|---|---|---|
| gaacaacatc | taataataca | aaactcattc | aagctgaagt | tatgaccacg | gaagagctca | 150780 |
| ccgaatcggt | aatctatgat | ggagaccatt | taatggaaac | tggtgaattg | gttgcaatga | 150840 |
| caggtgatat | tgaaatagaa | gacagagttg | actttgcatc | atttgtttca | tcaaacgtta | 150900 |
| aacagaaagt | agaatcatct | cttggaatta | ttgcgtcttg | catagatatt | acaaacatgc | 150960 |
| cttacaagtt | cgttcaagga | taaatcatgg | aacttattac | agaattattt | gacggcgctt | 151020 |
| cggcgccggt | tgttaactta | aatcctaagc | ataaaatacc | tcaaattttt | gctattcaag | 151080 |
| ccggtgaaga | aagcgtgctt | cctggattta | gattttgtac | atacacctct | ggcggtgata | 151140 |
| caaataaaaa | cgttaagccg | ggcgataaaa | tgatgcatat | cgtaatgata | ggtgtcaacg | 151200 |
| agaaattatc | gttagtcaag | cttagaaact | tgggtggaaa | tccaattggc | gtcattaatg | 151260 |
| ctgtttttga | tactgctctt | caaacaatga | aacagtataa | aatcgacgca | tgcctattcc | 151320 |
| gcgtactaaa | aagtaaaaca | aatggcgcag | ctcgtcaaat | gcaagttatt | gctgaccgtt | 151380 |
| tagtacgtac | taaaggagca | ggtcgatatg | ttcttttaaa | ggaaatctgg | ggctatgata | 151440 |
| agaaatatgc | atatattatg | gtttaccgta | aaaatgccaa | tttagaagac | attccaggtg | 151500 |
| tacctcctat | ttcaactgag | ttattcacaa | aagttgaatc | aaaggttggt | gatgtttatg | 151560 |
| tagacgttaa | aacaggtaat | gctgttccta | aagctgtcgc | tgttgctgct | tctattgctt | 151620 |
| tagaaaatga | taagcgcacg | gatcaagctg | ttattcagaa | aactaaaatt | agtcgtcgat | 151680 |
| tagcagcaca | agctcaatat | tctactgttg | atgcttcact | tcagggtgat | agcttcgctg | 151740 |
| ctaagaaata | tcaagagttt | gaatctaaag | ttccggtata | taaagcagaa | ggtccgatga | 151800 |
| actctggcgt | tattcagatt | ggttcaaact | ttagcaaagg | agctatcggt | ggtatgagaa | 151860 |
| gtgcttctcg | ttttaaatct | aacgattatg | aactagaaag | tttccgaaat | catattgcat | 151920 |
| tagcccatgc | acgtttacgt | gatccatcta | tcaagttgca | gagcgatata | acatatcaag | 151980 |
| gttctcaaga | atatttaaag | aataaagaat | tctttgatta | taaaactgat | aaaattttaa | 152040 |
| gcgatcttgc | tgacattaat | atttctaata | gctttgatgt | tattaagaaa | attatcaatg | 152100 |
| atttagttaa | aggttctaaa | gctacaccag | atgaaaagac | agctattatt | caatttgtca | 152160 |
| tgaatggcat | ttataaattg | attaatgaat | ctgccgctca | ggcatatgaa | tacgcaagca | 152220 |
| ctgaagtaac | tccaaaagga | ttaactcagg | ctgagtctga | tgtaattgaa | gattattgtg | 152280 |
| cagattcata | tgttgaaatg | aactcgttcc | ttttaggtaa | acctgattct | acccgtgaag | 152340 |
| aatatatgga | acgagctatt | aaacacatcg | agacgttgga | ttctgcattt | gctaaaggtt | 152400 |
| cagttcttcc | tccaggaact | actctttatc | gtgggcaaga | agttaccttt | aaaactttgc | 152460 |
| gtcataacat | tgaaaataaa | atgttctatt | tcaagaactt | cgtatccaca | tcgcttaaac | 152520 |
| caaatatctt | cggtgagcat | ggtaaaaact | atatggctct | agatgattct | ggcgcagtat | 152580 |

FIG. 17DDDD sequence.txt

| | | | | | |
|---|---|---|---|---|---|
| tttctggtga | aggagaaggt | tccattgatg | cagaagattt | gatgcatatg | ggtagtcatt | 152640 |
| ctacatatgt | taatgaagat | gctgaaacta | gcgtgggtat | ggtaattaaa | ggagctgagc | 152700 |
| gaatcaaagt | tatcgttcca | ggtcatttat | caggatttcc | atcagaagct | gaagttattc | 152760 |
| taccacgtgg | aattttactg | aagattaata | aagtaagtac | ttactttatg | aaagaaactg | 152820 |
| cttataacaa | gtatctaatc | gaaggtacaa | tcgttcctcc | ttctgaacaa | ttagaggaat | 152880 |
| cagtatatga | tggcgatcat | ttgatggaaa | ctggtgaagt | tcgtccaatg | actggattta | 152940 |
| atcaattcct | tgtagaagaa | tcaaaagaag | aggaaaacga | agtttctcaa | atcttagctt | 153000 |
| ctttggttaa | catcaacgga | atgtctaaaa | agttcaaaat | gtagtttaca | agtccctcat | 153060 |
| gttgtgttat | agtagtctta | ctgacataac | atgaggaaca | caaaatgaaa | tcttctttgc | 153120 |
| gcttttgggg | tcaagaactt | gtagttgaag | gcgttattcc | tgctgataat | gcttttaatg | 153180 |
| aagcagttta | caatgaattt | atcaaaattt | ttggaacaga | taaaaagttc | ggaatttttc | 153240 |
| cttctgaaaa | tttttcaaag | ccagaacaga | ctgaaagtat | tttccaaggt | gtagtaacag | 153300 |
| gtaaatttga | gtcagaagct | ccggtaaaaa | ttgaggttta | tattgaagac | agtttagttg | 153360 |
| cttcagttgc | tgcttttatt | tcattccgta | aataaaaata | tggggaccga | aaggtcccca | 153420 |
| ttgttatatt | gctcctaata | ttttactttg | cgaattgaca | attcctgtca | tagtattaat | 153480 |
| gtttgaaatg | cttcctgcag | ttccccctaa | tctactgagt | cgtgaaagcg | aattagatag | 153540 |
| tccagtaaca | cctccactat | ttccgagaac | gctttgaata | ccatttatag | cagcagattc | 153600 |
| aagccattca | agcgcagctt | gcctatcaac | tgctccagcc | tgcatcactc | tatacgcaaa | 153660 |
| agtaacgtca | aatgtagtta | tttggttatc | tccatcatat | gataactcag | gagcgctcac | 153720 |
| tgatattgga | atgcatccag | tgaacatcac | cgcagtatga | ggcaatccat | tacgagaatg | 153780 |
| aagattaacc | tgaatatctg | cctcgacatc | ctgtggcaaa | gcacgcagtc | cagttactgg | 153840 |
| gtcttgaacg | gagttaaccc | agtcttgcat | tgcacgatag | ttacaagctt | ctgaatccat | 153900 |
| tctaaatgaa | ataaccaaag | ggtctaattc | tctcccagtt | atacgaatat | taggagaatt | 153960 |
| atagttccag | tcagtttcat | aggataatct | attctctggc | attttacag | agtatatcat | 154020 |
| caatccagat | gagttatatg | ccatgttaaa | gaagtcaatt | aaatatgtac | caactgtaaa | 154080 |
| tgagcctaat | aaactttgaa | ctgtacgttg | actcatggca | ccaataagat | atttactaac | 154140 |
| ccctgatttt | cttatcagtt | tttgtgtgcc | agcagtaatt | agcgtggtaa | ttccctgatt | 154200 |
| aatatcacct | tgagtcaatc | ctaaccaatc | tgaattaggg | cccaagttat | tataagaaaa | 154260 |
| gttgctaatt | gaacttatca | acgaagagct | tttagttgat | ggagttgttg | caaaaacgca | 154320 |
| gctaaacata | ttattacgtt | ggaaatctgc | gtttattgct | tgattattaa | attcctctaa | 154380 |
| agaatacatt | aaaaagtccc | cgcatataaa | gaagcacggt | ttaacgtgat | aatttctctc | 154440 |
| atagtaatct | cgagagtaaa | tgtactaggg | aggtttggag | caatagctaa | tccgttaaag | 154500 |

FIG. 17EEEE sequence.txt

| | | | | | | |
|---|---|---|---|---|---|---|
| ttaccattag | gtgttttgtc | aaatctgata | ctctggattt | gacatggacc | gaatatttcc | 154560 |
| gttttccat | caaacttaga | tgttgcacca | aagtttttca | ccatccaaat | tgtcgggttt | 154620 |
| gaaactacaa | gaacgttagt | taaactcgat | gtcattttct | caaataacgt | cttatttta | 154680 |
| actgcatctt | ctggagttaa | cggctcaata | aaagtagaac | ggtaccactc | atctaaatat | 154740 |
| ccttttattt | cagcagcata | ttgagattta | ccagtttcac | cgtaagaaaa | atagttaaaa | 154800 |
| tactgataga | tattaataat | agccattaaa | tcttctgttg | agcgcggagt | caaatcccaa | 154860 |
| gtgaacactt | tagttctatt | ttcagcaccg | ccgtacatgc | ttctggctgt | cgtataaatc | 154920 |
| tgttcattat | tatcagccat | tataccttgt | gttatacttt | ccagcgctcc | aaatactgcg | 154980 |
| gttgaagcca | tattgcttag | cacaccagta | gcagtacctc | cacctttgt | aataagacta | 155040 |
| tcttgaacat | cattaaatct | atgtgatgac | gtatcgacgt | cagatttaga | tctaggtaaa | 155100 |
| agaatatttg | caacaggaac | tttacttatt | gttcctgaat | tattatctga | tattagtcca | 155160 |
| tttgatagtt | ttgatactgt | attactgata | gtgtttctgg | ctgtacgtaa | aatactcgaa | 155220 |
| gatgaagaag | agtagttaga | tctcatcgtt | ctaagacttc | cagaatccct | agatgacata | 155280 |
| ttgtatgcag | taaataataa | tccattctta | tatagatctg | ttacctggaa | gtccctgta | 155340 |
| gtgtcattac | cactagcacg | cccagttgga | aactgggcag | tgtatgtttt | agttgctact | 155400 |
| tctgatttag | tactctgtcc | ggctgaaatt | ttctcaccgg | actttttaat | taaatcagca | 155460 |
| gttatttctt | taacaattgc | catattattc | cttaattaac | tccagtcgca | tcaaatacac | 155520 |
| caggagcagt | cgtgctcgtt | acgggtgtca | tattatgaac | gacagtattt | ttcttaataa | 155580 |
| cattattagt | attattgatt | gaaggagatg | cttgttgaat | aggagcttgc | tgtgcttgt | 155640 |
| tcttttctat | tacctggact | tgttttgctt | ctggcgattt | agcagaagtt | tgaggtttgg | 155700 |
| cattaggctg | attttcttg | agctcttgat | aagtagcatc | aattttagaa | aatctagcag | 155760 |
| caagttcttt | tttaactgcc | ggtgaattat | ttaaatccgg | gtcatccatt | cgttttttaa | 155820 |
| ggtcttcata | ggcagcttca | actgatttaa | ccgttgagtc | tttactcata | tcagctgaat | 155880 |
| tagcgtattc | atcaaaacga | ttcatagcag | cacgagcttc | attagctttc | attaaagcaa | 155940 |
| ttttagcttc | ctccggagaa | agttgcttta | attttcttc | ttcctctgct | ctctcttcat | 156000 |
| cagtcgttag | tgcttcttta | ttatcaacac | cacgaatcca | gttagatgca | cgagttttcc | 156060 |
| agttcgcaat | tttgtctagc | ccttttgcta | ttggaccaag | atcgtcattc | attctttat | 156120 |
| attgataatt | tgcaactttt | tcttggtctt | ctttgctaag | agaagcattt | gtagtatttt | 156180 |
| ggaaattttc | tagtgctctt | ccttctactt | catcagcagt | atccttcata | ccaggaataa | 156240 |
| ctcgaagaat | tgccgcagat | aatttagcca | ttccaagttg | aataagctct | cctaaattaa | 156300 |
| aaagaacctt | tccaagtcct | tcgacaatag | ctactgtcaa | tccgccccag | tctccagctt | 156360 |

FIG. 17FFFF

```
                                sequence.txt
cccacagctt cttaatttta tcaatagaac caaagatgct ctgtaataaa ggacccacg   156420
ttccggtttc gctagagaat ttggtaaagt ttgtactaaa caaatcccat gcctgcgaaa  156480
atttatctga ccaatatttg aagtgaacca tcaacagatc tattccaaca acaacagcca  156540
atatcattgc agtcatttta gcagcttcaa tagcagcact aacggtatac ttaaataaca  156600
tgcttgatat tttatcacta attgaaatag atttcttaaa tccaaaatca acagtctttg  156660
ttaatttatc taaagcttga gataatttta agttaaatgc ttcttttttc tgttttcttt  156720
ctggcgattc ttgtttaggt tcaactggct gaggggtagg gaaaaaatca gcatcaggat  156780
cattattaac tgcttcagga gctggtaata aaggacccac ggattcagct gtatcgtcct  156840
caacaacttt aacaggaata gcgctttcaa ccgtagctaa actagttcct gtttgttgaa  156900
ttccggctgt ctggattttt tgctcgagta aactcgttaa tttatctaat ttacttccga  156960
gcgattcacc gatttcttta ttaatattat tgccaatttc gacagtttca gcaattaact  157020
cagaaccagc agtagtatca ctcactgcgc tttctacatt gtcaattgct ccaattattt  157080
cattcgattt ttcttcaaca gtttgagcaa ttaattcaga agcagcttga gcatcatcca  157140
atttcgtaga tatatcgtta agtccagata aagtgttaga agcggattta gccgcttcct  157200
gtgttggttt attatctgaa ataactttc tacgcatcgt ttgcatttct tgtggctttt   157260
tcattcaaat aatccaataa tattgccaat tccggttatt ggaccattag ggccaggaat  157320
tgctaaagtt gtaaaaatat catttgccca ttttaaaacg aatgctggca tctcaagaaa  157380
attaatttct ttaacttcat cattgacctt aagcaagcat ttggataaca tatcgctcac  157440
cgttaaaaat tgttcaaatt ttccaggagg tctaaaataa aatgtatttc cttggtattg  157500
aaattctaat ctttggcaca cataaacatc attaatgtca taagtataac catctatttc  157560
tttacgagat ttaatctttc cattaaattc caataaatga atggaaacga aatcaacttc  157620
tgccggtgat aaatttggac aaatagaatc aataagaagc tttaaatttt catcaggacc  157680
tttaacatct tttaaaatgt tataatgttt aagaccatc ttaggaatag aaacttcttt   157740
attacttatc ggaagaacta ctttcttcag tggtagtatc agttttaaat tcattttaa   157800
ccttaactgg gtcgattgtt tccagtttcg ttgcattagt gaacatatat agatgagtta  157860
cggaattatt atttgataat tcgtgaataa cttcatcaac gtaaaattct gttttaaatt  157920
ggtttttact atcattaaaa ataattttaa cgccaggagt caagttaaaa ttaccgacag  157980
tagaacattt agcatagccg tcatattgcg ccatagtctg aagacgaata gcttcttcat  158040
atccatttct ataagtcatt tcagaataag cacctgacct tgacactaca atagagtttt  158100
caccctttcc tgtagtaatc attggtaatg aagaatctaa aaatgaatga gcatagatag  158160
tagcattttt cattggatca cgtttatgcg ggtttgattt agtcaaccaa acaaaatcat  158220
atgctaatgg atatttcaat tcttggacga attgacctat taaagttggc tcacctacaa  158280
```

FIG. 17GGGG sequence.txt

| | | | | | |
|---|---|---|---|---|---|
| tcattggata | tggttcttga | tttatcatca | tatcatagtc | catcatgtta | actcccatga | 158340 |
| tgtcttgcca | tacaaatacg | aacttatcgc | ttcctaccgc | tagagcaact | tctcttacat | 158400 |
| atgacaaata | gttttcaaat | gtgctagtcc | atggaatatc | aggaacataa | gcattaatag | 158460 |
| catttatcgc | tggagttaat | aatgtacgat | cttgataaat | tacgccaagc | atttcctta | 158520 |
| tagattcacc | ggcatcaggg | aaaaatggtc | taccaaattt | aagattttct | atagaatgaa | 158580 |
| tagttcccaa | ttcaatagca | atgatgttat | cacctttga | atctacagat | acagaaaaat | 158640 |
| gcttacatcc | ataaattctt | gttttaacat | tattaatatc | gtttgcatta | gctacagaaa | 158700 |
| tctgaattat | ttcatttcca | tccatttttg | tatggatatt | tttagaatca | taaaattgta | 158760 |
| gcattccttc | atttcgacca | taaagagaat | cccgcatagt | taatgtggta | atagtagcag | 158820 |
| ctaattcaac | aaatctatta | ttactccaag | cgtcataact | ctcaaataat | ttaacgctga | 158880 |
| gatttggata | tccaggacgt | tgtaacatac | tcattgatgt | ttatccttct | caatcagttt | 158940 |
| taatacgaat | ccgcgctcgg | caggaatcat | tttcattatt | gaatttaagc | tataattact | 159000 |
| ttttacaagc | gtgtgattaa | tttgataaaa | agtaaatatc | tcatctggat | taactaatag | 159060 |
| cttaaacaca | tctactatat | cagtgtattt | tttaatgtac | ttatcacaac | acgacatgtg | 159120 |
| caatgttaaa | ttaataggat | tcattgcatc | gagaattttt | tctaatgttt | ctatctcgat | 159180 |
| ggcgtcaact | agttctattt | gactggactc | gctaatttcc | ttccaatcat | accatatttc | 159240 |
| atctacttga | acagaatgaa | tattttcagt | aatcatcttt | gctttatttt | cataaaactc | 159300 |
| agaaggaaac | tttaatttaa | ttttaacatt | agctacatca | aaaacaggtt | cctttaattc | 159360 |
| tttttgatat | atttcaaatg | gaactgtctt | ttctttttta | cattttggac | atacaaatgt | 159420 |
| gactggtact | ttagttttac | ctattgaacc | tacaaatacc | tgcaaaaata | taaatggttg | 159480 |
| ccaagtcttc | ggatagtctc | caaataatc | atcaattaaa | tcagtaatta | tttcttttg | 159540 |
| ttcttgtggt | gaccgatgtt | ctatatcgtt | tcgaactaac | aaaaaatctc | gataatcttc | 159600 |
| taccgtaaat | ggtttaaaac | gatgaacacc | atctggtaat | ttacaacgaa | taatgtttgc | 159660 |
| catagatgct | cctttattc | tatttataaa | tatgataaat | aaaggagcta | aatatgtatg | 159720 |
| aatacaaatt | tgatgtgaga | gttggttcta | aaataatcaa | ctgtcgcgca | tttactctta | 159780 |
| aagaatatct | agaacttatt | actgccaaaa | ataatggttc | tgtagaagta | attgttaaaa | 159840 |
| agctaatcaa | agactgtaca | aatgcaaaag | atttaaaccg | ccaagaatca | gaactattac | 159900 |
| tgattcattt | atgggcgcat | tctcttggtg | aagttaatca | cgaaaactct | tggaagtgca | 159960 |
| cctgtggaac | tgaaatacca | acccatataa | atctattaca | tacacaaata | gatgcaccag | 160020 |
| aagacctctg | gtatacactg | ggtgacatta | aaattaaatt | ccgatacct | aaaattttg | 160080 |
| atgataaaaa | tatagcccac | atgatagtat | catgcataga | aacgattcat | gctaacgggg | 160140 |

FIG. 17HHHH sequence.txt

```
aaagcattcc agttgaagac ttaaatgaaa aggaactaga agatttatat tctatcatca    160200
cagagtcaga tattgtagct ataaaagata tgcttttaaa acctaccgtt tatttggctg    160260
ttccaattaa gtgtccagag tgtggaaaaa cccatgctca tgtaataaga ggcctcaaag    160320
agttctttga gttactataa tggcaaatat taataagctt tattctgaca ttgacccaga    160380
aatgaaaatg gattggaaca aagatgtttc cagatcgctt ggattaaggt caattaaaaa    160440
cagtcttttg ggaattatta caacaagaaa aggttcaaga ccgtttgacc ctgaatttgg    160500
atgtgattta tcagaccagc tttttgaaaa tatgactcct cttactgctg atactgttga    160560
gcgtaatatc gaaagcgcag taagaaacta tgagccacgt attgataaat tagcagttaa    160620
tgtaataccg gtttatgatg attatacttt gatagtagaa atacgctttt cagtcatcga    160680
taaccctgat gatattgagc agataaaact acaactggct tccagtaata gagtataatg    160740
cttcacgtat aaacgtggta taatgaatct aagtccatcc aataacaatt gaatagagaa    160800
caatatgaga ttagaagatc ttcaagaaga attgaagaaa gatgtgttta tagattcgac    160860
taaattacag tatgaagcag ctaataatgt gatgttatat agtaaatggc ttaataagca    160920
ttcaagtatt aaaaaggaaa tgcttagaat tgaagcacag aaaaaagttg ctcttaaagc    160980
taaattagac tactactcgg gacgaggaga tggtgatgaa tttagtatgg atcgttacga    161040
gaaatcagaa atgaagacag ttctatcagc tgataaggat gttttaaagg ttgatacctc    161100
gttacagtat tgggggattt tattagattt ctgtagcgga gctcttgatg ctattaaatc    161160
acgtggattt gctattaagc atattcaaga catgcgagca tttgaggctg gaaaataatg    161220
agatataaca ttgatgatgc ttttaattat gaagaagaat ttgaaacgga aattcaattc    161280
ttaatgaaaa agcataatct taagcgtcag gatattcgta tcctggccga ccacccgtgc    161340
ggtgaagatg ttctttatat taaaggaaaa tttgccggat atcttgatga atattttat    161400
tctaaagata tgggcattga tatgcatatg agagttgtat aaatagatat ataattcaga    161460
ggagacaatc atgtcagata agatttgtgt tgtctgtaaa actccaatcg attctgcatt    161520
ggttgttgaa acagacaaag gtcctgtaca tcctgggcct tgctataatt acattaaaga    161580
actaccagtt tcagaaagtt cggaagaaca attaaatgaa acgcaacttt tgctatagtg    161640
tgacctttag tctatagttt tggcccttcc ttttggttg ggccttttt aatttaaaag    161700
cttcttcta cttcatcgtc tgaatcttct aattcagctc ttttttcctgc caaagcatct    161760
ctgactgaga tgtcatcagt atcttttaat tcagtttctt taactctttt cttataataa    161820
gcttcaagtt cttctaaacc ttctaatgtt tgacaagagg caattttacc cataaattca    161880
tcaatagaag cttcataaag aaattgttta aattctagta acatcttttt ctccaaaggg    161940
ccgaagccct tataaattaa ctgttttcat tacgtaatta aatttttcat ctgcgtagcg    162000
ctgaatacga tcaatgccgt gttttaaaag atagttcaag tgaacatatt tcttttttagt    162060
```

FIG. 17IIII sequence.txt

| | | | | | | |
|---|---|---|---|---|---|---|
| attagcagat | tttggcttga | caccacagtc | atctatgagg | tcccagactg | ttgcgattgt | 162120 |
| tttagaacca | tgcttacgta | atacacgacc | gattgtttgt | aatacaatga | tttttgattt | 162180 |
| aacaccgtgc | gctaaaacaa | cgtgatgcag | atttttaact | gaaataccag | tagaaaatac | 162240 |
| accataacta | gctactataa | ttattccttt | accattttca | gctaaggttt | tcattatatt | 162300 |
| gcgggtttcg | gtatcaactt | cccctgatac | gtaataaact | ttatcgtatt | catttttaat | 162360 |
| taaatcgaaa | atagctttac | catgtgatac | atgtttaaac | atgacaaaag | cgttttcatc | 162420 |
| tttttgtgca | agcttaatag | ccaatttagc | gatccattta | tttcttttac | taagcccgt | 162480 |
| aataattttt | atttcttctt | gataagtttt | tcctttaat | ttagtagtga | actcatcggg | 162540 |
| atagcgaaga | aaaatactat | taattttag | ctcagttact | tgtccatctt | ccattaactt | 162600 |
| agaagtcgtt | actggcttaa | atatttcacc | aaacattcca | acatactgca | tgatattggc | 162660 |
| tttgccatca | cgtaatgaac | cagatagacc | aaatttgaac | atgcagttat | ttaaacctga | 162720 |
| tatgatagat | gaaatacttt | ttcctgtagc | aagatggcat | tcatcattca | tcatcattcc | 162780 |
| aaactgtgag | aaccattctt | tcggttgttt | tactacagtt | tgccatgtac | caacaacgac | 162840 |
| tggtgcatca | tttttatatt | tatcatcttt | tgatgctccg | ccaccaattt | tctttatcat | 162900 |
| tgcatgactg | aataaacgat | agtcaacgaa | gtcatcagcc | atctgagttg | ttagagcagt | 162960 |
| tgttggaaca | atgataagaa | ttttaccttc | ataattttcc | aaataatatc | gcgcaagcaa | 163020 |
| agcttgaatt | aacgatttac | cagcggatgt | tggaagatta | agaattctac | gacgattaac | 163080 |
| taatccttcg | aacactgcat | cttttgata | ccaatgcggt | tcaattcttt | tatttcctga | 163140 |
| atagatttct | aatttagaaa | gccattcatc | aaaatctttt | cttgataatt | cttctttttc | 163200 |
| gttaatctgt | gggtcaatcc | aggctttata | gccaaagtta | tcgcagaact | ttttaatttg | 163260 |
| cccgactaaa | ccgaatggaa | gaaggcgatt | ataatctaaa | agacgaattc | gtccatccca | 163320 |
| gtggccatat | ttgtacttcg | gattaaaacg | atacccatca | gcttcaaagc | taaagaaatc | 163380 |
| acggagttca | tgaaatgtac | tttcttcgca | atcaattctc | acgtgactaa | aatcataaaa | 163440 |
| atgtacttta | atgtcagtca | tgtctaaata | ccatgtaata | aatatatcta | tatttatact | 163500 |
| gaggaaatat | tatgatagat | aaagattata | ttgcagagct | gaaggctctt | gatgataata | 163560 |
| aagaagctaa | agctaaatta | gctgaatatg | ctgaacagtt | tggtataaag | gtcaaaaaga | 163620 |
| ataaatcttt | tgataatatc | gttaatgata | ttgaagaagc | tctccagaag | ctcgctagtg | 163680 |
| aacctatgcc | ggagactgat | gggttatcta | ttaaagactt | aattgatgct | gctgatgctg | 163740 |
| cagaggggtt | aaaatatgac | gatgaagaag | tcaatccaga | agcagcactt | ttgattgatt | 163800 |
| ctccggttaa | atctgacatt | aaaattgaag | tagtagaaac | agataaaatt | cctgaaaata | 163860 |
| ccgatgtttt | gattgaagat | actccatttg | ttgaagaaaa | atttgaacag | gctgtagctg | 163920 |

FIG. 17JJJJ

```
                                   sequence.txt
agattattga atctgaaaag ccgtctgtat ttactcttcc ggaaaacttt agcccgaatc   163980
ttcagttgat tggaaaaaat ccaggattct gtactgttcc ttggtggatt tatcaatgga   164040
ttgctgaaac tcctgattgg aaatctcacc caactagttt tgaacatgcg tcagcacacc   164100
aaactttatt tagcttaatt tattatatta accgtgacgg atcagttcta attcgtgaaa   164160
cacgcaactc ttctttcgta acattaaaat aaggataact tatgactttt acagttgata   164220
taactcctaa aacaccgaca ggggttattg atgaaactaa gcagtttact gctacaccca   164280
gtggtgaaac tggaggcgga actattacat atgcttggac tgtagacgac gctccacagg   164340
aagaaacgtc agcaactttt agttatgtac taaaaggacc tgccggtcaa aagactatta   164400
aagtagttgc aaccaatcaa gttgcagaat ctgaacctga aacagctgaa attagtacaa   164460
ctatcacagt tcaaaataag acacaaacaa ctactttggc agtaactcct ggtagccctg   164520
atgctggagt gattggaact ccaattgaat ttaccgctgc cttagcttca cagccatcag   164580
gtgcaaacgc tacgtatcaa tggtacgttg acggttctcc tgtgggcgaa gcaactagca   164640
ctacattcaa ttacactcct gacgcaagcg gagttaaaac aattaagtgc gtagctcaag   164700
taaccgcgac agattatgat acaaaggaag ttacttccaa tgaagtgtca ctgactgtta   164760
ataaaaagac gcagacaact actttggcag taactcctga tagtcctcca gcgggagtaa   164820
tcggaacccc agttcaattt actgctgcct tagcttctca acctgatgga gcgtctgcta   164880
cgtatcagtg gtatgtagat gattcacaag ttggtggaga aactaactct acatttagct   164940
atactccaac tacaagtgga gtaaaaagaa ttaaatgcgt agcccaagta actgctgaaa   165000
attacaatga aaaggaagtt acttctaatg aagtatcatt gacagttaat aagaagacaa   165060
tgaatccaca ggttacattg actcctcctt ctattaatgt tcagcaagat gcttcggcta   165120
catttacggc taatgttacg ggtgctccag aagaagcaca aattacttac tcatggaaga   165180
aagattcttc tcctgtagaa gggtcaacta acgtatatac tgtcgatacc tcatctgttg   165240
gaagtcaaac tattgaagtt actgctgtcg ttactgcaac tgattacgat agcaaaacta   165300
ttacagcaga aggtcaagtt caggtaactg ataaagttgc tccagaacca gaaggtgaac   165360
taccttatgt tcatcctctt ccacatcgta cttcagctta tatctggtgc ggttggtggg   165420
ttatggatga atccaaaaa atgaccgaag aaggtaaaga ttggaaaact gacgacccag   165480
atagtaaata ttacctacat cgttacactc ttcagaagat gatgaaagac tatccagaag   165540
ttgatgttca agaatcgcgt aatggataca tcattcataa aactgcttta gaaactggta   165600
tcatctatac ctatccataa tcataagggg cttcggcccc tttcttcatt ttgaaagcac   165660
acaaaacaca atcagaaaat gatgtatata atggcaccaa ctcgataaca tgagattgat   165720
tatgagaact gaggttgtgg tgtttactct tcatgagtct ggaaagtcat tcattgaaat   165780
tgctcgtgaa ttaaacttac aggcaaaaga agtggctgta ttatgggctc gagctatgac   165840
```

FIG. 17KKKK sequence.txt

```
tgctaaaaat aaatttgaaa ctcgagaaaa agtcgtctat agaaaaagac atatcaataa    165900
aaaggtgaaa aatggaacag tatgatcttt atgaaaatga atcttttgct aatcaattgc    165960
gcgaaaaagc acttaaaagt aaacagttta agctagagtg ttttattaaa gatttttcgg    166020
aacttgctaa taaagcagct gaacaaggta aaacacattt tagttattat tgtattgctc    166080
gtgataaatt gattactgaa gaaattggtg attggctgag aaaagaagga ttcagcttta    166140
aagtcaatag tgatcagcgt gatggtgatt ggttagaaat tacattttga ggattaatta    166200
tgtttaaaaa gtatagcagt cttgaaaatc attacaactc taaatttatt gaaaaacttt    166260
atagcttggg attgactggt ggggagtggg tagctcgtga aaagattcac ggcacaaatt    166320
tctcattgat tattgagcgt gataaagtaa cttgcgctaa acgtactgga ccgattcttc    166380
ctgctgaaga tttctttggg tatgaaatta ttctaaagaa ttacgaagat tctattaaag    166440
cagtacaaga tattatggaa acctcagcgg ttgtatctta tcaagtcttt ggcgaattcg    166500
ctggacctgg cattcagaag aatgtcgatt atggcgataa agatttttat gtatttgaca    166560
ttattgtcac tacagaaagt ggtgatgtga cttatgtcga tgattatatg atggaatcat    166620
tttgtaatac atttaaattt aaaatggctc cacttttagg tcgcggtaaa tttgaagagc    166680
ttattaaatt gccaaatgat ttagattctg tcgtccaaga ttataatttt acagtagacc    166740
atgctggatt agttgacgct aacaaatgtg tttggaaagc tgaagccaaa ggcgaagtat    166800
ttaccgctga aggatatgta ttgaaacctt gttatccttc ttggcttcat aatggaaatc    166860
gtgtagccat caaatgcaag aattccaaat ttagtgaaaa gaaaaagtct gataagccta    166920
ttaaagctaa agttgaacta tcagaagctg ataacaaatt ggtgggaatt ttagcttgct    166980
acgttacact gaaccgagta aataacgtta tttctaaaat tggtgaaatt ggtccgaagg    167040
attttggaaa ggtgatggga ctaactgttc aagatatttt ggaagaaact tctcgtgaag    167100
gtattactct aactcaagca gataatcctt cttttggttaa aaaggaatta gttaaaatgg    167160
tacaagatgt acttcgtccg gcttggattg aattggtaag ttaaataaaa agggaccgaa    167220
aggtcccttt gttttattca tcaacgataa ttttggtag cttaacacct aataaaacag    167280
acaaa                                                                167285
```

FIG. 18A sequence.txt

<210> 4
<211> 43313
<212> DNA
<213> Unknown

<220>
<223> Description of Unknown: Bacteriophage F510/08

<400> 4

| | | | | | | |
|---|---|---|---|---|---|---|
| cctactcaac | gaggccgtgg | ctagcaaggt | gctaaactcc | cgcctgggct | ggtccgcagt | 60 |
| cggcgagtat | gtcgaactgt | tcaaccgcac | gcaatcccgc | gtggccgggt | tgattcccga | 120 |
| gtagctcaag | ccgagtacct | gcatagtcgg | gtgctccact | ggaactactg | gaatttttat | 180 |
| tgagattggc | tggaggttgg | ctgtctgtgg | ctgggggggg | tagttactcc | gggtctaatt | 240 |
| ttggtatcgt | cgtgtgagaa | ccctcccgac | tctgatcagc | ccaccccttcc | cccgtaggcc | 300 |
| ctccgcctgg | tgggccatcc | ctcgcattgc | ctgggtgttg | cttcctagcc | tcctgggagc | 360 |
| ttccagctcc | gctgggtggc | gtgggcttcc | ctgccctgtc | gccgaccatt | ctacgcatcc | 420 |
| tgtcgggagt | gtcaacccctt | gggctggccg | tagtgcctgg | agcgctccag | cgcttccctg | 480 |
| tgcttggtca | gcgctaccgc | gtactcctgg | gatgcctggc | gcttccgcca | cggtgctgcg | 540 |
| tagtgccggt | ggtcctgcgc | tgcccacgtc | gctatctgcc | tctgccatgc | tgcgtcctgc | 600 |
| tggtgccagg | ctcgctcgcc | tctgtcctgt | ctgctcagca | tcctgtgcct | cctgtggcct | 660 |
| ctgctggtcc | tgtcgggtgg | tggtgcggga | gtggctggcc | ttgcctcttg | tggtattgcc | 720 |
| tcctggctgt | acctggcgtt | gcctgggtgg | tcccggctct | gcctggggcc | tacctggcca | 780 |
| ctccctctag | gccacgtact | ctacccgcct | gcctctgcct | tgtctagtcc | ctcctggctg | 840 |
| gtgcctgggt | gctggtctgt | ctcaccctgg | ctcactctgt | ctctacctgt | gccctgcctg | 900 |
| gctctgtcct | ggctaccgct | ggtcctgctg | tcttgcctcg | ccgctccctc | gcatgctcgg | 960 |
| tcgcacctgc | ggcgctgatg | gactcctgtt | tgtccattgt | gtgtgacata | accgcagccc | 1020 |
| tagtgccacg | cgggttccag | ggcggtgggt | cgggtgcctg | ggtggcggct | gtcgctccct | 1080 |

FIG. 18B sequence.txt

| | | | | | |
|---|---|---|---|---|---|
| ggtaacgcaa | atcctggcta | gctagactaa | gcctcgcacg | tgggtctcta | tacgtgtggg | 1140
| aaggctccag | ggagcgccct | gggagggttg | acacgtgggc | agtaggtctg | tagagttcgc | 1200
| cctgtcttca | cgcaacaacg | cctctacagg | cagcctggag | acggggttga | cacactgcca | 1260
| gggcatcggt | agagtacgca | gccagaacga | cgggagattg | caaccttcca | agcgcggcac | 1320
| aagccatagg | cgcaagggac | acggcaaact | cttagggcag | gaaccgcagt | gtgtaaggcc | 1380
| ggcaggcatc | actgagggga | ttgacacggt | gcaggacacg | cggtacagtt | cgcaccacct | 1440
| gatggccact | cagcaaaagg | gcctatgcca | gagaactgga | cgaactaatc | cccgacagag | 1500
| gattgacaag | acaagcgcaa | gtctctaaca | tgcgcagcaa | gacgaaagga | tggttcagcc | 1560
| atctggcggt | agaggttcga | agcttcacca | gcggtacatg | gactggtgcg | gtaggttgac | 1620
| cgaagctgca | actggttagg | cagggtccca | gggaatacct | gtcgggtgct | gaagactcac | 1680
| ccaaaagagt | ctgagcggga | agcctcccg | tccacggtta | agcaaaggca | cgttagtgcc | 1740
| ggtgggaacg | aacagagtgt | cagtgggatc | gagaactaga | aacctcggtt | aatcgcgact | 1800
| gacagtatgc | tgggtagtat | cggcgggccg | attgaacaag | gccaggcaga | tagcgcaaag | 1860
| ggtacggggg | atgagtgctg | acgatcccga | agagtatgcg | caggacaagc | cagaaccgct | 1920
| gatactacag | ggactatgcc | aatgccaagg | tttgtccctt | gaggcccttc | caccgagggg | 1980
| attcaagaga | cagacctagt | gaggattgcc | gatggcacac | ttcaaggcta | aggctcccaa | 2040
| gtcgcccttt | gctgctcagg | tagcgtactg | gcgggactgg | gaagccaaac | gtactaagct | 2100
| catcgcacag | gataacgtcg | aagggcgtaa | agagcttcgc | aagatgcgtg | acgtgcgcta | 2160
| cgccaccgac | ccggagccag | cgccaggacg | ctaccataac | cctgaacaga | aggctttcgt | 2220
| gaagggtagc | gaaggcaagg | cgcggaacat | cctgaaggga | tggaacgcta | agaagtcgca | 2280
| agggaagggt | ttgtaatgcc | acgtgtgaat | gaactgacgc | cgcgtcaacg | caaggccgcc | 2340
| aaggctcgcc | gcgacaaggc | tcgccggatt | gatctagcgc | acaggatgcc | gaaaggtgcc | 2400
| gactgcccga | tcttccgcaa | ggctgagcag | gcgcaagcta | agcagccacg | agtcgatacc | 2460
| ctgaccactc | cccgcagtgc | tggctacctg | gccgccgctg | cttacctgaa | caaatccatc | 2520
| tgaggtacat | accatgacca | acgcaatctc | caaaaccgta | atcgcattcc | gtggcaccga | 2580
| agagatcaac | cgcgctatcg | acgccatccg | tgtccgtggc | aaggaactcg | acgaagccat | 2640
| ccaactgacc | ggcctgtcga | tcatccacca | catcgaccag | tgcggcgacg | tgaccgtagt | 2700
| caaggcgctg | tatgaagcca | tgccgaaggg | cagccgccgc | aatgcgctgg | tcgagtggct | 2760
| ggtgctgcac | ggcaaggtac | aggttaacac | tgacaagaaa | tcgaacaagg | acctgccctt | 2820
| cctgtacaac | aagttcggca | agaccgatct | cgtcggcgcc | accaacagcc | cgtggtacag | 2880
| cttcaagcct | gagaaagcgc | tggaccagga | gttcaacctg | gctgctgccc | tggccacgat | 2940

FIG. 18C sequence.txt

```
caaaaagcag gtgctccagg ctcagaccaa gggcaaggtg atcgtcggta tggaactgct    3000
gggtgacttg gaagcgctgg ccgccaaggc tgcacccatc gccgagcaga gcaagcgcgc    3060
tgccgcccat tgactcaagt cgaacgcctg ctaagcgggc gttccgctgg aatcaatgac    3120
aactggagaa acacgatgag cttcaaacaa cgcctgcaac gtcaaatcgc cctggcacag    3180
tacagccgcc cggctcagtt cccgtatggc gagcaagccg tccaggcgaa gggggagtga    3240
ccatggactt ctggatcgcc cttcccttcc tcgaactcgg cctcaacctc ggcgaggatg    3300
aactgcgcat gttgtggttc agcggcctga cgatattctt catccacctc ctgaagcggt    3360
gactcaagtc atggccctgg cgggcgaccc tcgcctactc cggggccatc gctggactca    3420
tcacaagcga gaactaaacc atgcaagctt tgaataccct gttgattgca atccccaagg    3480
acccgaccgc aggcatgcac gccgccgaca aggtgctgtg cgcccacgga ttccgcatgg    3540
gtgacctgaa taccgcgcac gtcctgaccc caggcgggtt cgtggtagtg ggcgccggcg    3600
tgactgtgaa ccgctatgac gaagcgtatc gtatgagccg gaacctcgac tccgaaggct    3660
tcgacgtgct gctggtccag ggcagcccgc tgtccgggcg tgtcacctgc caggcgtacg    3720
gatggatcaa cgccgagtac cacaagggct gtgcgaatgg ccgtcccatc ttcgacatcg    3780
caggaacctc gtaccatgtc atcgcgtgac ccgtaccgca tcggccaccg cgttgggctg    3840
gtgaactaca gcgaccgcta cctgggtgcc gacgcggcag gcaccaaggg catcatcgag    3900
gccataaccc gaccgtcgcg ctgtatgacg gtctaccacg ttcgctgcga gcggaccctg    3960
cgcctgatcg aggcagaggc ccgcaacgtg cgattcatcc gacagcgggc ggagcggtga    4020
gctggcgcat cgtggtagtg acgccaggca acgggtgcgc cttcgtgtgg acccgtcgca    4080
agcgcgtccg gcctctgaga ttctactccc gcaaggccgc taaacgctgg ctccgtaggc    4140
accgccgccc ggcgatcctc ggtagccagt acctgatcgt gaactggagc aaacgtatat    4200
gaccctcgtg gccaccgtag tagacagcgc gcacaacctg gaagtcgacg acctcaccgc    4260
cggcaacctg tatgccgcca gctcgcccag cgggaacatg ttcatcgtgg tagtgggtaa    4320
tcacaatggg cgcaggcttc ccgtagtcct gtcatccacc gatacccgca ccatcgggga    4380
cgtgataagc aacactgggt tccggtacag tgagatcgcc gggttctccg taaacctggc    4440
acagggagat tatgactgat ggtcacccgt actgtatacg tcacgcctga agacccgacg    4500
ccgccgatct tgtccgtggg ccgactggct ccgggagaac tctacaaggt ggtggcaccc    4560
agctcggcgg aaggtatcat tgtgctggcg accaagcaga cgccggcgct agcccaagca    4620
gccgtcgtac tgcacagcat gaaccctgcg cagtatcccg caggttcggc tatcctcaac    4680
acggcctgga agtgccgccg cctgggagtg ggcgagtacg tcaagctcgt ccaaggggag    4740
gaggactgat ggccgtggca atactcatcc tggccgtgtg gttgatcggc ggcgccctgc    4800
tattcctgcc gttcgacctt gtggtctcac cgcgcttgcc gctatcagac gaggccctca    4860
```

FIG. 18D sequence.txt

| | | | | | | |
|---|---|---|---|---|---|---|
| accgaaccgc | actgtacacc | gtgctttggc | cggtaaccct | acctaccctg | atcgccataa | 4920 |
| ccgtggttgt | catgctgcat | tccgcgtaca | ggggcgccat | cgaactctac | caggagatga | 4980 |
| aatcatgatc | cgtacccata | cccacaacgt | cgagcgcaca | ccgcaccgac | tgtaccggca | 5040 |
| cactgagctg | gcgtctggcg | agctgtaccg | tgtagtgcag | cccgactcca | agcgcggcac | 5100 |
| gttggtggtc | ggcgtagcgg | cctgggacag | ccagggccgg | cccgcagtgc | tgcccgtggt | 5160 |
| catccatgac | gatggtgacg | ccaaggtgac | ctgcgcacgt | cctaccgtac | tgcgcaacga | 5220 |
| cgggtggcgc | atggtcctcg | ccgacaaggg | gacccaggtg | acactcaccg | ccgagtgacc | 5280 |
| aaggcgaagg | ctggtgcgcc | agccttccac | cgtggccatt | cctgccgcg | aaccaactca | 5340 |
| actgaggagc | tacaacatga | ccaacgtcaa | caccaccacc | gaaaccacca | ccgctgctgt | 5400 |
| cctgggtgcc | aagctgatca | agaagccggc | caccgtcgag | gacttccgca | acaacgtggt | 5460 |
| cttccaccat | agcgccctga | ccaaactgac | cgaggtctac | aacgaagcgg | tcgccgccct | 5520 |
| gcaaaccgcc | gagcgcctgt | ccagcctcgt | cgccggtgac | gtgatcacct | tcgaccacgg | 5580 |
| caagggcgag | aaagccgaag | tgctgagcgg | cgaagtcatc | agcgtggtcg | ccggcgtcta | 5640 |
| tcaggtgctg | gtccgcttca | gcgacagcgc | accggccaag | ctgctggacg | tgaaggccag | 5700 |
| cgccatccgc | gccgtccagt | cgtcggcagc | ccaggctgca | accctcgacg | aagccatcgc | 5760 |
| ccagggcgag | taaggcccgc | acgtaatagg | cccggccctc | cgggcctatt | gcgagctagc | 5820 |
| cataccatag | gaggaatcac | catgagcaag | cgcaaccccg | aacacatcaa | cggcaccgtt | 5880 |
| cgtagcgtca | gcgtccagaa | gttggcggcc | acccaggaac | tggaggatcg | tctggaggct | 5940 |
| gccctggccg | tgtgccagca | gcgggcagag | gacatcgacc | tgctgagccg | ccgtctccag | 6000 |
| gccgccgagc | gcgcccgtcg | ctgggagatc | gacgagattc | gcaaccacca | ggcgaccatc | 6060 |
| cgcctgttgc | aaaacgatct | gaacgctgcg | catgatgccc | acgaggcaca | agagcgccgc | 6120 |
| gctcgcaagg | caaccatcat | ggcctgggta | tgcctgctga | ccgcaggttt | ggccgtcacc | 6180 |
| ctgaagctgg | caggagtctg | accatgcagt | gcaaagacct | ttacgaac | ctcgcgtcgg | 6240 |
| gcatgttcaa | cgtgccgtgc | tcccaggtga | ccccggagat | gcgacgggta | gccaagagcc | 6300 |
| gggcattcgc | ccacgcctat | acgcccaaga | aacaggcttc | gggcgggact | tacaccgccc | 6360 |
| gtgtgagcgg | cgtcacctgt | gacggtggta | aggtggaggt | gcgcctggat | aacgtggagc | 6420 |
| gcgtcagcac | cttcgactat | gccgagctgg | agacgcgggt | agcggccagt | ctgtgccagg | 6480 |
| ccgacgcgaa | gcgcgccgct | gaatacgaaa | agctactgct | gaaagcgttc | ccgtcggtat | 6540 |
| ccccgaagga | tggcccgctg | tccgccaagg | acttcgaatt | gcgcctgcat | gatctgtgct | 6600 |
| caaccaagct | ggtagtgctt | cgtgccttgc | gtgatgccgg | gatagagatg | gacggtccgc | 6660 |
| tgcgcagccg | ggtacggaag | ctggcggatc | ggaataacgt | gatgggtgct | gagttgttca | 6720 |

FIG. 18E sequence.txt

```
gcctcaagca ggagttggca caactggtcg cggtcggcca aaaggctgga ctgaattggg      6780
acggggcgga gactcagcgc ctgctgacgg tggccccgac caaggctctc tgtcgactca      6840
tcagcgcgct gaccggcgtg cggtataccc accacaccgt cgtagccaag gccgaggctg      6900
aggcgcgcga gcgggcaaag gccgaggcca aggattcatt gcaggcggca accttcgcag      6960
ccgccatcgc tggtggcgtc gtcggcagcg ccctgatgtt cctgctcggc tagggcgacc      7020
agggcctact ccggggtcaa atccgagggc gttcctagag cgccctctcg tgtgagtctg      7080
gaggatcacg aacatgcaat accacttcac gcattacaac ggataccgct cggcgtcga      7140
gctggaggac gaggctgtct tcccgtgcat cgacggtaag cgggcgacct gggacaaggt      7200
ggcggcatgt gccggtagcc ttgtgcatta catggcgcag gacctgatcg actttggcca      7260
gcgcaagtta agggagtttg aagatgagca agacgagcct gtatccgctg aacctgcatc      7320
ccggcctgat tcaaatcagg acgattcacg tattcagcat ccaagccccg agcaacgccg      7380
agaactggtg gcagtggttc ctctggcagc ggaagtacca cccgctccgg gaaagcctga      7440
gtccagccgg ggagctgagt gcgagtatcg ccgagtgtgt gctccacctc cgccggaatg      7500
gctggcaaga tagcgacatc tggcgcaaga agggaggcgt gctggccctc ggtgccttcg      7560
acctgtccgg cctgatggta ggttcctgcc tcgtagtagg tggtgagctg aaggccctgt      7620
gcgttgatga ccggcacagc aggcagggta tcggcgctga gctggtgcgg gccgctgagc      7680
tggctggtgc cgagtatctg acctgcttcg agttcctgga gccgttctac gccgacttgg      7740
gctggagcac cacccaccgc gaggcgaact ggacagcagg agagccggac gtgctgcaca      7800
tgagggcacc cggtcatgac gtatgaggtg atgacatggc ttatcgagaa caaaccgctg      7860
gtcatcggag tcgccttcag tctggtggcc ctgggcgtgc tgctcacaca gaacaacggc      7920
ggcccgccta cggcgcccgc atgacctggc acctccagga catgttcgag gcccgaggcg      7980
ggctgcggcc tttgtgggag gaatggtacc aatggcactg cgccgtgact cctggctaaa      8040
gcaagcgcaa tccctggcgg tcggtcaggc gggtcgattc cgccacgtcc tgggatgcca      8100
gagcatgagc cggggcggga ccaacatgac ctgcaagaac cttcctgacc gctgggtggc      8160
ttactgctac tcctgtcagg agggtggcgt ggtcgagaaa acgcatgtgc ggagggtaca      8220
atgcgcggat caagaacgct tcatgccctg gcccgaggat gcctcggact ggacgcaagc      8280
cgactgctat caatcgcttt atggtttgct gctgtccaag ggcatagact acaacgtgat      8340
gacgccaggg ctgccgctgc tgtacagcga aaggcagcat cggcttatct tccctaccga      8400
cgcgggctgg attgggcgcg ctactgccga ccaaaatccc aagtgggtgg gttacgggta      8460
tcctgccccg gattaccatg gatggcccca ggaattatca atgggcaggc catgggtgct      8520
gacggaagac tacttgtcgg cgctgaaggt gcggtgggcc tgtcccgaag tctttgctgt      8580
cggtctgaac ggtacaaggc tgcgcgacag gctggcggcg atcatgttgc agcagacctg      8640
```

FIG. 18F sequence.txt

```
caagcgcgcc ttcatcttct tggatggcga ccgggcaggt gtccgtggta gtgcaggcgt      8700
gatgcgccgg ctccggtccc tgcttatcga aggccaagtc ataccaacgc cggacgggtt      8760
cgaccccaag gacctgaccc gcgagcagat aaggagccta gtaattggac gtattgacgc      8820
ttcacgcact gagtgaccgg gaccgcttcc gcacattgcg gagtgtggtg cccgaaggaa      8880
tgatggggcc ggagacgtgc ttcgtcatcg actggatcga gcagtattgg aaggtctacc      8940
cggcgcatca gaaggtagac ccgcaggcac tgcgcgaact gatcaagctg cgaggtggct      9000
accagccgga gcaactggcg gtggtcctga acctcgtcaa ccaactggac aagccggtgg      9060
acccggactc gctacagggc gtcgtgtccc agctcaacga actggatttc tcagggcggg      9120
tggatgccct cctggcgcag tacaaccagg gcgaggacat cgacctggcg tatgagctgc      9180
gccggctgag cgacgaggcc ctgcgccgcg aggggtcag cacgccgacc gactacgtga       9240
cggacgacgt gtttgatatc ctcgcggagg agcagggtga ccacggcatc aagctgccgg      9300
ggctggtgct accggcgtac atgaagggcc tccacgccgg ggcctcggtg ctggtggcag      9360
cgccgccgga tgcgggcaag acctcgttca tggcctggat cgctgtccat atcgcgccgc      9420
agctcaagcg gtacttcgac cccggacgac ccatcctgtg gctgaacaac gagggcaagg      9480
gccggcggat caagccgcgc ctgtactcgg cagccttggg catgaccgtg ggcgagattc      9540
ttgccctgga cccggaggaa gttcgcagga tgtacgccga gaaaatcggc ggcgactctg      9600
agctgatccg catcaaggac ttccacggcg ggtccctggc ccaggccgag caggtcattg      9660
acgcgatgaa gccgtcggtg gtgttttggg acatgatggc tcacgtcaag ggtggacagc      9720
gcaaggacca gaaccgcacc gacgagatgg agtacaaggt ggccgaggtc cgcgagatgg      9780
cggtgcgcca cgacttcatc agcttcatga cgtggcagat tagcaacgac ggccacgacc      9840
agttgttccc accgcagtcc tgcctcaagg attcgaagac agcagtgcag ggtgcggtag      9900
atgtgcaaat ccacctgggc cgtctcaacg gtgcggatca acaggtcatg cgtggcctgt      9960
ccctgccgaa gaacaagttc cagatggacg ggaagccttc gaacgtggag gctatgatta     10020
acttcgacgc cgcacggtgt cgattcttcg agagtgtaga ccatgcaagc taagcatagc     10080
cgggtgctcg aaggcaccaa agaaattccg ctgggtagca tcgagccgtt actgggcagc     10140
gtcgcgggcc tgctgttgtg cctgtactcc gacgcaactc acgaggaggg cgtcgccttg     10200
gccggtgggt tccctcgcga cttgatgcac ggcgccactc ccaaggacgt ggatgtggcc     10260
ctgtatagca tgacctgggg gcgggcagag cacctgatcc agaaggcact cccggtcctg     10320
aaccccatct tcgtccggga tggtgggtgg cgctcggact acgctgatgg tggtgacggt     10380
ggtatcttca agggcgtgat gtccctcgtg ggctgccgtg ggttgaatgg catggacttg     10440
gactttaact actacgacgc cgacagcctc ggtcgagtga tggagtcgtt cgacttcacc     10500
```

FIG. 18G

```
                                    sequence.txt
atcaaccagg taggcatcgc gtacaactgg cccgaccccg agggtgggcc gcgcctgggt    10560
gcgtacctgc acaaggacgt tacctggggc gtgaacaagg aagtcggtgc cggctcacgt    10620
ctgccggaac gatgcgagaa aatgcgagcc aaggccgcgt actacggatg ggagaacgtg    10680
tgatgagcaa gcgcgacgtg gtactggata tcgagaaagg catctggcgt ggtgttgacc    10740
agaacgacaa ggccgtcgag gccatcatca agaagaacgg gtacgtgatc gtcgagccta    10800
agatcgacgg gtgccgtgcc atcgtcggtg cgcatggcgt ggtgtcccgc agtgggcgcc    10860
gcttcccggc cctggatggc ttggaagacc gcatcatcga gcgactggcc cgaccggggc    10920
tggactccgg cctggtgctg gactgcgaga tgtacctggc cggcatgccc ttcagcgagg    10980
cgactggccg catgtcgagt aagacccgc tgaccgagga agagctggag tgcctgcact    11040
tcgcggtatt cgacgccacc catatcgacg tgctccgaaa ggcgcgcacc tcacacctgg    11100
tatacgaaga gcgccgagcc atggccagca gcctcctggc agcctgtcgg ctcagcgaca    11160
ctccgacgtt cttccaggtg gggttcaccg tctgccggag aatgtctgac gtttaccgcc    11220
agtacaagtt caaccgggag gtgggctacg agggatcaat ggagaaagac cccagcctgg    11280
tctaccgcaa cggcaaggtc gccggctgct acaagcgcaa gccgggcatc accgtagatg    11340
gccgcatcgt cgggtacgtg atgggcaaga ctggcaagaa cgtgggccgc gtcgtgggct    11400
accgcgtgga gctggaagat ggttccggca ccgtggccgc caccggcctg agcgaggagc    11460
acatccagct cctgacctac gcccacctca cgcccacat cgacgaggcc atgccgaact    11520
acggtcgtat cgtcgaggtc tccgcgatgg agcgctcagc caacaccctc cgccatccca    11580
gcttcagtcg cttccgcgac ctggccagta atccaggagt caaggtatga agattcgaaa    11640
gtcccgtaac cgcaactacc cggaagatat ggtgtaccac gccaccaacc gggattcact    11700
gctgtatccg aagtacgtca tgggttccgt gttcatcagc caggacggaa cattccgcat    11760
ctgcgtcatg gcagggacct gggaccacgt tgggtcgaa gttctgcatc atgcacggga    11820
catccaatcc cttggcgccg gtcgccgtaa gttgcaccgg gtcatgcgac ggctgcgccg    11880
caatctgcaa caggtaggag tcaaggtatg agaatgccaa ccgaagaaga acgcacgatc    11940
cgctgcctgc tggcagatat ccacgaaccc ttgaacctgc tgttccccgg tatccgtgta    12000
aaggccgaga caatgcccct gggctgggga gatagtatct gtgccctggt actccgggtg    12060
agctacgaac atctcacgct ggggcgcctg gagtacatgc acgaggtccc catcctgcac    12120
ctgtcgcagt ggggccggga cggcctgcta cagcacctga tgaacgagat tccccgtcgg    12180
gtgctggatg gcatgctacg tcaggcacag aaatacagcc agagtaactg gtacagcaaa    12240
tgacgactat ccgaatcctc gacctcgaaa ccgagagcta cgagcacaaa gggcgcaagg    12300
cgtcgccctt tgaccccgc aactatatcg tcatggccgg ctggcgtgac gatgttgacg    12360
gcaaggtcgg ccagaaggtg gagcatcgct ccgcagccg ggccgaagcc gaagacccga    12420
```

FIG. 18H sequence.txt

```
acaaccgctg gttcaacctc gacggcgtgg acgtgatcgt agcgcacaac gccatgttcg    12480
aatcgaactg gttcttcacc cgctaccggg acgagtacct ggccttcctg cgacgtggtg    12540
gccgggtctg gtgtacccag caggccgagt atctgctgag tcatcagacg tggctgtacc    12600
cggcgctcga cgagctggcc ccgaagtacg gcggcaccca caaggtggac ggcatcaaga    12660
tgctgtggga ccagggtgtg ctcacctcgg agatggacca ggacctgctg agcgaatacc    12720
tgtctggccc gtgcggcgac atcgagaata ccgccctcgt attctacggt cagttgatga    12780
agctccaggc ccgtggcatg tgggctggtt acctggagcg ctgcgaggcc ctgatcggtt    12840
tctcggcgat ggagtgcgcc ggcctgaagg tggacctcga agtcgccaag gtgaaccacg    12900
ccaagcaact ggaagaggtg gccgggatcg aggccgagct gaagaagctg atgcccgact    12960
tcccggaata cttcgagttc aagtatacca gcctctacca tatgagcgca tggctatacg    13020
gtggcgaggt gcggtacaag ggccgggtgc cctacgaaga tggccggatg gagaaagccg    13080
acttcgtgcg cttcggcaca gccaagcggg ggactcctat cgagagtacc tcggtacggg    13140
tcccgatcca cgaagtgacc gaccagggtg aatggcactg gccaccatcc accgagctgg    13200
cgaccaagca cggtccggtc atcacgttct ccgccggcaa gaacaagggc agcgtcaaag    13260
tgttccgtga ggatacggac atcccggcga ccaagtggga cgatgaccag cgattccggt    13320
tccccggcct gatcaacctg accaacctgc cggaagtagt gcgtgagaaa ttcctgggca    13380
agcgcccgga gttccagtgc gccctcaccc tggcggatgg atcgcccgtg ttcagcacca    13440
gcggcgacgc cctcaaggct ctggagaaac agggcttcga ggcggccaag ctgttgatgc    13500
gcctggccga gctgcacaag gacaactcct cgttctacat cacccacacc tacaacaagg    13560
atgggacgat taaggacacg aaggggatgc ttcagtacgt ggacgatgat ggtatcatcc    13620
accactcgct gaatacgacg gcgacggcga caacgcgtct gtcgtccagc cgcccgaacc    13680
tccagcagct cccgtcgaag gacgaggacg acccggaagc cggcagccgc gtgaaggaga    13740
tgttcgtgtc tcgcttcggc gcagacggga tgatcggcga gaccgactat accgccctgg    13800
aggtggtgat gttggcggcc ctgtcgaagg accggaacct cctggcgaaa ctgatggccg    13860
gcactgacat gcacttgtac cgcctggcag ggaagcacaa caactggaac gggttcgact    13920
acgaccagct cgtggccatc aagaaggacc ccaaccaccc gtggcacggt cgcatgatgc    13980
aggctcgaaa gaacatcaag cccaaggcat tctcggcgca gtacggcgcg agtgcggctg    14040
gtatcgcatt caacaccggc tgtaccgtgg aagaggccca ggaattcctg gacaacgagg    14100
cggccctgtt cccagagtcc atcgcattcc ggcagatcgt ccgagacagt gcagaggcca    14160
ccagcctcgt catgtacaag gccgaggacc agatgccggc aggcgccttc agcgagatgg    14220
ggccggatgg caactggcgc cagtaccgcc ggggattctg gcaagcgccg ggtggcacct    14280
```

FIG. 18I sequence.txt

```
gctacagctt ccgccaacag gagcgctggg acaaggaaca gcgcaagacg gtcatggact     14340
tcaaggacac gcagatcgcc aactactgga accagggcga ggctgggttc atgatgaccg     14400
tgagcgtagg gcgcatcttc cgttggatgc tgcatcgccc aggattcatg gtcaccgagt     14460
tcctgatcaa caacgtacac gatgccgtgt acaccgactg ccacaaggac accgccgccg     14520
aggtcaacaa gggcgtgcgc gacatcatgg ccgacgctgc ccgctacatg agcgagcgcc     14580
tgggctacga catcgccgac gttccgttcc cagcagtggc tgagatgggg ccgaacatgt     14640
tcaatatgga ggtgatccag tgaaagaact gcacccgctg cacacgcctg agttcgtcaa     14700
gacattcctg gaccagaccg ggtgcctgcc gggagtacgc cgtacgggtc gcaccaccgg     14760
cattgctcta caggccattg gcatggcgct gtcccatccg agggaaaccc tgacgttcgt     14820
ggaccacccg gacggcagcg cggcagcact ggtggccagc attgaaacca tactggcgac     14880
cctgggctac aagaacgtcc tcgttcgacc cacaacccgt gcggatgggc gcagcgtgag     14940
catcgtcttc aagacgctgc cgaacgcctg acgaccttc cctactccgg ccttaaatct     15000
tcatccgaca cgagagagac cacgcatgac tcaacaactc aacgctctgc aagccgccct     15060
cgccctggcc aacaaggctg ccgagaccgc aaccatcgac atgtccgaaa cctccaccgg     15120
cggtggcggc ggtcgcatct tcccggcggg caccgccatg ggccgcttct gcatctacat     15180
cgagctgggt gaccacgcca aggaattcca gggcaagctc aagaacccgg cgcctcaaat     15240
ccgcctgggc ttcgcactgt ggggcgacgt gaacccgcag gccggtaacc cgcagagccg     15300
cccggacgac ctgttccaca cttacgaggc cgacggctcg atcaagcccg gcctgttccg     15360
taccttcgag atgacccteg gcaacaacga aaagtccaag accaagctgg ccttcgacaa     15420
gatgaactgg agcgggcagc atacccactt cgctcagatg ctcggccagg cgttcatcat     15480
cccgatcaag cgcaccaaga tcaccaaggg caacaacgcc ggcaaggaac gcaacgacat     15540
cgattggggc ggcatcatga agccctacaa cccggtcgat ggcagcccgt acaacgtgcc     15600
ggaactgccg atggacctgt tgcagtattt cttcttcgac gcgccgacca aggagacctg     15660
ggacgccctg tatatcgagg gcacctcgga caacggcaag tccaagaact tcctgcaaga     15720
gaccattcgc tcggccacca acttccccgg ctcggccctg cacatcatgt tgggcggcgg     15780
cgacgatctg atcatcaagc caacgagcca ggccgcaggc agcaacctgc cggcagtgcc     15840
caacgtggcc gccgatgcag gcgtagcagc agcccctgcc gtcccggcag tccgcaggc      15900
agtggctcag acggccccca gcgtgcccca ggtggcgaat gtggctgccc ctgtggtagg     15960
tactgccgag gcgcagaacg tgctgcctga cgtgcccag gtggctcaga cggcggctcc      16020
ggcagcggtc gaagtcccgg cggtcccggt agtgccggca gtaccgcagg tctaatgcgc     16080
ctgccatcgg aagagttcct ggcaggacta tccgcgcagt tcgaccgcag catggcaggc     16140
gggacgttgg tgtgtgacgc cgatggaccc gcctacgtgg ctgcggccac tgctaagacc     16200
```

FIG. 18J sequence.txt

```
ctggacactg cactccgaag attctggaag ctcattttgg agcagcagtt cctagcgcac    16260
tgcacaggga cacgggttca cctcacggca gcaggtgggg cgaaggcgta ccgcgacacg    16320
tatccgacca tgaaaccgta ccagggccag cgcaagggca aggcaaagcc cgcgctgctg    16380
gagccactgc ggcgggccgt ggcggacgtg catgagcgag gcggggcgcc ggaggggatc    16440
gatgtcatcc tgcacacgtt cttcgaggcg gacgacggca tgatgatgga cgcctacgcc    16500
atgcaggaca aggccatcat ccggtccgac gacaaagacc tgcggatgac gatctacccg    16560
tattgggaga tcgatacggc gtgtgtgagc aggatcgaag gcggcttcgg ctacctcaag    16620
gaagcgtaca cgccttccgg ccagttcaag ctcaagggcc atggacggaa gttcttcttg    16680
gcgcagtggc tcggcggcga caccgctgac aacatccgag ggatcgatcg attcaacggt    16740
aagctctgcg gtatgaagac ggccttcgac atcctccatc cgatcacgga tgaggacgag    16800
gccatcgaca tgatcctgga ggcgtacgcc aagatcaagc aaaacccgct ggcagaggcc    16860
gaggtgctgt ggatgcgccg aacgcctacc gacaacgcag cgcagtacct gttaagccgc    16920
gaccttcgtc cggccttccg ccagtggatc atcgagctgg acgcctacca cgaggcgctg    16980
ctccagaagc ggagggagag cgattatgac gagtgagccg aaggtctacc agataccgcg    17040
cagtcaacag cgcaccttca ccctgaagct atgggccgag cagaacaagc tgtgcccgct    17100
ctgcggcaag cccatcgata tcagcgtgaa gggcgaagcg gtgatggacc acgaccacga    17160
aacggggctg gtgcggggcg tcctgcaccg gtcctgtaac accgcagaag gcaagataac    17220
gaatgcggca ggttcctggg gatgcaagtc gatgaagtat tcagacatca tccctacct    17280
tcgtgccctc ctgacgtatc tggaggggcc gaagcatccg ctgatctacc ccctgcacaa    17340
gaccgacgag gagaaacacg aagcgaagct ggccaagcgc cggcaggcag ccgccaaacg    17400
caaggcggcg atggccgtcg caaagcacaa cgcgaggaac gtatgagcaa actccgcaag    17460
caattcacca atgagtacct gcgaaacgtc tatgtcgagc tgggcctcaa gaagggtgcc    17520
gagcacctga ccgagcattc gcgcttcggt gaggtgagcc gccagtgctt ccgcaactgg    17580
tgcatcaagc tgggcttcca cgacagcagg acgcgcggca tgtacgccaa gaagggcgcg    17640
atgcactggc tgggccgcaa ggctgccgag gtagtgcgca agttccctgg cgccgtgggc    17700
aacgtggtag gccagggtcc gaaggtgctg agcctggaca tcgagacctc gcctatcgag    17760
ggctgggtct ggtcgctctg gaagcagaac gtgggcctca accagatcaa gcgggactgg    17820
accatcctgt cgttctgtgc gaagtggatg cacagcgacg aggtgatcta catggactgc    17880
cagggtgatc ccttggacga catgcacctg ctggtcgcgc tgcacaagct gttggacgag    17940
gccgacatca tcatcgtcca gaacggcaag cgcttcgacg tgcccaagat caacgcccgg    18000
ttcttcctga acaagatgcc gccgccgcga ccgttcaagg tgatcgacac cttgatcatc    18060
```

FIG. 18K

```
                                 sequence.txt
gccaagcagc aattcgcgtt caccagccgc aagctggagt acatgaccca caaggcatgc    18120
accatcaaga agcgactgca cggcaagttc cccggattcg acctgtgggc ggcctgcctc    18180
caggacaacc cggaggcgtg ggaagagatg cgcctgtaca acatcgacga cgtacggtcg    18240
atggaagagc tgtacatcct gatgcgtcca tggttcgtcg gccaccccaa cgtggccgtg    18300
tacttcaatg acgccgaacc gaccatccgc tgcccgaagt gcggcgacac ggatgttaag    18360
caagaaggct gggtgcatac gcagaccggc aagtacgagc actatcactg cggtggctgc    18420
ggtggctgga gccgagggcg gtacacccgc aacacctcgg aacagcgcaa agccctgctg    18480
agcaactaag gaggtagcat gagcctagca ttcccggact cttacgagtc gacgatcacg    18540
actgaaccgt accgcaaagg tgcgagtctg aagaacgca aggtcggcaa gcttcccatg    18600
cacctggtag tcgaggggtt cccgctgctg aagcgggagc ttgctcgaat gatgcaatgg    18660
gctgccgagg tcaaggggta tctgccgcac gactggaaga agatgacggt gggcgagttc    18720
aagtccgccc aacacaggca cgagtccaag cggctgatcg acgggccgct ggatgacgag    18780
tccaacctga tgcacctggt gcatgaggca ttcaacgcaa tggccgccgc cgaggtggcc    18840
ctgatggacc gggagaaagg caatgagtaa aatctgttgg tgtacccgac cgcacgagac    18900
cgatgaaggt gttcgggtca tctgggcctt caacgagcgg ggcatcgggg tcaactacgt    18960
cacagcgtac atcacgccgg cgatggtcag ccatcgggac tggagcgatg tcatactccc    19020
ggacattctc cgggagatgg cggagcgcct ggagcgggaa gtgaagctgg tggaactgcg    19080
ctggttccgc gctgagattc tgagctgcgg ggaatggcgt gactaccgag cgatgacgct    19140
ggaggggggcg gttagcctgg ccgaggccga gtggggtccc gaggatatcg ggcgcgtaat    19200
cgaaagacga taggagatgg aatggacctg atacagcagc agatcgccca cgaagaggcc    19260
ctggtcgggg cggcgcagaa tgacgcccgc attgccttgg aaaaggcgat tgcccaaggg    19320
tccatcgacc gcatcccgag ggcgcgcatc atgttgatgc ggatgctccc catcgtgacc    19380
gaagcgatct tcgcccacca ggaagcgaag gcggcggggc cggcagcgaa gcttcggcac    19440
ctgctgcgga tcatcgacgc ccaggacctc gcggtcatgg cgctgcgggc tgggctgtcg    19500
atgctcatca actacccaac gatcacagcg acgaagtatt acacccacat gggtaagata    19560
ctctgtcgag agatcgaagt gcggttggcc ttcaaggtca accaaccctc ttacgaccgg    19620
acgctggact acctcaagac cagcaggact cgcagcgtcc ggcacatcca aagacgatg    19680
gacgctcttc tggacgcggt actaccggaa gaggcacgta tcgacctgcc ggatggcgac    19740
tacctgcgcc tcggcaagtt catcggtgat ccgctgatac agtgcggcct gttcgagccg    19800
aaccgcttca caggtcgtgg aggtactagc gtccacctgg agccgtcgcc ggaagccaag    19860
gagttcctgc aagacccttc ggcggcgatg acctggggag gcccaggccg tagcgtgatg    19920
ctggcaccgc cgcgaccatg gaacgactgg tgcgatggcg gttactacag cgctaaggcg    19980
```

FIG. 18L sequence.txt

```
cagaaacacc atgtgctagt gcgccgtacc aagcaccaga ccaagcgggc gcgccagatg    20040
cagctacgcc acctgggccg ggacaagatg cccagggtgt atgaggcggt caacgcgctg    20100
caatcagtgg cctacgagat caaccacgac gtgtacgaga tcatcgagcg cgtcttcact    20160
tccggcggcg gtgtgctggg catccctcag cgcacctacc cggacaaacc tgagttcccg    20220
ctcggcgacg agtgggccaa ggagaacgcc agtgaacaag agctggaagc cttcaaccgc    20280
tggaagcgat ccgtccaccg atggtacacc ggcgagcggg agcataccgc caagcttcgc    20340
gagtttgctg cactctaccg agttgttcga gagcatcatg gcaaggcagt gtacttcccg    20400
atgcacgttg actcccgtgg ccgcatgtac tattggggca caccgaatcc ccaggggtcc    20460
gacatcgcca aggcatgtct gcgattccac gaaaagcgtg ccctcggtaa gcgcggactg    20520
tactggctca aggtccacgt cgccaactcc ctcggatgcg acaaggtgta cttcgacgac    20580
cgagcagcct gggtcgatga gcgctgggac gacttccagc gagcgctcga cgaagggccg    20640
gagaactatc cgaatctctt ccccgaagac gagtccccac tgtgcgccat cgcaggtctg    20700
ctggagttgc gggcggccta cgcttccggc aatcccgagg gctacgccag tggtttcatc    20760
gtccacatgg acgccacctg ctccggcctc aacactact cggctattct ccgcgacgag    20820
atcggcgggg cctacgtcaa cctgctgcca cctggacttg caaaagctga tatctactcc    20880
cgagtgctcg gactcgttaa tgagtctctg gagagagacc gagcggaagg cgcggatggc    20940
gaggcgcggg gttatgccat tctatgggat aaagctggtc tgacgcggag cctgaccaag    21000
aagccctgca tgacgctggt gtacggcacc acgttcaagg gcgtcgtgga ccactgcctg    21060
gactacctcg acgagtccgg tgtggagatt cccgagggtg tgccgtcata ccgcctagga    21120
agctacatgg cgacgctcat actggacgca atccgcgaga cagtaccatc ggcagtcttc    21180
gccatggagt ggctccagcg gcttgctagg gcccttcctg acgcatccaa ggatttgcac    21240
tggaccacgc cgctcggcat gcaggtcttc cagtcctacc cgaagaccga ggaggtgcga    21300
gtacggctgc gcgccgaggc tgtcgagtac gtcaccctgt acgaggccaa ggacgagctg    21360
gacccggtac gcaacgccaa cggcatcgct ccgaacttcg tccacgggct ggacagcagc    21420
cacctgggcc tgacggcctt ggcatgcgcg gcagagggaa tcccgatcca ggccatccac    21480
gacagcatgg gcacttatgc ggcagacgtg gaccggatgc acgttcacat cagggagcag    21540
ttcatcgcca tgtacagtgg ccccgtgtgt ctcgtagagc tggcaaagca gcttggtata    21600
gaggctaccc cgccccggag aggatcgttg aatctggagg ctgtacggga ctcctgggcg    21660
ttcttctgct gaggcggatt atgtcaccca cataggagca agtgcatccg tccaaggccc    21720
tcgtagaggg agcggggagc aggagaggtc agggaagacc tggtagagga gaggtgaaga    21780
tgagaatgga tgactacgaa ggattctaga tagaatagac taaccagcat aggagatatg    21840
```

FIG. 18M

```
                                    sequence.txt
atagatggct actatgaaga cccaccgccc tacggttatg tcacccacag tggaaggatc    21900
gagaacaggc aagggtacgg cccgtcctgt cacgttcacc tctcagcaga tcgagtggtt    21960
agaacagacc ttccccgaac atcagatcgg tcctggaacc acgatggaag acatccagtt    22020
ccaggccggt aggcgagacg tggtgcgagc agtacgcctg cgccgacgcg atgccatcgc    22080
agtggagctg aagtgatgaa caagtccatc tggcgagtcc acgcaaaggc cggcactccc    22140
tcggaactcc agggcctgtg ctggctggcg atacaggagt tggaggagtt caccctcttc    22200
cgctcgaaag acgacgccct gaatgcgatg ctggacagta tcgagggcaa tgatcgaacc    22260
gagctgttgg tattccgcga tggccagttg gctggcggtg cctgcattgt gttcgaggac    22320
gatccccacg tcggcccgtg cgtcacagca cagtggcagt acgtcctacc gcgctaccgc    22380
aatacaggcg tggtccggga gttcatccgc gaactccacc gtcaggccgg ctggggtcaa    22440
atcccctcg tgtgctggag ccatcgtgaa agcgatagcc ggtacacgat ccactaccgg    22500
agagccaagc cttatgggca agaaagtaaa gaaggtgctg ggcaagacca tcatcggcaa    22560
actcgctgat ggcctgctgg gcaccgacct gagcggcgca caatccgatg cccgcaagat    22620
ggaagagcag aaccgcctaa tgcagcagca ggcggaccag ctcgcacgaa accagcaggt    22680
tgacctcacc gccgagaacg tggcgcaggt tgacctagga gcgatggccg atgccactgg    22740
caccggcacg cgacggcgcc ggaatcaggc gggcacaggc gtatcgcaaa ccctcggtat    22800
caactactga cgaggtacgc catgaaaacc accgcagcta tgctgtggga gaaacttcgg    22860
gatgggagcg tggagagtcg agccatcgag ttcgccaaga ccacgcttcc ctacctgatg    22920
gtcgatccca tgtccggcag ccggggagtc gtagagcatg acttccagtc cgccggtgcc    22980
ctcctggtga acaacctcgc cgccaagctg gcgagatcgc tgttccccac ggggattccg    23040
ttcttccgat ccgaactcac tgatgcgatc cgccgcgagg ccgacagccg gacacagac     23100
attaccgaag tgaccgctgc cttggctcgg gtggatcgca aagcaacaca gcgcctgttc    23160
cagaacgcct ccctggcggt cctgacgcag gtgatcaagc tactgatcgt gactggcaat    23220
gctctgctgt accgagacag cgccgccgct acggtggtcg catggtcgct ccgctcctat    23280
gcggtgcgtc gagatgcgac tggccgctgg atggatatcg tcctaaagca gcgctacaag    23340
tccaaggacc tggatgaaga gtacaagcag gacctgatgc gcgcaggccg caacctatcc    23400
ggttcgggca gcgtggacct gtacacccac gtacagcgca agaagggcac ggcgatggaa    23460
tacgccgagc tgtaccacga gatcgacggc gtgcgtgtgg caaggaggg ccgctggcct     23520
atccacctgt gcccgtacat cgtgccgacc tggaacctcg cacctggcga gcactacggt    23580
cgaggccacg tcgaggacta catcggcgac ttcgccaagc tgtccctgct gagcgagaaa    23640
ctcggcctgt acgagctgga gtcgctggag gtcctgaacc tcgtggacga ggccaagggt    23700
gcggtggtcg atgactacca agacgccgag atgggtgact acgtgccagg tggcgcggag    23760
```

FIG. 18N sequence.txt

| | | | | | | |
|---|---|---|---|---|---|---|
| gccgtccgtg | cttacgagcg | tggcgactac | aacaagatgg | ctgctataca | gcagagcttg | 23820 |
| caagccgtag | tcgtccgcct | gaaccaggcg | ttcatgtatg | gtgccaacca | gcgcgacgcc | 23880 |
| gagcgcgtta | ctgccgagga | agtccgcatc | actgcggagg | aggcagagaa | cacgctgggt | 23940 |
| ggtacatact | cgctcttggc | tgagaacctc | cagtcgcccc | tggcctacgt | ctgcctatcc | 24000 |
| gaggtggatg | acgcgctact | ccagggcttg | atcaccaagc | agcacaagcc | ggctatcgag | 24060 |
| acgggcctcc | cagctctgtc | ccgctccgcc | gctgtgcaga | gcatgctcaa | cgcttcccaa | 24120 |
| gtcatcgctg | gcttggcccc | gattgctcag | ctcgatcccc | gcatctcgct | accgaagatg | 24180 |
| atggacacga | tttgggcagc | cttcagtgtc | gatacgtcgc | agttctacaa | gagcgccgac | 24240 |
| gaactggaag | ccgaggcaga | acagcagcgc | cagcaggccg | cacaggccca | ggcagcgcag | 24300 |
| gagaccttgc | tggaaggcgc | ttccgacatg | accaatgcac | tcgcaggagt | ctgatagatg | 24360 |
| acccaaccga | acgatcagca | actgccaccg | ggcctcgcta | acctggttgc | caacgtaccg | 24420 |
| cccgccgccg | cgccgacccc | gagtcatgtg | caggtgttgc | cgaacccggt | gatccagccg | 24480 |
| caggctccgg | tccagcccgg | ccaggtaggt | gcgccgcagc | aactggccat | cccgacccag | 24540 |
| cagccgcaac | ccgttccgac | cagcgccatg | acgcccact | accagccggt | agcggtgccc | 24600 |
| gtcgccggtc | aacccgttgt | tccgcaagca | cccgctcagc | cggccccggt | agctccgccg | 24660 |
| gctgcgggtg | cagttcttcc | cgagaacctg | gaagtcccgc | cgcctccggc | cttcactccc | 24720 |
| aacggggaga | tcgtaggcac | cctggcaggg | aacctcgaag | gcgacccgca | gttggcgccc | 24780 |
| tctatcagct | atctggaagc | attctctgac | aagctggata | ccgtccgtgc | cttcggcaag | 24840 |
| gccgccgaga | accgcgatcc | gcgattcatc | gacgagcact | atctgaagga | agtcctgggt | 24900 |
| ccggcccagg | cacagcacgt | catcaacgtg | gccaagggcg | tcctgaccta | tgtcgatgcg | 24960 |
| cagaccaagg | ccgtcctgaa | tcagacctat | gccgccgtcg | gcggtgaggc | cgtcctgaag | 25020 |
| caggctgccg | gagtcttcaa | ccagcacgct | gacccggcca | ccaaggccgc | catcggtcgg | 25080 |
| ctgatggact | cgggcgatgc | ccaggccatg | cagtacgcag | cgaagcaaat | tgtggccttc | 25140 |
| gcacaaggct | cgggtgccgt | ggtacaggct | accggccaac | ccctgggtgc | tgcggcacct | 25200 |
| gcactggcag | ctctgagcgc | tgagcagtac | cgcttggaag | tatctaagct | gccgctgaac | 25260 |
| gcatccgaag | ccgagatggc | tgcgctgcgc | gagcgtcgta | aggcaggcat | ggcgcagggt | 25320 |
| atctaacgac | cctgccctac | tccggcctta | aacccacatc | caaaagagag | agaatcgcat | 25380 |
| gagctttctg | aacgacctga | ctcgtccgaa | ctacgctggc | aagaacgcgg | acgttgacat | 25440 |
| ccacctggaa | gagcacctcg | gcatcgtcga | taagcacttc | gcctacacct | ccaagttcgc | 25500 |
| accgctgatg | aacatccgcg | acctgcgtgg | ctcgaacgtg | gtccgcctgg | atcgcctggg | 25560 |
| taacgtcgag | gccaagggtc | gccgcgccgg | tgaagagctg | gagcgcagcc | gagtcgtgaa | 25620 |

FIG. 180 sequence.txt

| | | | | | |
|---|---|---|---|---|---:|
| cgacaagtgg | aacctgaccg | tcgacaccct | gctgtacctc | cgccaccagt | tcgaccacca | 25680 |
| ggacgagtgg | acccaatcct | tcgacatgcg | caaggaagtc | gccgagctgg | acggccagga | 25740 |
| actggctcgc | aagttcgacc | aagcctgcct | gatccaggtg | atcaaggctg | ccgcgatgga | 25800 |
| cgcgccggtg | gacctggaag | atgcgttctc | gccgggcgtg | ctggagaaac | tggacctgac | 25860 |
| cggcctgacc | gccaagcagg | ctgccgacaa | gatcgtccgc | atgcaccgcc | gcgtagtcga | 25920 |
| gaccttcatc | gaccgcgacc | tgggcgatgc | ggtttactcc | gagggcctga | ccccgatgtc | 25980 |
| gccgcgtgtg | ttcagcctgc | tgctggagca | cgacaagctg | atgaacgtcg | agtaccaggc | 26040 |
| aaccggcgcg | accaacgact | acgtgaagtc | ccgcgtggcc | atcctcaacg | cgtcaaggt | 26100 |
| gctggagact | ccgcgcttcg | ccaccaaggc | aatcgcagcc | cacccgctgg | gccgtcactt | 26160 |
| caacgtgagc | gccgaggagt | ccgagcgcca | gatcgccctg | ttcctcccga | gcaagaccct | 26220 |
| gatcaccgcc | caagtggcgc | cggtccaggc | caagctgtgg | gaagacaacg | agaaattctc | 26280 |
| gtgggtcctg | gataccttcc | agatgtacaa | catcggtgcc | cgtcgtccgg | acaccgctgg | 26340 |
| tgccatcgaa | ctgaagggta | tcggcgcctt | cgacatcacc | gcgtgatgcc | acgaaccc | 26400 |
| gcacttcggt | gtggggtttc | ttcaaagcct | aacgaccgc | gcagattccc | tgcgtgggtt | 26460 |
| tttgcgcttt | aggagaaacc | ctatgctact | actcgacgca | gtgaatgtca | tcctgcgcaa | 26520 |
| gatcggcgag | ctgccgattc | cgagcatgga | tgagacgtat | cccaccatgg | ccattgccct | 26580 |
| cccggagttg | gaggaccagc | gcatccagtt | gctgacgcaa | ggctggtggt | tcaacacctg | 26640 |
| gtggaagcac | aagctgacac | ctgacccgca | gggtcgcatc | aacctgccca | aggatacctt | 26700 |
| ggcattctac | cccgactccc | cggacctcca | gtgggacggc | ctgggagtac | gggatgccaa | 26760 |
| caccggcgac | gaccgtatcg | gcaagtcggt | cgagggtcgg | ctggtgctgt | cccgcgagtg | 26820 |
| ggaccgtatc | ccggagattg | cgcagcgcgt | cattgcgcac | caagccgccc | ttgcggtata | 26880 |
| cacccacgag | attggcccgg | acgagaccgc | ccaggtcatc | gcccaggaat | tgcaggcgta | 26940 |
| tcagaacgaa | ctgtctcgca | tgcacactcg | atcccgtccg | ctgaacaccc | aggccaagcg | 27000 |
| tagcttcagc | cggtggcggc | gtagcttgag | gacctgagca | tgagctacaa | gcaatccgcg | 27060 |
| tatcccaatc | tgctgatggg | cgtgagccaa | caggtgccct | tcgagcgcct | gcccggccag | 27120 |
| ctcagcgagc | agatcaacat | ggtatccgac | cccgtgtcgg | gactgcggcg | gcgcagtggt | 27180 |
| atcgagctga | tggctcacct | gctgcatacc | gaccagccct | ggccgaggcc | gttcctctac | 27240 |
| cacacgaacc | taggtggccg | cagcattgcg | atgctggtgg | cccaacaccg | tggcgagctg | 27300 |
| tacctgttcg | acgagcggga | tggacgcctg | ctgatgggcc | agccgctggc | ccacgactac | 27360 |
| ctcaaggccg | acgactatcg | gcagctacgg | gccgctacgg | tggcagatga | cctgttcatc | 27420 |
| gccaacctga | gcgtgaagcc | cgaggccgac | cgcaccgatg | tcaagggtgt | agaccccaac | 27480 |
| aaagcgggct | ggctgtacat | caaggccggg | cagtattcga | aggcattctc | tatgaccatc | 27540 |

FIG. 18P sequence.txt

| | | | | | | |
|---|---|---|---|---|---|---|
| aaggtcaagg | acaacgccac | gggcaccacc | tacagccata | ccgccactta | cgtgacgccg | 27600 |
| gacaacgcca | gcacgaaccc | caacctcgct | gaggcgccat | tccaaacgag | cgtaggctac | 27660 |
| atcgcgtggc | agctctacgg | caagttcttt | ggtgcgccgg | agtacactct | gcccaactcg | 27720 |
| acgaagaagt | acccgaaggt | ggacccggac | gccaacgcgg | caaccatagc | cggctacctc | 27780 |
| aaccaacggg | gcgtgcagga | cgggtacatc | gcgttccgtg | gtgatgccga | tatcgtggtc | 27840 |
| gaagtgtcca | cggacatggg | caacaactac | ggcatagcct | ccggcggtat | gagcctcaac | 27900 |
| gccacggcag | acctgccagc | cttactgccg | ggcgcgggtg | ctcctggcgt | gggtgtgcag | 27960 |
| ttcatgggcg | gcgctgtcat | ggccaccggc | tccaccaagg | ccccggtata | cttcgagtgg | 28020 |
| gattccgcta | accgccgctg | ggcagagcgg | gccgcctacg | gcaccgattg | ggtcctgaag | 28080 |
| aagatgccac | tggccctgcg | ctgggatgag | gctaccgaca | cctacagctt | gaacgagctg | 28140 |
| gagtatgatc | gacgtggctc | cggcgacgag | gatacgaacc | ccacgttcaa | cttcgtcacc | 28200 |
| cgaggcatca | ccggcatgac | gaccttccag | ggtcgcctcg | tcctcctgtc | gcaggagtac | 28260 |
| gtctgcatgt | cggccagtaa | caatccgcac | cgctggttca | agaagtcggc | agccgcgctg | 28320 |
| aacgacgatg | atcctatcga | gatcgcagcc | caggggagcc | tgactgaacc | gtacgagcac | 28380 |
| gcggtcacct | tcaacaagga | cttgatcgtc | ttcgccaaga | agtatcaggc | cgtggtcccc | 28440 |
| ggtggcggca | ttgtaactcc | ccgcacggcg | gttatcagca | tcaccacgca | gtacgacctc | 28500 |
| gataccaggg | cggcacctgc | cgtgactggc | cgcagtgtgt | acttcgctgc | ggagcgtgcc | 28560 |
| ctgggtttca | tgggcctgca | tgagatggcc | ccgtctccgt | ccacggacag | ccactacgtc | 28620 |
| gccgaagacg | ttaccagcca | catcccgagc | tacatgccgg | ggcctgctga | gtacatccag | 28680 |
| gcggcggcct | ccagcggcta | cctggtgttc | ggcaccagca | cggcggacga | gatgatctgc | 28740 |
| caccagtacc | tctggcaggg | caacgagaaa | gtgcagaacg | cgtttcatcg | ctggacgttg | 28800 |
| cggcatcaga | tcatcggcgc | ctacttcact | ggcgacaacc | tgatggttct | gattcagaag | 28860 |
| ggccaggaga | tcgccctggg | acggatgcac | ctgaacagcc | tgccagcccg | tgagggtctg | 28920 |
| caatacccta | aatacgacta | ctggcggcgt | atcgaggcga | ccgtcgatgg | tgagctggaa | 28980 |
| ctgaccaagc | agcattggga | cctgatcaag | gatgcctctg | ccgtgtacca | gctacagcct | 29040 |
| gtggccggcg | cctacatgga | gcgtacccat | ctaggcgtga | agcgcgagac | gaatacgaag | 29100 |
| gtgttcctcg | acgtgcccga | ggccgtggtc | ggggcggtgt | atgtggtcgg | ctgcgagttc | 29160 |
| tggtcgaagg | tggagttcac | tccgccggtt | ctccgggacc | acaatggcct | gcccatgacc | 29220 |
| tcgacccgtg | cagtgcttca | tcggtacaac | gtaaacttcg | gctggaccgg | cgagttcctg | 29280 |
| tggcgcatca | gcgacacggc | tcgacccaac | cagccgtggt | acgacacgac | gccccttcgg | 29340 |
| ttgttcagcc | ggcaactcaa | tgccggggag | cctctggtgg | atagcgctgt | ggtgccgctg | 29400 |

FIG. 18Q sequence.txt

```
ccggcacggg tcgatatggc cacgtccaag ttcgagctga gctgtcacag tccgtacgac    29460
atgaacgttc gggctgtcga gtacaacttc aagtccaacc aaacctacag gagggtgtga    29520
tggctttctg gctaccacta ttggccgctg gcggcatgtc cgcccttcaa cagggattgg    29580
ccaacaagga agagcgcaac aagatcaagg ccgagaacaa ggctcgactg aagacggacc    29640
tcgacaacct gggcgccgct gcccgcgaca tcgccaacct cggagtcatg gctgctagct    29700
accgcaagca agccgtggcc tcgcaggtgg aggccaagcg ccaggggatg ctagccggcg    29760
gaagcgccga ggctcaggcc ggggcgttcg gcgtcaaggg tgcatccgtc gatgcggtgg    29820
ccctggatat cgagcgggag gtcggcgagg ccctgatcca gattgacgac aacctggaca    29880
atcagatgtg gaacctcgcc gagcaggcgc actccatcca ggctcaggct aaggccggcc    29940
tgctgggtca gaagagtacc acggcggggc aacggtcccc gctggtggcc ggtctgatgt    30000
cggcgggttc cctgtacgca agtcaatact tcaagttcgg cgccacgcct aaaggaggca    30060
actgatggcg gaatcgcaac gtgcttccca agagcttggg atcaacgtcg gacagacgca    30120
actccagccg ggccagagtg ctcggcgcgg agtgcgcgac tccgaggtca actacagcgg    30180
tccgagcgta ggctcgcaga ttctcgacgg catcctgggt gccggtcagc agatcgctgg    30240
caaatggttc gagcacaacg tgcagcagga agttctgcgc ggtgagcgtg cccgtatggc    30300
cggcgaggcg gaggaggcag tagacagcaa cgtactggcc aaaccattcg tgaagggtgg    30360
ttggcgtaag caggactacc gtatcgccca ggcggacttc agcctgaaga tgcagcgatt    30420
catcgccaac aagggccggg agatgactcc cgaggagttc cgcaagtacc tgtcccagga    30480
ggctacgcac gtcctggact cgaccgaggg catgaacccc aacgatgcct acaggcgct    30540
ggcgcagcag cagaaggccg aggaacagct cttcggcatg caggctaagg cgtacatgga    30600
ctggtccatc gaccaggccg cccgtggctt ccgtacccag ggtaacagta tcctggccaa    30660
ggctgtgcag gctcaggcca ccggcgacga actgtcccgg cagctcagcc tggaagaggc    30720
cggcctgttc tataccaaca tcatgacctc cgaggatatc ccgctggagg tgcgcgacaa    30780
ggtaggcatg cagttcctgg cggccagcct ggacatgaac cagcggggca tctatgaggg    30840
cctgcgcgat gccgggttcc tggacagtat gtcctttgac gaccggcgtg cgctcaacgg    30900
cctctatgaa aaatcgaagg cacagacccg tgccaaggaa tcgatggcta ccctgcgggc    30960
cgacgcggac ttccagcagc gggtggccaa cggcgccatc acagaccttg ccgaggttga    31020
agcgtactca cgaggcatgg tcgaggaggg ccgctggagc gacgctcagg ccatctcatt    31080
catgaccaag gccatgaccg gtctgggcaa tgcccaacgc atgcagggca tcatggcggc    31140
cctggaagcg ggggacatca acgccctaca cacgctgggg acgaacgtta ctgaggccct    31200
ggagcagtgg gacaagatgc aggccgccaa cggctcaagc ctgactgacc gtctcgtgca    31260
gggcacacag ctcggcctgc gcctggggac cttccccaag acctacggcg agtccgtggg    31320
```

FIG. 18R sequence.txt

| | | | | | | |
|---|---|---|---|---|---|---|
| cagcgcggtg | cgcatgatcc | aggccgccaa | agaaggcgag | gcaaacccgg | agctggtcaa | 31380 |
| cacgctgaac | agcatcttcg | agcaggtggc | ctcggcccag | gagatcaacc | cctccgccgg | 31440 |
| caacgtgatg | ctatccggca | tcccggaagc | cgagcaaggt | gccgtggcct | gggcactcaa | 31500 |
| gcagatgaag | atgggcatcg | caccagctca | agctctgcgc | gagttcagcg | ccaacgccga | 31560 |
| agtcgtgaaa | cagatggacg | agttcgagaa | aggccagaac | accaaggcat | tcaaggacaa | 31620 |
| cctcggcaag | caggtcaacg | acaagttcgt | gaacaacatc | ttcggtcggg | cctggaacat | 31680 |
| gctgaccggt | gaaagcgacc | tgagtaacaa | cgaggccgtt | ctcagcatgt | accgtcgagc | 31740 |
| aaccatcgac | gaggcgaact | ggctggccag | cgaccgcaag | catgcgggtc | tgctcaccag | 31800 |
| tgacacgggc | cgcgaggccc | tgctggagat | cgccgccgcc | aacgtgcgta | accgcaccat | 31860 |
| ccaggtaggc | gaaggtcgga | atctgaagga | aggggaccta | ttcagccgcc | gcgatagcgc | 31920 |
| gccgctgatc | ctgccgcgtg | gcaccaccgc | cgagcagcta | ttcgggacca | acgaccga | 31980 |
| gaccatcgga | accgtcctgg | ccgagcagca | caagccgcat | gtcgaaggac | tcctcggcta | 32040 |
| caagtcggta | gtcgccttcg | agtacgaccg | caccaggggc | agcctcctcg | ccgtcgagta | 32100 |
| cgacgagaac | ggtgtggccc | tggaccgcac | gcgggttgat | ccccaggcag | tcggtaacga | 32160 |
| ggtgctcaag | cgcaacgcgg | ataagctgaa | tgcgatgcgg | ggcgccgagt | acggtgccaa | 32220 |
| cgtcaaggtc | agcggcacgg | acattcgcat | gaacggggt | aacagtgccg | gcatgctgaa | 32280 |
| gcaggacgtg | ttcaactggc | ggaaggaact | ggctcagttc | gaggcttacc | gaggggaggc | 32340 |
| gtataaggat | gccgatggtt | atagtgtggg | cctggggcat | tacctgggca | gtggcaatgc | 32400 |
| tggggcaggc | actacagtca | cgcctgagca | agccgcgcag | tggttcgccg | aggacaccga | 32460 |
| ccgcgcactc | gaccagggtg | tgaggttggc | cgacgagctg | ggcgttacga | caatgcctc | 32520 |
| tatcctggga | ttggccggta | tggccttcca | gatgggcgaa | ggacgtgccc | ggcagttccg | 32580 |
| taacaccttc | caggcgatca | aggatcgcaa | caaggaagcc | ttcgaggctg | gtgtacgaaa | 32640 |
| cagcaagtgg | tacacgcaga | cgcccaaccg | ggccgaggca | ttcatcaagc | gcatggcgcc | 32700 |
| ccacttcgat | acaccgagtc | aaatcggtgt | cgattggtac | agcgccgcaa | cagcggagta | 32760 |
| agacatggca | aagcaattca | agggccgcat | gacgcccaag | tatccccttg | accaagtaca | 32820 |
| gctcgacgag | gcccaagtac | agggccaact | cgacgcggtg | cctaccgtgg | ggttcgacgc | 32880 |
| cctgacgggt | ggtgagatcg | gagaacggaa | cgtggcagcg | ggccaacgag | ccaatgcgcg | 32940 |
| ggaactggaa | cgcatcgtag | cggaccagga | actgccggcc | cttgaccgtg | cttccgcact | 33000 |
| ctggaaccag | tccaccctcg | tcggacgctg | ggtcgatgcg | ctccagctcg | acgcagacct | 33060 |
| tgcggcgaac | agtaccggcg | aggtggaccc | taacttcgac | gctgggacct | atggggtcca | 33120 |
| ggcgctccag | gcggcaggta | tccagccgac | tgataactac | cttcagatca | tggcccgtgc | 33180 |

FIG. 18S sequence.txt

| | | | | | |
|---|---|---|---|---|---|
| cggcaatgcc | gaggacgcgg | cctacctcct | atcgaggatt | caacggtatg | agcaggacga | 33240 |
| acaaatcgtg | cgggacaacc | catactggaa | cttcgcggtt | ggtatgctgg | acccggcagc | 33300 |
| cctggcagtt | gatgcggtta | cttcggcgc | tggccgtgct | ctgcggctcg | gtcgtgctgg | 33360 |
| catggctgct | gctggcggcg | ctgggcaagt | cgggtatgtt | gctgggctgg | atgccgcagg | 33420 |
| ggccgatgtg | gatgctggaa | cctacatcgt | ggcgggtgct | cttggcgctg | gcgtgggtgc | 33480 |
| tctgctgggg | tctggtgcgg | gacgcattgc | cgcagaggcc | caacgcaac | cgcatgtgcc | 33540 |
| cgaagtatcg | gcgcctactg | tcgggctgcc | agaagtagcc | atgaccgccg | aggaggccgc | 33600 |
| agcacgcggc | ttcaaggcag | gtgacgtggt | agacctgctg | gacgagggca | ctgtgctatc | 33660 |
| ccgtgtcagt | gcccgcgtgg | agcaggctga | gataccggct | attccgcgac | gtgacactgc | 33720 |
| cttcggcgac | gagctgcata | gcctgtcggg | ccggaagctg | tctgaggtcc | tggaccacat | 33780 |
| caagacccac | gcagaggtgc | ccaagccgct | ccagggcatc | gccgccaagg | tggctgacac | 33840 |
| tatcaggacc | ctggagggcc | tggggcagcg | taccgcgttc | cgtgtggtgc | agggcggtga | 33900 |
| cactgccagc | tctgccttcc | tcaaaccggg | tacggcgggg | attcactcca | cccagggcct | 33960 |
| cgacaccctg | gtccaggtac | gcggcagcac | cgcacctggt | cgagttggca | ccaacccggt | 34020 |
| gaccgtgctc | cacgaggcgg | ttcacgctgc | caccgtgggc | gtgatgaacg | ccgccctgcg | 34080 |
| caaccccggt | gcgatgagtc | cgaaggtggc | tcaggccatg | cagaccctgg | agaatgtccg | 34140 |
| gggtaacgtg | ctcaacgccc | tgaagcagga | ccgcgccgcc | ggtcggcaac | tgtccgagtt | 34200 |
| cgaagagaca | ctgctggccg | gtaactccaa | caccctggcc | aacgtcaagg | aactggtagc | 34260 |
| ctggggcctg | acggataccc | gcttccagcg | gaccctgaat | cgcctccgct | acagcgacgg | 34320 |
| cgggccgggc | ctgtggtccc | gcttcgtgga | gggcatccgc | accctgctgg | gtctgcggtc | 34380 |
| cgatgctgac | acggccctga | ccgcgtcct | ggccgcctct | gagacgatta | tggaggccat | 34440 |
| gcccggttac | actaaggcac | aggccaagtg | ggccaacaag | ggcgctccgg | taaccgagga | 34500 |
| ggccagcctg | gagaccatcg | tccggtccac | cagggagcgc | gcccgcgagg | gtgccggctt | 34560 |
| cgtgaacagg | ttcttcagcg | aggcagacct | cctggcacag | cccggagagg | gcgcacggcg | 34620 |
| actcctgagc | cgtcttattg | acgacccggt | acgtcgggat | gggttcagca | cgaacgacaa | 34680 |
| cgcagcgagc | tatctccgcc | gctatcggaa | cgagttcgag | ggctacgtga | agtcctacga | 34740 |
| cgagatgatg | gccaaggcaa | tggctgagca | gggtgtgggc | ctgacggcac | gtgcgctgaa | 34800 |
| ctcccgccgc | gccatggcag | tccgggacca | gctcaacgag | caggtcaccc | gcgagctgct | 34860 |
| gcgccgggac | cgggagtgga | ccgcctacgg | cagcgtccgc | gtggaccta | acctacctcc | 34920 |
| gaccatcaag | gccctggccg | accgctcaga | cgagattcat | ggtctgatgg | ccagcgtgc | 34980 |
| cagggaagct | ggggtgcgcg | ggttcgagaa | cttcgcaccg | cgaccgggat | acttccaccg | 35040 |
| ctcgtggaac | tggtcgaaga | tggcgcagat | ggacgaggcc | gcccctggcc | tggcccgccg | 35100 |

FIG. 18T sequence.txt

```
tgccatcagt gaggccgtgt tccgtggcat ccctgggctg gagcgcgccg acgccgatac    35160
catcgcacag gccattgtgc agcgggcgcg ggatcgggcc accggaatcc gctccgagtt    35220
catgggcgcg atgggcgtgg cggacacggc attcatccgg caggcgctgg aggaggccaa    35280
cgtgtcccag gccaagttcg acagcatcat ggccaagatc gagcagaagc agtccgacca    35340
gggcaccgtc aagtacggca agggccggct gtcgctggac atgaccgccg agatcaacca    35400
caacggcacc gtgtatcgtg tgcaagacct gatcgaccgg gacctcgacc ggctgatgga    35460
gaactacgcc ggcagtatgt cgggccgctc agcattggcc cgcgcaggca tgccggggga    35520
ctcggagatc gaagccttca tccgggagta ccagcgagag gcagcccacc tgggcaccga    35580
taaggtgcag gagctgacgg ggcaactgcg gggagtcttc ggggacttca ccggcaacgt    35640
gccgagggag catcagctcg gcccggttgc tcagcgggcc agcggcctaa ccagcgccac    35700
catgctggga ttctccggcg tgtaccagct cgccgaactg gccacgatgg cgcaccgtca    35760
aggcgtcttc aacgtcatga aggccatgct gaactcccgc ctgggagact tcgtgggcgc    35820
catgcgtcgc gaccccggacc tcgctgacga gatgcagacc gtcctcggcc tgaacctcgc    35880
caacgatatc cggatgaagc cctggaagcg gcagttcgac accttcctgg tcagccaaga    35940
caccttcatg gatcgcttcc tccacgcagg taagcaggct gtcccagtgc tcaacggcat    36000
gaagttcatc cacaactggc aatcccgtat gaacgccaac ctcaccttga acaaggtggc    36060
gcgggcggcg caggggggatg aagcagccct tcgcgtgctc cagcagtacg ggaaggacgt    36120
ggactggacg ccagtcctgg cgcgggttcg cggttatgtc acatacagag gaaggaacgc    36180
ccgatccatg aattggggcg cctggagcca agcagacgtg aacactgtca tgaacaccgc    36240
actgcggatc atggacgact cactcctgta cggtagggtc ggtcagaact cgggcttcgc    36300
tcggtctccg gtcggtcaaa tcctgggcca gttccgcagc tttgtggcct tcgcacacaa    36360
caagctcctc cggggaacct atgagaactc cggcgtgctt ggcgtggcct cgctcctcgc    36420
attccagtat ccgctcaccg cgctgatgat gggtgccaag gcagcgatca acggcaagtt    36480
cgacacctct gatgaaggca tccgcaagat ggccatcgac ggcatcggtt acactgccgg    36540
cctcggcttc accgccgaca tgtggggtgt gatcaccggg cactcccgga tgtccgcacc    36600
ggtctttggc ctggcggagc actccaacga ggtgttccgc ggcgtcaagg acctagtaac    36660
cggcgacgac cccgcagccg ccaccggcga tatcgtcaac ggcgccgcag gggcactgcc    36720
tttcgtcaac gtattcccgg cgaccaagtt gctgctggaa tccatcaaag gggaataacg    36780
tggctcggtt caagaatccc gagaccatcc acgtcgcaga tggggtcgag gctgtcttca    36840
gtctcgactt cccgttcctg cggcgtgagg acgtattcgt ccaggtcgat aagatactcg    36900
tcaccgacta tacgtgggta gacgacacca acattcaatt ggccgtggtg ccgaagaagg    36960
```

FIG. 18U

```
                                    sequence.txt
atcaagaggt ccgcatcttc cgcgacacac ccgcccaggt cccggacact cagttcagcc    37020
agggcatccc gttcctgcct cgatacatcg acgcgaacaa caagcagctc ctgtacgctg    37080
tgcaggaagg catcaacacc gcgaacctcg ctctcgacgg cgtactcgac gcgatccgca    37140
tcgccgagga agctcgtcgc ctggcacagg aagcactcga cgccgccaat gaggcgctgc    37200
gccgtgccct aggcttcgcc gagattcgca ccgtgaccga ggactcggac atcgatccga    37260
gctggcgtgg ttactggaac cgctgcatca cctccgagca gtccctgact ctgaccatgc    37320
agatggagga cccggacgag ccttggatcg agttcagcga ggtccacttc gaacaggcgg    37380
gcattcgcga cctcaacatc gtggccggcc ctggcgtgac catcaaccgc ttgcagaaca    37440
ccaccatgca gctctatggc gagaacggtg tgtgtaccct gaagcgcctc ggccctaacc    37500
actggatcat cttcggggcg atggaggacg actaatgcgt ggcattatcg caggtgtggt    37560
ggcgtcgcag attcgccggc ccaagccggt gctgaccacc atcacctacc cgcagtcttc    37620
ctcggatcgt gggggtatga cgtttcatgc catcgccggg atcatccaag ataccgtgaa    37680
gttcgcggat agtaaggacc tgggtagtta tgagatgctt gtgcgggacg ctaccctgaa    37740
gagcatggtc attacactca ctgaggttaa ggacagtagc gtctggagta tgggtgtgct    37800
gagtgcggca atcaaatccg tagttcagtt cttgacacca gtcgaggaga atcctcgtt    37860
ggatatgagc atcatccacg gcgagcacaa gcaatcggtc attccatact cccgctgggc    37920
tgaggctggg tccctgtcca tgggtatcac agagggtaaa gtttatgtac catagcagca    37980
ccattcgagg tgagttcgat ctggagattg tacgtcctga cggtacagtc cgccagcacc    38040
tgcacttcaa gaacctgatc accgacttgg cccttgaggc catgagttcc aagggcgtcc    38100
cgagtggcgg ctggacgaac atgttcgccg gcactggcaa ccgtaccccg gtccccgctg    38160
acgtgtccct cgtggcgcct gtggctaatg ccagtgcctc gctgaactac ggcaaccgcg    38220
cagtgtggga ttccaccact ggcgagaaag tgcatactgg cacggggacc ttccgcgcag    38280
gttccttcca aggccagtcc ctggccgagg taggaatcgg tcgggtagtc tctgagctgt    38340
actcccgatc cctgatcaag gacgccaacg gcgatcctac cacgatcacg gtgctggtgg    38400
atgaggaact gcgtgtgacc tacactctgc ggattgctcc gccggcgtcc agtgaagtca    38460
agatcacgat gaagggtatc gagtacaccc tgagcatgcg ggaccgccgt accttccggg    38520
acttatcgcc cgagcctgcg gctgagtttg gcactcgcgg cagtctgtcg tggagcgcta    38580
tcagtgcgcc ggacagtaac ggccagacca agaccgccaa cttgagcggc gacgccggga    38640
ccgggattat ccaggttcct gcacagtctg cacagatcat gcgtatccag cccgccgatg    38700
ccaactggac ggaaggtatt cagtacctcc gctgggagac tccggcagga cgtgagctgg    38760
agatcaagct ggacccgcct ctggtcaaga acagcttgga gcgcgtggac atcaccgtaa    38820
cccacatctt caatcgggta tgattcagtt caagttcggt gactaccgga cccgtgtgcc    38880
```

FIG. 18V sequence.txt

| | | | | | | |
|---|---|---|---|---|---|---|
| cttccagggt | gcgcgggacc | ggcgggatat | caacgaccgc | agcgactacg | tggacggtgg | 38940 |
| cgtcgccatc | caagacccta | gtcaaggtct | gttgtatcag | gagtggcacg | ccgagctact | 39000 |
| cgaagacggc | atctacctga | cacctgagaa | agagcgagtg | actaccgca | tcggaccagg | 39060 |
| tatcaatgaa | ggcgtggcta | gtatggcggt | cacgttcgac | cagaacatga | actatgtcct | 39120 |
| ggtgtatacc | aagcaaggcg | aaggcttcat | cgacttcttc | gattccgcta | ccgaagagcg | 39180 |
| caatgtgatg | aaccttgggc | cggtggacta | tatcaagaca | gacctagacg | atcggcggcc | 39240 |
| agagggcagc | gcctgggcgc | aggttctggt | ctgctacaca | cggcagggaa | acttctacgt | 39300 |
| ccgagccagc | tcaactcgct | ttactgaaga | ggagcttatc | gtcggtacgg | gcaaagtgac | 39360 |
| ccggcctatc | gtcaaatgcg | gaatggcagc | gaactggaga | ttccaggtcc | tgttccgagg | 39420 |
| gagaatgtaa | tgagcaagaa | gcagaccgcg | agtgctgagc | ggctgggcct | gctacatgag | 39480 |
| ctggtctgca | ccgccatcga | gcgtaacttc | aagtggtaca | tggacaacga | catcccgatc | 39540 |
| cccgcatcgg | atatcgctgc | cgccaccaag | ttcctcaagg | acaacgagat | cacctgcgat | 39600 |
| ccgtccgaca | ccatcaacat | cgaccgcctc | cgcgaggaga | tgcggcaggc | gcaggcggag | 39660 |
| aatcgccgta | tcgcgctgga | gggcttcatc | gccggtgaga | cggacgatga | gatggaacgc | 39720 |
| ctgtacaccc | actaaggagg | cagcatgacg | ccgcaagaac | gattccagat | agcccacgag | 39780 |
| gtgcgggaca | tgtacccgcg | cttccgggac | ttctgcctgg | acgccatgct | gttcctcggc | 39840 |
| ttcaagatga | cgtggatgca | gctcgacatc | gccgacttca | tgcaggactc | gcccaacaag | 39900 |
| gcgatggtcg | ctgcacagcg | cggcgaagct | aagtccacca | tcgcctgtat | ctatgtggtg | 39960 |
| tggtgcataa | cgcagaaccc | ggctacccgc | gccatgctgg | tatccggttc | cggtgacaag | 40020 |
| gccgaggaga | acggccagtt | gatcacgaag | ctgatcatgc | attgggacct | gctggcgtac | 40080 |
| ctgcgccccg | aggcccgcat | gggtgaccgt | acctcggcca | ccagcttcga | cgtgaactgg | 40140 |
| gcgttgaagg | gtgtcgagaa | atcggcctct | atcaactgca | tcgggatcac | cgctgccctc | 40200 |
| cagggctacc | gggctgacat | cctgatccct | gacgacatcg | agaccacgaa | gaacggcctc | 40260 |
| accgccaccg | agcgggccaa | gctgacgcgg | cagtcgcagg | agttcacctc | tatctgtacc | 40320 |
| cacggtaaga | ttctctacct | gggcacgccg | cagtcccgtg | agtcgatcta | caacggtctg | 40380 |
| ccggcgcggg | gcttcctgat | gcgcatctgg | ccgggccgct | tcccgaccct | ggatgagcag | 40440 |
| gaacgctacg | gtgactggct | cgcaccttcc | atcctagcgc | gcattgcccg | cctggaggag | 40500 |
| aaaggccaca | acccgcgtac | tgcaagggc | ctggatggca | ctcgtggctg | ggcggctgat | 40560 |
| ccgcagcgct | acaacgaaga | ggacctgctc | gacaaggagc | ttgaccaagg | ccccgagggc | 40620 |
| ttccagcttc | agtacatgct | ggacaccagc | ctcgccgacg | agcagcgtat | gcagctcaag | 40680 |
| ctgcgcgacc | tgctgttcat | cgacgccacg | catgagagcg | tgccggagca | agtggcctgg | 40740 |

FIG. 18W

```
                                   sequence.txt
gctgccgacg agcgcttcaa gctcaagttc gacgcccacc gattcccggt catcaagcct    40800
gagctgtacc tgccggcgct gatggctggc ggctgggcac cactccagca aatgacgatg    40860
ttcgtggacc ctgccggcga cggtggcgac gagctgtcgt atgccgtggg cgggactctt    40920
ggcccgtaca tccacgtcgt gagcatcggc ggctggaagg gtggctttgc tgaggagaac    40980
ctggagaaat gtattgccct agctgcgcgt tatggcgtca aggtgatcta tgtcgagaaa    41040
aacctcggcg ctggtgcagt tggccagctc ttccgcaacc acatgcgatc catcgacccg    41100
gacaccaaca agccccgcta tgaggggatc ggcgtagaag accgccagaa gtccggacag    41160
aaagagcgtc gtatcatcga caccctgcgg cccatcatgc agcggcaccg tctgatcttc    41220
cacgtatcgg cgatggattc cgaccacgtg gcctgccagc agtacccagc ggacaagcgc    41280
aatgagcgct ccgtgttcca ccagattcac aacatcacca ccgaccgagg ctcactgccg    41340
aaggacgacc ggatcgatgc ccttgagggc cttgtccgcg agctagcacc cacgctcgta    41400
aaggacgacg aagccgcaac ccgcgctcgt gaagaggctg ccaagaagga atggctgaac    41460
aacccgatgg gttacactaa gtctgtcctt cggtctctcg gcatgggccg ggagcgtcgc    41520
aagggccgcc caaaaggacg aagactatga tgctcgatac cgccaccgag gcgggcaaag    41580
gcaccctcgc cgtcactggc gtggggatcg ccgtttactc gccctatgag atcgccagcc    41640
tctgtgctgc ggtactcacc gcgctctatg tgggcgccca gctcatcacc ctgctcccga    41700
agatgctcga tagcatcgcg gagcttcgcc ggaggttcaa gaagtgaaca agcccctgcg    41760
cggcgcagcc cttgcggctg ccctcgccgg ccttgtcgcc ctggaaggta gtgagaccac    41820
tgcctaccgg gacatcgccg gcgtgcccac catctgttct ggcaccactg ccggggtcaa    41880
gatgggtgac aaagccacac cggagcagtg ctaccagatg acgctcaagg actaccagcg    41940
cttcgagcgc atcgtcctgg acgccatcaa ggtgccgctg aacgtcaacg agcagaccgc    42000
cctgacgttc ttctgctaca cgtgggtcc agtctgtaca accagcacag cgttcaagcg    42060
cttcaaccaa ggccgcgcca ctgagggctg ccaagccctg gccatgtgga acaaggtcac    42120
gatcaacggc cagaaggtcg tatccaaggg cctcgtgaat cgccgcaacg cggagatcaa    42180
gcaatgcctc gaaccatcgt cgcaatactc gtccttgctg tggtagccct gggagcctca    42240
tacggcttcg tccagagcta ccgggccttg ggtatcgccc aggaggagat caagcggcag    42300
acggcccgtg cggaggccct ggaggtgcgt tatgccacct tgcagcgcca cgtcaaggag    42360
gtcgctgcca ggaccaacac ccagcgccag gaggtggacc gtgccctgga ccagaaccgc    42420
ccgtgggctg accggcctgt tcctgctgct gtcgttgaca gcctgtgcaa ccgccccggc    42480
gcccgctgtg ctgtgcgaac acccactgat tgaccctacc acccaggctg gcctgatccg    42540
cgctgtagcg gcctatcagg acgccctgga cctatgcaac gccttgaatc aaggagactg    42600
acatggcgaa cacccgtgag caatacctcg ctggccgtaa caccggcctg accttctacc    42660
```

FIG. 18X sequence.txt

| | | | | | | |
|---|---|---|---|---|---|---|
| aggtctgcca | gcccggcacc | gacaaccgca | tcgccctgca | cgacatggac | gaggccgatg | 42720 |
| tcaaggccaa | ggccaccgcc | gtaatcgcag | cagccaccgc | cctgggcggc | gaaggtggcg | 42780 |
| ctactccacc | ggacccgctc | accgcctaca | aggtgaagaa | cggtgacacc | ctgcccgtgg | 42840 |
| acggcggtgg | ttccgtgaag | gtgaccgtag | ccaacggtgc | tatcaccaag | gtcgtgtaca | 42900 |
| ccgcaccggc | gggctgagct | acagcccgtc | ccacctgact | ccatccctaa | cacaaggaac | 42960 |
| tgaaccatgg | caaccttcgc | cgctgcaact | cagaaagacc | tccgcgcctt | cgccggcgct | 43020 |
| atcgagaacc | tgatccgccc | tctggaagaa | gcggccttgg | gttccggctt | caccgaggtg | 43080 |
| atcaccatca | ccaagggcac | cgatggcaac | gagactcgca | cctccgagcg | taaggtacgt | 43140 |
| cccgagctgg | tcgctaacct | cgacgccctg | atggccgctg | tcgagaccgc | caaagccgcc | 43200 |
| gtctacaagt | aaggggacac | catgagcaaa | gccaaactac | gagtcatcgc | cgacaccccg | 43260 |
| gagctggagt | cagtgctaaa | agcattgctg | accgccacct | acgctatcga | gga | 43313 |

FIG. 19A sequence.txt

<210> 560
<211> 137360
<212> DNA
<213> Unknown

<220>
<223> Description of Unknown: Bacteriophage F44/10

<400> 560

| | | | | | | |
|---|---|---|---|---|---|---|
| aatttcatta | gaaaagaatt | ttttctttt | tctatagtat | ctttcttgtt | atcgtattct | 60 |
| gaatacatca | taaattctat | aaatatacta | tttctgtcag | atgaaaacat | atctatagaa | 120 |
| aacggacaat | caaaacttat | gtcatcttta | ttaatactaa | aacattcagt | aacatttaag | 180 |
| tcatttattt | catatacctc | aaagtatcca | tcaactcttt | taagttctat | agcactatta | 240 |
| tatctataat | aacgttgttc | ctctattaac | ttatcttttg | ttagataggg | atattcattt | 300 |
| ataaatatag | gattacttgt | tccatagtta | ttttaatat | attcagcatc | ttctaaggaa | 360 |
| tcagtataac | ctaaaacttc | gtaacttgtt | gtatacacag | tatcctcttc | ccacaagtca | 420 |
| tagtccattt | cctctatttc | ttcctctagt | atataaattt | ttttcatata | ttactcccaa | 480 |
| acaccaataa | gatttttaag | tttagctata | acttcttctt | ctgtttgata | agaaaatact | 540 |
| cctgtaatgt | gtccatagtt | acctataatt | tcataatcct | gtgtaccatg | tttgtctact | 600 |
| agatatgagt | tacccataac | atttaaacta | tcctccgagt | aactgaaatt | tatattatag | 660 |
| tctactaaaa | aattaataat | tttttcatt | tacataacct | ctcctatcgg | atattgtcct | 720 |
| aacattcttg | ttccatttc | gttatagaag | gtatattcta | ctacaataat | attcattata | 780 |
| tcgacatata | tagcttctat | ataaggtgta | atattctctt | cttcttgtat | gtgtttacct | 840 |
| ataatattat | ataataattc | agagtgtatt | cttttatctc | tcattataga | cctccgtaag | 900 |
| aaatgataca | gtcttatctt | ttaaagattt | ttctactagt | tccatagcat | ctttataatg | 960 |
| ttttatatta | gattcattag | acttcagttt | atcttttact | tcttgaatta | gaggttcaac | 1020 |
| tttagtaact | aaatcttttt | tattttctat | actcacattg | cttcttttat | tatctaatac | 1080 |
| ttcctttggc | atatacttaa | cttttgcaaa | gtctttatag | ctaacattta | agttatctaa | 1140 |
| atcatctaat | aaatcattat | aatattctaa | atgattatag | aatgtgtaaa | acttaacaag | 1200 |
| gtctttacct | gctagctctt | cttttttag | tatattattg | atattaccaa | taacagaata | 1260 |
| tgctataggc | ttaaaattag | ccctaacata | agttaaaaat | ataaaatcat | cataaaacaa | 1320 |
| gtctaaaaca | gttttattga | atctagtatt | tttagcttgc | tctaattgag | cacataaatt | 1380 |

FIG. 19B sequence.txt

| | | | | | |
|---|---|---|---|---|---|
| aagaacatta | tcaaacccac | tctttaatac | caaagagata | aatctttcca | ctgcatagta | 1440 |
| cctagatact | tcagtatgtt | tgcttgcttt | ttcactattt | ctaaaaatag | tatctgataa | 1500 |
| aggttgaact | actaaactca | tataatcttt | atctgaatat | tcatccgatg | ttccttgata | 1560 |
| agtacttcca | aattctattg | tagataataa | aaaactttt | tctaaattca | ttataacatc | 1620 |
| ctccttttac | ttgttattat | aatactaaca | catatgttta | ttaatgtcaa | acattaaata | 1680 |
| tcttctgttg | tgtcaacttc | atcttgtata | tacttaaagt | attcataaat | tttaaatagt | 1740 |
| ataactccta | gtgttattaa | tcctaaaata | tatttcataa | caatcctcct | taaaagtatt | 1800 |
| tatccttccc | atcctgataa | agcatccata | gccatatcat | actcttcttc | atttttagtt | 1860 |
| cttataattt | tctctatttc | ttttttttgct | tgtttagagt | tcataaaatc | aatatctact | 1920 |
| gtatctaaat | ttgtataatc | aatatttct | ctaataaagt | tcttttgact | tggtgttata | 1980 |
| gaattaactc | gtacgttttc | gtgatttaaa | aattgataga | agtccatact | attcaccttc | 2040 |
| ttttaaacag | tctgccatat | cttttaaagt | attaagtaca | tatttcaaat | ctctataata | 2100 |
| actatcagaa | aaactaataa | cagcatatgg | tgtcatatca | ctatagtgtg | cacaatcaaa | 2160 |
| acctaatacc | ctatagtcac | cctcatgttc | atcgtatgtt | atacctccat | gggaacaatc | 2220 |
| ttctatacta | ttaaactgtt | ctttggttat | attcgtaggc | acattaatat | aaccatttag | 2280 |
| atgtcctgaa | tgagggtgac | gtttaacagt | taggtttatt | cccttataat | ctatatttaa | 2340 |
| agttaagtcc | tctcctaata | tattatcctc | tttatctata | atttccataa | tatgttctgg | 2400 |
| agcttttcca | aacatcataa | ttcctcccctt | ttctttatac | tcttactata | cactactttt | 2460 |
| tctattttgt | caacaaaaaa | aggctactaa | ttaaagtagc | ctaagaatta | attatttagc | 2520 |
| attatatttc | cattgccaat | aaccattttt | ctgtgagaac | tcaaagtgaa | aaccgtcata | 2580 |
| gtcaaattca | atattatagt | ctccatcttg | aagtggtttt | gaatttagta | caggactatt | 2640 |
| actctttgcc | aattctgcta | gaaactcatg | atttactttt | tccatagggt | ttattcctcc | 2700 |
| taattattct | tacagtacta | atatatcaca | ggtctttttc | taggtcgttt | ttaaatttct | 2760 |
| cctcataaga | actagcataa | gttacttcat | aacctattac | cttagtataa | tctatgcaaa | 2820 |
| gtaatttata | attggactttt | attttaatat | cctctgattg | ttctattta | ttgataactt | 2880 |
| catttagctc | attcgaagag | taatgtttat | tatcaacttt | tattgttttt | ccttgggtat | 2940 |
| agatatcaat | ttcttgtatc | atcatttcat | ccttttgatt | attcattatt | tgattataag | 3000 |
| tctctaaatc | atcaatgtta | tctgtatctg | aaccttttac | taaccattct | cctctcttct | 3060 |
| taaggaggtc | atcaaatttc | tcatgttctt | taattatctt | ctctacttca | ctcggtatta | 3120 |
| gaacagctct | agcgtaattt | atatgccaca | tagacatatt | atcaataaga | taattaacca | 3180 |
| ttcttataag | ttccttctca | tttgccatat | accaacctcc | ttatatctaa | tactaatata | 3240 |

FIG. 19C sequence.txt

```
agagaaaagc agacttatta aaagtctgct tctgtaccta attctaatct tttattttc     3300
atatgaggaa tcatttttct atctcctgtt aatagagata attctctagc tttttcttta    3360
gataatgtta atagtccatt ataattatct actttcttat tatattccat aattaagcgc    3420
tctagctcat atgatatatc ttcgagttct cctgatttaa ctccaagtaa ctttctatac    3480
atatcataat cttcagaaag actttctact ttatttttag atacagaatc ataaactgct    3540
tgtaaattac cttcttcaat aagtttaaag ttatgttcac ctatgattaa ttcctcctca    3600
gaagaatcaa gcgttactaa tccgcttgta ttacctgtaa agtcaccttt ataatctaca    3660
acaatacctt cagttacttt gtcacctaat tcaatagtcc catcttcatt ttctttaaat    3720
ttatgagcat catatacttc tactttgtca cctaatctca aatcttgagt taagttatgt    3780
ttaccaataa ttctatccat tactcaatct ctcctttatt aatagggtct tgtgttaaga    3840
acatttctag attctctttt gtaataggta accaaaaata tttactttcc ggaattgtaa    3900
ttgtatagaa atcctcatct ttgttaactt taatattaac atctgtaaac tcatcctgca    3960
ttaaccaatg agttacagtt aagttatatg aaccatcact aacatacCCT aaatcaatat    4020
catgtctaaa agccaaatct tctaaatgtt ctaataaatc gttcttttca ttatgttttt    4080
cttcttctgt attatttta attgggttaa ttaactctgt gcaaacaata tcgtacaatt     4140
caccatctgt aacctcatag ttcttttcaa ttaatacatc ttgtatttta ttgattgagt    4200
ttgtaactac tttcccatat tcttcttctg taaacttaca tttatctaaa tcaacatctg    4260
taattaattc tgcaatccat ttatttaaaa ttgatactgc cattgttcta gaaataatac    4320
tgtcgtatac catatttatt taatctcctt atttaggtga atgtggtctt ctaatgaaaa    4380
atcaaaaggc gctacaccat ttcttttatt atttgtttct ttttaagta taacataagt     4440
tagtgaaaaa gtcaagatag ttactacaac cattgataaa aatttaatca ggttttcat     4500
aattactcta actccttaag tttattttt actttctctt tatcgtactt ataatcttta    4560
ctagagtttt cattttttc tttctcttct tcattaagtt ctctatactg agcctcttct    4620
acctcttgtt ctttattatc attccttct tctgcttttt gaatttctac attttacta    4680
ctaccaccat ttacctttt tctaaaaaga aaccaaagta ttaataaaat gatgagtaaa    4740
ataataatgc ttaatacaac agcccaaata ttattaacca ttacaaccta cctccgaata    4800
gtttttttac ggctcttaag ttttcagatg aatcattatt tatatcaata cctatgctag    4860
aatcaaaaat tacagcatta tcaagtatat gctctgtcaa tttattaccg taactacttt    4920
tacttaccac actaccataa ccatgattag ttaggtcaac catatcaggt tcaacttcta    4980
gtactctaaa agatattcta cgtaagaatg aaggatttac caagtaaaag gaagatttaa    5040
aaacatttaa tctttgataa gaatgtttta tattaacaac aaaccctgtt aacttatttt    5100
catattctga atttgataac ttacctaggt aaaggtttat actatatcct tttgtttcta    5160
```

FIG. 19D sequence.txt

| | | | | | | |
|---|---|---|---|---|---|---|
| atgtttgaat | agcacttaac | attatagccc | ctctataagc | aaggttttca | gggtcttcca | 5220 |
| tccaactaat | actagaatta | taaaatacat | caataacttt | cttctctgct | ttaactcttt | 5280 |
| gctgagacat | catagaatta | ggtaaccctt | ttatagcatt | aggtacgtga | ggttgatacc | 5340 |
| cttccggagc | tacgacaggt | tttcttttta | ctgacttatc | cattctaaat | aatgcatctg | 5400 |
| tcattttttt | aagtttaact | accatatcat | atgattctct | atcaccctta | accattaagt | 5460 |
| tataggcttc | ttgaaaacta | tgagttcctg | taaaatcata | gctacctgta | tctgatgaat | 5520 |
| tttctctacc | tgaaactcta | ttcttttta | aagcagaaaa | gaaatcaggt | agaccatcat | 5580 |
| atttaattac | atttaattct | gagttatcta | ttaatcgtct | acccattgat | tttcctccta | 5640 |
| ttctaatcct | aacttatcca | taattgtatc | aaagtccatt | gaatcttttg | atgtactatt | 5700 |
| agattttcta | ggttcctgtt | taggttcttg | ttgcatacct | aaaagctttc | ttgttgcttc | 5760 |
| tgtatatctg | ttaccttcag | gtaaagagct | aataaattga | ttaatctcat | ctttcggtac | 5820 |
| agatttaaag | ataatacttt | ctacaacaaa | ctcatcttcc | attactccat | ctaatttact | 5880 |
| accattaata | attgcacgca | ttgagaatac | ataaggtaat | ccttttcat | cattctcatg | 5940 |
| tcttaattgt | tgtacaaagt | ttactaagtc | ttcattgctt | gatagttgat | gttccacctt | 6000 |
| agtatcatag | tcaaattcaa | cttgagcaaa | gcggtctaat | gtagctccat | ctaattgttg | 6060 |
| tctacctaca | taaatatggt | ctgctcctgt | tcccatagta | ttacctgctg | acacaactct | 6120 |
| gaaatcttca | tgagctgtta | cacgtccaat | agggaagtca | aagtatttat | ttgcaatagc | 6180 |
| tgaattaaga | attaatagta | cttcaggaat | agatgcatcc | atttcatcta | agaagaataa | 6240 |
| cccaccttt | gtaaatgctt | tatagaattg | agtttcatga | aacttaccat | ttgcatcaat | 6300 |
| aaatcctgtt | aatttaaatt | cttgagtaat | tgcattacta | aaatagaaat | ctaaatctag | 6360 |
| ggcttctgct | acttgttcca | atacatggtt | cttacctgaa | cctgctccgc | cttttaaaaa | 6420 |
| tactggaata | ttttggttaa | ctaactttag | tatatcttga | tatctgtaat | ggaagattcc | 6480 |
| tgagatatct | ttaattgttt | ttccttcttg | ttgtaattca | attttaactg | gtaaattact | 6540 |
| aagttgttct | tctacatact | cttcaatttg | ttttttaaca | tcagtaataa | taatttctct | 6600 |
| actctcagtt | cctgctttct | caacaattgc | atctacaatt | gcttgttcat | acggattaga | 6660 |
| gttttctct | cctagttttt | ttgctaaatc | tgctgttgtt | tccatttgtt | gctctaccaa | 6720 |
| tctctctaat | cttcaatag | tatcttgctt | tgccatattt | atcattctcc | tttgatttgt | 6780 |
| tatacattta | ttatattaca | agtatttgaa | tttgtcaaca | actttctaaa | acttttttag | 6840 |
| ttgctaataa | aaaaatacct | tacacctata | acttaacata | gggtaaggta | attgtcaaca | 6900 |
| cttttgttaa | aaatacatta | atttaaaaaa | atcatcaata | tctttagttc | catgtgtatc | 6960 |
| catatcatac | ataaacatac | aattatatgt | atgactattc | attatttcta | acatgttatg | 7020 |

FIG. 19E

```
                              sequence.txt
catagaagtt gcattattga attcctctaa atcaatagtt accgtaagtt cttgaccttc    7080
ataaagtatg tttgctatat aatatttcct aacaccttcc attgttccat gggaagtttc    7140
attatgatta agtacttcta cacctagtga aggtaaatat tctgaaaagt aatatttaca    7200
gaaatatata aaattgtctg ttcttttaga cacgagtact atctccgtac tttatatttc    7260
tttctaatcg tacataatat gttttaattt tttgtacttc tttatctact gcatcctttc    7320
ttcctaacct tgtagtatat tttacaatat taaatatcat agaatcaaca aagccatcat    7380
aagaaaaatg ttcttctaga aaagaaataa catccttact acctttataa tgttcaggta    7440
aatgtgcatc tacttgtata ttataataat cttctaaaag acctatactc tcaccaagac    7500
tagataaagc gtaacctaaa tcatttgaat cattagacca ttctttagat actgatagtg    7560
catcttctat aattgttact tttaatttat ctaaataatc ttctacttga gcttgtgttt    7620
tcataaattc ttttgcgttc atgtaatacc ctcctaaatt atataaaaaa aacaccctgc    7680
ttggatacaa gcaaggtgaa aaaggaaaga tattatggaa gtgtactatc taagtacacc    7740
tcataatata acagttttcc ttgctagtta ttacttattt tttaaggtct tcttctttga    7800
caaacactcc gttaataagc ttacctttcc tttcttttat ctcatcataa gccatatcaa    7860
tacactcttc aatatctata tctaactgta aacatagtac tgttaatact acaaaaatat    7920
ccccaacact atctcttgtt acatggtcat tacttttagc aatacctgaa gctaattctc    7980
ctgcttcttc taataatttt aacatttgac cctcgggttt acctgtttgt aagtttctat    8040
cttttgccca ttgtttaata agttctactt tttccattat tctatatctc ctttaatttc    8100
tgtatctttg ataattaggt tatcagagtc acttgttaca tttaagttat cttcaactaa    8160
ttcatgtaga ttattagtaa tatcttcttc atacctataa cctacacgaa cataagcttt    8220
aactctgata tctatattaa cataatcttc ttggaatttt tccatttcta acttcccttta   8280
ttatatcata ttattatact attgtcaatt aatctgagta gtttcccttta gcaagttgat    8340
acttttgtg taattcttca tataattctc tcataccttc gtagtttctc atatcatctt    8400
ccaagaaact aagataatct aataatactt ttacatcctc aggttctaaa gttataactg    8460
gttttaccat taggcaacct ccttaaattc ttctttattt attttcttaa tatcttttc     8520
taatgcttct tttaattcat taggtaattt ataggcatca attgattgtt gttgacctaa    8580
tacatatcca ttatctgtga tacgtatttc cactgtaaac catgaattat ctaaatcttc    8640
ttctaatctt gctaataata ttaaacaact atttttaaa attctattag catcccgcc     8700
aacacaatga gataacattt taccttcatc tttaagttta cttacagtat ctgcaggaag    8760
gaattttact tttctaccat cttttaattt ataagtttta tcaattattt tttctaattt    8820
attatcatat ttagctttaa gttccgcatc atctaattgt tgttgtatag attgtttctc    8880
atctgtaact atatcatgtt ctagttttaa tgagaatggt gttaggttaa cactttctaa    8940
```

FIG. 19F sequence.txt

```
tgttctataa ccttctctta ttaatattga taaatcatgt aagtaatcta agtaatagtt    9000
atctagtgca tatcctgtta tacgttgtct gtcttgagca tctacatcta aatagtgagt    9060
catcttttttg tagttagcaa aagatataga taatatttca tttacaatag gttttacttt    9120
taaagcattt gtaacatctc ttgaatctct aaccattaaa aaggtatcgt caaataattg    9180
gtgtaaatta acttcattgt gtaaatgatt atagttctta tagagagtat tagcaaatct    9240
taagtaatta ccttgctcaa atttatttaa agttagtagc tttttataag tctgttttgt    9300
aagattgaag gcttcatgaa cttttccattt aggggttttta ggtatatgga atagtaatgc    9360
atttctttca aataatccaa attcttctaa gttatttatt ttatcaatat ttttaacaat    9420
atctgttaaa gttattaagt aattagaagt tgaatttttct cctataaaaa tcctatactt    9480
atcccctcta taatttatat gaccataaac atctatatta tcaggacacc aactagaaaa    9540
atcaaaatta tgatgctcta atgtttgttc tattatcttt attataattc ctctatttaa    9600
gttaggttgt gaatagtttt ttaaaataac atttaataaa acagataatg tcaattcatt    9660
tttgtattca cttttactaa tatcatcttt ataggttt aaagctattt ctttattaac    9720
aagactatct gttaagaaaa ccttgactgc tcctgtctta acgtcaaatg aacttttatt    9780
ttctaaaacc catttgttac ccatattatg cttatccctg atatgtctaa ctttaagacc    9840
aaaagatgaa ttattctcag tacttgggtg catgtaccaa acacgactat acaatgaatc    9900
tgacatttcc ttataatact cactagaacc ttttctata tcttcattca taacaataat    9960
agatgaattt ataagaacat atttaccttg gtctagtaca tccatgatat cattatttaa    10020
actatctact gcttccttat actcatctaa ttgtctagct tcatatcccc ataaacggtt    10080
ttcatttttct aattctttaa ttttttcttc aacataccct ttagattgta tttgtttttct    10140
acgtctacta ccatataaag gaaaatcttt tctttctcct ctatcagctt caatatactc    10200
tttgtaattt cttcctttat tattaccaat cacaccttca actaattttt caactgtttc    10260
atagggtca ccttcaaagt ttgttacttc tttattacca catagggcta aaaataaatg    10320
tatttctgta gctgtatcaa aactaaatat attatgaata tctctaaata attctttaga    10380
acctaagtta attatattat ttttcttttt cttaagaaat acatcttctt ctcctatata    10440
gatacatcct ttattaacct taggtaaatt aataatttct tgttctgtta atccttttttg    10500
tttataagtt attgccattt aaaatcactc cttatttgtt atgtactaat cataccatag    10560
taaataatat ttgtcaacaa aaaaagaaga actttttaaa gttcttctaa atgagtttcg    10620
tatataactt tttgaatttt atttaatggt tctaaatcta aattcctaat aagttttttca    10680
tactttcttg aattttaaa attgatagta tttggcatag caagagcttc atcaacatct    10740
ttagtatagc ttacaacatc tgaatagata tctacttctt ttacatatag accttgagtt    10800
```

FIG. 19G

```
                                    sequence.txt
aaactcctaa atactacctc attatgtgct ataatttctt cttcttttc tatgctcatt    10860
tataaacctc ctggtctact ctacacaaac aagtacgtat tctaaattag ttaaagaaac    10920
tgatttaata ttgtttaatt cttgtaattt cttaatttcc acatcatagt tcttacttat    10980
agtccataat gtctctcctg ctcttacttt gtgataatat ttatttccct ctttgataag    11040
gtcattcaat attacctacc tccttgagta ataattagct tgtagataac ataagtat     11100
aagaacaaag tttacaaatt cagtagctat aatatgaaca taggtatgtg ttaaaaccat    11160
acttacaatt aatgaagcta atcctaatcc aataataaga aatagaaatc tatttgttcc    11220
ttctgcactt ttagttttat aaaaggttgt tatctgagtt acatacgcaa ggataatagt    11280
aatagttgct acagtttgtg ttaaggctgt aaagtcactt aataaaaata gtaacagtga    11340
gaacacaata ataaaaggta tagagaaata gtccttttt ctatatgaag ctactaataa     11400
gcaaacaata cctagagtta aattaagacc aactgatact acttgaaaca tcgtagcatc    11460
agttagaagt aaattgtaaa aactaatacc tactgtagct acaattaaat accaaaaata    11520
actactaaca cctttaacac tatctgactt aactagggct attaaacctg gtatataacc    11580
tactgtaact aatatagcat ataatatact taagtaatgt gataaattat ccatcttgtt    11640
cccctaattt ctctaatcta ttagtaactt cttcccatga aataaatcct tctccgtttg    11700
ttaattctaa aaccatacca tacacaaatt ggtttgtact aaattcagct ctgtcagggt    11760
cattgtatgg tttaccatga ccctgtctaa tatcagagca gtagattaat acgggttttt    11820
ttaaaatata ttcctgctct ccaatttgtc cttgtaaaat atcatatgtt tctgatagtt    11880
catctatctc attgaactta ataactcag actgttcttt taattgtttt attgtttctt     11940
gtgcttgatg tttcataacct aataaaatac ctagttctgc aattgttcct aatccttcat    12000
taagaacatc aaatacaaaa atatctgatt cttgcatagc cttaaagtca ttagttaaaa    12060
tacgttctgc tagcttagtt tgttctgcat tagctttatc atttattgac ttatctttgt    12120
gagggctata cggagttact cctacaatgc catctacttc tttatgttgt ttatctctgt    12180
aatctaccat agcttcattt aggatatgtc cacccatata aattactttg tctttaattt    12240
tattaaccat ctatagtatc tcctttttct tctaaaattt ctcttaaaat atgtggcatt    12300
tttttcttaa tttgtttatc tactatttc agtatattt ctttttcttc ttccataata     12360
tcatcaacaa agttttgacc tacttgtttc ataattagac cgaagttttc taattctaaa    12420
tcatcttcag ataatctatc ttcttctata gcccctaaaaa tcattttttc cattcttgct    12480
cttgtaatgg cataatctgc cactgactcg ttctttttta cttctgtttt cattttttga    12540
cgactaaatt ctttaaactc attagatact aatttaaagt agtcatcata ttctgattta    12600
ccatctaagt atttaattac tataccttca cccttatcag gttaactgt catgtcagat     12660
tttcctacta attcttgaat ttcttcaggt tttaaatcat ttaagtagtg agatggttta    12720
```

FIG. 19H sequence.txt

```
gctactagca aagtttttaac tgtttttaac cctaaatgat gtgcaattac attcatgtct   12780
tctattgata aataaacttc attttcttta tcataaacat caaatacata aaaattgttg   12840
taaaattctt ctttgtactg aatcttatgt ttgactaacc attcaccaaa aataatgtat   12900
ttttctaagg ctgatacgta cgtatttctt acatttatat tttcatgtac ccaatcataa   12960
aaaccattta aagtttcatt ctcatttaat ttttttctac gtgaaaaaca tactaattca   13020
ccattttcta ctgtgaagct tgcattactt ccatctaatt tttcttgtac aactagacct   13080
cttctcttaa atttatctag tacaatacct ttattttta ctttagtata cgatttcatt   13140
aattatcctc ctttgaatta tgtactatag aaaacaaaat aagacttaca ctagctaaaa   13200
atgctaatac tactaaacca ggtaaattaa gaactgttga taagaataat gatattgcac   13260
ttataacata aactagaccg cttagaaata aagttaataa tacaattgtt ataagtttca   13320
ccaaccaatt attattaata aataccttag ctaaataatt cataaaaaaa tcctccttag   13380
ttattataga ataactatac cataactaag gggatttgtc aacatattat tttaccattt   13440
aaaattgtct gcatattgtg caagcttaga gcggaaatta actgtaaaat tatgaaatac   13500
tgctccttca taatttttaa agtattccat ataatctcca aaacctgatt tactttcgtt   13560
ctttaaatct atttgtttaa aattaccttc tactattaca gtagaatttt ttgtatgaac   13620
ccttgtaaga acttttttaa gttcactgcg tttaaagttc tgtgcttcat ttataattat   13680
agtagcatct cttagatttc cacctcttag gaataaatgg gatatttgag atacccaaca   13740
atctcctagt ttatcttctt taacattatc ttccatcatt aacatttcag ttatttgttg   13800
ttcaggattc atattaagtt caataagggc atcgtgtaat cccatgaaat aagccatttc   13860
tttttctgtc tgattacctg gtctgcttcc taaatcttct gatactggtg aaattataaa   13920
tactagcttt ctatttttat taagatagtc tgcgtaagca caggctactg agcacattgt   13980
tttacctgta ccggcttgac tctcattcca aagtatttca acattatcat taaagaaatc   14040
ctcacagaaa tctaactgct cggttgtagc tttttcaagg aattcattaa agattagatg   14100
ttctcccatg ttgtatctta cattaggata atcttttaac ttaaagtcta actcttttag   14160
ttgtattgcc atattttaaa gttccctat ctataaatag ttttactctc ttttaatata   14220
gtactaattt ccgatatatt ctcctgttga agagcaataa ttactacatt cacattcagg   14280
gtagttatca caaacatctt catcttctac atcatcataa ccaatatcat aattattata   14340
attaaaatct acaatacaat tttcactatt acctttagat aatcctgtat aaataatatc   14400
atccacagaa tcccaatcgt tatctgccaa gtaatttaca ctatctagta ctgattcatt   14460
atcaggtaaa taaatactac cgtctgaaaa tttaattaaa atatcacctt gaggtaaggt   14520
atcattaatt aaatcaatct ctgtttcttc ttcaatagtg aatacagttc cttctaatct   14580
```

FIG. 19I

```
                                    sequence.txt
ttccggtgta gtatgtgtta aatgtttac  agtatcccct gattcttcat agaatcctac    14640
tgcattcata tctttattat attttgcaat aaatttacca ttgtcactta ccaaatattg    14700
actagttgca ttatagtcgt ttgcgtcatc tactgtcatg caagggttat aatctttaac    14760
ataataacta attttcctaa catctgctgt ttgtactttc ttaccttcac ctttaattac    14820
tgaattaatt ttcttcataa tattttctcc tttttatata tcaattgatt tttttgcaag    14880
attatcggca tagtcattcc atttgtcatt tgaatggctc tttacttta  caaagtttat    14940
atctattact ttttggtatt ctcgtatcat attaatatat gttttactta gaatatttct    15000
tgcagaccaa gtaccttcat accaatgtat taaaccaata taatctatat aaactattgc    15060
ctgattgtat cctagtttta tagcctcttc aataccataa caacaagcca atatttcacc    15120
cgcaacatta ttatacttta ttaatcctgg tttgtcaaca cttttactaa tttccgatat    15180
tatatttcct tctttactta ccaagacagc acctgagcct actttacctt tattatatga    15240
ggagctaccg tctgtgtata tatttacact atcctgcata cttataatcc tccataaatt    15300
gagggaattc acaatctgaa tagacttctc tgcaaaaaga tactgagata tagttaaaat    15360
caaaacattt gaaacagtgt tcttgaactt cttttttatc tttagcaatc acattaaatt    15420
taaaaccatc agctatgact gtaaatactc cttttttcat aaaacaaata cctccactaa    15480
ttttatttta aattaataac taactcaata aatgatttaa tagttttatt tttaccttca    15540
tcaatatctg aaaagaaatt aattaaactg tcatcctcat caaataaatc ttcaacatca    15600
tcaaatttat ttaatatgtc tgtaacactg taaccctctt ctgatatata ctcatgtaag    15660
tcttctccat cttctgacag tgttgcttct attttaccat ttttactttc aattaaatat    15720
aaagtattta atactttaac agaatctaca actacactgt agttactaat agtaggatac    15780
tctgtataaa gtatttctat attagtattc atataactat caattacaga gttaactgta    15840
tctctttta  gctcagatac attatgtttt cgtatagtag ggaattcttc atcatattct    15900
actaattctt ttctatctgt attcaataac ttgtctaaag aagacaacaa tactatttta    15960
tattggttat caggaagact gtctgtaatt tccattattg ttaaaaacgt atcttcacct    16020
agaactttgt ttatatcttg taattcaaat gaatctacca tttcaatagt atcatctata    16080
tcatctgtag tcattaaaaa attaactaaa ttattattct ccatcgtctt cctccaattc    16140
tttaaataac tcttttcctg gagtatttaa cgctttctct aaccgcatta aattagcact    16200
tcttggtttc ttttttccat actcccaata agatataaga gagtaatgaa cacctatctc    16260
agaagctaga cttcttaacg tatgtccttt ttctactcta atttttgaa  ggtttagagg    16320
tttactttcc tttttttcat ccataattat ttctcctcta cttttaaaaa tttaaaatcc    16380
tcagattctt ttgcattttt tagtatatac tcttgtgatt tatttcttgc ctctgcctta    16440
cttttagcat ataactctat atgaaataca tgaggttttt ttaaagacgg tgactcgtat    16500
```

FIG. 19J sequence.txt

| | | | | | |
|---|---|---|---|---|---|
| ctccaataaa | ctttaaaaag | tagtgtttct | tttttaaaa | cattaattcg | aaaccatctt | 16560 |
| ttaaatttat | tcattcatta | tcctcctcta | tttatttgtt | aaactaatta | tagcatagtt | 16620 |
| aacttatgaa | gtcaactata | atatacaaaa | aagactaaga | aattaatctt | agccttaata | 16680 |
| tattaataac | tattatgtgc | gttgtggtat | gcaagagctc | ctgatgttga | accgtaacgg | 16740 |
| tcaatcatat | attgttttgc | acctttagtt | tgttctgcta | tagaaccacc | actccatgat | 16800 |
| ttacctaatc | cttggaatag | tccttgagct | cctgatgatg | cattaacagc | attagggttc | 16860 |
| attgtagatt | cacgcatagc | aatttcaatc | attgcctcgt | ctccacctgc | ttgtctaatc | 16920 |
| tgttctgcta | cagagcctcc | tgtagaacta | gttgattgtg | taggttgttt | agtttccttt | 16980 |
| tgaactggtg | ctgatgttgt | ttgtacttct | tttttagtat | cttgtttatt | ttgagtatca | 17040 |
| aattgtgctt | gttgttggtc | tactttttgt | tcaggtgttt | gttcttctcc | tgctaatcta | 17100 |
| gatactgtat | tatctacttg | agttgagcct | gaatggtatt | cataaccaaa | gttaccatta | 17160 |
| taattataga | aatgataagt | aaattcaccg | tcactaaatg | agaaatcata | attaccttct | 17220 |
| tgaattggtt | ttgtattgac | ttctgctgaa | tttgatttag | cctgttctgc | taacttatta | 17280 |
| taatcaattt | cgtctgcact | agcttcgttt | gtagcaatac | ctccaaaagt | aatagctgta | 17340 |
| cctaatgcta | atgttgcaaa | aattgttttc | ttcataaatt | taaaactcct | taaataattt | 17400 |
| tttagaattg | tttatttgta | aaccgacata | agtaatcata | acatatatct | ttaaataacg | 17460 |
| caagtataat | atagcactaa | ttagtgtaat | attattaagg | ttttattaca | aacattacag | 17520 |
| ttatcagata | attaaataca | aaaaaaagag | aggtattaac | ctctctaatt | tattattttc | 17580 |
| ctgttacatc | tacaatagtt | ccgtctccgc | caatttgaat | aggttgttta | ccatcccatt | 17640 |
| tttcaattaa | ctgttgacgt | aatatcttat | cagataagga | agattctcta | atctcattgg | 17700 |
| cttttttatc | accattagcc | tctacttctt | ttttcttagc | attttgttca | gcaatttgtt | 17760 |
| tatcaacttt | agtacgttct | aattcttggt | tagctttaac | tcgactgtca | attgcttttt | 17820 |
| gagtattctt | atctgcttta | gggctagata | atgcaatgtc | ctcaattaca | aatccttgtt | 17880 |
| tttctaagtt | gtcattcaag | ctatctaaag | tatcttttt | aatttcccct | gttttaactc | 17940 |
| caaatgcatc | aattacagaa | tacttagata | ctgcttgacg | gacattatct | tgtacccgtg | 18000 |
| aacgtaaata | tccttttct | agttcttcga | tatctgcact | accaaaacga | ttaaataaat | 18060 |
| ctacagcttt | agttgcatct | actttataag | atacatcaat | atccatttgt | aaattcttgc | 18120 |
| catctgaagt | tgctacattt | aaatctttat | atttatgtgt | ttgtgtttta | gttgggtatt | 18180 |
| tatttacctt | atcaaaaggt | gctgttaaat | gccaacctgg | tgatttagta | tcttccttaa | 18240 |
| caccatttac | tgagtataca | actccaacat | gaccttgtgg | aatcttagta | atacacatta | 18300 |
| ataaaataat | aaaccctata | attgctaaaa | accctaatac | tcctgaaata | actactgact | 18360 |

FIG. 19K

```
                                sequence.txt
ttctcattac atttctcctt tttctatttc ttttattaag ctatttaaag cttttcctc      18420
ttggtctatt tcttgtttat cggctctagt tacaattgat tgtctacggt catttaagaa     18480
ttgttttta  tactttacat attgttctaa accgtattca tctaatgtac cttgcctaac     18540
taattccctg tattgttttc ttatgttact cttcttctct ttcattgaaa gaaaatcaaa     18600
taaataactt ataccaaaac ctacaaggac tagaaaaaca ataaaaatag caaaatatgt     18660
taaaagtagt gccatgtaat tcctccttta tttgattaca tatataacta tacactatgt     18720
atttaatttt gtcaacactt ttttgcaaaa aaaaatagac ggattttaaa tccgtctaaa     18780
tttatattct atttgaatac tccccaggca acgccaggta tttgattagg tggaacacct    18840
tgacaagttc taacagggca atatactctg ttaccgttgt aagcattata acctatccaa    18900
atatgacctg cttggataca aacttcgtca tatacaattg tagcccctgc cggtaagtta    18960
ccgcctactg gagcatttaa gaatggagaa cctattctgg ttactatagg ttggttacca   19020
ttaacaaatg ttgcgctttc cggtttatac caagttccga actggttctt tttccaagaa   19080
cctgtaactg gtctagttgc cggtgtactt gcactacttg ttttaccatc tttaactaca   19140
gtagagcttg aagttccgtt actcatgtag tttttaattt gtttaatgaa gtaatctttt   19200
aacttattca ttattgcttg tgatggtctt ccttgtgtta ctgggttaaa tcctgtatga   19260
agaaccatcg aacggtgagg gcaggcagtt ggtacaaatt ccatatgcaa tcttacagtt   19320
ttacggttag gagtaagacc ccattcttta aatttctctg ctgtaaattg gaatactgct   19380
tgttcatttt taaggaattg agcatcacta gcactcattg attgacagac ttcaatacct   19440
gcaaatctaa agttacctga gtttgctcct gttccatccc ctgtgtgcca agcaatttga   19500
ttcttagcat ctattgcttc ccatacataa ccttcagagc catagtaatg agcaatacca   19560
ttagcatatc tagcataacc tgcattagct aatgaattct cgtattgttg tcctgaagaa   19620
cgacctgcat cgttgtgtat taccattcct tcaggttttt taccacgttt atccattgta   19680
tagttaatgt gattcttaga aactttagt gttgctttct ttttaggtgc aggtgtttta    19740
cttgcgcttt tcttagctgt ttcttttta acagtagttc ctgcttttac aggtatttca    19800
atgaagtgag ttaatccgta ataattatct acacgttttg taggtttttt attagcataa   19860
ccattccagt tttgctctaa aatagtaaat gtagaagtat tacctccatc atatacaata   19920
cctatgtgac cccactgttc ataactaccg gatgtaaata ccgcaatcca acctttttta   19980
ggtacagtag aaggtttatt ttcatgtatt ttaaatccag taccataact ctgtttaatt   20040
tggtctttag cattacccca agttctaact ttattatctg ttaaccataa aacatagtct   20100
gtaataaggt cttgacattg agcgtgatag tagccatctg cgtcaatggc tcctgcttcc   20160
attacaccaa atgacgggtc ataacttgta gctttttaa ctctgtaagg gctatctact    20220
gttcctttg cataagcgtc taaacgttta tttatttctg cttgagtctt agccattact    20280
```

FIG. 19L sequence.txt

```
taacttcctc ctctgcaaat actttaccat gttcctcggt atcttcttca tcttgagaag    20340
gtgctgaacc accatcaatt tcatcttcaa tagcaggtac ttcatcacta tcatctgtgt    20400
caggttctgc attgttttcg tagctgtcta tctcaaaagt actagcgtta tttgcgtttg    20460
tttgccattg aacgaactca ttagggtctt tactatcacg aggtttaacg taatctgttt    20520
gaacaatatc actgtctcta agacctttag tattattatc aacaataata cctaaacctg    20580
ctaataatgt tagtatagaa cctacaatat ttacaccttg ctcaatttga gctgagtagt    20640
ctaaaccgaa agcacctgta atttggttag caaataatgc tactgctgat ataattgcta    20700
cccaaaatgt tttgctctta gttcttgtgc taaggtttat tcctccaaca actttaggtt    20760
gtttagtttc attagccatt aaaaaaccga cctttctatt atatttattt ctaacaataa    20820
tataacagta ggtcggtcat gtttatctat attaatttaa cacttactca ttaatttggt    20880
ttagtttttt gataacttca gacatttgtt tgttatctaa atcttctaat ttagtttccg    20940
gaagtagctc taacttatcc caaacttctt ctttattaga tactttatta ttaataattg    21000
ccttaccaac taaactttcc gtataatata attgttttgc tgatgccatt tgtatctctc    21060
cttttaaata tgtaaagtat atagctagta tcgtatccta ggaacaaaca cttgcgctat    21120
atactcaatg aaatcctacc ctcattcgag gacacagcaa accggttcgt caaccgcaca    21180
tatgaattct aagatttcat ttatgtaaaa cacaccctct tgatttgca caaagactaa    21240
gggttttgga gaccccttgta ctactaatta tactaagggt gtttattatg gtttctattg    21300
gatttgaacc aatgacacct agagcttcaa tctagtgctc taccatctga gctaagaaac    21360
cttaaaacga cccatacgag actcgaactc gtactctctg ccgtgacagg gcagtgtgtt    21420
aaccagttac accaatgagc caaaattata atgctatacc ctaaccttac cttaatgtat    21480
agcaggtttt ctcttaggct cgaagcaacg attattacca ctcataacaa ctatatatta    21540
agtgaaagga ggtgaaatga acaaaacgtg gtaattggta cctaagaagg taatatgtat    21600
aatctacaag gagtaagtta ttggttcata aaggagtgtg aacaataaat acatgaaaga    21660
gtgaaagttt actccctgta gattcttttt taattatcaa tcaaaggagg aaactgataa    21720
ttgttaataa taaactataa agaggaaaat atttatagtc acattctgat ataatgcaac    21780
taaatatcca agcataaccc gtctcacgag gaacctacct ataagacctg ttattaagtg    21840
aatcactacg attgactcta ttaaggagct accttaagtc catctcacgc aatttaaaag    21900
ggacttacaa accgtaaaac ggtaataagt ttattaaata atgtgatatt aacatattag    21960
ttaataactt tcacatggtc gaagaaaagt aaatttattt gattaccaaa ttatttttat    22020
caaatatagc tcttttgaac ctgtagattt atgctactca tactgataac ctctattatc    22080
taacacattt ctgtgctcca actacagtta gtcgttacag cgtatctttc taggattccg    22140
```

FIG. 19M

```
                           sequence.txt
ctaagaccct agaaagaaat taaaccctag ccgttatcat actctacaga ccttataagt    22200
aagtaccaag tataccaatc gtatttaaca atactaatga cgacccatcc taccgatata    22260
tctccgataa gttttgattc gtttgattat cttgtacctt atgactacca aatcattatt    22320
cagtcactat gctcagatat ttagttgtat tatttatata ttaattataa catagttttt    22380
attacttgtc aagttaattt caaaaaaatt atagaagtag ggacgcttac ctacttccat    22440
ttaatttaca caaggatgat aacattgtta ttgttttata ctggaaaaca atgtaagaaa    22500
aacagtgatg tgtaaggtat ttgttttatt gttaattaca ttatagcata tactgatacc    22560
tttgtcaagt taatttaata cttttttaaa atattagtta tcttttgtta attcttcctg    22620
aatagcatcc catcttcttt ctgcttcact acgattatct tctatatgtt ttgtagtttt    22680
acaacatttg atacaatata tatctttgat atgaccttct tctctttttat ttgctctttt    22740
tcttggtact ttgaatacat ttccacattc tttacatatt aaacttgagt aaaacatttt    22800
ttgtcttttc ataattaatc aattcctttt ctcttttatt tgataattta actatatact    22860
atattgataa ataagtcaac agttttctaa aaataattta aattattttg aagaatcctt    22920
taatatcaag ggttacaaga gaaaaagtac gtatttagaa aataaggagt actcctatta    22980
tatataatta tattctgata tagagtaata aataatatta aatatataat tataattaat    23040
aaggttggga aaattgatat aaacataact gatattgctt atagatactc agtataaaag    23100
taaaatccct tagtatcagt acttacaggc aaaaaagtac gtatttagaa aataaggaac    23160
tctcctatta tagttatata tattaattac tattattaat tactatttaa atatataatt    23220
ataattaaca atgttagaaa gtcaacaata gtataaataa aaaagtgact acttaaagtc    23280
actcaataat tagaatacta ttttaaaaga ttctattctg tttggattaa tatatacttg    23340
aggtgaagtt atagcacttt cagtatatac ttttatagag gtttcatcca ttcctcttaa    23400
catataatct atatcttgcc tattgtaact cttttcatca gtagatacta aaaagtattt    23460
agctccactt gacattgtta tttcaatatg ttttgacatc tacaatctct cctatgcaaa    23520
tttgttaaag acaaaggata atatagctcc tagaacaagt aaaagaactt tctcagttgt    23580
atccttcttc ttagtatcct tagttttttgt acttccagca agttctgaaa tcttttcatc    23640
aagtctttct aattggacgt aaattgctga ttgtttttca ctattgacag ctacatcttt    23700
atctatacta actatcattt ttcttagttc agctacctca acttctaaat ctttgaaagt    23760
ccctctatct atataattac cttcttgtat cttagactta atagtttcta cttgagaaac    23820
aaggttgttt atctccttat ccaactagaa tcacctctaa ggtctaaccg tttcagattc    23880
agaatggata tcataatttt ctaagaaatc attgataatc tccatataat tatccgtaac    23940
gacttttccg taagatgttt ttgtatcaat ttcaaaccta agcttaccaa aactttggag    24000
gtctaattct tttattacaa tattagggtc atcagaagga aggtaataat agtcgaagta    24060
```

FIG. 19N sequence.txt

| | | | | | |
|---|---|---|---|---|---|
| tataattgag | ccatttatta | atactctgtc | tattctatag | acgtggaaat | agcgtctgtc | 24120 |
| tcttttaaaa | tgggctagtg | catctttaaa | ctctaactta | aggatatcct | tatatttagt | 24180 |
| caaagtggta | acctccttac | tattaatttt | taaatttact | tattttgtgg | tataatagtt | 24240 |
| atgataaagg | cagttattat | aattatatta | agaataatga | taataattat | tttttctgag | 24300 |
| aaaataagcc | aaatactaaa | aacagataaa | gcatagatag | ctgatagata | tactatatta | 24360 |
| agagttacct | tacttttatc | ttttctatag | atagaataac | ctaaagacgt | tgtaacacca | 24420 |
| ctaagtataa | aataatagaa | acaaaaaaga | ggtatagaca | gaaaaaaaga | tacgataatc | 24480 |
| attgttaaac | acctatttct | ttttgaccta | ttatttctag | aacttttaga | ttacaccact | 24540 |
| aatataacat | taaaagccag | tcataaaagt | caattgttag | attaataata | taataaaaaa | 24600 |
| agacaatagg | aggttaaagt | ggttgaataa | taacatagct | atattcatat | tcaaaacact | 24660 |
| ggttatcatt | atattcttac | tactaatttt | gtctgttatt | aattccttgt | cccttattta | 24720 |
| ctcaataaga | ccgagtgtag | ttatgacata | ctttatcttt | ggtggtattg | tttctaatgt | 24780 |
| cgcacttact | gtaacagata | agttcttact | gaagaaagaa | gaccccctac | ctgaatatgt | 24840 |
| tcttaaaaaa | gtagagataa | atgataaaga | aataagaata | atcaagaaaa | tcatagaaag | 24900 |
| taattacgga | ataacagcag | aagagataaa | agttagggct | aaagcacaaa | gaagaataga | 24960 |
| ggaagatagt | aaaaaggaag | attacgatga | aaacaaagaa | agaaattaaa | gaacaaagga | 25020 |
| aagagcttaa | ggatggtgct | acatctgttt | ctttagtaaa | aaaaggagat | aagagaatag | 25080 |
| ctagccctag | tagaatttgt | agtctatgtg | gtcagcagtt | atcaggtatg | aattacacta | 25140 |
| aaggaaaagc | attatcaaaa | gttaatcatt | ttcatttaca | gtattctaag | tatatttatt | 25200 |
| ttgatatttg | cgcagatatc | aacaattgtt | ataaaaattt | aagaaaacga | ggtgaaatgg | 25260 |
| attgagtgca | gaaaatatta | gagatataat | taacaagaaa | aagttagaag | aagaggatac | 25320 |
| aagaaaatat | atagctgatg | gatttatgaa | tggtatcggt | aaattaatgt | acgaattcaa | 25380 |
| taaaaagta | gataataaag | aaatagaagt | taaagaccct | aatgatttat | ataaattatt | 25440 |
| tgtgatattc | tctcaaatgc | aaaatatggt | caatgaaact | tctgaaggtg | gagcaatacc | 25500 |
| tcaactatct | agacctcaac | aggaattatt | tgatgagatt | acaacagaag | atagtaatgg | 25560 |
| agaatctaca | gttgatttac | agaagatatc | agaaatgtca | gcagaagata | ttacagcaat | 25620 |
| gatttctgaa | aaggaaaaag | taatgaatga | ggaaaattca | gaaacattct | aaggagaaag | 25680 |
| atataaatgg | atggaaaaga | actaattaag | atagcacaag | aaacatttca | aactgaaaaa | 25740 |
| ataacaagag | aacagataga | ccatataatc | aatatgctaa | acccttctac | ctatatgctt | 25800 |
| aagtatcata | cactgagagg | tcatcctata | acttttagta | ttcctaacag | ggatagaagt | 25860 |
| aaagcacagg | ctcatagacc | ttggcaaact | aggattgtaa | atgatactca | tcctaataag | 25920 |

FIG. 19O sequence.txt

| | | | | | |
|---|---|---|---|---|---|
| gctgtaataa | aatcacgtca | gttaggtctt | agtgaaatgg | gtgtaatgga | aatggttcat | 25980 |
| tttgcagata | tgcatagtta | tgctaacgca | aagtgtctgt | atacattccc | tacaaatgaa | 26040 |
| caaatgaaaa | aatttgttca | gtcacgtttg | aaccctgttt | tagagaaaga | atatttaga | 26100 |
| gacattgttg | attgggataa | agactcgtta | ggttttaaaa | agataagaaa | ctctagttta | 26160 |
| ttctttagaa | caagttctaa | agcaagtacc | gtagagggtg | tggatattga | ttatttatct | 26220 |
| ttagatgagt | atgatagggt | aaacttatta | gcagaatcgt | ctgcactaga | atcaatgtct | 26280 |
| tcatcacctt | ttaagattgt | gagaagatgg | agcacacctt | ctgtacctgg | gatgggtata | 26340 |
| cacaaattat | accaacaatc | agaccagtgg | tattacggtc | atagatgtca | acattgtgat | 26400 |
| tacttaaatg | aaatgagtta | taatgattac | aaccctgata | atcttgaaga | aagtggaaat | 26460 |
| atgttatgtg | ttaatcctga | aggtgtagat | gagcaagcta | aaacagtaca | gaatggcagt | 26520 |
| taccaatttg | tttgtcaaaa | atgtggtaaa | ccattggata | gatggtataa | cggtgagtgg | 26580 |
| cattgtaagt | accctgagcg | tacaaaaggt | aataaagggg | tacgaggata | cctaataaca | 26640 |
| caaatgaacg | ctgtatggat | ttctgctgat | gaattaaaag | agaaagaaat | gaatacagaa | 26700 |
| tctaagcaag | cattctacaa | ctatatttta | ggttatcctt | ttgaagatgt | taaacttaga | 26760 |
| gttaatgaag | aagatgttta | tggtaacaaa | tcacctattg | cagaaacaca | attaatgaaa | 26820 |
| cgagatagat | attctcatat | agctattggt | atagattggg | gaaatactca | ctggataact | 26880 |
| gttcatggta | tgttacctaa | tggtaaggta | gacttaatac | gattattctc | tgttaaaaaa | 26940 |
| atgacaagac | ctgatttagt | tgaagcagat | ttagaaaaaa | taatttggga | aatatctaag | 27000 |
| tacgaccctg | atattataat | tgcagataac | ggggactcag | gtaataacgt | tttaaaactc | 27060 |
| attaatcatt | ttggaaaaga | taaagtattt | gggtgtactt | ataaatcttc | tcctaaatct | 27120 |
| acagggcaat | taagacctga | atttaatgag | aacaataata | gggttacagt | agataaatta | 27180 |
| atgcagaata | aaagatatgt | acaagcactt | aagacaaagg | atataagtgt | ttatagtaca | 27240 |
| gtagatgatg | atttaaaaac | tttcttaaaa | cattggcaga | atgttgttat | tatggatgaa | 27300 |
| gaagatgaaa | aaactggaga | aatgtaccaa | gttatcaaac | gtaaaggtga | cgaccactat | 27360 |
| gcacaagcaa | gtgtctacgc | ctatatagga | ttaacaagaa | taaaagaact | tcttaaagaa | 27420 |
| ggaaacggta | caagctttgg | ttctacattt | gtttctactg | attacaatca | agaaggaaat | 27480 |
| aaacaattct | actttgatga | atagaggtga | aatagacttg | acagataaat | tatttttatgg | 27540 |
| tacaattagt | aatgaagaaa | ttaataaaag | tgtattgaat | ttgttattgg | gtgaggaatt | 27600 |
| atccttagat | tatgtttcta | aaaatagtga | tactttagat | gttaaatatg | aacatgttta | 27660 |
| taaatctcta | ggattcgata | atttctttga | ttgtttttta | tatgctaata | gagagcctga | 27720 |
| aatagtccat | aaaggtggag | ataaaaatct | tggtggacta | aataaggtta | aacgtactgt | 27780 |
| tattcgtaat | ggtaaagaaa | tggaaatgac | agtttacgaa | gatggtaata | aagagaacga | 27840 |

FIG. 19P sequence.txt

| | | | | | | |
|---|---|---|---|---|---|---|
| tagtaaagaa | aaacaagaag | gaaaagaaga | agttagtaga | agtgcagtag | gagcaagggc | 27900 |
| tatttctaat | ggtgaagaag | gaaaggtaaa | ccctaaaaag | gtagcaaatt | cattatctaa | 27960 |
| tttaagtaaa | aaggtgtag | atgtatcaca | tattaataca | aactcatcat | tgtataaaga | 28020 |
| gtttgttgat | gataacggtg | atacattagg | aattacatct | tttaaacgaa | ctgaaaatga | 28080 |
| tataatatta | gaatcttatg | caagttcaca | tgattcagat | ggtgtaggag | caagagctat | 28140 |
| tatggaatta | ttacgtttaa | gtattaagga | aaataaaaat | gcagttgtgt | atgatataga | 28200 |
| attacctgaa | gcagtagagt | atttaaaaac | tttaggattt | aaacctaata | aagatggata | 28260 |
| catcttaaga | aaaaagatg | taaaacaatt | cttaggtgat | tatagtgatt | ttatttagca | 28320 |
| ctatagtcat | ctattctatt | gtatttattc | tatatattgt | attaaaaaca | atttatataa | 28380 |
| agtctaatat | gagtagaata | gataacacaa | ctgaattatt | aaaaatatta | caggaagata | 28440 |
| ttgaaggtaa | gataaaaaag | gaaggaagaa | ataaatgact | ttagaagaaa | ataaattaac | 28500 |
| attagaagaa | tcaataactc | cacttagcaa | agaggagaaa | gaagatagta | ttaaagaatt | 28560 |
| tagcagttta | ttatgtgaaa | tggtaaatag | actatataag | tcttataatg | tatttagaca | 28620 |
| agaccctatg | gatgaaactc | aacgtctaga | tggctcttta | atggtctttc | aaagtagatt | 28680 |
| aaatgaccct | ttaacaggag | atttacatga | taagatgtat | aaacttgctt | tttcaaaacg | 28740 |
| tattgatatt | ttcgaagcta | ataagcaatt | tagaaaagat | gtagaagcag | gtaaagcaat | 28800 |
| tgagttaggt | gatgtagcta | ttatagatac | agcattaagt | aacatccttt | caggcaatga | 28860 |
| gttccaagga | agtatttcat | ttatgcttag | aaaagacttt | gaagaaaaag | aacgaattag | 28920 |
| aaaagaagaa | gaagagaaac | ttaataactt | ataaaaggga | agaattatga | gactatataa | 28980 |
| aatgaggtat | cataattgaa | aaagaaacca | caaggcaatg | aggtaatcat | aaccataata | 29040 |
| acggttatga | tagcagtatt | tgtagtcatt | atgaccatat | tttttaataa | atatcaagat | 29100 |
| gctaaagaag | ataaagatag | atatcaaaga | ttagtagaga | tttataaaaa | agcagatgat | 29160 |
| aatgatggtg | agactaaaaa | gaaatatgtt | aaaagattaa | ataaggctga | agaagaactt | 29220 |
| aaaaaagtaa | aaaagaaaca | aattataaag | attataataa | gaagtcaagt | aaagaaagac | 29280 |
| aaaaagaaga | taaagaaact | agagagaaaa | tatatgatgt | aactggtgat | gatgacttaa | 29340 |
| tattagtaaa | aaataatatt | gagtttagtg | ataaagtaga | caagcccgaa | atacttatta | 29400 |
| gtgaagatgg | aattggtacg | ataactgttc | ctgtagatag | tgggtatgaa | aaacaaacag | 29460 |
| taggttctat | tattactagt | gtattaggtt | ctcctttcct | atcacctggt | tcaaatagta | 29520 |
| tagatggttt | aagtgttatt | aacgataatg | tttatccaaa | tacagtagat | agcatagtag | 29580 |
| aagatacaaa | accttctatt | aacttaccaa | cggataatcc | tattataaca | aatccagttg | 29640 |
| aaccaactat | accttcagat | attatacctc | ctattgataa | tccttcagtt | ccgatatctc | 29700 |

FIG. 19Q sequence.txt

```
ctgagaaccc aggagataat aatcaaggaa atacagataa tccaaatcct cccctccag    29760
ggtacacaga tgaagatggt ggaagaggct ccggtggtgg aggaaattct gaaccaccat   29820
caacggaaga accttcggat aatggtaaca ccggaggagg agattgggaa gaaaaacctg   29880
acccaggaga agaaccttca gataatggta atacaggagg aaatggtgga gaagttacgc   29940
ctgaacctga acctgaacct gaacctgaac ctgaacctga acctgaacaa ccgaatgaaa   30000
atcctgatga aggtaatgaa gaaaaaccat ctgaaccgtc tgacaatcct gatgaaaatg   30060
gaggatggga aactgaacca actgaacctg agtcaccttc agagccggac gataaagtgg   30120
acgaagaaga taaaaatgaa gatactacag atgataaaca gcccactgaa caaccggacg   30180
ataacaacat agataatgaa gataaaactg aagaggagta attactcctc tttttgttt    30240
gctatattaa ataagagcta aatataaaaa aattgaacat tacggtggtg aaaactttgt   30300
taggaatgaa tattataacg tcactatcag tagtatttac ttgtttaagt cttttaactt   30360
taatgatttt tgttcatagt aagttctcta gtaaaaacgt ttttgttttg tatgtaattt   30420
atgctataat aggaataggt acatacatag ttttaactat gtttcaaaca acatctgtac   30480
ttattaagaa tgatgtaata gattccatag aaaatactga acattatatt ggattcaatg   30540
accctataat tatatttact ataagtttta taggtgcaat acttggagga atttggtaca   30600
agatgatgaa aattattaaa aagagtaact ttaaagataa aaaataaaaa agacggtgaa   30660
taggttgata ttctctaaag ataaaaaatg ggatgaagca aaagatttca tcaaaggtca   30720
aggtatgcaa gataattgga tagagattgt agattattat agacagatag gtggaaaaca   30780
cgtagctgtt tttattgctt taaacaaagt aaaatacatg attctagaag caacaaaaga   30840
caataaggta atattagtag ataaagataa taatatacta ttagaagatt atgatattgt   30900
tatggaaagt aagaagatgt tttattacat tgaagaaccg ttcgaggtta aaataaatat   30960
ccctcaacat attagagatg taacttataa taatactgtt gtattaacta cagtaagagg   31020
gagtagaggt gactagtaat tggcagattt atttaagcaa ttcagattag gtaaagacta   31080
tggtaataat agtaccattg ctcaagttcc tattgatgaa ggattacaag ctaacattaa   31140
aaaaatagaa caagacaata aagagtatca agatttaact aagtctttat acggacagca   31200
acaggcttat gcagagccat ttatagaaat gatggatacg aatcctgaat ttagagataa   31260
gagaagttac atgaagaacg aacataactt acatgatgtt ttgaaaaagt ttggtaataa   31320
ccctatcctt aatgctatca tacttacacg ttcaaatcaa gtagctatgt attgtcaacc   31380
tgcaagatat tcagagaaag gtttaggttt tgaggtaaga ttaagagacc tagatgcgga   31440
acccggtaga aaagaaaaag aagaaatgaa acgtatagaa gattttattg ttaatacagg   31500
taaagataaa gatgtagata gagattcatt tcaaactttc tgtaagaaaa ttgttagaga   31560
tacttacatc tatgaccaag ttaactttga aaaagtattt aataagaata taaaactaa    31620
```

FIG. 19R

```
sequence.txt
attagaaaaa ttcatagcag tagacccttc tactattttt tatgcaacag ataaaaaagg    31680
taaaattatt aagggtggta agagatttgt tcaagtagta gataaaagag tagtagctag    31740
ttttacttct agagagttag ctatgggtat aagaaaccct agaactgaat tatcttcttc    31800
aggatatgga ttatcagaag tagagatagc tatgaaagag tttattgcct acaataacac    31860
tgaatcattt aatgatagat tcttctccca cggtggtact actagaggta ttttacagat    31920
acgttcagac caacaacaat cacaacatgc attagagaac tttaagcgtg aatggaaatc    31980
tagtttatca ggtatcaacg gttcatggca ataccagtg gtaatggcag atgatattaa    32040
atttgtcaat atgacaccaa ctgctaatga tatgcaattt gagaaatggt taaattacct    32100
tatcaatatt atatctgctt tatatggtat tgaccctgca gaaattggtt tccctaatag    32160
aggaggagct acaggttcta aaggtggttc tactttaaat gaggctgacc cgggtaaaaa    32220
acaacaacaa tctcaaaata aaggtttaca acctttactt agatttattg aagacttagt    32280
taatagacat attatatcag aatatggaga taagtataca ttccaattcg taggtggaga    32340
tactaagagt gctactgata aacttaatat tcttaaacta gagactcaaa tatttaaaac    32400
agttaatgag gctagagaag agcaaggtaa gaaacctatt gaaggtggag acattattct    32460
agatgcttca ttcttacaag gaacagccca attacaacaa gataaacaat ataatgatgg    32520
taaacaaaaa gaacgtttac aaatgatgat gagtttacta gaaggagaca atgatgattc    32580
tgaagaaggg caatcaacag attctagtaa tgatgataaa gagataggaa cagatgcaca    32640
aataaaaggt gacgataatg tttatcgtac tcaaacatct aataaaggtc aaggaagaaa    32700
aggagaaaaa tcttctgact ttaaacatta attaataagc ctagaataaa tctaggcttt    32760
gtttatttt ttcgtaattt aattttgata aatgtaataa ctatgatata ctatatgtaa    32820
ttgatattaa tacataaaaa atattaatat ttcacttaca agttattatt gttatattat    32880
taacgtaaaa gtaaataaaa taacaagtgg aggtgtagac acctttggaa gaaataaaat    32940
ttaatgcttt tgtacctatg gatttgaaga aatctgtatc aacagcttct gatactaatg    33000
agtattctat cgtttcagga tgggctagta ctccaagtat ggatttacag aatgatatag    33060
ttaatcctaa aggaatagat atagagtatt ttaagtcaca agggtacatt aattatgagc    33120
atcaaagtga taaagttgta ggtataccta cagagaattg ctatgtggat atagaaaaag    33180
gtttatttat tgaagcaaag ctatggaaga atgacgaaaa tgttgttaag atgcttgatt    33240
tagctgagaa attagaaaaa tcaggtagtg gaagacgttt aggtttttct attgaaggtg    33300
cagttaaaaa acgtaatata aatgacaatc gagttattga tgaagttatg ataaccggag    33360
ttgcattagt taaaaaccct gctaatcctg aagcaacatg ggaaagcttt atgaaatcat    33420
ttttaactgg tcatggtaca tcacctgaca ctcaagttga tgcaggagct ttaagaaaag    33480
```

FIG. 19S sequence.txt

| | | | | | |
|---|---|---|---|---|---|
| aagaaatagc | atctagcatt | acaaatttag | cttacgtcac | taagattaaa | gatttaaaag | 33540 |
| agtttaatga | tgtatggaat | ggcgttgttg | aagatttgag | taaatctaat | agtatgggat | 33600 |
| atgaggaatc | agtccttacg | ttacaactag | ctaaaggttt | atctcgtaaa | gatgcagaac | 33660 |
| tagcagtaat | ggatataaac | aaacaaaaac | tagaataggt | aaggagaata | cattctatga | 33720 |
| gtaaagaaat | gcaaaatatt | ttagaagagt | atgataagtt | aaatgctcaa | gaggcagttt | 33780 |
| cgaaatctgt | agaagatgat | gaaaagaata | cagtagaatc | taccgaagag | caagtagcag | 33840 |
| aaacaactga | agaacctgct | aaagaacctg | aaaaagtatc | tgaggaagat | gctaaagaag | 33900 |
| cacaagagca | aggtgaaaaa | gttgaatctg | aagaggtagc | agagggcaat | gaagatgagg | 33960 |
| aagttgaaaa | atcagctaaa | gaatcaaaag | accctgtaga | ccaaaaagat | actaagacag | 34020 |
| aaaataaaga | caacgagaaa | cgtaaaaata | aaaaagataa | aaaagaagat | tctgacgatg | 34080 |
| aagataaaga | tactgacgat | gataaagata | agaaagaaga | taagaaggaa | aaaacttcta | 34140 |
| aatcaatttc | tgatgaagat | atcacaacag | tatttaaatc | tatcttaaca | tcttttgaaa | 34200 |
| acttaaataa | agagaaagaa | aactttgcta | ctaaagaaga | tttaagtgaa | gttagtaaat | 34260 |
| ctattaatga | gttatcagca | aaaatttctg | aaatccaagc | tgaagatgtt | tctaaatcag | 34320 |
| tagacactga | tgaagaagct | gtagaaaaat | cagtaacatc | tacaaacgga | gagcaagaaa | 34380 |
| aagtagaagg | ttacgtttct | aaatcagtag | acactgaaga | acaagctgaa | actggtgaag | 34440 |
| caaaatcaga | agaagctgaa | gaagtacaag | aagataacac | atttaaagga | ttaagtcaag | 34500 |
| aagaacgaac | taagttcatg | gattcttaca | aagcacaagc | taaagaccct | agagcttcta | 34560 |
| aacatgactt | acaatcagct | taccaatctt | acttgaacat | taacactgac | cctactaatg | 34620 |
| catcagagaa | agatattaaa | actgtaaaag | actttgcaca | aatttaatta | atgcacaaag | 34680 |
| ttgtgttata | ttatacggtg | taactaaaga | atataaatag | ggtacatttt | actgtaccct | 34740 |
| acataaaata | aaaagaacac | aaatgaaagg | tgataaattt | atatgactat | cgaaaagaac | 34800 |
| ctgtcagacg | ttcaacaaaa | gtacgctgac | caattccaag | aagacgtagt | aaagtcattc | 34860 |
| caaactggtt | atggaatcac | tcctgataca | caaattgacg | caggagcttt | acgtagagaa | 34920 |
| attttagatg | accaaatcac | aatgttaaca | tggactaatg | aagacttaat | cttctatcgt | 34980 |
| gatatctcac | gccgtcctgc | tcaatctaca | gtagtaaaat | acgaccaata | tttacgtcat | 35040 |
| ggtaacgtag | gtcactctcg | tttcgttaaa | gaaatcggag | tagcaccagt | atctgaccca | 35100 |
| aatatccgtc | aaaaaactgt | atcaatgaaa | tacgtttctg | atactaaaaa | tatgtcaatt | 35160 |
| gcatcaggtt | tagtaaataa | cattgctgac | ccatcacaaa | tccttacaga | agatgctatc | 35220 |
| gcagttgttg | caaaaacaat | tgagtgggct | tcattctacg | gtgacgcttc | attaacttct | 35280 |
| gaagttgaag | gtgaaggtct | agagtttgat | ggtttagcta | aattaattga | caaaaataac | 35340 |
| gtaattaacg | ctaaaggtaa | tcaattaact | gagaaacact | taaatgaggc | ggcggtacgt | 35400 |

FIG. 19T sequence.txt

| | | | | | | |
|---|---|---|---|---|---|---|
| atcggtaaag | gtttcggtac | agctacagat | gcttacatgc | ctatcggtgt | acacgcagac | 35460 |
| ttcgttaact | caatcttagg | tcgtcaaatg | caattaatgc | aagacaacag | cggtaacgtt | 35520 |
| aacactggtt | acagcgtaaa | tggtttctac | tcatctcgtg | gattcattaa | attacatggt | 35580 |
| tctacagtaa | tggaaaatga | actaatctta | gatgaatcat | acaaccatt | accaaatgct | 35640 |
| ccacaacctg | ctaaagttac | agctactgtt | gaaactaagc | aaaaggtgc | ttttgaaaat | 35700 |
| gaagaagacc | gtgcaggatt | atcatataaa | gtagtagtta | actcagatga | cgctcaatca | 35760 |
| gctccttctg | aagaagtaac | agctacagta | tctaacgtag | acgatggtgt | taaactttca | 35820 |
| attaatgtta | acgctatgta | ccaacaacaa | ccacaattcg | tttctatcta | ccgtcaaggt | 35880 |
| aaagaaacag | gtatgtactt | cctaatcaaa | cgtgtaccag | ttaaagatgc | acaagaagac | 35940 |
| ggaacaatcg | tattcgtaga | taagaacgaa | acattgcctg | aaacagcaga | cgtatttgtt | 36000 |
| ggtgaaatgt | caccacaagt | agttcactta | ttcgaattac | ttccaatgat | gaaattacca | 36060 |
| ttagctcaaa | ttaatgcttc | tattacattt | gcagtattat | ggtatggtgc | attagcatta | 36120 |
| cgtgctccta | aaaatgggc | tcgtattaaa | aacgttcgtt | atatcgcagt | ttaatagaat | 36180 |
| aagaaaaact | gaatacaaga | gaatagggat | aaacttaggg | tttatccctt | ttttattaaa | 36240 |
| ataaacttga | agggatttaa | taaatatgtt | atactataag | aaactattag | ataaaaaaat | 36300 |
| ggctactgtt | tatggtacag | tggagattga | caaagatgga | gtagttaaag | gattaactaa | 36360 |
| agagcaagaa | aaagaatttg | caaatgttcc | aggttttgaa | tttgaagaag | aaaagaaaac | 36420 |
| tactagaaaa | caatcagctt | ctactagtaa | agaagaagag | cctaaggaag | aggaaaagaa | 36480 |
| agcctctact | agaaaaacta | caagtactac | tagaaaatct | acagcacgta | aaacaacagc | 36540 |
| caaaaagat | gaaaataagt | aaagggtgaa | ttaaatggtt | aactcaatgt | ttggagggga | 36600 |
| cttagaccct | tatgaaaaat | cattaaacta | tgaatatcct | tatcatccta | gtggtaatcc | 36660 |
| taaacatata | gacgtaagtg | agatagataa | tttaacatta | gctgattatg | gatggtcacc | 36720 |
| ggatgcagtt | aaagcatata | tgttcggtat | cgtagttcaa | aatcctgata | caggacagcc | 36780 |
| tatgggtgat | gagttttata | accatatatt | agaaagagcg | gtaggtaaag | ctgaaagagc | 36840 |
| attagatata | tctatactac | ctgacactca | acatgagatg | agagattatc | atgagacaga | 36900 |
| gtttaatagt | tatatgtttg | tacatgctta | cagaaaacct | atattacagg | tagagaactt | 36960 |
| acagctacag | tttaatggta | gaccaatata | taaatacct | gctaactggt | ggaaagtaga | 37020 |
| gcatctagca | ggacatgttc | aattatttcc | tacagcactt | atgcaaacag | gacaatcaat | 37080 |
| gtcatatgat | gctgtattca | atgggtatcc | tcaattagca | ggtgtatacc | cgccatcagg | 37140 |
| ggcaacattt | gcacctcaaa | tgatacgatt | agaatatgta | tcaggtatgc | ttccacgtaa | 37200 |
| aaaagcagga | agaaataaac | cttgggaaat | gcctcctgag | ttagaacagt | tagttataaa | 37260 |

FIG. 19U sequence.txt

| | | | | | | |
|---|---|---|---|---|---|---|
| atatgcattg | aaagaaatat | accaagtatg | gggtaactta | atcattggtg | ccggtattgc | 37320 |
| taataaaaca | ttagaagtag | acggtattac | agagacaata | ggtactactc | aatcagctat | 37380 |
| gtatggtgga | gctagtgcac | agatacttca | aataaatgaa | gatataaaag | aactattaga | 37440 |
| tggtttaaga | gcttactttg | gatataatat | gataggatta | taaggagggt | tagaaaatgg | 37500 |
| aaaaaccgta | tatgatagga | gccaactcta | accctaatgt | tattaataag | tcaacaacat | 37560 |
| atactactac | aacacaagca | gatgaacaag | ataaacctaa | gtatactact | agactagagt | 37620 |
| ttgatacgat | tgacatgatt | aggtttatta | atgaccgagg | tataaaagta | ttatgggaag | 37680 |
| aagcatattt | ctgtccttgt | cttaatcctg | atacaggaca | tcctagggta | gattgcccta | 37740 |
| gatgtcatgg | taaagggatt | gcatatctac | ctcctaaaga | gactataatg | gcaatacagt | 37800 |
| ctcaagagaa | aggaactaac | cagttagata | taggtatatt | agacacaggt | actgcaatag | 37860 |
| gtaccactca | attagaaaag | agaatttcct | atagagatag | gtttactgtt | cctgaggtat | 37920 |
| tgatgcctca | acaaatgatt | tattttgtga | ataaagatag | aattagaaaa | ggtatacctc | 37980 |
| tatactacga | tgtaaaagaa | gtaacttata | tagctactca | agatggtaca | gtctatgaag | 38040 |
| aagattatga | aattaagaat | aacagattgt | atttaaatga | aaaatatgag | aaccatacag | 38100 |
| taactttaaa | gatacttatg | actttaagat | atgtagtatc | agatatacta | aaagaaagtc | 38160 |
| gttatcaata | tactaagttt | aatcaaccta | aatcaaaatt | tgaaaactta | cctcaaaaat | 38220 |
| tacttcttaa | aagggaagat | gttattgtac | tacaagaccc | ttataaagtt | aatgatggca | 38280 |
| tagaagaaga | cctagaaatt | caagtagatg | accctaaggc | ttcagcatct | aatcctagta | 38340 |
| atttaggtgg | attcttcgga | ggtgcattta | ataatgcca | gttcacggaa | agagacctaa | 38400 |
| tttatttaaa | aataaaaact | ataagcaggt | aggtaagaga | acaattgatg | gtatgcgttc | 38460 |
| agaagttctt | gataaattac | aagcaacagc | acagcaagta | gagaatacta | gtattaaacg | 38520 |
| tatgcctact | tacctacaaa | taacagagaa | aaagcttgaa | aaagaaggag | tagtagacct | 38580 |
| taaaaaagct | tttgctcact | catctaaaaa | gaaaactagt | aaagatggcg | gatggtattt | 38640 |
| aactgtacca | atccgcatca | aaactagtag | aatgaataac | agtacttacc | aagatatgag | 38700 |
| aactttaaaa | gtagataaag | gtacaggttc | agtctctaag | ataactgatt | acctagaagg | 38760 |
| acgtagaaag | aatgtaagcc | atccttcaat | gaagcctgaa | cctatgactc | ataatatgac | 38820 |
| taaagttaaa | agaggaaagc | aatcttctta | ctttatattt | agaactgttt | ctagtaagtc | 38880 |
| acctgctagt | tcttggatac | ttaacagaga | taagttaat | gaagataact | tctctaaaac | 38940 |
| aactctaaaa | actgttaagc | aattaatgaa | ctggaagatg | aaaaatttaa | attaagagga | 39000 |
| gggttagtat | taaatggcaa | taacatcagt | tgattcatat | ttattatcag | aaataaagcc | 39060 |
| tagacttaac | actgtgctag | agaattgtta | tattatagat | gaagttttaa | aagactttga | 39120 |
| ttatcaaact | agagagagct | ttaaagaagc | tttctgtggt | aagaatgcac | aacatgaagt | 39180 |

FIG. 19V sequence.txt

```
aacggtagga tttaacttcc caaaatttaa aaataactat gaagctcatt acttgataca    39240
attaggtcaa ggacaagaga caaaaaactc tttagggagt attcagtcat cttactttga    39300
ggcaacagga gataccttag tcgaatcttc tacagcaata agagaagatg ataagttagt    39360
ttttactgtt tctaaaccaa taggagagtt aataaaggta aagatatag agtttgctaa     39420
atacgataat ctccaagttg aaggtaataa ggtatcattt aagtatcaaa caaatgaaga    39480
ttatgagaac tacaatgcta acattatatt taccgaaaag aaaaatgatt ctaaaggttt    39540
agtaaaagga ttcacagttg aagaacaagt aacagttgta ggtctttcat ttaatgtaga    39600
cgttgcaaga tgtttagatg ctgtactgaa aatgatttta atatctatga gagatagtat    39660
agaagagcaa caaacattcc aattacagaa tttgtctttt ggtgatattg caccaataat    39720
agaagatggt gactcaatga tttttggtag accaacaatt attaagtaca caagttctct    39780
agatttggat tatactatta cacaagatat taataaacta acttttaaag aaagaaagga    39840
ttggaagtag gatggctaga aaaagacac ctgaaaataa cactcctaaa tttaatggtt     39900
atgttcatat agatacattc cttgatactg caaaacccct ttttaatatg aaggattcac    39960
aagtagcagg atttaaagct tatatggaag gtagtcatta tttgtttagt gagcaagaat    40020
tcttaccatc attagagaag tatctaggta ggaaattaga tatataataa cattcagata    40080
aggagaatta aatatggcag tagaaccatt cccaagaaga cctattaccc gtcctcatgc    40140
atctattgaa gtagatactt caggtatcgg tggctcagca ggttcaagtg aaaaagtatt    40200
ttgcttaatc ggtcaggctg aaggcggaga accaaataca gtttatgaat tacgtaacta    40260
tgcacaagct aaacgtttat tccgttcagg agaattactt gatgcaatag aattagcatg    40320
gggttctaac cctaactata cagcaggtaa gattttagct atgcgtatag aagatgctaa    40380
acctgcttca gcggaaatcg gtggattaaa agtaacatct aaaatctatg gtaatgttgc    40440
taacaacatt caagtaggat tagaaaagaa tacattaagt gattcattac gtttaagagt    40500
aatcttccaa gatgaccgtt tcaatgaggt ttatgataat atcggtaata tcttcacaat    40560
caagtacaaa ggagaagaag ctaacgcaac tttctctgta gaacatgatg aagaaactca    40620
aaaagcaagt cgtttagtat taaaagttgg agaccaagaa gttaagtcat atgatttaac    40680
tggtggagct tatgactaca ctaatgctat tattacagac attaatcaat tacctgattt    40740
cgaagctaaa ttatcacctt tcggagataa gaacttagaa tctagtaaat tagataaaat    40800
tgaaaatgca aatatcaaag ataaagctgt atatgtaaaa gcagtttttg gtgacttaga    40860
aaaacaaaca gcttacaacg gtatcgtatc tttcgagcaa cttaatgcag aaggagaagt    40920
accaagtaat gtagaggttg aagcaggaga agaatcagct acagtaactg ctacttcacc    40980
tattaaaact attgagccgt ttgagttaac taagttaacg ggcggtacta atggagaacc    41040
```

FIG. 19W sequence.txt

```
acctgctaca tgggcagaca agttagataa atttgcacat gaaggcggat actacattgt    41100
cccattatca tctaaacaat cagttcatgc agaggtagct tcttttgtta aagaacgttc    41160
tgatgcaggg gaaccaatga gagctattgt tggtggagga ttcaatgaat ctaaagaaca    41220
attgttcggt agacaagcat cattatctaa tccacgagta tcattagtag ctaactcagg    41280
tacttttgtt atggatgatg gacgtaaaaa ccacgtacct gcttacatgg tagccgtagc    41340
tctaggtggt cttgcaagtg gtttagaaat tggtgaatca atcacattca aaccactacg    41400
tgtaagttca ttagaccaaa tctatgagtc aatagactta gatgaattaa atgaaaatgg    41460
tattattagt atagagtttg ttcgtaaccg tactaataca ttcttcagaa tcgttgatga    41520
cgtaactaca ttcaatgata aatcagaccc agttaaggct gaaatggctg ttggggaagc    41580
taatgacttc ttagtaagtg agcttaaagt tcaacttgaa gaccaattta ttggtactcg    41640
tactatcaat acaagtgctt caatcattaa agactttatc caatcttact gggtcgtaa    41700
gaaacgtgat aatgaaattc aagacttccc tgctgaagac gtacaagtta ttgttgaagg    41760
taacgaagca agaatttcaa tgacagttta cccaatcaga agcttcaaga aaatttctgt    41820
tagcttggtt tacaagcaac aaacattaga agcctagtct aggtgatgga gtacctggat    41880
taggtactcc tattaatata atttgaatac tttaggagag tgaatacaga tggcatcaga    41940
agctaaacaa accgtccata ctggtaatac cgtcctactt atgattaaag gtaaaccggt    42000
aggaagagca caatcagcat caggtcaacg tgaatacggt acaactggtg tatacgaaat    42060
cggttctatc atgcctcaag aacacgtata tttacgttat gaaggtacaa ttacagtaga    42120
acgtttacgt atgaaaaaag aaaactttgc agatttagga tatgcttcac ttggtgaaga    42180
aattcttaag aaagatatca ttgatatttt agtggtagat aacttaacga acaagttat     42240
tatctcatat catggttgct ctgcaaataa ctacaatgaa acttggcaga caaatgaaat    42300
tgtaacagaa gaaatcgagt tcagttacct ttaactaata gaggctatgt ttggtgacaa    42360
gcatagaaaa cactttaaat tgcgtgaaag tcttaaagac tagataacta caacgtaact    42420
cgaaagggta agcgtgaatg ttgagaaatc agaaaaaata tctagtatag tataaggtta    42480
aatcctaagt acagtaaaat agatgatacg caggcaagcc tacaaatgtg ggaagcttca    42540
acgactataa taggtgagtc ttagttacac attaagatta tggtatagtc tactcccttt    42600
aaaatatatc gaaagatagg gtacaaagga cagcatcaga taaagctaga acttaaattt    42660
cttattaaga ccaacaataa aagttggtct tatattttat acttgctttg tctgaggcag    42720
tgtgctataa ttaaaataca aggaggtaat aatatgggaa aaaatcaata tacatttaat    42780
attaaagaaa ataaaaataa atggtatgaa tggtgtaaac tacaaaacgt aaaacctta     42840
gtagaatatg aaaatgcaca acaaatattt tattttgaat ttcttgaagg taaatttaaa    42900
ggactaatag gaaaaacata ttgggctagt ataaatagag gttctaatat gcgtatgagt    42960
```

FIG. 19X sequence.txt

| | | | | | |
|---|---|---|---|---|---|
| tgtttaacat | cagaaagtaa | agataaatat | ttaaaaaatt | taggaaaaag | aaaaggtata | 43020
| gaggtagtag | aagactataa | gggtggcaga | aaattaaaac | ataaatttat | agttttagaa | 43080
| ggtaagtacc | aaggatgtga | agggtatata | actttaaatg | atttagagaa | tttaggtaga | 43140
| gtagataata | gaagtttatc | tgaaaaagga | aggaaacaat | actttgataa | acaggcaaga | 43200
| cttagagatt | gtattattct | agagtaccct | aaagactata | gaataaaaac | taaagataag | 43260
| atagtagtaa | aagataaaga | agggcatgtt | cataatatta | ttgttcagga | cttttttgag | 43320
| aaatcatctt | tattggagtt | atcttgtgct | agtgaaggag | agaaaatagt | taaagaaata | 43380
| cttactaaaa | attctataaa | atttgaaaaa | gaaaaatcat | ttagaaacaa | agaaggtaaa | 43440
| gtacaaagat | ttgatttta | tattaatgaa | aataataaag | aatatgcaat | agagtacaat | 43500
| ggtgcacagc | actacataga | ttctacagga | tatcttaaag | atactttgga | aacaacccag | 43560
| aaaagagata | aactaaaaaa | agaatacagt | aaagataaag | gtataaattt | attaattatt | 43620
| ccttacacaa | taacagataa | gaaagaaatg | gaaaaaatta | ttttaaattt | tttaaacaaa | 43680
| taacccttga | cactccctca | agggatatgt | tattataata | acaggttagg | agtaataagt | 43740
| atgaataata | ggcaagctaa | actaaaagga | tataaccaat | ttcattatta | tgattttcca | 43800
| acaactaaag | gtaagtttaa | agatataatg | aaaagaaaat | ctagaacaga | acttaaaaaa | 43860
| gatttacaaa | aagaaaggaa | gtattatctt | gacaaataag | agaaaaacga | taggtaagat | 43920
| gagtaacaca | agagcaacat | ggaatattaa | tccggtaact | aaagttaaaa | aagataaaac | 43980
| aaaatattct | agaaaaaata | aacataaagg | tcttgacaat | tataattaac | taaggtatat | 44040
| tattagtata | acaaaaaaag | gagatgttat | aatatgagaa | tttatataag | taatgactat | 44100
| aacaaagagc | tattagataa | atgtttatca | gatattaaca | aagataaagg | taatataaac | 44160
| tacagtatta | attatggtga | aggtaacatt | aaagaagcag | atgtagaaat | tattaaacta | 44220
| gataagaatc | tattagaaac | agaatcaaga | gcatttgctt | attcgaagtt | tgttgaagat | 44280
| tgtatatttt | tatttcctta | taagattgct | ttacttagag | ggggtaaaat | agagttaaga | 44340
| tttgattgga | atgaaatatt | ataacaaaaa | aaggagatgg | atatatgagt | acattttggt | 44400
| cagaaagaag | aacaactaat | aaagataggc | aagttaaaaa | acattatact | caaatgagta | 44460
| tgtatgaaag | aaagaaatgt | gtagagttat | tacaagagac | aattactgaa | aatagaatta | 44520
| ttaattttac | acgacatagt | gcaaaaaaag | ttaaaggtaa | accaacaaca | aatataccta | 44580
| aattaatagg | ttttattttt | aaaaataagt | ttgcctacga | aaatatcata | gagtacaata | 44640
| acacagatta | taatggtaat | attgagagga | gaattgttgt | taaacatccc | aaagttataa | 44700
| ctgtagaagg | aaaacttagc | tatcagtttt | tgacaattag | tcttgaagat | gctagagtta | 44760
| ttacggtgtg | gtataacagt | gtagatgata | cacatagaac | actagattta | aattattata | 44820

FIG. 19Y

```
                                    sequence.txt
gtaaagactt gacaattcaa taaggaggag ttataatggg attaacaata gtaaatggtt      44880
atttctttct atcaagtatt atatttattg tagtaagtat actaaatgga aaaggtacag      44940
ttacaaggga atcactagct atgagtcaag cattagtgat aataacatcc attcaatttt      45000
tagcattttt aattataaat ggcatttatt actcattaaa atatatgtaa taaaaggag       45060
tacaaatgga aatatacatt gtaatagact taagaggaag cacagaagaa gaaacaagta      45120
tggattttaa agcttttaga aaattacaag atgctataac atatgtagat ggtaatggta      45180
acagggattt acatataatt cctctagaat tagaataaaa gtattgacaa attaaaacta      45240
ataattata ataaggtat aacaaattaa aggagaagat ataaaatgtc acaagataaa        45300
ttaagagcaa tttacacaga aatgaaagta gaattacaca aatttcctaa agaggtagat      45360
gtaacaagta aatcaactgc aattgcaatc aatcagattt tagataaatt caaaacatta     45420
acagaacaag caggaaagat tactagaaaa tatttagaag gtcaagaaat attaactatt     45480
gattatgagt actatgattc attacaagaa tactatattt acctacttag aaatagtgaa     45540
aaaattgaac aaagtttaca agaaattact aagcgtacag gtgaatatgt aaagtaattt     45600
tgatttaaaa acaaaatatg atatactatg tttaaagtag taagcctaca ctagtccgtg     45660
ttatattaat attgaatcgg ataagcgtag gctttattaa tatttaaaaa aaggaaggta     45720
tatcatatta tggcagaaga aattaaaaag gaacaagatg tacaagaaac aactaaagaa     45780
gaaaaaaaag atgttagcaa aatgacaccg gaagaaatag ataaattaaa atatcaagac    45840
aagcaagaaa aagaacaagt tattaacaaa gttattaaag gtgttaatga tacttgggaa     45900
aaagaatata actttgaaga attagactta agatttaaag ttaaaattaa attacctaac     45960
gcacgagagc aaggtaatat atttgcgtta cgttctgctt acttaggtgg tatggatatg     46020
taccaaacag accaagtaat tagagcatat caaatgttag ctacattaca ggaagtaggt     46080
attgaagttc ctaaggaatt ccaagaccct gacgatattt ataacttata tcctttaact     46140
gttatgtatg aagattggtt aggattctta aactcctttc gttactaata gtatagaaac     46200
actagataaa gatatagaac gattgggcgg tatggaatca attgttaaac aacctttatc    46260
tagaaatcta tgggctatta tgaaagagtt taatgtttta cctactgagc aaagatttaa    46320
ggacttagat gattatcaga tagagtttat tattgggaat atgaacagag atgtttatga    46380
acataacaaa caacttaaac aagctcaaaa aggtggaaaa ttcgatagtc aatttgaaga    46440
tgatgatagt agttggtgga atgaatctca tgaagacttt gacccagtac ctgatttctt    46500
agatgctgat gatttagcac aacagatgga agctaaatta tccgatagag ataaggaaga    46560
aagagctaag agaaacgatg cagagttaaa tgatgaaaca gaaggactta ctacacaaca    46620
tctagctatg atggaataca tcagacagaa acaacaagaa ttagatgatg aagtaggaaa    46680
tggtaagact agtgaagatg acgctactat atcacaagat agcgttaata aagcactaga    46740
```

FIG. 19Z sequence.txt

| | | | | | |
|---|---|---|---|---|---|
| agacctagat | gatgactggt | atatgtaaag | ggtggtaggt | gatactacca | tccttatttt | 46800 |
| tttaaaatgg | atggtgaata | atgatggcaa | tgaatgacga | ttatagattg | gtcttgtccg | 46860 |
| gtgatagttc | ggatttagag | aatagtctaa | aggcaataga | actttatatg | gattctttag | 46920 |
| agtctaagaa | tattgatgct | cctttagata | atttcttaaa | aaaattaaaa | gtaattgcta | 46980 |
| aagaagttaa | aaatgtacag | aacgcaatgg | ataaacaaga | tggtaaatct | gttatatctt | 47040 |
| ctaaagacat | ggatgaatct | attaaatcca | ctcaatctgc | tacaaagaat | ataaatgaat | 47100 |
| taaagaaagc | tttagatgac | cttcaaaaag | agaatatatc | taaaggtatt | gcacctgacc | 47160 |
| ctgaagttga | aaaagcatat | gctaagatgg | gtaaagttgt | agatgaaact | caagaaaaac | 47220 |
| ttgagaaaat | gtcttcacaa | aaaataggtt | ctgatgctag | tattcaaaat | agaattaagg | 47280 |
| aaatgaaaac | cttaaatcaa | gtaactgaag | aatacaataa | aataagtaaa | gattctagcg | 47340 |
| caactaaaga | ttatacaaaa | cgattaagag | ctaatcgtaa | tatgactaga | ggttacatgg | 47400 |
| agcgttcaga | aggaacagga | cgtttgacat | atgaccaagg | tgcacgagtt | agaagtgaac | 47460 |
| taggtaaagt | aagttcttat | gagagccaaa | gaaaacaaaa | ccaacgtaat | ttgggacaag | 47520 |
| caagagaaca | atatagcaac | tatagaaacc | aacaacaaga | cttgactaaa | cgtagagcta | 47580 |
| gcggtcaaat | taataaggca | caatatgaac | aagagttagc | ttctattaaa | caggaaatga | 47640 |
| aagctagaga | agaacttata | tctaactatg | agaaattagg | agcagaactt | gataaaacag | 47700 |
| ttcagtatta | taagggttca | gttcaaaagg | atttccaatc | tagagacgta | gaccaacaaa | 47760 |
| gaggaacatt | tggtagaatg | gttcaagaac | gtttgccatc | tattggttct | catgctatga | 47820 |
| tgggtactac | agctatggct | acaggtttat | acatgaaggg | tgcctcacta | agtgaaacta | 47880 |
| atagacctat | ggttacatca | ttaggtcaaa | attccgataa | tatggatata | gattctgtaa | 47940 |
| gaaatgcata | tggagacttg | tcaattgata | acaaattagg | ttataatagt | actgacatgt | 48000 |
| tgaaaatggc | tacttcatat | gaagcatcag | taggacataa | aagtgatgag | gacacaatgg | 48060 |
| caggaactaa | acagcttgct | attggaggac | gttctttagg | cattaaagac | caagaagctt | 48120 |
| atcaagagtc | tatgggtcaa | atcatgcata | ccggcggagt | aaattctgat | aacatgaagg | 48180 |
| aaatgcaaga | tgcattctta | ggtggtatta | aacagtcagg | tatggttggt | cgtcaagatg | 48240 |
| aacaacttaa | agcactaggt | tctatagcgg | aacaatcagg | agaaggaaga | actctaacta | 48300 |
| aagaccaaat | gagtaatctt | actgccatgc | aatctacttt | tgcagagtca | ggaagtaaag | 48360 |
| gattacaagg | tgaacaaggt | gccaatgcta | ttaacagtat | agaccaagga | cttaaaaatg | 48420 |
| gtatgaatag | ttcttatgct | cgtatagcaa | tgggatgggg | aacgcaatac | caaggtcttg | 48480 |
| aaggtggata | tgatttacaa | aaacgtatgg | atgaaggtat | atctaatcct | gaaaacttga | 48540 |
| cagatatggc | tgatatggct | actcaaatgg | gtggcagtga | aaagaacaa | aaatacctat | 48600 |

FIG. 19AA

```
                                    sequence.txt
ttaatagaag tatgaaagaa ataggcgcta acctaactat ggagcaatct gatgaaatat    48660
ttaaggactc taaagaagga aaactgtcta aagaagagtt agctaagaaa gctaagaaaa    48720
tggaaaaaga aggtaaaaaa gaaggagaag ataacgccac tgattataaa gaatctaaat    48780
caggaaaaaa tgaccaaaat aaatctaaga ctgatgataa agcagaagat acttatgata    48840
tggctcaacc actaagagat gctcatagtg ctttagcagg tcttcctgcc cctatatatt    48900
tagctattgg tgctatagga gcatttacag cttcactaat tgcatctgca agtcaatttg    48960
gagcaggtca cttaattggt aaaggagcca aaggacttag aaataaattt ggtagaaata    49020
aaggtggtag ctccggtggt aaccctatgg caggtggaat gcctagtggt ggtggttcac    49080
ctaagggtgg aggctcacct aaaggtgggg gcactcgttc tactggagga aaaatacttg    49140
atagcgctaa aggtcttgga ggattcctag taggtggcgc aggatggaaa ggtatgtttg    49200
gcggggagtc taaaggtaaa ggatttaaac aaacatctaa agaagcctgg tcaggtacta    49260
gaaaagtatt taatagagat aatggtagaa aagccatgga taaatctaaa gatatagcta    49320
aaggtaccgg tagtggtctt aaagatatct ataatgatag tatatttggt aaagaaagaa    49380
gacaaaacct aggagaaaaa gctaaaggtt ttggtggcaa agctaagggt ctctatggta    49440
agtttgctga taagtttggt gacggaggta aaaatggtat cctttcacaa tcaccaaaag    49500
caggtggaag tggcataggg aaacttggaa aacttgcagg tggacttgga aaaggagccg    49560
gagttttagg tgttgctacg tctgccttat cattaatacc tgctttagct tccggagata    49620
gtaaagctat cggcggagga ataggctcta tgggtggagg aatggcaggt gcatcagcag    49680
gagcttctat aggagcttta tttggtggtg taggtgcaat ccctggagct ttaataggtg    49740
gagctatagg ttctttcggt ggaggagctg ttggtgaaaa agtaggagac atggctaaga    49800
aggctaacac taaagaagga tggaacctag gatggactaa tggagataaa gacggtaaga    49860
ataaattcca agattcttta ttaggaaaac ctatatctaa agcatggagt ggtataacag    49920
gtctctttga taatgacgct gaagcatctg aagaaaatag caaagataag aaaaaaggcg    49980
ttaaaggtgt taaaggggat actaagaaga aagaaaaaat gacagcagaa caacttagag    50040
aaaaaaataa ccaatctgaa actaagaacc ttaaaatcta tagtgattta cttgatagag    50100
ctcagaaaat tattgagagt gctaaaggta ttaatataga tggaggaact tctgatagtg    50160
gttctgatag tggaggctct gcatctgatg taggaggaga aggtgcagag aaaatgtata    50220
agttccttaa aggaaaagga ctatctgata accaggtagg agctgttatg gggaacttac    50280
aacaagaatc taaccttgac cctaatgcta agaacccttc aagtggagca tttggtattg    50340
ctcaatggtt aggtgctaga aaaacaggat tagataactt tgctaagtct aaaggtaaaa    50400
aatccagtga tttagatgtt caattagact acctatggaa agaaatgcaa tctgattatg    50460
aaagtaaaaa cctcaagaat gcaggttgga gtaaaggtgg aagtctagaa cagaatacaa    50520
```

FIG. 19BB sequence.txt

| | | | | | | |
|---|---|---|---|---|---|---|
| aagcatttgc | taccgggttt | gaacgtatgg | gagcaaatga | ggctatgatg | ggtactcgtg | 50580 |
| ttaacaatgc | caaggaattc | aagaagaaat | atggaggttc | cggcggagga | ggcggagggg | 50640 |
| gcgctatgtc | ctctacttac | caagaagcta | tgagtaaccc | tgtattaacc | actggttcca | 50700 |
| actacagagg | ctctaacgat | gcttctaatg | cttctacaac | taacagaata | acagttaatg | 50760 |
| ttaacgttca | aggcggaaat | aatcctgaag | aaactggaga | cattatcgga | ggaagaatta | 50820 |
| gagaagtttt | agacagcaac | atggatattt | ttgcaaatga | acataagaga | agttattagt | 50880 |
| gattttgtat | tgacacaaga | gtagtatagt | agtatactac | tcttatacat | ataaaaataa | 50940 |
| aaggaagtat | gtgtatatga | aaagattaag | aagacctaag | gtaagaatag | agatagttac | 51000 |
| agatgataat | acatttacat | taagatttga | agatacacgt | gactacaatg | gtgatgagtt | 51060 |
| tggagctaaa | cttttaggct | ttcaaactaa | aaactctatg | gaagatgata | gttctgtatt | 51120 |
| ccaaatcaat | atggcaggag | atacttactg | ggataagtta | gttatggcta | atgatataat | 51180 |
| cagaatattt | attacaccta | atgatgaccc | taatgataaa | gaaggtcgtc | aagaacgttt | 51240 |
| aatacaagta | ggtatggtat | cacaagtatc | aaaagtaggt | agctatggta | atgaccaaac | 51300 |
| tcaatttaga | ataacaggtc | aatcttttgt | aaaaccettt | atgaaatttg | gattaggtgt | 51360 |
| tattcaagag | gttcaagctg | tattacctga | agtaggttgg | cttattgatg | gtgatgggga | 51420 |
| taatgaagta | aaatttactg | gtagttcggc | acatgaagtt | atgacaggta | ttatccgaag | 51480 |
| atttgttcct | tatatgaaat | ataactatac | agaaaaaaca | tataatacaa | tagatagtta | 51540 |
| ccttgattat | gatgatttaa | gtagttggga | tgaatttgaa | aatctgacag | aagtatctgc | 51600 |
| ttttactaat | tttgatggct | cattaaaaca | gttgatggat | atggtaacag | ctagaccttt | 51660 |
| caatgagtta | ttcctttaaaa | actccgaaaa | aacaccaggt | aaagcacagc | ttgttttaag | 51720 |
| aaaaactcct | tttaatccta | ctgagtggag | agctttggat | atgattaaag | tacctactga | 51780 |
| agactttatt | gaagaggatg | tgggtaaaag | tgacgtagaa | acatactcta | tatttacagc | 51840 |
| tacacctgca | ggtatgttaa | aagaacttaa | tggtgatgta | ttttctaaac | cacaatttca | 51900 |
| ccctgaattg | actgatagat | atgggtatac | taaatttgaa | gtagagaata | tctatcttag | 51960 |
| tactaaatca | ggttcagcta | ctgaagactc | agattcttcg | ggtgatgata | atggtactga | 52020 |
| aagaggaact | tattctaaaa | ttatgaaaga | tttaagtaac | tatggaagag | ataatatatc | 52080 |
| taaggtata | gataagtata | caagtaaatt | atcctcaaaa | tataaaaact | taaaaaagcc | 52140 |
| caagctaaaa | aaattataga | gaagtttgtc | aaagaaggaa | aagtaacaga | aaaagaatat | 52200 |
| gaaaagataa | caggtaataa | ggtagatgat | gaattaacat | cagataacag | accgaagttg | 52260 |
| acaaaagata | aattaaagag | tatactaaaa | gagaagttta | aaacacaaga | tgattttaat | 52320 |
| aattctaaaa | aagaaaaaa | gctaaaacag | atgcacttaa | agaattgaca | actaaatatc | 52380 |

FIG. 19CC sequence.txt

```
gttttggtaa taaaacacat gctacaactt tgttagatga atatattaaa tacaaaggag    52440
aaccacctaa tgatgaggct tttgataaat atcttaaagc tattgaaggt gttagtaata    52500
tagctacaga tacaggttca gatgcaagtg atagtccttt agttatgttc tctagaatgc    52560
tatttaactg gtatcatggc aaccctaact tctatgcagg agatattatt gttttaggag    52620
accctaagta tgacctaggt aaaagattat ttattgaaga taagcaacga ggagacactt    52680
gggagttcta tattgaatct gtagaacata aattcgatta taaacaaggg tattatacaa    52740
ctgtaggagt aactagaggt ttaaaagatg ctattctaga agacggtaaa ggtagtcctc    52800
atagatttgc aggactatgg aaccaatcat cagacttcat gggaggtctt atgggtgaag    52860
atacttctaa agaacttaaa gaaaaaggtg tatcagagaa acaaagcagt ggagataaag    52920
acggtggctc tgatagtggt ggcgctcaag atggtggctc tttagattca cttaaaaaat    52980
ataatggcaa acttcctaag catgacccaa gttttgttca acctggtaac cgacattata    53040
agtatcagtg tacatggtat gcttataata gaagaggtca attaggcatt cctgtgcctt    53100
tatggggggga tgccgccgac tggataggcg gtgctaaagg agcaggttat ggagtaggta    53160
gaacacctaa acaaggtgct tgtgttatat ggcaaagagg agtacaagga ggtagtgctc    53220
aatatgggca tgttgctttt gttgagaaag ttttagacgg aggtaaaaaa atatttatct    53280
ccgaacataa ctgggctact cctaatggat atggtactag aacaatagat atgagctcag    53340
ctataggtaa gaatgctcaa ttcatttacg ataagaaata aaggaggata gtctatggca    53400
acagataaag aagctaaaga tgttattgac aagtttatag ataatgtatt taatttgat    53460
gtattaacta tggaaagagt taaagaaaaa gatgaagaaa ttaaaaaaat aactacagat    53520
gatatgtatg aaaaggttgt gtatatacga ccttatgttg gagtaataca aagccttaac    53580
cctcaacatg tacagtatga atcattttct aataatggtt atgatataga ggcagaatta    53640
agtttcagga aagtaagtta tttagttgat aaagggtcta tacctacaga ttcttttatct    53700
actttaacag ttcatttagt agaaagaaat caagagctat taatagatta ctttgatgag    53760
atacaagatg tgttgtacgg agaatatgtg gaagaagaat atgtattcga tgaagatgta    53820
cccttaagta cgatactagc attagactta aatgataatc ttaaatcctt atcaaatata    53880
aagtatatgt tcaaggtgc tcctaaagag aatccatttg gaacagataa agatgtttat    53940
atagatactt ataacttatt atactggtta tatttaggtg aagatgaaga gttagcatac    54000
cctatgaata ttaattattt ctttacagag ggtagattct ttactatatt tggtaaaggg    54060
cataagtaca aggtagatgt tagtaaattt atagttggag atatattatt ctttggtaga    54120
agtgatacta atataggtat ttatgtaggt gatggagagt ttatatctat gataggtaaa    54180
tttcctaaag atgaaacacc tataggaaaa tataaacttg atgattactg gaatgaattt    54240
aacggaagag ttatgagatt cgatgaagag gtgtatattt aatggtagta agattccaat    54300
```

FIG. 19DD sequence.txt

| | | | | | | |
|---|---|---|---|---|---|---|
| cttccatggg | aagaagttta | aaaagagtag | attcagatga | tttaaatgta | aaaggattag | 54360 |
| ttttagctac | agttagtaaa | attaattata | aatatcaatc | agtagaagtt | aaagttaaca | 54420 |
| acctaacttt | gggaagtcgt | ataggtgacg | atggtagctt | agctgtacct | tatcctaaat | 54480 |
| ctttcatagg | aagaacaccg | gaaggaagcg | tattcggtac | aaaacctctt | attactgaag | 54540 |
| gttctgtagt | attaataggg | ttcctaaatg | atgatataaa | tagccctata | atcttaagtg | 54600 |
| tttacggtga | taatgaacaa | aataaaatga | ttaatacgaa | tcctttagat | ggaggtaaat | 54660 |
| ttgatacaga | cagtgtttat | aaatatagta | gtgcactata | tgaaatttta | ccatctttaa | 54720 |
| attataagta | tgatgatgga | gaaggtacaa | gtattaagac | ctataatggt | aagtcattct | 54780 |
| tctccatgac | atcaggtgaa | gaagaaaaac | ctcaggcaac | agatttttac | actggaactg | 54840 |
| agtatcaaga | tttatttact | tcttattatg | gtaataagac | attaattgag | cctagaatac | 54900 |
| aaaaggctcc | taatatgtta | tttaaacatc | aaggagtttt | ttatgatgat | ggtacaccgg | 54960 |
| ataatcatat | aactacttta | tttatatctg | aaagaggaga | tataagagct | tcagttttaa | 55020 |
| atacagaaac | acagaaaaga | accacacagg | aaatgtcaag | tgatgggtct | tatagggtta | 55080 |
| tcaaacaaga | tgacgattta | atgttggatg | aagctcaagt | ttggattgag | tatggtatta | 55140 |
| gtgaagataa | taaattttat | attaaaaatg | acaagcataa | atttgaattt | actgatgagg | 55200 |
| gaatctatat | agatgataag | cctatgttag | aaaacttaga | tgagagtata | gcagaggcta | 55260 |
| tgaagaattt | gaatgaaata | caaaaagaac | tcgatgatat | aaactacctt | ctcgagggtg | 55320 |
| tgggtaaaga | caatttagaa | gaattaatag | agtctacaaa | agagtctata | gaagcttcta | 55380 |
| aaaaagcaac | ttcagatgtc | aatagactta | caactcagat | agcagaagtt | agtggtagaa | 55440 |
| ctgaaggtat | tataacacag | ttccaaaaat | ttagagatga | gacttttaaa | gatttttatg | 55500 |
| aagatgcttc | tactgttatt | aatgaagtaa | atcagaattt | ccctactatg | aaaacagatg | 55560 |
| ttaatacctt | aaagactaaa | gttgataacc | tagagaaaac | tgaaatacca | aacattaaaa | 55620 |
| ctagattaac | agaactagag | aacaataata | acaatgccga | taaaataatc | tcagatagag | 55680 |
| gagagcatat | aggtgctatg | atacagttag | aagaaaatgt | tactgtaccg | acaagaaact | 55740 |
| atatgccaat | accttggagt | aaagttactt | ataataatgc | agagttttgg | gattctaata | 55800 |
| atcctactcg | attagtagta | cctaaaggaa | taacaaaagt | aagagttgca | ggtaatgttt | 55860 |
| tgtgggactc | taacgccaca | ggacaacgta | tgttgagaat | attgaaaaat | ggtacttata | 55920 |
| gtctagggtt | accttataca | agagatgtag | ctatatctac | agcccctcag | aacggtacta | 55980 |
| gtggagttat | tcctgttaaa | gaaggagatt | actttgagtt | tgaagctttc | caagactcag | 56040 |
| aaggtgacag | acaattcaga | gcagaccctt | atacatggtt | tagtattgaa | gctatagaat | 56100 |
| tagaaactga | aactatggag | aaagacttta | tgcttatagg | acatagagga | gcaaccggat | 56160 |

FIG. 19EE sequence.txt

| | | | | | | |
|---|---|---|---|---|---|---|
| acacagatga | gcacacgata | aaaggatatc | aaatggcttt | agataaaggt | gcagattata | 56220 |
| tagaattgga | tttacaatta | acaaaagata | ataagttatt | gtgtatgcat | gattctacta | 56280 |
| tagacagaac | aacaacagga | acaggtaagg | taggagatat | gactttatct | tatatacaaa | 56340 |
| ctaactttac | atctcttaat | ggtgagccga | taccatctct | tgatgatgta | ttaaatcatt | 56400 |
| ttggaacaaa | agttaaatat | tatatagaaa | ctaaacgtcc | gtttgatgct | aatatggata | 56460 |
| aagaattatt | aactcaatta | aaagcaaaag | gattaatagg | aatagggtca | gagagattcc | 56520 |
| aagtaattat | tcaatcattt | gctagagaat | cattaattaa | tattcataat | caattctcta | 56580 |
| atataccttt | agcttattta | acaagtacat | tctctgaaag | tgaaatggat | gattgtttaa | 56640 |
| gttatggttc | ttatgctatt | gctcctaagt | atacaactat | aactaaagaa | ttagtagatt | 56700 |
| tagctcatag | taaaggtctt | aaagtacacg | catggacggt | aaacacaaaa | gaagaaatgc | 56760 |
| aaagcttaat | acaaatgggt | gtagatggat | tctttacaaa | ctacttagat | gaatataaaa | 56820 |
| agatttaata | ttaaagacct | attaatttag | gtctttttt | agttgtaatt | taaactagtt | 56880 |
| cgtgatatat | tagtagtatg | agatttatat | acatactgaa | aaggagagga | taaaatgcca | 56940 |
| caatcagatg | gaataagtaa | tcttcataga | atagctttac | gcttccctaa | agaaggcggt | 57000 |
| ggttatgata | tgtatagatt | taaagttaac | cccgagaact | acacaataga | ttcaccacaa | 57060 |
| cgtacgacag | caattaaaac | aaaatcagat | attgtaatag | aagattatgg | taaagacata | 57120 |
| gaagttatta | acttcacagg | tacaactggt | tttagacctg | ttagagaagc | agacggatta | 57180 |
| aaaacaggta | agcagaaaat | ggaagagtta | caaagtagag | ttagtgaata | tgctatgcaa | 57240 |
| ggtggtagtg | gtaatgtaag | tggttcttac | ttacaatttt | ttaactttac | agatgatagc | 57300 |
| tactataaag | ttcatttagc | tcctcaaggg | ttaaagataa | ctaggtctaa | agatgaacca | 57360 |
| ttactttta | gatatgaaat | aacattagta | gttattggtt | cgttaacaga | agcagataga | 57420 |
| agtgctgtaa | caacagaaga | gtttggtaat | gttaaaccta | atgcttctca | aagagtagat | 57480 |
| gagggtataa | aagaattaga | taaaaatgct | cgtaaaacga | gagatagaaa | taatcaagaa | 57540 |
| atatctaaaa | gagaaaatac | aatacctaaa | tctacaggag | ataatacgaa | tgagggtaat | 57600 |
| agacttaagc | aaagcttccc | tagtagttct | atatataatc | ctagacaatc | tactaacgga | 57660 |
| ttaaagggga | atattgacaa | tatggctctg | ataataggtt | acggtgatgg | aggtgtatct | 57720 |
| agctaatgaa | taatttttata | ccacaacctc | aaggtctact | cagattttta | aatgccctag | 57780 |
| atgcagattt | aacttcttct | cacatgaatt | tactggatga | agaggtatca | tttgtatcta | 57840 |
| aattttacac | accacagcta | caattaagtg | aattagcaaa | aaaagtattg | acaaatataa | 57900 |
| agacagatga | tatacctgta | ttagaaagag | aatttaatga | taatacaatt | atccataaag | 57960 |
| ctaatgatac | attactaaaa | gtacaggctc | caagaatgta | tatgattcta | cagtctattg | 58020 |
| tgcttgaagc | atatgctatt | gttaattgct | ttgtagaaaa | tccaagctct | ttaaaatact | 58080 |

FIG. 19FF sequence.txt

```
taactgaaga agatgttagt ataacacgag aaaatttaaa ttatgtagct gactacttag    58140
gtaactatga tgactacaat agtgttgtct tagacttaag agatttagac ttatgtttta    58200
gtgctataga attacaatta cctctaatta aaaaggaggc taatgtataa tgagatttaa    58260
gaaacacgta gttcaacatg aagaaacgat gcaagcaata gcacagagat actatggtga    58320
tgttagttat tggatagacc tagtagagca taataatcta aagtatccct atttagtaga    58380
aactgatgaa gaaaaaatga aagaccctga acgattggct tctacaggtg atacactgat    58440
tatacctata gaatctgatt taacagatgt atcagcaaaa gaaattaatt ctagagataa    58500
agatgtacta gttgaattag ctttaggaag agatttaaat attactgcag atgaaaagta    58560
tttaatgaa catggtacta gtgataatat actagcattc agcacaaacg gtaatggaga    58620
tttagatact gtaaaaggca tagataatat gaaacagcaa ttacaggcac gtttattaac    58680
tcctagaggt tctttaatgc tacatcctaa ttatggttca gatttgcata atttatttgg    58740
tcttaatata cctgaacaag ctacattaat agaaatggaa gtattgagaa cattaacatc    58800
agataataga gtaaaatctg ctaatctaat tgattggaaa atacaaggta atgtttattc    58860
aggtcaattt tcagtggaaa taaaatctgt tgaagaatca ataaattttg tcttaggaca    58920
agatgaggaa ggaattttg ctttatttga ataggaaagg attaaattat gaaaactaga    58980
aaattaacta acatactatc aaaattaata gataagacaa tggcaggtac aagcaagata    59040
acagacttta ctcctggttc agcttcccgt tcattattag aagctgtatc attagagata    59100
gagcaattct atatcctaac aaaagaaaat attgattggg gtatacaaga aggtatcatt    59160
gaagctttg attttcaaaa aagacaatct aaaagagctt atggtgatgt tactattcaa    59220
ttctaccaac ccttagatat gagaatgtat atacctgcag gaacaacttt tacttcaaca    59280
cgacaagaat atcctcagca atttgaaaca ttagttgatt attatgcaga gcctgattct    59340
actgagattg ttgttgaagt ttattgtaaa gaaacagggg ttgcaggtaa tgttcctgaa    59400
ggaacaatta atactatagc atcaggttct agtttgatta gaagtgttaa taacgagtat    59460
tcttttaata caggaactaa agaagagagc caagaagact ttaagcgcag attccactct    59520
tttgtagaat ctagaggtag agcaactaat aaatcagtaa gatatggtgc attgcagata    59580
cctgatgtag aaggtgttta tgtttatgaa gaaacaggac atattacagt atttgctcat    59640
gatagaaatg gtaatttatc agataccta aagaagata taatcgatgc tttacaagac    59700
tatagaccaa gtggtataat gttagatgtt acaggtgtag aaaaagaaga agttaatgtt    59760
tctgctacag taactatatc taataaatct agaattggtg atacattaca aaaacatatc    59820
gaaggtgtta ttagaagcta tttaaataat ctaaaaactt ctgatgactt aataattaca    59880
gaccttattc aagctataat gaatattgat gatgtactaa tatatgatgt gtcatttgat    59940
```

FIG. 19GG sequence.txt

```
aacctagatg agaacattat agtaccacca caaggaatta ttagagcagg agaaataaaa   60000
gtagaactaa agtaaagaga ggtgaaactt aagtcgtggc taattttta aagaatcttc    60060
atccattatt aagaagagat agaaacaaaa aagataatca agaccctaac tttgctctca   60120
tagatgcact caatgaagag atgaatcaag tagagaaaga tgctatagaa agtaaattac   60180
aatcctctct aaagacatct acaagtgaat atttagataa gtttggggat tggtttggag   60240
tttatcgtaa gactgatgag aacgatgatg tttatagagc aagaattata aaatatttac   60300
tcttgaaaag aggaactaat aatgctataa tagatgctat aaaagattat ttaggtagag   60360
atgatattga tgtaagtgta tatgaacctt ttacaaatat tttctatacg aacaaatcac   60420
atttaaatgg tgaagaccac ttaatgggat actattatag atttgctgtt attaatgtct   60480
ctataggtga ttatttccct gtagagatta tagatgtaat taatgaattc aaacctgcag   60540
gtgtaactct gtatgtcact tatgatggag cttctactat tagaggtgga gcaattatta   60600
agtggttaga tgggttacct aaaatagaaa cataccaaga gtttgatagg tttacaggat   60660
acgatgatac attctatggt catattaaca tgaatcaaag taaagatact gataatagta   60720
catcagatat ttttaaaaca aaccatagct taattaatag tttagatgtt ttaacaggtt   60780
cctctagcgt aggtagacag tatgttaact atggatatat aacatcatat gtttataatc   60840
caggtatgac atcttctgta aatcaaataa gcgctagtac agaaggtaga gggcaagaag   60900
tacctactga ctattatatg tatactagta ctaagaataa caatacagta gaacttagta   60960
tgcaaactac ttccggtgtg tcttatttat ataataactt taattttagg gattatatga   61020
gtaaatatag acctcaagta aatttacaat ctgatgaggc tagaagaatt gtatctgatt   61080
atataaaaga attaagtatt gattattatc tcagtgctgt aatacctcct gatgaaagta   61140
tagaaattaa attacaagtt tatgattttt ctattaatag atggcttaca gtatcaatta   61200
ataatttatc tttctatgaa aaaaatatcg gtagcaatat aggatatata aaagattatt   61260
taaacagtga attaaatatg tttactagat tagagataaa cgcaggtaaa agagattcag   61320
tagatattaa agttaattac ttagatttaa tgttttatta ctatgaacga ggtatttata   61380
caataaaacc ttataaagcc ttagtagaaa attatttaga tatatctaga gagacttacg   61440
tagaggcatt taaaatatca tcgttatcta atggagatat tataactaaa acaggttatt   61500
tacctatagg ttatctaaga gtatcaggag acattgataa cttaagtaac catatagaaa   61560
ttattaccat agataataat actaatagta ttacaagtac tcttttagaa gatgactcta   61620
atagtttgat attatcatat ggtaacgtca aaaccaatat acacagtttt gaattaaata   61680
gtgatgcttc aatttcaaat attaaatttg aatactctta ttatggtgat gcttgggaag   61740
aactgacagt attaactgaa atatctgagg gtgaaactat agtacctaat atactaatag   61800
atttatatgg attacagaca gtagattatt ctaatataaa tccaatgtca aaagtatcat   61860
```

FIG. 19HH sequence.txt

| | | | | | |
|---|---|---|---|---|---|
| tacgttctat | ttggaatgtt | aaattaggtg | aacttaataa | taaagaaggt | tctttatcaa | 61920 |
| atatgcctaa | cgattatttt | aatgctgtat | ggcaagatat | agataaacta | tcagatattg | 61980 |
| atttaggctc | tatgagaatg | attaaagaca | ctgagggtgg | agtatttgat | ggagctacag | 62040 |
| gtgaaattat | taaagctact | ttatttaatg | ttggtgtata | tactgattta | gatatgttag | 62100 |
| cctacacttt | aactaactat | actgaaccaa | taactttagg | ttctagtcga | ttaataagtg | 62160 |
| aacttaaaga | agaactatta | acatcagaat | catttaatgt | cgataataga | attaaagtaa | 62220 |
| ttgactcaat | atctgagcag | ttacctaata | acaatatatt | aagtaactct | taccaaacac | 62280 |
| aaactattac | acagaatgga | tttgctaagt | ataatttgaa | agaacctata | gagcagagaa | 62340 |
| aacaatacaa | tctaagaata | catggagatt | ttaaagaagg | attagaaaga | ttagctatag | 62400 |
| gtaattctaa | tggttcattt | aatgaagtat | ttgtttaccc | tgaaaatatt | aagatggta | 62460 |
| tagtagatat | tacttacact | tctagagatg | ataattacgc | agaagggaaa | caaagactta | 62520 |
| ataatgatta | tagagtttac | gctcaaccat | acgatagtga | agtagtaaca | atttacagtt | 62580 |
| tagagttaat | aaaagtttaa | taaataagtt | gacagaaagt | taataatatg | gtatacttat | 62640 |
| aaagtaatat | ttagtgggta | taccatgtta | tattaataaa | gaaaacaaca | gatgaaagga | 62700 |
| attaaaaaat | atggcaattg | caacgtataa | ttctcatgtt | gagttagcaa | aatatctagt | 62760 |
| tagtaaagct | gattcagttt | acttaacaat | tggaagagc | acaccgtggt | ctaatgaaac | 62820 |
| aaacccaccg | caacctgatg | aaaatgcaac | agtattacag | gaggttatag | gatacaaaaa | 62880 |
| agctactaaa | gtaactttag | ttagaccttc | taaatcacct | gaagatgata | ataagaattt | 62940 |
| aatttcttat | ggtaataaat | catgggtaga | agtaacacct | gaaaatgcta | aagatgaagg | 63000 |
| agctaaatgg | gtttacttag | aaagcagtat | tgttggtgac | gaactacctc | ttggaacata | 63060 |
| tagacaagta | ggatttgtta | tggacttagt | agcaaaaagt | ggtattagta | aatttaactt | 63120 |
| agtacctagt | gaagtagaat | caactggaac | attattattc | tttgataata | aacaattcca | 63180 |
| aaatagaagt | gagcaaacaa | ctgctaaaga | aagattatt | gtagaagttt | aaagaaaggg | 63240 |
| agataattct | aaatggcaat | taattttaaa | ggttcacctt | atttagatag | atttgacccg | 63300 |
| tctaaagata | gaacaaaagt | attatttaat | cctgatagac | tctacaaca | ggcagaatta | 63360 |
| aatgaaatgc | agtctataga | ccaatattat | ttaaaaaatc | taggagacgc | tattttaaa | 63420 |
| gacggagata | aacaatcagg | tcttggattc | acattatctg | aagataatgt | attgacagta | 63480 |
| aatcctggtt | atgtatatat | caacggtaaa | ataagatatt | acgataatga | cgattcagtt | 63540 |
| aaaataactg | gcgtaggtaa | agaaactatc | ggtattaagt | taacagaacg | tattgttaca | 63600 |
| cctgatgaag | atgctagcct | actagaccaa | actagtggag | taccaagtta | cttctctaaa | 63660 |
| ggtgcagata | gattagaaga | aaagatgtca | ttaactgtta | atgaccctac | atcagcaact | 63720 |

FIG. 19II sequence.txt

| | | | | | | |
|---|---|---|---|---|---|---|
| atttatactt | tcatggacgg | agatttatat | atccaatcaa | ctaatgctga | gatggataaa | 63780 |
| atcaataaag | tattagctga | acgtacttat | gatgagtcag | gttcatataa | agtaaatggt | 63840 |
| tttgagttat | tctcagaagg | taatgctgaa | gatgatgacc | acgtttctgt | agttgtagat | 63900 |
| gcaggtaaag | cctatgtaaa | aggttttaaa | gtagataaac | ccgtatcaac | aagaattagt | 63960 |
| gtacctaaat | cttatgactt | aggaacagca | gaaaatgaaa | gtactatctt | taataagtct | 64020 |
| aataattcta | ttagtttagc | taatagccct | gtaaaagaaa | ttagacgtgt | tacaggtcaa | 64080 |
| gtacttattg | aaaaagaacg | agttacaaga | ggagcccaag | gtgatggtca | agattttctt | 64140 |
| tcaaataata | cagcatttga | aattgtaaaa | gtttggactg | aaacaagccc | tggagttact | 64200 |
| acaaaagagt | ataaacaagg | agaagacttc | agattaacag | atggtcaaac | gattgactgg | 64260 |
| tcacctcaag | gtcaagaacc | ttcaggaggt | acttcatact | atgtttctta | taaatataat | 64320 |
| aaacgtatgg | aagtcggtaa | agattatgaa | gtaacaactc | aaggagaagg | gttaagtaag | 64380 |
| aaatggtata | ttaattttac | acctgaaaat | ggtgctaaac | ctattgacca | aacagtagta | 64440 |
| ttagtagatt | atacttatta | cttggctcgt | aaagattcag | tgtttattaa | taagtatggt | 64500 |
| gatattgcaa | tattacctgg | tgaacctaat | attatgagat | tagttacacc | accattaaac | 64560 |
| acagaccctg | agaatttaca | attaggtaca | gttacagtat | tacctgattc | agatgaagcc | 64620 |
| gtatgtattt | catttgcaat | cactagattg | tctatggaag | acttacagaa | agttaaaaca | 64680 |
| agagtagata | acttagagta | taaccaagca | gtaaatgcct | tagatgatgg | tgctatggaa | 64740 |
| ggacagaacc | ctctaacatt | acgttcagta | tttagtgaag | gtttcattag | tcttgataaa | 64800 |
| gcagatatta | cccatcctga | cttcggaata | gtatttagtt | ttgaagacgc | agaagctact | 64860 |
| ctagcttata | cagaagccgt | taaccaacct | aaaattattc | ctggagatac | aacagctcat | 64920 |
| atttggggta | gattaatttc | agcaccattt | actgaggaac | gtacaatcta | tcaaggtcaa | 64980 |
| gcatcagaaa | cattaaatgt | taacccttat | aatatcccta | ataagcaagg | tgtacttaag | 65040 |
| ttaacaccta | gtgaggataa | ttggattgat | actgaaaatg | ttacaattac | tgagcaaaaa | 65100 |
| actaagaaag | taactatgaa | acgattttgg | agacacaatg | aaagttacta | cggtgagact | 65160 |
| gaacactact | tgtactctaa | tttacaatta | gacgcaggtc | aaaagtggaa | aggtgaaact | 65220 |
| tacgcttatg | acagagagca | tggtcgtaca | ggtacattac | tagaatcagg | cggtcaacgt | 65280 |
| actttagaag | agatgattga | attcattaga | attagagatg | tatccttcga | ggttaaaggt | 65340 |
| ctaaacccta | atgataataa | cttatattta | ttatttgatg | gtgtaagatg | tcctattact | 65400 |
| cctgcaactg | gttacagaaa | aggttctgaa | gatgggacta | ttatgacaga | tgcaaaagga | 65460 |
| acagctaaag | gtaaatttac | tattcctgca | ggtattcgtt | gtggtaaccg | agaagttaca | 65520 |
| ctcaagaatg | ctaactctac | aagtgctaca | acttacacag | ctcaaggacg | taaaaaaatc | 65580 |
| gttcaagata | ttattattag | aactcgtgta | acagtaaact | tagtagaccc | gttagcacaa | 65640 |

FIG. 19JJ sequence.txt

```
tcattccagt atgatgagaa cagaactata tcatcattag gtttatactt tgcttctaaa    65700
ggagataagc aatctaacgt tgttatccaa attagaggta tgggtgacca aggttatcct    65760
aataaaacaa tctatgcaga gacagttatg aatgcagatg atattaaagt atctaataat    65820
gctagtgctg aaactagagt atactttgat gaccctatga tggcagaagg cggtaaagaa    65880
tacgctattg ttattattac tgagaacagt gattatacaa tgtgggtagg tactagaact    65940
aagcctaaga ttgataaacc taatgaggtt atctcaggta atccatatct tcaaggtgtg    66000
ttattcagtt catcaaacgc atcaacatgg actcctcatc aaaactctga ccttaaattt    66060
ggtatctata cttctaaatt taatgaaaca gcaacaattg aattcgaacc aattaaagat    66120
gtatctgcag atagaatagt tcttatgtct acgtacttaa ctcctgagag aacaggatgt    66180
acatgggaaa tgaaattaat tctagatgac atggcatctt ctacaacatt cgaccagttg    66240
aaatgggaac ctattggtaa ctatcaagac ttagatgttt taggtctagc aagacaagtt    66300
aagttaagag caactttcga atctaataga tatatctcac cattaatgag ctctagtgat    66360
ttaacattca ctacattctt aacagagtta acaggttcat atgttggtag agctattgat    66420
atgacagagg ctccttacaa tacagtaaga tttagttatg aagctttctt acctaaaggt    66480
actaaagttg ttcctaagta ttctgcggat gatggaaaaa cttggaaaac atttactaaa    66540
tccccctacaa ctactagagc caataatgag tttacacgct atgtcattga cgagaaagta    66600
aaatcatcag gaacaaatac taaactacaa gttagattag atttatcaac tgaaaatagc    66660
ttttttacgtc ctcgtgttcg tagacttatg gttactacta gggatgaata aactagaggg    66720
gttgattgac ccctctttat ttaataagga gagatttata tgcctagaga agttagagac    66780
ccttattctc aagctaaatt atttatacct acagttgagg aaaaatcaat taaggaatta    66840
gaaaaaacat acaaagaaaa aattgatgaa gctactaagt taatcaatga attaaagaaa    66900
gagagaggag aaaaatagat ggcatttaac tacacgcctc ttactgaaac acagaagtta    66960
aaagatatgt atcctaaagt taatgatata ggtaactttt taaaaacaga agttaacctt    67020
agtgatgtaa aacaaatatc acaacctgac tttaataata ttttagcatc tatacctgat    67080
agtggtaact actatgtaac taattcaaaa ggtgctccta gtggagaagc tacggcagga    67140
tttgtaagat tggataaacg aaatgtaaat tattataaaa tttattattc accatatagt    67200
agtaataaaa tgtatatcaa gacttatgct aatggtactg tatatgattg gattagtttt    67260
aaattagatg aaggtaactt atacaatgaa ggtaatactt tgaatgtaaa ggaacttact    67320
gaatctacaa ctcaatatgt aacactagtt aatcctccaa aagagaactt aaatacaggt    67380
tgggttaatt acaaagaaag taaaaatggt gtttcttctt tagtagaatt taacccagtt    67440
aactctacct caactttcaa gatgataaga aagttaccag tacaagaaca aaagcctaac    67500
```

FIG. 19KK sequence.txt

```
ttattgaaag atagtttatt tgtttatcct gaaactagct cttcaaatat taaaacagat    67560
aattggaata caccctccttt ttggggatac acagctaata gtggtcgttc aggggttaga    67620
tttagaggag agaatactat acagattgat gatggtagta gcacatatcc tactgcaatg    67680
actaatagat ttaagatggg taatgagctt tctgtaggtg atacaattac tgtatctgta    67740
tatgctaaaa ttaatgaccc tgcattactt aaagataact tagtttactt tgaactagcg    67800
gggtatgata tggtagatag aactgataat ccttatacag gaggacgtag agaaataaca    67860
gcaagtgaga taacaactga gtggaaaaag tactccttca cattcacgat acctgaaaat    67920
acaattggag catcaggcgt taaagttaat tacgtatctt tactcttaag aatgaattgt    67980
tcatctagta aaggtaatgg tgctgtggta tactatgctc tacctaaatt agaaaaatca    68040
tctaaagtta caccgtttat cacacatgca actgatgttc gtaagtatga tgagatttgg    68100
tctaactggc aagaagttat tagtaaagat gaattaaaag gtcactctcc tgtagatata    68160
gaatataatg attactttaa gtaccaatgg tggaaatctg aagttaatga aaagagttta    68220
aaagatttag ctatgacagt acctcaagga tatcatacat tttattgcca aggctctatt    68280
gccgggacac ctaggggacg ttctattaga ggaaccattc aggtagatta tgacaaaggt    68340
gaccctaca gagctaataa gtttgttaaa ttattgttta ctgacacaga aggtatacct    68400
tatacattat actacggagg gtataatcaa ggttggaaac tcttaaagca atcagaaact    68460
tctactttac tatgggaagg tactttagat tttgggtcta cggaagctgt taacttaaat    68520
gactcattag ataattatga tttaattgag gtaacttatt ggactcgttc agcaggacat    68580
ttttctacaa aaagattaga tataaaaaat acatcaaatt tactgtatat tagagatttt    68640
aatatttcaa atgatagtac aggttctagt gtagactttt ttgaagggta ttgcactttt    68700
cctactagaa catcagtaca acctggtatg gtaaaatcta aactttaga cgggtctaca    68760
aatacaacaa aagtagcatc atggaatgaa aaggaacgta taaaggtata caatattatg    68820
ggaattaata gaggataaag aaaggtggaa taaaaaaaac tatggctgtt aaatatgata    68880
taggtaataa tgagatagta ttacatttaa gagaaggtaa atatataaca gggtttacaa    68940
cagtaggagg gtatgataag gagttaggac aagtaaaagt taatagagaa atcttacctg    69000
cttacttctt tgataatttt gcctatgaaa gatacttgta ttatagtaaa cctgaagagg    69060
ttatagagaa taaaaactat gtaccacctc aaatcaataa tggtgatgag gaatctcaac    69120
aaaatactgt acctaaagaa caatatgata gtttaaaaga agaactagaa cttatgagaa    69180
aacaacaaga agctatgatg gaaatgcttc aaaaactctt aggtcaaaag gggtaataat    69240
aaatggcatt aaattttact acaataacgg aaaacaatgt tattaaagac ctgactactc    69300
aggtcaataa cattggggaa gaattaacaa agaaagaaa tatatttgac attacagatg    69360
atttagttta taatttaat aaatcacaga agattaaact aactgatgat aaaggattaa    69420
```

FIG. 19LL sequence.txt

| | | | | | | |
|---|---|---|---|---|---|---|
| ctaaatcgta | tggaaacata | acagctctta | gagatataaa | agaaccaggt | tactactata | 69480 |
| taggcgctag | aacattagca | acattattag | atagacctga | tatggagtct | cttgatgttg | 69540 |
| ttttacatgt | agtacctctt | gatacttcta | gtaaggtagt | tcaacattta | tatacactat | 69600 |
| ctactaacaa | taaccaaatt | aaaatgttat | atagatttgt | ctcaggaaac | tctagttcag | 69660 |
| aatggcaatt | tattcaagga | ttaccgagta | ataaaaatgc | tgttatatca | ggaactaata | 69720 |
| ttctagatat | agcttcacca | ggtgtttatt | ttgttatggg | aatgacagga | gggatgccta | 69780 |
| gtggtgtaga | ttcaggtttt | ttagatttaa | gtgtagatgc | taatgacaat | agattagcta | 69840 |
| gactaactga | tgctgaaact | ggtaaagaat | atactagtat | taagaagcct | acagaagtat | 69900 |
| acacagcttg | gaaaaagaa | tttgagccaa | agatatgga | gaaatattta | ctaagtagta | 69960 |
| tcagagacga | tggtagtgca | tcattcccac | tcctagttta | tactagtgat | aataaaacgt | 70020 |
| ttcaacaagc | tattatagac | catatagata | gaacaggtca | aacaaccttt | actttctacg | 70080 |
| ttcaaggtgg | tgtatcaggt | tcccctatgt | ctaatagttg | tcgaggtcta | ttcatgtcag | 70140 |
| atacacctaa | cacttctagt | ttacatggtg | tctataatgc | tataggtaca | gatggtagaa | 70200 |
| atgtaacagg | ttcagtggta | ggaggtaatt | ggacttcacc | aaagacatca | ccttcccata | 70260 |
| aagaattatg | gacgggagca | caatcattcc | tatctgtagg | tactactaag | aatctagcag | 70320 |
| atgatattag | taattactct | tatgtagagg | tttatactaa | acataagaca | gtagagaaga | 70380 |
| ctaaaggtaa | tgatgactcg | ggtacaattt | gccacaagtt | ctacttagat | ggtagcggta | 70440 |
| cttacgtttg | ctcaggaact | tttgtttcag | gagatagaac | agatacaaaa | ccacctgtta | 70500 |
| cagagttcta | tagagtaggt | gtatctttca | aaggttcaac | atggacgctt | gtagatagtg | 70560 |
| cagtacaaaa | tagtaaaact | caatacgtta | caagaattat | aggtattaat | atgccataga | 70620 |
| ctaggataag | tttcctagtc | ttttttttctt | gacttgaaaa | ggattctatg | gtatactata | 70680 |
| actcgtgtaa | ggatataagg | agattaaaat | gagattaaga | attaagaact | tatataccta | 70740 |
| tgtagaattt | gaggaggatg | ataaatactt | aaaagatata | tttttaaaga | gagttcatac | 70800 |
| aactatagga | gcaaggcaag | aaggttttca | gtatagccct | gcttacaaaa | gaggcagttg | 70860 |
| ggatgggtat | gtagactttt | atgtttatga | ggaagataaa | ttccctactg | gactttttatt | 70920 |
| taaaattgag | ttattattag | gtgagctaca | atcaagatat | aacttccagt | ttgaaacaat | 70980 |
| tgatgagcgt | gatgaaagtt | tcttatctga | agaagatatt | gatgacgaga | taacattgct | 71040 |
| tgataataat | gtaggtcaaa | ttaccttacg | agattatcaa | tatgaggcag | tgtacaacag | 71100 |
| cttaacattt | tacaatggta | ttgctcattt | agctactaat | ggaggtaaaa | ctgaggttgc | 71160 |
| tagtggtatt | atagaccaac | tattacctca | attagaaaaa | ggtgaaagag | tagcattctt | 71220 |
| cacaggctct | acggagatat | tccatcagtc | tgcagataga | ctacaagaac | gtttaaatat | 71280 |

FIG. 19MM sequence.txt

| | | | | | | |
|---|---|---|---|---|---|---|
| ccctattggt | aaagtgggtg | caggtaagtt | tgatgttaag | caggttacag | ttgtaatgat | 71340 |
| acctacttta | aatgcaaacc | ttaaagaccc | aacacaaggg | gtaaaggtta | cacctaaaca | 71400 |
| aaatattagt | aaaaagattg | ctcaagagat | attaccgaaa | tttgaaggcg | gtacaaatca | 71460 |
| aaaaaaatta | ctaaaagtat | tacttgataa | cacaacacct | aaaacaaaag | tagaacaaaa | 71520 |
| cgtattaagt | gccttagaga | taatttacca | aaatagtaag | acagatgcag | aagtttatt | 71580 |
| aaacttaaga | aatcataatg | cacattttca | aaaaattgtt | agagaaaaaa | acgaaagaa | 71640 |
| atatgataaa | tatcaagata | tgagagattt | tttagactca | gttacagtta | tgatagttga | 71700 |
| tgaggcacac | cattctaaat | ctgattcctg | gtacaacaat | ctaatgacat | gtgaaaaagc | 71760 |
| tttataccga | attgcattaa | cagggtctat | agataaaaaa | gatgaattac | tttggatgag | 71820 |
| attgcaggct | ctattcggta | atgttattgc | acgaactact | aataagtttt | taattgatga | 71880 |
| aggtcattct | gctagaccaa | caataaatat | tatacctgta | gctaatccta | atgacataga | 71940 |
| tagaattgat | gattataggg | aagcttatga | taaaggtata | acaaataatg | attttagaaa | 72000 |
| taaacttatt | gcaaaactaa | cagaaaagtg | gtataatcaa | gataaaggta | cattgattat | 72060 |
| tgtaaacttc | attgaacatg | gagacacaat | atcagaaatg | ttaaatgatt | tagatgtaga | 72120 |
| gcactacttc | ttacatggag | aaatagactc | tgaaactagg | agagaaaaat | taaatgatat | 72180 |
| gagaagtggt | aaacttaaag | taatgatagc | tacatcactt | attgatgagg | gtgtagatat | 72240 |
| atccggtatt | aacgcactaa | tattaggtgc | aggaggcaag | tcattaagac | aaacattgca | 72300 |
| acgtattggt | cgtgctttgc | gtaagaaaaa | agacgataat | acaacacaaa | tatttgattt | 72360 |
| taatgatatg | acaaatagat | ttttatatac | tcacgctaat | gagcgtagga | aaatttatga | 72420 |
| agaggaagat | tttgaaataa | aagacttagg | aaaataggag | ggtaagagat | ggcaacaaaa | 72480 |
| acacaaagaa | agctatacca | atatctagag | gaaaatgcta | cagaaaataa | atttcatatt | 72540 |
| tctactaaga | aagagttagc | agattctcta | ggtgtttcca | tctctgctct | atccaataac | 72600 |
| cttaaaaagt | tagaagaaga | aaataaagtc | gttactgttt | ctaaaagagg | aaaaaacggt | 72660 |
| ggagtaataa | taactttagt | tagagagtat | gacacagaag | aattgaaaga | atttaataat | 72720 |
| tctacagata | atattattac | ttccgattta | cagtatgcta | aggcattaag | agaaaagcac | 72780 |
| ttcccttctt | atagatatga | gagaaaagaa | caacgtagac | gtactaagat | agaaatggca | 72840 |
| caatacaatg | ctattaagga | tgagaagaga | agaattatag | cagatatgaa | tttctattca | 72900 |
| gaaggtcttc | cttacccttc | taaagatatt | tttaatatgt | cttatgaccc | ggaaggtttt | 72960 |
| tataaagcat | acatcttatg | taagttatat | gaccaatatg | ctatttctca | tatggatgct | 73020 |
| aaacatacaa | gtcatcttaa | agcaatgagt | aaggcaacaa | ctaaagatga | atatgactac | 73080 |
| catcaacata | tgtctgaata | ctatagaaat | aaaatgattc | aaaatttacc | tagaaatagt | 73140 |
| gttagtgata | atttctttgg | tagtaaaatg | tttaatactt | tttataattt | ttatttaaaa | 73200 |

FIG. 19NN sequence.txt

```
ataaaagata aaaatattaa tgtatttaaa tatatgaaaa acgtatttaa aaatgtaaca    73260
ttttattacg agaacggtat gcaacctaat ccaatacctt ctcctaactt ctttagttca    73320
gataagtatt ttaaaaacta taataattat attaaggaa taaaaaagg cattaacagt      73380
acgaatagac acctaggtga tacagacagc atcattaatt catcagacta tgtgaaaaac   73440
cctgctgtat tacatctaca ccaactatat actacaggat taaattctac tttacatgat   73500
attgatacta tgtttgaaca agccttagac cttgagaatg cttcttatgg attatttgga   73560
gatatgaaac atattatctt actacagtat aattctatga ttgaagaaga aattaagaat   73620
ttacctatag aagagaagga tattattaat aaatatgtaa aacaatgcat aattaataat   73680
tactcaccaa caagtatttc accatctgca agattatcaa tgtttactat gcagaaagag   73740
catatagttt ataataagca attaaataag ggaatcaaga gagaggattt attaccatta   73800
agtctaggag gtatagtgaa taaagattca ttaagtagta tggatataca aaacttagaa   73860
cagaatggca atgaatacct atatatgaga caacatactt caacttatta tatactaaga   73920
atgtttggtg actatttagg gtatgaggta aatttaagag aagtaaaata tattgtagag   73980
aaatataatt taattgataa aataccattg acaaaagagg gtatgttgga ttataataaa   74040
cttatacatt tagtagagga agaggttaat aactatgagt aagaagataa aggagcttat   74100
ccttcataaa tcaatgaagg atatacattt tgcaagagaa gtattagata acttacctaa   74160
gaacttattt tcagcagagt ctgaagacat gggttactta tttacagcca taaagagaac   74220
agcacatatt tccgataaga tgtcaaatga agcattagca attaaagtag aacagcttat   74280
gggtaataac aaggaagatg aggagaaagt aaccaagaca ttaacttact tagaagattt   74340
atataaagta gacgttaatg aaaaagatga atctgttaat tatgaaatag agaagtatat   74400
taaaacagaa atgtcaaaag aagttttagt taaatttatt gcagaaaata aacaagaaga   74460
ctctgataat ctacatgaac ttgtagacaa actaaagcaa atagaagtaa gtgacatctc   74520
aggaggtaat ggggagttta ttgacttctt cgaagataca gaaaagaaac aagaactatt   74580
gagtaattta gctacaaata aattctctac tggatttact tctattgaca accatattga   74640
aggtggtata gcaagaggag aggttggatt aatcatagct cctaccggta gaggtaaatc   74700
attaatggct tcaaacttag ctaagaatta tgttaaaagt ggattaagtg ttttatatat   74760
tgccttagag gaaaaaatgg atagaatggt tttgcgtgct gagcaacaaa tggcaggagc   74820
agaaaagagt caaattgtaa atcaggatat gtctttaaat aataaagttt atgatgcaat   74880
acaaaatcat tatcagaaga atagaaagtt attaggtgac ttttatattt ctaaacatat   74940
gccgggtgaa gttacaccaa accaattaga gcaaattatt gtcaatacaa caattaagaa   75000
agataaaaat attgatgttg ttattattga ctatcctcat ttaatgagaa atccttatgc   75060
```

FIG. 1900

```
                                sequence.txt
taaatatcat tcagaatcag atgcaggcgg aaaattgttt gaagatattc gtagattatc   75120
acagcaatat ggatttgttt gttggacgtt agctcaaact aaccgtggtg cttatggttc   75180
agatgttatt acaagtgagc atgtagaagg ttctcgtaaa attgtcaatg ctgttgaggt   75240
gtctttagca gtaaaccaaa aagatgaaga attcaagagt ggtttcttaa gattatattt   75300
agataaaatt cgtaatagct ctaacacagg agaacgattt gttaatctta agtagaacc    75360
aactaagatg attgtaagag atgaaacacc tgaagaaaaa caagagcata tacaattgct   75420
atcagataat ggaaagaag acacaagtaa atttcaaaat aaagataata aaatagaagc    75480
tataaataac acattcggag gattaccggg agtttaattt tttaaaatat accacttgac   75540
attttatatg ttaggtggta taattatttt ataaagaata aaggagagat taataatgaa   75600
atttgtattc tttacagata gtcattttca cctatttact aactatgcta aacctgataa   75660
tgaatttgtg aatgatagat ttaaagaaca gatagaagca ttacagaaag tttttgatat   75720
tgctaaaaaa gaagaagcaa cagttatatt tggtggagat ttattccata acgtaactc    75780
ggtagatact agagtatata acaaagtatt tagtacattt gccaaaaata atgaggttcc   75840
tgtattatta cttagaggta atcatgatgc tacaactaat tcattatata ctgattcaag   75900
tatagataca tttgagtatc tacctaatgt aaatgtaata aaatcattaa atacaatttt   75960
aaaagataat gttaatattg tgtttactgc ttatggggat gagacgaagg aaataaagac   76020
atacattaat agtaattatg ataaagatat ggtcaatata ctagtaggtc atttaggtgt   76080
agaaggttca ttaactggaa aaggctctca tagattagaa ggggcatttg gataccagga   76140
tttattacct gataaatatg atttcatttt actaggtcat tatcaccgta gacagtattt   76200
ccaaaatccg aatcatttt atggtggctc attaatgcaa caatcatttt ctgatgaaca    76260
agaagctaat ggtgttcatt taatagatac agacaaaatg actacagaat tcattccaat   76320
tcatacacgt agatttatta ctattcaagg agaagatatt cctgataact ttgaacaatt   76380
aatagaggaa gataatttta ttagagttat tggtacagca atcatgctaa ggttttaga    76440
aatggatgac agtatgaaag ataagaatgt tgaagttcaa attaaaaaag agtatactgt   76500
agagaaacgt attgatagtg atgtatctga tgaccctcta acaattgcta gtacctatgc   76560
taaacaatac tcacctgaat cagaacaaga aatccttgaa tgtttgaagg aggttttata   76620
atgaaaaaat atagagaata tctaaataag acagatgcag aaaatttagc agaggattgg   76680
gagaaagtaa ccgaagattt atggaaagtg tttaaagata tgaaacctaa aattaataca   76740
ttagatatca gtaatgtagg aagtaaagat ttagataaaa gtaaacctat actacaattc   76800
caagattcag atggagtaat agagaatatt tgtaatgttg aaggtttaga agatggtcta   76860
agtaaaatga aaaagatttt tgatgatagt aattttgaaa agcattatta caatagagta   76920
gtagaccatg atgggtatta ctggattgat tatggttctc atcattgttt ctttagagtt   76980
```

FIG. 19PP sequence.txt

| | | | | | | |
|---|---|---|---|---|---|---|
| acgaaagggg | ataagtaatg | gttgtattta | aacaagtaga | agttaataat | tttttagcaa | 77040 |
| ttaaagaagc | tacactagag | ttagacaata | gaggtttaat | tctcattgag | ggtgagaata | 77100 |
| aatccaatga | gtcatttcat | tcaaacggct | caggtaaatc | aactttaata | tctgccatta | 77160 |
| cttatgcttt | atatggtaaa | actgaaaaag | ggctaaaagc | ggatgatgta | gtaaataata | 77220 |
| ttgagaagaa | aaatacgtct | gtgaaactta | agtttgatat | cggggaagat | agctatttaa | 77280 |
| ttgaacgtta | tcgtaaggac | aaagagaata | agaataaagt | aaaattattc | gttaatgaaa | 77340 |
| aagagattac | aggttcaaca | aatgacgtta | ccgataaaca | aatacaagac | ttatttggta | 77400 |
| ttgagtttaa | tacttatgtt | aatgccatca | tgtatggtca | aggtgatatt | cctatgttct | 77460 |
| ctcaagcaac | agataagggt | aagaaagaaa | ttcttgaatc | tattactaag | acagatgtat | 77520 |
| ataaacaagc | gcaagatgta | gcaaaagaga | aagttaaaga | agtagaagaa | caacaaaata | 77580 |
| atataagaca | ggaaatctat | aaactaggtt | atcagttatc | tacaaaagat | gagtacttcc | 77640 |
| aaagagaaat | agaacaatat | aatcagtata | agaacaatt | ggttcagata | gaaaatagta | 77700 |
| ataaggaaaa | agatagatta | agagaacaag | aggagaagca | aatagaagct | caaatagagc | 77760 |
| aattagcttc | acagatacca | acaatacctg | aagatgaatt | taagcactca | gaggagtata | 77820 |
| ataaagcctc | tcaaagccta | gatttacttt | ctaataaatt | aacggagtta | aatcaagtat | 77880 |
| actcagaata | taataccaaa | gaacaagtac | taaaatctga | aatagctaca | ttaagcaata | 77940 |
| gtctaaatca | gttagatata | aatgaccatt | gtcctgtttg | tggctcccct | atagataatt | 78000 |
| ctcataaatt | aaaagaacag | gaaaatatca | gcaatcagat | tgagaataag | aaacaagaga | 78060 |
| ttactagtgt | attagaaatg | aaagatacgt | ataaagaagc | tattgataaa | gtaaaagata | 78120 |
| aatcacaaga | aattaaagat | aaaatgtcac | aggaagacca | acaagaacga | gagcacaata | 78180 |
| ataagattaa | cagtatcatt | caagaggctt | ctaggattaa | atcagacatt | agttcattag | 78240 |
| agaataataa | aacttattta | aaagtgaaat | accaacatca | atctgttcaa | ggattagaga | 78300 |
| gagaagaacc | aagtaaagaa | aaacatgagg | aagataaaaa | agaattacaa | gaatctattg | 78360 |
| acaaacatga | agagaatata | gtacaattag | aaactaagaa | agggaaatat | caacaagctg | 78420 |
| tagatgcttt | tagtaataaa | ggtatacgtt | cagtagtgtt | agactttatt | acaccattct | 78480 |
| taaatgagaa | agcaaatgag | taccttcaaa | ctttatcagg | ttcagatatt | gaaatagagt | 78540 |
| tccaaactca | agtgaagaat | gctaaaggag | aactaaaaga | taagtttgat | gttattgtta | 78600 |
| agaataacaa | gggtggaggc | tcctacaaat | ccaattcagc | aggagaacaa | aaacgtattg | 78660 |
| atttagcaat | tagttttgca | attcaggatt | taattatgag | taaagatgag | atatctacga | 78720 |
| acattgcact | ttacgatgag | tgttttgatg | gattagatac | tatcggttgt | gaaaacgtga | 78780 |
| ttaaattatt | aaaagataga | cttaatacag | taggaacgat | atttgtaatt | actcataata | 78840 |

FIG. 19QQ sequence.txt

| | | | | | |
|---|---|---|---|---|---|
| ccgaacttaa | acccctattt | gaacaaacaa | ttaaaatagt | aaaagaaaat | ggagtatcaa | 78900
| aactggagga | aaaataatga | aattaaagat | tttagataaa | gataatgcaa | cacttaatgt | 78960
| gtttcatcgt | aataaggagc | ataaaacgat | agataatgta | ccgactgcta | atttagttga | 79020
| ttggtaccct | ctaagtaatg | cttatgaata | caagttaagt | agaaatggag | aatacttaga | 79080
| attaaaaaga | ttacgttcta | ctttaccttc | atcttatggt | ttagatgata | ataaccaaga | 79140
| tattattaga | gataataacc | atagatgtaa | aataggttat | tggtacaacc | ctgcagtgcg | 79200
| taaagataat | ttaaagatta | tagagaaagc | taaacaatat | ggattacctg | ttataacaga | 79260
| agaatatgat | gctaatactg | tagagcaagg | atttagagat | attggagtta | tattccaaag | 79320
| tcttaaaact | attgttgtta | ctagatatct | agaaggtaaa | acagaggaag | aattaagaat | 79380
| atttaacatg | aaatcagagg | aatcacaatt | gaatgaagca | cttaaagaga | gtgattttc | 79440
| tgtagactta | acttatagtg | acttaggaca | aatttataat | atgttgttat | taatgaaaaa | 79500
| aattagtaaa | tagtaaggaa | ggatattatg | aggtttgaag | acttttaac | ccaagaatta | 79560
| ggagaaccaa | aagaaaatac | tataggtgag | ctaagatact | gttgtccgtt | ttgtggagaa | 79620
| aaaagttata | agttctatgt | taagcaagcc | ctagactcta | gtaatggtca | gtatcattgt | 79680
| aaaaaatgtg | atgaaacagg | caaccctatt | acatttatga | agacttatta | taacattaca | 79740
| ggtaagcaag | cttttgattt | attagagtct | aagaatatag | atatagagag | agccccttta | 79800
| cttacaacta | ataataagga | tttaacagaa | tcagagaaac | ttatattaat | gcttagaggt | 79860
| gtgcaccaag | ataaaggaac | tactagtatt | aaacctcctc | gattacctga | aggatataaa | 79920
| ttattaaaag | ataatttaaa | taataaagag | attataccttt | ttttaaaata | cttaaaaggt | 79980
| agaggtataa | ctttagaaca | aatcattaat | aacaatatag | gctatgttat | taatggtagc | 80040
| ttttataaag | ttgacgggga | atccaaagta | tcattaagga | atagtattat | atttttact | 80100
| tatgataaca | atggaaacta | ccagtactgg | aatacaagaa | gtatagagaa | gaaccttat | 80160
| attaaatcta | ttaatgctcc | tgctaaacaa | gatgaagtag | ggagaaaaga | tgtcatattt | 80220
| aatttgaata | tagcaagaaa | gaaaaagttc | ttagttataa | ctgaaggtgt | atttgatgct | 80280
| ttaaccttc | atgaatatgg | agtagcaaca | ttaggtaaac | aagtaactga | gaatcaaata | 80340
| aaaaaaataa | ttgattacgt | tagtatagat | acatcaatat | atattatgtt | agacactgat | 80400
| gcattagata | ataatataga | cttagcttat | aagttaaaaa | cacattttaa | taaagtttac | 80460
| tttgtaccac | atggtgatga | agatgcaaat | gatatgggaa | caaggaaagc | ttttgagtta | 80520
| ttaaaacaga | accgggtgtt | agtaacacct | gaaagtatac | agagttacaa | aatacaacaa | 80580
| aaacttaaac | tttaggcttg | accttagaga | agttttatgt | tatactagta | attaagtaat | 80640
| taataaagga | gaaaaaaata | atgtcaaata | gtaaaaaaga | tattttagaa | tttgtagatg | 80700
| aatacattac | agctttaaga | gttggtaatg | agcaacgaca | acaccaatta | gaagaaatgg | 80760

FIG. 19RR sequence.txt

```
gtaaagaaga aacagcaaca ttaacagatg tagctaaagc tattactaac cttatgttag     80820
gtgttaatga gcagatgaca gacttagaat ataataacga gttaaactta aatatttttaa    80880
ttgacgcttt atataaagca gagcttatta atgaagatgt attagactac attcaagaat     80940
caattgataa atcacaagaa gaacctaaaa atgaagaaga aaaaggagaa caagaataat     81000
ggaaaaaaat attagcacac acacaaaagg tattagtcaa gcagacatgg agaaatggat     81060
tgaagctgta gtacaaggaa ctgttgatgg taaacaagtt gatgagaaaa cagctaaaca     81120
attagataga attggttcac gtagtgtttc tttagaagaa gcaactcgta ttgctaaagt     81180
tcttaatgct gtaacagctc aagaggttac aggagactt aatgatgcat ttaatgcaat      81240
tgacttaatg atgattatca tggaagatga gctaggagta actcaagaaa aagtgggtaa     81300
agctaaagat aaactaaatg aaaaacgaga agcttaccta aaagagaaac aagaagaatt     81360
acgccaaaaa caacaagaag aggcacaaaa agaaactgaa tctgacagca atgagaaagt     81420
aattcagttg aagaaaaatg acgaacagta agaaaaaagg ggatacattc gaacgtaaaa     81480
tagctaaaga attaactgct tggtggggat accaattcaa taggtctcct caatcaggtg     81540
gtgcttcatg gggtaaagat aataatgctg tcggagatat agtagtacct caggaagcta     81600
atttccttt agtagtagaa tgtaaacata gagaagaatg gactatagat aacgttcttt      81660
taaacaacag agagccacat acatggtggg agcaagtcat taatgatagt agcaaggtgg    81720
ataagacacc ttgcttaata tttactagaa acagagctca gagttatgtt gctttacctt    81780
atgatgagaa agtatatgaa gatttgagaa ataatgaata ccctgtcatg agaacagatt    81840
ttattattga taatattaga aaagataaat tttttttatga tgtacttata actaccatga   81900
atgggttgac ctcatttaca ccttcttata ttatatcttg ctacgacaaa aaagatataa    81960
aaccatacaa gaaggtcgag tctaatttat ctgaggtaag taagcatgaa gatgaattga    82020
ttaatgacct tcttagtgat atataaggaa ggtaagataa gtatgacaag taaagaaaga    82080
ccattaatcg tatattttc aggtacaggg caaacagaaa gattagtaaa taaaattaat      82140
attaataatt catttgaaac atttaggggtt aagagtggaa aagagaaagt aaataaacct   82200
tttatactaa taacacctac ttatatgaaa ggtgcaatac ctaaacaaat agaaagattc    82260
ctagaaatta atgggagccc taaagaagtt attggtacag gaaataaaca atggggctct    82320
aatttctgtg gagcaagtaa aaagatttca gagatgttta agattccttt aattgctaaa    82380
gtagagcaat caggacactt taacgagata caaccaatat tagaacactt tagtaataaa    82440
tataaagtag cgtaaaggat gagagatata tggcaacata tggaaaatgg attgagttaa    82500
ataatgaaat aactcaatta gatgacaatg gaaaaataa actctataaa gaccaagaag      82560
ctttagatga gtatttaaaa tatattgaag acaatacaag aaagtttaat agtgaagtag    82620
```

FIG. 19SS

```
                          sequence.txt
aaagaattag agtattgaca aaagaaggaa catatgataa aatatttgac aaggttcctg    82680
atactattat tgatgagatg actaagttag cttacagttt taattttaaa ttccctagtt    82740
tcatggcagg gcaaaagttt tatgaatctt acgcatcaaa acagtatgat gaaaacaaaa    82800
aacctatttt tgttgaagac tatgagcaac ataatgttcg agtagcttta tatttatttc    82860
aaaatgacta tgtaaaggct agagaattac tagtacaact tatggagcaa acattccaac    82920
catctacacc tacgtataac aactcagggc aagctaatag aggtgaacta agttcatgtt    82980
atctatttgt agtagatgat tcaattgagt ctttaaactt tgttgaggat agcgtagcta    83040
atgctagttc taatggtggc ggagttgcaa ttgatttaac tagaattaga cctaaaggag    83100
ctccagtacg taatagacct aattcaagta aaggtgttat tgcttttgct aaagctattg    83160
aacataaagt tagtatttat gaccagggcg gtgtaagaca gggtagtggt gcagtttacc    83220
taaatatatt ccacaatgat atcttggatt tattaagctc taagaaaatc aatgccagtg    83280
agtctgttag actagataaa ttatctattg gtgttacaat ccctaacaaa tttatggagt    83340
tagttaaaga aggtagacct ttctatactt tcgatactta cgacattaat aaagtgtatg    83400
gtaagtattt agatgagcta aacattgatg aatggtatga taagttatta aataatgata    83460
gtatcggtaa agtaaaacat gatgctagag aagttatgac agatattgct aaaacgcaat    83520
tagaatcagg ctacccttat gtattctata ttgataatgc taatgataat cacccattga    83580
aaaacctagg taaagttaaa atgagtaact tatgtacaga aatttcacaa ttacaagagg    83640
tatcagaaat ttatccgtac tcttacagta atcagaatgt tattaataga gatgttgttt    83700
gtacattagg ttctcttaac ttggttaatg tagttgaaaa aggtttattg aatgaatctg    83760
tagatattgg tacaagagca ttaacaaaag ttactgatat tatggattta ccttacttac    83820
ctagtgttca aaaagcaaat gatgatatta gagctatcgg tttaggttca atgaatttac    83880
atggactttt agctaagaat atgattagtt atggttctag agaagcatta gacctagtaa    83940
acagtttata tagtgctatt aacttccagt ctattaagac atctatgtta atggctaaag    84000
aaacaggaaa accatttaaa ggctttgaga agtctgatta cgctacaggt gaatactttg    84060
taagatatat tagagaatcc aatcaaccta agacagataa agctaagaaa gtcttagata    84120
aggtttatat tccaacacaa gatgattggg atgaattagc taaagcagta aaagtacatg    84180
gcttgtataa tggttataga aaagcagaag cacctactca atctatatct tatgtacaga    84240
atgctacaag ttctattatg ccagtcccta gtgctataga gaatagacaa tatggagata    84300
tggagacata ttacccaatg ccttacctaa gtcctataac tcagttcttc tatgaaggag    84360
aaacagctta taagattgac aataaacgta ttattaatac aagcgcagtt gttcagaaac    84420
atacagacca agcagtgtct acaatacttt atgtagagtc agaaatccct actaataaac    84480
tagtatcatt atactattat gcttgggaac aaggattaaa atcattatac tatacacgtt    84540
```

FIG. 19TT sequence.txt

| | | | | | | |
|---|---|---|---|---|---|---|
| cacgtaaact | ttctgttatt | gaatgtgaaa | catgttcggt | ttagaaagga | aatagatatg | 84600 |
| gatattacac | aaaaagtaaa | acaacataat | aaaaatgctg | tattaaaagc | aacaaactgg | 84660 |
| aatattgaag | atgacggtat | gtctgatatt | tattgggagc | aaggaatctc | ccaattttgg | 84720 |
| actcctgaag | agtttgatgt | atcaagagat | ttaagttctt | ggaatagttt | aactgaaagt | 84780 |
| gaaaagaaca | cttataagaa | agtccttgca | gggctcacag | gtctcgatac | aaagcaagga | 84840 |
| ggagaaggta | tgaacttagt | atcctaccat | gaaccaagac | ccaaatacca | agctgtattt | 84900 |
| gcgtttatgg | gtggtatgga | agagatacat | gctaaatcct | atagtcatat | ctttacaaca | 84960 |
| ttactaagta | ataaagaaac | aagctatcta | ttagatactt | gggtcgaaga | aaatgacttt | 85020 |
| ttaaaagtaa | aagctcagtt | tatcggatat | tactatgacc | aactattaaa | acctaaccct | 85080 |
| actgtatttg | atagatatat | ggctaaagta | gctagtgcct | ttttagaaag | tgcactattc | 85140 |
| tactcaggat | tttattatcc | tttacttctt | gcaggaagag | gtcagatgac | acaatcagga | 85200 |
| gctattattt | ataaaattac | tcaagatgaa | gcttaccatg | gttcagcagt | aggattaaca | 85260 |
| gctcaatatg | attataatct | tctaacagaa | gaagagaaaa | aacaagcaga | taaagaaact | 85320 |
| tatgaattat | tagatattct | ttacactaat | gaagtagcgt | atacacatag | tctatatgac | 85380 |
| ccactagaat | taagtgaaga | cgtaattaac | tatgttcagt | ataattttaa | tagagctctt | 85440 |
| caaaaccttg | gaagagagga | ctattttaat | cctgaacctt | ataaccctat | tgtagaaaat | 85500 |
| caaactaatg | tagacagatt | acgaaatgtt | gatttcttta | gtggtaaagc | agactatgaa | 85560 |
| aaatctacaa | atatcaaaga | cattaaagat | gaagatttct | cattcttaga | tagtaaagaa | 85620 |
| tacaatactg | ccaaggaatt | cctataaaaa | ggagaaaaga | tattatggat | agaaaagaag | 85680 |
| caatggattt | actaagtaaa | gcagaaatat | tatttaaaaa | acatgatgag | ttttcatgtg | 85740 |
| taagtgatat | taatgacccc | atgaagttat | tcagtagctc | taaggatgct | aaagctgatg | 85800 |
| atacgtctaa | gtcttttcag | ctagagttta | tgcatgatat | gaccatgtat | actttatctt | 85860 |
| atggctcagg | acagttaaaa | cttattgatt | tagcagaagg | ttatgaagca | caaaaagcta | 85920 |
| cagtagttaa | ctcatttccc | gaattatta | aaacattaga | aaggatgat | tcagaagatg | 85980 |
| gaaaaaatga | atagtttagt | agatttaaat | acagcaatta | gacaaaagaa | agatgttatt | 86040 |
| gtcatgatta | cacaagataa | ttgtggtaag | tgtgagattt | taaaagtgt | aatccctatg | 86100 |
| tttcaagagt | caggtgacat | taaaaaacct | atcttaacat | taaatctaga | tgctgaagat | 86160 |
| gtagatagag | aaaaagctgt | taagttattc | gatatcatga | gtacaccagt | attaattggg | 86220 |
| tataaagatg | gtcagttagt | taaaaagtat | gaagaccaag | ttacacctat | gcaattacaa | 86280 |
| gaattagagt | cactttaatt | tggaatttcc | tactatctgt | gctatactat | aatagtacaa | 86340 |
| ggtagtagga | ttttttaatg | gaaggaagat | gacatatcgc | aaagaataaa | acattaacga | 86400 |

FIG. 19UU sequence.txt

```
tatataatag tgatagatat tttaatatac acacaaaaga taaagataaa attaatgagg      86460
ctattaaagt cacacatggt aatgaagaag aaattgagaa gaatatggat gaattaatat      86520
ctaagtctag acgatatatc atgagagatg aaaatcatta catgttattt aatgagaagt      86580
ataataatga tagacttata gaaaaagtat gtaaacatgg cggtaaagtt acatactata      86640
ctgattcagt attaccttat tatgttttaa aagacttatc tagtcaccct gactcagaag      86700
ttgtttatcg tatgcgcaat ggttttactg caaaagaagt agataatata gctttatcat      86760
tcatgggtac aaaagttatt attgatattt ctgtagtatt tccttatgta aacccttatg      86820
atattattag aagtttacat gatattaaaa caaatgtaga tgaagttcat ttatcatttc      86880
cacgaatatt agaggtagat gaaaaacaag aaaagttttta tttctttgat ggtgaagctt      86940
atgatttaaa acctgaatat aaagtcgatt ttgcagataa aattagagta tctttatcag      87000
tatggaaaat gtatatctat atcttaacaa gtagtcgtga ttttgaggat gtagacaatg      87060
taattacgaa attaaaacaa caacgaaaga ttaagatata aggtgattat atgagtacag      87120
caaatagaag agatatagca agaaagatat cagagaatac aggttactat atccaagatg      87180
tagaggaaat actaagtgca gagacagatg ctatttctga cttactagaa gaaggatata      87240
ctaaagtaaa gaatcataaa tttatgcaaa tagaagttat tgaaagaaaa ggtaaaaaag      87300
cgtgggatgg tctgaataaa gaatacttcc atttacctaa tagaaaagct ataaaattca      87360
aaccactaaa agaactagaa gaggttattg atagacttaa tgaagaagag aaataattct      87420
cttcttttt tattgacaag gtttaaaata tatggtatag tattattaag ttaaaaaagg      87480
agaggaatta aatgaaagta ttaatcttat ttgaccacat tagagaagag cattttttctg     87540
taagtaaaga tgggagtgtg aaatctaatg tactaaatac acctaatgga aaaacactta      87600
agaaattact tgagaagtgt tctaacttaa agagagataa gacaaacaga gattatgata      87660
ttgattttct ctacaatgca gtacctacac ctatcagaaa tgactacggt aaaatcatta      87720
aatatcaaga tgttaaacaa gcagaagtaa agccatacta tgagagaatg aacaatatta      87780
ttattgataa ttccttatgat atggtaattc ctgtaggtaa actaggtgtt aaatacctat      87840
taaatgttac agctatcggt aaagtaagag gagtcccaag taaagtaact attgaaaatg      87900
aaacatcttc tcatgacgtg tgggtattac ctacttacag tattgaatat actaatgtaa      87960
ataaaaatag tgaacgtcat gtagtatcag atttacaaac agttggtaag tttgtagagc      88020
aaggagaaga ggcatttaaa cctaaggaag tatcttacga gttggtagat aacattgaaa      88080
gagtaagaga aatattcaat aaggaagtaa agaacgacaa ttatgatggc gtagatatta      88140
ccgcatggga cttagagact aactcattaa aacctgataa agaaggaagt aaacctttag      88200
tactatctct atcatggaga aacggtcaag gtgtaactat acctttatat aaatcagact      88260
ttaactggga aaatggtcaa gatgatattg atgaagtctt agaattgctt aagaattggt      88320
```

FIG. 19VV sequence.txt

| | | | | | | |
|---|---|---|---|---|---|---|
| tagctagtaa | agaagacatt | aaagtagcac | acaacggtaa | atgatttgct | gttgtaaaat | 88380 |
| ccctctcata | tcgggcatag | ctttaagaag | ctgataagag | aacctaagtc | ctgtaataag | 88440 |
| gatagtggta | atcccgagcc | tacattattg | gtgacaatag | atggggtgta | gagactgagc | 88500 |
| tgaggttttg | tagaccaagg | tgagacatag | tgtatcaact | taatagaggt | ggtacagtga | 88560 |
| aaaaagatta | tatgacatca | gttaaaaata | acaaaaaagt | atgtagaaga | tgtaatgaag | 88620 |
| aattagactt | atctaatttt | aaaacatata | aaagaatga | taaaatttat | tatcagagta | 88680 |
| tgtgtatacc | ttgtagaaag | gaatacaata | aattagataa | aactaaaaat | actattaaaa | 88740 |
| aatgttatga | taaaaatgga | gataagtatc | ggaaacaagg | taatgagtat | aacacttctg | 88800 |
| atagaggaag | agaactaaat | aaaaagcgtt | caagaaaata | cagagaaaat | aattctttaa | 88860 |
| aagctaaagc | tagaaactct | gtaagaactg | cattaagaaa | tggttctcta | ttaagaccta | 88920 |
| gtaaatgttc | agagtgtaat | aaggaatgta | ttcctgaagc | tcatcatcct | gattataaca | 88980 |
| aacctttaga | aataaaatgg | ttatgtaaat | catgtcatga | agatacacat | cataaaaaat | 89040 |
| aatcacacta | tgtaaatgag | ggacatcaag | cccatttagg | taactacaaa | caaacctaat | 89100 |
| ggtaagggct | tatgaaggta | tagtccgttc | tgtatagaaa | tatacaggct | aaaacgaaat | 89160 |
| atgatattaa | attcttaatg | agtactgaaa | actttaaaga | ttttgagagt | attcaggata | 89220 |
| ctaaagtagg | ttggtaccta | gccgttaccc | aggaagttaa | agaatcttta | agattatctg | 89280 |
| atttagctta | cgaggttacg | gatgtcggag | gatatgataa | accattagaa | gactttaaat | 89340 |
| tatggtttgt | tactaagtta | ttaagattct | tctcagataa | aattaaagag | atacagaaag | 89400 |
| aaaataaaaa | aattgctaag | aaagagtatg | atgttaaagc | tcctgaatat | aaagaatggt | 89460 |
| tagagaataa | actaaatgaa | acagtagtag | aactagatga | tactgagaag | aaatttagag | 89520 |
| tcagtgaatt | agagaaaaag | tatattcaac | taggtctttc | acctgaaatt | gtaaatatga | 89580 |
| atttagttat | gaataacgat | gagtttataa | gtattgcaga | acaatcacct | gagtacatgg | 89640 |
| ggttatctga | ctacgctaag | tcttacacat | taaatactgc | aattaattta | attaatgagt | 89700 |
| atagagatgt | aaaagatgta | gttaatgata | ttgatggagg | taactttaat | tatgattggt | 89760 |
| tccctattga | gttaatgcat | ccatatgctt | caggagatac | tgatgtatgt | agaagaattc | 89820 |
| attgtgatgt | agttaaaaaa | cttaagaac | aagatagacc | taaatcaatg | catttattag | 89880 |
| aagttaatta | tccaagactt | actaagtctt | tagctaggat | tgaatcaaat | ggtttatatt | 89940 |
| gtgacttaga | ttatatgaaa | gaaaatgatg | agtcatacga | gtctgagatg | gctaaaaatc | 90000 |
| atgctacaat | gagagagcac | tgggctgtta | aagaatttga | agaataccaa | tacaatcttt | 90060 |
| accaaatggc | gttagaagaa | catgagaaaa | agccaaaaga | tagagataaa | gatatccatc | 90120 |
| agtatagaga | taaatttaaa | gatggtaaat | ggatgttttc | cccaagttcc | ggagaccata | 90180 |

FIG. 19WW

```
                              sequence.txt
aaggtagagt aatttatgat attttaggaa ttcaattacc ttatgataaa gaatatgtta    90240
aggaaaaacc atttaatgct aatgttaaag aagcagacct tacttggcag gactataaaa    90300
cagacaagaa agctattggt tatgcgttag ataatttaga attaaaagat gatgttagag    90360
aacttcttga gttacttaaa tatcatgcta gtatgcagac aaaacgtaat tcatttacta    90420
agaaattacc taatatgatt aataaacaaa acgaacatt acatggttct ttttctgaga    90480
caggtacaga gacatcaaga ctaagtagta gtaaccctaa cttgcaaaac ttaccggcac    90540
acacatcaga tgtaaacaag tttgattaca acatccaat taaacgttca tttgtttcta    90600
gatttgaaaa tggagtacta ctgggagccg actatagcgc cctagagatg cgtattattg    90660
gattatttac taaagaccct gatatgctac aatcattctt aaatggggaa gatattcata    90720
aggctactgc aagtattgtt tataataaac cagtagaaga ggtaactaag gaagaacgac    90780
aagcaactaa agcagttaac ttcgggttag ccttcggtga atcacccttc tcatttgcag    90840
gtaaaaataa tatggaagta agtgaagcag aagaaatatt tgaaaagtac ttccaaacaa    90900
aaccaagtgt aaaaacttct attgacaatg tacatgagtt tgtgcaacaa tatggttatg    90960
ttgatacaat gcacggacat agaagattta tccgttcagc ccaatcaaca gataaaaaga    91020
taaaaaatga aggtctaaga cagtcattta acactattat ccaaggttca ggtagtttct    91080
taacaaacat gtctttaact tacttagatg attttatcca atctcgtaac ttaaaatcaa    91140
aagttattgc cacagtacat gatagtatct taattgattg tcctcctgaa gaagctaaaa    91200
ttatggctaa agtgacaatt catattatgg aaaacttacc atttgatttc ttaaaagcag    91260
aaattgatgg aaaagaagta caatacccta ttgaagctga tatggaaatc gggttaaact    91320
ataatgatat ggttgaatat gatgaggaag aaatagatac atttaattct taccaaggtt    91380
atattaagta tatgatgaat ttacagacct tagaagatta taaagagtca ggtaaactaa    91440
cagatgaaca atttgaaaag gctactaacg ttgttaaaag tgaaaaacat atttaccaag    91500
aaatttaata aaagtattga caatatattt aacttatgtt atactatata ggtaataaat    91560
ataaggagga aaaagagtga atacaggaga gattagattt aatcgttcta tggatgaatg    91620
gattataaca agtatgtacc aggatgagct aggtgatatg aatattgttg ttacattcta    91680
taatagagaa gaaaataaac acggttctac agttttaccc acagagtcat ctactggaga    91740
agtaacagag gaattggcaa atcttgaaga agaatatcct ctagctttac ctttaagtag    91800
tatctcagtt aatatttaaa aggaggaact gataaatgga aatacacatt gattccctag    91860
attttacaaa ctttactatt aaagatagaa atgggaactc acaagagttt gatattacag    91920
atgagttaag aattacagag tatacaatac aagaggactt tatgcaacaa tcagctaaat    91980
atgctttttg ggcttctata ttagagaagg taagagcata ttctgaaatg gaacaaagaa    92040
atctagaaac aattggtagt aagctaaacc ttacaattag acaagagtac gaacaacaag    92100
```

FIG. 19XX sequence.txt

| | | | | | |
|---|---|---|---|---|---|
| gtaaaaagcc | tactaaagat | atgattgaat | ctagtgttta | tattcatgat | tcttaccaac | 92160 |
| aacaacttaa | agttgttgag | gcttggaatt | ataaagttaa | acaacttcaa | tatgttgtaa | 92220 |
| aagcttttga | gacaagaaga | gatatgatga | ttcaattagg | tgcagaatta | cgacaaacaa | 92280 |
| ataaaaatgg | tggaattact | aatccatttt | cacattaaaa | aataaagtaa | agaatataat | 92340 |
| tgacaaatat | aaaaaactat | gttataataa | ataagtaaat | taattaaaag | gagaaaagat | 92400 |
| aattatggat | ttcaatcaat | ttattaacaa | tgaggcaagc | aaattagaaa | gcaataacag | 92460 |
| ttcttttaac | aataatgtag | agagctacaa | acctaaaaac | cctgtactac | gtttaggtaa | 92520 |
| tattaaagat | gcaaacggaa | ataaggttgt | taagaaaaat | gcttttgtac | gagtattacc | 92580 |
| tcctgcacaa | ggaacaaatg | ttttctttaa | agaatttaga | acaacaggta | ttaactattc | 92640 |
| taagaaagat | ggttctcaag | gattcacagg | attaacatta | cctgcagaag | aaggttcatc | 92700 |
| tgtccttgac | ccgtacattc | aggactggat | aacaaatggt | gttcaattta | gtagattccc | 92760 |
| taataaacca | ggagtacgct | attacattca | tgtgattgaa | tactttaata | acaatggtca | 92820 |
| aattcaacca | aaaacggatg | ctcaaggaaa | tgtaatgatt | caacctatgg | aattatctaa | 92880 |
| cacaggatat | aaagaattat | tagctaactt | aaaagatact | atgttaaaac | catcacctaa | 92940 |
| tgcacctcat | agctttatct | cagcaaatga | agcattctta | gttaatattg | ttaaagctaa | 93000 |
| gaaaggtgaa | atgtcatgga | aagtaagtgt | ttatcctaat | gctcctttag | gtgcgttacc | 93060 |
| gcaaggttgg | gaacaacaat | tatctgacct | agaccaatta | gcaaaaccaa | cagaagaaca | 93120 |
| aaatcctaat | tttgttaact | tcttaatcaa | taatgttaat | aacacagagt | taagtcatga | 93180 |
| taactttaaa | tttaaccgtg | aaacaaatgt | cttaggtgaa | gaaccttcag | agcctaaaca | 93240 |
| agcacctacg | caacaagatg | tagatagtca | aatgccaagt | aatatgggag | gacaacctaa | 93300 |
| tcagcctcag | caaggtcaag | taggtcagta | tgcacaacaa | ggtcaaagta | atggtcaagg | 93360 |
| acagcagtta | caaggtacac | aacaacctat | caataacacg | caatttggtc | aaggaactcc | 93420 |
| ttcaggacaa | caaccaagta | acacaggttc | tgttgattgg | gataacttag | cgcaacaaca | 93480 |
| atcacaacct | gattcaaacc | cattcaatga | ttttgatgtt | agcagtgttg | atgattcaca | 93540 |
| ggtaccttt | gagacacaac | ctcaaaatac | acaacaagca | cctgaaccac | accaaactac | 93600 |
| acaagagcct | ccaaaacaaa | aacaaacgca | aagtattgac | gatgtattag | gtggtctaga | 93660 |
| cttagataac | ctataagata | tagagtgcct | tagagcactc | ttttatttga | gatataatta | 93720 |
| ctaggaggat | attaaatggc | aagagcaaaa | aaaggtaaag | aagtagattt | aacagattta | 93780 |
| aatacaattg | atttaggtaa | agaattagga | ttaacattgc | tatcagatac | aaacagagca | 93840 |
| gatattaaaa | acgttatacc | tacaatggtt | cctcagtatg | actatatttt | aggtggaggt | 93900 |
| attccattag | gtcgattaac | agaagtttac | ggtttaactg | gtagtggtaa | atctactttt | 93960 |

FIG. 19YY sequence.txt

```
gcagttcact tatctagaat tgcaacacaa ctaggtgtta tcactatttg gattgatatt    94020
gaaggaacag cagataacaa tcgtatggaa caacttggtg tagatgtttc aaaactattc    94080
tctattcaat caggagaagg tagacttaaa aatacagtag aattatctgt agagcaagta    94140
ggtaaagaat tagaatactg gattgacact ttcaatgaaa agattccagg agtacctatt    94200
gtatttattt gggactcatt aggggctaca agaactcaga aagagattga tggcggtatt    94260
gatgagaagc aaatgggtct caaagcatca gctactcaaa aagtaattaa tgcagtaaca    94320
cctaaactaa atgatacaaa cacagggtta attgttatta accaagcccg tgatgatatg    94380
aacgcaggta tgtatggtga ccctattaaa tctacaggtg gtagagcttt tgaacatagt    94440
gctagtttac gtattaaggt tcataaagca tctcagttaa acagaagag tgagttaact     94500
ggtaaagatg aataccacgg tcacattatg cgtattgaaa ctaagaaatc taaactatca    94560
cgaccagggc aaaaagctga agcagactta ctatctgatt atatggtagg taaagaagat    94620
gaccctatct tattaaatgg tatcgactta gaacataccg tatataaaga agcagttgaa    94680
agaggtttaa ttactaaagg agcatggaga aactatgtta cattgaatgg tgaggaaatt    94740
aaacttagag atgctgaatg ggttcctgta cttaaagata atagagagtt atatctagaa    94800
ttgtttagta gagtttatgg agaacacttc cctaatggtt actcaccatt acttaataac    94860
aaagtaatcg taactcaatt agaagagtat caagctcttg aaaactacta taagaatgg    94920
gctacagata ataaacaaga agaacaagag gaagaactaa aaggagaatc tcaagaaaag    94980
gattctgaat aatagatgga taatttaata gataaaaaca tgagtcaggt aaaagaatct    95040
ttggggaacg caaattcctc agatgttctt cctttacctt ataaagatat agcaaagaaa    95100
tttgaagaag taaaagaaaa aggtgaatca attatcattg aagaaggtgg attcccttat    95160
acagattcta cagtgatgta tatagaacat gtaacagata gatgggcagg aggatattcc    95220
ttaattagac atgaaggtga ggaagtaaaa gtacctaaga ctatccattt ctctgatata    95280
tatgttaaag ataaatcaca caaagtaaga ataatcttcg aggggctaa tccttatgaa    95340
gaaagctaat aatggtaata gatatgtaat agatatagat ggtataccgt ttgattttga    95400
aagagattta gatagtttac ttaataggta taaaaacctt agatggtctt tatatcatag    95460
atacgcaggg attttatcta atgattttga aagacaagaa ctaagagaat atattgatga    95520
gcaatttatt aaattagtta aagaatataa tattagaagt aaagtggatt ttcctggata    95580
tattaaagct aaactaactt taagagttca aaatagttat gttaagaaga atgaaaaata    95640
taaacgtact gaaattatcg gtaaaaaaga ttatacagta gagtccttaa cagaagattt    95700
aaatgaagac ttcgaggata atcaaattat gagttatgta tttgatgata tagaatttac    95760
agaggttcaa agtgagttac ttaaagaatt acttattaac cctgaaagag aagatgatgc    95820
ctttatcgtt tctcaagtag cggaaaagtt tgatatgaaa agaaaagaag tagcaagtga    95880
```

FIG. 19ZZ sequence.txt

| | | | | | | |
|---|---|---|---|---|---|---|
| gttgacagaa | ctcagagact | atgttagatt | taaaataaat | gcataccatg | agtactatgc | 95940 |
| taagaaagaa | ttaaataacc | atagagttaa | tactgaaaat | catatttggg | aaaactagtt | 96000 |
| acagtgcctt | ccttgtgtta | tattattatc | gagaattcaa | taataaagca | tagggaaggc | 96060 |
| ttttttctat | gtcttataga | atgctttaaa | atagattact | aaaataaaga | ttggagatta | 96120 |
| agcttatggc | taaaaagaat | gttaatgatg | tattacaaca | agaatctgtt | acagtagcag | 96180 |
| ataagtattt | acaagttaaa | gttaaccgtg | acggttatac | tcgtacacat | gaaggacaat | 96240 |
| atgcgtacaa | agtagtttca | gagggagaag | aattattctt | ataccctgta | caaacagatg | 96300 |
| gtaaaggtac | attaaatgta | atgaagaaat | cacctattgc | ttacactgat | ggagacaata | 96360 |
| tccatttcgt | agtaaacaca | gtagtagacc | cttataatca | ctcatttatc | cgtactgaag | 96420 |
| atattaaagg | attagataaa | ggtaaacaac | ttattcaagc | tttcttagct | ttcgttgaag | 96480 |
| accgtttcaa | atttggtgtt | tataacgtat | ttgttgcaaa | caacaaagag | gatgtattat | 96540 |
| ctattgtaga | ccctacagat | aatgatgcag | atgaagttaa | agatagttta | gagcacgcac | 96600 |
| atgaagatgt | aattgcggat | ttccctgcta | gccctgctcg | taaggacgtt | aaaggcgtag | 96660 |
| attcaggaga | aggtcaagga | gacacttcag | aaccatcagc | acctaagaac | gttcaagtta | 96720 |
| ctcctaagga | agacggagca | gacgtatcag | cagaataata | tatagataag | gatggtaaat | 96780 |
| ttggctaagt | taaatttata | caaaggtaat | gagttactaa | acagcgtaga | aaaaacagaa | 96840 |
| ggaaaatcaa | caatcacgat | tgagaattta | gatgctaata | cggattaccc | taaaggtact | 96900 |
| tttaaagtat | cattctcaaa | tgattcagga | gagtcagaga | aggtcgatgt | tcctcagttt | 96960 |
| aagacaaaag | caattaaagt | tatttcagtt | acccttgacg | ttgatagttt | agaccttaca | 97020 |
| gttggagata | ctcaccaact | atcaacaact | atcacgccta | gtgaagcatc | taacaaaaat | 97080 |
| gtgtcatttg | aatcagacaa | atcaggtgtt | gctagcgtaa | catcagaaga | cttaattgaa | 97140 |
| gcagttagtg | caggaacagc | taatgttact | gtaactactg | aagatggtag | tcacactgat | 97200 |
| attgttgctg | taacagttaa | ggaacctatt | cctgaagcac | ctgcagacgt | aacagttgaa | 97260 |
| cctggtgaaa | atagcgcaga | tattactgta | taagaggaca | ataaagaatg | gaaaagacat | 97320 |
| taaaagttta | tagtaatggt | gaagttgtgg | gctctcaagt | agctaataac | gatggagcta | 97380 |
| ctacagtatc | tattacaggc | ttagaagccg | gaaaaactta | tgctaaagga | gattttaaag | 97440 |
| tagcatttgc | taatgattca | ggtgaatcag | aaaaagtaga | tgttcctgaa | tttacaacta | 97500 |
| aaactcctac | tgaagaacct | tcaggagacg | cataataatt | aagaccaact | aaaagttgg | 97560 |
| tcttttttta | ttgacaattt | ataatatcta | tgatacacta | tataagaatt | aagaaaagga | 97620 |
| ggggaaagta | atggatattc | caacaatatt | atttagaaat | ccatatgatt | atacgaaagt | 97680 |
| aaaaaaatta | atggaaaaca | aagagcagta | tattgtagta | aagtttgatt | ctgtttctgt | 97740 |

FIG. 19AAA

```
                              sequence.txt
tcataattta aatgttcaag gtatgatgaa tgtcatccaa gattacctac acatctatgg    97800
ttacagagtt aaagagtacg gacaagaaaa ttcttctaaa gatgatgaaa gagacgttaa    97860
aggctactta tatgaaagag taggtgagta gggtatggga attatagtaa actccaacca    97920
tattcaatca gacactttat atgagtatga tagcttttt gatattgaga aagtagatac     97980
atttgaagaa ggattgcttt caatacagga tgagccaact gttttagcag gattcatcta    98040
tgatgatatc acatttaata aggtcattaa ttctaattca gatattgatg actatattaa    98100
gaataatgat atttattatg tctctgatat aggattactt cctgatactt ttatcactgt    98160
tgattctgat agaaaatatt attcattatt acaacagata actgagttaa gtaaagaccc    98220
ttttcctaaa tgggtagagg atgatgcaaa aggtttaact aagtattata actttcaaga    98280
ttttgaagat gtatttgatt taaatagttt ttacaaaaaa gaagttgaca tggtaagaga    98340
aaagtgctat aataatggta atgtatattt attatatgag gttctgcctg attataaatt    98400
acctctagct tatagtttac tttcaaacaa ggagcatggt attgttatta tcggttcaca    98460
gacacgttct aataatgata tactgacttt ttatgttaaa ggtatggatg ctaaggcaat    98520
agctagtatg ttcaatgtag aacatgatta tgattctaat attttccata catttgtaaa    98580
cagtcacatt aatatttag gaaatcaaat aactaagttt ataagagaga aaggaagcag     98640
ttatgagtaa ctataaaaca atagaagaag tacaagcagt tattattggg gtattattta    98700
aagatgaagg taaaattata acatctaagt ttaataaaat tactaaagag tttggtttag    98760
atagaatcgg taaagatgac cttaaagaaa ttgtagagga tatccgacaa gacgcttatc    98820
taaatgaact taaaaacaaa gcaattaaag gtaaagtaac gttaggtgat ttaaaagatg    98880
ttgcagataa ccaagtattc gaaggtaata actaccatga agaagtatct acttatgtag    98940
tagctaaaga aaaagaattg tctcacttaa gagaacagcg taagcacaat aggcatactg    99000
catacctca aattatgttt gatgaactta agaacatat ggttaaggaa ttacaagggg       99060
aaacattagt agaacatcac ggaagtaaag ctaatattaa tgatacagag ctaattgtgt    99120
tactatcaga tttccatatt ggaagtattg tatctgatat gactaatggt aaatatgatt    99180
ttgaagttct taaagcaaga ttaaatcatt ttattaatac aacagttaaa gaaattgaag    99240
atagagaaat ttctaatgta actgtttact ttgttgggga cttagtagaa catattaata    99300
tgagagatgt taaccaagca tttgaaacag agtttacttt agcagaacaa atctctaaag    99360
gtactcgatt acttattgat atcctgaatg tactatctaa tgtagtttca ggagaactaa    99420
gatttggtat tattggtggt aaccatgacc gtatgcaagg taacaagaat cagaagattt    99480
ataatgataa cattgcttat gtagtgttag attctttatt gttattccaa gaacaaggac    99540
tattaaatgg tgtagatatt attgataatc gtgaagatat ttatactatt agagatacct    99600
ttggcggtaa atctattatc attaaccacg gagatgggtt aaaaggtaaa ggtaatcata    99660
```

FIG. 19BBB sequence.txt

```
tcaataaatt tatcttagat agtcatattg acttattaat tacaggtcat gtacatcatt    99720
tctcagtaaa acaagaagat tttaatagaa tgcacatcgt agcttcatct ccgatgggat    99780
ataataacta tgctaaagag ttacatttat caaaaactaa accttcacag cagttattat    99840
tcataaataa ggaaaataaa gatattgata ttaaaacagt attttagat taaggatggt     99900
taataaatgg atacaatttt tattataggt gtagcgttta taacttttgc aacatttaac    99960
atagtcttta gattatttga tttatggact acagagaaaa aaatggtaag tcaaggacaa   100020
cctccactaa gtaactttga gtactatcat gtgatagtac cttacttagt aggtgttatt   100080
gttattatac tgagtattat ttttagggat tccttgtatt ccgcacaatc agggttcggt   100140
gttattatta caagctttat ttacatgcta gtttatgtta taattggtct tgtagggtca   100200
tttgtactta caatattcca agctagaaaa gctagacagt atcaaacaca ggaggataat   100260
aatgaagttc aatgatattt atgagcaatt aattaaaaat gatacagtac aaaacattca   100320
tgagtctcaa gatgacaaag gaaatattta tacaatacag tttgataaag gtaatgataa   100380
gtatttattt aatgttatta atgatggatt cttgaaagaa atgacaaatg gtatggtaga   100440
ccatcctgaa ggtcagccat attcagtaag tttaatcaat aaagaaacac ctagtatgtc   100500
agtgaaacaa tatttaacag atgtagaaga tattgtacct actattagaa aaatggaaaa   100560
ggatttctta tagagtcaag tctttacttg actctttta ctatatatgg tatattaata    100620
tagaggtgac ttaaaaatgg atttaatt tagtgctttt gataatagct cattagcaat     100680
gagaattagt gagggtgtat actatttcaa tgatacgcct tattacttta ttgagcatgt   100740
agaagaagaa atgtctgagt atgttattgt atatgacata catgacagag aggaaaaaga   100800
aaatcctcag aagaaatata gaatagaacc ttaccaacgt acaataccgg gaggaacacc   100860
tcttagtaat ttaattaaga gtatgatgcc tcaacgtaag tatcctaaga aggttacaga   100920
agaccctata tttgtagcta atgttattcc tttaggaaca gatacagtaa caggtaaaac   100980
cggtaaagga tttttttgaaa gagataagga tagaactatc tattctcaaa aggaaccaac   101040
taaagtcgtt catggtcaat acacaggtgt ttttataggt ctaacaagtg ttaagtggaa   101100
tagaacatat accccttag aaagtgttgt tgagtactac aaaagggtta aaggagatag    101160
gttaaatgtc taatgatgta gttaagttct atgaaaaaga tattaaagac cttatcagaa   101220
ctaaaaaaca catgttcaaa gacgatgaaa taactagtga tataaacgat atacgaatct   101280
ttaatgagaa agtcatttgt caaggtaaat gtagaacaga ttgtttagtg ttagaccgta   101340
atggtacagt aatgggtata gagataaaaa cagaacgaga ctctacacaa agattaaata   101400
accaattaaa atattatagt ctagtatgta agtatgtata tgtaatgtgc catgacaaac   101460
atgtacctaa agtagaacaa atacttaaaa ggtataaaca taatcatgta ggtataatga   101520
```

FIG. 19CCC sequence.txt

```
gttacattag ttttaaaggc aaacctgttg taggcaaata caaagatgct acaccatcac    101580
cacatagaag cccttatcat acaatgaata tattatggaa gacaaactta atgacaatac    101640
ttagattgat tagagaccct catacgtata gaacagggta tagctataat gctagtggta    101700
gatatagtgg aggggaaggt aatttctccc aaacaactca aagtaaaaga atgaaaaaac    101760
ctgctattat taaccaaata attcattatg taggggtaga taatacttat aaactcttta    101820
caagaggtgt tatctatggt tataataata ggtgggaagt tatagaagaa gatttcttta    101880
atactatgaa gaatggggta agagtaatta atgagcaaag acaaaccaaa tagacgtaaa    101940
gagatacagc atcaacctgt taactttgcc cctacgaata ctttaacagg agctaataat    102000
agtttctttg ctaaaaatcc ttcagagcct aaagatgcaa catctgttat tgaatatcgt    102060
atactattta ttaaaagatt tgataacgta acaagtacag atgtgaaatt acagaaaaag    102120
tatgcactaa atcttattag tgaagcactt gatgttaaag aaacttactt gtctcttaag    102180
caaaaaggaa aaaaaacaga atctattttg catacagata gagtttatta tgttcataga    102240
ggtaaaaaac ttattggaaa gtgtagtatc agagagcaaa gaacatttaa gggtaaacat    102300
ttgatattta tattcaaaac aagacataga gttaaagcag aaaggaaaga taaataatgt    102360
taaaaggatt ttcagaacat gtagacaaac ctacaactag taagacctta tacaagacct    102420
taacaagtgg taaagtagaa ttactaggtg tatcttacga tagtgattac ttcccttcag    102480
gtgttacagt acaatcttac attgaggata taggtaatga agatgagggt ctacagtttg    102540
ttaataaggt aaatgtagta gaatcaatga acaggctgt agtaggtatg aataatcaat    102600
taggttcttc aggtcttggc tatgtgagaa ctgaacaact taaaaaagag ttggaagaga    102660
ctggactaat gacagattta cttgctagag gtactaactt aacctctact aagaaagtag    102720
atattgtaag tacttttatt gagcctgagg taacatacca aaatattact atagctaaag    102780
atattaaact acgtttgtat aaagtagaag aagaatcacc attaaatggt tacactcata    102840
ttgtatactt acttactaca gaaaaactat atgatggtca aacactcttc ggtatgctct    102900
ctaaaaaaga taagttatct aaaggagata ctgataaatt attagcattc ttcagaaaca    102960
atagtttaat aagtaaaagt gtatttgtg ttaagttatt aagtaaagac tactactta    103020
atttatataa tacacatgag acagggatat tcttttttaga agacacagat gttattacta    103080
ttgcttgtgg tcagtcatat gttaaagtta acactaaaga tattaagtct agttatgtta    103140
aaattgaaga taagactcat aaattaactg agctagtaat taacctaaag ggtgacgaca    103200
cattaactat tttattctag gaaaatgtta taaatatgtg ataattaagt ataaatatac    103260
gttatataag aagttttcat aatgtttta atacagaaac tagttaagtt ttttctactt    103320
gctctagttt ctgtgaaatt atatttatga aaagttaaaa tatcttttag gtaaaggctt    103380
tgtaaatagt taaaaaatat attaaaattt tatacaaagt agttaataaa attatattac    103440
```

FIG. 19DDD sequence.txt

```
atttatatat tatgaaataa taacagaaat tgtgatatat tatatagtgt aaccttgaaa    103500
cagttgatgt tgtagggttt gtttatgttc gttaaactgg tttcaaaaca tcagttacca    103560
taaataaatg acagttaagg agagctatat aatggctaga aaaagaatt tacgaaataa     103620
aaacagtgat ataaaagttg ttcctgataa agaaaaagaa agtatattat ctaagctata    103680
ccataataaa ttactacgtt ctaaggtaga taatgcatta gatgaagata tgagttatga    103740
tgatattata gaactatgta aagaatatga tttagaattg tctaaatcag ctattacaag    103800
atacaaaagt aaaagaaaag aagctattga aaatggttgg gatttaggag aattaattga    103860
taaacgtaaa aaaacaagtg taaaagatat taaggaaaaa gaaactccta tattagaaga    103920
ggagcaactt tctccattcg aacaatcaaa acatcacaca caaacaattt atgatgatat    103980
tcaagtacta gatatgatta tttctaaagg tgcaaaagga ttagagtttg tggaaacttt    104040
agaccctgct ttaatgatac gtgcaatgga aactaaagat aagattaccg gaaatcaatt    104100
aaaaggtatg tcatttattg gacttagaga attacaatta aaacaaacag ctcaagatac    104160
agctatgagt gaagtattat tagaatttat acctgaagag aaacatgaag aggtattaca    104220
acgattagaa gaactacaaa atgaattcta caaaaatcta gatttagatg aggaaagtag    104280
aaaattaaaa gaagctcttg atagagtagg ctatacaatt tagatagtga ggttagagta    104340
atggcagatg agattagttt aaatccaata caagatgcta agccaattga cgatatagta    104400
gatatcatga catacttaaa aaacgggaaa gtactgagag ttaaacaaga caaccaagga    104460
gatatccttg ttagaatgag tccagggaaa cacaaattta ctgaagtatc tagagactta    104520
gataaagaat cattctacta taaaagacat tgggttctct ataatgtatc tgttaactct    104580
cttataacat ttgatgttta tctagatgaa gaatattcag aaacaactaa ggttaagtat    104640
cctaaagata ctattgtaga atatacaaga gaagaccaag aaaaagatgt tgctatgatt    104700
aagaaaatac ttacagataa taatggtaat tatttctatg cacttacagg agaaacaatg    104760
ctctttgatg aaaataaatt aaataaagtt aaagattagg gttgacagct tctatagttt    104820
atgatatagt atatgtatac taaaaataaa ggagctaaca attatgttta tttcattaaa    104880
tcaagaagag aaagaattat taactaaaga ggaaagtaaa tacacaccac tagaaacatc    104940
aagagagttt aacacaccta aagaagaatt cattgtaaca agttataacg aaggtaaacc    105000
cttagattac attgcaaaag aagctaaggt aagtatggga ttaatttaca cagttctaaa    105060
ctactataaa gtaggtaagc gtaataagaa atcacctgta gaagaaagaa ttgcacatat    105120
cttaaaagat aaaaacttag tcaaagagat tattaaggat taccaatata tgaatttaca    105180
ggacatttat agtaaatata atcttcataa gaatggttta tattacatct tagatttata    105240
ccatgtagaa agaaaatctg aacttaagga caaagcatta gaagaggata atattgtcgt    105300
```

FIG. 19EEE sequence.txt

| | | | | | | |
|---|---|---|---|---|---|---|
| tgagtaagta | aagaggttat | aatatgagaa | ataaaaaatc | atttcaagag | cagttaaatg | 105360 |
| acatgcgtaa | taaagagaaa | tgggtatctg | aagaggagtt | cactgaagaa | gtggctcctt | 105420 |
| ctgaagaacc | tgaagtagaa | gaagaaaaac | tatatacttt | aaatgagtta | aagagaact | 105480 |
| tactagatgc | tcaaggatta | aaagatgttg | tagctgattt | tcctgcatct | aaagatttat | 105540 |
| atgaacctaa | taaactatat | atttgtacaa | taccaaaagg | atatcgttct | acagaagtac | 105600 |
| aaccaggtca | atatattggt | atcagtacag | gattattatc | agaatcagaa | gatttagtc | 105660 |
| atttaagagg | tcaaatgcct | agaaatcttt | atgaaacttc | tcatgtttta | aaacctttag | 105720 |
| tacgtattaa | taatacaaat | ctcgaatatc | aacagcatga | gttacttgaa | gatattaaag | 105780 |
| atgacaagaa | gatatacgat | gttgaattag | aagacctgag | attagtaaca | ggagaagaaa | 105840 |
| tatcccattt | agaaattgtc | gatagtaagt | tttttgaaag | tcgtattaat | gaaattctag | 105900 |
| accgctatac | tgaattaacg | gattccgatg | atttgcttat | atactatagt | aaattacgag | 105960 |
| aattagttgg | tagtgacaaa | atgatttatt | gttcactttt | agataaatgt | gttaaaatta | 106020 |
| tagattaata | gttagtctcc | tcttatatta | taactgtaag | aggagacatt | tttgtataga | 106080 |
| ggtgttaatt | atgtcaagaa | aagcaagtat | attctatata | ctagtggtta | ttgttttggc | 106140 |
| tttttctatt | tcatcttatt | atatatcttc | tttcatgtat | cacgacaaag | caaagaatga | 106200 |
| agtctctact | gagttatcaa | acacgggaaa | gattaaagaa | gaaaagaacg | tagaatttgt | 106260 |
| cggtgactat | acacttaaaa | aagtggaaaa | taataaagct | tattttatgg | aaacattacc | 106320 |
| tacttaccta | cccggtagaa | caggagataa | cagcatagat | atgaggtact | acaaaacaag | 106380 |
| tagatttaaa | gaagggtaa | atttcaagct | tattagggta | tatactgaag | atggggaaga | 106440 |
| taatccaatt | cataagtata | ggtttgaagc | agtaccaacc | aaaaagtaat | aaggaggtga | 106500 |
| cttaaatgac | aacattaatt | gtcgtcatct | ttattgctat | catttattac | ttatggaaca | 106560 |
| gtgattgagt | caagttaatt | cttgactctc | ttttgtttt | atggtatatt | aatatataga | 106620 |
| aaggagagat | taattatgga | aatggcagat | ttagaaagat | tcgatacgtt | tgtaagatta | 106680 |
| gtttcagatg | atgagctttc | ggaggagaga | gcattagaat | taagtgtaga | cttattaaat | 106740 |
| ccgatactag | aaggaggtac | agcttaccaa | gctaaaaaac | gcattagaag | taagttcggt | 106800 |
| aaaatagaag | caaaaaactt | taaagaaat | tataaattct | tactcaagtc | gatagctcaa | 106860 |
| atagaccaaa | ggagatagga | caatgataga | aagggaaaag | ttagttaaag | aaattgaaga | 106920 |
| tgctaataga | gacatacaat | tgaggttaaa | agaagtagat | gattataagg | atagtatacg | 106980 |
| ttctaaagga | acaagaaact | atgtatctac | taaggtatta | gattcagtta | tggtagggct | 107040 |
| aattataagt | ttctttattc | ttgtaatgtt | acgtgtactt | gaatattttg | taacaggtaa | 107100 |
| tgctgtttat | tcacctttag | cacccgcagt | tattattatg | tttgttttag | ccttaggtac | 107160 |
| atggaaagta | agtaaaatga | ataaaatagt | atcctatagg | ggaactatta | agatgtactg | 107220 |

FIG. 19FFF sequence.txt

| | | | | | | |
|---|---|---|---|---|---|---|
| ggaattaagt | aatgctgaac | agaaccaagc | taaggtattt | aagtatccta | atgatgaagt | 107280 |
| agatattgta | tcaaaacata | acttaagaca | aataactttt | agtgagatta | atatacttca | 107340 |
| tcttaaatat | atgagatata | ataaggcagt | agaacagcat | actaagttat | ctaaagaact | 107400 |
| tttttaaaaaa | gataaagaaa | ctgttgacaa | gaataaataa | gtgtagtata | gtattactaa | 107460 |
| aggaggagag | atattatggt | tatacctagt | attaaagcac | aaaacaaatt | caagaatgaa | 107520 |
| ttagagtatt | ataagcaagg | tcacattagt | gaaagtaaaa | tgttagaatt | agcttttgat | 107580 |
| tacattcaag | aattagaaca | aaataatgaa | tacgttacta | atttgctaga | agaggagaga | 107640 |
| tacggtgagt | aaatttattg | gagtgtactt | atttaattta | ttagtagtag | cactaattta | 107700 |
| cacagtagga | tttttattct | tttatggtgt | agctagctta | gttattattt | taactcatgc | 107760 |
| tactattgac | ccgttcgtat | tagctacttt | cttaggaata | ggattcttag | ttattagaac | 107820 |
| tgcacacaga | atcatggcac | gagtaattaa | tgatgcagta | gctaaagcta | ttaaggataa | 107880 |
| agaaaatgaa | taaaggggaa | tttattatgg | ataaaacatt | accaaagttt | agtgtatatg | 107940 |
| aagttattgt | aaagactgta | attatgacac | caacagaagg | aagttctgac | ctagaatcat | 108000 |
| tttactttc | aactagagag | ttagcagaaa | gatttgttga | agaaaataca | gtggaaacaa | 108060 |
| aaaacggtaa | acgtgtatct | tttgctgtta | aagaacgtaa | agtaaatcaa | ccaggctaac | 108120 |
| attaatttgt | tagcttttt | tattgacaaa | tcattttata | tagtgtatag | taatattata | 108180 |
| cagaaaagga | ggaattatta | tgaaagtttc | agaagaagta | aaacagagtt | atctagagaa | 108240 |
| tagagctaat | actaaaatgg | ataagataag | ttggtctgag | ttaaggtcta | gtcctttagg | 108300 |
| tattaccta | ggtgatatta | tatttatag | tgtggttatt | atagataaca | ttatagctat | 108360 |
| tattttaact | ttaaccttaa | taggtactat | tactgactca | attgagagta | ctttagccca | 108420 |
| aataatcgta | gggatgttca | taatcattac | tatatatgga | atcctatcag | cgttaatacc | 108480 |
| tattctagtt | cataaagctg | tatcaccggg | atggagctat | actgaatgga | atgaatccta | 108540 |
| ttacatcaga | ttacctggag | aagagaacta | caagtactat | agtaaatggt | atttagattt | 108600 |
| attaggagtt | aaagaatttt | actataagag | agacaatgga | gaagaagtaa | aagaaaaaat | 108660 |
| atatcatggg | cttttcaagc | tgaagtaaaa | agacctgaag | atgttaacca | ctggaaaaac | 108720 |
| caattgctta | ctaatagacc | tttaacaatt | ttagaatata | aaaaattaaa | gaaattagat | 108780 |
| aaggaaagtg | aaattaggaa | acaagaagat | ttagaagaat | ataaacaata | caatagtaat | 108840 |
| taaagaggtg | gaaagcaatg | ataagctcat | ttgatagtat | actacttgtc | atatacatta | 108900 |
| ttatagcttt | tgcagtagct | atggcaatta | tctacttagt | atttaaaggt | atgactattc | 108960 |
| tactagataa | gctaatgatg | ttattattaa | gtaaaactac | attagatgta | gaagcttgct | 109020 |
| ctatgataat | ggcagtcatc | agtacaattg | tgtttggaat | tatttgtactt | ttaatatggc | 109080 |

FIG. 19GGG

```
                         sequence.txt
tagcagtaaa taatatttta ctataaggag atttactatg gattttaatg actttataaa    109140
cagtgaatcg datagggtag gtaagcctaa acaaaagaag aaggtagaga ataagctacc    109200
ttcttctact cctattgaag ataaggaaaa gaaattaaaa gagataagaa agaaatcatt    109260
atatattgat ttaaggagaa aaagaaatga ctaaagaaac aaatgtactt tacaaagata    109320
agtatagaga ttatactata gttgtaagat tagcagggaa tattattgtt actgaagtag    109380
ataagaaaca taaaacagca tttacaccta ttatatttga caatggtgta gaaggcgtag    109440
agcttgtaat gcgtataggt tctgtagagc ttagcatgac agatttacgt gagttcacaa    109500
aggaagtatc tacagctcag aaagctttag aatattttaa taaaaaactt tatattaaag    109560
gcttgacaga tgaagcattt taatatatac taaaagtata aataaaataa agaaaagagg    109620
aatgattatt atgttattag gaatttttatg gtttatatgg ggatttgtat cgtactttgt    109680
attgatgttt ggaattgagt tttggaaaga tagatggatg ccaggtgtta tcggagcagg    109740
agctttacta ctattcttat tttggattat gaaatctatt cataatgcta tgacagtagt    109800
atacttgtat taggaggttg tatagatgat tgatatacta gttattcact atgaagaaac    109860
aaataaacgg gttttaaaag aaacaataca aacaatacaa aatcatttaa atgatgaaca    109920
tggtttggtt aagatgacag caacaaaact tagcagagag aatatagaga aaagatttaa    109980
taactataat atagtcattg cagaagatga ccctgataat tcttatcatt acggtgaagc    110040
tgtagaagac gcagatttta ttatagacat accaatttca tatttagata tacatgcagg    110100
aatagaatgg gatgttgata atcctgtaga tatgctagat aggaatcctg atttttataga   110160
agctgtaaat aaactaaatg aagacttaat gttataagga ggaaatagaa tgctaaatga    110220
aaaactaaaa aacctggaag atacaaaagt atacatgatt aatagtattg caagtttact    110280
aagcgcaagt acaggaaaat caagtaaagt attttttgat gaaggaacta ttaaaattgt    110340
aagtggtgaa acaaaagcag tagaagttat tgataactta gttcaccctc actcaggacg    110400
tttacctatt aaaacaacag aacgtattgc gctaggtaga ttaacagatt ctttacagtt    110460
tgttatctca gaaatagaag tagttaaaga ccaaattata gatgaagaaa atgaagctta    110520
cattgatttt gtgatggaag actggaactg ggattaatgc ctatggactt attaactatt    110580
gcttctgttg cttttatagc tgtagtcatt attgatttga ttaatgatga tatgagctat    110640
atgcttactg gtactgcaat cttaataaat atttgggcgg gattttatgg atggttttc     110700
ttactacaag caggtatgtt actttctta ttattagcta ggaaggttaa agatgataag    110760
gagtcaatac tatattccag tgcttcatta atatgtgcac taggaatgat aataaatctt    110820
ctttcatttt cttaaaaata agtattgaca cctttgtact tttgtattat acttagtata    110880
taacaagtac aggagatgat taatatgagt aaagaaacaa tcagaagaca attttcaaat    110940
gcaattgaga ttatggcaac aactaaagaa tggtggaact ccctaaaag ttttgatacg     111000
```

FIG. 19HHH sequence.txt

| | | | | | | |
|---|---|---|---|---|---|---|
| aataaagaat | ttaaaattaa | aacttttaaa | aatgatacac | ttgtatttga | agttagagaa | 111060 |
| ggtagtagaa | acttaggaag | ctttgtagtt | tttacaaaca | ttgattttga | ttatgataaa | 111120 |
| ctagaaggaa | cttcaacaca | atatatgatt | aattactttg | ctaagaaatt | aactaaagat | 111180 |
| atgtttaact | atcataagtt | acaattatag | taggaggtgg | aaagatgaga | gaagagttaa | 111240 |
| aaccttttaa | taggaaacaa | gttaatgtta | aagggtattt | agatgatgtt | aagtactcaa | 111300 |
| agcgtagaag | acataagggt | aatcaacatg | ggtgtgttaa | aatcacagtt | actgatgtaa | 111360 |
| agattaatgg | tatacctatt | gaccacgtta | acattgaagt | tggtatctct | ttctatgaaa | 111420 |
| aactaaagga | gcttcaagga | aagagaatcc | aatttgtagg | cactgtttac | aagtatgtta | 111480 |
| aacatgctag | agggcgcaaa | ggtagaatta | aaggatttta | taaagaggat | tatagcgtaa | 111540 |
| ctttagataa | gaagttacaa | aaggaggaaa | aataatgact | gaatggtatg | ctttatgcta | 111600 |
| ttatgataaa | gtaggtaaaa | agaaaatacc | taggcaagtt | agagcgcaca | gagatatttc | 111660 |
| agtattagaa | gaattaaaag | aaagattaga | agaaagaaat | cctaatacag | aatactctat | 111720 |
| aaaaacaaca | aaagaatttg | atgaggagag | ataaggatgt | taacaccaca | acaaaaagat | 111780 |
| tcattaaaag | aacaacaaaa | gaaattaagt | aaaaagaaga | ataactgtt | gacaaatgag | 111840 |
| tgtgcatagg | ttatacttaa | gttaacaaat | aaagaggagg | tatgacctat | gttattcata | 111900 |
| attttattc | tagcagtatt | ctttgtacta | ggatttatta | acggatggaa | ctcagaagac | 111960 |
| taaaaagga | gtggttatag | tgaagttaga | agataaagta | ttagaaagaa | ttgattctct | 112020 |
| tggaggtaag | ttaggtgata | ttagccaaca | tgcttgggaa | gctttagtaa | agtaccaaat | 112080 |
| tatatatggt | attatagacc | ttatagtagg | tattgtagtt | atagcattaa | ctttattttt | 112140 |
| atggaaggta | tttattaatc | aacataagaa | ggtaaatgat | atggatagag | atgatgatta | 112200 |
| tagtttacta | tttgaagatt | gtgaagattt | atcaggcata | ggtttgtttt | atgtaatagt | 112260 |
| tacatcatta | atatcactat | ttgcatttat | atacttaatc | tatggaatac | ctatggatat | 112320 |
| tataaagata | ttaaaccctg | aagtatttgc | agtaaaagac | ttaatagaac | aagctaaagg | 112380 |
| aggaaattaa | tatgaaacaa | agagatttcg | aatttgaaga | ggattttgta | ttaacttatg | 112440 |
| aatgtgagga | ttgcaaacat | ttcgaggatt | ggggtcatga | tgaagagcct | gaagaatgca | 112500 |
| gtgaatgtgg | tagtagtgac | ttaattaaca | atacaagtca | tgaagacact | gagtgtgata | 112560 |
| tgtgtaaagg | atacattgat | atgtggcaag | atggttatag | atacatggga | gataataaag | 112620 |
| cataccttga | aaaagaagat | tcaggtttaa | tttgtgaaga | ttgctatgag | aaattagata | 112680 |
| tttaataagg | aggaatttat | atgaataaag | cagtagaaca | agcaagtaac | gcagtaggtc | 112740 |
| aaggattttc | agccatggta | tggcatcaag | tattagtagg | tctagggttt | attttattag | 112800 |
| ggttgatatt | atccttacta | gtttgggtac | tagtgaaaaa | atttcatgta | cctttaatc | 112860 |

FIG. 19III

```
                                  sequence.txt
acccaacagc ttttgttgta tattcaatta tgttagttag tattgttgct agttttattt    112920
ggggcggttt acatgtaatt aaccccgagt attacgctat cttagaactt aaaggtttta    112980
taaagtagga ggaattctat gactaaagaa gagttagagc aaagagtaaa agaacttgaa    113040
gcagagaata aagaacttaa aaaacaaata gaacgttttg aagacgaggg aggaaaaaca    113100
aaagatgaat agtagacaaa agaaaatttt aacattaaca gtaagtaact ttttaattct    113160
agccttagat actgtagcac taattagata taaaaaaggt aaaattaaac aagagaatta    113220
taacacaggg caaattacaa gaatgatagc tacaacagct aactcattag gtattcttta    113280
cttagaagag caagagcgta aagaagttaa agatattaaa gtaggtactt ttgaaattgg    113340
agccttaaaa agatttacaa ataataaata aaaaagttt aagaaaccta ttgacattag     113400
gtttcttttta ttatatacta atattataag aaataaggag gttaacttat gaaaggtatt   113460
atcatatttt acaaggaaga gaccaaagag gattaggat atttcttgg gtttataaac     113520
tttaagctag aaggattatc ttacacaact gaaggtactt tagtagataa tgatgtagta   113580
gttttaaagg ataaccaaat taatgaggat aatttagagc agtttagtat gtcaaacaat   113640
aatttagtta ttggaatact aggtcattca tctcttcag tacgcatcta tgaaaaaggt    113700
attagacaag agtttgatag agtagaagaa tatttagagg agttgagaca ataatgatat   113760
ttatattaat ttttggttta ctatttattt tatctttact aggtattttt atttattcta   113820
tagttttacg aaagaaaaaa caattaatag aagaaagaga atcatttggt atttataata   113880
gaacaaaaga aaaactgggt gatgtaacac gtttagggta tgaggaagat gtatataagt   113940
taatccataa ccaatctaat aaaacaatca tagaggataa aaagagtaaa gttgtagata   114000
caattaaaaa gatgtatgaa ttagaattaa catctgtaga tgtttctaag gtagaaggat   114060
tatctccact tgatacagaa cctatgacaa atatgaaatt actttcatat aagctagata   114120
gagaaggatt atatagttta agtaaattta tttaggagtg atacaatgga atttatagat   114180
aaaaataatg taattaaagc ttatgatata ccaaatgttt atttaaaagg ttatgtatta   114240
caggcatgtg ataaaaatgg agatacaaca gcttatgatg gttatgacca aatacactat   114300
aaagaaggta gagtattaac attccctttt gataaaccat taagaaagat aaatgtacta   114360
tcaggatatt acaaactatt taaaaggag gacataatat gatttatttt gttagtgatt    114420
tacatttcgg tcatgataat attagagaat tcgaagcacc tacaagaagt cactggaact   114480
cagtagaaga aatgaatgaa ggtttaattg agttgtggaa taatacaatt acaaataacg   114540
atattgttta taacattgga gacttctttt tcaatatgaa accttctaaa gtagaagata   114600
tacttaatag actaaattat aaagagatga tactgattgc aggtaaccat gaccataaga   114660
aacttataaa actatatgaa cgtaatggta ttacagtaaa gtacgcagac atgattaaaa   114720
aggatggtaa gagattttat ctaagccatt atcctacact aataggtaga aaaacatgt   114780
```

FIG. 19JJJ sequence.txt

| | | | | | | |
|---|---|---|---|---|---|---|
| ttaatattca | tggtcatata | cactcacaat | taatgggtac | tgaatatcac | atcaatgtag | 114840 |
| gttatgatgt | agagggtaaa | attgcctata | gttttgatga | tattataagt | agagcaggtg | 114900 |
| aatataatgg | agaaattcaa | aggtaaagat | ttatataaaa | ctagaattag | aaaacaaaca | 114960 |
| attaaaaatt | tagttataaa | aacagagaag | ctacataata | aacacggaaa | gtatagacct | 115020 |
| attggtcatg | tttattatta | tccaaaaaca | aaagagttta | ctttatctaa | acctgagcag | 115080 |
| aaaatattta | tagagtatat | gaaggcatta | ggttttagtg | ttaaacataa | gagacgtaag | 115140 |
| aaaataatta | tagtatacaa | gaatgtgtta | gatgaatatc | ttagtatgta | tcaggaagca | 115200 |
| attgaaagta | cgtgttgaca | attaaggtat | actatgctat | agtatagaaa | aggaggttaa | 115260 |
| ctgatgaagc | attttatttt | gattttaggt | attgtaattc | tagttattgc | attaggtatt | 115320 |
| gttttacctg | catggatttt | acaattagta | ttatctgcat | tcggtgttaa | agtaagtatt | 115380 |
| tgggtatgta | tcgggatatt | tattttaatc | agtgcagtag | gaagtatgtt | tagtagaaat | 115440 |
| taaaggagga | actataaatg | gcaaaatatg | aatcaaatat | caatggagaa | aattatattg | 115500 |
| caacaccgtc | acaagcttta | agagaggcat | tggcagaatt | aattagagaa | gaaaagaatt | 115560 |
| ttgcagagta | tcaaactaag | ggtgaggaac | agtatgaatc | acagttacaa | ctaagacact | 115620 |
| ttgattcaat | gatttctcag | tatgaagagg | ctattcgagt | actagaggat | agatattcac | 115680 |
| ctcagatttt | tattccaaaa | gataataagg | aggaaaagta | attatgaaag | cagaatcaat | 115740 |
| agcaagattt | tttcaggata | aggtattaca | aatagaaggg | tataaagtaa | gattcactca | 115800 |
| agctagttca | tcatatattt | tagatataga | tactatggat | gaatcagtat | tgttttaga | 115860 |
| tactgtagtt | ttcactctat | caggcaagta | cttattagat | acgcacatta | caattaataa | 115920 |
| acctgagaca | ctaagttcta | atgaattata | cacagagatt | agtaataaac | tacaagagat | 115980 |
| tgtaggagac | caaactaaaa | cagatataga | gttatcaaaa | tactttaagg | aggtaaaata | 116040 |
| aatgagttca | gaagctatta | caaatcattt | attaaattta | aatcaaataa | aaattaaaga | 116100 |
| atataatatt | catgcttaca | ttaaaaaatc | tgtttgttcc | ggtattgaaa | atgcagattt | 116160 |
| tgaagtaaga | ataaactata | tagcagacaa | agaccctaac | tatattagaa | ctattaattc | 116220 |
| tattattttt | gttgattaca | gtaaccgtaa | tccaaaagaa | attttactac | agtttaaaga | 116280 |
| aaaaattctt | tctattgtaa | aagaacaggt | agagattgat | aatgattta | ttgaggctat | 116340 |
| taaagatatt | aatacaaatc | atgaactaga | gaaattagaa | cctttatta | ataaagaata | 116400 |
| ctattctatg | tttaagtcat | ctattgaaaa | agaggtacca | gtagctttat | catctgaagt | 116460 |
| acttaataga | tgtacaggta | aaacaagcac | actagcttat | ttagctattg | aaaaggattt | 116520 |
| acctttaatt | gtgtctaaca | attctatgat | gaaaatgctt | aaaaaagatt | acccttctgt | 116580 |
| taaagtttcg | tctgttgaag | atttctcaaa | ctataatatt | aaaggtgaaa | ttgtacttat | 116640 |

FIG. 19KKK sequence.txt

| | | | | | | |
|---|---|---|---|---|---|---|
| agatgaagta | gatgtagacc | agttatatag | tgcagataga | gtttctgttg | atgcactact | 116700 |
| agtaggtatc | ataaaaaatt | aaataaattt | gtaaatacct | gttgacagca | ggtattttt | 116760 |
| atagtatact | ttagatgtaa | agaaaaagga | ggtagtaata | tggttggtat | tataatttta | 116820 |
| attgtcggtt | taatattatt | tttagctagt | ggatataaat | tagttttagg | taaatattat | 116880 |
| gatgacatag | atttaaagat | gttatttaca | atctttggta | ttggtgctat | actattactt | 116940 |
| acaggattta | tattataaag | gaggaaatta | caaatgaact | ataaagaagt | actagaagtt | 117000 |
| attaaaaaga | ataagccatg | taaggttaga | tttactggaa | gtattttagc | aatcgttaat | 117060 |
| aaggaattta | atgcagatac | tgataaaggt | atactacaaa | ttgatgtatc | aaatattaat | 117120 |
| aaaaatgact | acattaagtt | acaacagtat | tgtttagaaa | gagatgatta | tactgtagca | 117180 |
| ggagctattt | tattttaagg | aggagtaatt | atgaattata | gagattttat | tacggattgt | 117240 |
| attagttgtg | gttataaagt | ccacattagt | gttactgaga | aaagagttca | cattatttca | 117300 |
| gaaatgacat | cagcatctta | tccaaagaaa | gaaattaatt | tggatgaatt | acaagcttat | 117360 |
| gtttattata | tgaataattt | tggaagtcag | attacaacgg | agggattata | aatggaatta | 117420 |
| gttattaata | ttatagcagt | attaattggt | atgtatggta | tttacttta | tgttacaaaa | 117480 |
| tttagtactg | gtctatcagg | tatcttaatt | gtactaggta | tggctgtagg | tctttacttt | 117540 |
| tacttagatt | acttaaatgt | tagagagaat | gttattcgat | tagtatctgt | aatgtttggt | 117600 |
| gctttcttat | ttagtatcga | gatgatttat | aataagatta | tgtttgaaat | taaaaaatct | 117660 |
| aagtatgata | agactgttag | aacgtacaga | ggagaccaat | aagaattta | ctataaagag | 117720 |
| tacttaaaat | aggttaagtg | ccctatatgg | taccttaaaa | tggcttagaa | ttgaaattaa | 117780 |
| ggagatgaaa | agttattata | gctactaaat | atattgtatc | tattgaacga | tggtaaataa | 117840 |
| ggaggagtag | ttatgaatgc | taggaaagca | cgtaagaaca | ctaaaaatca | taaagactct | 117900 |
| agtgtagtaa | ctaaggagca | acacctaact | tatatctata | ataagataaa | ctacttgatt | 117960 |
| gcaaatagta | gtagtcaggg | taagacatat | gtggtaatga | acctaagaac | aggttatcct | 118020 |
| gacgagttct | ctttatctaa | attaaaatat | ctaaagaaa | ttaaacagca | ctataaagac | 118080 |
| ctaggattta | ccgtacaaac | tcaagtaaga | aagtcacggt | ggtcagagaa | aagtataatc | 118140 |
| aggtactact | ttaacttagg | ttatatagat | agcgtgttag | ttcctattat | acacattagt | 118200 |
| tggtaattac | aaggaggaat | agttatggat | aatccaaact | taaataaaaa | gacactgaga | 118260 |
| gctgtaataa | gagaaatgga | taagatata | gaagaaagag | cagaagcatt | aagaagagaa | 118320 |
| gagactagat | taagtattgc | tagggataat | agaaaaaggc | tttacattga | attagagtct | 118380 |
| atactagagg | aggaataatt | atggattta | atttgaaaga | ctatgctgta | agacctataa | 118440 |
| cagacaaaga | aggaaatatg | gtagtaagaa | cagtgtatgt | gtgtttaaag | agagaataca | 118500 |
| gtgattgggt | agtagataaa | gtatatggta | gacaagagag | ttctgaaacg | tggttaaaat | 118560 |

FIG. 19LLL sequence.txt

| | | | | | | |
|---|---|---|---|---|---|---|
| ttatgcaaga | aattagaaac | atagagagag | caaaactaag | agtggagaaa | tggcaagtta | 118620 |
| attagaataa | ttagttaaag | gagggaaaga | tatgagttta | tcagaattat | tagagtatca | 118680 |
| taaaaatagt | ggtaaggaac | gagcagagta | tataagtgat | aatggtaatt | gtagagtagc | 118740 |
| tattatgcat | tatgataaat | gggcagttgt | aggagattta | gagaatgcag | tctttacaat | 118800 |
| tgagaagtaa | tagttatgta | cttatttgct | aaaataatta | ttatatctat | tgatgttata | 118860 |
| cccttaatgt | ctattattgt | tgtacagtta | attacagatt | ataatgatag | acattaagta | 118920 |
| tcgaatattg | ttgactagta | agaagaagaa | aatattacta | ttaagaagtt | aaagttaccc | 118980 |
| gggaatattg | ttgactaaca | ataataagaa | gaaaaaaata | ttattactat | taagtacctg | 119040 |
| ggaattcttt | tacctctccc | actcagccta | ttacttacta | ccgacttccc | taactactta | 119100 |
| ttctatagtt | atagtattca | tttattatac | aatacttaaa | ctatagtatt | ctaaccttaa | 119160 |
| tctatgctga | agcggtatta | atctattgtt | attatataat | aatcttatct | aatagtggta | 119220 |
| taatctaggt | tattacatta | gaatgattct | aatctagtat | tttaatcttt | agaccctagg | 119280 |
| aaaagtggta | ctaaaatata | gaaccctata | ggtacgggat | tcttattttt | aaaattacta | 119340 |
| aaaagtatta | ggttttccct | agggtaaagt | tttaatgtac | ttaaaatcgt | aagtagctcc | 119400 |
| ttatcattta | ggtctgttta | attgagaata | ttagaagata | tccgcttcaa | ttacaattaa | 119460 |
| gtgttgacaa | tcatgaagcg | gtatgttata | cttagtatat | aaattaatag | gagatgaatt | 119520 |
| aaatgattat | accattaatt | atactcatga | tgaccttcgg | tacatttgca | ttcagttatg | 119580 |
| ttgcacatga | tgcatacagg | gtagatgaaa | aaggtatcat | gtatgctatg | gtagttggta | 119640 |
| ttgtagttat | aaatgtaatt | ggtttagaaa | tgataattgt | agaatgttta | tagaggagat | 119700 |
| gatttaatat | gattgatatt | tatttacaca | gtgaatatga | taaagataag | ttaaaattta | 119760 |
| tccttaaagc | aataagggat | ttttctccta | gagaattaac | ctacgatttt | aggaatccaa | 119820 |
| aagcggatgt | tagtatccag | gaactactag | gagatgacat | agacatattt | gaatctatag | 119880 |
| cattagatta | ccctaatgat | attaatatcc | ttgtaggaga | tagtggatac | tcgatagttt | 119940 |
| atcagaatga | ttttcttaca | attagtggat | tgagtacggc | tatgaaggag | gtaataggat | 120000 |
| gataggattc | acaatattaa | gtacaataat | ggttatctta | gttatagcta | tgtacactca | 120060 |
| ggtgttagta | gatatgattc | agtcaatcag | gtatgataga | tttgataagg | tacttaacat | 120120 |
| agtaacgttt | atagttatga | cagttgtact | agtatcaggt | attttaatta | tgtttgacat | 120180 |
| ttagagctta | tttaagaagc | ggttaagtag | ttaaggataa | attggtctag | aaatatacta | 120240 |
| ccgcttctct | atggctcttt | aaataggctt | agaattgaaa | ggagatggaa | taatgaaagc | 120300 |
| aattgtatat | tgtgctaaaa | gatatagtaa | gcatacactg | aagcatattt | tagaggaatt | 120360 |
| agaagcggag | aatagtgact | taacatttag | tacagaaata | tcagatttag | gggaagtaga | 120420 |

FIG. 19MMM sequence.txt

| | | | | | | |
|---|---|---|---|---|---|---|
| tattgttgta | caacatacta | aattaccttt | ctcagaacta | atggatttgt | gtagtaaagt | 120480 |
| aagtaaaggg | tctgaccgct | tctatgtatt | tgttggtaat | cactcagggt | attatataaa | 120540 |
| cggtgattta | tatatcaacg | agataggtaa | gtttattaca | tctagagaaa | ctaatgttat | 120600 |
| gatgtagagg | aggagatatt | atgatagaaa | ttagattagt | tgaaggctat | gataaaagtc | 120660 |
| agttgaagtt | tatgttaaag | aaaattaaga | gagtagcacc | tagggaatta | acttatgata | 120720 |
| tagaagcggg | gatagattcg | gtagatgtta | atattgaaga | tgtacttcct | cataaatcac | 120780 |
| cccaggagta | tgaaagatat | tcaatgttac | ttgaagaaga | cttatggata | gttatacttg | 120840 |
| agtcaggtta | tatagcttac | tgggatggaa | agaagtatgg | tggtgaagct | ttagatgata | 120900 |
| ttatatataa | tatgtttaaa | gggagaggga | gactataatg | atagaagtat | ttttaagtaa | 120960 |
| agattatgat | aaggatttac | tcaaagctta | tttagagtat | attagaaagt | ccgcttcaag | 121020 |
| agagttaaag | tataatacta | accatactaa | aggaacggat | gttaatattg | aaaatattat | 121080 |
| tagttatact | aatcaagagg | ttcatcattt | tagctcttac | ggtatgtata | gagatgactt | 121140 |
| atgtgtattc | atagataata | caagagtatc | tgagtatctt | aatggtgaac | ctgtaggggt | 121200 |
| agatacaata | tataaatata | taaggagat | gtaatggatg | tttaaagtat | attatacagt | 121260 |
| ttatcataga | caaagtatga | agactattaa | ggataagtta | gatagaagcg | gtttaatcta | 121320 |
| tttcttatat | gaaacttggt | ataaagatat | aaataatgta | tgtccttcta | actataaccc | 121380 |
| ggaatttggt | agtcttaata | aagatataga | catagataga | ttaattgaag | cggttaatga | 121440 |
| agaagggata | ctacttatta | accatggtaa | ttatgttaca | gtagaagagt | ggtaggatgt | 121500 |
| tgacaaatca | taagtagtgt | ggtatgatta | aggtagaaat | tttacgataa | actcgtagga | 121560 |
| taaaaccgta | ggataaaaaa | ggaggataga | atatgataga | tattgagata | aaaatttggg | 121620 |
| atgaaaccct | taggatgcag | gttgaagaag | aggatgtact | ttccttctta | tctaagttta | 121680 |
| aaaataaaac | aacaggtgat | aaagaagaat | cttatggagt | agggttagat | gaatctaaat | 121740 |
| ggaaagtaca | cccattctat | acacgttatg | aggtacaccc | tgaaggatac | gttaggttga | 121800 |
| aggatactaa | aacacctgta | atatttacta | agtatagaaa | agaacttcac | cataaaccac | 121860 |
| agtttattag | ctctaatata | atggatgatg | aaggtaagca | tacagtagct | ctacataagt | 121920 |
| tagttgctga | tacatttata | cctattccat | ggtatttaca | gggatataac | tatacagatt | 121980 |
| tatcagtagg | cttgaaggat | ggagattatg | aaaataaaga | agcggttaaa | gcatataact | 122040 |
| tagcttggta | tgtaggaagg | atacgaggta | atgctccaat | gattaaactt | atggacttag | 122100 |
| aagatgatag | agtattatac | tttgctagta | ttcctcaaat | agagaacttt | attagagata | 122160 |
| ataaattaga | ccctaaacgt | tttaattaca | aaactgaata | aatgataagt | agagagggct | 122220 |
| taagtagtcc | tcttttattt | aggttagaat | aattagtaag | tagctcctcg | taatactaag | 122280 |
| tagttcctga | tttttgata | tagttgtaag | tagtcccctg | gtaatccccc | cagtttatcc | 122340 |

FIG. 19NNN sequence.txt

| | | | | | |
|---|---|---|---|---|---|
| caaccgcttc | aagcagaccg | caataagaat | ccccaggaat | tatattccca | gggatttcta | 122400 |
| taattttttt | atttaattaa | gatatgtttc | aatatattct | tcataaattg | cacttgctaa | 122460 |
| atcattgtac | ccgtctttt | gtttttcctc | cattaaccaa | ttgtaatcta | cacttaaact | 122520 |
| gaataaataa | tcttttctt | ttacatcaat | taaatttctt | aattcattct | caaagatatt | 122580 |
| aacttgatac | acatagttta | cttttttaa | taggttgtgc | acctctttat | tcaattcttc | 122640 |
| tttagttccc | tcaaatttaa | attccattgt | tatcaatcct | tttcatttag | ttgttaaggt | 122700 |
| gtttgattac | cttacaaata | ctattatatc | agattgagga | taaattgcaa | taggttttg | 122760 |
| aaacttttt | aaattctttt | tgtgttgact | tgatcgacct | ataacaacta | tttagtaggc | 122820 |
| tttttgaat | atgtttttc | tgtttcttcc | attataaaca | aaaaataggc | tcataaaact | 122880 |
| ttttaaaaga | atttgtaaat | atgtattgac | ttattaatca | tatgatagta | atataaaggt | 122940 |
| acagcaaggg | aacagcaaca | agatattaga | attatataaa | aaaattattt | aattggagat | 123000 |
| gatttaaatg | gatgtaaaag | aaattgcaaa | tactataatg | gagttgtggc | aaatggacgg | 123060 |
| ctacagatgt | acagaaccac | cattatatga | aagcacatta | aaccatacac | gcacatatac | 123120 |
| ggctttaatc | gtaagcatta | aaggaaacta | tgacactgtt | caaatgttcc | gcaaaacgcc | 123180 |
| tataatgagc | atgagagggc | aagcccaacc | ggctagtatg | ttagtaaatg | taattgatga | 123240 |
| tgtgattata | atcgtatatg | aaaatgttgt | ttacggggta | cagaataaag | aaataaaatt | 123300 |
| tattgaagaa | atttaaaaat | aggggttgca | atacccctta | agatgtagta | atataataga | 123360 |
| tgtaagggat | agcaacacac | cttaaaaaac | tttttaaaaa | gttaaaaaaa | gtgttgacac | 123420 |
| cttacaagat | acatgttatt | attagtatag | aagttaagac | aagccacata | gcaaataacg | 123480 |
| aaattaaata | aaaaaattat | agaataggat | ttgattatta | tgacaaacaa | aaattactta | 123540 |
| tatgaagaag | ctcacacagt | acagggaac | gaaattacgg | ctttcagaat | tccaaatgac | 123600 |
| gcaaacggca | acccacgtta | tgtagtgcat | ttcatggatt | taaatattaa | actagcagac | 123660 |
| tatgacaaca | tcaataaact | ttacggattt | aataaatatc | gtgctaaatg | gtttggcggt | 123720 |
| ggtgtagtat | tccaaagcta | taatatagaa | gatacattaa | attttgcact | agataaagtt | 123780 |
| aaagaaatag | aagcggttaa | gaattaaaac | cgcttctgaa | ttaaataaaa | aatttatata | 123840 |
| aaaaggatat | gataatatga | aatttaaaat | agaaaaaaat | aacagtgata | taaaaacttt | 123900 |
| atggaattta | gctaaaaatg | gatatatgag | ttatcaaact | gtacacaata | tatttaaaaa | 123960 |
| tgaatcagat | gaatttatta | tatttaacag | taaacaaact | tataataaat | ttatggaatt | 124020 |
| aagatataat | agaagtgcaa | tccaatagta | taaaaaaatt | atacaattcc | ctgggattaa | 124080 |
| attcctaggg | atttttattt | gttttaattt | atataaaaaa | attatttaat | aaataagtta | 124140 |
| gtgtaaaatt | gactattgac | aaggttgtat | tttttatggt | ataatgaagt | gaagaccttt | 124200 |

FIG. 19000

```
                                     sequence.txt
tttagtataa aaaaattatt atataaaaaa tttatattaa atggttttaa agcgggtctt    124260
tctcccaacc ttgtcattta tatagcggaa gggttaggct ggttaccgct gttttacttt    124320
ctatatatag aatactatga ataatggtaa ttgtcaacac ctttcagaaa ctttttttac    124380
tttcttttat tattatataa aaaaattata catattttag ggctccactt ccattatata    124440
ataattcggt attaatgtca atagataaat gtaaaaaagt tttttaaatt aatttcatta    124500
aatccattga cttgtgtttc tttctatagt aatatatagg tataccaaca agggaggcaa    124560
tacaaatgct aaaattcaaa tggaaaaaca aaacaattaa atcaactcaa aaaacggata    124620
acattctatt acttattata ggtggtttag ttgcaacaat cacacctaaa cttgtaaact    124680
ggttttact actacaagat aatataaata ttttttttaag ataactattg acaacctaga    124740
aacaacatgt taatattaag ataacaaata aatcaataaa ggaaatgata aaaatgaaaa    124800
aaatcacaac aactttaaac ttaatcggca tgaaaaataa tgaaaggttt acagaagagt    124860
taaaaaacta ccgtcaagat gttactttct tgaaagcaaa taaaattgta aaatattcaa    124920
aataaggctt gacaacttaa acactacatg ttattattaa ggtacaaggt aagggaagcg    124980
gtcaaccgct tccaacctaa ataaaaaagt ttaaaaaaac tattgacagt cacttgaaac    125040
catgatatta ttaagataac aaaaaacaaa cagaaaagga attgattata atgaaattta    125100
tcaaaactat cgaaaactta ttaactaaag cagaaaacaa agggcaagca attttaaacg    125160
gtcgttatta tgacggatat agaaacggtg agcttgaaga aaaatacgca atcgaaattg    125220
agggaaacaa attagttatg cgtcactggg gaacacaaac aattgagatt gacttaggta    125280
tgaaagaaat tgtttcatac tatggagaaa gcaactcaga ccgtgacagt ttaaacacac    125340
ttgtatattg cttaggaatt gcgccaaact ttagatactt accaagcaaa gacttattta    125400
tttacgaaaa ttaattaaat aaagggcttg acttccaagc cctaccatgt tattattaaa    125460
ttgtaaggta atcaagcaca acgacaaaat aaactgaaaa ggaattgatg aaaatgttca    125520
aattacaaaa taaagtggaa attatcgtac ctaaatatac taatagtggt aaagagattt    125580
caagccctgc aattaaagaa gcggttaaca atgcaactaa aatatgtgga ggttgtacga    125640
taactgaaat caagggacaa tggtggtcag acgatgaaca acgtattatg gaagatgaca    125700
acttaaatct tgagtggtac tatgacaaag gtatgcaaga catgaacgac caacaagggt    125760
tattacaagc cttatcaaag attgctagac aattgattgt attctatgaa caagaggcaa    125820
tcagtataaa aattaatggt acactatata ttatagatta tgaagattta gatttattat    125880
cttatgactt atatgaatta atgtttaaaa attaaataaa aattttatat aaaccgcttc    125940
ggattaaatt cttgaagcgg ttttttatgt aaaatttatg cttgacaaat gtattaaaaa    126000
atgagataat agagtgacaa ctttttttag tataaaaata atattatata aaaaagttat    126060
agagttttta aggctccaag tccattatat caatttact actggttgtc aatactttct    126120
```

FIG. 19PPP sequence.txt

| | | | | | | |
|---|---|---|---|---|---|---|
| tttttatat | aataatttaa | ttatcttaaa | gataccgtcc | acctccatta | tctcaaattt | 126180 |
| tgcccccaaa | gtcaagaact | ttctttcaaa | taatttattt | aaaaaagttt | ataaaagggg | 126240 |
| ttgacttatt | ttgtactata | gtgtaatata | taaagtgtag | taaggaagcg | gaggaaataa | 126300 |
| cctaaaaaaa | gaatttaaaa | aacttttaaa | aaggtgttga | caaacttcca | aatacatgat | 126360 |
| aatattaaga | tagttagaaa | aacaaaaaac | gaaaaggaat | tgataattat | gaacagatta | 126420 |
| gaaatagtaa | aagatacggc | aatggaatat | atccttatga | tggataacag | tgttatggac | 126480 |
| ggcgttatga | cacaagagga | atacaacgaa | gcggttagct | ttgaaaaggt | gtatgactat | 126540 |
| actctatcag | aagcaaatca | agaatgtaaa | ttcttaggtg | gtaaggtttt | aactttccta | 126600 |
| gtacatgaag | caatcgaaga | atacgcataa | aaaaacttaa | taaagggggt | tgaatgtcaa | 126660 |
| cccctaccat | gttaatatta | atatatacca | aatgagagga | attgataatt | atgagatacg | 126720 |
| aaatcgtaac | attagttaat | ggagaattat | tcatgtttgc | aacatttaag | aaagcagagg | 126780 |
| cagaaaataa | atatcaagaa | tggtgtgact | tgtacggtca | agaaaatgtg | agcatggaaa | 126840 |
| aaaattaaaa | taagcggttg | acaaactaac | cgcttcatgg | taatattaaa | ctatactaaa | 126900 |
| gaaaaggaaa | tgattacaat | gacaaaaaca | atcaaacaat | tagaaagcca | acttgaaaga | 126960 |
| ctagaaagaa | aatcagatga | gcaactagca | aacggatatt | atgaagcctt | tgaaagaact | 127020 |
| tgcgcacaaa | ttagagaatt | agacctacaa | atcgaattaa | aaaagaattc | agaaactgtt | 127080 |
| taaaaaaatt | aaataagggg | ttgacactta | accccttaga | tgttattatt | aatacataag | 127140 |
| gtaaaacaaa | taaggagga | aaacaaaatg | atgatttgga | tattgatttt | tatggtaatc | 127200 |
| cctttgtac | ttggattcat | taacggttgg | aactcagaag | aagaaaatta | aaaaaagtgt | 127260 |
| tgacacttta | aaaaatacat | gttaatataa | atatatacta | aagaaaagga | attgataaaa | 127320 |
| atgaaattat | taaacagaga | caatgaaatc | gtaattagca | tagcaacatt | agagagcgta | 127380 |
| aaacaagcct | taatttggga | atacatcgac | cacatagata | ataacatcct | agacagtgaa | 127440 |
| atctatgacc | aagaagcggt | tgtcgttact | tctaagactc | tacaatcaat | aaaatttgca | 127500 |
| gacactatgg | aagacctgca | ggaatacatt | gcagatatca | attggaaatt | agtttaaaaa | 127560 |
| agttttaaat | aactgttgac | accttagcaa | atagatggta | atataagagt | ataagaaaa | 127620 |
| acaaaaaaac | gaaaaggatt | tgattataat | gacaaacaca | ataaaggat | ttttacaaac | 127680 |
| agaagaagca | agcacagtta | aggacgtagc | aactcacgga | gtacaaagcg | gagcaattgg | 127740 |
| cagattaatc | tatacatcgg | acgtagtaaa | attctttgat | agacattatt | cagatattga | 127800 |
| agcggtagta | ttagacttct | tagaaggctt | tacaggtcaa | agatactatg | acctattaga | 127860 |
| ttatgacttg | atgagagaac | tcgaagagca | tgcaaatgta | gagtttgaag | acgaagacga | 127920 |
| atataataat | attcaatttg | acttagcaga | aaatattgct | tctgatgaga | ttgaaggatt | 127980 |

FIG. 19QQQ sequence.txt

| | | | | | | |
|---|---|---|---|---|---|---|
| cgaagacatg | gacgaagccg | agcaggcgga | tgcagttatc | gaagctatgg | acgatgtaga | 128040 |
| attagagata | ctagacacgg | ataaggtgca | gtttgttaac | ttagcagttg | agattgtagc | 128100 |
| acaacaaatg | caagaagcat | aagaccctgc | aggaagcaca | cagagacaca | cagagaagct | 128160 |
| taaccgcttc | tctaatataa | aactattagg | agatgttgaa | catgacaatt | aaagagatta | 128220 |
| taaaccaatt | acaagcagta | gaaaataagg | aacttgaact | attcgtatgt | gacaaggaag | 128280 |
| gaaataacat | ttcaattaaa | gatattactt | tgtttgatag | tgaagcggag | cacacagaaa | 128340 |
| acaacccatt | agggattaac | tattaggagg | tttataattg | aacattagag | aggttcataa | 128400 |
| tgtcgttaag | agtgcaaaga | gcaaactcct | acaggagcag | aataatatta | ataatgtaat | 128460 |
| gatagatgac | tacatcacag | aagagcttca | cagacgcaca | cagagaagcg | gaacaataca | 128520 |
| gatgaacaat | aacaccgctt | catatagtaa | tggctcatat | ggtagcttag | aagagattag | 128580 |
| agaagcttat | gacctatctt | cattatctac | taatgagatt | aaagaactgc | ttgaaacatt | 128640 |
| tgtttaaatt | attttatcaa | aacgctttac | aactatttaa | tttgtatgat | ataatgaact | 128700 |
| taacaaatta | aaagaaaagg | aaatgatgaa | catgagagac | ttacaagaaa | gaaaaagaga | 128760 |
| attgaaaaca | ttactattta | acttagctat | agagaagaac | agagcaactg | acgagacact | 128820 |
| aagaagtgta | ttagaagaag | cccatcaaga | ggtaggaaac | caactaagaa | aagtaagaaa | 128880 |
| agaaattgaa | attttagttg | aagaaaaaga | aagagaattt | tggaacgatt | tcgactttaa | 128940 |
| tggattagac | taagagggaa | taaaatccct | cttttatttt | tatcctatta | tataattttt | 129000 |
| ttatattata | cgggggcagg | ggtaaaatgc | cactcaatgg | gggtgggtct | atataccct | 129060 |
| atggtctacc | caggtactta | tttttgggg | aaaattatga | aaataaatat | tctaaaagtc | 129120 |
| aacaccccc | tattataagt | caacattaca | accctaccct | ataagtcaac | aatttataat | 129180 |
| ataaatagat | agcccttaaa | tataaagtca | acatatctaa | aataaaaaag | ccaccccttt | 129240 |
| aggagtgact | tagtgttta | atattttatt | tcttctccta | aaatgagttt | gttttgataa | 129300 |
| ctacctaatc | ttgtatatat | cttactatta | gggtctgatg | aatttatact | atttgtgcta | 129360 |
| ccataagcta | tacaactatc | taaccacata | tgactacctg | atgaagtttg | gaaatctttg | 129420 |
| ccttggtaac | tttcgaaagc | ggtacatcct | aaattccaag | attctgtacc | ttcatttaca | 129480 |
| tctgcgacat | taccgccatc | atttctagca | taaataccgt | ttactcgtat | agctttaaga | 129540 |
| ccatcatgag | ttgtggaacc | attatttgat | ttagtacctg | ctgttccttt | ttcgaatcca | 129600 |
| ttttctaaag | ctgtacaatt | aatttcaata | actaaaggtt | tagagctatc | tgcacctata | 129660 |
| tgataattaa | atccatccat | atagttatta | ttagctacac | tattattgac | gataacttct | 129720 |
| ttacctccaa | caatttctaa | accattacca | ttgacttggg | aagcatagct | cagtacacag | 129780 |
| ttattaatat | atacgctatt | gtcttggttt | aattcaaacc | tagcaggtct | agctccaccg | 129840 |
| tacagattta | aattttcaat | ataaagtca | gttggtacac | tagatactat | taggtgttgg | 129900 |

FIG. 19RRR sequence.txt

```
gatgataata gcggtacaac ttttttgtta ggttctatgg aaccgttatt aacataaact    129960
tttgtaccat cagagtacca agaaaaaagt gtcgtatcta ctttatctaa ggaggtaaca    130020
tttgtaaact ccctatcatt attaaaatct actaccttc taacggcgga acgtgtaaat     130080
tcataagtgc tatctctacc tgatgtttta gtccaagttg gctcatctgc cataaataag    130140
tttacatttg agcccaaacc aataatatta atactcttat tacttattgg tggaagcaat    130200
gtgcctccta ctctaaagta atcccgtca ctaacataaa gtgtatcccc attatttatt     130260
atgccttgag ctttttaaa tgttttaaag ggggttgatt gagaaagacc gtcattagta     130320
tcattaccat tttctccatc aacatagtaa gatttacctc ccctaagttt aaagttctcc    130380
atatttaaag aagtggaaaa cttacctaaa ccatctgtaa aaatattatt gacaagcggg    130440
tggtctttaa ttaagtaatc tacaggagtg aaaacaggta ttttatacga tgtttctttt    130500
ttcatagaaa ttttcatatt atcaatttct ttgattaatc ctttaatgaa ttcctcatta    130560
ttaactgttt gtattttctt agtagaagaa ccatcaaaaa gtagaaactg ttttatattt    130620
acaggtgaag taacttgtct tgtatctatt cttaaactaa ttttgcttga attttccggg    130680
atatttatat tattaattgc aaatgtcgtg tcatttattt tattaagttg agtaattgtt    130740
tgtatatatg aaccatcaga atcttgtatt gaatactcaa atgatgcttt cgggtcaggt    130800
acgtcatctg ttattatttt agcactaaat gttttacctg gtgcaagttt ttcaacagct    130860
ttaactgtgt aaaataacca accatttgaa ttaagtgtaa aagaaccatc ggggttcatg    130920
gtattttccg gtatactgtt tctaattgta atattagaga aatatgtttt atctactgtt    130980
gatgggtata aacgaatgtc ttctccatta tcagggtaca ctattaaact atcttccatt    131040
gttttattta cttcttgtaa attagagtca ctaggattaa caaaaactct caatgaatct    131100
aattgttctt cggtaaatct atcaaaagta aagtctttac ctggttcccc tgttttacct    131160
ggctctcctg gttttcctgg ctctcctggt tttcctggct ctcctggttc acctttaatg    131220
gacttaaccc attcttcttc tgtacctgta aaaccattat ctactgctat atcataagct    131280
gttttaggtt taacagttaa gatgtcttta gcataaaaag taatttcttt gtaagaagat    131340
tctaatgtag taaattcagg aactacagtt ttttccgact catagttatc cccttcccaa    131400
gaaacataaa actccccttg agggtactta gtatgaggtt ttaaatttgg tataataact    131460
gaaccttgct cagtatatac attataacct atggctagta tattgccttc tttatcataa    131520
gcttttaaat gtggcattta taaatctcct attctaatgt gttagtacat ataatatatc    131580
aaattgaata aaagaagagt attagttacc cttctttatg tttatatcgc agtctacgat    131640
attaagttca tgaatagtaa tcatatccat tccatcgaat cctcttgggt ctcctttaat    131700
gaactcttgt tctcctctat aattagtctc ttccctatac ccttcttctt taatacgttt    131760
```

FIG. 19SSS sequence.txt

```
aattaatttt tccttatttg tatatacatt gtcttctcta aaatgaaaat tatcttcata    131820
aggttcacaa ttatcatgtt ctacttgata tagtttcatt catttgtcct cctttactct    131880
ctataataat catatatttc taagtaaggt gaaaatggtg aatcacctct agtattaata    131940
ataacttcac cttcatgttt acttatctct gtaagctctt ctagactatt aatttctaca    132000
caccatcgtt ctagtgtaaa tggattacct ttttggtcta caagttctag tttctttata    132060
taggcaccct ctataggctt tttattaatg gtgcttgtcc tatctataaa aaattccatt    132120
agttttcctc cttttcataa gaccattcac catattctgc gttaaaatgg gctgtatccg    132180
tacccctcgtc ttcatattct acactatacc atgcatcctc ttctgtttct gcatctatat   132240
atcttacttc ctctgtagta ataatacgtt ttactttaaa tctctccata ttagttttcc    132300
tccttatatt ctttataact tttaataaca atcttacaga tacctctatt aacagctaaa    132360
aacaataaaa atgataacag agttataact gctctagtat ctcctgtgaa aggtaatact    132420
ttaaatagta aaacactttc taaaacactt gtagctgtga tagttgttag gtataagata    132480
gttagtaaat aatcttttaa ttttagctta acaaaaggtt ttttattatc ttgagttctt    132540
actataccat atagaattat aaaccattct acagttacga gcatagttat aaagtaatta    132600
tttatgtcta atgcatataa accataaatg atacctgcag gaataccaat aatgaatgct    132660
aaaaatacag agagtataat tagcattata agaagagcta caaggaatcc taagccttgt    132720
tttgagtact ctagtgtatt cttccctatg gctttaaaga atgttttatt catctgctac    132780
ctccttgtaa tatacagtat ctatatggat aatattgtct ttgaaccata tagatgtatc    132840
acctttgtta gattctaaaa atttaacacc attaaaaaca agaccccga taaaagaatt     132900
taaattagtt ttagtatctt tttgctttat aatagtagaa gtccctgata catcatgaat    132960
ccttataaaa ttaatatctt ttttacttc ctcttcttta tgttttttaa atatcattat     133020
tcttcctcct ttatattctc ttctaatatt tgttttaacg tctgacaatc ttttggtct     133080
aaagtattcc aactttctag attttgtaat tgatagtgaa attcatttac aatttcatcg    133140
aaggcttctg ctttttggta gacttcttgt aactcttcta attcttttc attatcaata     133200
caccagtagt tctcgttgtc agttataata tcttgaattt tattttata ttcataagcc     133260
attatttatc cctcctcttc tatagaatta ctttccgtaa tagttacctc tagcatgtta    133320
ttgtaatact cattcttttg attgatattg tagtagtcat tatattcatt aaagtctaca    133380
taagtgtatt catttgtatc atcatcataa ataatatcta tagctgtaat atctgagtat    133440
gctgtaatca tttcataagc atttgtatta tccggataag caaaaccaac ttgagatatt    133500
tctttagggt tatcaataag aataccaaaa taagtacatc tacgtgttcg acttatatgt    133560
gaagtaccat agtaatctat accttctgta attccatcta catggaacct tttacatct     133620
ttaggttcta gtcttacaac atcacaattt tctaatacta atcaatata ttttatattc     133680
```

FIG. 19TTT sequence.txt

| | | | | | | |
|---|---|---|---|---|---|---|
| attttaattc | tcctctttat | ttaaacctat | tatatacgca | atggactcta | acatcttcca | 133740 |
| ttactttacc | taatagattc | tgacctttcc | agttgctttc | atctaatatc | ttagggtcat | 133800 |
| ttgctttaat | acctacaccc | catattttat | catagggtga | tgcttctacg | aaatctttac | 133860 |
| gtaaatctgt | atctagtatt | ttttgtttta | agtgtgtagt | cataaattta | tctttaacca | 133920 |
| cttctaccat | aatgtcatat | ctcaccttat | tccattgctc | ttcattaaaa | ttacgaactt | 133980 |
| tacgacctag | acttttagca | tggttcggat | gcttagcatt | taatatttct | cctgctattt | 134040 |
| gccagtcttt | aaaatattga | gctttacgcc | acataaaggc | ttgttctgag | ttattaaatg | 134100 |
| ttcttccttt | gtgtttaaat | gttattgggt | aaaagttaga | atagatatct | tccttacccc | 134160 |
| aaaacataat | gtattcttta | gtctctttca | tattatctct | cctttaattc | cataatgatg | 134220 |
| gtaatacgat | tttaaagtta | tctagaattt | tgttttgtac | ctgttcaatc | tcgtcctcat | 134280 |
| tatcaacatc | aaagctatcc | attgattcgt | ggtagaattg | aattaaactt | aatatatgct | 134340 |
| ttatcatatc | tatctgtgtt | cttttctttc | cttctatatc | agtaaatgta | tggtactcca | 134400 |
| tatccacatg | attactactt | tctacaaaag | catttaaatc | agcatatagt | tgaataaaga | 134460 |
| aggacatatc | atagttccaa | tatttaggtt | catttctacc | taattcttta | ttcatttttt | 134520 |
| tgtatttttt | attcttttt | aatccaaaaa | cttcttttc | aaagtcattt | aatttaagtc | 134580 |
| ctttaaaata | tcttttcttc | atgagtttcc | ctccaattta | ataaaaggta | aatctatatc | 134640 |
| cctgaataca | gcacctacat | cacacattaa | catgtctcca | ttaatttcta | cttctccact | 134700 |
| gtcagttggt | gtatgaccac | atacataggt | aaaaccatct | tttctaggtt | gaaagtctct | 134760 |
| tgaccatatt | aattggtcaa | ttgtttgttc | ttctacaggc | ttccaactaa | ccccgcctga | 134820 |
| atgagagaat | atatacttgt | cttctttata | gtactttcta | caattaacca | taagtatttt | 134880 |
| aaattttcta | tagtcgtctg | attctttaag | tttctttagt | tcactttaa | taaaatcata | 134940 |
| attacttctt | aggttttctt | ctacactact | atactttaaa | gttaccgtac | tcacaccgta | 135000 |
| agagttaagt | gtttctatac | aatatcttga | gagccattca | atatcataga | tacttaatcg | 135060 |
| gtctacgttt | tccataacat | tataaaactc | atcatcatgg | ttccctaaca | gagttactac | 135120 |
| attatcatca | ttagacatta | aatcaaatat | atagttaaca | acgtcttttg | acctttacc | 135180 |
| tctatctaca | taatccccta | aaaatactat | tgtttcttta | ggttttcttt | cattgtttat | 135240 |
| tttatccata | attgttaata | attttggta | ttctccatga | atatcgggaa | caacgtatat | 135300 |
| agccatctaa | tctcctcctt | attgtatata | actatcttac | catacttagt | aaaaaaagtc | 135360 |
| aataaaaaaa | cacctattaa | tttaataggt | gtttatcatt | taatgttatt | ttaaagtatc | 135420 |
| attaccatgt | gctaattttt | tatcatctat | tgcatggtca | ttataaatat | atttaacctc | 135480 |
| tatatactgg | tcttcacttt | tcagtgcatc | tactatagaa | gcattattag | ttattgagct | 135540 |

FIG. 19UUU sequence.txt

```
tgttctaggg taagtaaatt tttgaccgtc agataaaata atagtaacat caacttcaaa  135600
gttaacaggt agtctgtatc cataatcttc caaataatta ataaagttat taagagaaaa  135660
tggtttatac ttgccatcta aggtatagtc aatatattca tttaatgcat cagtaagttc  135720
tgattctgtt aactccattg tatcataatc tttttcgtta tagaatacta caacattatg  135780
ttgttctata ctagaatctc cgtctttata cttagatata aaaaatccaa tatttccttt  135840
atgctctaaa taatctgctt tcataatttt aaatacttct tctgctatag gttttgctaa  135900
tagtgttacc cattcacctt tttctgcgtc ataaacacta ggtagtacgt ttaccatcat  135960
ttaaatctcc tcttcttaat ttattggttt aaaccacaat ttactcttat cacttggttc  136020
tgtttcacta actacgaaag agttagaatc aatgtttaaa gtattaaaaa caatttcttg  136080
tttgtcttca ttacttttttg ttgtaaattc gggaacatct gttaatatag actctttacc  136140
attaatagtc catgatattt taaaagaccc ttggctatac actgtattcg gtgtcagttt  136200
ttcaattata attttagcgg atgcacctgt aatttttttct gaagattta ataatttacc  136260
tttggaatca tataagttta atgttctctc cacaaattt atctccttta ctatattttg  136320
tacaattaat ataacaaaaa aacacctatt agtttaaata ggtgtccgac agagctcccg  136380
tacttagatt acggtaata atattttacg caactatat gagaccctct gtcgttgaaa  136440
ctcttgtcac tgcgttattc cacaagatat tttagaaggt agcttgtgga agaagattgt  136500
ttttaaaggt acaattagcg tttttaagcc tattcgatac ccaggacact atgtccgtac  136560
taactattac gtcaataaag gttctacggt ctcaattacc tactctttat tgttaaaact  136620
aaaattaagc ttgagtgctc tagaagccaa aatcaattaa ttaactatag atacggaatg  136680
gagggacact accatccgga gtctacggtc agatacaaag cctctgccgg gcaacatacg  136740
gtatctctcg tacatcaggt tgactagacc tttagagttt ttcactcctt ctcttataac  136800
cagtaactta ggagaaatag gttttactta gtagatatga aacaataaat ccacatacaa  136860
tattaaatca tagtcaagtg attgcacata tgtctaatac ctataagttt tttgctagcc  136920
tggtatatgg actctgcagg attcgaacct acagtcaaac cgttatgagc ggttggcttt  136980
acctttaagc taagagtcct agaaatatcc tgagagagga ctcgaacctc aacgactagg  137040
tagctacatc tagccaatgc cattactcag gattgctagt aacgctaaat agaattataa  137100
cgttaccgta gacctttct acgcttggta gataggtaaa atataatgat ttcaaagtac  137160
ccatatagtt aggctcttat tctcattata aggttaaaaa ggctaactgt gtttagcatt  137220
atataagagg ctttagttaa ctactatact aatagtatac cataaataat acttaatgtc  137280
aagttaattt atcaattgaa tccataattt ttgatgtact tcttatatcc gcttctttac  137340
tgtgtttaag aagatatttt                                              137360
```

FIG. 20A sequence.txt

<210> 781
<211> 166679
<212> DNA
<213> Unknown

<220>
<223> Description of Unknown: Bacteriophage F387/08

<400> 781

| | | | | | |
|---|---|---|---|---|---|
| cgttagcacc | tttataaccg | atggtgaagt | aatcctgacg | agcatactgg | tcgatgtata | 60 |
| cacggtagcg | accacccaga | acaccagcaa | atactgcttt | agtggtgtcg | gtattataac | 120 |
| cacgacccag | accctgagct | gccggagata | cgttggtatc | aacagctgcc | agtacgttaa | 180 |
| ctacgttacg | ggaagcgata | atgaagttac | cttcaccgcg | accggtctga | cgagcgattt | 240 |
| cagcggattc | tttgtcaatc | tggaacagca | gagctttaaa | gctttcacct | gcccaacgag | 300 |
| caccgcggat | atcaatcggg | tcttggaagt | cgaatacacc | agctttagaa | ccaacagtct | 360 |
| gggtcatacc | agatttacca | acctgagcgg | agtagttaat | ccagtcaaca | acttcacggt | 420 |
| tgatttccag | cataatttcg | gtagccagga | ttgaactcaa | ttcagcatca | gcgtccatac | 480 |
| cgtgaacagc | acggaggtcc | tgagccagtt | cgatggaata | ctgtgctttc | agctgacgag | 540 |
| atttcgcttc | gatagtttgt | ttatcgatac | ggaagcccat | ttcattccac | gggttatctt | 600 |
| tagaaccgtt | aaatgcttct | tgcagttcag | caacggaagt | agccatacct | tcggcgattt | 660 |
| ctacaacttt | accagcttcc | agagcagcag | taactgcagc | gtccagttta | gcagcatcgg | 720 |
| tagcaccagc | gtctacagtg | aaatcttcaa | caacctgcag | atgagcacga | ccggtctgtg | 780 |
| cgaaatcgtg | aacaacgata | tcaccaacag | tcagagcagc | accagcttta | actgcttcaa | 840 |
| acttctcggt | tgcaccctga | ccagagaaca | ttgcatccgg | agcgtacatc | ggatggaaag | 900 |
| cttctttagc | accagcagcc | agagggtctt | tgccgtaaac | agcgcggaga | gcgaatacct | 960 |
| gaccggttgg | gttagacatc | ggctgtacac | cacagatatc | gaaagcaatc | aggttaggga | 1020 |

FIG. 20B sequence.txt

```
tagcacgacg aaccatacccc ataactgccg ggccaatctg ggttacagca ccagaggtct    1080
gaccagctgc gatgttctgt gcatcataac cgtggtcacc gccaatttct gcttcagaca    1140
ggaaagaacc aaatgcttca gcgattttt  catcgcggta ttctggagcc tgattaatat    1200
cagcttcctg gttttcaaaa atcttagcga tcagagcttt tttgctagcg ccaacaattt    1260
ccggcagagc ttcgttctca agcagcggct gccattttc  gataagttta ttcttttca    1320
tgtgttgtat aaccttttaa attaagaaag acgagccgct tgggccacat aagcatccat    1380
aacggatggg gttttagtcg caggagtttc ttctactgct tcagttgtga agtttaaacc    1440
gtctgcttct ttgtcgatag tatttatatc ggcagattcc gttacagact gctctacaga    1500
accctgcacc atttcaacaa tagctttcag cttagttgaa aatgcgtcag aataatccat    1560
gccctctgtc agagaaacta ctttctcttt ttgggtatca gtcagttcac gggttgcttc    1620
ttggatagca tactcacgtt gggcataatt gatatactca tcgcgcttag aaacttcttc    1680
aaataaacga gcagtttctg cttttttgctc agcaagttct tcttccatct cagctactac    1740
gtctactgat tcttcaggaa ttacaacgtt gtgctcaaca aacagctctt tcataccgac    1800
aaacatggat tcaaacaggt cagctttaat accgcggtca accgccagct ggttttctgc    1860
catccattct gcagcgatat ggtcaaagta tttagaagca gcttctttca gctcttcgcg    1920
agcttcttct ttagcttttt cttttttcttc ttctactttt tcttctgctt tctcagcaat    1980
ctttttcaatg tgagattctg ccagagctac ggcgtgtttt ttgactgttg cttcgaatac    2040
agtgctgaag ttagcttttag cttccggaga aagctgaact gattcgaaaa tactgtcaag    2100
agcgacggaa gcatcgatag ttttagcttc ggtcattaaa agttctttaa gcatttttga    2160
tgtcctgtgt taagttacat aattatttat aacgctttta acttctctgc gagagccata    2220
aaagcatcat cagcactatt ggcaacttgt gccgaggtat tttccgaaat ttgtttcggt    2280
tgtacccatg catccggagc actaggaccc caaactgcgt ctacaccaac agtcaggcga    2340
aagccttctt gtacgatgtt atatccttt  cctgagtctt ttaaagaacc gagcccgcgg    2400
cttgatacac caggaatcca accagcacgg atgttagcgg ctaatttatc acctggaccg    2460
tggtctcctt cgatgattct tgcacgccca taaacatcgt tgcctttcca ccacatatct    2520
tcgataatga ttgcggcttg catcgggtca acatttgcgc gaggtggatg gtttaattct    2580
cctagagcct gacgagtagc aacctgttcc ttaatataac gacttaccgc agtctcaaga    2640
atgcgttttg gataaagacg tttattacgg tttactactt ctgcctgcat aaaaacacct    2700
tcaatataca gaccaggttt taagccagat tcatttcgc  cttcaacgat aatagattct    2760
agcatgggtt taccatcaat tacatcgccc ggttgacccc aatgctcaat taaaagttgt    2820
tcattgaggt tttccattaa cttagcccca gagcctgacg gcgtttaagt gctttcttac    2880
```

FIG. 20C

```
                                   sequence.txt
gtttacgtaa tccacgagtt tgagccgatg gattagcacg ttttgatttt actgctttac    2940
gcgcgatttg acggcgttta gctttagaaa gtccagttgt ttggaacgcg ttacgctcac    3000
gtgttttacg atccttagta cgtgtaatag tacctttaga atcaacatgt ttaacgataa    3060
attcatttag ttgtagagat tcattgattg aacctaaagc aattgctaaa tcaggctcag    3120
aaacaacaag attctctaca attttattta tatcatcttt agagagcgct gcggacaact    3180
tatcaaaacg cgcctgggct tcaggaagaa gagcttcgac agtgtcgata actaattcat    3240
gattttcagg cagtataagc attactcgtc ctcttcgtcg tcttcgtctt tatcagactt    3300
atcttcgtct tcgtcgtctt catcttcgtc ctcatcgggc tcttcaccct caatcatgac    3360
agacgctgcg ataaattttt tgcgctcttc aattaaacca gatgtccgtt cagccataat    3420
tgcaccaaaa gctttttttgg ctgctacgag gtctctggat tcaattgcgg aaatataatt    3480
ttccattaga aatcctcttc attttcttgg tcttggaagc gagcctcttt agactctaat    3540
tcaatttgct tggcttcttg ttcaatttct tcatctgaca tctgaaggaa gtctttcatt    3600
gctgtcttat gagaaatata cttgccgata aacggttcag ccattgtgag catattgatt    3660
ctacgctcca taacttcagc atctttcaac tcggtgaaat atgaatcttt atggaacaca    3720
atcttaatat tatttatttc gtcttcccac tcatctttag acaaaacttt tttaagaatt    3780
agattagtgc gaagtggatc aagcataatc tcttcgaatt tatgctgtaa tctacgaata    3840
aatttagcaa aatcaagctc atcgcgagta attgctgtgc cagcatcaaa ctgcacaccg    3900
ccttgattat ttgcatccgg catgcgcgaa agaggaactc gcaatgccat gtataacgct    3960
gttctaaagt aacggacgtc atccatatca ctcatacctg ataccagg aagagtatct    4020
acttcagtaa ctgctttacc atctctacgc tgcaaccaat agtcttctgt cattgacata    4080
ttatgttgct gatttttaat cttaccggtt gatgcatcat atacaacgcg attttttcatc   4140
gtgttcataa tatgttgcat atgagctgcc gctttacgag aaggcatatt accagtgtca    4200
atgtaaaaca cacgacggtc aggagcacga gtaatacgat aaattaccaa cgcatcttct    4260
aatagcttta actggttggc gggtttaacg gctcggtgta ataaccgat gatgttttga    4320
cctgaacaat caactagtcc agaatgtgca tatacgatag catcgcgtgg aattttaatt    4380
ttcgttccgg cggaatataa tctgccatct gcataataac tttctttgcc agtatcgtaa    4440
atgaaatact ctttgtaccc cttaacgatt ttagtaccag cgtcatcagc agtaacgatt    4500
tcacggatga attgtaagtt gcgcgggtca agacgtctca gttcctgaat tccgtctttc    4560
attttcttgg tgttgacgat tttatggaag aatattcttg agtcaacata ccaacggcgg    4620
aaatggtcag cgccctttcg ctcgaaatta aggcatgtta aaactgtatt aaactcttca    4680
agaatgcggt ctttaattgc ttgactgaag tcagtagaat ctaaatcaag agaaactact    4740
ggatgaccgt cttcgtatac aactgcgtca gaaactattt cttcaacagc attgtcaact    4800
```

FIG. 20D sequence.txt

```
tcgtagttat tcattaaact acgataagtg ttgattaaat cagcagttgt tttcattcca   4860
ggttcattgg aaccaaacat catttggttg aatgaattgt actggatttc gttttcgttt   4920
gattcaactt cacgagctcc atcatcaaat tttggagcag tgattgactc taggtcattg   4980
ttgatttgtt gcttatattc agcttcgtcg cgttttccc acggagcgaa taagtccaaa   5040
atatgaaagg ccattggagt ctccgaaatt atctataagt atatttatat cgaagataaa   5100
catgctttat gatatctcat aattgcacta cgtgttgact ccactccgca tactggacaa   5160
gtcattcgtg gctggtttat cttttttcct ttgttagggt gctcttttcc gaacatagga   5220
tttctttcac ccgacattgc tttagaatgg tcaggtcgtt ttcttccgga taatttaata   5280
gagtgatctg gacgttttat tcctaaccgc tgatgacgtt gttttctttt agactcttca   5340
ctcatttttc ttcctttagt tgacatccca aagaaaccgt ttggttgtgc taaagccata   5400
tttatatacg aactggattt aactacgtcg tattttattt gcaactcaag ttcagcttta   5460
gaagcttcct ctcgagtttc atatgtgttt aatatccggg ttttgaataa atgaggatta   5520
tcatgttgct cactcttcca gaggtcttta tatttcttgg atttaactga gccatgataa   5580
ttttcatcaa taattcgtga tacactagta gaaccgatgt agcgacgggg aagtttattc   5640
cccgtgtata ttgtcaaata agtacagaac attaatacct ccacttcgtt gttagaggta   5700
tttattcagc attattccca ccaatcgata gcaaaggtag tttcaaacgt ttctatctca   5760
ttattcgaat cccaatccat ctgtacttca ccaacgttag ttggccacag accagtaatg   5820
gtgtgttcat ttgtgatagt tttgccatca cgactaaact ggcgtaccgt agcaaccttt   5880
ttgtaatcgg ctggagtcat accagagata tcattgcctt gagcgtgggc ctgagcctgc   5940
caagcaataa ttgccttacg tacttcgtgt ttatcatcgt tatagatggt aacagtccag   6000
tcgtcataag tacggtcacc agcgacgtta atcttacggt tcatgtaccc gactggaact   6060
ttttctacga tacctgccgg catcggtgct gctttacatt tgaaactgaa gttacgaccc   6120
agataaggaa tttctacctc aaacaggtta ggacgcgcaa agtcaccaga ttcaaacgca   6180
cgagtgatgt ctgttaattc catcgttgtt tcctatagat atttatatag cctctcgatt   6240
gactacatca tcgtagaggc tattaaagtg tgcggtaata taatttatca tctaaagatt   6300
agatgacccc agaatgtcct ggggttcata ttactgtggt ccgattaact catcgaaatc   6360
tgcaccagtt gccgtagcaa cgaagttcag agtgatatag ttaattgaac gtgccggctt   6420
gatgtagaag ctcgctacaa actcgttgcg gtcgataact gctggagtgt tattcgtggt   6480
atcacataca actcggaagt catatacacc acccagagct ttaatacctg cgaggtattg   6540
gctggtttcc atacggaaag aactacgggt aaagttatcg tttaattcaa acagctgcca   6600
cttagaagaa tcaccgatgt tgttcttcag catgttaaac aagcgacgaa cgttaattcg   6660
```

FIG. 20E

```
                              sequence.txt
gtcaaacggt gttggaacag tggttgcagt cttatcaccg aacagaatga aaccttcacc       6720
tgtaccttga ccagtcactg ggttaatacc tgcttggtac atgcggtcac gatgtgcctg       6780
acgcggttca attgccaatt tgatgcaatt taaaatctga ccacgacgat atccagctgg       6840
tgacatccaa ggctgagcaa tatcatcagt acgagcacac aggcctgcaa tatcagcagc       6900
taacggaacc caacggttta cgtcgttata tttatcatac tgatatttat agttaccatc       6960
aattgctgcg tacgtagtat tgatgttcat gttagcagaa tcataagttc catcgccttg       7020
gcgccagtcg attaaattat caacagcacg agtcagagga atatttacaa tcgttgacct       7080
tggaggcgaa atgagtgcta agcagtcttg acgctcatct gcaatagacg aaacgtgttt       7140
ttgtactgta cttgcgattt catcggtttc accagcacaa gcaccagcaa tcagaaggtt       7200
tacacgcaat gcttcacggt caccaaataa atcccagcct tgaattaaat cgccagccgt       7260
aactgattca ttagctgaaa ccccaccacc cagacgaata acgccggaaa atccttcagg       7320
ccatccttgc gcagtagcaa atacatagcg tgaagaaccc ttggagaaat aatcgtccat       7380
aaagatgttg tttccgtaga tatctttatc ttggcggctt gttgataaca ccgctgattc       7440
aactacagca ccatctctac gaacaatgat agcgtactga gtatcggtct gaggaccata       7500
tccaaatacg gcttttgcgg ttgatgcacg ctgtccacca ctcggataaa tcgtcagttg       7560
ttcgccttta tcaaaagcgg cttttgatac aatttcaatt tccagttggt ttccgagctc       7620
gccaggatac gcagctacaa ttccaggcat tttatattgc gcaagcgcag tctggaattc       7680
agttttgtc atttcttcat gggcagtttc atgttcagtc agtagaactg tagactcaga       7740
aataatttta cctaaagtaa tgacagcgga acaccagaa ctctgtgaag taatggtagt       7800
tgtccacgaa gaccctaaat caggatattg attaatgctt tttgcatatg caataatctt       7860
cgatgtcgga atgaacaccg acttaatttt tccgtcacta tctacttcag taactgaacc       7920
ggtgtcatct acggtttggt ctgcatattt aaccgtaatt ttatcaccaa cttcatagtt       7980
actaccagca gtagtgatag tccattcaat attatcaacc aatggagatg cgttttagc       8040
agcttcacgg ttaactacac ggacggtgcg tagatcatta ccatattgca gaaagttcat       8100
tgctgacata agtaatcag cagtttggtt attagggccg ccaaacatat caaccagttc       8160
aacttcatta gtgatttgag taacttgata tgcaggaccc cattggaact tcccgacaat       8220
tgcggcacga cctgtagcgt taagtactac cgtgctctgt acgctcgttt ctttgagctc       8280
aattccagga gagactaaag gcatgatata tcctcaatgt tgtttgcttt ttattattta       8340
tacaaatgaa agaccatgtt cttgaggcgc atattctgcg ctattcacgg cgtcaacgaa       8400
cactacagga gcgtaatcgt cgttcatatc ttctaattcg cgtttaaaaa cttcagatgc       8460
taaacgcatt tcatctttat ccacgaaatc agcaatttt tgctgtgttg ttaaccatgc       8520
gaaaattacg agtgacataa ttaaatcgtc atgatatcca tcttctgccg cccaggatac       8580
```

FIG. 20F sequence.txt

```
tcctttctca gagaaagtac gaaattcttg aacagtagca cgatggtgaa taatgagttt      8640
atcttttcg  ataaggtctt ttagtgcaga acatccaacg gcttttgacc ttttcgtctg      8700
tttcattcct aaatcaacta ttgaatcgca aatgacattc tcatattcta aatccatata      8760
aagactcttc gctacagaaa cacctgtaga gttaagttct atatagatcg gagcttcgtt      8820
gtactccatt agatatttaa taactatatc cgggaggatt aagtgagaaa ttgtattaga      8880
atgtaatact ccaacttgtt cccattcaga tgtagtaacg tcaataatat ttagtgcatg      8940
gtaatcctga ccgcgtcctt cagcagagtc aagagttgca atatatttgt ggtctgcttc      9000
cgcttcttta aatttataaa acccgtgcga gtcaggagta acttcaatcc aatccatatt      9060
ggcaagtttc ataccggaaa tgagagtacc ggatgtgcca tgaaattccg cacagtgctc      9120
ttgtttaaac tgttcaagag aagaagcact gatagtttga agtgaccatt gccacccatc      9180
atcaaacata tcttcgtcgt tatatagacg ttctttaacc gagttccaaa ttgcagtata      9240
aggcgtaaag ccggatttac cttcaacagc tgcagtccaa atatcataga agtggtttaa      9300
tccacttggt gtagtcgtga taataatttt agaacgacga cctgatgaaa taacaggttg      9360
gatagcaagc catgcatcta tgaagtttgg aataaacgca cattcgtcaa tgtaaatcat      9420
tgcaaatgag ttaccacgaa cggcatcagg actcgaagcg tatgcccaa  tagatgagcc      9480
attatctaat tcgattgagc ctttgttcca ttcaacaata ccaggctgaa gaaagtcagg      9540
aagtaattca attgcttgct tagtacggtc gagaacttcc gcagacattg agcctttatg      9600
cgcaagaata cctactgctt tatccttatt aaaacacacg aagtgcgcaa gaaagattgc      9660
tactacagta gttttaccga gctgacgact gaggttacaa caagtcatac gtttggctgc      9720
catgatttcc agcatgtccc tctggtaatc acgaagctgg actttaatgg taccatagtc      9780
aatgtgagta attgcacagt aggtctctgc gaagtacaca atatcgtctc ggcatttctt      9840
ccattctgca actatttcac gggttagttg cattttaata tttgctcgtt taaggtttgg      9900
caatcccata tagcgggtgc gcttattatt tttgtcctta aacgtttgga aatgagctgg      9960
gtcttcacct tgcaaacgaa ttttaactat cccatgcaac ttaagatagt cttcaaattt     10020
ctcaggatac cacttatcat cccattgcga tttaaagaaa cgaactccgt tttcaatttt     10080
cgtttccatt tcagacgggt gacgaataac cgtcagtttc ccgtcattta aaggatgggc     10140
atcactcaga acgttaaacg gttgagtctg ttccatttac tatttctct  cgagcttctt     10200
gtgcttcata ggcatcaccg aattcatcca tcatatcagc ggtagaccct acaaagactg     10260
ttgcattttg aatattcatt ccttgctgag gattagctcc cttccggtg  ccaacctgct     10320
cagaagtaat gtctttcatt tctttatgaa gcttaagaat ttctttgttg gttgtagtca     10380
tctgacccat aagagttgca aatacttcca tatgtctagg agaatcagca ttcttagcag     10440
```

FIG. 20G

```
                                sequence.txt
tttccaaaaa tattttagct gcgtccatta acatctgttg ttggaagtgc atgttcttgc    10500
gaacaaccga ataatcatct tcgaggtcag gtttacggtc atttggatta gatttaactt    10560
caactaattc aagtttttca taaactggaa tttcttgtcc ttctattcca ggaattcctt    10620
cgatgtctaa taatttagcc atatctaatt gtaattcact cattttttcac ctctcggtcc    10680
aggagcctcc ggatttaccg gaataggaat atcgtgagaa taagtttgtt tactagaacc    10740
atcccaattt tcgtgttgaa catctcgtgg agtgacttcg ctatctactg attcaaagtt    10800
tccttctgga gttaactcct tgctgttagc gaagaaatct aaataaatgg ttctaatttc    10860
gccatcaatt tcagctacag gcggatacaa ccagccattg acttcaaaca tcagcgacca    10920
ttctaatcta cggcgagtga tattatctcc atcaacagct tcatcctgag aaaatgactg    10980
taatacaatt ctaacatcac gattaaagct tgtgtctttg tcgtaaagct cagttatagt    11040
cgtgttaaaa tgcggctgaa ataaggaac gatttgctcg atgatttgat acatatcatc    11100
ttgattgcgt gtataaattc ccaattcaaa aatcatctta atcggagtag gattatactg    11160
agatgtaatt tttgaagggg ttttatatga tttggttcta ttcaactgtg atgttttata    11220
catcgcattg tattgcatat caaccaagtg caaattcatt cttggcaaaa cagtttctat    11280
ctttgcttta ttctcggtag actgaatagc agtccatttt ccgagttgag aaaggaactt    11340
ttcctttgaa gcataagtga taggtacttt aatatatttt agtccagtgt cttcacgcca    11400
acgagcaatt tgtacatgag aaaataaatc tccaagcaat acaatgtatc ggcgtaagga    11460
cgaattatac caatgtccaa acatgatttc tcctaaggga cccaaaggtc ccatctttat    11520
tttatttatt cgaagaaccc gtcatcaaac gaatctgctt taggagggga ctcaagtcct    11580
cttccgttat taacataata cggatgaaca tattcagagg cttctttatt gatttcatca    11640
ctttctgcgt attgtatatc agaaatatca gcaagagcat ctatattttt gattggttct    11700
aaatcaagct cagaaaattc aggaatatta atgccttcat tacgttgcaa ttctggctga    11760
agctgctcac cagaataaat gtattttgt gcagtaatct tgcgttgaac attttgacct    11820
aactgataaa atggatcgta tggctgaacc cagttaattt cgaataatga gttatccata    11880
ggaaaataaa ttaggtcacc ggcttttggt tcagaattat tagtttgatg cttgaatagg    11940
ttgggattaa tagtcaaatt gacttcatca ttaaccatca taccaaattt actaaagaat    12000
gtgttatcgc cagaatatcc ttcaaatgaa tctaaataag cagcaaattt ccaagctttg    12060
gtgaatttac ttgatgggtc ttctccaaaa agcaaatcag gattgttata ttcacgagga    12120
aggaaataaa actcaattcc tctcatttga atagcctcag ccgataaagc atctgctaac    12180
gtttggctat ttctgtgatt ataaaaattc acataaggat tgagaatttc agtctcatta    12240
gttttattat atcctcgata atcttcgagt ttagcgaaga gcctagaatc aaatgtagac    12300
atcttttacc ccaacagaat aggacaaccc gggtcaagta aatcaagttc ctctcggagc    12360
```

FIG. 20H sequence.txt

```
ctctcgattt cttcttgggc ctctacctta agtgtttgac catcaactgt aactccacct     12420
gccaattgca gaccctgatg tttaaaaaga atttcacccc acagctttt  agttaatgct    12480
gtagcataat cttttaccca acgattatta tatgcgcctt ctctatttgt attaccttca     12540
ccagcatatt gaccattatt acgaaggtca ggattctgat atctatctcc taatccccaa     12600
tgatcagcag tttgcggccc agcaaatccg tatcctgctg tattgcctac catcgcatct     12660
gtattcataa atgatttggt ccagcattca cagacaatga tgtcacccatt catgaagttg     12720
cccattactt taagcatttc attatcagag ttataccaat aatccgggag aggagcaagt     12780
aaatcttgca tcattgacca gtaagtcatc aattgagtaa aatagccaag gtcagcacca     12840
aacgcatttg gcccatagct tttattacag cttgacccca ttccgccatt aattcctgcc     12900
attcccatta gaaagtcggt aaaccatggg tatgtcgcat taccatccat tgaagttaat     12960
gaacctacat ttgttctaac aatttgggtg acagcaaata cattacggcc gcgcaaatca     13020
aatacgccgt tcaaaaatct tgcgttgtca gcttcgtctt ttccaatata aaaaacttga     13080
taacctttat tcaatccgtt aaagtggtat tcaccataca actctaatgc tcgttgaata     13140
caatcataaa tttggtcttc agttacttct acattaatta ccggcgctcc tagacgtcga     13200
agtatagcgt ctttaagcgt ttttgggttg tacgtgttgt atgacatatg aactcctctt     13260
tatattccta tttatacgaa aaagggaccc gaaggtccct tttgttatac agctggatga     13320
atagtaatat ccaaagattt aattttaaca agaacctgtg attcttctga agcagctcta     13380
tacacgattt tgattgcatc accagatgaa aactcaatga gtttcttggt tttaatcaac     13440
tgttcgcccg ttacagcctt aacaccgagc ccgtaggaaa acacctcgat gttattaacg     13500
agaataacaa ttttcacgcc tttatctgaa tcagaagctt cgataaccgt atcagtttct     13560
acgcaaaata cgccatcgtc atcaacaaca atgtcatcga caatacgaat gccagcattg     13620
aatggagcag cgaccaatga gttaggattt accaatgcat cagaacttaa atcaacagtg     13680
aaatcttctt tactgaattc acctattgat gaaggttttt taaaccattc gccctgttta     13740
cggaggtatg ctccagcttg ttctacgtca gtaactgcag tcacgaattt atcttgcaat     13800
tctactacag tagcgtatac accatcacgt tgaactgggt tttctgacga aaagtcacca     13860
ttcatttgag tctgtaatgt aaatacagaa cccttta acc cttcattgtt attgccaagt     13920
tctacttgaa tgtcctgaat agcagactgt tgagagtttt gcataccttc aacattggtc     13980
attctcgcta aaattgaccc aggaggaatc ggctgctcgc taggaacaat accaacctgt     14040
tggtttatcc atgctacttg accctgaagc cctgatgaag tatcacgtcc tacaacatca     14100
gaaatgtacc cttggtcagt tgaaagagaa ctaattttc  cttcaatagt atcaggctta    14160
tcagaagacc ctaaacgagc atcaatatta ttgacacgag gaactaaccc ggtttgtgca     14220
```

FIG. 20I sequence.txt

```
aagttaagtg ttgcgtcaac tatacgataa tcgttttcta atctagtagt acgagctcca    14280
attttactg gattggtaaa atcaatggct tggttaatag caaagatttc attattagct     14340
gcggaaatag catcagcgtt attcacaagc cttgcataaa ttgaagctga cgtagctccg    14400
gatttaggac caacttcttt acgcaggtcg tttacttcaa tagtcagaga acctacgtct    14460
gaatcattgt atgcatcctc tagcgcctga atacgctcgt catgttttac tatagctgac    14520
gcattattga tgattcggta tttcatacca gaacccggag agtcttgctt cggctgtccg    14580
ttaatatctt gcccaggata cgcaccaatt tcacgtttaa cccaaactat attatcacga    14640
actgttctgt aatagtcatc tttactagaa tcataaacac ctacatcctc ttcgagaaaa    14700
tcaaggtcag ttcgaagttt ttcggtgtct tcttctaatt taagaatttg tccatcatgc    14760
ttttcaatat tcttttatt gatataaacc tgctcaatgg cgtcagaaga acctgtaatt    14820
tctaacgatt ttttgatttg gtctacatct acttgaatat tttctacagc agttccaacg    14880
ttgttcaaat cgttatgtac ctgaacaacg ttttctgga tttgaacaga agctctattc    14940
agttctccat catttccata gcgggttgaa gccccattaa gaggctctgt attttttatc    15000
cagttaattc tctgttgaaa atcgtctgga attccgtcta cgaacggaag cgaatctact    15060
agtttggtca tattgttcct tacggtctat ttgtacagaa tgtaagcatg cagtcataaa    15120
atataatacg actgtcttct gttggtctta tttgaacagt ggcatttgga ggaatgttat    15180
tgaagaaaaa gttgctagat gcgtaagctt caaatctcca tgaatgacca tttcgtccgc    15240
ctttagtatt ttcgatgtta agagtaagtt caccgcccca tggggaaccg ttaactatta    15300
caacaaatct gaaaatacga ttgtcatatc cgtcgttgtt acgctcaaat tttacattaa    15360
catttagagc taatctacta gaagcttccc atggtgcatt acatgtaaac gttgcacctc    15420
gactaatcca agattgacct tcaacccaag taacattacc tactctggtt ccagctggca    15480
tgtaacgccc gtcagattct tgtcttgtat aacaattaat atcattgtta gtaatcgtta    15540
tgtcattgtc aagagttttt ccgtttattc tacgggtttt aaagactgca tctgttgcag    15600
ccgctgccaa tgaagcatca gtagttggag aacctgataa tctggttaat ccatatttat    15660
ccttggtgga ttttagcgct tgaagacttt ttggagtaac agccaaattg ttagaagtag    15720
ctgaagccac atctgagtct ttagcaaatt ttactatacc aaatacgctg tcagacgctt    15780
ttgatgccat gaaggttttt ggagttactg cgtatccatc gtgaacagca cctgctgcta    15840
cctgggcttg ggttgcgaca cgaactaatc ccaagttgct ttctgtcgca gaggtataac    15900
taggaggact gacactgaac tttccaatca tttctacaac acgcttagga gttactgcgg    15960
tagtttcgtc agttcctgct tgcgcttgag ccgcagtagt taacctaaca gttccatcta    16020
cgttttcttg ggctttcaca gttttaaaca catgaccgag agccgccgcg gtaatagttc    16080
tatttcctgc ggttaatgct gcggcttcag tattagtagc ataccgtgtt aagccaagaa    16140
```

FIG. 20J sequence.txt

```
ctgttgtagt tgcttcagga cgggtaactg tggattttaa tgtagcagga gttaccgcag    16200
cattaccaat agttccagca tcaacttcag cctgtgttgc tgtgcgaatt acaccggcta    16260
ctgtaggaga tgctacaggt aatccggtat cagttcttgc ccagctacca atcagctcta    16320
acgctgattg gacgtctttt atagcaacag gccattgtgt atttgttggg tcaaatatcg    16380
tatatttggc caaatcactg tagtgattat agttattctg ggccattatc ccatccttct    16440
aaaatagtgg aaagtaaatg tgttcgcgcc gaaggttta gattcgttgc cgatagcatc    16500
ccattgccca taacctgctt tagctggtga agtaatagta aattcaacag ttaaaccata    16560
cttttatat gtttcaaaat tatggttctg ataatctaaa tgaataatat caacatactg    16620
tggtgttgcc ggcgattgag taacctgttg aacaaccttt ccaacagctt ctaattcttt    16680
tactttatca taccaacgtg ttgctactgc tgcaaagtca tcaccgtttg caattctaat    16740
tggtaagcca agaatatgaa ttattactgg gtcaccgaca gagccgtctt cttttggctc    16800
taacgcaacg acacctgaaa aagtagcacg cgtaatttgc tgtgcgggct gtggagatat    16860
tccagtgtca ttgcaaataa tagttccaat ttctgctgac tgcaatgaca tcaaatcatt    16920
aatagcagct tcagtatttg gataccaaac ccctaaatcc atttgttcaa aggttaggct    16980
ccctatagga gccgtatttc ctaccgcaat attttgcggg tcaacgcgat attctgaaaa    17040
agcagctaat cttgaattaa ctttagctcc ttcacgagtt ttagtttcaa tcgtcatttt    17100
aacctaccct aatccaacga taaacggtga ttgttggctg aattttagtg atgtcatttg    17160
gaactacacc gttgtttacc gcaacagtgt cttcacggta tttagaataa cctggtccct    17220
gcgcgtctgg gtctaattga catccaccga taactacgct tccatgttca gggtctgaaa    17280
ttagaacttt atctcttgac attagttcag gaatgtgttc ttttcctaac gtaaatgtca    17340
aatctccaac cgttccacct gctgttaatg atggctgacc attttcgttt aagttattgt    17400
tgttacgcga aaaataagga tcagatgaat cattattcca accagcagta acacggcctt    17460
gtgaataaag cttccacacc ccaaatccca tatagtcagc agggtttgcg tggttgtgag    17520
cgttttcata aatcgtgcca atcggataaa ttacgtcaaa aaatgctgca atattattga    17580
ctttaatcat aatatcgtca gcaaccggac gcatattttt ctgattaggt tcatcataat    17640
ttgtgtattc aatgcgattt tttagagtta ctaattgctc agcattcata tacacttggt    17700
cggtttctgc catgatatcg tcaatatcca tagtagtacc gatgttatta ttgaaccaac    17760
ggacggtaag aaggtcttta tcttcaaacg cctcaccaaa aataatagct tcgacgttag    17820
taccagttga gtcaaattcc agtctatagt cttggttaga atttacccat tgaccaccat    17880
tgtttataca gtcttctgcg tatccacctt ccgcaccttc acaataaaat aaaggaagac    17940
ctgcagttcc agcttcgagt aattccttc cgttcaacga aatttcaagc gaattgggat    18000
```

FIG. 20K

```
                                sequence.txt
tcacacccac acctggaagt acacccatat catctagagt gattcttcga agagcagtaa    18060
ggttatctac tataattgac ccaggaatcg tctgggatgt agtctgggct gaatctcgta    18120
tctggatagc caacttgttg tatgaagacc gataaacacc aattccatct aggaaggttt    18180
caaatgttat tacttcccct tcaacacatg gaacttttaa acgaatgtct ttaccgttta    18240
attctaccaa ttgacctgct actgttccag gagaaccgta atcagcattg gctttatcca    18300
taacgctggt ttcaccgtaa tataaaatat taccacgacg atatacatta agcgagtctt    18360
cgttatattc tacgccatca aaaatgttaa gaaagtcagt ctgacccgca gtagcaataa    18420
ttgattttt cgctacagta cttaagttac cattagttag cttatctaca gttttatttt    18480
caatatattc ccagcggcca ggggcgcaat aaaccaattc caaatcttgg aagttagtat    18540
tgaaaatttt aggagaagct gaacccttta atgtatcgcc ttgagcagga ataactgtga    18600
ttgggcttaa tcgccaggtt gaccaaacat cacgaagttt aataactttg ttatagtcgt    18660
tggctgtacc ctttggaagc tgaacgttaa ctcttgctgc ctgggtatta atagcaaagg    18720
cctgaccaaa cttagcattt aaagtagttc cagtagggct agctttaaaa gttttccatg    18780
cacctgctgc gaatggaact gaaccatcac ctaactctga atataaatca tcaaagttgt    18840
tattaatttt aagaccacct ttacggaggt aatcaccaga cccatcatct actgattggc    18900
ctactatcaa attttgtttc attattgaga taccctacg gtctgtgtag caataacttt    18960
aactgccaaa cgtgcgtttc cataagatgt tgaagctgtg catattaaat ctttctgcgc    19020
gttaatagag tatgaaatag aatacatctt ttcattttca gatgattcac cacttcttaa    19080
cactgcatat tcagtgtcaa atactcttcc gtttggcgct gatgaagtaa tagtcgggtc    19140
aatcataagc atgacttcag atgattgcct tttgatggtt tgaccacctg gatttgcgct    19200
gaagcttaat agcaàtttaa cagtagagta atcatcatta tatccaagtc gaatattaat    19260
aggagaactc gttaaattat atgtagcttc taacggcgaa tatgtgctgc caaacatact    19320
tgaaattgaa taatcccaaa cagcagcacc gttagctttt acctcaacac accacaattc    19380
aattctacat cttggtgtgt tgataatcaa ttctcgcgat ccgtctttaa atgcatctgc    19440
tacgccttcg ccgtttgttg ttattttat ggatctagct tttgatgctg agccattact    19500
atttacaacg aatacagctt ctcccgcttt accttttgaa agacgtattt gaactgcgcc    19560
ttctgaacaa tcagcatcta tgcatgaccc cattggaact gtccctgcag agttagcatc    19620
tccaaatttt atctttggt aatagcttgt tgcatgaatt ttttggttca atgctccgcc    19680
gccagctgca aataatcgtt ggtcggcgaa ggcgttgtaa atggcgtcga agttatcatt    19740
aattttcaca ccgccatcat acagaatgtc gccggtagaa gcattaccaa tctcaccgac    19800
gtcaattatt ttttaccct tatctgtata cataggttaa cctcatatca aagtatagtc    19860
ttatttatat aaaatgggga gccaaaggct ccccataatt aaaactcgaa aattaagttt    19920
```

FIG. 20L sequence.txt

| | | | | | |
|---|---|---|---|---|---|
| aattcttccg | tttggtccat | tgaacgaata | ataggttgcc | gattttccat | gtaaatcatt | 19980 |
| tcacctgact | gtctttcaag | accagaagca | ctataccagc | cttttcagc | cttaacatta | 20040 |
| ggtgaatttg | gcattggctt | aacttcaagc | ggattagtta | taattgacag | ctgtctaaat | 20100 |
| ccagtatttc | ccggaagact | gaactccgga | aaataaaccg | catcaagata | cgctttaaac | 20160 |
| ctgatagtat | tgcatttcat | gcgataaatc | aaattaaagt | cgttttgttg | ccaagttaag | 20220 |
| ttgtttttgaa | atccccaacg | ggctggagat | tcttcaatct | cttctggcca | aggaactacg | 20280 |
| atatattcat | ttgtacatct | gttaattgat | acgtcggctg | gaatttcata | tagatattcc | 20340 |
| caaagatatc | catcgcccaa | atcgacggta | ccatttgcat | caccacgacc | tcgaggagct | 20400 |
| gaaccagaaa | tagtggatgg | tgtccattta | cccccaagct | taatacattc | ttctttgctt | 20460 |
| gtaagattgc | caattgaaca | cattccatcc | tttggaacat | caatacatct | ataccatc | 20520 |
| catccaaatc | cagcatcagt | tctgttatat | ggcgcagagt | tagcaacaac | gatatcgcca | 20580 |
| attagaaatg | tgcgtgggtt | aggatatctt | gtatctcccc | agtctcttct | tggaacaaca | 20640 |
| cagtcaagca | ttgatgattc | aattttgacc | gcgcccatca | tatttgtcca | aacatcaact | 20700 |
| accccatctc | cattatcagc | gggatatgga | ggtgcaaatc | cgggttcaga | ttcgttatct | 20760 |
| gaccacggag | tgcttttgcc | aaatgaaaca | tacagtgtgt | tttggtccgt | tcccggacca | 20820 |
| atcgatttat | aaaatgtgta | catcttttca | gttctaaact | tagatgtaat | gatagcacga | 20880 |
| taaatcgtgc | tacgcgttga | acttgctctt | gttgaattac | tcatcaattt | ttacctgtgt | 20940 |
| cggatttca | ggatcgcgag | gattacctgc | atcgtcttta | agacgttggt | taactaaatc | 21000 |
| gcgataatta | gcaaacgtta | ctgctgattg | gtcaaacgta | ggacttaacg | gtttacgtcg | 21060 |
| ttgtccaggg | ttttgtccag | cgataatgct | gttattattt | tcttgattgt | agttagcagg | 21120 |
| taacgggaaa | ggttcaccag | cttgagcacg | tgaagaatac | ctaggctcat | tggttattgg | 21180 |
| gtctctttct | attgtatcat | ctgaagcgat | aatagcaact | ctatcaggat | aaactgatgg | 21240 |
| cagtcctgca | tcccatttat | agttcttgag | tttatttatg | atagtctcaa | catgcttcat | 21300 |
| atttaagcca | ctattgataa | acattgtcag | caatgttata | ccaatgaaac | cgaaacctac | 21360 |
| cggatgaaca | aaccttaata | catcgtcgcg | gaaacgagaa | gtaggaagct | gagacttaat | 21420 |
| tttcataaca | tagtaagaac | ggctgcggtt | tatataatca | atgttattac | tcagcatatc | 21480 |
| cttttccacga | acaccttgaa | ctataatacc | ctcaaagtcc | gtacgctctg | atttaatttc | 21540 |
| ctggccttca | atgaaccgtc | ctgataagtt | atgaatagta | atacgccata | acagacgacc | 21600 |
| atcccggtat | tctctctcga | tataagtcac | attactacga | ccggaagcag | tataaatcgt | 21660 |
| acgaccaact | aaatcgtcag | aaatatttgt | actttcaaca | ataatgtcat | attcggtagt | 21720 |
| gttctttgac | tcaatatcga | tttcaacatc | ttcattataa | agaagtttaa | acaagaattt | 21780 |

FIG. 20M sequence.txt

| | | | | | |
|---|---|---|---|---|---|
| gtatgagtct | tcaattcctt | tggtagcata | gaaatcattc | ttacgggctt | caaagaaacg | 21840
| gacaacagca | tcgcgagcgt | ctttactcag | ataaatattg | cgtttataaa | cttctgacca | 21900
| caggtattcc | catgcatttt | cttcacgagg | atatttgttc | ttaacaagat | taacgagact | 21960
| gttgtaatgc | gttccatttc | cgtctgaaag | gaattggaga | tagtacttac | aaaattgctc | 22020
| aaaattacta | tcttgtagca | agtaactatc | cggcatcatt | ttagtaagat | acggacgcaa | 22080
| atctgggtca | cgtaagcctg | gagtatgttc | aggtgtccag | tcttcttccc | gtgtttggtt | 22140
| ctgcagaaac | gctttaaaca | ttacatcagt | cggtttccag | ttaagcgtta | cctggtcacg | 22200
| aacacgataa | tcaaatgcgt | aatagcctat | cagttttccg | tctggttcgt | gaaacatgat | 22260
| gccagaagca | tactgcaaaa | atccattaaa | tgaaactgga | gggcaataaa | acgttgcgtc | 22320
| acctttatcc | cacacttccg | aaagaacacg | ctcggtagtt | ccctgcgccg | ctgcatctac | 22380
| tcttttttga | taaagaatat | cattataaat | gacaactgca | tggtcagctg | tacttatcca | 22440
| gcatctgtta | ccttcacgag | ccatccagac | aaaccaaggc | tcagcataaa | acctcatcgg | 22500
| tccaggaaca | aatgtttccc | atcttgaaaa | ttcatctgct | ctgaaactca | tcatgtgata | 22560
| atgcttatca | gagtgatact | gaattggatt | aacattttta | actgcagtag | aaattagttc | 22620
| tggatatttc | gtctcaagtt | caatatcctg | ggtgtactct | gttgtcttaa | aattagctga | 22680
| tgaaaagaat | atttcctttc | cgtcagttga | catagacgtc | cataaatgct | ctatacgacg | 22740
| tttttcttca | tctgtattac | cgaatacacg | tttccatgta | tttgtgtctt | cttgataaac | 22800
| atagacgcct | ttagtagcag | aatccacaac | attccgcggg | tctgttgggt | ctaatcctaa | 22860
| ggtttttaact | tctccggtaa | taagagcgaa | gattttgcct | ccgacagaat | ccattttaaa | 22920
| gcatacagat | ttaggattgc | ctgttatatg | agatgcttct | ttttcgaaca | cttttttcacc | 22980
| aaatgtaggg | cttaaagggt | cagtgtctat | tggagcatct | tttaatttaa | ctctgcgtac | 23040
| tgtatccttt | gcaactacat | ataagtggtc | atcattgcat | gtaaaggctt | ctgcatattt | 23100
| ggtaacatca | gcaggtagtg | atgcatatgt | accaaataac | tctacttcaa | atcccagttt | 23160
| taactggtct | cccaatttag | caaatgtaac | ttcgttatcg | ctaaatttaa | cctcatttga | 23220
| tgaccagcgt | acgtcagatg | attttcttcc | gtaaaagatt | ttatcatagc | ctaaaacata | 23280
| tgatgtggta | cttgattgat | aaattaccac | tctagaaacc | ggatttccta | cacggtcatt | 23340
| aaataactga | acgtattgcc | agttctgtcc | tttatcgttt | gatactttaa | ccatatgttg | 23400
| gaatctttca | aacagataca | aaattccgtc | tatttctcct | agcatggttc | tatttttatc | 23460
| aacacagact | gcttcaatag | gtccctgaat | ttcatgatat | ccagattcgc | ctactacgaa | 23520
| attttcaata | gctgacaaat | gagaatattc | aggactaaat | tgaaaagact | cagtcatcaa | 23580
| agatgccatc | atggcagatg | tgttgaagtt | aacatacgac | atgttatttta | aagaaaactt | 23640
| ctgcttaatg | aattctttca | ctaaactgaa | ttcttgcata | tgctcaaacg | tgtacgcgtt | 23700

FIG. 20N sequence.txt

| | | | | | | |
|---|---|---|---|---|---|---|
| ttcttcaaaa | gtttggaact | cttctgtttc | aacccattca | gacggttcaa | atcctgctga | 23760 |
| cgtagtttga | acacgcattt | tataataggt | aagcggttca | atacgatttt | gttcgaacca | 23820 |
| atcattatcc | gcggtataac | ccagtgaaga | ccaactcaaa | ttatcagcgg | ggataatttc | 23880 |
| ccccgctctg | tttcgagttt | cggccagttc | tacaaaatag | tagaagtttg | caccaacgtc | 23940 |
| atcccaacga | atattgacct | gattcgcaga | tagcttatga | attcgtaagc | tggtgacgaa | 24000 |
| cggtgcaatt | gtcattgagt | aataggctcc | aatttaatag | ttgtgtattg | aggacgaagg | 24060 |
| tcattctcaa | atacgataag | tgttccatcg | cgggcgaaga | cgatatcctg | ggtaggagta | 24120 |
| gaataaagct | caatactttg | gtcttcaaac | tgaagaggat | cggctccaat | ggctccaaga | 24180 |
| ctccagtaaa | tgttatcacc | ataataatct | acttcaccga | ttttatacca | gcgagttctt | 24240 |
| tcgccgatgg | tagttctatc | aaaatcgttt | tcagtatatg | gctggatatg | agtattctct | 24300 |
| ttaatatcac | ctggtttaaa | tggtccaata | accatatttc | ctttgccatt | tttatctggg | 24360 |
| tcagttccaa | cgatattaac | tgaatacggt | tcagcagttg | gggtaacagt | aaagaccaaa | 24420 |
| tcaccagaac | gtaacgtccg | cggagtaata | gtattatagt | atttaatacc | tgcgctagga | 24480 |
| agagtgaaat | agttgacaat | ttcacgaacc | atctgaatat | ccacagaaga | accgatgatt | 24540 |
| gagtggtcag | tgtcatcaat | gtaagtcaac | aacttagatt | tactgaaatt | tttgttgaac | 24600 |
| atttcaactt | catcaacgta | atatctatta | atcgagtcta | taattttga | ctgtaaccac | 24660 |
| tgctctgatt | cttgcaactt | attcaatgca | taagaagctt | taatattatg | acgaatgaat | 24720 |
| aagtaatctg | ggctcattac | cgaaggggta | atcggagcaa | gacagaaagg | ttttagataa | 24780 |
| tcctgaatgt | cttcccgttg | aaccgcagtt | aactgcaacc | cagattttgg | tttgattgcg | 24840 |
| ataaatgcat | atccgggttt | gtcctgatca | gtaaagcatt | gtactgcttg | tacgatagaa | 24900 |
| ccaaagcgtg | aactaacgaa | tgattcatag | tcagttttag | acacgcatcg | catttgagat | 24960 |
| tcgcgcttaa | tctgtgcgag | ctcacgaata | cgctcgatgt | cttcaggttc | accaccgcca | 25020 |
| tcagcgccaa | cataatcagg | agaatctgac | cagttttcaa | tgattctatt | tactacgata | 25080 |
| tattgcagag | tatccgcata | actaaattca | gtcgcgccat | tagcagcttc | accgtcagta | 25140 |
| cgaatatatt | caataacgac | ttgcgcaccc | ttagtaggct | tcaatccacc | gatgaagttg | 25200 |
| ctttcaagaa | ctcctcctgc | cacagatgct | tctgccacac | cctcaccaaa | gaagaattct | 25260 |
| gtatttccat | cgacagtttc | acgcatataa | taaattgttg | aaatagacga | agcatgaacc | 25320 |
| attgatcggt | ctgtccagtt | agtccattca | gcgccatcca | cccacagctt | aacttgcttg | 25380 |
| cggtcaattg | attgatcgcg | aataacaata | ggtttcttcg | ggtcatatga | caactgagta | 25440 |
| cgaataatac | gtccctgcgc | caaattgaca | ataggccaat | attttggtc | attatcacga | 25500 |
| atagccacaa | cgttttcagt | aacaacgaag | ttatatgggt | tggctttatc | ggattttgag | 25560 |

FIG. 20O

```
                                  sequence.txt
tatgctaaaa atttagttcc tcgtggaatt acaactctca acgtgctgct cgggttcatg    25620
tgagttacct caagcataat agatgcagta gccgctgatt tggaacttgg caaatacccg    25680
ttttgctgag ctgcttgaac aacggaactt ctcaagttag ctgttccaat aaagctttcg    25740
tataaagcag tattactaaa ttgctgtatg taaagcgtgt tatatgctaa taagtctaat    25800
agcacgttta aacgcgaacc agcaaaatca aagtcctgaa actcttttg accgctaagc     25860
cagttaataa gctgatttt aatttcgtcg aatgttgctc cagtaaatgc gtctgggata     25920
gcgtttgcag tacgcgttaa ctgataattt aagggttctt taatagccat tagtgtatga    25980
ataccttga acttgattgc gcgacagtgt cgccacaaga aattggatcg gccatttgaa     26040
cagctttttt gcctgttaca aataccttgg atgtgcgagg ttgaacaact cctccatgcg    26100
tatcatgagg gtcaaccgtc ttggtgtgtg gggtaattga gtcgccatca actaataccg    26160
ctattccacc agtgaatact ttactttgtg tagcatttac ttctgtcgga ggatacgcac    26220
tatgcccggc agttaagcat ttattaaatg atagtccagc catttaattc cccgcatata    26280
cataagcacg aagttggtcg ccccatctac tccagttgcc tttaacggtt tgagagtaaa    26340
tcttttgctt tttatgttct gttatgattg gagcgctaga acctccggat gaacctccag    26400
acgattcttc tgtcactgta tatattatct caactgtata ggtaaatgtc ttctctagtg    26460
ttctggggc tttccataga tacaaatcag cagttttggg attaggtaaa tcctcccacg     26520
ctgaagcgga ctttagctca tcaccttcac ggtatttaag cacatcgttt ccaaaagtaa    26580
aaactgagtt ataattacct ttataatgag tttcagacac agagatatca gatactggtt    26640
gatagtcgat aatatttatt gattttaatg tttcgttagt agataattga gcagtaaagt    26700
actgctcaac atattcacct tctattactt cacgtaacgt tgtattaata ggaagtatat    26760
cagccatgat taacctacat caattcgtga accatcaaca gtgtattgac cttgggcgat    26820
tgagctcata gaagccattg tttcagtcca agccccacca acattccaat tcacagtacc    26880
tgctacttgc caagttaaat taccaccgac ggtcacgtcg tggttgccat ctactttagt    26940
agtggcatca ccattgactt ggatatcagc atttccttca acgactatct taatgttacc    27000
cttgacaaaa atagtaccat tgccttcaat cgttttagtt tcatttccac gtacgtaaag    27060
cgtgttatcg ccatcaattt gctgtcgacg attatacatg ttataatagg tctcgttccc    27120
tccaacgtta accttcttat caccagagat taaaatattt ccatcaccct gagtcatgtc    27180
atataaatca gctacagttt ttctggtacg acgtccatca ggagcaactt cttcatatga    27240
accggttgga tgaacaatac gatagcgttc atagccaggc gtatcatcaa attcttggat    27300
atggcctgat tctgtttcca tcgtatgtac atatggatat tgaccattat atgaagactc    27360
aggttctttg aaaagaattc ttgaatcctc tggggtccac gggtcttcag gattaccacc    27420
agacttcggt tctacataag ccgcagacag gttttttcct tctggctttg gagcaggaac    27480
```

FIG. 20P sequence.txt

```
tccatatgat tccatattac ctgttagaat aatcatggaa acacgagaag cacgaccttt      27540
tgtctggtta aaccacacgg agtttcttgc ttcagtatag gctgttttcc aatcaccaat      27600
gagcatggca tcaagcattt taccaaattt tgctaatcca cctacaccca tttgaaaact      27660
catattttct aaagccattt gccttgattt gttgacttta gcataccg gtcctacgcg        27720
tgaattcgtt ttaatatcag aaagcatttt atcacgatct ttcttaaata gtgcaactgc     27780
ttcgtccatt gtaatgatac cgggatttcc tgtaacagta cgaccaacct gattagataa     27840
agttttatta atgacagaca tatcacgtac tttttgtgcc atgataaggt gtccaatacc     27900
tacagtagga tatccttctg tatcccaata gactttcaat ctaagacctt catccctatt     27960
aagcatatct gttattgtaa ttgcaggatt tgggtcttca ggaatatcgc ttaggtcagc     28020
atcgtcagga ttaatgccaa tatccaagtt tctatcttgg atgatgtttg gtatagcact     28080
atacccagtt tcatcgcctt gaactagtgg gttggtatct gacccaacct gtctaggata     28140
ttgacctgtg gggtcagaaa aaccttccgt gtagtttggc ttagtttttc tgtgcgcaga    28200
atatgttcct attactaatc ctgctgtttt gaattcatca agccataagc caaataccga    28260
tgttccttcc accattccag ttatagacga gccaactccg gaaattccag ctgagtttgt    28320
aggctgaatc actgacatcc aaggaaggtc ttcggtagga agaccggtta tagctccttg    28380
tacctttca aacggatgaa gcccgtaaac acgtactcgc actcttcctt gctttaacgg     28440
gtcttgtctg tcttcaacaa caccagtaaa ccattttaat gaatcgttca tttcaatcat    28500
aaaacttctc cgatggtagt ctgggatttg tatcggcctg attcgtattc gctgtcaggt    28560
gcttttttcca tttctcgtat aatatcagaa agaaatgcct caatatcact aggattgata  28620
atgtttattt ggcgcagttt ttcattttct atgatagagt cttcataaat gtcaacacca   28680
gccaaagcac cagtatattg aggatactga tgattaaagt ccccttttatc ataccaaaca   28740
cctgaatttt caggatattg ctcgagattg taatagcgat tgccatacgc atccacgtga   28800
tagagtattt ggtctccacc tacatctgca tattttgct gcgcaaattg atagcatgca    28860
tcttgggttt taatccaatc tctgaatggg tcatatacat tattacacat taaaagaatc    28920
cagtacagct gactatttcc ataaagaata tatgctaatt cttctggtct aggagctcca   28980
cttatgtaat atgtttgtaa aagatagttt tctgccacag tgtcaaaata tttgcgataa   29040
ttacgaaata tgtcagcggt tgggatagct tttgccttag caccttttac ggtctttgca  29100
gaataatcta tcggactaaa aaatgagaag agcatagttt atcctcttat aaatattaat    29160
aacagtattt ataaggaggc cactatggca tattccggca aattcatgcc gcagaatctc   29220
cacaaatata aaggcgactt cagaaagatt acttatcgtt ctacgtggga acagtacatg   29280
atgagatggc ttgacaatca tccagatgta gttcaatgga acagcgaaga ggtagtcatt   29340
```

FIG. 20Q sequence.txt

| | | | | | | |
|---|---|---|---|---|---|---|
| ccatactta | gtaatgcaga | tggaaagaaa | cgccggtatt | tcatggattt | ctgggctaag | 29400 |
| ttttctaatg | gtcaacagtt | cttttttgaa | gttaagccga | agaaagaaac | tagacctccg | 29460 |
| gtcaaaccca | caaagttgac | gacatcagcg | aagaaacggt | acattgatga | aatttacaca | 29520 |
| tggtctgtaa | acgttgataa | gtggaaagca | gctcaagcta | ctgccagtaa | aatgggtata | 29580 |
| gaatttaggt | taattaccga | agattcactt | aaaaaattag | gatggaaagg | ctgatggcta | 29640 |
| tatttgaatt | tatcactgaa | gctgcagaat | cgcctaaagc | taaatcccgt | agtgaaaatc | 29700 |
| aatgggtagc | attaggagtt | gaatactctg | ctgctcgtaa | aaaaggcatg | acatcaaaat | 29760 |
| catttgctga | aagtaaagga | ataaatcctg | ctacgttcag | taaagctatg | gctcgtcatg | 29820 |
| catcaagaat | taaaacggca | attaaagtag | cagaaattga | gaaaaaacct | gctaacaaaa | 29880 |
| tgaccaaaca | agagcgtgct | cttgtgatgg | taaattcatt | tcgaagctct | atcaaagata | 29940 |
| aaattcgtaa | tgaaggcgca | gcagtaaaca | ataaatctgc | taaatggttt | gcagaaacta | 30000 |
| taaagaaaaa | tatacgtggt | cattctgtaa | ccaagcctca | acctggaaag | ctatatgctt | 30060 |
| acatgtatga | cgctaagcac | aaagacactc | ttccattctg | ggataaattt | cctttgatag | 30120 |
| tttatcttgg | tcttggaaag | caaggtacaa | ccacattgat | gtatgggtta | aaccttcact | 30180 |
| acattccgcc | aaaggctcgt | cagcagtttt | tagaagaact | tctgaaacag | tatgctaata | 30240 |
| cgccagtgat | atctaataag | accagattaa | agataaactg | gagccaggtt | aaaggatttg | 30300 |
| ctggcgctga | caaaatgatt | aaagcatata | ttcctggtaa | tataaagggt | gctttaattg | 30360 |
| agataaaacc | ggctgattgg | gcgaatgtag | tcatgttacc | actgcagcag | ttcatgtcga | 30420 |
| aaggcaaacg | ctactctgct | acttctgtat | ggaaatcata | atgtctactg | gactgtttaa | 30480 |
| tcaaactaac | acaactaact | ttatattaga | ggtccctgac | gggggcctca | cccaagcgtt | 30540 |
| taaagctaat | cttcaaacag | ctgtagttcc | tggaattcat | attcctgcta | ctgatactgt | 30600 |
| gggttcgccg | caaggcatgc | accgtgctaa | attgcctggg | tctacctttg | aatttgacgc | 30660 |
| tgttcctgtt | agatttttag | tagacgaaaa | ccttgattca | tgggtacaaa | tgtacaaatg | 30720 |
| gatgttaagc | tgtcaaaact | acattgaccg | agacaagtct | ggatggaata | acggcggtga | 30780 |
| aggatttcct | ggtgcagttt | taatgcatgt | tcttgataac | gataaacatg | atatagtatt | 30840 |
| aactgtccgc | tacatcggag | gttgggtgag | tgatttatct | gaaattgagt | attctttaac | 30900 |
| cgaagaatcc | gacccagcaa | tggtatgtgt | agcaactttg | cagtacaaat | acattgaagt | 30960 |
| tgaaaagat | ggtataataa | ttactggtag | accttctgtc | aatgatactc | gcgaatccca | 31020 |
| gtatcaacag | aaagttatgg | gaatgcatcc | ttctatgagg | taataatttg | aagcttttat | 31080 |
| ttttgattgg | taaaaacgt | agtggcaaag | atacaactgc | tgactacatt | atggataact | 31140 |
| ataacgcaac | aaagcatcag | ttagcaggtc | caattaaaga | tgctttggct | gatgcaatgc | 31200 |
| ttactgagtg | gtatcgcgat | acgtctcgtg | agtttccgcg | cattactcgg | tctatgattg | 31260 |

FIG. 20R sequence.txt

```
agggcattga ttacgatcgc gaacaagatt taaatctgtc tactaaagac gtgattcgta    31320
tcatggcgaa tgcgattgaa tatgttcatc atgatttgcc tttacctggc gtggtttatg    31380
ataacaaacg taaaatactt gacggcgata cgatggaagt catccgtaaa gttgtaataa    31440
ataaacctgt tgagccatgg tcaattcgtc gtctcatgca gacccttggg actgacattg    31500
tctgtgataa gctcgatcgc atgtattggg taaaacgatt cactttggtt atggctgata    31560
cttttggtga ttatgattat ttcattgtcc cagatactcg tcaagaccat gaacttgatg    31620
tagccagggc gatgggtgct acagttattc atgtagttcg tcctgagcaa gaaggttcta    31680
aaaaagatac tcacgtcaca gagcgtggac ttccgattcg cgaaggcgat atcgtaataa    31740
ctaacgacgg ttctctagaa gaactttatt caaaaatcaa cactatatta ggaattcaaa    31800
atgactactg aacaactgca agcccaagtc gatactctga aagttcgtgt atttgacctg    31860
tctgaaacta tccaaggcct ttctgctctg cgtgcacaat atgaagaagt actgcagaag    31920
ctgattgctg tatccggcgt tgaaattggc gaagacggcc aggttaaact tgatgacctg    31980
gttgcaaaaa tcgaagcaca gttcgcagaa gaaactactg aagaatctga gtgatgaaat    32040
tcagtgattt tagcactggc ttatatgtag ctgctaaatt ctctgagaaa actcttgatg    32100
ctattgagga ccttcagcgt gaattgaagg tccctaatcc tgtacctcgt cataagattc    32160
atacgacgat atgctattca agagttcatg ttccatacgt ttgtgcttca ggaagttttg    32220
aagttgctac atcaggtaaa cttgaagtat gggacacaca agacggacgt acgctagttc    32280
ttaagctaga ttcagaatac ttaaaattcc gtcaccaata tgcaagagct ttgggagcaa    32340
ctcatgattt cccagattac tcaccgcaca ttactctcag ctacaatgta ggtccagctc    32400
acttcgaggg tgaagttcaa gtacctgtag tgcttgatag agagtaccaa gagccactaa    32460
aactgaactg gtcagaggac cttaaatgaa gtcataccaa gaatttttaa tggaaactga    32520
ggctcttttg gagtctactc tgccagatta catgattgta aaaagcttta atgtaaaaaa    32580
tggctacgta attaaatttc ctatcgctag tgtcaagcct ggtgctgaca tgtcaaatga    32640
tgctggcatt agtgttaaag ttaatgtaca gtttattaat tacaactctg ctaaaaagtc    32700
gtatgatgct aaaatgactt tttccggtgg cgaaaaggta gttaaaaaca ttaagttaga    32760
ttacgatgaa tccgcagaaa gtgtcaagaa acgctttggt gataaactgg taaaatctat    32820
catggttcat ccaactttca aacgcgattt cacggaactt tataaataaa aagttgttta    32880
cttttcctcga gggctatgat actatagccc tatcaaaaca aatgaggata aaacatgaaa    32940
cgctgtgaac tgataagaaa tgttgcttct gctatttgcc ttactgctgt gggcactagc    33000
attttcggtg ccatctttat gggtgcaaaa gaaataatgg ttgtgttagt agctgcattt    33060
cttatgggtt caatttcatt tattatggat aaaatttctc atgaaaaga ttaaacaatg    33120
```

FIG. 20S sequence.txt

| | | | | | | |
|---|---|---|---|---|---|---|
| gtttgttaag | acctatgatt | taggccgtga | agaagtaact | aagtatgatt | atgttactttt | 33180 |
| gggtgtagga | ctaggtgcac | tactggcagc | attgcattca | tcattacttg | ccattgcagt | 33240 |
| gcttcttatt | ttggctcact | acagctggaa | acgtaagtaa | tgtatgcact | tttaacttgg | 33300 |
| tctaattatt | atcctgctcc | tggctctgac | caaatcagag | gtgtttactc | tacagtagaa | 33360 |
| gaatgctatg | aagccctcca | gggaacgtat | caggactatt | ttgagatact | gaactctcgg | 33420 |
| tttgagaccg | ttgctaaagg | ttcaactgaa | gcatacaaag | attaattgtg | aggaaattgt | 33480 |
| gatgaatatc | agagctgcat | ttaatacttt | ctaccaagag | aattataagc | ttctttccca | 33540 |
| tgaatactat | gatgcacaag | gcgttccaat | tcctagtgat | ttagttacgc | ctaagcatgt | 33600 |
| caaaaccgat | tctcttgaca | atgaaattca | acctggtgat | ttggtatcat | actattgtgg | 33660 |
| cgggtcactt | tctgcagcaa | gcgttggtat | tttgctagga | tttacgccta | aaggttatcg | 33720 |
| tgtggttcct | ttccatacaa | gtccaattcc | tgagcaccgg | gtattgctct | ctcatatgga | 33780 |
| ttcaccgcat | agggtattcc | tggttaaatc | aaagagctca | ccgattgtgt | aatatgcttt | 33840 |
| aggttttctt | tgttattatt | aatctatcaa | ctgctctgat | taatttcagg | gcagtataaa | 33900 |
| taaaattacc | caatggggag | ttagaccgta | ggggtagcgg | gacagactgt | aaatctgttg | 33960 |
| ctcaaaaggc | tcgagtggtt | cgactccatt | actccccacc | aaatttaagg | gatactagct | 34020 |
| cagttggtta | gagcaccgga | cttttaatcc | gggtgtacga | agttcgaatc | ttcggtgtcc | 34080 |
| caccaaattc | gggtcgttgg | ctgagagggt | aagcgacgga | ctgttaatcc | gtgtcagaaa | 34140 |
| tgactaggca | ggttcgatac | ctgcacggcc | cgccaaatga | agaagtcaga | agacgttctg | 34200 |
| ataaatcgtc | ggcatagaat | tccctggcat | ggcgtttgta | ttaaggagta | tgatttcatc | 34260 |
| ctgcttaata | cttgttcatg | ttataatttc | ttacggcgtt | gaaagttcgc | tttcagggat | 34320 |
| acatcttaga | acagagtgct | aaacaagatt | catctggtac | caaggtgatg | agagtcctgt | 34380 |
| tcccctttgc | ttcggcatag | tgccagagta | tctctgaaag | cgaattatag | tgctgtagtc | 34440 |
| gagatggtta | agacactccc | ctgtcacggg | agagatcgcg | ggttcgacac | ccgtcagcac | 34500 |
| tgccaaatac | gagagcaaca | tgaaagatta | tgaaaagtac | cgcatgcaaa | aagtgcatgc | 34560 |
| caaataaaga | ggtattgaat | ttaaattgac | atttgatgaa | tggttatcat | ggtggaaagc | 34620 |
| tactggcaaa | tatcatttgc | ggggtagagc | atcagataac | tattgcatgt | gtcgtaaagg | 34680 |
| agatgttgga | ccatattctt | tagataacat | ctattgcgca | actaatgcgc | aaaacgctaa | 34740 |
| agacgctggc | gctaacggaa | gaataatatc | tactggtttt | actggacata | accattctga | 34800 |
| tgaaacaaaa | ataaaaatat | cagaaaacca | tgcacacaag | ttaaatgcag | acgaaatttc | 34860 |
| tttgcgaata | gacctgtata | attctataga | ttttacacag | cgtggtgcac | tagtaaaatt | 34920 |
| tgcaaataaa | cttggaatta | gtcatactca | agctagaaag | ttcataaata | agtttataaa | 34980 |
| gtaacgtggc | agttcttgaa | gatgagtttg | agtcctgtaa | gataatgccg | aggacgaagc | 35040 |

FIG. 20T sequence.txt

| | | | | | | |
|---|---|---|---|---|---|---|
| ggtttgttcc | cacggaataa | gctctatatt | cgtaagatta | tatctttagc | gtgttctaca | 35100 |
| tcaagctact | tgttagtact | tcaagaaccc | ggataaatgc | ggagtaactt | cagttggtag | 35160 |
| aatgttgggc | tcatatcccg | acacgcgcag | gttcgagtcc | tgcctccgcc | tccaaacaat | 35220 |
| tgaatcatag | ccaagttggt | aaggcagtag | gttttgatcc | tacgatccct | ggttcgagtc | 35280 |
| caggtggttc | agccaaatta | atattcattc | aacgcgatgt | gtaggcagaa | gtcatgaacc | 35340 |
| tgctttagct | accgtatgaa | gtcctcatga | tggatggagt | gaatattgat | gtggtcgtag | 35400 |
| ttcagttggt | agaacccgag | gttgtgatcc | tcgatgtcac | ggattcgaat | tccgtcggcc | 35460 |
| accccaacaa | tgaaggaatg | gtggaaaaat | acacggcccg | caaaacgctg | tggctgtcgc | 35520 |
| taagcgaatt | gtgtctataa | tggcacttcc | ttcaccaatt | aatggagagt | agcgctagtg | 35580 |
| gtagcaaacc | ggacttgaaa | tccgggccac | cggaaacggt | gagggttcaa | ctcctttact | 35640 |
| ctccgccaaa | tttatgaaag | ttaaacgctg | cccatagcag | tggtacatca | acaattagat | 35700 |
| gattagcttt | ccatgggagt | atagctcatt | tggtagagct | ctcgaccgat | aatcgagcgg | 35760 |
| tgactggttc | gagtccagtt | actcccacca | aataacaggt | tcttagtata | atggctatta | 35820 |
| tgctgggctc | caaacccagt | gatgagggtt | cgattccttc | agggcctgcc | aaatttgcat | 35880 |
| ccatcgtata | gcggatatta | tgtctggctt | ccacccagaa | gatgggagtt | cgattctccc | 35940 |
| tggatgctcc | aaattactcc | gtatagctca | gcctggtaga | gcgctccatt | tgggatggag | 36000 |
| aggtcgaatg | ttcgagtcat | tctatggaga | ccaaattaac | ggtatgacac | aatacaagat | 36060 |
| ggtgtaagct | gagtagcggg | attgcagtct | cgttcagata | tgctatcgag | tatgggtgat | 36120 |
| atattaaaca | cacggattct | gcaaagtcca | tgtgactcgg | ttcgagaccg | ggcataccgt | 36180 |
| ccaatcactt | gccattgaga | attatattat | gaaatattac | ggcttcaaaa | catcccattt | 36240 |
| cgggaaagca | tatcgtacag | aaaacattga | tagacgtcga | gcatattacg | aatcactgca | 36300 |
| taaagcagga | cgttctcgtg | cacgacaaga | aggccaaaaa | caagcgaagg | aaatagaatg | 36360 |
| aatattttta | ttggtgttgc | aaataacgta | aatgctatta | cggtgaaatt | acaatggaat | 36420 |
| cgtccaacta | attttgcttt | aggattatgt | aaatctgaac | gtgatttaat | gcttcatgct | 36480 |
| gattttgcat | acacttttga | tgaacgcaaa | ggtatgtggg | tatggattaa | atgcagatac | 36540 |
| gaagcattaa | tcaaatatga | gtacttcagt | gagcgtgata | ttcaagaagt | tattgcttat | 36600 |
| cattctggct | gtaaagtaag | taaactgcgt | caagttattc | cgtttactaa | tgcttcaaat | 36660 |
| gtagaagagc | taattactga | ttttaaacga | atttatcagg | cgaaatatga | tgaaagattc | 36720 |
| taaaggtcga | gacgtacaag | ttggtgatat | cgttttctat | ggagaacgta | catacaataa | 36780 |
| aggcggtcgt | ggttctatgc | gctgtggtcg | tattactgat | attgcttcag | gattggctaa | 36840 |
| agtagataac | gactacgttg | caatgcgaag | caaatcattc | gttaaggttt | ctcctatgtt | 36900 |

FIG. 20U sequence.txt

| | | | | | |
|---|---|---|---|---|---|
| cgcaacaatg | tgggaaaacg | gaacgatttt | cgagatttaa | tgctacaaga | ataacctgtt | 36960 |
| attattacta | catcaaaaca | aacaaggaaa | aagaatgaaa | cgtatcgcac | tgattgttga | 37020 |
| ccaagaagct | atgttcgctg | ctaccggtaa | atttcatccg | gtgagtaaat | ttgttgctcg | 37080 |
| cagcgagaaa | atcgttggtc | tggtagaaac | tgtcgcaggt | gatgtaattg | tttctattaa | 37140 |
| aacgtctgaa | atttctccag | tagttaaagt | agcagttgaa | aatgacttct | gggaagtagc | 37200 |
| tgattttatg | tgtgagtaat | tctgcctagc | aggtggataa | gcccgacaag | gcgccctctt | 37260 |
| cggagggctt | ttataaaagt | cataagattt | ctataaaggc | cctgtagctc | aattggtaga | 37320 |
| gcgttcccct | cataagggat | tggttgcatg | ttcgagtctt | tgccagggtc | accaaattaa | 37380 |
| tgaggaaaat | attatgatgc | gattagttaa | agtagttgta | gaagaatctg | aatacatggg | 37440 |
| cgatagccga | atgattgaag | aattcgttac | tgttgaggca | gattctgaat | ctgaaatcgt | 37500 |
| tgataaagtt | tatcgtcatt | ttgataatat | gtctgattcg | tatggcacaa | tgtatagcat | 37560 |
| ttatcgttta | gatgtaatag | tacatatcaa | ctgaggaaat | tgaaatgcat | attagatttg | 37620 |
| gacaagttat | tcctaaaggc | ttagcaatgg | caattaccac | ttgggaaaac | gatgctgatc | 37680 |
| ggtattctac | ccaaatggtt | tatggcttag | aaaaagaaga | gattaatcaa | gtaattcacg | 37740 |
| ttcttgaatg | gttctcttct | aatggtcggc | gtggtgaata | ccttggaaat | aatgattaca | 37800 |
| accatgaagc | aattcttgaa | aagcttcata | ctgaacagaa | gtatgtaact | cctgaatttt | 37860 |
| ccaagaaatt | ctttggcgtt | gatgttcctg | catatgattg | cacagacgaa | gagtttgatg | 37920 |
| cttatttaga | taaccactat | tcttgttcaa | atgaagttat | gtatgctatt | caggcttggt | 37980 |
| tgggtaatcc | aattgaatat | gattatgatt | tcatgcgagt | atttgagaaa | gtagaaatct | 38040 |
| ttgacattaa | agaagaaatt | cgtattcctg | atgctccagt | tgcattccat | gttggaatta | 38100 |
| cgtataaaca | aaaagaaagt | ccattaaaag | ttgattggtt | gaaatacgtg | aaggaaaagt | 38160 |
| aatggatatt | ggttcaggca | gttcatatcc | atcatgtgct | ttgagcaact | ttgctcctca | 38220 |
| taaatttatc | tatgatggcg | tagaatgtgc | ctcaatggag | ggattcttgc | agtccctcaa | 38280 |
| attttcttcg | cctgaaatgc | aagcacatgt | atgtacacta | gtcggaaagt | ccgctaaatt | 38340 |
| taaaggtaag | aagaaacgtt | ggtggccaac | tcaaacactt | tattggaaag | gcgtgccaat | 38400 |
| ccatcgtgct | tcagaagcgt | atcagaattt | actgacagga | gcatacgatg | cacttagtaa | 38460 |
| aaatgaagga | ttcagaaaag | ctttggctgc | tacccggaat | gctacgctca | ctcacagtat | 38520 |
| gggtaaaaat | aaaatttctg | aaacgatttt | gactgaacgc | gaattctgta | atcaacttta | 38580 |
| tcgtttgaga | aatgctataa | ataatcagta | atataattat | cttgttcagt | gttgaaatcg | 38640 |
| gtagacatgg | tgacgggcac | cttttgagct | cgcatattgc | atcatatgct | ggcgatggtg | 38700 |
| gtaaatcgcc | gacggaatca | gtcgtgcagg | ttcgagtcct | gcctgaacaa | atatttgcgt | 38760 |
| cgatgttgga | attggtagac | aaaggagact | taaaatctcc | cgggattaaa | cccgtacgag | 38820 |

FIG. 20V sequence.txt

| | | | | | | |
|---|---|---|---|---|---|---|
| ttcgagtctc | gttcgacgca | ccaaagccct | tatagtgtaa | tggatagcac | acgatcgttc | 38880 |
| taaggtcggt | agtccgggtt | cgagtcctgg | tgggggtacc | acgccgattt | agctcagttg | 38940 |
| gtagagcgct | tcacttgtaa | tgaagatgcc | gcgggttcga | ctcctgcaat | cggcaccaaa | 39000 |
| ttcgaaggga | aacttgcgta | taccctcgtt | gagtcgtcag | atagaagaga | atggttcgtc | 39060 |
| cattgccgca | agtcggttgt | tccctgtcgc | aagcataacc | tcctgacgct | atacttcttt | 39120 |
| ggatgagact | gatgcctccg | agtccaaaga | aatgaatttc | gcaggtcatc | tgccagtggg | 39180 |
| tgatgctgtc | gattattaga | gccctgtctt | cggacggggc | ttttagtat | aaatagtaat | 39240 |
| ttaatcggca | ctaaggattt | ttttgcaatg | aaatttaaag | attttttaac | cgaagaagag | 39300 |
| cttttttgaag | cagctcctgg | ccgcatgact | aaatcgaaat | ggcgtgacgc | tctggtattg | 39360 |
| gttccacgtg | gtgaacgcca | tgattttagc | aaatttgcgg | cttctgtgga | aaagatttat | 39420 |
| ggtattggga | ttagcgatcc | taaagactat | gctaaggtag | cagctgcctt | tgaaagttta | 39480 |
| ggcggaaagg | ttactacacc | tgcacgtgga | gcttctccgg | cacaagcacc | ggccgcaaaa | 39540 |
| ccggctccgg | ttaaagcgaa | acctaaaaat | attcctggcc | ttaaaattag | tggagaccat | 39600 |
| ggagacatca | ttggttcagg | tgaactgttt | aaagctattg | ataaagctct | tccactagta | 39660 |
| agagataatg | gtcctctttta | taaagcagtt | caattctatt | tcgataatct | gtggaagtat | 39720 |
| cgtgaatccc | aaggtgctaa | accttctgca | cgtgaaactc | agcatatcgg | tgaagtgaaa | 39780 |
| acacttttag | ctaaactgaa | tcatcacctt | gttgaactca | gtcgtcagac | agaattatcg | 39840 |
| tacaatgtat | aataaaatgt | aatcctacag | ccctagaatt | catctagggc | attttttgtat | 39900 |
| cctcggctgt | ataaatccat | tctatcttcc | agaaagttcc | tccagatgcc | ctaaaaattt | 39960 |
| ttgcacaaag | ttgtttactt | cctctatcaa | ctcggttact | atagctccat | caaaacaaaa | 40020 |
| cagagtaacg | gagaataaaa | tgtctaaatt | caactttatc | caaattgaac | gtggttataa | 40080 |
| caattacggt | actcctgatc | gttatcgcgc | gatttggatt | aaaggtgaac | atgaacacgc | 40140 |
| agtgttcaat | gtagcagaaa | ctcgtgaact | taaagatttg | attaagcatg | ttcgtaaaga | 40200 |
| ttggcctgct | gttgaagagt | actacgttcg | agtttaccat | gaagaagctc | ctaccgaaac | 40260 |
| tgttcaaatt | aaattcgcaa | aaactgctag | tgctttaacc | aaacgaattg | aagctgtaat | 40320 |
| taactgctaa | taattttggg | gagttataat | gaactcccca | cctactgagg | aaataaaatg | 40380 |
| tctattctga | aaaaacttgt | tgaattcatc | cgttctaaat | tcggtacctt | tgttgcacag | 40440 |
| aacacttctg | ttgaagacca | gtatacgatg | gcagcaaacc | gtattattga | tgaaatcact | 40500 |
| aaactgcgta | ccacgcatgt | taaatcagta | aatgaagaaa | agcgtctgct | gaaacttgct | 40560 |
| gatgaaaaag | accaagcggg | tgcttctaaa | gagcgtgaaa | ttcgtcgctt | gatggcagaa | 40620 |
| ggtatgaatg | tagaaaccca | tgctaaactg | ggtcttctgt | atcgtcgtac | tgctaaggct | 40680 |

FIG. 20W sequence.txt

```
ttacgtgata aagctgccga atataaagaa atgcgggccc aaattgaaga aaccgtagtt      40740
aagcttgatg accaacgtct tgatttggca gtgaaactcg aatacatccg tgagacccgt      40800
aatgcttctg ctctgggtat tacctctgct gacgacgtga ttgaaatcgc agaactcgct      40860
aaagtagatg tacaagacat catgatgaaa gttgaaacct tcagcggtac tcagcctggt      40920
attgaaacca ccactgctga tgtccaggaa tatctggaaa gtctgaagta attttaccgg      40980
ggccttcggg cccctaact tggataataa aatgttatat gaatgcgctg gagatattcc       41040
aatggcaaca cctcaaatta aagaattaat tgcagcagga ttcccaacag aaatcactga      41100
tattcttgga aaatttgctt atcctgatac tcggcctgaa aattggaaaa ctcgctataa      41160
cgggtataac accacagttt taccgcgggc tatcgttctt aaagactatt ccaagctgaa      41220
aaacttaatt tctaatattt cgtctatttc cgacggagtt aagcttgtgg atattttttgc    41280
acttcggtac ggaatctact cttttaacga ttctccatca aatttaaaat cagcccgtac      41340
taatgccggt gaatactcta cttctggttc aacaacgtac accatagtta ttgagattat      41400
tcataataaa aatagctatc gtcttggtat taacctagtt aaatatgtga catctcagga      41460
tgattatagc aattatttaa attactgtgt taatgaattg ccatcaaagg ttatgagtat      41520
gtttgactct aacaacatgg taggcaaaca attaatcatt gatgaattta tcaaatactg      41580
ccgtgagagg gtgcagaaat gagtaactta tatctgccaa gtgaacctcc cgtttataat      41640
tatgtctata aatttgatca gattgattat gcccttgttc ctggtattgg tgcaactgtc      41700
ggcgcaatgt gtacctttgc cgcgattgat atcatgcatt taactgatat tacaccggca      41760
gtgttattcg gaattctgct tgcatggtgg ggaactagtt tgctcatcat gggattaatt      41820
gaatgttccc gatgggttaa atggtctcgc aataattata agcgtaaagc tgaatggaaa      41880
gaacagtgca agaatttaac tcttgaatgg aatcgcaaaa agtcgtttga gtttattaaa     41940
gaggtgagaa gaaaatgaat gaatataaac ccgacggatt ttggaatcaa gatgggctcg      42000
cgccaggttt tggaattgtg acatggcttt tatattgtgc tttcgtaatt gttggaggga     42060
cattctttgg attgaacgtc tcagagttta tgattatgct tttattttta ggtgttttcg     42120
cattcagcct catgtggatg ctaattatcg cgttgattaa ttgctgtaca tttttagctt     42180
accgaatgaa atacaagaag tggaaagaaa aagaagattt caacacctgg attaggagct      42240
gcagaaaatg attaaaactt gctaccgtgg aatgattaaa agcgatgagc ctgggtattt      42300
cttcctattt ctgcttattt ggttttcatt atcagccttt gttggatttg aacattctg      42360
ggggttctac ttcttttctc cagtatttgg cgatgcgtta tattacatag gctggatgtc      42420
aggtgttgga acttggtttg caatacttgc ccggtggttg caattcgttt cccagcggca      42480
gaggggtgta ttcgataagc ccaaagtaaa gaaagaaaaa tctaaagatg actctcgtag      42540
tgaaaccttta tcctggatta aggagatgaa ataatggctg ttgcagtgca tgtaaaattt     42600
```

FIG. 20X sequence.txt

| | | | | | | |
|---|---|---|---|---|---|---|
| gaaaatggtg | atactcgcct | tctgtgttac | agtgataatg | aatcactgag | cggtatcgag | 42660 |
| atttcactca | aagaagaact | gcttggtatt | aatggaccta | tctgtgattt | ctcggtagaa | 42720 |
| ggttcggata | attgtaatga | tgatttggag | tctatggtct | atactgccat | ggaagatatt | 42780 |
| cttgaagaaa | gttggaacga | atgccaatga | aagagctcag | tgcaggaatt | ttattcttta | 42840 |
| ccgatgacaa | acggctttta | atgggtcgta | tgacaaatac | atatgtccag | ggcagaggct | 42900 |
| ctagatggga | tattccaaaa | ggacatgttg | agcctggtga | aacaccaaaa | gaagctgcta | 42960 |
| ttcgcgaatg | caaggaagag | actggattta | ctgagtttga | ccaagacctc | ttatatgacc | 43020 |
| ttggacgaca | tgattatgca | agcaataagg | atatccatct | gtttggatat | atgctccctg | 43080 |
| taagcccaga | aatgttcaga | aattgccgtt | gtacagctta | ccataaagat | gaaaatggaa | 43140 |
| ttaattttcc | tgaaatcgat | gcatttgctt | taattaaacc | aagccagtgg | aaatatgtga | 43200 |
| tgggaccaag | tttatacaaa | atcatgacgc | aaatgtatag | cacagctcag | tgaggttatt | 43260 |
| atggaagaag | ccgttgaatt | aggcattcca | cacatttata | aacatgagct | acgatttatt | 43320 |
| cacgatggaa | aatggattag | catatttcat | cctagggata | aatgtcgcg | tatactaatg | 43380 |
| aaatcacggt | atgtcttcag | tgatagtgag | tatataaaat | cagcatatta | tatagcagaa | 43440 |
| cagctatatc | cgggatttag | tgaattgccc | gaggacgata | aaagagatta | tgtgtggtgg | 43500 |
| aaagataaat | ggacaccata | cgagaagtgt | agccttgagt | tattcatagc | caagtgcagg | 43560 |
| gccaaataaa | tactcctata | aattaatagg | aggtccttat | ggatatttt | ggcatgttgc | 43620 |
| gtattgatga | aggatacgac | agcaaaattt | ataaagatag | cgaagggtat | tggactatcg | 43680 |
| gtattggtca | cttactgact | aaagacccgt | caaaatcttt | ggctatttct | aatctggaca | 43740 |
| aactggtagg | tcgttctacc | ggtggccaaa | ttactcaggc | tgaggcagaa | gtaatttttg | 43800 |
| ccaaagatgt | tgagaaggca | attaaaggta | ttgttgctaa | tgctacatta | agcccggtat | 43860 |
| ataatatatt | agatgatgtt | cgtagagctg | ctctgattaa | catggtattc | caaatgggtg | 43920 |
| tgtctggtgt | agccgggttc | ccagcttcaa | tgaagttatt | actcgctaaa | aaatgggatg | 43980 |
| ctgctgccaa | ggaacttgca | aattcacgtt | ggtatcgtca | gacacctaat | cgtgctcgtc | 44040 |
| gtgtaattga | aactatgcgg | accggaactt | gggccgctta | tcaaggaaaa | taaatgaaaa | 44100 |
| cctatcaaga | atttttaaat | gaatcccgtt | tagcaacagt | tggcgtaatg | actgaatctg | 44160 |
| ttggaagtaa | tcttctgaaa | tttaaaaaag | gtcagaagat | gacagccacg | ctagaagatg | 44220 |
| gcacagaaat | tgaaatggac | gttgttggat | ataactacgt | agtagacggc | aagttatata | 44280 |
| ataagagcca | tgctaagttt | gattcattcg | atgattttgt | ctcttcggtt | gaagatgaat | 44340 |
| cttctcgcaa | agcagtagca | tctggcgatg | cacgctcttt | aatggcccat | ggacatatgc | 44400 |
| gtattaagtc | taagcagaac | aaacctggtg | aagataactt | tgcattagta | ggttatcagt | 44460 |

FIG. 20Y

```
                              sequence.txt
ctggtaaaac ttctaacggt taccagcgta cggttaccat gtacatgcgt aatggtaaaa    44520
ttgcattcgt aaacgatcgc ggcgctattc gttacgctaa atcaattaag taagcaattt    44580
cctaataaag ccgaacacga cctctcctca tgaacgtcga gtcctctgag tgaagtagct    44640
tttcctacct gtaataaggt cgagcgcaag tgcggtaagg ggtttacata gtgtgtcgat    44700
ggattaaaca tgtgccaagg aatggcccca tttaatttaa aacttttacc tttctggatt    44760
taaaaatgaa aacttataaa gaatttatca ctgaagcgcg agtgagtgca ggtaaattag    44820
aagccgctat aaataaaaag gcccattcat ttcatgattt gtcagataaa gaccgtaaga    44880
aacttgtaag cctttatatt gacaaagagc gtattctcgc tcttcctggc gctaatgaag    44940
gtaaacaggc caagcctttg aatgctgtcg aaaagaaaat tgataacttt gcttctaaat    45000
tcggtatgtc tatggatgac cttcagcaag cggctatcga agcagctaaa gtaattaaag    45060
gtaaataaca gtttactttc tcctagaatt gtgatagtat attcatattt acatttaaac    45120
aacattggaa taacctggac ctcatgattc tatgagggat tcccgcctac ctgtaataag    45180
gtcgagccca agtgtggcaa tgccagttac ataaggtatc ggaatggact cactccatgc    45240
gccaaggaat ggccccatta aaagagagct tatgaaatac ttaacaccaa tttatttgac    45300
cctgatgcat gctttcaaag acgctgcaga cagacgatta aataatccca actacagttt    45360
ttatgaaccg tcttgcctta tgcgagagta cggtaccctt cgtctagatg gtggaagaca    45420
aaccggaaag accgcagcct tatgccaatt cgctaccgat tggttgcttg aagatggttc    45480
ggttataatc ttatctactc gatacacaca atcatctgaa ctgatggaag gtattctacg    45540
agaatataat tcatcgcatt taattaataa attaccggct aacgagatag ctaaatcaat    45600
tgttccgatg acaatcaggg aatttctatc caatgattcc tcttataagt ttagaggaag    45660
aaagcttgga agagcattaa ttatcattga agaaccaatg aaagttcccg atatgatgaa    45720
gttctatgat atgtaccagg aagctatcag atggtctatg cctaatgata ccttaccttt    45780
attttcgtg ataggaatgc aatgatgaca cagacagaaa ttgttgatat gattacagtg    45840
atggaaaata caggatttgc cgatatgaag caattaataa caatggttac ggctggcaac    45900
ctgcttgagt acaagcgcta caagtttctg tctggcccgt tcaaaggcgc agaattcatt    45960
tctaatgctc ctaacacgaa gtggatgaat cgctatccta attttagaat tgagtttata    46020
tctggtaagc taaaaggcgt gattagttca agcttaatca catatgacca acgcattcaa    46080
gagaaaacaa tgcaatggct gaaattgtta taaggtgtcc tccacaccta gttgagagct    46140
tctgtgaatg gttcagtaat tctggtgagc aagatttta tgaagctcac cagaatggaa    46200
cttggaatga acaaccaaa cagtgggaag aagctacaac gtatataggc actcgcggat    46260
atggagttaa cgagcctatt gaaattgtgg aatacgataa agaaactgat gaagaagtta    46320
cttatcatga agataaaata acttatctag aagcagctgc aaagtttcat tcagacgaat    46380
```

FIG. 20Z sequence.txt

| | | | | | | |
|---|---|---|---|---|---|---|
| ggaataaaat | gagtgtaatt | accgcataca | tgcgtggttg | gaataaagaa | tctaattaag | 46440 |
| aggaaatatg | aaagcatatc | aaattcttga | aggtgaactt | aaaggcacca | tttacatcga | 46500 |
| agatggtgat | gacgcacgag | taatcgtttc | aaaagttctt | aaagaagata | ctattacgga | 46560 |
| tgctgaaact | ttttatggct | acaaggctcg | tgaagtagaa | attgaatacc | agccaacggt | 46620 |
| aaaaattgaa | ggcggtcagc | acctgaacgt | taacgtgctg | cgtcgcgaaa | ccctgctgga | 46680 |
| cgcggttgag | catccggaaa | aatacccgca | gctgaccatt | cgtgtttccg | gctacgctgt | 46740 |
| acgcttcaac | tccctgacgc | cggaacagca | gcgcgacgtt | atcgcccgta | ctttcacaga | 46800 |
| ggcactataa | tggcaattga | agatatcaaa | ggatataagc | cacataccga | tgaaaaaatt | 46860 |
| ggtaaagtga | atgctattaa | agacgcggaa | attcgtcttg | gattaatttt | caaagcgtta | 46920 |
| gaagaagaac | atgttgaaaa | gtacatgaat | ttagatgtta | gcacaatgag | cgacaaagaa | 46980 |
| tttgatttag | cacatgagcg | tattactcaa | attcgcaacg | cgattcaaca | cttgaaggaa | 47040 |
| gcttctatgt | gggcatgtcg | ttcagtgttt | caaccagaag | aaaaatatta | aaaagtagtt | 47100 |
| tactttcctt | acgggccatg | atactatggc | cctacaaaca | aaggagaatg | aactatgtca | 47160 |
| actaacccag | aagtattcat | ccgcagaact | aaaactacgtc | gtaagtttga | ggaagcattt | 47220 |
| cgctctttga | atttatcagt | tcgtgcccga | gctaaagctg | agggcaaaga | gcctttcttc | 47280 |
| actaagtact | ctgatcattt | gttggaccgt | gctatccaac | gtgaaattga | tgaagagtat | 47340 |
| gtattctctg | ttctttccaa | aattcctaat | catcttaaag | aaattaatga | attcttagca | 47400 |
| atgccttggc | ttccaattga | cccaaaggac | attgatgaaa | acattgagta | taagccaatg | 47460 |
| cggttagaaa | ttacggatgg | aaatctgtgg | ctagggttta | ctatggatat | tccaagacca | 47520 |
| ggaaaaggac | ctagtataaa | gtgtcgtatg | gcattcgtta | atgataaacg | tttgaaaggt | 47580 |
| aaaatcagca | caaaagttat | acacattaat | tgaggtaaac | atgaaaaaag | cgcttatcgg | 47640 |
| tctaatggcc | ttatgttcaa | cggcctttgg | gtctgagcca | actttcagta | atgttcaact | 47700 |
| tgacaacttg | cattacgcat | ataattttgg | tgaacaatat | caaaaatccg | gaaaagaaaa | 47760 |
| atctccgcat | aaccgatatg | ataataacgg | cttaggatat | ataatggctg | ctatatcatg | 47820 |
| gaaagaatct | tcggcaggag | ccaatttaaa | agcaggaaag | gggcatcatt | cttatggggt | 47880 |
| atttcaaaat | tacttgccta | cggttaaagc | cagagctaaa | ttagagggca | aaaaccttag | 47940 |
| tgattctgaa | ataagaaaaa | tgcttaaatc | tagacagaat | tccgcggaat | gggcatatat | 48000 |
| tgagctttca | tattggttaa | atatacataa | cggcaatatg | cgaaaagctc | ttgctagtta | 48060 |
| taatgcagga | tggaatgtca | aaaggggaaa | ctcttatgcg | tcagatgtcc | tagagaaagc | 48120 |
| taatttctta | aaaaaacata | aaatgctaca | tacaaaggtg | gaataatggt | aaagtacgcc | 48180 |
| gcgcttcttg | gattggtatt | ggcattctct | gctaatgctg | aaaattcaat | gacagattca | 48240 |

FIG. 20AA

```
                                   sequence.txt
cttcgtatcg ctaaaacatt ttgcaatacg aactctgaat gtgttgatat attagcgctt    48300
gaattagatt cagcattcag cgatggagta aaagattcac gtagcccggc tcagtggaca    48360
acactaataa atcgtaaggc taagagcatg aaagatttat gtgtcaatgc tcctaacgaa    48420
aatatatgtt taatgtatcg tgaccaatta atggctcgtt atatgtcagg actatcgtca    48480
aaatgaaaaa agcggctatt ttattatgct gcgcattttc agttaatgcc tgggaaaaac    48540
tcccaggcta tcctgaaact gtacttgcag cacagggtac taaaatagaa agcaatggcc    48600
cattcaagaa caacattgaa atagcatttg ttcctagcag cagaaaattg ctaatgtcat    48660
tttataatta tcaagataaa gatgaccagg tgatagttcc acttgtcgaa tataatgctc    48720
gtggatgtgg aatgcagagc gatggcgttt ctgttgatgg agtaatgcat cctaaagaac    48780
aaggagtgct gaaccctatc cttaattgta caatgctat atttttaaga gtatacaata    48840
atcttaatga atatgcaaca tataaaattc cataggtgaa taaatgatta ctggatatat    48900
taagggcaat attgtagaac tattcatgaa gcatgaatgc gatatcgctc atgggtgtaa    48960
ttgctttact acaatgggtg ctggtgtagc aggacaactt gctaaagcat atcctccaat    49020
tctcgatatt gacatcgatg aagaccgtta ttatgacaat aatttagcca agcttggaac    49080
tcatacacga gccattcaca aaaaaggcac tgcatattgc tataatctgt atactcagta    49140
tgctccaggt ccaaacgttg attacggcgc aatttttaat gcattccatg aactaaattc    49200
tggtcgtatt gtttataatc gtcctctata cattccaaaa attggagctg gtattgctgg    49260
cggtgattgg gaactaattg agaaattaat caatttagca acacctgata ttgacattat    49320
ggtggtagaa tatgaagaag ctaaaagcta aatccgtctt gtagaggtaa atagatgatt    49380
actgaagagc aaaaaactaa actgtggcag ttgattgacg attatgcagg tgccgagcaa    49440
gtagtagcta ttagtgccat ttacggaaat ggtctacctg aagaatacga tgaactcatt    49500
cgttctaaga atgctatttc tgattttatg gagacacttt aatggcacag ctttatttca    49560
actacgcgag catgaatgca ggcaaatcag ctaaccttct tacagcagct cataactata    49620
aagaacgcgg catgggaact ctcattctga aacctgctat tgatactcgg gattcggcaa    49680
cggaagttac ttctcgtatt ggtctacgtc atgaagctaa tacagtagac gaatctattg    49740
acatacttga atttttcaag tgggcacaaa cacaacgtga tattcattgt gtatttgtag    49800
atgaagcaca attcttgact gctgaacatg ttcttcagct atgtaaaatc gttgacttgt    49860
atgatgttcc agtaatggca tatgggcttc gcactgattt tcgcggcgag ttattcgaag    49920
gttctaaagc tcttctttct gtagccgata aacttgttga gctcaaggc gtttgccact    49980
gtggacgtaa ggctacaatg gtagctcgta ttgacgaaaa cggaaatgct attaccgatg    50040
gtgaagtagt agaacttggt ggtgaagaca aatacgtttc tctttgtcgt aaacactggt    50100
gcgaactggt aggtgtttat aatgaagcca agaacgtata acactatcct gatgctagtt    50160
```

FIG. 20BB sequence.txt

| | | | | | |
|---|---|---|---|---|---|
| ttaagtatgt | tattcatttg | gatgggtgta | gcagcatcta | ttcaaagcga | tagacgagaa | 50220
| gaacttcaaa | atcgtcttga | ttctggatgc | aaagtattag | ctcagggtaa | agactttatt | 50280
| gctaatacaa | atgggtgtta | tattaaatat | gagtagccta | tttgctatag | cgggtgtata | 50340
| gtactagtac | tcgtgattgg | gtttttacta | tacgtaatat | ttctttcgtt | attggtttaa | 50400
| tatgaaaaaa | tatgtgatgt | gctatcgttg | tcttcatgta | tatgattaca | acactgctcc | 50460
| aaagactgct | accaagcgtc | ttaaaaccaa | agaacctgaa | tgtccaaaat | gtaaatgcaa | 50520
| ggtcatctat | tcatgaatat | taaattttc | aaatcaggat | tttactatcg | ttgaggtaat | 50580
| ttaacttaac | gaggtaataa | tgtctagaac | aattcgccgt | aaaggctggc | atgtagtaaa | 50640
| atcttccaaa | tggaacgatc | agaataataa | cgaatttgct | tatattaaaa | gctataacga | 50700
| atacgttaaa | actcagaaag | ataaagaaaa | ccagcagaaa | tatgttgaac | tgcgtatttc | 50760
| tgaaaacagt | gaaagaccgt | tagaggccaa | gaaactgatc | gctaaatcaa | agcgcgatgg | 50820
| attctggaaa | actctacgtt | ggacccgtta | tgctatgccg | gttccgcgtt | tatttcataa | 50880
| agccgaaatt | aaacgtgcat | tgaagtatga | tgaagaatat | aactgggacg | aagctggtgc | 50940
| tagaaccatt | gagcaaggca | tctgcgaatg | gctttgggat | taagtaacac | atacttatat | 51000
| aaatactatt | actaactgat | gaggtgtata | tgcagcattt | aagtgaaaag | caacttcgta | 51060
| atcttactgt | agagcagctg | gacgaacttc | gtcgtgagat | tgggcatggt | atttcgcacc | 51120
| ttcaggaaga | aattcgtcaa | catagttcaa | aagcagatta | tacccgtaaa | cgtacgctgg | 51180
| aaaaatacct | caaagaagtt | aaggctgtac | ttcagcacaa | acgtaatact | ggacaaaaat | 51240
| aataggaggc | cgtatggcct | ttaatcacat | ttgcttagcc | ctggtgttgg | gctgcgggat | 51300
| ttcattccca | gctgcatcac | acgacgacat | ttcagattat | aattcgtatg | ttgagggagc | 51360
| tctacaagtt | tatgctaaat | ttaaggagcc | tagtaagcaa | gagtctgaac | agttctatgc | 51420
| tttcgtacaa | agtaaatgga | agagcgagtc | ttgttctaaa | gattgcgatt | ctttaggacg | 51480
| ttcagcaggt | gaagaatacg | ctaaccgtat | gaggatacaa | ttcgataatg | aagttcaatg | 51540
| attttgtaaa | ggacggtaaa | cttactccgc | aggatgaatt | catcggttta | cttatggtgt | 51600
| ctcaagcgta | ttttcattca | gcgcattttg | ataccaaatc | gtatgccaga | cataaagcgt | 51660
| atgaagtttt | ctttaacgag | attccagatt | tgatagatgc | ttttggtgag | cagtggttag | 51720
| gattctcagg | taagagttat | acaccggctt | taccatcgca | gaaagagctg | ccaaaggaca | 51780
| ccattgaaat | gctagacttc | attctggcta | aggccgatgg | tatctacaag | tccgttcctg | 51840
| ccgccctcca | aagtgttctg | gatgacatta | caggcctatg | ctacaagact | aagtatttgt | 51900
| tatcattgca | gtaatacct | ccgcctcctt | cgggaggcat | tttctttca | aaaagttgtt | 51960
| tacttcccctt | cattacatga | tactatagac | atatcaacaa | ccaaacgaga | aaaacattat | 52020

FIG. 20CC

```
                                      sequence.txt
gattaagtta actaccgagc ttcaacctgg aaaaatcttt tatcacgtgt gtggtgttaa      52080
tcgcacagaa actaaacccg gcgaaataac gcgttacatt gttgcttcag gcacatatga      52140
tgtagaactt ggtcttagtg gtgtatattc acgtaaatct cctttcttcc aagtgatttg      52200
tgaatatgaa aactatgctg gccaaactga aagctattca actgaacggt ctgcccatga      52260
tatggggtata ttcaagccag gtgaaaagcg ttcggttcat aatcttaatc gtgggttttg     52320
gacgcgtgaa gaagctgaac agttcatcaa agagctccaa gaaaataagt tcagcgatcc      52380
agatgatcaa gcatatgcag acagactgac cccttctgaa gatttccgcc gtcaacaaga      52440
atttatggat tcttatcttg acagttgtga ttatgattac tacgactttg atgatggcga      52500
agaatgagaa acgttttact tatcatctac attgtggtac aataccagca tccgatgttt      52560
acatataatt tggtgcaaat gattctggag agtttgaaat gaatggatgg ggcccatcag      52620
atgacggatt tgcaactcgc gaagctacaa tagcagacgg gattgaatgg gcccgtcttc      52680
agaaacaact ccaagaacag cgggaatccg aagagttctg tgttgattgt gatgaggaaa      52740
tcccagtagc tcgtcgtctg ttggttaaag gctgtcaacg gtgtgtagaa tgtcaaggaa      52800
agtgggatac agtaatgact tctgcttata atcgccgtgg ttcaaaagat tcacaattga      52860
ggtaattatg gaaagtattc ttgatagtac caatttagat aatccgtaca gcgatgtgca      52920
tgtaaaggtt gtgaattcgt attttactaa aaagttgagt cgtgtcgtgc taaaacaagg      52980
taatgatata attcatcttg atactaaaca aattgattca ttaattcaat tcttgataga      53040
ggcaaaagat ggcgagtaaa ttagtatggg acggaaaacc ccgtaaaggc gatgcagtaa      53100
ttgaagatga aagcccgcat gttattgatt tgtatcttac ggtattccac acgtatgaac      53160
ataatactat catcgaaatt gaacgtgacg gagattgtgt agctattgat aaaagcgacg      53220
ctattgaact ggtcaaatat cttaccgcaa tgattccaac tatgaaacag gataacttat      53280
aatgaatatc aataaaaatt cttggcattt caaaatgaac ctatggttta aatctggcaa      53340
tatatggaaa atgccaaaaa ctctatgtgg atacttttgg accacagtac ttcatattct      53400
gttctcttca gcaattgcta tattcattgg ttctgttgca tggatgttcg gttggccgct      53460
tatagcgcag acgggtattc tcgcttggat aggtgttagt ttatccgcct tttggctaaa      53520
tgttgtagca gtaccagttg gtgcagtgtt tatagcaaca tttgtgcttg cgtttgtagc      53580
aatagtgttt ggatttattt tcggtttaga aaaatttaaa gaataccgta aaaataaaca      53640
atttacgaag aaacttgctc gagtaaaagc tggtcttccg gcagaatccg aaccgttagt      53700
attcatccag tatttaaaag ctcgtaaacg gaaagtttgc ccaatgattg attatgtaga      53760
aggtaaaact agtgaagaat gatcaagttt atatcgtgaa cggccgaaag gccgtctttc      53820
gtgctaaaac tgaacgtggt ataatttcta catacctat tgccgaattt acttttgaag       53880
atggcgagca gattaaaatt aaatatgttc cgttatctca gacgtaccga ttcatcggcg      53940
```

FIG. 20DD sequence.txt

| | | | | | | |
|---|---|---|---|---|---|---|
| gcgaaattga | tttagacatt | tattatgaag | gtggcgtatg | gaaattgaaa | tcgtaacaac | 54000 |
| caaaaagaaa | ctctctatga | gcttgcttaa | gcagatgaaa | atggcaagct | cttctgaaat | 54060 |
| caaattcgca | atgtttgacc | gagttcatcg | tgttcttgga | tatgttaatg | cctttaaatg | 54120 |
| gaacaaaatg | gatatccaag | tagcaatcat | taacactggg | aacgattggg | cattagttcc | 54180 |
| tatgtatgat | acacatgtta | ttaaaaccgc | ccggcgcgaa | ccacatccag | acggtcaaga | 54240 |
| atatcatttc | catgacgtag | tatactacca | tactatgcag | aaaatcggga | atgttcatcg | 54300 |
| caattctaag | aagagtactg | ataaagaaca | tgttgaagcc | tgtgctaaag | cctcaaatga | 54360 |
| tttgattaaa | ttcgctaaag | ggaatcatat | ttacttatga | aaacaatcgt | aaaatcttat | 54420 |
| tttggttcac | atctgtatgg | tacttcaact | cccgagtcag | atgtggattt | taaagaaatc | 54480 |
| tttgtacctc | atccgcgtga | tattctaatg | tgtcaggcga | tgaaccacac | caattgtaat | 54540 |
| actaacaaca | gcgcaaccaa | aaatacgaaa | gacgacgtcg | accatgagct | gttcagctta | 54600 |
| aagtatttct | tcaagctcgc | tgctgacggt | gaaactgtcg | cgttggatat | gctgcatact | 54660 |
| ccaccggaat | tggtagttgc | atctgacctt | cctgaagtat | ggaaattcat | tcaagacaac | 54720 |
| cgagctcgtt | tctataccac | tgacatgaaa | gcttatctcg | gatatgtccg | taagcaagca | 54780 |
| ggtaagtatg | gtgttaaggg | ttctcgttta | gctgacctgc | ataaagtcct | ggatgttatc | 54840 |
| agagatgttc | ctgaatggaa | atatgacgat | cgtcctcagc | agaagggtat | caatgagcgt | 54900 |
| tggaaagtac | aggatatcgc | agagaaactt | cctctcggtg | aattcctcga | atggaccacc | 54960 |
| ttcgttgacc | acaaatcagg | cgagcagaag | ttttataacg | ttctgggtcg | taaattccag | 55020 |
| acgactatca | ctatcaaaga | gatgaagtat | tcccttgaga | agcttgatgc | tgaatacggt | 55080 |
| gaacgtgctc | gtaaggcaga | agctaacgaa | ggcgttgact | ggaaagcact | gagtcatgct | 55140 |
| cttcgtgcag | gtctgcagct | tcaggaaatc | tatatgactg | gtgaccttca | attccctctg | 55200 |
| acccatgcta | aaatggtcaa | gatggtcaaa | gcaggtgagt | taccgttcaa | agaagtacag | 55260 |
| gagcttctcg | agtctgtagt | agatgaagta | gaaattctag | ctcatactgc | tgaaaagaac | 55320 |
| ggaatgccta | agaaagtaga | catgaagttc | tgggacgatt | tcgtcgagaa | ggtttatctt | 55380 |
| gaaaaccaca | attcttacta | caaatgatac | aatgaaggtc | ttcttgaatt | atggaagacc | 55440 |
| tcataaaggt | agacggtggt | atttggaagc | agtttgcaga | gagactggtc | gtagagaaaa | 55500 |
| tgctaaattc | tctgctcgac | caactcgaaa | acaaatccac | caatttatgt | catgggccgg | 55560 |
| agaaactctc | cggttctcac | tttactgggc | tgaaatatga | ttttactttg | gagcgtagta | 55620 |
| gtgccaatcg | ttgttgcaat | aatttacttt | atcgtgggtt | ggtctgtctg | taaacatcta | 55680 |
| atcaaaaacg | gaactattga | gaaggtagga | gagtattggt | tctatctcat | cttttggttc | 55740 |
| cctgctttta | ttgttggagc | gattatcatg | ttcttccgct | gggcaggtaa | acttccaaag | 55800 |

FIG. 20EE sequence.txt

```
cgtatcgcag aaaacgctat caacaagcac gcataactga ggagccttcg ggctcctctt    55860
tttgtttcaa aagaatgcat aaagtagtat acaaactcgc gggctggtga tactatagac    55920
ctgtaccacc caaacagata cattggagaa taaaatgaaa actttagaaa tcgtcgtaaa    55980
caacattgat aaagccttta aagctgctga agcccacggt gtagaatttg aaccaatgat    56040
ggtgggagaa gcgttctcta agcttgctat catccgtggt gaaactgaca acttgattga    56100
ttttgtggat gacttctatc tcggttcaaa ggtccgtcct tactacatca atgaaatttt    56160
agaaaaataa ttaaaaagta gtttactttg gagctgtaga atgatactat agctccatca    56220
aaacaaaaca gagtaacgga gaataaaatg tcaactatca ccatcaagaa agggatttac    56280
ttcggcaaag agatttcagg tacttatgag ttactcggtg agtggttccc ggatagctta    56340
agtgctgaag attctcgcca gggtgatggt aaagtctttg ttgaactgaa tggcaaaaag    56400
cgtggtgttt gggtattcaa agatgatatc acaattgacg gagtagctgc taaaattgaa    56460
gttgttgaat ccgttgatga aatgaaagag cgtatcaaga aacgctttaa cgttatggga    56520
ttaatgacta acggtttaat ccacgggaac attcgttctc tgattatctc cggagcagca    56580
ggtatcggta agacttactc tttggataaa gcattacaac atgctcatga tactaacgct    56640
attgattaca aatcagtgaa cggtaaaatc tcaggaattg gtttatactg ccgtctttgg    56700
gaatcacgtg aagcaaattc agttctgctt attgatgatg tagatgtatt ctctgatatg    56760
gacattctta accttctgaa agctgctttg gattcagggg agaaacgtaa agtatgctgg    56820
agcactgcat cttctttctt ggaagataaa ggaattccta atgagtttga gtttgaaggt    56880
actgtggtct ttatcactaa cgttgatatt gaccgtgaat tagagcgcgg ttctaaactt    56940
gctccgcatc ttcaagcctt ggtatcacgt tcggtttatc ttgaccttgg tgttcacact    57000
aatgaagaga ttatggttcg tgttcaagat gtaataatga ctacttctat gttacagaac    57060
cgtgggttaa gaaattctga agttattgaa gttttggaat ttatgaaaga taacgtaaat    57120
cgtctgcgta acgtatctct ccgtactgct ctttatatcg gtgatttcgt tgcgactgac    57180
cgtaaaaatt ggcggacaat cgctgaagta acaatgctga ataatttaa acgggaggag    57240
aaatcctccc taactgagga aaatataatg gctactttaa tttctaatga tgtaaaacgt    57300
gttttgttta aaggcggaat gtatatcgtt gatactccta aaggtgatac ctcttcctgg    57360
actattaacg agtggattaa ttacattgat gaaaacggag cgtgggtaca atgagtttag    57420
cagctattaa agatattgaa tgttggttaa cgatattaa agtatatccg cctggtcata    57480
tctttgcagg taaacccaag ggtaaagcag agaaagcttg tgaagcaatc tgtgaaaaac    57540
tttataagtt taattttggc gataagaaaa atgtattagc tgaagtccat tcttcttatc    57600
atgaattacg tgtaatggta aacgtatttc gtgctcctcc attcattgag ctcaggaaag    57660
aatacgctaa taaagtattt gatactttcc ttgcaaatgt gcaggatgca gtaaagcatt    57720
```

FIG. 20FF sequence.txt

| | | | | | |
|---|---|---|---|---|---|
| tagacgaaat | gcataaacaa | caccaagatt | taaatgccta | ttataagcct | tggcgtaaat | 57780
| cataccaaga | gcttaaaaat | cgtattgaac | ttattcgtta | tgaggtgcta | aaatgaaaaa | 57840
| ctgggtaatg | acggaaagtg | aagcctatgc | agcgtatgtt | tcaccagacg | atcgtcgtag | 57900
| tgagttgttt | ggttattatg | gttcatattg | cgttgccgaa | gaagcagtta | agggcagtc | 57960
| ttggtggggc | tcagatggta | cagttaatcg | taagccaacg | gaactaatta | cattcaccga | 58020
| tgaaaatggc | gaatcatgga | cttttcctaa | aagcgctgct | attagtgttc | aggaagaaac | 58080
| acctgaagct | aagcgtaaac | ggttggaaaa | aattaaagaa | tccgctttgg | ctaaattaaa | 58140
| tcctgatgaa | cgcgaggcgc | tcggattatg | agtaaagaat | ttagtactac | tcgtatggta | 58200
| gatgcttttg | gatatccgtg | caacggttat | cgtgaattta | ttcacccgga | agttgaaaat | 58260
| caatttaaag | aagtcgtaag | aaatatttg | ctcaatgcat | ttaaaactca | aggaactaac | 58320
| ccgagagatt | taggcattta | tcttgaagaa | gccatcagag | acgtacaaaa | gagcgtatcg | 58380
| gctaaacttc | attgggctga | agaaaatatt | gcttggtcaa | acaagaaacg | ttctgattta | 58440
| aattggcccg | ctgatcgtga | acaaatcgtc | aattatgcta | aagggtaacc | catgtttaat | 58500
| actatagtgt | ctatacatgc | gtattacgaa | gggcagttaa | atgctgcccg | aaccaagtat | 58560
| aagcgaggaa | tggaggaatc | tgtggaatgc | cttaaagata | ttcagacatt | tgcccagaag | 58620
| acccagaacc | tcatcttgat | ggaccgtaaa | caggtctcat | tggctgaaga | gctaaaagcc | 58680
| tctaagatga | ttatagaaga | caataggaaa | caccaactga | aattgcttaa | acggcgacaa | 58740
| caccagtcgc | catggtttaa | cagtgatttc | cgatcttttt | aagggccttc | gggcccttt | 58800
| gttgtttaca | tcttagaaaa | gccatgataa | gatagcttcc | gttaactaat | gaggagattg | 58860
| aaatgaaagc | acctacttgg | aacgaacttc | aagaaatgtt | caatactgaa | gaagcttttg | 58920
| gaactatttc | tgaaatggtt | gagaatttag | tagattctcc | ttcagaagat | aatcttctgt | 58980
| gtttagcaca | gttcatcatt | gaaacttaca | tagagaatca | gaaatgacag | tatacgtaga | 59040
| tgtcttgatg | aatcatggtt | ggaaaatgag | aggtcatcaa | gtaaagaact | gccacatgtt | 59100
| tagcgacaat | cttgatgagt | tgcatgctat | ggcagaagcc | atcggaatga | acgttcttg | 59160
| gttccaggat | aagcgagttc | cacactatga | tttgcgtgat | gttcgtcgca | agcaagcagt | 59220
| tgctctagga | gcagtagaag | tatctcgtag | agacgcagtt | ctgctttgga | gaaaattttt | 59280
| cacaaagtag | tttactttcg | gcgaggctgt | tgataagatg | gtctcgtcaa | ccaaactgga | 59340
| gaataaaatg | aaaactttaa | ccgagattat | ctctgcactt | gttgaagaaa | atcgtgtagc | 59400
| ccgccaagca | caccgagcga | aagttgaaaa | acgcgccgag | gagttgaatg | ctggatgggc | 59460
| gaagacccgc | ttcggtcgtg | aatactttga | taaagtggta | gctcctactt | ggggcaaaga | 59520
| tgatcgtcct | catgctccct | ttgatggtta | tctttgggaa | aatgaattag | gtgaagttga | 59580

FIG. 20GG

```
                                    sequence.txt
agcttatcac gcaggcagtt acttgccgta tgttacagaa ttggattcac tggataagcc    59640
tgagtatacc ggtgaccacg gttggtggaa aatccgctta actcaagaag agtacaaaga    59700
acttcgggag tatggttatc ctcttgaagt acgcattcca tataaagagt ggaaattgca    59760
agatggcaca aatgttgtta tggcagaagt tagagctcat aagagcatct tagaggctat    59820
ccaggaacat tcaaaagagg tcttgataa tatattcaat gagctgaata agaataaagg     59880
ggatgcaccg gaaggacgag tgaccgtctc tggtacagta acgtcagtaa aagtttatga    59940
agactattac ggcgtacaat gtaagatgat ggttgtgctt gagaatggag ctacggttta    60000
cggctcccgtt ccaaaaagta ttccgtttga atacagaggc aaagtacagt ttactgctac   60060
atttgaatta gcgaaagatg ataaaactca tgctttctat aagcgtccaa gcaaagttat    60120
tatgcttgat gaatagttgt tgtataatgg gttcagggag attttgagat actctttgag    60180
cccagtccaa aatagaggaa aagataatga ataagaatga attaaagatg tttgtagaag    60240
ctgaattaa taagttgaaa gataaaactc tcacgaagcg tgagaaacat gttaaggtgt    60300
tatcagcttt acatgattta aatccaaggg cttatgatgt agcaattgct ggtaacgtag    60360
ctcgtcgtgt gctaaatagc atggcatcac atgaagccaa ttatgctggt tttgttgtag    60420
aaaacattcg tcgttctcgc tggttaggtg caatgtcagc agagaaacag ctcaaaaagt    60480
ttgctatcgg caatgctaaa atttacggtc agcgttatag ctttgcggca ggggcgttta   60540
aaactgaaga aagacatgac cgtagcgctg ctcaaatctt ctgttctgaa tttaatgcaa    60600
acctgcgccg tattcttaat cgttcaattt gcttgcttaa aggcgatgac cgcgtgaaat    60660
accaggcatc ttctactagt tctagaaatc ctaagggtgt ttcatttatt cgtgccgaag    60720
aacttgacaa tgtaactgta cgaattcata ttaatagcca tttatccagc ggaaagtatc    60780
cggctcgggc gcttttagcg caagttcgta ctgcattaga tcatatggat gtagttaaaa    60840
aatcatgctg taaacagcag ggtgaaaact catctgttct tgaagtacat ttggacccat    60900
ttaagatttt tcctaaaaca ttgagcacca ccccagttat tgatgaagat gtagcacata    60960
tgtatctcaa tgttgttaag cctcttccgt taacaccagt aaatcatatt gaaatcgcta    61020
agaatagtat tactgccgaa atggaatcgg ttaagcgatt tattgacaca aaagaagctg    61080
aattggctaa gcatgaattg acgatggcag atttggttaa atcgcttaac gaatacaaag    61140
agcgttatga atctctcgag tatgcccgga gcttactgtg aaaaatcaat taaagaaga    61200
catggtcgtt gatgataacg accttgaaat tgagtttgag tatccacctg tacctgaatt    61260
taaaattgac tgggacgcct gtcttgaaat ggtagaccgt cgagaagctg cagctaaaca    61320
agttgtgcct tgcgaaaaat gtggtagtat tcaagtacag cttgtcgatt ggacaaccga    61380
tattctgaaa atgaaatgcc ggacttgtaa acacagattt gagagaaaat taaaatgatt    61440
actaaaacta ttactggtgc taatactaag ttttttgtcg agtatgctaa taacctcata    61500
```

FIG. 20HH sequence.txt

```
aaagacaaaa actttgataa catcattgca gatatgattc ttgacgcata cgaaagtggc    61560
atcgaccta  tgcagcttaa agaatatctt cgagcgacaa tggattttac agttcttaac    61620
atgatgctta gaactgatac tgaattcaat gaaatgattg ctcgtcgtaa tgaaggcaag    61680
ttcaatttga ctgatgatga agtattagca tgcgctgctc acgaagcttg gaagaaggtg    61740
attaaatgaa aacaactggc gcgctttgga aagaattta  taacgatgaa gccttctggg    61800
aaggctatta tcatgatgac actttaatac tctttgatga tgttgaagta gaagaatatg    61860
aagacccttc gcctgatgcg gtagtaaaaa ttgaaagcgg atatgtttac aaaaccgatg    61920
atgattcctt cacttcccat gatttgagtc ttgaaacttt ctttaaacgt tggaaaaaga    61980
aacagaccac tcgcactatg gtagtcactg ttgataaaga tgacttcgcc aaagtatttg    62040
aaactatctc taatattcct ggagtgaaaa aggtaaaatg attgacatta aattagatac    62100
ttatgcagta cgccagttat tcccagaagg tacagcagcc cgtgctcaac tgcaacagtc    62160
agtaatcaat aacatcgtta aagaaatggt gttaaaagat tcacagaata agctgaagca    62220
agcagtacaa tctgaagtta atattgctgc tgtgactatt ccagatgtcc gagcagaagt    62280
taagaagcaa gttcagcaga tgttccatac tcgcggttgg aatgatatgt ctgctaaaga    62340
agaaatgtca cagatgatgc gtaacgctgc ccaatcatgc gctaaaaatg ctattgatga    62400
tatggttcgt caaactattg atgacgctgt taagcaagct gaaggtcgta ttaagatgtc    62460
tattgaaaga gctaatctcc gaattcaaga aatcattgtt aatgcaatga ataaaaattt    62520
cgctgatcaa attaacgctg ccattgctgc taaattggca gaacacttcc cggtaactgc    62580
taatggataa aattgatttt agcaaattaa atataccacg tatgggaatt cctgatgata    62640
ttgccaagca attagctagc gttcaaccaa tgccagataa ttgcatcaaa gatattttcg    62700
atgcgttaga tggtaaaaca ttagttataa ctactaaggc tgaaaatggc tcgtaaacga    62760
tatatggaag aagccgaacg agtaatgcta ctcatgtatt cggtttatta taatgagact    62820
ggtcaaatag ttgatagttc taaactcaaa ggagctatga ctcgtggccg aggttttgca    62880
caagcagcta ttgataaaga aattatttct cgccttggaa ttaagtatag ctccaagatg    62940
tatctccatc ctggctggaa ccaagttcaa gctcaagtat ttaaggaaat agaagaagat    63000
gttcacagtt tttggctacg acagcaacat ccataagtgt gtattttgcg ataatgcaaa    63060
gcgtctgctc gatgttaaga aacaagagta tgcattcatt aatgtaatgc cagaaaaagg    63120
cgtatttgat gaagtggtta tcagtgattt gcttcgtcgt ttaggtcgtg aatcacaggt    63180
tggattaact atgcctcaga tttttgctcc tgacggtaca catatcggcg ttttgatga    63240
actccgtaaa ttcaaattca atgcatgatt atcgtggaac cctccttcgg gagggtgata    63300
ttgtagccct ttattatggc tatggcggat tagaaaccgg tgagattaaa caaatcaaaa    63360
```

FIG. 20II

```
                                sequence.txt
atcatcgagc aaaggtagag gtaacttact ctaatggagt taaggttatg tctaaatgga    63420
aatacggtga gtgtatggtg aaattatgat tagcatgagg aagagttatg agttatgata    63480
ttggtgattt aaaagctccg tgcacggtaa caatttcagc agaagagttc atccgcttgc    63540
aagctattga agaactgttg tgggaaattg aatgtgcgct tccgtctggt ttagaaagct    63600
ggattgatga tgaagaccta caaaaactgc gaggttaaaa tgactaacgc tgaattagta    63660
aaagaaatca agcatatcgc tggtgtcact ggcgaatggg acgacaacta tgatttcgaa    63720
tatccgccta atgcaccaga cgatgatgca gaagaaatct ttgttttagt agaagatgat    63780
gaatggacac aggaccataa gtatcaaagc cgttctcaga tttggtatta cccagctcgc    63840
ggcgtccatt tcatggtatc agagtctcgt tcaggttcat atcataccga ttggtattat    63900
aatcctcctg aagtagatat cgtcactcgt cacgagaaag tagttactcg tactgaagtt    63960
gaatggcgta ttgaatacga ttctgttaat gattccgctc cggcaccatg caaagcagca    64020
aaggcataaa accttggtac acggctcgat gggaaactgt cgagccagag gaagatgcta    64080
ttcctgaaga agattataat acttctgaac ctaccattaa cgaactactt gattatgagg    64140
acaaagtgaa tggaacttat tggtaagcag tttgaagtta tagaaaatga tgatgaatta    64200
actgaacaat tccccagtt tgttcctgga tttaaatttc aggttatcaa tgcagttaat    64260
gaagatgacc ttgaaacatg tggcattaca gcagtaattg atttgctcac aaataaaatc    64320
atcacaatta atgacccaac tccattcggt gaatcttggt tctggtgctt ctatagtgaa    64380
gataccatgc accaaattaa agaaatcggc caaggtgaag acgttccaaa tatttctgaa    64440
attaaactcg accattttca tggaaaaatt gttccaatta ccaaagctct ttatgctttc    64500
gcaggtcaag aaaattgtga ttctgaagaa tacgatttaa tgcagaaagc agctgattat    64560
atcgtcgcct tggaaactcg tcttggagtt caatatgtct aaatcatgcg taaccaaaac    64620
tattacagta aaaattttgg attttgtga tattcatcgt attgcaaggg aaatcttacg    64680
tagtcatgga tataaaattg gtgacattat taaattcagt aatggatatt atgacgatga    64740
catcggtgga atggcttggc caaaaatgag tattattcac aaagaaacta attcatatat    64800
tgagttcaat gcggatgatt atgaaggcat ctatgctttc tgtacttctt tctgcataaa    64860
agagtctaat cataacatct atagtagtta ctcgttaatt taactataaa tactcttatc    64920
taatcgctga ggtaagagta tgttattaac cggtaagtta tataagaag aaaaagaaaa    64980
actatatcag gcacagaacg gattatgtcc ttgctgcaaa cgtcctttag atgaggatat    65040
tcaaaagaat cacctcgacc atgaccatgc gttagaaggt gacaatgcag gaaaggtcag    65100
aggcttgctc tgtaacctgt gtaatgcggc agaaggccaa atgaagcata gttcaaccg    65160
ctctggttta aaaggtcaag atattgacta cctcgaatgg ttagagaatt tgctggttta    65220
tctccgccag aatcgtaaag acagtaatat tcacccgcaa tatgttgccg atatggctaa    65280
```

FIG. 20JJ sequence.txt

| | | | | | | |
|---|---|---|---|---|---|---|
| acgcttttca | cgtcttggta | aacctgagat | gattgctgaa | atggaattgc | atgggtttac | 65340 |
| atacgaggaa | agtgatggaa | aatcacaact | tgcttcaaaa | tacaagaagc | agcttcgtaa | 65400 |
| gagtttaaaa | tgaatatcga | attagaaatc | cagggactta | ttaataaaac | caacaaggac | 65460 |
| ctcttaaacg | agaatgctaa | caaagattct | cgtgtttttc | ctacccaacg | tgacctgatg | 65520 |
| gctggtatcg | tatctaaaca | tatcgccaat | caggtcattc | ctttctctgt | aatggaagca | 65580 |
| cacaaagaag | gtgttatcca | ttttcatgat | atggactaca | gtccagcttt | gcctttcacc | 65640 |
| aactgctgtt | tggtagattt | gaaaggtatg | ttgcagaatg | gctttaaact | tggtaacgct | 65700 |
| caaattgaaa | ctcctaagag | tattggagta | gctactgcta | tcatggcgca | aatcactgca | 65760 |
| caagtagcat | ctcaccaata | tggtggaact | acttttgcta | atgtcgattt | agttctggct | 65820 |
| ccttatgtag | agaagacatt | cgctaaacat | gtacgtgatg | ctcgcaaata | tcaagtagca | 65880 |
| ttagtaaaag | attatgctat | ttcaaaaaca | gaaaagacg | tatttgatgc | tttccaggcg | 65940 |
| tatgaatatg | aagtgaatac | tttgttcagt | tcaaatggcc | aaactccatt | tgtgactatc | 66000 |
| acatttggta | tgggaacgtc | atgggaagaa | aaattaattc | aacgagctat | tcttgataat | 66060 |
| cgtattcgtg | gattaggacg | tgatggaatt | actccaatct | ttccaaagct | tgtgatgttt | 66120 |
| gtagaagaag | gcattaatct | acgcaaagaa | gacccgaact | atgatattaa | gcagcttgca | 66180 |
| ttagaatgcg | cagctaaacg | catgtatcct | gatatcatca | gtgctagaaa | taatagagca | 66240 |
| attacaggtt | cagaaactcc | tgtatctcca | atgggctgta | gaagtttcct | tggtgcttgg | 66300 |
| agagactctt | ctggcaaacc | cgttcttgac | ggccgtaata | atctaggggt | agtaacattg | 66360 |
| aacctcccta | ggatagctct | ggatgcaaat | tataaaagtt | cagatgatag | taataaactg | 66420 |
| ttcaaactac | tggatgaacg | tcttgatatt | tgtaaagaag | ctcttttaac | tagaattaaa | 66480 |
| tcccttgaag | gtgttactgc | gtcagttgct | cctattcttt | accaggaagg | tgcttttggt | 66540 |
| gtgcgtatga | aacctgatga | tgaaattctt | gagctattca | aaaatggacg | tagttcaatt | 66600 |
| tcattaggat | atattggcat | tcacgaattt | gatatgctta | cttttaaagg | aagcggtaaa | 66660 |
| ctcgtcctga | agtacatcaa | cactaagcta | aacaagtgga | cggaagaaac | cgggtatgcc | 66720 |
| tttagtttgt | attctactcc | ggctgaaagt | ctgtgctatc | gtttctgtaa | gattgaccaa | 66780 |
| gccaagtttg | gtgatgttaa | gggcgtaact | gataaaggct | ggtacactaa | tagtttccat | 66840 |
| gtgtcagtag | aagaaaacct | gtcgcctttt | gaaaagattg | accgtgaagc | accatatcat | 66900 |
| tccattgcta | aaggtggtca | tatttcttat | gttgaactgc | ctgacatgaa | gcgtaaccgt | 66960 |
| gaaggtcttg | aagtggtatg | ggactatgct | atcgagaagt | tggattattt | tggtgttaat | 67020 |
| atgccagtag | ataaatgtct | ttcttgcggt | tctactcatg | agatgacacc | tactgaaaac | 67080 |
| ggattcactt | gctcaatttg | cggtgaaact | gatccaagaa | aaatgaatac | aattcgtagg | 67140 |

FIG. 20KK sequence.txt

| | | | | | | |
|---|---|---|---|---|---|---|
| acttgcggct | atcttggtaa | tccttctgag | cgtgggttca | atcttggtaa | gaacaaagaa | 67200 |
| attatgcata | gggtaaaaca | tgttagagaa | accaatgaag | caagttgatt | ggaaccaact | 67260 |
| tagcgaatgg | ggattgattt | ggaaaatcaa | caaagaggtt | ctgcacccgc | ttggaattgc | 67320 |
| tataacccgt | gaccccgaaa | gtggattatc | ggctggggct | attcaaactg | atgagccctg | 67380 |
| gaaatatgat | gcagaagtag | aagcacgtaa | tgaggtaagg | ttcaatgaat | tcgacagaa | 67440 |
| tctacccttc | tgactttgtg | aatggccctg | gatgcagggt | cgttcttttt | gtcacagggt | 67500 |
| gtttgcataa | atgtgaaggg | tgttataata | aatctacttg | gaatgctcgt | aacggacagc | 67560 |
| tattcactat | gaatactgtt | aaagaaattg | catctcactt | aagcaaatcg | tatatccaag | 67620 |
| gccttacctt | aaccggtggt | gacccacttt | atccacagaa | ccgagaagag | atttcaaatt | 67680 |
| tagtttcttg | ggttaaagca | agatttccgg | agaaagatat | ctggatgtgg | acaggatata | 67740 |
| agtttgaaga | tatcaaagat | ttagatttgc | tacaacacat | cgatgttata | attgatggga | 67800 |
| aatatgagaa | atcactgcca | actactaaaa | actggcgcgg | ttctgacaac | caaagactct | 67860 |
| gggtaagaaa | tggttctacc | tggacacatg | attgaggaaa | tttatatgct | gacttacaaa | 67920 |
| attatgttta | ctctgaacca | catggctact | gaactgtttg | gaccggaatt | tctggctatg | 67980 |
| acagcgttca | tcttaactat | ttaaggaaaa | ttatgaaatt | tattaatgct | attcgtaaat | 68040 |
| ttatttctaa | cgttatcgct | ttggttgcat | taacggcagg | tgctttcgta | gcaattccgt | 68100 |
| ttattgttct | tattatcatc | gcagattgga | ttaatcctac | caagaaagat | gaaaagttat | 68160 |
| ctaatgaaga | atttcagaaa | cgagttaaca | ctctgactgc | taaactccaa | caggtcatga | 68220 |
| aatgatagaa | atctatggca | tccctgaaga | agtttggaga | tgccctggat | gtaaagcagt | 68280 |
| tcgtgacttg | ctcgataagc | tgcaacttcc | gtatgagttc | tataacgtaa | tcaatgaggt | 68340 |
| agacggtcaa | ccggtttatg | accgtccgtt | gattgagtca | cttgctaaac | gcatcgggtg | 68400 |
| ctatccatcg | cttgctattc | ggtatcctgt | cattttatg | gataacgtta | agcagtatga | 68460 |
| cattccaaca | ttcaaaacca | atcttattgc | tgctgggcat | gacccagata | tcatagaaga | 68520 |
| ttaaccggtt | cctttctaag | gtcatcttga | ccaccttctg | tatatttcta | tacccttcat | 68580 |
| ttagaggttc | ctgtgggacc | tctcttttat | tttaaatcca | tttcacaaag | ttgtttacaa | 68640 |
| gctagctgat | gagtgatact | atagctctat | caacggataa | cagcataccg | tttaactcga | 68700 |
| gaggaaaata | tgaactggtt | aaattggcaa | gaagctctag | aagctatgag | taaaggctgt | 68760 |
| aaagtaaagc | atgtgcattt | tactgatgac | gaatacttct | tgatgaagaa | caaagtcatc | 68820 |
| tgtgacgaaa | atggatatga | tatgactcgc | tggtacaagg | gtgagtcttg | gcaaaacgaa | 68880 |
| cattggtaca | tcgcatgaaa | acttttgctg | taggtgatat | cgtccgtacc | agaatttggg | 68940 |
| atgggcttca | atttgaagta | gttgtctacg | tcggttcaga | tggagttcta | cttcaccgaa | 69000 |
| ttaacaatct | gattaagtgg | caccttgaac | gcttcgtgaa | atatcatgaa | ttcaatagct | 69060 |

FIG. 20LL sequence.txt

```
accactgtac tgtagctccg gttgctagta aagaatacta cgatatgctc gaagagttaa    69120
aatctctcaa agattgattt gctacaggag atttgattta aaatctcctc tgtcaagaca    69180
atcactactg aggaaaataa catgtcccaa gcaattaaaa acgcactgaa cgctttcgca    69240
tactataaag tttctgcaat gctggaagaa ggacgttgtg taactccgtc tttgcttgat    69300
cagtgggaag ttgagcttca cggtacgatg aaagaagaag gacaaaaaat tggtaaagca    69360
cgcatccgtg aattagtggt tgcttatctt ctgtctgaat ttggtattaa agcctttggt    69420
gtagaaccca tcgtagttgg tgttggtgaa atttctgaat ccgctattcg caaaatgaaa    69480
aaccaacgca agaaaggttt tcgtgatgtg aaagcggtta aggcggcaaa atgaaactaa    69540
atcaaaacgg atgtccttct cgcgtacgat tttgcattct agaattacga tctaacattg    69600
tcgttattga cgaatacacc acgattgtag gtgtacaaca atatcttgat agacgttttg    69660
atacacgaac ccatatgaaa tatggatttc caggcaaatg taaattttat ccaatgagtg    69720
ctgatcatca atctgtagta aatgatgaat acaagtgggc agaaggtctt actttaaaag    69780
aacttgagga atatcttgat gcgtaaagtt attctataca cagaaatttt taccagccgt    69840
tgggtgtttg acagtgtcag aatttcaaac gcttcaaaag aagatgttcg taacgctcag    69900
cgattagcat acgatgaagc tggaaaatca ccagcatttg taaaaattga gtatatcatt    69960
actgattctg ctttaattca taatgtatca gaatcagtat taaagaagtt ctgcgttgat    70020
cgcatcaata aaggaacttc aatggaatat tttctattag cgagagaact gaaatggtag    70080
aagaacaaat tgcagaaatc ggtttactcg gatggttcgt gtctaaaact aaagacggca    70140
gaaacttgat tgaaactcca gaaggagaat tcattattga agaagatttt gacgcgtttt    70200
ggatttatga acgctctgga gagaatgaat acacatccgt ggatgctttc tctaaatttg    70260
aagatgctat tgactcggtg aaagcatggc taaagtaaac caaattatga ttgtagtaga    70320
aggcattggc ggatttacta tagattctta tatgggtgtt tggtttgaca atgaagaggg    70380
catgtattgg gaaacgcatg cctctatgtt aaatgaaact cattatgaaa gtttatactc    70440
ttcattcatg gaaatgatgc atgaagtaga tgaatctgat tggtttgaac ttagtttggt    70500
tgagttcaaa cgtatcatgg aacagctgtt ccaatgctat cgtattatga agggtgaact    70560
atgaaaattc aattgactct tacacatgaa aatattaaag gtgtgttctg tcttgaaaat    70620
agccaaataa cttttgcaca agatggaacg tactggtatg ctgaatcaga tgatatcgct    70680
ggttatggaa tggaacgtgt atttgaagat tttgaagccg tcattgatgt tccattagat    70740
ttcacgtata acgattttta tcgtatcatg atgaaattaa ttgcatgcgc tgaattgatt    70800
aagtaatgct ttaatcctct cgcttcccaa atttgttata atagatatta ttaattgaag    70860
cgaagaggca atatgagtaa ttatgtaaat aacaaggagt tgtataaatc aatctgttca    70920
```

FIG. 20MM

```
                              sequence.txt
tggaaagaga agtgtcggga gtctgaagct gctggcggtc ctcgagtagt aaaacagaac    70980
gatacgatcg gccttgctat tatgctgatc gcagaaggtc tgagtaagcg tttcaacttt    71040
tcaggataca cccaatcctg gaagcaagaa atgatttcag acgggattga agccgcaatt    71100
aaaggcttaa tcaacttcga tgaaactaag tatgataacc cgcatgcgta tataacccaa    71160
gcttgtttca atgcattcgt tcagcgtatc aaaaaagaac gcaaagaaat ggcaaagaaa    71220
tacagctatt ttgtccacaa cgtgtatgat tcacgggacg atgatatggt tgcgttagca    71280
gatgaaacct ttattcagga catctacgat aaaatgacgc agtatgaatc caccgcttat    71340
aaggcgccag ggtctgctaa aaagagcgaa cctacaagtg atggacctaa tctggaattt    71400
ttatatgagg ctgaagatta acctcgacgg gtttttagaa gatgtgcaag acctagacgc    71460
tatcccttat ttgctaaaga tgtatttaag ggaggtgctt gatcttgata ttcacattga    71520
cccgaaaaat ccacatgacg ctgatttcag atcagattct gctataattg aacatagtta    71580
taattggact gatactgaat tcacatttga aataaattac catccaaagg aataacatga    71640
acaatattac ccaggaagag cgcgacgaac tgcagcagaa actaatggaa gcggcagaag    71700
aacaagctat tgctcgagcc aacaaaattg ttcgtaaaaa ccgtcgtgaa attgagcgat    71760
taaaagctca tgctggagac gcggtattag acaacaattt ccctgcttac aagtatgcta    71820
ttgaaaaact gcgtactatt ttaaaacaac cttttaccga tgagattatt ctcacctgtt    71880
ggaataccct tcgtaaatct gtttgggaca ttctaaatgc tggtacaagt aaaatttaaa    71940
cgtgttcgta aagacgcagg atttactttg aacactgcta ctggaacaat ggcagtaaaa    72000
gtagcagata atcaatatcg cgtgttaggc tctaccgaag gatgtaagct aatagataag    72060
aactctcttg tctgggttga caccttccaa gttaaacggt ggtatgaatg gtaaatgaag    72120
agaattggga tgtatgacga atttgatggg ttctaatcct gggcatgatt ggcctgaagg    72180
aaattacgcg tgtcggtgta gtaattgttc agaacgttat acaggaccaa agcgtagtta    72240
cttctgctat aaatgcgata ccgccaggag agaagcaccc gctcccgatt atgaagcaat    72300
tcgtaatgct aagatagata tgctcaagcg ctttgaagaa gctaagcgta tatgcgaagc    72360
agcgggttat gttgtgtata agaaaattta aagggcttcg gccctttgc tttattacgg     72420
gaatggtaaa atatccaaaa ttaacaacaa aggtcaatat atgaagatta atattttaat    72480
ggctcgcgga cttgagggat gcggcgtaac caagttcagt ctcgagcatc gtgagtggtt    72540
agtaaaacat ggccatgaag taaatatcat ttacgctaaa gataaagcgt ttactcgtaa    72600
tagagcacat agctataaag atgtaactat tcctgtgtct ctggcagatg actacgataa    72660
gactttatct ctgcttaatg catgtgacat tcttatcatt aactcagtac ctgctgtcaa    72720
cgctccagaa gcagcgattg ataactataa gaagctcata gagaacatta aacctgaagt    72780
tcgggtagtc gtatatcaac atgaccatag agcattgtca cttcgtagaa atgctggtct    72840
```

FIG. 20NN sequence.txt

| | | | | | |
|---|---|---|---|---|---|
| tgaagaaacc | gttaagcgtg | ctgatgtact | gtttagtcat | agctcaaacg | gcgattttaa | 72900 |
| taccgtgcta | atggaagaat | attttccaag | cggcgggttg | agtttctttg | atgattctga | 72960 |
| ctcagctcct | ccggtttata | actttcaacc | tgctatgaac | atcaaagcaa | ttcgtgataa | 73020 |
| gtattggaaa | gacttctctg | ccattgattt | tgatatccat | cgttggattg | gtcgtactac | 73080 |
| tacgtggaaa | ggctatttct | tgatgtttga | ctttcatgaa | agtcatctgc | gtcccgcagg | 73140 |
| caaaacgact | atcttggaag | ggttagaacg | cagtcctgcg | tttattaaca | tcaaagaacg | 73200 |
| ctatgaaatt | gactattgcc | gtcattatca | tcaggttaaa | actgggccag | gtctgaatcc | 73260 |
| tcaagttctt | gaccgatatg | ttaactctga | aatgcttgag | cgtatgtctc | aatctggatt | 73320 |
| tggctatcag | ctgtcacgtc | ttccggataa | attccttgag | cgttcgttgg | aatatactca | 73380 |
| tttggaatta | ggtgcatgtg | gtactattcc | tgtgttccat | aaagccaccg | gtgatgcttt | 73440 |
| gaaattccga | gttgatggaa | agccattgac | ttctcatgat | tctggcattc | tgtggttgaa | 73500 |
| tgatgaaaat | aaaaatgaag | tctttgaacg | aatgaaacat | ctgtcatctg | accagaagct | 73560 |
| ctatgataaa | gagcgaaata | aagcatttga | attcctggta | gaacaccaag | attctgagca | 73620 |
| ttgctttaaa | gaacaatttg | agttaatgac | aaaataagta | atgggccttc | gggccctttt | 73680 |
| tgctattcat | ggaataatat | aaaattaaac | tctactagag | aggttatatg | aaaattattc | 73740 |
| actcaggcga | ttggcattta | ggtgtccgcg | cagatgaccc | gtgggtacag | gatgtacaac | 73800 |
| gacacggaat | taagcagcat | attgattatg | ccaaaaagca | tggaattaaa | actatcattc | 73860 |
| aatacggtga | tattttgat | gttcgtaaag | ctatcactca | taagacaatg | gaatttgctc | 73920 |
| gtgaaattgc | agagtctctt | gagaaagaag | gaattaactt | aattacgatc | gtcggaaatc | 73980 |
| atgacatgca | ctacaagaat | acgttgacgc | ctaatgcatc | aaccgaagtt | cttggtaagt | 74040 |
| ataagcatat | tactgttatt | gaaaagcccg | tgactatgga | ttttgatggg | actttgattg | 74100 |
| acttgtgtcc | atggatgtgt | gaagagaaca | catcagaaat | catgaagcat | atcaaagaat | 74160 |
| cgtctgctga | atactgcatt | ggtcattggg | agcttaatgg | cttttatttt | tataaaggaa | 74220 |
| tgaaatctca | tgggctggaa | ccagatttcc | tcaaaaagta | caaacaagta | tggtctgggc | 74280 |
| acttccacac | catatcaagc | gcagcaaacg | ttaagtacat | cggaacgcct | tggacgctta | 74340 |
| cagcgggtga | cgagaacgac | ccacgcggct | tctgggttca | agacactgaa | ttatcaacct | 74400 |
| ttgatttcgt | ccctaatgaa | atcacttggc | acagaaaact | gatttatcct | gtcacagggc | 74460 |
| aagttgattt | tgaagagttc | agaaatcttg | cagtgcgaat | tattatcact | gcggtcgatg | 74520 |
| aagaccttcc | taagtttgaa | tcagaacttg | aaaaggtagt | acatgaatta | agaactgttt | 74580 |
| ctaaagttga | caactcggtt | gagtctgaag | atggcgaaga | agtagaagtt | aaaagcttat | 74640 |
| tggatttaat | ggaagaatat | atccaagcac | ttgaagacct | gtccgcagat | gatatcaaag | 74700 |

FIG. 2000 sequence.txt

```
ccttaaaggt tatgtctaaa cagttataca ttgaggcaca aaatcagtga agacttttaa      74760
actaaatcgt gtcaagtata agaatataat gtcagttggc caagcggcca ttgacattca      74820
acttgataaa tgtcaaaaga ccttaatcac aggtaagaat ggtggtggca aaagtactat      74880
gcttgaagct attacttttg ccttatttgg taaaccattc cgtgatatta agaaaggtca      74940
attaattaac tcattcaata agaaggactc tgtagtagaa ctgtggatgg agtatgacgg      75000
tcatagtttc tacattaaac gtggacaaaa accgaatgtc tttgagattt tacgagatgg      75060
caataagctt gatgaagccg caagttcaaa ggattttcaa tcctactttg aaagcctcat      75120
cggcatgtca tacacatcgt ttaagcagat tgtcgtatta ggaacggcag gatatactcc      75180
gttcatgggg ttatcaactg ctaatagacg aaagctcgtt gaagatttgc ttgaagtgtc      75240
tcttttagct gatatggaca aactgaacaa gacacagata agagaaatca atcagcaaat      75300
ccaggttaat gatgttcagc gtgaagcatt gactaatgaa attaaaactc accatgagta      75360
tgcagaaaag cagaagaaac tttctggtga taacgttgct cgcctgcagg cgatgtatga      75420
tgaacaggtc aatgaagccc gtgggtataa agcagaatta gaaactcttc agagagaact      75480
gcttgagtta gtaattggag acgacccagc agagtcaatc caagaagttc aaggtaaaac      75540
atttaaaatt cggtctaaaa ttgaatcata ttcaaaggtt cttgggctgt atgataaagg      75600
tggtcattgc ccaacgtgct tgcaggattt gcattctaat gacactctaa tcactaagat      75660
taatcatcat gttgaagaat gtaataccat tcttggtgag ttaaagacgc gccagagtga      75720
actggatgaa ctagctcgcg agtataacac ggtccgggct cgcgctagag atatcaaaac      75780
ccaaatgggt agtttaaagc aaatgactat cactgctgtg gaaaaggcac gtcgtattaa      75840
agcagctatt gataaagcat ctcaggagtt tattgataac tcagacaaga ttaaactgct      75900
acaagaagaa ttagataaaa ttatcctcgt caaaactaat ttggttatgg aaaaatatcg      75960
tcgtggtatt ttaactgaaa tgctgaaaga ctccggtatt aaaggagcta tcatcaagaa      76020
gtacatcccg atgttcaata agcaaattaa cagctaccta aaaattatgg aagctgatta      76080
ttcgttcaca ctgaacgaag agttctctga acgattaaa tcacgtggac gagaagagtt      76140
tagttatgcc tcgtttagtc agggtgaaaa agccagaatt gatatagcat tactattcac      76200
gtggcgtgat attgctgaaa aagtttctgg tgttaaaata aactgtctgt ccttgatga      76260
agtttatgat tcggctaccg acgcagaagg tgttaaggca ataactgcta ttcttaataa      76320
gatggtagat gccaatgtgt ttattatttc tcaccgtgac cacgacccgc aggcatatgg      76380
ccaacacctt caaatgaaga aggtcggacg attcacggtg atggaatgaa tgagtttact      76440
acgggccaac atctgttggc ctttcctgaa ttaaagcgtt atgtgttagt taatttattt      76500
tctgatgaac gtcatcttgt aactgaagaa atgttacgag atgcttttac gggaaatgaa      76560
tataatagag tcatgtccaa caggaatccc ggttggatgg ttgaagatta ctacgattaa      76620
```

FIG. 20PP sequence.txt

```
ggtaaatata atgattaatt ttgttgatgt gaaagatatc caggttaaaa acgtacgtgc    76680
agattccaac ccgaataacc aaaatcgtat tcgtaaatct tgggttctgg ctctaactga    76740
agaaactaaa caggctatca aagataagat taaagattct gaagctcgct ttgctttcta    76800
taaatctatc gatgatgaag tcgcagaaaa atggattgaa ctgatgcgta agcattacaa    76860
tgaatcaatc aaggctggtg ctaaaattgt tactgatcgt cacggtggcg aacgtctaga    76920
aaatgattac tgtgtagatg ctgatgagca actcgttgcg gcaggtcaga ttgttgcaga    76980
agaattaact gctacattcg cagcttgata taattatcct gaacttaatt aaaaggtatt    77040
gaaatgaaat tctctaaaga aactctgaac attctgaaaa atttctccac catcaactct    77100
ggtatcatgc tgaaacctgg caattttatc atgactcgtg ctgttaatgg tacgacttat    77160
gctgaagcaa caatttctga taccatcgat actgatgtag caatttatga cctgaacagt    77220
ttcctgagca ttctgtcttt ggttggtgat gatgcagata ttatcatgca ggaagatggt    77280
aatctggcaa ttaaagatgc tcgctcaact atcttctggc cagcagctga cccgagcaca    77340
atcgtgttcc cgactaaacc aatcccattc ccggtggcaa acgtaattat cgattttaaa    77400
ggtgaagacc tgcaacagct gatgcgagta tctcgtggca tgcagattga cacaattgct    77460
atcaccaatg ttgatggtaa aattgttctg cgtggttata caaagtaga agatgctgca    77520
ctgacccgtc cgaagtattc tctgacactc ggtgattatg aaggtgaggg taacttcaac    77580
tttatcatca acatgagcaa tatgaagatg actatcggcg attataaact gatgctgtgg    77640
gcaaaaatga atggctccaa gaaacagact gccgcaaaat ttgaaggtgc atcagcctct    77700
tatgtagtag caatggaagc agacagtacc tttgattttg agtaataact tcggggcttc    77760
ggccccatct ttaatctgaa tgaggaaata taaatgaaat tgacagtaaa cgaagcagac    77820
ttcatgtggg aacagaaata tcgtccaggt actatttctg agtgtgtact tcctgctgaa    77880
gataaagaaa ttttttcagc tttagtagct aaaggaaaaa ttcctcattt aattctccat    77940
agcacttctc ctggtactgg taagactaca gtagctaaag cattatgtaa tgacattaat    78000
gctgaaatga tgttcgtgaa tggttctgac tgtaagattg atttcgttcg tggaccgtta    78060
actgcatttg caagttctgc ttctattgca ggcaagcaga aaattatcgt tattgatgaa    78120
tttgaccgtg caggtcttgc agaatctcaa cgacatctgc gttcattcat ggaagcgtat    78180
agcacaaact gtactattat cattactgca aacaatcttg atggtatcat taaacctctt    78240
cagtctcgtt gccgtgtaat taattttggt aaaccatctc catctgatgt taagccaatg    78300
caaatcgaga tgctcaagcg ttgtctcgca atttgtgaaa acgaaggcgt ggtagttgaa    78360
gataagaaag ttgtagctgc tttggtcaaa aagaattttc cagaattccg taagaccatt    78420
aacatgcttg accattattc ttctaagggt gtgattgatg caggtatctt gtctatcgtt    78480
```

FIG. 20QQ

```
                              sequence.txt
ctgaatgacc gtggttcaat tgaagatgtc atcgaagcta ttaaaactaa gaacatcaaa    78540
gaactccgtg ctcttgcccc gaaatatgca gcagactata cttggttcgt agataaactt    78600
tcttcggaac tgtatacaat ggttactggc ccaagcatta tccgaatgta tgaaatcatt    78660
ggtgaaaata accagtatca tggcatagca gcttcgattg aattacactt ggtttatatg    78720
cttattcaac ttgttgtaga gatgcagtgg aaatgatgag tttatttgaa gatgatgatc    78780
agtataacga gcaccaaata gcgtggttag gtaaagactg gacgaaagtc caggaattat    78840
ctgattcata taaagaaaaa gcagaaaatc aattcttcac aattattggg tctattaacg    78900
aaaagcaaga gcatttgaat atctcgacga tggattattc aaaattcatg gttgaaaacg    78960
ctctttctca acccctgac tgtatgcctt cggtttatgt tatgaacctt gttggtcaag    79020
ggttatctga ccaagcacac tataactata tgatggcctc tgttcctaga ggtcgtcggt    79080
atggtaaatg ggctaagtta acagaaaaca tccaggatgc attgattctt caagttataa    79140
tgacatatta caaggtcaat gcgattgacg ctaggatgta tagagagacc ctggaagcta    79200
aaaacaagct taaacctgct ctcaagaaaa tgaaaggtct tgtgactgat gaattggtca    79260
agacaatcac gaaaaacgtg aaagaacaga aaatcttaa gaaaacagca ttggaatggt    79320
aaagatgatt gaaattacac tgaaacagcc tgaagacttc ctgaaagtta agaaactct    79380
gacccgtatg ggaattgcta ataacaaaga taaggtacta tatcaaagct gccacattct    79440
tcagaaacaa ggtcgttact atattgttca ttttaaagaa atgttgaagc ttgatggccg    79500
ccctgttact attgatttgg aagatgaaat tcgtcgagac tcaatcgcac aactacttgc    79560
tgactggggt ctactgagta ttaatcgtgg tcaaactctt gctcagatgc agaataactt    79620
ccgggtcatt acgttcaagc agaaacatga atggacctta aaatctaaat atacgattgg    79680
tgcataatga cagaccaaga attttacgac aaacttaaaa atatcaggat tactgctcct    79740
gaatggttca gtcttcctat tgatgaacaa attcagtatc aggtaaaaga aactttagaa    79800
aaatatcctg gccgaaaagt tatgatgtgc ttcacatatg ataagaatcg agttcctcga    79860
attcagaagc aagtaattga agtttaagaa aaggccttcg ggcctttac tttataaaac    79920
tcggagtata attatcccac ctaaagacta ataactcggt ctataaacaa aggaaaccca    79980
tgaaagaatt ttatattagc gttgaatctc taggcaatga cattgtagaa cgttatatcg    80040
attctactgg tgaggaacgc atgcgtcgtg ttccgtattc tcctgtgatg tttagtcatt    80100
gcatggaaga aacaaagtac aaagatatct acggcaagta ttgcaagaaa aatacattcc    80160
caactatgaa agatgcccgc gattggatgc gtcgtatgga agatatggga atggaagcaa    80220
tgggtatgga tgatttcaaa ctcgcgtata tcagtgatac ttacggttca gaaatcgtct    80280
ataataaaaa attcatccga attgcaaact gtgacattga ggttactgca tctcaattcc    80340
cagacccaat gaaagcagaa tatgaaattg acgctatcac tcattatgat tcggttgatg    80400
```

FIG. 20RR sequence.txt

| | | | | | | |
|---|---|---|---|---|---|---|
| acaagttcta | cgtatttgat | ttactgcatt | ctctttatgg | ttctgtttcc | gagtgggaca | 80460 |
| agaaacttgc | tgctcgttta | gattctgaag | gcggtgatga | agttccacaa | catattcttg | 80520 |
| accgcgtagt | atatatgccg | ttcaattcag | aaaaagaaat | gatgcttgag | tacatcaatc | 80580 |
| tttgggaaca | gaaatgccca | gcaatcttta | ctggatggaa | cattgaagga | tttgatattc | 80640 |
| cgtacatcat | gaatcgtgtg | aaacagattc | ttggtgagcg | tgcgatgaaa | cggttctctc | 80700 |
| ctctgaataa | agtttcatct | aagattatca | caaacatgta | tggtgataaa | gaaatttatt | 80760 |
| ctatcatggg | tgtgactatt | cttgattaca | tggatttgta | taagaaattt | agtttcacga | 80820 |
| accaaccgac | gtataagttg | gatttcattg | cttattatga | aaccaagaaa | ggtaaattag | 80880 |
| catatgacgg | tccgatcaat | aaattgcgtg | aaactaacca | ccaacggtat | atttcgtata | 80940 |
| acatcatcga | cgttgaatca | gtacaagcga | ttgatgctgt | tcgtggatt | attgacctgg | 81000 |
| ctatctcgat | gtcttattat | gcgaagatgc | catatcaagg | tgtaatgagt | ccaattaaaa | 81060 |
| catgggacgc | aatcatcttt | aacagtctga | agaacaaga | caaggttatt | ccgcaaagtc | 81120 |
| gttctcatgt | taaacagtca | tatcctggtg | cgtatgttaa | ggaaccagtt | cctgctgcat | 81180 |
| atcgctatat | catgtcgttt | gacttgacat | ctctgtatcc | gtcaatcatc | cgacaagtta | 81240 |
| atatttcacc | agaaaccatc | gttggacagt | ttaaacttca | tccgttgggt | gagtacatta | 81300 |
| acaagactgc | tcctcgtccg | tctgatgaat | attcatgttc | accaaatggt | tggatgtatc | 81360 |
| gtaaagatgt | agatggtgtc | attccagttg | aaatcgcgaa | ggtattttat | cagcgtaaag | 81420 |
| agtggaaaaa | taaaatgatg | ggtgccaaac | gaaatcaaga | actgattaaa | aaggttctga | 81480 |
| atgataagaa | gtttggaact | atcgataaat | tcgcagaagt | taatgtctat | gaagatttct | 81540 |
| ctgatgatat | gaaagcagaa | ctgctgacat | ataccgaaga | gtgtcttgac | aaactgatgt | 81600 |
| ttgaatgtaa | acacgctgaa | atcttgggta | acactaacca | gttaaaccgt | aagattctga | 81660 |
| tcaactcact | ttatggtgca | ttgggtaaca | tttacttccg | ttattatgat | ttgcgcaacg | 81720 |
| catcagcaat | cacattgttt | ggtcaaatgg | caattcaatg | gattgaacgt | aaagttaatg | 81780 |
| aatacctcaa | caaggtatgt | ggcaccgaag | gacattcgtt | tgtagtagct | ggtgatactg | 81840 |
| actcaattta | cgtttgtgtt | gataaggtta | tcgagaaggt | aggtcttgag | cgtttcaaag | 81900 |
| aaactaacga | tttggtcgaa | ttcctgaacc | aattcggcaa | gaagaaaatg | gaaccatgga | 81960 |
| ttgaccaatc | atatcgtgag | atgtgtgaat | acatgaacaa | caaagaacat | ttaatgttca | 82020 |
| tggaccgtga | agctatttct | tgtcctccgt | tggggtcaaa | cggcattggc | ggattctgga | 82080 |
| aagcgaagaa | acgatatgct | ctgaacgtgt | atgatatgga | aggtactcga | tatgcagaac | 82140 |
| ctcatctgaa | aatcatgggt | atggaaactc | agcaaagttc | tacgccaact | gctgttcaga | 82200 |
| atgcattgga | agaatctatt | cggcgtatgc | tgcaggaagg | tgaagaatct | ttacagcaat | 82260 |

FIG. 20SS

```
                                 sequence.txt
attataagca gtttgagtct gaatatcgtg aacttgatta taaagtaatc gccgaagtta    82320
agactgcaaa caacatcggt aagtatgatg acggtgcagg atatccagat aaaggtacac    82380
catatcacgt taaaggtgct ttggcatata accgagcaac cgcaggattt gaaggtataa    82440
caccaatcat ggaaggtgag aaagtgatgg tcatcccgct gcgtgaaggt aacccgtacg    82500
gtgagaaatg catggcatgg ccatcgggca ctgagctgcc acaagaaatc cgacaggaag    82560
ttctagtgtg gcttgaccac agtgttctgt tccaaaaatc gttcgttaaa cctctgacgg    82620
gtatgtctga agcggcaggg ttagactatg aagagaaatc gtctcttctt gacatgttcg    82680
atttttaaaa aagttgttta ctttaccaca aggatgtggt actatagctc tcgaaataac    82740
atactgagga gattacaatg aaatcgttac ttgctgttat tgttgctctc acgctgactg    82800
gttgtcaaat gccacaaggt gatatcgtcc cggcttcttc tgttgggcag gtgcgagcaa    82860
ttggcggtac tgtaggatac tatcgtgcta gcaaccaggt ctctgctgaa tcgctcgcgg    82920
ttgagcgtcg gttggcgaaa gaaaaagcta atcctaatcg tcagctgtct gcgatggaac    82980
ttgacatgat tgagcagaat aagcatgaac tggaagaaat taagcgtctg cgtaaaactc    83040
aaaaagaacg tacgtgcact gctcaagcgg cagcagtgaa tgaccagatt cgtttaactg    83100
attttgctaa cggcggattg agttataatg agcataaaca acgtatggag cagttaaaat    83160
ctctccaaaa tcacatctac aacaaatgca tgtctaactg aggagattaa catggaagca    83220
gtatttggtt taatcattct tttcttcatc tattttttgc cgacctttgt agcttgcagt    83280
cgtaagcata aatcacgggg tggaatcttt atcacaaatc tagtattcgg ttggtccatt    83340
atcggttggt taattgcgct gatttggtct gcttctaacg cacagcagaa tacaattatt    83400
atccagcaag ttaaataaga ggtctcatga ttgtaactcc aatgacagta caagatatcc    83460
gtcaagaatt cgctgatgct ttgctcaaca aagaatttgt gattgataag acgggtgtga    83520
agactattga aatcgtaggt gcatcattta ttgcagatga aaacctaatt tttggcgcag    83580
ttaatgatgg atacattgct cgtgaacttg agtggtataa atctcaaagt ttattcgtta    83640
aagatattcc gggtgaaacc ccagctattt ggaaagcaat tgcatccaaa cacggcgaga    83700
ttaattctaa ctatggctgg gcagtttggt caacacaaaa ctattcacag tttgctaact    83760
gtgcgaaaga acttatcaat aatcctgatt ctcgccgcgg aattatgatt tatacacgac    83820
ctcaaatgca gtatgatttt gagcgcgatg gcatgagtga tttcatgtgt actaacaatg    83880
ttcagtatct gattcgtgat aatcgtgtgc atgctgtggt aaacatgcgt tcgaatgatg    83940
tcgtctttgg atatcgtaat gactatgcat ggcagctcta tgttttggaa cagttaacca    84000
aacttctgaa tgcatcaggt aaaaattatt cagttggtga cattatttgg aacgtcgggt    84060
ctttgcacgt atattctcga catttctatc tcgtagataa ttatgctcac acgggtgaaa    84120
ctcacatcgc aaagaaagac tataaaggtg aatggaaatg attcagtttg taattccaag    84180
```

FIG. 20TT sequence.txt

```
ttataagcgc gccggggcag ttactgccct gactatgttt cctgaaggtt atgttccaca    84240
tcttgtagta cgtgaatcag aaaaagaagc atacgaaact tggcacggtc atgctgctaa    84300
aatcgttact gtccccgatg atgtcgatgg aattgcggga actcgccgtc tgattactga    84360
aatgtatgca gggcaacgaa tttggatgct tgatgatgat acgaccattc atctgactga    84420
aattcgtgaa cgcgacgatc gccgggttcc acttggtgtc ggcgaggcaa tgagtcaaga    84480
ggtatttgat gatatggtca aatacgtcga gactgccatg gattgtggtt attatcacgg    84540
tcatgctcgc ttaccgattt tcaaaatcac atcaagctgg ggtcattatc gtgagaatag    84600
ctttgggttc accaatactt tctatgattt gactaaactt accgcagaag acattggcta    84660
cggaattatt gaccttaacg aagatgctta tgcttttcta aaattaatta acatgggtca    84720
tcctcatctg gctctgttta agtacctcgt taaatctggt aaggtgcagt cacctggtgg    84780
ttgttctaca cagcgtgata ctgctcgcca gaatagagcc cttgaacagc tgcatgctgc    84840
tttcccaaat caagcccgtt ggaaatctaa agacggtgaa agacgtggtt tattcggtga    84900
tgacgaacca ctaaaatcaa ttcgtatgtg tattaacact cgagtgaaat cccaggcctt    84960
ccatgaattt ggtaaggtag aaccatatct gtgagggcga aagccctcca aggacctctt    85020
atgaacatct atgataaatc tgatgtagct ggtaacatat tcaaggctga agaattcaga    85080
tgcttcgtat gtaaatctga tgagtttgtt catgaaggaa ctactggctc agatggaatg    85140
cattgctggt ggcacggcat gtgtgttgga tgtaaaatac actacgaaat agatatggaa    85200
acagtggttt ataacaccaa gaagaaatgg aacttctgtt aatagcttca agaacaaagt    85260
aatataatta ctctatcctt taacctgtga gaaaaatata atggagactt atggaatata    85320
atgaatgtct gacttaaaat ctcgcctgat taaagcatcc acttctaaaa tgacagcaga    85380
actgactaaa tcaaaattct ttaacgagaa agatgtagtt agaaccaaaa ttccgatgct    85440
taatatcgca atcagtggag cgttggatgg tggtatgcag tccggggttga ctatcttcgc    85500
aggtccatct aaacacttca aatctaacat gtctctgaca atggttagtg cttatcttaa    85560
taagtatcct gatgcggtct gcttgttcta tgattcagaa tttggtatca ctccagctta    85620
tctgaaatct atgggtgttg accctgaccg tgtaattcat acaccggttc agtcggttga    85680
acaattaaaa atcgatatgg ttaaccagct tgaagctatt gagcgtggtg aaaaagtcat    85740
cgtgtttatc gactctattg gtaacatggc gtctaaaaag gaaaccgaag atgctttgaa    85800
cgagaaatct gttgcagata tgactcgtgc gaaaagtctg aagtcgctct tccgtatcgt    85860
aactccttac ttctctatta agaacattcc ttgtgtagcg gttaaccaca caatcgagac    85920
tatcgagatg ttcagtaaga cggtaatgac aggtggtaca ggtcctatgt attctgcgga    85980
tactgtattc atcatcggta aacgtcaaat taaagatggt tctgagcttg agggatatca    86040
```

FIG. 20UU

```
                                sequence.txt
gtttgtcctg aacgctgaga aatcgcgtac tgtcaaagag aaaagtaagt tcttcatcga    86100
tgttaaattc gatggtggta tcgatccata tagtggtctg cttgatatgg ctctagatat    86160
cgggtttgtg gttaaaccga aaaatggatg gtatgcacga gaattcctgg atgttgaaac    86220
cggtgagatg attcgtgaag aaaaatcctg gcgggcaaaa gatacgagca gtacggaatt    86280
ttggggtcct ctgtttaagc atgagccatt ccgtgacgct atcaaagccc ggtatcagtt    86340
gggtgctatt gattcaaacg ctgcggttga tgaagcggta gcagaaatga ttaactcaaa    86400
agtttcaact aaggttgatg gtgttaaact tcctgagagt ggttcagtat cagctgctga    86460
agttgaagat gaattagaga acttcatgaa tgaagactga gtttgattta gaatctgaac    86520
tcgagaaatt tgaacaagaa tctccctcgg aagagggaga cttcgagcgt caagaacgag    86580
tgttcaagaa aagccatgaa ataatccaag aagctatgaa gactgttatc caagaaattg    86640
tgataaaatt aaatggtcaa tcacacttgg tttatgttca taaattaaat atttctcctt    86700
cggggggaagt aactattgag ttcagtacac catctgaagc tcataaggat gaactttatc    86760
ctcatgtgga agcttgtgtt aaacaacaaa tccagagtgc attaaagacc aagaaaaaat    86820
cattatggaa aatcttttaa gaggttaaag tggtagaaac aatcttagct aatctgattt    86880
acaaccaggc tttctttacg aaggtttggc catatatgga caaagagtac ttcgagcaag    86940
gacctgctca gacggtgttt aacataatta agaaacacgt taatgaatac acagcaattc    87000
cttcaaagac tgcgttatgt gtagcactgg ataattcgtc tataactgaa acggaacatg    87060
aaggtgcaaa gaaacttatt gataagttat ctgatgctcc tgaagatttg aattggttag    87120
ttaaggaaac agagaagtac gttcaagaaa aggctatgta caacgcaacg tctcgaatta    87180
ttgaaattca gactaatgcc cagcttgagc caaataaacg cgataagcgt cttcctgata    87240
ttggggctat tcctgatatc atgcgtgaag cgttatcagt atcgtttgat agctatattg    87300
gccatgattg gatggaagat tatgaagctc gttggttatc ataccagaat aaagctcgta    87360
aagttccgtt taaacttagc attctgaaca aaattactaa aggtggtgcc gagactggta    87420
cactgaacgt attgatggct ggcgtcaacg ttggtaaatc attaggatta tgttcattgg    87480
ctgcagacta tcttcagatg gggcataacg tcctttatat ttccatggaa atggccgaag    87540
aagtttgcgc taaacgtatt gatgctaact tgcttgatgt atcacttgat gatattgacg    87600
atggatgtgt atcatacgct gaatataaag gcaagatgga aaaatggcgt agttctagta    87660
ctcttggtcg tttaatcatt aaacagtatc cgactggtgg cgctaacgct aatacattcc    87720
gagctcttct gaatgagttg aaactcaaga agaactttaa accgactgtt atcatcattg    87780
actatcttgg tatttgtgct tcttgccgta ttcgtcaata tactgaaaac agttacacgt    87840
tagttaaagc tattgcagaa gaacttcgtg cattggctgt agaatctgaa actgttcttt    87900
ggaccgcagc tcaggtaggt cgttcagcgt gggatgcttc tgatatggac atgagtgata    87960
```

FIG. 20VV sequence.txt

| | | | | | |
|---|---|---|---|---|---|
| ttgcagaatc | tgcgggtcta | cctgctacgg | cagactttat | gctggctgtg | attgaaaccc | 88020
| ctgaacttgc | tcagatgaag | cagcaattaa | ttaagcagat | taaatcacgt | tacggtgata | 88080
| agaacatcaa | caataagttc | tctatgggtg | tacataaggc | taatcagcgt | tgggtagaaa | 88140
| ttgagcagca | aaacgaccca | actaagccta | atccaagcaa | taccgtccga | gaaggtgccg | 88200
| gtgcacagaa | ccgtgtagcc | gaatctaatc | gtcaagaacg | agtatcacgt | tctaagcttg | 88260
| atgctctagc | agaagagttg | aaattctagg | gtaaatttta | tgattttgt | gtttagcgta | 88320
| attcgcgacc | aatcaggtcg | ctcctttgtg | gtgacggcgt | ctgatagcgt | ccatcgtgga | 88380
| gtcatagctt | acaacaaagc | agatttatct | tcatatgact | atggtgaagt | taaggcatat | 88440
| aatgacgaag | gtatctgggt | taactctgcg | atataccttc | caaccaagaa | tttgacatcc | 88500
| gacgaagtcc | tcgaaaaatt | attcaaaaga | tagtttactt | ttaagtttgg | ccatgttatt | 88560
| atggccttac | tgaaacaaac | tgaggaaaac | aaaatgaaaa | agattgtact | tgctttaatc | 88620
| ttcgcagtat | caagttgctc | tgctgttccc | gctctggcga | actatgacaa | agacctctgc | 88680
| gaatggtcaa | tgactgcaga | tgaaaaagat | gttgctgagc | agattcgtgc | tgatgtaggt | 88740
| catatcattg | ataacactga | cccaagcaag | atgaaagaag | ttcaggcaga | aatctccaat | 88800
| gatggcgcag | caattaaact | gaactatgct | ctgtactgcg | atgctaattt | tgataacttc | 88860
| acaattgcaa | gctggattct | cggatgatta | catacgtatt | agtaatggct | ataatgactg | 88920
| gtgccggcgg | tgtttctact | gaaaagttat | cattcacagg | aatgaacgag | tcttcgctgg | 88980
| ctcagaaatg | tgaagatgcg | ggaaaacaat | ttactggcat | caaagccgat | tccgggttcg | 89040
| gttcaccatc | agtctacact | acgtacaagt | gtattcgtat | tgatggtgga | ataataaat | 89100
| agtttggagg | ctctatgaaa | acatttaaag | agtttgttaa | acttaatgag | gaaatggttg | 89160
| ctggcgatgc | cggcggtaat | cctcagaaca | ttgcatcagg | cactacttcg | ggcgcagtag | 89220
| taaataaagg | cccagaaact | ctcccaaaga | aaagcgaga | taaatcaaaa | cctgaaacgt | 89280
| gatacaatgg | ccttattagt | ttaaggccag | aggaatataa | tatgtcatgg | gttgataacg | 89340
| aattcgctat | ccgcgcaata | tctcacctac | ctaagtttag | acacgttact | acatcttcaa | 89400
| catttaagtt | aaactgccgt | tgcccaattt | gtggtgactc | acagaaagat | atcaataaag | 89460
| cccgattctg | gattttgat | gcgggtcaag | gattacgctg | ccattgcttc | aactgtgagt | 89520
| ataacaagtg | gctatcacaa | tatcttaaag | ataatgaacc | cgatctctat | cgagagtatc | 89580
| ttcttgagaa | aagaaggag | caggtctttg | ataagccaaa | gaccgtagaa | ccgtctgaga | 89640
| aaattaatgc | aaaactcccc | gtaatagaaa | aacttaattt | ctgtgagcga | ttagatagac | 89700
| ttcctaagga | acatccgata | gttaaatacg | tgactgccag | atgtattcca | agcacttctt | 89760
| ggaaaaggtt | atggtttact | aaccaatggc | cttctcttgt | taactccgtt | aatccaggaa | 89820

FIG. 20WW sequence.txt

| | | | | | | |
|---|---|---|---|---|---|---|
| cctataagaa | tgagacgaac | gaaccacgtt | tggttattcc | tatcttcaac | aagaaaggag | 89880 |
| agattgagtc | gtttcaagga | cgagcactac | gaaaaaatgc | tccacaaaaa | tacatcacaa | 89940 |
| tcaaagccca | tgaacacgcg | accaaaattt | atggtctcga | cactattgat | gagtcaaaac | 90000 |
| tcgtattcgt | catggaagga | ccaatagatt | cgttgttcat | tgataacgct | attgcaatca | 90060 |
| ctggcgggtc | tttagattta | gctcaagttc | catgccatga | taaccgagcg | tggattatgg | 90120 |
| accatgaacc | tcgtcatccc | gatacaatta | agcgtatgaa | acgtttagta | gatgctggtg | 90180 |
| aaaaggtagt | tttctgggat | aagtcgcctt | ggaaaagcaa | agatataaat | gatatgatta | 90240 |
| tgaaagaggg | ggcaactgct | tctgaaataa | cggattatat | taatcaaaat | atatcgcaag | 90300 |
| gtttaatggc | taaattacgt | cttgacaaat | atgcgaagat | atagggccca | aagcccctta | 90360 |
| aattaaagca | atcctccagt | cataataaac | gacacaactt | tttctaacgg | cattggagga | 90420 |
| agaactagcc | cgtgtgtgct | agctaatgga | actaccacat | aattccatgc | agctaaagca | 90480 |
| gcagtggcga | ttccgacgta | aagatatctt | ccaaatcctc | ctttgtcttt | acattctcgt | 90540 |
| ttcacttcag | acatgaatcc | tcctgctatt | tatgttaagt | gatataatat | ttatctaatt | 90600 |
| taattgaaag | gaaaaataat | atgccacatt | tcaacgaatg | tagtcaactg | atcgctggtg | 90660 |
| cagataaagc | tgaagctcga | tacgcaggta | tcgtacgcaa | agttggtggt | gaccctctgc | 90720 |
| aagtaatgct | tgatatgcaa | aaatctcttc | aggttcgtct | tgcaaatgac | aagcctggta | 90780 |
| ctaacatgca | tcctgatgaa | ttggcccaag | ccggtgatat | cgtgcagtgg | ctgcgtaacc | 90840 |
| aaaaagatta | cattgatgac | gaattccgcg | aattgctgac | gtctcttggc | ggtatgagta | 90900 |
| atggtgaaaa | ggcagctagt | gctgtgtgga | aaccatggaa | atctgaccac | gtcaaaatgc | 90960 |
| aggaaactta | tatcaaagac | ctgtctgata | aagaccagct | tgaaatcaaa | tttgaaatga | 91020 |
| ttgatatcct | gcactttgtt | ctgaatatgt | ttatggcgct | tggtctggat | tctgaagaaa | 91080 |
| tctttaagct | gtattatctg | aaaaacgccg | agaactttgc | tcgccaagac | agtggttact | 91140 |
| gatggccaaa | agaatatcta | agcgtcgttt | aaaaattatc | agaaaacaaa | aagaaagggc | 91200 |
| cttagtattg | gcccttcgag | aagaaatcac | tcgagaaatt | gataaagaaa | tattaaaggc | 91260 |
| gcttacagca | gctatataaa | tactcctgta | aactaaatag | gagattaaaa | tggcttacgt | 91320 |
| aaacatcaaa | acttttgacc | atacaactgc | tgatggtgaa | gttaaaggta | cagaagtatc | 91380 |
| tgtagctttt | aaggtgtatt | ctgattcaca | tcgcattgct | aacgcacagt | atcagatttt | 91440 |
| cccatctgaa | aaagctgctt | attcaacagt | agttgatgat | gctgcaactt | gggcaaccac | 91500 |
| caacgctaaa | atgtttgaag | ctgttccatc | tgatgcagaa | gtataaaaat | taaggactcc | 91560 |
| tccgggagtc | cttttatgct | atactgggaa | tagtatatta | ttcctactaa | ctgaggagaa | 91620 |
| gaaaatgata | tgttatacta | agccctggta | tcaatcgtca | ttaaagaagt | ctcattttga | 91680 |
| ttgttggtac | agaggtgtaa | gagctgcagc | gttattactc | aaagctgcgc | cggctttaat | 91740 |

FIG. 20XX sequence.txt

| | | | | | | |
|---|---|---|---|---|---|---|
| taaagcaaat | gataagtggt | ttgaagacaa | caacatgact | gaaggagctc | tttgtggcaa | 91800 |
| acgcaaaaat | ctataacgca | aaaatctata | aagtaagctt | acaacgcgca | gttcaatcaa | 91860 |
| gaagtgatgc | aaatggagtt | ttgcgtctag | accaagatag | aattttact | gttgctctat | 91920 |
| acagtacgtt | cgacaaagat | ttcaaagacc | tagttaataa | attcgaagcg | tttggttggt | 91980 |
| gtccttctga | agattatggc | attattaaga | ctgcccatgt | ctttgacgta | gatacagttc | 92040 |
| caggaagtcc | tgttgctata | ctacgtgctc | tccacttgaa | aggatacact | aatgtatgtc | 92100 |
| atgaaactag | cttatatgaa | tacgaaaatg | acataatttc | aagaggcaaa | aagattatca | 92160 |
| ttgatagcac | agattctcta | atagaattta | ctaagttagt | ttggttgtat | atgggcgcag | 92220 |
| attttatcaa | actgactcca | agcccgctgt | tgcaaaaagc | ggctgatgga | tataacagca | 92280 |
| gtagttgtct | gtatcgcaat | aatgagtggt | tcatgtgatg | gatttgtttg | aaatgatgga | 92340 |
| agagcctcag | gaagaggttc | aagttcatcc | agtgatttct | aaggacatca | aagacgaata | 92400 |
| ccgtataatt | atacagaagt | atggtattaa | agcccagaa | gctcttctag | atgaactagc | 92460 |
| ttcaatctgg | tctgacccgc | cgccctggtc | tccgtgggca | aaataatttc | acaaagtagt | 92520 |
| ttactcttcc | aaaagccatg | ataagatacc | tctcgtaacc | aaaaaatgga | gaatatcatg | 92580 |
| gctatttcat | taaacccatc | tatttcagta | aaattatcaa | aggttattcc | tatcgaaaaa | 92640 |
| cccattcgtt | ccattgatgt | tcttaacttc | gcgcgagaaa | gcaaaggatt | acctttatat | 92700 |
| gatttaagcg | tgtgggaagc | attagccaat | cgttttgact | gcaaagaaca | gtcaattcta | 92760 |
| tggcaatgca | tgaacaataa | gattggcgaa | gaatttcata | agaaacttga | ctctatcgtt | 92820 |
| agacgtcatc | aaattgataa | tagtgacatt | ctctatagag | gtctatcatg | ccgcgagtct | 92880 |
| aaagcctttt | atgacgccct | tattaaagga | gagaaatttg | gctttggaaa | ggttgcgtca | 92940 |
| ttcacaacag | atgaaacgat | cgccagagag | tttgcaggca | aatggcatta | ctcgaccttt | 93000 |
| gtagtcattg | aagtcaataa | ttgccatcaa | tcatttgatt | atcataccaa | catgaaatcg | 93060 |
| cttttaatta | ctgcaccaga | ttctgaattc | atgcgtccaa | atgatgtgat | tgataacatt | 93120 |
| gctcagcgca | gaagcgctga | catcgagatg | attgataaag | aacaagaaag | gatgctaccg | 93180 |
| atgggaacta | agttcaaagt | ggtgggtcat | aacaaagttg | aaaaatctgg | tttacttatg | 93240 |
| gactacttta | gtgttactat | agcttagtca | actagtgatt | atctagaact | agggacctag | 93300 |
| acccattata | ccgtccgtaa | gacgaaagca | tttttgagga | aaacatgatg | aaatttactg | 93360 |
| ctgaaaccgc | taagatttat | actcgcctga | ttacaacttt | aggttctgcc | cagcgtcgga | 93420 |
| acaaggagtt | caatcttacc | cctgagtatc | tgtttaacat | catgcaacag | actcattgcg | 93480 |
| catactcggg | tgaaaagttt | ggaaccgtca | aaggaaacca | tcctgacagc | atgacgcttg | 93540 |
| aacgctggaa | taatgacttg | ggatatgtaa | tggggaatgt | tattcctgtc | aagcaaaagt | 93600 |

FIG. 20YY sequence.txt

| | | | | | | |
|---|---|---|---|---|---|---|
| ataatacttt | gcgtggaaat | aatacgattg | aaggccttga | gcgaaaagcg | aatgaaatcg | 93660 |
| cagcacgcat | agttcgttct | tcagattctg | ttaagccaac | aagtgataaa | gaagcttctc | 93720 |
| gtttggaaaa | gattcgtgag | tatgaaaaaa | ctataacatc | aattaaaact | aacttacaca | 93780 |
| atcgtgaaaa | tcatctttct | caatttgtgc | aaaaagaaaa | gaatggaact | gcaacctcgg | 93840 |
| ctgatttaga | acttattaat | gcattgagaa | ctcgtatcag | cggtggtaag | tctgaattag | 93900 |
| ctaaagttga | gcgtaagtta | tctgctattt | tagcgtcagt | tccgaatcgt | ccgtcagatg | 93960 |
| ctgaaatccg | tgtacaatca | atacggttaa | ttgttagctc | acttcgtcgg | ttagaagaat | 94020 |
| gctcaatgtt | agataagtta | aaattgaaaa | aaggtcttcc | attgactgct | tccttcttcc | 94080 |
| aacttttgag | aggtaaaatg | taatgcaaca | ctatggatat | gtagtagcgt | ataaggataa | 94140 |
| agacggattt | gaccatccag | tcacaactga | tatgtatgat | ggagaacgat | gtgtagtctt | 94200 |
| cactaatgaa | gaatcagcca | ataaagcacg | gattcgtaca | atgtcggttt | taacagacaa | 94260 |
| attggcaaag | gggaatttta | ctgggaaaag | caaaaccaaa | gggatgcttt | ggtggaaaac | 94320 |
| aactgagcta | gtgtatgaac | cacttagcga | tgttgagcgt | gaaaaactca | aagcaaaaat | 94380 |
| taaaaatcta | catgtagtga | gggtaaaagt | ggcatgatta | cgtttgacca | attaaaagaa | 94440 |
| agtcaaaaag | cgatttttaa | taaagtcatt | gaaatggtca | acaaggagc | taaaggtcaa | 94500 |
| catattacga | ttaatggacc | cgccggtaca | ggtaaaacaa | ctttaaccaa | atttatcatt | 94560 |
| gacgctttga | tttctcaggg | tatctctgga | attgcattgg | cagcacctac | gcatggggcc | 94620 |
| aaaaaggttt | tatctaagct | cagcggaatg | caagccagta | ctattcatag | tcttctgaaa | 94680 |
| attaacccga | cgacatatga | agaaaacgtt | ctgtttgagc | aaaagaaagt | tccggatatg | 94740 |
| gcatctattc | gagttcttat | ctgtgatgaa | gcttcaatgt | atgaccgtaa | gctgtttaag | 94800 |
| attttgatgg | caactattcc | tgcctggtgt | attgtcattg | ccattggtga | taaggctcaa | 94860 |
| atacgtccgg | tagaacctgg | aagtaatgaa | cctgcactga | gtccattctt | cactcataaa | 94920 |
| gatttcttac | aacttcattt | gaccgaggtg | atgcggagta | atgctccaat | cattgaagtt | 94980 |
| gctactgaaa | tcagaacgg | tgggtggatt | cgtgactgtg | tagttgatgg | tcatggcgtc | 95040 |
| cgtggtttta | ctaaaggaac | cgcccttaaa | gattttatgc | taaattattt | taatttagtt | 95100 |
| aaaacaccag | aagatttatt | tgaaaacaga | atgcttgcat | tcactaataa | atctgtggat | 95160 |
| aaattgaacg | aaataatcag | acgcagaatc | tatgaaactg | aacgaccatt | cgtagtaggt | 95220 |
| gagattgttg | ttatgcaaga | acctcttacc | aaggaactta | aatttgaagg | gaagaaattc | 95280 |
| agcgaaattc | ttttcaataa | tggtcagttt | gttcgcatat | tagatgcaat | tgaaaccacg | 95340 |
| tcatttttag | gtgccagagg | tgttccaggt | gaatatctgg | ttcgtcattg | ggtattagat | 95400 |
| attgaaacct | atggcgacga | tgaagagtac | gctagagaga | aaatctgtgt | catctcatcc | 95460 |
| gaagaagaaa | tgaataagtt | tcaattcttc | ttggcaaaaa | cagcggatac | atataagaac | 95520 |

FIG. 20ZZ sequence.txt

| | | | | | | |
|---|---|---|---|---|---|---|
| tggaataaag | gcggtaaagc | accttggtct | gaattctggg | atgctaagcg | caagtttcat | 95580 |
| aaagtgaaag | cattaccagc | ttcgactttc | cataaggccc | agggcatctc | aattgacaga | 95640 |
| agcttcattt | atactccatg | cattcacatg | gcagatgctt | ctctcgcgca | acagttatta | 95700 |
| tatgttggta | ctactcgtgg | tcgctatgat | gtattctatg | tgtgaggtaa | tatgtttgaa | 95760 |
| ttgaaattag | aagaccttca | aacaatgatt | gttggcttac | aagaatctaa | gtttgaagca | 95820 |
| ccagataatg | ttaagcgtgc | tattaacatt | aaaattgata | tagttctgaa | tgagcttcgt | 95880 |
| gatatagcag | ataatgctaa | tgctattact | tggttcacag | gatatgaccc | aaaggtgtat | 95940 |
| ctgagcgaat | atattggttg | ccagttacgc | gaaattaaat | ttatgctaga | ggctcaaaat | 96000 |
| ggctaaagac | tttattattg | attttgaaac | attcggaaat | gtgtcaagct | cttctgtgat | 96060 |
| tgaccttgct | ctaatcacat | ttgattctga | ccccgaagtt | ttggaaagct | tcgatgaatt | 96120 |
| ggttaaacgt | ggtcatcgta | ttaagtttga | ccttaaatcc | cagaaaggtc | atcggttgtt | 96180 |
| tggtaagtct | actcttgagt | ggtggaagaa | acaatcagct | gaggcccgtg | ctaacctggc | 96240 |
| ctcaacgcca | gacgatttat | cagtaattgc | tggaattaaa | gaagctcagc | aatatctgat | 96300 |
| tgataatgga | attcacccat | gggattcctt | tggctggtgt | cgtggacaga | gctttgactt | 96360 |
| tccaattttt | gttgattgtc | ttcgcgatgt | tcaacgagcc | caaggaattt | ccgaagaaga | 96420 |
| aattgataca | tttaaagaag | aaccatgtaa | gttctggaat | cagcgtgata | ttcgtaccgc | 96480 |
| gattgaatca | ctgcttctta | cccgcgggct | gacaactacc | cctcttccaa | agggtactct | 96540 |
| caacgggttt | attgcgcatg | atagtatcca | tgactgtgct | aaagatattc | taatgcttaa | 96600 |
| atatgctcaa | cgctatgctc | taggcctaag | cgaagcacca | agtccagaag | ataccgatcc | 96660 |
| actgagttta | cctaaggggc | gtggctaatg | gaagagtttg | agttcgatga | aaactttgaa | 96720 |
| gagtggttca | accgggaaat | cctcccgaaa | atctctccaa | cgatggttct | ggtggccaag | 96780 |
| gctttgatgg | ctaaaggctg | ggacgcaggg | tatatgttcg | gcgtcgatgt | tgggtgtgaa | 96840 |
| atttctcacc | gatagctatt | tactttatga | aagagccgtt | atataatggc | tctacattaa | 96900 |
| caaactgaga | gaaacatgat | gaaaaatttg | gttgtaggcg | aaaacgttaa | agtaattggt | 96960 |
| ggtaagcata | tcggtaaaga | aggcgtaatt | gttggaatct | ttaaccgttc | taacaaaatg | 97020 |
| tcttcatatt | tgcttcaatt | ggaaaatgaa | gacaaagccg | tgtattcgct | gcaaaaattc | 97080 |
| gtagttgctc | tagaatcgcg | cgatttgctt | gattctatgt | ttaacgaaag | ctatctgcgc | 97140 |
| aagtgggtac | atgtgaattc | acttgacaat | gttattaccc | aatcggtgag | ttctactaat | 97200 |
| tcagccacta | atctgtcgct | gcataaaaat | gttcttgtca | ctgatgagtg | ggaagaagac | 97260 |
| ggtaaaaccc | tagtaaacgt | agtgtttcaa | ggcaactatg | cagttctgcc | taaagccgat | 97320 |
| gtagagccga | cagaatcgca | acgtcaaggt | ttagtataaa | aagttgttta | ctttgccaca | 97380 |

FIG. 20AAA

```
                             sequence.txt
aggatgtggt actattatct tatcaactac tgaggagaat aacatgaaaa ctgaaaacac    97440
cgtaaaaatt actgccgaag cttttgaaga cattctgttc aacccggact taatcgtcgt    97500
tcagaaagag aaaaccttcg gtaaagaaga gcattggacc tggttgtatg tattcgcgaa    97560
ccatggtgat atcgtcccag ttcgtacctt tgctcgtgta attacagttg atggcccaga    97620
atacatggag attgtgtaat gaattttaaa gaaggcgtac agtacaaatt cgtcaatgat    97680
gaagcggaag aagaattttc ttcacgttat gaggttaatg aagactttgt gtatgaactc    97740
tatgaaaatg gcgggagttt tactgttact aaagttgacc gccaaaataa tagagtatca    97800
ggaattatgt gggctaatgg cacagaatgt gatgaagtcg gcggtgaaga ccttgtaatt    97860
tttgatagcg aattcaaata ctttactgaa gttggaactt ccgcgaatgt aattccaacc    97920
gatttggtta tgaatctttc tattcataac cgtggtcaag caatcgctgc tattgcagca    97980
ctgcagagtg catatcaatg ttaaatttag ctcctatttt tgaagcatca aaactgtctt    98040
atcctattcc taaccgtagc attgggaatg tcatgctgca actttcttca gaaactggag    98100
aaatgtgtga ttggattaat cgtccatggc ggcagaaaga agagtttgaa ggtgagtgcg    98160
cagatgttat taactgtgta gtagatgcac tttggctgca tttcagaaat cgtcataaaa    98220
atgataccca tgtatcagat gatgaaatct ccatgatggt tactcgtgca ctaaatgagc    98280
aaatcatggt caaaacacaa aaatggaagg atgctgttaa tgccaatgta tgattacaag    98340
tgtgaagtct gtggaaaaaa gatagaaatt atgcgtaaaa tttcccatcg tgactatact    98400
gttaactgct ttaaccctaa gtgtgaaggt caaatgaagc gggtggtttc tgctccggca    98460
gttcactacg atggattaaa gagtggtgat tattgatggg aactaaagca cgcattacca    98520
tgaaacccgg agaaatccgg gttattaaag taggtaatat aacttatagg gttaaattga    98580
aatgaaaaag atttttaatta cagcgcttgc cttcatgatg attggatgca ctgacgctga    98640
taacgcaact cgagtattag aaaatgcagg attcactgaa gttgatatca ctggatacaa    98700
atttttctca tgttcagaag atgattttca gcataccggg ttcaaagcgg tcggtcctac    98760
cggaaagacg gttaaggta cagtgtgttc tgggattttc ttgaagaata gtactattcg    98820
ttttgaataa aaaggacctt cgggtccttt agttgtttac acgaatagtc ttctgcggta    98880
ttatagactt ataaactact ggagaataaa acatgaaata catcatctta actttaatcg    98940
cattagttat ctcaattgga gttctggttt ccttagcaga ttctacggaa tcttctaatg    99000
aagttcagaa aagctcaatt ggtattggtg tgaatggaca agttggtgtt aagatttcag    99060
ataatctttg tgttaatcct tctactggtg ctgctgaagt atgcttttaa aatgtattga    99120
tataatgcct ccactaactg aggaaatgta atgattaaga acgaaattaa aattctgagt    99180
gaccgagaac atatcattaa gcgcagcgga atgtacatcg gtagttctgc gtgtgaggca    99240
catgaccgtt ttcttttttgg taaattccaa tcagtaaagt atgttcctgg tattattaag    99300
```

FIG. 20BBB sequence.txt

| | | | | | | |
|---|---|---|---|---|---|---|
| cttattgatg | aaatcattga | taactctgtt | gatgaagcaa | ttcgtacaaa | ttttaaacat | 99360 |
| gccaataaaa | tttccgttga | tatcaaggga | aataagatta | tcgtaactga | taatggtcgt | 99420 |
| ggtcttccac | aggctccggt | agtaactcct | gaaggagaaa | ctattccagg | cccagtcgcc | 99480 |
| gcatggactc | gtcctcgtgc | gggtggtaac | tttggcgatg | atgctgagcg | taaaactggt | 99540 |
| ggtatgaacg | gtgtcggttc | tgcattaact | aacatctttt | cagtatcttt | cactggtgca | 99600 |
| acatgtgatg | gtaaaaatga | aatcattgtc | cgttgttcta | atggctcaga | aaatatctcc | 99660 |
| tgggaagaac | atccagcaaa | agacaaagaa | ttcatcaaag | ataagactgg | tactgtagta | 99720 |
| tcattcattc | cagatttcag | tcactttgaa | agcacaggat | tgactgatgt | tgaccaatca | 99780 |
| atcattcacg | atcgtctgat | gacattagca | gtagtttatc | ctgatattga | attcaaattc | 99840 |
| atgggtaaac | gtgttcaagg | taagtttaaa | gcttacgccc | agatgtatga | tgaaaatgcg | 99900 |
| gtagtgcagg | attctgatac | ttgtgctatt | gctattggtc | gctcagatga | tgggttccgc | 99960 |
| cagctttcat | atgttaataa | cattcacacc | aaaaatggtg | gtactcacgt | tgacctagtt | 100020 |
| cttgatgaac | tgagcaatga | acttattcca | gcattaaaac | gcaagtacaa | actagaagtt | 100080 |
| aataaagcac | gaattaaaga | gtgtctgact | gtcattatgt | ttattcgtga | catgtctaac | 100140 |
| atgcgatttg | attctcagac | taaagagcgt | ttgacttctc | cttggggcga | aattcgtagt | 100200 |
| catattgata | ttgattacaa | gaaacttgct | aacgctatta | tgaaatctga | agatattcat | 100260 |
| atgccgatta | ttgaggcgat | gttagctcgt | aaacttgctg | cagagaaagc | tgcagaaact | 100320 |
| aaagccgcca | agaaagcgca | gaaagctaaa | gtagctaagc | acatcaaagc | caacaaatat | 100380 |
| ggtaaagatg | ctgacaccac | tttattcttg | accgaaggtg | attctgcgat | tggttatcta | 100440 |
| ctcacaactc | gcgaccgtga | acttcatggt | ggatatcctc | tacgtggtaa | gttcatgaat | 100500 |
| acatggggaa | tgtctgctgc | agatgctatg | aagaacaagg | aagtatttga | catttgtgca | 100560 |
| atcaccggtt | tgacgattgg | tgagcctgct | gaaaatacta | actaccgaaa | tattgctatc | 100620 |
| atgaccgatg | cggatgttga | tggtgttggt | tcaattttcc | caagtctttt | agcgttttc | 100680 |
| agtaattggc | ctgaactgtt | tgaacaaggt | agaatccgct | ttgtgaaaac | tccggttatt | 100740 |
| attctcacca | aaggtaaaga | acaacgttgg | ttctattctc | ttggcgaata | tgaagaccat | 100800 |
| aaagatgatt | tcaaaggttg | gaaacttcgt | tatattaaag | gtcttggttc | tcttgaagaa | 100860 |
| gatgaatatg | aacgtgttat | tcaagacccg | gtttatgatg | tagtatctct | tcctgaaaac | 100920 |
| tggaaagaac | tgtttgaatt | aattatgggt | aatgatgctg | ctccacgtaa | gacctggatg | 100980 |
| agtgaataaa | tagtacgggt | aatattgccc | tgctatagaa | ggaattacta | tgcaacgtta | 101040 |
| ttggattact | ttggtctcag | gcgattacgg | atacatgttt | gccgaaaaga | aacctctccc | 101100 |
| tggtacttgg | gttactatct | gggtggaaaa | ctcggatggt | tctaaacatg | aggtgtatgg | 101160 |

FIG. 20CCC sequence.txt

| | | | | | | |
|---|---|---|---|---|---|---|
| ccgcgttagc | agagtgcatt | aatcccgagg | ggcttcggcc | cctcttttct | gaggaaatta | 101220 |
| ttatgaagtc | aactatcatt | tcaatactcc | gcactgaggc | actaaaatac | tcagtcgacc | 101280 |
| cctccaatga | ataccaagaa | cttttaatca | aacggttatt | aaattctata | gctgaccgtt | 101340 |
| tggaaagtaa | ccagagtgtc | cctattaatc | acagcctttt | tgctatgaaa | gtgatacgct | 101400 |
| ttttacgtcc | tgatattaaa | attgctgaca | tggtcaaagt | gattaaatcg | tcaggagcag | 101460 |
| taaaatgcta | aagaaaagtt | atgttccaaa | taaagaatta | tttgatgatg | ctatatatcg | 101520 |
| agagtatcgt | atcatccaac | gtttctttga | tatccaagca | gcagaggaat | tcaaagaccg | 101580 |
| ctttaaacaa | atcagtgata | aaattttttac | aactaacacc | gctactgctg | aagagctcct | 101640 |
| tgaagtagca | gaaatcatta | aacgacacaa | ttgataggaa | taaaatgaaa | attaaatgtg | 101700 |
| atgatgaagt | aattattggt | tcttctgacg | ctgaggattc | aacgtttacc | attaaagctt | 101760 |
| caggtaaagc | ttttgacatc | ttgtcaaaca | aactctataa | gtataaagtt | cgtgcggttg | 101820 |
| ttcgtgaact | ttctactaac | tgtgatgatg | ctcataaact | gaacggtaat | gaaaatcgtc | 101880 |
| cattttacat | caaagcacca | actcgtcttg | acccgcgctt | tgtaattcgt | gattatggtc | 101940 |
| caggtcttaa | tcataatgac | atgatgacga | tgtacaaaac | gttctttgaa | tctacaaaga | 102000 |
| ataatagtaa | tgatttcatc | ggtgctcttg | gtcttggttc | taaatcgcct | ttaagctata | 102060 |
| caagtacatt | taacgtagta | tcatatcata | atggtaaagc | caccggttat | actgtcatga | 102120 |
| aaaaccgcgg | tgaacctact | attcgtccga | tgtttgtcga | tgatatgaaa | gaagacgaag | 102180 |
| aaactggtct | tgaaattaca | gttccggtta | aagtagaaga | tattgatacc | tggcactatg | 102240 |
| aaatcgcata | tattttgcgt | acatttggtg | ctgtacctcc | aaaggtagat | tctcttcgcc | 102300 |
| gtgaaattga | atatttccca | gtagataaaa | ctgattggtt | tagcgttaat | agctcttacg | 102360 |
| aaagttatgg | cctgtatgca | gtttatggaa | aaatcgtata | tcctatcagc | ggtgtagatg | 102420 |
| ttaaggcaga | ttggctgctt | aatcgctatg | gtaaggttta | tgttcatttc | ccactgggtg | 102480 |
| aattggatat | cactccatct | cgtgaagagc | tttctcttga | cgaagaaaca | attgctaata | 102540 |
| tccagaagcg | tgtgaatgct | cttgaagaag | aggtaattac | cgcagatatt | aaagcgtttg | 102600 |
| aagcgtatga | atctgaccgt | gaattcctgc | gtgagttcaa | taagctgagt | tctaaggaac | 102660 |
| gctctattct | tcagagccgc | ggtattacca | ttgggaaccg | cgatattaaa | caagtagttg | 102720 |
| cgaagtataa | tcttgataaa | attcgttcat | actatgtaga | taacgaagta | tcagtttatg | 102780 |
| tttcatgcga | tgaacctgct | cgtcgtaaag | tgtcaagcag | ttcttggcat | cgtcataacc | 102840 |
| aagtaaacat | ttctgatatt | tgcggggttg | atagaactaa | agcgtttgtt | cttattgacg | 102900 |
| ataaagcggg | taagcgtatt | gctacggttc | gtgctctgtg | taaatctggg | ttagttccaa | 102960 |
| tctgggcaca | cattactgta | atcaaagaca | atgaagatga | attacatgtc | attgatgagc | 103020 |
| tgaagaaaat | catggatact | gatgaagttg | tagtattccg | tgtgtctgaa | cttgaagccc | 103080 |

FIG. 20DDD sequence.txt

```
agagaaaagc tcttcctgat tacgacactg gtccaaaaga gaaacgtcct aaatcaccaa    103140
atgtttctct gcattggatt gataaagacg ggtactggga agaagaccgt cagactttat    103200
tatcatctga aattactgag cttgaaggtt atgctatcgg tcgcaatcgt gatgaaatcc    103260
acactttccc agataatgtt tggtggtgga atatgagcat cacagatatg cgttctttgg    103320
cagaagcatg tggaattaag aaattctatg caattcgtcc gagtgctatg aaagccgcgg    103380
ccaaagctga tggattgctt tcatttgacc ggtttattat tgaccaatac atcaagtgta    103440
ttgataaggt agactacgac cagtacatgc catcaaatgc tactggaaac cgtatctgtg    103500
gaaatattgc gcattacgat aaattgaatt tcttgtcgag taagtttact gcgtctggaa    103560
tgaaaaatcc gttcctgaca aaactaaaca aaatcgctaa agtttgtcgt acaagtaaaa    103620
tcaaagatga aaatgatgaa acaatgatt tagctttatg taataaaatt tataataaac     103680
tgtctagtga tgctgagaca atcttctata aaagattga acagtttaaa gatgattatc     103740
ctgtcatcgc aagtgtcttg gatacttggc ggactgacag caaactcgtc gatgatatcg    103800
taaaaatcat ggagctcctt gatggagctt ctactcaaaa ttctgaaaat aaaggtgaat    103860
aaatggctgt tacctgtctg tctgaaatcc aaaaagatgc aatcgttaaa aacttcaaaa    103920
acggtctgta cactaagaaa gagctcgccg agaattatgg tgtttcccgt gacactattc    103980
ggcgtgtttt taaagagcgt gaagctcgag ctgccgcggc agctgttcct gctaaagtag    104040
aagctccagt tgagcgtgaa tttaaatggg cagcaagttc caaattcatt tcaattactg    104100
aaggccgtac tacttataac gctgatagcc aacatcccgg gtttaaatct gcactgcaga    104160
aacttgtaga tggtgatatc gctggtgcta ttgaccacat taacctggaa caaggcatca    104220
agaaattcgt tcagggtaac gtccgaattg aagatggtac tttgttctat aaagatatcg    104280
agctgaaatc tggtctgact gagcgtatcg ttcgagctat ggaagatggc gaagacttta    104340
aacgttatct gccttttcctg gaaaacctga tgctgaaccc gtctcgtcgt gcagtttatc    104400
gtctgtttga tttcctgaac gcaaacgata tcgacatcac tgatgatggc cacttcattg    104460
gttggaaagt agttcgttcc aattacttcg attgtgcttc aaacacattt gataactctc    104520
cgggtaaaac tgttacgatg ccgcgtaacc aggtagatga agatgatcag cgtacttgtt    104580
ccacaggtct gcatgtctgc tctaaatctt acatcggtca cttcggtagt ggttccgatc    104640
gtatcgtttc agttaaagtt catccgcgtg atgtagtatc tatcccggtt gattacaacg    104700
atgctaaaat gcgtacatgt ggttatgtag tacttgaaga tgtaaccgat cgttgggggtt    104760
cagaacttcg ctaattataa ggagccttcg ggctcctctt ttattatggg tgaaacatga    104820
ttaatccatt taacgtatct cattctaaag ttgttaatct tcgtggtact catcatgctg    104880
ctacggtatt ttgccatcat gtagttaaac atgaaggtga tgttcactat gcttggttgc    104940
```

FIG. 20EEE sequence.txt

| | | | | | |
|---|---|---|---|---|---|
| actgtgatga | actcgtagaa | cttggtgatg | attttgttgt | ggaaccagac | acatgtaacc | 105000
| acgacgatcg | tgtttatttt | ggtgaattac | atatcagagg | aatttatggc | attgatgaac | 105060
| aaagccctgc | agagattgaa | ccaactccgg | acatttaccc | tagatttgaa | taagctaagg | 105120
| ggtgaagcaa | aagtaaaaat | cattgatact | gccagatata | gcttagatat | cgatccatct | 105180
| caagatagaa | ttgacgttct | taaacgatgc | agaattgcta | taccggcaga | gtatgtggta | 105240
| gcggattttc | ttgatggata | cgtgaacgat | caagttgttg | accataataa | caacgaccca | 105300
| tatgaatggg | cctgggacgt | attagctcat | ccacactacc | aaggtgttag | ggttgaagtt | 105360
| aaaacacact | tgttcatga | ccgagcaaat | cataagccat | ggattaatgt | tacaactggt | 105420
| aaagacggtc | cattcccaga | tggaagtgga | ataaatctag | ggcccatgtt | taaacataaa | 105480
| gtcgcagact | gtataattat | attcgttgca | gaagaagtgt | cccagaatgt | catacggtac | 105540
| acaccaatgt | ttgccggcgg | tatcgaacag | ctcatggaag | tagtaaaacc | ttcacgtgtt | 105600
| ggagctggcg | ggtatatcat | gcacaaattt | taaaaagttg | tttacttccg | ggattggcca | 105660
| tgatactatg | gccctacaaa | ctgaacggga | gtaaaacatg | agttacttag | agctaaaatc | 105720
| acttcgagcc | aaacgcggaa | atgcttctat | taaagctgag | cttttgaaag | agtatagaat | 105780
| tctcgaatct | atgaattggc | attatgctat | cattgcttgt | gataatggcg | attcaactta | 105840
| cggtggattg | tatcccaatg | gagccgctgc | tgccgtgat | gagcataaag | ataaagttaa | 105900
| agccttagaa | gaaaaaattc | gtaacttgtg | catttaacgg | tttactttcc | tgttcttcgg | 105960
| tgatactata | atcttgttag | ctaaactgga | gaacaaaaat | gaaaagtta | cttacgattt | 106020
| tgaagaacac | ctttgtagta | ttctgcctta | tcgttacttt | cattggtgtt | ttcgcatggg | 106080
| atttagttaa | cgtttggatt | aatgctttca | tctgaggaaa | ataatgat | tcgtagtagt | 106140
| tttgatcgtc | gctttaactt | aatgagaact | gttgttctgt | cctttatcgt | tgcggtagcg | 106200
| cttggaattg | ttgctatatt | cgggttcgga | atttattttg | ctattcaagc | ggtagatatt | 106260
| attcagaccg | atggccttaa | atctttagta | gaaaccgtat | gggaaggtca | aaaatgaaac | 106320
| gacacatcgt | gtatcgtctg | ttggcttcgg | gtcttcttgc | attttgggtt | ggtatcgtga | 106380
| cagtggtagt | agtattttgg | taataagagg | ggcttcggcc | ccttatcgga | gaataaactt | 106440
| taatcaactg | aggaaattaa | catgcgtaat | attatgactt | ttgctgatct | cgataacgct | 106500
| ggtgcagaac | tgatcggttc | tattcgtaac | ggtgattggg | cagcaggtgc | tccatctcgt | 106560
| gaaattactg | agcgtgaagg | atttattttc | ctgatgttca | atgatggcaa | agcaggttat | 106620
| atcggtgcat | ctgctcgttt | ctttgtagct | aaacaacgtt | caaaggcagg | atttgagagt | 106680
| gttctttctc | atatccgttc | tggacgttct | cagttgggtc | gtaccttcg | ttcaaactgt | 106740
| gtaacatacg | gtgtgttctg | gattcctgcc | aataaaatga | aaccgctcac | caccggttat | 106800
| ggcaaaggtc | aacttgcact | ggcgtttact | cgtcagcatt | caagcgccgc | gcagacctac | 106860

FIG. 20FFF sequence.txt

| | | | | | | |
|---|---|---|---|---|---|---|
| tctgaactga | atcgtattct | gaatgataac | ttcatcttta | ctttgcagaa | atactaatga | 106920 |
| gaaccttctt | cgtgatgggc | tatgtgtttc | tgatggccct | aatgatttgc | tcaggaacat | 106980 |
| tcatgtggta | tggccttgtg | cctaccacta | aagtaatcgg | aagcattgcg | ttcactgcag | 107040 |
| catttattat | gtttgagcgc | atttgtaaaa | ttgtaggagt | ttacaaatga | ttaaaggaat | 107100 |
| tgctggcgga | atttgggctg | ctctatgcgt | atcgacattg | actaccggtg | aaacttctgt | 107160 |
| tatttcgcag | gcgttagcgc | aaggaacttt | atcaattatt | cttattatag | cagccttttc | 107220 |
| caatgattaa | gaaaattttg | attggagcgg | ctttagtagc | cgctttgctt | ttaattttgt | 107280 |
| actatggaat | gatttacggg | atgatttata | ttgtgctttt | catttccgat | gttatagtac | 107340 |
| aaatcggctc | actaatttgg | taggtacaat | ggatattttt | gacactctat | taaaacaagc | 107400 |
| aggttctatc | gatgatttgg | ctaaggcatc | aaatcttcgt | catcgcgatt | tgaaatctat | 107460 |
| cattgataat | gaagcaaaag | agtatgcgat | ttacactgta | gaaaccgtg | ctattccgaa | 107520 |
| cttgattgat | gggtttaaac | ctgtacagcg | ttttgttatt | gctcgggctc | ttgatttagc | 107580 |
| tcgtggtaat | aaagaaaaat | tccataagct | tgcgtctgtc | gccggtggtg | tagctgattt | 107640 |
| aggatatcat | catggcgaaa | cctctgctca | agatgctggt | gcattgatgg | caaacacatg | 107700 |
| gaataacaac | tatcctctgt | tagatggaca | aggtaacttc | ggttcgcgtc | tggttcaatc | 107760 |
| tgctgcggca | agtcgttata | ttttctgccg | gatttctgac | aacttccgta | aaatctacaa | 107820 |
| agacacagaa | atcgctccgg | tgcataaaga | caaagaacat | gttccacctg | cgtattatct | 107880 |
| tccggtaatt | ccgactgttc | ttctgaatgg | cgttcgcggt | attgcaacag | gttattcaac | 107940 |
| ttctattctt | ccgcatagtt | ttgaatctgt | tttggaatgc | actaaagcag | cacttcgtgg | 108000 |
| cgaaatgatg | gaacctgaag | tacagtttcc | taaatttaac | ggaaaaatcg | ttcaaacaga | 108060 |
| agacggttct | gttgagctgc | acggcgtgta | taagaaaact | tcacggaact | caatctatat | 108120 |
| cagtgaaatt | ccatacaagt | ttgaacgagc | ttcttacgtt | gaaaaagtac | ttgacccgtt | 108180 |
| ggaagatgca | ggatatatca | catatgatga | tgactgttct | aagactggct | ttggctttaa | 108240 |
| ggttaaattc | cgtaaagact | atgctttaag | cgaagaccct | gagcagcgtc | atgctaaaat | 108300 |
| catgaaggat | tttaaactca | ttgagaaaat | gagtcaatac | attgtggtca | tcgatgagaa | 108360 |
| tggtaagctg | aacgacaagt | tcaaaacttc | cggtgagctg | attcgtcatt | ttgtagaagt | 108420 |
| ccgtaagaca | ttcactgcca | aacgaatcga | gcataaaatc | gctgaaacta | agcaggcgtt | 108480 |
| taatcttgct | caggcaaaag | ctcaatttat | caaagaggtt | atcgcaggta | acatcgttat | 108540 |
| ccaaggtaaa | actcgcaagc | aactgactaa | agaaattgaa | caaaatgaac | tattcaaaga | 108600 |
| ccattctgaa | aaactcgttt | caatgaacat | ctatcacatc | actgatgatg | aagcgaagaa | 108660 |
| acttgctcag | gaagcaaaac | gcctagcaca | agaggttaag | tactgggaaa | agacaactcc | 108720 |

FIG. 20GGG sequence.txt

```
tgaagccgag tatctgaaag acctggaaga actatgatag aattttattt aattataggt    108780
tctgtaattg ccgtattagg tttagtttta ttgctcctca gttaatctag ggaacctgga    108840
ggtcatctcc aggtccttcc atataaatct atatccctcc aaaatccttc cttagaatgc    108900
cccaaattat tttcacaaag ttgtttacat gcttactcgg ttgtggtatt atagcaatat    108960
caaaacaaca cggagtaaaa caaaatgatt acatcattaa aatctgatat caaaaacatt    109020
ctttatattt ccactcaagc cgatggcact cgactgagcc actatgtcaa aggtaacatt    109080
gtggtgctcg atgagttcga agttaatcgc gagtatccta tgcgtcaggt aattcaagca    109140
agtaactatg aagacggtga agagtatcaa gtcgttcttt gtgtatatga tgatttctgg    109200
gtgcttaaac ttgagaatgg cgataagttc ttgatcttta acgtataaca tttttactgc    109260
tctttgaaga aaattttca gagagcagaa taaaatggtt tacaactgct ttaaaccatg    109320
gtattatagt ctcataccaa acaaactgaa taaaacatca tggagaatca caatgtctaa    109380
agtaacttac atcatcaaag cttccgaaga tgctctgaac gaaaaaactg ctgctatcct    109440
ggttcaggta gctaaaaagg atttcatcac ttcttctgaa ctgcgtgaaa tccttgaaga    109500
aaccatgaac gcaagttctg ttaactcaaa catcggcgtt ctgattaaga aggtctcat    109560
cgagaaatct ggtgacggtt taatcatcac tggtgaagca caggacatca tctctaaagc    109620
ggcagttatc tatgcagaag agaacaagcc tgaacttctt aagaaacgca atactcgtaa    109680
agctcgtcct ctgactgaag atatgaatga gcacaaagac ctgatgatga aacttctcgg    109740
tgagatggaa gatatcttgc ctttgaaaga actgactgtt taccgcagta actatatcgc    109800
agttctggaa aaacgtacct tcggtattcg tagtcttgaa gttaacaaca aaggtacttt    109860
ccgcatcttc ggttacaaga tttctgaaga gcatcagaaa cacttcactg acctcggaat    109920
gtcttgccgt gtagctgcaa caggcaatac ttacttagat atcgcccgta ctgctgaaaa    109980
cattgaaacc atcatccgct ctattaagga actgtaatgg aactttggga aattatatat    110040
gaagatgatg tgaatatcag aggcagcatc ttcattaagg ccctggacaa atatcacgcg    110100
attgaattgt ttgaacagtt acagcaacaa acttatatca atgaatcgcg ttatttaatt    110160
aaactcgcaa tgttttggt ggaataatga acaagtttaa agtattgaat gagcttcagc    110220
gttgtgttga aaaggttaac ttgaatgcta atatcccaac tgattgttgg gatgtatggt    110280
tccgtggaca ctttatcgga tacattgata agaaattcac aaaatgctat gctatctaca    110340
atgcagatgg taaacatatc atggatgtag ataattacca aaaggccctt gctaaatttg    110400
ttccattagc ggaagctgtt aactcaatgg aatggttaga gaaaatacag ggtgaacctg    110460
ttattcgcca gattggtatt cgtgaaaaga aaagtttgtg gcagaaaatt aaaggattct    110520
ttaaatgagc aagttttccg aacaaatgaa taaatttgtt gatgcttctc gtcacggtgc    110580
tctaattaat gaaccagaag aagttagtat tcctgaaatt tgctttaaag tagctgattg    110640
```

FIG. 20HHH sequence.txt

| | | | | | | |
|---|---|---|---|---|---|---|
| gtgggatgga | cgattacttc | aacgccgtat | cgtttgtgca | gcaaatcgtt | ttgaattgaa | 110700 |
| atctggtgga | acaattgtgg | ttccaggcac | tcgccattat | tctgttgata | tggcgaacgt | 110760 |
| tctagatatg | ttccgtgaca | aactggtttc | tgaccatgtc | catggagaca | atcaaggatt | 110820 |
| tgtcgaccag | tggggtgagt | acttcacacg | tgaagaagca | ttaatcatcg | ctacacatgc | 110880 |
| aggtcaagtt | aatacagttc | gtcctaaatc | aggacccgcc | aatgaattat | tctcagagga | 110940 |
| tttatactaa | tgattagtac | attaaagaat | aacattacgc | ttttaaaaat | tcaacgtaaa | 111000 |
| tcgcttcagc | gctcattaga | aatgatggac | gataattggg | gtacatatac | caatgaagcc | 111060 |
| gggtttaaaa | tggcagatag | caaattcatg | aaaactctca | tggataagga | atacatctgc | 111120 |
| ccgtttagcc | atccatttaa | tggcggtgct | aagccatttc | ttgctgaaat | gtacaaaata | 111180 |
| atgacagaag | aaatgattaa | agatattgac | tattacatca | aggaacttga | atgcaaggaa | 111240 |
| gataaagtgt | gagagcaata | agcgccaagg | cagattactt | caatagctta | aatcgttcag | 111300 |
| aaaaggctca | aattaaacgg | tttatcttgg | aattgggata | tgtgcatgcc | ggagatttaa | 111360 |
| aagcacatat | ccaagaatgt | ggtattgcta | agcgttttga | tattacacgc | aactgcttaa | 111420 |
| atgaggtaat | tgcacatgta | caacccagta | gcgaagaatg | actttaacaa | aggaggcgcg | 111480 |
| cataaagata | aaaagcgtgc | tgctaaagaa | tcaaaacgta | agcaaaaaca | taaaggtaaa | 111540 |
| gacaatgcgc | attctgaata | attctaaatg | tactacttta | accattattt | gtgatgacct | 111600 |
| agaagctctc | cataaaaaat | taggggacca | ttctggatta | gtagcagata | tccattctga | 111660 |
| actaatggaa | gacctccaga | atgctggata | tggggactgg | atggtacatg | attggaataa | 111720 |
| tggtaccttt | actgtagcta | ttattgctaa | cgttgaacct | gaagaagttc | ttgaacaatt | 111780 |
| tcagaaatgc | gttgatgctt | atgatattgg | agattatcta | tgaatactga | aactttacgc | 111840 |
| agagaagatg | aagccaaggc | atatcataaa | cgtgttgaat | tactttcagc | aattaaagta | 111900 |
| gaatacactt | tacaagttag | gcttaaagtt | cttaactctt | gggctaatga | cttagaagta | 111960 |
| aaacatttag | aacaagcagt | aatgtttacg | tttactcagg | aagcttctaa | accgtttagt | 112020 |
| ctatcagcag | atttccacac | gtatggaatt | attactatta | aagcaaagga | tagaggtgac | 112080 |
| attataagtg | gagttgagta | tattgaaagc | attttaggta | atcgcggaga | ggttgtttta | 112140 |
| gcatgagtca | taacttagaa | tctgtcattg | aatcacaaag | atatctcgaa | gcgttaatga | 112200 |
| ataaaatcgc | gcttggaagt | ctaatcgact | tgtcctttca | ggaggcaatg | gacgtatgtc | 112260 |
| actggatgaa | tcgtagggtt | cgtccaattg | gaaaggaatg | gtatttaacg | gctaaagtaa | 112320 |
| aagatggtcg | ctacgggctc | tggatgtcct | ctggtgctga | gtatatcact | accaaggaag | 112380 |
| atttgaattc | tcgtttggga | ttggcataaa | ctggtttaca | acgtggtatc | aagatgatac | 112440 |
| tataatcaca | taatccatta | tgttgtagga | aaaataatga | ctaagtttga | aattgtccaa | 112500 |

FIG. 20III

```
                                     sequence.txt
gaaattgtta   ccgttgcttc   tattctgact   aagttcaatg   ctgaacatat   catggagaag      112560
cgagatgaat   ttattgcgtt   cttgaacgaa   attggaatca   agaacgagca   ggggcgtcag      112620
ttaaatcaga   gcaacttccg   taaaatggtt   tctgagttaa   ctgacgaaga   gaagagaatt      112680
ctcgttgaag   aatacaacga   gggatttgag   tctatctatc   gaacaatggc   tatgcatagt      112740
aataagtaat   cacttagctc   ttcctagagc   tctaaccgcc   tgaccacata   tcgatgttag      112800
tctttcgtta   gataatgcag   gtttggaatt   gtaccagtac   atttcaacag   ttccagcata      112860
aacattgtct   aaattgaaat   acggacagct   aaacatgtac   gatatttcag   gtggttttct      112920
ttttgtcggt   aagaaaacaa   attccttatc   cgtccaaaaa   tatctacccg   ataaatgcgt      112980
gctatattca   gcagacgttt   tgtcgattgg   atatcctccc   aggtttttag   aatctaccgt      113040
gctaggtaaa   gtcccctcat   aagcaattaa   gtctacgaag   tagttcaagt   ttttaggtct      113100
gaacgtaaag   accgcagaaa   aatctgcacc   acttgagata   tgtactatct   ggagttgttc      113160
gagtgctgta   ttatcaaatc   gggtatccct   atcctttga    accagtttat   catacttgtc      113220
atatgtacta   tcgacgtaag   cagtaataag   actatctgac   ttataaccag   caaacgccaa      113280
caatgctaaa   agtatgacaa   caaaaacacg   ggaaaagaga   actcttcccg   tggctccatc      113340
tttgaataat   agctcgagca   acccaagaaa   catatcaaaa   aatggtattg   attgtttgct      113400
tgccatattg   ctctccttac   agagctattt   attgctatct   tctagttata   agaccttgcc      113460
agtattggtc   agttctgtca   ctaaaccagt   ttttaagctt   attagcttcg   tcatttgaag      113520
ctatttgata   gtttcttaca   tctccatcca   ttttacctgg   agtaaaatca   aaggtagtgc      113580
catctgacat   cattacccga   agatttattg   cgtcgccatt   tcttattccc   aaggttgtac      113640
cttgagggtc   accgttccaa   tagttaaccc   caccttgtcc   agatacagac   acaaataaag      113700
taacctcttt   accttcgaag   ttaccttgta   ctgtattttt   ggttgtcggt   ttagggctcc      113760
agttccagcc   accaacttgc   catgaacctc   tatagtaaat   attgttccag   ttacgatatt      113820
gcactgttaa   actaaagtta   aaaacacttc   gtcctatcat   attagacatc   cagaaaggtg      113880
ttcctagtct   taatttggct   ccggcttggg   ccatccacgg   ctcgccggtt   tcagccttcg      113940
cggaacttcc   aacccatggt   cctgttactg   ccatgatatc   tccttaaaga   tggggccgaa      114000
gccccatgca   ttatttagat   ttaagttctt   caatttccgc   tttaaggcct   ttaacctcag      114060
cagaaagctc   tttaacagat   tcaacaagaa   gtgcaattac   tgagttgtaa   ttcagacgca      114120
ataatccgcc   gtccgcttca   atatcttgag   taactgcttc   cggaagaact   tcttgaactt      114180
cttgagcaat   caacccagca   gaacgagtag   taccgccaga   agtattatga   agctcataag      114240
tattaccgct   taaggtctct   acttttccca   aagcgttttc   aataacttta   atatcagatt      114300
tagctctacg   gtcagaacga   atctcaacgt   tatcaaatga   accattgcga   gtacagatga      114360
agtcaccgcc   agctctgaaa   tagaaactgt   catctcgacc   gaatccatta   acattaatga      114420
```

FIG. 20JJJ sequence.txt

| | | | | | | |
|---|---|---|---|---|---|---|
| tagcttggtg | gaagttacca | acatattctt | ggaaatacag | agaggcataa | gcaccattac | 114480 |
| taaatctgct | tactaaccca | gcggtattgt | tatatgtgcc | attgggttgt | cctgcaggat | 114540 |
| aattagtagt | gctgctaatt | ccgttatagt | tagaaatggc | tcctgggaat | tgacatgaac | 114600 |
| cacttgccca | gaaattccat | actggtccag | aagcaccgcc | ggctcttata | ctaacattac | 114660 |
| caggctcatc | agcccaaaga | agacctttt | ctgtaccatc | tgctttacgg | aagaacacat | 114720 |
| ggctattacc | ggtgttctga | acgttaacag | aagtggatac | actgaactct | tgattaaacc | 114780 |
| tagcctttcc | atcaacagtt | aaaaccccat | taacggcagc | atctccggta | gtccatagag | 114840 |
| aagtagtttt | cagttgatta | cctgtaacta | ttaatgtacc | agttacagta | ccacctgcta | 114900 |
| atggaagata | agtatcgcca | gcattactaa | tagcagaagc | aaccttatca | tcaacatatt | 114960 |
| tcttgttggt | taggtgcgag | ttatcagtag | gagcttgacc | tgcaataaca | aacttaccag | 115020 |
| aagcgacgtt | gatgtttcca | tcagcattaa | tcacaccgct | gaagcgggaa | ttgccttaa | 115080 |
| ctatcaagtc | tgagttcaag | ttagtattac | ttgttactgt | aagctgcctg | ttaatttggg | 115140 |
| catttccgta | aacagtttgg | tttccgctag | catcaacttt | gaatatatcg | ctaaacgtgt | 115200 |
| cagcaggatt | aatttggttg | ttggtatttg | cagataccat | aacggtaaat | gagttagatt | 115260 |
| taccgatggc | cattttcct | ggcataccgt | ttttcttgac | taaaccaata | tcagagtttt | 115320 |
| tgccaagaac | gatcattctg | ttatcttcag | aaacgttcaa | gttgcctgtg | attttcgagt | 115380 |
| tctgggcctc | gaactcacca | ccgacagtca | ttttaccttt | ttggtcaata | actgtagctt | 115440 |
| ggttggaatc | atcgccgtta | ggtcttaaat | gaagagcttg | acctgttttt | gcgtagataa | 115500 |
| caaaagcacc | agagtcgttt | gaacgaatac | ccgggccata | ggaccactca | agcagaggct | 115560 |
| cagaaccgtt | agctttaact | ctaatctcag | acccagaaga | atcaccgaat | ggtctaaaag | 115620 |
| caatatattt | cgctgatgct | gcggctgtag | cagaagctga | catgatcaat | gcaccagtac | 115680 |
| taccaccttg | ggcttcacga | actactgcgc | cattttaaa | tgtgatagtt | ggatcacttg | 115740 |
| ttccgacgcc | attaacaact | aaccagccga | acttcacact | ctgtccttca | ccaacaccga | 115800 |
| ggttattacg | agcagcagcc | acagaagttg | ctccggtacc | gcccaagttg | attggttgaa | 115860 |
| cccctgcaac | aacctctttc | catgcagacc | atgtgccgtt | ttggcagtat | ctaacatatg | 115920 |
| tgccttcaac | attaccgttc | tttgtagtaa | aggtctgctt | acacgtccaa | tcactgtcag | 115980 |
| aaattttacg | caaagacaga | acttcaagaa | caaagttacc | atcagatgta | ggtttattag | 116040 |
| atatattaga | accaccacca | gatgatacac | atttatacag | ctgacagta | cctaaatcac | 116100 |
| tgcctttaat | aaccatgttg | ttaaggtcat | tagtcttatc | agtaatatta | attgcatctt | 116160 |
| cagtaccgcg | atatgtctga | ttaaaaacca | atccccttc | tacatcaagg | ccatcaggct | 116220 |
| taactcggat | gtacttgctg | ggagctggag | tagcaactgc | atcttgataa | ccaaactgca | 116280 |

FIG. 20KKK

```
                                                sequence.txt
cgtatccttc aggagtaatt ttaagcattg ctacggcagc gccagagcca actttacgtg    116340
caagggtcaa tctgctatac ttatctgagt tctctgaacc taaatcaacc attgatccat    116400
tagggttttc gactttaag ttagcgttaa tagtcaagtt accggtcatg gtatcaccag     116460
```



```
                                                sequence.txt
cgtatccttc aggagtaatt ttaagcattg ctacggcagc gccagagcca actttacgtg    116340
caagggtcaa tctgctatac ttatctgagt tctctgaacc taaatcaacc attgatccat    116400
tagggttttc gactttaag  ttagcgttaa tagtcaagtt accggtcatg gtatcaccag    116460
tcttgcttac ttgcttacta tcaccagtgg tgatatcatt tttaatagaa gtcaaatagt    116520
tgttaaggtt accgccaaac attgaaccag aggtaatatt cccgtctttg gttagcattg    116580
ctgctccacc aactttaact gctacaggaa catcaaggcg gccatcagaa cggaagctaa    116640
aatcaccggc agaaacatca ccagtagttt ttgcacgaat attaatctga cccaagtccg    116700
cggtattcgg agttgcccaa attacaccac gctcattacc tcctgttcta aaccatacat    116760
gagcgtttcc gcttcctgcg ttaacatata ctgatgcagt accagtgccg gaagcatgta    116820
aattaggaac agttaaatca ccagtcatgg tatcgccggc tttcttaact tgagtatcgt    116880
ttgtcagatt accaagtccg acatcagcct tagatggttt gtttgctgtg ccgtagagaa    116940
cattagaatt tactcttcca cttgctaaac cgctatcgtt tatagcaaat actctgacgt    117000
tgccagttgc ataatctata ttaagcgcag acattgtatc gccagttcta gaaaagaatc    117060
ctgcgccatg ggagtaataa ggagccccgg tataaccact cgctacgttg gctctaaatg    117120
ttgtaccacc aagagcctta aggcgagtca ttaaatcaac atcagaagta atatctacta    117180
gtgattttcc gttaccgcca ataccaaagg caccaacttc catcacattt ccgctggatt    117240
caccaacatc acgaacagcc gcagttctaa gacctaggtt atttctagca tctcctacgt    117300
tagtagcacc tgtaccacca cggttaaccg gaagagtacc ggtagtatcg ctgaaatctg    117360
gttttgagat actatcaaaa acctgtttca ttgaaacaag aatgcttcca gatggtgtag    117420
tagcaccagt atcttggcca gtttcataga taattacttt accgctatct tggccgttgt    117480
attcagcagt gtttagcact gtaacataaa gtccatttcc gtatcgagga actttagcgt    117540
aaaaatcaaa tgaagcctct gaatctgtag cagcatcatt tttaacaacg taatactctg    117600
gaacgtttcc tttattagga gaaccaatcc tgcgccattc aacccagtta tctaaattgc    117660
tagtgctcca ggatgttaaa ttgcgaccag ataacgtgat aaaatcaaca taatgccttc    117720
cgtgtccaga atcaatgcca ccagtaatca ttaaatctaa ctgcgaagat gcatctcctg    117780
ggtgtttaat tgtagctact ttaacccagc gcggagttcc agcggttgca gcagaaatta    117840
cgtattgcca tgcctgacgg ttgttttcta cattcgtcag aagagtaccg gatttaccag    117900
gacctcttcc gttcatggcg taataaacct gtgaatttct gaatgtcaga ttactgtcat    117960
tggttaattg aagaacacct acgcctcgtt ggttttaat gtaagcgtcg ttagagccta    118020
cacccatttc aaggacaagt gtgcttccat tgttaatttt aacagtttta ttagtggata    118080
atcttaaatc accaggaaga gtggtattac ccgagccgtc aagcaagacc agttttcggg    118140
cttcaacgtt gccgcttccg cgttgtacga attgaatagt ttcagcgcca tcgtcaatag    118200
```

FIG. 20LLL sequence.txt

| | | | | | |
|---|---|---|---|---|---|
| taccgatttc | aagaataccg | ctattgcttg | taccacctgc | accgatgtac | cagccatcgt | 118260 |
| tagtagcgca | tttgccgacg | atatgacgca | ctattgctcc | gcttaaatca | gtggcttcaa | 118320 |
| aattgatagc | tttattcgga | gaaatagtaa | cgttgtcttt | taatgtagta | attccatcaa | 118380 |
| cattaagatt | acctgcagta | tctaagaaag | gaacaccttt | acctgcaagc | tgaacaacgt | 118440 |
| tatcggcttc | atctttagtg | taaatggcaa | gagtacgccc | gtgtgtattc | aacacgattt | 118500 |
| cgccacgggc | tacgatatct | gcacctggtg | ctttattctc | tgtgctagtt | cttttaaatt | 118560 |
| gtatttgttt | taagttttga | tcggccatgg | ctacctctta | gtatgtgcca | aaatctattg | 118620 |
| ttaccccgcg | tgaaataacc | tgatctaatc | taggagcata | ttcaccggat | gttgctttat | 118680 |
| ttactataac | tacgccagcg | ttagctctaa | gtacaccggt | catggtgtcg | ccagctttct | 118740 |
| tgactgctgc | gttagctacg | ttgctaacag | tatttattag | ctcatcgaca | tagtctttgc | 118800 |
| gtgttaagtg | tgaatttgct | gttggagctg | cagccgcaac | agaaacttga | ttgttagaag | 118860 |
| tgattccacc | tttagtagta | atattaccag | atcgtaaatc | gaatgcgata | gttattccgt | 118920 |
| ttgaaccaga | attagattca | aatcccaagc | cccaccaagt | ttttattttg | gcattgacac | 118980 |
| catttaaagt | ggctccatca | actccgccat | ttacgagttc | catgcccccg | gagccagtag | 119040 |
| tttgaactct | taaacctgtt | tcaaacgtta | ctgttctaga | gtaacttccg | ccattagctt | 119100 |
| ttgacacaaa | gtcgttatct | gcggcttgtg | gtttatctat | ctcagtataa | accttttac | 119160 |
| ctctataagt | tagggagttt | cctgccggca | caagaggaaa | agtacccgcg | tgccaaatag | 119220 |
| gatttccgcc | aactgttgaa | cctgctttta | aatcggccat | agtttatcct | cttatatatt | 119280 |
| ttctatttat | acgaaaaaag | gaagccgaa | ggcttcctta | gtctgatgtt | tctctgaacg | 119340 |
| attgaactgg | aataacaccg | ctcggatcga | cttttgaatt | tggaagttcc | ataatcatag | 119400 |
| tagttcctcc | ttcaacgcct | ttattcattc | ttataccatt | cacaccaaac | tcctgaataa | 119460 |
| cactattcaa | ttgttcgcca | tgagaagttt | gaacaaatac | gaggtttttg | attttagagt | 119520 |
| caccaactac | agacgttttt | ggatatcgcg | ataccacgat | agtaaatcca | tcagcgtctg | 119580 |
| taggaacagc | ggtaaatctt | tcaaatctta | accatctatc | agctccattt | tttggaactt | 119640 |
| ctaatgatac | gtttgaagat | aataaagatg | taccctttgaa | ccaccgcaag | ctagctctag | 119700 |
| tagtagaacc | agcatcaaga | aggcttttag | atgcatacat | atcacatact | aaaaataccg | 119760 |
| aatccccagg | agatagtcca | taatcagcta | ttttgcttat | agattcattt | tgtactggat | 119820 |
| atcgtttata | ttcatatcca | gtagaatccg | agtattcatt | ggtatcttca | atagaacgat | 119880 |
| aaggacaccc | agtatatcct | acatctccta | cattgtcata | taccgtatct | actttagccc | 119940 |
| ttgaatcttc | tttaaccttt | ccgtcattcc | cataaaatga | ctcaattaat | atacgtcctt | 120000 |
| ttgctgctcc | gagcactcct | acataagcag | agtttggaaa | tgatttggaa | aaatcagaac | 120060 |

FIG. 20MMM sequence.txt

| | | | | | | |
|---|---|---|---|---|---|---|
| ctggccaaga | tgcagaccac | ttatttttaa | accatctgtc | tattaacggg | ctggattgaa | 120120 |
| atcgttcatg | cgtcattata | atatacaatc | ctgaagttaa | tccatttgca | tattctacaa | 120180 |
| acgctttgtt | attagcgttg | ttgtcatcag | tggtaacgtc | aaacgtttta | aagttaataa | 120240 |
| atctgtcacc | attaacttga | acaacattaa | tcccctccg | taaggaggag | gtcatatcaa | 120300 |
| aggcaccgtt | aatattcaat | tctggcttat | tcggaacagc | attagaatgt | gtagcataag | 120360 |
| cttttagcca | atacttcaca | gagtttgcct | cagagaggat | tcgtgtttcc | acgaaatcct | 120420 |
| caccaaaggc | tgccattaaa | attggatcag | ccattaatca | cctacccatt | caaatttgag | 120480 |
| agtttggttt | ggacggtctg | gccagatttt | aactggacca | agcttaatcc | attccaaaac | 120540 |
| ttcaagggtt | ttaacctgag | ttgatactga | gcttggagct | ccgatatcag | ctgcagttgg | 120600 |
| aggagtagca | gacgtgaaca | ctcgcatcca | atcatcaaac | ttattaaggt | ttggattata | 120660 |
| aatcctcatc | cacacagtat | gcgcgaaacg | cttatcagca | gtttcggttg | ttggaggata | 120720 |
| aggtgtccaa | agctgataag | tgttgtttgt | agttacacca | acctgagtta | aaacaccgcc | 120780 |
| agcagcagtt | ttttcttcat | atccggtcac | tactaaagtg | cttgggttag | cagggtcaat | 120840 |
| cggtgttctg | attggaacca | tataaccacg | aagacctttc | aatttagtag | cgtctttaat | 120900 |
| ttcagcagtc | caagaacctt | gtcgcaatac | agtatcatta | gtcggcacat | accacgattc | 120960 |
| agaacctgta | atgacgatag | ccgaactatt | tatgttaaga | ttgccggtca | tggtatcacc | 121020 |
| agctttcttg | acataacgac | catcagctaa | tcttgcgtag | ttttggtag | ttaaaatcgg | 121080 |
| atacgagtta | gtattatctc | gagcaaaaat | ttgcgtatca | gcgtcacgag | tatcaataaa | 121140 |
| cgcagagtga | gacctagcac | caataatagc | attttgggtt | tcaatagtta | atagaaccgt | 121200 |
| atcttttacc | ataacagttc | cgccaactat | tgtatttcca | gaagacctca | gagttttagt | 121260 |
| tgatacttca | ttaggaacat | ccagcgtgcc | gtttccacca | aatgtgtagg | tctggcttgc | 121320 |
| agcagtagtt | cctgttccgt | ttttgacacg | aacttttaaa | tttccagctg | aagctgtttg | 121380 |
| ggtttctgca | taaattatac | cgcgttcagt | tccatctcta | ttttgaaaac | gaacatgcgc | 121440 |
| atttccagtg | tcagcagttg | gagaaatttt | tacttcgcca | ccattagcgt | ataaaatatt | 121500 |
| ctggacagaa | atgttgttat | taaacacagt | atcctggcta | aatgtccaag | ctccagaaat | 121560 |
| tgtctgcgct | atatcgcgac | gagcatattt | gtctggggtt | tgaccaccta | gcattccggt | 121620 |
| gtcatacgct | ttaccaagac | gaggcaagta | atgtttcaac | gtgaggttca | attcatacgg | 121680 |
| agacactgcg | acgcccttag | aggcataccc | gttatccgga | agagttgagc | cattggtatc | 121740 |
| attacctttc | cacgttccat | cgcctgtaga | tagcctgacg | gtccctctaa | cgctgtctgt | 121800 |
| agcttgccat | gactctgtta | cctgaatagt | ttgtttcaag | taagcaggag | gaacaattct | 121860 |
| atcacttaat | gtgcctgcat | caacttgcgc | ctgtgtagca | tactgagcaa | gaccgatagc | 121920 |
| tccttcggtt | gctgttttcg | cgtgcaacgt | ggcagcagta | actattttct | tggcgtcggt | 121980 |

FIG. 20NNN sequence.txt

| | | | | | | |
|---|---|---|---|---|---|---|
| gccggtctg | acctcagcag | cagttgcaag | agtagttgta | cctctttgag | aagtacttgc | 122040 |
| ttcctgtatg | ttgatggtat | aatggtccca | gaggttccca | gtaatagtta | agccagaact | 122100 |
| agtattaact | tggatacgac | tagtattagc | aaatttatcg | aacagtaatt | tagggtttac | 122160 |
| cattactgta | cttgaagtac | cagcttcaaa | ttcaccctgg | gcaccaggtg | tcgcgaagcg | 122220 |
| agcaatacca | gtacgatcgt | tagttgctgt | acggtcattt | aatgttttag | gtgtaactgc | 122280 |
| tttattagtc | acgccaccag | cattaacttc | tgtctgtgta | gctatttgga | ttaaaccaat | 122340 |
| tgctccatca | gtagcaactt | ttttatgcaa | agattctggt | gtaacaaccg | taggaatatt | 122400 |
| tgaagaagca | ggagttccgt | ttctaacttc | gctatcactt | gctaaccaaa | ctattcctga | 122460 |
| ctgatttaca | gtagctttat | actcacgaag | agttttgga | gtaactgcat | ttttgtaatc | 122520 |
| agaatgatcg | aatataccgg | tgccagcaga | agaacgatca | gcagttgtgt | taggagcacc | 122580 |
| accagttttt | actaactgaa | taacacctaa | ccgtgaatcc | gacgtagtac | gataaagcaa | 122640 |
| cttcttagga | gtaacaattg | taaaatcgtc | tgttcctgca | tccattttag | cattagacgc | 122700 |
| aatttcagct | aaacctctac | gagtttcagt | agcagatctt | tcgttaagct | ttttaggagt | 122760 |
| aacgattacg | ttatccaagt | aagaagcagt | tgttgcctga | ttaacttcgc | cggaagttgc | 122820 |
| aattcttgct | ataccagtct | gagtttcagt | agaacgacgt | ccatttaaag | tttctggagt | 122880 |
| aattgctaat | tcttttctg | gatttgactc | cgcgttggct | tgagcttgcg | tagcaagagc | 122940 |
| aataacacct | aatcgtgctc | tggtagtatt | gtctttagca | tcaacacgtt | ctacagtagg | 123000 |
| gtcagattca | gttacaatcc | aatagctttt | tccggatgct | ttatcttcaa | tatatgcaag | 123060 |
| ctcaagaaca | ggaacatatg | acgtagttcc | attaaaggta | atcgagcttg | attgaaccca | 123120 |
| tgctgcatca | ggtggatact | ctgagcgttt | tggaaactgc | agtaaattca | aattactagc | 123180 |
| gatggtatca | ccatcagaag | ctttaattac | tactgtctgt | cctttacgca | tataattcat | 123240 |
| tgcgattttg | acagtatccc | caacagctac | gtcagtaggt | aaagtaatgt | taattgtttt | 123300 |
| aactgtacta | ttatctgcgc | caaatacaga | aatatgctca | ttaggcatta | aagtaacgtc | 123360 |
| agaagtaatt | attcttacac | gtgtacgtaa | atcattttca | aagatgcgcc | atattttgtc | 123420 |
| aatagcgtca | tacaccaaaa | atccactacc | tgaagtacgt | acttgaattt | ccgtttgtcc | 123480 |
| aggagtccca | attgagatag | ttgggtcaaa | cgtacgcaca | gtcatatggt | taatcggcga | 123540 |
| tgtaccatca | aggtcagtaa | aattaatgat | atcgtttgaa | ttagcgaaca | acggcagagt | 123600 |
| aataaaaatc | tctgagttgg | aagtataacg | acgaactacg | ttatcacctg | actgtacctg | 123660 |
| ggttggaaca | atcccgttcg | gaactaccat | tttagcagta | tcgccaaaat | cggttaaact | 123720 |
| agcacgccat | gcaccattac | taaacgtaag | cataatttgt | gaatacggac | gagtaagtct | 123780 |
| tacctcacgc | agacgcgatt | caccaaatac | gatagacgca | ccagtatctt | gtgctttaat | 123840 |

FIG. 2OOOO sequence.txt

| | | | | | | |
|---|---|---|---|---|---|---|
| taagattccg | ttatagccag | gacgacctcc | aatatcacga | actacaatgg | tatcgccttc | 123900 |
| gtctggtgct | aacggaagaa | gtagtgtagc | attaccggca | gcgttcgagt | caacgttgat | 123960 |
| gaactgacca | gattgaattt | caaactctcc | tttacggacg | gtataaatcc | agttcgggtc | 124020 |
| aacacgtaaa | gaagtccaat | tggcctgatt | aaattctccg | gctggttttg | gaatatcttt | 124080 |
| gtttgcaatc | caaatgcgtc | gtccataagt | cacagcaaaa | tcggtgagat | acccacgcgt | 124140 |
| cgggtcatat | ttttggatag | tattttcttg | aataacgtac | tcgacagaga | cgccgtcggt | 124200 |
| tttaacgttg | cggtcagcga | gtgccacatt | tataacttta | tttccgccgg | catccaaacc | 124260 |
| gttagttgca | cggaaatgtt | gtttcagtaa | atcgctcata | gagtctccta | tggggttatg | 124320 |
| cttcattata | gaagtattta | taatggctgt | actaactaat | tgaacgaggt | tcaaatgtct | 124380 |
| gatttaaatt | gcttattcgc | cgaagaagac | caagtaaaag | aaggtgtcat | tctgattgac | 124440 |
| ttgtcgcaaa | tcgcaatggc | gacaattctt | catacgtata | agaaggaga | taaactaacc | 124500 |
| actcctatgg | ttcgtcatct | tattctttct | actttaaaat | ttaatgcttt | taagtggaag | 124560 |
| aaagatgggt | acactaaaat | tgtcatttgt | gttgataacg | cagttaatgg | atattggcgc | 124620 |
| cgagatgtag | cgtactacta | taaaaagaac | cgtgctaaag | cccgcgaaga | atcaaattgg | 124680 |
| gattgggaag | gttactttga | aggtcttcgt | actgtaattg | atgaatttaa | gcagtatatg | 124740 |
| ccttattacg | tcattgatat | tgataaagca | gaagctgatg | atagtattgc | tgtactgacc | 124800 |
| aaaaagttca | gtctcgaagg | ccatccagtc | atgattgttt | cttcggatgg | tgactttact | 124860 |
| caattgcata | agtatcctaa | tgttaagcaa | tggtcaccaa | tgcagaagaa | attagtgaaa | 124920 |
| tctaaaaccg | gctctcctgc | tttagattgc | atggttaaaa | ttattaaggg | tgataagaaa | 124980 |
| gataacgtag | cttctattaa | agttcgttca | gattttggt | acacccatgt | tgatggcgag | 125040 |
| cgtactcctt | caacgaaaat | gacgtttgtt | gaagagtgtc | ttgatgctgg | cgaaaacatc | 125100 |
| aaagatttgc | ttaccgaaga | acagtataag | cgtttcttag | aaaaccgagt | gttaatcgat | 125160 |
| tttgattata | tccgtgaaga | cattgttgct | aacattttag | attgttataa | taattatcaa | 125220 |
| ctaccgggtc | gtggtaaaat | ttatagctac | tttgttaaat | ccggtctgtc | taaattaatg | 125280 |
| aaagaaataa | acaacttta | aggtgaatat | aatggctaag | aaagaaaaag | agcaagtagt | 125340 |
| atttgatgaa | gcagtacacg | gacaggctct | gcgagatatg | attaaggaag | cctcaggtaa | 125400 |
| taagctaaaa | gcagaaagct | atcttgagct | taacaaagac | attaaagacc | gcgccaagaa | 125460 |
| agaacttggc | gtagaaggca | aattatttaa | tcagctgctt | gccctgttcc | ataaaggtac | 125520 |
| acgcgatcgt | tttgaaactg | aaaaagatga | agtggtagaa | gcttatgact | ctattttcgc | 125580 |
| ttaaagatga | ggggacaca | tccccctccg | aatccattaa | ccagctgcta | gataagcaag | 125640 |
| ctaatggatt | tgctatcgaa | tctatggtaa | cagaacttgg | aatggggtat | ctcgaggcaa | 125700 |
| cgacacaatg | gctagaagaa | aattctattc | ctgagggaaa | cttcagtaga | tatattccac | 125760 |

FIG. 20PPP sequence.txt

```
ctgcaatcat agaaaaaatt atgtcagaag cattagaaga aaatatgctt cgaccatcat   125820
ttagtcaaac acataaaacg aatagtctgg attttttatt atgattcgtc tacgcatgcc   125880
ccaaaacaat aatagatacg ttaacggtaa gagcgtttat cttttatatt taatgctcaa   125940
acaacactt  gccggtcgtt atgatgttgt taagtataat tgggtcatgc gtgtctctga   126000
taaagcttat caaaagcgca gagacaaata cttctttgag aaacttgccg agaagtatac   126060
gctaaaggaa ttgactctga tattcatgag caatcttgta gctaatcaag atgcttggat   126120
tggtgatatc agtgacgctg atgcgttgat attctatcgt gaatacatcg gtaagttgaa   126180
gcaaatcaaa actacattct ctgaagatgt aaagaatatt tactactttg ctaagaaagt   126240
taatgtagat aagcttcatg atattttga  atataatgag aaagtcggaa catcttatgt   126300
gttcaaactt cttcagtcaa acgttatatc tttcgagaca ttcatcatgc ttgactcgtt   126360
tttagatata ataaatacac atgatactgc aacggataac ttagtttgga gtaattactc   126420
cactaaatta aaagcttata aaaacttt   aaacgttgac ggtgctgaag ctaagaaact   126480
ctttattagc ataatcaaat cttgtaaaga aattagtata taattaatct atcgtccagt   126540
tgcaaggacc catgttgcaa caacaactgt taaattaaaa aggtaatcat atgttcaagc   126600
gtaaaaatcc tgctcaactt caacaacaac tggctggtct gaaaggtggt tcttctttct   126660
ctaatgaaga taaaaacgaa tggaaactga agaccgataa tgctggtaat ggtcaagcag   126720
taattcgctt cctgcctggt aaagatgaaa actctctacc gtttgtaaaa ctgatcaatc   126780
acggtttcaa acatgctggt aaatggtaca tcgaaaattg tacttctacc cacggtgatt   126840
ttgattcttg cccggtttgt gctcatctga gcaaaaacga ttcttataac agcaacccag   126900
ctgaatataa actgctgaaa cgtaaaactt ctttctggtc taacatcctg gttattaaag   126960
acccggctaa cccagaaaac gaaggtaaag tatttaaatt ccgtttcggt cagaaaatta   127020
tggacaaaat caacgcgatg gttgaagtcg atgttgatat gggtgaaact ccggttgatg   127080
taacttgtgt gtatgaaggt gcaaacttcg tcatgaaagt taagaaagtc ggtggtttcc   127140
agaactatga tgaatgtaaa ttccttggtc agtccgagat tgcaaacatc aatgatgaag   127200
aaactcagaa attcctgacc gaaaatatgg ctgacctcag cgaaattgtg gctccatctc   127260
agtttaaatc gtttgaagtt aacgaagcta aatttaaaca gattatgggt acagcagctc   127320
ttggtggtgc cgcggcaaaa gcagcagctc aagccgataa aattggtgat gacctggatt   127380
cctttgacaa agacctgtct gattttgaat ccaaaccgac ctcttctcgt tccgcagacg   127440
atatcatggg cgatgctggt gacagtgttg gcgatgacga tctgaatgat attttgaacg   127500
acctctaata taaagggacc ttcgggtccc tttttcttta tccctccaaa aatattttca   127560
caaaattgtt tacaagccag ttgatgagtg atactatatc tacatcgaaa caaaacgagt   127620
```

FIG. 20QQQ sequence.txt

| | | | | | |
|---|---|---|---|---|---|
| agaggaaaac | atcatgggta | aattaaacat | tgatatcgtg | gcagaacctt | acatcaataa | 127680 |
| atcaggattt | tgtactgatt | taatttttga | agatggttca | cgttttatg | acactgacca | 127740 |
| tggtattgat | tttgatttag | ttatcaaaga | aggccctggt | ggtggttggc | caaatattga | 127800 |
| cctccgcggt | tctaaagaag | cagttcgtgc | ttggttagaa | gcaaacgagt | gggaagatat | 127860 |
| tgatttgatg | atggaagact | ggaaagagta | attacctttg | gggacttcgg | tccccacttt | 127920 |
| gaggaaatga | taatggcaca | ggttactgta | gaaatatatg | attatgaaca | cttcattgaa | 127980 |
| accattgaaa | aatacggttt | gattgaagtt | agtaacaagt | ctgccccatg | gggaggaaac | 128040 |
| gaaatcactg | tagaaggtga | tactcctacc | ctatggttat | ggcttgaaca | agaatatttt | 128100 |
| cctggcatgg | atgatgaatg | ccgtgaagat | acattaacga | cttttagcgg | gtaaattatg | 128160 |
| aaactgaaca | cagaatatcg | cattatccca | agtcttgctg | ccgagtggga | cctttcatct | 128220 |
| agcggaaatc | gccggatgcg | cttgatgatt | gaagaacatg | gtggttcgtt | cttcctact | 128280 |
| aaaatgctcg | acgaagataa | tagtttcatc | acagaagtaa | aatttaaaga | tggaacaact | 128340 |
| gctgacgctg | aaggatttgg | agatgcatac | tttgaaatat | ctgattatga | attcaaatac | 128400 |
| ttcgaaccag | tatatgaaat | tggtagtgca | atccaacctg | gtcctactcg | cttggacttg | 128460 |
| atcgttaccc | cagaaaatgc | agaagaaatg | attgacttga | tcaaaaagt | tttcaaaaag | 128520 |
| tagtttacac | ggagctatgc | ttgtgatagt | atagctccat | aatctactgg | agaataaaaa | 128580 |
| tgaaacttca | acgtcaaagc | attaaacttg | gttctgaata | tcgtggtaaa | tggaatttct | 128640 |
| gcatttgcga | taaaaaccca | gaagaattag | agcgtgttga | agaagtactg | tgccaaatgg | 128700 |
| aagctccatt | cactatgggt | ggtgaaactg | tctattggaa | tgattactgt | gataactgcc | 128760 |
| catgctatga | agatgggtat | ggctcaggct | tctggattcc | agttgaagat | gttgaagaat | 128820 |
| tcaaaaaagc | atttaaactt | gctaaggcca | agaaatgatt | gaggctgaat | tagtagtttt | 128880 |
| gttaatttct | gttactgtcg | cttttattag | cggcgttata | ttaggattat | ttttatatgt | 128940 |
| ctaaatttag | tgtaacggga | tatcctcgcg | ttaatattcg | ctgccagttt | gatgaaattc | 129000 |
| ctggagtaac | tcatattgag | ctcgtatttg | accctcattc | gcgatgcaat | caggtttcag | 129060 |
| gtaaaattga | ttcagcgtat | ggcgaatttt | taattaatga | ccaagttgtg | gtttcagcta | 129120 |
| tttctggtga | acaagcaggt | tcgttgtata | ttctgaaaag | ggaagtattt | gaggaaattt | 129180 |
| cagaagccat | aaaagaaggg | tttaaaactc | ttcagagcat | gattaaagct | agtgagtaca | 129240 |
| agtcatgtgg | attttaactg | actgggattg | taagtactgt | ggcggtagct | tatggcaatt | 129300 |
| aggtggccgg | tgttttaagt | gtggaatgag | gcaaggttaa | tggaaaattt | cgcagtagat | 129360 |
| gattacgatg | atttgatttg | gtgggacggc | cgtgaatggg | taactatctg | cgcaatgtcc | 129420 |
| aatatcgata | gcgctatcaa | acgtctccaa | gagcttcaac | agaagtggga | agacggtaat | 129480 |
| gttgaacggg | ttgaatttta | ttgaggttta | aatgattcaa | atagtttatg | cctttgctcc | 129540 |

FIG. 20RRR sequence.txt

| | | | | | |
|---|---|---|---|---|---|
| tacaaaaact | gtagacggca | aaaatgaaaa | tgctttcggt | ttaggcgatg | gtcttccatg | 129600 |
| gaaacatatt | tcccaggaca | tgaaaaactt | tgctaatcgt | actcgagata | ctatcttgat | 129660 |
| ttgcggagca | aagacttta | tgagttttcc | tgaacctctt | cctgggcgta | agacaatcgt | 129720 |
| tgtccaagac | atgagtcgtg | cgttggcaac | tgctaaaaat | ggcttctttg | cagatgctta | 129780 |
| tgtaagtgaa | ttagaattta | tcggtttctt | gggtggtgac | attatggccg | ctcatacttc | 129840 |
| ttacaacagt | actatcactt | taatagaga | ccttaattat | tctatcatag | gtggtgccgg | 129900 |
| aatcatccag | aaggcatatc | catacgcgga | tagggttatc | caaacaatca | ttagaaaaag | 129960 |
| tcatagagtg | aattctgatg | tcactctacc | tgctgaattt | gtaacagctc | ctacttggcc | 130020 |
| agaatcagga | ttcattacta | aagaaaatca | ctggtatcat | attgatgaag | tgactaacat | 130080 |
| ttcagaggtg | gtctatgagc | gcaaactatg | atatcactca | gctatcagaa | gacaaagtcc | 130140 |
| aaaagaggtg | gaaaagattt | ccatttaagc | atggtattca | tcttctagtt | ttcagttata | 130200 |
| atggtcttag | cacttataac | ggttcaacta | cagtatataa | ccgaaatgga | aatataccta | 130260 |
| ttgaaattga | acgtgattat | aagaagatgt | tcatcggaat | gtcacacggt | aatgtgacgg | 130320 |
| ttaatgatga | tgtagtgtct | attattgggc | gatttgaaaa | gcgtggtgat | cagcttttct | 130380 |
| ttacacctct | tcaggaaaaa | tttaatgcgt | gaataccaag | aattaattaa | agacatttt | 130440 |
| gaaaacggct | atgagacgga | tgaccgtact | ggtaccggta | ctattgcaaa | gtttggtact | 130500 |
| caacaccggt | ttgatttaca | agaaggattt | ccggcagtaa | ctaccaagcg | tcttgcgtgg | 130560 |
| aaagcgtgca | ttgcggagct | gatttggttc | atgtgtgggt | ctactaatgt | gcatgaatta | 130620 |
| cgtcttattc | agcatgactc | attactagaa | ggtaaaactg | tctgggacga | caactatgaa | 130680 |
| aaccaggcaa | aagacatggg | gtattccggt | ggtgagctag | gtcctgtgta | tggtaagcaa | 130740 |
| tggcgtgatt | tcatgggtgt | tgaccaactg | aaattgatca | ttgatcgtat | caagcaactt | 130800 |
| ccatatgacc | gtcgtcagat | tgtgactgct | tggaacccgg | ttgatttgga | taagatggca | 130860 |
| ttgccaccat | gtcatttgct | gtatcaattt | aacgttcgtc | aggggcatct | tgacctccaa | 130920 |
| tggtatcagc | gttctgtaga | tgtattcctt | ggcctcccct | tcaatattgc | gtcatatgca | 130980 |
| gcattggttc | atatcattgc | taaaatgaca | aatcttaaac | ctgggcattt | ggtattcact | 131040 |
| ggtggtaaca | ctcatatta | cctgaaccat | attgagcaat | gtaaagaaat | cttgcgtcga | 131100 |
| gagccaaaag | agttgtgtga | acttgaaatt | gcattcccag | atacgtatga | aacttggcag | 131160 |
| actagttctc | agattcgttg | gttagaacaa | tttgcacgtc | ctcatcattt | tgaactagtt | 131220 |
| gggtataaat | cccatccaac | aattaagggg | aaaatggcta | tatgaatatt | cgatttgttc | 131280 |
| gtaaaggaca | tcagtctaaa | accgtattag | gagaaatgca | ggacgcattc | tctagtgatt | 131340 |
| tgcctgaggt | taatgacacg | atagtttttg | acggaaccga | acaacgtgtt | ttatctgtca | 131400 |

FIG. 20SSS sequence.txt

```
ttaaatcata tgaatggtct attggcaaaa cacaattaat ctgctggttt gaagttgata   131460
taacatgaag atatgtcggg tggttaataa ataccattcc gacttcgatg taaatatcca   131520
acgtggaaca atgtggggaa attacgtcgg taaagattgc gataatcgtc ctgatgctat   131580
tgcggcattt aaggacgatt ttattgctaa gattcggaac ggagaaataa agcgagagca   131640
cttagaaact ttaagaggaa tgagattagg atgcacctgc aaaccgcttc cttgccatgg   131700
tgatataata gctcttgtag tgaataaact ttttaaagat acatttgaat tagaggactt   131760
atgcaagtaa ttaagagctc aggtgttagt caagaatttg acatgcagaa aatcattaaa   131820
gtcctcgaat gggcgtgcga aggaactaaa gtagacccat acgagttgta tgaaattatt   131880
aaatctcatc tgcgtgatgg catgagcact gcagatatcc agaagactat cgttaaggta   131940
gcggcgaata gcatttctat tgatgagcca gattatcaat atgtagcatc caatgcagca   132000
atgtttgaaa tccgtaaacg tgtttatgga cagtttgaac cgcctgcatt tattgaccac   132060
atttcacgtt gtgttaacgc aaataagtac gataagaaaa ttctaagtaa gtggtctgca   132120
gaagaaatta ctttgcttga ttcttatatt aagcatgagc gtgatttcac tatgacttat   132180
gctggaacaa tgcagcttat cgagaagtat ctcgtaaaag accgtcatac tggtgaattg   132240
tatgaaactc cacagtttgc ctttatgctg atcggtatgt gcttgcacca agatgatggc   132300
gaaaatcgtt tagcaaacgt tattcgtttc tatgatgcag tttctactaa aaagatttca   132360
ttgccaacac caattatgtc tggtgttcgt actccgacac gccagttcag ttcatgcgtg   132420
gttattgaag gtggtgacag tcttaattca attaacgaag ctgctgcgtc aattacgaaa   132480
tacatcagta agcgtgcagg tattggtatt aatgcaggca tgattcgcgc agagggttca   132540
aaaattggat ttggtgaagt caaacatact ggagttattc ctttctggaa acacttccag   132600
acagcagtta atcctgctc ccaaggtgga gtccgtggtg cgcggcgac actgtactat   132660
ccaatctggc acttggaagt tgaaaacctc ctcgtactta agaacaacaa aggtgtagat   132720
gaaaaccgta ttcgtcattt agattatggt gttcagatta ataacctaat gattgaacgc   132780
ttgattaaga atgattacat cactctgttt agtcccgatg tatgtcttgg cgcgctgtac   132840
acagaatact tccgtgatgc acaagcgttc cgtactttat acgaagagct ggaaaagaac   132900
ccagatataa gaaagaaacg tattaaagcc cgtgaactgt ttgagttgtt ccttactgag   132960
cgtgctggta ctgctcgaat ttacccgtac atggtagata acgttggtga atatggtcct   133020
tttattcgtg atgtggctac ggttaagcaa tcaaacctct gcctcgaaat tgcgttacca   133080
acttcggatg ttggccaaga agatggcgaa atcgcgctgt gtacactcgc agcattcgtg   133140
ctcgacaact tcaactggca agaccaagaa gaagttaacg aaatcgcaga agtaatggta   133200
agagctttgg ataaccttt ggattaccaa gattatccag tagacaaagc gttaaaagca   133260
aaagaccgca gagcattagg tgttggcatt actaactatg cagcttggtt agcaagtaac   133320
```

FIG. 20TTT sequence.txt

| | | | | | | |
|---|---|---|---|---|---|---|
| tttgcttcat | acgcagatgc | taatgatatt | actcacgaaa | tgatggaacg | tattcaatat | 133380 |
| gcactcatca | aagcctcagt | taaacttgct | agcgaaaaag | gtccgtgcgc | gctttacaaa | 133440 |
| gaaacacgat | atggacgtgg | cgaactgcct | attgactggt | acaataaacg | aattgaccaa | 133500 |
| ctcgcagctc | caaactatgt | ctgtgactgg | gaactcctgc | gagaagacct | caagcgatac | 133560 |
| ggtatccgaa | attcaacgtt | atctgcgctt | atgccatgcg | aatcgtctag | tcaggtatca | 133620 |
| aactctacca | acggtattga | accaccacgt | ggaccagtgt | cagttaaaga | atcaaaagaa | 133680 |
| ggaagcttca | accaagtcgt | tccaaatgtt | gaacacaatg | cttcccttta | tgattatgcc | 133740 |
| tggcagctcg | cgaaacaggg | taataagcct | tatctgaacc | aggttctgat | tatgcagaaa | 133800 |
| tttgtagacc | aaagcatctc | tgctaatact | tattcgacc | cggcgaattt | ccctaaaggt | 133860 |
| aaagttgaaa | tgtcggtaat | gatggacgac | ttgctttatt | tctggtactt | tggcggtaag | 133920 |
| actctttact | atcataacac | ccgtgatggt | tccggtaacg | atgatatgat | tcaagactct | 133980 |
| gctgactgcg | cggcctgtaa | attataatga | attatcaaaa | cgtatataat | agtttaatct | 134040 |
| cccgggctag | agcccgggaa | tctttattag | gatataaaga | gactcatcat | ataattccta | 134100 |
| gatgcatagg | aggttctgat | gataaagaaa | acttagttga | attaacaggt | agagaacatt | 134160 |
| ttatagcgca | ctggctttta | tgtaaaatat | atgaagcgcc | gggattaaag | aaagcctttg | 134220 |
| gtttaatgtg | tttgaccggt | aaaaatcgct | catataaagt | ttcctctcaa | ttgtatgaat | 134280 |
| taggcaaacg | gcgtttatct | gaagctgcta | caggacgtaa | agcttctata | gaaaccagag | 134340 |
| aaaagataag | caaatctctt | aaaggaaggg | aatttaccga | agagcattta | gccaacatga | 134400 |
| gaaagcctaa | aactgaagaa | accaaaaaga | atatagctgc | tgctaaagtg | ggcgtgctta | 134460 |
| atcctatgta | tggtaaaatt | tctccaacaa | gagatgttcc | ccatactaaa | gaaacccgtg | 134520 |
| atgtgatttc | tttgagaact | aagcaaggta | cagagtatcc | accttgtcca | cattgcggca | 134580 |
| agaaagttaa | taaaggtaat | gctcttcgtt | ggcattatga | taaatgtaaa | tttaaggacc | 134640 |
| ctaaatgagt | acagttttta | ataaagaacc | cgtagacatt | atgaacgaac | cgatgttctt | 134700 |
| aggctctggt | ctaggaatcg | ctcgttatga | tgtccaacgg | cacaaagtat | ttgaagaact | 134760 |
| tattgagaag | tctttatcat | ttttctggcg | tcctgaagaa | gttaacgtta | tgatggaccg | 134820 |
| tggtcagttt | gaaaaactcc | cagaacacca | gcgtaatatc | ttcactgata | acttgaagta | 134880 |
| ccaatctctt | cttgattcaa | ttcaaggacg | agctccagca | gcagttttat | ctgcacttat | 134940 |
| ttctgaccca | agcctagata | cttggaacca | gacttggacg | ttcagtgaaa | ctattcacag | 135000 |
| ccgttcgtac | acgcatatca | tgcgtaacct | ttatgtagac | ccagctaaaa | tctttgatga | 135060 |
| aatcgttctt | gacgaagcaa | tcatgaaacg | cgctgagtca | attggtgttt | actatgatga | 135120 |
| tgttatagcg | aagactcgcg | catgggaaaa | tgccaaaaat | cgctgcttta | atcaagataa | 135180 |

FIG. 20UUU sequence.txt

| | | | | | | |
|---|---|---|---|---|---|---|
| tatcgaaatt | aaagaagcta | aacgtgattt | aatgaaatct | ctttatcttt | gcttacatgt | 135240 |
| tattaacgca | ttagaagcta | ttcgtttcta | tgttagtttt | gcatgtacct | tcaacttcca | 135300 |
| taaaaatatg | gaaatcatgg | aaggtaatgc | taaaatcatg | aagttcattg | ctcgcgatga | 135360 |
| acaacttcat | ctgaagggca | cacagtacat | tctgcgtcaa | cttcaaactg | gaactgatgg | 135420 |
| cgaagaatgg | gttgagattg | ctaaagagtg | tgaacaagaa | gcaattgaaa | tcttcatgga | 135480 |
| agttaaccgc | caagaaaaag | attgggctat | tcatcttttc | cgcaatggtg | gtcttccggg | 135540 |
| tctgaatgtt | aaaattcttc | atgacttcat | tgactatctg | actgtatctc | gtatgcgtag | 135600 |
| ttgtggtctt | ccttgtccga | ttactgatgc | accaactcgt | catcctattc | cttggattcg | 135660 |
| cgaatatctt | aactctgatg | cagtccaatc | tgctcctcag | gaagttgaga | taagttctta | 135720 |
| tctggtagct | cagattgaca | atgatgtcac | tgatgatgtt | ctaattggat | ttaaaaggta | 135780 |
| cttataagga | aagggcttc | ggcccctctt | tattatgaat | gatattgcta | acgagttttc | 135840 |
| ttttataaaa | tatgttcaac | ttgagttaga | accagatttc | agtattaaac | ctgttttggt | 135900 |
| agcaaacaag | ttgaatgtag | tttatgccat | cgcagttgat | gatgaactag | tttacattgg | 135960 |
| taagactaaa | aatcttcgta | aacgtataaa | ttattataga | actgctatta | atcggaaaga | 136020 |
| ccaaacctct | gattcggcta | aatctgccaa | gattttgaa | gcactaatgg | ctggcaaaaa | 136080 |
| agtagagttc | tatgctcgtc | agtgttttaa | tcttttgatt | aataatgaac | ttggcgagat | 136140 |
| gtcaatatcc | actatggact | tggaagaacc | gatgtttatt | aaaaagttca | atcctccatg | 136200 |
| gaacacacaa | cataaggtaa | agaaatgtta | gagctatata | aaaatttaat | gaatctatgt | 136260 |
| gaaagctcag | aagttgcaaa | attcttttat | aaagatttta | ccggtcctat | ggatggtaag | 136320 |
| ttcagagtgt | tttcatacca | ctatgcaagc | tacagtgagt | ggttaaaacc | tgatgctctt | 136380 |
| gagtgccgcg | gtatcatgtt | tgagatggat | ggcgataccc | caattcgaat | tgcttcgcgt | 136440 |
| ccgatggaaa | aattcttcaa | tttgaatgaa | aacccactaa | cgatgggaat | tgatattagt | 136500 |
| gatgtagaat | acattatgga | taaggctgat | ggttctctag | tatcatctta | tgtcgatgat | 136560 |
| gggtatctat | accttaagtc | aaaaacatct | ctctacagtg | accaggcaag | acaagcttca | 136620 |
| gctttgctta | acagtgaaga | atattcttcg | cttcatcagg | ttattcttga | gctagcgcta | 136680 |
| gatggttata | cggtaaacat | ggaatttgtt | tcacctaata | atcgcgttgt | tttagcatat | 136740 |
| caggagccac | agctgtttgt | gttaaacgtc | cgtaataaca | caactggcga | gtatattaaa | 136800 |
| tatgatgatt | tgtacgctaa | tgctaagatt | cgtccttatt | taattaatgc | ttacggaatt | 136860 |
| tctgatccca | caacttgggt | tgaaggtgtt | cgtgaacttg | aaggcgtaga | agggtacatt | 136920 |
| gcagttctaa | acactgggca | gagatttaag | gttaaaaccg | aatggtattc | tgctcttcat | 136980 |
| cacactaaag | actcaataac | gtcaaatgaa | agactgtttg | cgtctgtcgt | atctgcaaat | 137040 |
| tccgacgatt | tgcgttctct | ttttgctgga | gatgaataca | caattaagaa | aatttctgcg | 137100 |

FIG. 20VVV sequence.txt

| | | | | | | |
|---|---|---|---|---|---|---|
| tttgagcaag | cttatctaga | ttacctcgga | aagtcacttg | agctgtgtca | gtcattctat | 137160 |
| gatgaataca | gaggtcgtgc | tcgtaaagat | tatgctattg | ctgctcagaa | agcaacggtt | 137220 |
| aatcagcgcc | atcttttgg | tgttatcatg | aacatgtacg | aaggaactgt | agatgtagat | 137280 |
| aaactgctta | aagacctcga | aagggtgttc | ttgaagtact | gggcaggata | tgttccaaaa | 137340 |
| gagtacgaaa | aggaaattga | aatttccgaa | gaataattgt | ttacatcctc | atcagggtgt | 137400 |
| gataccatag | acttacacca | actgatgagg | ataatgaaat | ggatatgcaa | gcaattactt | 137460 |
| tagatatggt | tgttaacaaa | tacggtactc | attctgacgg | gattttgtg | tggaatggta | 137520 |
| ccaagaaagt | gggattcgtc | actgatctac | gtacccatat | ggctcgcaag | gaagctgctc | 137580 |
| gtaagaagca | aaaagagtac | actaatcgtg | tgaacgagca | gcgtgccgaa | gcccttcctg | 137640 |
| aagccgtaga | tgaaatgatt | gatttcctag | ataatcatct | cgcgaagtat | ggtgcagagg | 137700 |
| tgttcaagaa | catcacccag | ccaaacgttc | atgctaacgg | gtgcaaatgc | tatgtaatcg | 137760 |
| ttgacccgat | ttatggtaag | catcgtcttg | gtattatgca | tcgtgagctg | aattattctg | 137820 |
| agatggcaga | atatgtagaa | gcgtgcttca | agtgttctcc | ttcggaaagt | tctgatcgtc | 137880 |
| acatcctcat | ttcgggatta | tcccgtgatg | atatcgtaga | ggttatcctt | aaactatgct | 137940 |
| caaaataaac | acaacttggt | tgttgattgg | agtgttagca | ttatccgcag | gaggattgaa | 138000 |
| atatctttcg | tggcgggtag | aaaatcttaa | agctgacctc | aaagtcgtcc | aagatgaatc | 138060 |
| tgatcgacaa | gcaaaagaaa | tagaaaatat | tggtgtttct | ataaaaaatc | tgcagacaac | 138120 |
| atataaaggc | tatcaggaaa | accgagcagc | tcgtgatact | tctaacgcta | agatgaataa | 138180 |
| agattctaag | cgtggaaacg | tagttgcagc | caaacctgga | ttagttgaaa | aacagattaa | 138240 |
| tgcaagcttc | aataagtttg | cagaagatat | ccaggaggct | accagatgaa | acgaagtcta | 138300 |
| ttagccatgt | gtattatcag | cttattagct | ggatgctctt | ctagtgcccc | agatgttccg | 138360 |
| gttttacatc | ctgagtggcc | agatccaatt | caaaaatggg | aaggacattg | ggaagtaaaa | 138420 |
| gtaattgacg | gtaaagcctg | ggttggtatg | ccgtttgaag | agtcgcaaga | atatcgtatc | 138480 |
| tggatgaatg | acattttacg | atatactaaa | gatgctaatg | gaatgatatg | ttattatcgt | 138540 |
| tctgaactta | agaacctcg | ttgcgttaag | taaactaaac | aagaggaaaa | tattatggaa | 138600 |
| ccgtcacatt | tttattctta | ctttgtaaaa | gacgcatcgc | atctttatc | gattaaaaat | 138660 |
| acacagctca | gaaatatgct | agctgttggg | tcgtgccagt | taactcctct | tgctaagaaa | 138720 |
| gctactgtta | taccggaaaa | tatttctaat | ggatatgttt | atacagtccg | tgttagtgtg | 138780 |
| cctggcgctt | taaagaaag | attgtttgag | cttaatgacc | aaacacgaat | ttcgtttgat | 138840 |
| gtgtggttta | aactattcat | ggtagaattc | atgtatcctg | atttcttgaa | gtttgttcag | 138900 |
| cgtaaagagg | cattgaagga | agcaatttct | gaattggaag | atgcctcaat | tgaatttggt | 138960 |

FIG. 20WWWW sequence.txt

```
aaggcactcc aatttgtaga aagtggcggt gtagagcaag atgctgttaa cgggtttttg    139020
aagaaatatg gaaagcgccg ctcattggcg catcgtaatc tttctaaaat ggtgatgtag    139080
tgaatcaaga acagtatgaa acacttaaag gattaattgc tgaaaatgaa ttggcgtgca    139140
tcgtgtttgg acgcgcagct gaaaattatg acaaaaatga tatactgtca atgaataagc    139200
cattgcgagc aattaaagaa aaatatcgtg ctaattgggg tgaaaagtct aaggctcttc    139260
atgattttat tgacactctt aaggacgtat aatgaaaaaa ttggttttga cacaggggc    139320
tccaggctct ggtaaaacaa cctgggctaa cgaatacgta gcagctaatc caggttggta    139380
tgttttgtct cgtgatgatt tgcgtgaagg catctttggc cttgataagc gtaatgatta    139440
caaatattct aagcttcgtg agaagtccgt atctgtatgc cagttttcta tggcgaagac    139500
tctactcgag atggaaacca ctaaaggtgt catcattgct gatactaacc ttaatccaac    139560
gactatcaag aagtggcaag agttggcata tgaaattgat ggtgtcaagt gggaaattaa    139620
acgctttgac gttccttgga ctgaactagt taagcgtaac ctctatcgtg gcgcgaatgc    139680
agttcctatt gaagtgctcc gtagcttcta ctctaagatg catccgtatg atttgtacat    139740
tccagatgaa tcattgccaa aagcagttat cttgaccttt gatggcacgt tagcagataa    139800
caatcatcgt tctccttatg acttggccaa atgtggtaaa gaccatccaa aggaaatggt    139860
aattgaattt cttaaaatgc ttcgtaacaa aggatataaa attcttactg tttctggtag    139920
agagtctgga actaaagaag accctacagt ttatcaacgt attacgaaga aatggctgtt    139980
ggaccatgtt ggcgaaacag gcgaacactt ccaacgtaag caaggcgatt cacgcaaaga    140040
cgatgtggta aaagaagaaa tcttctggga ccgaattgct gatcgttata atgtaaaact    140100
tgcagtagat gacagggcgc aggtagttga atgtggcgt cgtatcggtg ttgaatgctg    140160
gcaagtagcc cacggtgatt tttagaggaa agtataatgt ttccaaagta ttctgaagta    140220
gtaaaagtat catttacgca agttgttgct aatcatttaa cagatgagtt tactccggct    140280
gaagtagcca aaatgcatgc agagttttta tctgccatga atgcacttat tccaaatggc    140340
gaagttgtta aattttcaat tgaccgtcta ggcggttcgt ctgaaattaa aatttcttgt    140400
ggcgaaggtg aacacgactg gtttatcgtt ggaattattg ctaattttga aacccaacag    140460
gttgagactt atgttgtctg acgctaaatt ttcacatgat gaatttattt cgaaggttaa    140520
aatcttcgca caggaagtag caaaccgggt tcctggaagt aaagtgactc tccgacgaga    140580
gtcatccttt aactatgttg atgcttatat cattacagtt aataatggaa agagcaatca    140640
acatactcaa ttggctttaa ctggaacagg ccaagttgaa atgactaaca ttttaggaca    140700
tatctaatga cttacgtga agcggtagaa gctcttttaa ttgaacatgc tcgtggcatt    140760
aaagcagaaa tcagcccaaa tggtattcgg ctgatcagtg ctgttattgg ttctgaccaa    140820
ggtgtttggt caattccacg cgaagaatat gatgctattt tgtacagtaa cgttaatgtc    140880
```

FIG. 20XXX

```
sequence.txt
aaggaaggac aacctatgta tggttatgtc ttctctgact cgcttgaacg aggaaaccat    140940
ccgtttccag atggcacagg cattcgtact tctcgagtag agagttttgc ttctcctacc    141000
gacgagttaa aattggttaa aacaaataac acaacttatc tggtgattta aatgaaagcg    141060
tcgacggtac tacaaattgc gtatctcgta tctcaagagt caaaatgctg ctcgtggaaa    141120
gtcggcgcag taattgaaaa gaacggacga attatttcta ctggctataa cggttcacct    141180
tctggtggtg tgaactgttg tgaccatgca gcagaacaag gttggattgg tgaaattcct    141240
tacaaatcta cgggattgcg tcaagacgga ttccaagtca aaaaagtcgg attgctcaaa    141300
gaacatcgag cagcccactc tgcatggtct aaagtcaatg aaatccatgc tgagcttaat    141360
gctattcttt ttgctgcccg gaacggcagt agtattgatg gagcaacaat gtatgtcaca    141420
ctgtctccat gtccagattg tgcaaaagcc atcgctcagt ctggtattaa aaaattagta    141480
tactgtgaaa catacgacaa gaacgaacct ggctgggacg atattcttcg ttctgctgga    141540
atcgaggtgt tcaatgttcc aaaacgtaat ttggataagt tgaattggta taacattaaa    141600
gaattctgtg gaattgaata atgaaactta gaattgttga aattaataaa cttaacctaa    141660
gtggtgatgt tgttatatca tactcagtag aacgccggta ttggtttaaa tggaaaccat    141720
tagcaacatt taaatttgaa gatcaagcag ttcgattatt aaaagaatta tccaagcgca    141780
aatctgtaat tatcaaaact attaaagaga catcaaaatg aaactgacta ctgaacaaaa    141840
catccatatt cgtgaaactc tgaaggctgt gctgagcatg ggcgaatccc agattgtgtt    141900
tgaaaaagct gatggcacta ttcgtactct gcgctgtact cgtgataaag acattattcc    141960
atctgatttg gtagaaagca ctactaaatc tgctcgagca gaaagcacta cttcacttcc    142020
agtatatgat accgagaaag aaggttggcg ctcatttgcc tttgataaac tgatctcggt    142080
aaatggtatg aaagttgagc atctgctgca gatgatcggt aagtaatttg cttttaaactg    142140
accatgttaa tataactaca tggtcaaaca ataaaggtaa cacatggaac ttccaattaa    142200
agctctaggc gagtatgtaa ttctcgtatc tgaacctgca cagcaaggtg atgaaattgt    142260
ttctccttct ggtattattc ttggtaaaga agaacaagga caactgccgg atatgtgtga    142320
aatctattct atcggtgatg atgtaccgaa aggatttgtc gaggtcggtg atttgactcc    142380
gttgcctgtt ggtaatatca gaaacgtacc tcatccgtta gtagcagcag gtgtgaagaa    142440
acccaaagaa attcggcaga agtttgtgac ttgtcattat aagtcccttg catgcgtata    142500
taaataataa tatgaattgg gcgtcggaca attagttacc cgagcaattc tacgtggtgg    142560
atgcccgagc taaacctcgg ttaccgtcca ccaaatttta acctcatttg aggaacgatt    142620
caatgaacaa acaacttact aaagctctgg aactccaacg taatgcatgg aattccggtc    142680
acgaaaacta cggtgcttca atcgatatct atgcagaagc actggaagtt ctgaaagggt    142740
```

FIG. 20YYY sequence.txt

| | | | | | | |
|---|---|---|---|---|---|---|
| ttaaacacct | gaacccagca | caagctgaat | ttcgtgatac | tttagaagcg | atggacgaac | 142800 |
| tgaagtatgc | taagcatctt | ggttctgctg | ctcgcaaagc | tgttcgccac | tttgtggtaa | 142860 |
| cgctgaagta | atttgtacgc | ccaccatgtg | tacgcatggg | taacgtatga | tgtggacgtt | 142920 |
| gttggttatc | cccacgtaaa | acatccgaaa | ccaacggtga | tttgctacca | aagtgcagct | 142980 |
| agaaataaac | ggcaagtgca | tgctaccccg | aggcgatggc | caatcgggag | tacgcctcaa | 143040 |
| ggcctataca | tccatcggtg | tatatcttat | ccccgataaa | tcggacccgg | aacctttaag | 143100 |
| ctaacggtgt | gcaacagata | agagtttaaa | cgtacccctt | gagggctttc | gggagctaca | 143160 |
| accgaaagaa | ctgtcgaaag | aagttgaacc | tcggaagaac | gtgctcccat | gtatttctcc | 143220 |
| aaaatggaag | atgataaaat | ggctaaacaa | gctaaagcaa | aaactgcagt | aaaagaagtt | 143280 |
| gttggtacct | ctaaacgcgc | tggctacaag | cgtgggtcga | caagcgtat | caatcagacg | 143340 |
| gttgagaaaa | tcatgcgtcg | agctcgtgcg | gttcttcgcg | atgatgcttc | tcgttttggt | 143400 |
| aagccgaaag | cataagttca | gggactcctt | cgggagtccc | ttttttattt | tccacagaat | 143460 |
| gaaaaaagtt | gtttacttct | aggctcaaca | aggttactat | agacctgtac | cacccaaacg | 143520 |
| gacaacggag | aataaaatga | acttcactaa | cttcaaccgc | aaatacgtac | agaacaatgc | 143580 |
| ctgggacgtc | tctactactt | tgctgtggga | acacaacaac | ggcacagtgg | ctcaaatcga | 143640 |
| tatgtactgg | gaagataact | acgtattttt | cagctttgaa | aatggtccta | ctctggatat | 143700 |
| tcagttcaac | ggttctgaaa | tcaaagttgg | attccatgat | gaagttcgta | acgtgattt | 143760 |
| atcttcacat | ccgtcttgga | acacaaatcg | tcagctgctt | gttaaatttt | atctgcgcca | 143820 |
| catcctcggt | cgtaaaacaa | ccgaagaaca | acgtgaagca | atctgggata | tcgtttcaaa | 143880 |
| cgaaataaag | ttttaactaa | ctcggggctt | cggccccact | attgaggaaa | tgataatgga | 143940 |
| aaaaggtaaa | ttctataagc | ttaaaaagac | tccaagcttg | tctccaggcg | ctcttatcaa | 144000 |
| gggtgttttt | gagcaaatcg | gtaataatcc | aattaaaatt | accagaacct | ttaaatatgc | 144060 |
| ggaaaacact | ggattagttg | aatttgaaat | cattaagccc | gatggggaat | acaaacgcgt | 144120 |
| tagtatagat | gaagttcgct | tttctcgcat | gtggtgtatt | attactaatc | aagagtttca | 144180 |
| gcattatttt | gaagaaacca | cccacaaaga | acctgaaccg | aagaccgatg | acggaagcaa | 144240 |
| tgattggggt | gtttggacct | caaataaagg | aaatgatacc | tacaaaggtg | gattaacaaa | 144300 |
| ggaagaagct | gttaatcttg | caaagtaca | acgcctgaat | gcaactaaag | acacaaaagt | 144360 |
| tgtaatcatg | caaccttttg | ctgtccctgt | ggttcacgtt | aatattcgcc | cgttttaaga | 144420 |
| ggaaattgaa | atgattgtat | cagctttcta | tgattcacga | aagaaaaaag | ttgaaaccat | 144480 |
| tatcagcgat | acccgcgatg | gtacacctgc | taataaaaat | ggtgtgaaag | catacattga | 144540 |
| taagtattgc | cctcctgaat | ttcgtatgat | tgacggtgta | gattctctga | gcattaacat | 144600 |
| tataaatgct | aaaattgaat | ttattaatga | aactgtgcca | attgggtatt | ctgacggtga | 144660 |

FIG. 20ZZZ sequence.txt

```
tggctcaaat gctaaaatgc cgaaagaaaa attcataact aaattttgag gaaatcaaca   144720
tgattgtatc cgtgcctaaa tctaaagatg gtatttttc ttgcggcttg aaaaaccacc    144780
caatggttga tatcatgtca gctaacgtta aacaacacac cgttgagtat gaaattgatg   144840
ctccggattt ctttgaattg cctgaatggg cagtgaggct tgatgcatga aatatcatat   144900
cttcaataca gtaagattag caaatggaat tcctggagtt gtatgtgata cggctccagc   144960
cattaaagcc tactcggttg aaccttggta tgaagttaat tgggttgatg gcaatcgttc   145020
aatccatgca gaatccgagc tttatccaat tactcaatta agggctgcta acgacgatgt   145080
ctattaatcc tcacttcggt catatggttg cccgacgtat caccagggaa atgctaaaga   145140
ctgctgagta ttataatata gaattaattg atatagaacc ctcggacgct ccagggttaa   145200
tctggttcaa tttcaccggt gccgcaaata gcgtcgccaa atttaaacaa gcattgagga   145260
atttccccga atgtcaaaac cagtaatcgc aaccgatgtt gatggaatca tcgttaagtg   145320
gcaaagtggt ctgccttact ttgcccaaaa atataacctt ccggtagagc atatccttga   145380
tatgatgact actgaaaaat tcattaaacc cgctgagctg tttgattgtg aagaagacct   145440
ggctgttaag cttcttctga aatataacaa cagtgatttt attcgttatc tggcgccgta   145500
tgcggatgct ttagctacag ttaataagct caaagaaaaa tacgattttg tcgctatcac   145560
ggctcttggt aattcagtag atgctaacct taatcgtcgt ttcaatctga atgctttgtt   145620
ccctgatgca tttacagaaa tcatggtctg cgattatgat gaatctaaag atgctttact   145680
ggaaaaggct aaagtaaaat acggcgatcg catcgtctgc tatgtagatg atttgcctaa   145740
acatattgct gcggccagca aagtatttga agacactgaa acccgtgtgt tctatatgcc   145800
tcgtggtgag cgagagggtt cagtgactgc tcctggaatt atggttgaag attggcatca   145860
aattgtaact tgcctggaat ctttggaatc tgttaagaaa ccgcagaagt ctctttctag   145920
attgtgggaa gaagctatca aagaccaaat tcgtaaagag caacatcctt ttaattggcc   145980
tccacggcaa gttccaggag attggtggaa acaacctatc attccgttta gtcctagtcc   146040
gcatgttcct cctggaaacg actggtggaa taacggtcgt attacatgtg ataaccacca   146100
aattaattgc taacacactg ggtatggtat aatagccata ccctaggagg aaatatgttt   146160
gtagttcata ctaaggtagg taaacgttgg ttatcatgtg attatggcca tgttaatcag   146220
ttttatcgtt ggaatccaat ttggcgtgaa gcaaaggcgt gcccgatttg gaatgaatgc   146280
atcaataacg ggtttgttta tatcgatgga ttaacttatc atcgtagcgt aagcgaactt   146340
tcaaaagaat taggtgaata atgattttg atatcatcaa agcgattgaa gatgctaagg   146400
gttctaaagc caaaacccaa attctcattg acaataaaga taacgttgat ttaaaacgag   146460
cttatctgct ggcgtattcc gggcgattta agttctttat taagaaagtt ccagaatata   146520
```

FIG. 20AAAA sequence.txt

| | | | | | | |
|---|---|---|---|---|---|---|
| ctcccgttaa | atatccaaat | gttccttcaa | agacgttttc | tgatggtcta | gattacctcc | 146580 |
| aagacattct | ggcagcacga | gtacttactg | gtaatatggc | aatccagggg | ctagtagatt | 146640 |
| tgctctctaa | gatgaacgag | ggtgatgcta | gtgtactggt | ccgtgtactt | cttaaggata | 146700 |
| tgcgttgcgg | cgcttcaggt | tctattgcta | acaaggtatg | gaagaagtta | attcctgaga | 146760 |
| tgccacagat | gttagcatca | gcttattctg | agaaagcgct | atcgtatatt | aagttccctg | 146820 |
| catttgctca | gcttaaagcc | gatggagccc | ggtgcttcgc | tgaaatccgc | ggagatgatt | 146880 |
| tagatgatgt | aactcttctt | actcgttccg | gtaatgaata | cctgggtcta | gataaactta | 146940 |
| agcgtcaact | tatcgagatg | accaagaag | cccgagaacg | ccatcctaat | ggtgtgatga | 147000 |
| ttgatggcga | gttggtatat | catgtcgaag | tgaaagaaga | agaaaacgac | ctgtttgata | 147060 |
| tgtttaaaga | gcctgagctt | cctgaactaa | gtaaagctaa | ggaattccaa | cagacggctc | 147120 |
| gtacagaatc | aaacggcttg | gctaataagg | ccattaaagg | aacaatctct | gccgaagaag | 147180 |
| cagaaggcat | gagattccaa | gtttgggatt | atgttccgct | tgatgtagta | tattccgaag | 147240 |
| gtaaagttcc | tggatttgct | tatgatgtac | gcttccgtgc | actggaaatg | atgagcaaag | 147300 |
| gctatgacaa | gattattcta | attgaaaatc | atgtcgtaca | caacatccat | gaagctcgtg | 147360 |
| ctatctataa | gacatatgta | gaccaaggtc | tcgaaggtat | tatccttaag | aatatcggtg | 147420 |
| cttattggga | agataagcgt | tctaagaacc | tcgttaaatt | taaagaggtt | atcactgtag | 147480 |
| atttgaaatg | tgtcggttcg | tacgagcata | gaaaacaacc | tggtaaaatg | ggcggcttga | 147540 |
| tgttcgtatc | agaatgtggt | cgtattcgtg | ttaacgctgg | gtcaggtctt | aaagataagc | 147600 |
| ccgaagaact | gcacgagctt | gaccgtactc | atctatggaa | aattagagat | tctcttccag | 147660 |
| gaactatctg | ggaacttgaa | tgtaatggtt | gggtaactgc | tgaaggtcgt | gatgatggta | 147720 |
| cggtaggatt | gttcttgcct | atcattaaac | agcgcagata | tgataaagaa | gtggctaata | 147780 |
| cattcgaagc | cgcatttggc | gtgaacttta | cagaggcaac | aggaataaaa | tgaaagtatt | 147840 |
| atacgaagta | attgctaaaa | ctgatgatgg | gcgaggaggt | atttccgtcc | ataccgaagt | 147900 |
| tcttgatttt | gataatatcg | atgtattcaa | aaacttcaaa | gaaaacattg | aagagtatga | 147960 |
| gtctgtaaat | ggattacagg | tttggcgtac | tgccacaata | attaattaaa | ggccttcggg | 148020 |
| cctttttcg | tataaataga | ataaacaaac | gaggatatgt | catggaactt | ttaaatgaag | 148080 |
| ttttcgatga | agagaatagc | aaaatctatc | ctgtcgagaa | cgttaaacca | aaactaaagg | 148140 |
| tgcctcaggt | atttctgatt | aaggtgccgg | gtaataacaa | tctaatgatt | cgcttagtac | 148200 |
| atgggtcagg | tcaaggtgat | gcagttaaga | atatcaaaat | gggtgataaa | ttcattcagg | 148260 |
| tatatgtttt | ctctgtgtca | gaaaaaggta | atattggagc | cctcaagggt | gggttaggac | 148320 |
| aagacccgat | tggtgctatc | aatacaatct | ttgaaactgt | caacaaagta | gttaaacaaa | 148380 |
| ttaaagccga | tgcagtaatg | ttccgctttta | atccaaagaa | aatgcaagga | caagataaag | 148440 |

FIG. 20BBBB sequence.txt

| | | | | | | |
|---|---|---|---|---|---|---|
| ctattcaacg | cattcttgct | cggttgatta | ctactcgcac | cggtggtcgg | ttcaatctaa | 148500 |
| tgaaagatat | ggcttactat | aaaggtaagt | atgcttattc | cattatggtt | cacaaaggta | 148560 |
| agaagcttga | agagattgaa | ggaattcctg | aaatttcaga | tgagttatac | acaaaggttg | 148620 |
| aatccaaagt | aggtgaaatt | tatgtgtcta | agaaaccgg | cgaaagcgtt | accaaagccg | 148680 |
| aagcattggc | taattctatt | ggcgaaaaag | aagacaagaa | atctgaactc | gctgtaatga | 148740 |
| gtaaaatgaa | agtgtctcga | aaagatttaa | tccgagcaca | gtacggcaaa | tttgtttcat | 148800 |
| atgttgatga | agattggcca | gaaaataaac | gcgaacgttg | gtacgaatta | actactaaca | 148860 |
| ctccagtact | aaacgcagaa | ggcgatacgg | tagacctcca | aaaagatatc | aaagccggat | 148920 |
| tagaaaaatc | aattccttt | tatgttgatg | atatcaagca | ctatcgtgtt | cgtggcggat | 148980 |
| atggaagtaa | ttttggcgat | gcagttgaga | gattatttgt | aggccaaatg | tcgagaatgc | 149040 |
| atgacgactg | gaaggttttc | attccttcgg | gttcagacaa | aatgaaaatc | gctgaacaac | 149100 |
| gaatttcaga | cgttgctgac | gttattgctc | aagctaaaaa | tcctgcatct | atggaaacaa | 149160 |
| tgcgtaaaat | cgttgaagta | gctactcgtg | gatttgatat | gcctccagct | gacgatttcg | 149220 |
| gagctttgcg | tcaataccaa | aatcttgtca | attatatgat | atccgcttat | gtgtcaattg | 149280 |
| ttggcgattc | tatatccaaa | gcaattgaat | ataaccgtga | aatgcaatct | cgtttaagcg | 149340 |
| aagaagaaag | agatgcaata | catcattact | gtggttctgg | ttattcattt | gttaataact | 149400 |
| atcttattgg | tatggaaagc | ttaggcgatc | cgattattga | caagaaaatt | cgtccgctcg | 149460 |
| attctgcctt | tgaaaaaggt | ttgcgtcttg | aaccaggcac | tcttttgtat | cgtggtcagc | 149520 |
| gaggaaaata | tgaagacttt | aaagataaca | ttgagtctaa | aatgtttat | ttccagaact | 149580 |
| atgtttctac | ttcgttaagt | ccaattatct | ttggtgctta | ttcaaatgct | ggtgattcat | 149640 |
| taatgccaga | cgcacctagt | tctgatttag | aaaacaaaga | aacaactgct | aatgcggtat | 149700 |
| cttctgttat | tggaacagac | aacttggaaa | gagttgatag | aggcgaggaa | gttgcctatg | 149760 |
| gcgatgagtt | taagtttgga | ttcgttattc | atggggctga | taaagttaag | gtagttatcc | 149820 |
| caggtgtctt | gtcaagcttt | agcgatgagg | ctgaagttat | tcttcctcgc | gggttggcaa | 149880 |
| tgaaagtcaa | caaagtatgg | ggaactcctt | ttagaaatgg | agttggtgta | gcgaataaca | 149940 |
| agacattcat | ggtagaaatg | acggtagttc | cgccagagca | aatcgatgaa | tccgttcatc | 150000 |
| tctatgatgg | tgacatcttg | atggaacaag | gaaagtgga | acctcttgaa | gaaagcaagt | 150060 |
| tcaaaggctt | tttaaatgag | atttactttt | cgccagaccg | ttctacagat | aaggttagct | 150120 |
| acacacgtac | catggagcta | ctggctggtg | ctatcaacct | ggatggtatc | ccagaaaaac | 150180 |
| ttgcataaag | ttgtttactt | atcacaagga | cgtgatacta | tagacttaca | caaaccaatg | 150240 |
| aggaaattga | tatgaaacac | gtattccgct | ttaacggtat | tgaatggtct | gctgatgtta | 150300 |

FIG. 20CCCC sequence.txt

| | | | | | | |
|---|---|---|---|---|---|---|
| aagatgcaga | gaagttcaat | gaagaagttc | ttatcatgct | tgaagggttt | aacgaaggta | 150360 |
| ctccgacggt | tcttattcaa | gatatcttcc | gtaagccaac | tgaaccatcg | tttgttgaag | 150420 |
| cggttctaaa | cggtaaagca | gaaggtatta | ttccggtcaa | agtagtttgg | actactaaag | 150480 |
| aaatgaaact | tcttcgtact | gagccagggt | ttattggctg | cattgcataa | aacaaagggg | 150540 |
| ccataaggcc | cctaaattat | tctgcttgtt | gaagtagtga | tattagaaat | tccaccacct | 150600 |
| gccccgccta | aacgagacaa | tcttgaagca | gacgtactca | agccctgatt | tggattaatc | 150660 |
| gtctcaattt | tctgaatagt | tttatcttct | aaccaatcca | ttgcggcttg | ttttccgact | 150720 |
| gaacctgttt | gcatgctgcg | ataagcaaac | gtgacatcaa | acacagctat | tgtgttttct | 150780 |
| ccatcgtaag | taaattcggg | agctccacat | gctacaggca | tagcccctga | gaacaggcat | 150840 |
| acagtatgtg | gtaatccatt | tctagcatga | aggttaactt | ggatatcaca | ttctacgtct | 150900 |
| tgtggcaatc | ctcgcagacc | agtcaccggg | tcttcaactg | catttaccca | atcttgcatt | 150960 |
| gctctatagt | tgcttgcttc | tgggtccatc | ctaaatgaaa | gaaccaacgg | ctccatatct | 151020 |
| cttccagtga | tttttatgtt | aggagcgtta | tggaacttat | ccatttcata | tgacagtcta | 151080 |
| ttctctggta | ttttagcaga | atacaccatc | aagcctgctg | tcggaaatgc | catgttaaag | 151140 |
| aaatcaagca | gataagtacc | tactgtgaat | tcacctaaca | acgactgtac | aacacgctgt | 151200 |
| gtcattgcgc | caatcataaa | tgtattcaca | cctgatttgc | gaacaacctg | tcgagttcct | 151260 |
| tgtgtcacta | tggttgttat | accctgattg | aattcacctg | gtgtcaatcc | aagccaattt | 151320 |
| ccatctaaac | ccatattatt | atacagctct | ccgccaaagt | cgtttagaag | agcctgggtt | 151380 |
| ttactagagg | gtacagtagc | gaatacaaca | gagaacatat | tagttctctg | gaaatcgatg | 151440 |
| tcagcagctt | gactcttaaa | ttcttcgaga | gtaaacatta | ttcaatacct | ccgatataaa | 151500 |
| cgttccctct | attaagagta | agtatttcac | gcatagtaat | ttcaagcgta | aacgtgcttg | 151560 |
| gaaggttagg | agcgattgct | aacccattaa | aatgaccgtt | cggtgtttta | tcaaagcgga | 151620 |
| tgctctgaat | ttggcacgga | ccaaatatat | cctctctacc | atccattgat | gtagaatatc | 151680 |
| caaaattacg | aacagtccaa | atcgttgggt | tagaaactac | aataacattg | cttaaaaacg | 151740 |
| atgttatttg | ctcaaacaca | gtgttttcta | ctttagctcc | atccggtgct | gccgatttaa | 151800 |
| gtgttccttt | ataccattca | tcaatagcag | ctttaacttc | ttttgcatat | gatgaattcc | 151860 |
| ccgtcacacc | gtaagaatag | tagttaaaaa | tttcatagat | gcgaataatt | tgtataaggt | 151920 |
| catctgcaga | cctaggagtt | aaatcccaag | taaacacttt | cgttctatta | tcaggtccgg | 151980 |
| catacatact | acgggcagtg | ttataaattt | gctcaccgtt | atcggccatt | aatccctgcg | 152040 |
| ttaaagattc | tatcgaccca | aacaccgcag | tagaagccac | gttgcttaat | acaccagtag | 152100 |
| cagtaccgct | gccgcgagta | acaagagaat | cgccaacatc | attaaattta | tggctaaccg | 152160 |
| aatcaacgtc | tgacttagac | cgtggtaata | gaatattagc | taccggcgca | gtacttgtag | 152220 |

FIG. 20DDDD sequence.txt

| | | | | | |
|---|---|---|---|---|---|
| tagaacttga | tgaattagcc | agtgctgaca | ttggtgaatc | gaatacagac | gataacatta | 152280 |
| catctcgtct | aaatgaacgc | aaatcaggag | tagttcttcc | tttaaaatca | tatgctgtga | 152340 |
| ataataatcc | gttacgatac | aagtcatgta | ctctcatatc | ttgtgcggaa | tcgtttccgg | 152400 |
| ctgagcgttc | ggccggaaac | tgcgccacct | tagtggtagg | cgcattcgtc | agtttagatt | 152460 |
| taccttggga | aattcgagtt | cctgattttt | tgatgttttc | aaggccatcg | gccagttctt | 152520 |
| caaaaatcat | tgttttcct | taagaggttt | tcatagcgcc | ttgcattcca | ggagcagctg | 152580 |
| ttgaagtctg | tggaggcgtt | ctataaacgt | atgtgctatt | cttatttaca | gcggtattaa | 152640 |
| cctgaatagg | ttgcgactgt | gtattagatt | cacgtgtacg | agctgcttca | cgactatctg | 152700 |
| cggcggcttt | aatagaagca | gactgcttaa | cctcaggctg | ttctgttgca | ggtatagctt | 152760 |
| cggcagttgg | agcaggttct | gatattttag | aatcaagaag | cttttgcaat | tggtctaatt | 152820 |
| caacctttaa | atcttttgca | acttctggag | ataatttctc | caattcttta | tatctggtgg | 152880 |
| ttgtgctttg | tactgcatcc | ttagcagagt | ctaatcgagt | ggaatcagat | gcatcagttt | 152940 |
| tttcaacata | tgcttttgta | cgcttgagtt | ctgcctcagc | attattacga | gctgtgatga | 153000 |
| ttttgaggcg | ttcgtcttct | ggcaagtctg | catacgctga | ctgcttttc | tctccgctca | 153060 |
| gcaatttatt | atattcatcg | tcatcaatct | gaccggtgaa | tttttggaat | ttagcagaaa | 153120 |
| gctttctttt | ccattcaggt | tgttcgtcat | attctctttc | ttgacggtca | acatattttg | 153180 |
| ctctcatttt | agcatcttct | tcatctagtt | ctgccccagt | aacagtttga | aatctgtcta | 153240 |
| aagcagcgcc | ttcaatgtta | tctgccgaat | cgttaaatcc | taatgcgcgt | aacattccag | 153300 |
| cgagaagctt | actcattccg | agcataatag | tttctccgag | cttgtcaatt | acatcaacca | 153360 |
| agccagaacc | aatggcttta | gctaatccgc | cccaatcccc | tttgacgaat | gattttacta | 153420 |
| tttcattcga | catctcgctt | attgctgtta | atagcggacc | ccattctttg | gcttgcttgt | 153480 |
| taaattcaac | aaagttcttt | tcgaacagtt | tagtccaata | attaaaatga | acttaatta | 153540 |
| aatctataag | cattatcacg | cccaaaacca | tggcggcagt | tttcgccatt | tgagccaaag | 153600 |
| cgctaacagt | atagctaaat | agcatgctgc | taattttatc | tgttaatgaa | atagttttc | 153660 |
| caaaaccaga | tttaacactt | ttaattaatt | ctccaaattt | taggccaaga | aactttttat | 153720 |
| tcttatcctc | agtttctttg | ttaggttctt | ttctttcctc | ttgctcttct | gtgttaggaa | 153780 |
| agaaatccgc | gtcaggacgt | ctatcatcct | gtggaggaat | aagcctttcg | agtaattcct | 153840 |
| ctagcggctg | ctgaaccgga | gcatcaggta | cttgttccgt | tattgtttct | aacgatgttc | 153900 |
| cagtaccagt | cttttggaca | tcttgctgaa | catcatgctt | tttagataac | aagtcggcaa | 153960 |
| gtttcgtgag | cttatcatta | attaacgatg | ctgtatcatt | tagtttagag | acagcatctg | 154020 |
| ttgtgcgttc | tgaagcttca | gcagttaatt | caacaccagc | tgaaacatct | tctactgatt | 154080 |

FIG. 20EEEE sequence.txt

```
tgataatttc atttgattta gtttctatta catccgaaat caaatcagta gacgcttgtt    154140
ggtcgtctaa gcgacgacca atatcttcta gcgtattaat ctgagcatca gcttgagact    154200
cagccttttt ctgtggagcc gagtcagcaa taactcttct acgcattgaa ttcatttctg    154260
atttcttagt cattcaaata tttccattac gttaagcatg cctttgattg gtccttcagg    154320
tccatcaatg gctatagtgt ttactaagtc atcagcccac tttgttacaa aagctggaag    154380
cttcataaag tttatatcca ttggttttcc atctactgat tcaagaaatt cgcttaaaat    154440
tgaatctact gaacctagtt tggaataacg aggaggagct ctgaatttga attctttacc    154500
atctaaccgc tgagttaatc gttggcaaat gtaaacttta ttcaaatcgt aggtaaaatc    154560
atctttaaca accgtttctt ttattcggtt gttaaatgct aataaatgta gtacaacgat    154620
atcggattcg gctgccgtta atcctgggca aattgaatct aaaagaagat tcatgttttc    154680
gtctggtccc ttaacatctt tcatcagatt atggtgcttt aatccaagtt ttggaattga    154740
tatcgtcttt tcgtttatta ctattttctt aataggaaga atcacgttta agttcatttt    154800
tcaccttaat caaatctaca ggttcaaggg cagagccatt tgtgaacata tataagttag    154860
ttatagatgt gttatttgat atttcatgga taacttcatc tacataaaag tcagttctga    154920
actggtcctt taaatcaaca aaattgattt tcattccagg agttagttca aaattaccgt    154980
aacatttagt ttgagcatac ccgtcatatt gagccatcgt agaaatgcgt agtgcttctt    155040
catagccatt tctaaaaatc atgtcagaat atccgcctga cctattaatg aatacgctgt    155100
tttggccttc tccattaata attcgggtaa catctttgtc cacaaacgag tgtgcataaa    155160
atgttgcgtt tttcatggga tttctattat atctgtttga tttaacaagc cattcaaaat    155220
cccatgccaa tggatatttt aatcctgctg caaactgacc tattgtttga ggagctccaa    155280
acatgaatac atttgggttc tgggatatca ttgattcata atccatcatg ttaatcccag    155340
tgatatcttc ccatgcaaaa ataaattggt cgttatcagt agaaatgcct acgtttctaa    155400
cgtatcgcaa gtaatctttg agagtactag tccatggaac tcgtgggacg taggcgttaa    155460
ttccgttgat aggaggagca atcaatggtt ggtcaacata catcgcgcct atcatttctt    155520
ttatagtttc atatgcagaa ctaaaaaacg ctctactgaa cttgagattc attatgtcat    155580
gcagcgttcc aagctgaagg gtgataatgc tatcaccttt atcatcaaca ccgactgtaa    155640
agtgtttaat tccgtaaatt cgagtttgcg ttcttgatgt gttactgttt gcaacagata    155700
tttgaactag ttcatcaccg ttcatacgcg tgtgcatatt tttcgaatca taaaactgaa    155760
gtagaccctc attagtcccg cgtaatgaat ctctcattgt taatgtaata aatgtagctg    155820
ctaattcaac gaatctatta gctagccacg catcatatcc agaatataat tttatgctta    155880
tattaggata tcctaatctt tgtgctgtca tgatttaagg tcctttcaa  taagcgataa    155940
ggttatgcca cgttctatag gcagcatttt cattatagaa ttcaaatcgt atttaccctg    156000
```

FIG. 20FFFF sequence.txt

| | | | | | |
|---|---|---|---|---|---|
| agaaaccaat | ctatggttaa | tctgataaaa | tgtgaaaatc | tcgtcaggat | gtagcaatag | 156060 |
| cttaaaaata | tcgacaatgt | tatcatattt | taatattgtc | gtggtatcac | agcatgatgt | 156120 |
| ttttaattca | aaattaaagg | gcttcatctg | tgataaaatc | ttttccaagg | tttcaacatc | 156180 |
| tatagcatcg | ataacggtca | atttattgct | atcgctcaat | tcattccatg | cgtattcccc | 156240 |
| agatgaatcc | ttcacagata | taatgttatc | taaaatcatt | ttacctgtat | cgtcaattat | 156300 |
| ttctatgggt | tttttgaact | tgagcgttaa | tccagcaacc | tctacttttg | gatttaccaa | 156360 |
| tggaggttgg | ttaagattaa | aaagatactg | cttatatttt | ccgcattttg | ggcacttcat | 156420 |
| tctgacaggt | attttggttt | taccaatact | tgaaagaaat | accttaagaa | atatataagg | 156480 |
| acgatactcg | gcaggatggt | catgaaaata | atcatccatt | aattctgcta | taagttgttt | 156540 |
| ttgttcttct | tcagacttgg | tgttcatgtc | gtttctaacc | aataaaaggt | ctctataatc | 156600 |
| ttctactgta | aatggcttaa | aacgttggac | accatctggt | aattcgcatc | taactatatt | 156660 |
| ggccataagg | taatcctctt | tatactattt | ataaataatt | gaataagagg | agtggatatg | 156720 |
| aacatcacat | acaaatttga | aacaagaata | aatggcaaga | atatccagtg | ccgagctttt | 156780 |
| acactagaag | aatacgctaa | tttaattgca | gcgaagaaaa | acggcacaat | cgatgaatgc | 156840 |
| attaaagcat | tgctcagaga | atgcactaat | gccactgaat | taaacaaaca | ggaatcggaa | 156900 |
| ttacttatag | ttatactctg | ggcccatagt | attggcgagg | ttaatcacga | ggtgacctgg | 156960 |
| aattgcacct | gcgggcgtaa | aattcctgtg | ccattaaatt | atacacacgc | gcaaatcgat | 157020 |
| cctccagaag | acctctggta | tgacttaaag | ggatttaaaa | taaagttcaa | gtatccgagt | 157080 |
| cttttgacg | attcagacat | tccaatgatg | atatcaaaat | gcatagatta | tatcgtggtt | 157140 |
| ggaaatgagc | agatttactt | taatgattta | aacgatgcag | aaatcgatga | tttatattct | 157200 |
| gctattacaa | ccgaagatgt | agttaacatc | aaaaatatgc | tattgaagcc | gcaggttcaa | 157260 |
| ttagcagttc | ccattacttg | tgaatgcgga | atttctcaca | ttcatgtaat | taggggcttt | 157320 |
| aaagaattct | ttaagattat | gtcatgagca | atatcgataa | attatattct | gaccttgacc | 157380 |
| cagagatgcg | acttgcttgg | gatactgatg | tgtcaaaaac | ggtaggagca | cgatcggtta | 157440 |
| aaaatagcct | tcttggaata | ataaccacca | gaaaggggtc | tcggccattt | gacccagcgt | 157500 |
| ttggctgtga | tatcacaaac | gaattatttg | aaaacatgac | tccattaact | ggtgatacga | 157560 |
| taaagcgtaa | tatagtctct | gccgtgcgta | attatgagcc | taggattaat | cgtctatcgg | 157620 |
| ttgatgtgct | tccgttatat | gacgataatg | ctataattgt | tacggtgcag | ttttctatag | 157680 |
| tagacgaccc | tgatacgcta | gagcgtatac | gcatacagat | gcgtagtaat | gctaactcta | 157740 |
| gcagtagagt | ataatgggac | tagtccttcc | aaagaaacag | tagagtggag | atagaatgag | 157800 |
| attagaagaa | ttacaggatg | aattggataa | tgatttgatt | atcgaccaga | ctaaactaca | 157860 |

FIG. 20GGGG sequence.txt

| | | | | | |
|---|---|---|---|---|---|
| gtatgaagcg | gctaataacc | ctgttctgta | tggtaaatgg | gtgcgtaagc | actcgacttg | 157920 |
| tcgaaaagaa | atgttaagat | tagatgccct | caaaaagcaa | aatcttaaag | cacgattgga | 157980 |
| ttattacact | ggccgtggag | aggttggtgg | tgaagtatgc | atggatgtat | atgaaaaatc | 158040 |
| agaaatgaaa | actgttttaa | gcgctgataa | agaaatcttg | ggtgtagata | ctaaattgca | 158100 |
| atattggggga | attcttttgg | agttctgtag | cgatgcaatg | gatgctatca | agtcacgagg | 158160 |
| ttttagcatt | aagcacatta | ttgaccttcg | tcagtttgaa | gctggcgcgt | aataaataaa | 158220 |
| cttgtaaact | aaggagacaa | tcatgtcgaa | tacggtatgt | gtcgtctgta | aaggaccaat | 158280 |
| cgatgaagca | ttggttgtcc | aaacagacaa | aggcccggtt | catcccggag | cttgctataa | 158340 |
| ttatgcgatt | gaattgcctg | tcactgaaga | cacagaagag | caattacaag | aaacgcagct | 158400 |
| tttaatttag | tctagtgttg | atgtagccaa | ttggctttgc | ccttccttt | cggttggggc | 158460 |
| tttttttatat | cagaagtctt | cgtcttcgtc | atcttcagaa | tcagcttcaa | gagcctgtct | 158520 |
| acgccccgcc | aaagcatccc | gcacaatgat | gtcatcagaa | tcagcaagag | tagtttcttt | 158580 |
| agagcgctta | tcgtaatact | tctcgagttc | tttcagacca | tctaaggttt | ggcaagcatt | 158640 |
| aattttactc | atgaagttat | cgatagtagc | ctcacgaatt | gtggcttcgt | aaatatcttc | 158700 |
| aaatttaatc | atagatttac | cgttttcatt | acgtagttaa | attttttcatc | agcatatcgt | 158760 |
| tgaatacgct | ctaatgcatg | ttttaagcaa | tagtttaaat | gtgtgtattt | cttttttagca | 158820 |
| ttggctgact | tcggctttac | gcccaggtca | tcaatgatat | cccacactgt | agccaaagat | 158880 |
| ttatctttat | gcttacgaag | aacacgacca | atagtttgga | gtacgataat | cttcgattta | 158940 |
| actggatggg | ctaaaattac | atgatgcagg | tttttaacag | aaatacctgt | agaaaataca | 159000 |
| ccgtagcttg | cgacgataat | aattcccttt | ccgttttctg | ccatagcctt | taaagcatta | 159060 |
| cgtgtttcgg | tattaacttc | gcctgacaca | taatatacat | gctcatgacc | cgcagcttta | 159120 |
| atcatctcga | acagctcttt | accatgagct | acatgtttaa | acatcacaaa | ggcattttcg | 159180 |
| tcacgcgctg | caagtttagt | agcaagatta | gcaatccaac | gatttctttt | cttaacattg | 159240 |
| gtgatgaatt | taatttcttc | ttgatacgtt | ttgccttta | aagcgtttgc | ggctgcatct | 159300 |
| gggtatctta | agaagattgt | attaattta | agctcagtta | cttgtccatc | ttccattaac | 159360 |
| ttagaagttg | atactggacg | gaagatttca | ccaaacatac | caacatattg | catgatatta | 159420 |
| gctttgccgt | ctttaagaga | accagacagt | ccgtacttaa | acatgcaatt | tgtaagacct | 159480 |
| gcaatgattg | ttgaaattga | cttttcctgtt | gcaagatgac | attcatcatt | catcatcatg | 159540 |
| ccgaattgag | aaaaccattc | tttaggctgc | ttaacagcgg | tctgccaggt | agatacataa | 159600 |
| actaatgcat | tcgaatcacg | agcagtacca | cctcgaatac | ccagcatagc | attgcgagga | 159660 |
| aataaacgat | aatcacaaaa | atcatcaatc | atctggtcaa | ctaacgctgt | ggtaggaacg | 159720 |
| atgataagaa | ccttgccttc | gtaattttct | acataatatc | gagcaagtaa | tgcctggata | 159780 |

FIG. 20HHHH sequence.txt

| | | | | | | |
|---|---|---|---|---|---|---|
| agagacttac | cagcagatgt | tggaagatta | agaattctac | gccgattaac | tagaccttca | 159840 |
| tatacagcat | ctttctgata | ccagtgaggt | tcaatcttag | ttaatcctga | ataaatttct | 159900 |
| ttagttgata | accaattatc | aaaatcctcc | cgcgaaagag | tttcttgctc | gaatatagct | 159960 |
| ggatcgaaat | aaaccttata | tccgaattgg | tcagcgaatt | ttctgatttg | gccaacaaga | 160020 |
| ccaaacggta | agagacgatt | ataatctagc | agacgaattc | gtccatccca | atgtccatag | 160080 |
| cgatatttcg | ggttgaatct | gtatccatcg | gcttcgaagc | taaaatagtc | tctgagttca | 160140 |
| tagaaaatcg | agtcatcaca | ctcaatatga | acatgactaa | aatctttaaa | tttgacttgg | 160200 |
| atgtcgtgca | ctgtactatc | ctcagttata | aatacaatca | tatttataca | ttacatgagg | 160260 |
| cacacccaat | gctagataaa | gactatatta | aagaaattca | ggcactcgat | aaaaaagaag | 160320 |
| ctaaagataa | gctcgacgag | tatgcccaaa | ctttcggtat | taaactgaaa | aagacccgtt | 160380 |
| catttgacaa | tatggttgct | gacttagaaa | aagaactggc | taaattggcc | aatgagccta | 160440 |
| tgccagaaga | taatgatggg | ctgtcaattg | ctgatttaat | tcaagcagat | gatgaaattg | 160500 |
| agggtaaagc | agtatttaaa | gatgaagcgt | ctgatgaggc | aaaactactg | tttgacgctc | 160560 |
| cagttaatgt | tggtattaaa | attcatgata | ttgacccagg | tttttataaa | gaaacccta | 160620 |
| aggtaaatga | cccagggttt | gaagtaaaaa | caccttctat | caatgataaa | ggattttatg | 160680 |
| ctgaagctcc | tattggagac | agcgttattc | atatagatga | tgaaggacaa | gttaccaata | 160740 |
| ttccggttag | tatcacggac | cctgaagaat | tctccaaagc | aatggacaaa | gtagttaaaa | 160800 |
| ttattaaaac | agacgaaatc | attgagcttc | ctgaaaactt | tagtccaaat | atgcaattgc | 160860 |
| taggtaagaa | cccaggatat | attactcttc | catggtggat | ttaccaatgg | attaaagata | 160920 |
| acccagattg | gaaatctcgg | ccaacgtcgt | ttgaacaccc | atcagcacac | cagacactgt | 160980 |
| ttagtttaat | ctattacatc | aaaagaaacg | ggtctgttat | gattcgtgaa | acacgtaatt | 161040 |
| cttcatttgt | aactttaaaa | taaggaacac | ctatggctta | tagcgtatct | attgctcctt | 161100 |
| tggctgcttc | ggcagtcatt | ggagcaacaa | ccaattttac | tgcaacaact | tctggagccg | 161160 |
| cagctgaagg | cacagaaacg | tttgtatgga | cagtaaatgg | cgtaaaacaa | tcttctgtca | 161220 |
| ctgcagctat | gaattatgtc | actgcaggac | ctgccggtag | taagactgtt | aaagtagttg | 161280 |
| ctactgttac | cccagcagag | ggtgaggtag | aaaccgctga | agcagaaact | actttgacag | 161340 |
| ttaagaacaa | aactatgcct | gcgattactt | taactttgag | cccgacttct | gtttctaaag | 161400 |
| aaattggaca | atcacaagta | gtcacggctg | atgttactgg | cgcaccgtca | ggagcaagca | 161460 |
| ttgcttatgt | ttggaaacgt | ggctcttctg | ttatttccgg | tcaaactggt | aaaacaatta | 161520 |
| ccttaactga | atcaacggaa | accagctaca | cactgaattg | tgaagtgacg | gtttctgctc | 161580 |
| cagactataa | taatggaact | gcaactaaag | gtattgctgt | tgcttttact | aaaaagacca | 161640 |

FIG. 20IIII sequence.txt

| | | | | | |
|---|---|---|---|---|---|
| tgagtggtgt | ttcagttact | ttgagcccaa | cttctgtttc | taaagaaatt | ggccagtctc 161700 |
| aggtagttac | ggctaacgtt | gttggtgctc | cagaaggggc | aagtattgct | tatgtctgga 161760 |
| agcgtggtac | tgtcgttatt | gaaggtcaga | ctgctaaaac | gattaccata | actgagtcag 161820 |
| cagaggctaa | ttatactctg | aattgtgaag | caacagtttc | tgcaccagat | tacaatccag 161880 |
| tgactgtaag | caaaggtgct | agcgtaacca | tcactaaaaa | gacaatgagt | ggtgtttcag 161940 |
| ttactttgac | tcctgaatct | attacagtcg | agcagggggtc | tgatgcatct | tttaaagccg 162000 |
| acgttatcgg | ttctccagaa | ggtgcatccg | gaacttattc | atggaccaaa | gacggttccc 162060 |
| ctgttgaagg | ttcaactagt | actttagtga | ttgacacgtc | tgatataggg | tctcaagtga 162120 |
| ttggggtttc | tgttgaggtt | tccgcagaag | attataactc | agtcacagta | actacaactg 162180 |
| gtaatgtaac | tattaccaaa | agggtagctc | ctactcctaa | cggagagctt | ccgtatattc 162240 |
| atcctctgcc | gttccgtgaa | acagcttata | tctggtgcgg | ttggtgggta | atggatgaaa 162300 |
| tccagcgaat | gactgttgag | ggcaaagatt | ggaaactcga | cgaccctgac | agcgattatt 162360 |
| acctacaccg | atatactctg | gctaaaatgc | tagacgatta | tccagaagtc | gatgtacaag 162420 |
| aatctagaaa | tggatacatt | gttcatcgta | ctgcgctgga | agcaggtatt | atctatcctt 162480 |
| aatattcggg | agccttcggg | ctccctttt | gctattcata | gactggttta | atatgtcttc 162540 |
| atcacataga | tgaggttatt | atgaaagcaa | tacaagctca | cttgatgcat | gaaagtggta 162600 |
| aagatttcca | agaaattgcg | agagcattag | atatcactcc | agcggaagct | gctaaattgt 162660 |
| gggtctcagt | tgagaaagca | cacgaacggt | ttaagcaaaa | agaaaaagtc | gtatatcgga 162720 |
| aacgcttaac | aaacgttggt | ataaaatctc | gtcataagaa | acttgttaaa | cacatgagga 162780 |
| ctttatgatg | tctaaagtag | acccaattgt | agtagaacga | tttgaagaaa | tgctttctaa 162840 |
| gaaatttacg | ccagctgcta | atggggtaaa | tgtctggttg | tttgcatcta | aatttgttag 162900 |
| taaatgatg | gctgttcaga | gttcttacta | ctataaaagt | ggtgcacgta | aataacgga 162960 |
| tttgattaat | gaacggtatg | gaaaaattga | ttggatgctg | atggataaag | atattccatt 163020 |
| agtacttgag | gttggaagca | aaagtcaatt | tgaaatcatg | ctaactaaaa | gcggatatat 163080 |
| catgtatcgc | ttcgtgccga | gcggttatta | attgctttaa | aaatcgatgt | ggtataatgg 163140 |
| gctcagggga | atcctctga | taccattatc | cttatcccaa | gatagatgga | ctcctggttt 163200 |
| tatattattt | attgagagaa | aaattatgaa | ccttgcagat | agaatggcta | atacagctat 163260 |
| taatgttgct | acagaagaat | tgagtgcagc | aaaagaagaa | gtattaaccc | agattgagaa 163320 |
| aaccgcttta | gcgggtaagc | gtgagctaat | tatgtatcct | agcagtttag | ttaagaaaca 163380 |
| tatcacaaac | gttcttaatt | atttgcatga | tgaaggattt | gttacaaatt | ataccagtgc 163440 |
| ccagcgtaat | ggtgatactg | actttatgaa | aatcacattc | taaggaaatt | ataatgtttg 163500 |
| caaaatattc | tagtctcgag | aaccattaca | acaataagtt | catcgagaag | attcgtggtg 163560 |

FIG. 20JJJJ sequence.txt

| | | | | | |
|---|---|---|---|---|---|
| ctggttttga | tatgcatact | gttgagtggg | tggctcgtga | gaaaattcat | ggcactaact | 163620 |
| tcagtgtgat | tattacccct | accgaaattg | ttccggctaa | gcgtactggt | cctattttag | 163680 |
| aaggtgaaag | cttctttggt | catgagatta | tcatgaagaa | gtacaaggat | tctttcgtta | 163740 |
| agatgcagaa | catgctgaac | accatggatt | tagtatctgt | tcaaatcttc | ggtgaatttg | 163800 |
| ctggcggtgg | tattcagaaa | ggcgtagatt | atggtgataa | agatttctac | gtgtttgata | 163860 |
| tcctgtcgga | ttccggtaac | gaaaaagttt | attgggacga | ttatgtagta | gaatcgtttg | 163920 |
| ctactggtct | tggtcttaaa | ttagctccac | tgcttggtcg | tggttcattc | gctgagctat | 163980 |
| ctcagtatgt | aaatgacttt | aaatctattg | tcaattacta | taatgaactt | gttgacacga | 164040 |
| ctgaccttga | acatgcaaat | aaacatgtgt | tcggtccaca | ggcttcttct | gaaaccggtg | 164100 |
| tagctgaagg | ctatgttctt | aaaccggtta | atcctaaatt | ctttaataac | ggtacccgtg | 164160 |
| tagctattaa | gtgtaagaat | tctaagttca | gcgagaaagc | taaatctgat | aagcctatta | 164220 |
| aagctaaggt | tgaactcact | gatactgata | agcgtgttct | ggaaatcttt | tccgagtatg | 164280 |
| taacctggaa | ccgtgtaagt | aacgttctgt | ctcatattgg | tactgtaact | gccaaagatt | 164340 |
| ttggtcgagt | tatgggactg | actatgaaag | atatcattaa | cgaagcagct | cgtgaaggtc | 164400 |
| atgacatgct | attcgctgat | aatccttctg | ctgttaagaa | agaactgact | actttaattc | 164460 |
| aaaacactat | tcgtagcaaa | tggcatgagg | ttttagaata | atgaggctgg | cgctgattgg | 164520 |
| ttcaagagaa | gcgccacgca | gagttctgag | tctaatgact | ataatcggtc | aacgcctctc | 164580 |
| ggaagagggg | catttttcat | attcaggtgg | agctccgggt | tcagatgaag | cgtggttggc | 164640 |
| gaaatacgat | aggtcaaatt | cttgtaggat | tattccttat | tctggctttt | gtggccatgt | 164700 |
| tcctgataca | ggtgttgttg | tatggtctga | attatcaaac | gaagccaaaa | tcaaaagcat | 164760 |
| cattaaggcg | agagaagtta | cgtcgtactg | ggatgaatgc | tcgaagatag | tacagacact | 164820 |
| atttgcacgg | aattctatgc | aggtattggg | cctagaatgc | actgagcctg | tagataaggt | 164880 |
| attatattgg | gcgcctgaaa | aaagatgtgg | gagtgtatct | ggagggacga | gagtagctgt | 164940 |
| tgatatagcc | cgtagacatg | gaatagaatg | cgtcaacctc | tatgataaga | atgtgtttaa | 165000 |
| atccctcgag | gaggaatact | ccccgaggtt | tgacatattt | agtttataac | aaaaagggga | 165060 |
| gccgaagctc | cccataaatt | agtccgcaat | aagcttaggt | aacttaacac | cgagcagtac | 165120 |
| agacatctta | cttcttcctg | ccatcttatc | catatccgca | gcattaatca | cacgagcttc | 165180 |
| gtcctcgtcc | aatcctacag | tatatgggtt | aactgacaat | gcatatcgta | ccagtaaagc | 165240 |
| aacagaaggc | tgcaagctag | ctgggtcaac | aataacttta | aatgcaccaa | catgctcagg | 165300 |
| gtcgtctaaa | tccaagcctt | cggtatatgg | cgcataaaat | aaagaaccta | cagtttcctt | 165360 |
| cccaccaaat | tctgccttaa | caccaacaat | aacgtaatca | accggactgt | tagtatcaca | 165420 |

FIG. 20KKKK

```
                                      sequence.txt
ataaagaggt aaaccgttat tcagcatacc gtatgcgttt tccggaatac ttccatcatt    165480
cttctgtgtt aaccaaccgg aagctgcaag caccgcagca caacgagtag atgctactgc    165540
ataagtacca gaataagaag tattacgttg aactgctgaa ttcatttcac aaatgaaacg    165600
atacagagta cgaccttgtt ccggagcaga atcttgttta gttaaatcta atacacccttt   165660
atcggataca ccagctactt taaaccgaga agaaaccgta atcaatgatt gcaagatgtc    165720
tttattaatg tcttctgcca tttcagtagc aagtaaatca tcaataagtt ctggagcatc    165780
gaacccatta gcttctaaat cttgagctaa ttctaccgtt aaatctgttt taagcttacg    165840
tgatttaacc tgggtctgcc atttatcaat tttaaaactg gcttcggtga ttgggtctga    165900
atcgggtcct tcaaatttt cagtgactgc agcatctgac aacatacgaa tattattagc     165960
tgctactgct tcagacacaa ttccaaattc atcggtttct gctgtatcgg taaacgggct    166020
atctttaagt actttaaaga ccacattctg atatttgaac atatcgtctt tattgaatga    166080
gtctttattt gccatagtga gttcttcaat tgactcacgt tctggcgccc cgatttgacc    166140
tgcataagtt gcaccgtat taaacgtcag gtcaccatta gggttaagat atttgatacc     166200
atatagcgct gctacaggct gtttagtacg ctgtgtagca acaagatcgg tatagattaa    166260
tttagtagtt gcgcgcgtta atgcaacgag attagggcga ccaattaagt tgctactcgt    166320
tgtagttgac tcgcgcagaa gttcgttgat tttagccatt gcgcttcct ctgtggattt     166380
ataagtttat ttatatccat taaaacaact aaagggagcc cgaaggctcc cttattggta    166440
ttagatacct ttaacccata cacgacggaa gtaagcattc ttaccaacag agttgacgat    166500
agaaggcata ccagaggtaa tacgaccttt cggctgttga gcagcagaat cggcgaacgg    166560
gttaataccg ataccgtaac gggttttgaa ccccatgacc ggttggaagt tcttcggatc    166620
ggaaccacgc agcggggtca gtgcaacata cggagcatag tagataccag catccatttt   166679
```

FIG. 21A sequence.txt

<210> 1074
<211> 144994
<212> DNA
<213> Unknown

<220>
<223> Description of Unknown: Bacteriophage F125/10

<400> 1074

| | | | | | |
|---|---|---|---|---|---|
| ctttgttcaa | attcctatat | ttagtttaat | accaatacta | aggtataaat | tagaagaaca | 60 |
| aggtatagga | ttaatagaaa | cagaagaatc | ctacacaagt | aaaacgtctt | ttattgataa | 120 |
| tgaaaaacca | atcaaacata | atgtttataa | aggtaaaaga | gtaaaaagag | gtctctttaa | 180 |
| aacagaagag | ggtagaatat | taaatgctga | tgtaaatggt | gcatttcaaa | taatgaaaaa | 240 |
| agtattccct | gatgtagaaa | taccaaggga | taatgggttt | gtgtataacc | cattcttaat | 300 |
| aaattgttaa | aaaaacaaca | aaataagaaa | aaatttctca | aaaagtagca | ttatgtgaag | 360 |
| agaagtgtta | cattattatc | gagaattcaa | taataaagca | tagggaaggc | tttttctatg | 420 |
| tcttatagaa | tgctttaaaa | tagattacta | aaataaagat | tggagattaa | gcttatggct | 480 |
| aaaaagaatg | ttaatgatgt | attacaacaa | gaatctgtta | cagtagcaga | taagtattta | 540 |
| caagttaaag | ttaaccgtga | cggttatact | cgtacacatg | aaggacaata | tgcgtacaaa | 600 |
| gtagtttcag | agggagaaga | actattctta | taccctgtac | aaacagatgg | taaaggtaca | 660 |
| ttaaatgtaa | tgaagaaatc | acctattgct | tacactgatg | gggacaatat | ccatttcgta | 720 |
| gtaaacacag | tagtagaccc | ttataatcac | tcatttatcc | gtactgaaga | tatcaaagga | 780 |
| ttagataaag | gtaaacaact | tattcaagct | ttcttagctt | tcgttgaaga | ccgtttcaaa | 840 |
| tttggtgttt | ataacgtatt | tgttgcaaac | agcaaagagg | atgtattatc | tattgtagac | 900 |
| cctacagata | atgatgcaga | tgaagttaaa | gatagtttag | agcacgcaca | tgaagatgta | 960 |
| attgcggatt | tccctgctag | ccctgctcgt | aaggacgtta | aaggcgtaga | ttcaggagaa | 1020 |
| ggtcaaggag | acacttcaga | accatcagca | cctaagaacg | ttcaagttac | tcctaaggaa | 1080 |

FIG. 21B sequence.txt

```
gacggagcag acgtatcagc agaataatat atagataagg atggtaaatt tggctaagtt    1140
aaatttatac aaaggtaatg agttactaaa cagcgtagag aaaacagaag gaaaatcaac    1200
aatcacgatt gagaatttag atgctaatac ggattatcct aaaggtactt ttaaagtatc    1260
attctcaaat gattcaggag agtcagagaa ggtcgatgtc cctcagttta agacaaaagc    1320
aattaaagtt atttcagtta cccttgacgt tgatagttta gaccttacag ttggagatac    1380
tcaccaacta tcaacaacta tcacgcctag tgaagcatct aacaaaaatg tgtcatttga    1440
atcagacaaa tcaggtgttg ctagcgtaac atcagaaggc ttaattgaag cagttagtgc    1500
aggaacagct aatgttactg taactactga agatggtagt cacactgata ttgttgctgt    1560
aacagttaag gaacctattc ctgaagcacc tgcagacgta acagttgaac ctggtgaaaa    1620
tagcgcagat attactgcat aggaggacaa taaagaatgg aaaagacatt aaaagtttat    1680
agtaatggtg aagttgtagg ctctcaagta gctaataacg atggagctac tacagtatct    1740
attacgggct tagaagccgg aaaaacttat gctaagggag cttttaaagt agcatttgct    1800
aatgattcag gtgaatcaga aaaagtagat gttcctgaat ttacaactaa aactcctact    1860
gaagaacctt caggagaagc atagtaatta agaccaacta aaaagttggt cttttttat    1920
tgacaattta taatatctat gatacactat ataagaatta agaaaaggag ggaaagtaat    1980
ggatattcca acaatattat ttagaaatcc atatgattat acgaaagtaa aaaaactaat    2040
ggaaaacaaa gagcagtaca ttgtagtaaa gtttgattct gtttctgttc ataatttaaa    2100
tgttcaaggt atgatgaatg tcatccaaga ttacctacac atctatggtt atagggttaa    2160
agagtacggg caagaaaatg cttctaaaga tgatgaaaga gacgttaaag gttacttata    2220
tgaaagagta ggtgagtagg atatgggaat tatagtaaac tccaaccata ttcaatcaga    2280
cactttatat gagtatgata gcttttttga tattgagaaa gtagatacat ttgaagaagg    2340
attgctttca atacaagatg aaccaactgt tttagcagga ttcatctatg atgacatcac    2400
atttaataag gttattaatt ctaattcaga tattgatgat tatattaaga ataatgatat    2460
ttattatgtc tctgatatag ggttactccc tgatactttt atcactgttg attctgataa    2520
aaaatattat tcattattac aacaggtagt tgagttaagt aaagacccaa ttcctaaatg    2580
ggtagaggat gatgcaaaag gcttaactaa gtattataac tttcaagact ttgaagatgt    2640
atttgattta aatagttttt acaaaaaaga agttgacatg gtaagagaaa agtgctataa    2700
taatggtaat gtatatttat tatatgaggt tctgcctgat tataaattac ctctagctta    2760
tagtttactt tcaaacaaag agcatggtat tgttattatc ggttcacaga cacgttctaa    2820
taatgatata ctgacttttt atgttaaagg tatggatgct aaagcaatag ctagtatgtt    2880
caatgtagaa catgattatg attctaatat tttccataca tttgtaaaca gtcacattaa    2940
tattttagga aatcaaataa ctaagtttat aagagagaaa ggaagcagtt atgagtaact    3000
```

FIG. 21C sequence.txt

| | | | | | | |
|---|---|---|---|---|---|---|
| ataaaacaat | agaagaagta | caagcagtta | ttattggggt | attatttaaa | gatgaaggta | 3060 |
| aaattgtaac | atctaagttt | aataaaatta | ctaaagagtt | tggtttagat | agaatcggta | 3120 |
| aagatgacct | taaagaaatt | gtagaggata | ttagacaaga | cgcttatcta | aatgaactta | 3180 |
| aaaacaaagc | aattaaaggt | aaagtaacgt | taggtgattt | aaaagatgtt | gcagataacc | 3240 |
| aagtattcga | aggtaataac | taccatgaag | aagtatctac | ttacgtagta | gctaaagaaa | 3300 |
| aagaattgtc | tcacttaaga | gaacagcgta | agcacaatag | gcatactgca | taccctcaaa | 3360 |
| ttatgtttga | tgaacttaaa | gaacatatgg | ttaaagaatt | acaaggggaa | acattagtag | 3420 |
| aacatcatgg | aagtaaagct | aatattaatg | atacagagct | aattgtgtta | ttatcagatt | 3480 |
| tccatattgg | aagtattgta | tctgatatga | ctaatggtaa | atatgatttt | gaagttctta | 3540 |
| aagcaagatt | aaatcatttt | attaatacaa | cagttaaaga | aattgaagat | agagaaattt | 3600 |
| ctaatgtaac | tgtttacttt | gttggggact | tagtagaaca | tattaatatg | agagatgtta | 3660 |
| accaagcatt | tgaaacagag | tttactttag | cagaacaaat | ttctaaaggt | actcgattac | 3720 |
| ttattgatat | tctgaatgta | ctatctaatg | tagtttcagg | agaattaaga | tttggtatta | 3780 |
| ttggtggtaa | ccacgaccgt | atgcaaggta | acaagaatca | gaagatttat | aatgataata | 3840 |
| ttgcttatgt | agtgttagat | tctttattat | tattccaaga | acaaggatta | ctaaatggtg | 3900 |
| tagatattat | tgataaccgt | gaagatattt | atactattag | agatacccttt | ggcggtaaat | 3960 |
| ctattatcat | taatcacgga | gatgggttaa | aaggtaaagg | taatcatatc | aataaattta | 4020 |
| tcctagatag | tcatatcgac | ttattaatta | caggtcatgt | acatcatttc | tcagtaaaac | 4080 |
| aagaagattt | taatagaatg | catatcgtag | cttcatctcc | aatgggatat | aataactatg | 4140 |
| ctaaagagtt | acatttatca | aaaactaaac | cttcacagca | gttattattt | gtaaataagg | 4200 |
| aaaataaaga | tattgatatt | aaaacagtat | ttttagatta | aggatggtta | ataaatggat | 4260 |
| acaattttta | ttataggtgt | agcgtttata | acttttgcaa | cattaacat | agtctttaga | 4320 |
| ctatttgatt | tatggactac | cgagaaaaaa | atggtaagtc | aaggacaacc | cccgctaagt | 4380 |
| aattttgagt | actatcatgt | gatagtacct | tacttagtag | gtgttattgt | tattacacta | 4440 |
| agtattattt | ttagagattc | cttgtattcc | gcacaatcag | ggttcggtat | tattattaca | 4500 |
| agctttattt | acatgctagt | ttatgttata | attggtcttg | tagggtcatt | tatacttaca | 4560 |
| atattccaag | ctagaaaagc | tagacagtat | caaacacagg | aggataataa | tgaagttcaa | 4620 |
| tgatatttat | gagcaattaa | ttaaaaatga | tacagtacaa | aacattcatg | agtctcaaga | 4680 |
| tgacaaagga | aatatttata | caatccaatt | tgataaaggt | aatgataagt | atttatttaa | 4740 |
| tgttattaat | gatggattct | tgaaagaaat | gacaaacggt | atggtagacc | atcctgaagg | 4800 |
| tcagccatac | tcagtaagtt | taatcaataa | agaaacacct | agtatgtcag | tgaaacaata | 4860 |

FIG. 21D

```
                       sequence.txt
tttaacagat gtagaagata ttgtacctac tattagaaaa atggaaaagg atttcttata      4920
gagtcaagtc tttacttgac tcttttact atatatggta tattaatata gaggtgactt       4980
aaaaatggat tttaatttta gtgcttttga taatagctca ttagcaatga gaattagtga     5040
gggtgtatac tatttcaatg atactcctta ttactttatt gagcatgtag aagaagaaat    5100
gtctgagtat gttattgtgt atgacataca tgacagagag gaaaaagaaa atcctcagaa    5160
gaaatataga atagaacctt accaacgtac aatacctggg ggaacacctc ttagtaactt    5220
aattaagagt atgatgcctc aacgtaagta tcctaagaag gttacagaag accctatatt   5280
tgtagctaat gttattcctt taggaacaga tacagtaaca ggtaaaaccg gtaaaggatt    5340
ttttgaaaga gataaggata gaactatcta ttctcaaaag gaaccaacta aagtcgttca    5400
tggtcaatat acaggtgttt ttataggtct aacaagtgtt aagtggaata gaacatatac    5460
ccctctagaa agtgttgttg agtactacaa aagggttaaa ggggataggt taaatgtcta    5520
atgatgtagt taagttttat gaaaaagata ttaaagacct tatcagaact aaaaaacaca    5580
tgttcaaaga cgatgaaata actagtgata taaacgatat acgaatcttt aatgagaaag    5640
tcatttgtca aggtaagtgc agaacagatt gtttagtact agaccgtaat ggtacagtaa    5700
tgggtataga gataaaaaca gaacgagact ctacacagag actaaataac caattaaagt    5760
attatagtct agtatgtaag tatgtatatg taatgtgtca tgataaacat gtacctaaag    5820
tagaacaaat acttaaaagg tataaacata atcatgtagg tataatgagc tacattagtt    5880
ttaaaggcaa acctgttgta ggtaaataca aagatgctac accatcacca catagaagcc    5940
cttatcatac aatgaatata ttatggaaga caaacttaat gacaatactt agattgatta    6000
gagaccctca tacgtataga acagggtata gctataatgc tagtggtaga tatagtggcg    6060
gagaaggtaa tttctcccaa acaactcaaa gtaaaagaat gaaaaaacct gctattatta    6120
atcaaataat tcattatgta ggggtagata atacttataa actctttaca agaggtgtta    6180
tctatggtta taataatagg tgggaagtta tagaagaaga tttctttaat actatgaaga    6240
atggggtaag agtaatcaat gagcaaagac aaaccaaata gacgtaaaga gatacaacat    6300
cagcctgtta actttgcccc tatgaatact ctaacagggg ctaataatag tttctttgct    6360
aaaaagcctt cagagcctaa ggatgcaaca tctgttattg aatatcgtat actatttatt    6420
aaaagatttg ataacgtaac aagtacagat gtgaaattac agaaaaagta tgcactaaat    6480
cttattagtg aagcacttga tgttaaagaa acttacttgt ctcttaagca aaaggaaaa    6540
aaaacagaat ctattttgca tacagataga gtttattatg ttcatagagg taaaaaactt   6600
attggaaagt gtagtatcag agaacaaaga acatttaaag gtaaacattt gatatttata   6660
ttcaaaacaa gacatagagt taaagcagaa aggaaagata aataatgtta aaaggatttt    6720
cagaacatgt agacaaacct acaactacta agaccttata caagacctta acaagtggta    6780
```

FIG. 21E sequence.txt

| | | | | | | |
|---|---|---|---|---|---|---|
| aagtagaatt | actaggtgta | tcctacgata | gtgattactt | cccttcaggt | gttacagtac | 6840 |
| aatcttacat | tgaggatata | ggtaatgaag | atgagggtct | acagtttgtt | aataagataa | 6900 |
| atgtagtaga | atcaatgaaa | caggctgtag | taggtatgaa | taatcagtta | ggttcttcag | 6960 |
| gtcttggcta | tgtgagaact | gaacaactta | aaaagagtt | agaagagact | ggactaatga | 7020 |
| cagatttact | tgctagaggt | actaacttaa | cctctactaa | gaaagtagat | attgtaagta | 7080 |
| cttttattga | gcctgaggta | acataccagg | atattactat | agctaaagat | attaaactac | 7140 |
| gtttgtataa | attagaagaa | gaatcaccat | taaatggtta | cactcatatt | gtatacttac | 7200 |
| ttactacaga | aaagctatat | gatggtcaaa | cactattcgg | tatgctctct | aaaaagata | 7260 |
| agttatctaa | aggagatact | gataaattat | tagcattctt | cagaaacaat | agcttaataa | 7320 |
| gtaaaagtgt | attttgtgtt | aagttattaa | gtaaagacta | ctactttaat | ttatataaca | 7380 |
| cacatgagac | agggatattc | tttttagaag | acacagatgt | tattactatt | gcttgtggtc | 7440 |
| agtcatatgt | taaagttaat | actaaagata | ttaaatctag | ttatgttaaa | attgaagaca | 7500 |
| agactcataa | attaactgag | ctagtaatta | acttaaaagg | tgacgacaca | ttaactattt | 7560 |
| tattctaaga | gaatgttata | aatatgtgat | aattaagtat | aaatatacgt | tatatgagaa | 7620 |
| gttttcataa | tgttttaat | acagaaacta | gttaagtttt | ttctacttgc | tctagtttct | 7680 |
| gtgaaattat | atttatgaaa | agttaaaata | tcttttaggt | aaaggctttg | taaatagtta | 7740 |
| aaaatatat | taaaattta | tacaaagtag | ttaataaaat | tatattacat | ttatatatta | 7800 |
| tgaaataata | acagaaattg | tgatatatta | tatagtgtaa | ccttgaaaca | gttgatgttg | 7860 |
| tagggtttgt | ttatgttcgt | taaactggtt | tcagaacacc | agttaccata | aataaatgac | 7920 |
| agttaaggag | agctatataa | tggctagaaa | aaagaattta | cgaaataaaa | acagtgatat | 7980 |
| aaaagttgtt | cctgataaag | aaaaagaaag | catattatct | aagctatatc | ataataaatt | 8040 |
| actacgctca | aaggtagata | atgcattaga | tgaagatatg | agttatgatg | atattataga | 8100 |
| attatgtaaa | gaatatgatt | tagaattgtc | taagtcagct | attacaagat | ataaaagtaa | 8160 |
| aagaaaagaa | gctattgaaa | acggttggga | tttagaagaa | ttaattgata | aacgtaaaaa | 8220 |
| aacaagtgta | aaagatatta | aggaaaaaga | aactcctata | ttagaagagg | agcaactttc | 8280 |
| tccatttgaa | caatcaaaac | atcacacaca | aacaatttac | gatgatattc | aagtactaga | 8340 |
| tatgattatt | tctaaaggtg | caaaaggact | agaatttgta | gaaactttag | accctgcgtt | 8400 |
| gatgatacgt | gcaatggaaa | caaaagataa | gattaccgga | aaccaattaa | aaggtatgtc | 8460 |
| atttattgga | cttagagagt | tacaattaaa | acaaacagct | caagatacag | ctatgagtga | 8520 |
| agtattatta | gaatttatac | ctgaagagaa | acatgaagag | gtattacaac | gattagaaga | 8580 |
| actacaaaat | gaattctaca | aaacctaga | tttagatgag | gaaagtagaa | aattaaaaga | 8640 |

FIG. 21F sequence.txt

```
agctcttgat agagtaggct acacaattta gatagtgagg ttagagtaat ggcagatgag      8700
attagtttaa atccaataca agatgctaag ccaattgatg atatagtaga gattatgaca      8760
tatttaaaag acggaagagt actgagagtt aagcaagaca accaagggga tatccttgtt      8820
agaatgagcc cagggaaaca caaatttact gaagtatcta gagacttaga taaagaatca      8880
ttctactata aaagacattg ggttctctat aatgtatctg ttaactctct tataacattt      8940
gatgtttatc tagatgaaga atattcagaa acaactaagg ttaagtatcc taaagatact      9000
attgtagaat atacaagaga agaccaagaa aaagatgttg ctatgattaa agaaatactt      9060
acagataata atggtaatta tttctatgca cttacaggag aaacaatgct ctttgatgaa      9120
aataaattaa ataaagttaa agattagggt tgacagcttc tatagtttat gatatagtat      9180
atgtatacta aaaataaagg agctaacaat tatgtttatt tcattaaatc aagaagagaa      9240
agaattatta actaaagagg aaagtaaata cacaccacta gaaacatcaa gagagtttaa      9300
cacacctaaa gaagaattca ttgtaacaag ttataacgaa ggtaaacctt tagattacat      9360
tgcaaaagaa gctaaggtaa gtatgggatt aatttacaca gttctaaact actataaagt      9420
aggtaagcgt aataagaaat cacctgtaga agaaagaatt gcacatatct taaaagataa      9480
aaacttagtc aaagagatta ttaaggatta ccaatatatg aatttacagg acatttatag      9540
taaatataat cttcataaga atggtttata ttacatctta gatttatacc atgtagaaag      9600
aaaatctgaa cttaaggaca aagcattaga agaggataat attgtcgttg agtaagtaaa      9660
gaggttataa tatgagaaat aaaaaatcat ttcaagagca gttaaatgac atgcgtaata      9720
aagagaaatg ggtatctgaa gaggagttca ctgaagaagt ggctccttct gaagaacctg      9780
aagtagaaga agaaaaacta tatactttaa atgagttaaa agagaactta ctagatgctc      9840
aaggattaaa agatgttgta gctgattttc ctgcatctaa agatttatat gaacctaata      9900
aactatatat ctgtacaata cctaaaggat atcagtctac tgaagtacaa ccaggacaat      9960
atattggtat tagtactgga ttattatcag agtcagaaga cttcagtcat ttaagaggtc     10020
aaatgcctag aaatctttat gaaacttctc atgttttaaa acctttagtc cgtattaata     10080
atacaagtat cgaatatcaa cagcatgagt tacttgaaga tattaaagaa gacaagaatg     10140
tatatgatgt tgaattagaa gacttgagat tagcaacagg agaagaaatt tcttatttag     10200
agattgttga tagtaagttt tttgaaagtc gtattaatga agttcttgat ttttaccatg     10260
aactaacgga ttccgatgat ttgcttgagt attataacaa attacgagag ttagtcggaa     10320
atgatagaat gatttattgt ccgcttttaa ataaatgtgt taaaattata gattaatagt     10380
agtctcctct tatattataa ctgtaagagg agacattttt gtatagaggt gttaattatg     10440
tcaagaaaag caagtatatt ttatatacta gtggttattg ttttggcttt ctctatctca     10500
tcttattata tatcttcttt catgtatcac gacaaagcaa aaaatgaagt ctctactgag     10560
```

FIG. 21G sequence.txt

| | | | | | | |
|---|---|---|---|---|---|---|
| ttatcgaaca | caggaaagat | taaagaagaa | aagaacgtag | aatttgttgg | tgactacaca | 10620 |
| ttgaaaaaag | tggaagataa | taaagcttat | tttatggaaa | cattacctac | ttacctacca | 10680 |
| ggtagaacag | gagataacag | catagatatg | aggtactaca | aaacaagtag | atttaaggaa | 10740 |
| ggggtaaatt | tcaagcttat | tagggtatat | actgaagatg | gagaagataa | tccaattcat | 10800 |
| aagtataggt | ttgaagcagt | accaaccaaa | aagtaataag | gaggtgactt | aaatgacaac | 10860 |
| attaattgtc | gtcatcttta | ttgctatcat | ttattactta | tggaacagtg | attgagtcaa | 10920 |
| gttaattctt | gactctcttt | ttgttttatg | gtatattaat | atatagaaag | gagagattaa | 10980 |
| ttatggaaat | ggcagattta | gaaagatttg | atgcatttgt | aagactaatt | tcagatgatg | 11040 |
| agctttcgga | ggaaagaata | ctggagttaa | gcgtagactt | actaaacccg | atactagaag | 11100 |
| gaggtacagc | ttacagagct | aaaaaacgta | ttaaaagtaa | atttggtaag | ttagaagcaa | 11160 |
| aaaactttaa | acgaaactat | aaattcttac | ttaagtcgat | agctcaaata | gaccaaagga | 11220 |
| gataggacaa | tgacagaaag | ggaaaaatta | attaaagaga | ttgaagaggc | taacagagac | 11280 |
| atacagttac | agttaaaaga | agtagataat | tataaggata | gtatacgctc | taaaggaaca | 11340 |
| agaaattata | tctctacaaa | ggtattagat | tctattacgg | ttggtttcat | agttagtttt | 11400 |
| ttaatactca | ttataatgcg | tgtacttgaa | tactttgtaa | caggtaatgc | tgtttattca | 11460 |
| cctttagcgc | ctgcagttat | cattatgttt | gtttagcac | tcggtacatg | gaaagtaagt | 11520 |
| aagatgaaca | aaatagtatc | ttatagagga | actattaaga | tgtactggga | gctaagtaat | 11580 |
| gctgagcaaa | aacaagctaa | ggtatttaag | tatcctaatg | atgaagtaga | tattgtatca | 11640 |
| aaacataact | taaggcaaat | aacttttagt | gagattaata | tacttcatct | taaatatatg | 11700 |
| agatataata | aagcagtaga | acagcatact | aaattatcta | aagaactttt | taaaaaagat | 11760 |
| aaagaaacgg | ttgacaagaa | taaataagtg | tagtatagta | ttactaaagg | aggagagata | 11820 |
| ttatggttat | acctagtatt | aaagcacaaa | acaaattcaa | gaatgaatta | gagtattata | 11880 |
| aacaaggtca | cattagtgaa | agtaaaatgt | tagaattagc | ttttgattac | atccaagaat | 11940 |
| tagaacaaaa | taacgaatac | gttactaatt | tgctagaaga | ggagagatat | ggtgagtaaa | 12000 |
| tttatcggag | tgtacttatt | taatttacta | gtggtagctc | tagtttacac | agtaggattt | 12060 |
| ttattctttt | atggtgtagc | tagcttagtt | attattttaa | ctcatgctac | tattgacccg | 12120 |
| ttcgtattag | ctactttctt | aggaatagga | ttcttagtta | ttagaactgc | acacagaatt | 12180 |
| atggcacgag | taatcaatga | cgcagtagcc | caagccatta | aggataaaga | aaatgaataa | 12240 |
| aggggaattt | attatggata | aaacattacc | aaagtttagt | gtatatgaag | ttattgtaaa | 12300 |
| gactgtaatt | atgacaccaa | cagaaggaag | ttctgaccta | gaatcatttt | acttttcaac | 12360 |
| tagagagtta | gcagaaagat | ttgttgaaga | gaacacagtg | gaaacaaaaa | acggtaaacg | 12420 |

FIG. 21H

```
                              sequence.txt
tgtatctttt gctgttaaag aacgtaaagt aaatcaacca ggctaacatt aatttgttag    12480
cttttttttta ttgacaaatc attttatata gtgtatagta atattataca gaaaaggagg   12540
aattattatg aaagtttcag aagaagtaaa acagagttac ctagagaata aagctaatac    12600
taaaatggat aagataagtt ggtctgagtt aaaagctagt cctttaggta ttaccttagg    12660
tgatattata ttttatagtg tagttattat agataacatt atagctatta ttttaacttt    12720
aaccttgata ggtactatta ctgactcaat tgagagtact ttagcccaaa taatcgtagg    12780
ggtgttcata atcattacta tatatggaat cctatcagcg ttaataccta ttctaattca    12840
taaagctgta tcaccgggat ggagttatac tgaatggaat gaatcctatt acatcagatt    12900
acctggggaa gagaactaca aatactatag taaatggtat ttagatttat taggagttaa    12960
agaattttac tataaaagag atagtggaga agaagtaaaa gaaaaaaata tatcatgggc    13020
ttttcaagct gaagtgaaaa gacctgaaga tgttaaccac tggaaaaacc agttgcttac    13080
taatagacct ttaacaattt tagaatataa aaaattaaag aaattagata aggaaagtga    13140
aattaggaaa caagaagatt tagaagaata caaacaatac aatagtaatt aaagaggtgg    13200
aaagcaatga taagctcatt tgatagtata ctacttgtca tatacattat tatagctttt    13260
gcagtagcta tggcaattat ctacttagta tttaaaggta tgactatttt actagataaa    13320
ctaatgatgt tattattaag taaaactaca ttagatgtag aagcttgttc tatgataatg    13380
gcagtcatca gtacaattgt gtttggaatt attgtacttt taatatggct agcagtaaac    13440
aatattttac tataaggagt tttattatgg attttaatga ttttataaac agtgaatcgg    13500
atagagtagg taatcctaaa caaagaaga aggtagagaa taagctacct tcttctattc     13560
ctattgaaga tagagaaaag aaattaaaag agataagaaa gaaatcatta tatattgatt    13620
taaggagaaa aagaaatgac taaagaaaca aatgtacttt acaaagataa gtatagagat    13680
tatactatag ttgtaagact agcaggtaat attattgtta ctgaggtaga taagaaacat    13740
aaaacagcat ttacacctat tatatttgac aatggtgtag aaggcgtaga gcttgtaatg    13800
cgtataggtt ctgtagagct tagcatgaca gatttacgtg agttcacaaa ggaagtatct    13860
acagctcaga aagctttaga atattttaat aaaaaacttt acattaaagg cttgacagat    13920
gaagcatttt aatatatact aaagtataaa ataaataaa gaaagagga atgattatta     13980
tgttattagg aatttttatgg tttatatggg gatttgtatc gtactttgta ttgatgtttg    14040
gaattgagtt ttgtaaagat agatggatgc caggtgttat cggagcagga gccttactac    14100
tattcttatt ttggattatg aaatctatcc ataatgctat gacagtagta tacttgtatt    14160
aggaggttgt atagatggat atactaatta ttcattataa agaaacaaat aaacgagttt    14220
taaaagaaac aatacaaaca atacaaaatc atttaaatga tgaacatggt ttggttaaga    14280
tgacagcaac aaaacttagc agagagaata tagagaaaag atttaataac tataatatag    14340
```

FIG. 21I sequence.txt

```
tcattgcaga agatgaccct gataattcgt atcattacag tgaagctgta gaagaagcag    14400
attttattat agacatacca atttcatatt tagatataca tgcaggagta gaatgggatg    14460
ttgataatcc tgtagatatg ctagatagga atccggattt tatagaagct gtaaataaat    14520
taaatgaaga cttaatgtta taaggaggaa atagaatgct aaatgaaaaa ctaaaaaacc    14580
tggaagatac aaaagtatac atgattaata gtattgcaag tttactaagc gcaagtacag    14640
gaaaatcaag taaagtattt tttgatgaag gaactattaa aattgtaagt ggtgaaacaa    14700
aagcagtaga agttattgat aacttagttc acccacactc aggacgttta cctattaaaa    14760
caacagaacg tattgcgcta ggtagattaa cagattcttt acagtttgtt atttcagaaa    14820
tagaagtagt taaagaccaa attatagatg aagaaaatga agcttacatt gattttgtga    14880
tggaagactg ggactgggat taatacctat ggacttatta actattgctt ctgttgcttt    14940
tatagctgta gtcattattg atttgattaa tgatgatatg agctatatgc ttactggtac    15000
tgcaatctta ataaatattt gggcaggatt ttatggatgg ttttcttac tacaagcagg     15060
tatgttactt ttcttactat tagctaggaa agttaaagat gataaggagt caatactata    15120
ctctagtgct tcattaatat gtgcactagg aatgataata aatcttcttt cattttctta    15180
aaaataagta ttgacacctt tgtacttttg tattatactt agtatataac aagtacagga    15240
gatgattaat atgagtaaag aaacaatcag aagacaattt caaacgcaa ttgagattat     15300
ggcaacaact aaggaatggt ggaattttcc taaagttttt aatacaagta aagagtttaa    15360
aattaaaact tttaaaaatg acacacttgt atttgaagtt agggaaggta gtagaaattt    15420
aggaagcttt gtaatttta caaacattga ttttgattac gataaactag aaggaacttc    15480
aacacaatat atgattaatt actttgctaa gaaattaact aaagatatgt ttaactatca    15540
taagttacaa ttatagtagg aggtggaaag atgagagaag agttaaaacc ttttaatagg    15600
aaacaagtta atgttaaggg ttacttagat gatgttaagt attcaaagcg tagaagacat    15660
aaaggtaatc aacatgggtg tgttaaaatc acagttactg atgtaaagat taatggtata    15720
cctattgacc acgttaacat tgaagttggt atctctttct acgaaaaact aaaggagctt    15780
caaggaaaga gaattcaatt tgtaggtact gtttataagt atgttaaaca tgctagaggg    15840
cgcaaaggta gaattaaagg attttataaa gaggattata gcgtaacttt agataagaag    15900
ttacaaaagg aggaaaaata atgattaaaa gaagaaaaca tttagaccac tcattacagc    15960
ctgagaaagg atggagaaca gtaccttta atgggtatta tgaagcgcat cctacgggtt     16020
taattagaaa taagtaacg aaaagttaa ttaaaggtac acagacaaga aagaaccatc      16080
ctaagtggac tgctcatgag attgtatact taattaaccc taagaaaaca agttattcta    16140
ggggagtagt tattgcacat acattccctg aaatgattag ccaatcaaga ggagacctta    16200
```

FIG. 21J

```
                              sequence.txt
agaacggtca tgtgtgtttt aaagatggtg accgaagtaa ttgtcatgta gacaacatgt    16260
ttattggtaa aggtaatgtt aacaaaaata tctataaatt aaatgattct tatttaacta    16320
gaaaagatat tgaagaggat gttaataatt tagttaatga aagattattc tctcaattag    16380
aattattgat taagaaaaat gaaccggaaa gaattacacc tagtaatcac tttattaaaa    16440
gagataataa tgtgttcagt atcacagatt tatctaaaaa ctcactagta gagtttgagt    16500
tagaaatcaa gaatattaag taaggtggtt atataaatga atgagtggta tgctttatgt    16560
tattacgaca aagtaggtaa aaagaaaata cctaggcaaa ttaaagctca cagggatgta    16620
tctgtattag aggatttaaa agatagatta gaagaacaaa atcctaaaga agaatacaag    16680
attaaaacaa caaaagaatt tgataaggag agataattaa tgttaacacc tcaacaaaag    16740
gattcattaa aagagcaaca aaaaaaatta agtaaaaaga agaaataagt cttgacaatt    16800
gagtatacat aggttatact taagttaaca aataaagagg aggtatgacc tatgttattc    16860
gtaattttta tattggcagt actgtttgta cttggattta tgaatggatg gaactcagaa    16920
gactagataa ggagtggttg taatgaagtt agaagataaa gtgttagaga gaattgattc    16980
tcttggaaat aaagcaggta acttaagtaa tcaagcaatg gagtcattag taaagtatca    17040
aattacgtac ggtattatag atattgttgt aagtatttta gttattgcac taacaatatt    17100
tttaggtaag gtttacctta aagaatataa gaaggttaaa atggatttaa aagaaagctt    17160
attgtatgat gactacgata ttctctcttt acgcaatagt tgcaggtata ccaactgata    17220
ttatgagatt aattaatccg gaagtttatg cagtaaaaga tttaattgag caagttaaag    17280
gaggaaattg atatgaagca gagagatttt gaatttgaag aggatttgt attaacttac    17340
gagtgtgagg attgtaagca ttttgaagac tggggtcatg atgaagagcc tgaagaatgt    17400
agtgaatgtg gaagtagtga cttaatcaat aatacaagtc atgaagatac tgagtgtgat    17460
atgtgtcgag gatatattga tatgtggcaa gatggatata gatatatggg agataataaa    17520
gagtatattg aaaaagagga atcaggttta atttgtgaag attgttatga gaaattagat    17580
atttaataag gaggaaatta atatgaataa agcagtagaa caagcaagta atgcattagg    17640
tcaaggattt tcagctatgg tatggcatca agtattagca gggttagggt ttatttatt     17700
aggattggta ttatctttac tggtttgggt attagtaaaa aaattccatg tacctttaa     17760
tcacccgaca gcttttgtag tgtactcaat tatgttagtt agtattgttg ctagttttat    17820
ttggggcggt ttacatgtaa ttaaccctga gtattatgct attttagaac ttaaaggttt    17880
tataaagtag gaggaattct atgactaaag aagagttaga gcaaaaagta aagaacttg     17940
aagcagagaa taaagagctt aaaaaacaaa tagaacgttt tgaagacgaa ggaggaaaaa    18000
caaaagatga acagtagaca aagaaaatt ttaacattaa cagtaagtaa cttttaatt      18060
ctagccttag atactgtagc actaattaga tataaaaaag gtaaaattaa acaagagaat    18120
```

FIG. 21K sequence.txt

```
tataacacag ggcaaattac aagaatgata gctacaacag ctaactcatt aggtattctt      18180
tacttagaag agcaagagcg taaagaagtt aaagatatta aagtaggtac ttttgaaatt      18240
ggagccttaa aaagatttac aaataataaa taaaaaaagt ttaagaaacc tattgacatt      18300
aggtttcttt tattatatac taatattata agaaataagg aggttaactt atgaaaggta      18360
ttatcatatt ttacaaggaa gagaccaaag aggatttagg atattttctt gggtttataa      18420
actttaagct agaaggatta tcttacacaa ctgaaggtac tttagtagat aatgatgtag      18480
tagttttaaa ggataaccaa attaatgagg ataatttaga gcagtttagt atgtcaaaca      18540
ataatttagt tattggaata ctaggtcatt catctctttc agtacgcatc tatgaaaaag      18600
gtattagaca agagtttgat agagtagaag aatatttaga ggagttgaga caataatgat      18660
atttatatta attttggtt tactatttat tttatcttta ctaggtattt ttatttattt      18720
tatagtttta cgaaagaaaa aacaattaat agaagaaaga gaatcatttg gtatttataa      18780
tagaacaaaa gaaaaactgg gtgatgtaac acgtttaggg tatgaggaag atgtatataa      18840
gttaatccat aaccaatcta ataaaacaat catagaggat aaaaagagta agttgtaga      18900
tacaattaaa aagatgtatg agctagaatt aacgtcagta gatgtttcta aggtagaagg      18960
attatctcca cttgatacag aacctatgac aaatatgaaa ttactttcat ataagctaga      19020
tagagaagga ttatatagtt taagtaaatt tatttaggag tgatacaatg gaatttatag      19080
ataaaaataa tgtaattaaa gcttatgata taccaaatgt ttatttaaaa ggttatgtat      19140
tacaggcatg tgataaaaat ggagatacaa cagcttatga tggttatgac caaatacact      19200
ataaagaagg tagagtatta acattccctt ttgataaacc attaagaaag ataaatgtac      19260
tatcaggata ttacaaacta tttaaaaagg aggacataat atgatttatt ttgttagtga      19320
tttacatttc ggtcatgata atattagaga attcgaagca cctacaagaa gtcactggaa      19380
ctcagtagaa gaaatgaatg aaggtttaat tgagttgtgg aataatacaa ttacaaataa      19440
cgatattgtt tataacattg gagacttctt tttcaatatg aaaccttcta agtagaaga      19500
tatacttaat agactaaatt ataaagagat gatactgatt gcaggtaacc atgaccataa      19560
gaaacttata aaactatatg aacgtaatgg tattacagta aagtacgcag acatgattaa      19620
aaaggatggt aagagatttt atctaagcca ttatcctaca ctaataggta gaaaaaacat      19680
gtttaatatt catggtcata tacactcaca attaatgggt actgaatatc acatcaatgt      19740
aggttatgat gtagagggta aaattgccta tagttttgat gatattataa gtagagcagg      19800
tgaatataat ggagaaattc aaggtaaag atttatataa aactagaatt agaaaacaaa      19860
caattaaaaa tttagttata aaaacagaga agctacataa taaacacgga aagtatagac      19920
ctattggtca tgtttattac tatccgaaaa caaaagagtt tactttatct aagcctgaac      19980
```

FIG. 21L

```
                              sequence.txt
aaaagatatt tatagagtat atgaaagaat taggtttttaa tgtaaaacac aggagacgta    20040
agaaaacact tattatttat aagaatgcat tcactgaata cattagtatg tatcatgaag    20100
caatagagca gattgaagga gggacataat ggaatattta tttttattta taggtattgg    20160
catgataatt tggggtttca tagcacctta tcttgcattt gtagtttact ataaacatgt    20220
aagagaaaat cataatggat tcagtgatga ggaatctcta gaagaggcta cagtacttgg    20280
tatgggattc atgtttatag catttattcc tataggtata ctagttgtaa ttgaagaaat    20340
taagatttta ttctttaag tgttgacaac tacaatatag tgtgttacag tataaaaaag    20400
gaggttaact aatgaagcat tttattttaa ttttagggat tgtaatccta gttattgcat    20460
tagggattgt aatcctagtt attgcattag gtattgtttt accggcatgg attttacagc    20520
tagtattatc tgcattcgga gttaaagtaa gtatttgggt atgtatcgga atatttattt    20580
taatcagtgc aataggaagt atgtttagta gaaattaaag gaggaattac aaatggcaaa    20640
atatgaatca aatattaatg gagagaatta tattgcaaca ccgtcacaag ctttaagaga    20700
agcactagca aaattaataa ctgaggaaaa gagctttgca gagtaccaaa ctaaaggtgg    20760
ggaacagtat gaatcacagt tacaactaag acactttgat gcaatgatat ctcagtatga    20820
ggaagctatt agagtactag aagataaata tagacctcag attttttattc cgaaagataa    20880
taaggaggaa aattaattat gaaagcagaa tcaatagcaa gatttttttaa tgacaaagta    20940
ttacaaatag aaggttataa agtaagattt ccgcaggcta gttcatctta tattttagat    21000
atagatactg tagatgaatc agtattgttt ttagacgctc aagtatctac actttcaggt    21060
aagcatttat tagatacagc tattacaatt gagagacctg aaacattaag tgctaaagag    21120
ttatatacag aaattagtaa taaactgcaa gctattgtag gagaccaaac taaaacaact    21180
atagaactat caagatattt taaggaggaa aaataagtgt ctaataaaac tattacaaat    21240
catttattaa atttaaaagg aataaacatt gaaacgtata gtattattgc tcgtatcaag    21300
aaacaaacta gttggggtga taaggagat tcttttgaaa taagcataag ttataaagct    21360
gataaagacc ctagaacagt gagatatatt acaactgaaa ttactattga ttatagtagt    21420
aataatccaa aagaaatttt attacaatta aaagataaga ttttttctat tgttgaggaa    21480
caggtagaga ctgacaatga ttttattgaa tctattaaag aaattaattc aactaaagca    21540
ttagaaaaac taaagcctta tatcaataat gaatattatt caatgtttaa atcttctatt    21600
gaaaaggaaa tacctgtagc tttatcttct gaagtactca atagatgtac aggtaaaaca    21660
agcacattag cttatttagc actagaaaag gatttaccct tagtagtgtc aaatgaacct    21720
atgagaaaaa tgcttaaaaa taaattccct caccttagag tatcttctgc tgaagattat    21780
tcaaattatg atattaaagg tgaaattgta ttaatagatg aagtagatat tgaccagtta    21840
tatagtgctg ataaagtatc tgttgatgca ctattagtag gtatcattaa aaattaaata    21900
```

FIG. 21M sequence.txt

| | | | | | |
|---|---|---|---|---|---|
| aatttataaa | tacctgttga | caacaggtat | tttttatagt | atactttaga | tataaagaaa | 21960
| aaggaggtaa | tataatgata | cctataatag | ttatacttat | tggactcata | ttatttttat | 22020
| ctagtggtta | taagttggta | ttaggtaagt | actatgatga | tgtagattta | aaaatactat | 22080
| ttaccatatt | tggtgttggg | attgcattac | tacttggagg | atttatatta | taaaggagga | 22140
| aacaataaat | gaattatgaa | gaggtactaa | gaactattaa | ggaaaataaa | ccctgtaaag | 22200
| ttagattcac | aggaaatatt | ttagcaattg | ttaatgagga | atttaatgca | gatactgata | 22260
| aaggagtttt | acagcttgat | gtatcgaata | tcaacaaaga | gggctatata | agattacagc | 22320
| aatattgttt | agaaagagat | gactatacgg | tagtaggagc | tatttttatt | taaggagagg | 22380
| taaatatgaa | ttatagagat | tttattacag | attgtattag | cggtggttac | aacgtacaca | 22440
| tcagtgttac | agaaaaaaga | gtgcacatca | tttctgagat | gacatcagca | tcttatccta | 22500
| aaaaggaaat | taacttagat | gaactacaag | cttatgtgta | ctatatgaat | aactttggaa | 22560
| gtcaaattac | aacggagggg | ttataaatgg | aattggttat | taatattgta | gcagtattgg | 22620
| tcggtatgta | tgctatttat | ttctatgtta | caaaatttag | tactggctta | tcaggtattt | 22680
| taattgtttt | agggatggct | attggtcttt | acttctactt | agactattta | aatgtcagag | 22740
| aaaatgttat | tcgattagtt | tcagtaatgt | ttggagcttt | cctatttagt | attgaaatga | 22800
| tttataataa | aattatgttc | gaaattaaaa | aaagcaatgt | tcagaagact | gttagagtgt | 22860
| atgataaaga | gcagtaatga | tttttaccat | aaagagtatc | taaattactt | taagtgctct | 22920
| ctatggtacc | ttaaaatagc | ttagaattga | aattaaggag | atgaatattt | atgtatcctg | 22980
| aaatagatgt | agaaaaatta | gcgtacaagc | taaaaagtac | gagagaatat | ttagaaagca | 23040
| ttaaaataaa | agaagtagaa | atttatgaaa | tctatcatct | taaaacaggt | aagttagttt | 23100
| ttaaaggtga | atatattgaa | gtaaaagaat | tactgaggaa | aatgtataaa | gagaatttaa | 23160
| cacttgtaga | tgtagataca | atgttaagta | ttggtaaagg | atttattgat | gtaattaaga | 23220
| atatatcagc | agaaaatgta | ttccaaataa | catataaaaa | ggagctctca | acaaaatgat | 23280
| taaaatattt | tcagaagtag | ataaagaata | caaacccatt | attactgaaa | agtttcctaa | 23340
| tggtgagatt | aattttaaat | acgatgattt | aaagtattta | gtagaagaga | acttaagatt | 23400
| tgatgttttc | tttaaatggg | aaaatgacgc | agatttaatg | catttgtata | tgtttactaa | 23460
| gtatttagag | caactaggta | ttaaagataa | agctgaattt | ttagagattg | catatctacc | 23520
| ttatagcaga | atggatagag | tagaagaagg | gcataataat | atgttcagtc | ttaaatacat | 23580
| tacagaattt | attaataacc | ttaattataa | atcggtatgg | gtagtagaac | ctcatagtcc | 23640
| tgtaacagaa | gaattactta | ctaattctgt | tgctattgat | gttacactta | aattattaaa | 23700
| tcagtatatt | gaaatgtccg | aagagcctgt | aacaatagta | ctacctgata | aaggggcata | 23760

FIG. 21N

```
                                 sequence.txt
cgatagatat ctatttgatg tagaacgtat cttaatggaa tctaatattg aatcatattc    23820
aattgtatat ggtgagaaga aacgagattt tgaaacaggt aagattaaag gtattaaaat    23880
aattaaagat aaaaatactt tatatgataa ttgtattata ctagatgact taacaagtta    23940
cggcgggaca tttgtaggtt gtaaaaaagc ccttgacaaa cttaaggtaa gtagtgtatc    24000
attaatattg actcatgcag aacgagcttt tgcagaagga gcattactta gctcaggatt    24060
taaagatatt attgtaacag actctatgtt ccctaaaaat aattgggaaa aagctattgc    24120
taaacataga gctagaatca acggaactga attacaaata aaagatatcg aaagatattt    24180
ataaaaggag aaaaacaaat tatgctaaac ccaactttaa tgtgtgactt ctataaacta    24240
agtcacagag aacaatatcc tgaaggtaca gaaattgtat atagtacatt agtacctaga    24300
agtaataaat attatgaaca cagtgataat attgtagtat tcggtattca atcacttgtt    24360
aaaaaatatt ttattgatat gtttaataaa gagttcttta acagacctaa agaggaagtt    24420
attaatgaat acaaacgtac agttaaattt acactaggac aagaaaatcc tgatgctaaa    24480
cacttagaac aattcatgat cttaggttat ttacctattg atgtaagagc tttaaaagaa    24540
ggtactgttg ttcatcctaa cacacctgtt atgacaattg aaaatactca ctcagatttc    24600
ttttggttaa ctaattactt agaaacgatt attagtactc aaacatggca agcaatgact    24660
agtgctacac tagcatatga tatgcgtaaa atgctagata aatatgcaat ggaaacagta    24720
ggtaatattg aagcagtgga tttccagggt catgacttca gtatgcgtgg tatgagttct    24780
ttagaaacag ctcaattaag ttcagcaggt catgcaatta gttttaaagg cagtgataca    24840
gtacctgtag tggatttctt agaatcatat tacaatgcag acgtagagaa ggaaatggtt    24900
gttgcttcta tccctgctac tgagcactca gtaatgtgcg caaatggtaa ttatgaaacc    24960
atggatgagt atgaaacata taacgtatg ttaacagaaa tatatccaac aggaattttc     25020
tctattgtat ctgatacttg ggacttttgg ggtaatatga ctaaaacttt acctagatta    25080
aaggatatta ttatggaacg tgatggtaaa gtagtaatca gacctgatag tggagaccct    25140
gttaaaatta tttgcggaga ccctgatgca gatactgaat atgaacgtaa aggtgcagta    25200
gaagtacttt gggatacctt tggaggtact gaaactgaaa aagggtacaa agtattagat    25260
gaacatgtag gattaattta cggagactct attaactatg aacgtgctca acaaatttgt    25320
gaaggattaa aagaaaaagg ttttgcaagt attaatgttg tattaggtgt aggtagtttc    25380
tcttaccaat ttaatactcg tgatactcac gggtttgcaa tcaaagcaac gtatgctaag    25440
attaaaaatg aagaaaaact tatctataaa aatcctaaaa cagatagtgg taaacgttca    25500
cataaggtc gagtagctgt atataaagac ggttcatggg aagataactt aaccttacat    25560
caatggctaa acaaacaaaa tgttaatcaa ttagaaagag tatttgaaga tggtaagctt    25620
tatagagacc agtcgttaag tgaaattaga gaaataatta aaaataatta ataaatattt    25680
```

FIG. 210 sequence.txt

| | | | | | |
|---|---|---|---|---|---|
| aaactcccta | ttgacaaagg | gagtttttta | ttatatagta | gggttatagt | aaataaagga | 25740 |
| gtgaaagaaa | tgatttataa | aatatcaaaa | cataattact | atagtaggtt | tgaatattca | 25800 |
| tcttatttac | ctgatgaagg | atttgcatac | atagattatg | tagatgtcat | tcttataggt | 25860 |
| gtagataatc | cgaggaagag | aaaagttatt | actttaaaag | cagatgagtt | taatcctagt | 25920 |
| gattttaagg | ttggtcataa | atataatatt | ataaaaatac | tatggtttga | gaaatgggaa | 25980 |
| tggttacagc | catagggagg | agaggtatac | aatgattata | gataaattaa | atggagttaa | 26040 |
| attagagatt | ggcggtcatg | ttgtatcatt | tagtgtaagc | aaatttaaaa | cgattaatgg | 26100 |
| tgagagacaa | ttacttgatt | accaccatat | caaaagacgt | aaacagaaat | attttagaac | 26160 |
| tactgaagaa | ttctataatg | agtacaaaga | aataaaaccc | gataagaatg | aaatagatga | 26220 |
| aatgtttgaa | tctttaggtt | atgtagatac | taaactagaa | gatgtagtaa | gaaaccaaga | 26280 |
| gaaagtgaca | gagatattag | gagttagtga | acaatactta | aaccaattgt | cttataaggc | 26340 |
| tatagaggaa | tatgtagaca | aaatagttac | cttagaaatt | aaagaattaa | aaggagaaaa | 26400 |
| atagtatgag | taatagttgg | gaaaagaag | gagttaacta | ctgggaaaat | gaagattgcc | 26460 |
| ctagagaata | cttagagaaa | gcatttatag | aattagttga | atacgtagaa | ggtgttacag | 26520 |
| taccatctag | agatgttcag | cagttgagag | aggataagct | tagagaagat | attggatttt | 26580 |
| atgagtatgt | agcagataaa | taaatacaca | tctacctatt | gacttaggta | gatacttatt | 26640 |
| atataatagt | atacaaggag | atgaagtatg | atgaatggaa | aacaaattta | tgtattttta | 26700 |
| agtgaccagt | atagtaaaga | tatactcagt | ttacaattag | gacttattaa | ggaatggtct | 26760 |
| agaagagaac | taacttattc | agatgatgtc | gggtcagatg | cagatgttgt | tatttgtact | 26820 |
| gatatagtaa | gagatgattt | cgtaaaaaaa | ctaagtaaaa | ataatagcaa | tgcattattt | 26880 |
| gtgtttatta | gttcttttta | ttggataggt | tataaaggcg | gagaattttt | tgttgcagtt | 26940 |
| caagactatg | tgaaaggtat | gtaagatatg | aaaaaattat | taatattatt | tacattagct | 27000 |
| agtactttac | tattagcagg | atgtacaccg | gataatcatg | aaggaaaagt | tttaggaaca | 27060 |
| ggagaatata | gagagccaac | tacttatatc | aagtcaggaa | gtgttactgt | accagttatt | 27120 |
| ggtgaaatga | aatactatgt | agatttagaa | acagataaag | gtgaagaccg | tgtttatctt | 27180 |
| aatagagaag | tttatcataa | atttgataaa | ggtgatgatt | tctctaatgt | aggtaaaaaa | 27240 |
| gtatataaaa | atgatgaatt | aatatataaa | ggggactaat | tagtatgaaa | caatttatac | 27300 |
| atgataaaaa | agatagttat | aatagtacaa | atcgtaattt | tgatattcaa | tattataaag | 27360 |
| gtataccttt | acaacaaatt | gataggggat | atggtcaagc | aagagctagg | agatttacaa | 27420 |
| taaataatac | gaaccaaaat | atatggatac | ctatgacata | tttaaaacct | aatggtactc | 27480 |
| ttaaaaataa | cattgatata | gattggatac | ttgttaaaga | aaaatgtagt | ttaaagaaag | 27540 |

FIG. 21P

```
                              sequence.txt
caggattagt aataaaaata aaaattacag gagatgtatt ataatgtata tattagaaag    27600
aacaattaga ggttttgccg gtcaaacaga agatatttta ccttattact ttaaaagtaa    27660
gaaagaaatt gttaattttt taaaactaat ggagttcctt aaagaagaaa caaattattg    27720
ggttaaaaag aacggtaatt atactattat aatcagggct aaaaggatat tatacattga    27780
agaacatata cagaagttaa aggagtggga gaatgactta tgatgtttat gtattatata    27840
aaagaggaga acctattgca caaggtagta tggaacattg cttagatgtc tattattggg    27900
aaagggtaca cggttatagt aataaaggtt atgaactatt acctatggga tatgaacagg    27960
aggaataact aatgataaat atagaacatg attatacaat aagaactgta gataatagaa    28020
agtatactta ctatagtaaa catgaatctc cagttacttt atataaaaat attataggta    28080
aagattgtat tgaagtaact aaatacggga aagataaaaa agttattata gctactaaat    28140
atattgtatc tattgaacga tggtaaataa ggaggtataa ctaatgaatg ctaggaaagc    28200
acgtaagaac actaaaaact ataaggactc taatgtagta actaaagagc aacacctaac    28260
ttatatttat aataagttaa actacttgat tgcaaataat agtagtcagg gtaaaacata    28320
tgtggtaatg aacctaagaa cagattatcc tgatgagttt tctttatcta aattaaaata    28380
tctaaaagaa attaaacagc actataaaga cctagtattt aatgtgaaaa cgcaagtaag    28440
gaaggcacag tggtcagaga aaagtataat caggtactac tttaacctag gctatataga    28500
cagcgtgtta gtacctatta tacacattag ttggtaatta caaggagagg tagttatgtt    28560
ttttaaaaaa aagaagttaa gcaatgtaga gaaacaaata agacaaaacc gtaataaaga    28620
agacaaagaa agaaaagaac atcaagataa gttagataca gatatgtata aacatatga    28680
attagataaa attgtagaag aacatttaag aaagttaaac actatatccc ttgaagaatt    28740
ataattaact tcagtgtgtt tagggacaag acttgtttat tattactcaa taggtaagga    28800
ttggaataaa caagtatata gtttaaacga attagaatat atgaagaaga aatttaagaa    28860
attaggattt gaaactcaga taacaaacga agatataggg tttcaacctt atatttattt    28920
aagattatta tgggatgcat aagtaattat tattaaagga gggatagttg gtgctgtacc    28980
tctaatgact attattattg cacagttaat tacagattat catgatagac attaagtatt    29040
gaatactgtt gactaataag gaggatatat taagaagtta aagttacctg gtaatattgt    29100
tgactagcaa gaagaagaaa atattattac tattaagtac ctgggaaaac ttttacctct    29160
ctcactcagc ctattactta ctaccgactt ccctaactac ttattctata gttataatat    29220
tcatttatta tacaatggta aactatagta ttccacctgt aaactatgct gaagcggtag    29280
taatctattg ttattatata ataatcttat ataatggtac gttaatctag tatattacat    29340
tagaatgatt ctaatctagg attttaatct ttagacccta ggaaaagtgg tactaaaata    29400
taaaacccta taggtatggg attcttattt ttaaaattac taaaaagtat taggttttcc    29460
```

FIG. 21Q sequence.txt

| | | | | | |
|---|---|---|---|---|---|
| ctagggcaaa | gttttaatgt | acctaaaata | gtaagtagct | ccttatcatt | tagggttcta | 29520 |
| taattgagaa | tattgaaagc | taatccgctt | caattgtaat | taattgttga | caactatgaa | 29580 |
| gtgggtatgt | tatacttagt | atataaaata | ataggaggaa | ttaataatga | atctgacatt | 29640 |
| tgaagataag | ttagaagact | tactaaaaaa | ggtacgtagt | ggtgagatag | aacctatcga | 29700 |
| gtactctcaa | gttaatgatg | agcaccctaa | tggtaaaact | acttgtggcg | ttacttttaa | 29760 |
| gtttgatatc | gacacaccaa | ctaaatagga | atatgaagcg | gttaattccg | cttctcttac | 29820 |
| ttagagtata | taagtaactg | tatattgtaa | gtaggagtaa | tcaaatttag | gagatgagat | 29880 |
| agatgataat | attatttacg | caggattatg | ataaaaccct | aatgaaagtg | atattagggg | 29940 |
| atattaatac | tatgagacct | aattggaagt | acagtgttaa | ccatcctgag | aaagaagagg | 30000 |
| atgttcatat | acaagcttat | gaaggggaag | atatatttga | tgatatagag | gagttatcag | 30060 |
| atagtacaca | ggatatagtt | ataggtgtta | ctgaagatga | ttgtatatca | gagtctcctt | 30120 |
| atgactttaa | tggtgggctt | agattagtca | ctaaacatat | taaggaacat | atagagaaat | 30180 |
| tcttataggg | agtgataata | tgattgatat | atacttagga | gaaggttata | ataagaata | 30240 |
| cttgtctaag | gcactcagat | taatcaatga | ccatgctcct | agggagttaa | gttatgattt | 30300 |
| taataatgta | gaagcggatg | ttaatattca | cacgatgtta | tatgttaaac | ctgaagatag | 30360 |
| gtatgtctat | aaggatatat | cttatgactt | cccgggtgat | ttaattattt | gtatagttga | 30420 |
| agatgatgct | attgtgtatc | accaaggtaa | acaggtttca | ggtattagta | ttttaagaat | 30480 |
| aatagaagag | ctcatttaag | aagcagttaa | gtaaaaaagg | ataaattgta | ctagaaaatg | 30540 |
| tataccgctt | ctgtatggaa | ggctgagagg | gcttagaatt | gaaaggggag | atataatgat | 30600 |
| agagatatac | cttagtgaaa | attatgataa | ggatttatta | aaagcggaat | taaaatggat | 30660 |
| taaggagacc | gcttcaagag | aactaactta | tgatgttaat | aggaatccta | acttagatgt | 30720 |
| acatgttagc | ccatttagat | atactaaaga | tgaagtaaaa | gaaataagtt | tacatcctca | 30780 |
| atttgaagac | gatgtatgtg | tatttatagc | ggagacgtgg | atacatgaat | accatagagg | 30840 |
| taaatcaata | ggcgtagata | gtatggaaga | atatgtaaag | gagatgtaag | tatgtttaaa | 30900 |
| gtatattaca | cagtctacca | taaggtagt | atgaaaacaa | ttaaagataa | gctagataga | 30960 |
| agtagtttaa | tatacttctt | gtatgatact | tggtataaag | atattagtaa | tgtattccct | 31020 |
| aatcactata | ataaagagtt | tggaagtaat | agtgatgata | tagacataga | taaacttatt | 31080 |
| gaagcggtta | atgaggaggg | tatattactt | atcaatagag | gtaattatgt | tacaataaga | 31140 |
| gaatggtagg | ataggataaa | cttaggatag | aaaataattt | aggatgagtt | acgataggat | 31200 |
| aggatacgat | aggataggat | acgataggat | aggatacgat | aggataggat | aggggttaa | 31260 |
| gttaggatgg | ttactttaac | atacactatt | attcataaag | aatctgatag | ggtaatagct | 31320 |

FIG. 21R

```
                                   sequence.txt
agtggtttag atgagttaga ggttataaac ttagttcaaa ggatggtaaa tactaatcta   31380
gttactgata tatcattaga tgattatata cgcagaccaa gtggagatat agatgtactc   31440
aatttactag tagatattag aagacaaggc gtatttgatt tcaatcacac ttggcacgta   31500
ggataggagg gataggatga tagttatata tacagatgtt tctaaggatt atttaaaaga   31560
cgagttctta ccttggctta atgaaggga tagatactta gaagactata aagatgaatt    31620
acctgaggat atagattcct cttatattgt atcagttgta tactgtaagg atatggaagg   31680
tctattagaa agaaaagaca ttgttattgg taatagctat aatgaacctg tagctttatt   31740
aggtgttcct gagttttttg gtaattatag taattatttc tactatagag gagaaagtat   31800
tagtaaacat gacctaggag aaaattgttag gttaaaagct tggcaacgta tgggcggaga   31860
ttgactaagt agctctccct aatttcacta agtagctccc taggaattgc ctaagtagct   31920
cggtatgatt ttaccctaag tagctccctc tgttttctac tagtttattt taaccgcttc   31980
aggtgtctat atatagacgg ttggaataat agcagaccgc aaaaataaat acactaggat   32040
attattccca gtgtattata taattttttt atttaaatct ttttatattt ctatttattg   32100
ttattctact tacattatac atatttgata attcttcttg tgtaaaacct ttttcagtat   32160
ataatttata aatattttt ctttcattat ctgttaatga tttaccacgt ttaaaattgt    32220
ttattgtttc atctttatga tgtaaattat tatgttctgt agggctaata cattgtaaat   32280
tatttatatg gttattttgt ttattgccat ctatatggtg tatatgataa tcttgattaa   32340
aatcattgcc aaaatattca tatactaaac gatgtataga atgatgttta taattaattt   32400
taactatttt atagccttgc ttatgattat gaggttttac taacttttca atcatataat   32460
aattaccgtg tctttttatt ctaccatagt tagatactga ataattaaat atattattaa   32520
tattattttc tatgcgtttc catttctcat taggtaaatt attaatacta ttataatctt   32580
ttaaattgta ttgtaataaa gtatcaattt taactttct tgccttgttt atatcatctg    32640
tcatacgata aaagttattt ttatctttt taattcctt atttgttttc tttgaatata    32700
ctttgttttc ttttatatag tattttgaaa acatttcaat gttatttata ttatgtttca   32760
tcttctcaac tccttaacta tattctacta tataataggt aatttgtcaa gttaaaaaag   32820
ttttttaaaaa cctattgact tattacttt tagggtgtaa tatagatact gtaataaata    32880
acacgaaggg aattgatgaa aatggaaatc aaagaaattg ccgatacaat tatgtattta   32940
tttaatatgg atggttacag atgtgcagaa cctccattat atgaaagcac actaaaccac   33000
acacgcacac acacggcgtt aattgtttct attagggaa actatgacac agtgcagatg    33060
ttccgcaaaa cgcctataat gagcatgaga gggcaaagcc aaccggctag tatgttagta   33120
aatgtaattg atgatgtaat tataatagta tatgaaaatg tagtgtacgg agttcaaaac   33180
aaagaaataa aattcattga agaaatttaa aaatagggt tgcaatcctc aagcatctat    33240
```

FIG. 21S sequence.txt

```
agtaatataa taggtgtagg ggatagcaac acacctcaaa aaaactttt aaaaagtta   33300
aagaaaagtg ttgacacctt ataagataca tgttattatt aagataacaa ataagacaag  33360
ccacttagca aataacgaaa ttaaataaaa aaattataga ataggatttg attattatga  33420
caaacaaaaa ttacttatac gaagaaactc acacagtaca agggcaagac attacggctt  33480
tcagaattcc aaacgacaca aacggcaacc cacgttatgt agtgcatttc atggatttaa  33540
atattaaact agcagactat gacaacatca ataaactata cggatttaat aaatatcgtg  33600
ctaaatggtt tggcggtggt gtagtattcc aaagctataa tatagaagat acattaaatt  33660
ttgcactaga taaagttaaa gaaatagaag cggttaagaa ttaaaaccgc ttctgaatta  33720
aataaaaaaa ttatataaaa aggatatgat aatatgatat tagaaataga aactaaacca  33780
gttaaaacat tgaaagcaat taaagacgat acaaaaaata ttaaaaatag tatagcagaa  33840
catttaggat taaatagaga acaatttaaa ttatcaaatg gtttaataac tttaaaaggt  33900
tattcagaag aatttaaatg ttggtataat ttaactagca caattggtaa ttttcctaaa  33960
tatttaaaat cagaattata taatgaatat aaattatatt gtaatgtaga attaaaaact  34020
aaataaatta aataaaaaaa ttatacaatt ccctaggatt agatttctag ggatttttat  34080
ttattttaat ttatataaaa aatttattta ttaaataaat tagtgtaaaa ttgactattg  34140
acaaggttgt atttttatg gtataatgaa gtgaagacct tttttagtat aaaaaaatta  34200
ttatataaaa aatttatatt aaatgatttt agaaccgctc tttctcgtta cctcgtcatt  34260
tatatagcgc aagggatagg caacttagcg ctttgtttta ctttctatat atagtatact  34320
atgaataatg gtaattgtca acacctttca gaaactttt ttactttctt ttattattat  34380
ataaaaaaat tatacatatt ttatggctcc acttccatta tataataatt cagtcttaat  34440
gtcaatagat aaatgtaaaa aagttttta aattaatttc attaaatcta ttgacttgtg  34500
tttctttcta tagtaatata taggtatacc aacaagggag gcaatacaaa tgctaaaatt  34560
caaatggaaa aacaaaacaa ttaaatcaac tcaaaaaacg gataacattc tattacttat  34620
tataggtggt ttagttgcaa caatcacacc taaacttgta aactggtttt tactactaca  34680
agataatata aatattttt taagataact attgacaacc tagaaacaac atgttaatat  34740
taagatacaa ggtaagggaa gcggttgacc gcttccaacc taaataaaaa aagtttaaaa  34800
aaactattga cagtcacttg aaaccatgat attattaaga taacaaaaaa caaacagaaa  34860
aggaattgat gaaaatgttc aaattacaaa ataaagtgga aattatcgta cctaaggaag  34920
ataacaacgg cgttgagatt gcagacaaac gtattaaaga atatgtaaac agtatcacaa  34980
tggaagcggg cggttgcact attacagaaa ttaaggggca atggtattca gaagatgaaa  35040
agcgtatcat ggaagataac aacttaaatc ttgaatggta ctacattcca gaccgtgcaa  35100
```

FIG. 21T sequence.txt

```
aattcatgac agttgaatta aaaggcattg taagacgttt aattgaagtt tacggacaag   35160
aggcaatcag tattaaagtt aatggcacat tgtacattgt agaccaatca gacattgaag   35220
aattacacac aacattatta aatatcatga aataaaaaat ttatataaac cgcttcggat   35280
taaattcttg aagcggtttt tttatgtaaa atttatgctt gacaaatgta ttaaaaaatg   35340
agataataga gtgacgactt tttttagtat aaaaataata ttatataaaa aagttataga   35400
gtttttaagg ctccaagtcc attatatcaa ttttgctact ggttgtcaat actttctttt   35460
tttatataat aatttaatta tcttaaagat accgtccact tccattatct caaattttcc   35520
cccaaagtca agaactttct ttcaaataat ttatttaaaa aagtttacaa aaagggttga   35580
cttattttgt actatagtgt aatatataaa gtgtagtaag gaagcggagg aaataaccta   35640
aaaaagaat ttaaaaaaac ttttaaaaag gtgttgacaa acttccaaat acatgataat    35700
attaagatag ttaaaaaaac aaaaaaacga aaaggaattg ataattatga acagattaga   35760
aatagtaaaa gatacggcaa tggaatatat ccttatgatg gataacagtg ttatggacgg   35820
agttatgaca caagaggaat acaacgaagc ggttagcttt gaaaaggtgt atgactacac   35880
tctatcagaa gcaaataaag aatgtaaatt cttaggcggt aaagttttaa cttteetagt   35940
acatgaagca atcgaagaat acgcataaaa aaacttaata aaaggggttga acattcaacc   36000
cctaccatgt taatattaat atataccaaa tgagaggaat tgataattat gagatacgaa   36060
attgtaacgc tagttaatca agaattgttt atgtatgcaa cattcaacaa gcaggaagca   36120
gaagcaaaat atagtgaatg gtgtgaactg tacggtcaag aaaatgtaag catggaaaaa   36180
aattaaaata agctgttgac aaactaaccg cttcatgata atattaaact atactaaaga   36240
aaaggaaatg atacaaatga aattattaaa ccaagaaaac caaatcgtaa ttagcatagc   36300
aacattagag agtgtcaaac aagccctaat ttgggaatac atcgaccaca tagattataa   36360
catctggaac aatgaacttg atgacacaga agcggttgta aaaatttctg gtattcttca   36420
atcaatcaaa tttgcagaca ctatggaaga cctgcaggaa tatattgggg atattggttg   36480
gaaattaatt taaagaatt tcaaataact gttgacacct tagcagatag atggtaacat    36540
tagggtagtt aaaaaatact aaatgaaaag gatttgattt attatgaaaa aaaatgttaa   36600
agcaagcact attgaatggt tagaattgac tcaagggcat ggggagtttg atggtttcga   36660
tgaagaagat atggacttca gaaaactaga tgatgaagat attaaatggt atttttgaaaa   36720
ttggtacttt acagaggaaa aacaagaaca gattatagac gaaataggtc aagaggaatt   36780
tgaagaagcc tattcagatg atattaaaga atacaacaat taatacagga agcacacaga   36840
gacacacaga gaagcttaac cgcttctcta atattaaact attaggagat gtttataatg   36900
acaaaattta aattgattga taaaaatagc ttttacgtaa atgacaatta caataacgaa   36960
acttatttaa cttctcaaat tgttctatca ggtgaagcgg gtagattgtt agatgatatg   37020
```

FIG. 21U sequence.txt

```
atagaagatt gtgaagacga acacgacaaa gacaattaca agaaactaga cactaacaat    37080
attgatgata ttgattatat attggaatgt gctaacgttt atatttaccc ttacaataaa    37140
acggaattta aatattaaaa taggagatgt tgaatatgaa cacaagacgg gcaaataaag    37200
cgttaaacga agcggttaga ttattagata agcaaataga agacacacag aagaccatgc    37260
aggagctaaa caaacaacta gaacaacaaa taaaagctaa acaggaacta atgacactag    37320
ttgacgttat gactggtgat gatgagtaat gaacattaaa gaagctcaca aggtcgttag    37380
gagtgcaaag agcaaactcc tgcaggagca ggagcacata acaaaccata tcatagagga    37440
ctacatcata gaggagcttc acagacgcac acagggaagc ggaacaatac agatgaacaa    37500
taacaccgct tcatatagca atggctcata tggtagctta gaagagctta gagaagctta    37560
tgacctatcg tcattatcta ctggtgagat taaagaattg cttgaaacat ttgtttaaat    37620
ttatttaaaa aagtttagtc aaaactattg caatatcttc agaatactgt ataatagtac    37680
ttgtaagata aataaaacaa agaaaaggaa tgattaatta tgaaagaaca aatcaaacaa    37740
tttgagaaag aattagaaat ggcggtaaat aacttattcg tattacatga ttgtggcgta    37800
tcacaagcaa agattgaaga acaaaaccaa aaagttgtgt accttaaagc tatcgttgag    37860
aacatgaaag cctacgaaga aatcagagtt gagccaaaga gtgaagagca atttttcaaa    37920
gaacttgaag aagaacttga agaagaagaa aaaattttaa aaggaattta agaggagggc    37980
aaacgccctt ctttattttt atcctattat ataatttttt tatattatac gggggcaggg    38040
gtaaaatgcc actcaatggg ggtgggtcta tatacccta cggtctaccc aggtacttat     38100
tttttggagg aaattatgaa aataaatatt taaaagtcaa caccctatat gataagtcaa    38160
cattataacc ctaccctgta agtcaacaat ttatagtata aataagaagc ccttaaatat    38220
aaagtcaaca tatctaaaat aaaaaaagag aagaatatt attcttcctc tgaggtatta    38280
ttaataactt ctaattcatg aatagtaatc atatcttctc taaataatgg tacatcttct    38340
atattatctt tataatagta agtatacccg tcttgaaggt atccgcttat ttttttcttca    38400
tagccttctg ctttaatacg tttaattaag ttctccttat ttgtgtaaac tttatcttct    38460
ctgtaagaat agttatcttc atagggttca caattatcgt gttctacttg atatagtttc    38520
atattagtta tcctcccttt cataagacca ttcaccgtat tctgcactaa agtgggctgt    38580
gtctgtaccc tcatcttcat attctacact ataccatgca tcttcttctg tttctgcatc    38640
tatatatctt acttcttctg tagtaataat acgttttacc ttaaatctct ccatttgttt    38700
ttcctccttt atattttcct ctagtatttg ttttaatgtt tggcagtctt tttggtctag    38760
agtatcccaa ctctctagat tttgtaattg ataaagtaac tcatttacaa tttcatcgaa    38820
ggcttctgct tttctatata cttcttctag ttctgtttct gctaattttc tatcccctttt   38880
```

FIG. 21V

```
                                  sequence.txt
aatttgttct gctttagtta ctaagatatg ggctttattc atttcctcta taataaagtt      38940
tttatagttt tccattatta tttatccctt ctattttcta tccgttgttt tatctcttcc      39000
ctattgcggt ggtgctcctt actcatttct ttacgttcct tatttgttaa ccttattcta      39060
taaacaaggt aattaatgta tagggtgccg gctgaccata gtagcaagaa tgttattaga      39120
taagtccatg agatactaat ttctatcatt gtgattcctc cttatctatt gtaaaggatt      39180
tacctgttct agagaatagt ttaaacattt cttcttcaaa atgcccatca ctcatatctt      39240
tatctttcag catttcacag agtttgtccc atgcttctgc tttattataa attgtttcta      39300
cttctctatc tgtttcatca ctataatttt catatataat ttgtaataca aaatccttct      39360
catcgtaaca tttttcatta atatcatatc tcattataat tcctccttat attctttata      39420
gctcttgatg gctatttac aaatacctct atttacagca acaaatacta taatgataa       39480
tagtgttata actgctctta catctcctgt aaaaggtaat aattggaaga gcaaatagct      39540
ttctaaaaca ctaatagctg taatggtagt tagatataat atagatagta agtaatcctt      39600
taattttagt ttaacaaatg gttttttgtg ctcatctgtt cttacaatac cataaagtat      39660
tataaaccac ataacaggta ctaactgtat aataaaatca ttatctatat tcaatgcatg      39720
tagagcgtaa ataataactg caggaatacc tataatgaat gctaggaata cagaaaatat      39780
aattaacatt atagggaggg ctacaagaaa acctagcccc tgttttgaat actctaatgt      39840
gttttacct aggaacttaa aaaatgtttt attcatcttc ttcctccctg gaattacttt       39900
ctgtaattgt aatttctaac atattattgt aataatcatt cttttgattg atattatagt      39960
tatcattgta ttcattaaag tctacataaa tatattcatt tgcgtcattt tcataaataa      40020
tatctatagc tgtaatatct gaatatgctg taatcatttc ataagcgttc gtattatcag      40080
gataagcaaa accaacttga ggtatttcca taggcttatc aataagaata ccaaaataag      40140
tacagtgacg tgttcggctt atatttgaag tctctttata tgtaccgtag taatctatac      40200
cttctgtaat acctgatata tggaacctgc ttacgtcttt agattctaat cttacaacat      40260
cgcaattttc taatactaaa tcaatatatt tgatattcat tttaactctc cttttatatt      40320
aataattctt tccattcttt atcaacctt ttaagttctt ttttattata gtctccatct       40380
ttagttacta cagtgttcca ttgaaacttc tgtaataagc taaaattatt tataatccat      40440
atattacttt tactataata catattatct tcaaatctta tatctttttc tataaaatat      40500
ttatatattt tatatcttct ttcatctgca cctgatattt taataatttc attagtattt      40560
aattgagtgg ataactggaa gataacatct tttactttca ataggtcttt aacattacct      40620
ctacctacat ggtcattata ataatcgtac ttaacttttt tcttttgttt tctatcatta      40680
actacaatga atatattata tacgatataa gctttaaaat gggtataggt agtaggtgct      40740
tctgaatcat cacattcttt tcttaggtct gtacattgta tttttaacat aatattattt      40800
```

FIG. 21W sequence.txt

| | | | | | | |
|---|---|---|---|---|---|---|
| gatatgttga | ctacggtaga | accatcatgt | tttttattga | gatttatctt | atccatttta | 40860 |
| taattaccta | cttattgtag | atacaatgta | ctcgaacatc | ttccattact | ttgcctaata | 40920 |
| gattctgacc | tttccagtta | ctttgctcta | atattttagg | gtcatttgct | ttaagaccta | 40980 |
| ctccccatat | tttatcataa | ggtgaagctt | ctacgaaatc | tttacgtaca | tctgtgtcta | 41040 |
| atattctttg | ctttaggtgt | gtagtcataa | atttatcttt | aactacttct | accataatat | 41100 |
| catatcttac | tttattccat | tgctcttcat | taaaattacg | aactttacga | cctaaacttt | 41160 |
| tagcatggtt | tggattctta | gcatttagta | tttcacctgc | tatttgaaag | tcattaaagt | 41220 |
| atcttgcttt | acgccacata | aaggcttgct | ctgagttatt | aaatgttctt | ccttgatgtt | 41280 |
| taaactttat | agggtagaag | ttagaataaa | tatcctcttt | accccaaaac | ataatatatt | 41340 |
| cacttgtttc | tctcataata | tttctccttt | aattccatag | tgatggtaat | acaattttaa | 41400 |
| aattatctaa | tattttactt | tgtacctgtt | caagctcatc | atatttatcc | atatcaaaat | 41460 |
| catccatttc | tttatgataa | tattttatta | agcttaaaat | atgttttatc | atatctattt | 41520 |
| gtgttctttc | tttgccgtct | acatctacaa | aagtatggta | ttccatatcc | acatggttac | 41580 |
| tactctctac | aaatgcgttt | aagtcagcgt | ataactggat | aaagaaggac | atgtcataat | 41640 |
| tccaatactt | aggctcattt | ctacctagtt | ttttcttcat | tttcttatat | tttttattct | 41700 |
| tttttagtcc | aaaaacttct | ttttcaaagt | catttaattt | aagacccttta | aaatattttt | 41760 |
| tcttcatttc | ttaacctcca | atttaataaa | tggaaaatca | atgtttctaa | atactgcgcc | 41820 |
| gacatcacac | attaatatgt | ctccattaat | ttctacttct | ccactgtcag | ttggtgtatg | 41880 |
| accacataca | taggtaaaac | catcttttct | aggttgaaaa | tctcttgacc | atattaattg | 41940 |
| gtcaattgtt | tgttcttcta | caggcttcca | actaacccca | cctgaatgag | agaatatata | 42000 |
| cttgtcttct | ttatagtact | ttctacaatt | aaccataagt | attttaaatt | ttctatagtc | 42060 |
| gtctgattct | ttaagtttct | ttagttcact | tttaataaaa | tcataattat | ttcttagatt | 42120 |
| ttcctctaca | ctactatatt | ttaaagttac | cgtactcaca | ccgtaagagt | taagtgtttc | 42180 |
| tatacaatat | cttgagagcc | attcaatatc | atagatactt | aatcggtcta | cgttttccat | 42240 |
| aatattataa | aactcatcat | catggttccc | taacagagtt | actacattat | catcattaga | 42300 |
| cattaaatca | aatatatagt | taacaacatc | ttttgacctt | ttacctctat | ctacataatc | 42360 |
| tcctaaaaat | actattgttt | cttcaggttt | tctttcatta | tttattttat | ccataattgt | 42420 |
| taataatttt | tggtattctc | cgtgaatatc | gggaacaacg | tatatagcca | tctaatctcc | 42480 |
| tccttattgt | atataactat | cttaccatac | ttagtaaaaa | aagtcaataa | aaaaacctac | 42540 |
| cttagtaggt | aggtaattaa | aattatttat | atgttaattt | aatttcaaca | tttttatact | 42600 |
| ttttacgacc | atctgttcct | gttgactcta | gtgtaagaac | agatacaaaa | tctttaacct | 42660 |

FIG. 21X

```
                         sequence.txt
ccggtgttct gttattagtt gtaccttccg ttgcagtagg tactgttaac cagtaagggg    42720
agttagatgc taagcttgta ttattaacta gtgttttgcc attatattct aacttagtaa    42780
cagacttacc tgttaaatct aacttagttt tatctatatt aatcatgaaa ctttggtctt    42840
ctttccagta tatagctgtt ggtgtgaatg ttgctgtata cgtaccatca ccattactta    42900
caggtgttat agttcctgat gtatctcctg ttggtggtgt actggctgta gtatctttgt    42960
aacctacttg agtatattcc cctacaatat tagttttttgt tttatctaca tagataactt    43020
taatgtaatc tctcataaac tctagtcctt gagcattatc atctatagtt atgaaagcat    43080
ttaagaagtt ttgaacttcg gaaattctat tatatttgtt accatcttca taagcaggta    43140
aagtatacca gtaaggtgaa ttagatgtgt agccttcggg gtttatcaag ctcttaccat    43200
tataagaaac atttaatatc ttattagcag ttaagtctat atcatctgta ctcatgttca    43260
taacaaagct tgtatctttc ttccatctca ttccagttgg tctgattaat ttagaataaa    43320
caccattacc taaatcctta acagaagtgt caatagatgg tgggcttgct atagcaccta    43380
cagtaccttt actttctaag aatgattgta tagtgtatga tataaattca tgacctttag    43440
cattaggatg taagccatcc tccatgcctt ctttccaagc aaagaatgtt ttatttacat    43500
tgttatccca tactctaata ttactctccc tatataagtc taatacagga aatgaaaatt    43560
gttttgctat ttcttttata acatctacca attgtcctaa agtatatcct tgtccgtttt    43620
caacttcttt aaaaggatta ctttcaatcc taggtgttgg tgttagaaca acaataggta    43680
ctgtaggaaa aaccttagat agttgataat aagtataata gattgaacct gctactgtag    43740
tgtaagagtg ttctttagct gttcctaggg gttttgtttt accccaact aaaccatagt     43800
catttgtacc taacataacg caaattaaat caggtttatc tgtaatagtg taggctacgt    43860
ttttacggtc ttggtagcct gttccacttg tacctttatt aacatttatt aatcctgttc    43920
tgtcagcaat aaattggtgg tagttttttg ttgttcttgc atttacttcc gtaatactat    43980
ctcctatgaa tataactttc ttatctttca aaggtgagat agttgttgta cttggttgtt    44040
gtgttggttt attatcagct ataagcttat ttatttctgc cataaattct tcttttatat    44100
ggtcgttaaa ttgggtatct ataacatcct gtaaacctat aatattttct gcttttatat    44160
tcataggttc tacttcatta taagtaacaa taataagttt gtcctgggat gatgttaagg    44220
taacaaattt tggtatatct acttttattg attcttcacc attaatatcc caacaaattt    44280
taaagtgccc tgcttcgtat gttgtatcag gatttaaatt ctctataact atttgaccta    44340
ttgaatcttc tatgttttca cttgatttta aaagattatt ttcatagtca taaagcttca    44400
atttcttagt catatttact tctccttttta ttgaattttg tacaactata atatatcaaa    44460
aaaaatttaa aaaacacct atttaactta aataggtgtc cgacagagct cccgtactta    44520
gattacggtt aataatattt tacgacaatt atatgagacc ctctgtcgtt gaaacgctcg    44580
```

FIG. 21Y sequence.txt

```
tcactgcgtt atacctcaca agatattttg acagttagct tgtgagaaga agattgtttt    44640
ttattgtact tagtttatac actctcaaaa gtacatgtgt actatatatt tatacaccaa    44700
gcgtttggtg ttagatacgg aatggaggga cactaccatc cggagtctac ggtcagatac    44760
aaagcctctg ccgggcaaca tacggtatct ctcgtacatc aggttgacta aacctttaga    44820
gcttttcact ccttctctta taaccagtaa cttaagagaa ataggtttta cttagtagat    44880
atgaaacaat aaatccacat acaatattaa atcatagtca agtgattgca catatgtcta    44940
atacctataa gttttctgct agcctggtat atggactctg caggactcga acctacagtc    45000
aaaccgttat gagcggttgg ctttaccttt aagctaagag tcctagaaat atcctgagag    45060
aggactcgaa cctcaacgac taggtagcta catctagcca atgccattac tcaggattgc    45120
tagtaacgct aaatagaatt ataacgttac cgtagacctt ttctacgctt ggtagatagg    45180
taaaatataa tgatttcaaa gtacccatat agttaggctc ttactctcat tatcaggtta    45240
aaaaggctaa ctgtatttag cattatataa gaggctttag ttaactacta tactaataat    45300
ataccataaa ttatacttaa tgtcaagtta atttatcaat tgaatctata atttttgatg    45360
tgctacgtat atccgcttct ctactatgtt taaggagata ttttaatttc attaaaaaag    45420
aatttttttc tttttctata atatcttctt tatcattgta ttctgaaaac ataatgaatt    45480
ctatacctat actatttcta ttatgtgaaa acatatttat agaaaaaggt gaatcaaaat    45540
ttttatcatc tttattaata ctaaagtctt cagtaacatg taattcattt atttcagata    45600
ttcaaagta cccattaact cтттттaagтт caagataact attatatcta aaataacgct    45660
gttcttctat taacttctct tttgttagat aaggatactc atttataaat ataggattac    45720
ttgttccata gttatctcta atatattctg cgtcctctaa agaatcagta taacctaaaa    45780
cttcataact tgttgtatac actgtatctt cttcccacaa gtcatagtcc atttcctcta    45840
tttcttcttc taatatataa aтттттттcca tatattactc ccaaatacca ataagattt    45900
taagcttagc tataacctct тcттcтgтттт gataagaaaa tacccctgta atatgttcat    45960
agttacctac aatttcataa tcttgtgtac catgtttatc tactaagtat gagttattca    46020
taacatttaa actatcttct gagtaactaa aatttatgtt atagtctact aaaaaataa    46080
тaатaтттттт catttacata acctctccta tcggatattg tcctagcatt ctgtccat    46140
тттcатттaтa aaaagtatat tctactacaa taatattcat catatctaca тaтaтagcттт    46200
ctatatatgg tgtaatattt tcctcttctt gtatgtgctt acctatgata tcatataata    46260
attctgagtg tattctttta tctctcatta tagacctccg taaggaatgc tacagttttg    46320
tctttcaaag atttttctac taatcccata gcatctttat agtgtttgat atagatcca    46380
ttatacttaa gтттaтcтттт tactccttga attagaggct cтacттттaттт aaccaaatct    46440
```

FIG. 21Z sequence.txt

```
tttttctttt caatacttac attgcttctc ttattgtcta atacttcttt tggcatatat    46500
ttaacttttg caaagtcttt atagctaaca tttaagttat ctaaatcatc taataaatca    46560
ttatagtatt ctaaatgatt atagaatgta taaaacttaa caaggtcttt accagttaat    46620
tctcctttt  ttagtatgtt attaatatta ccgataaccg aatatgctat aggcttaaaa    46680
ttagctctaa cataagttaa aaatataaaa tcatcataaa ataaatctaa aacagtttta    46740
ttaaatctag tatttttagc ttgctctaat tgagcacata aattaagaac attatcaaac    46800
ccactttta  gcactaaaga gataaatctt tctactgcat agtatcttga tacttctgta    46860
tgcttacttg cttttcatt  attcctaaat atagtatctg ataaaggttg aacaactaaa    46920
ctcatgtaat ctttatctga atgctcatct gatgttcctt gataagtact tccaaattct    46980
attgttgata ataagaaact tttttctagg ttcattataa catcctcctt ttatttgtta    47040
tttaaataat aacatatatt gataataatg tcaatactta tatatcttct tctgtatcaa    47100
cttcatcttg tttatactta aagtgttcat agactttaaa tagtataatc cctagtgtta    47160
ttaatcctaa aatatatttc atagtaatcc tccttaataa ccatgtttag ttacccatcc    47220
tgctaaagca tccatagcca tatcatattc ttcttcattt ttaattctta taattttctc    47280
tatttcttcc tttgctttct tagaactaat aaaatcaata tcagtatcct ctaggttagt    47340
taattctaaa ttttctctaa taaaattctt ttgacttggt gttatagaat taactcttac    47400
attttcgtga tttagaaatt ggtaaaagtc catattactc atccttttta acgtattctg    47460
ccatatcttt taaaatactt agtacatact ctaaatctct atattggtca tctaatgacc    47520
ctataatagc atatggtgtc atatcccagg catgtgcaca gtcaaaccct aatactctct    47580
taccctcata gtcataatca tcgtaagtga tacctctatg agcacgtctt tctaaggagt    47640
catattcttt ttcattgata tctgaaggta aagttatata tccatttaga tgaccagttt    47700
cagggtgtct cttaacagtt agtttaactc ctttataata aatatcaaga cttaaatctt    47760
ctcctagaat attgttttct ttttctactt tttccataat gtattgaggt gcttttttaa    47820
acataatcag tcatctcctt tttatttata tctttactat acactatttt ttctattttg    47880
tcaacaaaaa aaggctacta attaaagtag cctaaatact aattatttag cattgtattt    47940
ccattgccaa taaccatttt tctgtgagaa ctcaaagtga aaaccatcat agtcaaattc    48000
aatattatag tctccatctt gaagtggttt tgaatttagt acaggactat tactctttgc    48060
caattctgct agaaactcat gatttacttt ttccataggg tttactcctc ctaattattc    48120
ttacagtact aatatatcat aggtcttttt ctaagtcatt tttaaaagtt tcctcgtagg    48180
aactagcgta agtaacctca taacccacta cgttagtata tcctacatat aatgacttat    48240
aattagattt tatcttaata tcttctgatt gttctagctt atttaagact tcatttaaat    48300
catctgagga atagtgttca ttatctattg ttattgtttt tccttgggta tagatatcaa    48360
```

FIG. 21AA sequence.txt

| | | | | | | |
|---|---|---|---|---|---|---|
| tttcttgtat | catcatttca | tcctttttgat | tattcattat | ttgattataa | gtttctaaat | 48420 |
| catcaatgtt | atctgtatct | gaacctttta | ctaaccattc | tcctctcttc | ttaaggaggt | 48480 |
| catcaaactt | ctcatgctct | ttaattatct | tttctacctc | acttggtatt | aacacagccc | 48540 |
| tagcatagtt | tatatgccac | atagacatat | tatcaataag | ataattaacc | attcttataa | 48600 |
| tctctttttc | atttgccata | taccaacctc | cttatatcta | ttattaatat | aagagaaaag | 48660 |
| cagacttatt | aaaagtctgc | ttctttacct | aattctaatc | ttctatttttt | catatgagga | 48720 |
| atcgttttttt | tatttcctgt | taataatgat | aattctctag | cttttttcttt | agataatgtt | 48780 |
| agtagtccat | tataattatc | tactttacta | ttatattgtc | tgactaagta | ctctagttca | 48840 |
| tcttctatac | ctgctagttc | tcctgattta | actccaagta | actttctata | catgtcataa | 48900 |
| tcttcagaaa | gactttctac | tttgttttta | gatacagaat | cataaactgc | ttgtaaatta | 48960 |
| ccttcttcaa | taagtttaaa | attatattca | ccaatgatta | attcttttttc | agaagagtca | 49020 |
| agggtaacta | aaccacttgt | attacctgta | aagtcacctt | tataatctac | aacaattcct | 49080 |
| tcagttattt | tatctcctaa | ttcaatagtc | ccatcttcat | tttctttaaa | tttatgagca | 49140 |
| tcataaactt | ctactttgtc | acctaatctc | aaatcttgag | ttaagttatg | tttaccgata | 49200 |
| attctatcca | ttacttaacc | tctcctttat | taatagggtc | ttgtgttaag | aacatttcta | 49260 |
| agttctcttt | tgtaataggt | aaccaaaaat | atttactttc | cggaattgta | actgtataga | 49320 |
| agtcttcatc | attattaact | ttgatgttaa | catctgtaaa | ctcatcttgc | attaaccaat | 49380 |
| gagttacagt | taagttatat | gacccatcac | taacataccc | taaatcaata | tcatgtctaa | 49440 |
| aagccaaatc | ttctaaatgt | tctaataaat | cattcttttc | attatgtttt | tcttcttctg | 49500 |
| tattattttt | aattgggtta | attaactctg | tacaaacgat | atcgtacaat | tcaccatctg | 49560 |
| taacctcata | gttcttttca | attaatacat | cttgtatttt | attgattgaa | tttgtaacta | 49620 |
| ctttcccata | ttcttcttct | gtaaatttac | atttatctaa | atcaacatct | gtaattaatt | 49680 |
| ctgcaatcca | tttatttaaa | attgatactg | ccattgttct | agaaataata | ctatcgtata | 49740 |
| ccatatttat | ttaatctcct | tatttaggtg | aatgtggtct | tctaatgaaa | aatcaaaagg | 49800 |
| cgctacacca | tttctttttat | tatttgtttc | ttttttaagt | ataacataag | ttagtgaaaa | 49860 |
| agtcaagata | gttactacag | ctattgataa | aagtttaatc | gggtttttca | tagttactct | 49920 |
| aactccttaa | gtttattttt | tactttctct | ttatcgtact | tataatcttt | actagagttt | 49980 |
| tcatttttttt | ctttctcttc | ttcattaagt | tctctatact | gagcttcttc | tacctcttgt | 50040 |
| tctttattat | cgttatttttc | ttctgctttt | tgaatttcta | cattttttact | attaccacca | 50100 |
| tttaccttttt | ttctaaaaag | aaaccaaagt | attaataaaa | tgatgagtaa | aataataatg | 50160 |
| cttaatacaa | cagcccaaat | attattagcc | attacaacct | acctccgaat | agttttttta | 50220 |

FIG. 21BB sequence.txt

| | | | | | | |
|---|---|---|---|---|---|---|
| cagctcttaa | attttcagat | gaatcgttat | ttatatcaat | ccctacgcta | gaatcaaaaa | 50280 |
| ttacagcatt | atcaagtata | tgctctgtta | atttattacc | ataactactt | ttacttacca | 50340 |
| cactaccata | accatgatta | gttaggtcaa | ccatatcagg | ttcaacttct | agtactctaa | 50400 |
| aagatattct | acgtaagaat | gaaggattta | ctaagtaaaa | ggaagattta | aaaacattta | 50460 |
| atctttgata | agaatgtttt | atattaacaa | caaaccctgt | taacttatct | tcataccctg | 50520 |
| aatttgataa | tttacctaag | taaggttta | tactatatcc | ttttgtttct | aatgtttgaa | 50580 |
| tagcacttaa | cattatagca | cctctataag | caagattttc | agggtcttcc | ctccaactaa | 50640 |
| tactagaatt | ataaaataca | tcaataactt | tcttctctgc | tttaactctt | tgctgagaca | 50700 |
| tcatagaatt | aggtaatcct | tttatagcat | taggtacgtg | aggttgatat | ccttccggag | 50760 |
| ctacgacagg | ttttcttttt | actgacttat | ccattctaaa | taatgcatct | gtcattttt | 50820 |
| taagtttaac | taccatatca | tatgactctc | tatcacccct | aaccattaag | ttataggctt | 50880 |
| cttgaaaact | atgagtccct | gtaaaatcat | agctacctgt | atcggatgaa | ttatctctac | 50940 |
| ctgaaactct | attcttttt | aaagcagaaa | agaaatcagg | tagaccatca | tatttaatta | 51000 |
| catttaattc | tgagttatct | attaatcgtc | tacccattga | tttgcctcct | attctaatcc | 51060 |
| taatttatcc | ataattgtat | caaaatccat | tgaatctttt | gatgtactat | cagattttct | 51120 |
| aggttcctgc | ttaggctctt | gttgcatacc | taaaagcttt | cttgttgctt | ctgtgtatct | 51180 |
| gttaccttca | ggtaaagagc | taataaattg | attaatctca | tctttcggta | cagatttaaa | 51240 |
| gataatactt | tctacaacaa | actcatcttc | cattactcca | tctaatttac | taccattaat | 51300 |
| aattgcacgc | attgagaata | cataaggtaa | tccttttttca | tcattctcat | gtcttaattg | 51360 |
| ttgtacaaag | tttactaggt | cttcattgct | tgatagttga | tgttccacct | tagtatcata | 51420 |
| gtcaaattca | acttgagcaa | agcggtctaa | tgtagctccg | tctaattgtt | gtctacctac | 51480 |
| ataaatatgg | tctgctcctg | ttcccatagt | attacctgct | gacacaactc | tgaaatcttc | 51540 |
| atgagctgtt | acacgtccaa | tagggaagtc | aaagtattta | tttgcaatag | ctgaattaag | 51600 |
| aattaatagt | acttcaggaa | tagatgcatc | catttcatct | aagaagaata | acccacctttt | 51660 |
| tgtaaatgct | ttatagaatt | gagtttcatg | aaacttacca | tttgcatcaa | taaatcctgt | 51720 |
| taatttaaat | tcttgcgtaa | ttgcattact | aaaatagaaa | tctaaatcta | gggcttctgc | 51780 |
| tacttgttcc | aatacatggt | tcttacctga | acctgctcca | ccttttaaaa | atactggaat | 51840 |
| attttggtta | actagcttta | gtatatcttg | gtatctataa | tgaaagattc | ctgagatatc | 51900 |
| tttaattgtt | tttccttctt | gttgtaattc | aattttaact | ggtaaattac | taagttgttc | 51960 |
| ttctacatat | tcttcaattt | gttttttaac | gtcagtaata | ataatttctc | tactctcagt | 52020 |
| tcctgctttc | tcaacaattg | catctacaat | tgcttgttcg | tacggattag | agttttttctc | 52080 |
| tcctagtttt | tttgctaaat | ctgctgttgt | ttccatttgt | tgctctacca | atctctctaa | 52140 |

FIG. 21CC sequence.txt

```
tctttcaata gtatcttgct ttgccatatt tatcattctc ctttgatttg ttatacattt    52200
attatattac aagtatttga atttgtcaac aactttctaa aacttttttt agttgctaat    52260
aaaaaaatac cttacaccta taacttaaca tagggtaagg taattgtcaa cacttttgtt    52320
aaaaatacat taatttaaaa aaatcatcaa tatctttagt ttcatgtgta tccatatcat    52380
acataaacat acaattatat gtatgattat tcattatttc taacatgtta tgcatagaag    52440
ttgcattatt gaattcctct aaatcaatag ttaccgtaag ttcttgacct tcataaagta    52500
tgtttgctat ataatatttc ttaacacctt ccattgttcc atgagaagtt tcattatgat    52560
taagtacttc tacacctagt gaaggtaaat attctgaaaa gtaatattta cagaaatata    52620
taaaattgtc tgttctttta gacacgagta ctatctccgt actttatatt tctttctaat    52680
cgtacataat atgttttaat ttttgtact tctttatcta ctgcatcctt tcttcctaac    52740
cttgtagtat attttacaat attaaatatc atagaatcaa caaagccatc ataagaaaaa    52800
tgttcttcta gaaaagaaat aacatccttg ctacctttat agtgctcagg taaatgtgca    52860
tctacttgta tattataata attttctaaa agacctatac tctcaccaag actagacaaa    52920
gcgtaaccta aatcatttga atcattagac cattccttag atactgatag tgcatcttct    52980
ataattgtta cttttaattt atctaaataa tcttctactt gagcttgtgt tttcataaat    53040
tcttttgcgt tcatgtaata ccctcctaaa ttatataaaa aaacaccctg cttggctaca    53100
agcaaggtga aaaaggaaag atattatgga agtgtactat ctaagtacac ctcataatat    53160
aacagttttc cttgctagtt attacttatt ttttaaggtc ttcttctttt acaaacactc    53220
cattaataag cttacctttt ctgtctttta tctcatcata agccatatca atacactctt    53280
caatatctat atctaactgt aagcatagta ctgttaatac tacaaaaata tccccaacac    53340
tatctcttgt tacatggtca ttacttttag caatacctga agctaattct cctgcttctt    53400
ctaataattt tagcatttga ccctcgggtt tacctgtttg taagtttcta tcttttgccc    53460
attgtttaat aagttctact ttttccatta ttctatatct cctttaatttt ctgtatcttt    53520
gataattagg ctatcagagt cacttgttac atttaaatta tcttcaacta attcatgtaa    53580
attattagta atatcttctt catacctata acctacacga ataagctt taactctgat     53640
atctatatta acataatctt cttggaattt ttccattcct aacttccttt attgtatcat    53700
attattatac tattgtcaat taatctgagt agtttccttt agcaagttga tactttttgt    53760
gtaattcttc ataattct ctcatacctt cgtagtttct catatcatct tccaagaaac     53820
taagataatc taataatact tttacatcct caggttctaa agttataact ggttttacca    53880
ttaggcaacc tccttaaatt cttctttatt tattttctta atatctttt ctaatgcttc     53940
ttttaattca ttaggtaatt tataggcatc aattgattgt tgttgcccta gtacatatcc    54000
```

FIG. 21DD sequence.txt

| | | | | | |
|---|---|---|---|---|---|
| attatctgta | atacgtattt | caactgtaaa | ccatgaatta | tctaaatctt | cttctagtct | 54060 |
| tgctaacaat | attaagcaac | tgttctttat | aattcgatta | gcatacccgc | caacacaatg | 54120 |
| agatagcatt | ttaccttcat | ttttcagttt | acttacggta | tctgcaggaa | ggaattttac | 54180 |
| ttttctacca | tctttaatt | tataagtttt | atcaattatt | ttttctaatt | tattttcata | 54240 |
| tttagattta | agctctgcat | catctaattg | ttgttgaata | gattgtttct | cgtctgtaac | 54300 |
| tatatcatgt | tctaatttta | gagagaatgg | tgttaagtta | acactttcta | atgttctata | 54360 |
| accttctcgt | attaatattg | ataaatcatg | aagataatct | aaatagtagc | tatccagtgc | 54420 |
| atatcctgtt | atacgttgtc | tatcttgagc | atctacatct | aaataatgag | tcattttttt | 54480 |
| gtaattagca | aaagatatag | ataatatttc | atttacaata | ggttttactt | ttaaagcatc | 54540 |
| tgtaacattt | cttacatcct | gaaccattaa | aaatgtatca | tcaaatagtt | gatgtagatt | 54600 |
| aacttcattg | tgtaaatgat | tatagtaatt | atacaatgta | tctgaaaatc | ttaaataatt | 54660 |
| actctgttca | aaattattta | atgttagtaa | tttttatac | gtttgctttg | taagattaaa | 54720 |
| tgcttcatgt | attttccact | taggatttt | aggtatatga | aatagtaatg | aatttctttc | 54780 |
| aaataattca | aattcctcta | agttatttat | tttgtcaata | tttttaacaa | tatctgttaa | 54840 |
| gattgttaag | taattagaag | ttgaattttc | tcctttgagt | ggtttatatt | tgtttcctcc | 54900 |
| ataatttaca | cgcccatata | catcaacctc | atcaaggcac | caactagaaa | gtccaaaacc | 54960 |
| atcatttctt | aatgtttctt | caattatttt | aataataaca | ttcttactta | aattaggtgt | 55020 |
| tgaataattt | tttaaaataa | catttaataa | aacagccaaa | tttaattcat | ttttatattc | 55080 |
| actttactta | atatcgtctt | tgtatagatt | taaagttatt | tctttattaa | caagactgtc | 55140 |
| tgttaagaaa | accttaactt | ctcctgtttt | aacatcaaat | gaacttttat | tttctaaaac | 55200 |
| ccatctattt | cccatattat | atttatctct | aatgtgtcta | actttaagac | caaaagatga | 55260 |
| actattctca | gtacttggat | gcatgtacca | agtactactg | tacaatgaat | ctgatatttc | 55320 |
| cttataatac | ttactagagc | cttttctgt | atcttcatta | agtctggaag | taatagatga | 55380 |
| ctttattaaa | ccgtacttac | cttggtataa | gatatccata | atatcattat | tcaaactatc | 55440 |
| tactacttcc | ttatactcat | ctaattgtct | agattcatac | caccttaaac | gggtttcatt | 55500 |
| ttctaattct | ttaattttt | cttctacata | acctttagat | tttatttgtg | ttatacgttt | 55560 |
| actaccatat | aaaggaaatt | cttttctttc | ttctctactg | gatgcaatat | attctttgta | 55620 |
| acttcttcct | ttattttctt | caattacacc | ttcaactaat | ttttcaattg | tttcataagg | 55680 |
| attacctgta | aagtttgtta | cttctttatt | accacatagt | gctaagaata | aatgtatttc | 55740 |
| tgtagcagta | tcaaaactaa | atatattatg | aatatctcta | aatagttcct | tagagcctaa | 55800 |
| gttaattata | ttattttttct | tcttcttaag | gaatacatct | tcttctccta | tatagataca | 55860 |
| tcctttatta | actttaggta | aattaataat | ttcttgttct | gttaatcctt | tttgtttata | 55920 |

FIG. 21EE sequence.txt

```
tgttattgcc atttaaaatc actccttatt tgttatgtac taatcatacc atagtaaata     55980
atatttgtca acaaaaaaag aagaactttt taaagttctt ctaagtgagt ttcgtagata     56040
accttttgaa ttttatttaa tggtttcaaa tctaaattac gaataagttt ttcgtacttt     56100
ctagaattttt taaaattgat agtatttggc atagcaagag cctcatcaat gtctttagta     56160
tagcttataa catctgaata aatatctact tcttttacat atagaccttg agttaaactt     56220
ttaaatacta cctcattatg tgctacaact tcttctttct tttctatgct cattttgta      56280
aacctcctgg tctattctac acaaacaagt acgtactcta aactagttaa tgttactgat     56340
ttaatattat ttaattcttg taatttctta atatctacac catagttttt acttatagtc     56400
cataatgtct ctcctgctct tactttatgg taatacttat tcccttcttt aataaggtca     56460
ttcaatatta cctacctcct tgagtaatag ttagcttgta gataacatat aagtataaga     56520
acaaagttta caaattcagt agctataatg tgaacataag tatgtgataa aaccatactt     56580
aatattaatg aagctaatcc taatccaata ataaggaata gaaatctgtt tgttccttct     56640
gcactttttag ttttatagaa tgttgttatc tgagttacat acgcaaggat aatagtaata     56700
gttgcaatag tttgtgttaa ggctgtaaag tcacttaata aaaatagtaa cactgagaac     56760
acaataataa aaggtataga gaaataatcc tttttttctat acgaagctac taataagcaa     56820
acaataccaa gagttaaatt aacaccaact gatactactt gaaacattgt agcgtcagtt     56880
ataagtaaat tgtaaaagct aatacctact gtagctacaa ttaaatacca aaaataacta     56940
ctaactcctt taacactatc tgatttaact aaagctatta gacctggtat ataacctact     57000
gtaactaata tagcatataa tatacttaag taatgtgata agttatccat cttgtcctcc     57060
taatttctct agtcttttta aaacttcttc ccaagaaata aaccttctc cattagttag      57120
gcttagcaca catccgtaaa taaattggtt cgtactaaat tcagccctat cagggtcatc     57180
ataacctttt ccatgtcctt gacgaatatc agagcaatag attaaaacag gtttatttac     57240
aatattataa gcttctaaaa tatcatattg tgttaagggc tctaagtctc taaagtctat     57300
atcttcatat ttatcaataa tttttgagc ttggtgtttc attcctaata aaataccaag      57360
ttctgcaatc gttcctagcc cctcattaag aatgtcaaat acaaaaatat ctgattcttg     57420
catagcttta aaatcattgt ttaagatacg ttcagctaat ccagtttgtt ctgcattagc     57480
tttatcgttg attgatttgt cctgatgagg gctataagga gttactccta caatacccstc     57540
tacttgttcg tgttgtttag ttctatattc taccatagct tggttaagta gatgacctcc     57600
catgtaacaa accttatctt tagtataatt aaccatctat agtatctcct ttttcttcta     57660
gaatacctct taaaatgtgt ggcatctttt tcttaatttg tttttctata attttcatca     57720
tattttcttt ttcttcttcc atgatatcat caacaaaatt ttgacctact tgtttcataa     57780
```

FIG. 21FF sequence.txt

| | | | | | |
|---|---|---|---|---|---|
| ttaaaccaaa | attttccaat | tctaaatcat | ctttagacaa | tctgttttct | tctatagctc | 57840 |
| taaaaatcat | tttttccatt | cttgattttg | tgatagcata | atctgctaca | gaatcattac | 57900 |
| ttctaacttc | tgatttcatt | ttcttacgac | taaactcttt | aaattcctta | gatactaatt | 57960 |
| taaaataatc | atcatgttct | gatttaccat | ctaaatattt | aataacaata | ccttctcctg | 58020 |
| tattaggttt | aacagtcata | tctgattttc | ctactaaatc | ttgaatttct | tgagggttta | 58080 |
| atttattaag | ataaaaagat | ggttctataa | tcattaaagt | ttttacagtt | ttcaaaccta | 58140 |
| atgtttctga | taaagaaatg | acttctgaat | aaggtaaata | ggtttcacta | tccttatcgt | 58200 |
| atacatcgaa | tacataaaaa | ttattataac | actcttcttt | ataatttacc | ttatgtttaa | 58260 |
| ctaaccattc | tccaaatata | ataataccett | ctaatataga | taaatctaat | ttatctgtca | 58320 |
| tgttttcatg | tacccaatta | taaaaaccgt | ttaatgtttc | gttttcattt | aatttttttc | 58380 |
| tacgagagaa | acatactaac | tcaccattct | ctgtagtaaa | acttgcgttg | cttccatcta | 58440 |
| atttttcttg | aactacaaaa | cctctatctt | taaatttgtc | taaagataat | cctttatttt | 58500 |
| ttactttagt | ataagatttc | attaattagt | tatcctcctt | tgaattatgt | actattgaaa | 58560 |
| ataaaataag | acttacactt | gccaaaaatg | ctaatactac | taaaccaggt | aaatttagaa | 58620 |
| ctgttgataa | gaataatgct | actgcactta | taacataaac | tagaccgcct | aataataaag | 58680 |
| ttaataatac | aattgttata | agttttacca | accagttatt | attaataaat | actttagcta | 58740 |
| aataattcat | aaaaaagcct | ccttagttat | tataatataa | gtataccata | tctaaggagg | 58800 |
| tttgtcaaca | tattatttta | ccatttgaaa | ttatctgcgt | attgggctaa | cttagaacgg | 58860 |
| aaattaactg | taaaattatg | gaatactgca | ccatcatatt | ttttaaaata | ctccatgtaa | 58920 |
| tccccaaaac | ctgatttact | ttcattttt | aaatctattt | gtttaaagtt | accttctact | 58980 |
| attacagtag | aattttttgt | atgaacccett | gtaagaactt | ttttaagttc | actacgttta | 59040 |
| aagttctgtg | cttcatttat | aattatagta | gaatctctta | gatttccacc | tcttaggaat | 59100 |
| agatgtgata | tttgagatac | ccaacaatct | cctagtttat | cttctttaac | attatcttcc | 59160 |
| atcattaaca | tttcagttat | ttgttgttca | ggattcatat | taagttcaat | aagggcatcg | 59220 |
| tgtaatccca | tgaaataagc | catttctttt | tctgtctgat | tacctggtct | gcttcctaaa | 59280 |
| tcctctgata | ctggtgaaat | tataaatact | agctttctat | ctttattaag | atagtctgcg | 59340 |
| taagcacagg | ctactgagca | cattgtttta | cctgtaccgg | cttgactctc | attccaaagt | 59400 |
| atttcaacat | tatcattaaa | gaaatcctca | cagaaatcta | actgctcggt | tgtagctttt | 59460 |
| tcaaggaatt | cattaaagac | tagatgttct | cccatgttgt | atcttacatt | aggataatct | 59520 |
| tttaacttaa | agtctaactc | ttttagttgt | attgccatat | tttaaagttc | ccctatctat | 59580 |
| aaatagtttt | actctctttt | aatatagtac | taatttccga | tatattctcc | tgttgaagag | 59640 |
| caataattac | tacattcaca | ttcagggtag | ttatcacaaa | cttcttcgtc | ttctacatca | 59700 |

FIG. 21GG sequence.txt

| | | | | | | |
|---|---|---|---|---|---|---|
| tcataaccaa | tatcataatt | attataatta | aaatctacaa | tacaattttc | actattacct | 59760 |
| ttagataatc | ctgtataaat | aatatcatcc | acagaatccc | aatcgttatc | tgccaaataa | 59820 |
| tttacgctat | ctaatactga | ttcattatca | ggtaaataaa | tactaccgtc | tgaaaattta | 59880 |
| attagaatat | caccttgagg | taaagtatca | ttaattaaat | caatctttgt | ttcttcttca | 59940 |
| atagtgaata | cagttccttc | taatctttcc | ggtgtagtat | gcgttaaatg | ttttacagta | 60000 |
| tctcctgatt | cttcatagaa | tcctactgca | ttcatatctt | tattatattt | tgcaataaat | 60060 |
| ttaccattgt | cacttaccaa | atattgacta | gttgaattat | agtcgtttgc | gtcatctact | 60120 |
| gtcatgcaag | ggttataatc | tttaacataa | taactaattt | tcctaacatc | tgttgtttgt | 60180 |
| actttcttac | cttcaccttt | aattactgaa | ttaattttttt | tcataatatt | ttctccttttt | 60240 |
| tatatatcaa | ttgattttttt | tgcaagatta | tcggcatagt | cattccattt | atcatttgaa | 60300 |
| tggctcttta | cttttacaaa | atttatatct | attacttttt | ggtattctct | tatcatattg | 60360 |
| atatatgttt | tacttagaat | atttcttgca | gaccaagtac | cttcatacca | atgtattaaa | 60420 |
| ccaatataat | ctatataaac | tattgcctga | ttgtatccta | gttttatagc | ctcttcaata | 60480 |
| ccataacaac | aagccaatat | ttcacctgca | acattattat | actttattaa | tcctggtttg | 60540 |
| tcaacacttt | tactaatttc | cgctattata | tttccttctt | tacttaccaa | gacagcacct | 60600 |
| gagcctactt | tacctttatt | atatgaggag | ctaccatctg | tgtatatatt | tacactatcc | 60660 |
| tgcatattta | taatcctcca | taaattgagg | gaattcacaa | tctgagtata | cttctctaca | 60720 |
| aaaagatact | gagatataat | taaaatcaaa | acatttgaaa | cagtgttctt | gaacttcttt | 60780 |
| tttatcttta | gcaatcacat | taaatttaaa | accatcagct | attactgtaa | atactccttt | 60840 |
| tttcataaaa | caaatacctc | caccaatttt | attttaaatt | aataactaat | tcaataaatg | 60900 |
| atttaatagt | tttattttta | ccttcatcaa | tatctgaaaa | gaagttaatt | aaactatcat | 60960 |
| cctcatcaaa | taaatcttca | acatcatcaa | atttatttaa | tatgtctgta | acactataac | 61020 |
| cttcttctga | tatatactca | tgcaagtctt | ctccatcttc | tgacagtgtt | gcttctattt | 61080 |
| taccattttt | actttcaatt | aaatataaag | tatttaacac | tttaacagaa | tctacaacta | 61140 |
| cactgtagtt | actaatagta | ggatattctg | tataaagtat | ttctacatta | gtattcatat | 61200 |
| aactatcaat | tacagagtta | actgtatctc | ttttttagctc | agatacatta | tgttttcgta | 61260 |
| tagtagggaa | ttcttcatca | tattctacta | attcttttct | atctgtgttc | aataacttgt | 61320 |
| ctaaagaaga | caacaatact | attttatact | ggttatcagg | gagactatct | gtaatttcca | 61380 |
| ttattgttaa | aaacgtatct | tcacctagaa | ctttgtttat | atcttgtaac | tcaaatgaat | 61440 |
| ctaccatttc | aatagtatca | tctatatcat | ctgtagtcat | taaaaaatta | actaaattat | 61500 |
| tattctccat | catcttcctc | caattctttg | aataactctt | ttcctggagt | atttaacgct | 61560 |

FIG. 21HH

```
                                    sequence.txt
ttctctaacc gcattaaatt agcgcttctt ggtttctttt ttccatactc ccaataagat    61620
ataagagagt aatgaacacc tatctcagaa gctaggctcc ttaatgtatg tccttttct    61680
actctaattt tttgaaggtt tagaggttta ctttccttt tttcatccat aattatttct    61740
cctctacttt taaaaattta aaatcctcag atgcttttgc attttttagt atatactcgt    61800
gtgacttatc tcttgcctct gccttgcttt tagcatataa ctctatatga aatacatgag    61860
gttttttaa agacggtgat tcatatctcc aataaacttt aaaaagtagt gtttctttt    61920
ttaaaacatt aattcgaaac catcttttaa atttattcat tcattatcct cctttattta    61980
tttgttaaac taattatagc atagttaact tatgaagtca actataatat acaaaaaaga    62040
ctaagaaatt aatcttagtc taaatcgtta ctaatagttt ccgttggcat tatggaagtt    62100
taaagctcct gatgttgaac cgtaacggtc aatcatatat tgttttgcac ctttagtttg    62160
ttctgctata gaaccaccac tccatgattt acctaatcct tggaataacc cttgggctcc    62220
tgatgttgga ttaacagcat tcgggttcaa tgtagattca cgcatagcaa tttcaatcat    62280
tgcttcatct ccgcctgctt gtctaatctg ttctgctaca gaaccacctg tacttttagt    62340
agctgtagtc ttagtttcta ctttaggagc ttctactgac ttaggagctt cttgagtagt    62400
tgtttcttgt ttaggttgtt ctactgcttt attttgtgta tcaaattgtg cttgttgttg    62460
gtctactttt tgttcaggtg tttgctcttc tcctgctaat ctagatactg tattatctac    62520
ttgagttgaa cctgaatgat attcataacc aaagttacca ttataattat agaaatgata    62580
agtaaattca ccatcactaa atgagaaatc ataattaccT tcttgaattg gttttgtatt    62640
aacttctact gaatttgatt tagcttgttc tgctaactta ttatagtcaa tttcgtctgc    62700
actagcttcg tttgtagcca tacctccaaa agtaatagct gtacctaatg ctaatgttgc    62760
aaaaattgtt ttcttcataa atttaaaact ccttaaataa tttttagaa ttgtttattt    62820
gtaaaccgac ataagtaatc ataacatata tctttaaata acgcaagtat aatatagcac    62880
taattagtgt aatattatta aggttttatt acaaacatta cagttatcag ataattaaat    62940
acaaaaaaga gaggtattaa cctatctaat ttattatttt cctgttacat ctacaatagt    63000
tccgtctccg ccaatttgaa taggttgttt tccatcccat ttttcaatta gctgttgttg    63060
taaaacttca tctgttaatg attcacttct gatatcatta gctttcttct cacctttgc    63120
ttctacttct tttttcttag catttttctt c agctatctgt ttatcgactt tgtacgttc    63180
taattcttga tttgctttta ctctttcgtc aattgctttt tgagtattct tatctgcttt    63240
aggactagat aatgcaatat cttcaattac aaatccttgt ttttctaaat tatcatttaa    63300
gctatctaaa gtatctttt taatttgtcc tgttttaaca ccaaatgcat caattactga    63360
gtacttagat actgattgac gtacattatc ttgtacacga gaacgtaagt aaccttttc    63420
taattcttca atgtcagcac taccaaaacg attaaataag tctacagctt tagttgcatc    63480
```

FIG. 21II sequence.txt

| | | | | | | |
|---|---|---|---|---|---|---|
| tactttatat | gaaacatcaa | tatccatttg | taaattctta | ccgtctgaag | ttgccacgtt | 63540 |
| taaatcttta | tatttatgtg | tttgtgtttt | agttggatat | ttgtttacct | tatcaaaagg | 63600 |
| tgctgttaag | tgccaacctg | gtgatttagt | atcttcctta | acaccattta | ctgagtacac | 63660 |
| aactccaaca | tgaccttgtg | gaatctttgt | aatacacatt | aataaaataa | taaatcctat | 63720 |
| aattgctaaa | aaccctatta | ctcctgaaat | aactactgac | ttcctcattt | acatttctcc | 63780 |
| ttttttctatc | tcttttatta | aactatttaa | agcttttttcc | tctttgtcta | tttcctgttt | 63840 |
| gtctgctttg | gtaacaagag | attgcctacg | gtcatttaag | aattgttttt | tatattttac | 63900 |
| atattgttct | aaaccgtatt | cttctaatgt | accttgccta | actaattccc | tgtattgttt | 63960 |
| tcttatgtta | cttttcttct | ctctcattga | aagaaaatca | aatacgtaac | tcataccaaa | 64020 |
| acctacaagg | actagaaaaa | caataaaaat | agcaaagtat | gttaaaaata | atgccatgta | 64080 |
| attcctcctt | tatttgatta | catatataac | tatacactat | gtattacgtt | ttgtcaacac | 64140 |
| ttttttgcaa | aaaaaataga | cggatttaaa | atccgtctaa | atttatactt | tatttaaata | 64200 |
| ttgttatact | tttagtttct | tcatactctt | tcaacattct | atctctaaga | tttattgctt | 64260 |
| cttttatact | atctacttga | tatgattggt | accttatatt | atttcttgtt | atagaaactc | 64320 |
| tatatttacc | attagttctt | tcttgtatgt | ttttaatcc | ttctagttta | gagggtctat | 64380 |
| taactatatt | ttcacttcta | gtagtccatc | tacaattttc | cggagaatag | ttaccatcat | 64440 |
| tatcttttct | atctaattgg | tatttatcag | aaggtctttt | acccatatca | tataaaaaag | 64500 |
| attcgaaaga | gtttttccat | ctatcacaaa | cttcaatacc | tcttcctcca | taatatggat | 64560 |
| aactgtcttg | attttgtta | tagcatcttt | ctttcatttt | tctccatact | gtatactcag | 64620 |
| gatgtttttt | agaaccatta | cgtgatttca | tacaaccaca | acttttataa | tagtataatt | 64680 |
| gacttttaga | taaaactcta | tccataccgc | aatcacataa | gcataaatat | aatttaccttt | 64740 |
| taatcttatc | tgaacctaca | tattcttcaa | caaataattt | ttctatttttt | ttacctataa | 64800 |
| tattttccat | aaaatctctc | ctttgaaaat | attataacat | atatataagg | ggtattgcaa | 64860 |
| cccctttatt | tattaacctt | tgaatacacc | ccaggcaact | ccaggtacat | gtgaaggtgg | 64920 |
| aacaccttga | caagttctaa | cagggcaata | tactctgtta | ccattgtaag | cattataacc | 64980 |
| tatccaaata | tgacctgctt | ggatacaaac | ttcgtcatat | acaattgtag | cccctgccgg | 65040 |
| taagttaccg | cctactggag | catttaagaa | tggagaacct | attctagtta | ctataggttg | 65100 |
| gttaccatta | acaaatgttg | cattttccgg | tttataccaa | gttccgtact | ggttctttttt | 65160 |
| ccaagagcct | gtaactggtc | tagttgccgg | tgtacttgcg | ctacttgttt | ttccatcttt | 65220 |
| aactactgta | gaacttgaag | tccctttatc | catgtagttt | ttaatttgtt | taatgaaata | 65280 |
| atcttttaat | ttattcatta | ttgcttgtga | tggtcttcct | tgtgttactg | gattaaatcc | 65340 |

FIG. 21JJ

```
                              sequence.txt
tgtatgaaga accatagaac ggtgagggca ggcagttggt acaaattcca tatgcaatct    65400
tacagttttca cggttaggag taagacccca ttctttaaat ttctccgctg taaattggaa   65460
tactgcttgt tcatttttaa ggaattgagc atcactagca ctcattgatt gacagacttc    65520
aatacctgca aatctaaagt tacctgagtt tgctcctgtt ccatctcctg tgtgccaagc    65580
aatttgattc ttagcatcta ttgcttccca tacataacct tcagagccgt agtaatgagc    65640
aataccatta gcgtatctag cataacctgc attagctaat gaattctcgt attgttgtcc    65700
tgaagaacga cctgcatcgt tgtgtattac cattccttca ggtttttac cacgtttatc      65760
cattgtatag ttaatgtgat tcttagaaac ttttagtgtt gctttctttt taggtgcagg    65820
agttttactt gcgcttttct tagctgtttc ttttttaaca gtagttcctg cttttacagg    65880
tatttcaatg aagtgagtta atccgtaata attatctaca cgttttgtag gttttttatt    65940
agcataacca ttccagtttt gctctaaaat agtaaacgta gaagtattac ctccatcata    66000
tacaatacct atgtgacccc actgttcata actaccggat gtaaataccg caatccaacc    66060
tttttttaggt acagtagaag gtttattttc atgtattta aatccagtac cataactctg    66120
tttaatttgg tctttagcat taccccaagt tctaacttta ttatctgtta accataaaac    66180
atagtctgta ataaggtctt gacactgagc gtgatagtaa ccatctgcgt caatggctcc    66240
tgcttccatt acaccaaatg atgggtcata acttgtagct tttttaactc tgtaagggct    66300
atctactgtt cctttttgcat aagcgtctaa acgtttattt atttctgctt gagtcttagc   66360
cattacttaa cttcctcctc tgcaaatact ttaccatgtt cctcggtatc ttcttcatct    66420
tgagaaggtg ctgaaccacc atcaatttca tcttcaatag caggtacttc atcactatca    66480
tctgtgtcag gttctgcatt gttttcgtag ctgtctatct caaaagtact agcgttattt    66540
gcatttgctt gccattgaac gaattcatta gggtctttac tatcacgagg tttaagatag    66600
tctgtttgaa caatatcact atctttaaga cctttagtat tattatcaac aataataacct   66660
aaacctgcta atagtgttag tatagaacct acaatattta caccttgctc aatttgagct    66720
gagtagtcta aaccgaaagc acctgtaatt tggttagcaa ataatgctac tgctgatata    66780
attgctaccc aaaatgtttt gctcttagtt cttgtgctaa ggtttattcc tccaacaact    66840
ttaggttgtt tagtttcatt agccattaaa aaaccgacct ttctattata tttatttcta   66900
acaataatat aacagtaggt cggtcatgtt tatctatatt aatttaacac ttactcatta    66960
atttggttta gttttttgat aacttcagac atttgtttgt tatctaaatc ttctaattta    67020
gtttcaggaa gtagctctaa cttatcccaa acttcttctt tattagatac tttattatta    67080
ataattgcct taccaactaa actttccgta taatataatt gttttgctga tgccattgt     67140
atctctcctt ttaaatatgt aaagtatata gctagtatcg tatcctagga acaaacactt   67200
gcgctatata ctcaatgaaa tcctacccctc attcgaggac acagcaaacc ggttcgtcaa   67260
```

FIG. 21KK sequence.txt

```
ccgcacatat gaattctcag atttcattta tgtaaaacac accctctttg atttgcacaa      67320
agactaaggg ttttggagac ccttgtacta ctaattatac taagggtgtt tattatggtt      67380
tctattggat ttgaaccaat gacacctaga gcttcaatct agtgctctac catctgagct      67440
aagaaacctt aaaacgaccc atacgagact cgaactcgta ctctctgccg tgacagggca      67500
gtgtgttaac cagttacacc aatgagccaa aattataatg ctatacccta accttacctt      67560
aatgtatagc aggtttttat ataagctcga agcaacgatt attaccactc ataacaacta      67620
tatattaagt gaaaggaggt gaaatgaaca aaacgtggta attggtactt atataggaaa      67680
tatgtataat ctacaaggag taagttattg gttcataaag gagtgtgaac aataaataca      67740
tgaaagagtg aaagtttact ccctgtagat tctttttttaa ttatcaatca aaggaggaaa     67800
ctgataattg ttaataataa actataaaga ggaaaatatt tatagtcaca ttctgatata      67860
atgcaactaa atatccaagc ataacccgtc tcacgaggaa cctacctata agacctgtta     67920
ttaagtgaat cactacgatt gactctatta aggagctacc ttaagtccat ctcacgcaat      67980
ttaaaaggga cttacaaacc gtaaaacggt aataagttta ttaaataatg tgatattaac     68040
atattagtta ataactttca catggtcgaa gaaaagtaaa tttatttgat taccaaatta     68100
tttttatcaa atatagctct tttgaacctg tagatttatg ctactcatac tgataacctc     68160
tattatctaa cacatttctg tgctccaact acagttagtc gttacagcgt atctttctag     68220
gattccgcta agaccctaga aagaaattaa accctagccg ttatcatact ctacagacct     68280
tataagtaag taccaagtat accaatcgta tttaacaata ctaatgacga cccatcctac     68340
cgatatatct ccgataggtt ttgattcgtt tgattatctt gtaccttatg actaccaaat     68400
cattattcag tcactatgct cagatattta gttgtattat ttatatatta attataacat    68460
aatttttatt acttgtcaag ttaattttaa aaaaaattat agaagtaggg acgtttacct    68520
acttccattt aatttacaca aggatgataa cattgttatt gttttatact ggaaaacaat    68580
gtaataaaaa cagtgatgtg taaggtattt gttttattgt taattacatt atagcatata    68640
ctgatacctt tgtcaagtta atttaatact tttttttaaaa tattagttat cttttgttaa   68700
ttcttcctga atagcatccc atcttctttc tgcttcacta cgattatctt ctatatgctt    68760
tgtagtttta caacatttaa tacaatatat atctttgata tgaccttctt ctctttttatt   68820
tgctcttttt cttggtactt tgaatacatt tccacattct ttacatatta aacttgagta    68880
aaacatttt tgtcttttca taattaatca attccttttc tcttttattt gataatttaa     68940
ctatatacta tactgataaa taagtcaaca gttttctaaa aaataattta aattattttg    69000
aagaatcctt taatatcagt acttacaaga gaaaagtac gtatttagaa ataaggagt      69060
actcctatta tatataatta tattctgata tacagtaatt aataatatta aatatataat    69120
```

FIG. 21LL sequence.txt

```
tataattaat agggttggga aaattgatat aaacataact gatactgttt ataaatactc    69180
agtataaaag taaaatccct tagtatcagt acttacaggc aaaaaagtac gtatttagaa    69240
aataaggagc tctcctatta tagttatata tatatattta ttactattat taattactat    69300
ttaaatatat aattataatt aacaatgtta gaaagtcaac aatagcataa ataaaaaagt    69360
gactacttaa agtcactcaa taattagaat actattttaa aagattctat tctgtttgga    69420
ttaatatata cttgaggtga agttatagca ctttcagtat atactttat agaggtttca     69480
tccattcctc ttaacatata atctatatct tgcctattgt aactcttttc atcagtagat    69540
actaaaaagt atttagctcc acttgacatt gttatttcaa tatgttttga catctacaat    69600
ctctcctatg caaatttgtt aaagacaaag gataatatag ctcctagaac aagtaaaaga    69660
accttctcag ttgtatcctt tttcttagta tccttagttt ttgtactttc agcaagttct    69720
gaaatctttt catcaagtct ttctaattgg acgtaaattg ctgattgttt ttcactattg    69780
acagctacat ctttatctat actaactatc attttcttta gttcagctac ctcaacttct    69840
aaatctttga agttcctct atctatataa ttaccttctt gtatcttaga cttaatagtt     69900
tctacttgag aaacaaggtt gtttatctcc ttatccaact agaatcacct ctaaggtcta    69960
accgtttcag attcagaatg gatatcataa ttttctaaga aatcattgat aatctccata    70020
taattatccg taacgacttt tccgtaagat gtttttgtat caatttcgaa tctaagttta    70080
ccgaagtctt ggaggtctaa ctctttttatt acaatattcg ggtcatcaga aggaaggtaa   70140
taatagtcga agtatataat tgagccattt attagtagac ggtctattct atacatatga    70200
aagaatcttc tgtctcgttt gaaatgagct agtgaatctt taaactctaa cttaagtata    70260
tccttatatt tagtcaaagt ggtaacctcc ttactattaa ttttttaaatt tacttatttt   70320
gtgttataat agttatgata aaggcagtta ttataattat attaagaata aagataataa    70380
ttattttttc tgagaaaata agccaaatac tacaaacaga taaaacatag atagctgata    70440
gatatactat attaatagtt accttacttt tatcttttct atagatagaa taacctaaag    70500
aagttgtaac accactaagt ataaaataat agaaacaaaa aagaggtata gacagaaaaa    70560
aagatacgat aatcattgtt aaacacctat ttctttttga cctattattt ctagaacttt    70620
tagattatac cactaatata acattaaaag ccagtcataa aagtcaattg ttagattaat    70680
aatataataa aaaaagacaa taggaggtta aagtggttga ataataacat agctatattc    70740
atattcaaaa cattggttat cattatattc ttactgctat ttttgtctgt tgttaattcc    70800
ttatccctta tttactcaat aagaccgagt gtagttatgg catactttac ctttggaggt    70860
attgtttctg atgtcgcact tactatgaca gataagttct tacttaagaa agaagaccct    70920
ctacctgagt atgttcttaa aaaagtagag ataaatgata aagaaataag cataattaag    70980
aaaatcatag aaagtaatta tgatataaca tcagaagaga taaaagttag agctaaagca    71040
```

FIG. 21MM sequence.txt

| | | | | | | |
|---|---|---|---|---|---|---|
| caacagagat | tagaggaaga | tagcaaagag | gaagataacg | atgaaaacga | agaaagaaat | 71100 |
| taaagaacaa | aggaaagaac | ttaaagacgg | tgctacaact | gtttctttag | taaaaaaagg | 71160 |
| ggataagaga | atagctagcc | ctagtagaat | ttgtagttta | tgtggtcagc | agttatcagg | 71220 |
| tatgagttac | actaaaggaa | aagcattatc | aaaagttaat | cattttcatt | tacagtactc | 71280 |
| taagtacatt | tattttgata | tttgtgcaga | tattaacaat | tgttataaaa | atttaagaaa | 71340 |
| acgaggtgaa | atggattgag | tgcagaaaat | attagagata | taattaataa | gaaaaagtta | 71400 |
| gaagaagagg | atacaagaaa | atatatagct | gatggattta | tgaatggtat | cggtaaatta | 71460 |
| atgtatgaat | tcaataaaaa | agtagataat | aaagaaatag | aagttaaaga | ccctaacgat | 71520 |
| ttatataaac | tatttgtgat | attctctcaa | atgcagaata | tggttaatga | acttctgaa | 71580 |
| ggtggagcaa | tacctcaact | atctagacct | caacaagaat | tatttgaaga | gattacaact | 71640 |
| gaagatagta | atggggagtc | tactgtagac | ttacaaaaaa | tatcagaaat | gtcagcagaa | 71700 |
| gatattacag | aaatgatttc | tgaaaaagag | aaagtaatga | atgaggaaaa | ttcaaaaaca | 71760 |
| ttctaagggg | aaagatataa | catggatgga | aaagaactaa | ttaaaatagc | acaagaaaca | 71820 |
| tttcaaacag | aaaaaataac | aagagagcag | atagaccata | taatcaatat | gttaaaccct | 71880 |
| tctacctata | tgcttaagta | tcacacgcta | agaggtcacc | ctataacttt | cagtattcct | 71940 |
| aataggata | gaagtaaagc | acaagcacac | cgaccttggc | aagtccgtaa | acatactatg | 72000 |
| cggactataa | accttttcta | aaattggaaa | ctcctaacaa | gtgaagttga | ggacaatcaa | 72060 |
| ttgctaaatc | gtaactaaga | taaatatttt | aattacgtaa | atgcctaacg | actaaatttc | 72120 |
| caagtaagca | ataaaatggt | attgtgtaga | attggaagag | agggaaaccg | taacgaaaag | 72180 |
| gacttttacg | cctaactgta | aaagtatgat | atagtctaat | ccctaataa | atatcgggaa | 72240 |
| accgagggta | gtaaatgata | gtaaatgaca | ctcatccaaa | caaagcagtt | attaaaagca | 72300 |
| gacaattggg | gcttagtgag | atgggtgtaa | tggaaatggt | tcattttgca | gatatgcata | 72360 |
| gctatgccaa | tgcaaaatgt | ttatatacct | ttaattagag | aggcttcacg | tagcaatgcg | 72420 |
| tgttgaaaaa | ccttgttaaa | cggggaaacc | cctaacgtaa | agacgagggc | aatcccgtgc | 72480 |
| taaatgttga | ctaacctaat | attatatgat | atattagtta | tagtcagcta | aatgccgaac | 72540 |
| gactaaattt | ctaggtaggt | atctaaatgg | aggtactgag | aactagataa | aaaaactact | 72600 |
| taaataatt | agacttaaaa | aaatactgtt | ggaaggagga | tatttaatgg | gaaaaaaatt | 72660 |
| aactaatact | gagtttttaa | atagagtatt | tcagttagtt | agtgatgaat | actcattttt | 72720 |
| agaagagtat | aaagggagac | ataccaaatt | aagatgtaaa | cataatttat | gtagttacga | 72780 |
| gtgggatgta | gaacctggag | cttttttagg | taataagaac | aaagcaggaa | gtagatgtcc | 72840 |
| tagttgttat | ggtaatgtta | ctaaaacaac | agataaattt | aaaaaagaaa | tatacaattt | 72900 |

FIG. 21NN

```
                                    sequence.txt
aactaaagat gaatataggt tactttctga gtatattaat gctaaaacaa aagtaaaaat     72960
taaacattct aaatgtggta atactttttc tatgacacct aatactttta taaatggaag     73020
tagatgtcct gaatgtaacc ctcaaaaacc gtataataca gattctgcta aagataggat    73080
aaataaagaa acgaatggta cttttgaact agttagtgaa tacaaaggtt gttatgagct    73140
tatgaagtta aagcatcatg aatgtggaaa tattgtagaa ataaatatgc agagtattga    73200
tagcaataga ctaaattgtc cttattgtta taataggtct agaggtgaat tactagtatc    73260
ctcatttctt cttteaaaaa ataccatt cgaagtccaa aaaagatttg atgggtttaa      73320
gaaatatcct tatgattttt atatagctga ttataatacg gttatagaat atcatggaga    73380
acaacattat aaacctatta agtttatgg tggagaagat agattggtaa ggcagaaaaa     73440
tatagattta aagaagaaaa atttgttga gggtaaaggt ataaattact tagaaatacc     73500
ttacacatta aacaatcaaa ataaagtaaa tgagtttta attaatatt ttaagtagaa      73560
gtaaagcaag gaacccttaa ccaaacttaa gggttatgat atagtctaaa ccgtatataa    73620
atactaggaa actagcggta taattgtcct acaaatgaac aaatgaagaa atttgttcag    73680
tctcgtttaa atcctgtatt agaaaagaa tattttaggg atattgttga ttgggataaa    73740
gactctttag gttttaaaaa gataagaaat tctagtttat tctttagaac aagttctaaa    73800
gcaagtactg tagagggtgt ggatattgac tatttatctt tagatgagta tgacagggta    73860
aacttattag cagaatcgtc tgcactagaa tcaatgtctt catcaccttt taagattgtg    73920
agaagatgga gcacaccttc tgtaccgggg atgggtatac acaaattata ccaacaatca    73980
gaccaatggt attacggtca tagatgtcaa cattgtgatt acttaaatga aatgagttat    74040
aatgattaca accctgataa tcttgaagaa agtggaaata tgttatgtgt taatcctgaa    74100
ggggtagatg agcaagctaa aacagtacaa aatggtagtt accaatttgt ttgccaaaaa    74160
tgtggtaaac cactagatag atggtataat ggtgagtggc attgtaagta ccctgagcgt    74220
acaaaaggta ataagggg acgaggatac ctaataacac aaatgaacgc tgtatggatt      74280
tctgctgatg aattaaaaga gaaagaaatg aatacagaat ctaaacaagc attctacaac    74340
tatatttag gttatccttt tgaagatgtt aaacttagag ttaatgaaga agatgtttat     74400
ggtaacaaat cacctattgc agaaacacaa ttaatgaaac gagatagata ttctcatata    74460
gctattggta tagattgggg aaatactcac tggataactg ttcatggtat gttacctaat    74520
ggcaaggtag acttaatacg attattctct gttaaaaaaa tgacaagacc tgatttagtt    74580
gaagcagatt tagaaaaat aatttgggaa atatctaagt acgaccctga tattataatt    74640
gcagataatg gagactcagg taataacgtt ttaaaactca ttaatcattt tggaaaagat    74700
aaagtatttg gatgtactta taatcttct cctaaatcta caggacaatt aagacctgaa    74760
tttaatgaga acaataatag ggttacagtg gataaattaa tgcagaataa aagatatgta   74820
```

FIG. 2100 sequence.txt

```
caagcactta agacaaagga tataagtgtt tatagtacag tagatgatga tttaaaaact    74880
ttcttaaaac attggcaaaa tgttgttatt atggatgaag aagatgaaaa aactggagaa    74940
atgtaccaag ttatcaaacg taaaggtgac gaccactatg cacaagcaag tgtttacgcc    75000
tatataggat taacaagaat aaaagaactt cttaaagaag gaaacggtac aagctttggt    75060
tctacatttg tttctactga ttacaatcaa gaaggaaata aacaattcta ctttgatgaa    75120
tagaggtgaa atagacttga cagataaatt attttatggt acaattagta atgaagaaat    75180
taataaaagt gtattgaatt tgttattggg tgaggaatta tccttagatt atgtttctaa    75240
aaatagtgat actttagatg ttaaatatga acatgtctat aaatctctag gattcgataa    75300
tttctttgat tgtttttat atgctaatag agagcctgaa atagtccaca aggtggaga    75360
taaaaatctt ggtggactaa ataaggttaa acgtactgtt attcgtaatg gtaaagaaat    75420
ggaaatgaca gtttacgaag acggtaataa agagaacgat agtaaagaaa aacaagaagg    75480
aaaagaagaa gttagtagaa gtgcagtagg agcaagagct atttctaatg gtgaagaagg    75540
aaaggtaaac cctaaaaaag tagcaaattc attatctagt ttaagtaaaa agggtgtaga    75600
tgtatcccat attaatacaa acttatcatt gtataaagag tttgttgatg ataacggtga    75660
tacattagga attacatctt ttaaacgaac tgaaaatgat ataatattag aatcttatgc    75720
aagttcacct gattcagatg gtgtaggagc aagagctatt atggaattat tacgtttaag    75780
tattaaggaa aataaaaatg cagttgtgta tgacatagaa ttacctgaag cagtagagta    75840
tttaaaaact ttaggattta aacctaataa agatgggtac atcttaagaa aaaagatgt    75900
aaaacaattc ttaggtgatt atagtgattt tatttagcac tatagtcatc tattctattg    75960
tatttattct atatattgta ttaaaaacaa tttatataaa gtctaatatg agtagaatag    76020
ataacacaac tgaattatta aaaatattac aggaagatat tgaaggtaag ataaaaaagg    76080
aaggaagaaa taatgacctt tagaagaaaa taaattaaca ttagaagaat caataactcc    76140
acttagtaaa gaggagaaag aagatagtat taaagaattt agtagtttat tatgtgaaat    76200
ggtaaatagg ctatacaagt cttataatgt atttagacaa gaccctatgg atgaaactca    76260
acgtctagat ggctctttaa tggtctttca aagtagatta aatgacccct taacaggaga    76320
tttacatgat aagatgtata aacttgcttt ttcaaaacgt attgatattt tcgaagctaa    76380
taagcaattt agaaaagatg tagaagcagg taaagcaatt gagttaggtg atgtagctat    76440
tatagataca gcattaagta acatcctttc aggcaatgag ttccaaggaa gtatttcatt    76500
tatgcttaga aaagactttg aagaaaaaga acgaattaga aagaagaag aagagaaact    76560
taataactta taaaagggaa gaattatgag actatataaa atgaggtatc ataattgaaa    76620
aagaaaccac aaggcaatga ggtaatcata accataataa cggttatgat agcagtattt    76680
```

FIG. 21PP sequence.txt

```
gtagtcatta tgaccatatt ttttaataaa tatcaagatg ctaaagaaga taaagataga    76740
tatcaaagat tagtagagat ttataaaaaa gcagatgata atgatggtga gactaaaaag    76800
aaatatgtta aaagattaaa taaggctgaa gaagaactta aaaaagtaaa aaaagaaaca    76860
aattataaag attataataa gaagtcaagt aaagaaagac aaaaagaaga taaagaaact    76920
agagagaaaa tatatgatgt aactggtgat gatgacttaa tattagtaaa aataatatt     76980
gattttagtg ataaagtaga caagcccgaa atacttatta gtgaagatgg aattggtacg    77040
ataactgttc ctgtagatag tgggtatgaa aaacaaacag taggttctat tattactagt    77100
gtattaggtt ctcctttcct atcacctggt tcaaatagta tagatggttt aagtgttatt    77160
aacgataatg tttatccaaa tacagtagat agcatagtag aagatacaaa accttctatt    77220
aacttaccaa tggataatcc tattataaca aatccggttg aaccaactat accttcagat    77280
actatacctc ctattgataa tccttcagtt ccggtatttc ctgagaatcc agtagataat    77340
aatcaaggaa atacagataa tccaaaccca ccgcctccag gatatacaga tgaagatggt    77400
ggaaggggct ccggtggtgg aggaaattct gaaccaccat caacggaaga accttcggat    77460
aatggtaaca ctggaggagg agattgggaa gaaaaacctg acccaggaga agaaccttca    77520
gataatggta atacaggagg caatggtgga gaagttacgc ctgaacctga ccctacccct    77580
tctgaacctg aacaaccgaa tgaaaattct gatgaaggta atgaagaaaa accatctgaa    77640
ccgtctgaca atcctgatga aaatggagga tgggaaactg aaccaactga acctgagtca    77700
ccttcagagc cggacgataa agtggacgaa gaggataaaa atgaagatac tacagatgat    77760
aaacagccca ctgaacaacc ggacgataac aacatagata atgaagataa aactgaagag    77820
gagtaattac tcctcttttt tgtttgctat attaaataag agttaaatat aaaaaaaatt    77880
gaacattacg gtggtgaaaa ctttgttagg aatgaatatt ataacgtcac tatcagtagt    77940
atttacctgt ttaagtcttt taactttaat gattttgtt catagtaagt tctctagtaa     78000
aaacgttttt gttttgtatg taatttatgc tataatagga ataggtacat acatagtttt    78060
aactatgttt caaacaacat ctgtacttat taagaatgat gtaatagatt ccatagaaaa    78120
tactgaacat tatattggat tcaatgaccc tataattata tttactataa gttttatagg    78180
tgcaatactt ggaggaattt ggtacaagat gatgaaaatt attaaaaaga gtaactttaa    78240
agataaaaaa taaaaaagac ggtgaatagg ttgatattct ctaaagataa aaaatgggat    78300
gaagcaaaag atttcatcaa aggtcaaggt atgcaagata attggataga gattgtagat    78360
tattatagac agataggtgg aaaacacgta gctgttttta ttgctttaaa caaagtaaaa    78420
tacatgattc tagaagcaac aaaagacaat aaagtaatat tagtagataa agataataat    78480
atactattag aagattatga tattgttatg gaaagtaaga agatgtttta ttacattgaa    78540
gaaccgttcg aggttaaaat aaatatccct caacatatta gagatgtaac ttataataat    78600
```

FIG. 21QQ sequence.txt

| | | | | | |
|---|---|---|---|---|---|
| actgttgtat | taactacagt | aagagggagt | agaggtgact | agtaattggc | agatttattt | 78660
| aagcaattca | gattaggtaa | agactatggt | aataatagta | ccattgctca | agttcctatt | 78720
| gatgaaggat | tacaagctaa | cattaaaaaa | atagaacaag | acaataaaga | gtatcaagat | 78780
| ttaactaagt | ctttatacgg | acagcaacag | gcttatgcag | agccatttat | agaaatgatg | 78840
| gatactaatc | ctgaatttag | agataagaga | agttacatga | agaacgaaca | taacttacat | 78900
| gatgttttga | aaagtttgg | taataaccct | atccttaatg | ctatcatact | tacacgttca | 78960
| aatcaagtag | ctatgtattg | tcaacctgca | agatattcag | agaaaggttt | aggttttgag | 79020
| gtaagattaa | gagacctaga | tgcggaacct | ggtagaaaag | aaaaagaaga | aatgaaacgt | 79080
| atagaagatt | ttattgttaa | tactggtaaa | gataaagatg | tagatagaga | ttcatttcaa | 79140
| actttctgta | agaaaattgt | tagagatact | tatatctatg | accaagttaa | ctttgaaaaa | 79200
| gtatttaata | agaataataa | gactagacta | gaaaaattca | tagcagtaga | cccttctact | 79260
| attttttatg | caacagataa | aaaaggtaaa | attattaagg | gtggtaagag | atttgttcaa | 79320
| gtagtagata | aaagagtagt | agctagtttt | acttctagag | aattagctat | gggtataaga | 79380
| aaccctagaa | ctgaattatc | ttcctcagga | tatggattat | cagaagtaga | gatagctatg | 79440
| aaagagttta | ttgcctataa | taacactgaa | tctttcaatg | atagattttt | ctcacatggt | 79500
| ggtactacta | gaggtatttt | acagatacgt | tcagaccaac | aacaatcaca | acatgcatta | 79560
| gagaacttta | agcgtgaatg | gaaatctagt | ttatcaggta | ttaatggttc | atggcaaatt | 79620
| ccagtagtaa | tggcagatga | tattaaattt | gtcaatatga | caccgactgc | taatgatatg | 79680
| caatttgaga | aatggttaaa | ttaccttatc | aatattatat | ctgctttata | tggtattgac | 79740
| cctgcagaaa | ttggtttccc | taatagagga | ggagctacag | gttctaaagg | tggctctact | 79800
| ttaaatgagg | ctgacccagg | taaaaaacaa | caacaatctc | aaaataaagg | tttacaacct | 79860
| ttacttagat | ttattgaaga | tttagttaat | agacatatta | tatcagaata | tggagataag | 79920
| tatacattcc | aattcgtagg | tggagatact | aagagtgcta | ctgataaact | taatattctt | 79980
| aaactagaga | ctcaaatatt | taaaacagtt | aatgaggcta | gagaagagca | aggtaagaaa | 80040
| cctattgaag | gtggagacat | tattctagat | gcttcattct | tacaaggaac | agcccaatta | 80100
| caacaagata | aacaatataa | tgatggtaaa | caaaagaac | gtttacaaat | gatgatgagt | 80160
| ttactagaag | gagacaatga | tgattctgaa | gaaggacaat | cagcagattc | tagtaatgat | 80220
| gataaaagta | accctgaagt | aggaactgac | tctcaaataa | aaggggattc | aaacgtttat | 80280
| agaacagaaa | cttctaacaa | gggtcaaggt | aaaaaagggg | aaaagtcttc | tgattttaaa | 80340
| cactaataag | gaggtaaaat | taaatgtcag | ttatatataa | agataataat | tggattgatt | 80400
| taactaatgt | tccttattta | caaaaggtg | atagtggata | tcgtaaagat | ataccaagga | 80460

FIG. 21RR sequence.txt

```
aaaattggaa aaagtgttta aatacagaag taagtttttc ttataaaggt aaaaagggtc    80520
tattttatgt aacttatcgt aaggaagata aaggaaaagt taaagttgaa tatgataagt    80580
atgttaagat aatagaccct catgatttaa agacactaaa tataaataaa atagttaatc    80640
ctcctaataa agctaagtat cgtgagcagg aagtaattaa tggtgatact gtaagaaata    80700
ttagaaaagt taagaataca ggaattgttt atactatgtt atgttcagag tatgaagaag    80760
aatatgatat aagagaaagt gatttattaa gagggagagg tagcccttat aaatcaggta    80820
gaaaagtatg ttataacaat tcattatatt ctgttgaaaa tttgagagaa tatatctgtg    80880
atttagaata tgctaaaact gtaactaagt tttcacataa agatataaaa tgcaagtgcc    80940
ctatatgtag tgaagagaaa gttatgaagg ttaataaatt agttaataac ggttttctt     81000
gtcatagatg tagctcaact ataacatatc ctgaacgatt aatgatagga ttactagaat    81060
taaataattt aaactatgaa tatcaaaaag tatttaaaga cctacctaat agaaaatttg    81120
attttatttt acctaaatta aatatggtta ttgaaactca tggattacaa cattataggg    81180
aattaaatgg ttacatgaat catgaaaaaa caaaggaatc ggatttagag aagtataact    81240
attgcaagaa taataatata gattatattg aaatagattg tagttacagt gatttatcct    81300
ttatattaag taatgttgag aatagtaagt taaatagcat acttaaaaat aagaattacg    81360
ataatcttag caattatatt ataagaagta aaaatgatga tgttaagtat aatatatatt    81420
tggattactg caaaggatta agcaagaaag aattgaaaga taaatataat aaaacgagtt    81480
attatataaa caggtctatt gagatattta acattaatt aataagccta gaataaatct     81540
aggctttgtt tattttttt gtaatttaat tttgataaat gtaataacta tggtatacta     81600
tatgtaattg atattaatac ataaaaaata ttaatatttc acttacaagt tattattgtt    81660
atattattaa cgtaaaagta aataaaataa caagtggagg tgtagacacc tttggaagaa    81720
ataaaattta atgcttttgt acctatggat ttgaagaaat ctgtatcaac agcttctgat    81780
actaatgagt attctatcgt ttcaggatgg gctagtactc caagtatgga tttacagaat    81840
gatatagtta atcctaaagg aatagatata gagtatttta agtcacaagg gtacattaat    81900
tatgagcatc aaagtgataa ggttgtaggg atacctacag agaattgcta tgtggatata    81960
gaaaaaggtt tatttattga agcaaagcta tggaagaatg acgaaaatgt tgttaagatg    82020
cttgatttag ctgagaaatt agaaaaatca ggtagtggaa gacgtttagg tttttctatt    82080
gaaggtgcag ttaaaaaacg taatataaat gacaatagag ttattgatga agttatgata    82140
accggagttg cattagttaa aaaccctgct aatcctgaag caacatggga aagctttatg    82200
aaatcatttt taactggtca tggtacatca cctgacactc aagttgatgc aggagcttta    82260
agaaaagaag aaatagcatc tagcattaca aatttagctt acgtcactaa gattaaagat    82320
ttaaaagagt ttaatgatgt atggaatggc gttgttgaag atttgagtaa atctaatagt    82380
```

FIG. 21SS sequence.txt

| | | | | | |
|---|---|---|---|---|---|
| atgggatatg | aggaatcagt | ccttacgtta | caactagcta | aaggtttatc | tcgtaaagat | 82440 |
| gcagaactag | cagtaatgga | tataaacaaa | caaaaactag | aataggtaag | gagaatacat | 82500 |
| tctatgagta | aagaaatgca | aaatatttta | gaagagtatg | ataagttaaa | tgctcaagag | 82560 |
| gcagtttcga | aatctgtaga | agatgatgaa | aagaatacag | tagaatctac | cgaagagcaa | 82620 |
| gtagcagaaa | caactgaaga | acctgctaaa | gaacctgaaa | aagtatctga | ggaagatgct | 82680 |
| aaagaagcac | aagagcaagg | tgaaaaagtt | gaatctgaag | aggtagcaga | ggacaatgaa | 82740 |
| gatgaggaag | ttgaaaaatc | agctaaagaa | tcaaaagacc | ctgtagacca | aaaagatact | 82800 |
| aagacagaaa | ataaagacaa | cgagaaacgt | aaaaataaaa | aagataaaaa | agaagattct | 82860 |
| gattctgacg | atgaagataa | agatactgac | gatgataaag | ataagaaaga | agataagaag | 82920 |
| gaaaaaactt | ctaaatcaat | ttctgatgaa | gatatcacaa | cagtatttaa | atctatctta | 82980 |
| acatcttttg | aaaacttaaa | taaagagaaa | gaaaactttg | ctactaaaga | agatttaagt | 83040 |
| gaagttagta | aatctattaa | tgagttatca | gcaaaaattt | ctgaaatcca | agctgaagat | 83100 |
| gtttctaaat | cagtagacac | tgatgaagaa | gctgtagaaa | aatcagtaac | atctacaaat | 83160 |
| ggagagcaag | aaaaagtaga | aggttatgtt | tctaaatcag | tagacactga | agaacaagct | 83220 |
| gaaactggtg | aagcaaaatc | agaagaagct | gaagaagtac | aagaagataa | cacatttaaa | 83280 |
| ggattaagtc | aagaagaacg | aactaagttc | atggattctt | acaaagcaca | agctaaagac | 83340 |
| cctagagctt | ctaaacatga | cttacaatca | gcttaccaat | cttacttgaa | cattaacact | 83400 |
| gaccctacta | acgcatcaga | gaaagatatt | aaaactgtaa | aagactttgc | acaaatttaa | 83460 |
| ttaatgcaca | aagttgtgtt | atattatacg | gtgtaactaa | agaatataaa | tagggtacat | 83520 |
| tttactgtac | cctacataaa | ataaaagaa | cacaaatgaa | aggtgataaa | tttatatgac | 83580 |
| tatcgaaaag | aacctgtcag | acgttcaaca | aaagtacgct | gaccaattcc | aagaagacgt | 83640 |
| agtaaagtca | ttccaaactg | gttatggaat | cactcctgat | acacaaattg | acgcaggagc | 83700 |
| tttacgtaga | gaaattttag | atgaccaaat | cacaatgtta | acatggacta | atgaagattt | 83760 |
| aatcttctat | cgtgatatct | cacgccgtcc | tgctcaatct | acagtagtaa | aatacgacca | 83820 |
| atatttacgt | catggtaacg | taggtcactc | tcgtttcgtt | aaagaaatcg | gagtagcacc | 83880 |
| agtatctgac | ccaaatatcc | gtcaaaaaac | tgtatcaatg | aaatacgttt | ctgatactaa | 83940 |
| aaacatgtca | attgcatcag | gtttagtaaa | taacattgct | gacccatcac | aaatccttac | 84000 |
| agaagatgct | atcgcagttg | ttgcaaaaac | aattgagtgg | gcttcattct | acggtgacgc | 84060 |
| ttcattaact | tctgaagttg | aaggtgaagg | tttagagttt | gatggtttag | ctaaattgat | 84120 |
| tgacaaaaat | aacgtaatta | acgctaaagg | taaccaatta | actgagaaac | acttaaatga | 84180 |
| ggcggcggta | cgtatcggta | aaggtttcgg | tacagctaca | gatgcttaca | tgcctatcgg | 84240 |

FIG. 21TT

```
                              sequence.txt
tgtacacgca gacttcgtta actcaatctt aggtcgtcaa atgcaattaa tgcaagacaa    84300
cagcggtaac gttaacactg gttacagcgt aaatggtttc tactcatctc gtggattcat    84360
taaattacat ggttctacag taatggaaaa tgaattaatc ttagatgaat cattacaacc    84420
attaccaaat gctccacaac ctgctaaagt tacagctact gttgaaacta agcaaaaagg    84480
tgcttttgaa aatgaagaag accgtgcagg attatcatat aaagtagtag ttaactcaga    84540
tgacgctcaa tcagctcctt ctgaagaagt aacagctaca gtatctaacg tagacgatgg    84600
tgttaaactt tcaattagtg ttaacgctat gtaccaacaa caaccacaat tcgtttctat    84660
ctaccgtcaa ggtaaagaaa caggtatgta cttcctaata aaacgtgtac cagttaaaga    84720
tgcacaagaa gatggaacaa tcgtattcgt agataagaac gaaacattgc ctgaaacagc    84780
agacgtattt gttggtgaaa tgtcaccaca agtagttcac ttattcgaat tacttccaat    84840
gatgaaatta ccattagctc aaattaatgc ttctattaca tttgcagtat tatggtatgg    84900
tgcattagca ttacgtgctc ctaaaaaatg ggctcgtatt aaaaacgttc gttatatcgc    84960
agtttaatag aataagaaaa actgaataca agagaatagg gataaactta gggtttatcc    85020
cttttttatt aaaataaact tgaagggatt taataaatat gttatactat aagaaactat    85080
tagataaaaa aatggctact gtttatggta cagtggagat tgacaaagat ggagtagtta    85140
aaggattaac taaagagcaa gaaaagaat ttgcaaatgt tccaggtttt gaatttgaag    85200
aagaaaagaa aactactaga aaacaatcag cttctactag taaagaagaa gagcctaagg    85260
aagaggaaaa gaaagcctct actagaaaaa ctacaagtac tactagaaaa tctacagcac    85320
gtaaaacaac agccaaaaaa gatgaaaata agtaaagggt gaattaaatg gttaactcaa    85380
tgtttggagg ggacttagac ccttatgaaa aatcattaaa ctatgaatat ccttatcatc    85440
ctagtggtaa tcctaaacat atagacgtaa gtgagataga taatttaaca ttagctgatt    85500
atggatggtc accggatgca gttaaagcat atatgttcgg tatcatagtt caaaatcctg    85560
atacaggaca acctatgggt gatgagtttt ataaccatat attagaaaga gcggtaggta    85620
aagctgaaag agcattagat atatctatac tacctgacac tcaacatgag atgagagatt    85680
atcatgagac agagtttaat agttatatgt ttgtacatgc ttatagaaaa cctatattac    85740
aggtagagaa cttacagcta cagtttaatg gtagaccgat atataaatac cctgctaact    85800
ggtggaaagt agagcatcta gcaggacatg ttcaattatt ccctacagca cttatgcaaa    85860
caggacaatc aatgtcatat gatgcggtat tcaatggata ccctcaatta gcaggtgtat    85920
acccaccatc aggagcaaca tttgcacctc aaatgatacg attagaatat gtatcaggta    85980
tgcttccacg taaaaaagca ggaagaaata aaccttggga aatgcctcct gagttagaac    86040
aattagttat aaaatatgca ttgaaagaaa tataccaagt atggggtaac ttaatcattg    86100
gtgccggtat tgctaataaa acattagaag tagacggtat tacagagaca ataggtacca    86160
```

FIG. 21UU sequence.txt

```
ctcaatcagc tatgtatggt ggagctagtg ctcagatact tcaaataaat gaagatataa    86220
aagaactatt agatggttta agagcttact ttggatataa tatgatagga ttataaggag    86280
ggttagaaaa tggaaaaacc gtatatgata ggagccaact ctaaccctaa tgttattaat    86340
aagtcaacaa catatactac tacaacacaa gcagatgaac aagataaacc taagtatact    86400
actagactag agtttgatac gattgacatg attaggttta ttaatgaccg aggtataaaa    86460
gtattatggg aagaagcata tttctgccct tgtcttaatc ctgatacagg acatcctaga    86520
gtcgattgtc ctagatgtca tggtaaaggg attgcatatc tacctcctaa agagactata    86580
atggcaatac agtctcaaga gaaaggaact aaccagttag atataggtat attagacaca    86640
ggtactgcaa taggtaccac tcaattagaa aagaggattt cctatagaga caggtttact    86700
gttcctgagg tattgatgcc tcaacaaatg atttattttg tgaataaaga tagaattaaa    86760
aaaggtatac ctctatacta cgatgtaaaa gaagtaactt atatagccac tcaagatggt    86820
acagtctatg aagaagatta tgaaattaag aataatagat tgtatttaaa tgaaaaatat    86880
gagaatcata cagtaacttt aaagatactt atgactttaa gatatgtagt atcagatata    86940
ctaaaagaaa gtcgttacca atatactaag tttaatcaac ctaaatcaaa atttgaaaac    87000
ttacctcaaa aattacttct taaaagggaa gatgttattg tactacaaga cccttataaa    87060
gttaatgatg gtatagaaga agacctagaa attcaagtag atgaccctaa ggcttcggca    87120
tctaatccta gtaatttagg tggattcttc ggaggtgcat ttaaataatg ccagttcacg    87180
gaaagagacc taatttattt aaaaataaaa actataagca ggtaggtaag agaacaattg    87240
atggtatgcg ttcagaagtt cttgataaat tacaagcaac agcacagcaa gtagagaata    87300
ctagtattaa acgtatgcct acttacctac aaataacaga gaaaaagctt gaaaagaag     87360
gagtagtaga cctaaaaaaa gcttttgctc actcatctaa aaagaaaact agtaaagatg    87420
gcggatggta tttaactgta ccaatccgca tcaaaactag tagaatgaat aacagtactt    87480
accaagatat gagaacttta aaagtagata aggtacagg ttcagtctct aagataactg     87540
attacctaga aggacgtaga aagaatgtaa gccacccttc aatgaagcct gagcctatga    87600
ctcataatat gactaaagtt aaaagaggaa agcaatcttc ttactttata tttagaactg    87660
tttctagtaa gtcacctgct agttcttgga tacttaacag agataaagtt aatgaagata    87720
acttctctaa aacaactcta aaaactgtta agcaattaat gaactggaag atgaaaaatt    87780
taaattaaga ggagggatag tattaaatgg caataacatc agttgattca tatttattat    87840
cagaaataaa gcctagactt aacactgtgc tagagaattg ttatattata gatgaagttt    87900
taaaagactt tgattatcaa actagagaga gctttaaaga agctttctgt ggtaagaatg    87960
cacaacatga agtaacggta ggatttaact tcccaaaatt taaaaataac tatgaagctc    88020
```

FIG. 21VV sequence.txt

```
attacttgat acaattaggt caaggacaag agacaaaaaa ctctttaggg agtattcagt    88080
catcttactt tgaggcaaca ggagatacct tagtcgaatc ttctacagca ataagagaag    88140
atgataagtt agttttact gtttctaaac caataggaga gttaataaag gtagaagata    88200
tagagtttgc taaatacgat aatcttcaag ttgaaggtaa taaggtatca tttaagtatc    88260
aaacaaatga agattatgag aactacaatg ctaacattat atttaccgaa aagaaaaatg    88320
attctaaagg tttagtaaaa ggattcacag ttgaagaaca agtaacagtt gtaggtcttt    88380
catttaatgt agacgttgca agatgtttgg atgctgtact gaaaatgatt ttaatatcta    88440
tgagagatag tatagaagag caacaaacat tccaattaca gaatttgtct tttggtgata    88500
ttgcaccaat aatagaagat ggtgactcaa tgattttgg tagaccaaca attattaagt    88560
acacaagttc tctagatttg gattatacta ttacacaaga tattaataaa ctaacttta    88620
aagaaagaaa ggattggaag taggatggct agaaaaaaga cacctgaaaa taacactcct    88680
aaatttaatg gttatgttca tatagataca ttccttgata ctgcaaaaac ccttttaat    88740
atgaaggatt cacaagtagc aggatttaaa gcttatatgg aaggtagtca ttatttgttt    88800
agtgagcaag aattcttacc atcattagag aagtatctag gtaggaaatt agatatataa    88860
taacattcag ataaggagaa ttaaatatgg cagtagaacc attcccaaga agacctatta    88920
cccgtcctca tgcatctatt gaagtagata cttcaggtat cggtggctca gcaggttcaa    88980
gtgaaaaagt attttgctta atcggtcagg ctgaaggcgg agaaccaaat acagtttatg    89040
aattacgtaa ctatgcacaa gctaaacgtt tattccgttc aggagaatta cttgatgcaa    89100
tagaattagc atggggttct aaccctaact atacagcagg taagattta gctatgcgta    89160
tagaagatgc taaacctgct tcagcggaaa tcggtggatt aaaagtaaca tctaaaatct    89220
atggtaatgt tgctaacaac attcaagtag gattagaaaa gaatacatta agtgattcat    89280
tacgtttaag agtaatcttc caagatgacc gtttcaatga ggtttatgat aatatcggta    89340
atatcttcac aatcaagtac aaaggagaag aagctaacgc aactttctct gtagaacatg    89400
atgaagaaac tcaaaaagca agtcgtttag tattaaaagt tggagaccaa gaagttaagt    89460
catatgattt aactggtgga gcttatgact acactaatgc tattattaca gacattaatc    89520
aattacctga tttcgaagct aaattatcac ctttcggaga taagaactta gaatctagta    89580
aattagataa aattgaaaat gcaaatatca aagataaagc tgtatatgta aaagcagttt    89640
ttggtgactt agaaaaacaa acagcttaca acggatcgt atctttcgag caacttaatg    89700
cagaaggaga agtaccaagt aatgtagagg ttgaagcagg agaagaatca gctacagtaa    89760
ctgctacttc acctattaaa actattgagc cgtttgagtt aactaagtta acgggcggta    89820
ctaatggaga accacctgct acatgggcag acaagttaga taaatttgca catgaaggcg    89880
gatactacat tgtcccatta tcatctaaac aatcagttca tgcagaggta gcttcttttg    89940
```

FIG. 21WW sequence.txt

```
ttaaagaacg ttctgatgca ggggaaccaa tgagagctat tgttggtgga ggattcaatg    90000
aatctaaaga acaattgttc ggtagacaag catcattatc taatccacga gtatcattag    90060
tagctaactc aggtactttt gttatggatg atggacgtaa aaaccacgta cctgcttaca    90120
tggtagccgt agctctaggt ggtcttgcaa gtggtttaga aatcggtgaa tcaatcacat    90180
tcaaaccact acgtgtaagt tcattagacc aaatctatga gtcaatagat ttagatgaat    90240
taaatgaaaa tggtattatt agtatcgagt tgttcgtaa ccgtactaat acattcttca    90300
gaatcgttga tgacgtaact acattcaatg ataaatcaga cccagttaag gctgaaatgg    90360
ctgttgggga agctaatgac ttcttagtaa gtgagcttaa agttcaactt gaagaccaat    90420
ttattggtac tcgtactatc aatacaagtg cttcaatcat taaagacttt atccaatctt    90480
acttgggtcg taagaaacgt gataatgaaa ttcaagactt ccctgctgaa gacgtacaag    90540
ttattgttga aggtaacgaa gcaagaattt caatgacagt ttacccaatc agaagcttca    90600
agaaaatctc tgttagcttg gtttacaagc aacagacatt acaagcctag tctaggtgac    90660
ggagtacctg gattaggtac tcctattaat ataatttgaa tactttagga gagtgaatac    90720
agatggcatc agaagctaaa caaaccgtcc atactggtaa taccgtccta cttatgatta    90780
aaggtaaacc ggtaggaaga gcacaatcag catcaggtca acgtgaatac ggtacaactg    90840
gtgtatacga aatcggttct atcatgcctc aagaacacgt atacttacgt tatgaaggta    90900
caattacagt agaacgttta cgtatgaaaa aagaaaactt tgcagattta ggatatgctt    90960
cacttggtga agaaattctt aagaaagata tcattgatat tttagtggta gataacttaa    91020
cgaaacaagt tattatctca tatcatggtt gctctgcaaa taactacaat gaaacttggc    91080
agacaaatga aattgtaaca gaagaaatcg agttcagtta cctttaacta atagaggcta    91140
tgtttggtga caagcataga aaacacttta aattgcgtga aagtcttaaa gactagataa    91200
ctacaacgta actcgaaagg gtaagcgtga atgttgagaa atcagaaaaa atatctagta    91260
tagtataagg ttaaatccta agtacagtaa aatagatgat acgcaggcaa gcctacaaat    91320
gtgggaagct tcaacgacta taataggtga gtcttagtta cacattaaga ttatggtata    91380
gtctactccc tttaaaatat atcgaaagat agggtacaaa ggacagcatc agataaagct    91440
agaacttaaa tttcttatta agaccaacaa taaagttgg tcttatattt tatacttgct    91500
ttgtctgagg cagtgtgcta taattaaaat acaaggaggt aataatatgg gaaaaaatca    91560
atatacattt aatattaaag aaaataaaaa taaatggtat gaatggtgta aactacaaaa    91620
cgtaaaacct ttagtagaat atgaaaatgc acaacaaata ttttatttg aatttcttga    91680
aggtaaattt aaaggactaa taggaaaaac atattgggct agtataaata gaggttctaa    91740
tatgcgtatg agttgtttaa catcagaaag taaagataaa tatttaaaaa atttaggaaa    91800
```

FIG. 21XX sequence.txt

| | | | | | | |
|---|---|---|---|---|---|---|
| aagaaaaggt | atagaggtag | tagaagacta | taagggtggc | agaaaattaa | aacataaatt | 91860 |
| tatagtttta | gaaggtaagt | accaaggatg | tgaaggatat | ataactttaa | atgatttaga | 91920 |
| gaatttaggt | agagtagata | atagaagttt | atctgaaaaa | ggaaggaaac | aatactttga | 91980 |
| taaacaggca | agacttagag | attgtattat | tctagagtac | cctaaagact | atagaataaa | 92040 |
| aactaaagat | aagatagtag | taaaagataa | agaagggcat | gttcataata | ttattgttca | 92100 |
| ggacttttt | gagaaatcat | ctttattgga | gttatcttgt | gctagtgaag | gagagaaaat | 92160 |
| agttaaagaa | atacttacta | aaaattctat | aaaatttgaa | aaagaaaaat | catttagaaa | 92220 |
| caaagaaggt | aaagtacaaa | gatttgattt | ttatattaat | gaaaataata | agaatatgc | 92280 |
| aatagagtac | aatggtgcac | agcactacat | agattctaca | ggatatctta | aagatacttt | 92340 |
| ggaaacaacc | cagaaaagag | ataaactaaa | aaagaatac | agtaaagata | aggtataaa | 92400 |
| tttattaatt | attccttaca | caataacaga | taagaaagaa | atggaaaaaa | ttattttaaa | 92460 |
| tttttaaac | aaataaccct | tgacactccc | tcaagggata | tgttattata | ataacaggtt | 92520 |
| aggagtaata | agtatgaata | ataggcaagc | taaaataaaa | ggatataacc | aatttcatta | 92580 |
| ttatgatttt | ccaacaacta | aaggtaagtt | taaagatata | atgaaaagaa | aatctagaac | 92640 |
| agaacttaaa | aaagatttac | aaaaagaaag | gaagtattat | cttgacaaat | aagagaaaaa | 92700 |
| cgataggtaa | gatgagtaac | acaagagcaa | catggaatat | taatccggta | actaaagtta | 92760 |
| aaaagataa | aacaaaatat | tctagaaaaa | ataaacataa | aggtcttgac | aattataatt | 92820 |
| aactaaggta | tattattagt | ataacaaaaa | aggagatggg | tatatgagta | catttggtc | 92880 |
| agaaagaaga | acaactaata | aagataggca | agttaaaaaa | cattatactc | aaatgagtat | 92940 |
| gtatgaaaga | aagaaatgtg | tagagttatt | acaagagaca | attactgaaa | atagaattat | 93000 |
| taattttaca | cgacatagtg | caaagaaagt | taaaggtaaa | ccaacaacaa | atatacctaa | 93060 |
| attaataggt | tttatttta | aaataagtt | tgcctacgaa | aatatcatag | aatacaataa | 93120 |
| cacagattat | aatggtaata | ttgagaggag | aattgttgtt | aaacatccta | agttataac | 93180 |
| tgtagaagga | aaacctagct | atcagttttt | gacaattagt | cttgaagatg | ctagagttat | 93240 |
| tacagtatgg | tacaacagtg | tagatgatac | acatagaaca | ctagatttaa | attattatag | 93300 |
| taaagacttg | acaattcaat | aaggaggtat | tataatgggt | atcacaatag | taaatagtta | 93360 |
| ttttattctg | tctaacatct | tcctcatcat | attaaccata | ttaaatggta | agggtactgt | 93420 |
| tacaagggaa | tcactaacta | tgagtaaaat | attagtagta | ataacatcaa | ttcaattttt | 93480 |
| agcatgttta | attattaatg | gtatttattg | gtcactaaaa | ttttagaata | aagtattga | 93540 |
| caaattaaaa | ctaataaatt | ataataaagg | tataacaaat | taaggagaa | gatataaaat | 93600 |
| gtcacaagat | aaattaagag | caatttacac | agaaatgaaa | gtagaattac | acaaatttcc | 93660 |
| taaagaggta | gatataacaa | gtaaatcaac | tgcaattgca | atcaatcaga | ttttagataa | 93720 |

FIG. 21YY sequence.txt

| | | | | | | |
|---|---|---|---|---|---|---|
| attcaaaaca | ttaacagaac | aagcaggaaa | gattactaga | aaatatttag | aaggtcaaga | 93780 |
| aatattaact | attgattatg | agtattatga | ttcattacaa | gaatactata | tttacctact | 93840 |
| tagaaatagt | gaaaagattg | aacaaagttt | acaagaaatt | actaagcgca | caggtgaata | 93900 |
| tgtaaagtaa | ttttgattta | aaaacaaaat | atgatatact | atgtttaaag | tagtaagcct | 93960 |
| acactagtcc | gtgttatatt | aatattgaat | cggataagcg | taggctttat | taatatttaa | 94020 |
| aaaaggaagg | tatatcatat | tatggcagaa | gaaattaaaa | aggaacaaga | tgtacaagaa | 94080 |
| acaactaaag | aagaaaaaaa | agatgttagt | aaaatgacac | cggaagaaat | agataaatta | 94140 |
| aaatatcaag | acaaacaaga | aaaagaacaa | gttattaaca | aagttattaa | aggtgttaat | 94200 |
| gatacttggg | aaaaagaata | taactttgaa | gaattagact | taagatttaa | agttaaaatt | 94260 |
| aaattaccta | atgcacgaga | acaaggtaat | atatttgcgt | tacgttctgc | ttacttaggt | 94320 |
| ggtatggata | tgtaccaaac | agaccaagta | attagagcat | atcaaatgtt | agctacatta | 94380 |
| caggaagtag | gtattgaagt | tcctaaggaa | ttccaagacc | ctgacgatat | ttataactta | 94440 |
| tatcctttaa | ctgttatgta | tgaagattgg | ttaggattct | taaactcctt | tcgttactaa | 94500 |
| tagtatagaa | acattagata | aagatataga | acgattgggc | ggtatggaat | caattgttaa | 94560 |
| acaaccttta | tctagaaatc | tatgggctat | tatgaaagag | tttaatgttt | tacctactga | 94620 |
| gcaaagattt | aaggacttag | atgattatca | gatagagttt | attattggga | atatgaacag | 94680 |
| agatgtttat | gaacataaca | aacaacttaa | acaagctcaa | aaaggtggaa | aattcgatag | 94740 |
| tcaattcgaa | gatgatgata | gtagttggtg | gaatgaatct | catgaagact | tgacccagt | 94800 |
| acctgatttc | ttagatgctg | atgatttagc | acaacaggtg | gaagctaaat | tatccgatag | 94860 |
| agataaggaa | gaaagagcta | agagaaacga | tgcggagtta | aatgatgaaa | cagaaggact | 94920 |
| tactacacaa | catctagcta | tgatggaata | catcagacag | aaacaacaag | aattagatga | 94980 |
| tgaagtagga | aatggtaaga | ctagtgaaga | ggatgctact | atatcacaag | atagcgttaa | 95040 |
| taaagcacta | gaagacctag | atgatgactg | gtatatgtaa | agggtggtag | gtgatactac | 95100 |
| catccttatt | tttttaaaat | ggatggtgaa | taatgatggc | aatgaatgac | gattatagat | 95160 |
| tggtcttgtc | cggtgatagt | tcggatttag | agaatagtct | gaaggcaata | gaactttata | 95220 |
| tggattcttt | agagtctaag | aatattgatg | ctcctttaga | taatttctta | aaaaaattaa | 95280 |
| aagtaattgc | taaagaagtt | aaaaatgtac | agaacgcaat | ggataaacaa | gatggtaaat | 95340 |
| ctgttatatc | ttctaaagac | atggatgaat | ctattaaatc | cactcaatct | gctacaaaga | 95400 |
| atataaatga | attaaagaaa | gctttagatg | accttcaaaa | agagaatata | tctaaaggta | 95460 |
| ttgcacctga | ccctgaagtt | gaaaaagcat | atgctaagat | gggtaaagtt | gtagatgaaa | 95520 |
| ctcaagaaaa | acttgagaaa | atgtcttcac | aaaaaatagg | ttctgatgct | agtattcaaa | 95580 |

FIG. 21ZZ sequence.txt

| | | | | | | |
|---|---|---|---|---|---|---|
| atagaattaa | ggaaatgaaa | accttaaatc | aagtaactga | agaatacaat | aaaataagta | 95640 |
| aagattctag | cgcaactaaa | gattatacaa | aacgattaag | agctaatcgt | aatatgacta | 95700 |
| gaggttacat | ggagcgttca | gaaggaacag | gacgtttgac | atatgaccaa | ggtgcacgag | 95760 |
| ttagaagtga | actaggtaaa | ataagttctt | atgagagcca | aagaaaacaa | aaccaacgta | 95820 |
| atttaggaca | agcaagagag | caatatagca | actatagaaa | ccaacaacaa | gacttgacta | 95880 |
| aacgtagagc | tagcggtcaa | attaataagg | cacaatatga | acaagaatta | gcttctatta | 95940 |
| aacaggaaat | gaaagctaga | gaagaactta | tatctaacta | cgagaaacta | ggagcagaac | 96000 |
| ttgataaaac | agtccagtat | tataagggtt | cagttcaaaa | ggatttccaa | tctagagatg | 96060 |
| tagaccaaca | acgaggaaca | tttggtagaa | tggttcaaga | acgtttgcca | tctattggtt | 96120 |
| ctcatgctat | gatgggtact | acagctatgg | ctacaggttt | atacatgaag | ggtgcctcat | 96180 |
| taagtgaaac | taatagaccg | atggttacat | cattaggtca | aaattccgat | aatatggata | 96240 |
| tagattctgt | aagaaatgca | tatggagact | tgtcaattga | caacaaatta | ggttataata | 96300 |
| gtactgacat | gttaaaaatg | gctacttcat | atgaagcatc | agtagggcat | aaaagtgacg | 96360 |
| aggacacaat | ggcaggaact | aaacaacttg | ctattggagg | acgttcttta | ggtattagag | 96420 |
| accaagaagc | ttatcaagag | tctatgggtc | aaatcatgca | tactggtgga | gtaaattctg | 96480 |
| ataacatgaa | ggaaatgcaa | gatgcattcc | taggtggtat | taaacaatca | ggcatggttg | 96540 |
| gtcgtcaaga | tgaacaactt | aaagcactag | gttctatagc | ggaacaatca | ggagaaggaa | 96600 |
| gaactctaac | taaagaccaa | atgagtaatc | ttactgccat | gcaatctact | tttgcagagt | 96660 |
| caggaagtaa | aggattacaa | ggtgaacaag | gtgccaatgc | tattaacagt | atagaccaag | 96720 |
| gacttaaaaa | tggtatgaat | agttcttatg | ctcgtatagc | aatgggatgg | ggaacacaat | 96780 |
| accaaggtct | tgaaggtgga | tatgatttac | aaaaacgtat | ggatgaaggt | atatctaatc | 96840 |
| ctgaaaactt | gacagatatg | gctgatatgg | ctactcaaat | gggtggcagt | gaaaaagaac | 96900 |
| aaaaatacct | atttaataga | agtatgaaag | aaataggcgc | taacctaact | atggagcaat | 96960 |
| ctgatgaaat | atttaaagat | gctcaatccg | gaaaactatc | taaagaagag | ttagctaaga | 97020 |
| aagctaagaa | aatggaaaaa | gaaggtaaaa | aagaaggaga | agataacgcc | actgattata | 97080 |
| aagaatctaa | atcaggaaaa | aatgaccaaa | ataaatctaa | gactgatgat | aaagcagaag | 97140 |
| atacttatga | tatggctcaa | ccattaagag | atgctcatag | tgctttagca | ggtcttcctg | 97200 |
| cccctatata | tttagctata | ggagctatag | gagcatttac | agcttcacta | attgcatctg | 97260 |
| caagtcaatt | tggagcaggt | cacttaattg | gtaaaggagc | caaaggactt | agaaataaat | 97320 |
| ttggtagaaa | taagggtggt | agctccggcg | gtaatcctat | ggcaggtgga | atgcctagtg | 97380 |
| gtggtggttc | acctaagggc | ggaggctcac | ctaaaggtgg | aggcactcgt | tctactggag | 97440 |
| gaaaaatact | tgatagcgct | aaaggtcttg | gaggattcct | agtaggtggc | gcaggatgga | 97500 |

FIG. 21AAA sequence.txt

```
aaggtatgtt tggtggggag tctaaaggta aaggctttaa acaaacatct aaagaagcct    97560
ggtcaggtac tagaaaagta tttaatagag ataatggtag aaaagccatg gataaatcta    97620
aagacatagc taaaggtact ggtagtggtc ttaaagatat ctataatgat agtatatttg    97680
gtaaagaaag aagacaaaac ctaggagaaa aagctaaagg ttttggtggc aaagctaaag    97740
gtctttatgg taaatttgct gataagtttg gtgacggagg taaaaatggt atcctttcac    97800
aatcaccaaa agcaggtgga agtggcatag ggaaacttgg aaaacttgca ggtggacttg    97860
gaaaaggagc cggagtttta ggtgttgcta cgtctgcctt atcattaata cctgctttag    97920
cttccggaga tagtaaagct atcggcggtg aataggctc tatgggtgga ggaatggcag     97980
gtgcatcagc aggagcttct ataggagctt tatttggtgg tgtaggtgca atacctggag    98040
ctttaatagg tggagctata ggttccttcg gaggaggagc tgttggtgaa aaagtcggag    98100
acatggctaa aaaagctaac actaaagaag gatggaacct aggatggact aatggagata    98160
aagatggtaa gaataaattc caagattctt tattaggaaa acctatatct aaagcatgga    98220
gcggtataac aggtctcttt gataatgacg ctgaagcatc cgaagaagat agtaaagata    98280
agaaaaaagg tgttaaaggc gttaaggag atactaagaa gaaagaaaaa atgacagcag     98340
aacaacttag agaaaagaat aaccaatctg aaactaagaa tcttaaaatc tatagtgatt    98400
tacttgacag agctcagaaa attattgaga gtgctaaagg tattaatata gatggaggaa    98460
cttctgatag tggttctgat agtggaggct ctgcatctga tgtaggtgga gaaggtgcag    98520
agaagatgta caagttcctt aaaggaaaag gactatctga taatcaggta ggagctgtta    98580
tggggaactt acaacaagaa tctaatcttg accctaatgc taagaatgct tctagtggag    98640
catttggtat tgctcagtgg ttaggagcta gaaaaacagg attagaaaac tttgctaaat    98700
ctaaaggtaa aaaatctagt gacatggatg ttcaattaga ttacctatgg aaagaaatgc    98760
agtctgatta tgaaagcaat aatcttaaaa atgcaggttg gagcaaaggt ggaagcttag    98820
aacagaatac aaaagcattt gctactggat ttgaacgtat gggagcaaac gaggctatga    98880
tgggtactcg tgttaacaat gctaaggaat tcaagaagaa atatggaggc tccggtggcg    98940
gaggtggtgg aggagcttta tcctctactt atcaagaagc tatgagtaat cctgtattaa    99000
ctactggttc taattataga ggctctaatg atgcttctaa tgcttctaca actaacagaa    99060
taacagtcaa tgttaatgtt caaggtggaa ataatcctga agaaactgga gacattatcg    99120
gaggaagaat tagagaagtt ctagatagta atatggatat ctttgcaaat gaacataaga    99180
gaagttatta gtaattttgt attgacacaa gagtagtatc atagtatact actcttatac    99240
atataaaaaa taaaaggaag tatgtgtata tgcgtagaat aagaagacct aaggtaagaa    99300
tagaaatcgt tacagatgat aatacattta cattgagatt tgaagataca cgtgactata    99360
```

FIG. 21BBB sequence.txt

```
atggtgatga gtttggagct aaacttttag gattccaaac taaaaactct atggaagatg    99420
atagttcagt tttccaaata aatatggcag gagatactta ttgggataag ctagttatgg    99480
ctaatgatat cataagaata tttattacac ctaatgatga ccccaacgat aaagaaggaa    99540
gacaagaacg acttatccag gtaggtatgg tttctcaagt atcaaaagta ggtagttacg    99600
gtaatgacca aactcaattt agaataacag gtcaatcttt tgtaaaacct tttatgaaat    99660
ttggattagg cgttattcag gaagttcaag ctgtattgcc tgaagtaggt tggcttattg    99720
atggtgatgg agataatgaa gtaaaattta ctggtagctc agctcatgaa gtaatgactg    99780
gcattatacg tagatttata ccttatatga aatataacta tactgaaaaa acatataata    99840
caattgataa ctatcttgat tatgatgatt taagtagttg ggatgagttt gaaaaactta    99900
cagaagtttc agcctttact aattttgacg ggtcattaaa acagttaatg gatatggtaa    99960
cagctagacc ttttaatgag ttattcttca aaaattcaga aaaacacct ggaaaggctc    100020
aacttgtatt aagaaagacc cctttaatc ctactgagtg gagagcttta gatatgatta    100080
aagtacctac tgaggatttt atagaagagg atgtaggtaa aagtgatgta gagacatatt    100140
ctatatttac agcaacacct gcaggtatgt tgaaagagct taacggtgat gtattttcca    100200
aaccacaatt ccatcctgaa ttaactgata gatacggtta taccaaattt gaagtagaaa    100260
atatttatct tagtacaaaa tcaggttcag ccactgagga ttcagattct tcaggtgatg    100320
ataatggtac agaacgagga acttactcta aaattatgaa agatttaagt aactatggaa    100380
gagataatat atctaaaggt atagataagt atacaagtaa attatcttca aaatataaaa    100440
acttaaaaaa agcccaagct aaaaaaatta tagagaagtt tgtcaaagaa ggaaaagtaa    100500
cagaaaaaga atatgaaaaa ataacaggta ataaggtaga tgatgaatta acatcagata    100560
acagaccgaa gttgacaaaa gataaattaa agagtatact aaaagagaag tttaaaacac    100620
aagatgattt taataattct aagaaaaaga aaaaagctaa gacagatgca cttaaagaat    100680
tgacaactaa atatcgtttt ggtaataaaa cacatgctac aactttgtta gatgaatata    100740
ttaaatacaa aggagaaccg cctaatgatg aggcttttga taaatatctt aaagctattg    100800
aaggtgttag taacgtagct acagacacag gttcagatgc aagtgatagc cctctagtta    100860
tgttttctag aatgttattt aattggtatc atggtaaccc taacttctat gcaggagata    100920
ttattgtttt aggagaccct aagtatgacc taggtaaaag attatttatt gaggataagc    100980
aacgaggaga cacatgggag ttctatattg aatctgtaga acataaattc gattataaac    101040
aagggtatta tacaactgta ggagtaacta gaggtttaaa agacgctatt ctagaagatg    101100
gtaaaggtag tcctcataga tttgcaggat tatggaatca atcatcagac ttcatgggag    101160
gtcttatggg tgaagatact tctaaagaac ttaaagaaaa aggtgtagca gagaaacaaa    101220
gtagtggagg taaagatggt ggttctgata gtggcggagc tcaagatggt ggctctttag    101280
```

FIG. 21CCC sequence.txt

| | | | | | | |
|---|---|---|---|---|---|---|
| attcacttaa | aaaatataac | ggcaaacttc | ctaaacatga | cccaagtttt | gttcaacctg | 101340 |
| gtaaccgaca | ttataagtat | cagtgtacat | ggtatgctta | taatagaaga | ggtcaattag | 101400 |
| gcattcctgt | gcctttatgg | ggggacgccg | ccgactggat | aggcggtgct | aaaggagcag | 101460 |
| gttatggtgt | aggtagaaca | cctaaacaag | gtgcttgtgt | tatatggcaa | agaggagttc | 101520 |
| aaggaggtag | cccacaatat | ggtcacgtag | cttttgtaga | gaaagtatta | gatggaggta | 101580 |
| aaaaaatatt | tatctctgaa | cataactatg | ctaccctaa | tggatatggt | actagaacaa | 101640 |
| tagatatgag | ttcagccata | ggtaagaatg | ctcaattcat | ttacgataag | aaataaagga | 101700 |
| ggatagtcta | tggcaacaga | taaagaagct | aaagatgtta | ttgataaatt | tatagacaat | 101760 |
| gtatttaatt | ttgatgtact | tacaaaagaa | agaataaaag | aaaaagatga | agaaattaaa | 101820 |
| aaaataacta | cagatgatat | gtatgaaaag | gttgtgtata | tacgacccta | cgttggagta | 101880 |
| atacaaagtc | ttaaccctca | acatgtgcag | tatgaatcat | tttctaataa | tggttatgat | 101940 |
| atagaggcag | aattaagttt | caggaaagta | agttatttag | ttgataaagg | gtctatacct | 102000 |
| acagattctt | tatctacttt | aacagttcac | ttagtagaac | gaaatcaaga | actattaata | 102060 |
| gattactttg | atgagataca | agatgtgttg | tatggagaat | atatggaaga | agaatatgta | 102120 |
| tttgatgaag | atgtaccatt | aagtacgata | ctagcattag | acttaaatga | taatcttaaa | 102180 |
| tccttatcaa | atataaagta | tatgttcaaa | ggtgctccta | aagagaatcc | atttggaaca | 102240 |
| gataaagatg | tttatataga | tacttataac | ttattatact | ggttatattt | aggtgaagat | 102300 |
| gaagagttag | catacctat | gaatattaat | tacttctttta | cagagggaag | attctttact | 102360 |
| atattcggta | aaggacataa | gtataaggta | gatgttagta | aatttatagt | tggagatata | 102420 |
| ttattctttg | gtagaagtga | tactaatata | ggtatttatg | taggagatgg | ggagtttata | 102480 |
| tctatgatgg | gtaaattccc | taaagatgaa | acacctatag | gaaaatataa | acttgatgat | 102540 |
| tactggaatg | aatttaacgg | aagagttatg | agattcgatg | aagaggtgta | tatttaatgg | 102600 |
| tagtaagatt | ccaatcttcc | atggggagaa | gtttaaaaag | agtagattca | gatgatttaa | 102660 |
| atgtaaaagg | attagtttta | gctacagtta | gtaaaattaa | ttataaatat | caatcagtag | 102720 |
| aagttaaagt | taacaactta | actctaggaa | gccgtatagg | tgacgatggt | agcttagctg | 102780 |
| taccttatcc | taaatctttc | ataggaagaa | cacctgaagg | aagcgtattc | ggtacaaaac | 102840 |
| ctcttattac | tgaaggttct | gtagtattaa | taggatttct | aaatgatgat | ataaatagtc | 102900 |
| ctattatttt | aagtgtttat | ggtgataatg | aacaaaataa | aatgattaat | accaatcctt | 102960 |
| tagatggggg | taagtttgat | acagaaagtg | tctataaata | tagtagttca | ctatatgaaa | 103020 |
| ttttaccatc | tttaaattat | aaatatgatg | atggagaagg | aacaagtatt | aggacttata | 103080 |
| atggtaaatc | attttctct | atgacatcag | gtgaagaaga | gaaacctcag | gcaacagatt | 103140 |

FIG. 21DDD

```
                                    sequence.txt
tttatactgg aactgagtat caagatttat ttacttctta ttatggtaat aagacattaa    103200
ttgagcctag aatacaaaag gctcctaata tgttatttaa acatcaaggc gtttttatg     103260
atgatggcac gccggataat catataacta ctttatttat atctgaaaga ggggatataa    103320
gagcctcagt tttaaataca gaaacacaga aaagaaccac acaggaaatg tcaagtgatg    103380
ggtcttatag ggttataaaa caagatgacg atttaatgtt ggatgaagct caagtttgga    103440
ttgagtatgg tattagtgaa gataataaat tctatattaa aaatgacaag cataaatttg    103500
aatttactga tgagggaatt tatatagatg ataagcctat gttagaaaac ttagatgaga    103560
gtatagcaga ggctatgaag aatttgaatg aaatacaaaa agaactcgat gatataaatt    103620
accttctcga gggtgtaggt aaggataact tagaagaatt aatagagtct acaaaagagt    103680
ctatagaagc ttctaaaaaa gcaacttcag atgtcaatag acttacaact cagatagcag    103740
aagttagtgg tagaactgaa ggtattataa cacagttcca aaaatttaga gatgagactt    103800
ttaaagattt ttatgaagat gcttctactg ttattaatga agtaaatcag aatttcccta    103860
ctatgaaaac agatgttaag accttaaaga ctaaagttga taacctagag aaaactgaaa    103920
taccaaatat taaaactaga ttaacagaac tagagaacaa taataacaat gctgataaaa    103980
taatatcaga tagaggagaa catataggtg ctatgataca gttagaggaa aatgtcactg    104040
tacctatgag aaaatatatg ccaataccat ggagcaaagt tacttataat aatgcagagt    104100
tttgggattc taataatcct actcgattag tagtacctaa aggaataaca aaagtaagag    104160
ttgcaggtaa tgttttgtgg gactctaacg ccacaggaca acgtatgttg agaatattga    104220
aaaatggtac ttatagtata ggattacctt atacaagaga tgtagctata tctacagcac    104280
ctcagaatgg tactagtgga gttattcctg ttaaagaagg agattacttt gagtttgaag    104340
cttcccaaga ctcagaaggt gacagacaat tcagagcaga cccttataca tggtttagta    104400
ttgaagctat agaattagaa actgaaacta tggagaaaga ctttatgctt ataggacata    104460
gaggagcaac cggatacaca gatgagcaca cgataaaagg atatcaaatg gctttagata    104520
aaggtgcaga ttatatagaa ttagatttac aattaacaaa agataataag ttattgtgta    104580
tgcatgattc tactatagac agaacaacaa caggaacagg taaggtagga gatatgacct    104640
tatcttatat acaaactaac tttacatccc tcaatggtga gccgatacca tctcttgatg    104700
atgtactaaa tcattttgga acaaaagtta aatattatat agaaactaaa cgtccgtttg    104760
atgctaatat ggataaagaa ttattaactc aattaaaagc aaaaggatta ataggaatag    104820
gttcagagag attccaagta attattcaat catttgctag agatcgtta attaatattc     104880
ataatcaatt ctctaatata cctttagctt acttaacaag tacattctct gaaagtgaaa    104940
tggatgattg tttaagttat ggttcttatg ctattgcgcc taaatataca actataacta    105000
aagaattagt agatttagct catagtaaag gcttaaagt ccacgcatgg acggtaaata     105060
```

FIG. 21EEE sequence.txt

| | | | | | | |
|---|---|---|---|---|---|---|
| caaaagaaga | aatgcaaagc | ttaatacaaa | tgggtgtaga | tggattcttt | acaaactacc | 105120 |
| tagatgaata | taaaaagatt | taatattaaa | gacctattaa | tttaggtctt | tttttagttg | 105180 |
| taatttaaac | tagttcgtga | tatattagta | gtatgagatt | tatatacata | ctgaaaagga | 105240 |
| gaggataaaa | tgccacaatc | agatggaata | agtaatcttc | atagaatagc | tttacgtttc | 105300 |
| cctaaagaag | gcggtggtta | tgatatgtat | agatttaaag | ttaaccctga | gaactacaca | 105360 |
| atagattcac | cacaacgtac | gacagcaatt | aaaacaaaat | cagatatcgt | aatagaagat | 105420 |
| tatggtaaag | atatagaagt | tattaacttc | acaggtacaa | ctggttttag | acctgttaga | 105480 |
| gaagcagatg | ggttaaaaac | aggtaagcag | aaaatggaag | agttacaaag | tagagttagt | 105540 |
| gaatatgcta | tgcaaggtgg | cagtggtaat | gtaagtggtt | cttacttaca | atttttaac | 105600 |
| tttacagatg | atagttatta | taaagttcat | ttagctcctc | aggggttaaa | gataactagg | 105660 |
| tctaaagatg | aaccattact | ttttagatat | gaaataacat | tagtagttat | tggttcatta | 105720 |
| acagaagcag | atagaagtgc | tgtaactact | gaagagtttg | gtaatgttaa | acctaatgct | 105780 |
| tctcaaagag | tagatgaagg | tataaaagaa | ttagataaaa | atgctcgtaa | aacgagagat | 105840 |
| agaaacaatc | aagaaatatc | tagaagagaa | aatacaatac | ctaaatccac | aggagataat | 105900 |
| acgaacgagg | gtaatagact | taagcaaagc | ttccctagta | gttctatata | taatcctaga | 105960 |
| caatctacta | atggattaaa | aggtaatatt | gacaatatgg | ctctgataat | aggttacggt | 106020 |
| gatggaggtg | tatctagcta | atgaataatt | ttataccaca | acctcaaggt | ctacttagat | 106080 |
| ttttaaatgc | cctagataca | gatttaactt | cttctcatat | gaatttactg | gatgaagagg | 106140 |
| tatcatttgt | atctaaattt | tatacaccac | agttacaatt | aagtgaatta | gcaaaaaaag | 106200 |
| tattgacaaa | tataaagaca | gatgatatac | ctgtattaga | aagggaattt | aatgataata | 106260 |
| caattatcca | taaagctaac | gatacattac | taaaagtaca | ggctccaaga | atgtatatga | 106320 |
| ttctacagtc | tattgtactt | gaagcatatg | ctattgttaa | ttgctttgta | gaaaatccaa | 106380 |
| gttctttaaa | atacttaact | gaagaagatg | ttagtataac | acgagaaaac | ttaaattatg | 106440 |
| tagctgacta | cttaggtaac | tatgatgact | acaatagtgt | tgtattagac | ttaagagatt | 106500 |
| tagacttatg | ttttagtgct | atagaattac | aattacctct | aattaaaaag | gaggctaacg | 106560 |
| tataatgaga | tttaagaagc | acgtagttca | acatgaagaa | acgatgcaag | caatagcaca | 106620 |
| gagatactat | ggtgatgtta | gttattggat | agacctagta | gagcataata | atttaaagta | 106680 |
| tccctatta | gtagaaactg | atgaagaaaa | aatgaaagac | ccggaacgat | tagcttctac | 106740 |
| cggtgataca | ctgattatac | ctatagaatc | tgatttaaca | gatgtatcag | caaaagaaat | 106800 |
| taattctaga | gataaagatg | tactagttga | attagcttta | ggaagagatt | taaatattac | 106860 |
| tgcagatgaa | aagtatttta | atgaacatgg | tactagtgat | aatatactag | cattcagcac | 106920 |

FIG. 21FFF

```
                              sequence.txt
aaatggtaat ggagatttag atactgtaaa aggcatagat aatatgaaac agcaattaca    106980
ggcacgttta ttaactccta gaggttcctt aatgttacat cctaattacg gttcagattt    107040
gcataattta tttggtctta atatacctga acaagctacg cttatagaaa tggaagtatt    107100
gagaacatta acatcagata atagagtaaa atctgctaat ttaattgatt ggaaaataca    107160
aggtaatgtt tattcaggtc aattttcagt ggaaataaaa tctgttgaag aatcaataaa    107220
ttttgtctta ggacaagatg aggaaggaat ttttgcttta tttgaatagg aaaggattaa    107280
attatgaaaa ctagaaaatt aactaacata ctatcaaaat taatagataa gacaatggca    107340
ggtacaagca agataacaga ctttactcct ggttcagctt cccgttcatt attagaagct    107400
gtatcattag agatagagca attctatatt ctaacaaaag aaaatattga ttggggtata    107460
caagaaggta tcattgaagc ttttgatttt caaaaaagac aatctaaaag agcttatggt    107520
gatgttacta ttcaattcta ccaaccctta gatatgagaa tgtatatacc tgcaggaaca    107580
acttttactt caacacgaca agaataccct cagcaatttg aaacattagt tgattattat    107640
gcagagcctg attctactga gattgttgtt gaagtttatt gtaaagaaac aggggttgca    107700
ggtaatgttc ctgaaggaac gattaatact atagcatcag gttctagttt gattagaagt    107760
gttaataatg agtattcttt taatacagga actaaagaag aaagtcagga agactttaaa    107820
cgtagattcc actcttttgt agaatctaga ggtagagcaa ctaataaatc agtaagatat    107880
ggtgcactgc agatacctga tgtagaaggt gtttatgttt atgaagaaac agggcatatt    107940
acagtatttg ctcatgatag aaacggtaat ttatcagata ccttaaaaga agatataatt    108000
gatgctttac aagactatag accaagtggt ataatgttag atgttacagg tgtagaaaaa    108060
gaagaagtta atgtttctgc tacagtaact atatctaata aatctagaat tggtgataca    108120
ttacaaaaac atatcgaaag tgttattaga agctatttaa ataatttaaa aacttctgat    108180
gacctaataa ttacagacct tattcaagct ataatgaata ttgatgacgt attaatatat    108240
gatgtgtcat ttgataactt agatgagaac attatagtac caccacaagg gattattaga    108300
gcgggagaaa taaaagtaga attaaagtaa agagaggtga aacttaagtc gtggctaatt    108360
ttttaaagaa tcttcatcca ttattaagaa gagatagaaa taaaaaagat aatcaagacc    108420
ctaactttgc tctgatagat gcactcaatg aagagatgaa tcaagtggag aaagatgcta    108480
tagaaagtaa attacaatcc tctctaaaga catctacaag tgaatattta gataagtttg    108540
gggattggtt tggagtttat cgtaagaccg atgagaacga tgatgtttat agagcaagaa    108600
ttataaaaata tttactcttg aaaagaggaa ctaataatgc tataatagat gctataaaag    108660
attatttagg tagagatgat attgatgtaa gtgtatatga gccctttaca aatatttttt    108720
atacgaacaa atcacattta aatggtgaag accatttaat gggatactat tatagatttg    108780
ctgttattaa tgtatctata ggtgattatt ttcctgtaga gattatagat gtaattaatg    108840
```

FIG. 21GGG sequence.txt

| | | | | | |
|---|---|---|---|---|---|
| aattcaaacc | tgcaggtgta | actctatatg | tcacttatga | tggagcttct | actattagag | 108900 |
| gtggagcaat | tattaagtgg | ttagatgggt | tacctaaaat | agaaacatac | caagagtttg | 108960 |
| atagatttac | aggttatgat | gatacattct | atggtcatat | taatatgaat | caaagtaaag | 109020 |
| atactgataa | cagttcatca | gatatttta | aaacaaatca | tagcttaatt | aatagtttag | 109080 |
| atgttttaac | aggttcatct | agtgtaggta | gacagtatat | taactatgga | tatgtaacat | 109140 |
| catatgttta | taatccaggt | atgacatcct | ctgtaaacca | aataagtgct | agtacagaag | 109200 |
| gtagaggtca | agaagtacct | actgattact | atatgtatac | tagtactaag | aataacaata | 109260 |
| cagtagaact | tagtatgcaa | actacttccg | gtgtgtctta | tttatataat | aactttaatt | 109320 |
| ttagagatta | tatgagtaaa | tatagacctc | aagtagattt | acaatctgat | gaggctagaa | 109380 |
| gaattgtatc | tgattatata | aaagaattaa | gtattgatta | ctatcttagt | gctgtgatac | 109440 |
| ctcctgatga | aagtatagaa | attaaactac | aagtttatga | tttttctatt | aatagatggc | 109500 |
| ttacagtatc | aattaataac | ttatctttct | atgaaaaaaa | tattgggagt | aatatagggt | 109560 |
| atataaaaga | ctatctaaac | agtgaattaa | atatgtttac | taggttagag | ataaatgcag | 109620 |
| gtaaaagaga | ttcagtagat | attaaagtta | attacttaga | tttaatgttt | tattactatg | 109680 |
| aacgaggtat | ttatacaata | aaaccttata | aagcattaat | agaaaattat | ttagatatat | 109740 |
| ctagagagac | ttatgtagaa | gcatttaaaa | tagcatcatt | atctaatgga | gatattataa | 109800 |
| ctaaaacagg | ttttcagcct | atagggtatt | taaaactagt | tggtaattat | gaaaatacaa | 109860 |
| gacctagcac | aataaatata | gtagctaaag | atacagataa | taaccctata | gaatctaatg | 109920 |
| aattagatgt | atataataca | gtagagaata | gaaatctatt | acaatcttat | aaaggtgcaa | 109980 |
| atacgatagc | tagagaaata | acttctacaa | aagagtttac | tgtatcagga | tgggctaaag | 110040 |
| agatatactc | aactaattat | cttctaaag | tattaaaacc | aggtaaagtg | tatacgttat | 110100 |
| cttttgatat | agaaataaca | ggtaatgacc | taactcttaa | atcttattct | gataatcatg | 110160 |
| gtatatattt | atacagtaat | actaagggaa | ttgttgttaa | tggtgttaaa | tctatggaac | 110220 |
| gtactatagg | taacaaagta | tccgtaactc | aaactttac | agcccctact | attactgacc | 110280 |
| atagattatt | aatatatact | ggaagatata | catctgatgg | taaagcatca | actcctccag | 110340 |
| tgttctttaa | tacagttaaa | attacggaat | taaaattgtc | tgagggtacc | tctaatctag | 110400 |
| agtactcacc | tgctccggaa | gataaaccta | acgtaataga | aaaaggaatt | aaatttaata | 110460 |
| atatcctaac | taatatacag | actttaagta | ttaattcgga | tactatctta | aaaaatgtaa | 110520 |
| cttttatatta | ttccttactat | ggtgataatt | gggtagaact | aaagactcta | ggaaatatta | 110580 |
| gtactggaga | aacaacagaa | accaataact | taatagattt | atatggatta | cagacagtag | 110640 |
| attattctaa | tataaatcca | atgtctaaag | tatcattacg | ttccatttgg | aatgttaaac | 110700 |

FIG. 21HHH

```
                                  sequence.txt
taggtgaatt gaacaatcaa gaaggttctt tatctaatat gcctaatgat tactttaatg   110760
ctgtatggca ggatatagat aaattatcag atattgagat aggttctatg agaatggtta   110820
aagacactga gggtggagta ttcgatggag ctacaggtga aattattaag gctactctat   110880
ttaatgtcgg ttcttatact gatttagaca tgttagctta tactttgact aactatactg   110940
aaccgttaac tttaggctct agtcgattaa taagtgagtt aaaagaagaa cttctaacat   111000
cagaatcatt taatgttgat aatagaatta aagtaattga ctcaatatat gaggagttac   111060
caaatacaag cattattaaa aatggatttg ttgaaagaga ggttacaggc tctaaatatt   111120
tagattatgg tttatatgag cctatagaag atggtactag atataaactt attgtcgaag   111180
gagaatttaa agataatata gaatttatat atttatacaa ttctaaccct aactttaatg   111240
aaacatttat atatccatca gagataatta atggagttgc tgaaaaagaa tttattgcaa   111300
aaccatccac cgaagacaaa ccaaggttaa atacagatgt tagaatatat atacgaccct   111360
atgattcaac tatctctaaa gtaagaagag tagaattaag gaaagtttaa taaataagtt   111420
gacagaaagt taataatatg gtatacttat aaagtaatat ttagtgggta taccatgtta   111480
tattaataaa gaaaacaaca gatgaaagga attaaaaaat atggcaattg caacgtataa   111540
ttctcatgtt gagttagcaa aatatctagt tagtaaagct gattcagttt acttaacaat   111600
tggaaagagc acaccgtggt ctaatgaaac aaacccaccg caacctgatg aaaatgcaac   111660
agtattacag gaggttattg gatacaaaaa agctactaaa gttactttag ttagaccttc   111720
taaatcacct gaagatgata ataagaattt aatttcttat ggtaataaat catgggtaga   111780
agtaacacct gaaaatgcta aagctgaagg agctaaatgg gtttacttag aaagtagtat   111840
tgttggtgac gaactgcctc ttggaacata tagacaggta ggatttgtta tggacttagt   111900
agcaaaaagt ggtattagta aatttaactt agtacctagt gaagtagaat caactggaac   111960
attattattc tttgataata aacaattcca aaatagaagt gagcagacaa ctgctaaaga   112020
aagatttatt gtagaagttt aaagaaaggg agataattct aaatggcaat taattttaaa   112080
ggttcacctt atttagatag atttgacccg tctaaagata gaacaaaagt attatttaat   112140
cctgatagac ctctacaaca ggcagaatta aatgaaatgc agtctataga ccaatattat   112200
ttaaaaaatc taggagacgc tatttttaaa gacggagata acagtcagg acttggattc   112260
acattgtctg aagataatgt attgacagta atcctggtt atgtatatat caacggtaaa   112320
ataagatatt acgataatga cgattcagtt aaaataactg gcgtaggtaa agaaactatc   112380
ggtattaagt taacagaacg tattgttaca cctgatgaag atgctagtct attagaccaa   112440
actagtggag taccaagtta cttctctaaa ggtgcagata gattagaaga aaagatgtca   112500
ttaacagtta atgaccctac atcagcaact atttatactt tcatggatgg agatttatat   112560
attcaatcaa ctaatgctga aatggataaa atcaataaag tattagctga acgtacttat   112620
```

FIG. 21III sequence.txt

```
gatgagtcag gttcatataa agtaaatggt tttgagttat tctcagaagg taatgctgaa    112680
gatgatgacc acgtttctgt agttgtagat gcaggtaaag cttatgtaaa aggttttaaa    112740
gtagataaac ctgtatcaac aagaattagt gtacctaaat cttatgactt aggaacagca    112800
gaaaatgaaa gtactatctt taataagtct aataattcta ttagtttagc taatagccct    112860
gtaaaagaaa ttagacgtgt tacaggtcaa gtacttattg aaaaagaacg agttacaaga    112920
ggagcccaag gtgatgggca agatttttctt tcaaataata cagcatttga aattgtaaaa    112980
gtttggactg aaacaagccc tggtgttact acaaaagagt ataaacaagg agaagacttc    113040
agattaacag acggtcaaac gattgattgg tcacctcaag gtcaagaacc ttcaggaggt    113100
acttcatact acgtttctta taaatataac aaacgtatgg aagccggtaa agattatgaa    113160
gtaacaactc aaggtgaagg tttgagtaag aaatggtaca ttaacttcac accttcaaat    113220
ggtgctaaac ctattgacca aacagtagta ttagtagact atacttacta cttggctcgt    113280
aaagattcag tgtttattaa taaatatggt gatattgcaa tattacctgg tgaacctaat    113340
attatgagat tagttacacc accattaaac acagaccctg agaatttaca attaggtaca    113400
gttacagtat tacctgattc agatgaagca gtatgtattt catttgcaat cactagattg    113460
tctatggaag acttacagaa agttaaaaca agagtagata acttagagta taaccaagca    113520
gtaaatgctc tagatgatgg tgctatggaa ggacagaacc cactaacatt acgttcagta    113580
tttagtgaag ggttcattag tcttgacaaa gcagatatta cacatcctga cttcggaatt    113640
gtatttagtt ttgaagatgc agaagctact ttggcttata cagaagcagt taaccaacct    113700
aagattattc caggagatac aacagctcat atttggggta gattaatttc agcaccattt    113760
actgaggaac gtacaatcta tcaaggtcaa gcatcagaaa cattaaatgt taacccttat    113820
aatattccta acaaacaagg tgtgttaaag ttaacaccta gtgaggataa ctggattgat    113880
actgaaaatg ttacaatcac tgaacaaaaa actaaaaaag taactatgaa acgatttgg    113940
agacataatg agagttacta tggtgagact gagcattact tgtattctaa cttacagtta    114000
gatgcaggac aaaagtggaa aggtgaaact tacgcttatg atagagagca tggacgtact    114060
ggtactttat tagaatcagg aggacaacgt actctagaag aaatgattga attcattaga    114120
atcagagatg tatccttcga agttaaagga ctaaaaccta atgataataa cttatatttta    114180
ttattttgatg gggtaagatg cgctataaca cctgcaactg gttatagaaa aggctctgaa    114240
gatggtacga taatgacaga tgctaaagga acagctaaag gtaaatttac tattcctgca    114300
ggtattcgtt gtggtaaccg agaagttaca cttaagaatg ctaactctac aagtgctaca    114360
acttacacag cccaaggacg taaaaaaacc gttcaagata ttattatcag aactcgtgta    114420
acagtaaact tagtagaccc attagcacaa tcattccaat atgatgagaa cagaactata    114480
```

FIG. 21JJJ sequence.txt

```
tcatcattag gattatactt tgcttctaaa ggtgataaac aatctaatgt tgttatccaa    114540
attagaggta tgggtgacca aggttatcct aataaaacaa tctatgcaga aacagttatg    114600
aatgctgatg atattaaagt atctaataat gctagtgctg aaactagagt atactttgat    114660
gaccctatga tggctgaagg cggtaaggaa tacgctattg ttattattac tgagaacagt    114720
gattatacaa tgtgggtagg tactagaact aagcctaaga ttgataaacc taatgaggtt    114780
atctcaggta acccatacct tcaaggtgta ttattcagtt catcaaatgc atcaacatgg    114840
actcctcatc aaaactctga ccttaaattt ggtatttata cttctaaatt taatgagaca    114900
gcaacaattg aattcgaacc aattaaagat gtatcggcag atagaatagt tcttatgtct    114960
acgtacttaa ctcctgagag aacaggatgt acatgggaaa tgaaattaat tctagatgat    115020
atggcatctt ctacaacatt cgaccaatta aaatgggagc ctatcggtaa ctaccaagat    115080
ttagatgttt taggtctagc aagacaagtt aagttaagag caactttcga atctaataga    115140
tatatctcac cattaatgag ctctagtgat ttaacattca ctacattctt aacagagtta    115200
acaggttcat atgttggtag agctattgat atgacagagg ctccttacaa tacagtaaga    115260
tttagttatg aagctttctt acctaaaggt actaagttg ttcctaagta ttctgcggat    115320
gatggaaaaa cttggaaaac atttactaaa tcccctacaa ctactagagc caataatgag    115380
tttacacgct atgtcattga cgagaaagta aaatcatcag gaacaaatac taaactacaa    115440
gttagattag atttatcaac tgaaaatagc tttttacgtc ctcgtgttcg tagacttatg    115500
gttactacta gggatgaata aactagaggg gttgattgac ccctctttat ttaataagga    115560
gagatttata tgcctagaga agttagagac ccttattctc aagctaaatt atttataccct    115620
acagttgaag aaaaatcaat taaggaatta gaaaaaacat acaaagaaaa aattgatgaa    115680
gctactaagt taatcaatga attaaagaaa gagagaggag aaaaatagat ggcatttaac    115740
tacacgcctc ttactgaaac acagaagtta aagatatgt atcctaaagt taatgatata    115800
ggtaactttt taaaaacaga agttaacctt agtgatgtaa aacaaatatc acaacccgac    115860
tttaataata ttttagcatc tataccctgat agtggtaact actatgtaac taattcaaaa    115920
ggtgctccta gtggagaagc tacggcagga tttgtaagat tggataaacg aaatgtaaat    115980
tattataaaa tttactattc accatatagt agtaataaaa tgtatatcaa gacttatgct    116040
aatggtactg tatatgattg gattagtttt aaattagatg aaggtaactt atacaatgaa    116100
ggtaatactt taaatgtaaa ggaacttact gaatctacaa ctcaatatgc aacactagtt    116160
aatcctccaa aagagaactt aaatacaggt tgggttaatt acaaagaaag taaaaatggt    116220
gtttcttctt tagtagaatt taacccggtt aactccactt caactttaa gatgataaga    116280
aagttaccag tacaagaaca aaagcctaac ttattgaaag atagtttatt tgtttatcct    116340
gaaactagct attctaatat taaaacagat aactgggata cgcctccatt ttggggatat    116400
```

FIG. 21KKK

```
sequence.txt
tcttctaata gtggtcgttc aggagttaga tttagaggag agaatacagt acagatagat    116460
gatgggtcta atacgtaccc tttagtagtt tctaataggt ttaaaatggg taaagaactt    116520
tctgtaggtg atactgtaac ggtatcagta tatgctaaaa ttaatgaccc tgctttactt    116580
aaagataact tagtttactt tgaattagca ggatacgata ctgtagatga tactagtaaa    116640
aatccttata caggaggacg tagagaaata acagcaagtg agataacaac tgagtggaaa    116700
aaatactctt tcacatttac gatacctgaa aatacaatcg gagcatcagg cgttaaagtt    116760
aattacgtat ctttactact aagaatgaat tgttcatcta gtaaaggtaa tggtgctgta    116820
gtatactatg ccttacctaa attagaaaaa tcacctaaag ttacaccatt tattacacat    116880
gaaaatgatg ttcgtaaata tgatgagatt tggtctaatt ggcaagaagt tattagtaaa    116940
gatgaattaa aaggtcactc tcctgtagat attgaatata atgattattt taaatatcag    117000
tggtggaaat ctgaagttaa tgaaaagagt ttaaaagatt tagctatgac agtacctcaa    117060
ggatatcata cattttattg tcaaggctct attgccggga cgcctaaggg acgttctatt    117120
agaggaacca ttcaggtaga ttatgacaaa ggtgacccct acagagctaa taagtttgtt    117180
aaattattgt ttactgacac agaaggtata ccttatacat tatactacgg agggtataat    117240
caaggttgga aactcttaaa gcaatcagaa acttctactt tactatggga aggtacttta    117300
gattttgggt ctacggaagc tgttaactta aatgactcat tagataatta tgatttaatt    117360
gaggtaactt attggactcg ttcagcagga cattttctaa caaaaagatt agatataaaa    117420
aatacatcaa atttactgta tattagagac tttaatattt caaatgatag tacaggttct    117480
agtgtagact tttttgaagg gtattgcact ttccctacta gagcatcagt acaacctggt    117540
atggtaaaat ctataacttt agacgggtct acaaatacaa caaaagtagc atcatggaat    117600
gaaaaggaac gtataaaggt atacaatatt atgggaatta atagaggata aagaaaggtg    117660
gaataaaaaa ctatggctgt taaatatgat ataggtaata atgagatagt attcacttta    117720
agagaaggta aatatataac agggtttaca acagtaggag ggtatgacaa ggagttaggg    117780
caagtaaaag ttaatagaga aatcttacct gcttacttct ttgataattt tgcctatgaa    117840
agatatttgt attatagtaa acctgaagag gttatagaaa ataaaaacta tgtaccacca    117900
caaatcaatg atgatgagga atcccaacaa attactgtac ctaaagaaca atatgatagt    117960
ttaaagaag agctagagct tatgagaaaa caacaagaag ctatgatgga aatgcttcaa    118020
aagctcttag gtcaaaaggg gtaattataa atggcattaa attttactac aataacggaa    118080
aacaatgtta ttagagacct gactactcag gtcaataaca ttggagaaga attaacaaaa    118140
gaaagaaata tatttgacat taccgatgat ttagtttata attttaataa atcacagaaa    118200
attaaactaa ctgatgataa aggattaact aaatcttatg gaaacataac agcccttaga    118260
```

FIG. 21LLL

```
                                    sequence.txt
gatataaaag aacctggtta ttactatata ggtgctagaa cattagcaac attattagat    118320
agacctgata tggaatctct tgatgttgtt ttacatgtag tacctcttga tacttctagt    118380
aaggtagttc aacatttata tacactatct actaacaata accaaattaa aatgttatat    118440
agatttgtct cagggaactc tagttcagaa tggcaattta ttcaaggatt acctagtaat    118500
aaaaatgctg ttatatcggg cactaatatt ctagatatag cttcaccagg tgtttacttt    118560
gttatgggaa tgacaggagg aatgcctagt ggagtaagct ccggattttt agacttaagt    118620
gtagatgcta atgataatag attagctaga ctaactgatg ctgaaactgg taaagaatat    118680
actagcatta agaaacctac aggaacatac acatcttgga aaaagaatt tgagccaaaa     118740
gatatggaga aatatttact aagtagtatc agagacgatg gtagtgcatc attcccactc    118800
ctagtttata ctagtgataa taaaacgttt caacaagcta ttatagacca tatagataga    118860
acaggtcaaa caacctttac tttctacgtt caaggtggtg tatcaggttc ccctatgtct    118920
aatagttgtc gaggtctatt catgtcagat acacctaaca cttctagttt acatggtgtc    118980
tataatgcta taggtacaga tggtagaaat gtaacaggtt cagtggtagg aggtaattgg    119040
acttcaccaa agacatcacc ttcccataaa gaattatgga cgggagcaca atcattccta    119100
tctgtaggta ctactaagaa tctagcagat gatattagta attactctta tgtagaggtt    119160
tatactaaac ataagacagt agagaagact aaaggtaatg atgactcggg tacaatttgc    119220
cacaagttct acttagatgg tagcggtact tacgtttgct caggaacttt tgtttcagga    119280
gatagaacag atacaaaacc acctgttaca gagttctata gagtaggtgt atctttcaaa    119340
ggttcaacat ggacgcttgt agatagtgca gtacaaaata gtaaaactca atacgttaca    119400
agaattatag gtattaatat gccatagact aggataagtt tcctagtctt tttttcttga    119460
cttgaaaagg attctatggt atactataac tcgtgtaagg atataaggag attaaaatga    119520
gattaagaat taagaactta tatacctatg tagaatttga ggaggatgat aaatacttaa    119580
aagatatatt tttaaagaga gtccatacta ctataggagc aaggcaagaa ggttttcaat    119640
atagccctgc gtacaaaaga ggtagttggg atggttatgt agactttat gtttatgagg     119700
aagataaatt ccctactgga cttttattta aaattgagtt attattaggt gagttacaat    119760
caaggtataa cttccagttt gaaacaattg atgagcgtga tgaaagtttc ttatctgaag    119820
aagatattga tgatgagata acattgcttg ataataatgt cggtcaaatt accttaagag    119880
attaccaata tgaagcagtg tacaatagct taacatttta caatggtatt gctcacttag    119940
ctactaatgg tggtaaaact gaggttgcta gtggtattat agaccaacta ttacctcaat    120000
tagaaaaagg tgaaagagta gcgttcttca caggctctac ggagatattt catcagtctg    120060
cggatagact acaagaacgt ttaaatattc ctattggtaa agtaggtgca ggtaaatttg    120120
atgttaaaca ggttacagtt gtaatgatac ctactttaaa tgcaaacctt aaagacccaa    120180
```

FIG. 21MMM sequence.txt

```
cacaaggggt aaaggttaca cctaaacaaa atattagtaa aaagattgct caagagatat    120240
tacctaaatt tgaaggtgga acaaatcaaa agaaattact aaaagtatta cttgataaca    120300
caacacctaa aacaaaagta gaacaaaacg tattaagtgc cttagagata atttaccaaa    120360
atagtaagac agatgcagaa gttttattaa acttaagaaa tcataatgca cattttcaaa    120420
aaattgttag agaaaagaac gaaaagaaat atgataaata tcaagatatg agagattttt    120480
tagactcagt tacagttatg atagttgatg aggcacacca ttctaaatct gattcttggt    120540
acaataatct aatgacatgt gaaaaagctt tatatcgaat tgcattaaca gggtctatag    120600
ataaaaaaga tgaattactt tggatgagat tacaggctct atttggtaat gttattgcac    120660
gaactactaa taagttttta attgatgaag gtcattctgc tagaccaaca ataaatatta    120720
tacctatagc taatcctaat gacatagata gaattgatga ttataggaa gcttacgata    120780
gaggtataac aaataatgat tttagaaata aacttattgc aaaactaaca gaaaagtggt    120840
ataatcaaga taaaggtaca ttgattattg taaacttcat tgaacatgga gacacgatat    120900
cagaaatgtt aaatgattta gatgtagagc actacttctt acatggagaa atagactctg    120960
aaactaggag agaaaaatta aatgatatga gaagtggtaa gcttaaagta atgatagcta    121020
catcacttat tgatgagggt gtagatatat ccggtattaa tgcactaata ttaggtgcag    121080
gaggtaagtc attaagacaa acattacaac gtattggtcg tgctttacgt aagaaaaaag    121140
acgataatac aacacaaata tttgatttta atgatatgac aaatagattt ttatatactc    121200
atgctaatga gcgtaggaaa atttatgaag aggaagattt tgaaataaaa gacttaggaa    121260
aataggaggg taagagatgg caacaaaaac acaagaaag ctataccaat atctagagga    121320
aaatgctaca gaaaataaat ttcatatttc tactaagaaa gagctagcag attctctagg    121380
tgtttccatc tctgctttat ccaataacct taaaaagtta gaagaagaaa ataaagtcgt    121440
tactgtttct aaaagaggaa aaaacggcgg agtaataata actttagtta gagagtatga    121500
tacagaagaa ttgaaagaat ttaataattc tacagataat attattactt ccgatttaca    121560
gtatgctaag gcattaagag aaaagcactt cccttcttat agatatgaga gaaaagaaca    121620
acgtagacgt actaaaatag aaatggcaca atacaatgcc attaaggatg agaagagaag    121680
aattatagca gatatgaact tctattcaga aggtcttcct tatccttcta agatattttt    121740
taatatgtct tatgacccgg aagggtttta taagcatac atcttatgta agttatacga    121800
ccaatatgct atttctcata tggatgctaa acatacaagt catcttaaag caatgagtaa    121860
ggcaacaact aaagatgaat atgactatca tcaacatatg tctgaatact atagaaataa    121920
aatgattcaa aatttaccta gaaatagcgt tagtgataat ttctttggta gtaaaatgtt    121980
taataccttt tataatttttatttaaaaat aaaagataaa aatattaatg tatttaaata    122040
```

FIG. 21NNN sequence.txt

```
tatgcaaaac gtatttaaaa atgtaacatt ttattatgag aatggtatgc aacctaatcc    122100
aataccttct cctaacttct ttagttcaga taagtatttt aaaaactata ataattatat    122160
taaaggaata aaaaaaggtg ttaacagtac gaatagacac ctaggtgata cagacagcat    122220
cattaattca tcagactacg tgaaaaaccc tgctgtatta catctacacc aactatatac    122280
tacaggatta aattctactt tacatgatat tgatactatg tttgaacaag ccttagacct    122340
tgaaaatgcc tcctatggac tatttggaga tatgaaacat attattttac tacagtataa    122400
ttctatgatt gaagaagaaa ttaagaattt acctagagaa gaaaaggata ttattaataa    122460
atatgtaaaa caatgcataa ttaatgatta ttcaccaaca agtatttcac catctgcaag    122520
gttatcaatg tttactatgc agaaagagca tatagtttac aataagcagt taaataaggg    122580
aatcaagaga gaggatttat taccattaag tctaggaggt atagtgaata aagattcatt    122640
gagtggtatg gatatacaaa acttagaaca gaatggtaat gaatacctgt atatgagaca    122700
acatacttca acttattata tattaagaat gtttggtgac tatttaggat atgaggtaaa    122760
cttaagagaa gtaaaatata ttgtagagaa atataattta attgataaaa taccattgac    122820
aaaagagggt atgttggatt ataataaact tatacattta gtagaggaag aggttaataa    122880
ctatgagtaa gaagataaag gagcttatcc ttcataaatc aatgaaggat atacattttg    122940
caagagaagt attagataac ttacctaaga atctattttc agcagagtct gaggacatgg    123000
gttacttatt tacagctata aagagaacag cacatatttc cgataagatg tcaaatgaag    123060
cattagcaat taaagtagaa cagcttatgg gtaataataa ggaagatgaa gagaaagtaa    123120
ccaagacatt aacttactta gaagatttat ataaagtaga cgttaatgaa aaagatgaat    123180
ctgttaatta tgaaatagag aagtatatta aaacagaaat gtcaaaagaa gttttagtta    123240
aatttattgc agaaaataaa caagaagact ctgataatct acatgaactt gtagacaaac    123300
taaagcaaat agaagtaagt gacatctcag gaggtaatgg agagtttatt gacttctttg    123360
aagatacaga aaagaaacaa gaactattga gtaatttagc tacaaataaa ttctctactg    123420
gatttacttc tattgacaac catattgaag gtggtatagc aagaggagaa gttggattaa    123480
ttatagctcc tactggtaga ggtaaatcat taatggcttc aaacttagct aagaattatg    123540
ttaaaagtgg attaagtgtt ttatatattg ccttagagga aaaatggat agaatggttt    123600
tgcgtgctga gcaacaaatg gcaggagcag aaaagagtca aattgtaaat caggatatgt    123660
ctttaaataa taagtttat gatgcaatac aaaatcatta tcagaagaat agaaagttat    123720
taggtgactt ttatattct aaacatatgc caggtgaagt tacaccaaac caattagagc    123780
aaattattgt taatacaaca attaagaagg ataaaaatat tgatgttgtt attattgact    123840
atcctcactt aatgagaaat ccttatgcta aatatcattc agaatcagat gcaggaggaa    123900
aattgtttga agatattcgt agattatcac agcaatatgg atttgtttgt tggacgttag    123960
```

FIG. 21000 sequence.txt

```
ctcaaactaa ccgtggtgct tatggttcag atgttattac aagtgagcat gtagaaggtt    124020
ctcgtaagat tgtcaatgct gttgaggtgt ctttagcagt aaaccaaaaa gatgaagaat    124080
tcaagagtgg tttcttaaga ttatatttag ataaaattcg taatagctcc aacacaggag    124140
aacgatttgt taatcttaaa gtagaaccaa ctaagatgat tgtaagagat gaaacacctg    124200
aagaaaaaca agagcatata caattgctat cagataatgg aaaagaagac acaagtaaat    124260
ttcaaaataa agataataaa atagaagcta taaataacac attcggagga ttaccgggag    124320
tttaattttt taaaatatac cacttgacat tttatatgtt aggtggtata attattttat    124380
aaagaataaa ggagagatta ataatgaaat ttgtattctt tacagatagt cattttcacc    124440
tatttactaa ctacgctaaa cctgataatg aatttgtgaa tgatagattt aaagaacaga    124500
tagaagcatt acagaaagtt tttgatattg ctaaaaaaga agaagcaaca gttatatttg    124560
gtggagattt atttcataaa cgtaactcgg tagatactag agtatacaac aaagtattta    124620
gtacatttgc caaaaatgat gaggttcctg tattattact tagaggtaat catgatgcta    124680
caactaattc attatatact gattcaagta tagatacatt tgagtatcta cctaatgtaa    124740
gtgtaataaa atcattaaat acaattttaa aagataatgt taatattgtg tttactgctt    124800
atggggatga gacgaaggaa ataaagacat acattaatag taattacgat aaagatatgg    124860
tcaatatact agtaggtcac ttaggtgtag aaggttcatt aactggaaaa ggctctcata    124920
gattagaagg ggcatttgga taccaggatt tattacctga taaatatgat ttcattttac    124980
taggtcatta tcaccgtaga cagtatttcc aaaatccgaa tcatttttat ggtggctcat    125040
taatgcaaca atcatttcct gatgaacaag aagctaatgg tgttcattta atagatacag    125100
aaaaaatgac tacagaattc atcccaattc atacacgtag atttattact attcaaggag    125160
aagatattcc tgagaacttt gaacagttaa tcgaggaagg taattttatt agggttatcg    125220
gtacagcaaa tcatgctaag gttttagaaa tggatgacag tatgaaagat aagaatgttg    125280
aagttcaaat taaaaaagaa tatactgtag agaaacgtat tgatagtgat gtatctgatg    125340
acccttaac aattgctagt acctatgcta aacaatactc acctgaatca gaacaagaaa    125400
tacttgagtg tttgaaggag gttttataat gaaaaatat agagaatacc taaataagac    125460
agatgcagaa aatttagcag aggattggga gaaagtaacc gaagatttat ggaaagtgtt    125520
taaagatatg aaacctaaaa ttaatacatt agatattagt aatgtagaaa gtaaaaactt    125580
agataaaagt aaacctatac tacaattcca agattcagat ggagtaatag agaatatttg    125640
taatgttgag ggtttagaag atggtttaag taaaatgaaa aaggttttg atgatagtaa    125700
ctttgaaaag cattattata gtagagtcgt agaccatgat gagtattact ggattgatta    125760
tggttctcat cattgtttct ttagagttac gaaaggggat aagtaatggt tgtatttaaa    125820
```

FIG. 21PPP sequence.txt

```
caagtagaag ttaataattt tttagcaatt aaagaagcta cgctagagtt agacaataga    125880
ggattaattc taattgaagg tgagaataaa tccaatgagt catttcattc aaacggttca    125940
ggaaaatcaa ctttaatatc tgccattact tacgctttat atggtaaaac tgaaaaagga    126000
ctaaaagcag acgatgtagt aaataatatt gagaagaaaa atacatctgt taaacttaag    126060
tttgatattg gggaagatag ctatttaatt gaacgttatc gtaaggacaa agagaataag    126120
aataaagtaa aattatttgt taatgaaaaa gagattacag gttcaacaaa tgacgttact    126180
gataaacaaa tacaagactt atttggtatt gagtttaata cttacgttaa tgctatcatg    126240
tatggtcaag gagatatccc tatgttctcc caagcaacag ataaaggtaa gaaagaaatt    126300
cttgaatcta ttactaagac agatgtatat aaacaagcgc aagatgtagc aaaagagaaa    126360
gttaaagaag tagaagaaca acaaaataac ataagacagg aaatctataa actaggttat    126420
cagttatcta caaaagatga gtacttccaa agagaaatag aacagtacaa ccagtataaa    126480
gaacaattgg ttcagataga aaacagtaat aaggaaaaag atagattaag agaacaagag    126540
gagaagcaaa tagaagctca aatagagcaa ttagcttcac agataccaac aatacctgaa    126600
gatgaattta agcactcaga ggagtataat aaagcttctc aaagcctaga tttactttct    126660
aataaattaa cggagctaaa tcaagtatac tcagaatata ataccaaaga acaagtacta    126720
aaatctgaaa tagctacatt aagcaatagt ctaaataagt tagatacaaa tgaccattgt    126780
cctgtttgtg gctcccctat agataattct cataaattaa agaacagga aatattaat     126840
aatcagattg agaataagaa acaagagatt actagtgtat tagaaatgaa agatacgtat    126900
aaagaagcta ttgataaagt aaaagataaa tcacaagaaa ttaaagataa aatgtcacag    126960
gaagaccaac aagaacggga gcacaataat aagattaaca gtataattca agaggcttct    127020
aggattaaat cagacattag ctcattagag aataataaaa cttatttaaa agtgaaatac    127080
caacatcaat ctgttcaagg attagagaga gaagaaccaa gtaaagaaaa acatgaggaa    127140
gataaaaaag aattacaaga atctattgac aaacatgaag agaatatagt acaattagaa    127200
actaagaaag gtaaatatca acaagctgta gatgctttta gtaataaagg tatacgttca    127260
gtagtgttag acttttattac accattctta aatgagaaag caatgagta ccttcaaact     127320
ttatcaggtt cagatattga aatagagttc caaactcaag tgaagaatgc taaaggagaa    127380
ctaaaagata gtttgatgt tattgttaag aatagcaagg gtggaggctc atacaaatct    127440
aattcagcag gagaacaaaa acgtattgat ttagcaatta gtttgcaat tcaggattta     127500
attatgagta aagatgagat atctacgaac attgcacttt acgatgagtg ttttgatggg    127560
ttagatacta tcggttgtga aaacgtgatt aaattattaa aagatagact taatacagta    127620
ggaacgatat ttgtaattac tcataatacc gaacttaaac cactatttga acaaacaatt    127680
aaaatagtaa aagaaatgg agtatcaaaa ctggaggaaa aataatgaaa ttaaagattt    127740
```

FIG. 21QQQ sequence.txt

| | | | | | | |
|---|---|---|---|---|---|---|
| tagataaaga | taatgcaaca | cttaatgtgt | ttcatcgtaa | taaggagcac | aaaacgatag | 127800 |
| ataatgtacc | aactgctaac | ttagttgatt | ggtaccctct | aagtaatgct | tatgaataca | 127860 |
| agttaagtag | aaatggagaa | tatttagaat | taaaaagatt | acgttctact | ttaccttcat | 127920 |
| cttatggttt | agatgataat | aaccaagata | ttattagaga | taataaccat | agatgtaaaa | 127980 |
| taggttattg | gtacaaccct | gcagtacgca | aagataattt | aaagattata | gagaaagcta | 128040 |
| aacaatatgg | attacctgtt | ataacagaag | aatatgatgc | taatactgta | gagcaaggat | 128100 |
| ttagagatat | tggagttata | ttccaaagtc | ttaaaactat | tgttgttact | agatatctag | 128160 |
| aaggtaaaac | agaggaagaa | ttaagaatat | ttaacatgaa | atcagaggaa | tcacaattga | 128220 |
| atgaagcact | taaagagagt | gattttctg | tagacttaac | ttatagtgat | ttaggacaaa | 128280 |
| tttataatat | gttgttatta | atgaaaaaaa | ttagtaaata | gtaaggaagg | atattatgag | 128340 |
| gtttgaagac | tttttaaccc | aagaattagg | agaaccaaaa | gaaaatacta | taggtgagct | 128400 |
| aagatactgt | tgtccgtttt | gtggagaaaa | aagttataag | ttctatgtta | agcaagccct | 128460 |
| agactctagt | aatggtcagt | atcattgtaa | aaaatgtgat | gaatcaggta | atcctattac | 128520 |
| atttatgaag | acttattata | acattacagg | taagcaagct | tttgatttat | tagagtctaa | 128580 |
| gaatatagat | atagagagag | cccctttact | tacaaccaat | aataaggatt | taacagaatc | 128640 |
| agagaaactt | atattaatgc | ttagaggtgt | gcatcaagat | aagggaacta | ctagtattaa | 128700 |
| acctcctcga | ttacctgaag | gatataaatt | attaaaagat | aacttaaata | ataaagagat | 128760 |
| tataccttt | ttaaaatact | taaaaggtag | aggtataact | ttagaacaaa | tcattaataa | 128820 |
| caatataggt | tatgttatta | atgggagctt | ttataaagtt | gacggggaat | ccaaagtatc | 128880 |
| attaaggaat | agtattatat | tttttactta | tgataatgat | ggaaactacc | agtactggaa | 128940 |
| tacaagaagt | atagagaaga | acccttatat | taatctatt | aatgctcctg | ctaaacaaga | 129000 |
| tgaagtaggt | agaaaagatg | tcatatttaa | tttgaatata | gcaagaaaga | aaaagttctt | 129060 |
| agttataact | gagggtgtat | ttgatgcttt | aacctttcat | gagtatggag | tagcaacatt | 129120 |
| aggtaaacaa | gtaactgaga | atcaaataaa | aaaaataatt | gattatgtta | gtatagatac | 129180 |
| atcaatatat | attatgttag | acactgatgc | attagataat | aatatagact | tagcttataa | 129240 |
| gttaaaaaca | catttaaca | aagtttactt | tgtaccacat | ggtgatgaag | atgcaaatga | 129300 |
| tatgggaaca | aggaaagctt | ttgagttatt | aaaacagaac | cgggtgttag | taacacctga | 129360 |
| aagtatacag | agttacaaaa | tacaacaaaa | acttaaactt | taggcttgac | cttagagaag | 129420 |
| ttttatgtta | tactagtaat | taagtaatta | ataaaggaga | aaaaaataat | gtcaaataat | 129480 |
| aaaaaagata | ttttagaatt | tgtagatgaa | tacattacag | ctttaagagt | tggtaatgag | 129540 |
| caacgacaac | atcaattaga | agaaatgggt | aaagaagaaa | cagcaacatt | aacagatgta | 129600 |

FIG. 21RRR sequence.txt

```
gctaaagcta ttactaacct tatgttaggt gttaatgagc agatgacaga cttagaatat    129660
aataacgagt taaacttaaa tattttaatt gatgctttat ataaagcaga gcttattaat    129720
gaagatgtat tagactacat tcaagaatca attgataaat cacaagaaga acctaaaaat    129780
gaagaagaaa aaggagaaca agaataatgg aaaaaaatat tagcacacac acaaaaggta    129840
ttagtcaagc agacatggag aaatggattg aagctgtagt acaaggaact gttgatggta    129900
aacaagttga tgagaaaaca gctaaacaat tagatagaat tggttcacga agtgtttctt    129960
tagaagaagc aactcgtatt gctaaagtcc ttaatgctgt aacagctcaa gaggttacag    130020
gagactttaa tgatgcattt aatgcaattg acttaatgat gattatcatg gaagatgagt    130080
taggagtaac tcaagaaaaa gtaggtaaag ctaaagataa actaaatgaa aaacgagaag    130140
cttacctaaa agagaaacaa gaagaattac gtcaaaaaca acaagaagag gcacaaaaag    130200
aaactgaatc tgacagcaat gaaaaagtaa ttcagttgaa gaaaaatgac gaacagtaag    130260
aaaaaagggg atacattcga acgtaaaata gctaaagaat taactgcttg gtggggatac    130320
caattcaata ggtctcctca atcaggtggt gcttcatggg gtaaagataa taatgctgtc    130380
ggagatatag tagtacccca ggaagctaat tttcctttag tagtagaatg taaacataga    130440
gaagaatgga ctatagataa cgttctttta aacaacagag agccacacac atggtgggag    130500
caagtcatta atgatagtag taaggtgaat aagacaccct gcttaatatt tactagaaat    130560
agagctcaga gttatgttgc tttaccttat aatgaaaaag tatatgaaga tttaagaaat    130620
aatgaatacc ctgtcatgag aacagatttt attattgata atattagaaa agataaattt    130680
ttttatgatg tccttataac taccatgaat gggttgacct catttacacc ttcttatatt    130740
atatcttgct acgacaaaaa agatataaaa ccatacaaga aggtcgagtc taatttatct    130800
gaggtaagta agcatgaaga tgaattgatt aatgaccttc ttagtgatat ataaggaagg    130860
taagataagt atgacaagca aagaagacc attaatcgta tattttcag gtacaggaca    130920
aacagaaaga ttagtaaaca aaattaatat taataattca tttgaaacat ttagggttaa    130980
gagtggaaaa gaaaagtaa ataaaccttt tatactaata cacctactt ataagaaagg    131040
tgcaataacct aaacaaatag aaagattcct agaaattaat gggagcccta aagaagttat    131100
tggcacagga aataaacaat ggggctctaa tttctgtgga gcaagtaaaa agatttcaga    131160
gatgtttaag attcctttaa ttgctaaagt agagcaatca ggacactta acgagataca    131220
accaatatta gaacacttta gtaataaata taagtagcg taaaggatga gagatatatg    131280
gcaacatatg gaaaatggat tgagttaaat aatgaaataa ctcaattaga tgacaatgga    131340
aaaaataaac tctataaaga ccaagaagct ttagatgagt attttaaaata tattgaagac    131400
aatacaagaa agtttaatag tgaagtagaa agaattagag tattgacaaa agaaggaaca    131460
tatgataaaa tatttgacaa ggttcctgac actattattg atgagatgac taagttagct    131520
```

FIG. 21SSS

```
sequence.txt
tacagtttta attttaaatt ccctagtttc atggcaggac aaaagtttta tgaatcttac    131580
gcatcaaaac agtatgatga aaacaaaaaa cctattttg ttgaagacta tgaacaacat     131640
aatgttcgag tagctttata tttatttcaa aatgactatg taaaggctag agaattacta   131700
gtacaactta tggagcaaac attccaacca tctacaccta cgtataataa ctcaggtcaa   131760
gctaatagag gtgaactaag ctcatgttat ctatttgtag tagatgattc aattgagtct   131820
ttaaactttg ttgaggatag cgtagctaat gctagttcta atggtggcgg agttgcaatt   131880
gatttaacta gaattagacc taaaggagct ccagtacgta atagacctaa ttcaagtaaa   131940
ggtgttattg cttttgctaa agctattgaa cataaagtta gtatttatga ccagggcggt   132000
gtaagacaag gtagtggtgc tgtttaccta aatatattcc acaatgatat cttggattta   132060
ttaagctcta agaaaatcaa tgccagtgaa tctgttagac tagataaatt atctattggt   132120
gttacaatcc ctaacaaatt tatggagtta gttaaagaag gtagaccttt ctatactttt   132180
gatacttacg acattaataa agtgtatggt aagtatttag atgagctaaa cattgatgaa   132240
tggtatgata agttactaga taatgatagt atcggtaaag taaaacatga tgctagagaa   132300
gttatgacag atattgctaa aacgcaatta gaatcaggat acccttatgt attctatatt   132360
gataatgcta atgataatca tccattgaaa aacctaggta agttaaaat gagtaactta    132420
tgtacagaaa tttcacaatt acaagaggta tcagaaattt atccgtactc ttacagtaat   132480
aagaatgtta ttaatagaga tgttgtttgt acattaggtt ctcttaactt ggttaatgtg   132540
gttgaaaaag gtttattgaa tgaatctgta gatattggta caagagcatt aacaaaagtt   132600
actgatatta tggatttacc ttacttacct agtgttcaaa aagcaaatga tgatattaga   132660
gctatcggtt taggttcaat gaatttacat ggacttttag ctaagaatat gattagttat   132720
ggttctagag aagcattaga cctagtaaac agtttatata gtgctattaa cttccagtct  132780
attaagacat ctatgttaat ggctaaagaa acaggaaaac catttaaagg atttgagaag   132840
tccgattacg ctacaggtga atactttgta agatatatta gagaatccaa tcaacctaag   132900
acagataaag ctaagaaagt cctagataag gtttatattc caacacaaga tgattgggat   132960
gaattagcta aagcagtaaa agtacatggc ttgtataatg gttatagaaa agcagaagca   133020
cctactcaat ctatatctta tgtacagaat gctacaagtt ctattatgcc agttcctagt   133080
gctatagaga atagacaata tggagatatg gagacatatt acccaatgcc ttacctaagt   133140
cctataactc agttcttcta tgaaggagaa acagcttata agattgacaa taaacgtatt   133200
attaatacaa gcgcagttgt tcagaaacat acagaccaag cagtatctac aatcctttat   133260
gtagagtcag aaatacctac taataaacta gtatcattat actattatgc ttgggaacaa   133320
ggattaaaat cattatacta tacacgttca cgtaaacttt ctgttattga atgtgaaaca   133380
```

FIG. 21TTT sequence.txt

```
tgttcggttt agaaaggaaa tagatatgga tattacacaa aaagtaaaac aacataataa    133440
aaatgctgta ttaaaagcaa caaactggaa tattgaagat gacgggatgt ctgatattta    133500
ttgggagcaa ggaatttccc aattttggac tcctgaagag tttgatgtat caagagattt    133560
aagttcttgg aatagtttaa ctgaaagtga aaagaacact tataagaaag tccttgcagg    133620
gctcacaggg ctcgatacca agcaaggagg agaaggtatg aacttagtat cctaccacga    133680
accaagacct aaataccaag ctgtatttgc gtttatgggt ggtatggaag agatacatgc    133740
taaatcctat agtcatatct ttacaacatt actaagtaat aaagaaacaa gctatctatt    133800
agatacttgg gtcgaagaaa acgactttt aaaagtaaaa gctcagttta tcggatatta    133860
ctatgaccaa ctattaaaac ctaaccctac tgtatttgat agatacatgg ctaaagtagc    133920
tagtgccttt ttagaaagtg cactattcta ctcaggattt tattatcctt tacttcttgc    133980
agggagagga cagatgacac aatcaggagc tattatttat aaaattactc aagatgaagc    134040
ttaccatggt tcagcagtag gattaacagc tcaatatgat tataatcttc taacagaaga    134100
agagaaaaaa caagcagata aagaaactta tgaattatta gatattcttt acactaatga    134160
agtagcgtat acacatagtc tatatgaccc attagaatta agtgaagacg taattaacta    134220
cgttcagtat aatttaata gagctcttca aaaccttgga agagaggact attttaatcc    134280
tgaaccttat aaccctattg tagaaaatca aactaatgta gacagattac gaaatgttga    134340
tttctttagt ggtaaagcag actatgaaaa atctacaaat attaaagata ttaaagatga    134400
agatttttca ttcttagata gtaaagaata cagtactgcc aaggaattcc tataaaaagg    134460
agaaaagata ttatggatag aaaagaagca atggatttac taagtaaagc agaaatatta    134520
tttaaaaaac atgatgagtt ttcatgtgta agtgatatca atgaccctat gaagttattc    134580
agtaactcta aggatgctaa agctgatgat acgtctaagt cttttcagtt agagtttatg    134640
catgatatga ccatgtatac tttatcttat ggctcaggac agttaaaact tattgattta    134700
gcagaaggtt atgaagcaca aaaagctaca gtagttaact catttcccga aattattaaa    134760
acattagaaa aggatgattc agaagatgga aaaaatgaat agtttagtag atttaaatac    134820
agcaattaga caaagaaag atgttattgt catgattaca caagataatt gtggtaagtg    134880
tgagatttta aaagtgtaa tccctatgtt tcaagagtca ggtgacatta aaaaacctat    134940
cttaacatta aatctagatg ctgaagatgt agatagagaa aaagctgtta agttattcga    135000
tatcatgagt acaccagtat taattggata taaagatggt cagttagtta aaaagtatga    135060
agaccaagtt acacctatgc aattacaaga attagagtca ctttaatttg gaatttccta    135120
ctatctgtgc tatactataa tagtacaagg tagtaggatt ttttaatgga aggaagatga    135180
catatcgcaa agaataaaac attaacgata tataatagtg atagatattt taatatacac    135240
acaaaagata aagataaaat taatgaggct attaaagtca cacatggtaa tgaagaagaa    135300
```

FIG. 21UUU sequence.txt

| | | | | | | |
|---|---|---|---|---|---|---|
| attgaaaaga | atatggatga | attaatatct | aagtctagac | gatatatcat | gagagatgaa | 135360 |
| aatcattaca | tgttatttaa | tgaaaagtac | aataatgata | gacttataga | aaaagtatgt | 135420 |
| aaacacggtg | gcaaagttac | atactatact | gattcagtat | taccctatta | tgttttaaaa | 135480 |
| gacttatcta | gtcaccctga | ctcagaagtc | gtttatcgta | tgcgcaatgg | ttttactgca | 135540 |
| aaagaagtag | ataatatagc | tttgtcattt | atgggtacaa | aagttattat | tgatatttct | 135600 |
| gtagtatttc | cttatgtaaa | cccttatgat | attattagaa | gtttacatga | tattaaaaca | 135660 |
| aatgtagatg | aagttcattt | atcatttcca | cgaatattag | aagtagatga | aaaacaagaa | 135720 |
| aaattttatt | tctttgatgg | tgaagcttat | gatttaaaac | ctgagtataa | agtagatttt | 135780 |
| gcggataaaa | ttagagtatc | tttatcagta | tggaaaatgt | atatctatat | cttaacaagt | 135840 |
| agtcgtgatt | ttgaggatgt | agacaatgta | attacgaaac | taaaacaaca | acgaaagatt | 135900 |
| aagatataag | gtgattatat | gagtacagca | aatagaagag | atatagcaag | aaagatatca | 135960 |
| gagaatacag | gttactatat | ccaggatgta | gaggaaatac | taagtgcaga | gacagatgct | 136020 |
| atttctgact | tactagaaga | aggatatact | aaagtaaaga | atcataaatt | tatgcaaata | 136080 |
| gaagttattg | aaagaaaagg | taaaaaagcg | tgggatggtc | tgaataaaga | atacttccat | 136140 |
| ttacctaata | gaaaagctat | aaaattcaaa | ccactaaaag | aactagaaga | ggttattgat | 136200 |
| agacttaatg | aagaagagaa | ataattctct | tcttttttta | ttgacaaggt | ttaaaatata | 136260 |
| tggtatagta | ttattaagtt | aaaaaaggag | aggaattaaa | tgaaagtatt | aatcttattt | 136320 |
| gaccacatta | gagaagagca | ttttctgta | agtaaagatg | ggagtgtgaa | atctaatgta | 136380 |
| ctaaatacac | ctaatggaaa | aacacttaag | aaattacttg | agaagtgttc | taatttaaag | 136440 |
| agagataaaa | caaacagaga | ttatgatatt | gattttctct | acaatgcagt | acctacacct | 136500 |
| atcagaaatg | actatggtaa | aattattaaa | tatcaagatg | ttaaacaagc | agaagtaaag | 136560 |
| ccatactatg | agagaatgaa | taatattatt | attgataatt | cttatgatat | gataattcct | 136620 |
| gtaggtaaac | taggcgttaa | atacttatta | aatgttacag | ctattggtaa | agtaagaggt | 136680 |
| gtaccaagta | aagtaactat | tgaaaatgga | acatcttctc | atgacgtgtg | ggtattacct | 136740 |
| acttacagta | ttgaatatac | taatgtaaat | aaaaatagtg | aacgtcatgt | agtatcagat | 136800 |
| ttacaaacag | ttggtaagtt | tgtagagcaa | ggagaagagg | catttaaacc | taaggaagta | 136860 |
| tcttacgagt | tggtagataa | cattgaaaga | gtaagagaaa | tattcaataa | ggaagtaaag | 136920 |
| aatgataatt | atgatggcgt | agatattacc | gcatgggact | tagagactaa | ctcattaaaa | 136980 |
| cctgataaag | aaggaagtaa | acctttagta | ctatctctat | catggagaaa | tggtcaaggt | 137040 |
| gtaactatac | ctttatacaa | atcagacttt | aactgggaaa | acggtcaaga | tgatattgat | 137100 |
| gaagtcttag | aattacttaa | gaactggtta | gctagtaaag | aagatattaa | agtagcacat | 137160 |

FIG. 21VVV

```
                                  sequence.txt
aatggtaagt acgatattaa attcttgatg agtactgaga actttaaaga ttttgagagt   137220
attcaagata ctaaagtagg ttggtaccta gctgttaccc aagaagttaa agaatcttta   137280
agattatctg atttagctta tgaggttaca gatgtcggag gttatgataa accattagaa   137340
gattttaaat tatggtttgt tactaagtta ttaagattct tctcagataa aattaaagag   137400
atacagaaag aaaataaaaa gattgctaag aaggagtatg atgttaaagc tcccgaatat   137460
aaagaatggc tagagaataa actaaatgaa acagtagtag aactagatga tactgagaag   137520
aaatttagag ttagtgaatt agagaaaaag tatattcaac taggtctttc acctgaaatt   137580
gtaaatatga atttagttat gaataacgat gagttcataa gtattgcaga acaatcacct   137640
gagtacatgg ggttatctga ctatgctaag tcttacacat taaatactgc aattaattta   137700
attaatgagt atagagatgt aaaagatgta gttaatgata ttgatggagg taactttaat   137760
tatgattggt tccctattga attaatgcat ccatacgcat caggagatac tgatgtatgt   137820
agaagaattc attgtgatgt agttaagaaa cttaaagaac aagatagacc taaatcaatg   137880
catttattag aagttaatta cccaagactt actaagtctt tagctagaat tgaatcaaat   137940
ggtttatatt gtgacttaga ttatatgaaa gaaaatgatg agtcatacga gtctgagatg   138000
gctaaaaatc atgctacaat gagagagcac tgggctgtta agaatttga agaataccaa    138060
tacaatcttt accaaatggc gttagaagaa catgagaaaa agccaaaaga tagagataaa   138120
gatatccatc agtatagaga taaatttaaa gatggtaaat ggatgttttc cccaagttcc   138180
ggagaccata aaggtagagt aatttatgat attttaggaa ttcaattacc ttatgataaa   138240
gaatatgtta aggaaaaacc atttaatgct aatgttaaag aagcagacct tacttggcag   138300
gactataaaa cagacaagaa agctattggt tatgcgttag ataatttaga attaaaagat   138360
gatgttagag aacttcttga gttacttaaa tatcatgcta gtatgcagac aaaacgtaat   138420
tcatttacta agaaattacc taatatgatt aataaacaaa acgaacatt acatggttct    138480
ttttctgaga caggtacaga gacatcaaga ctaagtagta gtaaccctaa cttgcaaaac   138540
ttaccggcac acacatcaga tgtaaacaag tttgattaca acatccaat taaacgttca    138600
tttgtttcta gatttgaaaa tggagtacta ctgggagccg actatagcgc cctagagatg   138660
cgtattattg gattatttac taaagaccct gatatgctac aatcattctt aaatggggaa   138720
gatattcata aggctactgc aagtattgtt tataataaac cagtagaaga ggtaactaag   138780
gaagaacgac aagcaactaa agcagttaac ttcgggttag ccttcggtga atcacccttc   138840
tcatttgcag gtaaaaataa tatggaagta agtgaagcag aagaaatatt tgaaaagtac   138900
ttccaaacaa aaccaagtgt aaaaacttct attgacaatg tacatgagtt tgtgcaacaa   138960
tatggttatg ttgatacaat gcacggacat agaagattta ccgttcagc ccaatcaaca    139020
gataaaaaga taaaaaatga aggtctaaga cagtcattta cactattat ccaaggttca    139080
```

FIG. 21WWWW sequence.txt

```
ggcagtttct taacaaacat gtctttaact tacttagatg attttatcca atctcgtaac    139140
ttaaaatcaa aagttattgc cacagtacat gatagtatct taattgattg tcctcctgaa    139200
gaagctaaaa ttatggctaa agtgacaatt catattatgg aaaacttacc atttgatttc    139260
ttaaaagcag aaattgatgg aaaagaagta caatatccta ttgaagctga tatggaaatt    139320
gggttaaact ataatgatat ggttgaatat gatgaggaag aaatagatac atttaattct    139380
taccaaggtt atattaagta tatgatgaat ttacagacct tagaagatta taaagagtca    139440
ggtaaactaa cagatgaaca atttgaaaag gctactaatg ttgttaaaag tgaaaaacat    139500
atttaccaag aaatttaata aaagtattga caatacattt aacttatgtt atactatata    139560
ggtaataaat ataaggagga aaacagagtg aatacaggag agattagatt taatcgttct    139620
atggatgaat ggattataac aagtatgtac caggatgagc taggtgagat gaatattgtt    139680
gttacattct ataatagaga agaaaataaa catggttcta cagttttacc aacagagtca    139740
tctactggag aagtagcaga ggaattggca agtcttgaag aagaatatcc tctagcttta    139800
cctttaagta gtatctcagt taatatttaa aaggaggaac tgataaatgg aaatacacat    139860
tgattcccta gattttacaa acttactat taaagataga aatgggaact cacaagagtt    139920
tgatattaca gatgagttaa gaattacaga gtatacaata caagaggact ttatgcaaca    139980
atcagctaaa tatgcttttt gggcttctat attagagaag gtaagagcat attctgaaat    140040
ggaacaaaga aatctagaaa caattggtag taagctaaac cttacaatta gacaagagta    140100
cgaacaacaa ggtaaaaagc ctactaaaga tatgattgaa tctagtgttt atattcatga    140160
ttcttaccaa caacaactta aagttgttga ggcttggaat tataaagtta acaacttca    140220
atatgttgta aaagcttttg agacaagaag agatatgatg attcaattag gtgcagaatt    140280
acgacaaaca aataaaaatg gtggaattac taatccattt tcacattaaa aaataaagta    140340
aagaatataa ttgacaaata taaaaaacta tgttataata aataagtaaa ttaattaaaa    140400
ggagaaaaga taattatgga tttcaatcaa tttattaaca atgaggcaag caaattagaa    140460
agcaataaca gttcttttaa caataatgta gagagctaca aacctaaaaa ccctgtacta    140520
cgtttaggta atattaaaga tgcaaacgga aataaggttg ttaaagaaaa tgcttttgta    140580
cgagtattac ctcctgcaca aggaacaaat gttttcttta agaatttag aacaacaggt    140640
attaactatt ctaagaaaga tggttctcaa ggattcacag gattaacatt acctgcagaa    140700
gaaggttcat ctgtccttga cccgtacatt caggactgga taacaaatgg tgttcaattt    140760
agtagattcc ctaataaacc aggagtacgc tattacattc atgtgattga atactttaat    140820
aacaatggtc aaattcaacc aaaaacggat gctcaaggaa atgtaatgat tcaacctatg    140880
gaattatcta acacaggata taagaatta ttagctaact aaaagatac tatgttaaaa    140940
```

FIG. 21XXX sequence.txt

```
ccatcaccta atgcacctca tagctttatc tcagcaaatg aagcattctt agttaatatt      141000
gttaaagcta agaaaggtga aatgtcatgg aaagtaagtg tttatcctaa tgctccttta      141060
ggtgcgttac cgcaaggttg ggaacaacaa ttatctgacc tagaccaatt agcaaaacca      141120
acagaagaac aaaatcctaa ttttgttaac ttcttaatca ataatgttaa taacacagag      141180
ttaagtcatg ataactttaa atttaaccgt gaaacaaatg tcttaggtga agaaccttca      141240
gagcctaaac aagcacctac gcaacaagat gtagatagtc aaatgccaag taatatggga      141300
ggacaaccta atcagcctca gcaaggtcaa gtaggtcagt atgcacaaca aggtcaaagt      141360
aatggtcaag gacagcagtt acaaggtaca caacaaccta tcaataacac gcaatttggt      141420
caaggaactc cttcaggaca acaccaagt aacacaggtt ctgttgattg ggataactta      141480
gcgcaacaac aatcacaacc tgattcaaac ccattcaatg attttgatgt tagcagtgtt      141540
gatgattcac aggtaccttt tgagacacaa cctcaaaata cacaacaagc acctgaacca      141600
caccaaacta cacaagagcc tccaaaacaa aaacaaacac aaagtattga cgatgtatta      141660
ggtggtctag acttagataa cctataagat atagagtgcc ttagagcact ctttatttta      141720
agatatataa ttactaggag gatattaaat ggcaagagca aaaaaaggta agaagtagaa      141780
tttaacagat ttaaatacaa ttgatttagg taaagaatta ggattaacat tattatcgga      141840
tagcaataga gcagacatta aaatattgt acctactatg gttcctcagt atgatagaat       141900
tctaggagga ggcatcccat taggtagatt gacagaggtt tacggattaa caggttcagg      141960
taaatcaagt tttgcagtcc atctctctag aatttcaaca cagttaggtg ttataactat      142020
ttggattgat attgaaggta ctgcggacaa taatcgtatg gaacagcttg gcgtagatgt      142080
ttcaaaacta ttctctattc aggcaggtga aggtagactt aaaaatacag tagagttatc      142140
tgtagagact gtaggtaagg aattagatta ctggatagat acttttcaacg agaaagcccc      142200
tggagtacct attttattta tttgggattc attaggagca acaagaactc aagcggagat      142260
tgaagaagga gtagaccata ggaaattagg gacaaaagcc acagctactc aaaaagttat      142320
caacgcagta tctcctaaat taaatgatac aaatacagga ttaattgtta ttaatcaagc      142380
tagagataac ttgaatatgt ctaacccctta tgatgaccct attaagtcca caggagggcg      142440
tgcgttcgag catggagcca gtctaagact taaaattact aaaggtaaag agtccgacct      142500
taaacaatct gattcaatga caggtaaacc tacctataaa ggtcatgtga tgagagtaga      142560
gactaaaaaa tctaaactat ctagaccagg acaaaaagca gaagcagact tactatcagg      142620
atatgaggta ggttctggtt cggatattac ccaactaaat ggaattgacc cttaccatac      142680
tatctataag gaagcagttg aaagaggtct aattacgaaa gggacttgga gaaattatat      142740
cacacttaat ggggaggaaa ttaaacttta tgataaagat tgggttcctc gtttaataga      142800
tgaccatgag ttatacttgg aattatttag tagagtctat ggagaacatt tccctaatgg      142860
```

FIG. 21YYY sequence.txt

```
ttattcacca ttacttaata ctaaagtaat tgtaactcag ttagaagaat atcaagcatt    142920
agagaattac tatgaagagt gggctaaaga taataaacaa gaagaacaag aggaagaatc    142980
aaaaggagaa tctcaagaaa aggattctga ataatagatg tataatttaa tagataaaaa    143040
catgagacag gtaaaagaat ctttggggaa tgcaaattcc tcagatgttc ttcctttacc    143100
ttataaagac atagcaaaga aatttgaaga agtaaaagaa aaaggtgaat caattatcat    143160
tgaagagggt ggattccctt acacagattc tacagtgatg tatatagaac atgtaacaga    143220
tagatgggca ggaggatact ccctaattag gcatgaaggt gaagaggtta aagtacctaa    143280
aactatccat ttctctgata tatatgttaa ggataaatca cataaagtaa gaataatctt    143340
cgaggggggct aatccttatg aagaaggcta aaaatggtaa tagatatgta atagatatag    143400
atggtattcc tgttgatttt gaaagagact tggatagttt acttaacagg tataaaaacc    143460
ttaggtggtc attatatcat aagtacgcag ggattttatc taatgatttt gaaagacaag    143520
aactaagaga atatattgat gagcaattta ttaaattagt taaagaatat aatattagaa    143580
gtaaagtgga ttttcctgga tatattaaag ctaaactaac tttaagagtt caaaatagtt    143640
atgttaagaa gaatgaaaaa tataaacgta ctgaaattat tggtaaaaaa gattatacag    143700
tagagtcctt aacagaagat ttaaatgaag acttcgagga taatcaaatt atgagttacg    143760
tatttgatga tatagaattt acagaagttc aaagtgagtt acttaaagaa ttacttatta    143820
atcctgaaag agaagatgat gcctttatcg tttctcaagt agcggaaaag tttgatatga    143880
aaagaaaaga agtagcaagt gagttgacag aactcagaga ctatgttaga tttaaaataa    143940
atgcatacca tgagtactat gctaagaaag aattaaataa ccatagagtt aatactgaaa    144000
atcatatttg ggaaaactag ttacagtgcc ttccttgtgt tatataagta ctactaataa    144060
tattattagt agtacttttg atatattatt tatgtagaag agaagtgaaa atagtgagaa    144120
tagaaaagca taaaataaag aataataaag taattaatga aatgtctata acagcaaata    144180
acctctataa tcatgctaat tttattttaa gacaaaattt ctttaataat aagactaata    144240
aaggatacag aaagttttta aattataata ctattcatag aatattaaaa aatatgaatg    144300
aagagaatta tattaaactc ccaagacaaa catctcaaca agtattaagg gatttaatta    144360
ataactggtc tagttttaga aaatcagaaa aagattattt taaaaaccct aataaataca    144420
gaaatagacc aaaaccacct aaatataaag ctaaaggcgg taaaggaaca attaagttta    144480
ctaatcaaca atgtagaatt cataaaaaag atggtttaat acatttacct acacctttac    144540
aagatataac tataaaacct tataaagcta agaatataag agaacttgtt tgtattccta    144600
aaagtgatta ttttgaagtt ttagtatgtt ataagaaga aaatagtaat aaaacactaa    144660
atgataacga aaacatagca agtattgatt taggtttaga taacttgata accatggttt    144720
```

FIG. 21ZZZ

```
                                          sequence.txt
ctattgtaga taaaccaata attataaatg gtaaaggtct aaaatctaaa aataaatatt    144780
ttaataaaaa aataaggtat tatcaaagtc tattacaaaa caatagttac tcttcgaaaa    144840
gaatattaaa atattgggaa aaaagacaca atattatact agattacttt cataaagcaa    144900
caaacgaagt tgttaaatac tgcgtaaaaa atgatattag taaagtagtt atagggtata    144960
ataaacagca aagtataaaa tctaaattaa aaaa                                144994
```

ANTIBACTERIAL PHAGE, PHAGE PEPTIDES AND METHODS OF USE THEREOF

1. RELATED APPLICATION

This application is a divisional application of U.S. patent application Ser. No. 13/823,519, filed on Oct. 28, 2013, which is a national stage application of PCT/PT2011/000031, filed on Sep. 19, 2011, which claims benefit of priority to U.S. Provisional Application No. 61/384,015, filed on Sep. 17, 2010, the contents of each of which are hereby incorporated by reference in their entirety.

2. SEQUENCE LISTING

The instant application contains a Sequence Listing which has been submitted in ASCII format via EFS-Web and is hereby incorporated by reference in its entirety. Said ASCII copy, created on Sep. 14, 2011, is named 16395US1.txt and is 3,295,858 bytes in size.

3. FIELD OF THE INVENTION

The present invention is directed to the field of phage therapy for the treatment and control of bacterial infections. In particular, the present invention is directed to the novel bacteriophage F387/08, F391/08, F394/08, F488/08, F510/08, F44/10, F125/10, isolated polypeptides thereof, compositions comprising one or more of the novel bacteriophage and/or isolated polypeptides; and methods for the treatment and prevention of bacterial infections caused by, e.g., *Staphylococcus aureus, Klebsiella pneumoniae, Acinetobacter baumannii, Escherichia coli*, and/or *Pseudomonas aeruginosa*, either alone or in combination with other therapies, e.g., antibiotics or other phage therapies.

4. BACKGROUND

Bacteriophage (phage) are viruses that specifically infect and lyse bacteria. Phage therapy, a method of using whole phage viruses for the treatment of bacterial infectious diseases, was introduced in the 1920s by Felix d'Herelle. Initially, phage therapy was vigorously investigated and numerous studies were undertaken to assess the potential of phage therapy for the treatment of bacterial infection in humans and animals. Early success prompted the development of multiple commercial phage preparations. For example, in 1940 Eli Lilly Company produced 7 phage products for human use, including phage preparations for treating different sicknesses caused by *Staphylococcus* sp., *E. coli* and other pathogenic bacteria. These preparations were used, for example, to treat infections that cause abscesses, purulent wounds, vaginitis, acute chronic upper-respiratory tract infections, and mastoid infections.

With the development of antibiotics in the 1940s, however, interest in phage-based therapeutics declined in the Western world. One of the most important factors that contributed to this decline was the lack of standardized testing protocols and methods of production. The failure to develop industry wide standards for the testing of phage therapies interfered with the documentation of study results, leading to a perceived lack of efficacy as well as problems of credibility regarding the value of phage therapy. Further, problems related to the production of phage samples/specimens complicated initial study and research. Diverse stabilizers and preservatives were initially used in attempts to increase the viability of the phage therapeutics. However, because the biology of both the phage and the various stabilizers were poorly understood, many of the ingredients added in an attempt to prolong the viability of phage preparations proved to be either toxic to humans or to negatively impact long term storage. Another problem in phage production related to the purity grade of the commercial preparations of the phage. At the time, phage therapy preparations generally consisted of raw lysates of host bacteria that had been treated with the phage of interest. Thus, many preparations contained what are now recognized to be undesired bacterial components, e.g., endotoxins. Accordingly, adverse events were often associated with the preparations, particularly in patients receiving them intravenously. Nevertheless, in Eastern Europe and the former Soviet Union, where access to antibiotics was limited, the development and use of phage therapy continued jointly with, or in place of, antibiotics.

With the rise of antibiotic resistant strains of many bacteria, however, interest in phage-based therapeutics has returned in the Western world. Even though novel classes of antibiotics may be developed, the prospect that bacteria will eventually develop resistance to the new drugs has intensified the search for non-chemotherapeutic means for controlling, preventing, and treating bacterial infections. There are three main phage-based strategies for using phage therapy in a clinical environment: 1) administering virulent phage; 2) using endolysins or purified lysins encoded by bacteriophage 3) using structural proteins of phage as metabolic inhibitors of key bacterial enzymes, such as enzymes that synthesize peptidoglycan.

There is therefore a need to develop novel bacteriophage and phage products as potential therapeutic and/or prophylactic agents for use in vivo against pathogenic bacteria. In particular, there is a need for bacteriophage capable of lysing nosocomial bacteria, including *Styphylococcus aureus, Klebsiella pneumoniae, Acinetobacter baumannii, Escherichia coli*, and/or *Pseudomonas aeruginosa*. Because most phage and phage peptides studied to date exhibit activity directed specifically against the species (or subspecies) of bacteria from which they are isolated, the novel phage-based therapies may find particular use in the hospital setting, selectively targeting nosocomial pathogens without affecting the normal surrounding flora.

5. SUMMARY OF THE INVENTION

The present invention is directed to isolated bacteriophage and to isolated antibacterial polypeptides of bacteriophage origin for the treatment, prevention, or management of conditions associated with infection by Gram-positive or Gram-negative bacteria. In particular, the isolated bacteriophage or polypeptides of the invention may be used in pharmaceutical compositions for the treatment, prophylaxis, or management of infection by nosocomial pathogens, e.g., Gram-negative bacteria including but not limited to *Klebsiella pneumoniae, Acinetobacter baumannii, Escherichia coli*, and *Pseudomonas aeruginosa*; and Gram-positive bacteria including but not limited to *Staphylococcus aureus*. In certain embodiments, the pharmaceutical compositions of the invention are of use in the treatment of conditions associated with infection by antibiotic resistant strains of bacteria, e.g., methicillin resistant strains of *Staphylococcus aureus* (MRSA). In particular embodiments, the isolated bacteriophage or polypeptides of the invention are used for the topical treatment of infection by nosocomial pathogens in a subject in need thereof. In other embodiments, the isolated bacteriophage or polypeptides of the invention are used for the diagnosis of the infective agent in a sample (e.g., tissue, blood, urine, sputum sample) derived from a patient. In other embodiments, the isolated bacteriophage or polypeptides of the invention are used as a prophylactic disinfectant or anti-infective for the preparation of solid surfaces, including skin or other epidermal surfaces.

In certain embodiments, the invention provides an isolated bacteriophage, F391/08, having a genome comprising the nucleic acid sequence of SEQ ID NO:1 (FIGS. 15A-15III) and exhibiting antibacterial activity against one or more strains of *Klebsiella pneumoniae*. In other embodiments, the invention provides an isolated bacteriophage, F394/08, having a genome comprising the nucleic acid sequence of SEQ ID NO:2 (FIGS. 16A-16Q) and exhibiting antibacterial activity against one or more strains of *Acinetobacter baumannii*. In yet other embodiments, the invention provides an isolated bacteriophage, F488/08, having a genome comprising the nucleic acid sequence of SEQ ID NO:3 (FIGS. 17A-17KKKK) and exhibiting antibacterial activity against one or more strains of *Escherichia coli*. In still yet other embodiments, the invention provides an isolated bacteriophage, F510/08, having a genome comprising the nucleic acid sequence of SEQ ID NO:4 (FIGS. 18A-18X) and exhibiting antibacterial activity against one or more strains of *Pseudomonas aeruginosa*. In still yet further embodiments, the invention provides an isolated bacteriophage, F44/10, having a genome comprising the nucleic acid sequence of SEQ ID NO:560 (FIGS. 19A-19UUU) and exhibiting antibacterial activity against one or more strains of *Staphylococcus aureus*. In still yet further embodiments, the invention provides an isolated bacteriophage, F387/08, having a genome comprising the nucleic acid sequence of SEQ ID NO:781 (FIGS. 20A-20KKKK) and exhibiting antibacterial activity against one or more strains of *Klebsiella pneumoniae*. In still yet further embodiments, the invention provides an isolated bacteriophage, F125/10, having a genome comprising the nucleic acid sequence of SEQ ID NO:1074 (FIGS. 21A-21ZZZ) and exhibiting antibacterial activity against one or more strains of *Staphylococcus aureus*.

The invention also encompasses isolated bacteria infected with one or more bacteriophage of the invention. In specific embodiments, the invention provides an isolated *K. pneumoniae* infected with a bacteriophage having a genome comprising or consisting of the nucleic acid sequence of SEQ ID NO: 1. In other embodiments, the invention provides an isolated *A. baumannii* infected with a bacteriophage having a genome comprising or consisting of the nucleic acid sequence of SEQ ID NO:2. In still other embodiments, the invention provides an isolated *E. coli* infected with a bacteriophage having a genome comprising or consisting of the nucleic acid sequence of SEQ ID NO:3. In yet other embodiments, the invention provides an isolated *P. aeruginosa* infected with one or more bacteriophage having a genome comprising or consisting of the nucleic acid sequence of SEQ ID NO:4. In still yet other embodiments, the invention provides an isolated *S. aureus* infected with one or more bacteriophage having a genome comprising or consisting of the nucleic acid sequence of SEQ ID NO:560. In still yet further embodiments, the invention provides an isolated *K. pneumoniae* infected with one or more bacteriophage having a genome comprising or consisting of the nucleic acid sequence of SEQ ID NO: 781. In still yet further embodiments, the invention provides an isolated *S. aureus* infected with one or more bacteriophage having a genome comprising or consisting of the nucleic acid sequence of SEQ ID NO: 1074.

The present invention encompasses polypeptides isolated from bacteriophage F387/08, F391/08, F394/08, F488/08, F510/08, F44/10, and/or F125/10, which polypeptides exhibit antibacterial activity against one or more species or strains of Gram-positive or Gram-negative bacterium, e.g., *K. pneumoniae, A. baumannii, E. coli, P. aeruginosa*, and/or *S. aureus*. In specific embodiments, the polypeptides of the invention isolated or derived from F387/08 and F3910/08 exhibit antibacterial or antimicrobial activity, e.g., lytic killing activity, against at least *K. pneumoniae*; those isolated or derived from F394/08, against at least *A. baumannii*; those isolated or derived from F488/08, against at least *E. coli*; those isolated or derived from F510/08 against at least *P. aeruginosa*; and those isolated or derived from F44/10 and F125/10 against at least *S. aureus*.

In certain embodiments, a polypeptide of the invention comprises or consists of an isolated lysin, or fragment thereof (e.g., a CHAP domain) that exhibits antibacterial activity against one or more species or strains of bacteria, e.g., Gram-positive bacteria, such as *S. aureus*; and/or Gram-negative bacteria, such as *K. pneumoniae A. baumannii, E. coli*, and/or *P. aeruginosa*. In specific embodiments, the polypeptide of the invention is an isolated lysin protein, e.g., an endolysin or tail lysin, comprising or consisting of the amino acid sequence SEQ ID NO: 20, SEQ ID NO: 80, SEQ ID NO: 192, SEQ ID NO: 282, SEQ ID NO: 547, SEQ ID NO: 556, SEQ ID NO: 557, SEQ ID NO: 598, SEQ ID NO: 1216, or SEQ ID NO: 1261. Predicted functions of said lysin proteins include, for example an Ig-like virion protein (SEQ ID NO: 20), cell wall hydrolase (SEQ ID NO: 80), N-acetylmuramoyl-L-alanine amidase (SEQ ID NO: 192), soluble lysozyme (SEQ ID NO: 282), T4-like lysozyme (SEQ ID NO: 547), endolysin (SEQ ID NO: 556), lambda Rz1-like protein (SEQ ID NO: 557), endolysin (SEQ ID NO: 598), endolysin (SEQ ID NO: 1216), and tail lysin (SEQ ID NO: 1261).

In other embodiments, a polypeptide of the invention comprises a fragment, variant or derivative of SEQ ID NO: 20, SEQ ID NO: 80, SEQ ID NO: 192, SEQ ID NO: 282, SEQ ID NO: 547, SEQ ID NO: 556, SEQ ID NO: 557, SEQ ID NO: 598, SEQ ID NO: 1216, or SEQ ID NO: 1261, wherein said fragment, variant or derivative has antibacterial activity or antimicrobial activity, e.g., lytic killing activity, against one or more strains of *K. pneumoniae A. baumannii, E. coli, P. aeruginosa*, and/or *S. aureus*. In specific examples in accordance with this embodiment, the variant, fragment or derivative of the amino acid sequence of SEQ ID NO: 20 and/or SEQ ID NO: 80 exhibits antibacterial or antimicrobial activity (e.g., lytic killing activity) against one or more strains of *K. pneumoniae*, for example, against the bacteriophage having a genome comprising or consisting of the nucleic acid sequence SEQ ID NO: 1. In other examples in accordance with this embodiment, the variant, fragment or derivative of the amino acid sequence of SEQ ID NO: 192 exhibits antibacterial or antimicrobial activity (e.g., lytic killing activity) against one or more strains of *A. baumannii*, for example, against the bacteriophage having a genome comprising or consisting of the nucleic acid sequence SEQ ID NO: 2. In other examples in accordance with this embodiment, the variant, fragment or derivative of the amino acid sequence of SEQ ID NO: 282 exhibits antibacterial or antimicrobial activity (e.g., lytic killing activity) against one or more strains of *E. coli*, for example, against the bacteriophage having a genome comprising or consisting of the nucleic acid sequence SEQ ID NO: 3. In other examples in accordance with this embodiment, the variant, fragment or derivative of the amino acid sequence of SEQ ID NO: 547, SEQ ID NO: 556, and/or SEQ ID NO: 557 exhibits antibacterial or antimicrobial activity (e.g., lytic killing activity) against one or more strains of *P. aeruginosa*, for example, against the bacteriophage having a genome comprising or consisting of the nucleic acid sequence SEQ ID NO: 4. In other examples in accordance with this embodiment, the variant, fragment or derivative of the amino acid sequence of SEQ ID NO: 598, SEQ ID NO: 1216, and/or SEQ ID NO: 1261 exhibits antibacterial or antimicrobial activity (e.g., lytic killing activity) against one or more strains of *S. aureus*, for example, against the bacteriophage having a genome comprising or consisting of the nucleic acid sequence SEQ ID NO: 560 or SEQ ID NO: 1074.

In specific embodiments, the isolated polypeptide of the invention comprises or consists of the CHAP domain of SEQ ID NO: 20, SEQ ID NO: 80, SEQ ID NO: 192, SEQ ID NO: 282, SEQ ID NO: 547, SEQ ID NO: 556, SEQ ID NO: 557, or SEQ ID NO: 598. In yet still other embodiments, a polypeptide of the invention comprises a fragment, variant or derivative of the CHAP domain of SEQ ID NO: 20, SEQ ID NO: 80, SEQ ID NO: 192, SEQ ID NO: 282, SEQ ID NO: 547, SEQ ID NO: 556, SEQ ID NO: 557, or SEQ ID NO: 598, wherein said fragment, variant or derivative has antibacterial activity or antimicrobial activity, e.g., lytic killing activity, against at least one or more strains of *K. pneumoniae A. baumannii, E. coli, P. aeruginosa*, and/or *S. aureus*.

In other embodiments, a polypeptide of the invention comprises or consists of an isolated tail protein (e.g., tail component, tail fiber protein, tail length tape measure protein, adsorption associated tail protein, major tail protein, major tail sheath protein, baseplate wedge subunit), or fragment thereof, having a biological function associated with the bacteriophage from which it is derived, e.g., antimicrobial or antibacterial activity (e.g., lytic killing activity), which function is directed against at least one or more species or strains of *K. pneumoniae, A. baumannii, E. coli, P. aeruginosa*, and/or *S. aureus*.

In specific embodiments, the polypeptide of the invention is an isolated tail protein comprising or consisting of the amino acid sequence SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266. In other embodiments, a polypeptide of the invention comprises a fragment, variant or derivative of SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266, wherein said fragment, variant or derivative exhibits a biological function associated with the bacteriophage from which it is derived, e.g., antimicrobial or antibacterial activity (e.g., lytic killing activity), which function is directed against one or more strains of *K. pneumoniae, A. baumannii, E. coli, P. aeruginosa*, and/or *S. aureus*.

Predicted functions of said tail proteins include, for example, a receptor-binding tail protein (SEQ ID NO: 15), major tail protein (SEQ ID NO: 26 and SEQ ID NO: 1077), minor tail protein (SEQ ID NO: 27), pore-forming tail tip protein (SEQ ID NO: 30), tail protein (SEQ ID NOs: 32-33), minor tail protein (SEQ ID NO: 34), phage tail protein (SEQ ID NO: 35), tail sheath protein (SEQ ID NO: 180), tail tape measure protein (SEQ ID NO: 183), tail protein (SEQ ID NO: 185), tail-fiber protein (SEQ ID NO: 190), tail tube protein (SEQ ID NO: 231), tail sheath monomer (SEQ ID NO: 232), tail sheath stabilizer and completion protein (SEQ ID NO:235), short tail fibers (SEQ ID NO: 239), base plate wedge completion tail pin (SEQ ID NOs: 240-241), base plate wedge completion tail fiber socket (SEQ ID NO: 242), base plate wedge subunit (SEQ ID NO: 243), base plate wedge initiator (SEQ ID NO: 244), base plate wedge (SEQ ID NO: 245), base plate hub subunit and tail lysozyme, cell-puncturing device (SEQ ID NO: 248), base plate wedge completion (SEQ ID NO: 249), tail completion and sheath stabilizer protein (SEQ ID NO: 252), chaperone long and short tail fiber assembly (SEQ ID NO: 254), tail fiber protein (SEQ ID NO: 433), tail fiber protein (SEQ ID NO: 434), hinge connecter long tail fiber (SEQ ID NO: 435), tail fiber hinge (SEQ ID NO: 436), proximal tail fiber subunit (SEQ ID NO: 437), base plate-tail tube initiator (SEQ ID NO: 489), base plate (SEQ ID NO: 490), baseplate hub subunit, tail length determinator (SEQ ID NO: 491), base plate distal hub subunit (SEQ ID NO: 492), base plate hub subunit (SEQ ID NO: 493), base plate hub assembly catalyst (SEQ ID NO: 494), baseplate hub subunit (SEQ ID NO: 495), baseplate wedge subunit (SEQ ID NO: 496), tail tubular protein (SEQ ID NOs: 544-545), tail fiber protein (SEQ ID NO: 549 and SEQ ID NO: 551), major tail sheath protein (SEQ ID NO: 629 and SEQ ID NO: 1250), major tail protein (SEQ ID NO: 686), tail tube protein (SEQ ID NO: 789), fibritin (SEQ ID NO: 796), short tail fibers (SEQ ID NO: 797), base plate wedge completion tail pin (SEQ ID NO: 798), base plate wedge subunit and tail pin (SEQ ID NO: 799), baseplate wedge tail fiber connector (SEQ ID NO: 800), baseplate hub subunit and lysozyme (SEQ ID NO: 806), lysozyme (SEQ ID NO: 854), holin (SEQ ID NO: 999 and SEQ ID NO: 1217), distal long tail fiber assembly catalyst (SEQ ID NO: 1000), L-shaped tail fiber protein (SEQ ID NO: 1001), hinge connecter of long tail fiber distal connector (SEQ ID NO: 1002), hinge connecter of long tail fiber proximal connector (SEQ ID NO: 1003), long tail fiber proximal subunit (SEQ ID NO: 1004), baseplate tail tube initiator (SEQ ID NO: 1053), baseplate tail tube cap (SEQ ID NO: 1054), baseplate hub subunit, tail length determinator (SEQ ID NO: 1055), baseplate distal hub subunit (SEQ ID NO: 1056), baseplate hub subunit (SEQ ID NOs: 1057 and 1059), baseplate hub assembly catalyst (SEQ ID NO: 1058), baseplate wedge subunit (SEQ ID NO: 1060), and baseplate protein (SEQ ID NO: 1266).

In certain embodiments, the invention encompasses a variant, fragment or derivative of the amino acid sequence of SEQ ID NO: 15, SEQ ID NO: 26, SEQ ID NO: 27, SEQ ID NO: 30, or SEQ ID NOs: 32-35, which exhibits a biological function associated with the bacteriophage having a genome comprising or consisting of the nucleic acid sequence SEQ ID NO: 1, e.g., antimicrobial or antibacterial activity (e.g., lytic killing activity), which function is directed against one or more strains of *K. pneumoniae*. In other embodiments, the invention encompasses a variant, fragment or derivative of the amino acid sequence of SEQ ID NO: 180, SEQ ID NO: 183, SEQ ID NO: 185, or SEQ ID NO: 190, which exhibits a biological function associated with the bacteriophage having a genome comprising or consisting of the nucleic acid sequence SEQ ID NO: 2, e.g., antimicrobial or antibacterial activity (e.g., lytic killing activity), which function is directed against one or more strains of *A. baumannii*.

In certain embodiments, the invention encompasses a variant, fragment or derivative of the amino acid sequence of SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-495, or SEQ ID NO: 496, which exhibits a biological function associated with the bacteriophage having a genome comprising or consisting of the nucleic acid sequence SEQ ID NO: 3, e.g., antimicrobial or antibacterial activity (e.g., lytic killing activity), which function is directed against one or more strains of E. coli. In certain embodiments, the invention encompasses a variant, fragment or derivative of the amino acid sequence of SEQ ID NO: 544, SEQ ID NO: 545, SEQ ID NO: 549, or SEQ ID NO: 551, which exhibits a biological function associated with the bacteriophage having a genome comprising or consisting of the nucleic acid sequence SEQ ID NO: 4, e.g., antimicrobial or antibacterial activity (e.g., lytic killing activity), which function is directed against one or more strains of P. aeruginosa. In still other embodiments, the invention encompasses a variant, fragment or derivative of the amino acid sequence of SEQ ID NO: 629 or SEQ ID NO: 686, which exhibits a biological function associated with the bacteriophage having a genome comprising or consisting of the nucleic acid sequence SEQ ID NO: 560, e.g., antimicrobial or antibacterial activity (e.g., lytic killing activity), which function is directed against one or more strains of S. aureus. In still other embodiments, the invention encompasses a variant, fragment or derivative of the amino acid sequence of SEQ ID NO: 789, SEQ ID NOs: 796-800, SEQ ID NO: 806, SEQ ID NO: 854, SEQ ID NOs: 999-1004, or SEQ ID NOs: 1053-1060, which exhibits a biological function associated with the bacteriophage having a genome comprising or consisting of the nucleic acid sequence SEQ ID NO: 781, e.g., antimicrobial or antibacterial activity (e.g., lytic killing activity), which function is directed against one or more strains of K. pneumoniae. In still other embodiments, the invention encompasses a variant, fragment or derivative of the amino acid sequence of SEQ ID NO: 1077, SEQ ID NO: 1217, SEQ ID NO: 1250, or SEQ ID NO: 1266, which exhibits a biological function associated with the bacteriophage having a genome comprising or consisting of the nucleic acid sequence SEQ ID NO: 1074, e.g., antimicrobial or antibacterial activity (e.g., lytic killing activity), which function is directed against one or more strains of S. aureus.

In certain embodiments, the invention provides for isolated polypeptides that exhibit antimicrobial or antibacterial activity (e.g., lytic killing activity) against one or more strains of bacteria, e.g., Gram-positive bacteria (e.g., S. aureus), Gram-negative bacteria (e.g., K. pneumoniae, A. baumannii, E. coli, and P. aeruginosa) or bacteria not classified as either Gram-positive or Gram-negative, wherein the isolated polypeptides have an amino acid sequence with at least 60%, 65%, 70%, 75%, 80%, 85%, 86%, 87%, 88%, 89%, 90%, 91%, 92%, 93%, 94%, 95%, 96%, 97%, 98%, 99%, or greater sequence identity to a second amino acid sequence of the same length (i.e., consisting of the same number of residues), which second amino acid sequence is of SEQ ID NO: 15, SEQ ID NO: 20, SEQ ID NO: 26, SEQ ID NO: 27, SEQ ID NO: 30, SEQ ID NOs: 32-35, SEQ ID NO: 80, SEQ ID NO: 180, SEQ ID NO: 183, SEQ ID NO: 185, SEQ ID NO: 190, SEQ ID NO: 192, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NO: 282, SEQ ID NOs: 433-437, SEQ ID NOs: 489-496, SEQ ID NO: 544, SEQ ID NO: 545, SEQ ID NO: 547, SEQ ID NO: 549, SEQ ID NO: 551, SEQ ID NO: 556, SEQ ID NO: 557, SEQ ID NO: 598, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1216, SEQ ID NO: 1217, SEQ ID NO: 1250, SEQ ID NO: 1261, SEQ ID NO: 1266, and/or a fragment thereof.

The invention further provides isolated polypeptides comprising or consisting of the amino acid sequence of any of SEQ ID NOs: 5-176, SEQ ID NOs: 177-223, SEQ ID NOs: 224-506, SEQ ID NOs: 507-559, SEQ ID NOs: 561-780, SEQ ID NOs: 782-1073, and SEQ ID NOs: 1075-1300. In other embodiments, isolated polypeptides of the invention recombinantly fused or chemically conjugated (e.g., covalent or non-covalent conjugation) to therapeutic agents (e.g., heterologous polypeptides or small molecules) are provided.

The invention also encompasses polynucleotides that encode the polypeptides of the invention. In a specific embodiment, the invention provides an isolated nucleic acid comprising a nucleic acid sequence encoding the polypeptide of any of SEQ ID NOs: 5-176, SEQ ID NOs: 177-223, SEQ ID NOs: 224-506, SEQ ID NOs: 507-559, SEQ ID NOs: 561-780, SEQ ID NOs: 782-1073, and SEQ ID NOs: 1075-1300. In other embodiments, the invention provides an isolated nucleic acid comprising a nucleic acid sequence encoding the polypeptide of any of SEQ ID NO: 15, SEQ ID NO: 20, SEQ ID NO: 26, SEQ ID NO: 27, SEQ ID NO: 30, SEQ ID NOs: 32-35, SEQ ID NO: 80, SEQ ID NO: 180, SEQ ID NO: 183, SEQ ID NO: 185, SEQ ID NO: 190, SEQ ID NO: 192, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NO: 282, SEQ ID NOs: 433-437, SEQ ID NOs: 489-496, SEQ ID NO: 544, SEQ ID NO: 545, SEQ ID NO: 547, SEQ ID NO: 549, SEQ ID NO: 551, SEQ ID NO: 556, SEQ ID NO: 557, SEQ ID NO: 598, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1216, SEQ ID NO: 1217, SEQ ID NO: 1250, SEQ ID NO: 1261, or SEQ ID NO: 1266, or active fragment, variant or derivative thereof, which polypeptide or active fragment, variant or derivative exhibits a biological function associated with the bacteriophage from which it is isolated and/or derived, e.g., antimicrobial or antibacterial activity (e.g., lytic killing activity). The invention also relates to a vector comprising one or more of said nucleic acids. In one specific embodiment, said vector is an expression vector. The invention further provides host cells containing a vector comprising one or more polynucleotides one or more encoding the polypeptides of the invention.

The present invention encompasses methods for the production of polypeptides of the invention or active fragments thereof, in particular for use in pharmaceutical compositions, i.e., antimicrobial compositions. For example, the polypeptides of the invention may be isolated directly from cell cultures (e.g., bacterial cell cultures) infected with bacteriophage F387/08, F391/08, F394/08, F488/08, F510/08, F44/10, and/or F125/10. Alternatively, the polypeptides of the present invention may be derived by recombinant means using expression vectors comprising nucleic acid sequence encoding polypeptides of the invention, e.g., SEQ ID NO: 15, SEQ ID NO: 20, SEQ ID NO: 26, SEQ ID NO: 27, SEQ ID NO: 30, SEQ ID NOs: 32-35, SEQ ID NO: 80, SEQ ID NO: 180, SEQ ID NO: 183, SEQ ID NO: 185, SEQ ID NO: 190, SEQ ID NO: 192, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NO: 282, SEQ ID NOs: 433-437, SEQ ID NOs: 489-496, SEQ ID NO: 544, SEQ ID NO: 545, SEQ ID NO: 547, SEQ ID NO: 549, SEQ ID NO: 551, SEQ ID NO: 556, SEQ ID NO: 557, SEQ ID NO: 598, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1216, SEQ ID NO: 1217, SEQ ID NO: 1250, SEQ ID NO: 1261, or SEQ ID NO: 1266, or active fragments, derivatives or variants thereof. The polypeptides of the invention or fragments thereof can be produced by any method known in the art for the production of a polypeptide, in particular, by chemical synthesis or by recombinant expression techniques.

In specific embodiments, the invention relates to a method for recombinantly producing a phage protein, e.g., a lysin protein, tail protein, or active fragment, variant or derivative thereof, said method comprising: (i) culturing under conditions suitable for the expression of said protein in a medium, a host cell containing a vector comprising a nucleic acid sequence encoding the amino acid sequence SEQ ID NO: 15, SEQ ID NO: 20, SEQ ID NO: 26, SEQ ID NO: 27, SEQ ID NO: 30, SEQ ID NOs: 32-35, SEQ ID NO: 80, SEQ ID NO: 180, SEQ ID NO: 183, SEQ ID NO: 185, SEQ ID NO: 190, SEQ ID NO: 192, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NO: 282, SEQ ID NOs: 433-437, SEQ ID NOs: 489-496, SEQ ID NO: 544, SEQ ID NO: 545, SEQ ID NO: 547, SEQ ID NO: 549, SEQ ID NO: 551, SEQ ID NO: 556, SEQ ID NO: 557, SEQ ID NO: 598, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, or SEQ ID NOs: 1053-1060, SEQ ID NO: 1077, SEQ ID NO: 1216, SEQ ID NO: 1217, SEQ ID NO: 1250, SEQ ID NO: 1261, or SEQ ID NO: 1266, or fragment thereof; and (ii) recovery of said protein from said medium. In certain embodiments, the nucleic acid sequence encoding the polypeptide of the invention is operably linked to a heterologous promoter.

The invention also encompasses methods for the diagnosis of the causative agent in a clinical presentation of bacterial infection. The isolated bacteriophage or polypeptides of the invention may be used to aid in the determination of species of bacteria in a patient sample by establishing susceptibility of the bacteria in the sample to the bacteriophage and/or polypeptides of the invention. Such methods further encompass methods of evaluation of antibacterial activity of the isolated bacteriophage and/or polypeptides of the invention. Antibacterial activity of the bacteriophage or the polypeptides of the invention, or susceptibility of an unknown sample to such activity, may be assessed by any method known in the art and/or described herein. In certain embodiments, antibacterial activity and/or susceptibility is assessed by culturing known bacteria and/or patient tissue, blood, fluid or swab samples according to standard techniques (e.g., in liquid culture or on agar plates), contacting the culture with bacteriophage and/or polypeptides of the invention and monitoring cell growth after said contacting. For example, in a liquid culture, the bacteria (e.g., *K. pneumoniae, A. baumannii, E. coli, P. aeruginosa*, and/or *S. aureus*) may be grown to a optical density ("OD") representative of a mid-point in exponential growth of the culture; the culture is exposed to one or more concentrations of one or more bacteriophage and/or polypeptides of the invention and the OD is monitored relative to a control culture. Decreased OD relative to a control culture is representative of a bacteriophage and/or polypeptide exhibiting antibacterial activity (e.g., exhibiting lytic killing activity) against the tested sample or bacterial species and/or strain in the culture. Similarly, bacterial colonies can be allowed to form on an agar plate, the plate exposed to a bacteriophage or polypeptide of the invention, and subsequent growth of the colonies evaluated relative to control plates. Decreased size of colonies, or decreased total numbers of colonies, indicates a bacteriophage and/or polypeptide with antibacterial activity against the tested sample and/or cultured species or strain.

The present invention is also directed to pharmaceutical compositions comprising or consisting of a bacteriophage having a genome comprising or consisting of the nucleic acid sequence SEQ ID NO: 1, SEQ ID NO: 2, SEQ ID NO: 3, SEQ ID NO: 4, SEQ ID NO: 560, SEQ ID NO: 781, or SEQ ID NO: 1074. In certain embodiments, the pharmaceutical composition of the invention comprises a bacteriophage having the genome comprising or consisting of the nucleic acid sequence SEQ ID NO: 1, SEQ ID NO: 2, SEQ ID NO: 3, SEQ ID NO: 4, SEQ ID NO: 560, SEQ ID NO: 781, or SEQ ID NO: 1074, in addition to one or more other bacteriophage. The one or more other bacteriophage may be one or more bacteriophage of the invention (e.g., having a genome comprising or consisting of a nucleic acid sequence of SEQ ID NO: 1, SEQ ID NO: 2, SEQ ID NO: 3, SEQ ID NO: 4, SEQ ID NO: 560, SEQ ID NO: 781, or SEQ ID NO: 1074), one or more strains thereof, or may be one or more bacteriophage known in the art other than a bacteriophage having a genome according to SEQ ID NO: 1, SEQ ID NO: 2, SEQ ID NO: 3, SEQ ID NO: 4, SEQ ID NO: 560, SEQ ID NO: 781, or SEQ ID NO: 1074. Further, the one or more bacteriophage in the pharmaceutical composition of the invention may target the same or different species or strains of bacteria. In certain embodiments, the pharmaceutical compositions comprising one or more bacteriophage of the invention further comprise one or more polypeptides of the invention and/or other phage products as described herein or known in the art.

In certain embodiments, the invention provides pharmaceutical compositions comprising polypeptides, or active fragments thereof, in particular those having anti-microbial and/or antibacterial activity, isolated from bacteriophage having a genome comprising or consisting of the nucleic acid sequence SEQ ID NO: 1, SEQ ID NO: 2, SEQ ID NO: 3, SEQ ID NO: 4, SEQ ID NO: 560, SEQ ID NO: 781, and/or SEQ ID NO: 1074. In specific embodiments, the pharmaceutical compositions of the invention comprise one or more polypeptides having an amino acid sequence of SEQ ID NO: 15, SEQ ID NO: 20, SEQ ID NO: 26, SEQ ID NO: 27, SEQ ID NO: 30, SEQ ID NOs: 32-35, SEQ ID NO: 80, SEQ ID NO: 180, SEQ ID NO: 183, SEQ ID NO: 185, SEQ ID NO: 190, SEQ ID NO: 192, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NO: 282, SEQ ID NOs: 433-437, SEQ ID NOs: 489-496, SEQ ID NO: 544, SEQ ID NO: 545, SEQ ID NO: 547, SEQ ID NO: 549, SEQ ID NO: 551, SEQ ID NO: 556, SEQ ID NO: 557, SEQ ID NO: 598, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1216, SEQ ID NO: 1217, SEQ ID NO: 1250, SEQ ID NO: 1261, or SEQ ID NO: 1266. In other embodiments, the pharmaceutical compositions of the invention comprise a polypeptide that is a variant, derivative or fragment of SEQ ID NO: 15, SEQ ID NO: 20, SEQ ID NO: 26, SEQ ID NO: 27, SEQ ID NO: 30, SEQ ID NOs: 32-35, SEQ ID NO: 80, SEQ ID NO: 180, SEQ ID NO: 183, SEQ ID NO: 185, SEQ ID NO: 190, SEQ ID NO: 192, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NO: 282, SEQ ID NOs: 433-437, SEQ ID NOs: 489-496, SEQ ID NO: 544, SEQ ID NO: 545, SEQ ID NO: 547, SEQ ID NO: 549, SEQ ID NO: 551, SEQ ID NO: 556, SEQ ID NO: 557, SEQ ID NO: 598, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1216, SEQ ID NO: 1217, SEQ ID NO: 1250, SEQ ID NO: 1261, or SEQ ID NO: 1266, wherein the variant, derivative or fragment retains a biological function of the polypeptide from which it is derived, e.g., antimicrobial or antibacterial activity (e.g., lytic killing activity), preferably against one or more strains of K. pneumoniae, A. baumannii, E. coli, P. aeruginosa, and/or S. aureus.

The pharmaceutical compositions of the invention may additionally comprise a pharmaceutically acceptable carrier, excipient, or stabilizer. In certain embodiments, the pharmaceutical compositions of the invention are antibiotic compositions (in that they exhibit antibacterial activity) or therapeutic compositions for the treatment, prevention, and/or amelioration of symptoms of a disease or disorder associated with infection by bacteria in a subject in need thereof. In specific embodiments, the pharmaceutical compositions of the invention are antibacterial compositions or therapeutic compositions for the treatment, prevention, and/or amelioration of symptoms of a disease or disorder associated with infection by K. pneumoniae, A. baumannii, E. coli, P. aeruginosa, and/or S. aureus. In certain embodiments, the subject receiving a pharmaceutical composition of the invention is a mammal (e.g., bovine, ovine, caprine, equid, primate (e.g., human), rodent, lagomorph or avian (e.g., chicken, duck, goose)).

The present invention provides for methods for the treatment or prevention of bacterial infection comprising administering to a subject in need thereof a pharmaceutical composition comprising one or more bacteriophage or phage products (e.g., an isolated bacteriophage polypeptide or active fragment, variant or derivative thereof), optionally in addition to one or more other bacteriophage or other phage products, as described herein. In the context of the present invention, "treatment" refers to both therapeutic treatment and prophylactic or preventative measures, wherein the object is to eliminate, lessen, decrease the severity of, slow the progression of or delay or prevent the symptoms or underlying cause (e.g., bacterial infection) associated with the pathological condition or disorder. The pharmaceutical compositions of the present invention may be used in the treatment or management of infections associated with any bacterial infection, including, but not limited to K. pneumoniae, A. baumannii, E. coli, P. aeruginosa, and/or S. aureus, as well as, in certain embodiments, S. epidermidis, S. auricularis, S. capitis, S. haemolyticus, S. hominis, S. saprophyticus, S. simulans, S. xylosis, M. luteus, B. subtilis, B. pumilus, E. faecalis, E. hirae, E. faecium, E. avium, and combinations thereof. In certain embodiments, the pharmaceutical compositions may be used to treat conditions or disorders associated with bacterial infections including, but not limited to, post-operative endophtalmitis, endocarditis, infections of the central nervous system, pneumonia, osteomylelitis, wound infections (e.g., diabetic foot ulcers), mastitis, septicemia, food poisoning, meningitis, skin infections, abscesses, toxic shock syndrome, bacteremia, and/or other conditions associated with nosocomial bacterial infections.

In certain embodiments, the invention provides for the use of a bacteriophage or an isolated phage product (e.g., an isolated phage polypeptide or active fragment, variant or derivative thereof) as a single agent therapy. In other embodiments, the invention provides for the use of a bacteriophage, or phage product (e.g., an isolated phage polypeptide or active fragment, variant or derivative thereof), in combination with a standard or experimental treatment for bacterial infection. Such combination therapy may enhance the efficacy of the standard or experimental treatment. Examples of therapeutic agents that are particularly useful in combination with a bacteriophage and/or polypeptide of the invention are anti-inflammatory agents, standard chemotherapeutic antibiotic agents (e.g., penicillin, synthetic penicillins, bacitracin, methicillin, nafcillin, oxacilin, cloxacillin, vancomycin, teicoplanin, clindamycin, co-trimoxazole, cephalosporin, polymyxin, cefaclor. Cefadroxil, cefamandole nafate, cefazolin, cefixime, cefmetazole, cefonioid, cefoperazone, ceforanide, cefotanme, cefotaxime, cefotetan, cefoxitin, cefpodoxime proxetil, ceftazidime, ceftizoxime, ceftriaxone, cefriaxone moxalactam, cefuroxime, cephalexin, cephalosporin C, cephalosporin C sodium salt, cephalothin, cephalothin sodium salt, cephapirin, cephradine, cefuroximeaxetil, dihydratecephalothin, moxalactam, loracarbef mafate and chelating agents), local anesthetic agents, and/or corticosteroids. In yet another embodiment, the compositions of the present invention may be combined with one or more bacteriophage or phage products known in the art. The combination therapies encompassed by the invention may be formulated into a single pharmaceutical composition or may be administered in separate compositions, but as part of an overall treatment regimen.

The pharmaceutical compositions of the invention may be administered by any method known in the art suitable for administration of an antibacterial compound, e.g., via oral or parenteral (e.g., inhalation, intramuscular, intravenous, or epidermal) delivery. In preferred embodiments, the pharmaceutical compositions of the invention are administered topically, e.g., in a topical formulation. The compositions of the invention may be used topically to treat and/or prevent common nosocomial infections, such as infections at surgical incision sites or associated with catheters or drains. In other embodiments, the compositions of the invention are use to treat bacterial infections of the skin or upper dermal layers (e.g., infections of diabetic ulcers of the foot or carbuncles).

The pharmaceutical compositions of the present invention may also be used for traditionally non-therapeutic uses such as antibacterial agents in cosmetics, or in sprays or solutions for use on solid surfaces to prevent the colonization of bacteria (i.e., as disinfectants).

The present invention is also directed to methods for screening peptides for antibacterial activity. In one embodiment the method comprises screening contiguous amino acid sequences of at least 6, 10, 15, 20 or 25 residues in length that are encoded by the open reading frames of the nucleic acid sequence SEQ ID NO: 1, SEQ ID NO: 2, SEQ ID NO: 3, SEQ ID NO: 4, SEQ ID NO: 560, SEQ ID NO: 781, or SEQ ID NO: 1074, for antibacterial activity, said antibacterial activity measured by the peptides ability to inhibit bacterial growth, e.g., in agar or liquid culture.

5.1 Definitions

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a protein. In a specific embodiment, the fragment is a functional fragment in that it retains at least one function of the protein from which it is isolated (e.g., antimicrobial or antibacterial activity (e.g., lytic cell killing)).

As used herein the terms "active bacteriophage products" and "bacteriophage products" refer to polypeptides, or fragments, variants or derivatives thereof, isolated from a bacteriophage of the invention, which polypeptide, or fragment, variant or derivative thereof, exhibits a biological function or activity associated with the bacteriophage from which it was isolated or derived (e.g., antimicrobial or antibacterial activity (e.g., lytic cell killing)).

As used herein, the term "isolated" in the context of a peptide, polypeptide, or fusion protein or refers to a peptide, polypeptide or fusion protein that is substantially free of cellular material or contaminating proteins from the cell or tissue source from which it is derived, or substantially free of chemical precursors or other chemicals when chemically synthesized. The language "substantially free of cellular material" includes preparations of a peptide, polypeptide or fusion protein in which the peptide, polypeptide or fusion protein is separated from cellular components of the cells from which it is isolated or recombinantly produced. Thus, a peptide, polypeptide or fusion protein that is substantially free of cellular material includes preparations of a peptide, polypeptide or fusion protein having less than about 30%, 20%, 10%, or 5% (by dry weight) of heterologous protein (also referred to herein as a "contaminating protein"). When the peptide, polypeptide or fusion protein is recombinantly produced, it is also preferably substantially free of culture medium, i.e., culture medium represents less than about 20%, 10%, or 5% of the volume of the protein preparation. When the peptide, polypeptide or fusion protein is produced by chemical synthesis, it is preferably substantially free of chemical precursors or other chemicals, i.e., it is separated from chemical precursors or other chemicals which are involved in the synthesis of the peptide, polypeptide, or fusion protein. Accordingly, such preparations of a peptide, polypeptide, fusion protein, or antibody have less than about 30%, 20%, 10%, 5% (by dry weight) of chemical precursors or compounds other than the peptide, polypeptide, or fusion protein of interest.

As used herein, the term "isolated" in the context of nucleic acid molecules refers to a first nucleic acid molecule which is separated from other nucleic acid molecules which are present in the natural source of the first nucleic acid molecule. Moreover, an "isolated" nucleic acid molecule, such as a cDNA molecule, is substantially free of other cellular material, or culture medium when produced by recombinant techniques, or substantially free of chemical precursors or other chemicals when chemically synthesized and may be free of other cDNA or other genomic DNA molecules, e.g., where it has been isolated from other clones in a nucleic acid library.

The term "purified" means that the peptide, polypeptide, fusion protein, or nucleic acid molecule has been measurably increased in concentration by any purification process, including but not limited to, column chromatography, HPLC, precipitation, electrophoresis, etc., thereby partially, substantially, nearly completely, or completely removing impurities, such as precursors or other chemicals involved in preparing the peptide, polypeptide, fusion protein, or nucleic acid molecule. One of skill in the art will appreciate the amount of purification necessary for a given use. For example, isolated protein meant for use in therapeutic compositions intended for administration to humans ordinarily must be of high purity in accordance with regulatory standards and good manufacturing processes.

As used herein, the term "derivative" in the context of polypeptides refers to a polypeptide that comprises an amino acid sequence which has been altered by the introduction of amino acid residue substitutions, deletions or additions. The term "derivative" as used herein also refers to a polypeptide that has been modified, i.e., by the covalent attachment of any type of molecule to the polypeptide. For example, but not by way of limitation, a polypeptide may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide may be produced by chemical modifications using techniques known to those of skill in the art, including, but not limited to specific chemical cleavage, acetylation, formylation, metabolic synthesis of tunicamycin, etc. Further, a derivative polypeptide may contain one or more non-classical amino acids. A polypeptide derivative possesses a similar or identical function as the polypeptide from which it was derived. The term "derived" as used in reference to a polypeptide "derived" from an organism may also refer to isolation of a polypeptide directly from said organism (e.g. bacterial cells or phage).

As used herein, the term "host cell" refers to the particular subject cell transfected with a nucleic acid molecule and the progeny or potential progeny of such a cell that contain the nucleic acid molecule or chromosomally integrated version thereof. Progeny of such a cell may not be identical to the parent cell transfected with the nucleic acid molecule due to mutations or environmental influences that may occur in succeeding generations or integration of the nucleic acid molecule into the host cell genome. For the expression of bacteriophage proteins and polypeptides, the host cell is preferably not of the same species or strain from which the bacteriophage was isolated or cultured.

As used herein, the term "in combination" refers to the use of more than one prophylactic and/or therapeutic agent. The use of the term "in combination" does not restrict the order in which prophylactic and/or therapeutic agents are administered to a subject with a disease or disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent (different from the first prophylactic or therapeutic agent) to a subject in need thereof, e.g., a subject with a disease or disorder.

As used herein, the terms "nucleic acids" and "nucleotide sequences" include single-stranded and double-stranded DNA and/or RNA molecules, or combinations thereof. As used herein, the term "encoded by the nucleic acid" refers to an amino acid sequence that results from the translation of the forward, reverse, complementary or reverse-complementary sequence of the referenced nucleic acid sequence using the standard genetic code (i.e., standard codon triplets) as well known in the art.

As used herein, the terms "prophylactic agent" and "prophylactic agents" refer to bacteriophage and/or polypeptides of the invention, which can be used in the prevention, treatment, management or amelioration of one or more symptoms of a disease or disorder, in particular, a disease or disorder associated with a bacterial infection.

As used herein, the terms "therapeutic agent" and "therapeutic agents" refer to bacteriophage and/or polypeptides of the invention that can be used in the prevention, treatment, management or amelioration of one or more symptoms of a disease or disorder, in particular, a disease or disorder associated with a bacterial infection.

As used herein, the term "therapeutically effective amount" refers to that amount of a therapeutic agent sufficient to result in amelioration of one or more symptoms of a disease or disorder, in particular, a disease or disorder associated with a bacterial infection.

As used herein, the terms "treat", "treatment" and "treating" refer to the amelioration of one or more symptoms of a disease or disorder, in particular, a disease or disorder associated with a bacterial infection, which results from the administration of one or more bacteriophage and/or polypeptides of the invention. As noted above, "treatment" and related terms refer to both therapeutic treatment and prophylactic or preventative measures, wherein the object is to eliminate, lessen, decrease the severity of, slow the progression of, or delay or prevent the symptoms or underlying cause (e.g., bacterial infection) associated with the pathological condition or disorder.

As used herein, the terms "antibacterial activity" and "antimicrobial activity" with reference to a bacteriophage, isolated bacteriophage protein (or variant, derivative or fragment thereof), or bacteriophage product, are used interchangeably to refer to the ability to kill and/or inhibit the growth or reproduction of a microorganism, in particular, the bacteria of the species or strain that the bacteriophage infects. In certain embodiments, antibacterial or antimicrobial activity is assessed by culturing bacteria, e.g., Gram-positive bacteria (e.g., *S. aureus*), Gram-negative bacteria (e.g., *K. pneumoniae, A. baumannii, E. coli*, and/or *P. aeruginosa*) or bacteria not classified as either Gram-positive or Gram-negative, according to standard techniques (e.g., in liquid culture or on agar plates), contacting the culture with a bacteriophage or polypeptide of the invention and monitoring cell growth after said contacting. For example, in a liquid culture, the bacteria may be grown to an optical density ("OD") representative of a mid-point in exponential growth of the culture; the culture is exposed to one or more concentrations of one or more bacteriophage or polypeptides of the invention, and the OD is monitored relative to a control culture. Decreased OD relative to a control culture is representative of a bacteriophage or polypeptide exhibiting antibacterial activity (e.g., exhibits lytic killing activity). Similarly, bacterial colonies can be allowed to form on an agar plate, the plate exposed to a bacteriophage or polypeptide of the invention, and subsequent growth of the colonies evaluated related to control plates. Decreased size of colonies, or decreased total numbers of colonies, indicate a bacteriophage or polypeptide with antibacterial activity.

As used herein, a "CHAP domain" refers to a conserved amidase domain found in several phage-encoded peptidoglycan hydrolases and stands for for "cysteine, histidine-dependent amidohydrolases/peptidases." See, e.g., Rigden D, et. al., Trends Biochem Sci. 2003 May 28(5): 230-4. It is found in a superfamily of amidases, including GSP amidase and peptidoglycan hydrolases. The family includes at least two different types of peptidoglycan cleavage activities: L-muramoyl-L-alanine amidase and D-alanyl-glycyl endopeptidase activity. CHAP domains generally contain conserved cysteine and histidine residues and hydrolyze γ-glutamyl-containing substrates. These cysteine residues are believed to be essential for the activity of several of these amidases, and their thiol groups appear to function as the nucleophiles in the catalytic mechanisms of all enzymes containing this domain. CHAP domains are often found in association with other domains that cleave peptidoglycan, e.g., acting in a cooperative manner to cleave specialized substrates. See also, Bateman A, et al., Trends Biochem Sci. 2003 May 28(5): 234-7.

6. BRIEF DESCRIPTION OF THE FIGURES

FIGS. 1A-1B: Schematic of the organization of the F391/08 genome, comprising the nucleic acid sequence of SEQ ID NO:1. The open reading frames ("ORFs") predicted in the approximately 113 kb genome are represented by arrows and numbered in black. The direction of an arrow indicates the direction of transcription. Color coding: Black—ORFs for which products a functional assignment could be made based on the known functions of homologous proteins; Gray—ORFs coding for products that are similar to proteins of unknown function; Empty—ORFs coding for proteins that share no significant homology with proteins in available databases. Functionally assigned ORFs are also listed in the figure. The information in the figure is also included in tabular form in FIG. 2.

FIGS. 2A-2II: Features of the bacteriophage F391/08 genome, including gene products and assignment of putative functions. The figure includes a listing of the ORFs of the genome and provides for each ORF (i) its position within the genome, (ii) the encoded amino acid sequence, (iii) a listing of homologous proteins and conserved domains within its encoded polypeptide and (iv) an assignment of putative function. ORFs 1-172 listed in FIG. 2 encode the amino acid sequences of SEQ ID NO:5-176, respectively.

Figure 3:
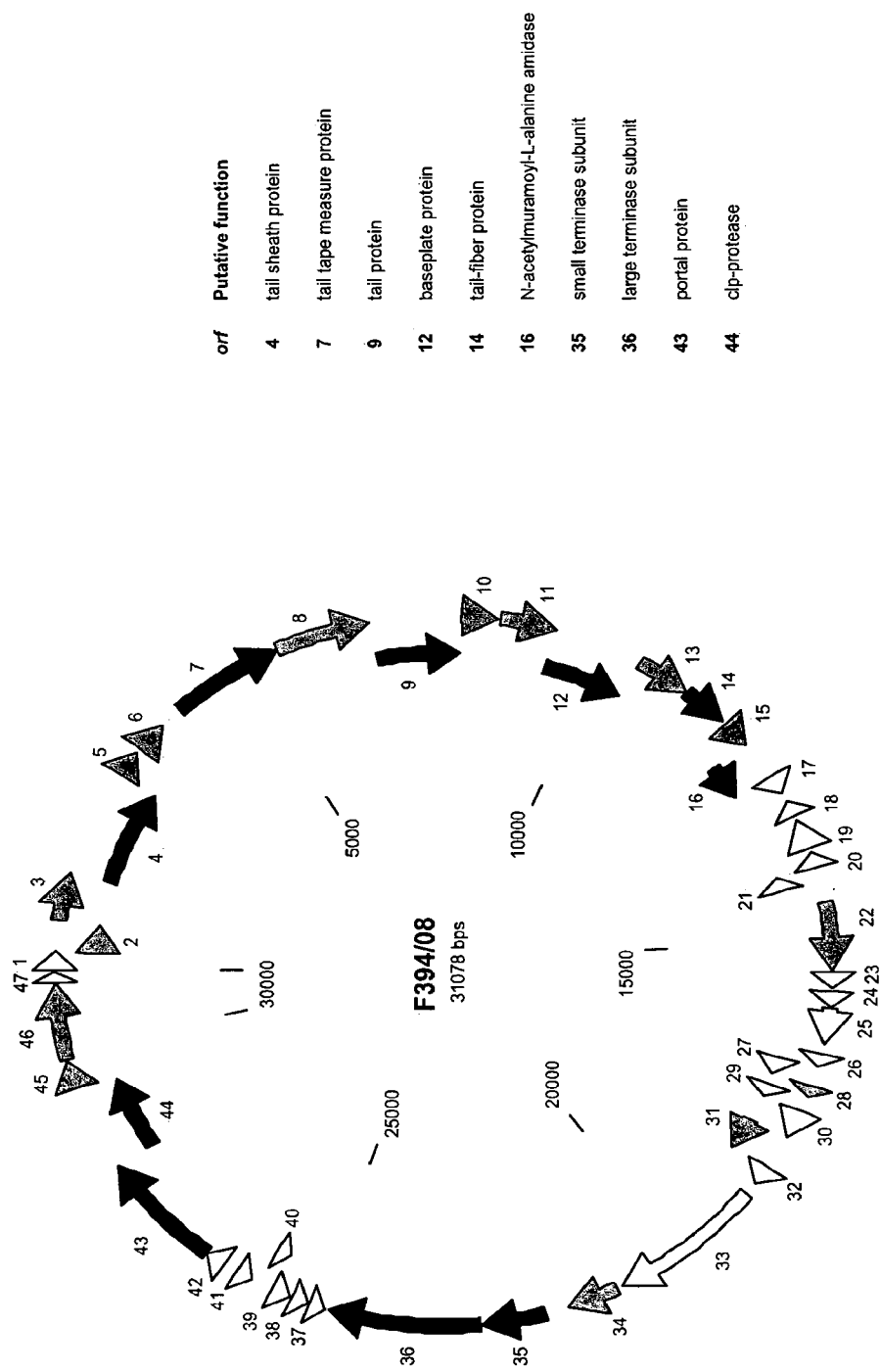

FIG. 3: Schematic of the organization of the F394/08 genome, comprising the nucleic acid sequence of SEQ ID NO:2. The open reading frames ("ORFs") predicted in the approximately 31 kb genome are represented by arrows and numbered in black. The direction of an arrow indicates the direction of transcription. Color coding: Black—ORFs for which products a functional assignment could be made based on the known functions of homologous proteins; Gray—ORFs coding for products that are similar to proteins of unknown function; Empty—ORFs coding for proteins that share no significant homology with proteins in available databases. Functionally assigned ORFs are also listed in the figure. The information in the figure is also included in tabular form in FIG. 4.

FIGS. 4A-4K: Features of the bacteriophage F394/08 genome, including gene products and assignment of putative functions. The figure includes a listing of the ORFs of the genome and provides for each ORF (i) its position within the genome, (ii) the encoded amino acid sequence, (iii) a listing of homologous proteins and conserved domains within its encoded polypeptide and (iv) an assignment of putative function. ORFs 1-47 listed in FIG. 4 encode the amino acid sequences of SEQ ID NO:177-223, respectively.

Figure 5A:
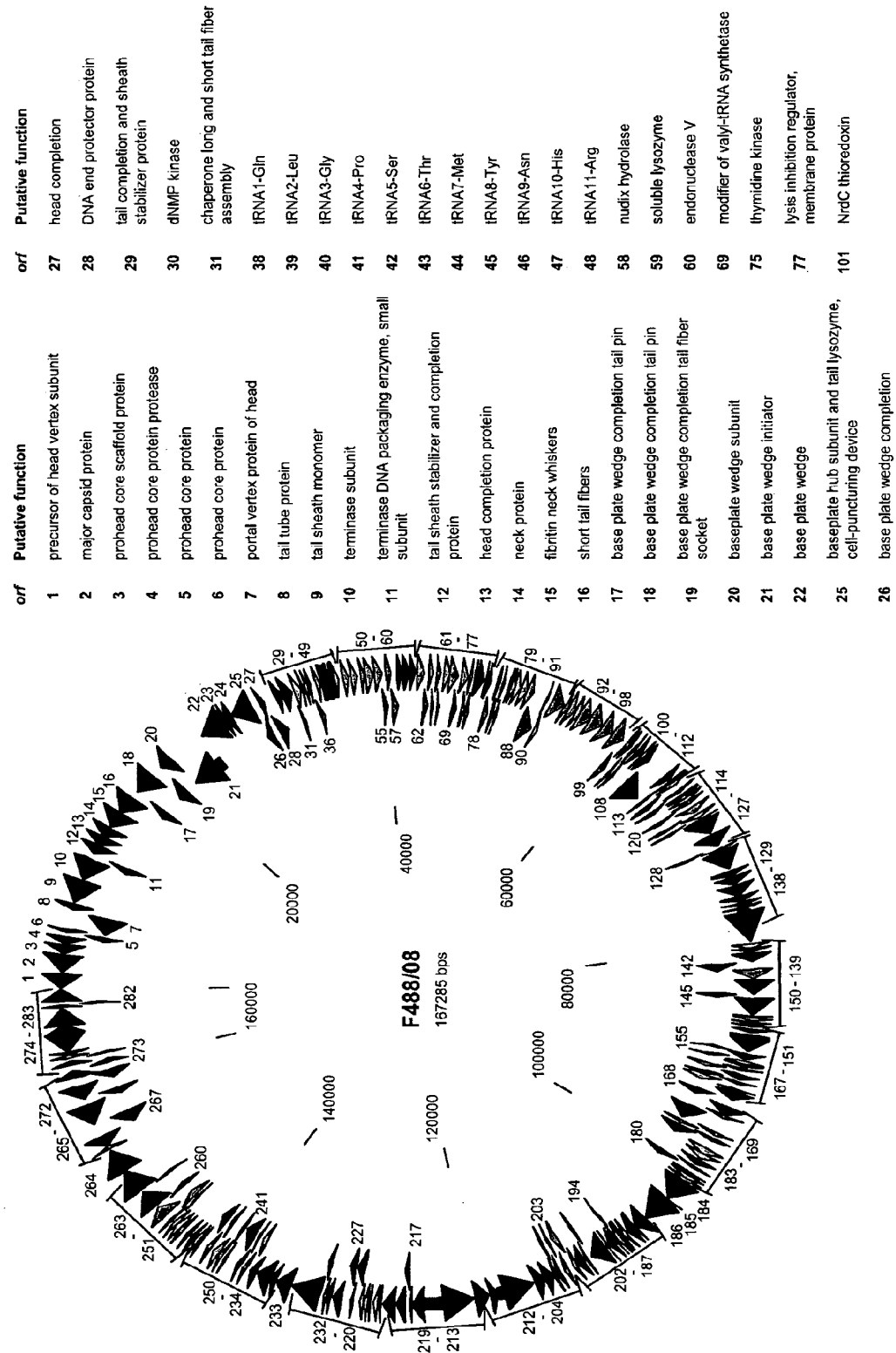

FIGS. 5A-5B: Schematic of the organization of the F488/08 genome, comprising the nucleic acid sequence of SEQ ID NO:3. The open reading frames ("ORFs") predicted in the approximately 167 kb genome are represented by arrows and numbered in black. The direction of an arrow indicates the direction of transcription. Color coding: Black—ORFs for which products a functional assignment could be made based on the known functions of homologous proteins; Gray—ORFs coding for products that are similar to proteins of unknown function; Empty—ORFs coding for proteins that share no significant homology with proteins in available databases. Functionally assigned ORFs are also listed in the figure. The information in the figure is also included in tabular form in FIG. 6.

FIGS. 6A-6DDD: Features of the bacteriophage F488/08 genome, including gene products and assignment of putative functions. The figure includes a listing of the ORFs of the genome and provides for each ORF (i) its position within the genome, (ii) the encoded amino acid sequence, (iii) a listing of homologous proteins, and conserved domains within its encoded polypeptide, and (iv) an assignment of putative function. ORFs 1-283 listed in FIG. 6 encode the amino acid sequences of SEQ ID NO:224-506, respectively.

Figure 7:
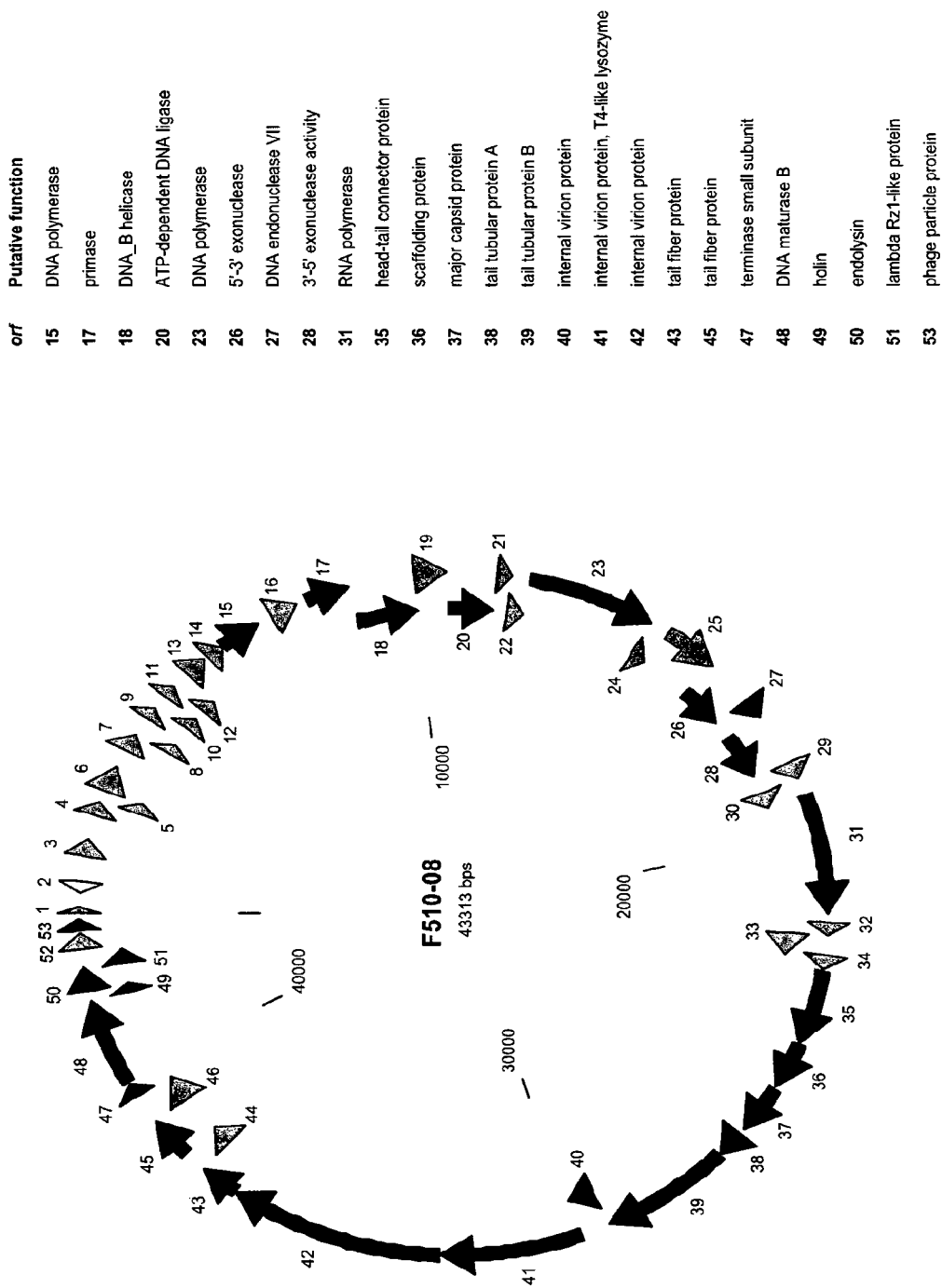

FIG. 7: Schematic of the organization of the F510/08 genome, comprising the nucleic acid sequence of SEQ ID NO:4. The open reading frames ("ORFs") predicted in the approximately 43 kb genome are represented by arrows and numbered in black. The direction of an arrow indicates the direction of transcription. Color coding: Black—ORFs for which products a functional assignment could be made based on the known functions of homologous proteins; Gray—ORFs coding for products that are similar to proteins of unknown function; Empty—ORFs coding for proteins that share no significant homology with proteins in available databases. Functionally assigned ORFs are also listed in the figure. The information in the figure is also included in tabular form in FIG. 8.

FIGS. 8 A-8S: Features of the bacteriophage F510/08 genome, including gene products and assignment of putative functions. The figure includes a listing of the ORFs of the genome and provides for each ORF (i) its position within the genome, (ii) the encoded amino acid sequence, (iii) a listing of homologous proteins, and conserved domains within its encoded polypeptide, and (iv) an assignment of putative function. ORFs 1-53 listed in FIG. 8 encode the amino acid sequences of SEQ ID NO:507-559, respectively.

Figure 9:
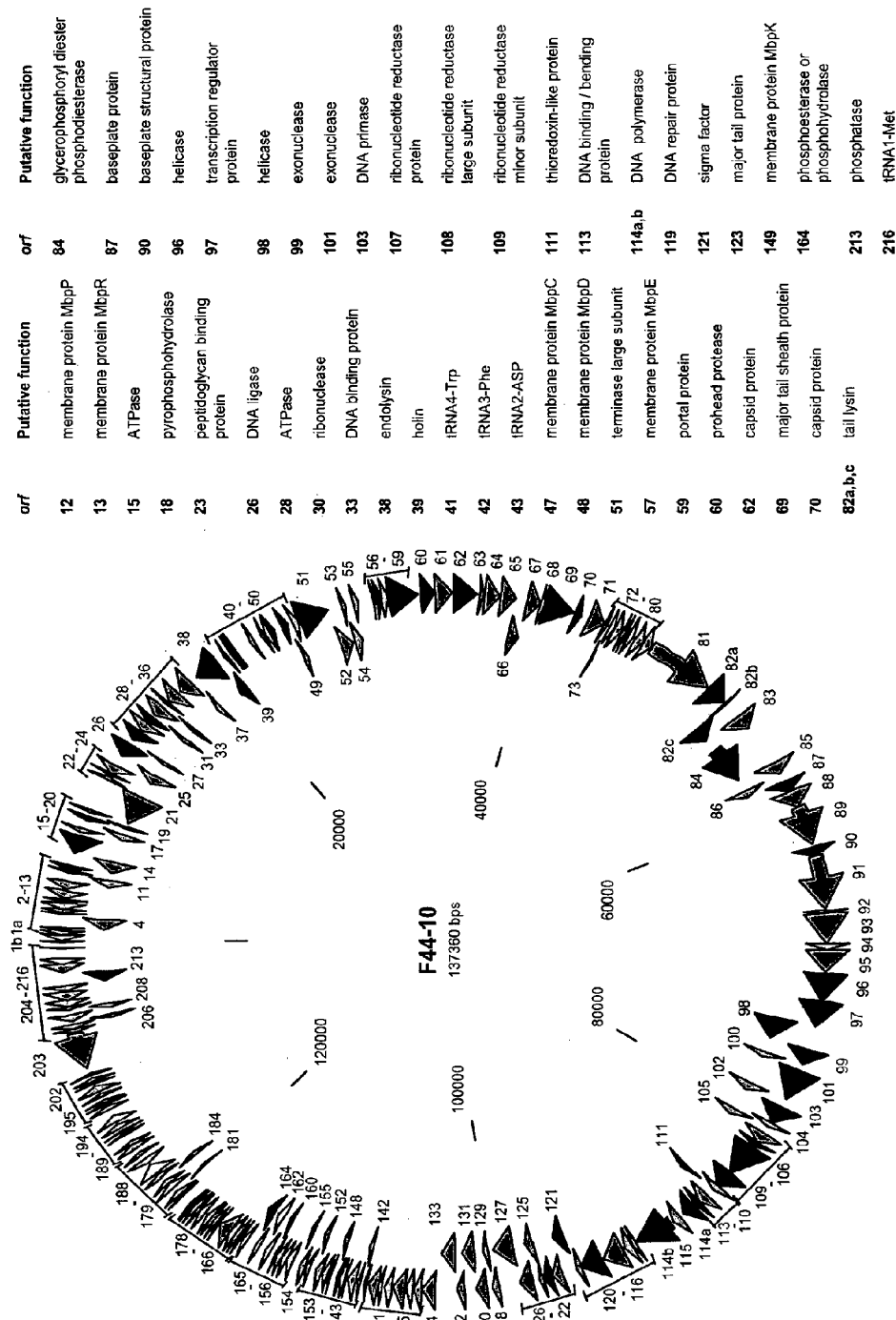

FIG. 9: Schematic of the organization of the F44/10 genome, comprising the nucleic acid sequence of SEQ ID NO:560. The open reading frames ("ORFs") predicted in the approximately 137 kb genome are represented by arrows and numbered in black. The direction of an arrow indicates the direction of transcription. Color coding: Black—ORFs for which products a functional assignment could be made based on the known functions of homologous proteins; Gray—ORFs coding for products that are similar to proteins of unknown function; Empty—ORFs coding for proteins that share no significant homology with proteins in available databases. Functionally assigned ORFs are also listed in the figure. The information in the figure is also included in tabular form in FIG. 10.

FIGS. 10A-10QQ: Features of the bacteriophage F44/10 genome, including gene products and assignment of putative functions. The figure includes a listing of the ORFs of the genome and provides for each ORF (i) its position within the genome, (ii) the encoded amino acid sequence, (iii) a listing of homologous proteins and conserved domains within its encoded polypeptide and (iv) an assignment of putative function. ORFs 1-216, including ORFs 1a, 1b, 82a, 82b, 82c, 114a, and 114b, listed in FIG. 10 encode the amino acid sequences of SEQ ID NO:561-780, respectively.

Figure 11A:
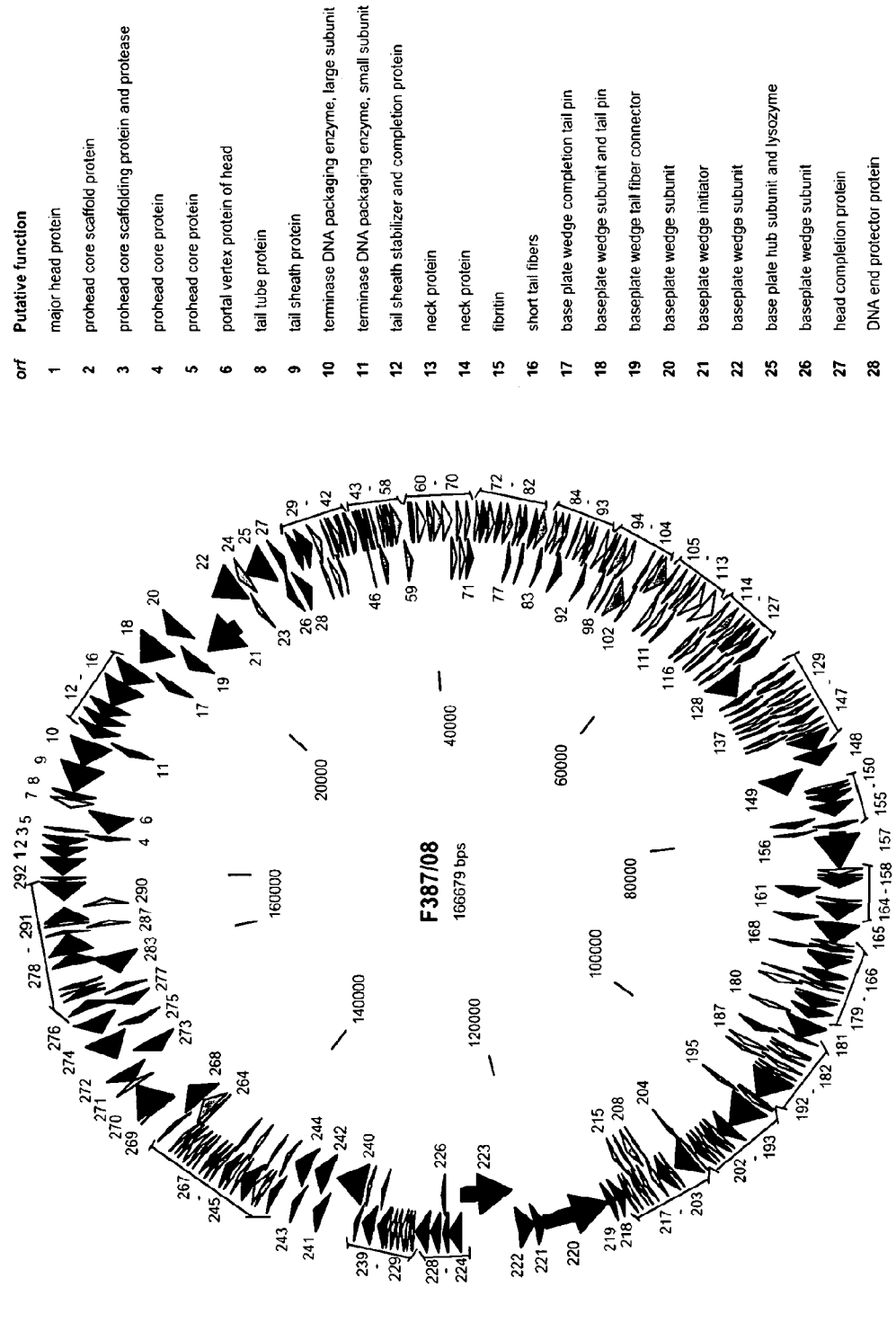

FIGS. 11A-11C: Schematic of the organization of the F387/08 genome, comprising the nucleic acid sequence of SEQ ID NO:781. The open reading frames ("ORFs") predicted in the approximately 167 kb genome are represented by arrows and numbered in black. The direction of an arrow indicates the direction of transcription. Color coding: Black—ORFs for which products a functional assignment could be made based on the known functions of homologous proteins; Gray—ORFs coding for products that are similar to proteins of unknown function; Empty—ORFs coding for proteins that share no significant homology with proteins in available databases. Functionally assigned ORFs are also listed in the figure. The information in the figure is also included in tabular form in FIG. 12.

FIGS. 12A-12UUU: Features of the bacteriophage F387/08 genome, including gene products and assignment of putative functions. The figure includes a listing of the ORFs of the genome and provides for each ORF (i) its position within the genome, (ii) the encoded amino acid sequence, (iii) a listing of homologous proteins and conserved domains within its encoded polypeptide and (iv) an assignment of putative function. ORFs 1-292 listed in FIG. 12 encode the amino acid sequences of SEQ ID NOs: 782-1073, respectively.

Figure 13A:
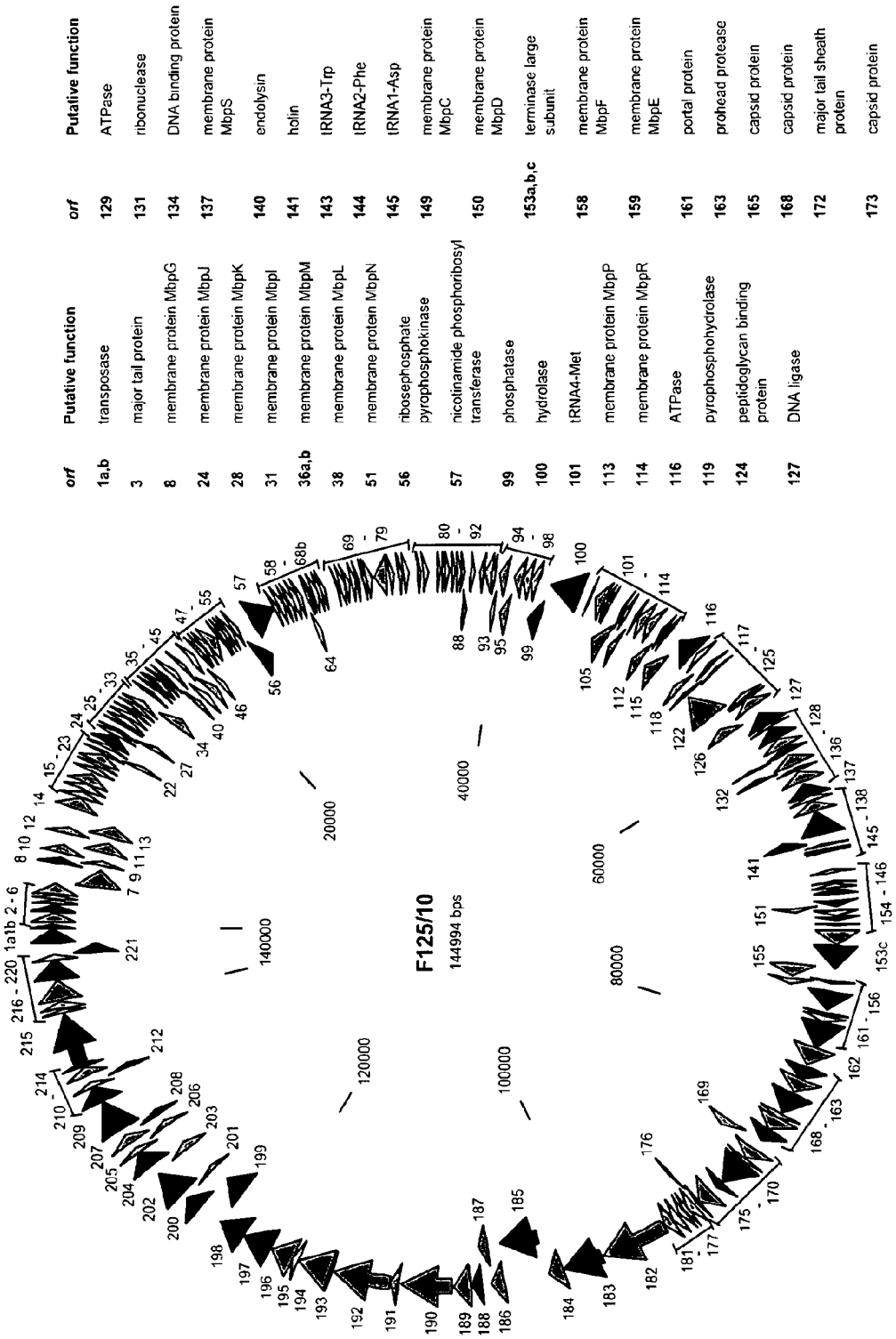

FIGS. 13A-13B: Schematic of the organization of the F125/10 genome, comprising the nucleic acid sequence of SEQ ID NO:1074. The open reading frames ("ORFs") predicted in the approximately 145 kb genome are represented by arrows and numbered in black. The direction of an arrow indicates the direction of transcription. Color coding: Black—ORFs for which products a functional assignment could be made based on the known functions of homologous proteins; Gray—ORFs coding for products that are similar to proteins of unknown function; Empty—ORFs coding for proteins that share no significant homology with proteins in available databases. Functionally assigned ORFs are also listed in the figure. The information in the figure is also included in tabular form in FIGS. 14A-14ZZZ

FIGS. 14A-14ZZZ: Features of the bacteriophage F125/10 genome, including gene products and assignment of putative functions. The figure includes a listing of the ORFs of the genome and provides for each ORF (i) its position within the genome, (ii) the encoded amino acid sequence, (iii) a listing of homologous proteins and conserved domains within its encoded polypeptide and (iv) an assignment of putative function. ORFs 1b-221, 1a listed in this Figure encode the amino acid sequences of SEQ ID NO:1075-1300, respectively, including 36a and 36b, 68a and 68b, and 153a and 153b.

FIGS. 15A-15III: The nucleotide sequence of the genome of bacteriophage F391/08 (SEQ ID NO:1).

FIGS. 16A-16Q: The nucleotide sequence of the genome of bacteriophage F394/08 (SEQ ID NO:2).

FIGS. 17A-17KKKK: The nucleotide sequence of the genome of bacteriophage F488/08 (SEQ ID NO:3).

FIGS. 18A-18X: The nucleotide sequence of the genome of bacteriophage F510/08 (SEQ ID NO:4).

FIGS. 19A-19UUU: The nucleotide sequence of the genome of bacteriophage F44/10 (SEQ ID NO:560).

FIGS. 20A-20KKKK: The nucleotide sequence of the genome of bacteriophage F387/08 (SEQ ID NO:781).

FIGS. 21A-21ZZZ: The nucleotide sequence of the genome of bacteriophage F125/10 (SEQ ID NO:1074).

6.1 DETAILED DESCRIPTION

The present invention is directed to isolated bacteriophage, and their isolated polypeptide products, having antibacterial activity against one or more species or strains of the nosocomial pathogens *Klebsiella pneumoniae, Acinetobacter baumannii, Escherichia coli, Pseudomonas aeruginosa*, and *S. aureus*. In one embodiment, isolated bacteriophage or polypeptides are provided that exhibit antimicrobial and/or antibacterial activity against methicillin-resistant strains of *S. aureus* (MRSA). In addition, the bacteriophage and polypeptides of the invention may exhibit antibacterial or antimicrobial activity against one or more species or strains of pathogenic bacteria including, but not limited to, *S. epidermidis*, *S. auricularis*, *S. capitis*, *S. haemolyticus*, *S. hominis*, *S. saprophyticus*, *S. simulans*, *S. xylosis*, *Micrococcus luteus*, *Bacilus subtilis*, *B. pumilus*, *E. hirae* and *E. avium*.

In some embodiments, the invention provides a bacteriophage having a genome comprising or consisting of the nucleic acid sequence of SEQ ID NO: 1. A specific example in accordance with this embodiment is the isolated bacteriophage F391/08, which targets a number of strains of *Klebsiella* species, including *K. pneumoniae* and *K. oxytoca*. A schematic organization of the F391/08 genome, comprising the nucleic acid sequence of SEQ ID NO: 1, is provided in FIG. 1. Open reading frames (ORFs) in the F391/08 genome are provided in FIG. 2. Also provided are the positions of the ORFs within the genome, the amino acid sequences encoded by the ORFs, homologous or similar proteins and conserved domains within the encoded polypeptide, and the assignment of putative functions. ORFs 1-172 listed in FIG. 2 encode the amino acid sequences of SEQ ID NOs: 5-176, respectively.

In some embodiments, the invention provides a bacteriophage having a genome comprising or consisting of the nucleic acid sequence of SEQ ID NO: 781. A specific example in accordance with this embodiment is the isolated bacteriophage F387/08, which targets a number of strains of *Klebsiella* species, including *K. pneumoniae* and *K. oxytoca*. A schematic organization of the F387/08 genome, comprising the nucleic acid sequence of SEQ ID NO: 781, is provided in FIGS. 11A-11C. Open reading frames (ORFs) in the F387/08 genome are provided in FIG. 12. Also provided are the positions of the ORFs within the genome, the amino acid sequences encoded by the ORFs, homologous or similar proteins and conserved domains within the encoded polypeptide, and the assignment of putative functions. ORFs 1-292 listed in FIG. 12 encode the amino acid sequences of SEQ ID NOs: 782-1073, respectively.

*Klebsiella pneumoniae* is a Gram-negative, non-motile, rod-shaped bacterium, found in the normal flora of the mouth, skin, and intestines. As an encapsulated, facultative anaerobe, the bacterium also naturally occurs in the soil and about 30% of strains can fix nitrogen in anaerobic conditions. Clinically, it is the most important member of the *Klebsiella* genus of Enterobacteriaceae, and also is closely related to *K. oxytoca*. *Klebsiella* infections tend to occur in people with a weakened immune system from improper diet, e.g. in alcoholics and diabetics. *Klebsiella* is also an opportunistic pathogen for patients with chronic pulmonary disease, enteric pathogenicity, nasal mucosa atrophy, and rhinoscleroma. New antibiotic resistant strains of *K. pneumoniae* are appearing, and it is increasingly found as a nosocomial infection, for example, due to contact with contaminated instruments.

In some embodiments, the invention provides a bacteriophage having a genome comprising or consisting of the nucleic acid sequence of SEQ ID NO: 2. A specific example in accordance with this embodiment is the isolated bacteriophage F394/08, which targets a number of strains of *Acinetobacter* species, including *A. baumanni*, *A. calcoaceticus*, and *A. Iwoffi*. A schematic organization of the F394/08 genome, comprising the nucleic acid sequence of SEQ ID NO: 2, is provided in FIG. 3. Open reading frames (ORFs) in the F394/08 genome are provided in FIG. 4. Also provided are the positions of the ORFs within the genome, the amino acid sequences encoded by the ORFs, homologous or similar proteins and conserved domains within the encoded polypeptide, and the assignment of putative functions. ORFs 1-47 listed in FIG. 4 encode the amino acid sequences of SEQ ID NOs: 177-223, respectively.

*Acinetobacter baumannii* is a species of bacteria that causes a number of severe clinical infections, particularly in individuals with compromised immune systems. *A. baumannii* is a pleomorphic aerobic gram-negative *bacillus* that is commonly isolated from the hospital environment and from hospitalized patients. The bacterium often enters the body open wounds, catheters, or breathing tubes. *A. baumannii* usually colonizes aquatic environments and is often cultured from hospitalized patients' sputum or respiratory secretions, wounds, and urine. In a hospital setting, *A. baumannii* commonly colonizes irrigating solutions and intravenous solutions. It is also known to be resistant to multiple antibiotics and the number of nosocomial infections caused by *A. baumanni* has increased in recent years.

In some embodiments, the invention provides a bacteriophage having a genome comprising or consisting of the nucleic acid sequence of SEQ ID NO: 3. A specific example in accordance with this embodiment is the isolated bacteriophage F488/08, which targets a number of strains of *Escherichia* species, including *E. coli*. A schematic organization of the F488/08 genome, comprising the nucleic acid sequence of SEQ ID NO: 3, is provided in FIG. 5. Open reading frames (ORFs) in the F488/08 genome are provided in FIG. 6. Also provided are the positions of the ORFs within the genome, the amino acid sequences encoded by the ORFs, homologous or similar proteins and conserved domains within the encoded polypeptide, and the assignment of putative functions. ORFs 1-283 listed in FIG. 6 encode the amino acid sequences of SEQ ID NOs: 224-506, respectively.

*Escherichia coli* is a Gram negative rod-shaped bacterium that is commonly found in the lower intestine of mammals, comprising the primaru facultative anaerobic of the human gastrointestinal tract. Most *E. coli* strains are harmless and may form part of the normal flora of the gut, where they may benefit their hosts, e.g., by producing vitamin K2 and/or by preventing the establishment of pathogenic bacteria within the intestines. Certain virulent strains of *E. coli*, however, may cause food poisoning, typically manifesting as a bout of diarrhea. More virulent strains, such as O157:H7, can cause serious illness and even death in the elderly, the very young, or the immunocompromised. Strains such as O157:H7, as well as O121 and O104:H21, produce potentially lethal toxins. Virulent strains of *E. coli* also can cause gastroenteritis, urinary tract infections, and neonatal meningitis, as well as, in rarer cases, haemolytic-uremic syndrome (HUS), peritonitis, mastitis, septicemia, and Gram-negative pneumonia. Further, if *E. coli* bacteria escape the intestinal tract through a perforation (for example from a ruptured appendix, and ulcer, or a surgical error) and enter the abdomen, they usually cause peritonitis that can be fatal without prompt treatment. Intestinal mucosa-associated *E. coli* also are observed in increased numbers in the inflammatory bowel diseases, Crohn's disease and ulcerative colitis.

Antibiotics that may be used to treat *E. coli* infection include amoxicillin as well as other semi-synthetic penicillins, many cephalosporins, carbapenems, aztreonam, trimethoprim-sulfamethoxazole, ciprofloxacin, nitrofurantoin, and the aminoglycosides. Nonetheless, as Gram-negative organisms, *E. coli* are resistant to many antibiotics that are effective against Gram-positive organisms and antibiotic resistance is a growing problem. Resistance to beta-lactam antibiotics, for example, has become a particular problem in recent decades, as strains of bacteria that produce extended-spectrum beta-lactamases become more common. These beta-lactamase enzymes can render many, if not all, penicillins and/or cephalosporins therapeutically ineffective. Extended-spectrum beta-lactamase producing *E. coli* strains that are resistant to an array of antibiotics result in infections that are particularly difficult to treat.

In some embodiments, the invention provides a bacteriophage having a genome comprising or consisting of the nucleic acid sequence of SEQ ID NO: 4. A specific example in accordance with this embodiment is the isolated bacteriophage F510/08, which targets a number of strains of *Pseudomonas* species, including *P. aeruginosa*. A schematic organization of the F510/08 genome, comprising the nucleic acid sequence of SEQ ID NO: 4, is provided in FIG. 7. Open reading frames (ORFs) in the F510/08 genome are provided in FIG. 8. Also provided are the positions of the ORFs within the genome, the amino acid sequences encoded by the ORFs, homologous or similar proteins and conserved domains within the encoded polypeptide, and the assignment of putative functions. ORFs 1-53 listed in FIG. 8 encode the amino acid sequences of SEQ ID NOs: 507-559, respectively.

*Pseudomonas aeruginosa* is a common Gram-negative rod-shaped bacterium found in soil, water, skin flora and most man-made environments. It thrives not only in normal atmospheres, but also with little oxygen as a facultative anaerobe, and can infect damaged tissues or immunocompromised individuals. When such colonisations occur in critical body organs such as the lungs, the urinary tract, and kidneys, the results can be fatal. Because it thrives on surfaces, this bacterium is also found on and in medical equipment including catheters, causing cross infections in hospitals and clinics. *P. aeruginosa* is one of the most relevant opportunistic, nosocomial pathogens, and it has been estimated that one in ten hosptical-acquired infections are from *Pseudomonas*. *P. aeruginosa* is also the most common cause of burn injury infections and the most frequent colonizer of medical devices, such as catheters.

In some embodiments, the invention provides a bacteriophage having a genome comprising or consisting of the nucleic acid sequence of SEQ ID NO: 560. A specific example in accordance with this embodiment is the isolated bacteriophage F44/10, which targets a number of strains of *Staphylococcus* species, including *S. aureus*. A schematic organization of the F44/10 genome, comprising the nucleic acid sequence of SEQ ID NO: 560, is provided in FIG. 9. Open reading frames (ORFs) in the F44/10 genome are provided in FIG. 10. Also provided are the positions of the ORFs within the genome, the amino acid sequences encoded by the ORFs, homologous or similar proteins and conserved domains within the encoded polypeptide, and the assignment of putative functions. ORFs 1-216, including 1a, 1b, 82a, 82b, 82c, 114a, and 114b, listed in FIG. 10, encode the amino acid sequences of SEQ ID NOs: 561-780, as indicated in the Figure.

In some embodiments, the invention provides a bacteriophage having a genome comprising or consisting of the nucleic acid sequence of SEQ ID NO: 1074. A specific example in accordance with this embodiment is the isolated bacteriophage F125/10, which targets a number of strains of *Staphylococcus* species, including *S. aureus*. A schematic organization of the F125/10 genome, comprising the nucleic acid sequence of SEQ ID NO: 1074, is provided in FIG. 13. Open reading frames (ORFs) in the F125/10 genome are provided in FIG. 14. Also provided are the positions of the ORFs within the genome, the amino acid sequences encoded by the ORFs, homologous or similar proteins and conserved domains within the encoded polypeptide, and the assignment of putative functions. ORFs 1-221, including 1a, 1b, 36a, 36b, 68a, 68b, 153a, and 153b, listed in FIG. 14, encode the amino acid sequences of SEQ ID NOs: 1075-1300, as indicated in the Figure.

*Staphylococcus aureus* is a Gram-positive spherical facultative anaerobe, which grows as grape-like clusters with a characteristic golden color, and the most common cause of staph infections. It is frequently part of the flora of human skin and responsible for a range of infections, including pimples, carbuncles, scalded skin syndrome, pneumonia, gastroenteritis, meningitis, osteomyelitis, endocarditis, toxic shock syndrome, bacteremia, and sepsis. It remains one of the five most common causes of nosocomial infections, often causing postsurgical wound infections. It has been estimated that about 50,000 patients in American hospitals contract a staph infection. Of particular concern are the methicillin-resistant *Staphylococcus aureus* strains (MRSA). MRSA remained an uncommon occurrence in hospital setting until the 1990's, when there was an explosion in MRSA prevalence in hospitals, where it now is considered endemic, especially in the UK. Johnson A. P., et al., *J. Antimicrobial Chemotherapy*, 48(1): 143-144 (2001). *S. aureus* has proven to be a very hardy bacterium, and was shown in one study that it could survive on polyester for almost three months, polyester being the main material used in hospital privacy curtains. Neely, A. N., et al., J. Clin. Microbiol., 38(2): 724-726 (2000).

The following organisms were deposited on Sep. 16, 20011, with NCIMB Limited, located at the Ferguson Building, Craibstone Estate, Bucksburn, Aberdeen, AB21 9YA, Scotland UK, under the provisions of the Budapest Treaty for the International Recognition of the Deposit of Microorganisms for the Purpose of Patent Procedure ("Budapest Treaty") and the NCIMB has assigned the corresponding NCIMB accession numbers as follows: host strain *Pseudomonas aeruginosa* 433/07 B2, NCIMB 41861; host strain *Staphylococcus aureus* 743/06 B1, NCIMB 41862; host strain *Acinetobacter baumannii* 1305/05 B3, NCIMB 41863; *Pseudomonas aeruginosa* phage F770/05, NCIMB 41864; *Acinetobacter baumannii* phage F1245/05, NCIMB 41865; *Staphylococcus aureus* phage F125/10, NCIMB 41866; *Staphylococcus aureus* phage F44/10, NCIMB 41867; and *Pseudomonas aeruginosa* phage F510/08, NCIMB 41868, all of which are incorporated by reference herein.

In certain embodiments, the bacteriophage of the invention comprises or consists of a genome having a sequence identity of at least 85%, 90%, 95%, 96%, 97%, 98% or at least 99% with the nucleic acid sequence of SEQ ID NO: 1, SEQ ID NO: 2, SEQ ID NO: 3, SEQ ID NO: 4, SEQ ID NO: 560, SEQ ID NO: 781, or SEQ ID NO: 1074, which bacteriophage exhibits at least one biological activity, e.g., antimicrobial or antibacterial activity (e.g., lytic killing activity), of one or more of bacteriophage F391/08, F394/08, F488/08, F510/08, F387/08, FF44/10, and F125/10. Alternatively or in addition, the bacteriophage of the invention may have a genome comprising a functional fragment of the nucleic acid sequence of SEQ ID NO: 1, SEQ ID NO: 2, SEQ ID NO: 3, SEQ ID NO:4, SEQ ID NO: 560, SEQ ID NO: 781, or SEQ ID NO: 1074, including the sequences of any of the open reading frames described in FIGS. 2, 4, 6, 8, 10, 12, and/or 14.

The invention also provides for isolated bacteria infected with one or more of the bacteriophage of the invention. In certain embodiments, the invention provides isolated *K. pneumoniae* infected with a bacteriophage having a genome comprising or consisting of the nucleic acid sequence of SEQ ID NO: 1 and/or SEQ ID NO: 781. In certain embodiments, the invention provides isolated *A. baumannii* infected with a bacteriophage having a genome comprising or consisting of the nucleic acid sequence of SEQ ID NO: 2. In certain embodiments, the invention provides isolated *E. coli* infected with a bacteriophage having a genome comprising or consisting of the nucleic acid sequence of SEQ ID NO: 3. In certain embodiments, the invention provides isolated *P. aeruginosa* infected with a bacteriophage having a genome comprising or consisting of the nucleic acid sequence of SEQ ID NO: 4. In certain embodiments, the invention provides isolated *S. aureus* infected with a bacteriophage having a genome comprising or consisting of the nucleic acid sequence of SEQ ID NO: 560 and/or SEQ ID NO: 1074.

The invention provides for methods of production and isolation of a bacteriophage having a genome comprising or consisting of the nucleic acid sequence of SEQ ID NO: 1, SEQ ID NO: 2, SEQ ID NO: 3, SEQ ID NO: 4, SEQ ID NO: 560, SEQ ID NO: 781, or SEQ ID NO: 1074. In certain embodiments, the invention provides for a method of producing and/or isolating a bacteriophage having a genome that comprises or consists of the nucleic acid sequence of SEQ ID NO: 1 and/or SEQ ID NO: 781 comprising (i) obtaining a culture of *K. pneumoniae*, (ii) infecting it with the bacteriophage having a genome comprising or consisting of the nucleic acid sequence of SEQ ID NO: 1 and/or SEQ ID NO: 781; (iii) culturing until significant lysis of the culture is observed; and (iv) isolating from the culture the bacteriophage. In other embodiments, the invention provides for a method of producing and/or isolating a bacteriophage having a genome that comprises or consists of the nucleic acid sequence of SEQ ID NO: 2 comprising (i) obtaining a culture of *A. baumannii*, (ii) infecting it with the bacteriophage having a genome comprising or consisting of the nucleic acid sequence of SEQ ID NO: 2; (iii) culturing until significant lysis of the culture is observed; and (iv) isolating from the culture the bacteriophage. In still other embodiments, the invention provides for a method of producing and/or isolating a bacteriophage having a genome that comprises or consists of the nucleic acid sequence of SEQ ID NO: 3 comprising (i) obtaining a culture of *E. coli*, (ii) infecting it with the bacteriophage having a genome comprising or consisting of the nucleic acid sequence of ID NO: 3; (iii) culturing until significant lysis of the culture is observed; and (iv) isolating from the culture the bacteriophage. In yet still other embodiments, the invention provides for a method of producing and/or isolating a bacteriophage having a genome that comprises or consists of the nucleic acid sequence of SEQ ID NO: 4 comprising (i) obtaining a culture of *P. aeruginosa*, (ii) infecting it with the bacteriophage having a genome comprising or consisting of the nucleic acid sequence of SEQ ID NO: 4; (iii) culturing until significant lysis of the culture is observed; and (iv) isolating from the culture the bacteriophage.

In yet still further embodiments, the invention provides for a method of producing and/or isolating a bacteriophage having a genome that comprises or consists of the nucleic acid sequence of SEQ ID NO: 560 and/or SEQ ID NO: 1074 comprising (i) obtaining a culture of *S. aureus*, (ii) infecting it with the bacteriophage having a genome comprising or consisting of the nucleic acid sequence of SEQ ID NO: 560 and/or SEQ ID NO: 1074; (iii) culturing until significant lysis of the culture is observed; and (iv) isolating from the culture the bacteriophage.

Bacteriophage may be isolated from a bacterial sample using any method described herein or known in the art (see, e.g., Carlson, "Working with bacteriophage: common techniques and methodological approaches," In, Kutter and Sulakvelidze (Eds) Bacteriophage: Biology and Applications, 5$^{th}$ ed. CRC Press (2005); incorporated herein by reference in its entirety).

The invention also provides for polypeptides isolated from bacteriophage of the invention. The isolated polypeptides may be full length bacteriophage proteins or may be fragments, variants or derivatives of the bacteriophage proteins provided that the fragment, variant or derivative exhibit at least one biological activity associated with the bacteriophage or polypeptide from which it is derived. In certain embodiments, the polypeptides of the invention are isolated from bacteriophage F387/08 or F391/08 (which typically infect *K. pneumoniae*), F394/08 (which typically infects *A. baumannii*), bacteriophage F488/08 (which typically infects *E. coli*), bacteriophage F510/08 (which typically infects *P. aeruginosa*) or bacteriophage F44/10 or F125/40 (which typically infects *S. aureus*).

In specific embodiments, the polypeptide of the invention is a lysin isolated from a bacteriophage having a genome comprising or consisting of SEQ ID NO: 1, SEQ ID NO: 2, SEQ ID NO: 3, SEQ ID NO: 4, SEQ ID NO: 560, SEQ ID NO: 781, or SEQ ID NO: 1074 (e.g., bacteriophage F391/08, F394/08, F488/08, F510/08, F44/10, F387/08, or F125/10, respectively). In specific embodiments, the polypeptide of the invention is a lysin, e.g., an endolysin or tail lysin, having the amino acid sequence comprising or consisting of SEQ ID NO: 20, SEQ ID NO: 80, SEQ ID NO: 192, SEQ ID NO: 282, SEQ ID NO: 547, SEQ ID NO: 556, SEQ ID NO: 557, SEQ ID NO: 598, SEQ ID NO: 1216, or SEQ ID NO: 1261. Predicted functions of said lysins include, for example an Ig-like virion protein (SEQ ID NO: 20), cell wall hydrolase (SEQ ID NO: 80), endolysin; N-acetylmuramoyl-L-alanine amidase (SEQ ID NO: 192), soluble lysozyme (SEQ ID NO: 282), T4-like lysozyme (SEQ ID NO: 547), endolysin (SEQ ID NO: 556), lambda Rz1-like protein (SEQ ID NO: 557), endolysin (SEQ ID NO: 598), endolysin (SEQ ID NO:1216), and tail lysin (SEQ ID NO: 1261).

In other embodiments, the isolated polypeptide of the invention is a fragment, variant or derivative of an endolysin or lysin isolated from a bacteriophage of the invention, which fragment, variant or derivative exhibits at least one biological activity, preferably antibacterial activity (e.g., lytic killing activity), of the endolysin, lysin or bacteriophage from which it is isolated or derived. Accordingly, in certain embodiments, the invention provides isolated polypeptides that are fragments, variants or derivatives of endolysins or lysins isolated from bacteriophage of the invention, which fragments, variants or derivatives exhibit antibacterial or antimicrobial activity (e.g., lytic killing activity) against one or more of *K. pneumoniae, A. baumannii, E. coli, P. aeruginosa,* or *S. aureus*. In other embodiments, the isolated polypeptides are fragments, variants or derivatives of endolysins or lysins isolated from bacteriophage of the invention that exhibit antibacterial or antimicrobial activity (e.g., lytic killing activity) against one or more species of bacteria other than *K. pneumoniae, A. baumannii, E. coli, P. aeruginosa,* or *S. aureus*. In certain embodiments, the polypeptide of the invention comprises or consists of the amino acid sequence SEQ ID NO: 20 and/or SEQ ID NO: 80, or a fragment, variant or derivative thereof, which polypeptide exhibits antibacterial or antimicrobial activity against one or more strains of *K. pneumoniae*, e.g., against the bacteriophage having a genome comprising or consisting of the nucleic acid sequence SEQ ID NO: 1. In other embodiments, the polypeptide of the invention comprises or consists of the amino acid sequence SEQ ID NO: 192, or a fragment, variant or derivative thereof, which polypeptide exhibits antibacterial or antimicrobial activity against one or more strains of *A. baumannii*, e.g., against the bacteriophage having a genome comprising or consisting of the nucleic acid sequence SEQ ID NO: 2. In yet still other embodiments, the polypeptide of the invention comprises or consists of the amino acid sequence SEQ ID NO: 282, or a fragment, variant or derivative thereof, which polypeptide exhibits antibacterial or antimicrobial activity against one or more strains of E. coli, e.g., against the bacteriophage having a genome comprising or consisting of the nucleic acid sequence SEQ ID NO: 3. In yet still other embodiments, the polypeptide of the invention comprises or consists of the amino acid sequence SEQ ID NO: 547, SEQ ID NO: 556, SEQ ID NO: 557, or a fragment, variant or derivative thereof, which polypeptide exhibits antibacterial or antimicrobial activity against one or more strains of P. aeruginosa, e.g., against the bacteriophage having a genome comprising or consisting of the nucleic acid sequence SEQ ID NO: 4. In yet still further embodiments, the polypeptide of the invention comprises or consists of the amino acid sequence SEQ ID NO: 598, or a fragment, variant or derivative thereof, which polypeptide exhibits antibacterial or antimicrobial activity against one or more strains of S. aureus, e.g., against the bacteriophage having a genome comprising or consisting of the nucleic acid sequence SEQ ID NO: 560. In yet still further embodiments, the polypeptide of the invention comprises or consists of the amino acid sequence SEQ ID NO: 1216 and/or SEQ ID NO: 1261, or a fragment, variant or derivative thereof, which polypeptide exhibits antibacterial or antimicrobial activity against one or more strains of S. aureus, e.g., against the bacteriophage having a genome comprising or consisting of the nucleic acid sequence SEQ ID NO: 1074.

In certain embodiments, the polypeptide of the invention comprises or consists of a CHAP domain isolated from an endolysin or lysin of bacteriophage F387/08, F391/08, F394/08, F488/08, F510/08, F44/10, or F125/10. Isolated CHAP domains have been demonstrated to retain the antibacterial activity, e.g., lytic killing activity, of the endolysin or lysin from which they are derived; CHAP domains may be identified and isolated by methods routine in the art (see, e.g., Rigden et al., 2003, Trends Biochem. Sci. 28:230-234; Bateman et al., 2003, Trends Biochem. Sci. 28:234-237, each of which is incorporated by reference herein in its entirety). In specific embodiments, the polypeptide of the invention comprises or consists of a CHAP domain isolated from a polypeptide having an amino acid sequence of SEQ ID NO: 20, SEQ ID NO: 80, SEQ ID NO: 192, SEQ ID NO: 282, SEQ ID NO: 547, SEQ ID NO: 556, SEQ ID NO: 557, SEQ ID NO: 598, SEQ ID NO: 1216, or SEQ ID NO: 1261. In other embodiments the invention provides for a fragment, variant or derivative of a CHAP domain of isolated from an endolysin or lysin of bacteriophage bacteriophage F387/08, F391/08, F394/08, F488/08, F510/08, F44/10, F125/10, which fragment, variant, or derivative exhibits at least one biological activity, e.g., lytic cell killing, of the CHAP domain from which it was derived.

In certain embodiments, a polypeptide of the invention comprises or consists of a tail protein (e.g., tail component, tail fiber protein, adsorption associated tail protein, tail length tape measure protein, baseplate wedge subunit), or fragment, variant, or derivative thereof, isolated from a bacteriophage having a genome comprising or consisting of SEQ ID NO: 1, SEQ ID NO: 2, SEQ ID NO: 3, SEQ ID NO:4, SEQ ID NO: 560, SEQ ID NO: 781, or SEQ ID NO: 1074 (e.g., bacteriophage F391/08, F394/08, F488/08, F510/08, F44/10, F387/08, or F125/10 respectively), wherein the tail protein, or fragment, variant, or derivative thereof has a biological function associated with the bacteriophage from which it is derived, e.g., antimicrobial or antibacterial activity (e.g., lytic killing activity). In specific embodiments, the antimicrobial or antibacterial activity of the tail protein is directed against at least one or more species or strains of K. pneumoniae, A. baumannii, E. coli, P. aeruginosa, and S. aureus. In specific embodiments, the polypeptide of the invention is a tail protein having the amino acid sequence comprising or consisting of SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629; SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266. In other embodiments, the isolated polypeptide of the invention is a fragment, variant or derivative of the amino acid sequence of SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629; SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266, which fragment, variant, or derivative exhibits at least one biological activity or function of the bacteriophage from which it is isolated or derived, e.g., antimicrobial or antibacterial activity (e.g., lytic killing activity). In preferred embodiments, the at least one biological activity or function of the fragment, variant or derivative is directed against one or more strains of K. pneumoniae, A. baumannii, E. coli, P. aeruginosa, and S. aureus.

Predicted functions of said tail proteins include, for example a receptor-binding tail protein (SEQ ID NO: 15), major tail protein (SEQ ID NO: 26), minor tail protein (SEQ ID NO: 27), pore-forming tail tip protein (SEQ ID NO: 30), tail protein (SEQ ID NOs: 32-33), minor tail protein (SEQ ID NO: 34), phage tail protein (SEQ ID NO: 35), tail sheath protein (SEQ ID NO: 180), tail tape measure protein (SEQ ID NO: 183), tail protein (SEQ ID NO: 185), tail-fiber protein (SEQ ID NO: 190), tail tube protein (SEQ ID NO: 231), tail sheath monomer (SEQ ID NO: 232), tail sheath stabilizer and completion protein (SEQ ID NO:235), short tail fibers (SEQ ID NO: 239), base plate wedge completion tail pin (SEQ ID NOs: 240-241), base plate wedge completion tail fiber socket (SEQ ID NO: 242), base plate wedge subunit (SEQ ID NO: 243), base plate wedge initiator (SEQ ID NO: 244), base plate wedge (SEQ ID NO: 245), base plate hub subunit and tail lysozyme, cell-puncturing device (SEQ ID NO: 248), base plate wedge completion (SEQ ID NO: 249), tail completion and sheath stabilizer protein (SEQ ID NO: 252), chaperone long and short tail fiber assembly (SEQ ID NO: 254), tail fiber protein (SEQ ID NO: 433), tail fiber protein (SEQ ID NO: 434), hinge connecter long tail fiber (SEQ ID NO: 435), tail fiber hinge (SEQ ID NO: 436), proximal tail fiber subunit (SEQ ID NO: 437), base plate-tail tube initiator (SEQ ID NO: 489), base plate (SEQ ID NO: 490), baseplate hub subunit, tail length determinator (SEQ ID NO: 491), base plate distal hub subunit (SEQ ID NO: 492), base plate hub subunit (SEQ ID NO: 493), base plate hub assembly catalyst (SEQ ID NO: 494), baseplate hub subunit (SEQ ID NO: 495), baseplate wedge subunit (SEQ ID NO: 496), tail tubular protein (SEQ ID NOs: 544-545), tail fiber protein (SEQ ID NO: 549 and SEQ ID NO: 551), major tail sheath protein (SEQ ID NO: 629); major tail protein (SEQ ID NO: 686); tail tube protein (SEQ ID NO: 789); fibritin (SEQ ID NO: 796); short tail fibers (SEQ ID NO: 797); base plate wedge completion tail pin (SEQ ID NO: 798); base plate wedge subunit and tail pin (SEQ ID NO: 799); baseplate wedge tail fiber connector (SEQ ID NO: 800); baseplate hub subunit and lysozyme (SEQ ID NO: 806); lysozyme (SEQ ID NO: 854); holin (SEQ ID NO: 999); distal long tail fiber assembly catalyst (SEQ ID NO: 1000); L-shaped tail fiber protein (SEQ ID NO: 1001); hinge connector of long tail fiber distal connector (SEQ ID NO: 1002); hinge connector of long tail fiber proximal connector (SEQ ID NO: 1003); long tail fiber proximal subnit (SEQ ID NO: 1004); baseplate tail tube initiator (SEQ ID NO: 1053); baseplate tail tube cap (SEQ ID NO: 1054); baseplate hub subunit, tail length determinator (SEQ ID NO: 1055); baseplate distal hub subunit (SEQ ID NO: 1056); baseplate hub subunit (SEQ ID NOs: 1057 and 1059); baseplate hub assembly catalyst (SEQ ID NO: 1058); baseplate wedge subunit (SEQ ID NO: 1060); major tail protein (SEQ ID NO: 1077); holin (SEQ ID NO: 1217); major tail sheath protein (SEQ ID NO: 1250); and baseplate protein (SEQ ID NO: 1266).

In certain embodiments, the invention encompasses a variant, fragment or derivative of the amino acid sequence of SEQ ID NO: 15, SEQ ID NO: 26, SEQ ID NO: 27, SEQ ID NO: 30, or SEQ ID NOs: 32-35, which exhibits a biological function associated with the bacteriophage having a genome comprising or consisting of the nucleic acid sequence SEQ ID NO: 1, e.g., antimicrobial or antibacterial activity (e.g., lytic killing activity), which function is directed against one or more strains of K. pneumoniae. In certain embodiments, the invention encompasses a variant, fragment or derivative of the amino acid sequence of SEQ ID NO: 789, SEQ ID NOs: 796-800, SEQ ID NO: 806, SEQ ID NO: 854, SEQ ID NOs: 999-1004, or SEQ ID NOs: 1053-1060, which exhibits a biological function associated with the bacteriophage having a genome comprising or consisting of the nucleic acid sequence SEQ ID NO: 781, e.g., antimicrobial or antibacterial activity (e.g., lytic killing activity), which function is directed against one or more strains of K. pneumoniae. In other embodiments, the invention encompasses a variant, fragment or derivative of the amino acid sequence of SEQ ID NO: 180, SEQ ID NO: 183, SEQ ID NO: 185, or SEQ ID NO: 190, which exhibits a biological function associated with the bacteriophage having a genome comprising or consisting of the nucleic acid sequence SEQ ID NO: 2, e.g., antimicrobial or antibacterial activity (e.g., lytic killing activity), which function is directed against one or more strains of A. baumannii.

In certain embodiments, the invention encompasses a variant, fragment or derivative of the amino acid sequence of SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-495, or SEQ ID NO: 496, which exhibits a biological function associated with the bacteriophage having a genome comprising or consisting of the nucleic acid sequence SEQ ID NO: 3, e.g., antimicrobial or antibacterial activity (e.g., lytic killing activity), which function is directed against one or more strains of E. coli. In certain embodiments, the invention encompasses a variant, fragment or derivative of the amino acid sequence of SEQ ID NO: 544, SEQ ID NO: 545, SEQ ID NO: 549, or SEQ ID NO: 551, which exhibits a biological function associated with the bacteriophage having a genome comprising or consisting of the nucleic acid sequence SEQ ID NO: 4, e.g., antimicrobial or antibacterial activity (e.g., lytic killing activity), which function is directed against one or more strains of P. aeruginosa. In certain embodiments, the invention encompasses a variant, fragment or derivative of the amino acid sequence of SEQ ID NO: 629 or SEQ ID NO: 686, which exhibits a biological function associated with the bacteriophage having a genome comprising or consisting of the nucleic acid sequence SEQ ID NO: 560, e.g., antimicrobial or antibacterial activity (e.g., lytic killing activity), which function is directed against one or more strains of S. aureus. In certain embodiments, the invention encompasses a variant, fragment or derivative of the amino acid sequence of SEQ ID NO: 1077, SEQ ID NO: 1216, SEQ ID NO: 1217, SEQ ID NO: 1250, SEQ ID NO: 1261, or SEQ ID NO: 1266, which exhibits a biological function associated with the bacteriophage having a genome comprising or consisting of the nucleic acid sequence SEQ ID NO: 1074, e.g., antimicrobial or antibacterial activity (e.g., lytic killing activity), which function is directed against one or more strains of S. aureus.

In certain embodiments, the isolated polypeptide of the invention is a variant of a bacteriophage polypeptide, which variant comprises or consists of a amino acid sequence having at least 60%, 65%, 70%, 75%, 80%, 85%, 86%, 87%, 88%, 89%, 90%, 91%, 92%, 93%, 94%, 95%, 96%, 97%, 98%, 99%, or greater sequence identity to a second amino acid sequence of the same length (i.e., consisting of the same number of residues), which second amino acid sequence is SEQ ID NO: 15, SEQ ID NO: 20, SEQ ID NO: 26, SEQ ID NO: 27, SEQ ID NO: 30, SEQ ID NOs: 32-35, SEQ ID NO: 80, SEQ ID NO: 180, SEQ ID NO: 183, SEQ ID NO: 185, SEQ ID NO: 190, SEQ ID NO: 192, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NO: 282, SEQ ID NOs: 433-437, SEQ ID NOs: 489-496, SEQ ID NO: 544, SEQ ID NO: 545, SEQ ID NO: 547, SEQ ID NO: 549, SEQ ID NO: 551, SEQ ID NO: 556, SEQ ID NO: 557, SEQ ID NO: 598, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1216, SEQ ID NO: 1217, SEQ ID NO: 1250, SEQ ID NO: 1261, SEQ ID NO: 1266 and/or a fragment thereof, and wherein the variant exhibits at least one biological function or activity of the bacteriophage from which it was derived (e.g., antimicrobial or antibacterial activity (e.g., lytic killing activity)) against one or more strains of bacteria, e.g., Gram-positive bacteria (e.g., S. aureus), Gram-negative bacteria (e.g., K. pneumoniae, A baumannii, E. coli, P. aeruginosa) or bacteria not classified as either Gram-positive or Gram-negative.

In certain embodiments, the invention provides an isolated polypeptide having an amino acid sequence of any of SEQ ID NOs: 5-176, SEQ ID NOs: 177-223, SEQ ID NOs: 224-506, SEQ ID NOs: 507-559, SEQ ID NOs: 561-780, SEQ ID NOs: 782-1073, and SEQ ID NOs: 1075-1300 and active biologic fragments thereof. In preferred embodiments, the variant polypeptide of the invention exhibits at least one biologic activity associated with the polypeptide or bacteriophage from which it was isolated or derived, e.g., lytic activity directed against at least one or more strains of K. pneumoniae, A. baumannii, E. coli, P. aeruginosa, and/or S. aureus.

In other embodiments, the invention provides an isolated nucleic acid sequence encoding the amino acid sequence of one of SEQ ID NOs: 5-176, SEQ ID NOs: 177-223, SEQ ID NOs: 224-506, SEQ ID NOs: 507-559, SEQ ID NOs: 561-780, SEQ ID NOs: 782-1073, and SEQ ID NOs: 1075-1300 and active fragments thereof. In other embodiments the invention provides the nucleic acid sequence encoding any of the open reading frames identified in FIGS. 2, 4, 6, 8, 10, 12, and/or 14.

In certain embodiments, the polypeptides of the present invention are recombinantly fused or chemically conjugated (including both covalently and non-covalently conjugations) to therapeutic agents, e.g., heterologous polypeptides or small molecules, to generate fusion proteins or chimeric polypeptides. The fusion does not necessarily need to be direct, but may occur through linker sequences or through chemical conjugation. Non-limiting examples of therapeutic agents to which the polypeptides of the invention may be conjugated are peptide or non-peptide cytotoxins (including antimicrobials and/or antibiotics), tracer/marker molecules (e.g., radionuclides and fluorophores) and other antibiotic or antibacterial compounds known in the art.

6.2 Antibiotic Compositions

The isolated bacteriophage or polypeptides of the present invention may be administered alone or incorporated into a pharmaceutical composition for the use in treatment or prophylaxis of bacterial infections, e.g., infections caused by bacteria including, but not limited to, *K. pneumoniae, A. baumannii, E. coli, P. aeruginosa* and *S. aureus*. The polypeptides may be combined with a pharmaceutically acceptable carrier, excipient, or stabilizer. Examples of pharmaceutically acceptable carriers, excipients and stabilizers include, but are not limited to, buffers such as phosphate, citrate, and other organic acids; antioxidants including ascorbic acid; low molecular weight polypeptides; proteins, such as serum albumin and gelatin; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™. The pharmaceutical compositions of the present invention (e.g., antibacterial compositions) can also include a lubricant, a wetting agent, a sweetener, a flavoring agent, an emulsifier, a suspending agent, and a preservative, e.g., in addition to the above ingredients.

The bacteriophage and/or polypeptides of the present invention may also be combined with one or more therapeutic and/or prophylactic agents useful for the treatment of bacterial infection as described herein and/or known in the art (e.g. one or more lysins). The pharmaceutical compositions of the invention may therefore comprise two or more isolated bacteriophage of the invention (with antibacterial activity against the same or different bacterial species or strains), the combination of a bacteriophage and a polypeptide of the invention or the combination of a bacteriophage and/or polypeptide of the invention and a bacteriophage and/or polypeptide known in the art. In specific embodiments, the therapeutic components of a combination target two or more species or strains of bacteria or exhibit differing enzymatic activity. For example, lysins in general exhibit one of amidase, endopeptidase, muramidase or glucosamidase activity. Accordingly, the combination of lysins exhibiting different activities may provide synergistic enhancement to the therapeutic activity of the pharmaceutical composition of the invention.

In some embodiments, a number of different bacteriophage are combined to provide a "phage cocktail." In some embodiments, the phage cocktail comprises at least 2 phage, at least 3 phage, at least 4 phage, at least 5 phage, at least 6 phage, at least 7 phage, at least 8 phage, at least 9 phage, at least 10 phage, or more. In some embodiments, the phage cocktail comprises 2-20 phage, 2-15 phage, 2-10 phage, 3-8 phage, or 4-6 phage.

In some embodiments, at least one phage of the cocktail is a phage with antibacterial activity against at least one Gram-negative bacteria, including but not limited to *Klebsiella pneumoniae, Acinetobacter baumannii, Escherichia coli*, and *Pseudomonas aeruginosa*; and/or against at least one Gram-positive bacteria including but not limited to *Staphylococcus aureus*. In certain embodiments, at least one phage of the cocktail is F391/08, having a genome comprising the nucleic acid sequence of SEQ ID NO:1 and exhibiting antibacterial activity against one or more strains of *Klebsiella pneumoniae*. In certain embodiments, at least one phage of the cocktail is F394/08, having a genome comprising the nucleic acid sequence of SEQ ID NO:2 and exhibiting antibacterial activity against one or more strains of *Acinetobacter baumannii*. In certain embodiments, at least one phage of the cocktail is F488/08, having a genome comprising the nucleic acid sequence of SEQ ID NO:3 and exhibiting antibacterial activity against one or more strains of *Escherichia coli*. In certain embodiments, at least one phage of the cocktail is F510/08, having a genome comprising the nucleic acid sequence of SEQ ID NO:4 and exhibiting antibacterial activity against one or more strains of *Pseudomonas aeruginosa*. In certain embodiments, at least one phage of the cocktail is F44/10, having a genome comprising the nucleic acid sequence of SEQ ID NO:560 and exhibiting antibacterial activity against one or more strains of *Staphylococcus aureus*. In certain embodiments, at least one phage of the cocktail is F387/08, having a genome comprising the nucleic acid sequence of SEQ ID NO:781 and exhibiting antibacterial activity against one or more strains of *Klebsiella pneumoniae*. In certain embodiments, at least one phage of the cocktail is F125/10, having a genome comprising the nucleic acid sequence of SEQ ID NO:1074 and exhibiting antibacterial activity against one or more strains of *Staphylococcus aureus*.

In certain embodiments, at least one phage of the cocktail is F170/08, having a genome as disclosed in WO 2010/090542, and exhibiting antibacterial activity against one or more strains of *Enterococcus faecalis* or *faecium*. In certain embodiments, at least one phage of the cocktail is F168/08, having a genome as disclosed in WO 2010/090542, and exhibiting antibacterial activity against one or more strains of *Enterococcus faecalis* or *faecium*. In certain embodiments, at least one phage of the cocktail is F770/05, having a genome as disclosed in WO 2010/090542, and exhibiting antibacterial activity against one or more strains of *Pseudomonas aeruginos*. In certain embodiments, at least one phage of the cocktail is F1245/05, having a genome as disclosed in WO 2010/090542, and exhibiting antibacterial activity against one or more strains of *Acinetobacter baumannii*.

In some preferred embodiments, the cocktail comprises a phage having biological activity against *Acinetobacter*. For example, the cocktail may comprise F394/08 and/or F1245/05, exhibiting antibacterial activity against one or more strains of *Acinetobacter baumannii*. In certain embodiments, the phage cocktail comprises at least one phage exhibiting antibacterial activity against one or more strains of *Acinetobacter baumannii* and at least one phage exhibiting antibacterial activity against a different bacteria. For example, in some embodiments, the phage cocktail comprises F394/08 and/or F1245/05 in combination with at least one other phage selected from F391/08, F488/08, F510/08, F44/10, F387/08, F170/08, F168/08, F770/05, and F125/10. In certain embodiments, the phage cocktail comprises at least one phage exhibiting antibacterial activity against one or more strains Klebsiella pneumoniae and at least one phage exhibiting antibacterial activity against a different bacteria. For example, in some embodiments, the phage cocktail comprises F391/08 and/or F387/08 in combination with at least one other phage selected from F394/08, F488/08, F510/08, F44/10, F1245/05, F170/08, F168/08, F770/05, and F125/10. In certain embodiments, the phage cocktail comprises at least one phage exhibiting antibacterial activity against one or more strains of Escherichia coli and at least one phage exhibiting antibacterial activity against a different bacteria. For example, in some embodiments, the phage cocktail comprises F488/08 in combination with at least one other phage selected from F391/08, F510/08, F44/10, F394/08, F387/08, F170/08, F168/08, F1245/05, F770/05, and F125/10.

In certain embodiments, the phage cocktail comprises at least one phage exhibiting antibacterial activity against one or more strains of Pseudomonas aeruginosa and at least one phage exhibiting antibacterial activity against a different bacteria. For example, in some embodiments, the phage cocktail comprises F510/08 and/or F770/05 in combination with at least one other phage selected from F391/08, F394/08, F488/08, F44/10, F387/08, F170/08, F168/08, F1245/05, and F125/10. In certain embodiments, the phage cocktail comprises at least one phage exhibiting antibacterial activity against one or more strains of Staphylococcus aureus and at least one phage exhibiting antibacterial activity against a different bacteria. For example, in some embodiments, the phage cocktail comprises F44/10 and/or F125/10 in combination with at least one other phage selected from F391/08, F394/08, F488/08, F510/08, F387/08, F170/08, F168/08, F770/05, and F1245/05. In certain embodiments, the phage cocktail comprises at least one phage exhibiting antibacterial activity against one or more strains of Enterococcus faecalis or faecium and at least one phage exhibiting antibacterial activity against a different bacteria. For example, in some embodiments, the phage cocktail comprises F170/08 and/or F168/08 in combination with at least one other phage selected from F391/08, F394/08, F488/08, F510/08, F44/10, F387/08, F770/05, F1245/05, and F125/10.

In certain embodiments, the phage cocktail comprises at least four (4) phage selected from the group consisting of F391/08, F394/08, F488/08, F510/08, F44/10, F387/08, F170/08, F168/08, F770/05, F1245/05, and F125/10. In certain embodiments, the phage cocktail comprises F391/08, F394/08, F488/08, and F510/08. In certain embodiments, the phage cocktail comprises F44/10, F387/08, F170/08, and F168/08. In certain embodiments, the phage cocktail comprises of F391/08, F394/08, F770/05, and F1245/05. In certain embodiments, the phage cocktail comprises F391/08, F394/08, F510/08, and/or F44/10. In certain embodiments, the phage cocktail comprises F391/08, F394/08, F44/10, and/or F387/08. In certain embodiments, the phage cocktail comprises F391/08, F394/08, F387/08, and/or F170/08. In certain embodiments, the phage cocktail comprises F391/08, F394/08, F170/08, and F168/08. In certain embodiments, the phage cocktail comprises F391/08, F394/08, F168/08, and/or F770/05. In certain embodiments, the phage cocktail comprises F391/08, F394/08, F770/05, and F1245/05.

In certain embodiments, the phage cocktail comprises F125/10, F391/08, F394/08, and F488/08. In certain embodiments, the phage cocktail comprises F125/10, F394/08, F488/08, and F510/08. In certain embodiments, the phage cocktail comprises F125/10, F488/08, F510/08, and F44/10. In certain embodiments, the phage cocktail comprises F125/10, F44/10, F387/08, and F170/08. In certain embodiments, the phage cocktail comprises F125/10, F170/08, F168/08, and F770/05. In certain embodiments, the phage cocktail comprises F125/10, F770/05, F1245/05, and F391/08. In certain embodiments, the phage cocktail comprises F125/10, F510/08, F44/10, F387/08. In certain embodiments, the phage cocktail comprises F125/10, F387/08, F170/08, F168/08. In certain embodiments, the phage cocktail comprises F125/10, F168/08, F770/05, and F1245/05. In certain embodiments, the phage cocktail comprises F125/10, F1245/05, F391/08, and F394/08.

In certain embodiments, the phage cocktail comprises F394/08, F488/088, F510/08, and/or F44/10. In certain embodiments, the phage cocktail comprises F394/08, F488/088, F44/10, and/or F387/08. In certain embodiments, the phage cocktail comprises F394/08, F488/088, F387/08, and/or F170/08. In certain embodiments, the phage cocktail comprises F394/08, F488/088, F170/08, and/or F168/08. In certain embodiments, the phage cocktail comprises F394/08, F488/088, F168/08 and/or F770/05. In certain embodiments, the phage cocktail comprises F394/08, F488/088, FF770/05, and/or F1245/05. In certain embodiments, the phage cocktail comprises F394/08, F488/088, F1245/05 and/or F391/08. In certain embodiments, the phage cocktail comprises F488/08, F510/08, F44/10, and/or F387/08. In certain embodiments, the phage cocktail comprises F488/08, F510/08, F387/08, and/or F170/08. In certain embodiments, the phage cocktail comprises F488/08, F510/08, F170/08, and/or F168/08. In certain embodiments, the phage cocktail comprises F488/08, F510/08, F168/08, and/or F770/05. In certain embodiments, the phage cocktail comprises F488/08, F510/08, F770/05, and/or F1245/05. In certain embodiments, the phage cocktail comprises F488/08, F510/08, F1245/05, and/or F391/08. In certain embodiments, the phage cocktail comprises F488/08, F510/08, F391/08, and/or F394/08.

In certain embodiments, the phage cocktail comprises F387/08, F170/08, F168/08, and/or F770/05. In certain embodiments, the phage cocktail comprises F387/08, F170/08, F770/05, and/or F1245/05. In certain embodiments, the phage cocktail comprises F387/08, F170/08, F1245/05, and/or F391/08. In certain embodiments, the phage cocktail comprises F387/08, F170/08, F391/08, and/or F394/08. In certain embodiments, the phage cocktail comprises F387/08, F170/08, F394/08, and/or F488/08. In certain embodiments, the phage cocktail comprises F387/08, F170/08, F488/08, and/or F510/08. In certain embodiments, the phage cocktail comprises F387/08, F170/08, F510/08, and/or F44/10. In certain embodiments, the phage cocktail comprises F387/08, F170/08, F44/10, and/or F387/08. In certain embodiments, the phage cocktail comprises F387/08, F170/08, F387/08, and/or F170/08. In certain embodiments, the phage cocktail comprises F387/08, F170/08, F170/08, and/or F168/08. In certain embodiments, the phage cocktail comprises F387/08, F170/08, F168/08, and/or F770/05. In certain embodiments, the phage cocktail comprises F387/08, F170/08, F770/05 and/or F1245/05. In certain embodiments, the phage cocktail comprises F387/08, F170/08, F1245/05, and/or F391/08. In certain embodiments, the phage cocktail comprises F387/08, F170/08, F391/08, and/or F394/08. In certain embodiments, the phage cocktail comprises F387/08, F170/08, F394/08 and/or F488/08. In certain embodiments, the phage cocktail comprises F387/08, F170/08, F488/08, and/or F510/08. In certain embodiments, the phage cocktail comprises F387/08, F170/08, F510/08, and/or F44/10.

In some embodiments, the phage cocktail comprises of F510/08, F44/10, F387/08, and/or F170/08. In some embodiments, the phage cocktail comprises F510/08, F44/10, F170/08, and/or F168/08. In some embodiments, the phage cocktail comprises F510/08, F44/10, F168/08, and/or F770/05. In some embodiments, the phage cocktail comprises F510/08, F44/10, F770/05, and/or F1245/05. In some embodiments, the phage cocktail comprises F510/08, F44/10, F1245/05, and/or F391/08. In some embodiments, the phage cocktail comprises F510/08, F44/10, F391/08, and/or F394/08. In some embodiments, the phage cocktail comprises F510/08, F44/10, F394/08, and/or F488/08.

In some embodiments, the phage comprises F44/10, F387/08, F170/08, and/or F168/08. In some embodiments, the phage comprises F44/10, F387/08, F168/08 and/or F770/05. In some embodiments, the phage comprises F44/10, F387/08, F770/05, and/or F1245/05. In some embodiments, the phage comprises F44/10, F387/08, F1245/05, and/or F391/08. In some embodiments, the phage comprises F44/10, F387/08, F391/08, and/or F394/08. In some embodiments, the phage comprises F44/10, F387/08, F394/08 and/or F488/08. In some embodiments, the phage comprises F44/10, F387/08, F488/08 and/or F510/08.

In some embodiments, the phage cocktail composition may or may not involve phage selected for increased in vivo half-life, e.g., as disclosed in U.S. Pat. No. 5,688,501, the contents of which are incorporated herein by reference.

In some embodiments, the cocktail comprises one or more polypeptides isolated from one or more phage, and/or a fragment, variant, or derivative thereof, in particular a polypeptide, fragment, variant, or derivative thereof which has antibacterial or antimicrobial activity. In some embodiments, the polypeptide, or fragment, variant, or derivative thereof comprises or consists of a lysin (or fragment thereof, e.g., a CHAP domain) and/or a tail protein. In more specific embodiments, the polypeptide corresponds to an isolated polypeptide, fragment, variant, or derivative thereof, as described herein and/or in WO 2010/090542, the contents of which are incorporated by reference herein. In some embodiments, the cocktail is administered in the absence of an isolated polypeptide, such as in the absence of a lyase.

Other examples of other therapeutic agents that may be used in combination with the polypeptide of the invention include, but are not limited to, standard antibiotic agents, anti-inflammatory agents, antiviral agents, local anesthetic agents, and corticosteroids. In some embodiments, the cocktail is administered in the absence of an antibiotic.

Standard antibiotics that may be used with pharmaceutical compositions comprising a bacteriophage and/or polypeptide of the invention include, but are not limited to, amikacin, gentamicin, kanamycin, neomycin, netilmicin, paromomycin, rhodostreptomycin, streptomycin, tobramycin, apramycin, rifamycin, naphthomycin, mupirocin, geldanamycin, ansamitocin, carbacephems, imipenem, meropenem, ertapenem, faropenem, doripenem, panipenem/betamipron, biapenem, PZ-601, cephalosporins, cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, cefcapene, cefdaloxime, cefdinir, cefditoren, cefetamet, cefixime, cefmenoxime, cefteram, ceftibuten, ceftiofur, ceftiolene, ceftizoxime, ceftriaxone, cefoperazone, ceftazidime latamoxef, cefclidine, cefepime, cefluprenam, cefoselis, cefozopran, cefpirome, cefquinome, flomoxef, ceftobiprole, azithromycin, clarithromycin, dirithromycin, erythromycin, roxithromycin, aztreonam, penicillin and penicillin derivatives, actinomycin, bacitracin, colistin, polymyxin B, cinoxacin, flumequine, nalidixic acid, oxolinic acid, piromidic acide, pipemidic acid, rosoxacin, ciprofloxacin, enoxacin, fleroxacin, lomefloxacin, nadifloxacin, norfloxacin, ofloxacin, pefloxacin, rufloxacin, balofloxacin, gatifloxacin, grepafloxacin, levofloxacin, moxifloxacin, pazufloxacin, sparfloxacin, temafloxacin, tosufloxacin, clinafloxacin, garenoxacin, gemifloxacin, stifloxacin, trovalfloxacin, prulifloxacin, acetazolamide, benzolamide, bumetanide, celecoxib, chlorthalidone, clopamide, dichlorphenamide, dorzolamide, ethoxyzolamide, furosemide, hydrochlorothiazide, indapamide, mafendide, mefruside, metolazone, probenecid, sulfacetamide, sulfadimethoxine, sulfadoxine, sulfanilamides, sulfamethoxazole, sulfasalazine, sultiame, sumatriptan, xipamide, tetracycline, chlortetracycline, oxytetracycline, doxycycline, lymecycline, meclocycline, methacycline, minocycline, rolitetracycline, methicillin, nafcillin, oxacilin, cloxacillin, vancomycin, teicoplanin, clindamycin, co-trimoxazole, and any combination thereof in amounts that are effective to additively or synergistically enhance the therapeutic effect of the bacteriophage and/or polypeptide of the invention for a given infection.

Local anesthetics that may be used in pharmaceutical compositions of the present invention include tetracaine, tetracaine hydrochloride, lidocain, lidocaine hydrochloride, dimethisoquin hydrochloride, dibucaine, dibucaine hydrochloride, butambenpicrate, and pramoxine hydrochloride. An exemplary concentration of local anesthetic is about 0.025% to about 5% by weight of the total composition.

Corticosteroids that may be useful in combination with the polypeptides, bacteriophage, and/or pharmaceutical compositions of the invention include betamethasone, dipropionate, fluocinolone, actinide, betamethasone valerate, triamcinolone actinide, clobetasol propionate, desoximetasone, diflorasone diacetate, amcinonide, flurandrenolide, hydrocortisone valerate, hydrocortisone butyrate, and desonide. An exemplary concentration of corticosteroid is about 0.01% to about 1% by weight of the total composition.

In certain embodiments, a formulation comprising a bacteriophage and/or polypeptide of the invention further comprises SM buffer (0.05 M Tris-HCl (pH 7.4-7.5); 0.1 M NaCl; 10 mM $MgSO_4$). In other embodiments, the formulation further comprises SM buffer and 10 mM $MgCl_2$. In still other embodiments, the formulation further comprises SM buffer and about 20% or about 30% ethanol.

Pharmaceutical compositions comprising a bacteriophage and/or polypeptide of the present invention can be formulated in a unit dose or multi-dose formulation. Suitable formulations can be selected from the group consisting of ointments, solutions, suspensions or emulsions, extracts, powders, granules, sprays, lozenges, tablets, or capsules; and additionally may include a dispersing agent or a stabilizing agent.

The pharmaceutical compositions of the invention can be administered by inhalation, in the form of a suppository or pessary, topically (e.g., in the form of a lotion, solution, cream, ointment or dusting powder), epi- or transdermally (e.g., by use of a skin patch), orally (e.g., as a tablet, which may contain excipients such as starch or lactose), as a capsule, ovule, elixirs, solutions, or suspensions (each optionally containing flavoring, coloring agents and/or excipients), or they can be injected parenterally (e.g., intravenously, intramuscularly or subcutaneously). For parenteral administration, the compositions may be used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner. In a preferred embodiment, a bacteriophage and/or polypeptide of the present invention is administered topically, either as a single agent, or in combination with other antibiotic treatments, as described herein or known in the art.

A bacteriophage and/or polypeptide of the present invention may also be dermally or transdermally administered. For topical application to the skin, the bacteriophage and/or polypeptides of the present invention may be combined with one or a combination of carriers, which can include but are not limited to, an aqueous liquid, an alcohol base liquid, a water soluble gel, a lotion, an ointment, a nonaqueous liquid base, a mineral oil base, a blend of mineral oil and petrolatum, lanolin, liposomes, proteins carriers such as serum albumin or gelatin, powdered cellulose carmel, and combinations thereof. A topical mode of delivery may include a smear, a spray, a bandage, a time-release patch, a liquid-absorbed wipe, and combinations thereof. The bacteriophage and/or polypeptide of the invention may be applied to a patch, wipe, bandage, etc., either directly or in a carrier(s). The patches, wipes, bandages, etc., may be damp or dry, wherein the phage and/or polypeptide (e.g., a lysin) is in a lyophilized form on the patch. The carriers of topical compositions may comprise semi-solid and gel-like vehicles that include a polymer thickener, water, preservatives, active surfactants, or emulsifiers, antioxidants, sun screens, and a solvent or mixed solvent system. U.S. Pat. No. 5,863,560 discloses a number of different carrier combinations that can aid in the exposure of skin to a medicament, and its contents are incorporated herein. The carrier may or may not involve a controlled-release formulation, e.g., as disclosed in US 2008/0260697, the contents of which are incorporated herein by reference. The carrier may or may not involve phage adsorbed on a matrix, e.g., as described in any one of US 2008/0038322, US 2008/0138311, US 2009/0130196, EP 1 812 025, EP 1 817 043, and EP 1 833 497, the contents of which are incorporated herein by reference. In some embodiments, the carrier may or may not involve a viscous formulation, e.g., a gel, e.g., as disclosed in US 2009/0191254, the contents of which are incorporated herein by reference.

For intranasal or administration by inhalation, the bacteriophage and/or polypeptide of the invention is conveniently delivered in the form of a dry powder inhaler or an aerosol spray presentation from a pressurized container, pump, spray, or nebuliser with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide, or other suitable gas. In the case of a pressurized aerosol, the dosage unit may be determined by providing a valve to deliver a metered amount. The pressurized container, pump, spray, or nebuliser may contain a solution or suspension of the active compound, e.g., using a mixture of ethanol and the propellant as the solvent, which may additionally contain a lubricant, e.g., sorbitan trioleate. Capsules and cartridges (made, for example, from gelatin) for use in an inhaler or insufflator may be formulated to contain a powder mix of the bacteriophage and/or polypeptide of the invention and a suitable powder base such as lactose or starch.

For administration in the form of a suppository or pessary, the therapeutic compositions may be applied topically in the form of a gel, hydrogel, lotion, solution, cream, ointment, or dusting powder. Compositions of the invention may also be administered by the ocular route. For ophthalmic use, the compositions of the invention can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

Dosages and desired drug concentrations of the pharmaceutical compositions of the present invention may vary depending on the particular use. The determination of the appropriate dosage or route of administration is within the skill of an ordinary physician. Animal experiments can provide reliable guidance for the determination of effective doses in human therapy. Interspecies scaling of effective doses can be performed by one of ordinary skill in the art following the principles described by Mordenti, J. and Chappell, W. "The use of interspecies scaling in toxicokinetics" in Toxicokinetics and New Drug Development, Yacobi et al., Eds., Pergamon Press, New York 1989, pp 42-96.

6.3 Therapeutic Use

The bacteriophage and polypeptides of the present invention have activity against a plurality of strains of *K. pneumoniae, A. baumannii, E. coli, P. aeruginosa*, and/or *S. aureus*, e.g., as described in Tables 1-7, in the Examples below. Therefore, the compositions of the present invention may find use in methods of preventing and/or treating infections associated with *K. pneumoniae, A. baumannii, E. coli, P. aeruginosa*, and/or *S. aureus* in both humans and animals. In other embodiments, the compositions of the present invention may be used to treat infection associated with related species or strains of these bacteria, including, but not limited to *S. epidermidis, S. auricularis, S. capitis, S. haemolyticus, S. hominis, S. saprophyticus, S. simulans, S. xylosis, Micrococcus luteus, Bacilus subtilis, B. pumilus, E. hirae*.

In specific embodiments, the subject receiving a pharmaceutical composition of the invention is a mammal (e.g., bovine, ovine, caprine, equid, primate (e.g., human), rodent, lagomorph or avian (e.g., chicken, duck, goose)). In the context of the present invention, "treatment" refers to therapeutic treatment, wherein the object is to eliminate, lessen, decrease the severity of, ameliorate, slow the progression of or prevent the symptoms or underlying cause (e.g., bacterial infection) associated with the pathological condition or disorder. "Treatment" refers to both therapeutic treatment and prophylactic or preventative measures, wherein the object is to eliminate, lessen, decrease the severity of, slow the progression of or delay or prevent the symptoms or underlying cause (e.g., bacterial infection) associated with the pathological condition or disorder. It is also contemplated that a bacteriophage and/or polypeptide of the invention acts as a prophylactic or preventative measure, preventing the onset of infection caused by one or more bacteria.

*K. pneumoniae, A. baumannii, E. coli, P. aeruginosa*, and *S. aureus* are responsible for many severe opportunistic infections, particularly in individuals with compromised immune systems. The pharmaceutical compositions of the present invention are contemplated for treating any infection associated with *K. pneumoniae, A. baumannii, E. coli, P. aeruginosa*, and/or *S. aureus*, or associated with other species or strains of bacteria, including, but not limited to, infections of the skin (including but not limited to skin ulcers, carbuncles, bed sores, and diabetic foot ulcers), infections in and around wounds, post-operative infections, infections associated with catheters and surgical drains, and infections of the blood.

Diabetic foot ulcer is one of the major complications of diabetes mellitus, occurring in about 15% of all diabetic patients and resulting in about 85% of all lower leg amputations. (Brem, et al., J. Clinical Invest., 2007, 117(5):1219-1222). Diabetes mellitus impedes the normal steps of the wound healing process. Non-healing chronic diabetic ulcers are often treated with extracellular matrix replacement therapy, advanced moist wound therapy, bio-engineered tissue or skin substitutes, growth factors, debridement, arterial revascularization, and/or negative pressure wound therapy. (Blume et. al, *Diabetes Care,* 2008, 31: 631-636). The ulcers may become infected with opportunistic bacteria, which further exacerbate the condition. Accordingly, foot ulcers in diabetes also often require antibiotics, e.g., against *Staphylococcus*, as well as other anaerobic bacteria, such as *Klebsiella pneumonia, Escherchia coli,* and/or *Pseudomonas aeruginosa.*

One or more compositions of the present invention find use in the treatment of diabetic foot ulcer. For example, an isolated phage or polypeptide of the invention can be used for the treatment of infections associated with diabetic foot ulcer, in a subject in need thereof. In particular embodiments, the composition used for treating diabetic foot ulcer is a topical composition, formulated for topical administration, e.g., a composition for direct application to an ulcer, wound, lesion, and/or sore associated with diabetic foot ulcer.

In certain embodiments, the composition for use with respect to diabetic foot ulcer comprises isolated F44/10, having a genome comprising the nucleic acid sequence of SEQ ID NO:560 and exhibiting antibacterial activity against one or more strains of *Staphylococcus aureus.* In some embodiments, a composition is used comprising a polypeptide isolated from bacteriophage F44/10, or a fragment, variant, or derivative thereof, which polypeptide, fragment, variant, or derivative exhibits antibacterial activity against one or more species or strains of *S. aureus.* In certain such embodiments, the polypeptide, or fragment, variant, or derivative thereof, is a lysin, a CHAP domain, or a tail protein, exhibiting antibacterial activity against one or more species or strains of *S. aureus.* In certain embodiments, the composition for use with respect to diabetic foot ulcer comprises isolated F125/10, having a genome comprising the nucleic acid sequence of SEQ ID NO:1074 and exhibiting antibacterial activity against one or more strains of *Staphylococcus aureus.* In some embodiments, a composition is used comprising a polypeptide isolated from bacteriophage F125/10, or a fragment, variant, or derivative thereof, which polypeptide, fragment, variant, or derivative exhibits antibacterial activity against one or more species or strains of *S. aureus.* In certain such embodiments, the polypeptide, or fragment, variant, or derivative thereof, is a lysin, a CHAP domain, or a tail protein, exhibiting antibacterial activity against one or more species or strains of *S. aureus.*

In certain embodiments, a composition comprising a phage cocktail is used, e.g., where the phage cocktail comprises at least one phage exhibiting antibacterial activity against one or more strains of *Staphylococcus aureus* and at least one phage exhibiting antibacterial activity against a different bacteria. In particular embodiments, the phage cocktail comprises F44/10 and/or F125/10 in combination with at least one other phage selected from F391/08, F394/08, F488/08, F510/08, F387/08, F170/08, F168/08, F770/05, and F1245/05. In particularly preferred embodiments, the phage cocktail comprises F44/10 and/or F125/10 in combination with one, two, three or more other phages selected from F391/08, F387/08, F488/08, F510/08 and/or F770/05.

In certain embodiments, the composition for use with respect to diabetic foot ulcer comprises isolated F391/08 and/or F387/08, having a genome comprising the nucleic acid sequence of SEQ ID NO:1 or SEQ ID NO: 781, respectively, and exhibiting antibacterial activity against one or more strains of *Klebsiella pneumoniae.* In some embodiments, a composition is used comprising a polypeptide isolated from bacteriophage F391/08 and/or F387/08, or a fragment, variant, or derivative thereof, which polypeptide, fragment, variant, or derivative exhibits antibacterial activity against one or more species or strains of *K. pneumoniae.* In certain such embodiments, the polypeptide, or fragment, variant, or derivative thereof, is a lysin, a CHAP domain, or a tail protein, exhibiting antibacterial activity against one or more species or strains of *K. pneumoniae.* In certain embodiments, a composition comprising a phage cocktail is used, e.g., where the phage cocktail comprises at least one phage exhibiting antibacterial activity against one or more strains of *Klebsiella pneumoniae* and at least one phage exhibiting antibacterial activity against a different bacteria. In particular embodiments, the phage cocktail comprises F391/08 and/or F387/08 in combination with at least one other phage selected from F394/08, F488/08, F510/08, F44/10, F170/08, F168/08, F770/05, F1245/05, and F125/10. In particularly preferred embodiments, the phage cocktail comprises F391/08 and/or F387/08 in combination with one, two, three or more other phages selected from F44/10, F488/08, F510/08 and/or F770/05.

In certain embodiments, the composition for use with respect to diabetic foot ulcer comprises isolated F488/08, having a genome comprising the nucleic acid sequence of SEQ ID NO:3 and exhibiting antibacterial activity against one or more strains of *Escherichia coli.* In some embodiments, a composition is used comprising a polypeptide isolated from bacteriophage F488/08, or a fragment, variant, or derivative thereof, which polypeptide, fragment, variant, or derivative exhibits antibacterial activity against one or more species or strains of *E. coli.* In certain such embodiments, the polypeptide, or fragment, variant, or derivative thereof, is a lysin, a CHAP domain, or a tail protein, exhibiting antibacterial activity against one or more species or strains of *Escherichia coli.* In certain embodiments, a composition comprising a phage cocktail is used, e.g., where the phage cocktail comprises at least one phage exhibiting antibacterial activity against one or more strains of *Escherichia coli* and at least one phage exhibiting antibacterial activity against a different bacteria. In particular embodiments, the phage cocktail comprises F488/08 in combination with at least one other phage selected from F394/08, F510/08, F44/10, F170/08, F168/08, F770/05, F1245/05, F391/08 F387/08, and F125/10. In particularly preferred embodiments, the phage cocktail comprises F488/08 in combination with one, two, three or more other phages selected from F391/08, F387/08, F44/10, F125/10, F510/08 and/or F770/05.

In certain embodiments, the composition for use with respect to diabetic foot ulcer comprises isolated F510/08 and/or F770/05, having a genome comprising the nucleic acid sequence of SEQ ID NO:4 or as disclosed in WO 2010/090542, respectively, and exhibiting antibacterial activity against one or more strains of *Pseudomonas aeruginosa.* In some embodiments, a composition is used comprising a polypeptide isolated from bacteriophage F510/08 and/or F770/05, or a fragment, variant, or derivative thereof, which polypeptide, fragment, variant, or derivative exhibits antibacterial activity against one or more species or strains of *P. aeruginosa.* In certain such embodiments, the polypeptide, or fragment, variant, or derivative thereof, is a lysin, a CHAP domain, or a tail protein, exhibiting antibacterial activity against one or more species or strains of *Pseudomonas aeruginosa.* In certain embodiments, a composition comprising a phage cocktail is used, e.g., where the phage cocktail comprises at least one phage exhibiting antibacterial activity against one or more strains of *Pseudomonas aeruginosa* and at least one phage exhibiting antibacterial activity against a different bacteria. In particular embodiments, the phage cocktail comprises F510/08 and/or F770/05 in combination with at least one other phage selected from F394/08, F488/08, F44/10, F170/08, F168/08, F1245/05, F391/08, F387/08, and F125/10. In particularly preferred embodiments, the phage cocktail comprises F510/08 and/or F770/05 in combination with one, two, three or more other phages selected from F44/10, F488/08, F391/08, and/or F387/08.

*K. pneumoniae, A. baumannii, E. coli, P. aeruginosa,* and *S. aureus* are also associated with infections that involve organ systems that have a high fluid content, and it is contemplated that the bacteriophage and/or polypeptides of the invention have therapeutic use in the prevention and treatment of these infections. For example, the pharmaceutical compositions of the invention may be used for the prevention or treatment of infections of the respiratory tract, of the cerebrospinal fluid, of peritoneal fluid, and of the urinary tract. The compositions of the invention may also be used to prevent and/or treat nosocomial pneumonia, infections associated with continuous ambulatory peritoneal dialysis (CAPD), catheter-associated bacterimia, and nosocomial meningitis.

In a preferred embodiment, a bacteriophage and/or polypeptide of the invention is used prophylactically in hospital setting, particularly to prevent infections associated with wounds, ulcers, and openings in the skin, e.g., due to catheterization and any other medical procedures or devices.

In certain embodiments, a bacteriophage and/or polypeptide of the invention is used as a single agent for treating or preventing infections associated with *K. pneumoniae, A. baumannii, E. coli, P. aeruginosa,* and/or *S. aureus*, and/or other bacterial species. In other embodiments of the invention, a bacteriophage and/or polypeptide of the invention is used in combination with other agents, including other bacteriophage (for example, that target a different species or strain of bacteria), or with antibiotics that target the same or different kinds of bacteria, including bacteria selected from any gram-positive bacteria, any gram-negative bacteria, and any other groups of bacteria that is not classified as gram-positive or gram-negative. The compositions of the invention may also be used in combination with any other means of treating bacterial infection known to one of skill in the art.

Also contemplated by the invention are methods of preventing and methods of treating an infection caused by bacteria including, but not limited to, *K. pneumoniae, A. baumannii, E. coli, P. aeruginosa,* and/or *S. aureus* comprising administering to a mammal in need thereof a composition comprising a lysin comprising or consisting of the amino acid sequence of SEQ ID NO: 20, SEQ ID NO: 80, SEQ ID NO: 192, SEQ ID NO: 282, SEQ ID NO: 547, SEQ ID NO: 556, SEQ ID NO: 557, SEQ ID NO: 598, SEQ ID NO: 1216, SEQ ID NO: 1261, or a fragment, variant, or derivative thereof, wherein the fragment, variant, or derivative exhibits antibacterial or antimicrobial activity against the species of bacteria from which the parent bacteriophage was isolated. In a specific example in accordance with this embodiment, the invention provides methods of preventing or treating an infection caused by a bacteria including, but not limited to, *K. pneumoniae, A. baumannii, E. coli, P. aeruginosa,* and/or *S. aureus*, comprising administering to a mammal in need thereof a composition comprising an isolated CHAP domain of a lysin, or a fragment, variant, or derivative thereof that exhibits at least one biologic activity of the CHAP domain from which it was isolated (e.g., lytic cell killing).

In certain embodiments, the invention provides methods of preventing and/or treating an infection caused by bacteria including, but not limited to, *K. pneumoniae, A. baumannii, E. coli, P. aeruginosa,* and/or *S. aureus*, comprising administering to a mammal in need thereof a composition comprising a tail protein comprising or consisting of the amino acid sequence of SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629, or SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, SEQ ID NO: 1266, or a fragment, variant, or derivative thereof, wherein the fragment, variant, or derivative exhibits a biologic activity associated with the bacteriophage from with it was derived.

In still other embodiments, the invention provides methods of preventing and/or treating an infection caused by bacteria including, but not limited to, *K. pneumoniae, A. baumannii, E. coli, P. aeruginosa,* and/or *S. aureus*, comprising administering to a mammal in need thereof a composition comprising bacteriophage having a genome comprising or consisting of the nucleic acid sequence of SEQ ID NO: 1, SEQ ID NO: 2, SEQ ID NO: 3, SEQ ID NO: 4, SEQ ID NO: 560, SEQ ID NO: 781, and/or SEQ ID NO: 1074. Combinations of the lysins (or fragments, variants, or derivatives thereof as described above) and tail proteins (or fragments, variants, or derivatives thereof as described above), optionally with one or more bacteriophage of the invention or with other treatments, such as antibiotics, are also contemplated, as well as methods of treating and/or methods of preventing a bacterial infection using one or more of the combinations herein described.

As used herein, the term "in combination" refers to the use of more than one prophylactic and/or therapeutic agent. The use of the term "in combination" does not restrict the order in which prophylactic and/or therapeutic agents are administered to a subject with a disease or disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent (different from the first prophylactic or therapeutic agent) to a subject with a disease or disorder.

6.4 Disinfectant and Anti-Infective Use

Bacterial pathogens most often infect at a mucous membrane site (e.g., upper and lower respiratory, intestinal, urogenital, ocular, and the like). The mucous membranes themselves are often the reservoir, sometimes the only reservoir, for many pathogenic bacteria found in the environment (e.g., pneumococci, staphylococci, and streptococci). There are very few anti-infectives that are designed to control the carrier state of pathogenic bacteria. However, studies have shown that by reducing or eliminating this reservoir in environments such as hospitals and nursing homes, the incidence of infections by these bacteria will be markedly reduced. The prevention of nosocomical infections involves routine and repeated cleaning of affected surfaces.

The bacteriophage and/or polypeptides of the present invention may be used in anti-infective compositions for controlling the growth of bacteria (e.g., Gram-positive bacteria (e.g., *S. aureus*), Gram-negative bacteria (e.g., *K. pneumoniae, A. baumannii, E. coli*, and *P. aeruginosa*), or bacteria not classified as either Gram-positive or Gram-negative), in order to prevent or reduce the incidence of nocosomial infections. In addition to use in compositions for application to mucous membranes, a bacteriophage and/or polypeptide of the present incorporation may also be incorporated into formulations such as gels, creams, ointments, or sprays for controlling or preventing colonization of bacteria on body surfaces (e.g., skin and mucus membranes) (e.g., for sterilization of surgical fields or of the hands and exposed skin of healthcare workers and/or patients) and other solid surfaces (e.g., appliances, countertops, and, in particular, hospital equipment).

6.5 Use in Nanotechnology

The bacteriophage and/or polypeptides of the present invention also may be used in nanotechnology, e.g., in the development of nanoscale devices. The combination of nanotechnology and molecular biology has led to a new generation of nanoscale-based devices, such as nanoscale conductors. Biological systems function based on the structure of macromolecules, mainly proteins and nucleic acids, which are structurally organized at the nanoscale. Accordingly, biological macromolecules may find use in nanoscale applications. In particular, proteins with highly organized structures can be used in the development of nanoscale devices.

In some embodiments, a polypeptide of the invention comprising or consisting of a tail protein (e.g., tail component, tail fiber protein, adsorption associated tail protein, tail length tape measure protein, baseplate wedge subunit), or fragment, variant, or derivative thereof, isolated from a bacteriophage having a genome comprising or consisting of SEQ ID NO: 1, SEQ ID NO: 2, SEQ ID NO: 3, SEQ ID NO:4, SEQ ID NO: 560, SEQ ID NO: 781, or SEQ ID NO: 1074 (e.g., bacteriophage F391/08, F394/08, F488/08, F510/08, F44/10, F387/08, or F125/10, respectively), may be used in nanotechnological applications. For example, tail proteins from tail fibers of the phage may have highly organized structures and may find use in nanoscale conductors. Such conductors may be used, e.g., to deposit gold and/or other ions.

In specific embodiments, the polypeptide of the invention used in nanotechonology is an isolated tail protein comprising or consisting of the amino acid sequence SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266. In other embodiments, the polypeptide of the invention comprises a fragment, variant or derivative of SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266, wherein said fragment, variant or derivative possesses a highly-organized structure. Such polypeptides find use, e.g., in nanoscale conductors, as described above.

6.6 Diagnostic Methods

The present invention also encompasses diagnostic methods for determining the causative agent in a bacterial infection. In certain embodiments, the diagnosis of the causative agent in a presentation of bacterial infection is performed by (i) culturing tissue, blood, or fluid samples of a patient according to standard techniques; (ii) contacting the culture with one or more bacteriophage and/or polypeptides of the invention; and (iii) monitoring cell growth and/or evidence of lysis after said contacting. Because the activity of bacteriophage and/or their isolated products (e.g., polypeptides, or biologically active fragments, variants, or derivatives thereof) tends to be species or strain specific, susceptibility, or lack of susceptibility, to one or more bacteriophage and/or polypeptides of the invention may be indicative of the species or strain of infective bacteria. For example, decreased growth of test cultures after contacting with a bacteriophage having a genome comprising or consisting of the nucleic acid sequence SEQ ID NO: 1 or 781, or with an isolated polypeptide thereof or derived therefrom, may be indicative of the test sample comprising *K. pneumoniae*. Similarly, a bacteriophage having a genome comprising or consisting of the nucleic acid sequence SEQ ID NO: 2, or an isolated polypeptide product thereof or derived therefrom, may be used to identify infection by *A. baumannii*; a bacteriophage having a genome comprising or consisting of the nucleic acid sequence SEQ ID NO: 3, or an isolated polypeptide product thereof or derived therefrom, may be used to identify infection by *E. coli*; while that having a genome comprising or consisting of the nucleic acid sequence SEQ ID NO: 4, or an isolated polypeptide product thereof or derived therefrom, may be used to identify infection by *P. aeruginosa*; and that having a genome comprising or consisting of the nucleic acid sequence SEQ ID NO: 560 or 1074, or an isolated polypeptide product thereof or derived therefrom, may be used to identify infection by *S. aureus*.

Additionally, in some embodiments, bacteriophage and/or polypeptides of the present invention may be used in biosensors in the scope of diagnostics. As used herein, "biosensor" refers an analytical device for the detection of an analyte that combines a biological component with a physicochemical detector component. In particular, proteins involved in the recognition of bacterial receptors can be used in the development of diagnostic biosensors.

In some embodiments, a polypeptide of the invention comprising or consisting of a tail protein (e.g., tail component, tail fiber protein, adsorption associated tail protein, tail length tape measure protein, baseplate wedge subunit), or fragment, variant, or derivative thereof, isolated from a bacteriophage having a genome comprising or consisting of SEQ ID NO: 1, SEQ ID NO: 2, SEQ ID NO: 3, SEQ ID NO:4, SEQ ID NO: 560, SEQ ID NO: 781, SEQ ID NO: 1074 (e.g., bacteriophage F391/08, F394/08, F488/08, F510/08, F44/10, F387/08, or F125/10 respectively), may be used in biosensor applications. For example, a phage tail protein may specifically recognize one or more bacterial species and/or strains, and thus may find use in biosensor diagnostics. The detection of a certain bacterial species and/or strain, by one or more bacteriophage and/or polypeptides of the invention, can indicate the species or strain of infective bacteria.

In specific embodiments, the polypeptide of the invention used in biosensor applications is an isolated tail protein comprising or consisting of the amino acid sequence SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266. In other embodiments, the polypeptide of the invention comprises a fragment, variant or derivative of SEQ ID NO: 15, SEQ ID NO: 26, SEQ ID NO: 27, SEQ ID NO: 30, SEQ ID NOs: 32-35, SEQ ID NO: 180, SEQ ID NO: 183, SEQ ID NO: 185, SEQ ID NO: 190, SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-496, SEQ ID NO: 544, SEQ ID NO: 545, SEQ ID NO: 549, SEQ ID NO: 551, SEQ ID NO: 629, SEQ ID NO: 686, SEQ ID NO: 789, SEQ ID NOs: 796-800, SEQ ID NO: 806, SEQ ID NO: 854, SEQ ID NOs: 999-1004, SEQ ID NOs: 1053-1060, SEQ ID NO: 1077, SEQ ID NO: 1217, SEQ ID NO: 1250, or SEQ ID NO: 1266, wherein said fragment, variant or derivative is capable of speceifically recognizing a bacteria, e.g., a specific species and/or one or more specific strains of the bacteria. Such polypeptides find use, e.g., in biosensors for detecting specific bacteria and/or diagnosing certain infections, as described above.

Generally, the phage tail protein for use in a biosensor will detect its host bacteria, or one or more specific species and/or specific strains of the host bacteria. Accordingly, in certain embodiments, the invention encompasses a tail protein corresponding to the amino acid sequence of SEQ ID NO: 15, SEQ ID NO: 26, SEQ ID NO: 27, SEQ ID NO: 30, or SEQ ID NOs: 32-35, or a variant, fragment or derivative thereof, which recognizes and can detect one or more strains of K. pneumoniae. Such detection may be indicative of a K. pneumoniae infection. In certain embodiments, the invention encompasses a tail protein corresponding to the amino acid sequence of SEQ ID NO: 180, SEQ ID NO: 183, SEQ ID NO: 185, or SEQ ID NO: 190, or a variant, fragment or derivative thereof, which recognizes and can detect one or more strains of A. baumannii. Such detection may be indicative of an A. baumannii infection. In certain embodiments, the invention encompasses a tail protein corresponding to the amino acid sequence of SEQ ID NO: 231, SEQ ID NO: 232, SEQ ID NO:235, SEQ ID NOs: 239-245, SEQ ID NO: 248, SEQ ID NO: 249, SEQ ID NO: 252, SEQ ID NO: 254, SEQ ID NOs: 433-437, SEQ ID NOs: 489-495, or SEQ ID NO: 496, or a variant, fragment or derivative thereof, which recognizes and can detect one or more strains of E. coli. Such detection may be indicative of an E. coli infection In certain embodiments, the invention encompasses a tail protein corresponding to the amino acid sequence of SEQ ID NO: 544, SEQ ID NO: 545, SEQ ID NO: 549, or SEQ ID NO: 551, or a variant, fragment or derivative thereof, which recognizes and can detect one or more strains of P. aeruginosa. Such detection may be indicative of a P. aeruginosa infection. In certain embodiments, the invention encompasses a tail protein corresponding to the amino acid sequence of SEQ ID NO: 629, SEQ ID NO: 686, SEQ ID NO: 1077, SEQ ID NO: 1217, SEQ ID NO: 1250, or SEQ ID NO: 1266, or a variant, fragment or derivative thereof, which recognizes and can detect one or more strains of S. aureus. Such detection may be indicative of an S. aureus infection. In certain embodiments, the invention encompasses a tail protein corresponding to the amino acid sequence of SEQ ID NO: 789, SEQ ID NOs: 796-800, SEQ ID NO: 806, SEQ ID NO: 854, SEQ ID NOs: 999-1004, or SEQ ID NOs: 1053-1060, or a variant, fragment or derivative thereof, which recognizes and can detect one or more strains of K. pneumoniae. Such detection may be indicative of a K. pneumoniae infection.

In some embodiments, the invention encompasses the use of more than one tail protein, e.g., a combination of two of more of the tail proteins provided above, in a biosensor for detecting more than one bacterial species and/or strains. The biosensor also may comprise additional proteins and/or other agents for detecting the same or different bacteria.

6.7 Amino Acid Variants

Amino acid sequence variants of the polypeptides of the invention can be created. In some embodiments, they may be substitutional, insertional and/or deletion variants. Deletion variants lack one or more residues of the native protein which typically are not essential for function (e.g., antimicrobial or antibacterial activity). Insertional mutants typically involve the addition of material at a non-terminal point in the polypeptide. Substitutional variants typically involve the exchange of one amino acid for another at one or more sites within the polypeptide, and may be designed to modulate one or more properties of the polypeptide, such as stability against proteolytic cleavage, preferably without the loss (or substantial loss) of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Once general areas of the gene are identified as encoding a particular antibacterial activity, e.g., as a lysin as described herein, point mutagenesis may be employed to identify with greater particularity which amino acid residues are important in the antibacterial activity. Thus, one of skill in the art will be able to generate, for example, single base changes in the DNA strand to result in an altered codon and/or a missense mutation that preserves desired function.

Preferably, mutation of the amino acids of a protein creates an equivalent, or even an improved, second-generation molecule. For example, certain amino acids may be substituted for other amino acids in a protein structure without detectable or substantial loss of function (e.g., antibacterial or antimicrobial activity). In making such changes, the hydropathic index of amino acids may be considered. The importance of the hydropathic amino acid index in conferring interactive biological function on a protein is generally understood in the art. It is accepted that the relative hydropathic character of the amino acid contributes to the secondary structure of the resultant protein, which in turn defines the interaction of the protein with other molecules, for example, interaction with a peptidoglycan within the outer coat of a gram-positive bacteria. Each amino acid has been assigned a hydropathic index on the basis of their hydrophobicity and charge characteristics; for example: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan 0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is also understood in the art that the substitution of like amino acids can be made effectively on the basis of hydrophilicity. Like hydrophobicity, values of hydrophilicity have been assigned to each amino acid: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). Equivalent molecules may be obtained by substitution of one amino acid for another where their hydropathic and/or their hydrophilicity indices are within ±2, preferably ±1, or most preferably ±5 of each other.

In certain embodiments, the invention encompasses isolated peptides that comprise 1, 2, 3, 4, 5, 6, 7, 8, 9, or 10 or more amino acid modifications (e.g., insertion, substitution, deletion, etc.) relative to an amino acid sequence disclosed herein. In preferred embodiments, the mutation(s) are made such that biological activity of the particular polypeptide is retained or substantially retained. For example, the present invention encompasses polypeptides isolated from bacteriophage F387/08, F391/08, F394/08, F488/08, F510/068, F44/10, and/or F125/10, which are mutated to comprise 1, 2, 3, 4, 5, 6, 7, 8, 9, or 10 or more amino acid modifications relative to an amino acid sequence listed herein, and which exhibit antibacterial activity against one or more species or strains of Gram-positive or Gram-negative bacterium, e.g., against *K. pneumoniae, A. baumannii, E. coli, P. aeruginosa*, and/or *S. aureus*. In specific embodiments, the polypeptides of the invention derived from F387/08 or F391/08 exhibit antibacterial or antimicrobial activity, e.g., lytic killing activity, against at least *K. pneumoniae*; those derived from F394/08 against at least *A. baumannii*; those derived from F488/08 against at least *E. coli*; those derived from F510/08 against at least. *P. aeruginosa*, and those derived from F44/10 or F125/10 against at least. *S. aureus*.

6.8 Polynucleotides Encoding Polypeptides of the Invention

The invention provides polynucleotides comprising a nucleotide sequence encoding a polypeptide of the invention. The invention also encompasses polynucleotides that hybridize under high stringency, intermediate, or lower stringency hybridization conditions, e.g., as defined supra, to polynucleotides that encode a polypeptide of the invention and that encode modified polypeptides that have antibiotic and/or other biological activity.

The polynucleotides may be obtained, and the nucleotide sequence of the polynucleotides determined, by any method known in the art. For example, a polynucleotide encoding a polypeptide of the invention may be generated from nucleic acid from a suitable source (e.g., bacteriophage F387/08, F391/08, F394/08, F488/08, F510/08, F44/10, and/or F125/10). Nucleotide sequences may be isolated from phage genomes by routine methods known in the art (see, e.g., Carlson, "Working with bacteriophage: common techniques and methodological approaches," In, Kutter and Sulakvelidze (Eds) Bacteriophage: Biology and Applications, 5$^{th}$ ed. CRC Press (2005); incorporated herein by reference in its entirety). If a source containing a nucleic acid encoding a particular polypeptide is not available, but the amino acid sequence of the polypeptide of the invention is known, a nucleic acid encoding the polypeptide may be chemically synthesized and cloned into replicable cloning vectors using any method well known in the art.

Once the nucleotide sequence of the polypeptide of the invention is determined, the nucleotide sequence of the polypeptide may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate polypeptides having a different amino acid sequence, for example to create amino acid substitutions, deletions, and/or insertions.

In some embodiments, a nucleotide sequence encoding one or more ORFs of FIGS. 2, 4, 6, 8, 10, 12, and 14 are provided. In some embodiments, a nucleotide sequence encoding a variant, fragment or derivative of one or more ORFs of FIGS. 2, 4, 6, 8, 10, 12, and 14 are provided, where the variant, fragment or derivative exhibits antibacterial or antimicrobial activity (e.g., lytic killing activity) against one or more strains of *K. pneumoniae*, for example, against the bacteriophage having a genome comprising or consisting of the nucleic acid sequence SEQ ID NO: 1 or SEQ ID NO: 781; and/or one against or more strains of *A. baumannii*, for example, against the bacteriophage having a genome comprising or consisting of the nucleic acid sequence SEQ ID NO: 2; and/or against one or more strains of *E. coli*, for example, against the bacteriophage having a genome comprising or consisting of the nucleic acid sequence SEQ ID NO: 3; against one or more strains of *P. aeruginosa*, for example, against the bacteriophage having a genome comprising or consisting of the nucleic acid sequence SEQ ID NO: 4; and/or against one or more strains of *S. aureus*, for example, against the bacteriophage having a genome comprising or consisting of the nucleic acid sequence SEQ ID NO: 560 or SEQ ID NO: 1074.

6.9 Recombinant Expression of Molecules of the Invention

Once a nucleic acid sequence encoding a molecule of the invention (e.g., a polypeptide) has been obtained, the vector for the production of the molecules may be produced by recombinant DNA technology using techniques well known in the art. Methods which are well known to those skilled in the art can be used to construct expression vectors containing the coding sequences for the molecules of the invention and appropriate transcriptional and translational control signals. These methods include, for example, in vitro recombinant DNA techniques, synthetic techniques, and in vivo genetic recombination. (See, for example, the techniques described in Sambrook et al., 1990, Molecular Cloning, A Laboratory Manual, 2d Ed., Cold Spring Harbor Laboratory, Cold Spring Harbor, N.Y. and Ausubel et al. eds., 1998, Current Protocols in Molecular Biology, John Wiley & Sons, NY).

The present invention provides expression vectors encoding the polypeptides of the invention. An expression vector comprising the nucleotide sequence of a molecule identified by the methods of the invention can be transferred to a host cell by conventional techniques (e.g., electroporation, liposomal transfection, and calcium phosphate precipitation) and the transfected cells are then cultured by conventional techniques to produce the molecules of the invention. In preferred embodiments, the host cell is other than the species of the parent bacteria from which the bacteriophage comprising the sequence was derived. In specific embodiments, the expression of the molecules of the invention is regulated by a constitutive, an inducible or a tissue, specific promoter. In specific embodiments the expression vector is pQE-30 (Qiagen) or pET-29(a) (Novagen).

The host cells used to express the molecules identified by the methods of the invention may be either bacterial cells (preferably non susceptible to the bacteriophage protein or variant, derivative, or fragment thereof of the invention). A variety of host-expression vector systems may be utilized to express the molecules identified by the methods of the invention. Such host-expression systems represent vehicles by which the coding sequences of the molecules of the invention may be produced and subsequently purified, but also represent cells which may, when transformed or transfected with the appropriate nucleotide coding sequences, express the molecules of the invention in situ. These include, but are not limited to, microorganisms such as bacteria that are not susceptible to the bacteriophage protein or variant, derivative, or fragment thereof of the invention (e.g., *B. subtilis*) transformed with recombinant bacteriophage DNA, plasmid DNA, or cosmid DNA expression vectors containing coding sequences for the molecules identified by the methods of the invention; yeast (e.g., *Saccharomyces Pichia*) transformed with recombinant yeast expression vectors containing sequences encoding the molecules identified by the methods of the invention; insect cell systems infected with recombinant virus expression vectors (e.g., baculovirus) containing the sequences encoding the molecules identified by the methods of the invention; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the molecules identified by the methods of the invention; or mammalian cell systems (e.g., COS, CHO, BHK, 293, 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter) containing sequences encoding the molecules identified by the methods of the invention.

In bacterial systems not susceptible to the bacteriophage protein or variant, derivative, or fragment thereof of the invention, a number of expression vectors may be advantageously selected depending upon the use intended for the molecule being expressed. For example, when a large quantity of such a protein is to be produced, for the generation of pharmaceutical compositions of a polypeptide, vectors which direct the expression of high levels of fusion protein products that are readily purified may be desirable. Such vectors include, but are not limited, to the *E. coli* expression vector pUR278 (Ruther et al., 1983, *EMBO J.* 2:1791), in which the protein sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, *J. Biol. Chem.* 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free gluta-thione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus preferably grows in *Spodoptera frugiperda* cells. The polypeptide coding sequence may be cloned individually into non-essential regions (e.g., the polyhedrin gene) of the virus and placed under control of an AcNPV promoter (e.g., the polyhedrin promoter).

Once a molecule of the invention (i.e., polypeptides) has been recombinantly expressed, it may be purified by any method known in the art for purification of polypeptides, for example, by chromatography (e.g., ion exchange, affinity, and sizing column chromatography), centrifugation, differential solubility, or by any other standard technique for the purification of polypeptides or antibodies.

Certain modifications and improvements will occur to those skilled in the art upon a reading of the foregoing description. It should be understood that all such modifications and improvements have been deleted herein for the sake of conciseness and readability but are properly within the scope of the following claims.

7. EXAMPLES

It is understood that the following examples and embodiments described herein are for illustrative purposes only and that various modifications or changes in light thereof will be suggestive to persons skilled in the art and are to be included within the spirit and purview of this application and the scope of the appended claims. All publications, patents, and patent applications cited herein are hereby incorporated by reference in their entirety for all purposes.

Unless otherwise indicated, the bacteriophage of the invention were isolated, processed and analyzed according to the following methods.

7.1.1 Purification of Phage

Stock preparations of bacteriophage isolated from clinical samples were prepared according to protocols described in Carlson, "Working with bacteriophage: common techniques and methodological approaches," In, Kutter and Sulakvelidze (Eds) Bacteriophage: Biology and Applications, $5^{th}$ ed. CRC Press (2005) ("Carlson," incorporated herein by reference in its entirety).

The bacteriophage stock preparations were concentrated by precipitation with PEG according to the protocol described in Carlson and Yamamoto et al., 2004, PNAS 101: 6415-6420. Briefly, the stock preparation was incubated in 1 M NaCl for one hour at 4° C. with agitation. Next, PEG 8000 (AppliChem, Cheshire, Mass.) was gradually added to a final concentration of 10% (w/v). The composition was then incubated overnight at 4° C. After the incubation period, the composition was centrifuged at 10000×g for 30 minutes at 4° C. The sediment was then re-suspended in SM buffer (0.05 M Tris-HCL at pH 7.4, 0.1 M NaCl, 10 mM $MgSO_4$) with gelatin at 1% w/v and centrifuged again at 1000 rpm at 4° C. for 10 minutes. The supernatant containing the suspended phage was saved for further purification. The supernatant was purified using a CsCl gradient according to the methods in Carlson.

CsCl was removed from the purified and concentrated phage stock by dialysis. A dialysis membrane, Cellu.Sep H1 High Grade Regenerated Cellulose Tubular Membrane (Cellu.Sep, River Street, USA), was prepared according to the manufacturers' instructions. The dialysis involved a first incubation of 30 minutes in 100 mM Tris-HCl and 3 M NaCl (pH 7.4) at 4° C. This was followed by a second incubation of 30 minutes in 100 mM Tris-HCl and 0.3 M NaCl (pH 7.4) at 4° C. After dialysis, the suspended phage was removed from the interior of the dialysis bag and stored at 4° C.

7.1.2 Extraction of Phage DNA

To 5 ml of the purified and concentrated bacteriophage samples was added 20 mM EDTA at pH 8.0, SDS at 0.5% (p/v) and Proteinase K at a final concentration of 40 µg/ml. The mixture was incubated at 56° C. for one hour. Successive extractions in phenol:chloroform:alcohol at a proportions of 25:24:1 were performed until the interface between the aqueous and organic phases was clear. The aqueous phase was then treated with an equal volume of chloroform and centrifuged at 13,0000×g for 10 minutes at 4° C. The aqueous phase was once again removed, and the DNA was precipitated by adding two volumes of absolute ethanol and incubating for thirty minutes at 20° C. The samples were then centrifuged at 11,000×g for 30 minutes at 4° C. The pellet was washed with 70% ethanol at room temperature and resuspended in 50 µl of ultra-pure water (Gibco, Calif.). DNA concentration was determined by measuring the absorbance at 260 nm in a ND-1000 Spectrophotometer. Integrity of the isolated phage DNA was analyzed by electrophoresis on a 1% agarose gel.

7.1.3 Analysis of Phage Genomes

Sequencing of the bacteriophage genome allowed identification of potential open reading frames (ORFs) within the genome. The putative ORFs of the bacteriophage were used to search the NCBI nucleotide collection database for homologous DNA sequences using the BLASTN program (see, e.g., Zhang et al., 2000, *J. Comput. Biol.* 7:203-214).

7.2 Example 1

Bacteriophage F391/08

Comparison of the putative ORFs of the bacteriophage F391/08 genome with the sequences in the NCBI nucleotide database revealed that only small portions of the genome (≤11% genome coverage) exhibited homology with known sequences. A schematic organization of the F391/08 genome is provided in FIG. 1. F391/08 ORFs, their encoded amino acid sequences, and known homologous proteins are provided in FIG. 2. Prediction of orfs was performed by integrating the results obtained with GeneMark.hmm and MetaGeneAnnotator programs (Besemer, J. and Borodovsky, M. 1999. Nucleic Acids Res., 27: 3911-3920; Noguchi, H. et al., 2008. DNA Res., 15: 387-396). Protein homology searches were carried out with BLASTP program (Alschul, S. F. et al., 1997. Nucleic Acids Res., 25: 3389-33402) using the NCBI non-redundant protein sequences database. Protein conserved domains were predicted using NCBI specialized BLAST (Marchler-Bauer, A. et al., 2007. Nucleic Acids Res. 35: 237-240). orfs whose products presented homology with the same protein(s) are indicated with the same number with the addition of a lowercase letter, in FIG. 2. Identification of putative transfer RNA genes (tRNA) was carried out using the tRNAscan-SE program (Lowe, T. M. et al., 1997. Nucleic Acids Res., 25: 955-964).

Table 1 below provides the results of spot tests that assessed the host range and activity of the bacteriophage F391/08 against 100 *Klebsiella* sp. strains (86 *K. pneumoniae* strains; 12 *K. oxytoca* strains; and 2 *Klebsiella* sp. strains) isolated from clinical samples. Each spot contained 5 µl of bacteriophage suspension with the indicated titers, prepared from a CsCl purified lysate. Sensitivity of each strain to the phage was evaluated based on a relative scale ranging from turbid (+) to clear (++++) lysis halos. Spots originating from isolated phage plaques are indicated as (pfu) and resistance to phage infection is indicated as (−). The percentage of strains displaying a particular sensitivity phenotype is indicated also.

TABLE 1

| Phage | Titer (pfu/ml) | Phage sensitivity (%) of *Klebsiella* sp. strains (n = 100) | | | | | | Total of infected strains (%) |
|---|---|---|---|---|---|---|---|---|
| | | ++++ | +++ | ++ | + | pfu | − | |
| F391/08 | $2.72 \times 10^{10}$ | 3 | 26 | 8 | 11 | 0 | 52 | 48 |
| | $2.72 \times 10^{8}$ | 1 | 5 | 6 | 1 | 0 | 87 | 13 |
| | $2.72 \times 10^{6}$ | 0 | 1 | 3 | 1 | 1 | 94 | 6 |
| | $2.72 \times 10^{4}$ | 0 | 0 | 0 | 0 | 3 | 97 | 3 |

7.3 Example 2

Bacteriophage F394/08

Comparison of the putative ORFs of the bacteriophage F394/08 genome with the sequences in the NCBI nucleotide database revealed no significant homologies with known sequences, other than that observed for small portions of the genome (≤1% genome coverage). A schematic organization of the F394/08 genome is provided in FIG. 3. F394/08 ORFs, their encoded amino acid sequences, and known homologous proteins are provided in FIG. 4. Prediction of orfs was performed by integrating the results obtained with GeneMark.hmm and MetaGeneAnnotator programs (Besemer, J. and Borodovsky, M. 1999. Nucleic Acids Res., 27: 3911-3920; Noguchi, H. et al., 2008. DNA Res., 15: 387-396). Protein homology searches were carried out with BLASTP program (Alschul, S. F. et al., 1997. Nucleic Acids Res., 25: 3389-33402) using the NCBI non-redundant protein sequences database. Protein conserved domains were predicted using NCBI specialized BLAST (Marchler-Bauer, A. et al., 2007. Nucleic Acids Res. 35: 237-240). orfs whose products presented homology with the same protein(s) are indicated with the same number with the addition of a lowercase letter, in FIG. 4. Identification of putative transfer RNA genes (tRNA) was carried out using the tRNAscan-SE program (Lowe, T. M. et al., 1997. Nucleic Acids Res., 25: 955-964).

Table 2 below provides the results of spot tests that assessed the host range and activity of the bacteriophage F394/08 against 100 *Acinetobacter* sp. strains (93 *A. baumannii* strains; 6 *A. calcoaceticus* strains; and 1 *A. lwoffi* strain) isolated from clinical samples. Each spot contained 5 µl of bacteriophage suspension with the indicated titers, prepared from a CsCl purified lysate. Sensitivity of each strain to the phage was evaluated based on a relative scale ranging from turbid (+) to clear (++++) lysis halos. Spots originating from isolated phage plaques are indicated as (pfu) and resistance to phage infection is indicated as (−). The percentage of strains displaying a particular sensitivity phenotype is indicated also.

TABLE 2

| Phage | Titer (pfu/ml) | Phage sensitivity (%) of *Acinetobacter* sp. strains (n = 100) | | | | | | Total of infected strains (%) |
|---|---|---|---|---|---|---|---|---|
| | | ++++ | +++ | ++ | + | pfu | − | |
| F394/08 | $2.2 \times 10^9$ | 67 | 3 | 1 | 0 | 0 | 29 | 71 |
| | $2.2 \times 10^8$ | 66 | 1 | 2 | 1 | 0 | 30 | 70 |
| | $2.2 \times 10^6$ | 9 | 38 | 8 | 0 | 0 | 45 | 55 |
| | $2.2 \times 10^4$ | 0 | 7 | 1 | 0 | 32 | 60 | 40 |

7.4 Example 3

Bacteriophage F488/08

Comparison of the putative ORFs of the bacteriophage F488/08 genome with the sequences in the NCBI nucleotide database revealed that approximately 94% of phage F488/08 DNA is highly similar to that of Enterobaceria phage RB 14, with individual ORF identities ranging from 70 to 100%. A schematic organization of the F488/08 genome is provided in FIG. 5. F4884/08 ORFs, their encoded amino acid sequences, and known homologous proteins are provided in FIG. 6. Prediction of orfs was performed by integrating the results obtained with GeneMark.hmm and MetaGeneAnnotator programs (Besemer, J. and Borodovsky, M. 1999. Nucleic Acids Res., 27: 3911-3920; Noguchi, H. et al., 2008. DNA Res., 15: 387-396). Protein homology searches were carried out with BLASTP program (Alschul, S. F. et al., 1997. Nucleic Acids Res., 25: 3389-33402) using the NCBI non-redundant protein sequences database. Protein conserved domains were predicted using NCBI specialized BLAST (Marchler-Bauer, A. et al., 2007. Nucleic Acids Res. 35: 237-240). orfs whose products presented homology with the same protein(s) are indicated with the same number with the addition of a lowercase letter, in FIG. 4. Identification of putative transfer RNA genes (tRNA) was carried out using the tRNAscan-SE program (Lowe, T. M. et al., 1997. Nucleic Acids Res., 25: 955-964).

Table 3 below provides the results of spot tests that assessed the host range and activity of the bacteriophage F488/08 against 100 *Escherichia coli* (ECO) strains isolated from clinical samples. Each spot contained 5 μl of bacteriophage suspension with the indicated titers, prepared from a lysate purified by ion exchange chromatography. Sensitivity of each strain to the phage was evaluated based on a relative scale ranging from turbid (+) to clear (++++) lysis halos. Spots originating from isolated phage plaques are indicated as (pfu) and resistance to phage infection is indicated as (−). The percentage of strains displaying a particular sensitivity phenotype is indicated also.

TABLE 3

| Phage | Titer (pfu/ml) | Phage sensitivity (%) of ECO strains (n = 100) | | | | | | Total of infected strains (%) |
|---|---|---|---|---|---|---|---|---|
| | | ++++ | +++ | ++ | + | pfu | − | |
| F488/08 | $1 \times 10^{10}$ | 0 | 60 | 1 | 2 | 0 | 37 | 63 |
| | $1 \times 10^8$ | 0 | 42 | 15 | 0 | 0 | 43 | 57 |
| | $1 \times 10^6$ | 0 | 8 | 10 | 7 | 0 | 75 | 25 |
| | $1 \times 10^4$ | 0 | 0 | 0 | 0 | 10 | 90 | 10 |

7.5 Example 4

Bacteriophage F510/08

Comparison of the putative ORFs of the bacteriophage F510/08 genome with the sequences in the NCBI nucleotide database revealed that approximately 95% of phage F510/08 DNA is highly similar to that of *Pseudomonas* phage LUZ19, with individual ORF identities ranging from 89 to 97%. A schematic organization of the F510/08 genome is provided in FIG. 7. F510/08 ORFs, their encoded amino acid sequences, and known homologous proteins are provided in FIG. 8. Prediction of orfs was performed by integrating the results obtained with GeneMark.hmm and MetaGeneAnnotator programs (Besemer, J. and Borodovsky, M. 1999. Nucleic Acids Res., 27: 3911-3920; Noguchi, H. et al., 2008. DNA Res., 15: 387-396). Protein homology searches were carried out with BLASTP program (Alschul, S. F. et al., 1997. Nucleic Acids Res., 25: 3389-33402) using the NCBI non-redundant protein sequences database. Protein conserved domains were predicted using NCBI specialized BLAST (Marchler-Bauer, A. et al., 2007. Nucleic Acids Res. 35: 237-240). orfs whose products presented homology with the same protein(s) are indicated with the same number with the addition of a lowercase letter, in FIG. 8. Identification of putative transfer RNA genes (tRNA) was carried out using the tRNAscan-SE program (Lowe, T. M. et al., 1997. Nucleic Acids Res., 25: 955-964).

Table 4 below provides the results of spot tests that assessed the host range and activity of the bacteriophage F510/08 against 100 *Pseudomonas aeruginosa* (PSA) strains isolated from clinical samples. Each spot contained 5 μl of bacteriophage suspension with the indicated titers, prepared from a CsCl purified lysate. Sensitivity of each strain to the phage was evaluated based on a relative scale ranging from turbid (+) to clear (++++) lysis halos. Spots originating from isolated phage plaques are indicated as (pfu) and resistance to phage infection is indicated as (−). The percentage of strains displaying a particular sensitivity phenotype is indicated also.

TABLE 4

| Phage | Titer (pfu/ml) | Phage sensitivity (%) of PSA strains (n = 100) | | | | | | Total of infected strains (%) |
|---|---|---|---|---|---|---|---|---|
| | | ++++ | +++ | ++ | + | pfu | − | |
| F510/08 | $5.7 \times 10^{10}$ | 35 | 18 | 4 | 10 | 3 | 30 | 70 |
| | $5.7 \times 10^8$ | 18 | 25 | 6 | 9 | 4 | 38 | 62 |
| | $5.7 \times 10^6$ | 13 | 14 | 4 | 2 | 4 | 63 | 37 |
| | $5.7 \times 10^4$ | 10 | 12 | 0 | 1 | 10 | 67 | 33 |

7.6 Example 5

Bacteriophage F44/10

Comparison of the putative ORFs of the bacteriophage F44/10 genome with the sequences in the NCBI nucleotide database revealed that approximately 81% of phage F44/10 DNA is highly similar to that of *Staphylococcus* phage K, with individual ORF identities ranging from 80 to 99%. A schematic organization of the F44/10 genome is provided in FIG. 9. F44/10 ORFs, their encoded amino acid sequences, and known homologous proteins are provided in FIG. 10. Prediction of orfs was performed by integrating the results obtained with GeneMark.hmm and MetaGeneAnnotator programs (Besemer, J. and Borodovsky, M. 1999. *Nucleic Acids*

Res., 27: 3911-3920; Noguchi, H. et al., 2008. *DNA Res.*, 15: 387-396). Protein homology searches were carried out with BLASTP program (Alschul, S. F. et al., 1997. *Nucleic Acids Res.*, 25: 3389-33402) using the NCBI non-redundant protein sequences database. Protein conserved domains were predicted using NCBI specialized BLAST (Marchler-Bauer, A. et al., 2007. *Nucleic Acids Res.* 35: 237-240). orfs whose products presented homology with the same protein(s) are indicated with the same number with the addition of a lowercase letter, in FIG. 10. As previously reported for *Staphylococcus* phage K, the putative polymerase gene (orf114a, orf114b) may contain an intron-like sequence. (O'Flaherty et al., 2004). Identification of putative transfer RNA genes (tRNA) was carried out using the tRNAscan-SE program (Lowe, T. M. et al., 1997. *Nucleic Acids Res.*, 25: 955-964).

Table 5 below provides the results of spot tests that assessed the host range and activity of the bacteriophage F44/10 against 100 *Staphylococcus aureus* (STA) strains isolated from clinical samples. Each spot contained 5 µl of bacteriophage suspension with the indicated titers, prepared from a CsCl purified lysate. Sensitivity of each strain to the phage was evaluated based on a relative scale ranging from turbid (+) to clear (++++) lysis halos. Spots originating from isolated phage plaques are indicated as (pfu) and resistance to phage infection is indicated as (−). The percentage of strains displaying a particular sensitivity phenotype is indicated also.

TABLE 5

| Phage | Titer (pfu/ml) | Phage sensitivity (%) of STA strains (n = 100) | | | | | | Total of infected strains (%) |
|---|---|---|---|---|---|---|---|---|
| | | ++++ | +++ | ++ | + | pfu | − | |
| F44110 | $2.25 \times 10^{11}$ | 53 | 35 | 10 | 1 | 1 | 0 | 100 |
| | $2.25 \times 10^{10}$ | 35 | 52 | 10 | 2 | 1 | 0 | 100 |
| | $2.25 \times 10^{8}$ | 19 | 51 | 5 | 5 | 1 | 19 | 81 |
| | $2.25 \times 10^{6}$ | 5 | 22 | 0 | 0 | 34 | 39 | 61 |
| | $2.25 \times 10^{4}$ | 0 | 0 | 0 | 0 | 42 | 58 | 42 |

7.7 Example 6

Bacteriophage F387/08

Comparison of the putative ORFs of the bacteriophage F387/08 genome with the sequences in the NCBI nucleotide database revealed no significant homologies with known sequences other than small portions of the genome (≤12% genome coverage). A schematic organization of the F387/08 genome is provided in FIGS. 11A-11C. Functionally assigned orfs are indicated on the right and in FIGS. 11B-C. DNA homology searches were carried out with BLASTN program (Zhang, Z. et al., 2000. J. Comput. Biol., 7: 203-214), using the NCBI nucleotide collection database.

F387/08 ORFs, their encoded amino acid sequences, and known homologous proteins are provided in FIG. 12. Prediction of orfs was performed by integrating the results obtained with GeneMark.hmm and MetaGeneAnnotator programs (Besemer, J. and Borodovsky, M. 1999. Nucleic Acids Res., 27: 3911-3920; Noguchi, H. et al., 2008. DNA Res., 15: 387-396). Protein homology searches were carried out with BLASTP program (Alschul, S. F. et al., 1997. Nucleic Acids Res., 25: 3389-33402) using the NCBI non-redundant protein sequences database. Protein conserved domains were predicted using NCBI specialized BLAST (Marchler-Bauer, A. et al., 2007. Nucleic Acids Res. 35: 237-240).

Table 6 below provides the results of spot tests that assessed the host range and activity of the bacteriophage F387/08 against 100 *Klebsiella* sp. strains (86 *K. pneumoniae* strains; 12 *K. oxytoca* strains; and 2 *Klebsiella* sp. strains) isolated from clinical samples. Each spot contained 5 µl of bacteriophage suspension with the indicated titers, prepared from a CsCl purified lysate. Sensitivity of each strain to the phage was evaluated based on a relative scale ranging from turbid (+) to clear (++++) lysis halos. Spots originating from isolated phage plaques are indicated as (pfu) and resistance to phage infection is indicated as (−). The percentage of strains displaying a particular sensitivity phenotype is indicated also.

TABLE 6

| Phage | Titer (pfu/ml) | Phage sensitivity (%) of KLE strains (n = 100) | | | | | | Total of infected strains (%) |
|---|---|---|---|---|---|---|---|---|
| | | ++++ | +++ | ++ | + | pfu | − | |
| F387/08 | $1.0 \times 10^{10}$ | 1 | 38 | 20 | 9 | 0 | 32 | 68 |
| | $1.0 \times 10^{8}$ | 0 | 10 | 14 | 9 | 0 | 67 | 33 |
| | $1.0 \times 10^{6}$ | 0 | 2 | 2 | 0 | 1 | 95 | 5 |
| | $1.0 \times 10^{4}$ | 0 | 0 | 0 | 1 | 2 | 97 | 3 |

7.8 Example 7

Bacteriophage F125/10

Comparison of the putative ORFs of the bacteriophage F125/10 genome with the sequences in the NCBI nucleotide database revealed that approximately 87% of phage F125/10 DNA is highly similar to that of *Staphylococcus* phage A5W, with individual ORF identities ranging from 77 to 99%. A schematic organization of the F125/10 genome is provided in FIG. 13. F125/10 ORFs, their encoded amino acid sequences, and known homologous proteins are provided in FIG. 14. Prediction of orfs was performed by integrating the results obtained with GeneMark.hmm and MetaGeneAnnotator programs (Besemer, J. and Borodovsky, M. 1999. *Nucleic Acids Res.*, 27: 3911-3920; Noguchi, H. et al., 2008. *DNA Res.*, 15: 387-396). Protein homology searches were carried out with BLASTP program (Alschul, S. F. et al., 1997. *Nucleic Acids Res.*, 25: 3389-33402) using the NCBI non-redundant protein sequences database. Protein conserved domains were predicted using NCBI specialized BLAST (Marchler-Bauer, A. et al., 2007. *Nucleic Acids Res.* 35: 237-240). orfs whose products presented homology with the same protein(s) are indicated with the same number with the addition of a lowercase letter, in FIG. 14. As previously reported for *Staphylococcus* phage K (O'Flaherty et al., 2004, *J. of Bacteriology* 186(9):2862-2871), and phage Twort (Landthaler et al., 2002, *Nucleic Acids Research* 30(9):1935-1943), introns interrupting genes involved in DNA metabolism were found; and the putative terminase large subunit gene (orf153a, orf153b) may contain an intron-like sequence (orf154*).

Table 7 below provides the results of spot tests that assessed the host range and activity of the bacteriophage F125/10 against 98 *Staphylococcus aureus* (STA) strains isolated from clinical samples. Each spot contained 5 µl of bacteriophage suspension with the indicated titers, prepared from a CsCl purified lysate. Sensitivity of each strain to the phage was evaluated based on a relative scale ranging from turbid (+) to clear (++++) lysis halos. Phage dilutions originating from isolated phage plaques are indicated as (pfu) and resistance to phage infection is indicated as (−). The percentage of strains displaying a particular sensitivity phenotype is indicated also.

TABLE 7

| Phage | Titer (pfu/ml) | Phage sensitivity (%) of STA strains (n = 198) | | | | | | Total of infected strains (%) |
|---|---|---|---|---|---|---|---|---|
| | | ++++ | +++ | ++ | + | pfu | − | |
| F125/10 | 8.30 × 10⁹ | 49 | 27 | 12 | 10 | 0 | 0 | 100 |
| | 8.30 × 10⁸ | 21 | 38 | 21 | 16 | 0 | 2 | 98 |
| | 8.30 × 10⁶ | 4 | 29 | 27 | 15 | 0 | 23 | 77 |
| | 8.30 × 10⁴ | 0 | 9 | 20 | 10 | 22 | 37 | 62 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09399049B2). An electronic copy of the "Sequence Listing" will also be available from the USPTO upon request and payment of the fee set forth in 37 CFR 1.19(b)(3).

What is claimed is:

1. A method of treating or reducing the incidence of a *Staphylococcus aureus* infection in a subject in need thereof, said method comprising administering to said subject an effective amount of a pharmaceutical composition, said pharmaceutical composition comprising:
   a pharmaceutically acceptable carrier; and
   a purified bacteriophage having a nucleic acid sequence of SEQ ID NO:560.

2. The method of claim 1, wherein said pharmaceutical composition further comprises
   (i) three additional purified phage selected from the group consisting of F391/08, F394/08, F488/08, F510/08, F387/08, F170/08, F168/08, F770/05, and F1245/05; or
   (ii) three additional purified phage selected from the group consisting of F391/08, F387/08, F488/08, F510/08 and/or F770/05.

3. The method of claim 1, wherein the infection is a nosocomial infection.

4. The method of claim 1, wherein the pharmaceutical composition is administered topically.

5. The method of claim 1, wherein the infection is an infection of the skin.

6. The method of claim 5, wherein the infection is an infection associated with at least one condition selected from the group consisting of diabetic foot ulcer, scalded skin syndrome, pimples, and carbuncles.

7. The method of claim 6, wherein the pharmaceutical composition is administered topically.

8. The method of claim 1, wherein the infection is pneumonia or other infection of the respiratory tract.

9. The method of claim 8, wherein the pharmaceutical composition is administered by inhalation.

10. The method of claim 9, wherein administration by inhalation uses a pump, a spray, or a nebulizer; or wherein the pharmaceutical composition for administration by inhalation comprises a dry powder inhaler or an aerosol spray.

11. The method of claim 1, wherein the infection is an infection associated with at least one condition selected from the group consisting of gastroenteritis, osteomyelitis, endocarditis, and peritonitis.

12. The method of claim 11, wherein the pharmaceutical composition is administered orally or parenterally.

13. The method of claim 1, wherein the infection is an infection associated with at least one condition selected from the group consisting of meningitis or other infection of the cerebrospinal fluid, toxic shock syndrome, bacteremia, and sepsis.

14. The method of claim 13, wherein the pharmaceutical composition is administered intravenously.

15. The method of claim 1, wherein the infection is an infection of the urinary tract.

16. The method of claim 15, wherein the pharmaceutical composition is administered by a catheter.

17. The method of claim 1, wherein the subject is a human.

18. The method of claim 1, further comprising administering to said subject an antibiotic for treating said bacterial infection.

19. The method of claim 1, wherein said pharmaceutical composition further comprises one of more additional bacteriophage known to have antibacterial or antimicrobial activity against *Staphylococcus aureus*.

20. The method of claim 1, wherein said pharmaceutical composition further comprises one of more additional bacteriophage known to have antibacterial or antimicrobial activity against a bacterium other than *Staphylococcus aureus*.

21. The method of claim 1, wherein said *Staphylococcus aureus* infection is an infection by a methicillin-resistant strain of *Staphylococcus aureus* (MRSA).

22. The method of claim 21, further comprising administering to said subject at least one antibiotic known to have antibacterial or antimicrobial activity against MRSA.

23. The method of claim 22, wherein said antibiotic is selected from the group consisting of vancomycin, teicoplanin, clindamycin, and trimethoprim-sulfamethoxazole.

* * * * *